(12) United States Patent
Boloor

(10) Patent No.: US 9,598,372 B2
(45) Date of Patent: *Mar. 21, 2017

(54) BROMODOMAIN INHIBITORS

(71) Applicant: Celgene Quanticel Research, Inc., San Diego, CA (US)

(72) Inventor: Amogh Boloor, San Diego, CA (US)

(73) Assignee: Celgene Quanticel Research, Inc., San Diego, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 14/789,881

(22) Filed: Jul. 1, 2015

(65) Prior Publication Data

US 2016/0115134 A1  Apr. 28, 2016

Related U.S. Application Data

(63) Continuation of application No. 14/658,048, filed on Mar. 13, 2015, now Pat. No. 9,115,114, which is a continuation of application No. 14/517,705, filed on Oct. 17, 2014, now Pat. No. 9,034,900.

(60) Provisional application No. 61/931,467, filed on Jan. 24, 2014, provisional application No. 61/893,133, filed on Oct. 18, 2013.

(51) Int. Cl.

| | | |
|---|---|---|
| *C07D 417/14* | (2006.01) |
| *C07D 217/24* | (2006.01) |
| *A61K 31/47* | (2006.01) |
| *C07D 498/04* | (2006.01) |
| *C07D 413/04* | (2006.01) |
| *C07D 401/04* | (2006.01) |
| *C07D 471/04* | (2006.01) |
| *C07D 405/04* | (2006.01) |
| *C07D 487/04* | (2006.01) |
| *C07D 211/94* | (2006.01) |
| *C07D 401/14* | (2006.01) |
| *C07D 213/64* | (2006.01) |
| *C07D 213/73* | (2006.01) |
| *C07D 213/74* | (2006.01) |
| *C07D 237/14* | (2006.01) |
| *C07D 239/54* | (2006.01) |
| *C07D 239/56* | (2006.01) |
| *C07D 241/20* | (2006.01) |
| *C07D 403/04* | (2006.01) |
| *C07D 405/12* | (2006.01) |
| *C07D 409/04* | (2006.01) |
| *C07D 413/06* | (2006.01) |
| *C07D 491/048* | (2006.01) |
| *C07D 495/04* | (2006.01) |

(52) U.S. Cl.
CPC .......... *C07D 217/24* (2013.01); *C07D 211/94* (2013.01); *C07D 213/64* (2013.01); *C07D 213/73* (2013.01); *C07D 213/74* (2013.01); *C07D 237/14* (2013.01); *C07D 239/54* (2013.01); *C07D 239/56* (2013.01); *C07D 241/20* (2013.01); *C07D 401/04* (2013.01); *C07D 401/14* (2013.01); *C07D 403/04* (2013.01); *C07D 405/04* (2013.01); *C07D 405/12* (2013.01); *C07D 409/04* (2013.01); *C07D 413/04* (2013.01); *C07D 413/06* (2013.01); *C07D 417/14* (2013.01); *C07D 471/04* (2013.01); *C07D 487/04* (2013.01); *C07D 491/048* (2013.01); *C07D 495/04* (2013.01); *C07D 498/04* (2013.01)

(58) Field of Classification Search
None
See application file for complete search history.

(56) References Cited

U.S. PATENT DOCUMENTS

| | | | |
|---|---|---|---|
| 3,816,422 A | 6/1974 | Stahle et al. |
| 4,711,956 A | 12/1987 | Atanassova et al. |
| 7,265,120 B2 | 9/2007 | Tsutsumi et al. |
| 8,513,232 B2 | 8/2013 | Bacon et al. |
| 8,969,341 B2 | 3/2015 | Furet et al. |
| 8,975,417 B2 | 3/2015 | Bordas et al. |
| 9,034,900 B2 | 5/2015 | Bennett et al. |
| 2006/0287341 A1 | 12/2006 | Wu et al. |
| 2007/0099911 A1 | 5/2007 | Kelly et al. |
| 2007/0213323 A1 | 9/2007 | Imogai et al. |
| 2009/0054434 A1 | 2/2009 | Hu et al. |
| 2010/0256698 A1 | 10/2010 | Trotter et al. |
| 2012/0208814 A1 | 8/2012 | Demont et al. |
| 2013/0331382 A1 | 12/2013 | Hubbard et al. |
| 2014/0349990 A1 | 11/2014 | Blank et al. |
| 2015/0005340 A1 | 1/2015 | Gong |
| 2015/0051208 A1 | 2/2015 | Engelhardt et al. |
| 2015/0183784 A1 | 7/2015 | Bennett et al. |

FOREIGN PATENT DOCUMENTS

| | | |
|---|---|---|
| CN | 103183675 A | 7/2013 |
| DE | 2011970 A1 | 11/1971 |

(Continued)

OTHER PUBLICATIONS

Gentile et al, Bioorganic & Medicinal Chemistry Letters (2011), 21(16), pp. 4823-4827.*
Alvarez et al. Product class 6: isoquinolinones. Science of Synthesis 15:839-906 (2005).
Becknell et al. Synthesis and evaluation of pyridone-phenoxypropyl-R-2-methylpyrrolidine analogues as histamine H3 receptor antagonists. Bioorganic & Medicinal Chemistry Letters 21(23):7076-7080 (2011).
Berti. A new type of electrophilic transposition: Passage of a phthalimidine derivative to an isocarbostyril. Gazzetta Chimica Italiana 90:559-72 (1960).

(Continued)

*Primary Examiner* — Zinna Northington Davis
(74) *Attorney, Agent, or Firm* — Wiley Rein LLP

(57) ABSTRACT

The present invention relates to substituted heterocyclic derivative compounds, compositions comprising said compounds, and the use of said compounds and compositions for epigenetic regulation by inhibition of bromodomain-mediated recognition of acetyl lysine regions of proteins, such as histones. Said compositions and methods are useful for the treatment of cancer and neoplastic disease.

31 Claims, No Drawings

(56) References Cited

FOREIGN PATENT DOCUMENTS

| | | | |
|---|---|---|---|
| DE | 2356005 A1 | 5/1975 |
| JP | 2005089352 A | 4/2005 |
| WO | WO-0023487 A1 | 4/2000 |
| WO | WO-2004029051 A1 | 4/2004 |
| WO | WO-2005030791 A2 | 4/2005 |
| WO | WO-2005063768 A1 | 7/2005 |
| WO | WO-2005095384 A1 | 10/2005 |
| WO | WO-2006030032 A1 | 3/2006 |
| WO | WO-2006112666 A1 | 10/2006 |
| WO | WO-2007012421 A1 | 2/2007 |
| WO | WO-2007012422 A1 | 2/2007 |
| WO | WO-2008077550 A1 | 7/2008 |
| WO | WO-2008077551 A1 | 7/2008 |
| WO | WO-2008077556 A1 | 7/2008 |
| WO | WO-2009097567 A1 | 8/2009 |
| WO | WO-2009158396 A1 | 12/2009 |
| WO | WO-2010069504 A1 | 6/2010 |
| WO | WO-2011044157 A1 | 4/2011 |
| WO | WO-2011112766 A2 | 9/2011 |
| WO | WO-2012000595 A1 | 1/2012 |
| WO | WO-2012171337 A1 | 12/2012 |
| WO | WO-2013064984 A1 | 5/2013 |
| WO | WO-2013142390 A1 | 9/2013 |
| WO | WO-2014191894 A1 | 12/2014 |
| WO | WO-2014191896 A1 | 12/2014 |
| WO | WO-2014191911 A1 | 12/2014 |
| WO | WO-2014206150 A1 | 12/2014 |
| WO | WO-2014206345 A1 | 12/2014 |
| WO | WO-2014210425 A1 | 12/2014 |
| WO | WO-2015022332 A1 | 2/2015 |

OTHER PUBLICATIONS

Berti et al. Mechanism of the cyclization of the amides of o-(2-chlorovinyl)benzoic acids. Annali di Chimica 49: 1253-68 (1959).
Berti et al. Ultraviolet spectra of some derivatives of 3- and 4-phenylisoquinoline. Annali di Chimica 49:2110-23 (1959).
Briet et al. Synthesis of novel substituted isoquinolones. Tetrahedron 58(29):5761-5766 (2002).
CAS Structure Search dated Jun. 25, 2013.
CAS Structure Search dated May 30, 2014.
Chao et al. Substituted isoquinolines and quinazolines as potential antiinflammatory agents. Synthesis and biological evaluation of inhibitors of tumor necrosis factor alpha. J. Med. Chem. 42:3860-3873 (1999).
Coskun et al. Novel Methods for the Synthesis of 4-Arylisoquinolinium Perchlorates and 4-Arylisoquinolin-1-ones. Synthetic Communications 35(18):2435-2443 (2005).
Couture et al. A new synthetic route to 2-alkyl-4-aryl-1(2H)-isoquinolones and 2-alkyl-4-aryl-1,2,3,4-tetrahydroisoquinolines. Tetrahedron 52(12):4433-48 (1996).
Couture et al. Base-induced cyclization of trimethoxy-o-aroyldiphenylphosphoryl methylbenzamide: a formal synthesis of (±) cherylline and (±) cherylline dimethylether. Tetrahedron Letters 37(21):3697-3700, (1999).
Couture et al. Total syntheses of (±)-cherylline and (±)-latifine. J. Chem. Soc., Perkin Trans. 1:789-794 (1999).
Dey et al. Brd4 marks select genes on mitotic chromatin and directs postmitotic transcription. Mol. Biol. Cell 20:4899-4909 (2009).
Filippakopoulos et al. Selective Inhibition of BET Bromodomains. Nature 468(7327):1067-73 (2010).
French et al. BRD4 bromodomain gene rearrangement in aggressive carcinoma with translocation t(15;19). Am J Pathol 159:1987-1992 (2001).
French et al. BRD4-NUT fusion oncogene: a novel mechanism in aggressive carcinoma. Cancer Res. 63:304-307 (2003).
Gore et al. Efficient synthesis of (±)-latifine dimethyl ether. Journal of the Chemical Society, Perkin Transactions 1: Organic and Bio-Organic Chemistry (3):481-3 (1972-1999) (1988).
Hares et al. Synthesis and Antibacterial Activity of Some 4-Oxopyrrolo [1,2-a] pyrimidine 3-Carboxylic Acid Derivatives. Egyptian Journal of Pharmaceutical Sciences 32(1-2) 303-14 (1991).
Hargreaves, et al. Control of inducible gene expression by signal-dependent transcriptional elongation. Cell 138:129-145 (2009).
Henry et al. Preparation and fluorescence of substituted 2-methyl-1-isoquinolones Journal of Organic Chemistry 40(12):1760-6 (1975).
Jang, et al. The bromodomain protein Brd4 is a positive regulatory component of P-TEFb and stimulates RNA polymerase II-dependent transcription. Mol Cell 19:523-534 (2005).
Kihara et al. New reduction reaction of benzylic alcohols with acid and proof of the intermolecular hydride shift mechanism. Heterocycles 53(2):359-372 (2000).
Kihara et al. Stereoselective intermolecular hydride shift mechanism of the new reduction of benzylic alcohols with acid. Heterocycles 48(12):2473-2476 (1998).
Leroy et al. The double bromodomain proteins Brd2 and Brd3 couple histone acetylation to transcription. Mol Cell 30:51-60 (2008).
Mishra et al. Diversely Substituted Imidazo[1,2-α]pyrazine-8-oxo-3carbaldehydes: An Iodine-Mediated Cyclization/Oxidation Approach. European Journal of Organic Chemistry 2013(4):693-700 (2013).
Moehrle et al. Carbinolamines from substituted tetrahydroisoquinolines, Archiv der Pharmazie (Weinheim, Germany) 321(10):759-64 (CAPLUS Accession No. 1989:23703) (1988).
Mukaiyama et al. Synthesis and c-Src inhibitory activity of imidazo[1,5-a]pyrazine derivatives as an agent for treatment of acute ischemic stroke. Bioorganic & Medicinal Chemistry 15(2):868-885, (2007).
Narasimhan et al. An Efficient Synthesis of 4Aryl-1,2,3,4-tetrahydrosisoquinolines. Journal of the Chemical Society, Chemical Communications (3):191-2 (1987).
Natsugari et al. Novel, Potent, and Orally Active Substance P Antagonists: Synthesis and Antagonist Activity of N-Benzylcarboxamide Derivatives of Pyrido[3,4-b]pyridine. Journal of Medicinal Chemistry 38(16):3106-20 (1995).
Nicodeme et al. Suppression of Inflammation by a Synthetic Histone Mimic. Nature 468(7327):1119-23 (2010).
PCT/US2014/61261 International Search Report and Written Opinion dated Jan. 21, 2015.
Phelps et al. Clinical response and pharmacokinetics from a phase 1 study of an active dosing schedule of flavopiridol in relapsed chronic lymphocytic leukemia. Blood 113:2637-2645 (2009).
Rahl et al. c-Myc regulates transcriptional pause release Cell 141:432-445 (2010).
Staehle et al. RingschluBreaktionen mit 2-Aminoimidazolinen. Liebigs Annalen Chemie, pp. 1275-1281 (1973) (English Abstract).
Svechkarev et al. Synthesis and spectral properties of new luminescent compounds with intramolecular proton phototransfer reaction which are derivatives of 2-(N-methylisoquinolon-1(2H)-4-yl)-3-hydroxychromone, Visnik Kharkivs'kogo Natsional'nogo Universitetu im. V. N. Karazina 770:201-207 (CAPLUS Accession No. 2008:1015841) (2007) (English Abstract).
Vachhani et al. A facile diversity-oriented synthesis of imidazo[1,2-a]pyrazinones via gold-catalyzed regioselective heteroannulation of propynylaminopyrazinones. Tetrahedron 69(1):359-365 (2013).
Wang et al. A novel synthesis of arylpyrrolo[1,2-a]pyrazinone derivatives. Molecules 9(7):574-582 (2004).
Xie et al. Synthesis, single-crystal characterization and preliminary biological evaluation of novel ferrocenyl pyrazolo[1,5-a]pyrazin-4(5H)-one derivatives. European Journal of Medicinal Chemistry 45(1):210-218 (2010).
Yang et al. Multisite protein modification and intramolecular signaling. Oncogene 24:1653-1662 (2005).
Yang et al. Recruitment of P-TEFb for stimulation of transcriptional elongation by the bromodomain protein Brd4 (2005) Mol. Cell 19:535-545.

* cited by examiner

BROMODOMAIN INHIBITORS

CROSS REFERENCE

This application is a continuation of U.S. application Ser. No. 14/658,048, filed Mar. 13, 2015, which is a continuation of U.S. application Ser. No. 14/517,705, filed Oct. 17, 2014, which claims the benefit of U.S. Provisional Application No. 61/893,133, filed Oct. 18, 2013, and U.S. Provisional Application No. 61/931,467, filed Jan. 24, 2014, the contents of which are hereby incorporated by reference in their entireties.

BACKGROUND

A need exists in the art for an effective treatment of cancer and neoplastic disease.

BRIEF SUMMARY OF THE INVENTION

Provided herein are substituted heterocyclic derivative compounds and pharmaceutical compositions comprising said compounds. The subject compounds and compositions are useful for epigenetic regulation by inhibition of bromodomain-mediated recognition of acetyl lysine regions of proteins, such as histones. Furthermore, the subject compounds and compositions are useful for the treatment of cancer, such as NUT midline carcinoma, Burkitts lymphoma, prostate cancer, breast cancer, bladder cancer, lung cancer and/or melanoma and the like. The substituted heterocyclic derivative compounds described herein are based upon isoquinolinones and related heterocyclic structures. Said isoquinolinones and related heterocyclic structures are substituted at the 4-position with a group such as an aryl, a heteroaryl and the like, and on the nitrogen atom of the isoquinolinone or related heterocyclic structure with a small alkyl group, such as a methyl group.

One embodiment provides a compound of Formula (I), or a pharmaceutically acceptable salt thereof,

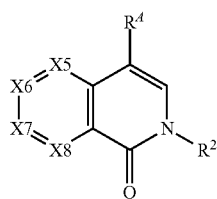

Formula (I)

wherein,
$R^2$ is selected from $CH_3$, $CH_2CH_3$, $CH_2CF_3$, $CH_2F$, $CHF_2$, $CF_3$, $CH_2D$, $CHD_2$, or $CD_3$;
X5 is C—$R^5$ or N;
X6 is C—$R^6$ or N;
X7 is C—$R^7$ or N;
X8 is C—$R^8$ or N; wherein no more than two of X5, X6, X7, or X8 may be N;
$R^5$ is hydrogen, halogen, —OH, —CN, —$OR^{61}$, —$NHR^{61}$, —$N(R^{61})_2$, alkyl, cycloalkyl, cycloalkylalkyl, aryl, aralkyl, heterocyclyl, heterocyclylalkyl, heteroaryl, or heteroarylalkyl, wherein each $R^{61}$ is independently selected from alkyl, cycloalkyl, cycloalkylalkyl, aryl, aralkyl, heterocyclyl, heterocyclylalkyl, heteroaryl, or heteroarylalkyl;
$R^6$ is hydrogen, halogen, —OH, —CN, —$OR^{61}$, —$NHR^{61}$, —$N(R^{61})_2$, alkyl, cycloalkyl, cycloalkylalkyl, aryl, aralkyl, heterocyclyl, heterocyclylalkyl, heteroaryl, or heteroarylalkyl, wherein each $R^{61}$ is independently selected from alkyl, cycloalkyl, cycloalkylalkyl, aryl, aralkyl, heterocyclyl, heterocyclylalkyl, heteroaryl, or heteroarylalkyl;
$R^7$ is hydrogen, halogen, —OH, —CN, —$OR^{61}$, —$NHR^{61}$, —$N(R^{61})_2$, alkyl, cycloalkyl, cycloalkylalkyl, aryl, aralkyl, heterocyclyl, heterocyclylalkyl, heteroaryl, or heteroarylalkyl, wherein each $R^{61}$ is independently selected from alkyl, cycloalkyl, cycloalkylalkyl, aryl, aralkyl, heterocyclyl, heterocyclylalkyl, heteroaryl, or heteroarylalkyl;
$R^8$ is hydrogen, halogen, or alkyl;
$R^A$ is

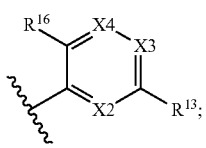

X2 is N or C—$R^{12}$, wherein $R^{12}$ is hydrogen, halogen, alkyl, or alkoxy;
$R^{13}$ is —Y—Z;
Y is selected from a bond, —$CH_2$—, —$CH(C_1-C_4$ alkyl)-;
Z is selected from —$SO_2R^{21}$, —$N(R^{22})SO_2R^{21}$, —$SO_2N(R^{22})_2$, —$N(R^{22})SO_2N(R^{22})_2$, —$CON(R^{22})_2$, —$N(R^{22})CO_2R^{21}$, —$N(R^{22})CON(R^{22})_2$, —$N(R^{22})COR^{21}$, —$COR^{21}$, —$OC(O)N(R^{22})_2$, —$OSO_2N(R^{22})_2$, or —$N(R^{22})SO_3R^{21}$;
X3 is N or C—$R^{14}$, wherein $R^{14}$ is hydrogen, halogen, —CN, alkyl, cycloalkyl, or alkoxy;
X4 is N or C—$R^{15}$, wherein $R^{15}$ is hydrogen, halogen, alkyl, —CN, or alkoxy;
$R^{16}$ is hydrogen, halogen, or —W—X, wherein W is a bond, —O—, —S—, or —NH—, and X is selected from alkyl, aryl, aralkyl, cycloalkyl, cycloalkylalkyl, alkynyl, cycloalkylalkynyl, heterocyclyl, heterocyclylalkyl, heteroaryl, or heteroarylalkyl;
each $R^{21}$ is independently selected from alkyl, cycloalkyl, cycloalkylalkyl, aryl, aralkyl, heterocyclyl, heterocyclylalkyl, heteroaryl, or heteroarylalkyl; and
each $R^{22}$ is independently selected from hydrogen, alkyl, cycloalkyl, cycloalkylalkyl, aryl, aralkyl, heterocyclyl, heterocyclylalkyl, heteroaryl, or heteroarylalkyl.

One embodiment provides a compound of Formula (II), or a pharmaceutically acceptable salt thereof,

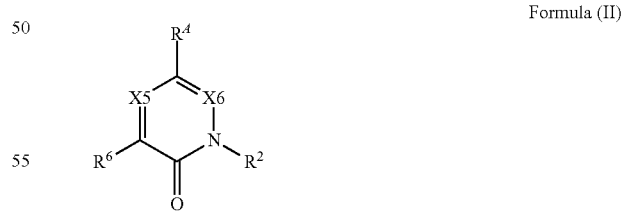

Formula (II)

wherein,
$R^2$ is alkyl, cycloalkyl, cycloalkylalkyl, heterocyclylalkyl, aralkyl, or heteroarylalkyl;
X6 is C—H or N;
X5 is C—$R^5$ or N; provided that if X6 is N, then X5 is C—$R^5$, and if X5 is N, then X6 is CH;
$R^5$ is hydrogen, halogen, —OH, —CN, —$OR^{61}$, —$NHR^{61}$, —$N(R^{61})_2$, alkyl, cycloalkyl, cycloalkylalkyl, aryl, aralkyl, heterocyclyl, heterocyclylalkyl, heteroaryl, or heteroarylalkyl, wherein each $R^{61}$ is independently selected from alkyl, cycloalkyl, cycloalkylalkyl, aryl, aralkyl, heterocyclyl, heterocyclylalkyl, heteroaryl, or heteroarylalkyl;

$R^6$ is hydrogen, halogen, —OH, —CN, alkyl, cycloalkyl, cycloalkylalkyl, amino, alkylamino, dialkylamino, cycloalkylalkylamino, alkoxy, —S-alkyl, cycloalkylalkoxy, heterocyclyl, aralkoxy, heteroaryloxy, aryloxy, alkynyloxy, or —N(H)COalkyl;

$R^4$ is

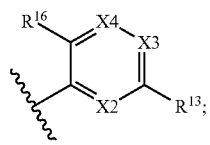

X2 is N or C—$R^{12}$, wherein $R^{12}$ is hydrogen, halogen, alkyl, or alkoxy;

$R^{13}$ is —Y—Z;

Y is selected from a bond, —CH$_2$—, or —CH(C$_1$-C$_4$alkyl)-;

Z is selected from —SO$_2$R$^{21}$, —N(R$^{22}$)SO$_2$R$^{21}$, —SO$_2$N(R$^{22}$)$_2$, —N(R$^{22}$)SO$_2$N(R$^{22}$)$_2$, —CON(R$^{22}$)$_2$, —N(R$^{22}$)CO$_2$R$^{21}$, —N(R$^{22}$)CON(R$^{22}$)$_2$, —N(R$^{22}$)COR$^{21}$, —COR$^{21}$, —OC(O)N(R$^{22}$)$_2$, —OSO$_2$N(R$^{22}$)$_2$, or —N(R$^{22}$)SO$_3$R$^{21}$;

X3 is N or C—$R^{14}$, wherein $R^{14}$ is hydrogen, halogen, —CN, alkyl, cycloalkyl, or alkoxy;

X4 is N or C—$R^{15}$, wherein $R^{15}$ is hydrogen, halogen, —CN, alkyl, alkoxy, aryloxy, aralkyloxy, cycloalkylalkyloxy, heterocyclyloxy, heteroarylalkyloxy, or alkynyloxy;

$R^{16}$ is hydrogen, halogen, —N(H)COX, or —W—X, wherein W is a bond, —O—, —S—, or —NH—, and X is selected from alkyl, aryl, aralkyl, cycloalkyl, cycloalkylalkyl, alkynyl, cycloalkylalkynyl, heterocyclyl, heterocyclylalkyl, heteroaryl, or heteroarylalkyl;

each $R^{21}$ is independently selected from alkyl, cycloalkyl, cycloalkylalkyl, aryl, aralkyl, heterocyclyl, heterocyclylalkyl, heteroaryl, or heteroarylalkyl; and each $R^{22}$ is independently selected from hydrogen, alkyl, cycloalkyl, cycloalkylalkyl, aryl, aralkyl, heterocyclyl, heterocyclylalkyl, heteroaryl, or heteroarylalkyl; and provided that when X6 is N, then $R^5$ and $R^6$ are not hydrogen.

One embodiment provides a pharmaceutical composition comprising a compound of Formula (I), or a pharmaceutically acceptable salt thereof, and a pharmaceutically acceptable excipient. One embodiment provides a pharmaceutical composition comprising a compound of Formula (II), or a pharmaceutically acceptable salt thereof, and a pharmaceutically acceptable excipient.

One embodiment provides a method of treating cancer in a patient in need thereof, comprising administering to the patient a compound of Formula (I), or a pharmaceutically acceptable salt thereof. One embodiment provides a method of treating cancer in a patient in need thereof, comprising administering to the patient a compound of Formula (II), or a pharmaceutically acceptable salt thereof.

INCORPORATION BY REFERENCE

All publications, patents, and patent applications mentioned in this specification are herein incorporated by reference to the same extent as if each individual publication, patent, or patent application was specifically and individually indicated to be incorporated by reference.

DETAILED DESCRIPTION OF THE INVENTION

As used herein and in the appended claims, the singular forms "a," "and," and "the" include plural referents unless the context clearly dictates otherwise. Thus, for example, reference to "an agent" includes a plurality of such agents, and reference to "the cell" includes reference to one or more cells (or to a plurality of cells) and equivalents thereof known to those skilled in the art, and so forth. When ranges are used herein for physical properties, such as molecular weight, or chemical properties, such as chemical formulae, all combinations and subcombinations of ranges and specific embodiments therein are intended to be included. The term "about" when referring to a number or a numerical range means that the number or numerical range referred to is an approximation within experimental variability (or within statistical experimental error), and thus the number or numerical range may vary between 1% and 15% of the stated number or numerical range. The term "comprising" (and related terms such as "comprise" or "comprises" or "having" or "including") is not intended to exclude that in other certain embodiments, for example, an embodiment of any composition of matter, composition, method, or process, or the like, described herein, may "consist of" or "consist essentially of" the described features.

DEFINITIONS

As used in the specification and appended claims, unless specified to the contrary, the following terms have the meaning indicated below.

"Amino" refers to the —NH$_2$ radical.
"Cyano" refers to the —CN radical.
"Nitro" refers to the —NO$_2$ radical.
"Oxa" refers to the —O— radical.
"Oxo" refers to the =O radical.
"Thioxo" refers to the =S radical.
"Imino" refers to the =N—H radical.
"Oximo" refers to the =N—OH radical.
"Hydrazino" refers to the =N—NH$_2$ radical.

"Alkyl" refers to a straight or branched hydrocarbon chain radical consisting solely of carbon and hydrogen atoms, containing no unsaturation, having from one to fifteen carbon atoms (e.g., C$_1$-C$_{15}$ alkyl). In certain embodiments, an alkyl comprises one to thirteen carbon atoms (e.g., C$_1$-C$_{13}$ alkyl). In certain embodiments, an alkyl comprises one to eight carbon atoms (e.g., C$_1$-C$_8$ alkyl). In other embodiments, an alkyl comprises one to five carbon atoms (e.g., C$_1$-C$_5$ alkyl). In other embodiments, an alkyl comprises one to four carbon atoms (e.g., C$_1$-C$_4$ alkyl). In other embodiments, an alkyl comprises one to three carbon atoms (e.g., C$_1$-C$_3$ alkyl). In other embodiments, an alkyl comprises one to two carbon atoms (e.g., C$_1$-C$_2$ alkyl). In other embodiments, an alkyl comprises one carbon atom (e.g., C$_1$ alkyl). In other embodiments, an alkyl comprises five to fifteen carbon atoms (e.g., C$_5$-C$_{15}$ alkyl). In other embodiments, an alkyl comprises five to eight carbon atoms (e.g., C$_5$-C$_8$ alkyl). In other embodiments, an alkyl comprises two to five carbon atoms (e.g., C$_2$-C$_5$ alkyl). In other embodiments, an alkyl comprises three to five carbon atoms (e.g., C$_3$-C$_5$ alkyl). In other embodiments, the alkyl group is selected from methyl, ethyl, 1-propyl (n-propyl), 1-methylethyl (iso-propyl), 1-butyl (n-butyl), 1-methylpropyl (sec-butyl), 2-methylpropyl (iso-butyl), 1,1-dimethylethyl (tert-butyl), 1-pentyl (n-pentyl). The alkyl is attached to the rest of the molecule by a single bond. Unless stated otherwise specifically in the specification, an alkyl group is optionally substituted by one or more of the following substituents: halo, cyano, nitro, oxo, thioxo, imino, oximo, trimethylsilanyl, —OR$^a$, —SR$^a$, —OC(O)—R$^a$, —N(R$^a$)$_2$, —C(O)R$^a$, —C(O)OR$^a$, —C(O)N(R$^a$)$_2$, —N(R$^a$)C(O)OR$^a$, —OC(O)—N(R$^a$)$_2$, —N(R$^a$)C(O)R$^a$, —N(R$^a$)S(O)$_t$R$^a$ (where t is 1 or 2), —S(O)$_t$OR$^a$ (where t is 1 or 2), —S(O)$_t$R$^a$ (where t is 1 or 2) and —S(O)$_t$N(R$^a$)$_2$ (where t is 1 or 2) where each R$^a$ is independently hydrogen, alkyl (optionally substituted with halogen, hydroxy, methoxy, or trifluoromethyl), fluoroalkyl, carbocyclyl (optionally substituted with halogen, hydroxy, methoxy, or trifluoromethyl), carbocyclylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl).

"Alkoxy" refers to a radical bonded through an oxygen atom of the formula —O-alkyl, where alkyl is an alkyl chain as defined above.

"Alkenyl" refers to a straight or branched hydrocarbon chain radical group consisting solely of carbon and hydrogen atoms, containing at least one carbon-carbon double bond, and having from two to twelve carbon atoms. In certain embodiments, an alkenyl comprises two to eight carbon atoms. In other embodiments, an alkenyl comprises two to four carbon atoms. The alkenyl is attached to the rest of the molecule by a single bond, for example, ethenyl (i.e., vinyl), prop-1-enyl (i.e., allyl), but-1-enyl, pent-1-enyl, penta-1,4-dienyl, and the like. Unless stated otherwise specifically in the specification, an alkenyl group is optionally substituted by one or more of the following substituents: halo, cyano, nitro, oxo, thioxo, imino, oximo, trimethylsilanyl, —OR$^a$, —SR$^a$, —OC(O)—R$^a$, —N(R$^a$)$_2$, —C(O)R$^a$, —C(O)OR$^a$, —C(O)N(R$^a$)$_2$, —N(R$^a$)C(O)OR$^a$, —OC(O)—N(R$^a$)$_2$, —N(R$^a$)C(O)R$^a$, —N(R$^a$)S(O)$_t$R$^a$ (where t is 1 or 2), —S(O)$_t$OR$^a$ (where t is 1 or 2), —S(O)$_t$R$^a$ (where t is 1 or 2) and —S(O)$_t$N(R$^a$)$_2$ (where t is 1 or 2) where each R$^a$ is independently hydrogen, alkyl (optionally substituted with halogen, hydroxy, methoxy, or trifluoromethyl), fluoroalkyl, carbocyclyl (optionally substituted with halogen, hydroxy, methoxy, or trifluoromethyl), carbocyclylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl).

"Alkynyl" refers to a straight or branched hydrocarbon chain radical group consisting solely of carbon and hydrogen atoms, containing at least one carbon-carbon triple bond, having from two to twelve carbon atoms. In certain embodiments, an alkynyl comprises two to eight carbon atoms. In other embodiments, an alkynyl has two to four carbon atoms. The alkynyl is attached to the rest of the molecule by a single bond, for example, ethynyl, propynyl, butynyl, pentynyl, hexynyl, and the like. Unless stated otherwise specifically in the specification, an alkynyl group is optionally substituted by one or more of the following substituents: halo, cyano, nitro, oxo, thioxo, imino, oximo, trimethylsilanyl, —OR$^a$, —SR$^a$, —OC(O)—R$^a$, —N(R$^a$)$_2$, —C(O)R$^a$, —C(O)OR$^a$, —C(O)N(R$^a$)$_2$, —N(R$^a$)C(O)OR$^a$, —OC(O)—N(R$^a$)$_2$, —N(R$^a$)C(O)R$^a$, —N(R$^a$)S(O)$_t$R$^a$ (where t is 1 or 2), —S(O)$_t$OR$^a$ (where t is 1 or 2), —S(O)$_t$R$^a$ (where t is 1 or 2) and —S(O)$_t$N(R$^a$)$_2$ (where t is 1 or 2) where each R$^a$ is independently hydrogen, alkyl (optionally substituted with halogen, hydroxy, methoxy, or trifluoromethyl), fluoroalkyl, carbocyclyl (optionally substituted with halogen, hydroxy, methoxy, or trifluoromethyl), carbocyclylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl).

"Alkylene" or "alkylene chain" refers to a straight or branched divalent hydrocarbon chain linking the rest of the molecule to a radical group, consisting solely of carbon and hydrogen, containing no unsaturation and having from one to twelve carbon atoms, for example, methylene, ethylene, propylene, n-butylene, and the like. The alkylene chain is attached to the rest of the molecule through a single bond and to the radical group through a single bond. The points of attachment of the alkylene chain to the rest of the molecule and to the radical group can be through one carbon in the alkylene chain or through any two carbons within the chain. In certain embodiments, an alkylene comprises one to eight carbon atoms (e.g., $C_1$-$C_8$ alkylene). In other embodiments, an alkylene comprises one to five carbon atoms (e.g., $C_1$-$C_5$ alkylene). In other embodiments, an alkylene comprises one to four carbon atoms (e.g., $C_1$-$C_4$ alkylene). In other embodiments, an alkylene comprises one to three carbon atoms (e.g., $C_1$-$C_3$ alkylene). In other embodiments, an alkylene comprises one to two carbon atoms (e.g., $C_1$-$C_2$ alkylene). In other embodiments, an alkylene comprises one carbon atom (e.g., $C_1$ alkylene). In other embodiments, an alkylene comprises five to eight carbon atoms (e.g., $C_5$-$C_8$ alkylene). In other embodiments, an alkylene comprises two to five carbon atoms (e.g., $C_2$-$C_5$ alkylene). In other embodiments, an alkylene comprises three to five carbon atoms (e.g., $C_3$-$C_5$ alkylene). Unless stated otherwise specifically in the specification, an alkylene chain is optionally substituted by one or more of the following substituents: halo, cyano, nitro, oxo, thioxo, imino, oximo, trimethylsilanyl, —OR$^a$, —SR$^a$, —OC(O)—R$^a$, —N(R$^a$)$_2$, —C(O)R$^a$, —C(O)OR$^a$, —C(O)N(R$^a$)$_2$, —N(R$^a$)C(O)OR$^a$, —OC(O)—N(R$^a$)$_2$, —N(R$^a$)C(O)R$^a$, —N(R$^a$)S(O)$_t$R$^a$ (where t is 1 or 2), —S(O)$_t$OR$^a$ (where t is 1 or 2), —S(O)$_t$R$^a$ (where t is 1 or 2) and —S(O)$_t$N(R$^a$)$_2$ (where t is 1 or 2) where each R$^a$ is independently hydrogen, alkyl (optionally substituted with halogen, hydroxy, methoxy, or trifluoromethyl), fluoroalkyl, carbocyclyl (optionally substituted with halogen, hydroxy, methoxy, or trifluoromethyl), carbocyclylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl).

"Alkynylene" or "alkynylene chain" refers to a straight or branched divalent hydrocarbon chain linking the rest of the molecule to a radical group, consisting solely of carbon and hydrogen, containing at least one carbon-carbon triple bond and having from two to twelve carbon atoms. The alkynylene chain is attached to the rest of the molecule through a single bond and to the radical group through a single bond. In certain embodiments, an alkynylene comprises two to eight carbon atoms (e.g., $C_2$-$C_8$ alkynylene). In other embodiments, an alkynylene comprises two to five carbon atoms (e.g., $C_2$-$C_5$ alkynylene). In other embodiments, an alkynylene comprises two to four carbon atoms (e.g., $C_2$-$C_4$ alkynylene). In other embodiments, an alkynylene comprises two to three carbon atoms (e.g., $C_2$-$C_3$ alkynylene). In other embodiments, an alkynylene comprises two carbon atoms (e.g., $C_2$ alkynylene). In other embodiments, an alkynylene comprises five to eight carbon atoms (e.g., $C_5$-$C_8$ alkynylene). In other embodiments, an alkynylene comprises two to five carbon atoms (e.g., $C_2$-$C_5$ alkynylene). In other embodiments, an alkynylene comprises three to five carbon atoms (e.g., $C_3$-$C_5$ alkynylene). Unless stated otherwise specifically in the specification, an alkynylene chain is optionally substituted by one or more of the following substituents: halo, cyano, nitro, oxo, thioxo, imino, oximo, trimethylsilanyl, —$OR^a$, —$SR^a$, —OC(O)—$R^a$, —N($R^a$)$_2$, —C(O)$R^a$, —C(O)O$R^a$, —C(O)N($R^a$)$_2$, —N($R^a$)C(O)O$R^a$, —OC(O)—N($R^a$)$_2$, —N($R^a$)C(O)$R^a$, —N($R^a$)S(O)$_t$$R^a$ (where t is 1 or 2), —S(O)$_t$O$R^a$ (where t is 1 or 2), —S(O)$_t$$R^a$ (where t is 1 or 2) and —S(O)$_t$N($R^a$)$_2$ (where t is 1 or 2) where each $R^a$ is independently hydrogen, alkyl (optionally substituted with halogen, hydroxy, methoxy, or trifluoromethyl), fluoroalkyl, carbocyclyl (optionally substituted with halogen, hydroxy, methoxy, or trifluoromethyl), carbocyclylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl).

"Aryl" refers to a radical derived from an aromatic monocyclic or multicyclic hydrocarbon ring system by removing a hydrogen atom from a ring carbon atom. The aromatic monocyclic or multicyclic hydrocarbon ring system contains only hydrogen and carbon from five to eighteen carbon atoms, where at least one of the rings in the ring system is fully unsaturated, i.e., it contains a cyclic, delocalized (4n+2) π-electron system in accordance with the Hückel theory. The ring system from which aryl groups are derived include, but are not limited to, groups such as benzene, fluorene, indane, indene, tetralin and naphthalene. Unless stated otherwise specifically in the specification, the term "aryl" or the prefix "ar-" (such as in "aralkyl") is meant to include aryl radicals optionally substituted by one or more substituents independently selected from alkyl, alkenyl, alkynyl, halo, fluoroalkyl, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, —$R^b$—$OR^a$, —$R^b$—OC(O)—$R^a$, —$R^b$—OC(O)—O$R^a$, —$R^b$—OC(O)—N($R^a$)$_2$, —$R^b$—N($R^a$)$_2$, —$R^b$—C(O)$R^a$, —$R^b$—C(O)O$R^a$, —$R^b$—C(O)N($R^a$)$_2$, —$R^b$—O—$R^c$—C(O)N($R^a$)$_2$, —$R^b$—N($R^a$)C(O)O$R^a$, —$R^b$—N($R^a$)C(O)$R^a$, —$R^b$—N($R^a$)S(O)$_t$$R^a$ (where t is 1 or 2), —$R^b$—S(O)$_t$$R^a$ (where t is 1 or 2), —$R^b$—S(O)$_t$O$R^a$ (where t is 1 or 2) and —$R^b$—S(O)$_t$N($R^a$)$_2$ (where t is 1 or 2), where each $R^a$ is independently hydrogen, alkyl (optionally substituted with halogen, hydroxy, methoxy, or trifluoromethyl), fluoroalkyl, cycloalkyl (optionally substituted with halogen, hydroxy, methoxy, or trifluoromethyl), cycloalkylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl), each $R^b$ is independently a direct bond or a straight or branched alkylene or alkenylene chain, and $R^c$ is a straight or branched alkylene or alkenylene chain, and where each of the above substituents is unsubstituted unless otherwise indicated.

"Aralkyl" refers to a radical of the formula —$R^c$-aryl where $R^c$ is an alkylene chain as defined above, for example, methylene, ethylene, and the like. The alkylene chain part of the aralkyl radical is optionally substituted as described above for an alkylene chain. The aryl part of the aralkyl radical is optionally substituted as described above for an aryl group.

"Aralkenyl" refers to a radical of the formula —$R^d$-aryl where $R^d$ is an alkenylene chain as defined above. The aryl part of the aralkenyl radical is optionally substituted as described above for an aryl group. The alkenylene chain part of the aralkenyl radical is optionally substituted as defined above for an alkenylene group.

"Aralkynyl" refers to a radical of the formula —$R^e$-aryl, where $R^e$ is an alkynylene chain as defined above. The aryl part of the aralkynyl radical is optionally substituted as described above for an aryl group. The alkynylene chain part of the aralkynyl radical is optionally substituted as defined above for an alkynylene chain.

"Aralkoxy" refers to a radical bonded through an oxygen atom of the formula —O—$R^c$-aryl where $R^c$ is an alkylene chain as defined above, for example, methylene, ethylene, and the like.

The alkylene chain part of the aralkyl radical is optionally substituted as described above for an alkylene chain. The aryl part of the aralkyl radical is optionally substituted as described above for an aryl group.

"Carbocyclyl" refers to a stable non-aromatic monocyclic or polycyclic hydrocarbon radical consisting solely of carbon and hydrogen atoms, which includes fused or bridged ring systems, having from three to fifteen carbon atoms. In certain embodiments, a carbocyclyl comprises three to ten carbon atoms. In other embodiments, a carbocyclyl comprises five to seven carbon atoms. The carbocyclyl is attached to the rest of the molecule by a single bond. Carbocyclyl may be saturated, (i.e., containing single C—C bonds only) or unsaturated (i.e., containing one or more double bonds or triple bonds.) A fully saturated carbocyclyl radical is also referred to as "cycloalkyl." Examples of monocyclic cycloalkyls include, e.g., cyclopropyl, cyclobutyl, cyclopentyl, cyclohexyl, cycloheptyl, and cyclooctyl. An unsaturated carbocyclyl is also referred to as "cycloalkenyl." Examples of monocyclic cycloalkenyls include, e.g., cyclopentenyl, cyclohexenyl, cycloheptenyl, and cyclooctenyl. Polycyclic carbocyclyl radicals include, for example, adamantyl, norbornyl (i.e., bicyclo[2.2.1]heptanyl), norbornenyl, decalinyl, 7,7-dimethyl-bicyclo[2.2.1]heptanyl, and the like. Unless otherwise stated specifically in the specification, the term "carbocyclyl" is meant to include carbocyclyl radicals that are optionally substituted by one or more substituents independently selected from alkyl, alkenyl, alkynyl, halo, fluoroalkyl, oxo, thioxo, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, —$R^b$—$OR^a$, —$R^b$—OC(O)—$R^a$, —$R^b$—OC(O)—$OR^a$, —$R^b$—OC(O)—N($R^a$)$_2$, —$R^b$—N($R^a$)$_2$, —$R^b$—C(O)$R^a$, —$R^b$—C(O)$OR^a$, —$R^b$—C(O)N($R^a$)$_2$, —$R^b$—O—$R^c$—C(O)N($R^a$)$_2$, —$R^b$—N($R^a$)C(O)$OR^a$, —$R^b$—N($R^a$)C(O)$R^a$, —$R^b$—N($R^a$)S(O)$_t$$R^a$ (where t is 1 or 2), —$R^b$—S(O)$_t$$R^a$ (where t is 1 or 2), —$R^b$—S(O)$_t$$OR^a$ (where t is 1 or 2) and —$R^b$—S(O)$_t$N($R^a$)$_2$ (where t is 1 or 2), where each $R^a$ is independently hydrogen, alkyl (optionally substituted with halogen, hydroxy, methoxy, or trifluoromethyl), fluoroalkyl, cycloalkyl (optionally substituted with halogen, hydroxy, methoxy, or trifluoromethyl), cycloalkylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl), each $R^b$ is independently a direct bond or a straight or branched alkylene or alkenylene chain, and $R^c$ is a straight or branched alkylene or alkenylene chain, and where each of the above substituents is unsubstituted unless otherwise indicated.

"Carbocyclylalkyl" refers to a radical of the formula —$R^c$-carbocyclyl where $R^c$ is an alkylene chain as defined above. The alkylene chain and the carbocyclyl radical is optionally substituted as defined above.

"Carbocyclylalkoxy" refers to a radical bonded through an oxygen atom of the formula —O—$R^c$-carbocyclyl where $R^c$ is an alkylene chain as defined above. The alkylene chain and the carbocyclyl radical is optionally substituted as defined above.

"Carbocyclylalkynyl" refers to a radical of the formula —$R^c$-carbocyclyl, where $R^c$ is an alkynylene chain as defined above. The carbocyclyl part of the carbocyclylalkynyl radical is optionally substituted as described above for an carbocyclyl group. In some embodiments the carbocyclyl group is a cycloalkyl group. The alkynylene chain part of the carbocyclylalkynyl radical is optionally substituted as defined above for an alkynylene chain.

As used herein, "carboxylic acid bioisostere" refers to a functional group or moiety that exhibits similar physical, biological and/or chemical properties as a carboxylic acid moiety. Examples of carboxylic acid bioisosteres include, but are not limited to,

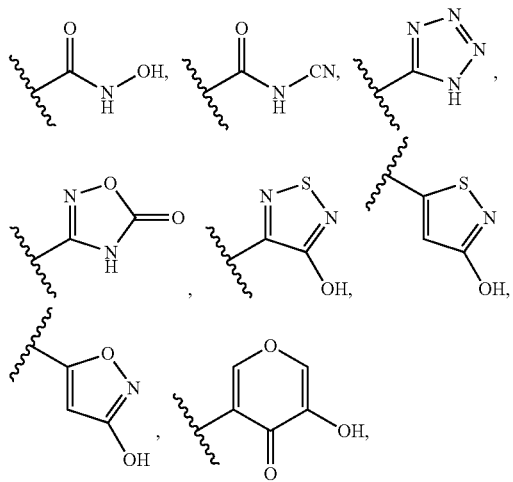

and the like.

"Halo" or "halogen" refers to bromo, chloro, fluoro or iodo substituents.

"Fluoroalkyl" refers to an alkyl radical, as defined above, that is substituted by one or more fluoro radicals, as defined above, for example, trifluoromethyl, difluoromethyl, fluoromethyl, 2,2,2-trifluoroethyl, 1-fluoromethyl-2-fluoroethyl, and the like. The alkyl part of the fluoroalkyl radical may be optionally substituted as defined above for an alkyl group.

"Heterocyclyl" refers to a stable 3- to 18-membered non-aromatic ring radical that comprises two to twelve carbon atoms and from one to six heteroatoms selected from nitrogen, oxygen and sulfur. Unless stated otherwise specifically in the specification, the heterocyclyl radical is a monocyclic, bicyclic, tricyclic or tetracyclic ring system, which may include fused or bridged ring systems. The heteroatoms in the heterocyclyl radical may be optionally oxidized.

One or more nitrogen atoms, if present, are optionally quaternized. The heterocyclyl radical is partially or fully saturated. The heterocyclyl may be attached to the rest of the molecule through any atom of the ring(s). Examples of such heterocyclyl radicals include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, and 1,1-dioxo-thiomorpholinyl. Unless stated otherwise specifically in the specification, the term "heterocyclyl" is meant to include heterocyclyl radicals as defined above that are optionally substituted by one or more substituents selected from alkyl, alkenyl, alkynyl, halo, fluoroalkyl, oxo, thioxo, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, —R$^b$—OR$^a$, —R$^b$—OC(O)—R$^a$, —R$^b$—OC(O)—OR$^a$, —R$^b$—OC(O)—N(R$^a$)$_2$, —R$^b$—N(R$^a$)$_2$, —R$^b$—C(O)R$^a$, —R$^b$—C(O)OR$^a$, —R$^b$—C(O)N(R$^a$)$_2$, —R$^b$—O—R$^c$—C(O)N(R$^a$)$_2$, —R$^b$—N(R$^a$)C(O)OR$^a$, —R$^b$—N(R$^a$)C(O)R$^a$, —R$^b$—N(R$^a$)S(O)$_t$R$^a$ (where t is 1 or 2), —R$^b$—S(O)$_t$R$^a$ (where t is 1 or 2), —R$^b$—S(O)$_t$OR$^a$ (where t is 1 or 2) and —R$^b$—S(O)$_t$N(R$^a$)$_2$ (where t is 1 or 2), where each R$^a$ is independently hydrogen, alkyl (optionally substituted with halogen, hydroxy, methoxy, or trifluoromethyl), fluoroalkyl, cycloalkyl (optionally substituted with halogen, hydroxy, methoxy, or trifluoromethyl), cycloalkylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl), each R$^b$ is independently a direct bond or a straight or branched alkylene or alkenylene chain, and R$^c$ is a straight or branched alkylene or alkenylene chain, and where each of the above substituents is unsubstituted unless otherwise indicated.

"N-heterocyclyl" or "N-attached heterocyclyl" refers to a heterocyclyl radical as defined above containing at least one nitrogen and where the point of attachment of the heterocyclyl radical to the rest of the molecule is through a nitrogen atom in the heterocyclyl radical. An N-heterocyclyl radical is optionally substituted as described above for heterocyclyl radicals. Examples of such N-heterocyclyl radicals include, but are not limited to, 1-morpholinyl, 1-piperidinyl, 1-piperazinyl, 1-pyrrolidinyl, pyrazolidinyl, imidazolinyl, and imidazolidinyl.

"C-heterocyclyl" or "C-attached heterocyclyl" refers to a heterocyclyl radical as defined above containing at least one heteroatom and where the point of attachment of the heterocyclyl radical to the rest of the molecule is through a carbon atom in the heterocyclyl radical. A C-heterocyclyl radical is optionally substituted as described above for heterocyclyl radicals. Examples of such C-heterocyclyl radicals include, but are not limited to, 2-morpholinyl, 2- or 3- or 4-piperidinyl, 2-piperazinyl, 2- or 3-pyrrolidinyl, and the like.

"Heterocyclylalkyl" refers to a radical of the formula —R$^c$-heterocyclyl where R$^c$ is an alkylene chain as defined above. If the heterocyclyl is a nitrogen-containing heterocyclyl, the heterocyclyl is optionally attached to the alkyl radical at the nitrogen atom. The alkylene chain of the heterocyclylalkyl radical is optionally substituted as defined above for an alkylene chain. The heterocyclyl part of the heterocyclylalkyl radical is optionally substituted as defined above for a heterocyclyl group.

"Heterocyclylalkoxy" refers to a radical bonded through an oxygen atom of the formula —O—R$^c$-heterocyclyl where R$^c$ is an alkylene chain as defined above. If the heterocyclyl is a nitrogen-containing heterocyclyl, the heterocyclyl is optionally attached to the alkyl radical at the nitrogen atom. The alkylene chain of the heterocyclylalkoxy radical is optionally substituted as defined above for an alkylene chain. The heterocyclyl part of the heterocyclylalkoxy radical is optionally substituted as defined above for a heterocyclyl group.

"Heteroaryl" refers to a radical derived from a 3- to 18-membered aromatic ring radical that comprises two to seventeen carbon atoms and from one to six heteroatoms selected from nitrogen, oxygen and sulfur. As used herein, the heteroaryl radical may be a monocyclic, bicyclic, tricyclic or tetracyclic ring system, wherein at least one of the rings in the ring system is fully unsaturated, i.e., it contains a cyclic, delocalized (4n+2) π-electron system in accordance with the Hückel theory. Heteroaryl includes fused or bridged ring systems. The heteroatom(s) in the heteroaryl radical is optionally oxidized. One or more nitrogen atoms, if present, are optionally quaternized. The heteroaryl is attached to the rest of the molecule through any atom of the ring(s). Examples of heteroaryls include, but are not limited to, azepinyl, acridinyl, benzimidazolyl, benzindolyl, 1,3-benzodioxolyl, benzofuranyl, benzooxazolyl, benzo[d]thiazolyl, benzothiadiazolyl, benzo[b][1,4]dioxepinyl, benzo[b][1,4]oxazinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzothieno[3,2-d]pyrimidinyl, benzotriazolyl, benzo[4,6]imidazo[1,2-a]pyridinyl, carbazolyl, cinnolinyl, cyclopenta[d]pyrimidinyl, 6,7-dihydro-5H-cyclopenta[4,5]thieno[2,3-d]pyrimidinyl, 5,6-dihydrobenzo[h]quinazolinyl, 5,6-dihydrobenzo[h]cinnolinyl, 6,7-dihydro-5H-benzo[6,7]cyclohepta[1,2-c]pyridazinyl, dibenzofuranyl, dibenzothiophenyl, furanyl, furanonyl, furo[3,2-c]pyridinyl, 5,6,7,8,9,10-hexahydrocycloocta[d]pyrimidinyl, 5,6,7,8,9,10-hexahydrocycloocta[d]pyridazinyl, 5,6,7,8,9,10-hexahydrocycloocta[d]pyridinyl, isothiazolyl, imidazolyl, indazolyl, indolyl, indazolyl, isoindolyl, indolinyl, isoindolinyl, isoquinolyl, indolizinyl, isoxazolyl, 5,8-methano-5,6,7,8-tetrahydroquinazolinyl, naphthyridinyl, 1,6-naphthyridinonyl, oxadiazolyl, 2-oxoazepinyl, oxazolyl, oxiranyl, 5,6,6a,7,8,9,10,10a-octahydrobenzo[h]quinazolinyl, 1-phenyl-1H-pyrrolyl, phenazinyl, phenothiazinyl, phenoxazinyl, phthalazinyl, pteridinyl, purinyl, pyrrolyl, pyrazolyl, pyrazolo[3,4-d]pyrimidinyl, pyridinyl, pyrido[3,2-d]pyrimidinyl, pyrido[3,4-d]pyrimidinyl, pyrazinyl, pyrimidinyl, pyridazinyl, pyrrolyl, quinazolinyl, quinoxalinyl, quinolinyl, isoquinolinyl, tetrahydroquinolinyl, 5,6,7,8-tetrahydroquinazolinyl, 5,6,7,8-tetrahydrobenzo[4,5]thieno[2,3-d]pyrimidinyl, 6,7,8,9-tetrahydro-5H-cyclohepta[4,5]thieno[2,3-d]pyrimidinyl, 5,6,7,8-tetrahydropyrido[4,5-c]pyridazinyl, thiazolyl, thiadiazolyl, triazolyl, tetrazolyl, triazinyl, thieno[2,3-d]pyrimidinyl, thieno[3,2-d]pyrimidinyl, thieno[2,3-c]pyridinyl, and thiophenyl (i.e. thienyl). Unless stated otherwise specifically in the specification, the term "heteroaryl" is meant to include heteroaryl radicals as defined above which are optionally substituted by one or more substituents selected from alkyl, alkenyl, alkynyl, halo, fluoroalkyl, haloalkenyl, haloalkynyl, oxo, thioxo, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, —R$^b$—OR$^a$, —R$^b$—OC(O)—R$^a$, —R$^b$—OC(O)—OR$^a$, —R$^b$—OC(O)—N(R$^a$)$_2$, —R$^b$—N(R$^a$)$_2$, —R$^b$—C(O)R$^a$, —R$^b$—C(O)OR$^a$, —R$^b$—C(O)N(R$^a$)$_2$, —R$^b$—O—R$^c$—C(O)N(R$^a$)$_2$, —R$^b$—N(R$^a$)C(O)OR$^a$, —R$^b$—N(R$^a$)C(O)R$^a$, —R$^b$—N(R$^a$)S(O)$_t$R$^a$ (where t is 1 or 2), —R$^b$—S(O)$_t$R$^a$ (where t is 1 or 2), —R$^b$—S(O)$_t$OR$^a$ (where t is 1 or 2) and —R$^b$—S(O)$_t$N(R$^a$)$_2$ (where t is 1 or 2), where each R$^a$ is independently hydrogen, alkyl (optionally substituted with halogen, hydroxy, methoxy, or trifluoromethyl), fluoroalkyl, cycloalkyl (optionally substituted with halogen, hydroxy, methoxy, or trifluoromethyl), cycloalkylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl), each $R^b$ is independently a direct bond or a straight or branched alkylene or alkenylene chain, and $R^c$ is a straight or branched alkylene or alkenylene chain, and where each of the above substituents is unsubstituted unless otherwise indicated.

"N-heteroaryl" refers to a heteroaryl radical as defined above containing at least one nitrogen and where the point of attachment of the heteroaryl radical to the rest of the molecule is through a nitrogen atom in the heteroaryl radical. An N-heteroaryl radical is optionally substituted as described above for heteroaryl radicals.

"C-heteroaryl" refers to a heteroaryl radical as defined above and where the point of attachment of the heteroaryl radical to the rest of the molecule is through a carbon atom in the heteroaryl radical. A C-heteroaryl radical is optionally substituted as described above for heteroaryl radicals.

"Heteroarylalkyl" refers to a radical of the formula —$R^c$-heteroaryl, where $R^c$ is an alkylene chain as defined above. If the heteroaryl is a nitrogen-containing heteroaryl, the heteroaryl is optionally attached to the alkyl radical at the nitrogen atom. The alkylene chain of the heteroarylalkyl radical is optionally substituted as defined above for an alkylene chain. The heteroaryl part of the heteroarylalkyl radical is optionally substituted as defined above for a heteroaryl group.

"Heteroarylalkoxy" refers to a radical bonded through an oxygen atom of the formula —O—$R^c$-heteroaryl, where $R^c$ is an alkylene chain as defined above. If the heteroaryl is a nitrogen-containing heteroaryl, the heteroaryl is optionally attached to the alkyl radical at the nitrogen atom. The alkylene chain of the heteroarylalkoxy radical is optionally substituted as defined above for an alkylene chain. The heteroaryl part of the heteroarylalkoxy radical is optionally substituted as defined above for a heteroaryl group.

The compounds disclosed herein may contain one or more asymmetric centers and may thus give rise to enantiomers, diastereomers, and other stereoisomeric forms that may be defined, in terms of absolute stereochemistry, as (R)- or (S)-. Unless stated otherwise, it is intended that all stereoisomeric forms of the compounds disclosed herein are contemplated by this disclosure. When the compounds described herein contain alkene double bonds, and unless specified otherwise, it is intended that this disclosure includes both E and Z geometric isomers (e.g., cis or trans.) Likewise, all possible isomers, as well as their racemic and optically pure forms, and all tautomeric forms are also intended to be included. The term "geometric isomer" refers to E or Z geometric isomers (e.g., cis or trans) of an alkene double bond. The term "positional isomer" refers to structural isomers around a central ring, such as ortho-, meta-, and para-isomers around a benzene ring.

A "tautomer" refers to a molecule wherein a proton shift from one atom of a molecule to another atom of the same molecule is possible. The compounds presented herein may, in certain embodiments, exist as tautomers. In circumstances where tautomerization is possible, a chemical equilibrium of the tautomers will exist. The exact ratio of the tautomers depends on several factors, including physical state, temperature, solvent, and pH. Some examples of tautomeric equilibrium include:

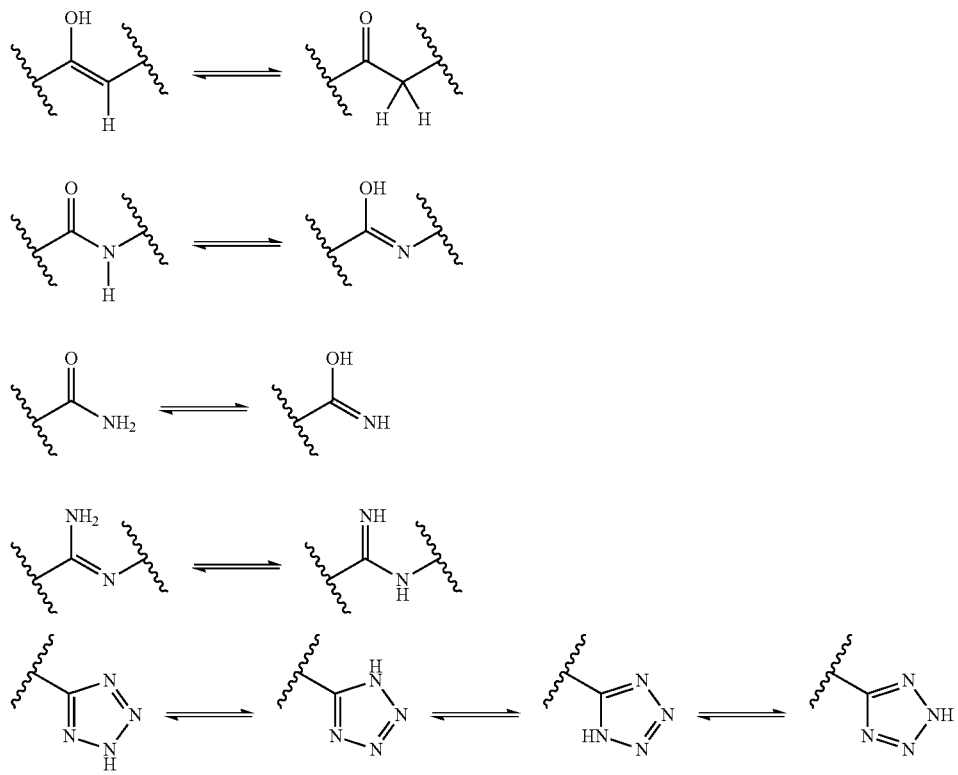

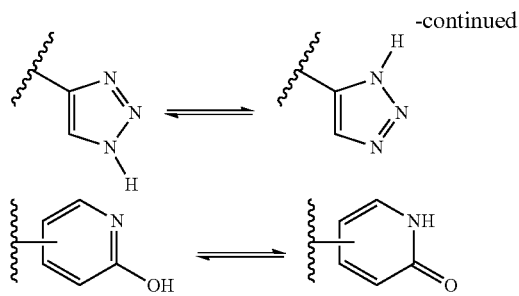

"Optional" or "optionally" means that a subsequently described event or circumstance may or may not occur and that the description includes instances when the event or circumstance occurs and instances in which it does not. For example, "optionally substituted aryl" means that the aryl radical may or may not be substituted and that the description includes both substituted aryl radicals and aryl radicals having no substitution.

"Pharmaceutically acceptable salt" includes both acid and base addition salts. A pharmaceutically acceptable salt of any one of the substituted heterocyclic derivative compounds described herein is intended to encompass any and all pharmaceutically suitable salt forms. Preferred pharmaceutically acceptable salts of the compounds described herein are pharmaceutically acceptable acid addition salts and pharmaceutically acceptable base addition salts.

"Pharmaceutically acceptable acid addition salt" refers to those salts which retain the biological effectiveness and properties of the free bases, which are not biologically or otherwise undesirable, and which are formed with inorganic acids such as hydrochloric acid, hydrobromic acid, sulfuric acid, nitric acid, phosphoric acid, hydroiodic acid, hydrofluoric acid, phosphorous acid, and the like. Also included are salts that are formed with organic acids such as aliphatic mono- and dicarboxylic acids, phenyl-substituted alkanoic acids, hydroxy alkanoic acids, alkanedioic acids, aromatic acids, aliphatic and. aromatic sulfonic acids, etc. and include, for example, acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Exemplary salts thus include sulfates, pyrosulfates, bisulfates, sulfites, bisulfites, nitrates, phosphates, monohydrogenphosphates, dihydrogenphosphates, metaphosphates, pyrophosphates, chlorides, bromides, iodides, acetates, trifluoroacetates, propionates, caprylates, isobutyrates, oxalates, malonates, succinate suberates, sebacates, fumarates, maleates, mandelates, benzoates, chlorobenzoates, methylbenzoates, dinitrobenzoates, phthalates, benzenesulfonates, toluenesulfonates, phenylacetates, citrates, lactates, malates, tartrates, methanesulfonates, and the like. Also contemplated are salts of amino acids, such as arginates, gluconates, and galacturonates (see, for example, Berge S. M. et al., "Pharmaceutical Salts," *Journal of Pharmaceutical Science*, 66:1-19 (1997)). Acid addition salts of basic compounds may be prepared by contacting the free base forms with a sufficient amount of the desired acid to produce the salt according to methods and techniques with which a skilled artisan is familiar.

"Pharmaceutically acceptable base addition salt" refers to those salts that retain the biological effectiveness and properties of the free acids, which are not biologically or otherwise undesirable. These salts are prepared from addition of an inorganic base or an organic base to the free acid. Pharmaceutically acceptable base addition salts may be formed with metals or amines, such as alkali and alkaline earth metals or organic amines. Salts derived from inorganic bases include, but are not limited to, sodium, potassium, lithium, ammonium, calcium, magnesium, iron, zinc, copper, manganese, aluminum salts and the like. Salts derived from organic bases include, but are not limited to, salts of primary, secondary, and tertiary amines, substituted amines including naturally occurring substituted amines, cyclic amines and basic ion exchange resins, for example, isopropylamine, trimethylamine, diethylamine, triethylamine, tripropylamine, ethanolamine, diethanolamine, 2-dimethylaminoethanol, 2-diethylaminoethanol, dicyclohexylamine, lysine, arginine, histidine, caffeine, procaine, N,N-dibenzylethylenediamine, chloroprocaine, hydrabamine, choline, betaine, ethylenediamine, ethylenedianiline, N-methylglucamine, glucosamine, methylglucamine, theobromine, purines, piperazine, piperidine, N-ethylpiperidine, polyamine resins and the like. See Berge et al., supra.

As used herein, "treatment" or "treating," or "palliating" or "ameliorating" are used interchangeably herein. These terms refers to an approach for obtaining beneficial or desired results including but not limited to therapeutic benefit and/or a prophylactic benefit. By "therapeutic benefit" is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient may still be afflicted with the underlying disorder. For prophylactic benefit, the compositions may be administered to a patient at risk of developing a particular disease, or to a patient reporting one or more of the physiological symptoms of a disease, even though a diagnosis of this disease may not have been made.

"Prodrug" is meant to indicate a compound that may be converted under physiological conditions or by solvolysis to a biologically active compound described herein. Thus, the term "prodrug" refers to a precursor of a biologically active compound that is pharmaceutically acceptable. A prodrug may be inactive when administered to a subject, but is converted in vivo to an active compound, for example, by hydrolysis. The prodrug compound often offers advantages of solubility, tissue compatibility or delayed release in a mammalian organism (see, e.g., Bundgard, H., Design of Prodrugs (1985), pp. 7-9, 21-24 (Elsevier, Amsterdam).

A discussion of prodrugs is provided in Higuchi, T., et al., "Pro-drugs as Novel Delivery Systems," A.C.S. Symposium Series, Vol. 14, and in Bioreversible Carriers in Drug Design, ed. Edward B. Roche, American Pharmaceutical Association and Pergamon Press, 1987.

The term "prodrug" is also meant to include any covalently bonded carriers, which release the active compound in vivo when such prodrug is administered to a mammalian subject. Prodrugs of an active compound, as described herein, may be prepared by modifying functional groups present in the active compound in such a way that the modifications are cleaved, either in routine manipulation or in vivo, to the parent active compound. Prodrugs include compounds wherein a hydroxy, amino or mercapto group is bonded to any group that, when the prodrug of the active compound is administered to a mammalian subject, cleaves to form a free hydroxy, free amino or free mercapto group, respectively. Examples of prodrugs include, but are not limited to, acetate, formate and benzoate derivatives of alcohol or amine functional groups in the active compounds and the like.

Unless otherwise stated, structures depicted herein are intended to include compounds which differ only in the presence of one or more isotopically enriched atoms. For example, compounds having the present structures except for the replacement of a hydrogen by a deuterium or tritium, or the replacement of a carbon by $^{13}$C- or $^{14}$C-enriched carbon are within the scope of the present disclosure.

The compounds of the present disclosure optionally contain unnatural proportions of atomic isotopes at one or more atoms that constitute such compounds. For example, the compounds may be labeled with isotopes, such as for example, deuterium ($^2$H), tritium ($^3$H), iodine-125 ($^{125}$I) or carbon-14 ($^{14}$C). Isotopic substitution with $^2$H, $^{11}$C, $^{13}$C, $^{14}$C, $^{15}$C, $^{12}$N, $^{13}$N, $^{15}$N, $^{16}$N, $^{16}$O, $^{17}$O, $^{14}$F, $^{15}$F, $^{16}$F, $^{17}$F, $^{18}$F, S, $^{34}$S, $^{35}$S, $^{36}$S, $^{35}$Cl, $^{37}$Cl, $^{79}$Br, $^{81}$Br, $^{125}$I are all contemplated. All isotopic variations of the compounds of the present invention, whether radioactive or not, are encompassed within the scope of the present invention.

In certain embodiments, the compounds disclosed herein have some or all of the $^1$H atoms replaced with $^2$H atoms. The methods of synthesis for deuterium-containing substituted heterocyclic derivative compounds are known in the art and include, by way of non-limiting example only, the following synthetic methods.

Deuterated starting materials are readily available and are subjected to the synthetic methods described herein to provide for the synthesis of deuterium-containing substituted heterocyclic derivative compounds. Large numbers of deuterium-containing reagents and building blocks are available commerically from chemical vendors, such as Aldrich Chemical Co.

Deuterium-transfer reagents suitable for use in nucleophilic substitution reactions, such as iodomethane-d$_3$ (CD$_3$I), are readily available and may be employed to transfer a deuterium-substituted carbon atom under nucleophilic substitution reaction conditions to the reaction substrate. The use of CD$_3$I is illustrated, by way of example only, in the reaction schemes below.

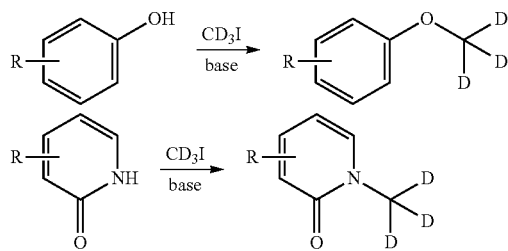

Deuterium-transfer reagents, such as lithium aluminum deuteride (LiAlD$_4$), are employed to transfer deuterium under reducing conditions to the reaction substrate. The use of LiAlD$_4$ is illustrated, by way of example only, in the reaction schemes below.

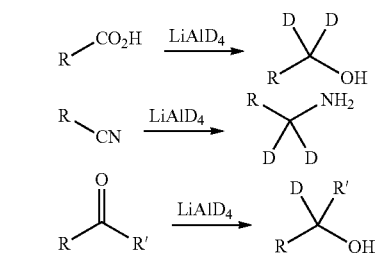

Deuterium gas and palladium catalyst are employed to reduce unsaturated carbon-carbon linkages and to perform a reductive substitution of aryl carbon-halogen bonds as illustrated, by way of example only, in the reaction schemes below.

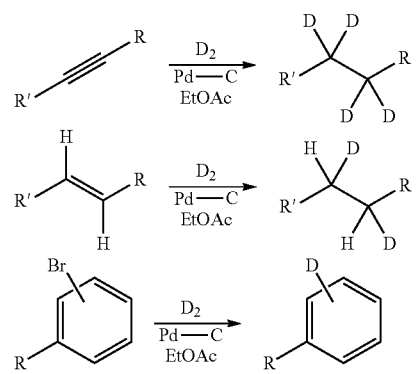

In one embodiment, the compounds disclosed herein contain one deuterium atom. In another embodiment, the compounds disclosed herein contain two deuterium atoms. In another embodiment, the compounds disclosed herein contain three deuterium atoms. In another embodiment, the compounds disclosed herein contain four deuterium atoms. In another embodiment, the compounds disclosed herein contain five deuterium atoms. In another embodiment, the compounds disclosed herein contain six deuterium atoms. In another embodiment, the compounds disclosed herein contain more than six deuterium atoms. In another embodiment, the compound disclosed herein is fully substituted with deuterium atoms and contains no non-exchangeable $^1$H hydrogen atoms. In one embodiment, the level of deuterium incorporation is determined by synthetic methods in which a deuterated synthetic building block is used as a starting material.

Substituted Heterocyclic Derivative Compounds

Substituted heterocyclic derivative compounds are described herein that are bromodomain inhibitors. These compounds, and compositions comprising these compounds, are useful for the treatment of cancer and neoplastic disease. The compounds described herein may, therefore, be useful for treating NUT midline carcinoma, Burkitts lymphoma, prostate cancer, breast cancer, bladder cancer, lung cancer and/or melanoma and the like.

One embodiment provides a compound of Formula (I), or a pharmaceutically acceptable salt thereof,

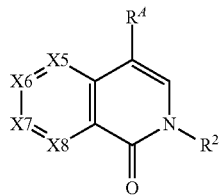

Formula (I)

wherein,
$R^2$ is selected from $CH_3$, $CH_2CH_3$, $CH_2CF_3$, $CH_2F$, $CHF_2$, $CF_3$, $CH_2D$, $CHD_2$, or $CD_3$;
X5 is C—$R^5$ or N;
X6 is C—$R^6$ or N;
X7 is C—$R^7$ or N;
X8 is C—$R^8$ or N; wherein no more than two of X5, X6, X7, or X8 may be N;
$R^5$ is hydrogen, halogen, —OH, —CN, —$OR^{61}$, —$NHR^{61}$, —$N(R^{61})_2$, alkyl, cycloalkyl, cycloalkylalkyl, aryl, aralkyl, heterocyclyl, heterocyclylalkyl, heteroaryl, or heteroarylalkyl, wherein each $R^{61}$ is independently selected from alkyl, cycloalkyl, cycloalkylalkyl, aryl, aralkyl, heterocyclyl, heterocyclylalkyl, heteroaryl, or heteroarylalkyl;
$R^6$ is hydrogen, halogen, —OH, —CN, —$OR^{61}$, —$NHR^{61}$, —$N(R^{61})_2$, alkyl, cycloalkyl, cycloalkylalkyl, aryl, aralkyl, heterocyclyl, heterocyclylalkyl, heteroaryl, or heteroarylalkyl, wherein each $R^{61}$ is independently selected from alkyl, cycloalkyl, cycloalkylalkyl, aryl, aralkyl, heterocyclyl, heterocyclylalkyl, heteroaryl, or heteroarylalkyl;
$R^7$ is hydrogen, halogen, —OH, —CN, —$OR^{61}$, —$NHR^{61}$, —$N(R^{61})_2$, alkyl, cycloalkyl, cycloalkylalkyl, aryl, aralkyl, heterocyclyl, heterocyclylalkyl, heteroaryl, or heteroarylalkyl, wherein each $R^{61}$ is independently selected from alkyl, cycloalkyl, cycloalkylalkyl, aryl, aralkyl, heterocyclyl, heterocyclylalkyl, heteroaryl, or heteroarylalkyl;
$R^8$ is hydrogen, halogen, or alkyl;
$R^4$ is

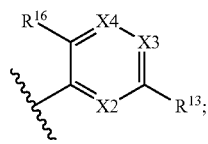

X2 is N or C—$R^{12}$, wherein $R^{12}$ is hydrogen, halogen, alkyl, or alkoxy;
$R^{13}$ is —Y—Z;
Y is selected from a bond, —$CH_2$—, —CH($C_1$-$C_4$ alkyl)-;
Z is selected from —$SO_2R^{21}$, —$N(R^{22})SO_2R^{21}$, —$SO_2N(R^{22})_2$, —$N(R^{22})SO_2N(R^{22})_2$, —$CON(R^{22})_2$, —$N(R^{22})CO_2R^{21}$, —$N(R^{22})CON(R^{22})_2$, —$N(R^{22})COR^{21}$, —$COR^{21}$, —$OC(O)N(R^{22})_2$, —$OSO_2N(R^{22})_2$, or —$N(R^{22})SO_3R^{21}$;
X3 is N or C—$R^{14}$, wherein $R^{14}$ is hydrogen, halogen, —CN, alkyl, cycloalkyl, or alkoxy;
X4 is N or C—$R^{15}$, wherein $R^{15}$ is hydrogen, halogen, alkyl, —CN, or alkoxy;
$R^{16}$ is hydrogen, halogen, or —W—X, wherein W is a bond, —O—, —S—, or —NH—, and X is selected from alkyl, aryl, aralkyl, cycloalkyl, cycloalkylalkyl, alkynyl, cycloalkylalkynyl, heterocyclyl, heterocyclylalkyl, heteroaryl, or heteroarylalkyl;

each $R^{21}$ is independently selected from alkyl, cycloalkyl, cycloalkylalkyl, aryl, aralkyl, heterocyclyl, heterocyclylalkyl, heteroaryl, or heteroarylalkyl; and
each $R^{22}$ is independently selected from hydrogen, alkyl, cycloalkyl, cycloalkylalkyl, aryl, aralkyl, heterocyclyl, heterocyclylalkyl, heteroaryl, or heteroarylalkyl.

Another embodiment provides a compound of Formula (I), wherein $R^2$ is $CH_3$. Another embodiment provides a compound of Formula (I), wherein $R^2$ is $CD_3$. Another embodiment provides a compound of Formula (I), wherein X5 is N. Another embodiment provides a compound of Formula (I), wherein X6 is N. Another embodiment provides a compound of Formula (I), wherein X7 is N. Another embodiment provides a compound of Formula (I), wherein X8 is N. Another embodiment provides a compound of Formula (I), wherein none of X5, X6, X7, or X8 is N. Another embodiment provides a compound of Formula (I), wherein $R^5$ and $R^8$ are hydrogen. Another embodiment provides a compound of Formula (I), wherein $R^5$, $R^6$, $R^7$ and $R^8$ are hydrogen. Another embodiment provides a compound of Formula (I), wherein $R^7$ is a halogen. Another embodiment provides a compound of Formula (I), wherein $R^6$ is a halogen. Another embodiment provides a compound of Formula (I), wherein $R^6$ is a heteroaryl. Another embodiment provides a compound of Formula (I), wherein $R^6$ is an aryl. Another embodiment provides a compound of Formula (I), wherein $R^6$ is an alkyl. Another embodiment provides a compound of Formula (I), wherein $R^6$ is an aryl.

Another embodiment provides a compound of Formula (I), wherein Y is a bond. Another embodiment provides a compound of Formula (I), wherein Y is a —$CH_2$—. Another embodiment provides a compound of Formula (I), wherein Z is —$SO_2R^{21}$. Another embodiment provides a compound of Formula (I), wherein Z is —$N(R^{22})SO_2R^{21}$. Another embodiment provides a compound of Formula (I), wherein Z is —$SO_2N(R^{22})_2$. Another embodiment provides a compound of Formula (I), wherein Z is —$N(R^{22})SO_2N(R^{22})_2$. Another embodiment provides a compound of Formula (I), wherein Z is —$CON(R^{22})_2$. Another embodiment provides a compound of Formula (I), wherein Z is —$N(R^{22})CO_2R^{21}$. Another embodiment provides a compound of Formula (I), wherein Z is —$N(R^{22})CON(R^{22})_2$. Another embodiment provides a compound of Formula (I), wherein $R^{21}$ is alkyl, cycloalkyl, or cycloalkylalkyl. Another embodiment provides a compound of Formula (I), wherein $R^{21}$ is alkyl. Another embodiment provides a compound of Formula (I), wherein $R^{14}$ is hydrogen, halogen, or alkyl. Another embodiment provides a compound of Formula (I), wherein X4 is C—$R^{15}$. Another embodiment provides a compound of Formula (I), wherein W is —O—. Another embodiment provides a compound of Formula (I), wherein W is —NH—. Another embodiment provides a compound of Formula (I), wherein X is alkyl. Another embodiment provides a compound of Formula (I), wherein X is aryl. Another embodiment provides a compound of Formula (I), wherein X is cycloalkylalkyl. Another embodiment provides a compound of Formula (I), wherein W is —O— and X is alkyl. Another embodiment provides a compound of Formula (I), wherein W is —O— and X is aryl. Another embodiment provides a compound of Formula (I), wherein W is —O— and X is cycloalkylalkyl. Another embodiment provides a compound of Formula (I), wherein $R^5$ and $R^8$ are hydrogen. Another embodiment provides a compound of Formula (I), wherein $R^5$ and $R^8$ are hydrogen, and $R^6$ is heteroaryl.

One embodiment provides a compound of Formula (Ia), or a pharmaceutically acceptable salt thereof, Formula (Ia)

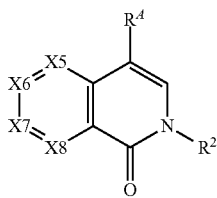

wherein, $R^2$ is selected from $CH_3$, $CH_2CH_3$, $CH_2CF_3$, $CH_2F$, $CHF_2$, $CF_3$, $CH_2D$, $CHD_2$, or $CD_3$;

X5 is C—$R^5$ or N;
X6 is C—$R^6$ or N;
X7 is C—$R^7$ or N;
X8 is C—$R^8$ or N; wherein no more than two of X5, X6, X7, or X8 may be N;

$R^5$ is hydrogen, halogen, —OH, —CN, —$OR^{61}$, —$NHR^{61}$, —$N(R^{61})_2$, alkyl, cycloalkyl, cycloalkylalkyl, aryl, aralkyl, heterocyclyl, heterocyclylalkyl, heteroaryl, or heteroarylalkyl, wherein each $R^{61}$ is independently selected from alkyl, cycloalkyl, cycloalkylalkyl, aryl, aralkyl, heterocyclyl, heterocyclylalkyl, heteroaryl, or heteroarylalkyl;

$R^6$ is hydrogen, halogen, —OH, —CN, —$OR^{61}$, —$NHR^{61}$, —$N(R^{61})_2$, alkyl, cycloalkyl, cycloalkylalkyl, aryl, aralkyl, heterocyclyl, heterocyclylalkyl, heteroaryl, or heteroarylalkyl, wherein each $R^{61}$ is independently selected from alkyl, cycloalkyl, cycloalkylalkyl, aryl, aralkyl, heterocyclyl, heterocyclylalkyl, heteroaryl, or heteroarylalkyl;

$R^7$ is hydrogen, halogen, —OH, —CN, —$OR^{61}$, —$NHR^{61}$, —$N(R^{61})_2$, alkyl, cycloalkyl, cycloalkylalkyl, aryl, aralkyl, heterocyclyl, heterocyclylalkyl, heteroaryl, or heteroarylalkyl, wherein each $R^{61}$ is independently selected from alkyl, cycloalkyl, cycloalkylalkyl, aryl, aralkyl, heterocyclyl, heterocyclylalkyl, heteroaryl, or heteroarylalkyl;

$R^8$ is hydrogen, halogen, or alkyl;

$R^A$ is

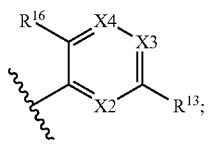

X2 is N or C—$R^{12}$, wherein $R^{12}$ is hydrogen, halogen, alkyl, or alkoxy;
$R^{13}$ is —Y—Z;
Y is selected from a bond, or —$CH_2$—;
Z is selected from —$SO_2R^{21}$, —$N(R^{22})SO_2R^{21}$, —$SO_2N(R^{22})_2$, —$N(R^{22})SO_2N(R^{22})_2$, —$CON(R^{22})_2$, —$N(R^{22})CO_2R^{21}$, —$N(R^{22})CON(R^{22})_2$, —$N(R^{22})COR^{21}$, —OC(O)N($R^{22})_2$, —$OSO_2N(R^{22})_2$, or —$N(R^{22})SO_3R^{21}$;
X3 is N or C—$R^{14}$, wherein $R^{14}$ is hydrogen, halogen, —CN, alkyl, cycloalkyl, or alkoxy;
X4 is N or C—$R^{15}$, wherein $R^{15}$ is hydrogen, halogen, alkyl, —CN, or alkoxy;
$R^{16}$ is hydrogen, halogen, or —W—X, wherein W is a bond, —O—, —S—, or —NH—, and X is selected from alkyl, aryl, aralkyl, cycloalkyl, cycloalkylalkyl, heterocyclyl, heterocyclylalkyl, heteroaryl, or heteroarylalkyl;
each $R^{21}$ is independently selected from alkyl, cycloalkyl, cycloalkylalkyl, aryl, aralkyl, heterocyclyl, heterocyclylalkyl, heteroaryl, or heteroarylalkyl; and
each $R^{22}$ is independently selected from hydrogen, alkyl, cycloalkyl, cycloalkylalkyl, aryl, aralkyl, heterocyclyl, heterocyclylalkyl, heteroaryl, or heteroarylalkyl.

Another embodiment provides a compound of Formula (Ia), wherein $R^2$ is $CH_3$. Another embodiment provides a compound of Formula (Ia), wherein $R^2$ is $CD_3$. Another embodiment provides a compound of Formula (Ia), wherein X5 is N. Another embodiment provides a compound of Formula (Ia), wherein X6 is N. Another embodiment provides a compound of Formula (Ia), wherein X7 is N. Another embodiment provides a compound of Formula (Ia), wherein X8 is N. Another embodiment provides a compound of Formula (Ia), wherein none of X5, X6, X7, or X8 is N. Another embodiment provides a compound of Formula (Ia), wherein $R^5$ and $R^8$ are hydrogen. Another embodiment provides a compound of Formula (Ia), wherein $R^5$, $R^6$, $R^7$ and $R^8$ are hydrogen. Another embodiment provides a compound of Formula (Ia), wherein $R^7$ is a halogen. Another embodiment provides a compound of Formula (Ia), wherein $R^6$ is a halogen. Another embodiment provides a compound of Formula (Ia), wherein $R^6$ is a heteroaryl. Another embodiment provides a compound of Formula (Ia), wherein $R^6$ is an aryl. Another embodiment provides a compound of Formula (Ia), wherein $R^6$ is an alkyl. Another embodiment provides a compound of Formula (Ia), wherein $R^6$ is an aryl.

Another embodiment provides a compound of Formula (Ia), wherein Y is a bond. Another embodiment provides a compound of Formula (Ia), wherein Y is a —$CH_2$—. Another embodiment provides a compound of Formula (Ia), wherein Z is —$SO_2R^{21}$. Another embodiment provides a compound of Formula (Ia), wherein Z is —$N(R^{22})SO_2R^{21}$. Another embodiment provides a compound of Formula (Ia), wherein Z is —$SO_2N(R^{22})_2$. Another embodiment provides a compound of Formula (Ia), wherein Z is —$N(R^{22})SO_2N(R^{22})_2$. Another embodiment provides a compound of Formula (Ia), wherein Z is —$CON(R^{22})_2$. Another embodiment provides a compound of Formula (Ia), wherein Z is —$N(R^{22})CO_2R^{21}$. Another embodiment provides a compound of Formula (Ia), wherein Z is —$N(R^{22})CON(R^{22})_2$. Another embodiment provides a compound of Formula (Ia), wherein $R^{21}$ is alkyl, cycloalkyl, or cycloalkylalkyl. Another embodiment provides a compound of Formula (Ia), wherein $R^{21}$ is alkyl. Another embodiment provides a compound of Formula (Ia), wherein $R^{14}$ is hydrogen, halogen, or alkyl. Another embodiment provides a compound of Formula (Ia), wherein X4 is C—$R^{15}$. Another embodiment provides a compound of Formula (Ia), wherein W is —O—. Another embodiment provides a compound of Formula (Ia), wherein W is —NH—. Another embodiment provides a compound of Formula (Ia), wherein X is alkyl. Another embodiment provides a compound of Formula (Ia), wherein X is aryl. Another embodiment provides a compound of Formula (Ia), wherein X is cycloalkylalkyl. Another embodiment provides a compound of Formula (Ia), wherein W is —O— and X is alkyl. Another embodiment provides a compound of Formula (Ia), wherein W is —O— and X is aryl. Another embodiment provides a compound of Formula (Ia), wherein W is —O— and X is cycloalkylalkyl. Another embodiment provides a compound of Formula (Ia), wherein $R^5$ and $R^8$ are hydrogen. Another embodiment provides a compound of Formula (Ia), wherein $R^5$ and $R^8$ are hydrogen, and $R^6$ is heteroaryl.

One embodiment provides a compound, or a pharmaceutically acceptable salt thereof, having the structure of Formula (Ib), Formula (Ib)

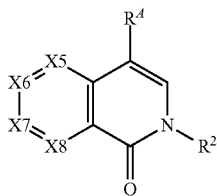

wherein,
R² is selected from CH₃;
X5 is C—H;
X6 is C—R⁶;
X7 is C—R⁷;
X8 is C—H;
R⁶ is hydrogen, or halogen;
R⁷ is hydrogen, or halogen;
R^A is

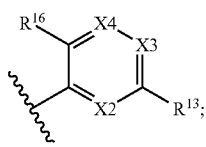

X2 is C—H;
R¹³ is —Y—Z;
Y is selected from a bond, or —CH₂—;
Z is selected from —SO₂R²¹, —N(R²²)SO₂R²¹, —SO₂N(R²²)₂, —N(R²²)SO₂N(R²²)₂, —CON(R²²)₂, —N(R²²)CO₂R²¹, —N(R²²)CON(R²²)₂, —N(R²²)COR²¹, —OC(O)N(R²²)₂, —OSO₂N(R²²)₂, or —N(R²²)SO₃R²¹;
X3 is C—R¹⁴, wherein R¹⁴ is hydrogen, halogen, C₁-C₃ alkyl, or C₁-C₃ alkoxy;
X4 is C—R¹⁵, wherein R¹⁵ is hydrogen, or halogen;
R¹⁶ is —W—X, wherein W is a bond, —O—, —S—, or —NH—, and X is selected from alkyl, aryl, aralkyl, cycloalkyl, cycloalkylalkyl, heterocyclyl, heterocyclylalkyl, heteroaryl, or heteroarylalkyl;
each R²¹ is independently selected from alkyl, cycloalkyl, cycloalkylalkyl, aryl, aralkyl, heterocyclyl, heterocyclylalkyl, heteroaryl, or heteroarylalkyl; and
each R²² is independently selected from hydrogen, alkyl, cycloalkyl, cycloalkylalkyl, aryl, aralkyl, heterocyclyl, heterocyclylalkyl, heteroaryl, or heteroarylalkyl.

Another embodiment provides a compound, or a pharmaceutically acceptable salt thereof, having the structure of Formula (Ib), wherein R⁶ is halogen, and R⁷ is hydrogen. Another embodiment provides a compound, or a pharmaceutically acceptable salt thereof, having the structure of Formula (Ib), wherein R⁶ is hydrogen, and R⁷ is halogen. Another embodiment provides a compound, or a pharmaceutically acceptable salt thereof, having the structure of Formula (Ib), wherein R⁶ is hydrogen, and R⁷ is hydrogen.

Another embodiment provides a compound, or a pharmaceutically acceptable salt thereof, having the structure of Formula (Ib), wherein Y is —CH₂—. Another embodiment provides a compound, or a pharmaceutically acceptable salt thereof, having the structure of Formula (Ib), wherein Y is —CH₂—, and Z is —SO₂R²¹, or —N(R²²)SO₂R²¹. Another embodiment provides a compound, or a pharmaceutically acceptable salt thereof, having the structure of Formula (Ib), wherein R²² is hydrogen or methyl.

Another embodiment provides a compound, or a pharmaceutically acceptable salt thereof, having the structure of Formula (Ib), wherein Y is a bond. Another embodiment provides a compound, or a pharmaceutically acceptable salt thereof, having the structure of Formula (Ib), wherein Y is a bond, and Z is —N(R²²)SO₂R²¹, or —N(R²²)SO₂N(R²²)₂. Another embodiment provides a compound, or a pharmaceutically acceptable salt thereof, having the structure of Formula (Ib), wherein Y is a bond, and Z is —SO₂R²¹. Another embodiment provides a compound, or a pharmaceutically acceptable salt thereof, having the structure of Formula (Ib), wherein Y is a bond, Z is —SO₂R²¹, and R²¹ is heterocyclyl, or heterocyclylalkyl. Another embodiment provides a compound, or a pharmaceutically acceptable salt thereof, having the structure of Formula (Ib), wherein Y is a bond, Z is —SO₂R²¹, and R²¹ is alkyl, cycloalkyl, or cycloalkylalkyl. Another embodiment provides a compound, or a pharmaceutically acceptable salt thereof, having the structure of Formula (Ib), wherein Y is a bond, Z is —SO₂R²¹, R²¹ is alkyl, and the alkyl is a C₁-C₄ alkyl.

Another embodiment provides a compound, or a pharmaceutically acceptable salt thereof, having the structure of Formula (Ib), wherein Y is a bond, and Z is —SO₂N(R²²)₂. Another embodiment provides a compound, or a pharmaceutically acceptable salt thereof, having the structure of Formula (Ib), wherein R²² is hydrogen or methyl. Another embodiment provides a compound, or a pharmaceutically acceptable salt thereof, having the structure of Formula (Ib), wherein Y is a bond, Z is —SO₂N(R²²)₂, and at least one R²² is alkyl, cycloalkyl, or aralkyl.

Another embodiment provides a compound, or a pharmaceutically acceptable salt thereof, having the structure of Formula (Ib), wherein R²¹ is heterocyclyl, or heterocyclylalkyl.

Another embodiment provides a compound, or a pharmaceutically acceptable salt thereof, having the structure of Formula (Ib), wherein R²² is hydrogen or methyl. Another embodiment provides a compound, or a pharmaceutically acceptable salt thereof, having the structure of Formula (Ib), wherein at least one R²² is alkyl, cycloalkyl, or aralkyl. Another embodiment provides a compound, or a pharmaceutically acceptable salt thereof, having the structure of Formula (Ib), wherein R²¹ is alkyl, cycloalkyl, or cycloalkylalkyl. Another embodiment provides a compound, or a pharmaceutically acceptable salt thereof, having the structure of Formula (Ib), wherein the alkyl is a C₁-C₄ alkyl. Another embodiment provides a compound, or a pharmaceutically acceptable salt thereof, having the structure of Formula (Ib), wherein the C₁-C₄ alkyl is a C₁ alkyl.

Another embodiment provides a compound, or a pharmaceutically acceptable salt thereof, having the structure of Formula (Ib), wherein R¹⁴ is hydrogen, and R¹⁵ is hydrogen.

Another embodiment provides a compound, or a pharmaceutically acceptable salt thereof, having the structure of Formula (Ib), wherein W is —NH—. Another embodiment provides a compound, or a pharmaceutically acceptable salt thereof, having the structure of Formula (Ib), wherein W is —S—. Another embodiment provides a compound, or a pharmaceutically acceptable salt thereof, having the structure of Formula (Ib), wherein W is a bond. Another embodiment provides a compound, or a pharmaceutically acceptable salt thereof, having the structure of Formula (Ib), wherein W is —O—.

Another embodiment provides a compound, or a pharmaceutically acceptable salt thereof, having the structure of Formula (Ib), wherein X is alkyl. Another embodiment provides a compound, or a pharmaceutically acceptable salt thereof, having the structure of Formula (Ib), wherein W is —NH—, and X is alkyl. Another embodiment provides a compound, or a pharmaceutically acceptable salt thereof, having the structure of Formula (Ib), wherein W is —O— and X is alkyl. Another embodiment provides a compound, or a pharmaceutically acceptable salt thereof, having the structure of Formula (Ib), wherein W is a bond, and X is alkyl.

Another embodiment provides a compound, or a pharmaceutically acceptable salt thereof, having the structure of Formula (Ib), wherein X is cycloalkylalkyl. Another embodiment provides a compound, or a pharmaceutically acceptable salt thereof, having the structure of Formula (Ib), wherein W is —NH—, and X is cycloalkylalkyl. Another embodiment provides a compound, or a pharmaceutically acceptable salt thereof, having the structure of Formula (Ib), wherein W is —O— and X is cycloalkylalkyl. Another embodiment provides a compound, or a pharmaceutically acceptable salt thereof, having the structure of Formula (Ib), wherein W is a bond, and X is cycloalkylalkyl.

Another embodiment provides a compound, or a pharmaceutically acceptable salt thereof, having the structure of Formula (Ib), wherein X is aryl. Another embodiment provides a compound, or a pharmaceutically acceptable salt thereof, having the structure of Formula (Ib), wherein W is —NH—, and X is aryl. Another embodiment provides a compound, or a pharmaceutically acceptable salt thereof, having the structure of Formula (Ib), wherein W is —O—, and X is aryl. Another embodiment provides a compound, or a pharmaceutically acceptable salt thereof, having the structure of Formula (Ib), wherein W is a bond, and X is aryl.

Another embodiment provides a compound, or a pharmaceutically acceptable salt thereof, having the structure of Formula (Ib), wherein Y is a bond, Z is —$SO_2R^{21}$, W is —O—, and X is aryl or cycloalkylalkyl. Another embodiment provides a compound, or a pharmaceutically acceptable salt thereof, having the structure of Formula (Ib), wherein Y is a bond, Z is —$SO_2R^{21}$, W is —O—, and X is cycloalkylalkyl.

One embodiment provides a compound of Formula (II), or a pharmaceutically acceptable salt thereof,

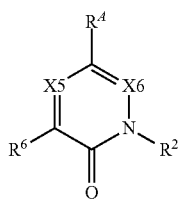

Formula (II)

wherein,
$R^2$ is alkyl, cycloalkyl, cycloalkylalkyl, heterocyclylalkyl, aralkyl, or heteroarylalkyl;
X6 is C—H or N;
X5 is C—$R^5$ or N; provided that if X6 is N, then X5 is C—$R^5$, and if X5 is N, then X6 is CH;
$R^5$ is hydrogen, halogen, —OH, —CN, —$OR^{61}$, —$NHR^{61}$, —$N(R^{61})_2$, alkyl, cycloalkyl, cycloalkylalkyl, aryl, aralkyl, heterocyclyl, heterocyclylalkyl, heteroaryl, or heteroarylalkyl, wherein each $R^{61}$ is independently selected from alkyl, cycloalkyl, cycloalkylalkyl, aryl, aralkyl, heterocyclyl, heterocyclylalkyl, heteroaryl, or heteroarylalkyl;
$R^6$ is hydrogen, halogen, —OH, —CN, alkyl, cycloalkyl, cycloalkylalkyl, amino, alkylamino, dialkylamino, cycloalkylalkylamino, alkoxy, —S-alkyl, cycloalkylalkoxy, heterocyclyl, aralkoxy, heteroaryloxy, aryloxy, alkynyloxy, or —N(H)COalkyl;
$R^A$ is

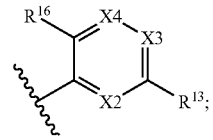

X2 is N or C—$R^{12}$, wherein $R^{12}$ is hydrogen, halogen, alkyl, or alkoxy;
$R^{13}$ is —Y—Z;
Y selected from a bond, —$CH_2$—, or —CH($C_1$-$C_4$alkyl)-;
Z is selected from —$SO_2R^{21}$, —$N(R^{22})SO_2R^{21}$, —$SO_2N(R^{22})_2$, —$N(R^{22})SO_2N(R^{22})_2$, —$CON(R^{22})_2$, —$N(R^{22})CO_2R^{21}$, —$N(R^{22})CON(R^{22})_2$, —$N(R^{22})COR^{21}$, —$COR^{21}$, —$OC(O)N(R^{22})_2$, —$OSO_2N(R^{22})_2$, or —$N(R^{22})SO_3R^{21}$;
X3 is N or C—$R^{14}$, wherein $R^{14}$ is hydrogen, halogen, —CN, alkyl, cycloalkyl, or alkoxy;
X4 is N or C—$R^{15}$, wherein $R^{15}$ is hydrogen, halogen, —CN, alkyl, alkoxy, aryloxy, aralkyloxy, cycloalkylalkyloxy, heterocyclyloxy, heteroarylalkyloxy, or alkynyloxy;
$R^{16}$ is hydrogen, halogen, —N(H)COX, or —W—X, wherein W is a bond, —O—, —S—, or —NH—, and X is selected from alkyl, aryl, aralkyl, cycloalkyl, cycloalkylalkyl, alkynyl, cycloalkylalkynyl, heterocyclyl, heterocyclylalkyl, heteroaryl, or heteroarylalkyl;
each $R^{21}$ is independently selected from alkyl, cycloalkyl, cycloalkylalkyl, aryl, aralkyl, heterocyclyl, heterocyclylalkyl, heteroaryl, or heteroarylalkyl; and
each $R^{22}$ is independently selected from hydrogen, alkyl, cycloalkyl, cycloalkylalkyl, aryl, aralkyl, heterocyclyl, heterocyclylalkyl, heteroaryl, or heteroarylalkyl; and provided that when X6 is N, then $R^5$ and $R^6$ are not hydrogen.

One embodiment provides a compound of Formula (IIa), or a pharmaceutically acceptable salt thereof,

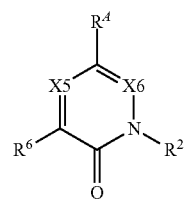

Formula (IIa)

wherein,
$R^2$ is $CH_3$, $CH_2CH_3$, $CH_2CF_3$, $CH_2F$, $CHF_2$, $CF_3$, $CH_2D$, $CHD_2$, or $CD_3$;
X6 is C—H or N;
X5 is C—$R^5$ or N; provided that if X6 is N, then X5 is C—$R^5$, and if X5 is N, then X6 is CH;
$R^5$ is hydrogen, halogen, —OH, —CN, —$OR^{61}$, —$NHR^{61}$, —$N(R^{61})_2$, alkyl, cycloalkyl, cycloalkylalkyl, aryl, aralkyl, heterocyclyl, heterocyclylalkyl, heteroaryl, or heteroarylalkyl, wherein each $R^{61}$ is independently selected from alkyl, cycloalkyl, cycloalkylalkyl, aryl, aralkyl, heterocyclyl, heterocyclylalkyl, heteroaryl, or heteroarylalkyl;
$R^6$ is hydrogen, halogen, —OH, —CN, alkyl, cycloalkyl, cycloalkylalkyl, amino, alkylamino, dialkylamino, cycloalkylalkylamino, alkoxy, or cycloalkylalkoxy;

$R^A$ is

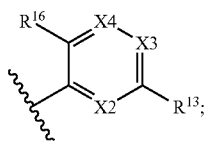

X2 is N or C—$R^{12}$, wherein $R^{12}$ is hydrogen, halogen, alkyl, or alkoxy;
$R^{13}$ is —Y—Z;
Y is selected from a bond, or —$CH_2$—;
Z is selected from —$SO_2R^{21}$, —$N(R^{22})SO_2R^{21}$, —$SO_2N(R^{22})_2$, —$N(R^{22})SO_2N(R^{22})_2$, —$CON(R^{22})_2$, —$N(R^{22})CO_2R^{21}$, —$N(R^{22})CON(R^{22})_2$, —$N(R^{22})COR^{21}$, —$OC(O)N(R^{22})_2$, —$OSO_2N(R^{22})_2$, or —$N(R^{22})SO_3R^{21}$;
X3 is N or C—$R^{14}$, wherein $R^{14}$ is hydrogen, halogen, —CN, alkyl, cycloalkyl, or alkoxy;
X4 is N or C—$R^{15}$, wherein $R^{15}$ is hydrogen, halogen, —CN, alkyl, or alkoxy;
$R^{16}$ is hydrogen, halogen, or —W—X, wherein W is a bond, —O—, —S—, or —NH—, and X is selected from alkyl, aryl, aralkyl, cycloalkyl, cycloalkylalkyl, heterocyclyl, heterocyclylalkyl, heteroaryl, or heteroarylalkyl;
each $R^{21}$ is independently selected from alkyl, cycloalkyl, cycloalkylalkyl, aryl, aralkyl, heterocyclyl, heterocyclylalkyl, heteroaryl, or heteroarylalkyl; and
each $R^{22}$ is independently selected from hydrogen, alkyl, cycloalkyl, cycloalkylalkyl, aryl, aralkyl, heterocyclyl, heterocyclylalkyl, heteroaryl, or heteroarylalkyl; and provided that when X6 is N, then $R^5$ and $R^6$ are not hydrogen.

Another embodiment provides a compound of Formula (IIa), wherein X2 is N. Another embodiment provides a compound of Formula (IIa), wherein X3 is N. Another embodiment provides a compound of Formula (IIa), wherein X4 is N. Another embodiment provides a compound of Formula (IIa), wherein X2 and X3 are N. Another embodiment provides a compound of Formula (IIa), wherein X2 is C—$R^{12}$, X3 is C—$R^{14}$, and X4 is C—$R^{15}$.

Another embodiment provides a compound of Formula (IIa), wherein $R^2$ is $CH_3$. Another embodiment provides a compound of Formula (IIa), wherein X6 is C—H. Another embodiment provides a compound of Formula (IIa), wherein X6 is N. Another embodiment provides a compound of Formula (IIa), wherein X5 is C—$R^5$. Another embodiment provides a compound of Formula (IIa), wherein X5 is N. Another embodiment provides a compound of Formula (IIa), wherein $R^5$ is hydrogen, halogen, or alkyl. Another embodiment provides a compound of Formula (IIa), wherein $R^6$ is hydrogen, halogen, or alkyl.

Another embodiment provides a compound of Formula (IIa), wherein Y is a bond. Another embodiment provides a compound of Formula (IIa), wherein Y is a —$CH_2$—. Another embodiment provides a compound of Formula (IIa), wherein Z is —$SO_2R^{21}$. Another embodiment provides a compound of Formula (IIa), wherein Z is —$N(R^{22})SO_2R^{21}$. Another embodiment provides a compound of Formula (IIa), wherein Z is —$SO_2N(R^{22})_2$. Another embodiment provides a compound of Formula (IIa), wherein Z is —$N(R^{22})SO_2N(R^{22})_2$. Another embodiment provides a compound of Formula (IIa), wherein Z is —$CON(R^{22})_2$. Another embodiment provides a compound of Formula (IIa), wherein Z is —$N(R^{22})CO_2R^{21}$. Another embodiment provides a compound of Formula (IIa), wherein Z is —$N(R^{22})CON(R^{22})_2$. Another embodiment provides a compound of Formula (IIa), wherein $R^{21}$ is alkyl, cycloalkyl, or cycloalkylalkyl. Another embodiment provides a compound of Formula (IIa), wherein $R^{21}$ is alkyl. Another embodiment provides a compound of Formula (IIa), wherein $R^{14}$ is hydrogen, halogen, or alkyl. Another embodiment provides a compound of Formula (IIa), wherein X4 is C—$R^{15}$. Another embodiment provides a compound of Formula (IIa), wherein W is —O—. Another embodiment provides a compound of Formula (IIa), wherein W is —NH—. Another embodiment provides a compound of Formula (IIa), wherein X is alkyl. Another embodiment provides a compound of Formula (IIa), wherein X is aryl. Another embodiment provides a compound of Formula (IIa), wherein X is cycloalkylalkyl. Another embodiment provides a compound of Formula (IIa), wherein W is —O— and X is alkyl. Another embodiment provides a compound of Formula (IIa), wherein W is —O— and X is aryl. Another embodiment provides a compound of Formula (IIa), wherein W is —O— and X is cycloalkylalkyl. Another embodiment provides a compound of Formula (IIa), wherein the $R^6$ is $CD_3$.

One embodiment provides a compound of Formula (IIb), or a pharmaceutically acceptable salt thereof, Formula (IIb)

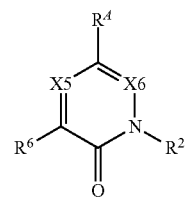

wherein,
$R^2$ is $CH_3$;
X6 is C—H;
X5 is C—$R^5$;
$R^5$ is hydrogen;
$R^6$ is halogen or alkyl;
$R^4$ is

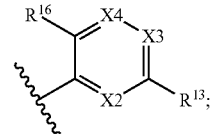

X2 is N;
$R^{13}$ is —Y—Z;
Y is selected from a bond, or —$CH_2$—;
Z is selected from —$SO_2R^{21}$, —$N(R^{22})SO_2R^{21}$, —$SO_2N(R^{22})_2$, —$N(R^{22})SO_2N(R^{22})_2$, —$CON(R^{22})_2$, —$N(R^{22})CO_2R^{21}$, —$N(R^{22})CON(R^{22})_2$, —$N(R^{22})COR^{21}$, —$OC(O)N(R^{22})_2$, —$OSO_2N(R^{22})_2$, or —$N(R^{22})SO_3R^{21}$;
X3 is N;
X4 is C—$R^{15}$, wherein $R^{15}$ is hydrogen, halogen, —CN, alkyl, or alkoxy;
$R^{16}$ is —W—X, wherein W is a bond, —O—, —S—, or —NH—, and X is selected from alkyl, aryl, aralkyl, cycloalkyl, cycloalkylalkyl, heterocyclyl, heterocyclylalkyl, heteroaryl, or heteroarylalkyl;
each $R^{21}$ is independently selected from alkyl, cycloalkyl, cycloalkylalkyl, aryl, aralkyl, heterocyclyl, heterocyclylalkyl, heteroaryl, or heteroarylalkyl; and each R²² is independently selected from hydrogen, alkyl, cycloalkyl, cycloalkylalkyl, aryl, aralkyl, heterocyclyl, heterocyclylalkyl, heteroaryl, or heteroarylalkyl.

Another embodiment provides a compound of Formula (IIb), wherein R⁶ is halogen. Another embodiment provides a compound of Formula (IIb), wherein R⁶ is alkyl. Another embodiment provides a compound of Formula (IIb), wherein R⁶ is C₁-C₃ alkyl. Another embodiment provides a compound of Formula (IIb), wherein R⁶ is C₁ alkyl.

Another embodiment provides a compound of Formula (IIb), wherein Y is a bond. Another embodiment provides a compound of Formula (IIb), wherein Y is a —CH₂—. Another embodiment provides a compound of Formula (IIb), wherein Z is —SO₂R²¹. Another embodiment provides a compound of Formula (IIb), wherein Z is —N(R²²)SO₂R²¹. Another embodiment provides a compound of Formula (IIb), wherein Z is —SO₂N(R²²)₂. Another embodiment provides a compound of Formula (IIb), wherein Z is —N(R²²)SO₂N(R²²)₂. Another embodiment provides a compound of Formula (IIb), wherein Z is —CON(R²²)₂. Another embodiment provides a compound of Formula (IIb), wherein Z is —N(R²²)CO₂R²¹. Another embodiment provides a compound of Formula (IIb), wherein Z is —N(R²²)CON(R²²)₂. Another embodiment provides a compound of Formula (IIb), wherein R²¹ is alkyl, cycloalkyl, or cycloalkylalkyl. Another embodiment provides a compound of Formula (IIb), wherein R²¹ is alkyl. Another embodiment provides a compound of Formula (IIb), wherein R²¹ is C₁-C₂ alkyl.

Another embodiment provides a compound of Formula (IIb), wherein W is —O—. Another embodiment provides a compound of Formula (IIb), wherein W is —NH—. Another embodiment provides a compound of Formula (IIb), wherein W is a bond. Another embodiment provides a compound of Formula (IIb), wherein X is alkyl. Another embodiment provides a compound of Formula (IIb), wherein X is aryl. Another embodiment provides a compound of Formula (IIb), wherein X is cycloalkylalkyl. Another embodiment provides a compound of Formula (IIb), wherein W is —O— and X is alkyl. Another embodiment provides a compound of Formula (IIb), wherein W is —O— and X is aryl. Another embodiment provides a compound of Formula (IIb), wherein W is —O— and X is cycloalkylalkyl. Another embodiment provides a compound of Formula (IIb), wherein W is a bond and X is alkyl. Another embodiment provides a compound of Formula (IIb), wherein W is a bond and X is aryl. Another embodiment provides a compound of Formula (IIb), wherein W is a bond and X is cycloalkylalkyl. Another embodiment provides a compound of Formula (IIb), wherein the R⁶ is CD₃.

One embodiment provides a compound of Formula (III), or a pharmaceutically acceptable salt thereof,

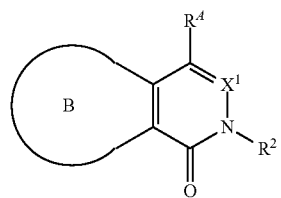

Formula (III)

wherein,
R² is CH₃, CH₂CH₃, CH₂CF₃, CH₂F, CHF₂, CF₃, CH₂D, CHD₂, or CD₃;
X1 is C—H or N;
ring B is an optionally substituted 5- or 6-membered heterocyclic ring containing at least one oxygen or nitrogen atom;
R⁴ is

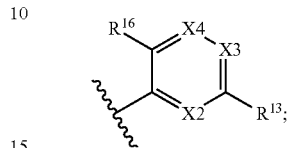

X2 is N or C—R¹², wherein R¹² is hydrogen, halogen, alkyl, or alkoxy;
R¹³ is —Y—Z;
Y is selected from a bond, —CH₂—, or —CH(C₁-C₄ alkyl)-;
Z is selected from —SO₂R²¹, —N(R²²)SO₂R²¹, —SO₂N(R²²)₂, —N(R²²)SO₂N(R²²)₂, —CON(R²²)₂, —N(R²²)CO₂R²¹, —N(R²²)CON(R²²)₂, —N(R²²)COR²¹, —OC(O)N(R²²)₂, —OSO₂N(R²²)₂, or —N(R²²)SO₃R²¹;
X3 is N or C—R¹⁴, wherein R¹⁴ is hydrogen, halogen, —CN, alkyl, cycloalkyl, or alkoxy; or optionally when X4 is C—R¹⁵, R¹⁴ and R¹⁵ connect to form a ring;
X4 is N or C—R¹⁵, wherein R¹⁵ is hydrogen, halogen, —CN, alkyl, or alkoxy;
R¹⁶ is hydrogen, halogen, or —W—X, wherein W is a bond, —O—, —S—, or —NH—, and X is selected from alkyl, alkynyl, aryl, aralkyl, cycloalkyl, cycloalkylalkyl, cycloalkylalkynyl, heterocyclyl, heterocyclylalkyl, heteroaryl, or heteroarylalkyl; or optionally when X4 is C—R¹⁵, R¹⁶ and R¹⁵ connect to form a ring;
each R²¹ is independently selected from alkyl, cycloalkyl, cycloalkylalkyl, aryl, aralkyl, heterocyclyl, heterocyclylalkyl, heteroaryl, or heteroarylalkyl; and
each R²² is independently selected from hydrogen, alkyl, cycloalkyl, cycloalkylalkyl, aryl, aralkyl, heterocyclyl, heterocyclylalkyl, heteroaryl, or heteroarylalkyl.

Another embodiment provides a compound of Formula (III), wherein X2 is N. Another embodiment provides a compound of Formula (III), wherein X3 is N. Another embodiment provides a compound of Formula (III), wherein X4 is N. Another embodiment provides a compound of Formula (III), wherein X2 and X3 are N. Another embodiment provides a compound of Formula (III), wherein X2 is C—R¹², X3 is C—R¹⁴, and X4 is C—R¹⁵.

Another embodiment provides a compound of Formula (III), having the structure of Formula (IIIa):

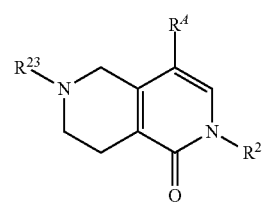

Formula (IIIa)

wherein,
ring B is a 6-membered ring having one nitrogen atom;
R²³ is selected from alkyl, aryl, aralkyl, cycloalkyl, cycloalkylalkyl, —COR²⁴, —CO₂R²⁴, CONH(R²⁴), —CON(R²⁴)₂, or SO₂R²⁴; and each $R^{24}$ is independently selected from alkyl, aryl, aralkyl, cycloalkyl, cycloalkylalkyl, heterocyclyl, heterocyclylalkyl, heteroaryl, or heteroarylalkyl.

Another embodiment provides a compound of Formula (III), wherein $R^2$ is $CH_3$. Another embodiment provides a compound of Formula (III), wherein X1 is C—H. Another embodiment provides a compound of Formula (III), wherein X1 is N.

Another embodiment provides a compound of Formula (III), wherein Y is a bond. Another embodiment provides a compound of Formula (III), wherein Y is a —$CH_2$—. Another embodiment provides a compound of Formula (III), wherein Z is —$SO_2R^{21}$. Another embodiment provides a compound of Formula (III), wherein Z is —$N(R^{22})SO_2R^{21}$. Another embodiment provides a compound of Formula (III), wherein Z is —$SO_2N(R^{22})_2$. Another embodiment provides a compound of Formula (III), wherein Z is —$N(R^{22})SO_2N(R^{22})_2$. Another embodiment provides a compound of Formula (III), wherein Z is —$CON(R^{22})_2$. Another embodiment provides a compound of Formula (III), wherein Z is —$N(R^{22})CO_2R^{21}$. Another embodiment provides a compound of Formula (III), wherein Z is —$N(R^{22})CON(R^{22})_2$. Another embodiment provides a compound of Formula (III), wherein $R^{21}$ is alkyl, cycloalkyl, or cycloalkylalkyl. Another embodiment provides a compound of Formula (III), wherein $R^{21}$ is alkyl. Another embodiment provides a compound of Formula (III), wherein $R^{14}$ is hydrogen, halogen, or alkyl. Another embodiment provides a compound of Formula (III), wherein X4 is C—$R^{15}$. Another embodiment provides a compound of Formula (III), wherein W is —O—. Another embodiment provides a compound of Formula (III), wherein W is —NH—. Another embodiment provides a compound of Formula (III), wherein X is alkyl. Another embodiment provides a compound of Formula (III), wherein X is alkynyl. Another embodiment provides a compound of Formula (III), wherein X is aryl. Another embodiment provides a compound of Formula (III), wherein X is cycloalkylalkyl. Another embodiment provides a compound of Formula (III), wherein X is cycloalkylalkynyl. Another embodiment provides a compound of Formula (III), wherein W is —O— and X is alkyl. Another embodiment provides a compound of Formula (III), wherein W is —O— and X is alkynyl. Another embodiment provides a compound of Formula (III), wherein W is —O— and X is aryl. Another embodiment provides a compound of Formula (III), wherein W is —O— and X is cycloalkylalkyl. Another embodiment provides a compound of Formula (III), wherein W is —O— and X is cycloalkylalkynyl.

One embodiment provides a compound of Formula (IV), or a pharmaceutically acceptable salt thereof,

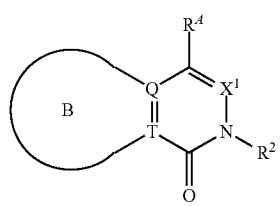

Formula (IV)

wherein,
Q is N and T is C, or Q is C and T is N;
Ring B is an optionally substituted 5-membered aromatic nitrogen-containing heteroaryl ring containing one or more nitrogen atoms;

$R^2$ is selected from $CH_3$, $CH_2CH_3$, $CH_2CF_3$, $CH_2F$, $CHF_2$, $CF_3$, $CH_2D$, $CHD_2$, or $CD_3$;
X1 is C—H or N;
$R^A$ is

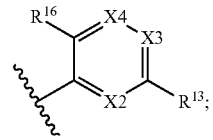

X2 is N or C—$R^{12}$, wherein $R^{12}$ is hydrogen, halogen, alkyl, or alkoxy;
$R^{13}$ is —Y—Z;
Y is selected from a bond, or —$CH_2$—;
Z is selected from —$SO_2R^{21}$, —$N(R^{22})SO_2R^{21}$, —$SO_2N(R^{22})_2$, —$N(R^{22})SO_2N(R^{22})_2$, —$CON(R^{22})_2$, —$N(R^{22})CO_2R^{21}$, —$N(R^{22})CON(R^{22})_2$, —$N(R^{22})COR^{21}$, —OC(O)N(R^{22})_2$, —$OSO_2N(R^{22})_2$, or —$N(R^{22})SO_3R^{21}$;
X3 is N or C—$R^{14}$, wherein $R^{14}$ is hydrogen, halogen, —CN, alkyl, cycloalkyl, or alkoxy;
X4 is N or C—$R^{15}$, wherein $R^{15}$ is hydrogen, halogen, —CN, alkyl, or alkoxy;
$R^{16}$ is hydrogen, halogen, or —W—X, wherein W is a bond, —O—, —S—, or —NH—, and X is selected from alkyl, aryl, aralkyl, cycloalkyl, cycloalkylalkyl, heterocyclyl, heterocyclylalkyl, heteroaryl, or heteroarylalkyl;
each $R^{21}$ is independently selected from alkyl, cycloalkyl, cycloalkylalkyl, aryl, aralkyl, heterocyclyl, heterocyclylalkyl, heteroaryl, or heteroarylalkyl; and
each $R^{22}$ is independently selected from hydrogen, alkyl, cycloalkyl, cycloalkylalkyl, aryl, aralkyl, heterocyclyl, heterocyclylalkyl, heteroaryl, or heteroarylalkyl.

Another embodiment provides a compound of Formula (IV), wherein X2 is N. Another embodiment provides a compound of Formula (IV), wherein X3 is N. Another embodiment provides a compound of Formula (IV), wherein X4 is N. Another embodiment provides a compound of Formula (IV), wherein X2 and X3 are N. Another embodiment provides a compound of Formula (IV), wherein X2 is C—$R^{12}$, X3 is C—$R^{14}$, and X4 is C—$R^{15}$.

Another embodiment provides a compound of Formula (IV), wherein the compound of Formula (IV) is selected from the group:

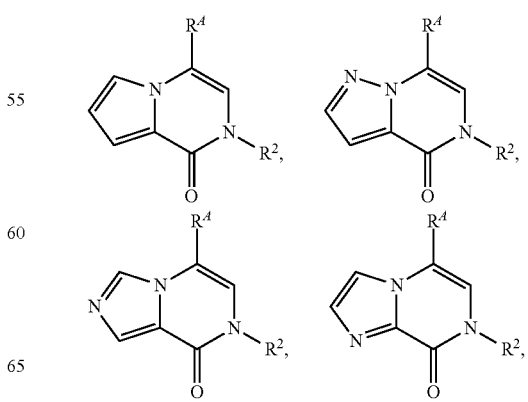

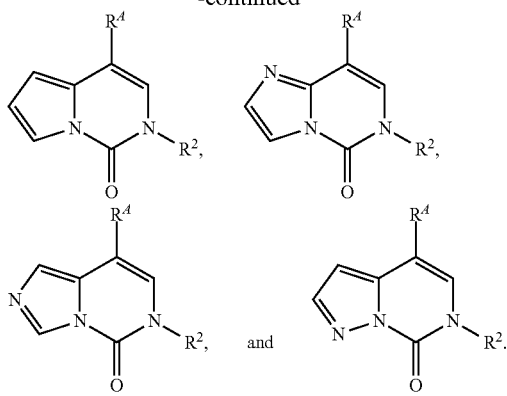

Another embodiment provides a compound of Formula (IV), wherein the compound of Formula (IV) has the structure:

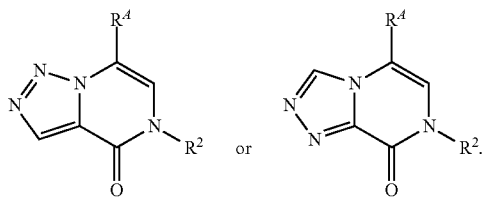

Another embodiment provides a compound of Formula (IV), wherein Q is N and T is C. Another embodiment provides a compound of Formula (IV), wherein Q is C and T is N. Another embodiment provides a compound of Formula (IV), wherein $R^2$ is $CH_3$. Another embodiment provides a compound of Formula (IV), wherein X1 is C—H. Another embodiment provides a compound of Formula (IV), wherein X1 is N.

Another embodiment provides a compound of Formula (IV), wherein Y is a bond. Another embodiment provides a compound of Formula (IV), wherein Y is a —$CH_2$—. Another embodiment provides a compound of Formula (IV), wherein Z is —$SO_2R^{21}$. Another embodiment provides a compound of Formula (IV), wherein Z is —$N(R^{22})SO_2R^{21}$. Another embodiment provides a compound of Formula (IV), wherein Z is —$SO_2N(R^{22})_2$. Another embodiment provides a compound of Formula (IV), wherein Z is —$N(R^{22})SO_2N(R^{22})_2$. Another embodiment provides a compound of Formula (IV), wherein Z is —$CON(R^{22})_2$. Another embodiment provides a compound of Formula (IV), wherein Z is —$N(R^{22})CO_2R^{21}$. Another embodiment provides a compound of Formula (IV), wherein Z is —$N(R^{22})CON(R^{22})_2$. Another embodiment provides a compound of Formula (IV), wherein $R^{21}$ is alkyl, cycloalkyl, or cycloalkylalkyl. Another embodiment provides a compound of Formula (IV), wherein $R^{21}$ is alkyl. Another embodiment provides a compound of Formula (IV), wherein $R^{14}$ is hydrogen, halogen, or alkyl. Another embodiment provides a compound of Formula (IV), wherein X4 is C—$R^{15}$. Another embodiment provides a compound of Formula (IV), wherein W is —O—. Another embodiment provides a compound of Formula (IV), wherein W is —NH—. Another embodiment provides a compound of Formula (IV), wherein X is alkyl. Another embodiment provides a compound of Formula (IV), wherein X is aryl. Another embodiment provides a compound of Formula (IV), wherein X is cycloalkylalkyl. Another embodiment provides a compound of Formula (IV), wherein W is —O— and X is alkyl. Another embodiment provides a compound of Formula (IV), wherein W is —O— and X is aryl. Another embodiment provides a compound of Formula (IV), wherein W is —O— and X is cycloalkylalkyl.

Another embodiment provides a compound of Formula (V), or a pharmaceutically acceptable salt thereof, Formula (V)

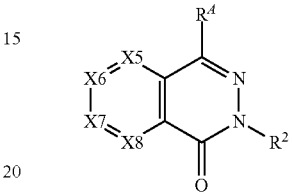

wherein,
$R^2$ is selected from $CH_3$, $CH_2CH_3$, $CH_2CF_3$, $CH_2F$, $CHF_2$, $CF_3$, $CH_2D$, $CHD_2$, or $CD_3$;
X5 is C—$R^5$ or N;
X6 is C—$R^6$ or N;
X7 is C—$R^7$ or N;
X8 is C—$R^8$ or N; wherein no more than two of X5, X6, X7, or X8 may be N;
$R^5$ is hydrogen, halogen, —OH, —CN, —$OR^{61}$, —$NHR^{61}$, —$N(R^{61})_2$, alkyl, cycloalkyl, cycloalkylalkyl, aryl, aralkyl, heterocyclyl, heterocyclylalkyl, heteroaryl, or heteroarylalkyl, wherein each $R^{61}$ is independently selected from alkyl, cycloalkyl, cycloalkylalkyl, aryl, aralkyl, heterocyclyl, heterocyclylalkyl, heteroaryl, or heteroarylalkyl;
$R^6$ is hydrogen, halogen, —OH, —CN, —$OR^{61}$, —$NHR^{61}$, —$N(R^{61})_2$, alkyl, cycloalkyl, cycloalkylalkyl, aryl, aralkyl, heterocyclyl, heterocyclylalkyl, heteroaryl, or heteroarylalkyl, wherein each $R^{61}$ is independently selected from alkyl, cycloalkyl, cycloalkylalkyl, aryl, aralkyl, heterocyclyl, heterocyclylalkyl, heteroaryl, or heteroarylalkyl;
$R^7$ is hydrogen, halogen, —OH, —CN, —$OR^{61}$, —$NHR^{61}$, —$N(R^{61})_2$, alkyl, cycloalkyl, cycloalkylalkyl, aryl, aralkyl, heterocyclyl, heterocyclylalkyl, heteroaryl, or heteroarylalkyl, wherein each $R^{61}$ is independently selected from alkyl, cycloalkyl, cycloalkylalkyl, aryl, aralkyl, heterocyclyl, heterocyclylalkyl, heteroaryl, or heteroarylalkyl;
$R^8$ is hydrogen, halogen, or alkyl;
$R^A$ is

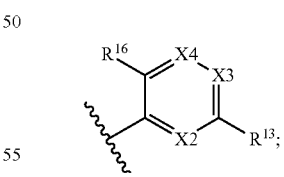

X2 is N or C—$R^{12}$, wherein $R^{12}$ is hydrogen, halogen, alkyl, or alkoxy;
$R^{13}$ is —Y—Z;
Y is selected from a bond, or —$CH_2$—;
Z is selected from —$SO_2R^{21}$, —$N(R^{22})SO_2R^{21}$, —$SO_2N(R^{22})_2$, —$N(R^{22})SO_2N(R^{22})_2$, —$CON(R^{22})_2$, —$N(R^{22})CO_2R^{21}$, —$N(R^{22})CON(R^{22})_2$, —$N(R^{22})COR^{21}$, —$OC(O)N(R^{22})_2$, —$OSO_2N(R^{22})_2$, or —$N(R^{22})SO_3R^{21}$;
X3 is N or C—$R^{14}$, wherein $R^{14}$ is hydrogen, halogen, alkyl, cycloalkyl, or alkoxy;

X4 is N or C—R$^{15}$, wherein R$^{15}$ is hydrogen, halogen, alkyl, or alkoxy;

R$^{16}$ is hydrogen, halogen, or —W—X, wherein W is a bond, —O—, —S—, or —NH—, and X is selected from alkyl, aryl, aralkyl, cycloalkyl, cycloalkylalkyl, heterocyclyl, heterocyclylalkyl, heteroaryl, or heteroarylalkyl;

each R$^{21}$ is independently selected from alkyl, cycloalkyl, cycloalkylalkyl, aryl, aralkyl, heterocyclyl, heterocyclylalkyl, heteroaryl, or heteroarylalkyl; and each R$^{22}$ is independently selected from hydrogen, alkyl, cycloalkyl, cycloalkylalkyl, aryl, aralkyl, heterocyclyl, heterocyclylalkyl, heteroaryl, or heteroarylalkyl.

Another embodiment provides a compound of Formula (V), wherein X2 is N. Another embodiment provides a compound of Formula (V), wherein X3 is N. Another embodiment provides a compound of Formula (V), wherein X4 is N. Another embodiment provides a compound of Formula (V), wherein X2 and X3 are N. Another embodiment provides a compound of Formula (V), wherein X2 is C—R$^{12}$, X3 is C—R$^{14}$, and X4 is C—R$^{15}$.

Another embodiment provides a compound of Formula (V), wherein R$^2$ is CH$_3$. Another embodiment provides a compound of Formula (V), wherein R$^2$ is CD$_3$. Another embodiment provides a compound of Formula (V), wherein X5 is N. Another embodiment provides a compound of Formula (V), wherein X6 is N. Another embodiment provides a compound of Formula (V), wherein X7 is N. Another embodiment provides a compound of Formula (V), wherein X8 is N. Another embodiment provides a compound of Formula (V), wherein none of X5, X6, X7, or X8 is N. Another embodiment provides a compound of Formula (V), wherein R$^5$ and R$^8$ are hydrogen. Another embodiment provides a compound of Formula (V), wherein R$^5$, R$^6$, R$^7$ and R$^8$ are hydrogen. Another embodiment provides a compound of Formula (V), wherein R$^7$ is a halogen. Another embodiment provides a compound of Formula (V), wherein R$^6$ is a halogen. Another embodiment provides a compound of Formula (V), wherein R$^6$ is a heteroaryl. Another embodiment provides a compound of Formula (V), wherein R$^6$ is an aryl. Another embodiment provides a compound of Formula (V), wherein R$^6$ is an alkyl. Another embodiment provides a compound of Formula (V), wherein R$^6$ is an aryl.

Another embodiment provides a compound of Formula (V), wherein Y is a bond. Another embodiment provides a compound of Formula (V), wherein Y is a —CH$_2$—. Another embodiment provides a compound of Formula (V), wherein Z is —SO$_2$R$^{21}$. Another embodiment provides a compound of Formula (V), wherein Z is —N(R$^{22}$)SO$_2$R$^{21}$. Another embodiment provides a compound of Formula (V), wherein Z is —SO$_2$N(R$^{22}$)$_2$. Another embodiment provides a compound of Formula (V), wherein Z is —N(R$^{22}$)SO$_2$N(R$^{22}$)$_2$. Another embodiment provides a compound of Formula (V), wherein Z is —CON(R$^{22}$)$_2$. Another embodiment provides a compound of Formula (V), wherein Z is —N(R$^{22}$)CO$_2$R$^{21}$. Another embodiment provides a compound of Formula (V), wherein Z is —N(R$^{22}$)CON(R$^{22}$)$_2$. Another embodiment provides a compound of Formula (V), wherein R$^{21}$ is alkyl, cycloalkyl, or cycloalkylalkyl. Another embodiment provides a compound of Formula (V), wherein R$^{21}$ is alkyl. Another embodiment provides a compound of Formula (V), wherein R$^{14}$ is hydrogen, halogen, or alkyl. Another embodiment provides a compound of Formula (V), wherein X4 is C—R$^{15}$. Another embodiment provides a compound of Formula (V), wherein W is —O—. Another embodiment provides a compound of Formula (V), wherein W is —NH—. Another embodiment provides a compound of Formula (V), wherein X is alkyl. Another embodiment provides a compound of Formula (V), wherein X is aryl. Another embodiment provides a compound of Formula (V), wherein X is cycloalkylalkyl. Another embodiment provides a compound of Formula (V), wherein W is —O— and X is alkyl. Another embodiment provides a compound of Formula (V), wherein W is —O— and X is aryl. Another embodiment provides a compound of Formula (V), wherein W is —O— and X is cycloalkylalkyl. Another embodiment provides a compound of Formula (V), wherein R$^5$ and R$^8$ are hydrogen. Another embodiment provides a compound of Formula (V), wherein R$^5$ and R$^8$ are hydrogen, and R$^6$ is heteroaryl.

One embodiment provides a compound of Formula (VIa), or a pharmaceutically acceptable salt thereof,

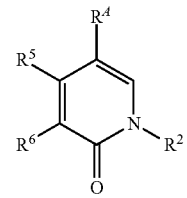

Formula (VIa)

wherein,

R$^2$ is CH$_3$ or CD$_3$;

R$^5$ is hydrogen or CH$_3$;

R$^6$ is hydrogen, CH$_3$, Cl, F, Br, NH$_2$, N(CH$_3$)$_2$, NH(alkyl), or CD$_3$;

R$^A$ is

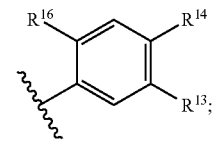

Y is selected from a bond or —CH$_2$—;

Z is —SO$_2$R$^{21}$;

R$^{14}$ is hydrogen, F, or Cl;

R$^{16}$ is —W—X, wherein W is —O— or —NH—, and X is selected from CH$_3$, CH$_2$CH$_3$, CH$_2$CH$_2$CH$_3$, CH(CH$_3$)$_2$, cyclopropyl, cyclobutyl, cyclopentyl, cyclohexyl, CH$_2$-(cyclopropyl), C$_6$H$_5$, 4-fluoro(C$_6$H$_4$), 2,4-difluoro(C$_6$H$_3$), 2-fluoro(C$_6$H$_4$), 4-tetrahydropyranyl, 3-tetrahydropyranyl, oxolan-3-yl, 4,4-difluorocyclohexyl, and 4-hydroxycyclohexyl; and each R$^{21}$ is CH$_3$ or CH$_2$CH$_3$.

Another embodiment provides a compound of Formula (VIa), wherein Y is a bond. Another embodiment provides a compound of Formula (VIa), wherein Y is —CH$_2$—. Another embodiment provides a compound of Formula (VIa), wherein W is —O—. Another embodiment provides a compound of Formula (VIa), wherein W is —NH—. Another embodiment provides a compound of Formula (VIa), wherein R$^2$ is CH$_3$. Another embodiment provides a compound of Formula (VIa), wherein R$^2$ is CD$_3$.

One embodiment provides a compound of Formula (VIb), or a pharmaceutically acceptable salt thereof, Formula (VIb)

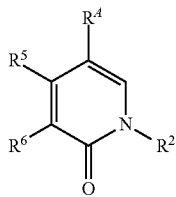

wherein,

R² is CH₃ or CD₃;

R⁵ is hydrogen or CH₃;

R⁶ is hydrogen, CH₃, Cl, F, Br, NH₂, N(CH₃)₂, NH(alkyl), or CD₃;

R⁴ is

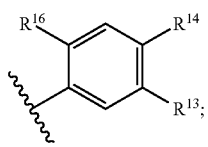

R¹³ is —NHSO₂R²¹;

R¹⁴ is hydrogen, F, or Cl;

R¹⁶ is —W—X, wherein W is —O— or —NH—, and X is selected from CH₃, CH₂CH₃, CH₂CH₂CH₃, CH(CH₃)₂, cyclopropyl, cyclobutyl, cyclopentyl, cyclohexyl, CH₂-(cyclopropyl), C₆H₅, 4-fluoro(C₆H₄), 2,4-difluoro(C₆H₃), 2-fluoro(C₆H₄), 4-tetrahydropyranyl, 3-tetrahydropyranyl, oxolan-3-yl, 4,4-difluorocyclohexyl, and 4-hydroxycyclohexyl; and each R²¹ is CH₃ or CH₂CH₃.

Another embodiment provides a compound of Formula (VIb), wherein W is —O—. Another embodiment provides a compound of Formula (VIb), wherein W is —NH—. Another embodiment provides a compound of Formula (VIb), wherein R² is CH₃. Another embodiment provides a compound of Formula (VIb), wherein R² is CD₃.

One embodiment provides a compound of Formula (VIc), or a pharmaceutically acceptable salt thereof, Formula (VIc)

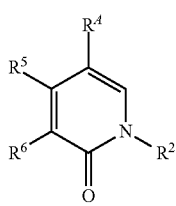

wherein,

R² is CH₃ or CD₃;

R⁵ is hydrogen or CH₃;

R⁶ is hydrogen, CH₃, Cl, F, Br, NH₂, N(CH₃)₂, NH(alkyl), or CD₃;

R⁴ is

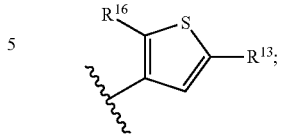

R¹³ is —Y—Z;

Y is selected from a bond or —CH₂—;

Z is —SO₂R²¹;

R¹⁶ is —W—X, wherein W is —O— or —NH—, and X is selected from CH₃, CH₂CH₃, CH₂CH₂CH₃, CH(CH₃)₂, cyclopropyl, cyclobutyl, cyclopentyl, cyclohexyl, CH₂-(cyclopropyl), C₆H₅, 4-fluoro(C₆H₄), 2,4-difluoro(C₆H₃), 2-fluoro(C₆H₄), 4-tetrahydropyranyl, 3-tetrahydropyranyl, oxolan-3-yl, 4,4-difluorocyclohexyl, and 4-hydroxycyclohexyl; and each R²¹ is CH₃ or CH₂CH₃.

Another embodiment provides a compound of Formula (VIc), wherein Y is a bond. Another embodiment provides a compound of Formula (VIc), wherein Y is —CH₂—. Another embodiment provides a compound of Formula (VIc), wherein W is —O—. Another embodiment provides a compound of Formula (VIc), wherein W is —NH—. Another embodiment provides a compound of Formula (VIc), wherein R² is CH₃. Another embodiment provides a compound of Formula (VIc), wherein R² is CD₃.

One embodiment provides a compound of Formula (VId), or a pharmaceutically acceptable salt thereof, Formula (VId)

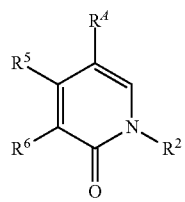

wherein,

R² is CH₃ or CD₃;

R⁵ is hydrogen or CH₃;

R⁶ is hydrogen, CH₃, Cl, F, Br, NH₂, N(CH₃)₂, NH(alkyl), or CD₃;

R⁴ is

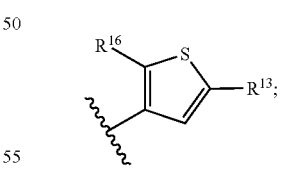

R¹³ is —NHSO₂R²¹;

R¹⁶ is —W—X, wherein W is —O— or —NH—, and X is selected from CH₃, CH₂CH₃, CH₂CH₂CH₃, CH(CH₃)₂, cyclopropyl, cyclobutyl, cyclopentyl, cyclohexyl, CH₂-(cyclopropyl), C₆H₅, 4-fluoro(C₆H₄), 2,4-difluoro(C₆H₃), 2-fluoro(C₆H₄), 4-tetrahydropyranyl, 3-tetrahydropyranyl, oxolan-3-yl, 4,4-difluorocyclohexyl, and 4-hydroxycyclohexyl; and each R²¹ is CH₃ or CH₂CH₃.

Another embodiment provides a compound of Formula (VId), wherein W is —O—. Another embodiment provides a compound of Formula (VId), wherein W is —NH—. Another embodiment provides a compound of Formula (VId), wherein $R^2$ is $CH_3$. Another embodiment provides a compound of Formula (VId), wherein $R^2$ is $CD_3$.

One embodiment provides a compound of Formula (VIe), or a pharmaceutically acceptable salt thereof,

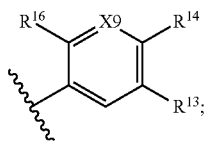

Formula (VIe)

wherein, $R^2$ is hydrogen, $CH_3$, or $CHF_2$;

$R^6$ is $CH_3$, $CD_3$, cyclopropyl, $NH(CH_3)$, $NH(CH_2CH_3)$, F, or Cl;

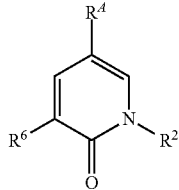

$R^A$ is $R^{13}$ is —Y—Z;

Y is selected from —NH— or —$CH_2$—;

Z is selected from —$SO_2R^{21}$;

$R^{14}$ is hydrogen, $CH_3$, or F;

X9 is N or CH;

$R^{16}$ is —W—X, wherein W is —O— or —NH—, and X is selected from $CH_3$, $CH_2CH_3$, $CH_2CH_2CH_3$, $CH_2$-(cyclopropyl), $CH_2CH_2CFH_2$, 2,4-difluoro($C_6H_3$), 2,3-difluoro ($C_6H_3$), 2-chloro-4-fluoro($C_6H_3$), 2-fluoro($C_6H_4$), and 2-chloro($C_6H_4$); and each $R^{21}$ is independently selected from $CH_3$, $CH_2CH_3$, $CH_2CH_2CH_3$, $CH_2CH_2CHF_2$, $CH_2$-(cyclopropyl), and cyclopropyl.

Another embodiment provides a compound of Formula (VIe), wherein Y is —NH—. Another embodiment provides a compound of Formula (VIe), wherein Y is —$CH_2$—. Another embodiment provides a compound of Formula (VIe), wherein W is —O—. Another embodiment provides a compound of Formula (VIe), wherein W is —NH—. Another embodiment provides a compound of Formula (VIe), wherein X9 is N. Another embodiment provides a compound of Formula (VIe), wherein X9 is CH. Another embodiment provides a compound of Formula (VIe), wherein $R^2$ is hydrogen. Another embodiment provides a compound of Formula (VIe), wherein $R^2$ is $CH_3$. Another embodiment provides a compound of Formula (VIe), wherein $R^2$ is $CHF_2$.

One embodiment provides a compound of Formula (VII), or a pharmaceutically acceptable salt thereof,

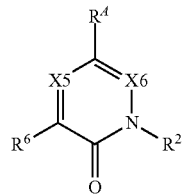

Formula (VII)

wherein, $R^2$ is $CH_3$, $CH_2CH_3$, $CH_2CF_3$, $CH_2F$, $CHF_2$, $CF_3$, $CH_2D$, $CHD_2$, or $CD_3$;

X6 is C—H or N;

X5 is C—$R^5$ or N; provided that if X6 is N, then X5 is C—$R^5$, and if X5 is N, then X6 is CH;

$R^5$ is hydrogen, halogen, —OH, —CN, —$OR^{61}$, —$NHR^{61}$, —$N(R^{61})_2$, alkyl, cycloalkyl, cycloalkylalkyl, aryl, aralkyl, heterocyclyl, heterocyclylalkyl, heteroaryl, or heteroarylalkyl, wherein each $R^{61}$ is independently selected from alkyl, cycloalkyl, cycloalkylalkyl, aryl, aralkyl, heterocyclyl, heterocyclylalkyl, heteroaryl, or heteroarylalkyl;

$R^6$ is hydrogen, halogen, —OH, —CN, alkyl, alkynyl, cycloalkyl, cycloalkylalkyl, cycloalkylalkynyl, amino, alkylamino, dialkylamino, heterocyclyl, cycloalkylalkylamino, alkoxy, cycloalkyloxy, cycloalkylalkoxy, alkyl-S—, cycloalkyl-S—, and cycloalkylalkyl-S—;

$R^A$ is

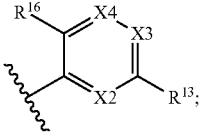

X2 is N or C—$R^{12}$, wherein $R^{12}$ is hydrogen, halogen, alkyl, or alkoxy;

$R^{13}$ is —Y—Z;

Y is selected from a bond, —$CH_2$—, or —$CH(C_1$-$C_4$ alkyl)-;

Z is selected from —$SO_2R^{21}$, —$N(R^{22})SO_2R^{21}$, —$SO_2N(R^{22})_2$, —$N(R^{22})SO_2N(R^{22})_2$, —$CON(R^{22})_2$, —$N(R^{22})CO_2R^{21}$, —$N(R^{22})CON(R^{22})_2$, —$N(R^{22})COR^{21}$, —OC(O)N($R^{22})_2$, —$OSO_2N(R^{22})_2$, or —$N(R^{22})SO_3R^{21}$;

X3 is N or C—$R^{14}$, wherein $R^{14}$ is hydrogen, halogen, —CN, alkyl, cycloalkyl, or alkoxy; or optionally when X4 is C—$R^{15}$, $R^{14}$ and $R^{15}$ connect to form a ring;

X4 is N or C—$R^{15}$, wherein $R^{15}$ is hydrogen, halogen, —CN, alkyl, or alkoxy;

$R^{16}$ is hydrogen, halogen, or —W—X, wherein W is a bond, —O—, —S—, or —NH—, and X is selected from alkyl, alkynyl, aryl, aralkyl, cycloalkyl, cycloalkylalkyl, cycloalkylalkynyl, heterocyclyl, heterocyclylalkyl, heteroaryl, or heteroarylalkyl; or optionally when X4 is C—$R^{15}$, $R^{16}$ and $R^{15}$ connect to form a ring;

each $R^{21}$ is independently selected from alkyl, cycloalkyl, cycloalkylalkyl, aryl, aralkyl, heterocyclyl, heterocyclylalkyl, heteroaryl, or heteroarylalkyl; and each $R^{22}$ is independently selected from hydrogen, alkyl, cycloalkyl, cycloalkylalkyl, aryl, aralkyl, heterocyclyl, heterocyclylalkyl, heteroaryl, or heteroarylalkyl.

Another embodiment provides a compound of Formula (VII), wherein X2 is N. Another embodiment provides a compound of Formula (VII), wherein X3 is N. Another embodiment provides a compound of Formula (VII), wherein X4 is N. Another embodiment provides a compound of Formula (VII), wherein X2 and X3 are N. Another embodiment provides a compound of Formula (VII), wherein X2 is C—$R^{12}$, X3 is C—$R^{14}$, and X4 is C—$R^{15}$.

Another embodiment provides a compound of Formula (VII), wherein $R^2$ is $CH_3$. Another embodiment provides a compound of Formula (VII), wherein X6 is C—H. Another embodiment provides a compound of Formula (VII), wherein X6 is N. Another embodiment provides a compound of Formula (VII), wherein X5 is C—$R^5$. Another embodiment provides a compound of Formula (VII), wherein X5 is N. Another embodiment provides a compound of Formula (VII), wherein $R^5$ is hydrogen, halogen, or alkyl. Another embodiment provides a compound of Formula (VII), wherein $R^6$ is hydrogen, halogen, or alkyl. Another embodiment provides a compound of Formula (VII), wherein $R^6$ is heterocyclyl. Another embodiment provides a compound of Formula (VII), wherein $R^6$ is cycloalkylalkynyl. Another embodiment provides a compound of Formula (VII), wherein $R^6$ is alkoxy, cycloalkyloxy, or cycloalkylalkoxy.

Another embodiment provides a compound of Formula (VII), wherein Y is a bond. Another embodiment provides a compound of Formula (VII), wherein Y is a —$CH_2$—. Another embodiment provides a compound of Formula (VII), wherein Z is —$SO_2R^{21}$. Another embodiment provides a compound of Formula (VII), wherein Z is —$N(R^{22})SO_2R^{21}$. Another embodiment provides a compound of Formula (VII), wherein Z is —$SO_2N(R^{22})_2$. Another embodiment provides a compound of Formula (VII), wherein Z is —$N(R^{22})SO_2N(R^{22})_2$. Another embodiment provides a compound of Formula (VII), wherein Z is —$CON(R^{22})_2$. Another embodiment provides a compound of Formula (VII), wherein Z is —$N(R^{22})CO_2R^{21}$. Another embodiment provides a compound of Formula (VII), wherein Z is —$N(R^{22})CON(R^{22})_2$. Another embodiment provides a compound of Formula (VII), wherein $R^{21}$ is alkyl, cycloalkyl, or cycloalkylalkyl. Another embodiment provides a compound of Formula (VII), wherein $R^{21}$ is alkyl. Another embodiment provides a compound of Formula (VII), wherein $R^{14}$ is hydrogen, halogen, or alkyl. Another embodiment provides a compound of Formula (VII), wherein X4 is C—$R^{15}$. Another embodiment provides a compound of Formula (VII), wherein W is —O—. Another embodiment provides a compound of Formula (VII), wherein W is —NH—. Another embodiment provides a compound of Formula (VII), wherein X is alkyl. Another embodiment provides a compound of Formula (VII), wherein X is alkynyl. Another embodiment provides a compound of Formula (VII), wherein X is aryl. Another embodiment provides a compound of Formula (VII), wherein X is cycloalkylalkyl. Another embodiment provides a compound of Formula (VII), wherein X is cycloalkylalkynyl. Another embodiment provides a compound of Formula (VII), wherein W is —O— and X is alkyl. Another embodiment provides a compound of Formula (VII), wherein W is —O— and X is alkynyl. Another embodiment provides a compound of Formula (VII), wherein W is —O— and X is aryl. Another embodiment provides a compound of Formula (VII), wherein W is —O— and X is cycloalkylalkyl. Another embodiment provides a compound of Formula (VII), wherein W is —O— and X is cycloalkylalkynyl. Another embodiment provides a compound of Formula (VII), wherein the $R^6$ is $CD_3$.

One embodiment provides a compound of Formula (VIIa), or a pharmaceutically acceptable salt thereof,

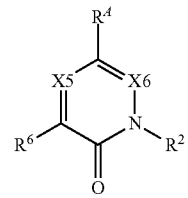

Formula (VIIa)

wherein,
$R^2$ is $CH_3$, $CH_2CH_3$, $CH_2CF_3$, $CH_2F$, $CHF_2$, $CF_3$, $CH_2D$, $CHD_2$, or $CD_3$;
X6 is C—H or N;
X5 is C—$R^5$ or N; provided that if X6 is N, then X5 is C—$R^5$, and if X5 is N, then X6 is CH;
$R^5$ is hydrogen, halogen, —OH, —CN, —$OR^{61}$, —$NHR^{61}$, —$N(R^{61})_2$, alkyl, cycloalkyl, cycloalkylalkyl, aryl, aralkyl, heterocyclyl, heterocyclylalkyl, heteroaryl, or heteroarylalkyl, wherein each $R^{61}$ is independently selected from alkyl, cycloalkyl, cycloalkylalkyl, aryl, aralkyl, heterocyclyl, heterocyclylalkyl, heteroaryl, or heteroarylalkyl;
$R^6$ is hydrogen, halogen, —OH, —CN, alkyl, alkynyl, cycloalkyl, cycloalkylalkyl, cycloalkylalkynyl, amino, alkylamino, dialkylamino, heterocyclyl, cycloalkylalkylamino, alkoxy, cycloalkyloxy, cycloalkylalkoxy, alkyl-S—, cycloalkyl-S—, and cycloalkylalkyl-S—;
$R^4$ is

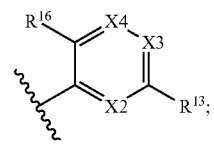

X2 is N or C—$R^{12}$, wherein $R^{12}$ is hydrogen, halogen, alkyl, or alkoxy;
$R^{13}$ is —Y—Z;
Y is selected from a bond, —$CH_2$—, or —$CH(C_1$-$C_4$ alkyl)-;
Z is selected from —$N(R^{22})SO_2R^{21}$, —$N(R^{22})CO_2R^{21}$, —$N(R^{22})COR^{21}$, or —$N(R^{22})SO_3R^{21}$;
X3 is N or C—$R^{14}$, wherein $R^{14}$ is hydrogen, halogen, —CN, alkyl, cycloalkyl, or alkoxy; or optionally when X4 is C—$R^{15}$, $R^{14}$ and $R^{15}$ connect to form a ring;
X4 is N or C—$R^{15}$, wherein $R^{15}$ is hydrogen, halogen, —CN, alkyl, or alkoxy;
$R^{16}$ is hydrogen, halogen, or —W—X, wherein W is a bond, —O—, —S—, or —NH—, and X is selected from alkyl, alkynyl, aryl, aralkyl, cycloalkyl, cycloalkylalkyl, cycloalkylalkynyl, heterocyclyl, heterocyclylalkyl, heteroaryl, or heteroarylalkyl; or optionally when X4 is C—$R^{15}$, $R^{16}$ and $R^{15}$ connect to form a ring;
each $R^{21}$ is independently selected from alkyl, cycloalkyl, cycloalkylalkyl, aryl, aralkyl, heterocyclyl, heterocyclylalkyl, heteroaryl, or heteroarylalkyl; or optionally when $R^{21}$ and $R^{22}$ are alkyl, $R^{21}$ and $R^{22}$ connect to form a ring; and
each $R^{22}$ is independently selected from hydrogen, alkyl, cycloalkyl, cycloalkylalkyl, aryl, aralkyl, heterocyclyl, heterocyclylalkyl, heteroaryl, or heteroarylalkyl.

Another embodiment provides a compound of Formula (VIIa), wherein X2 is N. Another embodiment provides a compound of Formula (VIIa), wherein X3 is N. Another embodiment provides a compound of Formula (VIIa), wherein X4 is N. Another embodiment provides a compound of Formula (VIIa), wherein X2 and X3 are N. Another embodiment provides a compound of Formula (VIIa), wherein X2 is C—R$^{12}$, X3 is C—R$^{14}$, and X4 is C—R$^{15}$.

Another embodiment provides a compound of Formula (VIIa), wherein R$^2$ is CH$_3$. Another embodiment provides a compound of Formula (VIIa), wherein X6 is C—H. Another embodiment provides a compound of Formula (VIIa), wherein X6 is N. Another embodiment provides a compound of Formula (VIIa), wherein X5 is C—R$^5$. Another embodiment provides a compound of Formula (VIIa), wherein X5 is N. Another embodiment provides a compound of Formula (VIIa), wherein R$^5$ is hydrogen, halogen, or alkyl. Another embodiment provides a compound of Formula (VIIa, wherein R$^6$ is hydrogen, halogen, or alkyl. Another embodiment provides a compound of Formula (VIIa), wherein R$^6$ is heterocyclyl. Another embodiment provides a compound of Formula (VIIa), wherein R$^6$ is cycloalkylalkynyl. Another embodiment provides a compound of Formula (VIIa), wherein R$^6$ is alkoxy, cycloalkyloxy, or cycloalkylalkoxy.

Another embodiment provides a compound of Formula (VIIa), wherein Y is a bond. Another embodiment provides a compound of Formula (VIIa), wherein Y is a —CH$_2$—. Another embodiment provides a compound of Formula (VIIa), wherein Z is —N(R$^{22}$)SO$_2$R$^{21}$. Another embodiment provides a compound of Formula (VIIa), wherein Z is —N(R$^{22}$)CO$_2$R$^{21}$. Another embodiment provides a compound of Formula (VIIa), wherein R$^{21}$ is alkyl, cycloalkyl, or cycloalkylalkyl. Another embodiment provides a compound of Formula (VIIa), wherein R$^{21}$ is alkyl. Another embodiment provides a compound of Formula (VIIa), wherein R$^{22}$ is alkyl. Another embodiment provides a compound of Formula (VIIa), wherein both R$^{21}$ and R$^{22}$ are alkyl and connect to form a ring. Another embodiment provides a compound of Formula (VIIa), wherein R$^{14}$ is hydrogen, halogen, or alkyl. Another embodiment provides a compound of Formula (VIIa), wherein X4 is C—R$^{15}$. Another embodiment provides a compound of Formula (VIIa), wherein W is —O—. Another embodiment provides a compound of Formula (VIIa), wherein W is —NH—. Another embodiment provides a compound of Formula (VIIa), wherein X is alkyl. Another embodiment provides a compound of Formula (VIIa), wherein X is alkynyl. Another embodiment provides a compound of Formula (VIIa), wherein X is aryl. Another embodiment provides a compound of Formula (VIIa), wherein X is cycloalkylalkyl. Another embodiment provides a compound of Formula (VIIa), wherein X is cycloalkylalkynyl. Another embodiment provides a compound of Formula (VIIa), wherein W is —O— and X is alkyl. Another embodiment provides a compound of Formula (VIIa), wherein W is —O— and X is alkynyl. Another embodiment provides a compound of Formula (VIIa), wherein W is —O— and X is aryl. Another embodiment provides a compound of Formula (VIIa), wherein W is —O— and X is cycloalkylalkyl. Another embodiment provides a compound of Formula (VIIa), wherein W is —O— and X is cycloalkylalkynyl. Another embodiment provides a compound of Formula (VIIa), wherein the R$^6$ is CD$_3$.

One embodiment provides a compound of Formula (VIII), or a pharmaceutically acceptable salt thereof,

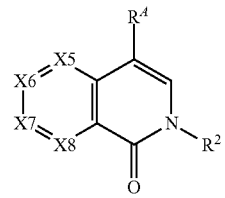

Formula (VIII)

wherein,
R$^2$ is selected from CH$_3$, CH$_2$CH$_3$, CH$_2$CF$_3$, CH$_2$F, CHF$_2$, CF$_3$, CH$_2$D, CHD$_2$, or CD$_3$;
X5 is C—R$^5$ or N;
X6 is C—R$^6$ or N;
X7 is C—R$^7$ or N;
X8 is C—R$^8$ or N; wherein no more than two of X5, X6, X7, or X8 may be N;
R$^5$ is hydrogen, halogen, —OH, —CN, —OR$^{61}$, —NHR$^{61}$, —N(R$^{61}$)$_2$, alkyl, cycloalkyl, cycloalkylalkyl, aryl, aralkyl, heterocyclyl, heterocyclylalkyl, heteroaryl, or heteroarylalkyl, wherein each R$^{61}$ is independently selected from alkyl, cycloalkyl, cycloalkylalkyl, aryl, aralkyl, heterocyclyl, heterocyclylalkyl, heteroaryl, or heteroarylalkyl;
R$^6$ is hydrogen, halogen, —OH, —CN, —OR$^{61}$, —NHR$^{61}$, —N(R$^{61}$)$_2$, alkyl, cycloalkyl, cycloalkylalkyl, aryl, aralkyl, heterocyclyl, heterocyclylalkyl, heteroaryl, or heteroarylalkyl, wherein each R$^{61}$ is independently selected from alkyl, cycloalkyl, cycloalkylalkyl, aryl, aralkyl, heterocyclyl, heterocyclylalkyl, heteroaryl, or heteroarylalkyl;
R$^7$ is hydrogen, halogen, —OH, —CN, —OR$^{61}$, —NHR$^{61}$, —N(R$^{61}$)$_2$, alkyl, cycloalkyl, cycloalkylalkyl, aryl, aralkyl, heterocyclyl, heterocyclylalkyl, heteroaryl, or heteroarylalkyl, wherein each R$^{61}$ is independently selected from alkyl, cycloalkyl, cycloalkylalkyl, aryl, aralkyl, heterocyclyl, heterocyclylalkyl, heteroaryl, or heteroarylalkyl;
R$^8$ is hydrogen, halogen, or alkyl;
R$^A$ is

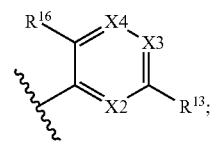

X2 is N or C—R$^{12}$, wherein R$^{12}$ is hydrogen, halogen, alkyl, or alkoxy;
R$^{13}$ is —Y—Z;
Y is selected from a bond, —CH$_2$—, or —CH(C$_1$-C$_4$ alkyl)-;
Z is selected from —SO$_2$R$^{21}$, —N(R$^{22}$)SO$_2$R$^{21}$, —SO$_2$N(R$^{22}$)$_2$, —N(R$^{22}$)SO$_2$N(R$^{22}$)$_2$, —CON(R$^{22}$)$_2$, —N(R$^{22}$)CO$_2$R$^{21}$, —N(R$^{22}$)CON(R$^{22}$)$_2$, —N(R$^{22}$)COR$^{21}$, —OC(O)N(R$^{22}$)$_2$, —OSO$_2$N(R$^{22}$)$_2$, or —N(R$^{22}$)SO$_3$R$^{21}$;
X3 is N or C—R$^{14}$, wherein R$^{14}$ is hydrogen, halogen, —CN, alkyl, cycloalkyl, or alkoxy; or optionally when X4 is C—R$^{15}$, R$^{14}$ and R$^{15}$ connect to form a ring;
X4 is N or C—R$^{15}$, wherein R$^{15}$ is hydrogen, halogen, —CN, alkyl, or alkoxy;
R$^{16}$ is hydrogen, halogen, or —W—X, wherein W is a bond, —O—, —S—, or —NH—, and X is selected from alkyl, alkynyl, aryl, aralkyl, cycloalkyl, cycloalkylalkyl, cycloalkylalkynyl, heterocyclyl, heterocyclylalkyl, heteroaryl, or heteroarylalkyl; or optionally when X4 is C—R$^{15}$, R$^{16}$ and R$^{15}$ connect to form a ring;

each $R^{21}$ is independently selected from alkyl, cycloalkyl, cycloalkylalkyl, aryl, aralkyl, heterocyclyl, heterocyclylalkyl, heteroaryl, or heteroarylalkyl; and each $R^{22}$ is independently selected from hydrogen, alkyl, cycloalkyl, cycloalkylalkyl, aryl, aralkyl, heterocyclyl, heterocyclylalkyl, heteroaryl, or heteroarylalkyl.

Another embodiment provides a compound of Formula (VIII), wherein $R^2$ is $CH_3$. Another embodiment provides a compound of Formula (VIII), wherein $R^2$ is $CD_3$. Another embodiment provides a compound of Formula (VIII), wherein X5 is N. Another embodiment provides a compound of Formula (VIII), wherein X6 is N. Another embodiment provides a compound of Formula (VIII), wherein X7 is N. Another embodiment provides a compound of Formula (VIII), wherein X8 is N. Another embodiment provides a compound of Formula (VIII), wherein none of X5, X6, X7, or X8 is N. Another embodiment provides a compound of Formula (VIII), wherein $R^5$ and $R^8$ are hydrogen. Another embodiment provides a compound of Formula (VIII), wherein $R^5$, $R^6$, $R^7$ and $R^8$ are hydrogen. Another embodiment provides a compound of Formula (VIII), wherein $R^7$ is a halogen. Another embodiment provides a compound of Formula (VIII), wherein $R^6$ is a halogen. Another embodiment provides a compound of Formula (VIII), wherein $R^6$ is a heteroaryl. Another embodiment provides a compound of Formula (VIII), wherein $R^6$ is an aryl. Another embodiment provides a compound of Formula (VIII), wherein $R^6$ is an alkyl. Another embodiment provides a compound of Formula (VIII), wherein $R^6$ is an aryl.

Another embodiment provides a compound of Formula (VIII), wherein Y is a bond. Another embodiment provides a compound of Formula (VIII), wherein Y is a —$CH_2$—. Another embodiment provides a compound of Formula (VIII), wherein Z is —$SO_2R^{21}$. Another embodiment provides a compound of Formula (VIII), wherein Z is —$N(R^{22})SO_2R^{21}$. Another embodiment provides a compound of Formula (VIII), wherein Z is —$SO_2N(R^{22})_2$. Another embodiment provides a compound of Formula (VIII), wherein Z is —$N(R^{22})SO_2N(R^{22})_2$. Another embodiment provides a compound of Formula (VIII), wherein Z is —$CON(R^{22})_2$. Another embodiment provides a compound of Formula (VIII), wherein Z is —$N(R^{22})CO_2R^{21}$. Another embodiment provides a compound of Formula (VIII), wherein Z is —$N(R^{22})CON(R^{22})_2$. Another embodiment provides a compound of Formula (VIII), wherein $R^{21}$ is alkyl, cycloalkyl, or cycloalkylalkyl. Another embodiment provides a compound of Formula (VIII), wherein $R^{21}$ is alkyl. Another embodiment provides a compound of Formula (VIII), wherein $R^{14}$ is hydrogen, halogen, or alkyl. Another embodiment provides a compound of Formula (VIII), wherein X4 is C—$R^{15}$. Another embodiment provides a compound of Formula (VIII), wherein W is —O—. Another embodiment provides a compound of Formula (VIII), wherein W is —NH—. Another embodiment provides a compound of Formula (VIII), wherein X is alkyl. Another embodiment provides a compound of Formula (VIII), wherein X is aryl. Another embodiment provides a compound of Formula (VIII), wherein X is cycloalkylalkyl. Another embodiment provides a compound of Formula (VIII), wherein W is —O— and X is alkyl. Another embodiment provides a compound of Formula (VIII), wherein W is —O— and X is aryl. Another embodiment provides a compound of Formula (VIII), wherein W is —O— and X is cycloalkylalkyl. Another embodiment provides a compound of Formula (VIII), wherein $R^5$ and $R^8$ are hydrogen. Another embodiment provides a compound of Formula (VIII), wherein $R^5$ and $R^8$ are hydrogen, and $R^6$ is heteroaryl.

One embodiment provides a compound of Formula (VIIIa), or a pharmaceutically acceptable salt thereof,

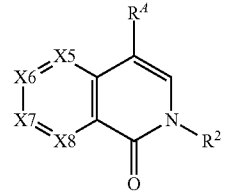

Formula (VIIIa)

wherein, $R^2$ is selected from $CH_3$, $CH_2CH_3$, $CH_2CF_3$, $CH_2F$, $CHF_2$, $CF_3$, $CH_2D$, $CHD_2$, or $CD_3$;

X5 is C—$R^5$ or N;

X6 is C—$R^6$ or N;

X7 is C—$R^7$ or N;

X8 is C—$R^8$ or N; wherein no more than two of X5, X6, X7, or X8 may be N;

$R^5$ is hydrogen, halogen, —OH, —CN, —$OR^{61}$, —$NHR^{61}$, —$N(R^{61})_2$, alkyl, cycloalkyl, cycloalkylalkyl, aryl, aralkyl, heterocyclyl, heterocyclylalkyl, heteroaryl, or heteroarylalkyl, wherein each $R^{61}$ is independently selected from alkyl, cycloalkyl, cycloalkylalkyl, aryl, aralkyl, heterocyclyl, heterocyclylalkyl, heteroaryl, or heteroarylalkyl;

$R^6$ is hydrogen, halogen, —OH, —CN, —$OR^{61}$, —$NHR^{61}$, —$N(R^{61})_2$, alkyl, cycloalkyl, cycloalkylalkyl, aryl, aralkyl, heterocyclyl, heterocyclylalkyl, heteroaryl, or heteroarylalkyl, wherein each $R^{61}$ is independently selected from alkyl, cycloalkyl, cycloalkylalkyl, aryl, aralkyl, heterocyclyl, heterocyclylalkyl, heteroaryl, or heteroarylalkyl;

$R^7$ is hydrogen, halogen, —OH, —CN, —$OR^{61}$, —$NHR^{61}$, —$N(R^{61})_2$, alkyl, cycloalkyl, cycloalkylalkyl, aryl, aralkyl, heterocyclyl, heterocyclylalkyl, heteroaryl, or heteroarylalkyl, wherein each $R^{61}$ is independently selected from alkyl, cycloalkyl, cycloalkylalkyl, aryl, aralkyl, heterocyclyl, heterocyclylalkyl, heteroaryl, or heteroarylalkyl;

$R^8$ is hydrogen, halogen, or alkyl;

$R^A$ is

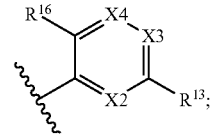

X2 is N or C—$R^{12}$, wherein $R^{12}$ is hydrogen, halogen, alkyl, or alkoxy;

$R^{13}$ is —Y—Z;

Y is selected from a bond, —$CH_2$—, or —$CH(C_1$-$C_4$ alkyl)-;

Z is selected from —$N(R^{22})SO_2R^{21}$, —$N(R^{22})CO_2R^{21}$, —$N(R^{22})COR^{21}$, or —$N(R^{22})SO_3R^{21}$;

X3 is N or C—$R^{14}$, wherein $R^{14}$ is hydrogen, halogen, —CN, alkyl, cycloalkyl, or alkoxy; or optionally when X4 is C—$R^{15}$, $R^{14}$ and $R^{15}$ connect to form a ring;

X4 is N or C—$R^{15}$, wherein $R^{15}$ is hydrogen, halogen, —CN, alkyl, or alkoxy;

$R^{16}$ is hydrogen, halogen, or —W—X, wherein W is a bond, —O—, —S—, or —NH—, and X is selected from alkyl, alkynyl, aryl, aralkyl, cycloalkyl, cycloalkylalkyl, cycloalkylalkynyl, heterocyclyl, heterocyclylalkyl, heteroaryl, or heteroarylalkyl; or optionally when X4 is C—$R^{15}$, $R^{16}$ and $R^{15}$ connect to form a ring;

each $R^{21}$ is independently selected from alkyl, cycloalkyl, cycloalkylalkyl, aryl, aralkyl, heterocyclyl, heterocyclylalkyl, heteroaryl, or heteroarylalkyl; or optionally when $R^{21}$ and $R^{22}$ are alkyl, $R^{21}$ and $R^{22}$ connect to form a ring; and each $R^{22}$ is independently selected from hydrogen, alkyl, cycloalkyl, cycloalkylalkyl, aryl, aralkyl, heterocyclyl, heterocyclylalkyl, heteroaryl, or heteroarylalkyl.

Another embodiment provides a compound of Formula (VIIIa), wherein $R^2$ is $CH_3$. Another embodiment provides a compound of Formula (VIIIa), wherein $R^2$ is $CD_3$. Another embodiment provides a compound of Formula (VIIIa), wherein X5 is N. Another embodiment provides a compound of Formula (VIIIa), wherein X6 is N. Another embodiment provides a compound of Formula (VIIIa), wherein X7 is N. Another embodiment provides a compound of Formula (VIIIa), wherein X8 is N. Another embodiment provides a compound of Formula (VIIIa), wherein none of X5, X6, X7, or X8 is N. Another embodiment provides a compound of Formula (VIIIa), wherein $R^5$ and $R^8$ are hydrogen. Another embodiment provides a compound of Formula (VIIIa), wherein $R^5$, $R^6$, $R^7$ and $R^8$ are hydrogen. Another embodiment provides a compound of Formula (VIIIa), wherein $R^7$ is a halogen. Another embodiment provides a compound of Formula (VIIIa), wherein $R^6$ is a halogen. Another embodiment provides a compound of Formula (VIIIa), wherein $R^6$ is a heteroaryl. Another embodiment provides a compound of Formula (VIIIa), wherein $R^6$ is an aryl. Another embodiment provides a compound of Formula (VIIIa), wherein $R^6$ is an alkyl. Another embodiment provides a compound of Formula (VIIIa), wherein $R^6$ is an aryl.

Another embodiment provides a compound of Formula (VIIIa), wherein Y is a bond. Another embodiment provides a compound of Formula (VIIIa), wherein Y is a —$CH_2$—. Another embodiment provides a compound of Formula (VIIIa), wherein Z is —$N(R^{22})SO_2R^{21}$. Another embodiment provides a compound of Formula (VIIIa), wherein Z is —$N(R^{22})CO_2R^{21}$. Another embodiment provides a compound of Formula (VIIIa), wherein $R^{21}$ is alkyl, cycloalkyl, or cycloalkylalkyl. Another embodiment provides a compound of Formula (VIIIa), wherein $R^{21}$ is alkyl. Another embodiment provides a compound of Formula (VIIIa), wherein $R^{22}$ is alkyl. Another embodiment provides a compound of Formula (VIIIa), wherein both $R^{21}$ and $R^{22}$ are alkyl and connect to form a ring. Another embodiment provides a compound of Formula (VIIIa), wherein $R^{14}$ is hydrogen, halogen, or alkyl. Another embodiment provides a compound of Formula (VIIIa), wherein X4 is C—$R^{15}$. Another embodiment provides a compound of Formula (VIIIa), wherein W is —O—. Another embodiment provides a compound of Formula (VIIIa), wherein W is —NH—. Another embodiment provides a compound of Formula (VIIIa), wherein X is alkyl. Another embodiment provides a compound of Formula (VIIIa), wherein X is aryl. Another embodiment provides a compound of Formula (VIIIa), wherein X is cycloalkylalkyl. Another embodiment provides a compound of Formula (VIIIa), wherein W is —O— and X is alkyl. Another embodiment provides a compound of Formula (VIIIa), wherein W is —O— and X is aryl. Another embodiment provides a compound of Formula (VIIIa), wherein W is —O— and X is cycloalkylalkyl. Another embodiment provides a compound of Formula (VIIIa), wherein $R^5$ and $R^8$ are hydrogen. Another embodiment provides a compound of Formula (VIIIa), wherein $R^5$ and $R^8$ are hydrogen, and $R^6$ is heteroaryl.

One embodiment provides a compound of Formula (IX), or a pharmaceutically acceptable salt thereof,

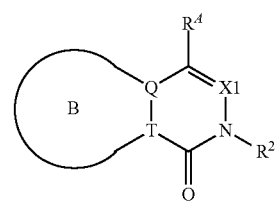

Formula (IX)

wherein,
Q is N and T is C, or Q is C and T is N;
Ring B is an optionally substituted 5-membered aromatic nitrogen-containing heteroaryl ring containing one or more nitrogen atoms;
$R^2$ is selected from $CH_3$, $CH_2CH_3$, $CH_2CF_3$, $CH_2F$, $CHF_2$, $CF_3$, $CH_2D$, $CHD_2$, or $CD_3$;
X1 is C—H or N;
$R^4$ is

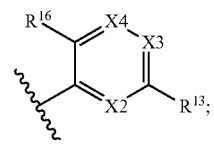

X2 is N or C—$R^{12}$, wherein $R^{12}$ is hydrogen, halogen, alkyl, or alkoxy;
$R^{13}$ is —Y—Z;
Y is selected from a bond, —$CH_2$—, or —$CH(C_1$-$C_4$ alkyl)-;
Z is selected from —$SO_2R^{21}$, —$N(R^{22})SO_2R^{21}$, —$SO_2N(R^{22})_2$, —$N(R^{22})SO_2N(R^{22})_2$, —$CON(R^{22})_2$, —$N(R^{22})CO_2R^{21}$, —$N(R^{22})CON(R^{22})_2$, —$N(R^{22})COR^{21}$, —$OC(O)N(R^{22})_2$, —$OSO_2N(R^{22})_2$, or —$N(R^{22})SO_3R^{21}$;
X3 is N or C—$R^{14}$, wherein $R^{14}$ is hydrogen, halogen, —CN, alkyl, cycloalkyl, or alkoxy; or optionally when X4 is C—$R^{15}$, $R^{14}$ and $R^{15}$ connect to form a ring;
X4 is N or C—$R^{15}$, wherein $R^{15}$ is hydrogen, halogen, —CN, alkyl, or alkoxy;
$R^{16}$ is hydrogen, halogen, or —W—X, wherein W is a bond, —O—, —S—, or —NH—, and X is selected from alkyl, alkynyl, aryl, aralkyl, cycloalkyl, cycloalkylalkyl, cycloalkylalkynyl, heterocyclyl, heterocyclylalkyl, heteroaryl, or heteroarylalkyl; or optionally when X4 is C—$R^{15}$, $R^{16}$ and $R^{15}$ connect to form a ring;
each $R^{21}$ is independently selected from alkyl, cycloalkyl, cycloalkylalkyl, aryl, aralkyl, heterocyclyl, heterocyclylalkyl, heteroaryl, or heteroarylalkyl; and
each $R^{22}$ is independently selected from hydrogen, alkyl, cycloalkyl, cycloalkylalkyl, aryl, aralkyl, heterocyclyl, heterocyclylalkyl, heteroaryl, or heteroarylalkyl.

Another embodiment provides a compound of Formula (IX), wherein X2 is N. Another embodiment provides a compound of Formula (IX), wherein X3 is N. Another embodiment provides a compound of Formula (IX), wherein X4 is N. Another embodiment provides a compound of Formula (IX), wherein X2 and X3 are N. Another embodiment provides a compound of Formula (IX), wherein X2 is C—$R^{12}$, X3 is C—$R^{14}$, and X4 is C—$R^{15}$.

Another embodiment provides a compound of Formula (IX), wherein the compound of Formula (IX) is selected from the group:

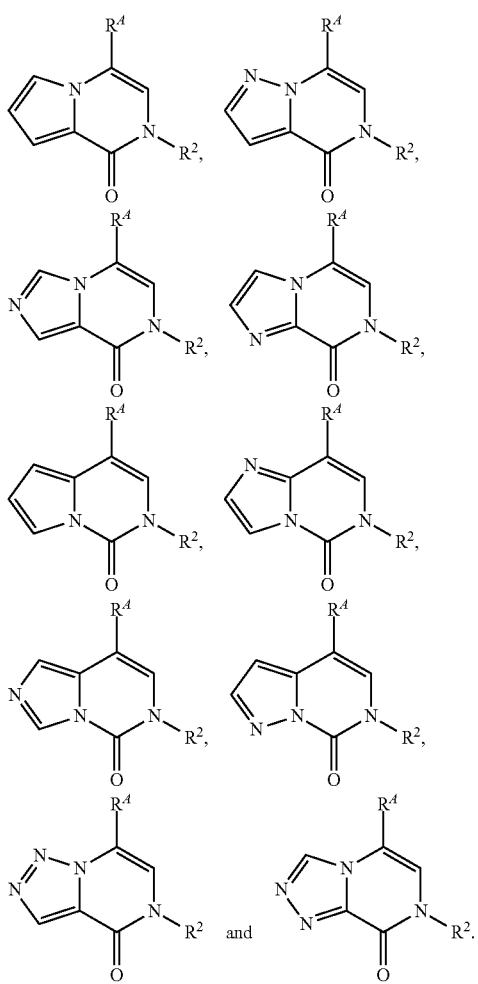

Another embodiment provides a compound of Formula (IX), wherein Q is N and T is C. Another embodiment provides a compound of Formula (IX), wherein Q is C and T is N. Another embodiment provides a compound of Formula (IX), wherein $R^2$ is $CH_3$. Another embodiment provides a compound of Formula (IX), wherein X1 is C—H. Another embodiment provides a compound of Formula (IX), wherein X1 is N.

Another embodiment provides a compound of Formula (IX), wherein Y is a bond. Another embodiment provides a compound of Formula (IX), wherein Y is a —$CH_2$—. Another embodiment provides a compound of Formula (IX), wherein Z is —$SO_2R^{21}$. Another embodiment provides a compound of Formula (IX), wherein Z is —$N(R^{22})SO_2R^{21}$. Another embodiment provides a compound of Formula (IX), wherein Z is —$SO_2N(R^{22})_2$. Another embodiment provides a compound of Formula (IX), wherein Z is —$N(R^{22})SO_2N(R^{22})_2$. Another embodiment provides a compound of Formula (IX), wherein Z is —$CON(R^{22})_2$. Another embodiment provides a compound of Formula (IX), wherein Z is —$N(R^{22})CO_2R^{21}$. Another embodiment provides a compound of Formula (IX), wherein Z is —$N(R^{22})CON(R^{22})_2$. Another embodiment provides a compound of Formula (IX), wherein $R^{21}$ is alkyl, cycloalkyl, or cycloalkylalkyl. Another embodiment provides a compound of Formula (IX), wherein $R^{21}$ is alkyl.

Another embodiment provides a compound of Formula (IX), wherein $R^{14}$ is hydrogen, halogen, or alkyl. Another embodiment provides a compound of Formula (IX), wherein X4 is C—$R^{15}$. Another embodiment provides a compound of Formula (IX), wherein W is —O—. Another embodiment provides a compound of Formula (IX), wherein W is —NH—. Another embodiment provides a compound of Formula (IX), wherein X is alkyl. Another embodiment provides a compound of Formula (IX), wherein X is aryl. Another embodiment provides a compound of Formula (IX), wherein X is cycloalkylalkyl. Another embodiment provides a compound of Formula (IX), wherein W is —O— and X is alkyl. Another embodiment provides a compound of Formula (IX), wherein W is —O— and X is aryl. Another embodiment provides a compound of Formula (IX), wherein W is —O— and X is cycloalkylalkyl.

One embodiment provides a compound of Formula (XII), or a pharmaceutically acceptable salt thereof, Formula (XII)

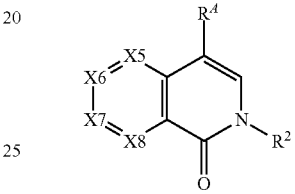

wherein,
$R^2$ is selected from $CH_3$, $CH_2CH_3$, $CH_2CF_3$, $CH_2F$, $CHF_2$, $CF_3$, $CH_2D$, $CHD_2$, or $CD_3$;
X5 is C—$R^5$ or N;
X6 is C—$R^6$ or N;
X7 is C—$R^7$ or N;
X8 is C—$R^8$ or N; wherein no more than two of X5, X6, X7, or X8 may be N;
$R^5$ is hydrogen, halogen, —OH, —CN, —$OR^{61}$, —$NHR^{61}$, —$N(R^{61})_2$, alkyl, cycloalkyl, cycloalkylalkyl, aryl, aralkyl, heterocyclyl, heterocyclylalkyl, heteroaryl, or heteroarylalkyl, wherein each $R^{61}$ is independently selected from alkyl, cycloalkyl, cycloalkylalkyl, aryl, aralkyl, heterocyclyl, heterocyclylalkyl, heteroaryl, or heteroarylalkyl;
$R^6$ is hydrogen, halogen, —OH, —CN, —$OR^{61}$, —$NHR^{61}$, —$N(R^{61})_2$, alkyl, cycloalkyl, cycloalkylalkyl, aryl, aralkyl, heterocyclyl, heterocyclylalkyl, heteroaryl, or heteroarylalkyl, wherein each $R^{61}$ is independently selected from alkyl, cycloalkyl, cycloalkylalkyl, aryl, aralkyl, heterocyclyl, heterocyclylalkyl, heteroaryl, or heteroarylalkyl;
$R^7$ is hydrogen, halogen, —OH, —CN, —$OR^{61}$, —$NHR^{61}$, —$N(R^{61})_2$, alkyl, cycloalkyl, cycloalkylalkyl, aryl, aralkyl, heterocyclyl, heterocyclylalkyl, heteroaryl, or heteroarylalkyl, wherein each $R^{61}$ is independently selected from alkyl, cycloalkyl, cycloalkylalkyl, aryl, aralkyl, heterocyclyl, heterocyclylalkyl, heteroaryl, or heteroarylalkyl;
$R^8$ is hydrogen, halogen, or alkyl;
$R^A$ is

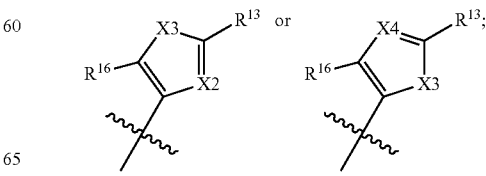

X2 is N or C—$R^{12}$, wherein $R^{12}$ is hydrogen, halogen, alkyl, or alkoxy;

$R^{13}$ is —Y—Z;

Y is selected from a bond, —$CH_2$—, or —CH($C_1$-$C_4$ alkyl)-;

Z is selected from —$SO_2R^{21}$, —$N(R^{22})SO_2R^{21}$, —$SO_2N(R^{22})_2$, —$N(R^{22})SO_2N(R^{22})_2$, —$CON(R^{22})_2$, —$N(R^{22})CO_2R^{21}$, —$N(R^{22})CON(R^{22})_2$, —$N(R^{22})COR^{21}$, —OC(O)N($R^{22})_2$, —$OSO_2N(R^{22})_2$, or —$N(R^{22})SO_3R^{21}$;

X3 is S;

X4 is N or C—$R^{14}$, wherein $R^{14}$ is hydrogen, halogen, alkyl, or alkoxy;

$R^{16}$ is hydrogen, halogen, or —W—X, wherein W is a bond, —O—, —S—, or —NH—, and X is selected from alkyl, alkynyl, aryl, aralkyl, cycloalkyl, cycloalkylalkyl, cycloalkylalkynyl, heterocyclyl, heterocyclylalkyl, heteroaryl, or heteroarylalkyl;

each $R^{21}$ is independently selected from alkyl, cycloalkyl, cycloalkylalkyl, aryl, aralkyl, heterocyclyl, heterocyclylalkyl, heteroaryl, or heteroarylalkyl; and each $R^{22}$ is independently selected from hydrogen, alkyl, cycloalkyl, cycloalkylalkyl, aryl, aralkyl, heterocyclyl, heterocyclylalkyl, heteroaryl, or heteroarylalkyl.

Another embodiment provides a compound of Formula (XII), wherein $R^2$ is $CH_3$. Another embodiment provides a compound of Formula (XII), wherein $R^2$ is $CD_3$. Another embodiment provides a compound of Formula (XII), wherein X5 is N. Another embodiment provides a compound of Formula (XII), wherein X6 is N. Another embodiment provides a compound of Formula (XII), wherein X7 is N. Another embodiment provides a compound of Formula (XII), wherein X8 is N. Another embodiment provides a compound of Formula (XII), wherein none of X5, X6, X7, or X8 is N. Another embodiment provides a compound of Formula (XII), wherein $R^5$ and $R^8$ are hydrogen. Another embodiment provides a compound of Formula (XII), wherein $R^5$, $R^6$, $R^7$ and $R^8$ are hydrogen. Another embodiment provides a compound of Formula (XII), wherein $R^7$ is a halogen. Another embodiment provides a compound of Formula (XII), wherein $R^6$ is a halogen. Another embodiment provides a compound of Formula (XII), wherein $R^6$ is a heteroaryl. Another embodiment provides a compound of Formula (XII), wherein $R^6$ is an aryl. Another embodiment provides a compound of Formula (XII), wherein $R^6$ is an alkyl. Another embodiment provides a compound of Formula (XII), wherein $R^6$ is an aryl.

Another embodiment provides a compound of Formula (XII), wherein Y is a bond. Another embodiment provides a compound of Formula (XII), wherein Y is a —$CH_2$—. Another embodiment provides a compound of Formula (XII), wherein Z is —$SO_2R^{21}$. Another embodiment provides a compound of Formula (XII), wherein Z is —$N(R^{22})SO_2R^{21}$. Another embodiment provides a compound of Formula (XII), wherein Z is —$SO_2N(R^{22})_2$. Another embodiment provides a compound of Formula (XII), wherein Z is —$N(R^{22})SO_2N(R^{22})_2$. Another embodiment provides a compound of Formula (XII), wherein Z is —$CON(R^{22})_2$. Another embodiment provides a compound of Formula (XII), wherein Z is —$N(R^{22})CO_2R^{21}$. Another embodiment provides a compound of Formula (XII), wherein Z is —$N(R^{22})CON(R^{22})_2$. Another embodiment provides a compound of Formula (XII), wherein $R^{21}$ is alkyl, cycloalkyl, or cycloalkylalkyl. Another embodiment provides a compound of Formula (XII), wherein $R^{21}$ is alkyl. Another embodiment provides a compound of Formula (XII), wherein W is —O—. Another embodiment provides a compound of Formula (XII), wherein W is —NH—. Another embodiment provides a compound of Formula (XII), wherein X is alkyl. Another embodiment provides a compound of Formula (XII), wherein X is aryl. Another embodiment provides a compound of Formula (XII), wherein X is cycloalkylalkyl. Another embodiment provides a compound of Formula (XII), wherein W is —O— and X is alkyl. Another embodiment provides a compound of Formula (XII), wherein W is —O— and X is aryl. Another embodiment provides a compound of Formula (XII), wherein W is —O— and X is cycloalkylalkyl. Another embodiment provides a compound of Formula (XII), wherein $R^5$ and $R^8$ are hydrogen. Another embodiment provides a compound of Formula (XII), wherein $R^5$ and $R^8$ are hydrogen, and $R^6$ is heteroaryl.

Another embodiment provides a compound of Formula (XII), wherein $R^A$ is

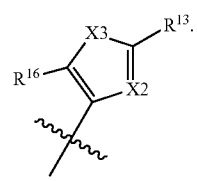

Another embodiment provides a compound of Formula (XII), wherein $R^A$ is

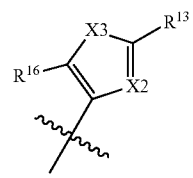

and X2 is N.

Another embodiment provides a compound of Formula (XII), wherein $R^A$ is

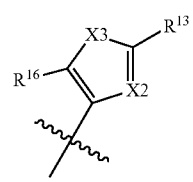

and X2 is C—$R^{12}$.

Another embodiment provides a compound of Formula (XII), wherein $R^A$ is

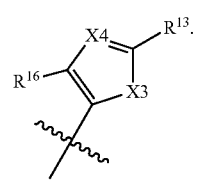

Another embodiment provides a compound of Formula (XII), wherein $R^A$ is

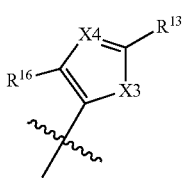

and X4 is N.

Another embodiment provides a compound of Formula (XII), wherein $R^A$ is

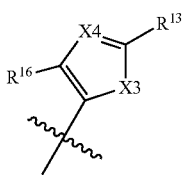

X4 is C—$R^{14}$.

One embodiment provides a compound of Formula (XIII), or a pharmaceutically acceptable salt thereof, Formula (XIII)

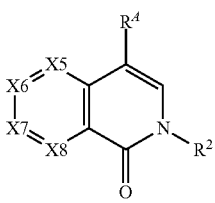

wherein, $R^2$ is selected from $CH_3$, $CH_2CH_3$, $CH_2CF_3$, $CH_2F$, $CHF_2$, $CF_3$, $CH_2D$, $CHD_2$, or $CD_3$;

X5 is C—$R^5$ or N;

X6 is C—$R^6$ or N;

X7 is C—$R^7$ or N;

X8 is C—$R^8$ or N; wherein no more than two of X5, X6, X7, or X8 may be N;

$R^5$ is hydrogen, halogen, —OH, —CN, —$OR^{61}$, —$NHR^{61}$, —$N(R^{61})_2$, alkyl, cycloalkyl, cycloalkylalkyl, aryl, aralkyl, heterocyclyl, heterocyclylalkyl, heteroaryl, or heteroarylalkyl, wherein each $R^{61}$ is independently selected from alkyl, cycloalkyl, cycloalkylalkyl, aryl, aralkyl, heterocyclyl, heterocyclylalkyl, heteroaryl, or heteroarylalkyl;

$R^6$ is hydrogen, halogen, —OH, —CN, —$OR^{61}$, —$NHR^{61}$, —$N(R^{61})_2$, alkyl, cycloalkyl, cycloalkylalkyl, aryl, aralkyl, heterocyclyl, heterocyclylalkyl, heteroaryl, or heteroarylalkyl, wherein each $R^{61}$ is independently selected from alkyl, cycloalkyl, cycloalkylalkyl, aryl, aralkyl, heterocyclyl, heterocyclylalkyl, heteroaryl, or heteroarylalkyl;

$R^7$ is hydrogen, halogen, —OH, —CN, —$OR^{61}$, —$NHR^{61}$, —$N(R^{61})_2$, alkyl, cycloalkyl, cycloalkylalkyl, aryl, aralkyl, heterocyclyl, heterocyclylalkyl, heteroaryl, or heteroarylalkyl, wherein each $R^{61}$ is independently selected from alkyl, cycloalkyl, cycloalkylalkyl, aryl, aralkyl, heterocyclyl, heterocyclylalkyl, heteroaryl, or heteroarylalkyl;

$R^8$ is hydrogen, halogen, or alkyl;

$R^A$ is

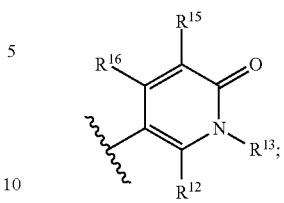

$R^{12}$ is hydrogen or $C_1$-$C_4$ alkyl;

$R^{13}$ is —Y—Z;

Y is selected from —$CH_2$—, or —$CH(C_1$-$C_4$ alkyl)-;

Z is selected from —$SO_2R^{21}$, —$SO_2N(R^{22})_2$, or —$CON(R^{22})_2$;

$R^{15}$ is hydrogen, halogen or $C_1$-$C_4$ alkyl;

$R^{16}$ is hydrogen, halogen, or —W—X, wherein W is a bond, —O—, —S—, or —NH—, and X is selected from alkyl, alkynyl, aryl, aralkyl, cycloalkyl, cycloalkylalkyl, cycloalkylalkynyl, heterocyclyl, heterocyclylalkyl, heteroaryl, or heteroarylalkyl; or optionally, $R^{16}$ and $R^{15}$ connect to form a ring;

each $R^{21}$ is independently selected from alkyl, cycloalkyl, cycloalkylalkyl, aryl, aralkyl, heterocyclyl, heterocyclylalkyl, heteroaryl, or heteroarylalkyl; and each $R^{22}$ is independently selected from hydrogen, alkyl, cycloalkyl, cycloalkylalkyl, aryl, aralkyl, heterocyclyl, heterocyclylalkyl, heteroaryl, or heteroarylalkyl.

Another embodiment provides a compound of Formula (XIII), wherein $R^2$ is $CH_3$. Another embodiment provides a compound of Formula (XIII), wherein $R^2$ is $CD_3$. Another embodiment provides a compound of Formula (XIII), wherein X5 is N. Another embodiment provides a compound of Formula (XIII), wherein X6 is N. Another embodiment provides a compound of Formula (XIII), wherein X7 is N. Another embodiment provides a compound of Formula (XIII), wherein X8 is N. Another embodiment provides a compound of Formula (XIII), wherein none of X5, X6, X7, or X8 is N. Another embodiment provides a compound of Formula (XIII), wherein $R^5$ and $R^8$ are hydrogen. Another embodiment provides a compound of Formula (XIII), wherein $R^5$, $R^6$, $R^7$ and $R^8$ are hydrogen. Another embodiment provides a compound of Formula (XIII), wherein $R^7$ is a halogen. Another embodiment provides a compound of Formula (XIII), wherein $R^6$ is a halogen. Another embodiment provides a compound of Formula (XIII), wherein $R^6$ is a heteroaryl. Another embodiment provides a compound of Formula (XIII), wherein $R^6$ is an aryl. Another embodiment provides a compound of Formula (XIII), wherein $R^6$ is an alkyl. Another embodiment provides a compound of Formula (XIII), wherein $R^6$ is an aryl.

Another embodiment provides a compound of Formula (XIII), wherein Y is a —$CH_2$—. Another embodiment provides a compound of Formula (XIII), wherein Z is —$SO_2R^{21}$. Another embodiment provides a compound of Formula (XIII), wherein Z is —$SO_2N(R^{22})_2$. Another embodiment provides a compound of Formula (XIII), wherein Z is —$CON(R^{22})_2$. Another embodiment provides a compound of Formula (XIII), wherein $R^{21}$ is alkyl, cycloalkyl, or cycloalkylalkyl. Another embodiment provides a compound of Formula (XIII), wherein $R^{21}$ is alkyl. Another embodiment provides a compound of Formula (XIII), wherein W is —O—. Another embodiment provides a compound of Formula (XIII), wherein W is —NH—. Another embodiment provides a compound of Formula (XIII), wherein X is alkyl. Another embodiment provides a compound of Formula (XIII), wherein X is aryl. Another embodiment provides a compound of Formula (XIII), wherein X is cycloalkylalkyl. Another embodiment provides a compound of Formula (XIII), wherein W is —O— and X is alkyl. Another embodiment provides a compound of Formula (XIII), wherein W is —O— and X is aryl. Another embodiment provides a compound of Formula (XIII), wherein W is —O— and X is cycloalkylalkyl. Another embodiment provides a compound of Formula (XIII), wherein $R^5$ and $R^8$ are hydrogen. Another embodiment provides a compound of Formula (XIII), wherein $R^5$ and $R^8$ are hydrogen, and $R^6$ is heteroaryl.

One embodiment provides a compound of Formula (XIV), or a pharmaceutically acceptable salt thereof,

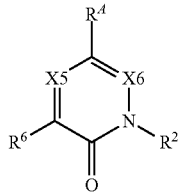

Formula (XIV)

wherein,
$R^2$ is $CH_3$, $CH_2CH_3$, $CH_2CF_3$, $CH_2F$, $CHF_2$, $CF_3$, $CH_2D$, $CHD_2$, or $CD_3$;
X6 is C—H or N;
X5 is C—$R^5$ or N; provided that if X6 is N, then X5 is C—$R^5$, and if X5 is N, then X6 is CH;
$R^5$ is hydrogen, halogen, —OH, —CN, —$OR^{61}$, —$NHR^{61}$, —$N(R^{61})_2$, alkyl, cycloalkyl, cycloalkylalkyl, aryl, aralkyl, heterocyclyl, heterocyclylalkyl, heteroaryl, or heteroarylalkyl, wherein each $R^{61}$ is independently selected from alkyl, cycloalkyl, cycloalkylalkyl, aryl, aralkyl, heterocyclyl, heterocyclylalkyl, heteroaryl, or heteroarylalkyl;
$R^6$ is hydrogen, halogen, —OH, —CN, alkyl, alkynyl, cycloalkyl, cycloalkylalkyl, cycloalkylalkynyl, amino, alkylamino, dialkylamino, heterocyclyl, cycloalkylalkylamino, alkoxy, cycloalkyloxy, cycloalkylalkoxy, alkyl-S—, cycloalkyl-S—, and cycloalkylalkyl-S—;
$R^A$ is

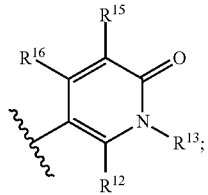

$R^{12}$ is hydrogen or $C_1$-$C_4$ alkyl;
$R^{13}$ is —Y—Z;
Y is selected from —$CH_2$—, or —CH($C_1$-$C_4$ alkyl)—;
Z is selected from —$SO_2R^{21}$, —$SO_2N(R^{22})_2$, or —CON$(R^{22})_2$;
$R^{15}$ is hydrogen, halogen or $C_1$-$C_4$ alkyl;
$R^{16}$ is hydrogen, halogen, or —W—X, wherein W is a bond, —O—, —S—, or —NH—, and X is selected from alkyl, alkynyl, aryl, aralkyl, cycloalkyl, cycloalkylalkyl, cycloalkylalkynyl, heterocyclyl, heterocyclylalkyl, heteroaryl, or heteroarylalkyl; or optionally, $R^{16}$ and $R^{15}$ connect to form a ring;

each $R^{21}$ is independently selected from alkyl, cycloalkyl, cycloalkylalkyl, aryl, aralkyl, heterocyclyl, heterocyclylalkyl, heteroaryl, or heteroarylalkyl; and
each $R^{22}$ is independently selected from hydrogen, alkyl, cycloalkyl, cycloalkylalkyl, aryl, aralkyl, heterocyclyl, heterocyclylalkyl, heteroaryl, or heteroarylalkyl.

Another embodiment provides a compound of Formula (XIV), wherein $R^2$ is $CH_3$. Another embodiment provides a compound of Formula (XIV), wherein X6 is C—H. Another embodiment provides a compound of Formula (XIV), wherein X6 is N. Another embodiment provides a compound of Formula (XIV), wherein X5 is C—$R^5$. Another embodiment provides a compound of Formula (XIV), wherein X5 is N. Another embodiment provides a compound of Formula (XIV), wherein $R^5$ is hydrogen, halogen, or alkyl. Another embodiment provides a compound of Formula (XIV), wherein $R^6$ is hydrogen, halogen, or alkyl. Another embodiment provides a compound of Formula (XIV), wherein $R^6$ is heterocyclyl. Another embodiment provides a compound of Formula (XIV), wherein $R^6$ is cycloalkylalkynyl. Another embodiment provides a compound of Formula (XIV), wherein $R^6$ is alkoxy, cycloalkyloxy, or cycloalkylalkoxy.

Another embodiment provides a compound of Formula (XIV), wherein Y is a —$CH_2$—. Another embodiment provides a compound of Formula (XIV), wherein Z is —$SO_2R^{21}$. Another embodiment provides a compound of Formula (XIV), wherein Z is —$SO_2N(R^{22})_2$. Another embodiment provides a compound of Formula (XIV), wherein Z is —CON$(R^{22})_2$. Another embodiment provides a compound of Formula (XIV), wherein $R^{21}$ is alkyl, cycloalkyl, or cycloalkylalkyl. Another embodiment provides a compound of Formula (XIV), wherein $R^{21}$ is alkyl. Another embodiment provides a compound of Formula (XIV), wherein W is —O—. Another embodiment provides a compound of Formula (XIV), wherein W is —NH—. Another embodiment provides a compound of Formula (XIV), wherein X is alkyl. Another embodiment provides a compound of Formula (XIV), wherein X is alkynyl. Another embodiment provides a compound of Formula (XIV), wherein X is aryl. Another embodiment provides a compound of Formula (XIV), wherein X is cycloalkylalkyl. Another embodiment provides a compound of Formula (XIV), wherein X is cycloalkylalkynyl. Another embodiment provides a compound of Formula (XIV), wherein W is —O— and X is alkyl. Another embodiment provides a compound of Formula (XIV), wherein W is —O— and X is alkynyl. Another embodiment provides a compound of Formula (XIV), wherein W is —O— and X is aryl. Another embodiment provides a compound of Formula (XIV), wherein W is —O— and X is cycloalkylalkyl. Another embodiment provides a compound of Formula (XIV), wherein W is —O— and X is cycloalkylalkynyl. Another embodiment provides a compound of Formula (XIV), wherein the $R^6$ is $CD_3$.

One embodiment provides a compound of Formula (XV), or a pharmaceutically acceptable salt thereof,

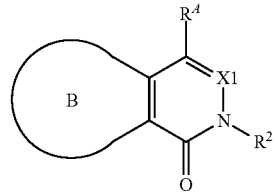

Formula (XV)

wherein,

Ring B is an optionally substituted 5-membered heteroaryl ring containing at least one oxygen or sulfur atom;

$R^2$ is selected from $CH_3$, $CH_2CH_3$, $CH_2CF_3$, $CH_2F$, $CHF_2$, $CF_3$, $CH_2D$, $CHD_2$, or $CD_3$;

X1 is C—H or N;

$R^A$ is

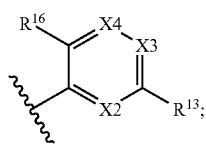

X2 is N or C—$R^{12}$, wherein $R^{12}$ is hydrogen, halogen, alkyl, or alkoxy;

$R^{13}$ is —Y—Z;

Y is selected from a bond, —$CH_2$—, or —$CH(C_1$-$C_4$ alkyl)-;

Z is selected from —$SO_2R^{21}$, —$N(R^{22})SO_2R^{21}$, —$SO_2N(R^{22})_2$, —$N(R^{22})SO_2N(R^{22})_2$, —$CON(R^{22})_2$, —$N(R^{22})CO_2R^{21}$, —$N(R^{22})CON(R^{22})_2$, —$N(R^{22})COR^{21}$, —$OC(O)N(R^{22})_2$, —$OSO_2N(R^{22})_2$, or —$N(R^{22})SO_3R^{21}$;

X3 is N or C—$R^{14}$, wherein $R^{14}$ is hydrogen, halogen, —CN, alkyl, cycloalkyl, or alkoxy; or optionally when X4 is C—$R^{15}$, $R^{14}$ and $R^{15}$ connect to form a ring;

X4 is N or C—$R^{15}$, wherein $R^{15}$ is hydrogen, halogen, —CN, alkyl, or alkoxy;

$R^{16}$ is hydrogen, halogen, or —W—X, wherein W is a bond, —O—, —S—, or —NH—, and X is selected from alkyl, alkynyl, aryl, aralkyl, cycloalkyl, cycloalkylalkyl, cycloalkylalkynyl, heterocyclyl, heterocyclylalkyl, heteroaryl, or heteroarylalkyl; or optionally when X4 is C—$R^{15}$, $R^{16}$ and $R^{15}$ connect to form a ring;

each $R^{21}$ is independently selected from alkyl, cycloalkyl, cycloalkylalkyl, aryl, aralkyl, heterocyclyl, heterocyclylalkyl, heteroaryl, or heteroarylalkyl; and each $R^{22}$ is independently selected from hydrogen, alkyl, cycloalkyl, cycloalkylalkyl, aryl, aralkyl, heterocyclyl, heterocyclylalkyl, heteroaryl, or heteroarylalkyl.

Another embodiment provides a compound of Formula (XV), wherein X2 is N. Another embodiment provides a compound of Formula (XV), wherein X3 is N. Another embodiment provides a compound of Formula (XV), wherein X4 is N. Another embodiment provides a compound of Formula (XV), wherein X2 and X3 are N. Another embodiment provides a compound of Formula (XV), wherein X2 is C—$R^{12}$, X3 is C—$R^{14}$, and X4 is C—$R^{15}$.

Another embodiment provides a compound of Formula (XV), wherein the compound of Formula (XV) has a formula selected from:

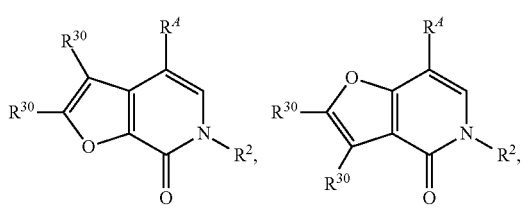

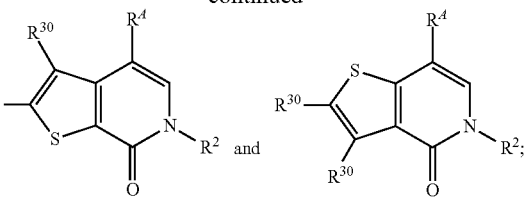

wherein each $R^{30}$ is independently selected from hydrogen, halogen, —CN, $C_1$-$C_4$ alkyl, —OH, —$OR^{31}$, —$NHR^{31}$, —$N(R^{31})_2$, —$CONHR^{31}$, —$CON(R^{31})_2$; and $R^3$ is $C_1$-$C_4$ alkyl.

Another embodiment provides a compound of Formula (XV), wherein the compound of Formula (XV) has a formula selected from:

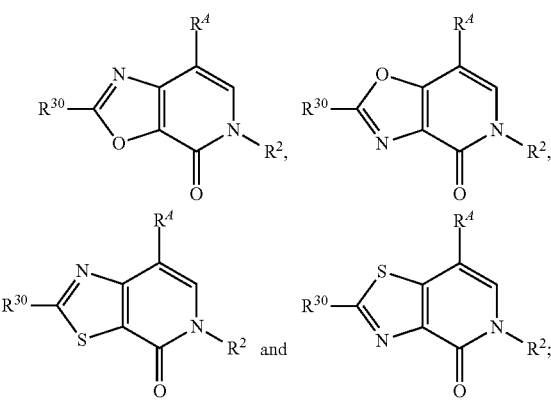

wherein each $R^{30}$ is independently selected from hydrogen, halogen, —CN, $C_1$-$C_4$ alkyl, —OH, —$OR^{31}$, —$NHR^{31}$, —$N(R^{31})_2$, —$CONHR^{31}$, —$CON(R^{31})_2$; and $R^{31}$ is $C_1$-$C_4$ alkyl.

Another embodiment provides a compound of Formula (XV), wherein the compound of Formula (XV) has a formula selected from:

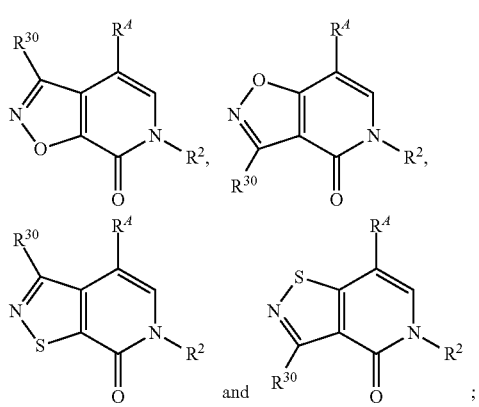

wherein each $R^{30}$ is independently selected from hydrogen, halogen, —CN, $C_1$-$C_4$ alkyl, —OH, —$OR^{31}$, —$NHR^{31}$, —$N(R^{31})_2$, —$CONHR^{31}$, —$CON(R^{31})_2$; and $R^{31}$ is $C_1$-$C_4$ alkyl.

Another embodiment provides a compound of Formula (XV), wherein $R^2$ is $CH_3$. Another embodiment provides a compound of Formula (XV), wherein X1 is C—H. Another embodiment provides a compound of Formula (XV), wherein X1 is N.

Another embodiment provides a compound of Formula (XV), wherein Y is a bond. Another embodiment provides a compound of Formula (XV), wherein Y is a —CH$_2$—. Another embodiment provides a compound of Formula (XV), wherein Z is —SO$_2$R$^{21}$. Another embodiment provides a compound of Formula (XV), wherein Z is —N(R$^{22}$)SO$_2$R$^{21}$. Another embodiment provides a compound of Formula (XV), wherein Z is —SO$_2$N(R$^{22}$)$_2$. Another embodiment provides a compound of Formula (XV), wherein Z is —N(R$^{22}$)SO$_2$N(R$^{22}$)$_2$. Another embodiment provides a compound of Formula (XV), wherein Z is —CON(R$^{22}$)$_2$. Another embodiment provides a compound of Formula (XV), wherein Z is —N(R$^{22}$)CO$_2$R$^{21}$. Another embodiment provides a compound of Formula (XV), wherein Z is —N(R$^{22}$)CON(R$^{22}$)$_2$. Another embodiment provides a compound of Formula (XV), wherein R$^{21}$ is alkyl, cycloalkyl, or cycloalkylalkyl. Another embodiment provides a compound of Formula (XV), wherein R$^{21}$ is alkyl.

Another embodiment provides a compound of Formula (XV), wherein X3 is C—R$^{14}$. Another embodiment provides a compound of Formula (XV), wherein R$^{14}$ is hydrogen, halogen, or alkyl. Another embodiment provides a compound of Formula (XV), wherein X4 is C—R$^5$. Another embodiment provides a compound of Formula (XV), wherein W is —O—. Another embodiment provides a compound of Formula (XV), wherein W is —NH—. Another embodiment provides a compound of Formula (XV), wherein X is alkyl. Another embodiment provides a compound of Formula (XV), wherein X is alkynyl. Another embodiment provides a compound of Formula (XV), wherein X is aryl. Another embodiment provides a compound of Formula (XV), wherein X is cycloalkylalkyl. Another embodiment provides a compound of Formula (XV), wherein X is cycloalkylalkynyl. Another embodiment provides a compound of Formula (XV), wherein W is —O— and X is alkyl. Another embodiment provides a compound of Formula (XV), wherein W is —O— and X is aryl. Another embodiment provides a compound of Formula (XV), wherein W is —O— and X is alkynyl. Another embodiment provides a compound of Formula (XV), wherein W is —O— and X is cycloalkylalkyl. Another embodiment provides a compound of Formula (XV), wherein W is —O— and X is cycloalkylalkynyl.

Another embodiment provides a compound of Formula (XVI), or a pharmaceutically acceptable salt thereof, Formula (XVI)

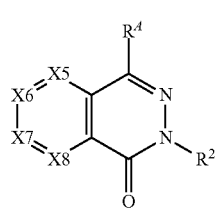

wherein,
R$^2$ is selected from CH$_3$, CH$_2$CH$_3$, CH$_2$CF$_3$, CH$_2$F, CHF$_2$, CF$_3$, CH$_2$D, CHD$_2$, or CD$_3$;
X5 is C—R$^5$ or N;
X6 is C—R$^6$ or N;
X7 is C—R$^7$ or N;
X8 is C—R$^8$ or N; wherein no more than two of X5, X6, X7, or X8 may be N;
R$^5$ is hydrogen, halogen, —OH, —CN, —OR$^{61}$, —NHR$^{61}$, —N(R$^{61}$)$_2$, alkyl, cycloalkyl, cycloalkylalkyl, aryl, aralkyl, heterocyclyl, heterocyclylalkyl, heteroaryl, or heteroarylalkyl, wherein each R$^{61}$ is independently selected from alkyl, cycloalkyl, cycloalkylalkyl, aryl, aralkyl, heterocyclyl, heterocyclylalkyl, heteroaryl, or heteroarylalkyl;
R$^6$ is hydrogen, halogen, —OH, —CN, —OR$^{61}$, —NHR$^{61}$, —N(R$^{61}$)$_2$, alkyl, cycloalkyl, cycloalkylalkyl, aryl, aralkyl, heterocyclyl, heterocyclylalkyl, heteroaryl, or heteroarylalkyl, wherein each R$^{61}$ is independently selected from alkyl, cycloalkyl, cycloalkylalkyl, aryl, aralkyl, heterocyclyl, heterocyclylalkyl, heteroaryl, or heteroarylalkyl;
R$^7$ is hydrogen, halogen, —OH, —CN, —OR$^{61}$, —NHR$^{61}$, —N(R$^{61}$)$_2$, alkyl, cycloalkyl, cycloalkylalkyl, aryl, aralkyl, heterocyclyl, heterocyclylalkyl, heteroaryl, or heteroarylalkyl, wherein each R$^{61}$ is independently selected from alkyl, cycloalkyl, cycloalkylalkyl, aryl, aralkyl, heterocyclyl, heterocyclylalkyl, heteroaryl, or heteroarylalkyl;
R$^8$ is hydrogen, halogen, or alkyl;
R$^A$ is

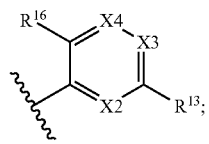

X2 is N or C—R$^{12}$, wherein R$^{12}$ is hydrogen, halogen, alkyl, or alkoxy;
R$^{13}$ is —Y—Z;
Y is selected from a bond, —CH$_2$—, or —CH(C$_1$-C$_4$ alkyl)-;
Z is selected from —SO$_2$R$^{21}$, —N(R$^{22}$)SO$_2$R$^{21}$, —SO$_2$N(R$^{22}$)$_2$, —N(R$^{22}$)SO$_2$N(R$^{22}$)$_2$, —CON(R$^{22}$)$_2$, —N(R$^{22}$)CO$_2$R$^{21}$, —N(R$^{22}$)CON(R$^{22}$)$_2$, —N(R$^{22}$)COR$^{21}$, —OC(O)N(R$^{22}$)$_2$, —OSO$_2$N(R$^{22}$)$_2$, or —N(R$^{22}$)SO$_3$R$^{21}$;
X3 is N or C—R$^{14}$, wherein R$^{14}$ is hydrogen, halogen, —CN, alkyl, cycloalkyl, or alkoxy; or optionally when X4 is C—R$^{15}$, R$^{14}$ and R$^{15}$ connect to form a ring;
X4 is N or C—R$^{15}$, wherein R$^{15}$ is hydrogen, halogen, —CN, alkyl, or alkoxy;
R$^{16}$ is hydrogen, halogen, or —W—X, wherein W is a bond, —O—, —S—, or —NH—, and X is selected from alkyl, alkynyl, aryl, aralkyl, cycloalkyl, cycloalkylalkyl, cycloalkylalkynyl, heterocyclyl, heterocyclylalkyl, heteroaryl, or heteroarylalkyl; or optionally when X4 is C—R$^{15}$, R$^{16}$ and R$^{15}$ connect to form a ring;
each R$^{21}$ is independently selected from alkyl, cycloalkyl, cycloalkylalkyl, aryl, aralkyl, heterocyclyl, heterocyclylalkyl, heteroaryl, or heteroarylalkyl; and
each R$^{22}$ is independently selected from hydrogen, alkyl, cycloalkyl, cycloalkylalkyl, aryl, aralkyl, heterocyclyl, heterocyclylalkyl, heteroaryl, or heteroarylalkyl.

Another embodiment provides a compound of Formula (XVI), wherein X2 is N. Another embodiment provides a compound of Formula (XVI), wherein X3 is N. Another embodiment provides a compound of Formula (XVI), wherein X4 is N. Another embodiment provides a compound of Formula (XVI), wherein X2 and X3 are N. Another embodiment provides a compound of Formula (XVI), wherein X2 is C—R$^{12}$, X3 is C—R$^{14}$, and X4 is C—R$^{15}$.

Another embodiment provides a compound of Formula (XVI), wherein R$^2$ is CH$_3$. Another embodiment provides a compound of Formula (XVI), wherein R$^2$ is CD$_3$. Another embodiment provides a compound of Formula (XVI), wherein X5 is N. Another embodiment provides a compound of Formula (XVI), wherein X6 is N. Another embodiment provides a compound of Formula (XVI), wherein X7 is N. Another embodiment provides a compound of Formula (XVI), wherein X8 is N. Another embodiment provides a compound of Formula (XVI), wherein none of X5, X6, X7, or X8 is N. Another embodiment provides a compound of Formula (XVI), wherein $R^5$ and $R^8$ are hydrogen. Another embodiment provides a compound of Formula (XVI), wherein $R^5$, $R^6$, $R^7$ and $R^8$ are hydrogen. Another embodiment provides a compound of Formula (XVI), wherein $R^7$ is a halogen. Another embodiment provides a compound of Formula (XVI), wherein $R^6$ is a halogen. Another embodiment provides a compound of Formula (XVI), wherein $R^6$ is a heteroaryl. Another embodiment provides a compound of Formula (XVI), wherein $R^6$ is an aryl. Another embodiment provides a compound of Formula (XVI), wherein $R^6$ is an alkyl. Another embodiment provides a compound of Formula (XVI), wherein $R^6$ is an aryl.

Another embodiment provides a compound of Formula (XVI), wherein Y is a bond. Another embodiment provides a compound of Formula (XVI), wherein Y is a —$CH_2$—. Another embodiment provides a compound of Formula (XVI), wherein Z is —$SO_2R^{21}$. Another embodiment provides a compound of Formula (XVI), wherein Z is —$N(R^{22})SO_2R^{21}$. Another embodiment provides a compound of Formula (XVI), wherein Z is —$SO_2N(R^{22})_2$. Another embodiment provides a compound of Formula (XVI), wherein Z is —$N(R^{22})SO_2N(R^{22})_2$. Another embodiment provides a compound of Formula (XVI), wherein Z is —$CON(R^{22})_2$. Another embodiment provides a compound of Formula (XVI), wherein Z is —$N(R^{22})CO_2R^{21}$. Another embodiment provides a compound of Formula (XVI), wherein Z is —$N(R^{22})CON(R^{22})_2$. Another embodiment provides a compound of Formula (XVI), wherein $R^{21}$ is alkyl, cycloalkyl, or cycloalkylalkyl. Another embodiment provides a compound of Formula (XVI), wherein $R^{21}$ is alkyl. Another embodiment provides a compound of Formula (XVI), wherein $R^{14}$ is hydrogen, halogen, or alkyl. Another embodiment provides a compound of Formula (XVI), wherein X4 is C—$R^{15}$. Another embodiment provides a compound of Formula (XVI), wherein W is —O—. Another embodiment provides a compound of Formula (XVI), wherein W is —NH—. Another embodiment provides a compound of Formula (XVI), wherein X is alkyl. Another embodiment provides a compound of Formula (XVI), wherein X is aryl. Another embodiment provides a compound of Formula (XVI), wherein X is cycloalkylalkyl. Another embodiment provides a compound of Formula (XVI), wherein W is —O— and X is alkyl. Another embodiment provides a compound of Formula (XVI), wherein W is —O— and X is aryl. Another embodiment provides a compound of Formula (XVI), wherein W is —O— and X is cycloalkylalkyl. Another embodiment provides a compound of Formula (XVI), wherein $R^5$ and $R^8$ are hydrogen. Another embodiment provides a compound of Formula (XVI), wherein $R^5$ and $R^8$ are hydrogen, and $R^6$ is heteroaryl.

One embodiment provides a compound of Formula (XVII), or a pharmaceutically acceptable salt thereof,

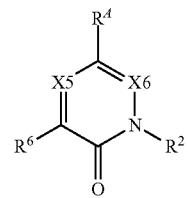

Formula (XVII)

wherein, $R^2$ is $CH_3$, $CH_2CH_3$, $CH_2CF_3$, $CH_2F$, $CHF_2$, $CF_3$, $CH_2D$, $CHD_2$, or $CD_3$;

X6 is C—H or N;

X5 is C—$R^5$ or N; provided that if X6 is N, then X5 is C—$R^5$, and if X5 is N, then X6 is CH;

$R^5$ is hydrogen, halogen, —OH, —CN, —$OR^{61}$, —$NHR^{61}$, —$N(R^{61})_2$, alkyl, cycloalkyl, cycloalkylalkyl, aryl, aralkyl, heterocyclyl, heterocyclylalkyl, heteroaryl, or heteroarylalkyl, wherein each $R^{61}$ is independently selected from alkyl, cycloalkyl, cycloalkylalkyl, aryl, aralkyl, heterocyclyl, heterocyclylalkyl, heteroaryl, or heteroarylalkyl;

$R^6$ is hydrogen, halogen, —OH, —CN, alkyl, alkynyl, cycloalkyl, cycloalkylalkyl, cycloalkylalkynyl, amino, alkylamino, dialkylamino, heterocyclyl, cycloalkylalkylamino, alkoxy, cycloalkyloxy, cycloalkylalkoxy, alkyl-S—, cycloalkyl-S—, and cycloalkylalkyl-S—;

$R^A$ is

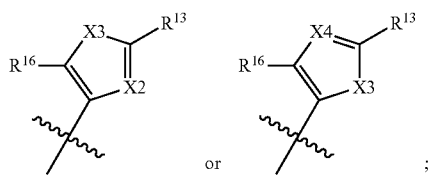

X2 is N or C—$R^{12}$, wherein $R^{12}$ is hydrogen, halogen, alkyl, or alkoxy;

$R^{13}$ is —Y—Z;

Y is selected from a bond, —$CH_2$—, or —$CH(C_1$-$C_4$ alkyl)-;

Z is selected from —$SO_2R^{21}$, —$N(R^{22})SO_2R^{21}$, —$SO_2N(R^{22})_2$, —$N(R^{22})SO_2N(R^{22})_2$, —$CON(R^{22})_2$, —$N(R^{22})CO_2R^{21}$, —$N(R^{22})CON(R^{22})_2$, —$N(R^{22})COR^{21}$, —$OC(O)N(R^{22})_2$, —$OSO_2N(R^{22})_2$, or —$N(R^{22})SO_3R^{21}$;

X3 is S;

X4 is N or C—$R^{14}$, wherein $R^{14}$ is hydrogen, halogen, alkyl, or alkoxy;

$R^{16}$ is hydrogen, halogen, or —W—X, wherein W is a bond, —O—, —S—, or —NH—, and X is selected from alkyl, alkynyl, aryl, aralkyl, cycloalkyl, cycloalkylalkyl, cycloalkylalkynyl, heterocyclyl, heterocyclylalkyl, heteroaryl, or heteroarylalkyl;

each $R^{21}$ is independently selected from alkyl, cycloalkyl, cycloalkylalkyl, aryl, aralkyl, heterocyclyl, heterocyclylalkyl, heteroaryl, or heteroarylalkyl; and each $R^{22}$ is independently selected from hydrogen, alkyl, cycloalkyl, cycloalkylalkyl, aryl, aralkyl, heterocyclyl, heterocyclylalkyl, heteroaryl, or heteroarylalkyl.

Another embodiment provides a compound of Formula (XVII), wherein $R^A$ is

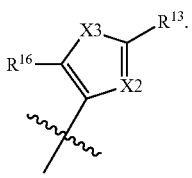

Another embodiment provides a compound of Formula (XVII), wherein $R^4$ is

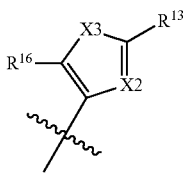

and X2 is N.

Another embodiment provides a compound of Formula (XVII), wherein $R^4$ is

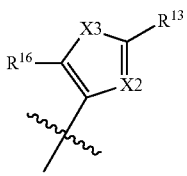

and X2 is C—$R^{12}$.

Another embodiment provides a compound of Formula (XVII), wherein $R^4$ is

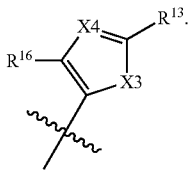

Another embodiment provides a compound of Formula (XVII), wherein $R^4$ is

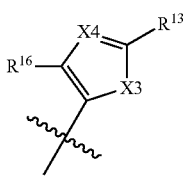

and X4 is N.

Another embodiment provides a compound of Formula (XVII), wherein $R^4$ is

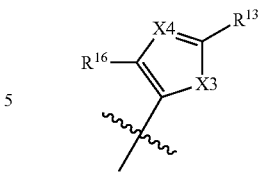

and X4 is C—$R^{14}$.

Another embodiment provides a compound of Formula (XVII), wherein $R^2$ is $CH_3$. Another embodiment provides a compound of Formula (XVII), wherein X6 is C—H. Another embodiment provides a compound of Formula (XVII), wherein X6 is N. Another embodiment provides a compound of Formula (XVII), wherein X5 is C—$R^5$. Another embodiment provides a compound of Formula (XVII), wherein X5 is N. Another embodiment provides a compound of Formula (XVII), wherein $R^5$ is hydrogen, halogen, or alkyl. Another embodiment provides a compound of Formula (XVII), wherein $R^6$ is hydrogen, halogen, or alkyl. Another embodiment provides a compound of Formula (XVII), wherein $R^6$ is heterocyclyl. Another embodiment provides a compound of Formula (XVII), wherein $R^6$ is cycloalkylalkynyl. Another embodiment provides a compound of Formula (XVII), wherein $R^6$ is alkoxy, cycloalkyloxy, or cycloalkylalkoxy.

Another embodiment provides a compound of Formula (XVII), wherein Y is a bond. Another embodiment provides a compound of Formula (XVII), wherein Y is a —$CH_2$—. Another embodiment provides a compound of Formula (XVII), wherein Z is —$SO_2R^{21}$. Another embodiment provides a compound of Formula (XVII), wherein Z is —$N(R^{22})SO_2R^{21}$. Another embodiment provides a compound of Formula (XVII), wherein Z is —$SO_2N(R^{22})_2$. Another embodiment provides a compound of Formula (XVII), wherein Z is —$N(R^{22})SO_2N(R^{22})_2$. Another embodiment provides a compound of Formula (XVII), wherein Z is —$CON(R^{22})_2$. Another embodiment provides a compound of Formula (XVII), wherein Z is —$N(R^{22})CO_2R^{21}$. Another embodiment provides a compound of Formula (XVII), wherein Z is —$N(R^{22})CON(R^{22})_2$. Another embodiment provides a compound of Formula (XVII), wherein $R^{21}$ is alkyl, cycloalkyl, or cycloalkylalkyl. Another embodiment provides a compound of Formula (XVII), wherein $R^{21}$ is alkyl. Another embodiment provides a compound of Formula (XVII), wherein W is —O—. Another embodiment provides a compound of Formula (XVII), wherein W is —NH—. Another embodiment provides a compound of Formula (XVII), wherein X is alkyl. Another embodiment provides a compound of Formula (XVII), wherein X is alkynyl. Another embodiment provides a compound of Formula (XVII), wherein X is aryl. Another embodiment provides a compound of Formula (XVII), wherein X is cycloalkylalkyl. Another embodiment provides a compound of Formula (XVII), wherein X is cycloalkylalkynyl. Another embodiment provides a compound of Formula (XVII), wherein W is —O— and X is alkyl. Another embodiment provides a compound of Formula (XVII), wherein W is —O— and X is alkynyl. Another embodiment provides a compound of Formula (XVII), wherein W is —O— and X is aryl. Another embodiment provides a compound of Formula (XVII), wherein W is —O— and X is cycloalkylalkyl. Another embodiment provides a compound of Formula (XVII), wherein W is —O— and X is cycloalkylalkynyl. Another embodiment provides a compound of Formula (XVII), wherein the $R^6$ is $CD_3$.

One embodiment provides a compound of Formula (XVIII), or a pharmaceutically acceptable salt thereof,

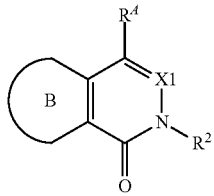

Formula (XVIII)

wherein,
$R^2$ is $CH_3$, $CH_2CH_3$, $CH_2CF_3$, $CH_2F$, $CHF_2$, $CF_3$, $CH_2D$, $CHD_2$, or $CD_3$;
X1 is C—H or N;
ring B is an optionally substituted 5- or 6-membered heterocyclic ring containing at least one oxygen or nitrogen atom;
$R^4$ is

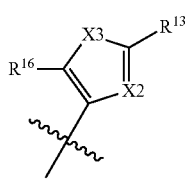 or 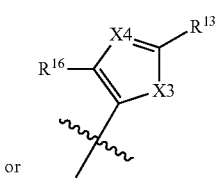 ;

X2 is N or C—$R^{12}$, wherein $R^{12}$ is hydrogen, halogen, alkyl, or alkoxy;
$R^{13}$ is —Y—Z;
Y is selected from a bond, —$CH_2$—, or —CH($C_1$-$C_4$ alkyl)-;
Z is selected from —$SO_2R^{21}$, —N($R^{22}$)$SO_2R^{21}$, —$SO_2$N($R^{22}$)$_2$, —N($R^{22}$)$SO_2$N($R^{22}$)$_2$, —CON($R^{22}$)$_2$, —N($R^{22}$)$CO_2R^{21}$, —N($R^{22}$)CON($R^{22}$)$_2$, —N($R^{22}$)COR$^{21}$, —OC(O)N($R^{22}$)$_2$, —$OSO_2$N($R^{22}$)$_2$, or —N($R^{22}$)$SO_3R^{21}$;
X3 is S;
X4 is N or C—$R^{14}$, wherein $R^{14}$ is hydrogen, halogen, alkyl, or alkoxy;
$R^{16}$ is hydrogen, halogen, or —W—X, wherein W is a bond, —O—, —S—, or —NH—, and X is selected from alkyl, alkynyl, aryl, aralkyl, cycloalkyl, cycloalkylalkyl, cycloalkylalkynyl, heterocyclyl, heterocyclylalkyl, heteroaryl, or heteroarylalkyl;
each $R^{21}$ is independently selected from alkyl, cycloalkyl, cycloalkylalkyl, aryl, aralkyl, heterocyclyl, heterocyclylalkyl, heteroaryl, or heteroarylalkyl; and
each $R^{22}$ is independently selected from hydrogen, alkyl, cycloalkyl, cycloalkylalkyl, aryl, aralkyl, heterocyclyl, heterocyclylalkyl, heteroaryl, or heteroarylalkyl.

One embodiment provides a compound of Formula (XIX), or a pharmaceutically acceptable salt thereof,

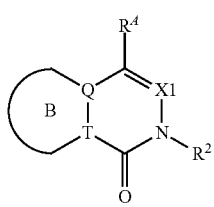

Formula (XIX)

wherein,
Q is N and T is C, or Q is C and T is N;
Ring B is an optionally substituted 5-membered aromatic nitrogen-containing heteroaryl ring containing one or more nitrogen atoms;
$R^2$ is selected from $CH_3$, $CH_2CH_3$, $CH_2CF_3$, $CH_2F$, $CHF_2$, $CF_3$, $CH_2D$, $CHD_2$, or $CD_3$;
X1 is C—H or N;
$R^4$ is

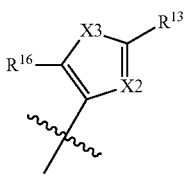 or 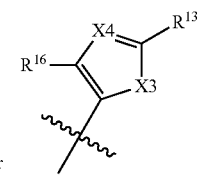 ;

X2 is N or C—$R^{12}$, wherein $R^{12}$ is hydrogen, halogen, alkyl, or alkoxy;
$R^{13}$ is —Y—Z;
Y is selected from a bond, —$CH_2$—, or —CH($C_1$-$C_4$ alkyl)-;
Z is selected from —$SO_2R^{21}$, —N($R^{22}$)$SO_2R^{21}$, —$SO_2$N($R^{22}$)$_2$, —N($R^{22}$)$SO_2$N($R^{22}$)$_2$, —CON($R^{22}$)$_2$, —N($R^{22}$)$CO_2R^{21}$, —N($R^{22}$)CON($R^{22}$)$_2$, —N($R^{22}$)COR$^{21}$, —OC(O)N($R^{22}$)$_2$, —$OSO_2$N($R^{22}$)$_2$, or —N($R^{22}$)$SO_3R^{21}$;
X3 is S;
X4 is N or C—$R^{14}$, wherein $R^{14}$ is hydrogen, halogen, alkyl, or alkoxy;
$R^{16}$ is hydrogen, halogen, or —W—X, wherein W is a bond, —O—, —S—, or —NH—, and X is selected from alkyl, alkynyl, aryl, aralkyl, cycloalkyl, cycloalkylalkyl, cycloalkylalkynyl, heterocyclyl, heterocyclylalkyl, heteroaryl, or heteroarylalkyl;
each $R^{21}$ is independently selected from alkyl, cycloalkyl, cycloalkylalkyl, aryl, aralkyl, heterocyclyl, heterocyclylalkyl, heteroaryl, or heteroarylalkyl; and
each $R^{22}$ is independently selected from hydrogen, alkyl, cycloalkyl, cycloalkylalkyl, aryl, aralkyl, heterocyclyl, heterocyclylalkyl, heteroaryl, or heteroarylalkyl.

Another embodiment provides a compound of Formula (XIX), wherein X2 is N. Another embodiment provides a compound of Formula (XIX), wherein X4 is N. Another embodiment provides a compound of Formula (XIX), wherein X2 is C—$R^{12}$. Another embodiment provides a compound of Formula (XIX), wherein X4 is C—$R^{14}$.

Another embodiment provides a compound of Formula (XIX), wherein the compound of Formula (XIX) is selected from the group:

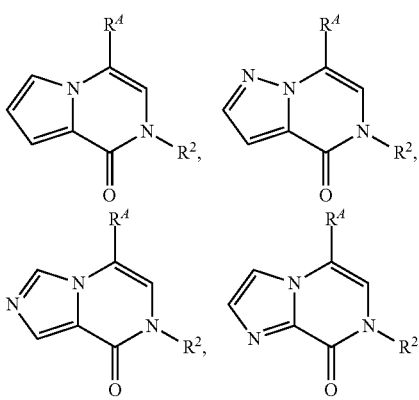

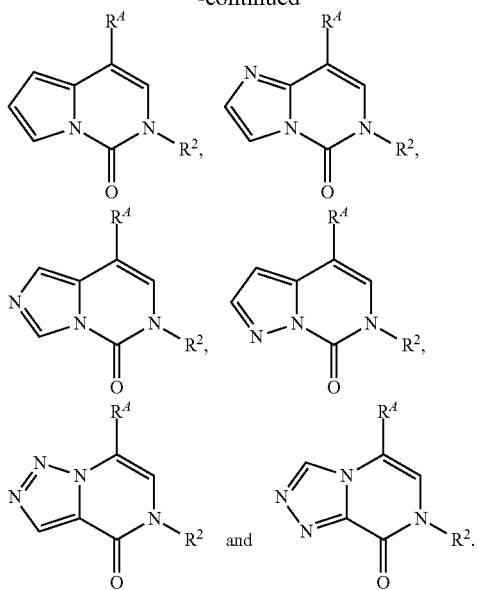

and

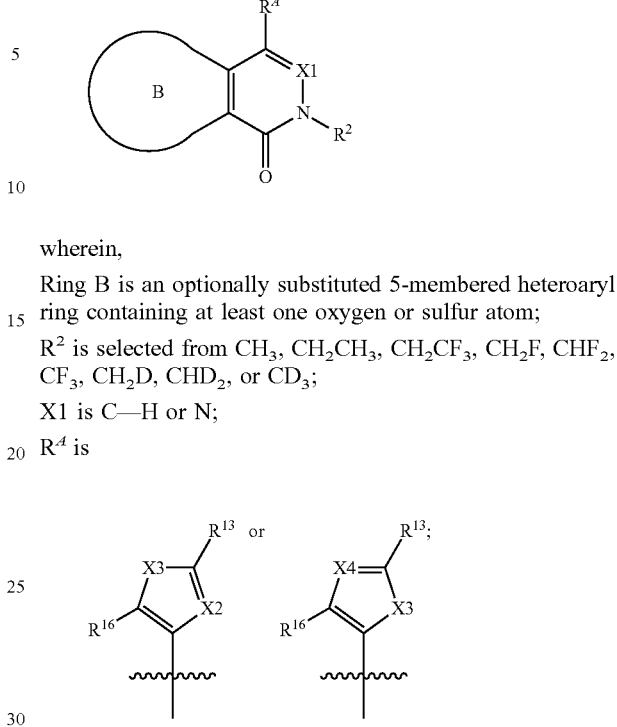

Another embodiment provides a compound of Formula (XIX), wherein Q is N and T is C. Another embodiment provides a compound of Formula (XIX), wherein Q is C and T is N. Another embodiment provides a compound of Formula (XIX), wherein $R^2$ is $CH_3$. Another embodiment provides a compound of Formula (XIX), wherein X1 is C—H. Another embodiment provides a compound of Formula (XIX), wherein X1 is N.

Another embodiment provides a compound of Formula (XIX), wherein Y is a bond. Another embodiment provides a compound of Formula (XIX), wherein Y is a —$CH_2$—. Another embodiment provides a compound of Formula (XIX), wherein Z is —$SO_2R^{21}$. Another embodiment provides a compound of Formula (XIX), wherein Z is —$N(R^{22})SO_2R^{21}$. Another embodiment provides a compound of Formula (XIX), wherein Z is —$SO_2N(R^{22})_2$. Another embodiment provides a compound of Formula (XIX), wherein Z is —$N(R^{22})SO_2N(R^{22})_2$. Another embodiment provides a compound of Formula (XIX), wherein Z is —$CON(R^{22})_2$. Another embodiment provides a compound of Formula (XIX), wherein Z is —$N(R^{22})CO_2R^{21}$. Another embodiment provides a compound of Formula (XIX), wherein Z is —$N(R^{22})CON(R^{22})_2$. Another embodiment provides a compound of Formula (XIX), wherein $R^{21}$ is alkyl, cycloalkyl, or cycloalkylalkyl. Another embodiment provides a compound of Formula (XIX), wherein $R^{21}$ is alkyl.

Another embodiment provides a compound of Formula (XIX), wherein W is —O—. Another embodiment provides a compound of Formula (XIX), wherein W is —NH—. Another embodiment provides a compound of Formula (XIX), wherein X is alkyl. Another embodiment provides a compound of Formula (XIX), wherein X is aryl. Another embodiment provides a compound of Formula (XIX), wherein X is cycloalkylalkyl. Another embodiment provides a compound of Formula (XIX), wherein W is —O— and X is alkyl. Another embodiment provides a compound of Formula (XIX), wherein W is —O— and X is aryl. Another embodiment provides a compound of Formula (XIX), wherein W is —O— and X is cycloalkylalkyl.

One embodiment provides a compound of Formula (XX), or a pharmaceutically acceptable salt thereof, wherein, Ring B is an optionally substituted 5-membered heteroaryl ring containing at least one oxygen or sulfur atom;

$R^2$ is selected from $CH_3$, $CH_2CH_3$, $CH_2CF_3$, $CH_2F$, $CHF_2$, $CF_3$, $CH_2D$, $CHD_2$, or $CD_3$;

X1 is C—H or N;

$R^A$ is $R^{13}$ is —Y—Z;

Y is selected from a bond, —$CH_2$—, or —$CH(C_1$-$C_4$ alkyl)-;

Z is selected from —$SO_2R^{21}$, —$N(R^{22})SO_2R^{21}$, —$SO_2N(R^{22})_2$, —$N(R^{22})SO_2N(R^{22})_2$, —$CON(R^{22})_2$, —$N(R^{22})CO_2R^{21}$, —$N(R^{22})CON(R^{22})_2$, —$N(R^{22})COR^{21}$, —$OC(O)N(R^{22})_2$, —$OSO_2N(R^{22})_2$, or —$N(R^{22})SO_3R^{21}$;

X3 is S;

X4 is N or C—$R^{14}$, wherein $R^{14}$ is hydrogen, halogen, alkyl, or alkoxy;

$R^{16}$ is hydrogen, halogen, or —W—X, wherein W is a bond, —O—, —S—, or —NH—, and X is selected from alkyl, alkynyl, aryl, aralkyl, cycloalkyl, cycloalkylalkyl, cycloalkylalkynyl, heterocyclyl, heterocyclylalkyl, heteroaryl, or heteroarylalkyl;

each $R^{21}$ is independently selected from alkyl, cycloalkyl, cycloalkylalkyl, aryl, aralkyl, heterocyclyl, heterocyclylalkyl, heteroaryl, or heteroarylalkyl; and each $R^{22}$ is independently selected from hydrogen, alkyl, cycloalkyl, cycloalkylalkyl, aryl, aralkyl, heterocyclyl, heterocyclylalkyl, heteroaryl, or heteroarylalkyl.

Another embodiment provides a compound of Formula (XX), wherein X2 is N. Another embodiment provides a compound of Formula (XX), wherein X4 is N. Another embodiment provides a compound of Formula (XX), wherein X2 is C—$R^{12}$. Another embodiment provides a compound of Formula (XX), wherein X4 is C—$R^{14}$.

Another embodiment provides a compound of Formula (XX), wherein the compound of Formula (XX) has a formula selected from:

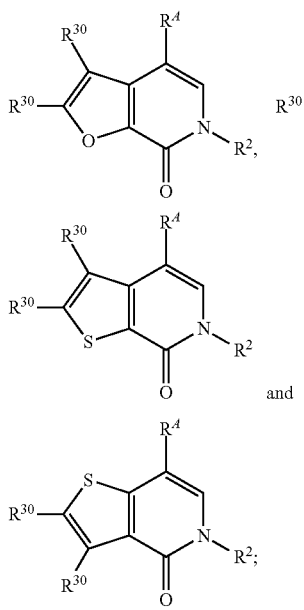

wherein each $R^{30}$ is independently selected from hydrogen, halogen, —CN, $C_1$-$C_4$ alkyl, —OH, —$OR^{31}$, —$NHR^{31}$, —$N(R^{31})_2$, —$CONHR^{31}$, —$CON(R^{31})_2$; and $R^3$ is $C_1$-$C_4$ alkyl.

Another embodiment provides a compound of Formula (XX), wherein the compound of Formula (XX) has a formula selected from:

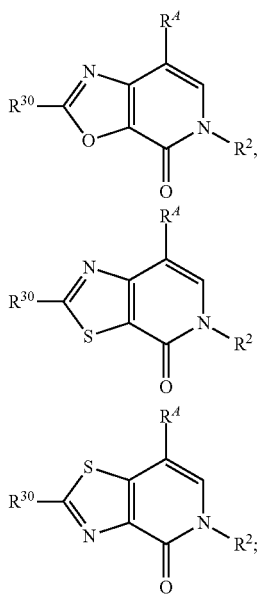

wherein each $R^{30}$ is independently selected from hydrogen, halogen, —CN, $C_1$-$C_4$ alkyl, —OH, —$OR^{31}$, —$NHR^{31}$, —$N(R^{31})_2$, —$CONHR^{31}$, —$CON(R^{31})_2$; and $R^3$ is $C_1$-$C_4$ alkyl.

Another embodiment provides a compound of Formula (XX), wherein the compound of Formula (XX) has a formula selected from:

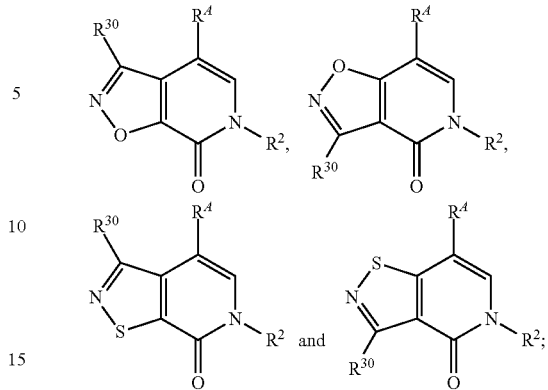

wherein each $R^{30}$ is independently selected from hydrogen, halogen, —CN, $C_1$-$C_4$ alkyl, —OH, —$OR^{31}$, —$NHR^{31}$, —$N(R^{31})_2$, —$CONHR^{31}$, —$CON(R^{31})_2$; and $R^{31}$ is $C_1$-$C_4$ alkyl.

Another embodiment provides a compound of Formula (XX), wherein $R^2$ is $CH_3$. Another embodiment provides a compound of Formula (XX), wherein X1 is C—H. Another embodiment provides a compound of Formula (XX), wherein X1 is N.

Another embodiment provides a compound of Formula (XX), wherein Y is a bond. Another embodiment provides a compound of Formula (XX), wherein Y is a —$CH_2$—. Another embodiment provides a compound of Formula (XX), wherein Z is —$SO_2R^{21}$. Another embodiment provides a compound of Formula (XX), wherein Z is —$N(R^{22})SO_2R^{21}$. Another embodiment provides a compound of Formula (XX), wherein Z is —$SO_2N(R^{22})_2$. Another embodiment provides a compound of Formula (XX), wherein Z is —$N(R^{22})SO_2N(R^{22})_2$. Another embodiment provides a compound of Formula (XX), wherein Z is —$CON(R^{22})_2$. Another embodiment provides a compound of Formula (XX), wherein Z is —$N(R^{22})CO_2R^{21}$. Another embodiment provides a compound of Formula (XX), wherein Z is —$N(R^{22})CON(R^{22})_2$. Another embodiment provides a compound of Formula (XX), wherein $R^{21}$ is alkyl, cycloalkyl, or cycloalkylalkyl. Another embodiment provides a compound of Formula (XV), wherein $R^{21}$ is alkyl.

Another embodiment provides a compound of Formula (XX), wherein W is —O—. Another embodiment provides a compound of Formula (XX), wherein W is —NH—. Another embodiment provides a compound of Formula (XX), wherein X is alkyl. Another embodiment provides a compound of Formula (XX), wherein X is alkynyl. Another embodiment provides a compound of Formula (XX), wherein X is aryl. Another embodiment provides a compound of Formula (XX), wherein X is cycloalkylalkyl. Another embodiment provides a compound of Formula (XX), wherein X is cycloalkylalkynyl. Another embodiment provides a compound of Formula (XX), wherein W is —O— and X is alkyl. Another embodiment provides a compound of Formula (XX), wherein W is —O— and X is aryl. Another embodiment provides a compound of Formula (XX), wherein W is —O— and X is alkynyl. Another embodiment provides a compound of Formula (XX), wherein W is —O— and X is cycloalkylalkyl. Another embodiment provides a compound of Formula (XX), wherein W is —O— and X is cycloalkylalkynyl.

One embodiment provides a compound of Formula (XXI), or a pharmaceutically acceptable salt thereof,

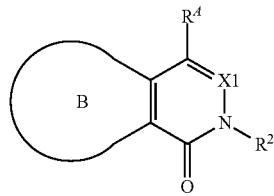

Formula (XXI)

wherein,
$R^2$ is $CH_3$, $CH_2CH_3$, $CH_2CF_3$, $CH_2F$, $CHF_2$, $CF_3$, $CH_2D$, $CHD_2$, or $CD_3$;
X1 is C—H or N;
ring B is an optionally substituted 5- or 6-membered heterocyclic ring containing at least one oxygen or nitrogen atom;
$R^A$ is

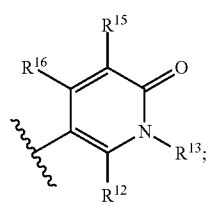

$R^{12}$ is hydrogen or $C_1$-$C_4$ alkyl;
$R^{13}$ is —Y—Z;
Y is selected from —$CH_2$—, or —$CH(C_1$-$C_4$ alkyl)-;
Z is selected from —$SO_2R^{21}$, —$SO_2N(R^{22})_2$, or —$CON(R^{22})_2$;
$R^{15}$ is hydrogen, halogen or $C_1$-$C_4$ alkyl;
$R^{16}$ is hydrogen, halogen, or —W—X, wherein W is a bond, —O—, —S—, or —NH—, and X is selected from alkyl, alkynyl, aryl, aralkyl, cycloalkyl, cycloalkylalkyl, cycloalkylalkynyl, heterocyclyl, heterocyclylalkyl, heteroaryl, or heteroarylalkyl; or optionally, $R^{16}$ and $R^{15}$ connect to form a ring;
each $R^{21}$ is independently selected from alkyl, cycloalkyl, cycloalkylalkyl, aryl, aralkyl, heterocyclyl, heterocyclylalkyl, heteroaryl, or heteroarylalkyl; and
each $R^{22}$ is independently selected from hydrogen, alkyl, cycloalkyl, cycloalkylalkyl, aryl, aralkyl, heterocyclyl, heterocyclylalkyl, heteroaryl, or heteroarylalkyl.

One embodiment provides a compound of Formula (XXII), or a pharmaceutically acceptable salt thereof,

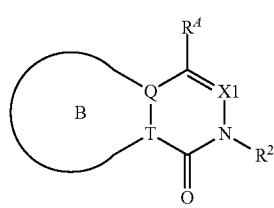

Formula (XXII)

wherein,
Q is N and T is C, or Q is C and T is N;
Ring B is an optionally substituted 5-membered aromatic nitrogen-containing heteroaryl ring containing one or more nitrogen atoms;
$R^2$ is selected from $CH_3$, $CH_2CH_3$, $CH_2CF_3$, $CH_2F$, $CHF_2$, $CF_3$, $CH_2D$, $CHD_2$, or $CD_3$;
X1 is C—H or N;
$R^A$ is

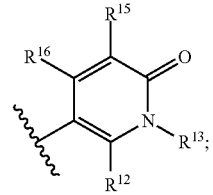

$R^{12}$ is hydrogen or $C_1$-$C_4$ alkyl;
$R^{13}$ is —Y—Z;
Y is selected from —$CH_2$—, or —$CH(C_1$-$C_4$ alkyl)-;
Z is selected from —$SO_2R^{21}$, —$SO_2N(R^{22})_2$, or —$CON(R^{22})_2$;
$R^{15}$ is hydrogen, halogen or $C_1$-$C_4$ alkyl;
$R^{16}$ is hydrogen, halogen, or —W—X, wherein W is a bond, —O—, —S—, or —NH—, and X is selected from alkyl, alkynyl, aryl, aralkyl, cycloalkyl, cycloalkylalkyl, cycloalkylalkynyl, heterocyclyl, heterocyclylalkyl, heteroaryl, or heteroarylalkyl; or optionally, $R^{16}$ and $R^{15}$ connect to form a ring;
each $R^{21}$ is independently selected from alkyl, cycloalkyl, cycloalkylalkyl, aryl, aralkyl, heterocyclyl, heterocyclylalkyl, heteroaryl, or heteroarylalkyl; and
each $R^{22}$ is independently selected from hydrogen, alkyl, cycloalkyl, cycloalkylalkyl, aryl, aralkyl, heterocyclyl, heterocyclylalkyl, heteroaryl, or heteroarylalkyl.

Another embodiment provides a compound of Formula (XXII), wherein the compound of Formula (XXII) is selected from the group:

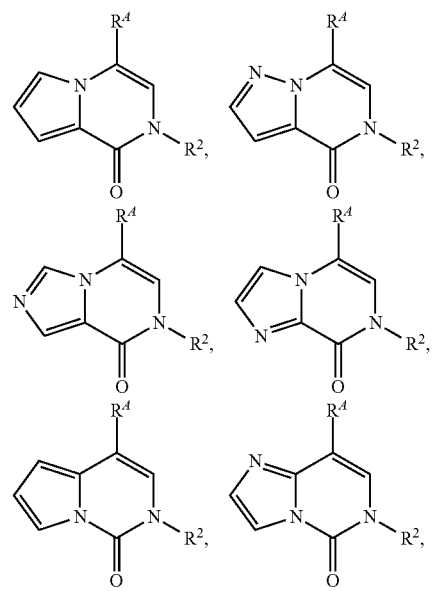

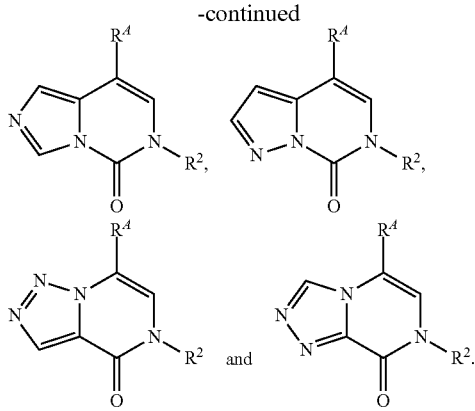

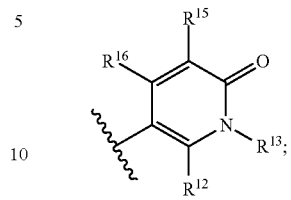

Another embodiment provides a compound of Formula (XXII), wherein Q is N and T is C. Another embodiment provides a compound of Formula (XXII), wherein Q is C and T is N. Another embodiment provides a compound of Formula (XXII), wherein $R^2$ is $CH_3$. Another embodiment provides a compound of Formula (XXII), wherein X1 is C—H. Another embodiment provides a compound of Formula (XXII), wherein X1 is N.

Another embodiment provides a compound of Formula (XXII), wherein Y is a —$CH_2$—. Another embodiment provides a compound of Formula (XXII), wherein Z is —$SO_2R^{21}$. Another embodiment provides a compound of Formula (XXII), wherein Z is —$SO_2N(R^{22})_2$. Another embodiment provides a compound of Formula (XXII), wherein Z is —$CON(R^{22})_2$. Another embodiment provides a compound of Formula (XXII), wherein $R^{21}$ is alkyl, cycloalkyl, or cycloalkylalkyl. Another embodiment provides a compound of Formula (XXII), wherein $R^{21}$ is alkyl.

Another embodiment provides a compound of Formula (XXII), wherein W is —O—. Another embodiment provides a compound of Formula (XXII), wherein W is —NH—. Another embodiment provides a compound of Formula (XXII), wherein X is alkyl. Another embodiment provides a compound of Formula (XXII), wherein X is aryl. Another embodiment provides a compound of Formula (XXII), wherein X is cycloalkylalkyl. Another embodiment provides a compound of Formula (XXII), wherein W is —O— and X is alkyl. Another embodiment provides a compound of Formula (XXII), wherein W is —O— and X is aryl. Another embodiment provides a compound of Formula (XXII), wherein W is —O— and X is cycloalkylalkyl.

One embodiment provides a compound of Formula (XXIII), or a pharmaceutically acceptable salt thereof, Formula (XXIII)

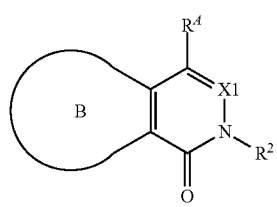

wherein,
Ring B is an optionally substituted 5-membered heteroaryl ring containing at least one oxygen or sulfur atom;
$R^2$ is selected from $CH_3$, $CH_2CH_3$, $CH_2CF_3$, $CH_2F$, $CHF_2$, $CF_3$, $CH_2D$, $CHD_2$, or $CD_3$;
X1 is C—H or N;
$R^A$ is $R^{12}$ is hydrogen or $C_1$-$C_4$ alkyl;
$R^{13}$ is —Y—Z;
Y is selected from —$CH_2$—, or —$CH(C_1$-$C_4$ alkyl)-;
Z is selected from —$SO_2R^{21}$, —$SO_2N(R^{22})_2$, or —$CON(R^{22})_2$;
$R^{15}$ is hydrogen, halogen or $C_1$-$C_4$ alkyl;
$R^{16}$ is hydrogen, halogen, or —W—X, wherein W is a bond, —O—, —S—, or —NH—, and X is selected from alkyl, alkynyl, aryl, aralkyl, cycloalkyl, cycloalkylalkyl, cycloalkylalkynyl, heterocyclyl, heterocyclylalkyl, heteroaryl, or heteroarylalkyl; or optionally, $R^{16}$ and $R^{15}$ connect to form a ring;
each $R^{21}$ is independently selected from alkyl, cycloalkyl, cycloalkylalkyl, aryl, aralkyl, heterocyclyl, heterocyclylalkyl, heteroaryl, or heteroarylalkyl; and
each $R^{22}$ is independently selected from hydrogen, alkyl, cycloalkyl, cycloalkylalkyl, aryl, aralkyl, heterocyclyl, heterocyclylalkyl, heteroaryl, or heteroarylalkyl.

Another embodiment provides a compound of Formula (XXIII), wherein the compound of Formula (XXIII) has a formula selected from:

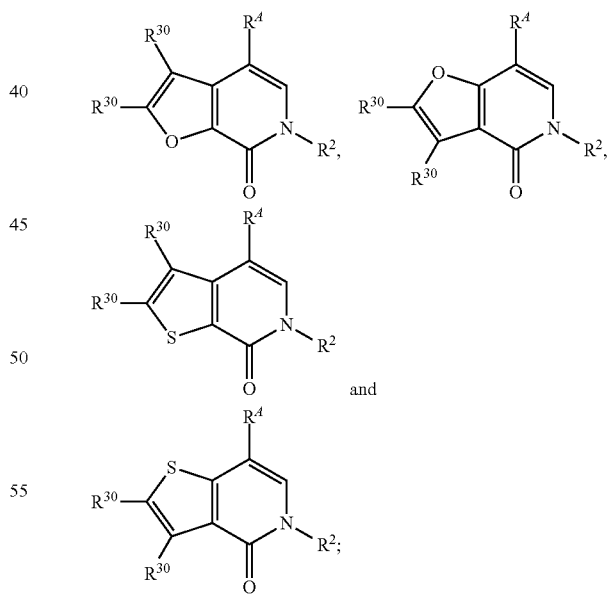

wherein each $R^{30}$ is independently selected from hydrogen, halogen, —CN, $C_1$-$C_4$ alkyl, —OH, —$OR^{31}$, —$NHR^{31}$, —$N(R^{31})_2$, —$CONHR^{31}$, —$CON(R^{31})_2$; and $R^{31}$ is $C_1$-$C_4$ alkyl.

Another embodiment provides a compound of Formula (XXIII), wherein the compound of Formula (XXIII) has a formula selected from:

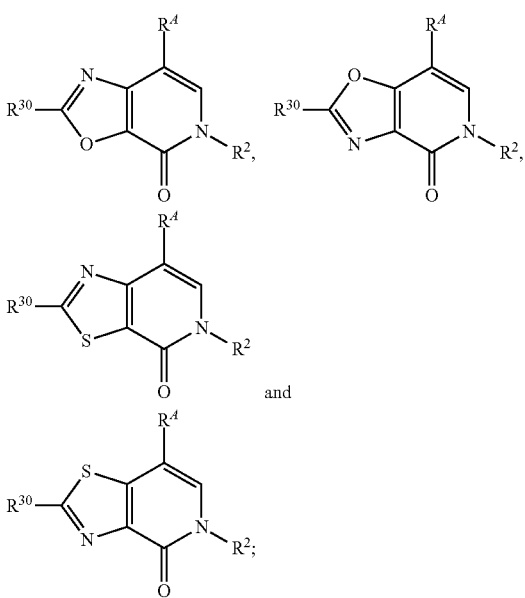

wherein each $R^{30}$ is independently selected from hydrogen, halogen, —CN, $C_1$-$C_4$ alkyl, —OH, —$OR^{31}$, —$NHR^{31}$, —$N(R^{31})_2$, —$CONHR^{31}$, —$CON(R^{31})_2$; and $R^3$ is $C_1$-$C_4$ alkyl.

Another embodiment provides a compound of Formula (XXIII), wherein the compound of Formula (XXIII) has a formula selected from:

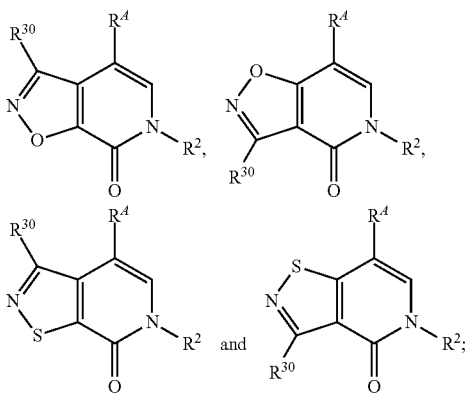

wherein each $R^{30}$ is independently selected from hydrogen, halogen, —CN, $C_1$-$C_4$ alkyl, —OH, —$OR^{31}$, —$NHR^{31}$, —$N(R^{31})_2$, —$CONHR^{31}$, —$CON(R^{31})_2$; and $R^3$ is $C_1$-$C_4$ alkyl.

Another embodiment provides a compound of Formula (XXIII), wherein $R^2$ is $CH_3$. Another embodiment provides a compound of Formula (XXIII), wherein X1 is C—H. Another embodiment provides a compound of Formula (XXIII), wherein X1 is N.

Another embodiment provides a compound of Formula (XXIII), wherein Y is a —$CH_2$—. Another embodiment provides a compound of Formula (XXIII), wherein Z is —$SO_2R^{21}$. Another embodiment provides a compound of Formula (XXIII), wherein Z is —$SO_2N(R^{22})_2$. Another embodiment provides a compound of Formula (XXIII), wherein Z is —$CON(R^{22})_2$. Another embodiment provides a compound of Formula (XXIII), wherein $R^{21}$ is alkyl, cycloalkyl, or cycloalkylalkyl. Another embodiment provides a compound of Formula (XXIII), wherein $R^{21}$ is alkyl.

Another embodiment provides a compound of Formula (XXIII), wherein W is —O—. Another embodiment provides a compound of Formula (XXIII), wherein W is —NH—. Another embodiment provides a compound of Formula (XXIII), wherein X is alkyl. Another embodiment provides a compound of Formula (XXIII), wherein X is alkynyl. Another embodiment provides a compound of Formula (XXIII), wherein X is aryl. Another embodiment provides a compound of Formula (XXIII), wherein X is cycloalkylalkyl. Another embodiment provides a compound of Formula (XXIII), wherein X is cycloalkylalkynyl. Another embodiment provides a compound of Formula (XXIII), wherein W is —O— and X is alkyl. Another embodiment provides a compound of Formula (XXIII), wherein W is —O— and X is aryl. Another embodiment provides a compound of Formula (XXIII), wherein W is —O— and X is alkynyl. Another embodiment provides a compound of Formula (XXIII), wherein W is —O— and X is cycloalkylalkyl. Another embodiment provides a compound of Formula (XXIII), wherein W is —O— and X is cycloalkylalkynyl.

One embodiment provides a compound of Formula (XXIV), or a pharmaceutically acceptable salt thereof,

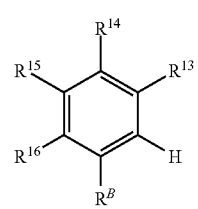

Formula (XXIV)

wherein,
$R^{13}$ is —Y—Z;
Y is selected from a bond, or —$CH_2$—;
Z is selected from —$SO_2R^{21}$, —$N(R^{22})SO_2R^{21}$, —$SO_2N(R^{22})_2$, —$N(R^{22})SO_2N(R^{22})_2$, —$CON(R^{22})_2$, —$N(R^{22})CO_2R^{21}$, —$N(R^{22})CON(R^{22})_2$, —$N(R^{22})COR^{21}$, —$COR^{21}$, —$OC(O)N(R^{22})_2$, —$OSO_2N(R^{22})_2$, —$N(R^{22})SO_3R^{21}$, or —$N(R^{22})_2$;
$R^{14}$ is hydrogen, halogen, $C_1$-$C_3$ alkyl, or $C_1$-$C_3$ alkoxy;
$R^{15}$ is halogen or U—V, wherein U is a bond, —O—, or —$CH_2$—; and V is —CN, alkyl, alkynyl, aryl, aralkyl, cycloalkyl, cycloalkylalkyl, heterocyclyl, heterocyclylalkyl, heteroaryl, or heteroarylalkyl;
$R^{16}$ is hydrogen;
each $R^{21}$ is independently selected from alkyl, cycloalkyl, cycloalkylalkyl, aryl, aralkyl, heterocyclyl, heterocyclylalkyl, heteroaryl, or heteroarylalkyl;
each $R^{22}$ is independently selected from hydrogen, alkyl, cycloalkyl, cycloalkylalkyl, aryl, aralkyl, heterocyclyl, heterocyclylalkyl, heteroaryl, or heteroarylalkyl;
$R^B$ is

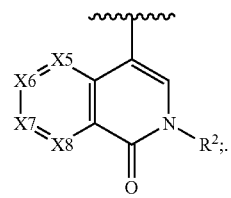

wherein
R² is CH₃;
X5 is C—H;
X6 is C—R⁶;
X7 is C—R⁷;
X8 is C—H;
R⁶ is hydrogen, or halogen;
R⁷ is hydrogen, or halogen; or
R^B is

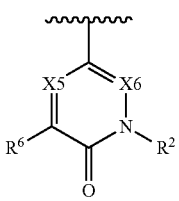

wherein
R² is CH₃;
X6 is C—H;
X5 is C—R⁵;
R⁵ is hydrogen, or halogen;
R⁶ is hydrogen, alkyl, alkoxy, or halogen; or
R^B is

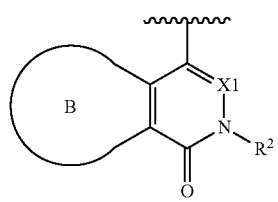

wherein
Ring B is an optionally substituted 5-membered heteroaryl ring containing at least one oxygen or sulfur atom;
R² is CH₃; and
X1 is C—H.

Another embodiment provides a compound of Formula (XXIV), or a pharmaceutically acceptable salt thereof, wherein Y is —CH₂—. Another embodiment provides a compound of Formula (XXIV), or a pharmaceutically acceptable salt thereof, wherein Y is a bond.

Another embodiment provides a compound of Formula (XXIV), or a pharmaceutically acceptable salt thereof, wherein Z is —SO₂R²¹, —N(R²²)SO₂R²¹, or —N(R²²)₂.

Another embodiment provides a compound of Formula (XXIV), or a pharmaceutically acceptable salt thereof, wherein Z is —SO₂R²¹ or —N(R²²)SO₂R²¹. Another embodiment provides a compound of Formula (XXIV), or a pharmaceutically acceptable salt thereof, wherein Z is —N(R²²)SO₂R²¹. Another embodiment provides a compound of Formula (XXIV), or a pharmaceutically acceptable salt thereof, wherein Z is —SO₂R²¹.

Another embodiment provides a compound of Formula (XXIV), or a pharmaceutically acceptable salt thereof, wherein R²¹ is heterocyclyl or heterocyclylalkyl. Another embodiment provides a compound of Formula (XXIV), or a pharmaceutically acceptable salt thereof, wherein R²¹ is alkyl, cycloalkyl, or cycloalkylalkyl. Another embodiment provides a compound of Formula (XXIV), or a pharmaceutically acceptable salt thereof, wherein R²¹ is alkyl, and the alkyl is a $C_1$-$C_4$ alkyl.

Another embodiment provides a compound of Formula (XXIV), or a pharmaceutically acceptable salt thereof, wherein R²² is alkyl, cycloalkyl, or aralkyl. Another embodiment provides a compound of Formula (XXIV), or a pharmaceutically acceptable salt thereof, wherein R²² is hydrogen or methyl.

Another embodiment provides a compound of Formula (XXIV), or a pharmaceutically acceptable salt thereof, wherein R¹⁴ is hydrogen.

Another embodiment provides a compound of Formula (XXIV), or a pharmaceutically acceptable salt thereof, wherein U is a bond. Another embodiment provides a compound of Formula (XXIV), or a pharmaceutically acceptable salt thereof, wherein U is —O—.

Another embodiment provides a compound of Formula (XXIV), or a pharmaceutically acceptable salt thereof, wherein U is —CH₂—.

Another embodiment provides a compound of Formula (XXIV), or a pharmaceutically acceptable salt thereof, wherein V is alkyl. Another embodiment provides a compound of Formula (XXIV), or a pharmaceutically acceptable salt thereof, wherein V is aryl. Another embodiment provides a compound of Formula (XXIV), or a pharmaceutically acceptable salt thereof, wherein V is aralkyl. Another embodiment provides a compound of Formula (XXIV), or a pharmaceutically acceptable salt thereof, wherein V is cycloalkylalkyl. Another embodiment provides a compound of Formula (XXIV), or a pharmaceutically acceptable salt thereof, wherein V is heterocyclylalkyl. Another embodiment provides a compound of Formula (XXIV), or a pharmaceutically acceptable salt thereof, wherein V is heteroaryl. Another embodiment provides a compound of Formula (XXIV), or a pharmaceutically acceptable salt thereof, wherein V is heteroarylalkyl. Another embodiment provides a compound of Formula (XXIV), or a pharmaceutically acceptable salt thereof, wherein V is alkynyl.

Another embodiment provides a compound of Formula (XXIV), or a pharmaceutically acceptable salt thereof, wherein Y is a bond, Z is —N(R²²)SO₂R²¹, U is —O—, and V is aryl, aralkyl or cycloalkylalkyl. Another embodiment provides a compound of Formula (XXIV), or a pharmaceutically acceptable salt thereof, wherein Y is a bond, Z is —SO₂R²¹, U is —O—, and V is aryl, aralkyl or cycloalkylalkyl.

Another embodiment provides a compound of Formula (XXIV), or a pharmaceutically acceptable salt thereof, wherein R^B is

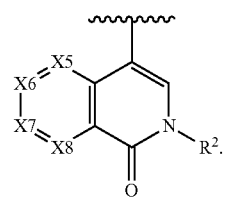

Another embodiment provides a compound of Formula (XXIV), or a pharmaceutically acceptable salt thereof, wherein R⁶ is halogen, and R⁷ is hydrogen. Another embodiment provides a compound of Formula (XXIV), or a pharmaceutically acceptable salt thereof, wherein R⁶ is hydrogen, and R⁷ is halogen. Another embodiment provides a compound of Formula (XXIV), or a pharmaceutically acceptable salt thereof, wherein $R^6$ is hydrogen, and $R^7$ is hydrogen.

Another embodiment provides a compound of Formula (XXIV), or a pharmaceutically acceptable salt thereof, wherein $R^B$ is

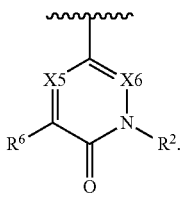

Another embodiment provides a compound of Formula (XXIV), or a pharmaceutically acceptable salt thereof, wherein $R^5$ is hydrogen, and $R^6$ is alkyl. Another embodiment provides a compound of Formula (XXIV), or a pharmaceutically acceptable salt thereof, wherein $R^6$ is methyl.

Another embodiment provides a compound of Formula (XXIV), or a pharmaceutically acceptable salt thereof, wherein $R^B$ is

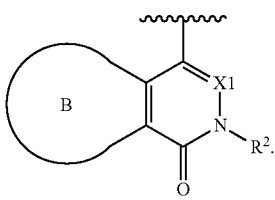

Another embodiment provides a compound of Formula (XXIV), or a pharmaceutically acceptable salt thereof, wherein Ring B is an optionally substituted 5-membered heteroaryl ring containing one oxygen.

One embodiment provides a compound of Formula (XXV), or a pharmaceutically acceptable salt thereof,

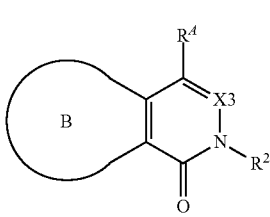

Formula (XXV)

wherein,

Ring B is an optionally substituted 5-, 6-, or 7-membered, non-aromatic carbocyclyl ring;

$R^2$ is selected from $CH_3$, $CH_2CH_3$, $CH_2CF_3$, $CH_2F$, $CHF_2$, $CF_3$, $CH_2D$, $CHD_2$, or $CD_3$;

X3 is C—H or N;

$R^A$ is

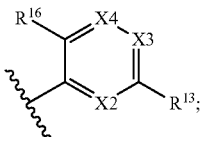

X2 is N or C—$R^{12}$, wherein $R^{12}$ is hydrogen, halogen, alkyl, or alkoxy;

$R^{13}$ is —Y—Z;

Y is selected from a bond, or —$CH_2$—;

Z is selected from —$SO_2R^{21}$, —N($R^{22}$)$SO_2R^{21}$, —$SO_2N(R^{22})_2$, —N($R^{22}$)$SO_2N(R^{22})_2$, —CON($R^{22})_2$, —N($R^{22}$)CO$_2R^{21}$, —N($R^{22}$)CON($R^{22})_2$, —N($R^{22}$)COR$^{21}$, —OC(O)N($R^{22})_2$, —OSO$_2$N($R^{22})_2$, or —N($R^{22}$)SO$_3R^{21}$;

X3 is N or C—$R^{14}$, wherein $R^{14}$ is hydrogen, halogen, —CN, alkyl, cycloalkyl, or alkoxy;

X4 is N or C—$R^{15}$, wherein $R^{15}$ is hydrogen, halogen, —CN, alkyl, or alkoxy;

$R^{16}$ is hydrogen, halogen, or —W—X, wherein W is a bond, —O—, —S—, or —NH—, and X is selected from alkyl, aryl, aralkyl, cycloalkyl, cycloalkylalkyl, heterocyclyl, heterocyclylalkyl, heteroaryl, or heteroarylalkyl;

each $R^{21}$ is independently selected from alkyl, cycloalkyl, cycloalkylalkyl, aryl, aralkyl, heterocyclyl, heterocyclylalkyl, heteroaryl, or heteroarylalkyl; and each $R^{22}$ is independently selected from hydrogen, alkyl, cycloalkyl, cycloalkylalkyl, aryl, aralkyl, heterocyclyl, heterocyclylalkyl, heteroaryl, or heteroarylalkyl.

Another embodiment provides a compound of Formula (XXV), or a pharmaceutically acceptable salt thereof, wherein Ring B is an optionally substituted 5-membered, non-aromatic carbocyclyl ring. Another embodiment provides a compound of Formula (XXV), or a pharmaceutically acceptable salt thereof, wherein Ring B is an optionally substituted 6-membered, non-aromatic carbocyclyl ring. Another embodiment provides a compound of Formula (XXV), or a pharmaceutically acceptable salt thereof, wherein Ring B is an optionally substituted 7-membered, non-aromatic carbocyclyl ring.

Another embodiment provides a compound of Formula (XXV), or a pharmaceutically acceptable salt thereof, wherein $R^2$ is $CH_3$.

Another embodiment provides a compound of Formula (XXV), or a pharmaceutically acceptable salt thereof, wherein X3 is C—H. Another embodiment provides a compound of Formula (XXV), or a pharmaceutically acceptable salt thereof, wherein X3 is N.

Another embodiment provides a compound of Formula (XXV), or a pharmaceutically acceptable salt thereof, wherein Y is a bond. Another embodiment provides a compound of Formula (XXV), or a pharmaceutically acceptable salt thereof, wherein Y is a —$CH_2$—.

Another embodiment provides a compound of Formula (XXV), or a pharmaceutically acceptable salt thereof, wherein Z is —$SO_2R^{21}$. Another embodiment provides a compound of Formula (XXV), or a pharmaceutically acceptable salt thereof, wherein Z is —N($R^{22}$)$SO_2R^{21}$.

Another embodiment provides a compound of Formula (XXV), or a pharmaceutically acceptable salt thereof, wherein Z is —$SO_2N(R^{22})_2$. Another embodiment provides a compound of Formula (XXV), or a pharmaceutically acceptable salt thereof, wherein Z is —N($R^{22}$)$SO_2N(R^{22})_2$. Another embodiment provides a compound of Formula (XXV), or a pharmaceutically acceptable salt thereof, wherein Z is —CON($R^{22})_2$. Another embodiment provides a compound of Formula (XXV), or a pharmaceutically acceptable salt thereof, wherein Z is —N(R$^{22}$)CO$_2$R$^{21}$. Another embodiment provides a compound of Formula (XXV), or a pharmaceutically acceptable salt thereof, wherein Z is —N(R$^{22}$)CON(R$^{22}$)$_2$.

Another embodiment provides a compound of Formula (XXV), or a pharmaceutically acceptable salt thereof, wherein R$^{21}$ is alkyl, cycloalkyl, or cycloalkylalkyl. Another embodiment provides a compound of Formula (XXV), or a pharmaceutically acceptable salt thereof, wherein R$^{21}$ is alkyl.

Another embodiment provides a compound of Formula (XXV), or a pharmaceutically acceptable salt thereof, wherein R$^{14}$ is hydrogen, halogen, or alkyl. Another embodiment provides a compound of Formula (XXV), or a pharmaceutically acceptable salt thereof, wherein X4 is C—R$^{15}$. Another embodiment provides a compound of Formula (XXV), or a pharmaceutically acceptable salt thereof, wherein W is —O—. Another embodiment provides a compound of Formula (XXV), or a pharmaceutically acceptable salt thereof, wherein W is —NH—.

Another embodiment provides a compound of Formula (XXV), or a pharmaceutically acceptable salt thereof, wherein X is alkyl. Another embodiment provides a compound of Formula (XXV), or a pharmaceutically acceptable salt thereof, wherein X is aryl. Another embodiment provides a compound of Formula (XXV), or a pharmaceutically acceptable salt thereof, wherein X is cycloalkylalkyl.

Another embodiment provides a compound of Formula (XXV), or a pharmaceutically acceptable salt thereof, wherein W is —O— and X is alkyl. Another embodiment provides a compound of Formula (XXV), or a pharmaceutically acceptable salt thereof, wherein W is —O— and X is aryl. Another embodiment provides a compound of Formula (XXV), or a pharmaceutically acceptable salt thereof, wherein W is —O— and X is cycloalkylalkyl.

In some embodiments, the substituted heterocyclic derivative compound disclosed herein has the structure provided in Table 1.

TABLE 1

| Chemical Synthesis Example | Structure | Name |
|---|---|---|
| 2 | 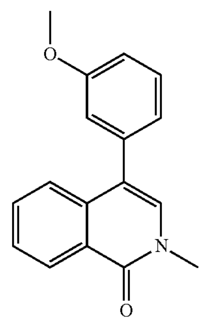 [SMILES: COc1cccc(-c2cn(C)c(=O)c3ccccc23)c1] | 4-(3-methoxyphenyl)-2-methylisoquinolin-1-one |
| 3 | 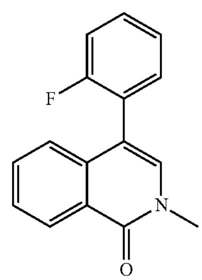 [SMILES: Cn1cc(-c2ccccc2F)c2ccccc2c1=O] | 4-(2-fluorophenyl)-2-methylisoquinolin-1-one |
| 4 | 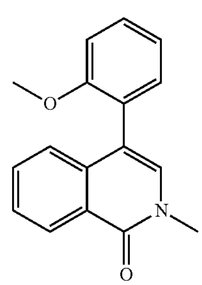 [SMILES: COc1ccccc1-c1cn(C)c(=O)c2ccccc12] | 4-(2-methoxyphenyl)-2-methylisoquinolin-1-one |

TABLE 1-continued

| Chemical Synthesis Example | Structure | Name |
|---|---|---|
| 5 | 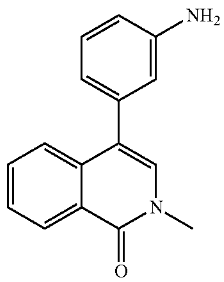 [SMILES: Cn1cc(-c2cccc(N)c2)c2ccccc2c1=O] | 4-(3-aminophenyl)-2-methylisoquinolin-1-one |
| 6 | 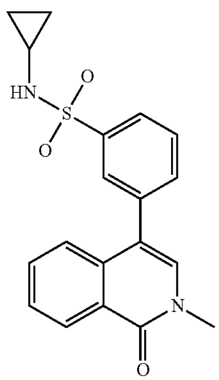 [SMILES: Cn1cc(-c2cccc(S(O)(O)NC3CC3)c2)c2ccccc2c1=O] | N-cyclopropyl-3-(2-methyl-1-oxoisoquinolin-4-yl)benzenesulfonamide |
| 7 | 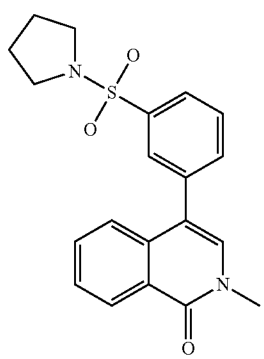 [SMILES: Cn1cc(-c2cccc(S(O)(O)N3CCCC3)c2)c2ccccc2c1=O] | 2-methyl-4-(3-pyrrolidin-1-ylsulfonylphenyl)isoquinolin-1-one |
| 8 | 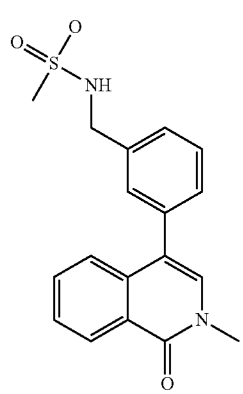 | N-[[3-(2-methyl-1-oxoisoquinolin-4-yl)phenyl]methyl]methanesulfonamide |

TABLE 1-continued

| Chemical Synthesis Example | Structure | Name |
|---|---|---|
| 9 | 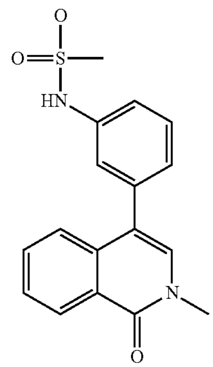 | N-[3-(2-methyl-1-oxoisoquinolin-4-yl)phenyl]methanesulfonamide |
| 10 | 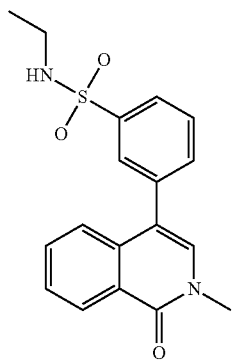 [SMILES: CCNS(O)(O)c1cccc(-c2cn(C)c(=O)c3ccccc23)c1] | N-ethyl-3-(2-methyl-1-oxoisoquinolin-4-yl)benzenesulfonamide |
| 11 | 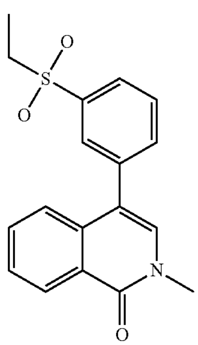 [SMILES: CCS(O)(O)c1cccc(-c2cn(C)c(=O)c3ccccc23)c1] | 4-(3-ethylsulfonylphenyl)-2-methylisoquinolin-1-one |
| 12 | 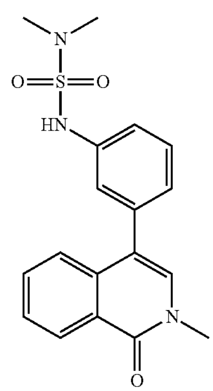 [SMILES: CN(C)S(=O)(=O)Nc1cccc(-c2cn(C)c(=O)c3ccccc23)c1] | 4-[3-(dimethylsulfamoylamino)phenyl]-2-methyl-1-oxoisoquinoline |

TABLE 1-continued

| Chemical Synthesis Example | Structure | Name |
|---|---|---|
| 13 | 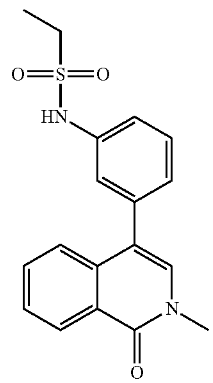 [SMILES: CCS(=O)(=O)Nc1cccc(-c2cn(C)c(=O)c3ccccc23)c1] | N-[3-(2-methyl-1-oxoisoquinolin-4-yl)phenyl]ethanesulfonamide |
| 14 | 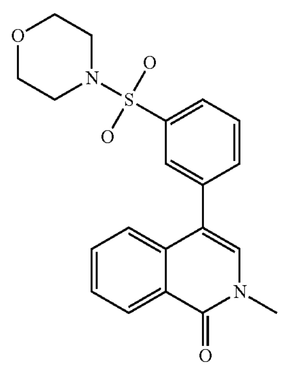 [SMILES: Cn1cc(-c2cccc(S(O)(O)N3CCOCC3)c2)c2ccccc2c1=O] | 2-methyl-4-(3-morpholin-4-ylsulfonylphenyl)isoquinolin-1-one |
| 15 | 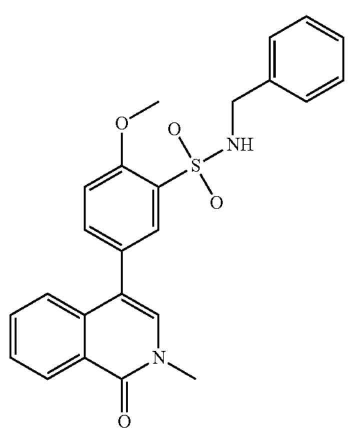 [SMILES: COc1ccc(-c2cn(C)c(=O)c3ccccc23)cc1S(O)(O)NCc1ccccc1] | N-benzyl-2-methoxy-5-(2-methyl-1-oxoisoquinolin-4-yl)benzenesulfonamide |
| 16 | 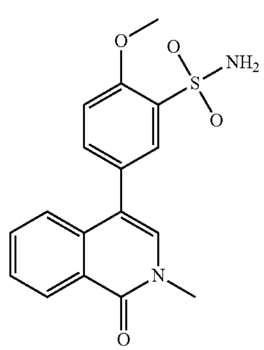 [SMILES: COc1ccc(-c2cn(C)c(=O)c3ccccc23)cc1S(N)(O)O] | 2-methoxy-5-(2-methyl-1-oxoisoquinolin-4-yl)benzenesulfonamide |

TABLE 1-continued

| Chemical Synthesis Example | Structure | Name |
|---|---|---|
| 17 | 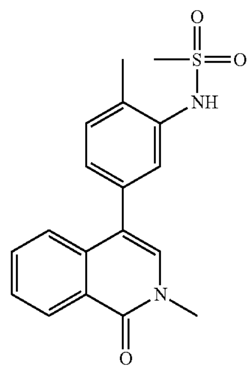 [SMILES: Cc1ccc(-c2cn(C)c(=O)c3ccccc23)cc1NS(C)(=O)=O] | N-[2-methyl-5-(2-methyl-1-oxoisoquinolin-4-yl)phenyl]methanesulfonamide |
| 18 | 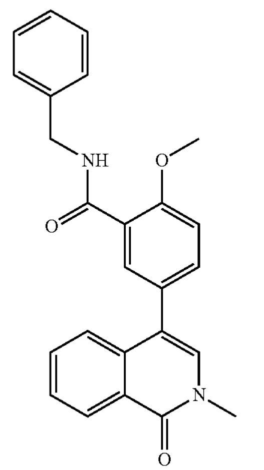 [SMILES: COc1ccc(-c2cn(C)c(=O)c3ccccc23)cc1C(=O)NCc1ccccc1] | N-benzyl-2-methoxy-5-(2-methyl-1-oxoisoquinolin-4-yl)benzamide |
| 19 | 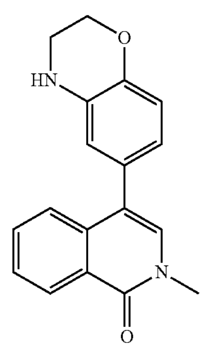 [SMILES: Cn1cc(-c2ccc3c(c2)NCCO3)c2ccccc2c1=O] | 4-(3,4-dihydro-2H-1,4-benzoxazin-6-yl)-2-methylisoquinolin-1-one |
| 20 | 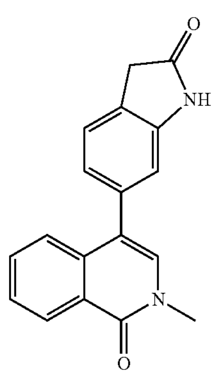 [SMILES: Cn1cc(-c2ccc3c(c2)NC(=O)C3)c2ccccc2c1=O] | 2-methyl-4-(2-oxo-1,3-dihydroindol-6-yl)isoquinolin-1-one |

TABLE 1-continued

| Chemical Synthesis Example | Structure | Name |
|---|---|---|
| 21 | 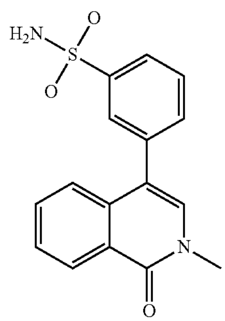 | 3-(2-methyl-1-oxoisoquinolin-4-yl)benzenesulfonamide |
| 22 | 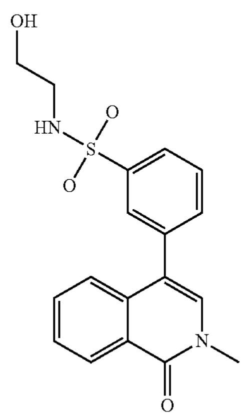 [SMILES: Cn1cc(-c2cccc(S(O)(O)NCCO)c2)c2ccccc2c1=O] | N-(2-hydroxyethyl)-3-(2-methyl-1-oxoisoquinolin-4-yl)benzenesulfonamide |
| 23 | 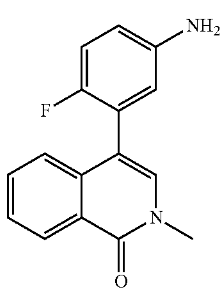 [SMILES: Cn1cc(-c2cc(N)ccc2F)c2ccccc2c1=O] | 4-(5-amino-2-fluorophenyl)-2-methylisoquinolin-1-one |
| 24 | 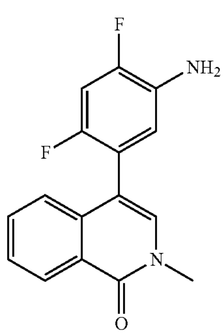 [SMILES: Cn1cc(-c2cc(N)c(F)cc2F)c2ccccc2c1=O] | 4-(5-amino-2,4-difluorophenyl)-2-methylisoquinolin-1-one |

TABLE 1-continued

| Chemical Synthesis Example | Structure | Name |
|---|---|---|
| 25 | 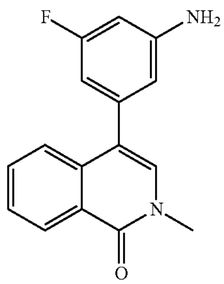 [SMILES: Cn1cc(-c2cc(N)cc(F)c2)c2ccccc2c1=O] | 4-(3-amino-5-fluorophenyl)-2-methylisoquinolin-1-one |
| 26 | 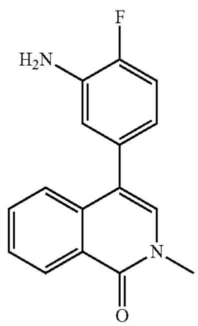 [SMILES: Cn1cc(-c2ccc(F)c(N)c2)c2ccccc2c1=O] | 4-(3-amino-4-fluorophenyl)-2-methylisoquinolin-1-one |
| 27 | 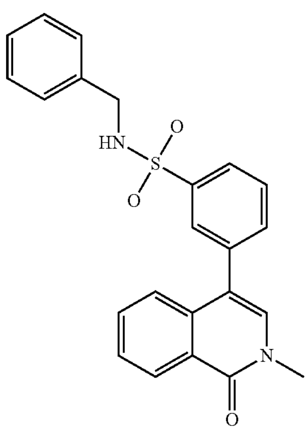 [SMILES: Cn1cc(-c2cccc(S(O)(O)NCc3ccccc3)c2)c2ccccc2c1=O] | N-benayl-3-(2-methyl-1-oxoisoquinolin-4-yl)benzenesulfonamide |
| 28 | 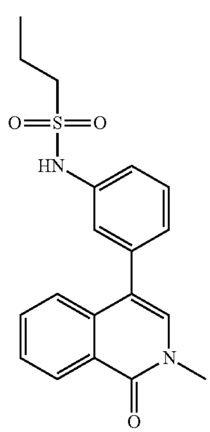 [SMILES: CCCS(=O)(=O)Nc1cccc(-c2cn(C)c(=O)c3ccccc23)c1] | N-[3-(2-methyl-1-oxoisoquinolin-4-yl)phenyl]propane-1-sulfonamide |

TABLE 1-continued

| Chemical Synthesis Example | Structure | Name |
|---|---|---|
| 29 | 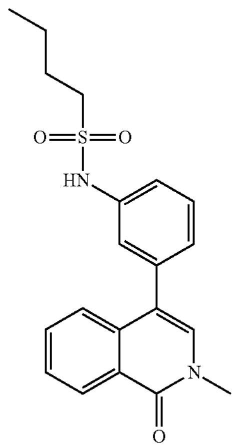 [SMILES: CCCCS(=O)(=O)Nc1cccc(-c2cn(C)c(=O)c3ccccc23)c1] | N-[3-(2-methyl-1-oxoisoquinolin-4-yl)phenyl]butane-1-sulfonamide |
| 30 | 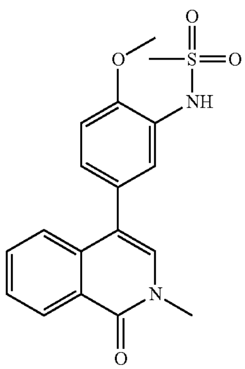 [SMILES: COc1ccc(-c2cn(C)c(=O)c3ccccc23)cc1NS(C)(=O)=O] | N-[2-methoxy-5-(2-methyl-1-oxoisoquinolin-4-yl)phenyl]methanesulfonamide |
| 31 | 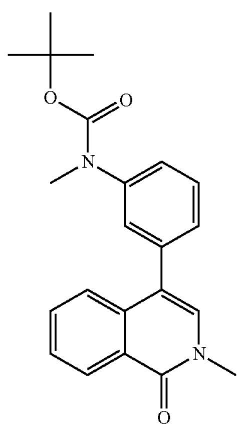 [SMILES: CN(C(=O)OC(C)(C)C)c1cccc(-c2cn(C)c(=O)c3ccccc23)c1] | tert-butyl N-methyl-N-[3-(2-methyl-1-oxoisoquinolin-4-yl)phenyl]carbamate |
| 32 | 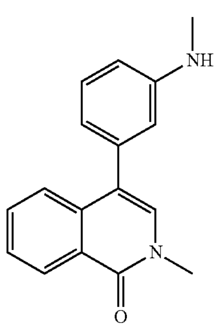 [SMILES: CNc1cccc(-c2cn(C)c(=O)c3ccccc23)c1] | 2-methyl-4-[3-(methylamino)phenyl]isoquinolin-1-one |

TABLE 1-continued

| Chemical Synthesis Example | Structure | Name |
|---|---|---|
| 33 | 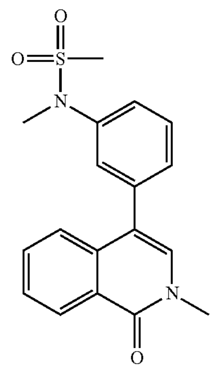 [SMILES: CN(c1cccc(-c2cn(C)c(=O)c3ccccc23)c1)S(C)(=O)=O] | N-methyl-N-[3-(2-methyl-1-oxoisoquinolin-4-yl)phenyl]methanesulfonamide |
| 34 | 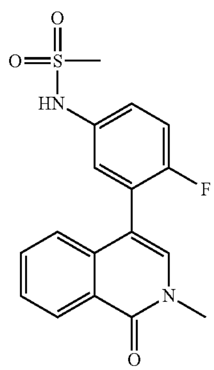 [SMILES: Cn1cc(-c2cc(NS(C)(=O)=O)ccc2F)c2ccccc2c1=O] | N-[4-fluoro-3-(2-methyl-1-oxoisoquinolin-4-yl)phenyl]methanesulfonamide |
| 35 | 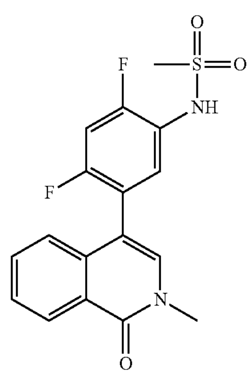 [SMILES: Cn1cc(-c2cc(NS(C)(=O)=O)c(F)cc2F)c2ccccc2c1=O] | N-[2,4-difluoro-5-(2-methyl-1-oxoisoquinolin-4-yl)phenyl]methanesulfonamide |
| 36 | 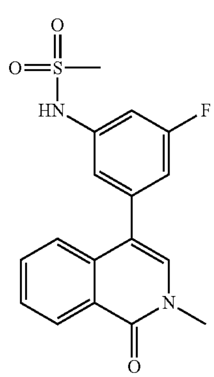 [SMILES: Cn1cc(-c2cc(F)cc(NS(C)(=O)=O)c2)c2ccccc2c1=O] | N-[3-fluoro-5-(2-methyl-1-oxoisoquinolin-4-yl)phenyl]methanesulfonamide |

TABLE 1-continued
| Chemical Synthesis Example | Structure | Name |
|---|---|---|
| 37 | 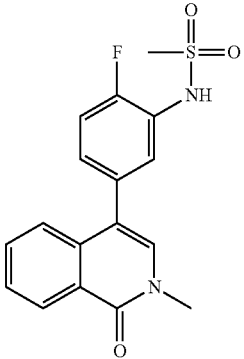 [SMILES: Cn1cc(-c2ccc(F)c(NS(C)(=O)=O)c2)c2ccccc2c1=O] | N-[2-fluoro-5-(2-methyl-1-oxoisoquinolin-4-yl)phenyl]methanesulfonamide |
| 38 | 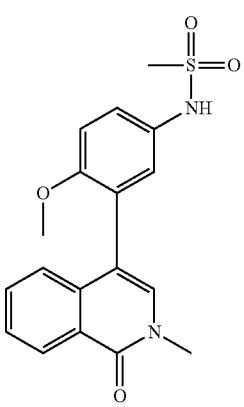 [SMILES: COc1ccc(NS(C)(=O)=O)cc1-c1cn(C)c(=O)c2ccccc12] | N-[4-chloro-3-(2-methyl-1-oxoisoquinolin-4-yl)phenyl]methanesulfonamide |
| 39 | 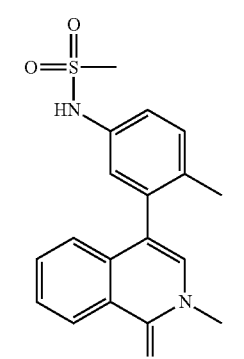 | N-[4-methyl-3-(2-methyl-1-oxoisoquinolin-4-yl)phenyl]methanesulfonamide |
| 40 | 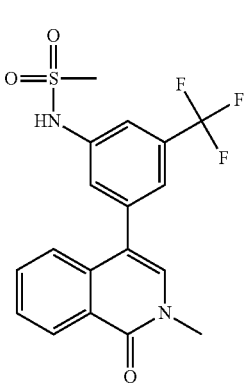 [SMILES: Cn1cc(-c2cc(NS(C)(=O)=O)cc(C(F)(F)F)c2)c2ccccc2c1=O] | N-[3-(2-methyl-1-oxoisoquinolin-4-yl)-5-(trifluoromethyl)phenyl]methanesulfonamide |

TABLE 1-continued

| Chemical Synthesis Example | Structure | Name |
|---|---|---|
| 41 | 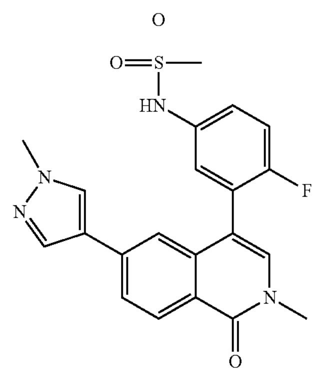 | N-[4-fluoro-3-[2-methyl-6-(1-methylpyrazol-4-yl)-1-oxoisoquinolin-4-yl]phenyl]methanesulfonamide |
| 42 | 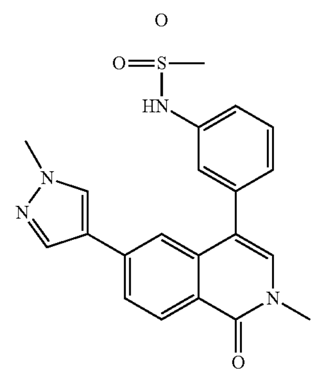 | N-[3-[2-methyl-6-(1-methylpyrazol-4-yl)-1-oxoisoquinolin-4-yl]phenyl]methanesulfonamide |
| 43 | 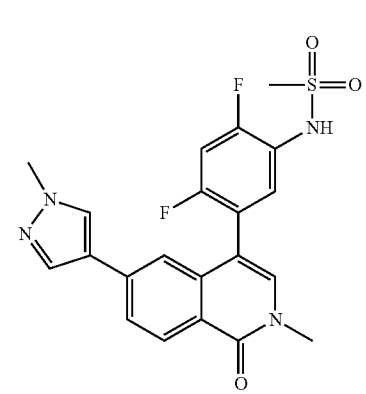 [SMILES: Cn1cc(-c2ccc3c(=O)n(C)cc(-c4cc(NS(C)(=O)=O)c(F)cc4F)c3c2)cn1] | N-[2,4-difluoro-5[2-methyl-6-(1-methylpyrazol-4-yl)-1-oxoisoquinolin-4-yl]phenyl]methanesulfonamide |
| 44 | 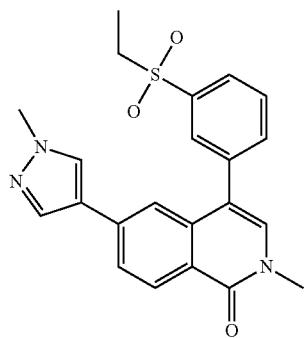 [SMILES: CCS(O)(O)c1cccc(-c2cn(C)c(=O)c3ccc(-c4cnn(C)c4)cc23)c1] | 4(3-ethylsulfonylphenyl)-2-methyl-6-(1-methylpyrazol-4-yl)isoquinolin-1-one |

TABLE 1-continued

| Chemical Synthesis Example | Structure | Name |
|---|---|---|
| 45 | 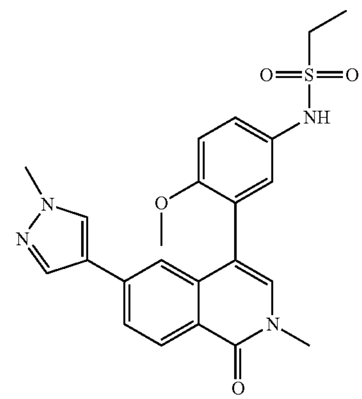 [SMILES: CCS(=O)(=O)Nc1ccc(OC)c(-c2cn(C)c(=O)c3ccc(-c4cnn(C)c4)cc23)c1] | N-[4-chloro-3-[2-methyl-6-(1-methylpyrazol-4-yl)-1-oxoisoquinolin-4-yl]phenyl]ethanesulfonamide |
| 46 | 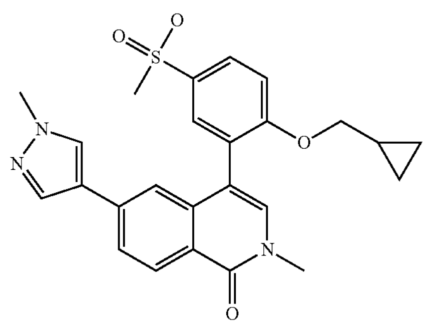 | 4-[2-(cyclopropylmethoxy)-5-methylsulfonylphenyl]-2-methyl-6-1-methylpyrazol-4-yl)isoquinolin-1-one |
| 47 | 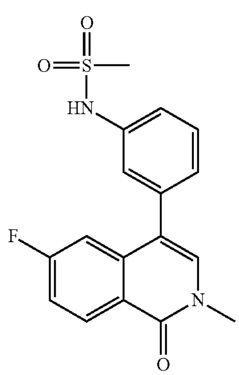 [SMILES: Cn1cc(-c2cccc(NS(C)(=O)=O)c2)c2cc(F)ccc2c1=O] | N-[3-(6-fluoro-2-methyl-1-oxoisoquinolin-4-yl)phenyl]methanesulfonamide |
| 48 | 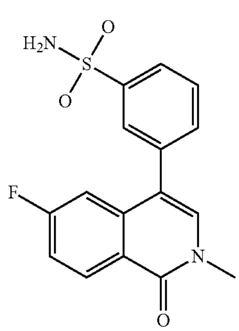 [SMILES: Cn1cc(-c2cccc(S(N)(O)O)c2)c2cc(F)ccc2c1=O] | 3-(6-fluoro-2-methyl-1-oxoisoquinolin-4-yl)benzenesulfonamide |

TABLE 1-continued
| Chemical Synthesis Example | Structure | Name |
|---|---|---|
| 49 | 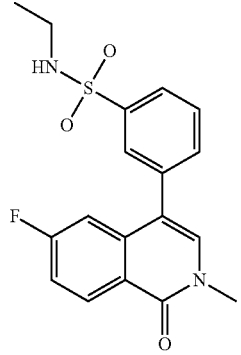 [SMILES: CCNS(O)(O)c1cccc(-c2cn(C)c(=O)c3ccc(F)cc23)c1] | N-ethyl-3-(6-fluoro-2-methyl-1-oxoisoquinolin-4-yl)benzenesulfonamide |
| 50 | 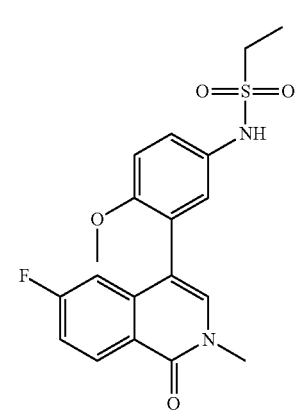 [SMILES: CCS(=O)(=O)Nc1ccc(OC)c(-c2cn(C)c(=O)c3ccc(F)cc23)c1] | N-[4-chloro-3-(6-fluoro-2-methyl-oxoisoquinolin-4-yl)phenyl]ethanesulfonamide |
| 51 | 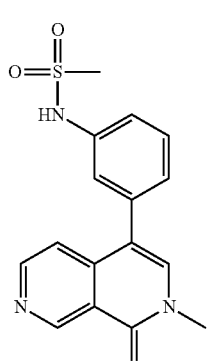 | N-[3-(2-methyl-1-oxo-2,7-naphthyridin-4-yl)phenyl]methanesulfonamide |
| 52 | 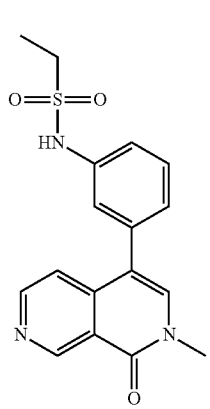 [SMILES: CCS(=O)(=O)Nc1cccc(-c2cn(C)c(=O)c3cnccc23)c1] | N-[3-(2-methyl-1-oxo-2,7-naphthyridin-4-yl)phenyl]ethanesulfonamide |

TABLE 1-continued
| Chemical Synthesis Example | Structure | Name |
|---|---|---|
| 53 | 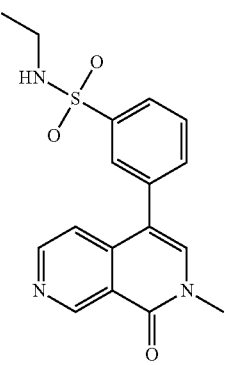 | N-ethyl-3-(2-methyl-1-oxo-2,7-naphthyridin-4-yl)benzenesulfonamide |
| 54 | 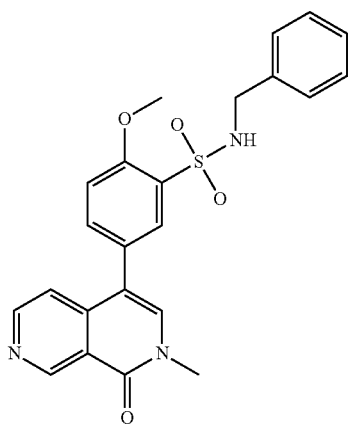 [SMILES: COc1ccc(-c2cn(C)c(=O)c3cnccc23)cc1S(O)(O)NCc1ccccc1] | N-benzyl-2-methoxy-5-(2-methyl-1-oxo-2,7-naphthyridin-4-yl)benzenesulfonamide |
| 55 | 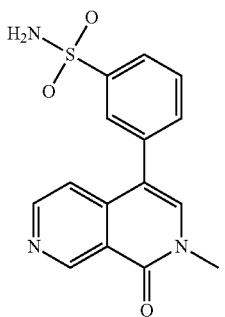 | 3-(2-methyl-1-oxo-2,7-naphthyridin-4-yl)benzenesulfonamide |
| 56 | 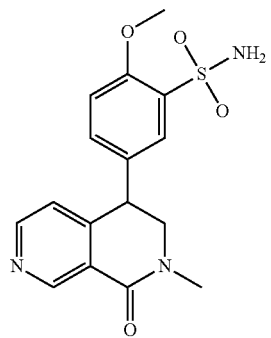 [SMILES: COc1ccc(C2CN(C)C(=O)c3cnccc32)cc1S(N)(O)O] | 2-methoxy-5-(2-methyl-1-oxo-2,7-naphthyridin-4-yl)benzenesulfonamide |

TABLE 1-continued

| Chemical Synthesis Example | Structure | Name |
|---|---|---|
| 57 | 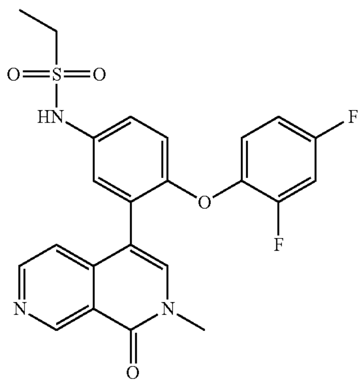 [SMILES: CCS(=O)(=O)Nc1ccc(Oc2ccc(F)cc2F)c(-c2cn(C)c(=O)c3cnccc23)c1] | N-[4-(2,4-difluorophenoxy)-3-(2-methyl-1-oxo-2,7-naphthyridin-4-yl)phenyl]ethanesulfonamide |
| 58 | 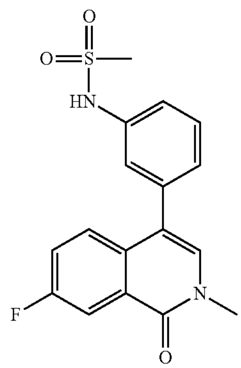 [SMILES: Cn1cc(-c2cccc(NS(C)(=O)=O)c2)c2ccc(F)cc2c1=O] | N-[3-(7-fluoro-2-methyl-1-oxoisoquinolin-4-yl)phenyl]methanesulfonamide |
| 59 | 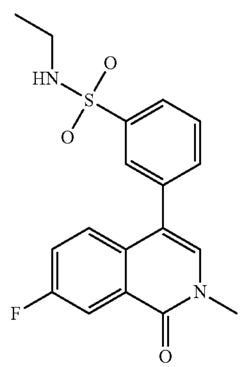 [SMILES: CCNS(O)(O)c1cccc(-c2cn(C)c(=O)c3cc(F)ccc23)c1] | N-ethyl-3-(7-fluoro-2-methyl-1-oxoisoquinolin-4-yl)benzenesulfonamide |
| 60 | 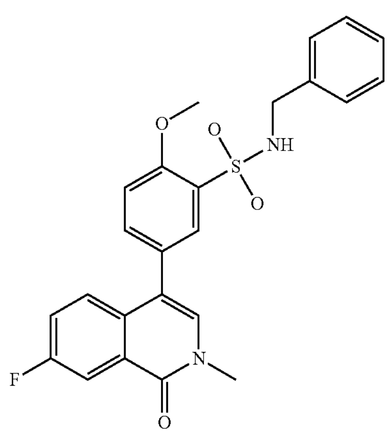 [SMILES: COc1ccc(-c2cn(C)c(=O)c3cc(F)ccc23)cc1S(O)(O)NCc1ccccc1] | N-benzyl-5-(7-fluoro-2-methyl-1-oxoisoquinolin-4-yl)-2-methoxybenzenesulfonamide |

TABLE 1-continued

| Chemical Synthesis Example | Structure | Name |
|---|---|---|
| 61 | 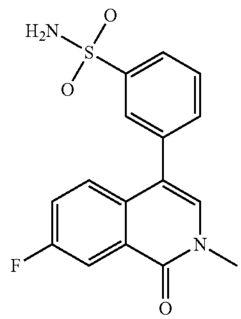 [SMILES: Cn1cc(-c2cccc(S(N)(O)O)c2)c2ccc(F)cc2c1=O] | 3-(7-fluoro-2-methyl-1-oxoisoquinolin-4-yl)benzenesulfonamide |
| 62 | 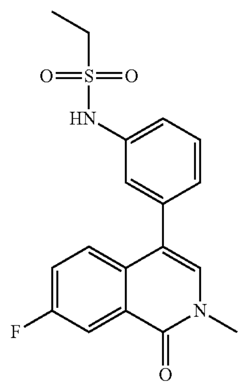 [SMILES: CCS(=O)(=O)Nc1cccc(-c2cn(C)c(=O)c3cc(F)ccc23)c1] | N-[3-(7-fluoro-2-methyl-1-oxoisoquinolin-4-yl)phenyl]ethanesulfonamide |
| 63 | 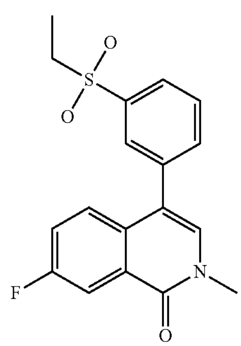 [SMILES: CCS(O)(O)c1cccc(-c2cn(C)c(=O)c3cc(F)ccc23)c1] | 4-(3-ethylsulfonylphenyl)-7-fluoro-2-methylisoquinolin-1-one |
| 64 | 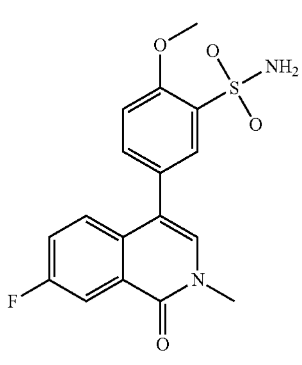 [SMILES: COc1ccc(-c2cn(C)c(=O)c3cc(F)ccc23)cc1S(N)(O)O] | 5-(7-fluoro-2-methyl-1-oxoisoquinolin-4-yl)-2-methoxybenzenesulfonamide |

TABLE 1-continued

| Chemical Synthesis Example | Structure | Name |
|---|---|---|
| 65 | 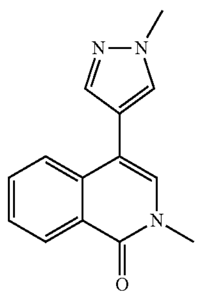 [SMILES: Cn1cc(-c2cn(C)c(=O)c3ccccc23)cn1] | 2-methyl-4-(1-methylpyrazol-4-yl)isoquinolin-1-one |
| 66 | 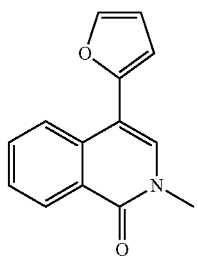 [SMILES: Cn1cc(-c2ccco2)c2ccccc2c1=O] | 4-(furan-2-yl)-2-methylisoquinolin-1-one |
| 67 | 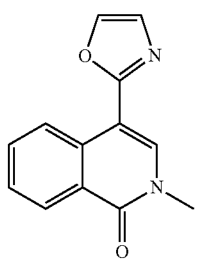 [SMILES: Cn1cc(-c2ncco2)c2ccccc2c1=O] | 2-methyl-4-(1,3-oxazol-2-yl)isoquinolin-1-one |
| 68 | 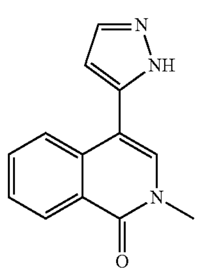 [SMILES: Cn1cc(-c2ccn[nH]2)c2ccccc2c1=O] | 2-methyl-4-(1H-pyrazol-5-yl)isoquinolin-1-one |
| 69 | 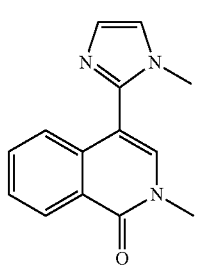 [SMILES: Cn1ccnc1-c1cn(C)c(=O)c2ccccc12] | 2-methyl-4-(1-methylimidazol-2-yl)isoquinolin-1-one |

TABLE 1-continued

| Chemical Synthesis Example | Structure | Name |
|---|---|---|
| 70 | 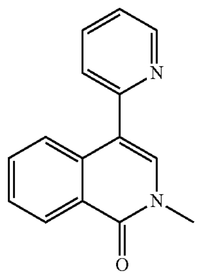 [SMILES: Cn1cc(-c2ccccn2)c2ccccc2c1=O] | 2-methyl-4-pyridin-2-ylisoquinolin-1-one |
| 71 | 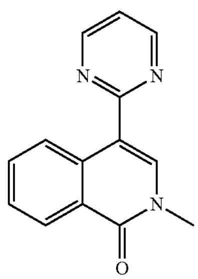 [SMILES: Cn1cc(-c2ncccn2)c2ccccc2c1=O] | 2-methyl-4-pyrimidin-2-ylisoquinolin-1-one |
| 72 | 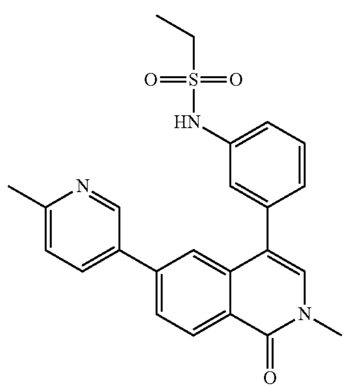 | N-[3-[2-methyl-6-(6-methylpyridin-3-yl)-1-oxoisoquinolin-4-yl]phenyl]ethanesulfonamide |
| 73 | 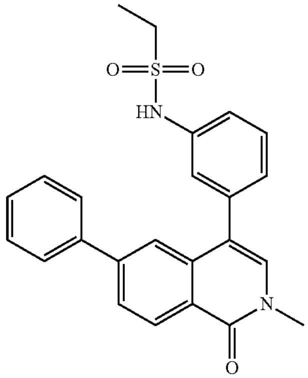 [SMILES: CCS(=O)(=O)Nc1cccc(-c2cn(C)c(=O)c3ccc(-c4ccccc4)cc23)c1] | N-[3-(2-methyl-1-oxo-6-phenylisoquinolin-4-yl)phenyl]ethanesulfonamide |

TABLE 1-continued

| Chemical Synthesis Example | Structure | Name |
|---|---|---|
| 74 | 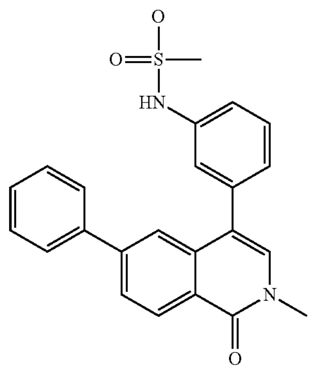 | N-[3-(2-methyl-1-oxo-6-phenylisoquinolin-4-yl)phenyl]methanesulfonamide |
| 75 | 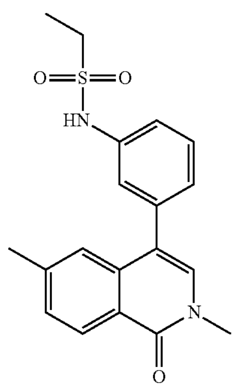 | N-[3-(2,6-dimethyl-1-oxoisoquinolin-4-yl)phenyl]ethanesulfonamide |
| 76 | 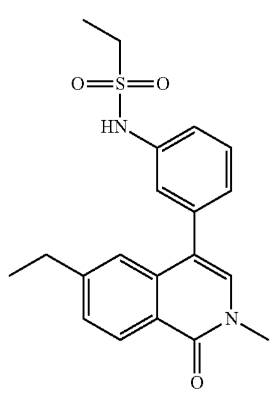 [SMILES: CCc1ccc2c(=O)n(C)cc(-c3cccc(NS(=O)(=O)CC)c3)c2c1] | N-[3-(6-ethyl-2-methyl-1-oxoisoquinolin-4-yl)phenyl]ethanesulfonamide |
| 77 | 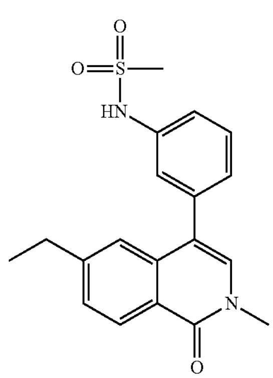 [SMILES: CCc1ccc2c(=O)n(C)cc(-c3cccc(NS(C)(=O)=O)c3)c2c1] | N-[3-(6-ethyl-2-methyl-1-oxoisoquinolin-4-yl)phenyl]methanesulfonamide |

TABLE 1-continued

| Chemical Synthesis Example | Structure | Name |
| --- | --- | --- |
| 78 | 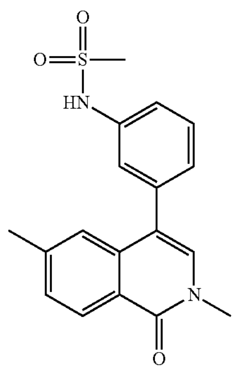 | N-[3-(2,6-dimethyl-1-oxoisoquinolin-4-yl)phenyl]methanesulfonamide |
| 79 | 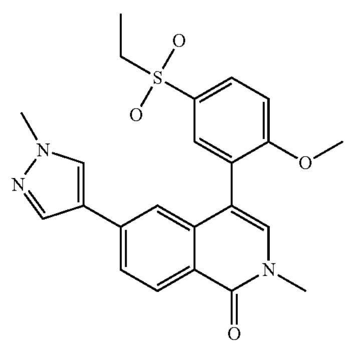 [SMILES: CCS(O)(O)c1ccc(OC)c(-c2cn(C)c(=O)c3ccc(-c4cnn(C)c4)cc23)c1] | 4-(5-ethylsulfonyl-2-methoxyphenyl)-2-methyl-6-(1-methylpyrazol-4-yl)isoquinolin-1-one |
| 80 | 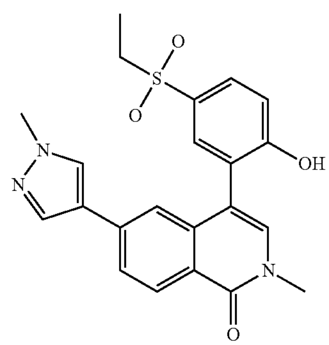 [SMILES: CCS(O)(O)c1ccc(O)c(-c2cn(C)c(=O)c3ccc(-c4cnn(C)c4)cc23)c1] | 4-(5-ethylsulfonyl-2-hydroxyphenyl)-2-methyl-6-(1-methylpyrazol-4-yl)isoquinolin-1-one |
| 81 | 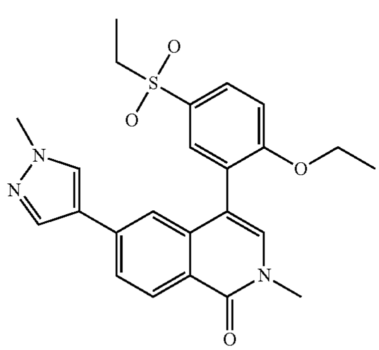 [SMILES: CCOc1ccc(S(O)(O)CC)cc1-c1cn(C)c(=O)c2ccc(-c3cnn(C)c3)cc12] | 4-(2-ethoxy-5-ethylsulfonylphenyl)-2-methyl-6-(1-methylpyrazol-4-yl)isoquinolin-1-one |

TABLE 1-continued

| Chemical Synthesis Example | Structure | Name |
|---|---|---|
| 82 | 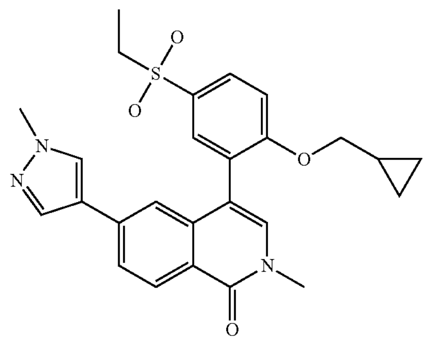 [SMILES: CCS(O)(O)c1ccc(OCC2CC2)c(-c2cn(C)c(=O)c3ccc(-c4cnn(C)c4)cc23)c1] | 4-[2-(cyclopropylmethoxy)-5-ethylsulfonylphenyl]-2-methyl-6-(1-methylpyrazol-4-yl)isoquinolin-1-one |
| 83 | 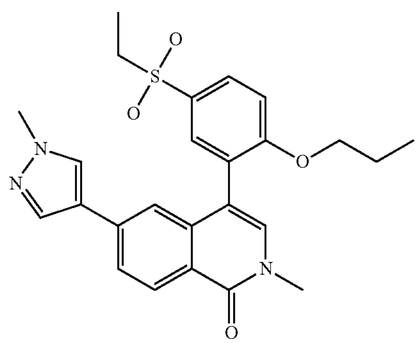 [SMILES: CCCOc1ccc(S(O)(O)CC)cc1-c1cn(C)c(=O)c2ccc(-c3cnn(C)c3)cc12] | 4-(5-ethylsulfonyl-2-propoxyphenyl)-2-methyl-6-(1-methylpyrazol-4-yl)isoquinolin-1-one |
| 84 | 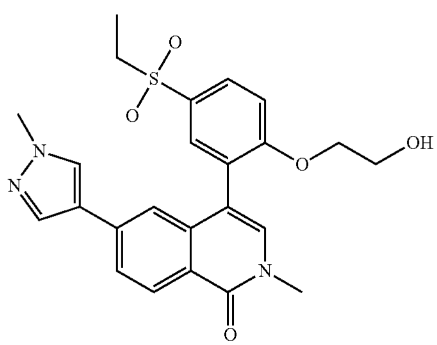 [SMILES: CCS(O)(O)c1ccc(OCCO)c(-c2cn(C)c(=O)c3ccc(-c4cnn(C)c4)cc23)c1] | 4-[5-ethylsulfonyl-2(2-hydroxyethoxy)phenyl]-2-methyl-6(1-methylpyrazol-4-yl)isoquinolin-1-one |
| 85 | 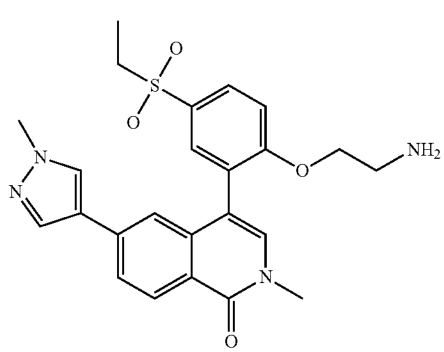 [SMILES: CCS(O)(O)c1ccc(OCCN)c(-c2cn(C)c(=O)c3ccc(-c4cnn(C)c4)cc23)c1] | 4-[2-(2-aminoethoxy)-5-ethylsulfonylphenyl]-2-methyl-6-(1-methylpyrazol-4-yl)isoquinolin-1-one |

TABLE 1-continued

| Chemical Synthesis Example | Structure | Name |
|---|---|---|
| 86 | 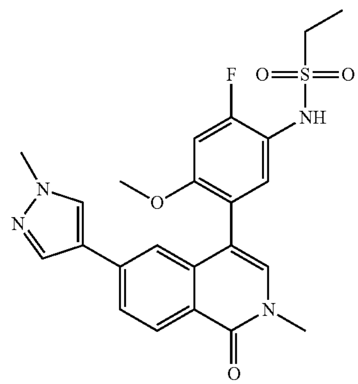 [SMILES: CCS(=O)(=O)Nc1cc(-c2cn(C)c(=O)c3ccc(-c4cnn(C)c4)cc23)c(OC)cc1F] | N-[2-fluoro-4-methoxy-5-[2-methyl-6-(1-methylpyrazol-4-yl)-1-oxoisoquinolin-4-yl]phenyl]ethanesulfonamide |
| 87 | 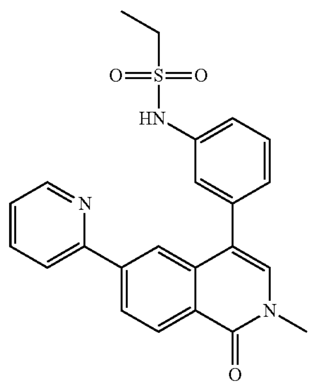 [SMILES: CCS(=O)(=O)Nc1cccc(-c2cn(C)c(=O)c3ccc(-c4ccccn4)cc23)c1] | N-[3-(2-methyl-1-oxo-6-pyridin-2-ylisoquinolin-4-yl)phenyl]ethanesulfonamide |
| 88 | 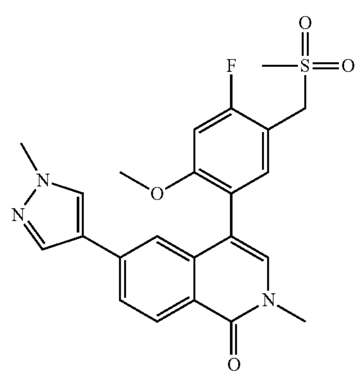 [SMILES: COc1cc(F)c(CS(C)(=O)=O)cc1-c1cn(C)c(=O)c2ccc(-c3cnn(C)c3)cc12] | 4-[4-fluoro-2-methoxy-5-(methylsulfonylmethyl)phenyl]-2-methyl-6-(1-methylpyrazol-4-yl)isoquinolin-1-one |
| 89 | 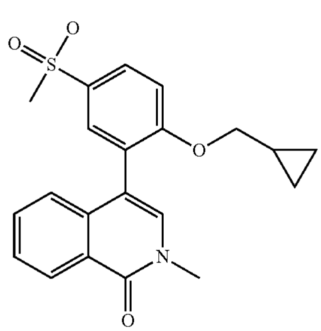 | 4-[2-(cyclopropylmethoxy)-5-methylsulfonylphenyl]-2-methylisoquinolin-1-one |

TABLE 1-continued

| Chemical Synthesis Example | Structure | Name |
|---|---|---|
| 90 | 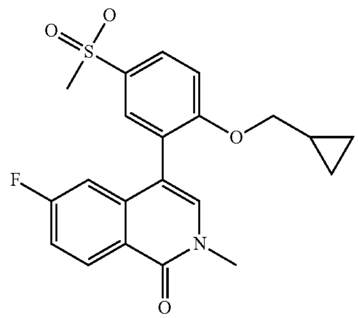 | 4-[2-(cyclopropylmethoxy)-5-methylsulfonylphenyl]-6-fluoro-2-methylisoquinolin-1-one |
| 91 | 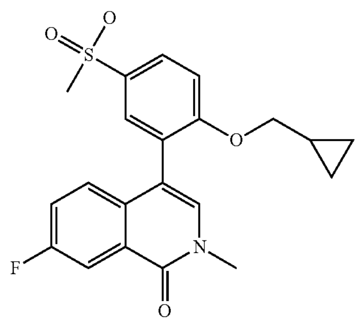 | 4-[2-(cyclopropylmethoxy)-5-methylsulfonylphenyl]-7-fluoro-2-methylisoquinolin-1-one |
| 92 | 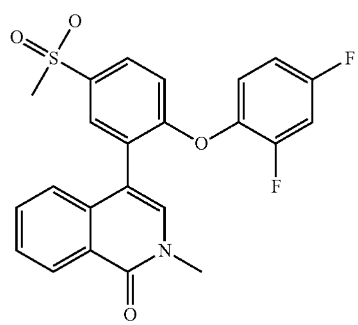 | 4-[2-(2,4-difluorophenoxy)-5-methylsulfonylphenyl]-2-methylisoquinolin-1-one |
| 93 | 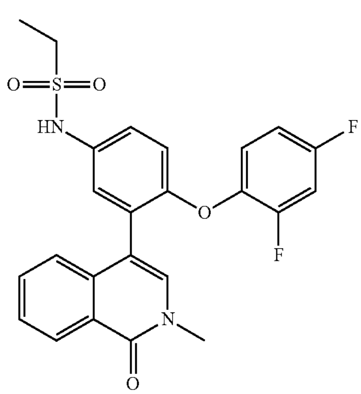 [SMILES: CCS(=O)(=O)Nc1ccc(Oc2ccc(F)cc2F)c(-c2cn(C)c(=O)c3ccccc23)c1] | N-[4-(2,4-difluorophenoxy)-3-(2-methyl-1-oxoisoquinolin-4-yl)phenyl]ethanesulfonamide |

TABLE 1-continued

| Chemical Synthesis Example | Structure | Name |
|---|---|---|
| 94 | 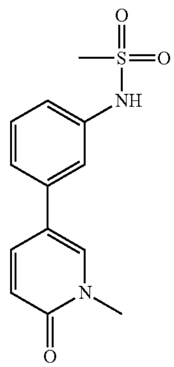 [SMILES: Cn1cc(-c2cccc(NS(C)(=O)=O)c2)ccc1=O] | N-[3-(1-methyl-6-oxopyridin-3-yl)phenyl]methanesulfonamide |
| 95 | 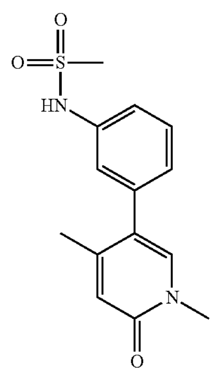 [SMILES: Cc1cc(=O)n(C)cc1-c1cccc(NS(C)(=O)=O)c1] | N-[3-(1,4-dimethyl-6-oxopyridin-3-yl)phenyl]methanesulfonamide |
| 96 | 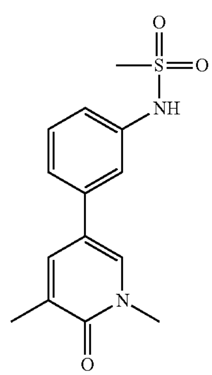 [SMILES: Cc1cc(-c2cccc(NS(C)(=O)=O)c2)cn(C)c1=O] | N-[3-(1,5-dimethyl-6-oxopyridin-3-yl)phenyl]methanesulfonamide |
| 97 | 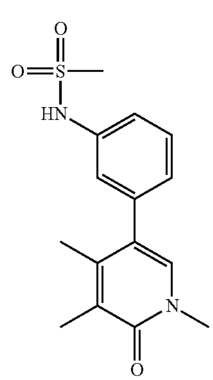 [SMILES: Cc1c(-c2cccc(NS(C)(=O)=O)c2)cn(C)c(=O)c1C] | N-[3-(1,4,5-trimethyl-6-oxopyridin-3-yl)phenyl]methanesulfonamide |

TABLE 1-continued

| Chemical Synthesis Example | Structure | Name |
|---|---|---|
| 98 | 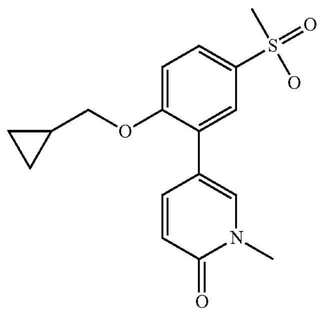 | 5-[2-(cyclopropylmethoxy)-5-methylsulfonylphenyl]-1-methylpyridin-2-one |
| 99 | 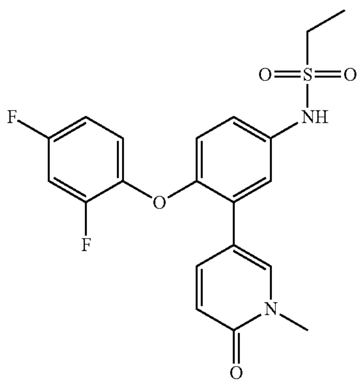 [SMILES: CCS(=O)(=O)Nc1ccc(Oc2ccc(F)cc2F)c(-c2ccc(=O)n(C)c2)c1] | N-[4-(2,4-difluorophenoxy)-3-(1-methyl-6-oxopyridin-3-yl)phenyl]ethanesulfonamide |
| 100 | 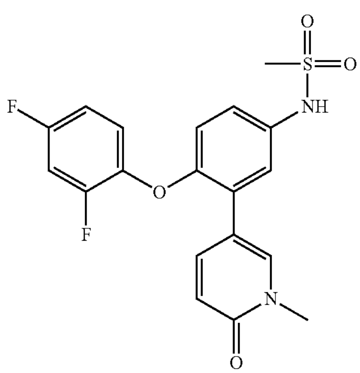 [SMILES: Cn1cc(-c2cc(NS(C)(=O)=O)ccc2Oc2ccc(F)cc2F)ccc1=O] | N-[4-(2,4-difluorophenoxy)-3-(1-methyl-6-oxopyridin-3-yl)phenyl]methanesulfonamide |
| 101 | 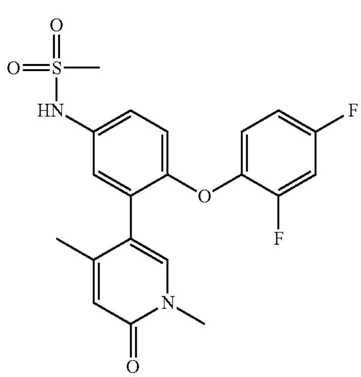 [SMILES: Cc1cc(=O)n(C)cc1-c1cc(NS(C)(=O)=O)ccc1Oc1ccc(F)cc1F] | N-[4-(2,4-difluorophenoxy)-3-(1,4-dimethyl-6-oxopyridin-3-yl)phenyl]methanesulfonamide |

TABLE 1-continued

| Chemical Synthesis Example | Structure | Name |
|---|---|---|
| 102 | 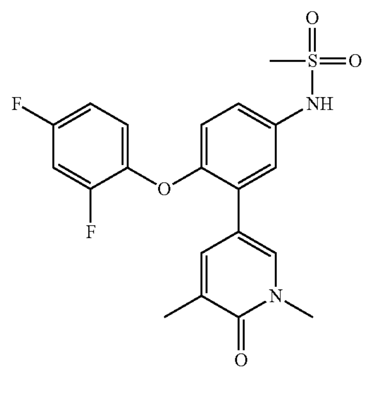 [SMILES: Cc1cc(-c2cc(NS(C)(=O)=O)ccc2Oc2ccc(F)cc2F)cn(C)c1=O] | N-[4-(2,4-difluorophenoxy)-3-(1,5-dimethyl-6-oxopyridin-3-yl)phenyl]methanesulfonamide |
| 103 | 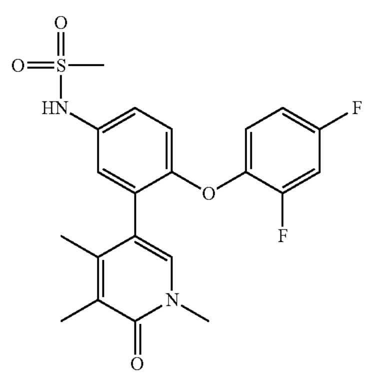 [SMILES: Cc1c(-c2cc(NS(C)(=O)=O)ccc2Oc2ccc(F)cc2F)cn(C)c(=O)c1C] | N-[4-(2,4-difluorophenoxy)-3-(1,4,5-trimethyl-6-oxopyridin-3-yl)phenyl]methanesulfonamide |
| 104 | 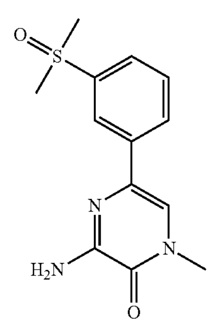 | 3-amino-1-methyl-5-(3-methylsulfonylphenyl)pyrazin-2-one |
| 105 | 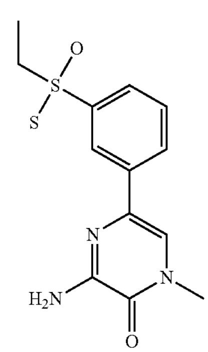 [SMILES: CCS(O)(S)c1cccc(-c2cn(C)c(=O)c(N)n2)c1] | 3-amino-5-(3-ethylsulfonylphenyl)-1-methylpyrazin-2-one |

TABLE 1-continued

| Chemical Synthesis Example | Structure | Name |
|---|---|---|
| 106 | 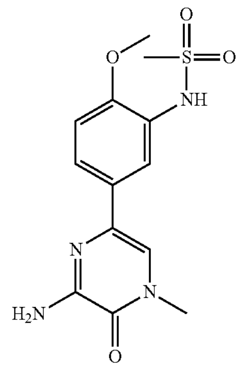 [SMILES: COc1ccc(-c2cn(C)c(=O)c(N)n2)cc1NS(C)(=O)=O] | N-[5-(6-amino-4-methyl-5-oxopyrazin-2-yl)-2-methoxyphenyl]methanesulfonamide |
| 107 | 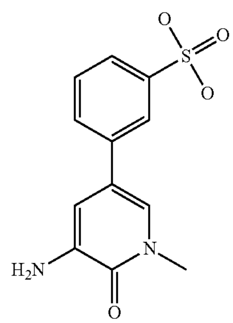 | 3-amino-1-methyl-5-(3-methylsulfonylphenyl)pyridin-2-one |
| 108 | 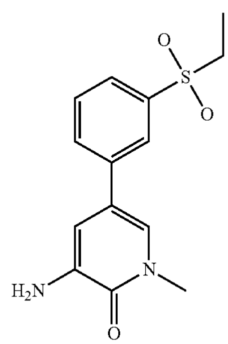 [SMILES: CCS(O)(O)c1cccc(-c2cc(N)c(=O)n(C)c2)c1] | 3-amino-5-(3-ethylsulfonylphenyl)-1-methylpyridin-2-one |
| 109 | 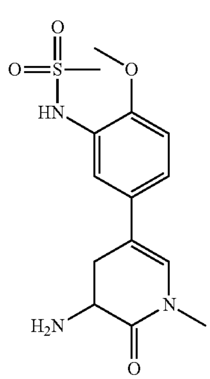 [SMILES: COc1ccc(C2=CN(C)C(=O)C(N)C2)cc1NS(C)(=O)=O] | N-[5-(5-amino-1-methyl-6-oxopyridin-3-yl)-2-methoxyphenyl]methanesulfonamide |

TABLE 1-continued

| Chemical Synthesis Example | Structure | Name |
|---|---|---|
| 110 | 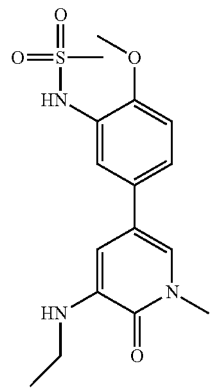 [SMILES: CCNc1cc(-c2ccc(OC)c(NS(C)(=O)=O)c2)cn(C)c1=O] | N-[2-methoxy-5-[1-methyl-5-(methylamino)-6-oxopyridin-3-yl]phenyl]methanesulfonamide |
| 111 | 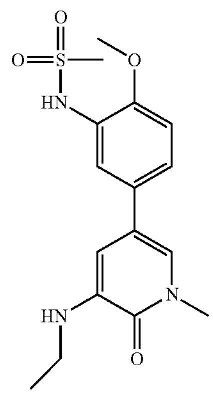 [SMILES: CCNc1cc(-c2ccc(OC)c(NS(C)(=O)=O)c2)cn(C)c1=O] | N-[5-[5-(ethylamino)-1-methyl-6-oxopyridin-3-yl]-2-methoxyphenyl]methanesulfonamide |
| 112 | 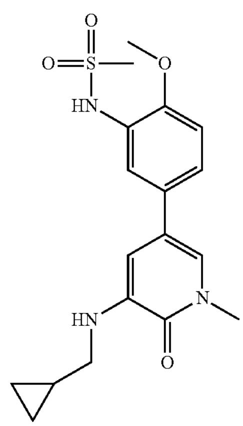 [SMILES: COc1ccc(-c2cc(NCC3CC3)c(=O)n(C)c2)cc1NS(C)(=O)=O] | N-[5-[5-(cyclopropylmethylamino)-1-methyl-6-oxopyridin-3-yl]-2-methoxyphenyl]methanesulfonamide |
| 113 | 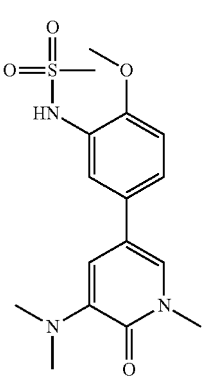 [SMILES: COc1ccc(-c2cc(N(C)C)c(=O)n(C)c2)cc1NS(C)(=O)=O] | N-[5-[5-(dimethylamino)-1-methyl-6-oxopyridin-3-yl]-2-methoxyphenyl]methanesulfonamide |

TABLE 1-continued

| Chemical Synthesis Example | Structure | Name |
|---|---|---|
| 114 | 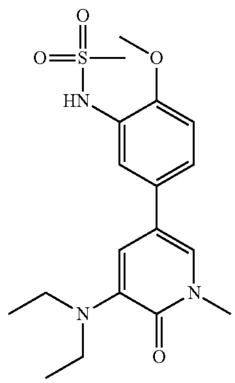 [SMILES: CCN(CC)c1cc(-c2ccc(OC)c(NS(C)(=O)=O)c2)cn(C)c1=O] | N-[5-[5-(diethylamino)-1-methyl-6-oxopyridin-3-yl]-2-methoxyphenyl]methanesulfonamide |
| 115 | 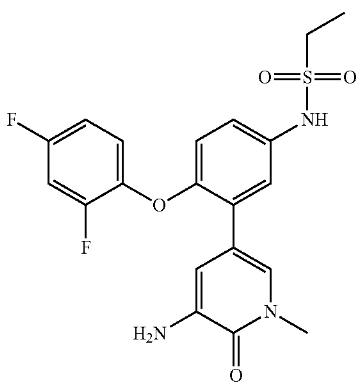 [SMILES: CCS(=O)(=O)Nc1ccc(Oc2ccc(F)cc2F)c(-c2cc(N)c(=O)n(C)c2)c1] | N-[3-(5-amino-1-methyl-6-oxopyridin-3-yl)-4-(2,4-difluorophenoxy)phenyl]ethanesulfonamide |
| 116 | 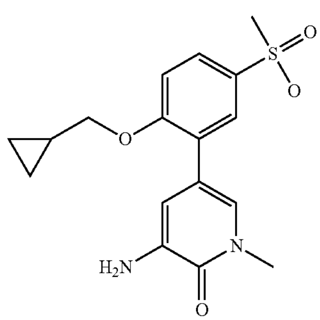 | 3-amino-5-[2-(cyclopropylmethoxy)-5-methylsulfonylphenyl]-1-methylpyridin-2-one |
| 117 | 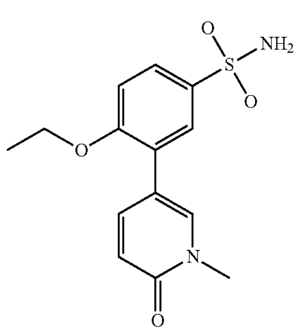 [SMILES: CCOc1ccc(S(N)(O)O)cc1-c1ccc(=O)n(C)c1] | 4-ethoxy-3-(1-methyl-6-oxopyridin-3-yl)benzenesulfonamide |

TABLE 1-continued

| Chemical Synthesis Example | Structure | Name |
|---|---|---|
| 118 | 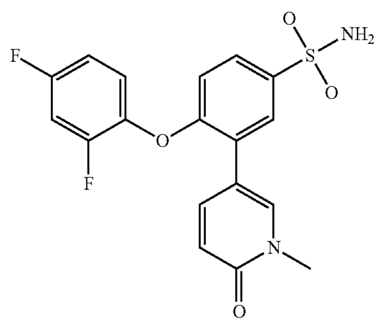 [SMILES: Cn1cc(-c2cc(S(N)(O)O)ccc2Oc2ccc(F)cc2F)ccc1=O] | 4-(2,4-difluorophenoxy)-3-(1-methyl-6-oxopyridin-3-yl)benzenesulfonamide |
| 119 | 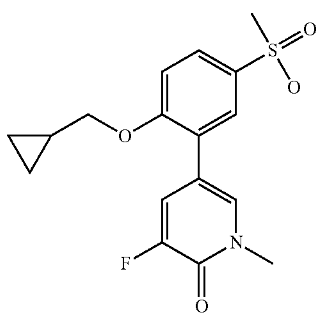 | 5-[2-(cyclopropylmethoxy)-5-methylsulfonylphenyl]-3-fluoro-1-methylpyridin-2-one |
| 120 | 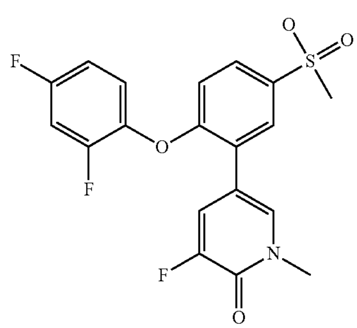 | 5-[2-(2,4-difluorophenoxy)-5-methylsulfonylphenyl]-3-fluoro-1-methylpyridin-2-one |
| 121 | 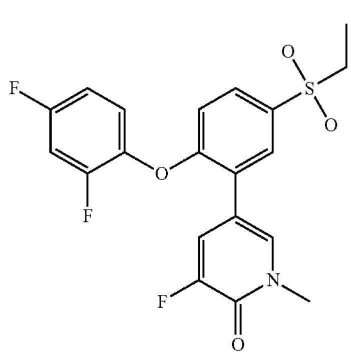 [SMILES: CCS(O)(O)c1ccc(Oc2ccc(F)cc2F)c(-c2cc(F)c(=O)n(C)c2)c1] | 5-[2-(2,4-difluorophenoxy)-5-ethylsulfonylphenyl]-3-fluoro-1-methylpyridin-2-one |

TABLE 1-continued
| Chemical Synthesis Example | Structure | Name |
|---|---|---|
| 122 | 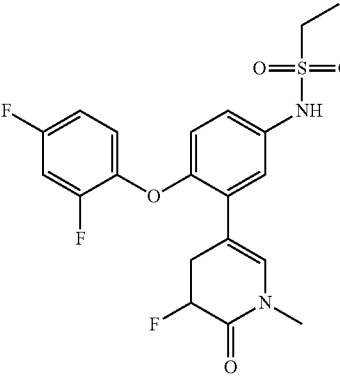 | N-[4-(2,4-difluorophenoxy)-3-(5-fluoro-1-methyl-6-oxopyridin-3-yl)phenyl]ethanesulfonamide |
| 123 | 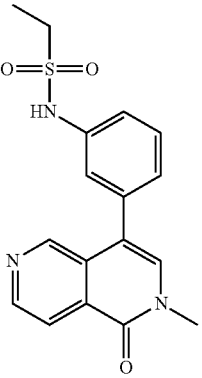 [SMILES: CCS(=O)(=O)Nc1cccc(-c2cn(C)c(=O)c3ccncc23)c1] | N-[3-(2-methyl-1-oxo-2,6-naphthyridin-4-yl)phenyl]ethanesulfonamide |
| 124 | 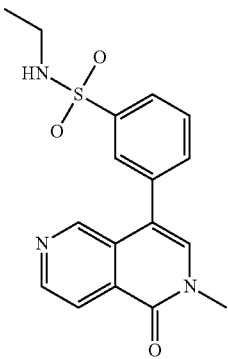 | N-ethyl-3-(2-methyl-1-oxo-2,6-naphthyridin-4-yl)benzenesulfonamide |
| 125 | 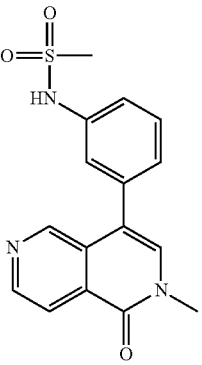 [SMILES: Cn1cc(-c2cccc(NS(C)(=O)=O)c2)c2cnccc2c1=O] | N-[3-(2-methyl-1-oxo-2,6-naphthyridin-4-yl)phenyl]methanesulfonamide |

TABLE 1-continued
| Chemical Synthesis Example | Structure | Name |
|---|---|---|
| 126 | 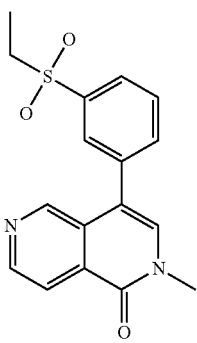 [SMILES: CCS(O)(O)c1cccc(-c2cn(C)c(=O)c3ccncc23)c1] | 4-(3-ethylsulfonylphenyl)-2-methyl-2,6-naphthyridin-1-one |
| 127 | 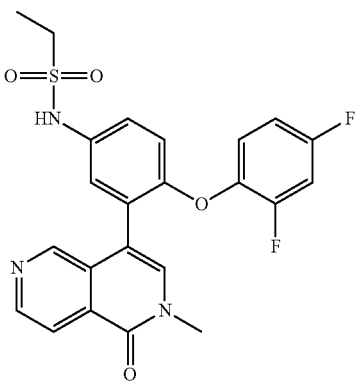 [SMILES: CCS(=O)(=O)Nc1ccc(Oc2ccc(F)cc2F)c(-c2cn(C)c(=O)c3ccncc23)c1] | N-[4-(2,4-difluorophenoxy)-3-(2-methyl-1-oxo-2,6-naphthyridin-4-yl)phenyl]ethanesulfonamide |
| 128 | 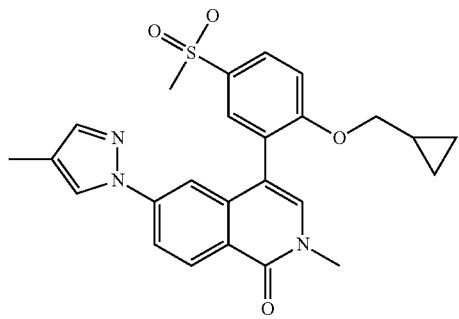 | 4-[2-(cyclopropylmethoxy)-5-methylsulfonylphenyl]-2-methyl-6-(4-methylpyrazol-1-yl)isoquinolin-1-one |
| 129 | 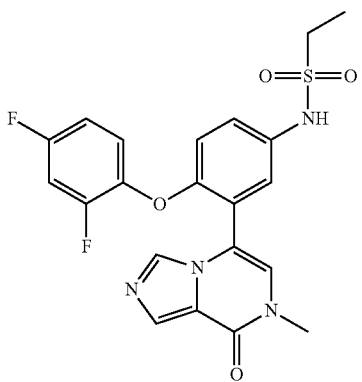 [SMILES: CCS(=O)(=O)Nc1ccc(Oc2ccc(F)cc2F)c(-c2cn(C)c(=O)c3cncn23)c1] | N-[4-(2,4-difluorophenoxy)-3-(7-methyl-8-oxoimidazo[1,5-a]pyrazin-5-yl)phenyl]ethanesulfonamide |

TABLE 1-continued

| Chemical Synthesis Example | Structure | Name |
|---|---|---|
| 130 | 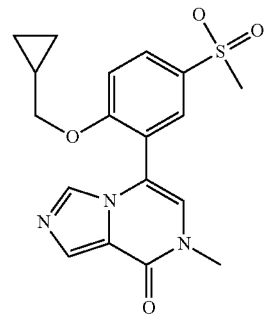 | 5-[2-(cyclopropylmethoxy)-5-methylsulfonylphenyl]-7-methylimidazo[1,5-a]pyrazin-8-one |
| 131 | 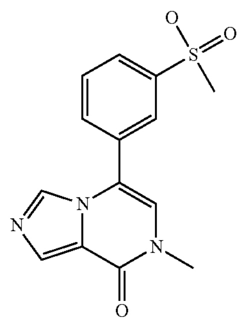 | 7-methyl-5-(3-methylsulfonylphenyl)imidazo[1,5-a]pyrazin-8-one |
| 132 | 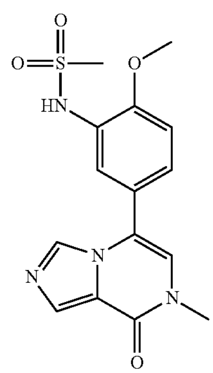 [SMILES: COc1ccc(-c2cn(C)c(=O)c3cncn23)cc1NS(C)(=O)=O] | N-[2-methoxy-5-(7-methyl-8-oxoimidazo[1,5-a]pyrazin-5-yl)phenyl]methanesulfonamide |
| 133 | 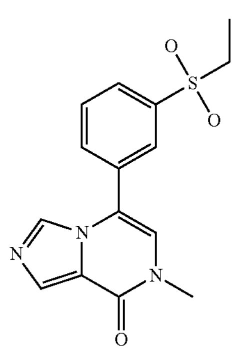 [SMILES: CCS(O)(O)c1cccc(-c2cn(C)c(=O)c3cncn23)c1] | 5-(3-ethylsulfonylphenyl)-7-methylimidazo[1,5-a]pyrazin-8-one |

TABLE 1-continued

| Chemical Synthesis Example | Structure | Name |
|---|---|---|
| 134 | 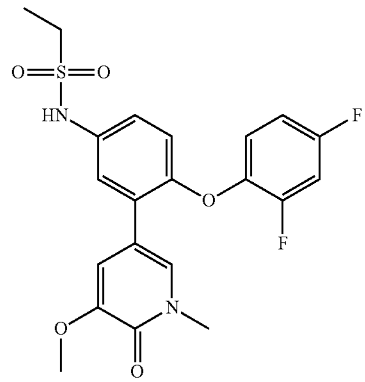 [SMILES: CCS(=O)(=O)Nc1ccc(Oc2ccc(F)cc2F)c(-c2cc(OC)c(=O)n(C)c2)c1] | N-[3-(5-chloro-1-methyl-6-oxopyridin-3-yl)-4-(2,4-difluorophenoxy)phenyl]ethanesulfonamide |
| 135 | 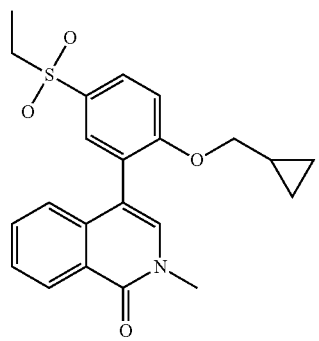 [SMILES: CCS(O)(O)c1ccc(OCC2CC2)c(-c2cn(C)c(=O)c3ccccc23)c1] | 4-[2-(cyclopropylmethoxy)-5-ethylsulfonylphenyl]-2-methylisoquinolin-1-one |
| 136 | 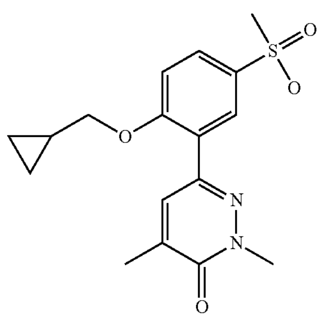 | 6-[2-(cyclopropylmethoxy)-5-methylsulfonylphenyl]-2,4-dimethylpyridazin-3-one |
| 137 | 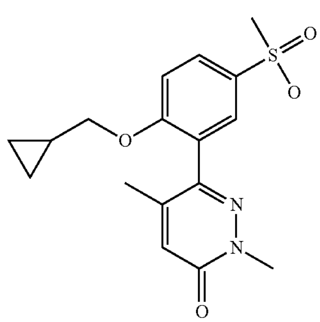 | 6-[2-(cyclopropylmethoxy)-5-methylsulfonylphenyl]-2,5-dimethylpyridazin-3-one |

TABLE 1-continued

| Chemical Synthesis Example | Structure | Name |
|---|---|---|
| 138 | 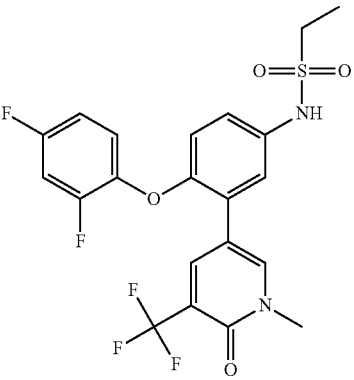 [SMILES: CCS(=O)(=O)Nc1ccc(Oc2ccc(F)cc2F)c(-c2cc(C(F)(F)F)c(=O)n(C)c2)c1] | N-[4-(2,4-difluorophenoxy)-3-[1-methyl-6-oxo-5-(trifluoromethyl)pyridin-3-yl]phenyl]ethanesulfonamide |
| 139 | 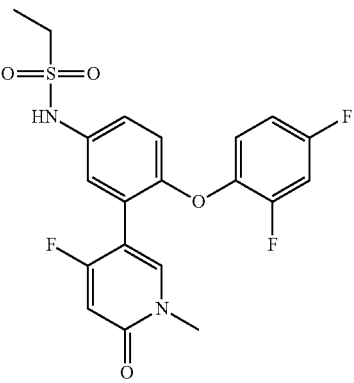 [SMILES: CCS(=O)(=O)Nc1ccc(Oc2ccc(F)cc2F)c(-c2cn(C)c(=O)cc2F)c1] | N-[4-(2,4-difluorophenoxy)-3-(4-fluoro-1-methyl-6-oxopyridin-3-yl)phenyl]ethanesulfonamide |
| 140 | 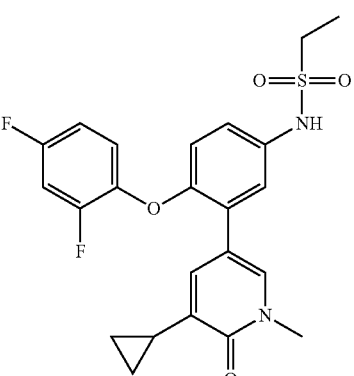 | N-[3-(5-cyclopropyl-1-methyl-6-oxopyridin-3-yl)-4-(2,4-difluorophenoxy)phenyl]ethanesulfonamide |
| 141 | 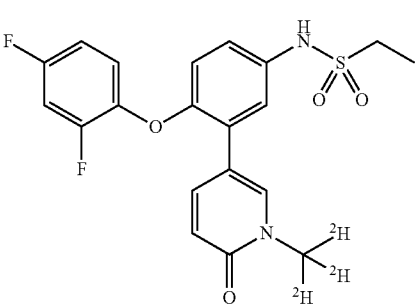 [SMILES: [2H]C([2H])([2H])n1cc(-c2cc(NS(=O)(=O)CC)ccc2Oc2ccc(F)cc2F)ccc1=O] | N-{4-(2,4-difluorophenoxy)-3-[1-($^2$H$_3$)methyl-6-oxopyridin-3-yl]phenyl}ethanesulfonamide |

US 9,598,372 B2

TABLE 1-continued

| Chemical Synthesis Example | Structure | Name |
|---|---|---|
| 142 | 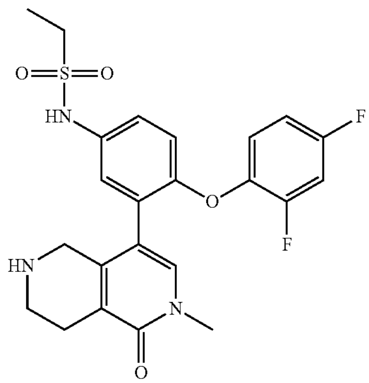 [SMILES: CCS(=O)(=O)Nc1ccc(Oc2ccc(F)cc2F)c(-c2cn(C)c(=O)c3c2CNCC3)c1] | N-[4-(2,4-difluorophenoxy)-3-(2-methyl-1-oxo-5,6,7,8-tetrahydro-2,6-naphthyridin-4-yl)phenyl]ethanesulfonamide |
| 143 | 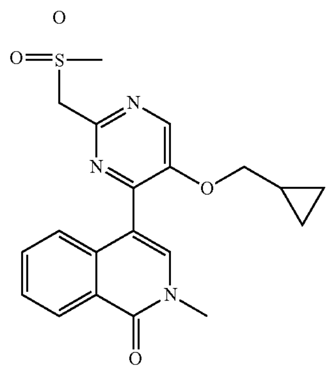 | 4-[5-(cyclopropylmethoxy)-2-(methylsulfonylmethyl)pyrimidin-4-yl]-2-methylisoquinolin-1-one |
| 144 | 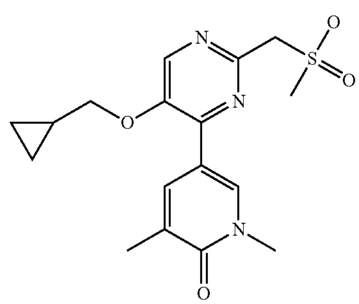 | 5-[5-(cyclopropylmethoxy)-2-(methylsulfonylmethyl)pyrimidin-4-yl]-1,3-dimethylpyridin-2-one |
| 145 | 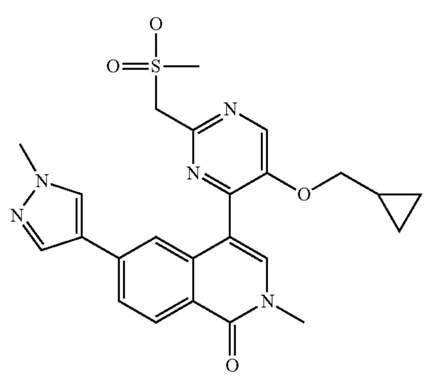 | 4-[5-(cyclopropylmethoxy)-2-(methylsulfonylmethyl)pyrimidin-4-yl]-2-methyl-6-(1-methylpyrazol-4-yl)isoquinolin-1-one |

TABLE 1-continued

| Chemical Synthesis Example | Structure | Name |
|---|---|---|
| 146 | 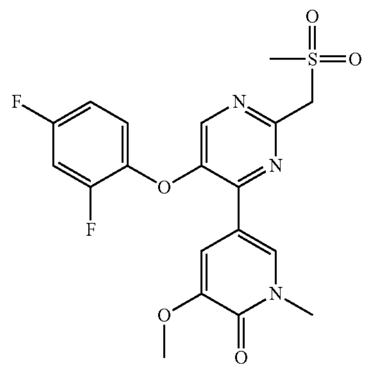 [SMILES: COc1cc(-c2nc(CS(C)(=O)=O)ncc2Oc2ccc(F)cc2F)cn(C)c1=O] | 5-[5-(2,4-difluorophenoxy)-2-(methylsulfonylmethyl)pyrimidin-4-yl]-3-methoxy-1-methylpyridin-2-one |
| 147 | 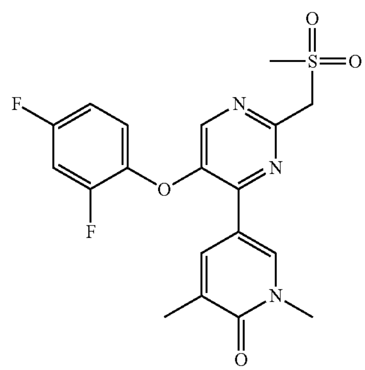 [SMILES: Cc1cc(-c2nc(CS(C)(=O)=O)ncc2Oc2ccc(F)cc2F)cn(C)c1=O] | 5-[5-(2,4-difluorophenoxy)-2-(methylsulfonylmethyl)pyrimidin-4-yl]-1,3-dimethylpyridin-2-one |
| 148 | 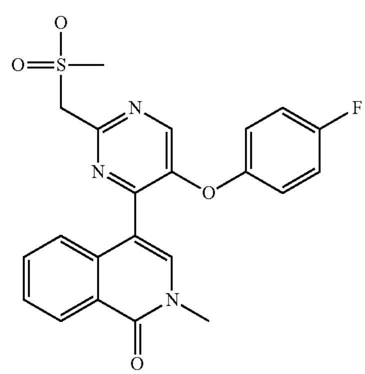 | 4-[5-(2,4-difluorophenoxy)-2-(methylsulfonylmethyl)pyrimidin-4-yl]-2-methylisoquinolin-1-one |
| 149 | 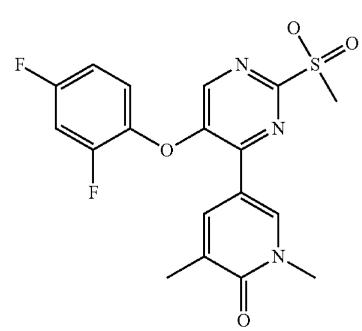 | 5-[5-(2,4-difluorophenoxy)-2-methylsulfonylpyrimidin-4-yl]-1,3-dimethylpyridin-2-one |

TABLE 1-continued

| Chemical Synthesis Example | Structure | Name |
|---|---|---|
| 150 | 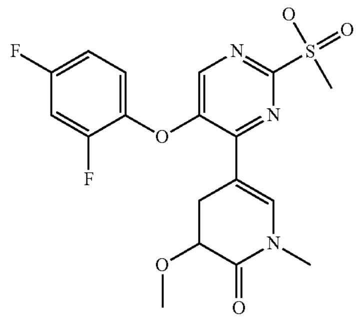 | 5-[5-(2,4-difluorophenoxy)-2-methylsulfonylpyrimidin-4-yl]-3-methoxy-1-methylpyridin-2-one |
| 151 | 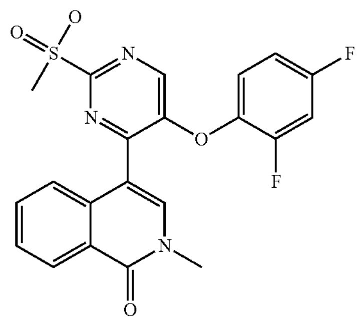 | 4-[5-(2,4-difluorophenoxy)-2-methylsulfonylpyrimidin-4-yl]-2-methylisoquinolin-1-one |
| 152 | 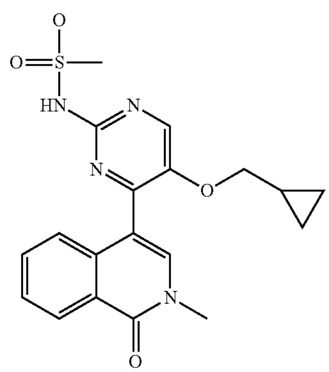 | N-[5-(cyclopropylmethoxy)-4-(2-methyl-1-oxoisoquinolin-4-yl)pyrimidin-2-yl]methanesulfonamide |
| 153 | 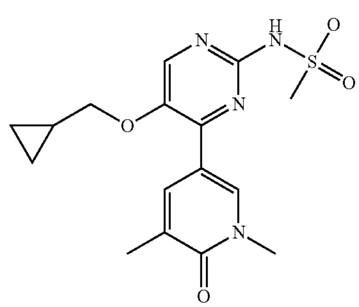 | N-[5-(cyclopropylmethoxy)-4-(1,5-dimethyl-6-oxopyridin-3-yl)pyrimidin-2-yl]methanesulfonamide |

TABLE 1-continued

| Chemical Synthesis Example | Structure | Name |
|---|---|---|
| 154 | 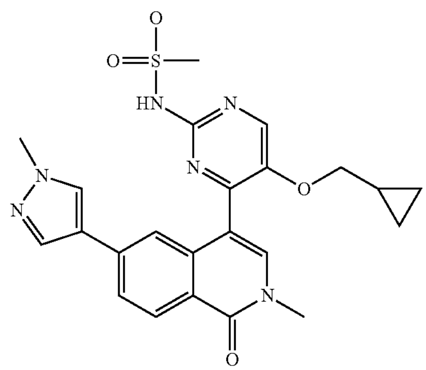 | N-[5-(cyclopropylmethoxy)-4-[2-methyl-6-(1-methylpyrazol-4-yl)-1-oxoisoquinolin-4-yl]pyrimidin-2-yl]methanesulfonamide |
| 155 | 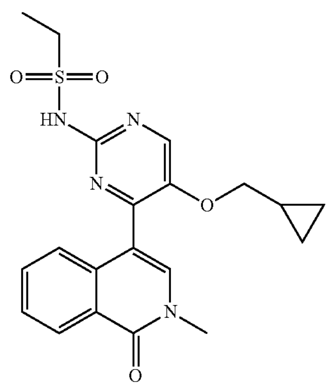 [SMILES: CCS(=O)(=O)Nc1ncc(OCC2CC2)c(-c2cn(C)c(=O)c3ccccc23)n1] | N-[5-(cyclopropylmethoxy)-4-(2-methyl-1-oxoisoquinolin-4-yl)pyrimidin-2-yl]ethanesulfonamide |
| 156 | 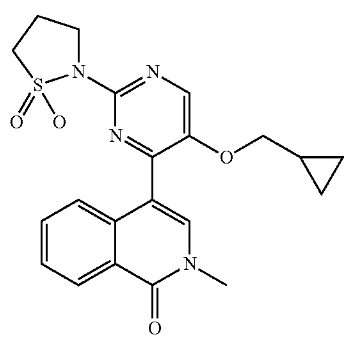 | 4-[5-(cyclopropylmethoxy)-2-(1,1-dioxo-1,2-thiazolidin-2-yl)pyrimidin-4-yl]-2-methylisoquinolin-1-one |
| 157 | 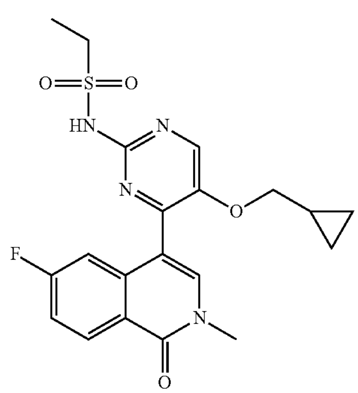 [SMILES: CCS(=O)(=O)Nc1ncc(OCC2CC2)c(-c2cn(C)c(=O)c3ccc(F)cc23)n1] | N-[5-(cyclopropylmethoxy)-4-(6-fluoro-2-methyl-1-oxoisoquinolin-4-yl)pyrimidin-2-yl]ethanesulfonamide |

TABLE 1-continued

| Chemical Synthesis Example | Structure | Name |
|---|---|---|
| 158 | 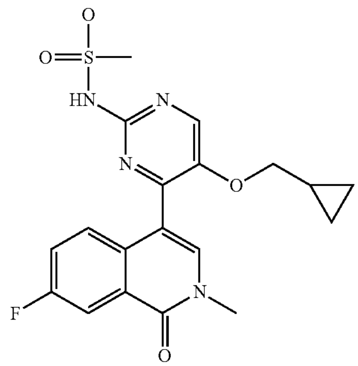 | N-[5-(cyclopropylmethoxy)-4-(7-fluoro-2-methyl-1-oxoisoquinolin-4-yl)pyrimidin-2-yl]methanesulfonamide |
| 159 | 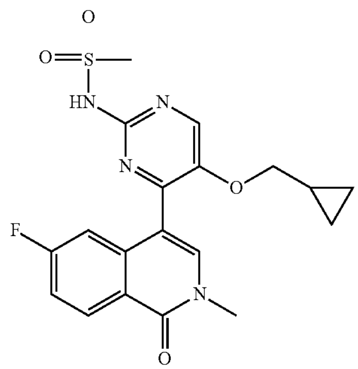 | N-[5-(cyclopropylmethoxy)-4-(6-fluoro-2-methyl-1-oxoisoquinolin-4-yl)pyrimidin-2-yl]methanesulfonamide |
| 160 | 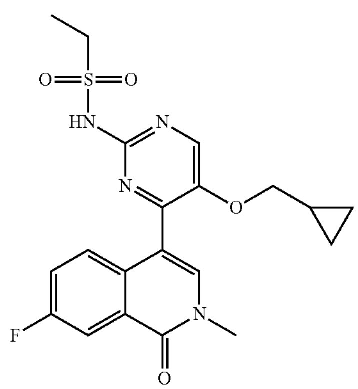 [SMILES: CCS(=O)(=O)Nc1ncc(OCC2CC2)c(-c2cn(C)c(=O)c3cc(F)ccc23)n1] | N-[5-(cyclopropylmethoxy)-4-(7-fluoro-2-methyl-1-oxoisoquinolin-4-yl)pyrimidin-2-yl]ethanesulfonamide |
| 161 | 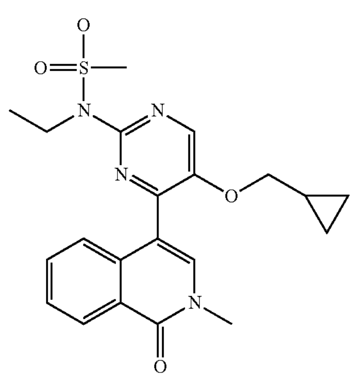 | N-[5-(cyclopropylmethoxy)-4-(2-methyl-1-oxoisoquinolin-4-yl)pyrimidin-2-yl]-N-ethylmethanesulfonamide |

TABLE 1-continued

| Chemical Synthesis Example | Structure | Name |
|---|---|---|
| 162 | 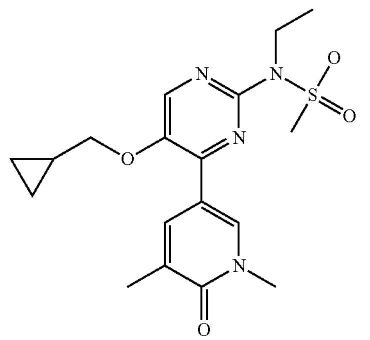 | N-[5-(cyclopropylmethoxy)-4-(1,5-dimethyl-6-oxopyridin-3-yl)pyrimidin-2-yl]-N-ethylmethanesulfonamide |
| 163 | 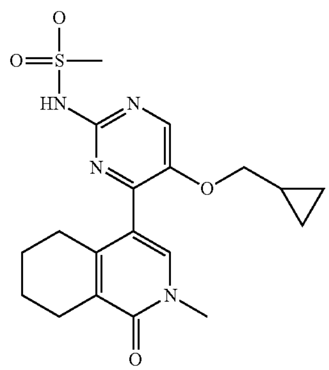 | N-[5-(cyclopropylmethoxy)-4-(2-methyl-1-oxo-5,6,7,8-tetrahydroisoquinolin-4-yl)pyrimidin-2-yl]methanesulfonamide |
| 164 | 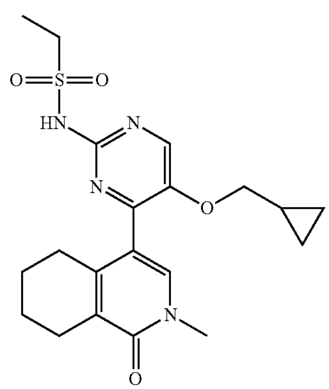 [SMILES: CCS(=O)(=O)Nc1ncc(OCC2CC2)c(-c2cn(C)c(=O)c3c2CCCC3)n1] | N-[5-(cyclopropylmethoxy)-4-(2-methyl-1-oxo-5,6,7,8-tetrahydroisoquinolin-4-yl)pyrimidin-2-yl]ethanesulfonamide |
| 165 | 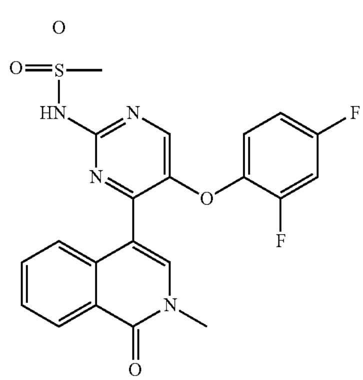 | N-[5-(2,4-difluorophenoxy)-4-(2-methyl-1-oxoisoquinolin-4-yl)pyrimidin-2-yl]methanesulfonamide |

TABLE 1-continued

| Chemical Synthesis Example | Structure | Name |
|---|---|---|
| 166 | 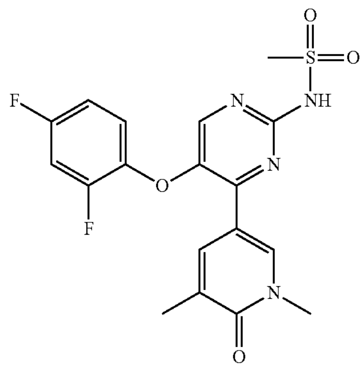 [SMILES: Cc1cc(-c2nc(NS(C)(=O)=O)ncc2Oc2ccc(F)cc2F)cn(C)c1=O] | N-[5-(2,4-difluorophenoxy)-4-(1,5-dimethyl-6-oxopyridin-3-yl)pyrimidin-2-yl]methanesulfonamide |
| 167 | 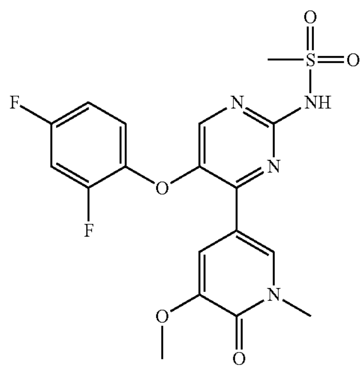 [SMILES: COc1cc(-c2nc(NS(C)(=O)=O)ncc2Oc2ccc(F)cc2F)cn(C)c1=O] | N-[5-(2,4-difluorophenoxy)-4-(5-methoxy-1-methyl-6-oxopyridin-3-yl)pyrimidin-2-yl]methanesulfonamide |
| 168 | 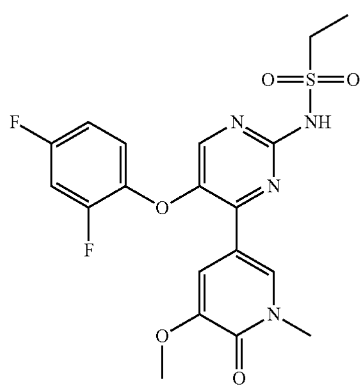 [SMILES: CCS(=O)(=O)Nc1ncc(Oc2ccc(F)cc2F)c(-c2cc(OC)c(=O)n(C)c2)n1] | N-[5-(2,4-difluorophenoxy)-4-(5-methoxy-1-methyl-6-oxopyridin-3-yl)pyrimidin-2-yl]ethanesulfonamide |
| 169 | 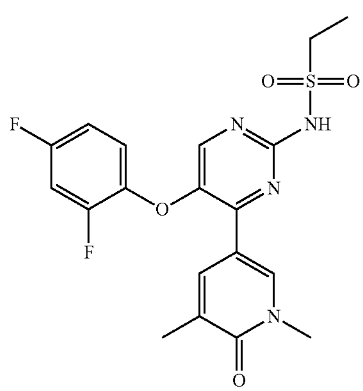 [SMILES: CCS(=O)(=O)Nc1ncc(Oc2ccc(F)cc2F)c(-c2cc(C)c(=O)n(C)c2)n1] | N-[5-(2,4-difluorophenoxy)-4-(1,5-dimethyl-6-oxopyridin-3-yl)pyrimidin-2-yl]ethanesulfonamide |

TABLE 1-continued

| Chemical Synthesis Example | Structure | Name |
|---|---|---|
| 170 | 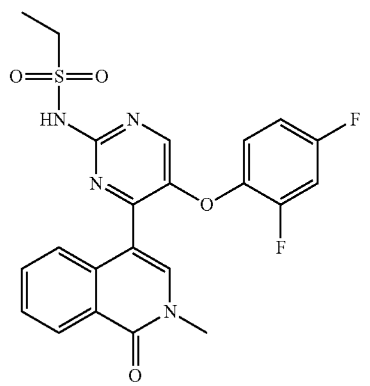 [SMILES: CCS(=O)(=O)Nc1ncc(Oc2ccc(F)cc2F)c(-c2cn(C)c(=O)c3ccccc23)n1] | N-[5-(2,4-difluorophenoxy)-4-(2-methyl-1-oxoisoquinolin-4-yl)pyrimidin-2-yl]ethanesulfonamide |
| 171 | 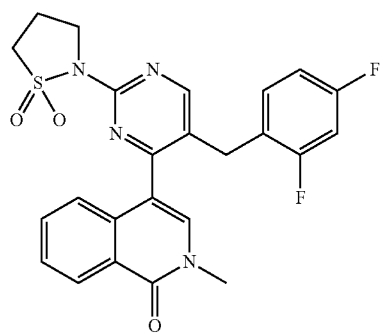 | 4-[5-(2,4-difluorophenoxy)-2-(1,1-dioxo-1,2-thiazolidin-2-yl)pyrimidin-4-yl]-2-methylisoquinolin-1-one |
| 172 | 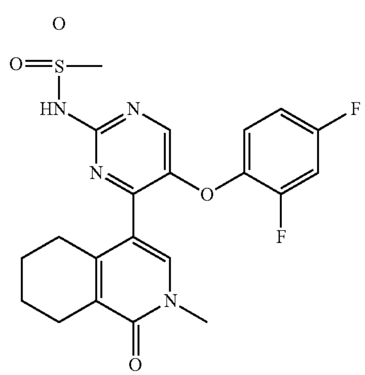 | N-[5-(2,4-difluorophenoxy)-4-(2-methyl-1-oxo-5,6,7,8-tetrahydroisoquinolin-4-yl)pyrimidin-2-yl]methanesulfonamide |
| 173 | 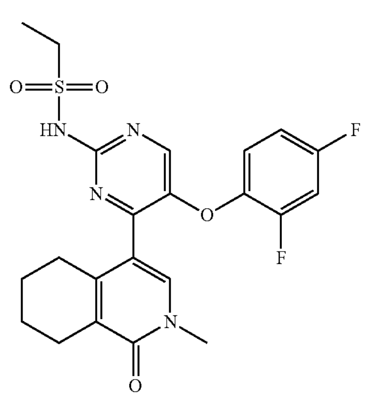 [SMILES: CCS(=O)(=O)Nc1ncc(Oc2ccc(F)cc2F)c(-c2cn(C)c(=O)c3c2CCCC3)n1] | N-[5-(2,4-difluorophenoxy)-4-(2-methyl-1-oxo-5,6,7,8-tetrahydroisoquinolin-4-yl)pyrimidin-2-yl]ethanesulfonamide |

TABLE 1-continued

| Chemical Synthesis Example | Structure | Name |
|---|---|---|
| 174 | 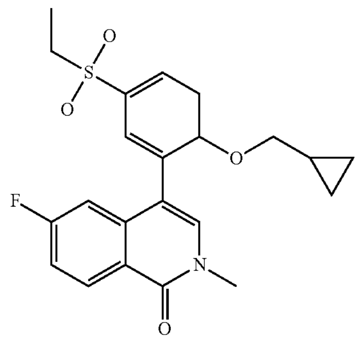 [SMILES: CCS(O)(O)C1=CCC(OCC2CC2)C(c2cn(C)c(=O)c3ccc(F)cc23)=C1] | 4-[2-(cyclopropylmethoxy)-5-ethylsulfonylphenyl]-6-fluoro-2-methylisoquinolin-1-one |
| 175 | 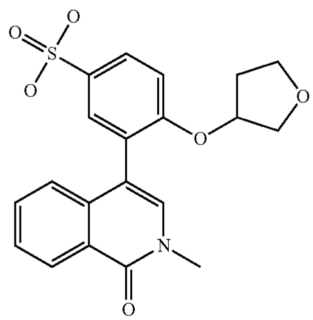 | 2-methyl-4-[5-methylsulfonyl-2-(oxolan-3-yloxy)phenyl]isoquinolin-1-one |
| 176 | 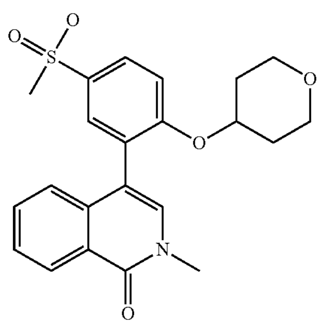 | 2-methyl-4-[5-methylsulfonyl-2-(oxan-4-yloxy)phenyl]isoquinolin-1-one |
| 177 | 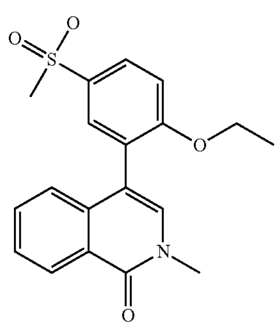 | 4-(2-ethoxy-5-methylsulfonylphenyl)-2-methylisoquinolin-1-one |

TABLE 1-continued

| Chemical Synthesis Example | Structure | Name |
|---|---|---|
| 178 | 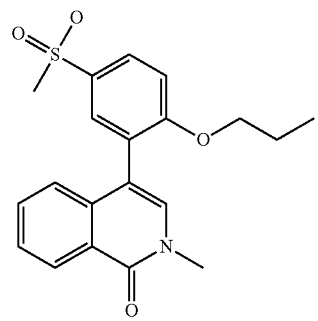 | 2-methyl-4-(5-methylsulfonyl-2-propoxyphenyl)isoquinolin-1-one |
| 179 | 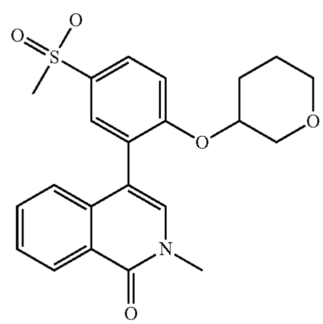 | 2-methyl-4-[5-methylsulfonyl-2-(oxan-3-yloxy)phenyl]isoquinolin-1-one |
| 180 | 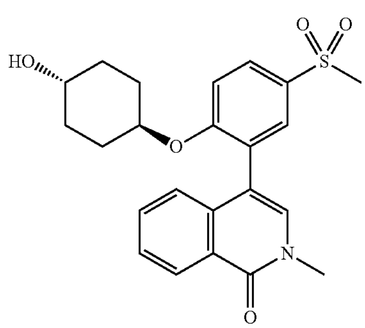 [SMILES: Cn1cc(-c2cc(S(C)(=O)=O)ccc2O[C@H]2CC[C@H](O)CC2)c2ccccc2c1=O] | 4-[2-(trans-4-hydroxycyclohexyl)oxy-5-methylsulfonylphenyl]-2-methylisoquinolin-1-one |
| 181 | 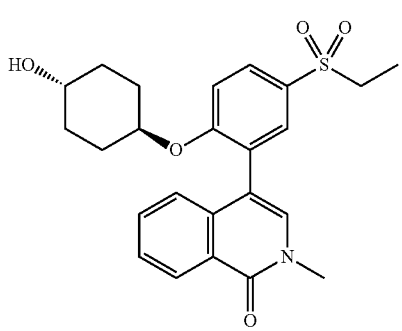 [SMILES: CCS(=O)(=O)c1ccc(O[C@H]2CC[C@H](O)CC2)c(-c2cn(C)c(=O)c3ccccc23)c1] | 4-[5-ethylsulfonyl-2-(trans-4-hydroxycyclohexyl)oxyphenyl]-2-methylisoquinolin-1-one |

TABLE 1-continued

| Chemical Synthesis Example | Structure | Name |
|---|---|---|
| 182 | 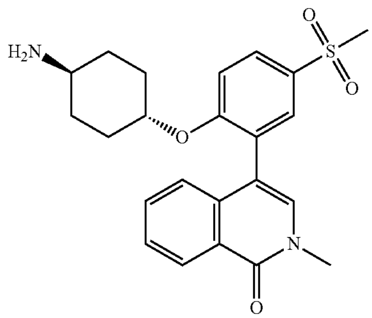 [SMILES: Cn1cc(-c2cc(S(C)(=O)=O)ccc2O[C@H]2CC[C@H](N)CC2)c2ccccc2c1=O] | 4-[2-(trans-4-aminocyclohexyl)oxy-5-methylsulfonylphenyl]-2-methylisoquinolin-1-one |
| 183 | 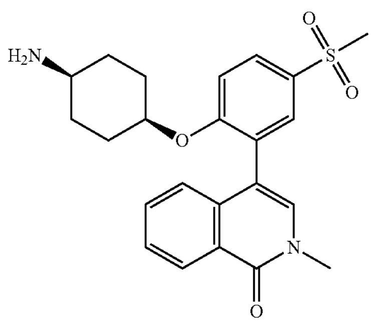 [SMILES: Cn1cc(-c2cc(S(C)(=O)=O)ccc2O[C@H]2CC[C@@H](N)CC2)c2ccccc2c1=O] | 4-[2-(cis-4-aminocyclohexyl)oxy-5-methylsulfonylphenyl]-2-methylisoquinolin-1-one |
| 184 | 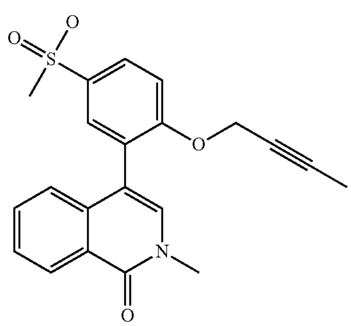 | 4-(2-but-2-ynoxy-5-methylsulfonylphenyl)-2-methylisoquinolin-1-one |
| 185 | 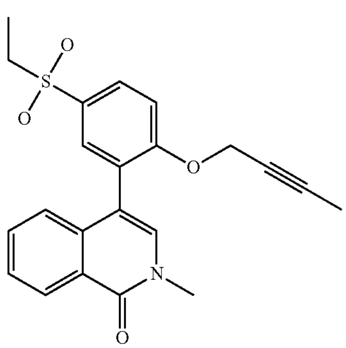 [SMILES: CC#CCOc1ccc(S(O)(O)CC)cc1-c1cn(C)c(=O)c2ccccc12] | 4-(2-but-2-ynoxy-5-ethylsulfonylphenyl)-2-methylisoquinolin-1-one |

TABLE 1-continued

| Chemical Synthesis Example | Structure | Name |
| --- | --- | --- |
| 186 | 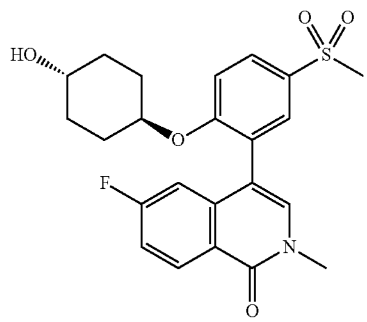 [SMILES: Cn1cc(-c2cc(S(C)(=O)=O)ccc2O[C@H]2CC[C@H](O)CC2)c2cc(F)ccc2c1=O] | 6-fluoro-4-[2-(trans-4-hydroxycyclohexyl)oxy-5-methylsulfonylphenyl]-2-methylisoquinolin-1-one |
| 187 | 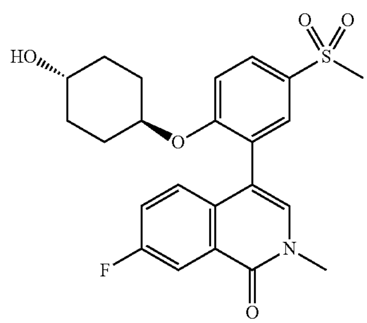 [SMILES: Cn1cc(-c2cc(S(C)(=O)=O)ccc2O[C@H]2CC[C@H](O)CC2)c2ccc(F)cc2c1=O] | 7-fluoro-4-[2-(trans-4-hydroxycyclohexyl)oxy-5-methylsulfonylphenyl]-2-methylisoquinolin-1-one |
| 188 | 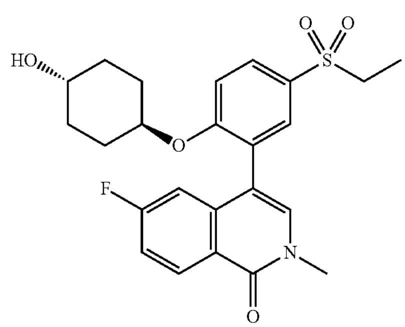 [SMILES: CCS(=O)(=O)c1ccc(O[C@H]2CC[C@H](O)CC2)c(-c2cn(C)c(=O)c3ccc(F)cc23)c1] | 4-[5-ethylsulfonyl-2-(trans-4-hydroxycyclohexyl)oxyphenyl]-6-fluoro-2-methylisoquinolin-1-one |
| 189 | 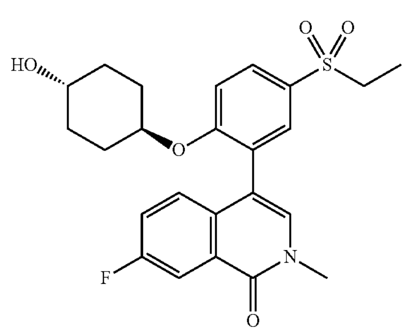 [SMILES: CCS(=O)(=O)c1ccc(O[C@H]2CC[C@H](O)CC2)c(-c2cn(C)c(=O)c3cc(F)ccc23)c1] | 4-[5-ethylsulfonyl-2-(trans-4-hydroxycyclohexyl)oxyphenyl]-7-fluoro-2-methylisoquinolin-1-one |

TABLE 1-continued

| Chemical Synthesis Example | Structure | Name |
|---|---|---|
| 190 | 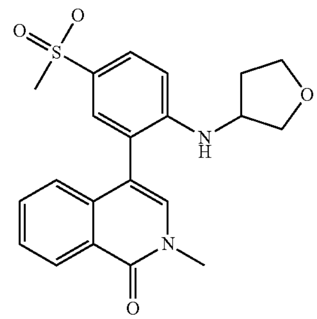 | 2-methyl-4-[5-methylsulfonyl-2-(oxolan-3-ylamino)phenyl]isoquinolin-1-one |
| 191 | 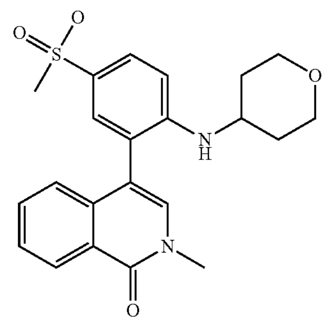 | 2-methyl-4-[5-methylsulfonyl-2-(oxan-4-ylamino)phenyl]isoquinolin-1-one |
| 192 | 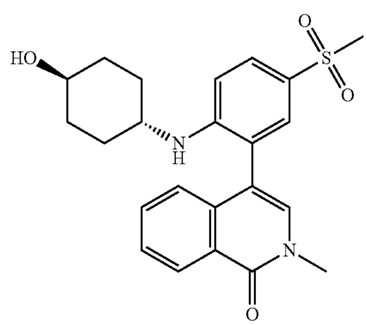 [SMILES: Cn1cc(-c2cc(S(C)(=O)=O)ccc2N[C@H]2CC[C@H](O)CC2)c2ccccc2c1=O] | 4-[2-[(trans-4-hydroxycyclohexyl)amino]-5-methylsulfonylphenyl]-2-methylisoquinolin-1-one |
| 193 | 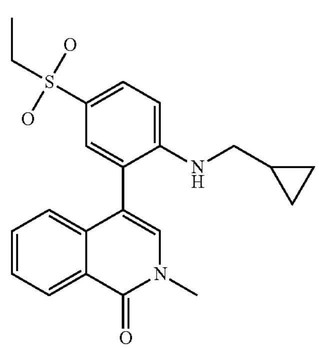 [SMILES: CCS(O)(O)c1ccc(NCC2CC2)c(-c2cn(C)c(=O)c3ccccc23)c1] | 4-[2-(cyclopropylmethylamino)-5-ethylsulfonylphenyl]-2-methylisoquinolin-1-one |

TABLE 1-continued

| Chemical Synthesis Example | Structure | Name |
|---|---|---|
| 194 | 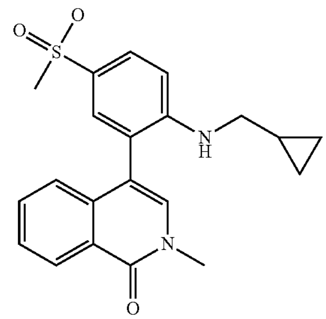 | 4-[2-(cyclopropylmethylamino)-5-methylsulfonylphenyl]-2-methylisoquinolin-1-one |
| 195 | 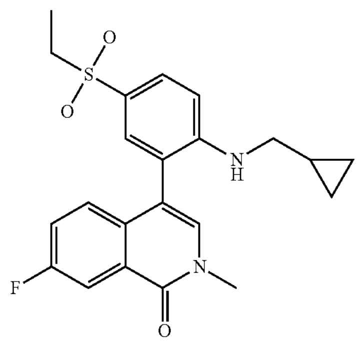 [SMILES: CCS(O)(O)c1ccc(NCC2CC2)c(-c2cn(C)c(=O)c3cc(F)ccc23)c1] | 4-[2-(cyclopropylmethylamino)-5-ethylsulfonylphenyl]-7-fluoro-2-methylisoquinolin-1-one |
| 196 | 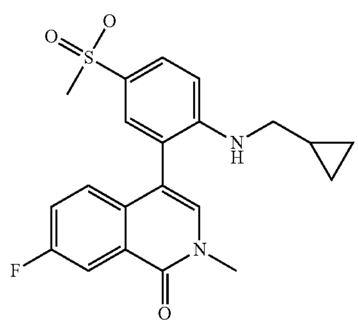 | 4-[2-(cyclopropylmethylamino)-5-methylsulfonylphenyl]-7-fluoro-2-methylisoquinolin-1-one |
| 197 | 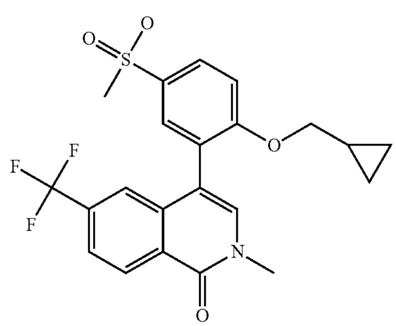 | 4-[2-(cyclopropylmethoxy)-5-methylsulfonylphenyl]-2-methyl-6-(trifluoromethyl)isoquinolin-1-one |

TABLE 1-continued

| Chemical Synthesis Example | Structure | Name |
|---|---|---|
| 198 | 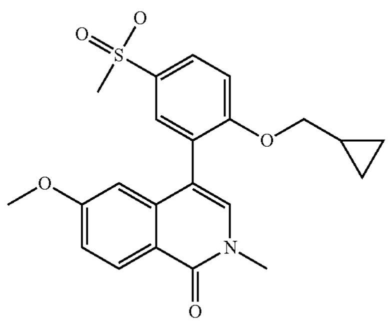 | 4-[2-(cyclopropylmethoxy)-5-methylsulfonylphenyl]-6-methoxy-2-methylisoquinolin-1-one |
| 199 | 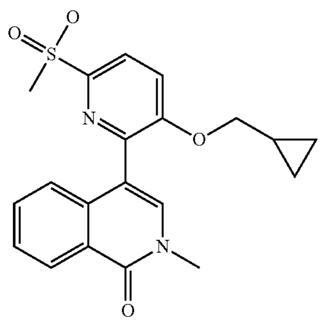 | 4-[3-(cyclopropylmethoxy)-6-methylsulfonylpyridin-2-yl]-2-methylisoquinolin-1-one |
| 200 | 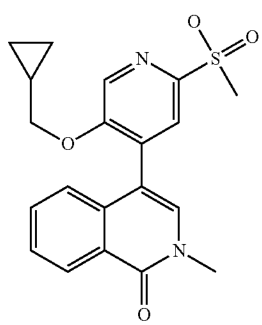 | 4-[5-(cyclopropylmethoxy)-2-methylsulfonylpyridin-4-yl]-2-methylisoquinolin-1-one |
| 201 | 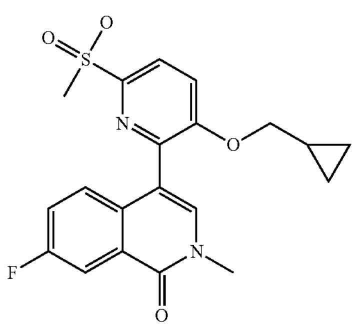 | 4-[3-(cyclopropylmethoxy)-6-methylsulfonylpyridin-2-yl]-7-fluoro-2-methylisoquinolin-1-one |

TABLE 1-continued

| Chemical Synthesis Example | Structure | Name |
|---|---|---|
| 202 | 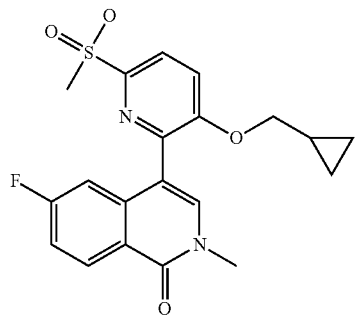 | 4-[3-(cyclopropylmethoxy)-6-methylsulfonylpyridin-2-yl]-6-fluoro-2-methylisoquinolin-1-one |
| 203 | 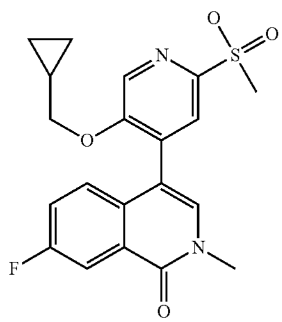 | 4-[5-(cyclopropylmethoxy)-2-methylsulfonylpyridin-4-yl]-7-fluoro-2-methylisoquinolin-1-one |
| 204 | 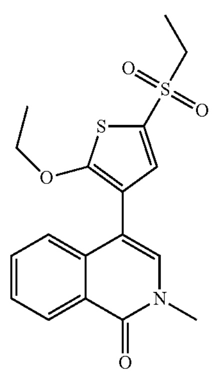 [SMILES: CCOc1sc(S(=O)(=O)CC)cc1-c1cn(C)c(=O)c2ccccc12] | 4-(2-ethoxy-5-ethylsulfonylthiophen-3-yl)-2-methylisoquinolin-1-one |
| 205 | 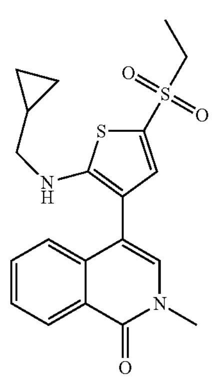 [SMILES: CCS(=O)(=O)c1cc(-c2cn(C)c(=O)c3ccccc23)c(NCC2CC2)s1] | 4-[2-(cyclopropylmethylamino)-5-ethylsulfonylthiophen-3-yl]-2-methylisoquinolin-1-one |

TABLE 1-continued

| Chemical Synthesis Example | Structure | Name |
| --- | --- | --- |
| 206 | 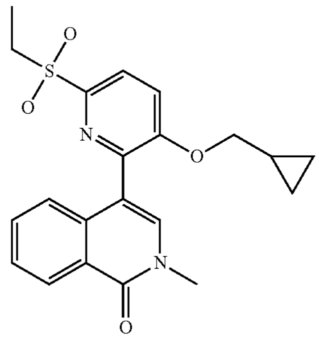 [SMILES: CCS(O)(O)c1ccc(OCC2CC2)c(-c2cn(C)c(=O)c3ccccc23)n1] | 4-[3-(cyclopropylmethoxy)-6-ethylsulfonylpyridin-2-yl]-2-methylisoquinolin-1-one |
| 207 | 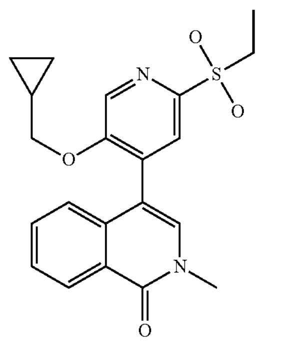 [SMILES: CCS(O)(O)c1cc(-c2cn(C)c(=O)c3ccccc23)c(OCC2CC2)cn1] | 4-[5-(cyclopropylmethoxy)-2-ethylsulfonylpyridin-4-yl]-2-methylisoquinolin-1-one |
| 208 | 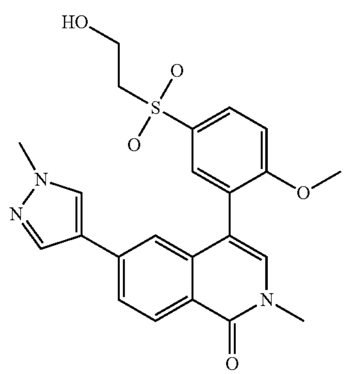 [SMILES: COc1ccc(S(O)(O)CCO)cc1-c1cn(C)c(=O)c2ccc(-c3cnn(C)c3)cc12] | 4-[5-(2-hydroxyethylsulfonyl)-2-methoxyphenyl]-2-methyl-6-(1-methylpyrazol-4-yl)isoquinolin-1-one |
| 209 | 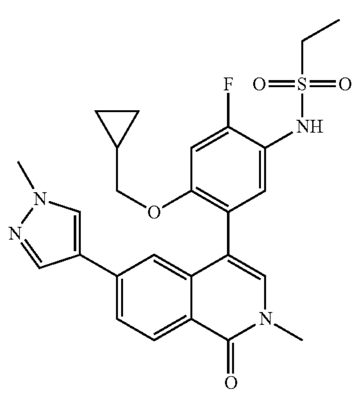 [SMILES: CCS(=O)(=O)Nc1cc(-c2cn(C)c(=O)c3ccc(-c4cnn(C)c4)cc23)c(OCC2CC2)cc1F] | N-[4-(cyclopropylmethoxy)-2-fluoro-5-[2-methyl-6-(1-methylpyrazol-4-yl)-1-oxoisoquinolin-4-yl]phenyl]ethanesulfonamide |

TABLE 1-continued

| Chemical Synthesis Example | Structure | Name |
|---|---|---|
| 210 | 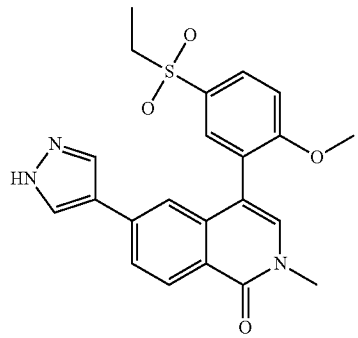 [SMILES: CCS(O)(O)c1ccc(OC)c(-c2cn(C)c(=O)c3ccc(-c4cn[nH]c4)cc23)c1] | 4-(5-ethylsulfonyl-2-methoxyphenyl)-2-methyl-6-(1H-pyrazol-4-yl)isoquinolin-1-one |
| 211 | 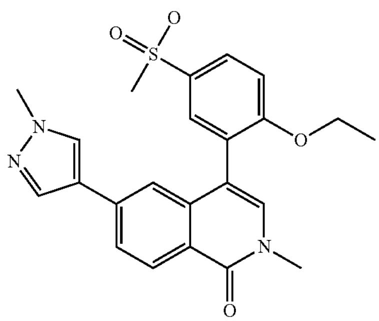 | 4-(2-ethoxy-5-methylsulfonylphenyl)-2-methyl-6-(1-methylpyrazol-4-yl)isoquinolin-1-one |
| 212 | 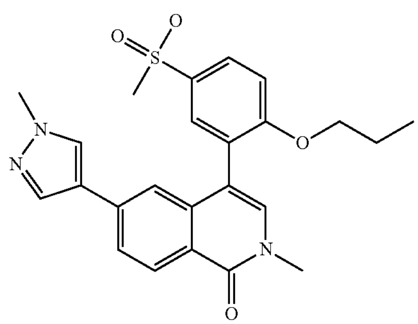 | 2-methyl-6(1-methylpyrazol-4-yl)-4(5-methylsulfonyl-2-propoxyphenyl)isoquinolin-1-one |
| 213 | 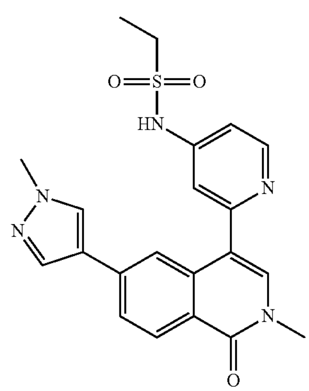 [SMILES: CCS(=O)(=O)Nc1ccnc(-c2cn(C)c(=O)c3ccc(-c4cnn(C)c4)cc23)c1] | N-[2-[2-methyl-6-(1-methylpyrazol-4-yl)-1-oxoisoquinolin-4-yl]pyridin-4-yl]ethanesulfonamide |

TABLE 1-continued

| Chemical Synthesis Example | Structure | Name |
|---|---|---|
| 214 | 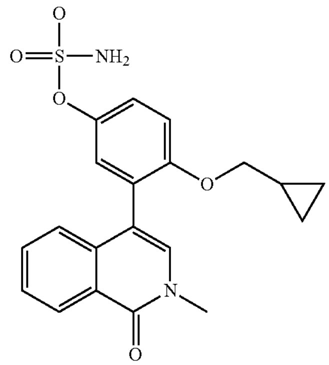 | [4-(cyclopropylmethoxy)-3-(2-methyl-1-oxoisoquinolin-4-yl)phenyl] sulfamate |
| 215 | 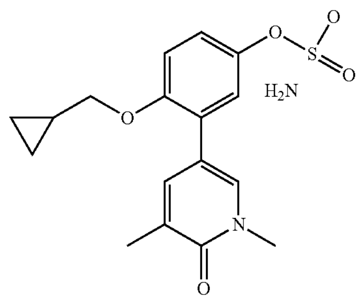 | [4-(cyclopropylmethoxy)-3-(1,5-dimethyl-6-oxopyridin-3-yl)phenyl] sulfamate |
| 216 | 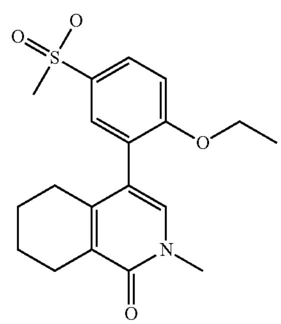 | 4-(2-ethoxy-5-methylsulfonylphenyl)-2-methyl-5,6,7,8-tetrahydroisoquinolin-1-one |
| 217 | 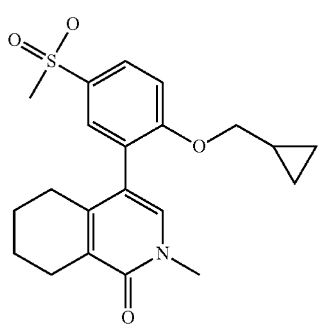 | 4-[2-(cyclopropylmethoxy)-5-methylsulfonylphenyl]-2-methyl-5,6,7,8-tetrahydroisoquinolin-1-one |

TABLE 1-continued

| Chemical Synthesis Example | Structure | Name |
|---|---|---|
| 218 | 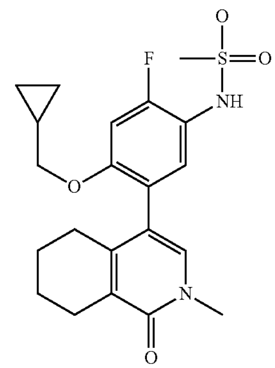 | N-[4-(cyclopropylmethoxy)-2-fluoro-5-(2-methyl-1-oxo-5,6,7,8-tetrahydroisoquinolin-4-yl)phenyl]methanesulfonamide |
| 219 | 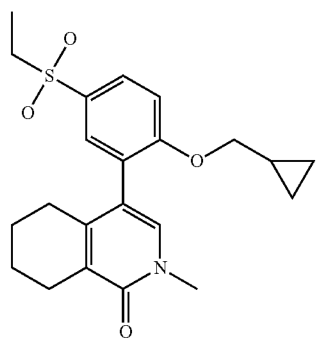 [SMILES: CCS(O)(O)c1ccc(OCC2CC2)c(-c2cn(C)c(=O)c3c2CCCC3)c1] | 4-[2-(cyclopropylmethoxy)-5-ethylsulfonylphenyl]-2-methyl-5,6,7,8-tetrahydroisoquinolin-1-one |
| 220 | 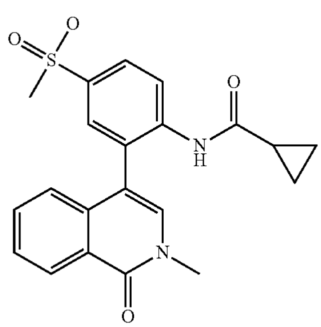 | N-[2-(2-methyl-1-oxoisoquinolin-4-yl)-4-methylsulfonylphenyl]cyclopropanecarboxamide |
| 221 | 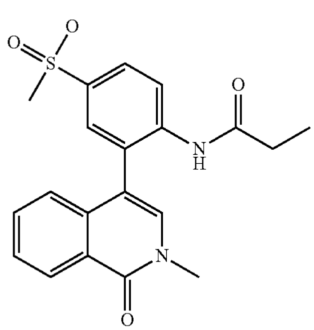 | N-[2-(2-methyl-1-oxoisoquinolin-4-yl)-4-methylsulfonylphenyl]propanamide |

TABLE 1-continued

| Chemical Synthesis Example | Structure | Name |
|---|---|---|
| 222 | 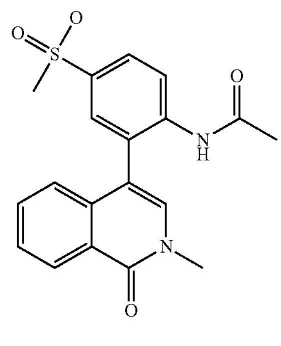 | N-[2-(2-methyl-1-oxoisoquinolin-4-yl)-4-methylsulfonylphenyl]acetamide |
| 223 | 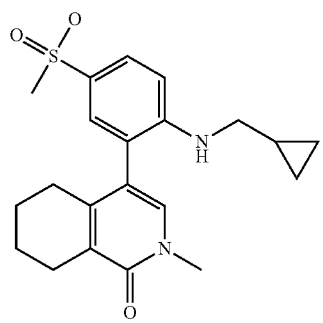 | 4[2-(cyclopropylmethylamino)-5-methylsulfonylphenyl]-2-methyl-5,6,7,8-tetrahydroisoquinolin-1-one |
| 224 | 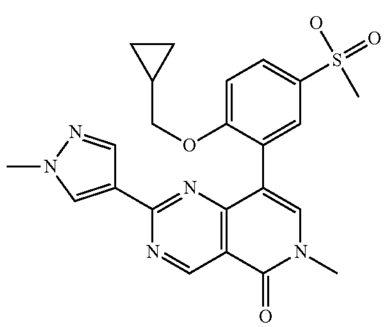 | 8-[2-(cyclopropylmethoxy)-5-methylsulfonylphenyl]-6-methyl-2-(1-methylpyrazol-4-yl)pyrido[4,3-d]pyrimidin-5-one |
| 225 | 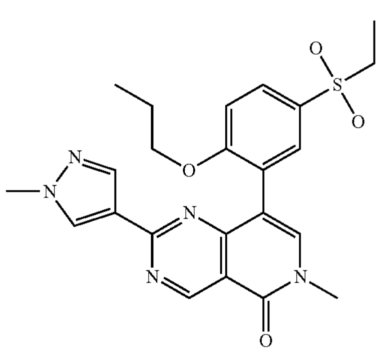 [SMILES: CCCOc1ccc(S(O)(O)CC)cc1-c1cn(C)c(=O)c2cnc(-c3cnn(C)c3)nc12] | 8(5-ethylsulfonyl-2-propoxyphenyl)-6-methyl-2(1-methylpyrazol-4-yl)pyrido[4,3-d]pyrimidin-5-one |

TABLE 1-continued

| Chemical Synthesis Example | Structure | Name |
|---|---|---|
| 226 | 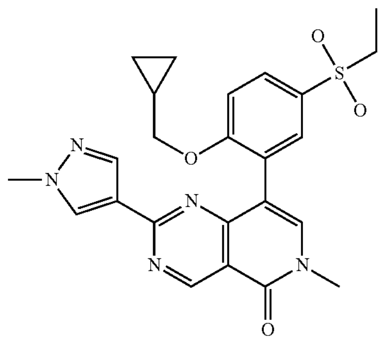 [SMILES: CCS(O)(O)c1ccc(OCC2CC2)c(-c2cn(C)c(=O)c3cnc(-c4cnn(C)c4)nc23)c1] | 8-[2-(cyclopropylmethoxy)-5-ethylsulfonylphenyl]-6-methyl-2-(1-methylpyrazol-4-yl)pyrido[4,3-d]pyrimidin-5-one |
| 227 | 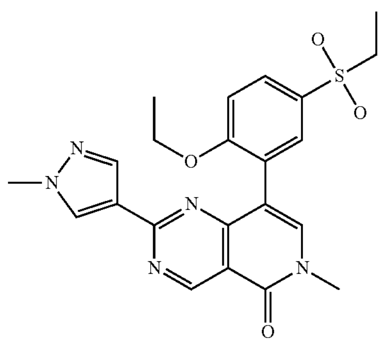 [SMILES: CCOc1ccc(S(O)(O)CC)cc1-c1cn(C)c(=O)c2cnc(-c3cnn(C)c3)nc12] | 8-(2-ethoxy-5-ethylsulfonylphenyl)-6-methyl-2-(1-methylpyrazol-4-yl)pyrido[4,3-d]pyrimidin-5-one |
| 228 | 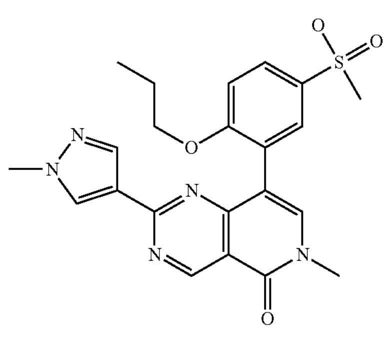 | 6-methyl-2-(1-methylpyrazol-4-yl)-8-(5-methylsulfonyl-2-propoxyphenyl)pyrido[4,3-d]pyrimidin-5-one |
| 229 | 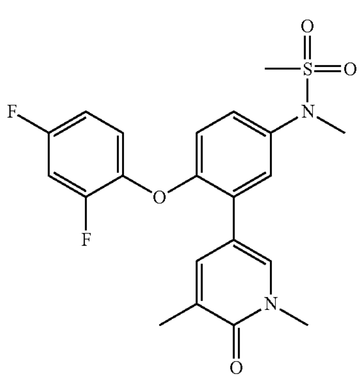 [SMILES: Cc1cc(-c2cc(N(C)S(C)(=O)=O)ccc2Oc2ccc(F)cc2F)cn(C)c1=O] | N-[4-(2,4-difluorophenoxy)-3-(1,5-dimethyl-6-oxopyridin-3-yl)phenyl]-N-methylmethanesulfonamide |

TABLE 1-continued

| Chemical Synthesis Example | Structure | Name |
|---|---|---|
| 230 | 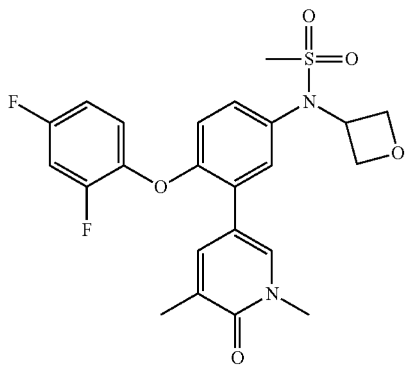 [SMILES: Cc1cc(-c2cc(N(C3COC3)S(C)(=O)=O)ccc2Oc2ccc(F)cc2F)cn(C)c1=O] | N-[4-(2,4-difluorophenoxy)-3-(1,5-dimethyl-6-oxopyridin-3-yl)phenyl]-N-(oxetan-3-yl)methanesulfonamide |
| 231 | 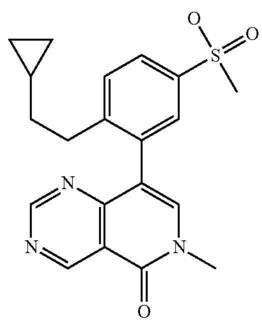 | 8-[2-(cyclopropylmethoxy)-5-methylsulfonylphenyl]-6-methylpyrido[4,3-d]pyrimidin-5-one |
| 232 | 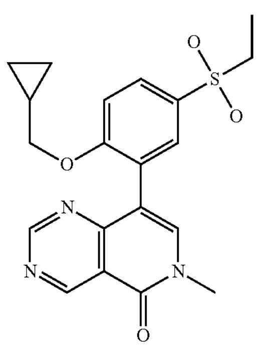 [SMILES: CCS(O)(O)c1ccc(OCC2CC2)c(-c2cn(C)c(=O)c3cncnc23)c1] | 8-[2-(cyclopropylmethoxy)-5-ethylsulfonylphenyl]-6-methylpyrido[4,3-d]pyrimidin-5-one |
| 233 | 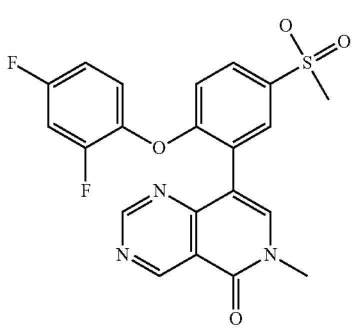 | 8-[2-(2,4-difluorophenoxy)-5-methylsulfonylphenyl]-6-methylpyrido[4,3-d]pyrimidin-5-one |

TABLE 1-continued

| Chemical Synthesis Example | Structure | Name |
|---|---|---|
| 234 | 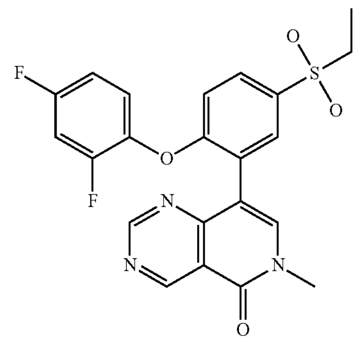 [SMILES: CCS(O)(O)c1ccc(Oc2ccc(F)cc2F)c(-c2cn(C)c(=O)c3cncnc23)c1] | 8-[2-(2,4-difluorophenoxy)-5-ethylsulfonylphenyl]-6-methylpyrido[4,3-d]pyrimidin-5-one |
| 235 | 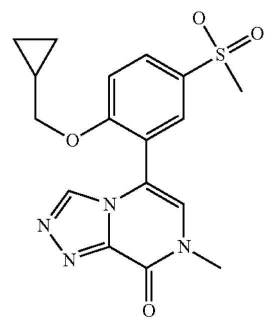 | 5-[2-(cyclopropylmethoxy)-5-methylsulfonylphenyl]-7-methyl-[1,2,4]triazolo[4,3-a]pyrazin-8-one |
| 236 | 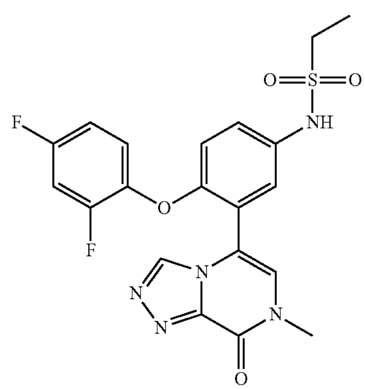 [SMILES: CCS(=O)(=O)Nc1ccc(Oc2ccc(F)cc2F)c(-c2cn(C)c(=O)c3nncn23)c1] | N-[4-(2,4-difluorophenoxy)-3-(7-methyl-8-oxo-[1,2,4]triazolo[4,3-a]pyrazin-5-yl)phenyl]ethanesulfonamide |
| 237 | 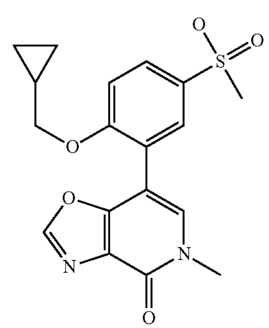 | 7-[2-(cyclopropylmethoxy)-5-methylsulfonylphenyl]-5-methyl-[1,3]oxazolo[4,5-c]pyridin-4-one |

TABLE 1-continued

| Chemical Synthesis Example | Structure | Name |
|---|---|---|
| 238 | 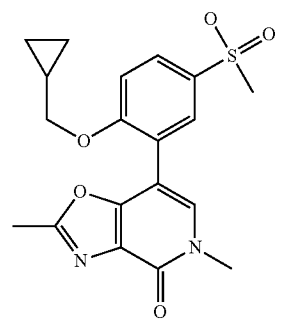 | 7-[2-(cyclopropylmethoxy)-5-methylsulfonylphenyl]-2,5-dimethyl-[1,3]oxazolo[4,5-c]pyridin-4-one |
| 239 | 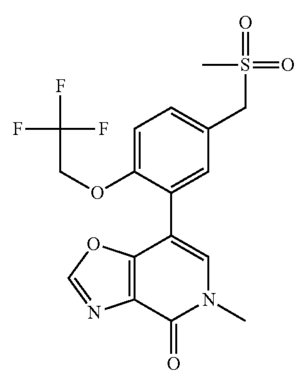 [SMILES: Cn1cc(-c2cc(CS(C)(=O)=O)ccc2OCC(F)(F)F)c2ocnc2c1=O] | 5-methyl-7-[5-(methylsulfonylmethyl)-2-(2,2,2-trifluoroethoxy)phenyl]-[1,3]oxazolo[4,5-c]pyridin-4-one |
| 240 | 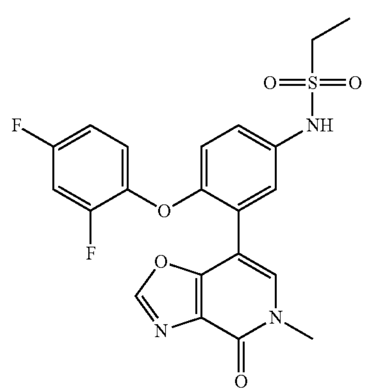 [SMILES: CCS(=O)(=O)Nc1ccc(Oc2ccc(F)cc2F)c(-c2cn(C)c(=O)c3ncoc23)c1] | N-[4-(2,4-difluorophenoxy)-3-(5-methyl-4-oxo-[1,3]oxazolo[4,5-c]pyridin-7-yl)phenyl]ethanesulfonamide |
| 241 | 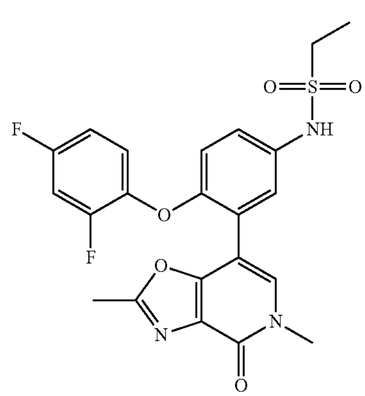 [SMILES: CCS(=O)(=O)Nc1ccc(Oc2ccc(F)cc2F)c(-c2cn(C)c(=O)c3nc(C)oc23)c1] | N-[4-(2,4-difluorophenoxy)-3-(2,5-dimethyl-4-oxo-[1,3]oxazolo[4,5-c]pyridin-7-yl)phenyl]ethanesulfonamide |

TABLE 1-continued

| Chemical Synthesis Example | Structure | Name |
|---|---|---|
| 242 | 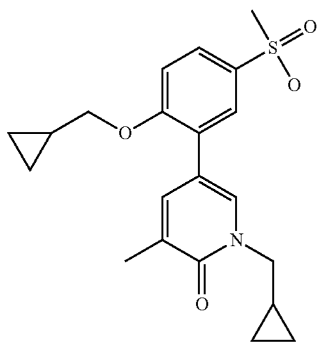 | 5-[2-(cyclopropylmethoxy)-5-methylsulfonylphenyl]-1-(cyclopropylmethyl)-3-methylpyridin-2-one |
| 243 | 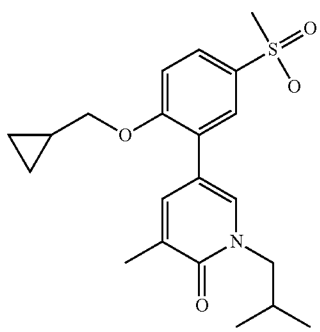 | 5-[(cyclopropylmethoxy)-5-methylsulfonylphenyl]-3-methyl-1-(2-methylpropyl)pyridin-2-one |
| 244 | 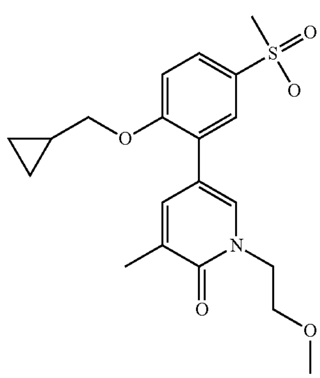 | 5-[2-(cyclopropylmethoxy)-5-methylsulfonylphenyl]-1-(2-methoxyethyl)-3-methylpyridin-2-one |
| 245 | 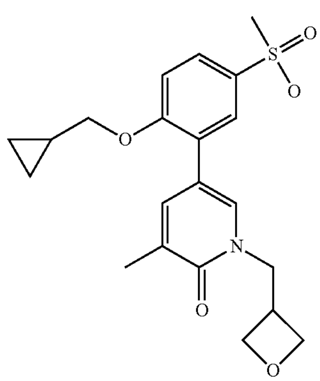 | 5-[2-(cyclopropylmethoxy)-5-methylsulfonylphenyl]-3-methyl-1-(oxetan-3-ylmethyl)pyridin-2-one |

TABLE 1-continued
| Chemical Synthesis Example | Structure | Name |
|---|---|---|
| 246 | 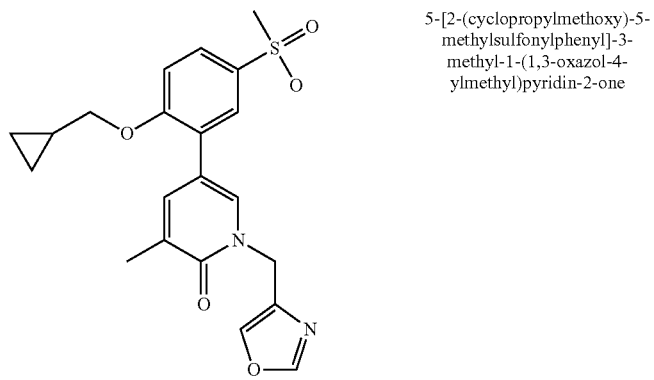 | 5-[2-(cyclopropylmethoxy)-5-methylsulfonylphenyl]-3-methyl-1-(1,3-oxazol-4-ylmethyl)pyridin-2-one |
| 247 | 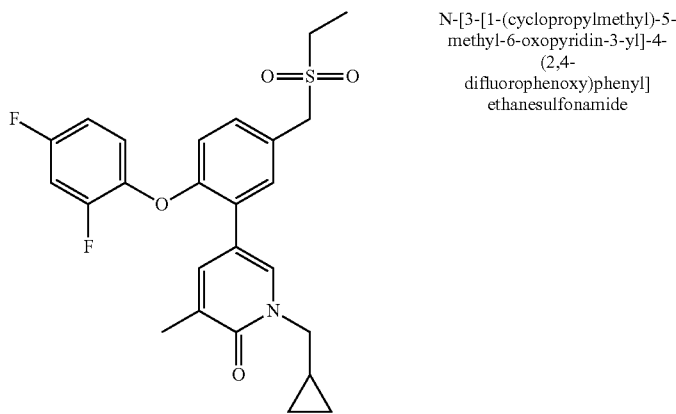 | N-[3-[1-(cyclopropylmethyl)-5-methyl-6-oxopyridin-3-yl]-4-(2,4-difluorophenoxy)phenyl]ethanesulfonamide |
| 248 | 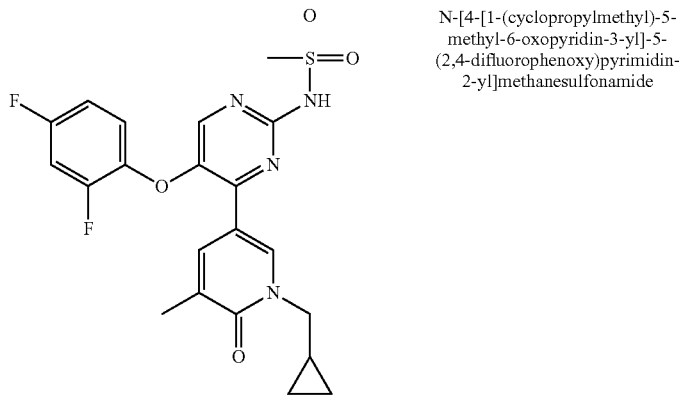 | N-[4-[1-(cyclopropylmethyl)-5-methyl-6-oxopyridin-3-yl]-5-(2,4-difluorophenoxy)pyrimidin-2-yl]methanesulfonamide |

TABLE 1-continued

| Chemical Synthesis Example | Structure | Name |
|---|---|---|
| 249 | 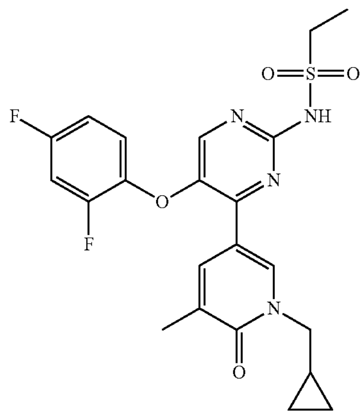 [SMILES: CCS(=O)(=O)Nc1ncc(Oc2ccc(F)cc2F)c(-c2cc(C)c(=O)n(CC3CC3)c2)n1] | N-[4-[1-(cyclopropylmethyl)-5-methyl-6-oxopyridin-3-yl]-5-(2,4-difluorophenoxy)pyrimidin-2-yl]ethanesulfonamide |
| 250 | 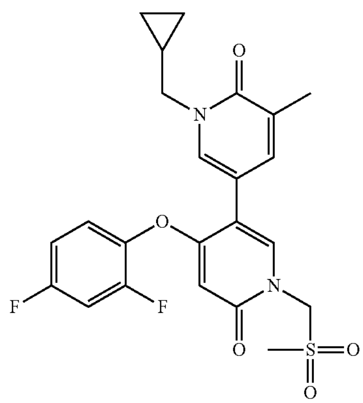 [SMILES: Cc1cc(-c2cn(CS(C)(=O)=O)c(=O)cc2Oc2ccc(F)cc2F)cn(CC2CC2)c1=O] | 1-(cyclopropylmethyl)-5-[4-(2,4-difluorophenoxy)-1-(methylsulfonylmethyl)-6-oxopyridin-3-yl]-3-methylpyridin-2-one |
| 251 | 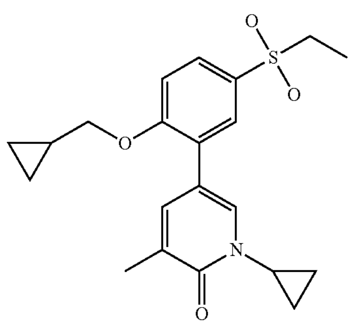 [SMILES: CCS(O)(O)c1ccc(OCC2CC2)c(-c2cc(C)c(=O)n(C3CC3)c2)c1] | 1-cyclopropyl-5-[2 (cyclopropylmethoxy)-5-etylsulfonylphenyl]-3-methylpyridin-2-one |
| 252 | 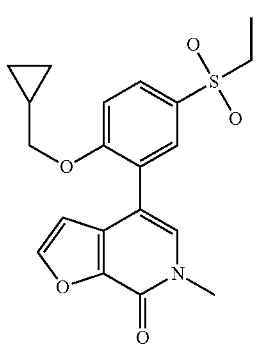 [SMILES: CCS(O)(O)c1ccc(OCC2CC2)c(-c2cn(C)c(=O)c3occc23)c1] | 4-[2-(cyclopropylmethoxy)-5-ethylsulfonylphenyl]-6-methylfuro[2,3-c]pyridin-7-one |

TABLE 1-continued

| Chemical Synthesis Example | Structure | Name |
|---|---|---|
| 253 | 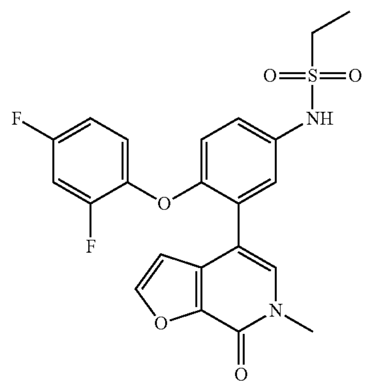 [SMILES: CCS(=O)(=O)Nc1ccc(Oc2ccc(F)cc2F)c(-c2cn(C)c(=O)c3occc23)c1] | N-[4-(2,4-difluorophenoxy)-3-(6-methyl-7-oxofuro[2,3-c]pyridin-4-yl)phenyl]ethanesulfonamide |
| 254 | 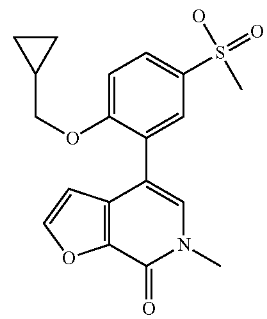 | 4-[2-(cyclopropylmethoxy)-5-methylsulfonylphenyl]-6-methylfuro[2,3-c]pyridin-7-one |
| 255 | 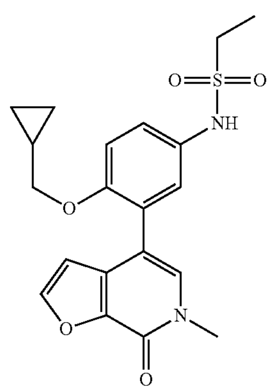 [SMILES: CCS(=O)(=O)Nc1ccc(OCC2CC2)c(-c2cn(C)c(=O)c3occc23)c1] | N-[4-(cyclopropylmethoxy)-3-(6-methyl-7-oxofuro[2,3-c]pyridin-4-yl)phenyl]ethanesulfonamide |
| 256 | 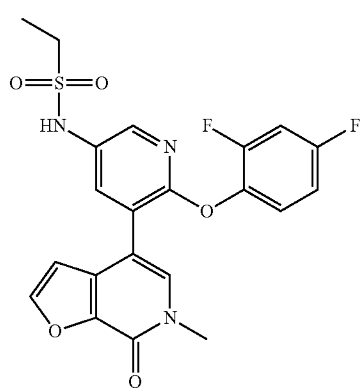 [SMILES: CCS(=O)(=O)Nc1cnc(Oc2ccc(F)cc2F)c(-c2cn(C)c(=O)c3occc23)c1] | N-[6-(2,4-difluorophenoxy)-5-(6-methyl-7-oxofuro[2,3-c]pyridin-4-yl)pyridin-3-yl]ethanesulfonamide |

TABLE 1-continued

| Chemical Synthesis Example | Structure | Name |
|---|---|---|
| 257 | 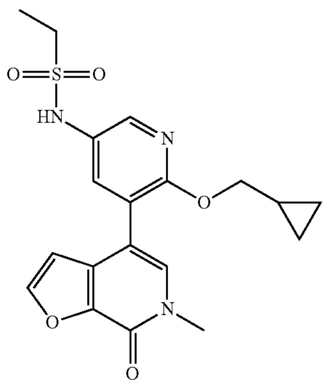 [SMILES: CCS(=O)(=O)Nc1cnc(OCC2CC2)c(-c2cn(C)c(=O)c3occc23)c1] | N-[6-(cyclopropylmethoxy)-5-(6-methyl-7-oxofuro[2,3-c]pyridin-4-yl)pyridin-3-yl]ethanesulfonamide |
| 258 | 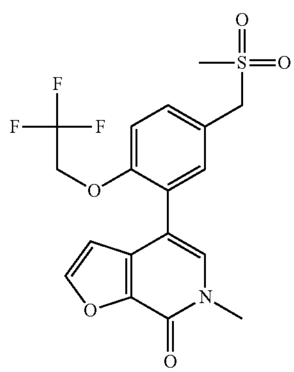 [SMILES: Cn1cc(-c2cc(CS(C)(=O)=O)ccc2OCC(F)(F)F)c2ccoc2c1=O] | 6-methyl-4-[5-(methylsulfonylmethyl)-2-(2,2,2-trifluoroethoxy)phenyl]furo[2,3-c]pyridin-7-one |
| 259 | 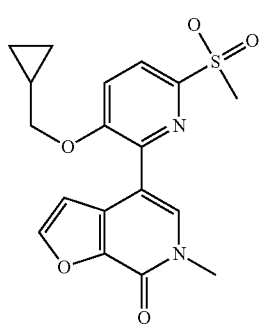 | 4-[3-(cyclopropylmethoxy)-6-methylsulfonylpyridin-2-yl]-6-methylfuro[2,3-c]pyridin-7-one |
| 260 | 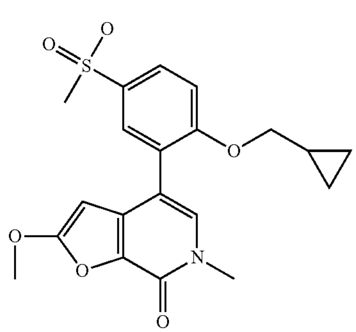 | 2-chloro-4-[2-(cyclopropylmethoxy)-5-methylsulfonylphenyl]-6-methylfuro[2,3-c]pyridin-7-one |

TABLE 1-continued

| Chemical Synthesis Example | Structure | Name |
|---|---|---|
| 261 | 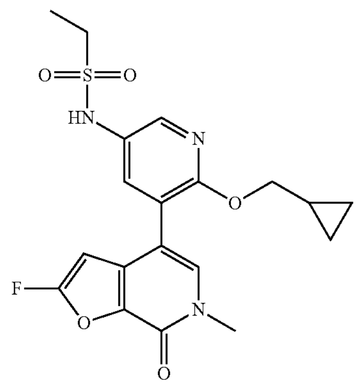 [SMILES: CCS(=O)(=O)Nc1cnc(OCC2CC2)c(-c2cn(C)c(=O)c3oc(F)cc23)c1] | N-[6-(cyclopropylmethoxy)-5-(2-fluoro-6-methyl-7-oxofuro[2,3-c]pyridin-4-yl)pyridin-3-yl]ethanesulfonamide |
| 262 | 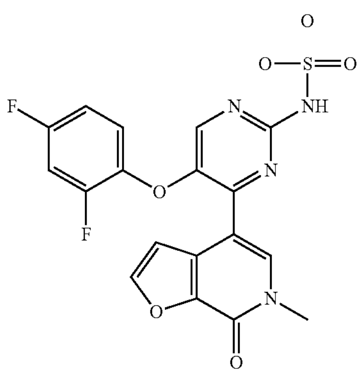 | N-[5-(2,4-difluorophenoxy)-4-(6-methyl-7-oxofuro[2,3-c]pyridin-4-yl)pyrimidin-2-yl]methanesulfonamide |
| 263 | 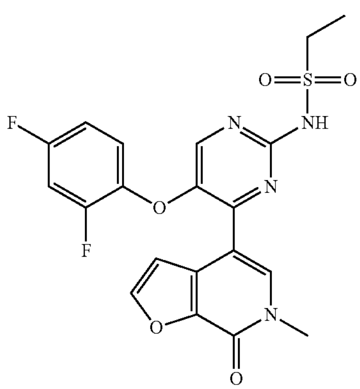 [SMILES: CCS(=O)(=O)Nc1ncc(Oc2ccc(F)cc2F)c(-c2cn(C)c(=O)c3occc23)n1] | N-[5-(2,4-difluorophenoxy)-4-(6-methyl-7-oxofuro[2,3-c]pyridin-4-yl)pyrimidin-2-yl]ethanesulfonamide |
| 264 | 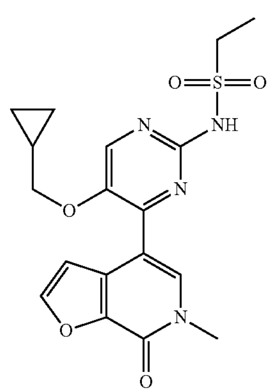 [SMILES: CCS(=O)(=O)Nc1ncc(OCC2CC2)c(-c2cn(C)c(=O)c3occc23)n1] | N-[5-(cyclopropylmethoxy)-4-(6-methyl-7-oxofuro[2,3-c]pyridin-4-yl)pyrimidin-2-yl]ethanesulfonamide |

TABLE 1-continued

| Chemical Synthesis Example | Structure | Name |
|---|---|---|
| 265 | 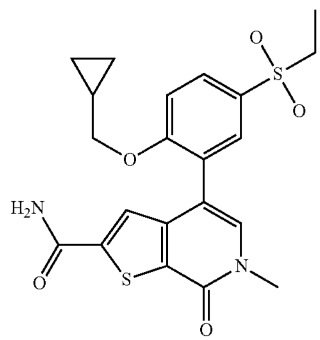 [SMILES: CCS(O)(O)c1ccc(OCC2CC2)c(-c2cn(C)c(=O)c3sc(C(N)=O)cc23)c1] | 4-[2-(cyclopropylmethoxy)-5-ethylsulfonylphenyl]-6-methyl-7-oxothieno[2,3-c]pyridine-2-carboxamide |
| 266 | 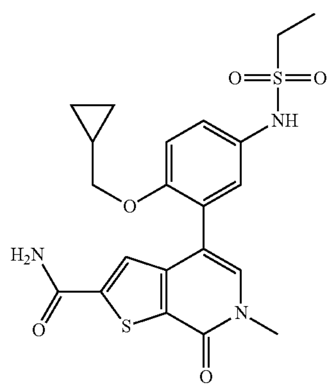 [SMILES: CCS(=O)(=O)Nc1ccc(OCC2CC2)c(-c2cn(C)c(=O)c3sc(C(N)=O)cc23)c1] | 4-[2-(cyclopropylmethoxy)-5-(ethylsulfonylamino)phenyl]-6-methyl-7-oxothieno[2,3-c]pyridine-2-carboxamide |
| 267 | 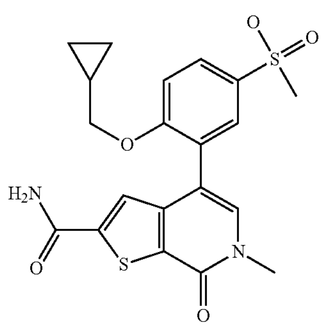 | 4-[2-(cyclopropylmethoxy)-5-methylsulfonylphenyl]-6-methyl-7-oxothieno[2,3-c]pyridine-2-carboxamide |
| 268 | 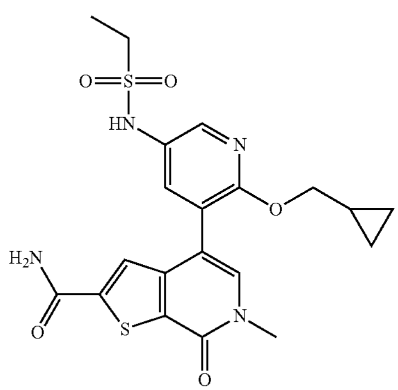 [SMILES: CCS(=O)(=O)Nc1cnc(OCC2CC2)c(-c2cn(C)c(=O)c3sc(C(N)=O)cc23)c1] | 4-[2-(cyclopropylmethoxy)-5-(ethylsulfonylamino)pyridin-3-yl]-6-methyl-7-oxothieno[2,3-c]pyridine-2-carboxamide |

TABLE 1-continued

| Chemical Synthesis Example | Structure | Name |
|---|---|---|
| 269 | 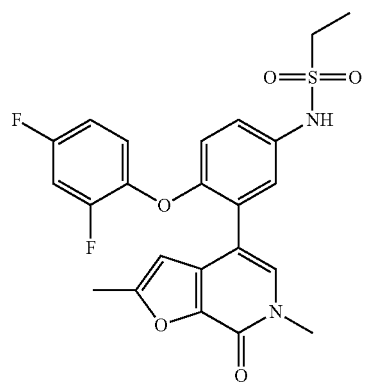 [SMILES: CCS(=O)(=O)Nc1ccc(Oc2ccc(F)cc2F)c(-c2cn(C)c(=O)c3oc(C)cc23)c1] | N-[4-(2,4-difluorophenoxy)-3-(2,6-dimethyl-7-oxofuro[2,3-c]pyridin-4-yl)phenyl]ethanesulfonamide |
| 270 | 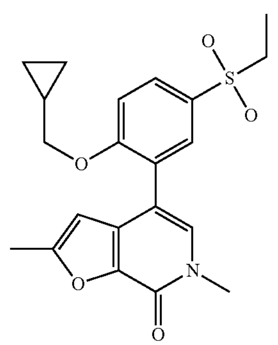 [SMILES: CCS(O)(O)c1ccc(OCC2CC2)c(-c2cn(C)c(=O)c3oc(C)cc23)c1] | 4-[2-cyclopropylmethoxy)-5-ethylsulfonylphenyl]-2,6-dimethylfuro[2,3-c]pyridin-7-one |
| 271 | 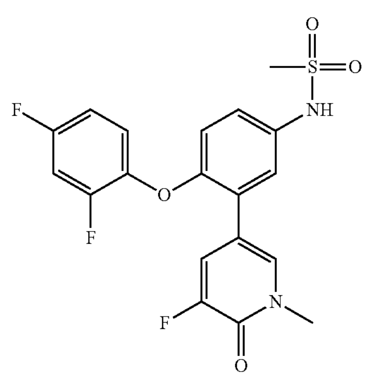 [SMILES: Cn1cc(-c2cc(NS(C)(=O)=O)ccc2Oc2ccc(F)cc2F)cc(F)c1=O] | N-[4-(2,4-difluorophenoxy)-3-(5-fluoro-1-methyl-6-oxopyridin-3-yl)phenyl]methanesulfonamide |
| 272 | 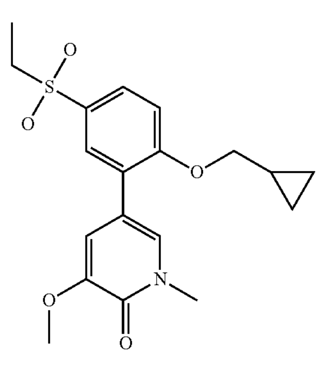 [SMILES: CCS(O)(O)c1ccc(OCC2CC2)c(-c2cc(OC)c(=O)n(C)c2)c1] | 3-chloro-5-[2-(cyclopropylmethoxy)-5-ethylsulfonylphenyl]-1-methylpyridin-2-one |

TABLE 1-continued

| Chemical Synthesis Example | Structure | Name |
|---|---|---|
| 273 | 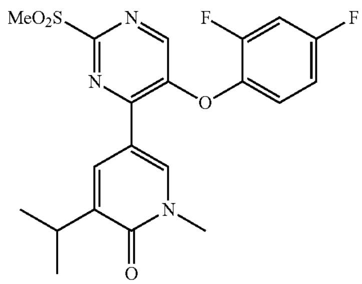 [SMILES: CC(C)c1cc(-c2nc(S(C)(=O)=O)ncc2Oc2ccc(F)cc2F)cn(C)c1=O] | 5-[5-(2,4-difluorophenoxy)-2-methylsulfonylpyrimidin-4-yl]-1-methyl-3-propan-2-ylpyridin-2-one |
| 274 | 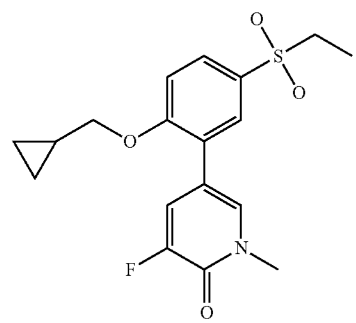 [SMILES: CCS(O)(O)c1ccc(OCC2CC2)c(-c2cc(F)c(=O)n(C)c2)c1] | 5-[2-(cyclopropylmethoxy)-5-ethylsulfonylphenyl]-3-fluoro-1-methylpyridin-2-one |
| 275 | 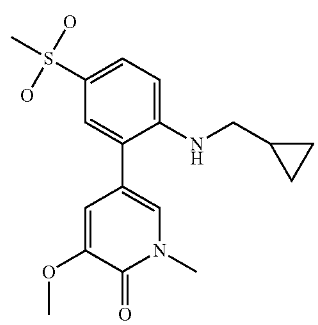 [SMILES: COc1cc(-c2cc(S(C)(O)O)ccc2NCC2CC2)cn(C)c1=O] | 3-chloro-5-[2-(cyclopropylmethylamino)-5-ethylsulfonylphenyl]-1-methylpyridin-2-one |
| 276 | 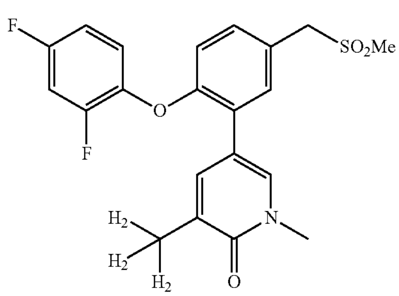 | 5-[2-(2,4-difluorophenoxy)-5-(methanesulfonylmethyl)phenyl]-3-($^2$H$_3$)methyl-1-methyl-1,2-dihydropyridin-2-one |
| 277 | 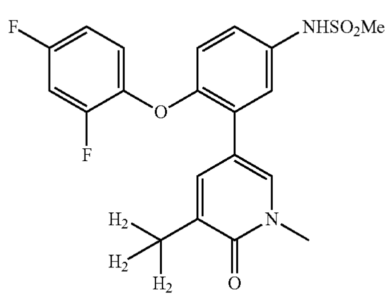 | N-[4-(2,4-difluorophenoxy)-3-[5-($^2$H$_3$)methyl-1-methyl-6-oxo-1,6-dihydropyridin-3-yl]phenyl]methanesulfonamide |

TABLE 1-continued

| Chemical Synthesis Example | Structure | Name |
|---|---|---|
| 278 | 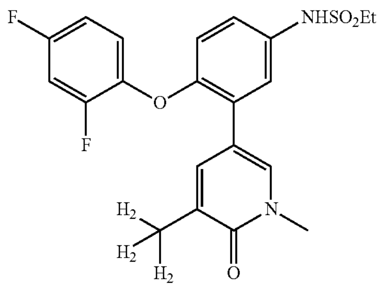 | N-[4-(2,4-difluorophenoxy)-3-[5-($^2$H$_3$)methyl-1-methyl-6-oxo-1,6-dihydropyridin-3-yl]phenyl]ethane-1-sulfonamide |
| 279 | 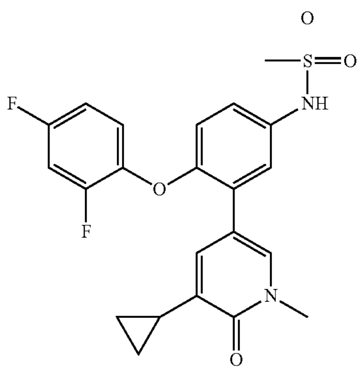 | N-[3-(5-cyclopropyl-1-methyl-6-oxopyridin-3-yl)-4-(2,4-difluorophenoxy)phenyl]methanesulfonamide |
| 280 | 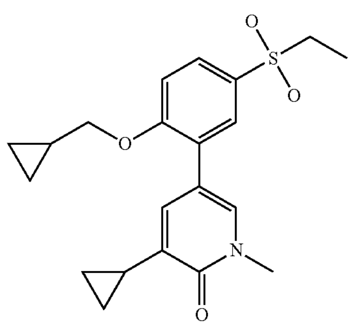 [SMILES: CCS(O)(O)c1ccc(OCC2CC2)c(-c2cc(C3CC3)c(=O)n(C)c2)c1] | 3-cyclopropyl-5-[2-(cyclopropylmethoxy)-5-ethylsulfonylphenyl]-1-methylpyridin-2-one |
| 281 | 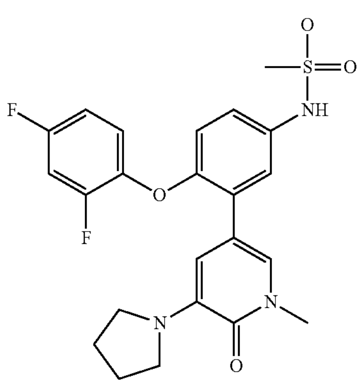 | N-[4-(2,4-difluorophenoxy)-3-(1-methyl-6-oxo-5-pyrrolidin-1-ylpyridin-3-yl)phenyl]methanesulfonamide |

TABLE 1-continued

| Chemical Synthesis Example | Structure | Name |
|---|---|---|
| 282 | 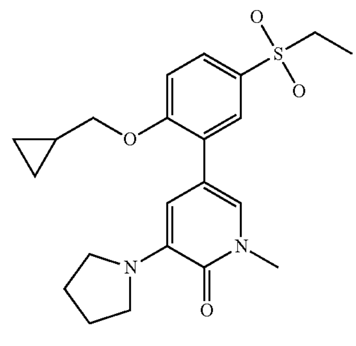 [SMILES: CCS(O)(O)c1ccc(OCC2CC2)c(-c2cc(N3CCCC3)c(=O)n(C)c2)c1] | 5-[2-(cyclopropylmethoxy)-5-ethylsulfonylphenyl]-1-methyl-3-pyrrolidin-1-ylpyridin-2-one |
| 283 | 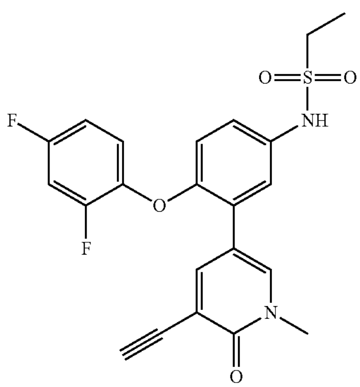 [SMILES: C#Cc1cc(-c2cc(NS(=O)(=O)CC)ccc2Oc2ccc(F)cc2F)cn(C)c1=O] | N-[4-(2,4-difluorophenoxy)-3-(5-ethynyl-1-methyl-6-oxopyridin-3-yl)phenyl]ethanesulfonamide |
| 284 | 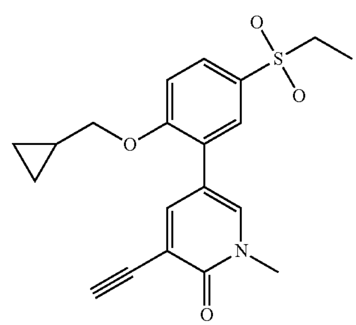 [SMILES: C#Cc1cc(-c2cc(S(O)(O)CC)ccc2OCC2CC2)cn(C)c1=O] | 5-[2-(cyclopropylmethoxy)-5-ethylsulfonylphenyl]-3-ethynyl-1-methylpyridin-2-one |
| 285 | 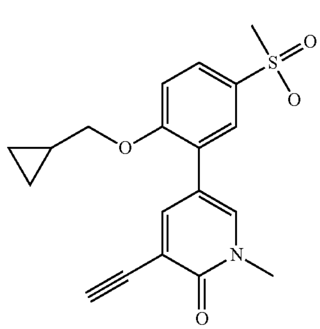 | 5-[2-cyclopropylmethoxy)-5-methylsulfonylphenyl]-3-ethynyl-1-methylpyridin-2-one |

TABLE 1-continued

| Chemical Synthesis Example | Structure | Name |
|---|---|---|
| 286 | 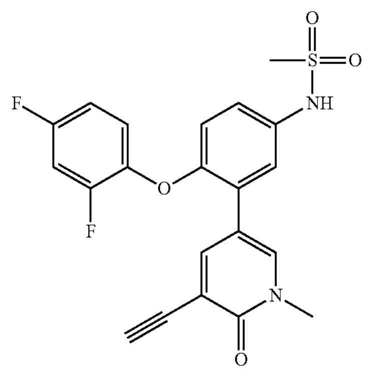 [SMILES: C#Cc1cc(-c2cc(NS(C)(=O)=O)ccc2Oc2ccc(F)cc2F)cn(C)c1=O] | N-[4-(2,4-difluorophenoxy)-3-(5-ethynyl-1-methyl-6-oxopyridin-3-yl)phenyl]methanesulfonamide |
| 287 | 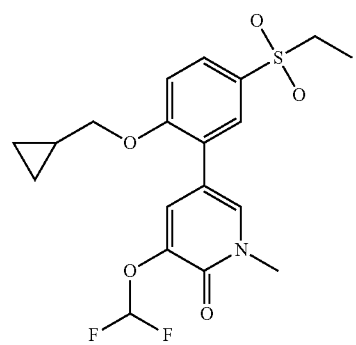 [SMILES: CCS(O)(O)c1ccc(OCC2CC2)c(-c2cc(OC(F)F)c(=O)n(C)c2)c1] | 5-[2-(cyclopropylmethoxy)-5-ethylsulfonylphenyl]-3-(difluoromethoxy)-1-methylpyridin-2-one |
| 288 | 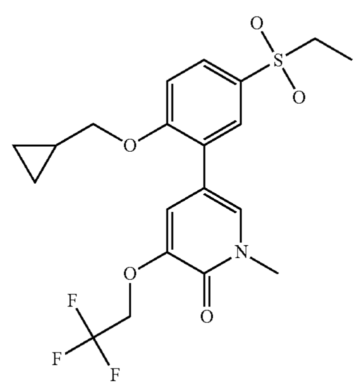 [SMILES: CCS(O)(O)c1ccc(OCC2CC2)c(-c2cc(OCC(F)(F)F)c(=O)n(C)c2)c1] | 5-[2-(cyclopropylmethoxy)-5-ethylsulfonylphenyl]-1-methyl-3-(2,2,2-trifluoroethoxy)pyridin-2-one |
| 289 | 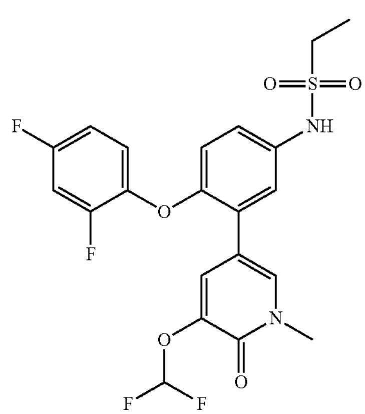 [SMILES: CCS(=O)(=O)Nc1ccc(Oc2ccc(F)cc2F)c(-c2cc(OC(F)F)c(=O)n(C)c2)c1] | N-[3-[5-(difluoromethoxy)-1-methyl-6-oxopyridin-3-yl]-4-(2,4-difluorophenoxy)phenyl]ethanesulfonamide |

TABLE 1-continued
| Chemical Synthesis Example | Structure | Name |
|---|---|---|
| 290 | 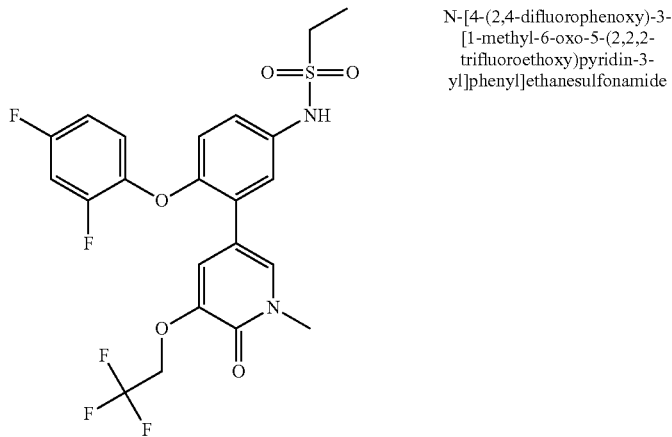 | N-[4-(2,4-difluorophenoxy)-3-[1-methyl-6-oxo-5-(2,2,2-trifluoroethoxy)pyridin-3-yl]phenyl]ethanesulfonamide |
| 291 | 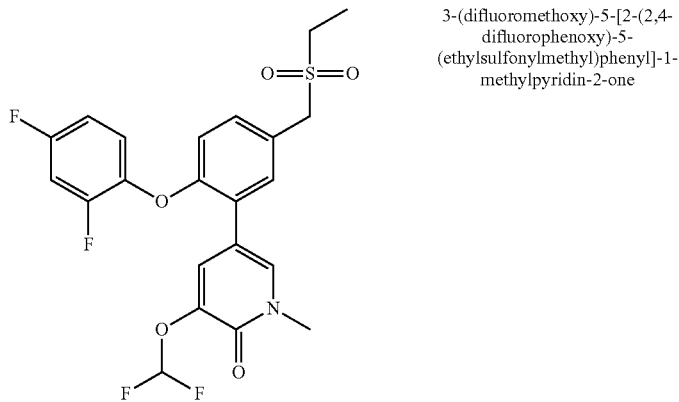 | 3-(difluoromethoxy)-5-[2-(2,4-difluorophenoxy)-5-(ethylsulfonylmethyl)phenyl]-1-methylpyridin-2-one |
| 292 | 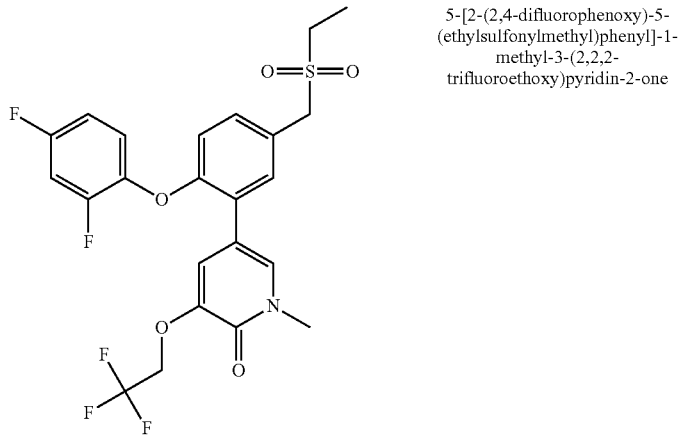 | 5-[2-(2,4-difluorophenoxy)-5-(ethylsulfonylmethyl)phenyl]-1-methyl-3-(2,2,2-trifluoroethoxy)pyridin-2-one |

TABLE 1-continued
| Chemical Synthesis Example | Structure | Name |
|---|---|---|
| 293 | 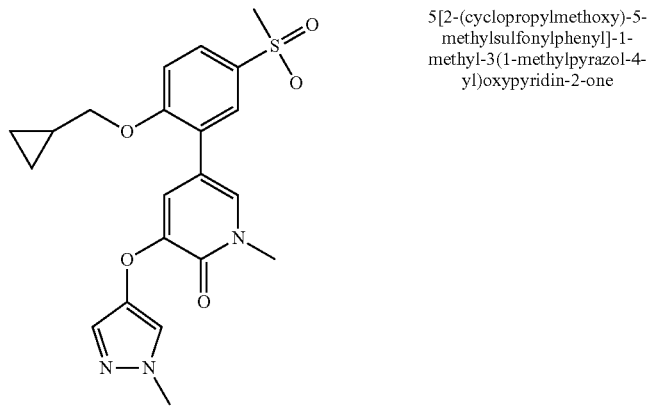 | 5[2-(cyclopropylmethoxy)-5-methylsulfonylphenyl]-1-methyl-3(1-methylpyrazol-4-yl)oxypyridin-2-one |
| 294 | 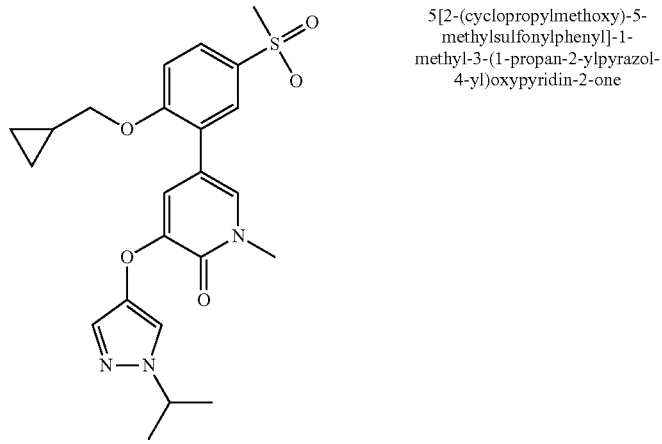 | 5[2-(cyclopropylmethoxy)-5-methylsulfonylphenyl]-1-methyl-3-(1-propan-2-ylpyrazol-4-yl)oxypyridin-2-one |
| 295 | 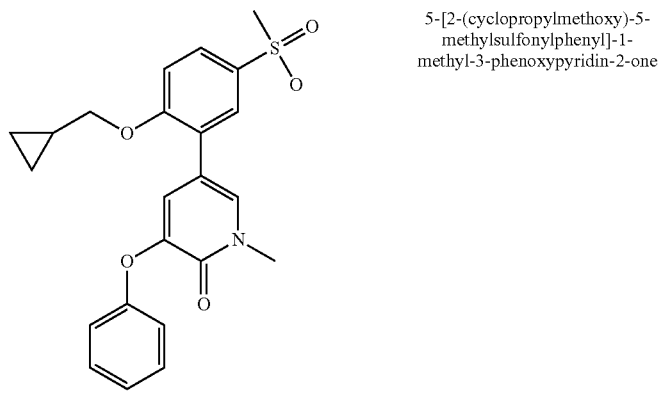 | 5-[2-(cyclopropylmethoxy)-5-methylsulfonylphenyl]-1-methyl-3-phenoxypyridin-2-one |

TABLE 1-continued
| Chemical Synthesis Example | Structure | Name |
|---|---|---|
| 296 | 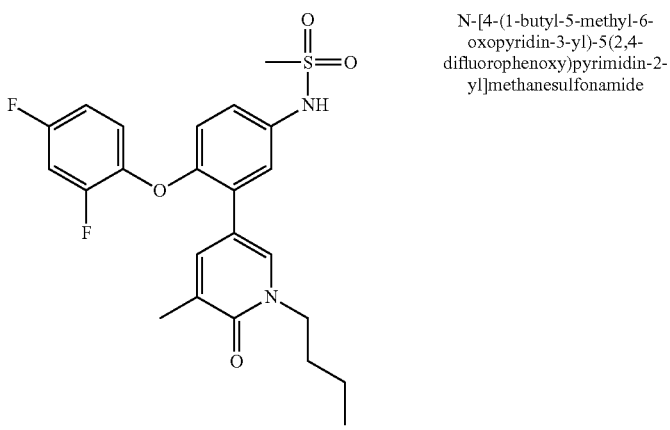 | N-[4-(1-butyl-5-methyl-6-oxopyridin-3-yl)-5(2,4-difluorophenoxy)pyrimidin-2-yl]methanesulfonamide |
| 297 | 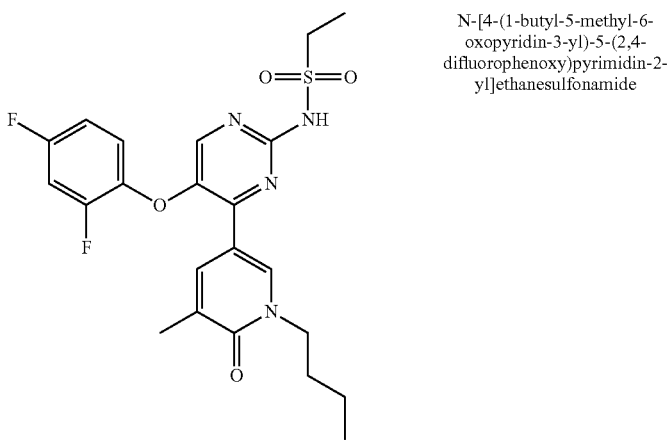 | N-[4-(1-butyl-5-methyl-6-oxopyridin-3-yl)-5-(2,4-difluorophenoxy)pyrimidin-2-yl]ethanesulfonamide |
| 298 | 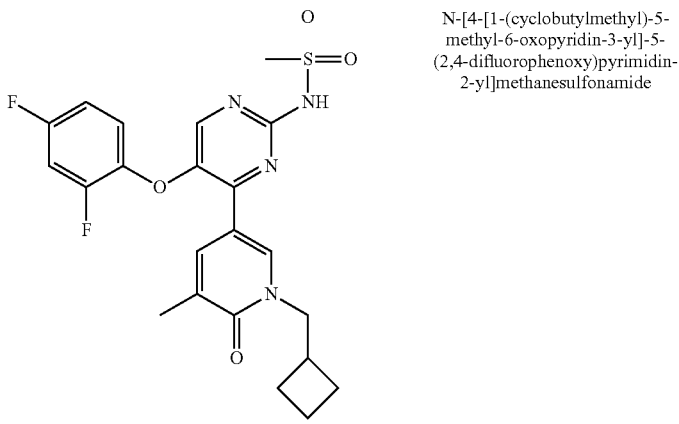 | N-[4-[1-(cyclobutylmethyl)-5-methyl-6-oxopyridin-3-yl]-5-(2,4-difluorophenoxy)pyrimidin-2-yl]methanesulfonamide |

TABLE 1-continued

| Chemical Synthesis Example | Structure | Name |
|---|---|---|
| 299 | 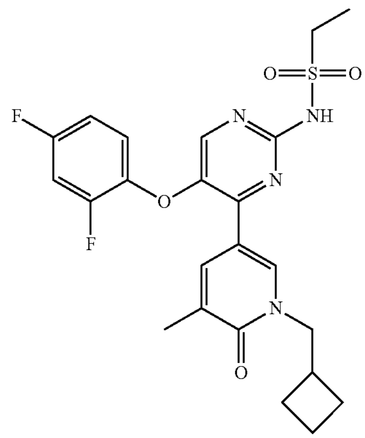 [SMILES: CCS(=O)(=O)Nc1ncc(Oc2ccc(F)cc2F)c(-c2cc(C)c(=O)n(CC3CCC3)c2)n1] | N-[4-[1-(cyclobutylmethyl)-5-methyl-6-oxopyridin-3-yl]-5-(2,4-difluorophenoxy)pyrimidin-2-yl]ethanesulfonamide |
| 300 | 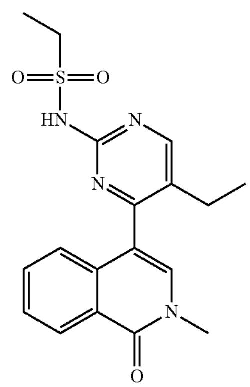 [SMILES: CCc1cnc(NS(=O)(=O)CC)nc1-c1cn(C)c(=O)c2ccccc12] | N-[5-ethyl-4-(2-methyl-1-oxoisoquinolin-4-yl)pyrimidin-2-yl]ethanesulfonamide |
| 301 | 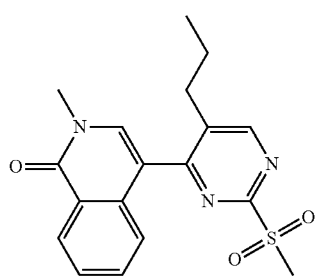 [SMILES: CCCc1cnc(S(C)(=O)=O)nc1-c1cn(C)c(=O)c2ccccc12] | 2-methyl-4-(2-methylsulfonyl-5-propylpyrimidin-4-yl)isoquinolin-1-one |
| 302 | 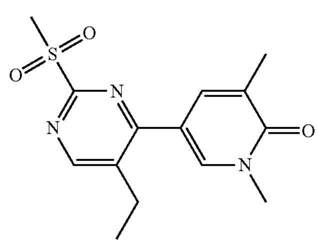 [SMILES: CCc1cnc(S(C)(=O)=O)nc1-c1cc(C)c(=O)n(C)c1] | 5-(5-ethyl-2-methylsulfonylpyrimidin-4-yl)-1,3-dimethylpyridin-2-one |

TABLE 1-continued

| Chemical Synthesis Example | Structure | Name |
|---|---|---|
| 303 | 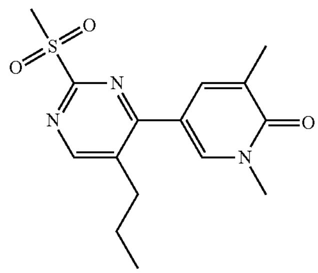 [SMILES: CCCc1cnc(S(C)(=O)=O)nc1-c1cc(C)c(=O)n(C)c1] | 1,3-dimethyl-5-(2-methylsulfonyl-5-propylpyrimidin-4-yl)pyridin-2-one |
| 304 | 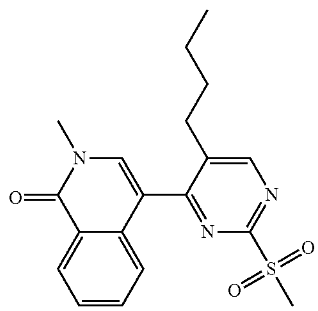 [SMILES: CCCCc1cnc(S(C)(=O)=O)nc1-c1cn(C)c(=O)c2ccccc12] | 4-(5-butyl-2-methylsulfonylpyrimidin-4-yl)-2-methylisoquinolin-1-one |
| 305 | 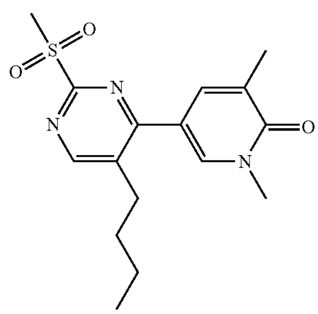 [SMILES: CCCCc1cnc(S(C)(=O)=O)nc1-c1cc(C)c(=O)n(C)c1] | 5-(5-butyl-2-methylsulfonylpyrimidin-4-yl)-1,3-dimethylpyridin-2-one |
| 306 | 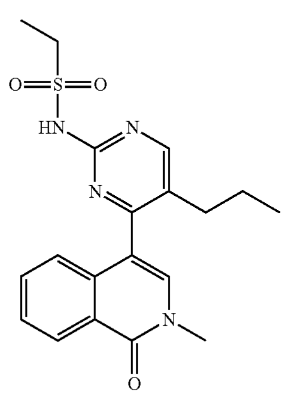 [SMILES: CCCc1cnc(NS(=O)(=O)CC)nc1-c1cn(C)c(=O)c2ccccc12] | N-[4-(2-methyl-1-oxoisoquinolin-4-yl)-5-propylpyrimidin-2-yl]ethanesulfonamide |

TABLE 1-continued

| Chemical Synthesis Example | Structure | Name |
|---|---|---|
| 307 | 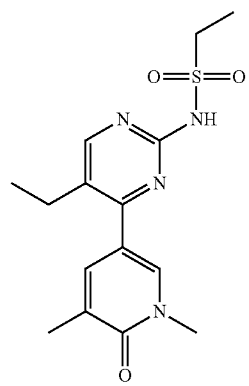 [SMILES: CCc1cnc(NS(=O)(=O)CC)nc1-c1cc(C)c(=O)n(C)c1] | N-[4-(1,5-dimethyl-6-oxopyridin-3-yl)-5-ethylpyrimidin-2-yl]ethanesulfonamide |
| 308 | 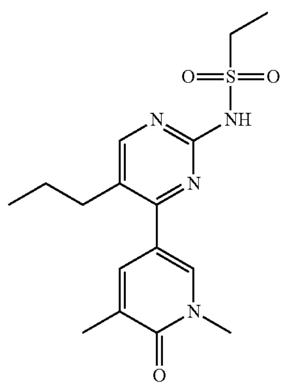 | N-[4-(1,5-dimethyl-6-oxopyridin-3-yl)-5-propylpyrimidin-2-yl]ethanesulfonamide |
| 309 | 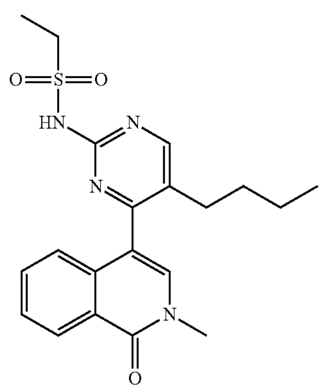 [SMILES: CCCCc1cnc(NS(=O)(=O)CC)nc1-c1cn(C)c(=O)c2ccccc12] | N-[5-butyl-4-(2-methyl-1-oxoisoquinolin-4-yl)pyrimidin-2-yl]ethanesulfonamide |
| 310 | 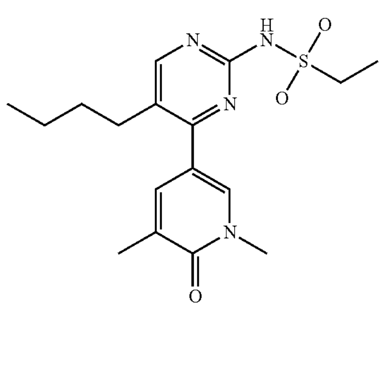 [SMILES: CCCCc1cnc(NS(O)(O)CC)nc1-c1cc(C)c(=O)n(C)c1] | N-[5-butyl-4-(1,5-dimethyl-6-oxopyridin-3-yl)pyrimidin-2-yl]ethanesulfonamide |

TABLE 1-continued

| Chemical Synthesis Example | Structure | Name |
|---|---|---|
| 311 | 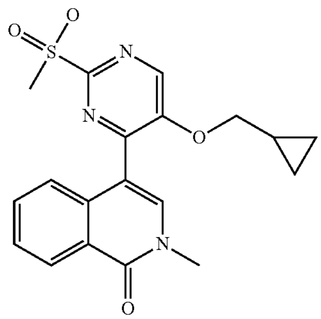 | 4-[5-(cyclopropylmethoxy)-2-methylsulfonylpyrimidin-4-yl]-2-methylisoquinolin-1-one |
| 312 | 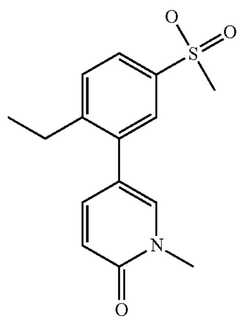 | 5-(2-ethyl-5-methylsulfonylphenyl)-1-methylpyridin-2-one |
| 313 | 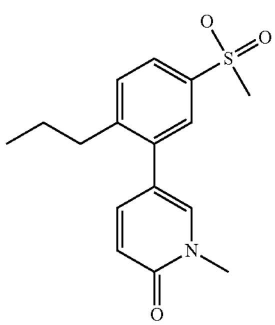 | 1-methyl-5-(5-methylsulfonyl-2-propylphenyl)pyridin-2-one |
| 314 | 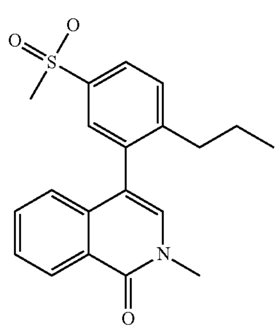 | 2-methyl-4-(5-methylsulfonyl-2-propylphenyl)isoquinolin-1-one |

TABLE 1-continued

| Chemical Synthesis Example | Structure | Name |
|---|---|---|
| 315 | 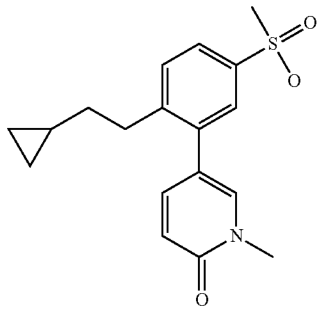 | 5-[2-(2-cyclopropylethyl)-5-methylsulfonylphenyl]-1-methylpyridin-2-one |
| 316 | 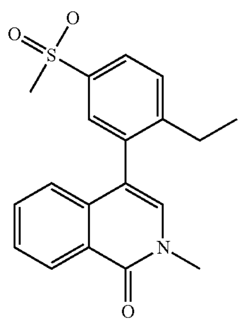 | 4-(2-ethyl-5-methylsulfonylphenyl)-2-methylisoquinolin-1-one |
| 317 | 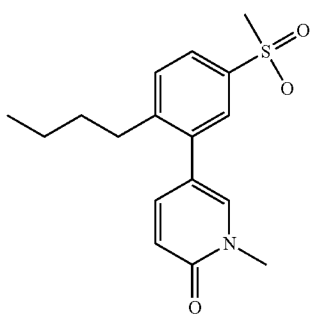 | 5-(2-butyl-5-methylsulfonylphenyl)-1-methylpyridin-2-one |
| 318 | 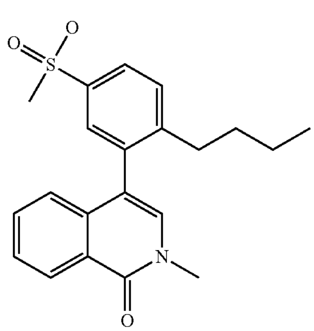 | 4-(2-butyl-5-methylsulfonylphenyl)-2-methylisoquinolin-1-one |

TABLE 1-continued

| Chemical Synthesis Example | Structure | Name |
|---|---|---|
| 319 | 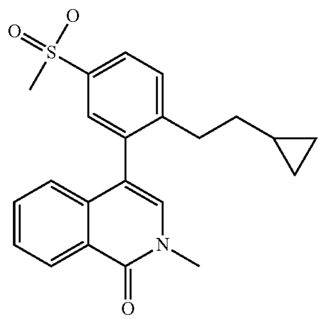 | 4-[2-(2-cyclopropylethyl)-5-methylsulfonylphenyl]-2-methylisoquinolin-1-one |
| 320 | 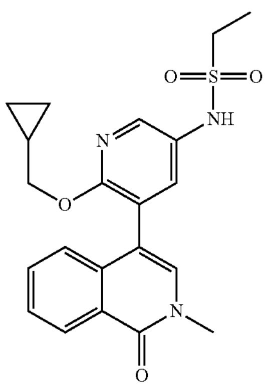 [SMILES: CCS(=O)(=O)Nc1cnc(OCC2CC2)c(-c2cn(C)c(=O)c3ccccc23)c1] | N-[6-(cyclopropylmethoxy)-5-(2-methyl-1-oxoisoquinolin-4-yl)pyridin-3-1-yl]ethanesulfonamide |
| 321 | 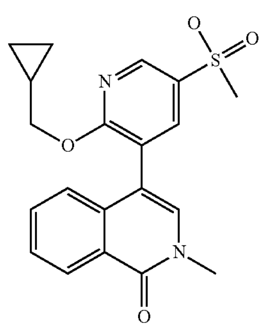 | 4-[2-(cyclopropylmethoxy)-5-methylsulfonylpyridin-3-yl]-2-methylisoquinolin-1-one |
| 322 | 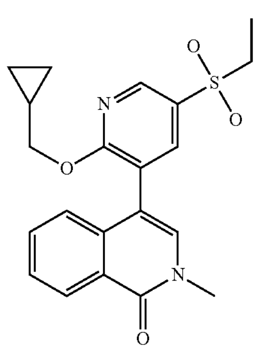 [SMILES: CCS(O)(O)c1cnc(OCC2CC2)c(-c2cn(C)c(=O)c3ccccc23)c1] | 4-[2-(cyclopropylmethoxy)-5-ethylsulfonylpyridin-3-yl]-2-methylisoquinolin-1-one |

TABLE 1-continued
| Chemical Synthesis Example | Structure | Name |
|---|---|---|
| 323 | 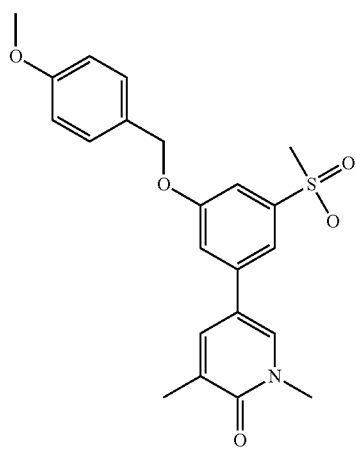 | 5-[3-[(4-methoxyphenyl)methoxy]-5-methylsulfonylphenyl]-1,3-dimethylpyridin-2-one |
| 324 | 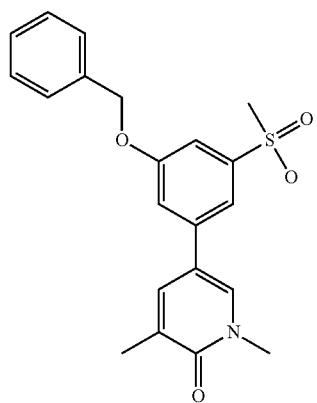 | 1,3-dimethyl-5-(3-methylsulfonyl-5-phenylmethoxyphenyl)pyridin-2-one |
| 325 | 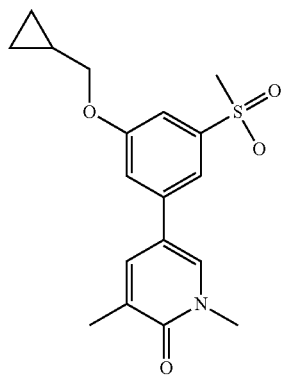 | 5-[3-(cyclopropylmethoxy)-5-methylsulfonylphenyl]-1,3-dimethylpyridin-2-one |

TABLE 1-continued

| Chemical Synthesis Example | Structure | Name |
|---|---|---|
| 326 | 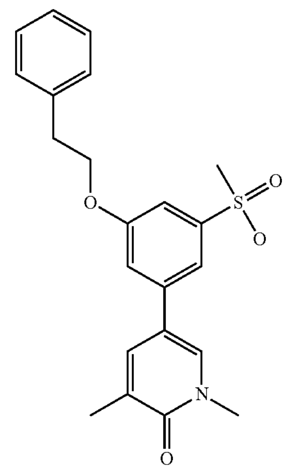 | 1,3-dimethyl-5-[3-methylsulfonyl-5-(2-phenylethoxy)phenyl]pyridin-2-one |
| 327 | 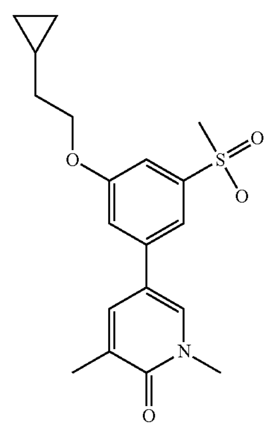 | 5-[3-(2-cyclopropylethoxy)-5-methylsulfonylphenyl]-1,3-dimethylpyridin-2-one |
| 328 | 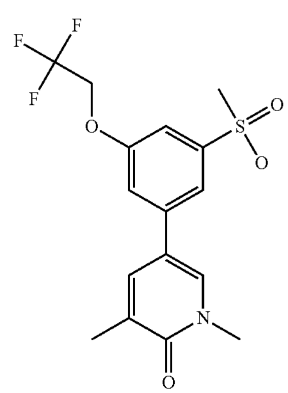 | 1,3-dimethyl-5-[3-methylsulfonyl-5-(2,2,2-trifluoroethoxy)phenyl]pyridin-2-one |

TABLE 1-continued
| Chemical Synthesis Example | Structure | Name |
|---|---|---|
| 329 | 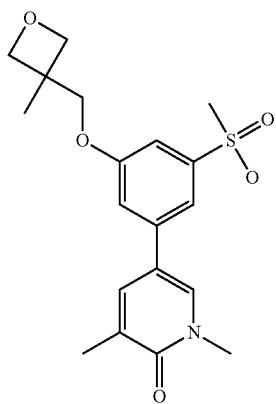 | 1,3-dimethyl-5-[3-[(3-methyloxetan-3-yl)methoxy]-5-methylsulfonylphenyl]pyridin-2-one |
| 330 | 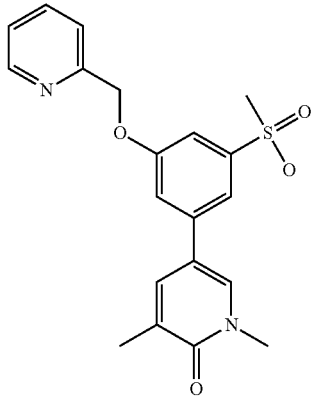 | 1,3-dimethyl-5-[3-methylsulfonyl-5-(pyridin-2-ylmethoxy)phenyl]pyridin-2-one |
| 331 | 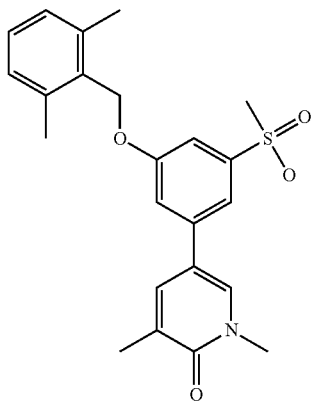 | 5-[3-[(2,6-dimethylphenyl)methoxy]-5-methylsulfonylphenyl]-1,3-dimethylpyridin-2-one |

TABLE 1-continued

| Chemical Synthesis Example | Structure | Name |
|---|---|---|
| 332 | 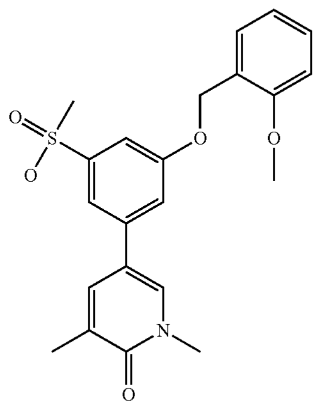 | 5-[3-[(2-chlorophenyl)methoxy]-5-methylsulfonylphenyl]-1,3-dimethylpyridin-2-one |
| 333 | 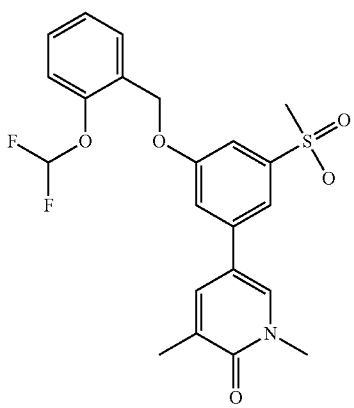 | 5-[3-[[2-(difluoromethoxy)phenyl]methoxy]-5-methylsulfonylphenyl]-1,3-dimethylpyridin-2-one |
| 334 | 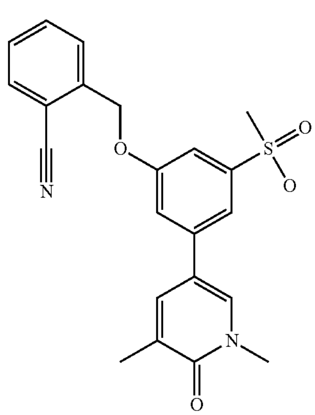 | 2-[[3-(1,5-dimethyl-6-oxopyridin-3-yl)-5-methylsulfonylphenoxy]methyl]benzonitrile |

TABLE 1-continued

| Chemical Synthesis Example | Structure | Name |
|---|---|---|
| 335 | 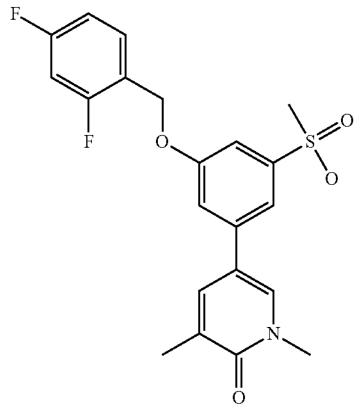 | 5-[3-[(2,4-difluorophenyl)methoxy]-5-methylsulfonylphenyl]-1,3-dimethylpyridin-2-one |
| 336 | 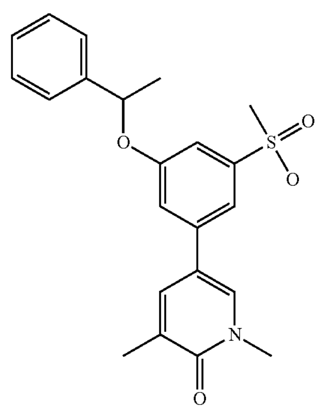 | 1,3-dimethyl-5-[3-methylsulfonyl-5-(1-phenylethoxy)phenyl]pyridin-2-one |
| 337 | 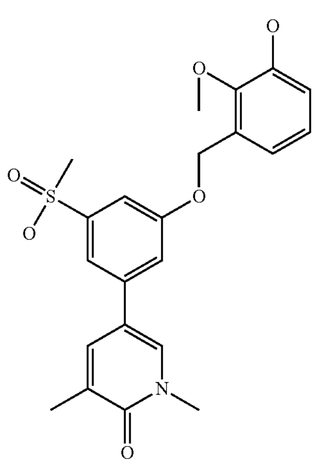 | 5-[3-[(2,3-dichlorophenyl)methoxy]-5-methylsulfonylphenyl]-1,3-dimethylpyridin-2-one |

TABLE 1-continued

| Chemical Synthesis Example | Structure | Name |
|---|---|---|
| 338 | 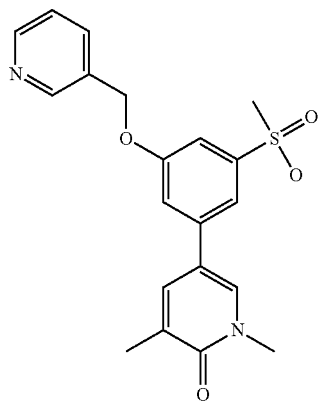 | 1,3-dimethyl-5-[3-methylsulfonyl-5-(pyridin-3-ylmethoxy)phenyl]pyridin-2-one |
| 339 | 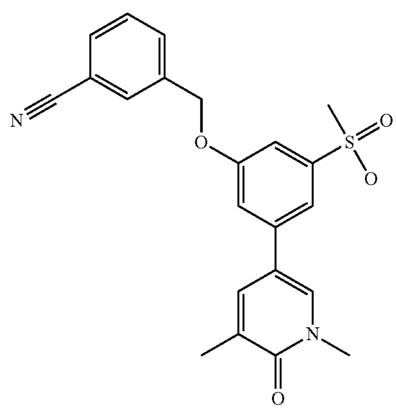 | 3-[[3-(1,5-dimethyl-6-oxopyridin-3-yl)-5-methylsulfonylphenoxy]methyl]benzonitrile |
| 340 | 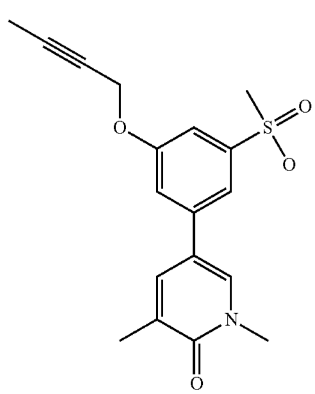 | 5-(3-but-2-ynoxy-5-methylsulfonylphenyl)-1,3-dimethylpyridin-2-one |

TABLE 1-continued

| Chemical Synthesis Example | Structure | Name |
|---|---|---|
| 341 | 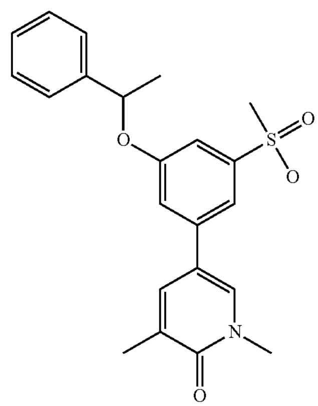 | 1,3-dimethyl-5[3-methylsulfonyl-5-(1-phenylethoxy)phenyl]pyridin-2-one |
| 342 | 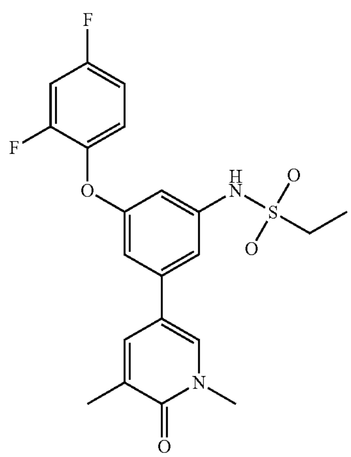 [SMILES: CCS(O)(O)Nc1cc(Oc2ccc(F)cc2F)cc(-c2cc(C)c(=O)n(C)c2)c1] | N-[3-(2,4-difluorophenoxy)-5-(1,5-dimethyl-6-oxopyridin-3-yl)phenyl]ethanesulfonamide |
| 343 | 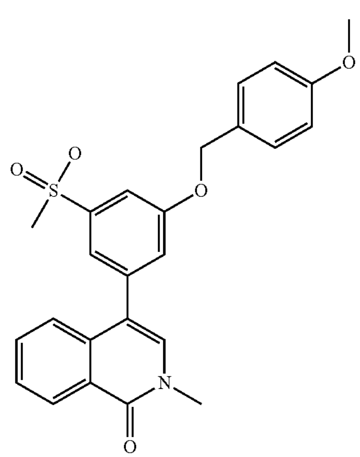 | 4-[3-[(4-methoxyphenyl)methoxy]-5-methylsulfonylphenyl]-2-methylisoquinolin-1-one |

TABLE 1-continued

| Chemical Synthesis Example | Structure | Name |
|---|---|---|
| 344 | 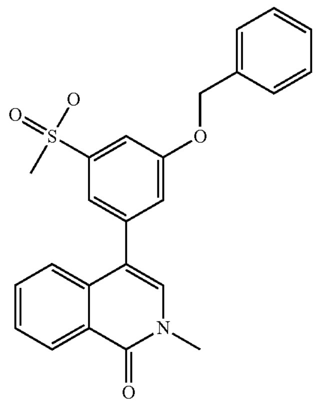 | 2-methyl-4-(3-methylsulfonyl-5-phenylmethoxyphenyl)isoquinolin-1-one |
| 345 | 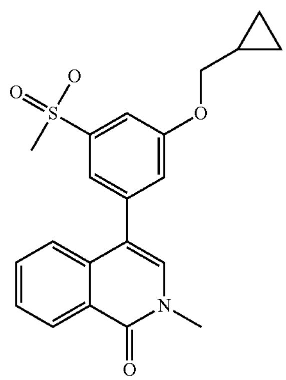 | 4-[3-(cyclopropylmethoxy)-5-methylsulfonylphenyl]-2-methylisoquinolin-1-one |
| 346 | 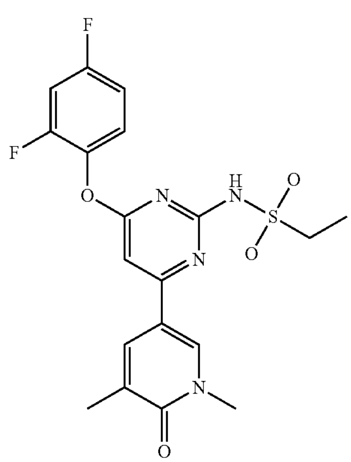 [SMILES: CCS(O)(O)Nc1nc(Oc2ccc(F)cc2F)cc(-c2cc(C)c(=O)n(C)c2)n1] | N-[4-(2,4-difluorophenoxy)-6-(1,5-dimethyl-6-oxopyridin-3-yl)pyrimidin-2-yl]ethanesulfonamide |

TABLE 1-continued

| Chemical Synthesis Example | Structure | Name |
|---|---|---|
| 347 | 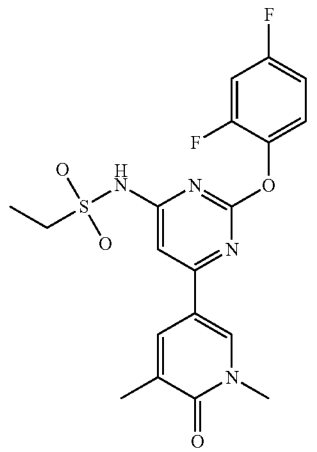 [SMILES: CCS(O)(O)Nc1cc(-c2cc(C)c(=O)n(C)c2)nc(Oc2ccc(F)cc2F)n1] | N-[2-(2,4-difluorophenoxy)-6-(1,5-dimethyl-6-oxopyridin-3-yl)pyrimidin-4-yl]ethanesulfonamide |
| 348 | 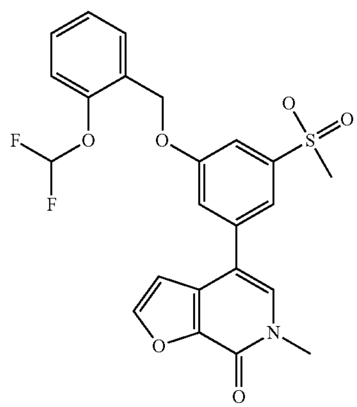 | 4-[3-[[2-(difluoromethoxy)phenyl]methoxy]-5-methylsulfonylphenyl]-6-methylfuro[2,3-c]pyridin-7-one |
| 349 | 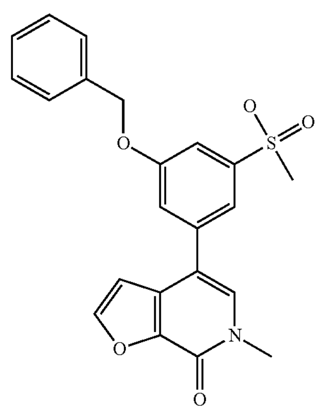 | 6-methyl-4-(3-methylsulfonyl-5-phenylmethoxyphenyl)furo[2,3-c]pyridin-7-one |

TABLE 1-continued

| Chemical Synthesis Example | Structure | Name |
|---|---|---|
| 350 | 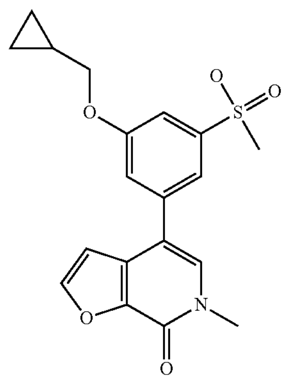 | 4-[3-(cyclopropylmethoxy)-5-methylsulfonylphenyl]-6-methylfuro[2,3-c]pyridin-7-one |
| 351 | 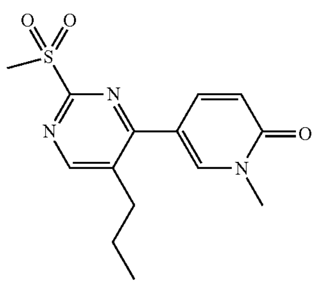 [SMILES: CCCc1cnc(S(C)(=O)=O)nc1-c1ccc(=O)n(C)c1] | 1-methyl-5-(2-methylsulfonyl-5-propylpyrimidin-4-yl)pyridin-2-one |
| 352 | 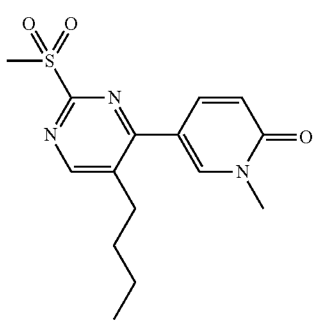 [SMILES: CCCCc1cnc(S(C)(=O)=O)nc1-c1ccc(=O)n(C)c1] | 5-(5-butyl-2-methylsulfonylpyrimidin-4-yl)-1-methylpyridin-2-one |
| 353 | 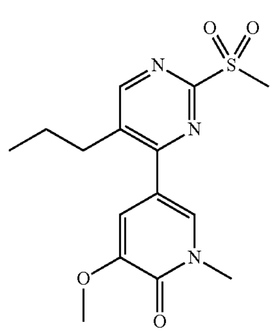 [SMILES: CCCc1cnc(S(C)(=O)=O)nc1-c1cc(OC)c(=O)n(C)c1] | 3-chloro-1-methyl-5-(2-methylsulfonyl-5-propylpyrimidin-4-yl)pyridin-2-one |

TABLE 1-continued

| Chemical Synthesis Example | Structure | Name |
|---|---|---|
| 354 | 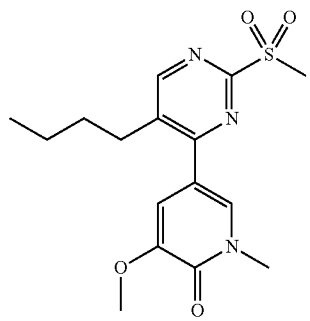 [SMILES: CCCCc1cnc(S(C)(=O)=O)nc1-c1cc(OC)c(=O)n(C)c1] | 5-(5-butyl-2-methylsulfonylpyrimidin-4-yl)-3-chloro-1-methylpyridin-2-one |
| 355 | 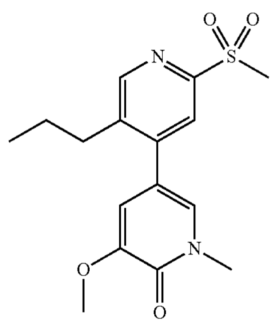 [SMILES: CCCc1cnc(S(C)(=O)=O)cc1-c1cc(OC)c(=O)n(C)c1] | 3-methoxy-1-methyl-5-(2-methylsulfonyl-5-propylpyrimidin-4-yl)pyridin-2-one |
| 356 | 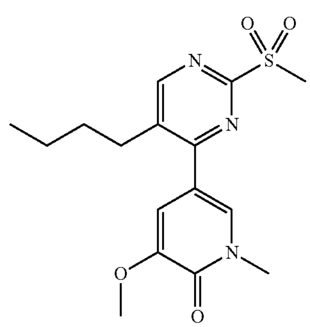 [SMILES: CCCCc1cnc(S(C)(=O)=O)nc1-c1cc(OC)c(=O)n(C)c1] | 5-(5-butyl-2-methylsulfonylpyrimidin-4-yl)-3-methoxy-1-methylpyridin-2-one |
| 357 | 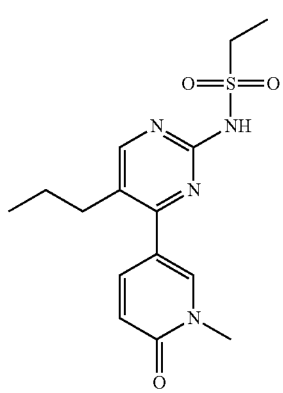 [SMILES: CCCc1cnc(NS(=O)(=O)CC)nc1-c1ccc(=O)n(C)c1] | N-[4-(1-methyl-6-oxopyridin-3-yl)-5-propylpyrimidin-2-yl]ethanesulfonamide |

TABLE 1-continued
| Chemical Synthesis Example | Structure | Name |
|---|---|---|
| 358 | 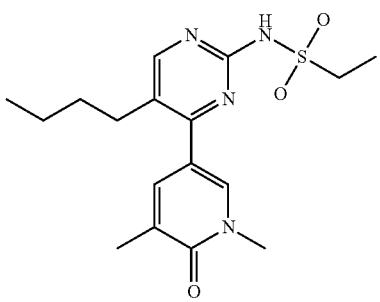 [SMILES: CCCCc1cnc(NS(O)(O)CC)nc1-c1cc(C)c(=O)n(C)c1] | N-[5-butyl-4-(1-methyl-6-oxopyridin-3-yl)pyrimidin-2-yl]ethanesulfonamide |
| 359 | 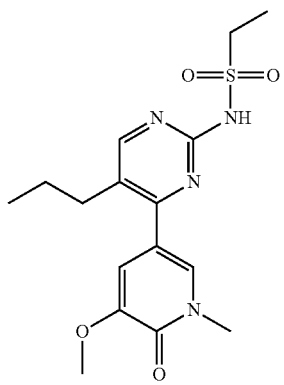 [SMILES: CCCc1cnc(NS(=O)(=O)CC)nc1-c1cc(OC)c(=O)n(C)c1] | N-[4-(5-chloro-1-methyl-6-oxopyridin-3-yl)-5-propylpyrimidin-2-yl]ethanesulfonamide |
| 360 | 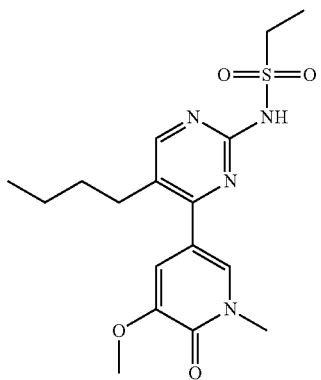 [SMILES: CCCCc1cnc(NS(=O)(=O)CC)nc1-c1cc(OC)c(=O)n(C)c1] | N-[5-butyl-4-(5-chloro-1-methyl-6-oxopyridin-3-yl)pyrimidin-2-yl]ethanesulfonamide |
| 361 | 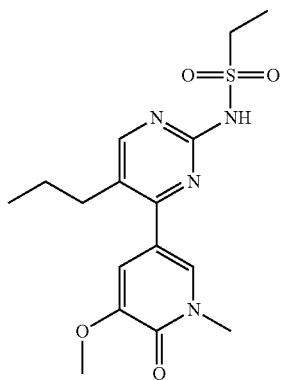 [SMILES: CCCc1cnc(NS(=O)(=O)CC)nc1-c1cc(OC)c(=O)n(C)c1] | N-[4-(5-methoxy-1-methyl-6-oxopyridin-3-yl)-5-propylpyrimidin-2-yl]ethanesulfonamide |

TABLE 1-continued

| Chemical Synthesis Example | Structure | Name |
|---|---|---|
| 362 | 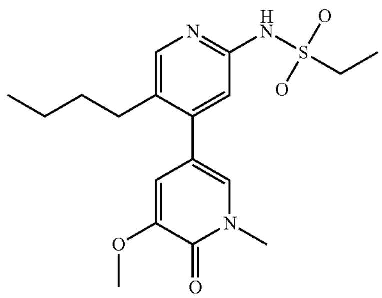 [SMILES: CCCCc1cnc(NS(O)(O)CC)cc1-c1cc(OC)c(=O)n(C)c1] | N-[5-butyl-4-(5-methoxy-1-methyl-6-oxopyridin-3-yl)pyrimidin-2-yl]ethanesulfonamide |
| 363 | 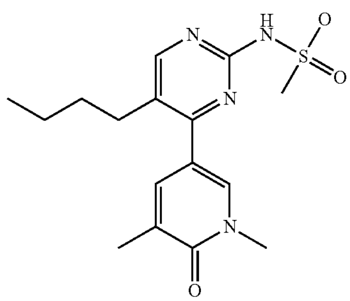 | N-[5-butyl-4-(1,5-dimethyl-6-oxopyridin-3-yl)pyrimidin-2-yl]methanesulfonamide |
| 364 | 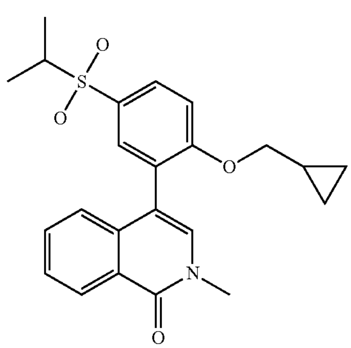 [SMILES: CC(C)S(O)(O)c1ccc(OCC2CC2)c(-c2cn(C)c(=O)c3ccccc23)c1] | 4-[2-(cyclopropylmethoxy)-5-propan-2-ylsulfonylphenyl]-2-methylisoquinolin-1-one |
| 365 | 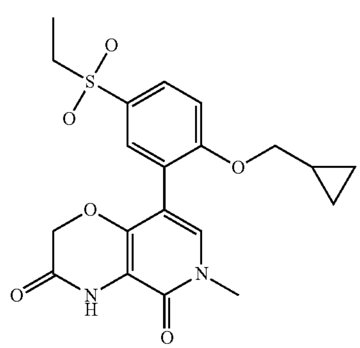 [SMILES: CCS(O)(O)c1ccc(OCC2CC2)c(-c2cn(C)c(=O)c3c2OCC(=O)N3)c1] | 8-[2-(cyclopropylmethoxy)-5-ethylsulfonylphenyl]-6-methyl-4H-pyrido[4,3-b][1,4]oxazine-3,5-dione |

| Chemical Synthesis Example | Structure | Name |
|---|---|---|
| 366 | 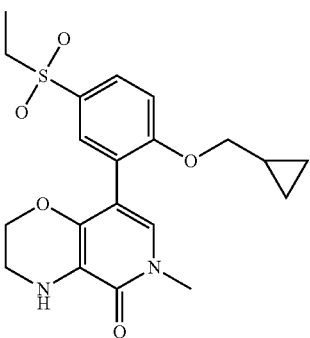 [SMILES: CCS(O)(O)c1ccc(OCC2CC2)c(-c2cn(C)c(=O)c3c2OCCN3)c1] | 8-[2-(cyclopropylmethoxy)-5-ethylsulfonylphenyl]-6-methyl-3,4-dihydro-2H-pyrido[4,3-b][1,4]oxazin-5-one |
| 367 | 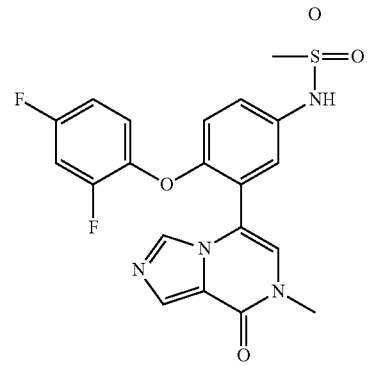 | N-[4-(2,4-difluorophenoxy)-3-(7-methyl-8-oxoimidazo[1,5-a]pyrazin-5-yl)phenyl]methanesulfonamide |
| 368 | 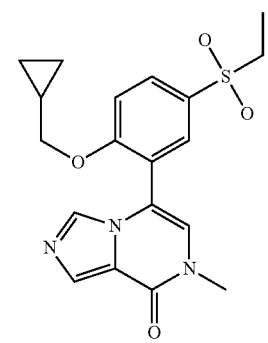 [SMILES: CCS(O)(O)c1ccc(OCC2CC2)c(-c2cn(C)c(=O)c3cncn23)c1] | 5-[2-(cyclopropylmethoxy)-5-ethylsulfonylphenyl]-7-methylimidazo[1,5-a]pyrazin-8- |
| 369 | 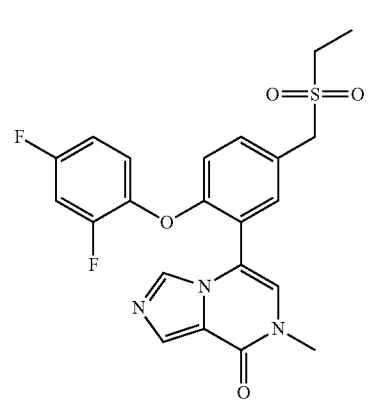 [SMILES: CCS(=O)(=O)Cc1ccc(Oc2ccc(F)cc2F)c(-c2cn(C)c(=O)c3cncn23)c1] | 5-[2-(2,4-difluorophenoxy)-5-(ethylsulfonylmethyl)phenyl]-7-methylimidazo[1,5-a]pyrazin-8-one |

TABLE 1-continued

| Chemical Synthesis Example | Structure | Name |
|---|---|---|
| 370 | 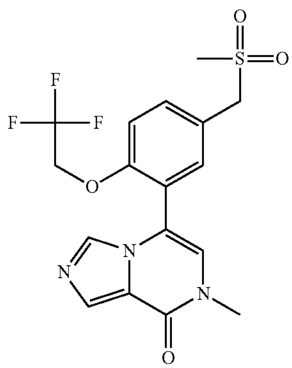 [SMILES: Cn1cc(-c2cc(CS(C)(=O)=O)ccc2OCC(F)(F)F)n2cncc2c1=O] | 7-methyl-5-[5-(methylsulfonylmethyl)-2-(2,2,2-trifluoroethoxy)phenyl]imidazo[1,5-a]pyrazin-8-one |
| 371 | 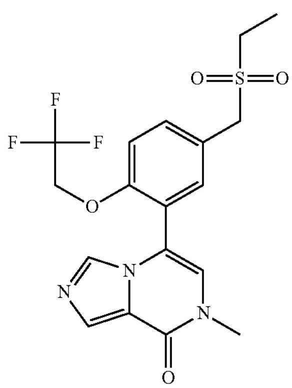 [SMILES: CCS(=O)(=O)Cc1ccc(OCC(F)(F)F)c(-c2cn(C)c(=O)c3cncn23)c1] | 5-[5-(ethylsulfonylmethyl)-2-(2,2,2-trifluoroethoxy)phenyl]-7-methylimidazo[1,5-a]pyrazin-8-one |
| 372 | 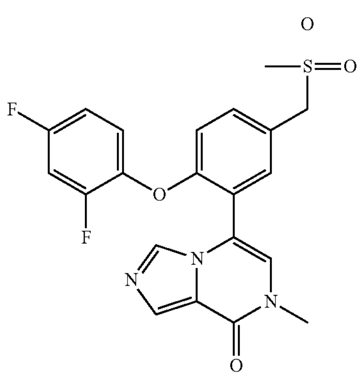 | 5-[2-(2,4-difluorophenoxy)-5-(methylsulfonylmethyl)phenyl]-7-methylimidazo[1,5-a]pyrazin-8-one |
| 373 | 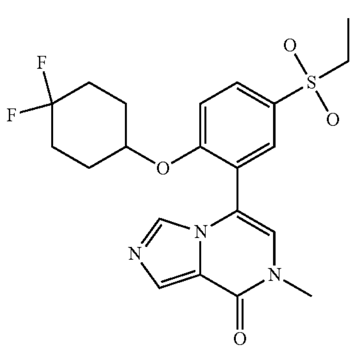 [SMILES: CCS(O)(O)c1ccc(OC2CCC(F)(F)CC2)c(-c2cn(C)c(=O)c3cncn23)c1] | 5-[2-(4,4-difluorocyclohexyl)oxy-5-ethylsulfonylphenyl]-7-methylimidazo[1,5-a]pyrazin-8-one |

TABLE 1-continued
| Chemical Synthesis Example | Structure | Name |
|---|---|---|
| 374 | 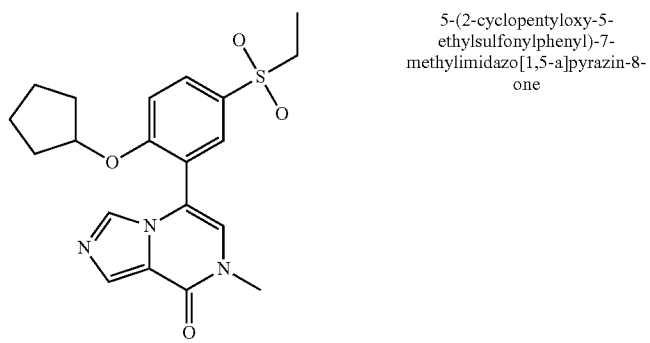 | 5-(2-cyclopentyloxy-5-ethylsulfonylphenyl)-7-methylimidazo[1,5-a]pyrazin-8-one |
| 375 | 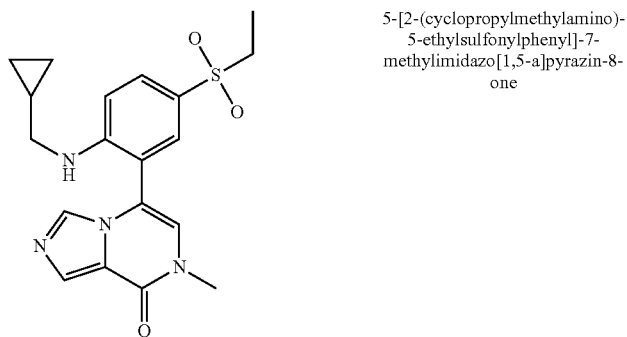 | 5-[2-(cyclopropylmethylamino)-5-ethylsulfonylphenyl]-7-methylimidazo[1,5-a]pyrazin-8-one |
| 376 | 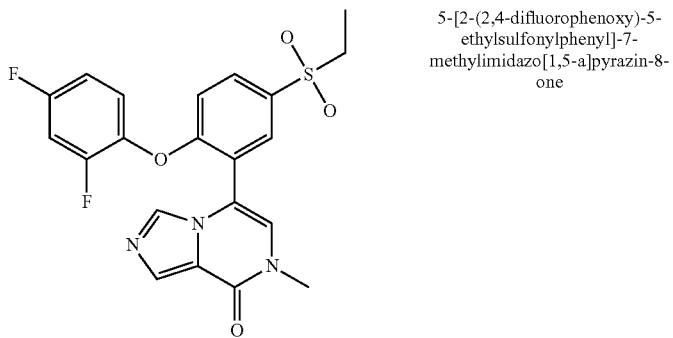 | 5-[2-(2,4-difluorophenoxy)-5-ethylsulfonylphenyl]-7-methylimidazo[1,5-a]pyrazin-8-one |
| 377 | 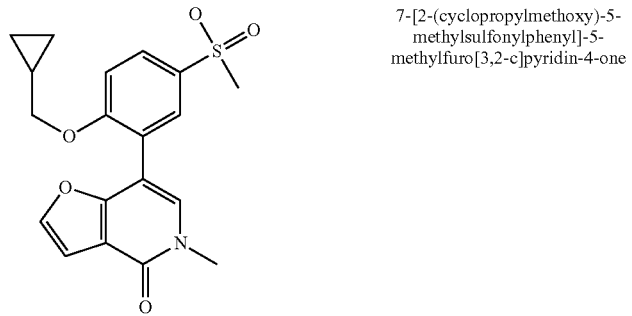 | 7-[2-(cyclopropylmethoxy)-5-methylsulfonylphenyl]-5-methylfuro[3,2-c]pyridin-4-one |

TABLE 1-continued

| Chemical Synthesis Example | Structure | Name |
|---|---|---|
| 378 | 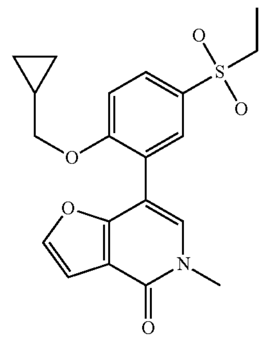 [SMILES: CCS(O)(O)c1ccc(OCC2CC2)c(-c2cn(C)c(=O)c3ccoc23)c1] | 7-[2-(cyclopropylmethoxy)-5-ethylsulfonylphenyl]-5-methylfuro[3,2-c]pyridin-4-one |
| 379 | 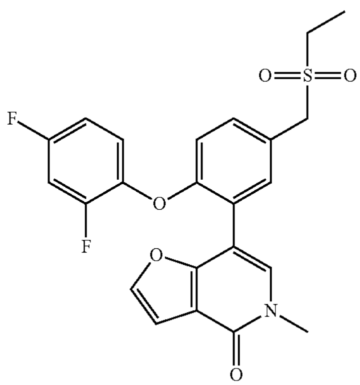 [SMILES: CCS(=O)(=O)Cc1ccc(Oc2ccc(F)cc2F)c(-c2cn(C)c(=O)c3ccoc23)c1] | N-[4-(2,4-difluorophenoxy)-3-(5-methyl-4-oxofuro[3,2-c]pyridin-7-yl)phenyl]ethanesulfonamide |
| 380 | 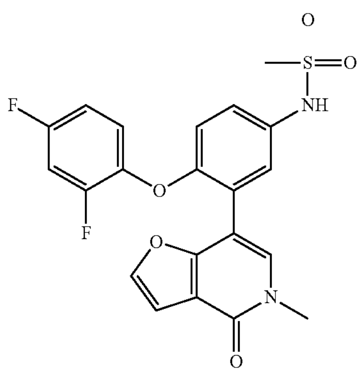 | N-[4-(2,4-difluorophenoxy)-3-(5-methyl-4-oxofuro[3,2-c]pyridin-7-yl)phenyl]ethanesulfonamide |
| 381 | 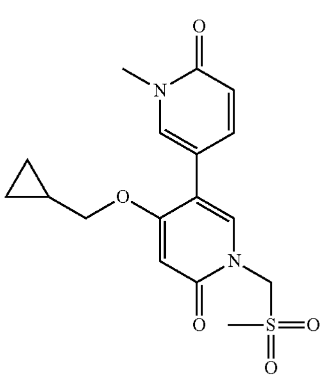 [SMILES: Cn1cc(-c2cn(CS(C)(=O)=O)c(=O)cc2OCC2CC2)ccc1=O] | 4-(cyclopropylmethoxy)-5-(1-methyl-6-oxopyridin-3-yl)-1-(methylsulfonylmethyl)pyridin-2-one |

TABLE 1-continued

| Chemical Synthesis Example | Structure | Name |
|---|---|---|
| 382 | 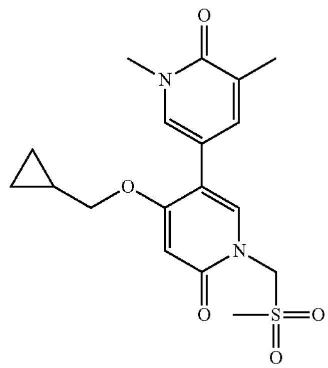 [SMILES: Cc1cc(-c2cn(CS(C)(=O)=O)c(=O)cc2OCC2CC2)cn(C)c1=O] | 5-[4-(cyclopropylmethoxy)-1-(methylsulfonylmethyl)-6-oxopyridin-3-yl]-1,3-dimethylpyridin-2-one |
| 383 | 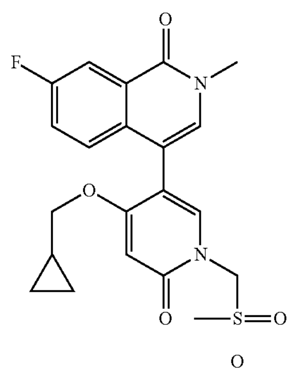 | 4-[4-(cyclopropylmethoxy)-1-(methylsulfonylmethyl)-6-oxopyridin-3-yl]-7-fluoro-2-methylisoquinolin-1-one |
| 384 | 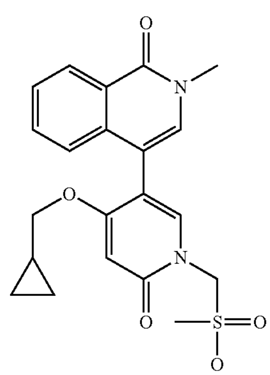 | 4-[4-(cyclopropylmethoxy)-1-(methylsulfonylmethyl)-6-oxopyridin-3-yl]-2-methylisoquinolin-1-one |
| 385 | 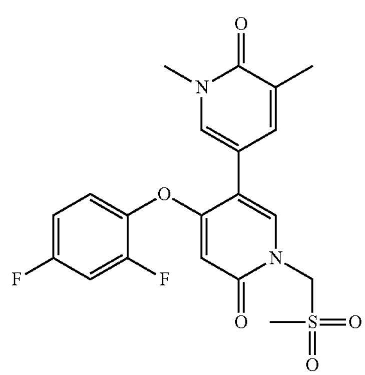 [SMILES: Cc1cc(-c2cn(CS(C)(=O)=O)c(=O)cc2Oc2ccc(F)cc2F)cn(C)c1=O] | 5-[4-(2,4-difluorophenoxy)-1-(methylsulfonylmethyl)-6-oxopyridin-3-yl]-1,3-dimethylpyridin-2-one |

TABLE 1-continued

| Chemical Synthesis Example | Structure | Name |
|---|---|---|
| 386 | 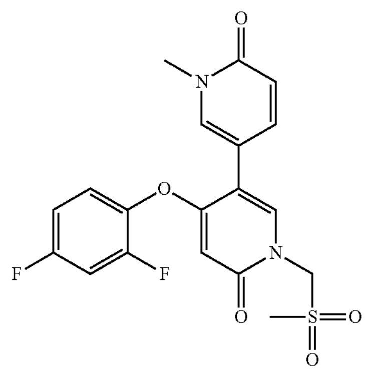 [SMILES: Cn1cc(-c2cn(CS(C)(=O)=O)c(=O)cc2Oc2ccc(F)cc2F)ccc1=O] | 4-(2,4-difluorophenoxy)-5-(1-methyl-6-oxopyridin-3-yl)-1-(methylsulfonylmethyl)pyridin-2-one |
| 387 | 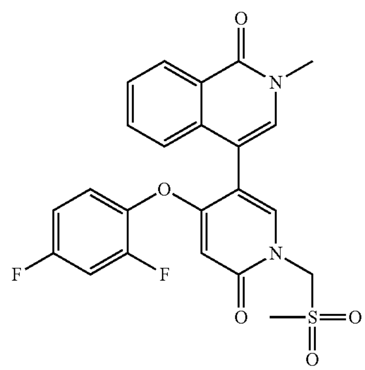 [SMILES: Cn1cc(-c2cn(CS(C)(=O)=O)c(=O)cc2Oc2ccc(F)cc2F)c2ccccc2c1=O] | 4-[4-(2,4-difluorophenoxy)-1-(methylsulfonylmethyl)-6-oxopyridin-3-yl]-2-methylisoquinolin-1-one |
| 388 | 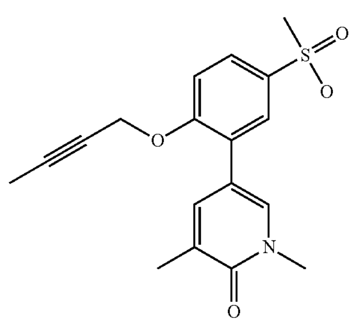 | 5-(2-but-2-ynoxy-5-methylsulfonylphenyl)-1,3-dimethylpyridin-2-one |
| 389 | 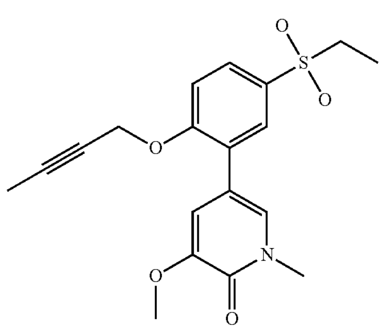 [SMILES: CC#CCOc1ccc(S(O)(O)CC)cc1-c1cc(OC)c(=O)n(C)c1] | 5-(2-but-2-ynoxy-5-ethylsulfonylphenyl)-3-methoxy-1-methylpyridin-2-one |

TABLE 1-continued

| Chemical Synthesis Example | Structure | Name |
| --- | --- | --- |
| 390 | 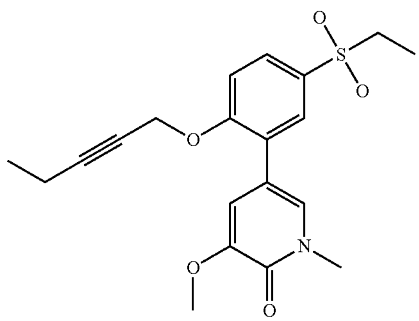 [SMILES: CCC#CCOc1ccc(S(O)(O)CC)cc1-c1cc(OC)c(=O)n(C)c1] | 5-(5-ethylsulfonyl-2-pent-2-ynoxyphenyl)-3-methoxy-1-methylpyridin-2-one |
| 391 | 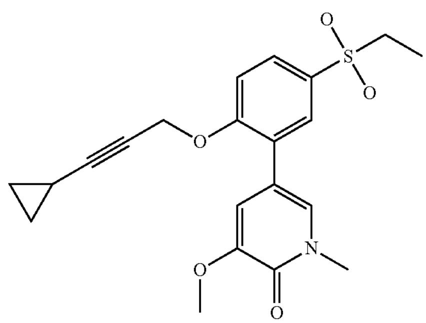 [SMILES: CCS(O)(O)c1ccc(OCC#CC2CC2)c(-c2cc(OC)c(=O)n(C)c2)c1] | 5-[2-(3-cyclopropylprop-2-ynoxy)-5-ethylsulfonylphenyl]-3-methoxy-1-methylpyridin-2-one |
| 392 | 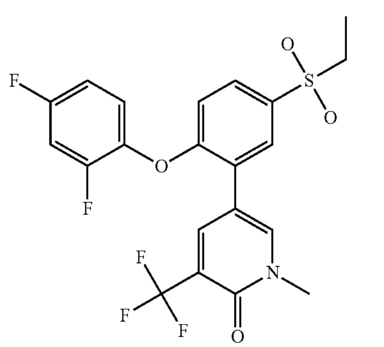 [SMILES: CCS(O)(O)c1ccc(Oc2ccc(F)cc2F)c(-c2cc(C(F)(F)F)c(=O)n(C)c2)c1] | 5-[2-(2,4-difluorophenoxy)-5-ethylsulfonylphenyl]-1-methyl-3-(trifluoromethyl)pyridin-2-one |
| 393 | 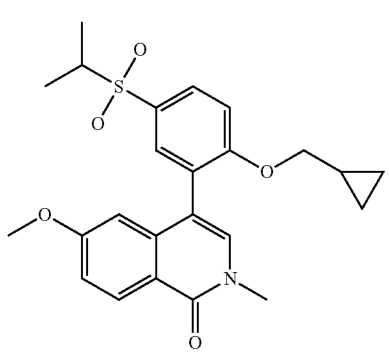 [SMILES: COc1ccc2c(=O)n(C)cc(-c3cc(S(O)(O)C(C)C)ccc3OCC3CC3)c2c1] | 4-[2-(cyclopropylmethoxy)-5-propan-2-ylsulfonylphenyl]-6-methoxy-2-methylisoquinolin-1-one |

TABLE 1-continued

| Chemical Synthesis Example | Structure | Name |
|---|---|---|
| 394 | 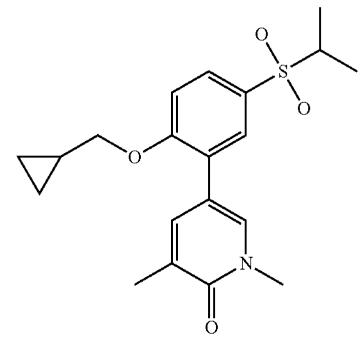 [SMILES: Cc1cc(-c2cc(S(O)(O)C(C)C)ccc2OCC2CC2)cn(C)c1=O] | 5-[2-(cyclopropylmethoxy)-5-propan-2-ylsulfonylphenyl]-1,3-dimethylpyridin-2-one |
| 395 | 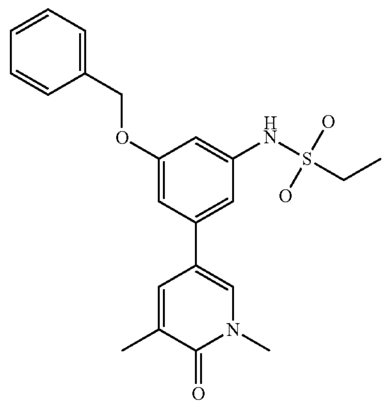 [SMILES: CCS(O)(O)Nc1cc(OCc2ccccc2)cc(-c2cc(C)c(=O)n(C)c2)c1] | N-[3-(1,5-dimethyl-6-oxopyridin-3-yl)-5-phenylmethoxyphenyl]ethanesulfonamide |
| 396 | 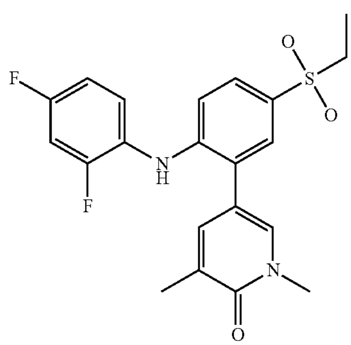 [SMILES: CCS(O)(O)c1ccc(Nc2ccc(F)cc2F)c(-c2cc(C)c(=O)n(C)c2)c1] | 5-[2-(2,4-difluoroanilino)-5-ethylsulfonylphenyl]-1,3-dimethylpyridin-2-one |
| 397 | 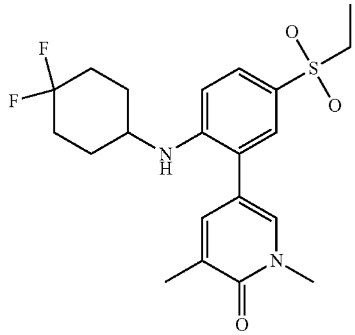 [SMILES: CCS(O)(O)c1ccc(NC2CCC(F)(F)CC2)c(-c2cc(C)c(=O)n(C)c2)c1] | 5-[2-[(4,4-difluorocyclohexyl)amino]-5-ethylsulfonylphenyl]-1,3-dimethylpyridin-2-one |

TABLE 1-continued

| Chemical Synthesis Example | Structure | Name |
|---|---|---|
| 398 | 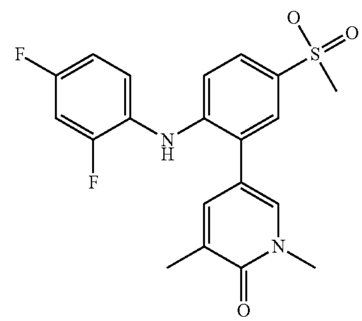 | 5-[2-(2,4-difluoroanilino)-5-methylsulfonylphenyl]-1,3-dimethylpyridin-2-one |
| 399 | 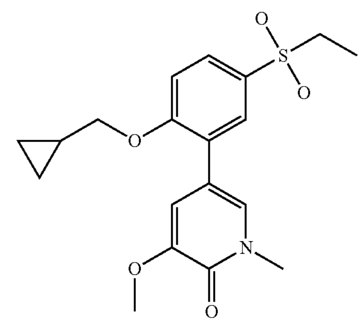 [SMILES: CCS(O)(O)c1ccc(OCC2CC2)c(-c2cc(OC)c(=O)n(C)c2)c1] | 5-[2-(cyclopropylmethoxy)-5-ethylsulfonylphenyl]-3-methoxy-1-methylpyridin-2-one |
| 400 | 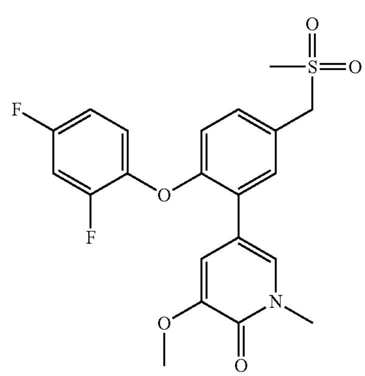 [SMILES: COc1cc(-c2cc(CS(C)(=O)=O)ccc2Oc2ccc(F)cc2F)cn(C)c1=O] | 5-[2-(2,4-difluorophenoxy)-5-(methylsulfonylmethyl)phenyl]-3-methoxy-1-methylpyridin-2-one |
| 401 | 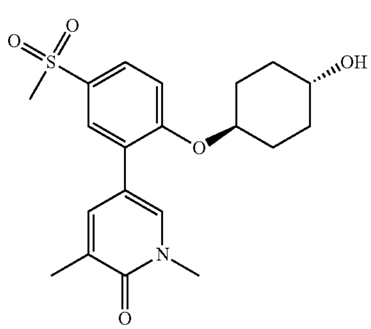 [SMILES: Cc1cc(-c2cc(S(C)(=O)=O)ccc2O[C@H]2CC[C@H](O)CC2)cn(C)c1=O] | 5-[2-(trans-4-hydroxycyclohexyl)oxy-5-methylsulfonylphenyl]-1,3-dimethylpyridin-2-one |

TABLE 1-continued

| Chemical Synthesis Example | Structure | Name |
|---|---|---|
| 402 | 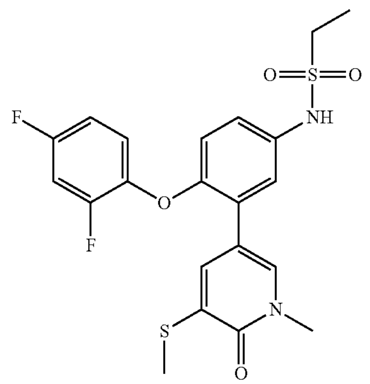 [SMILES: CCS(=O)(=O)Nc1ccc(Oc2ccc(F)cc2F)c(-c2cc(SC)c(=O)n(C)c2)c1] | N-[4-(2,4-difluorophenoxy)-3-(1-methyl-5-methylsulfanyl-6-oxopyridin-3-yl)phenyl]ethanesulfonamide |
| 403 | 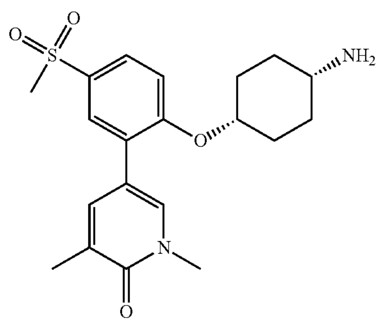 [SMILES: Cc1cc(-c2cc(S(C)(=O)=O)ccc2O[C@H]2CC[C@@H](N)CC2)cn(C)c1=O] | 5-[2-(cis-4-aminocyclohexyl)oxy-5-methylsulfonylphenyl]-1,3-dimethylpyridin-2-one |
| 404 | 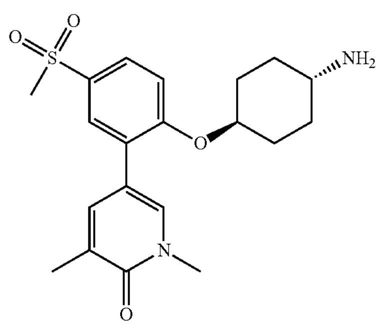 [SMILES: Cc1cc(-c2cc(S(C)(=O)=O)ccc2O[C@H]2CC[C@H](N)CC2)cn(C)c1=O] | 5-[2-(trans-4-aminocyclohexyl)oxy-5-methylsulfonylphenyl]-1,3-dimethylpyridin-2-one |
| 405 | 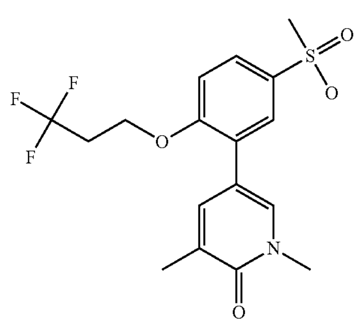 | 1,3-dimethyl-5-[5-methylsulfonyl-2-(3,3,3-trifluoropropoxy)phenyl]pyridin-2-one |

TABLE 1-continued

| Chemical Synthesis Example | Structure | Name |
|---|---|---|
| 406 | 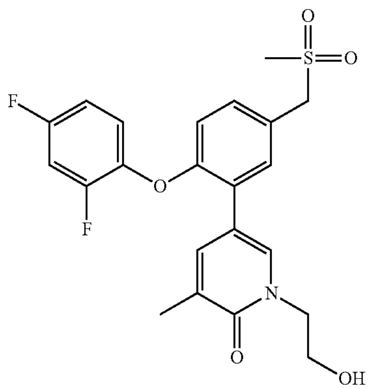 [SMILES: Cc1cc(-c2cc(CS(C)(=O)=O)ccc2Oc2ccc(F)cc2F)cn(CCO)c1=O] | 5-[2-(2,4-difluorophenoxy)-5-(methylsulfonylmethyl)phenyl]-1-(2-hydroxyethyl)-3-methylpyridin-2-one |
| 407 | 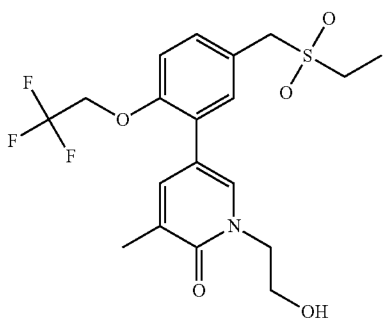 [SMILES: CCS(O)(O)Cc1ccc(OCC(F)(F)F)c(-c2cc(C)c(=O)n(CCO)c2)c1] | 5-[5-(ethylsulfonylmethyl)-2-(2,2,2-trifluoroethoxy)phenyl]-1-(2-hydroxyethyl)-3-methylpyridin-2-one |
| 408 | 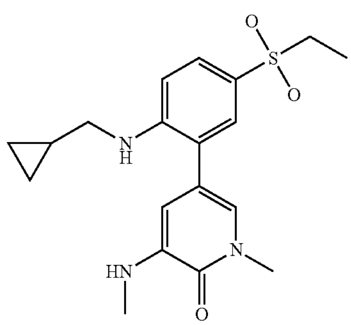 | 5-[2-(cyclopropylmethylamino)-5-ethylsulfonylphenyl]-1-methyl-3-(methylamino)pyridin-2-one |
| 409 | 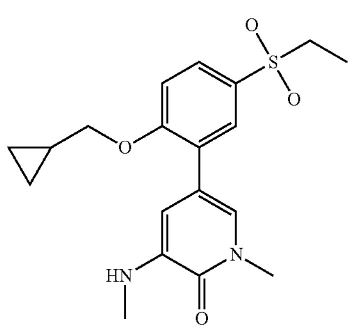 [SMILES: CCS(O)(O)c1ccc(OCC2CC2)c(-c2cc(NC)c(=O)n(C)c2)c1] | 5-[2-(cyclopropylmethoxy)-5-ethylsulfonylphenyl]-1-methyl-3-(methylamino)pyridin-2-one |

TABLE 1-continued

| Chemical Synthesis Example | Structure | Name |
|---|---|---|
| 410 | 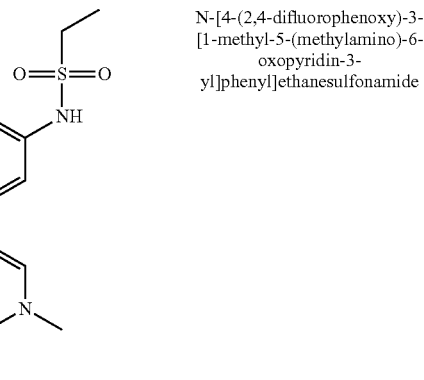 | N-[4-(2,4-difluorophenoxy)-3-[1-methyl-5-(methylamino)-6-oxopyridin-3-yl]phenyl]ethanesulfonamide |
| 411 | 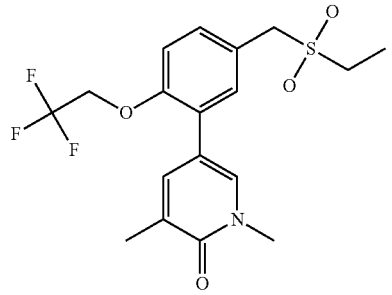 [SMILES: CCS(O)(O)Cc1ccc(OCC(F)(F)F)c(-c2cc(C)c(=O)n(C)c2)c1] | 5-[5-(ethylsulfonylmethyl)-2-(2,2,2-trifluoroethoxy)phenyl]-1,3-dimethylpyridin-2-one |
| 412 | 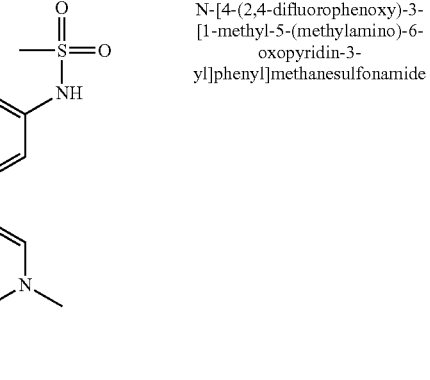 | N-[4-(2,4-difluorophenoxy)-3-[1-methyl-5-(methylamino)-6-oxopyridin-3-yl]phenyl]methanesulfonamide |
| 413 | 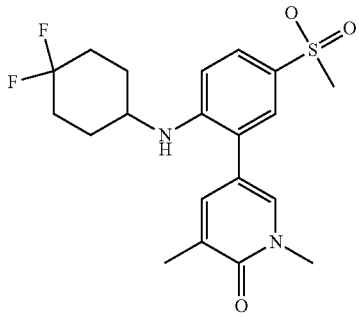 | 5-[2-[(4,4-difluorocyclohexyl)amino]-5-methylsulfonylphenyl]-1,3-dimethylpyridin-2-one |

TABLE 1-continued

| Chemical Synthesis Example | Structure | Name |
|---|---|---|
| 414 | 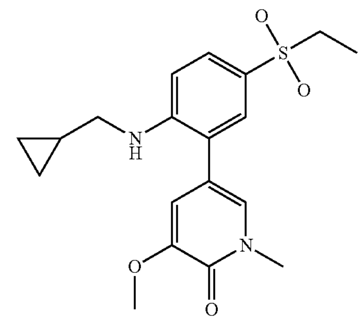 | 5-[2-(cyclopropylmethylamino)-5-ethylsulfonylphenyl]-3-methoxy-1-methylpyridin-2-one |
| 415 | 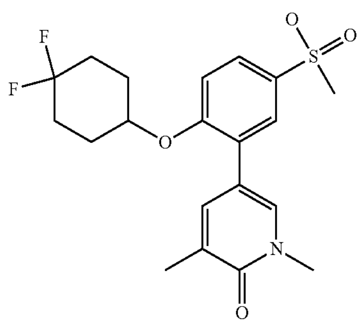 | 5-[2-(4,4-difluorocyclohexyl)oxy-5-methylsulfonylphenyl]-1,3-dimethylpyridin-2-one |
| 416 | 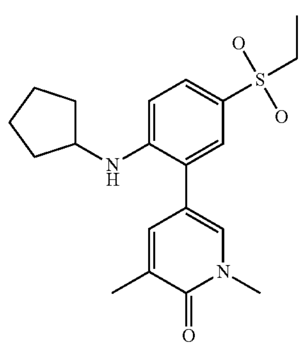 [SMILES: CCS(O)(O)c1ccc(NC2CCCC2)c(-c2cc(C)c(=O)n(C)c2)c1] | 5-[2-(cyclopentylamino)-5-ethylsulfonylphenyl]-1,3-dimethylpyridin-2-one |
| 417 | 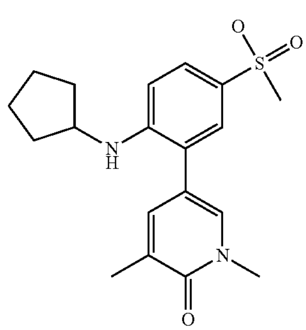 | 5-[2-(cyclopentylamino)-5-methylsulfonylphenyl]-1,3-dimethylpyridin-2-one |

TABLE 1-continued

| Chemical Synthesis Example | Structure | Name |
|---|---|---|
| 418 | 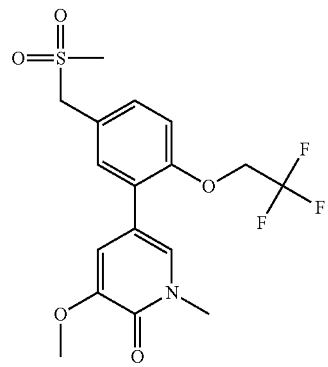 [SMILES: COc1cc(-c2cc(CS(C)(=O)=O)ccc2OCC(F)(F)F)cn(C)c1=O] | 3-chloro-1-methyl-5-[5-(methylsulfonylmethyl)-2-(2,2,2-trifluoroethoxy)phenyl]pyridin-2-one |
| 419 | 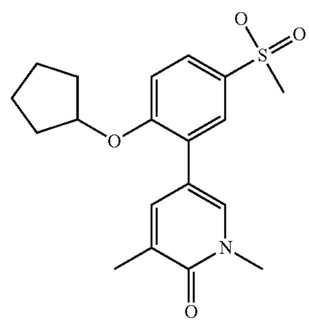 | 5-(2-cyclopentyloxy-5-methylsulfonylphenyl)-1,3-dimethylpyridin-2-one |
| 420 | 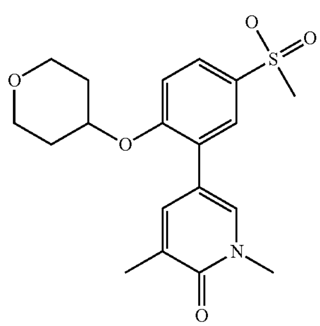 | 1,3-dimethyl-5-[5-methylsulfonyl-2-(oxan-4-yloxy)phenyl]pyridin-2-one |
| 421 | 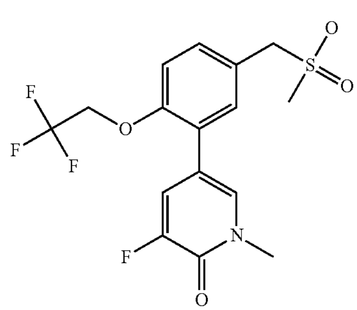 | 3-fluoro-1-methyl-5-[5-(methylsulfonylmethyl)-2-(2,2,2-trifluoroethoxy)phenyl]pyridin-2-one |

TABLE 1-continued

| Chemical Synthesis Example | Structure | Name |
|---|---|---|
| 422 | 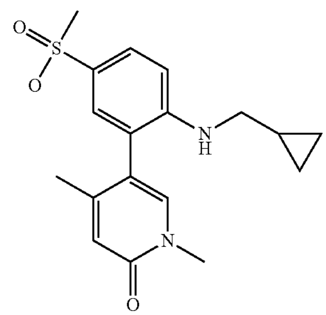 | 5-[2-(cyclopropylmethylamino)-5-methylsulfonylphenyl]-1,4-dimethylpyridin-2-one |
| 423 | 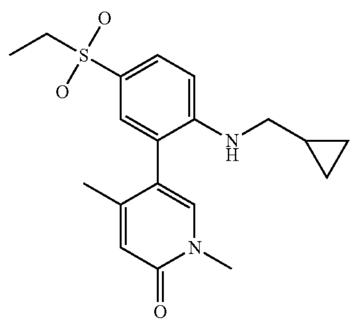 [SMILES: CCS(O)(O)c1ccc(NCC2CC2)c(-c2cn(C)c(=O)cc2C)c1] | 5-[2-(cyclopropylmethylamino)-5-ethylsulfonylphenyl]-1,4-dimethylpyridin-2-one |
| 424 | 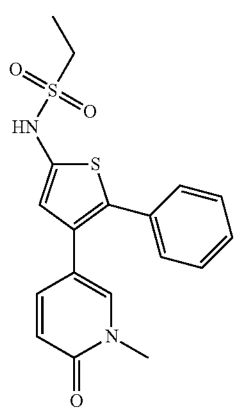 [SMILES: CCS(=O)(=O)Nc1cc(-c2ccc(=O)n(C)c2)c(-c2ccccc2)s1] | N-[4-(1-methyl-6-oxopyridin-3-yl)-5-phenylthiophen-2-yl]ethanesulfonamide |
| 425 | 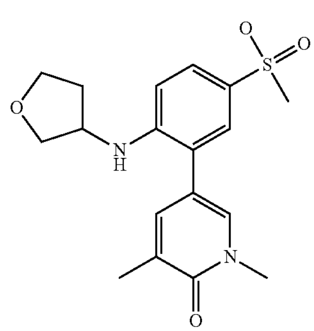 | 1,3-dimethyl-5-[5-methylsulfonyl-2-(oxolan-3-ylamino)phenyl]pyridin-2-one |

TABLE 1-continued

| Chemical Synthesis Example | Structure | Name |
|---|---|---|
| 426 | 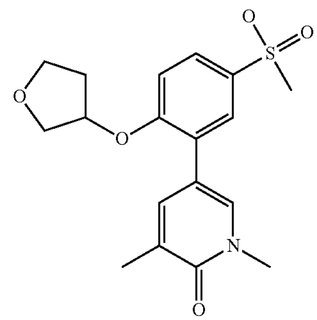 | 1,3-dimethyl-5-[5-methylsulfonyl-2-(oxolan-3-yloxy)phenyl]pyridin-2-one |
| 427 | 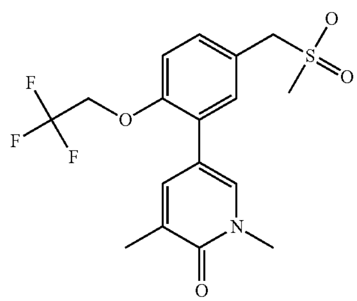 | 1,3-dimethyl-5-[5-(methylsulfonylmethyl)-2-(2,2,2-trifluoroethoxy)phenyl]pyridin-2-one |
| 428 | 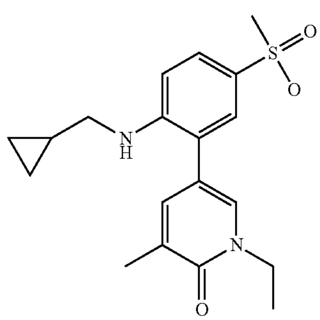 | 5-[2-(cyclopropylmethylamino)-5-methylsulfonylphenyl]-1-ethyl-3-methylpyridin-2-one |
| 429 | 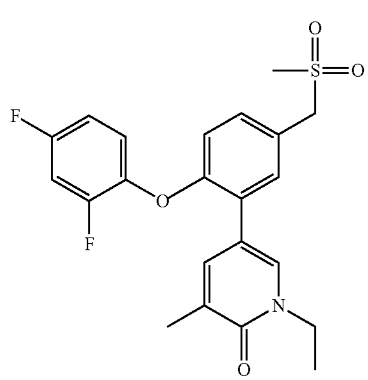 | 5-[2-(2,4-difluorophenoxy)-5-(methylsulfonylmethyl)phenyl]-1-ethyl-3-methylpyridin-2-one |

TABLE 1-continued

| Chemical Synthesis Example | Structure | Name |
|---|---|---|
| 430 | 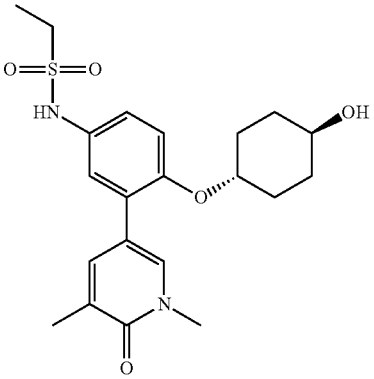 [SMILES: CCS(=O)(=O)Nc1ccc(O[C@H]2CC[C@H](O)CC2)c(-c2cc(C)c(=O)n(C)c2)c1] | N-[3-(1,5-dimethyl-6-oxopyridin-3-yl)-4-(trans-4-hydroxycyclohexyl)oxyphenyl]ethanesulfonamide |
| 431 | 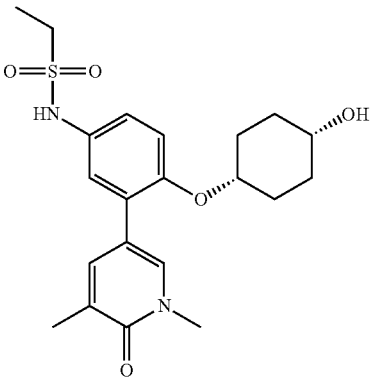 [SMILES: CCS(=O)(=O)Nc1ccc(O[C@H]2CC[C@@H](O)CC2)c(-c2cc(C)c(=O)n(C)c2)c1] | N-[3-(1,5-dimethyl-6-oxopyridin-3-yl)-4-(cis-4-hydroxycyclohexyl)oxyphenyl]ethanesulfonamide |
| 432 | 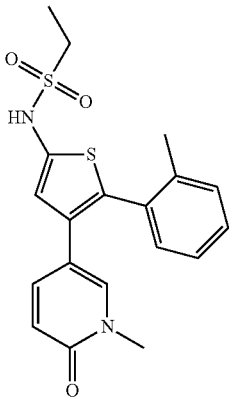 [SMILES: CCS(=O)(=O)Nc1cc(-c2ccc(=O)n(C)c2)c(-c2ccccc2C)s1] | N-[4-(1-methyl-6-oxopyridin-3-yl)-5-(2-methylphenyl)thiophen-2-yl]ethanesulfonamide |
| 433 | 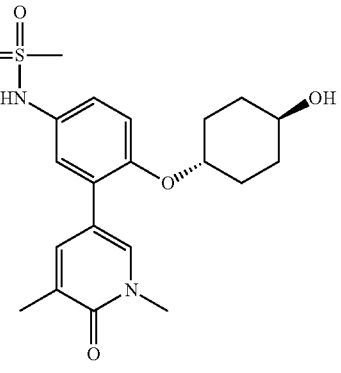 | N-[3-(1,5-dimethyl-6-oxopyridin-3-yl)-4-(trans-4-hydroxycyclohexyl)oxyphenyl]methanesulfonamide |

TABLE 1-continued

| Chemical Synthesis Example | Structure | Name |
|---|---|---|
| 434 | 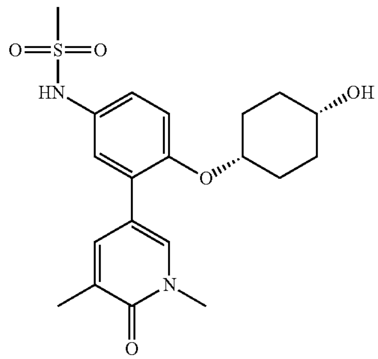 [SMILES: Cc1cc(-c2cc(NS(C)(=O)=O)ccc2O[C@H]2CC[C@@H](O)CC2)cn(C)c1=O] | N-[3-(1,5-dimethyl-6-oxopyridin-3-yl)-4-(cis-4-hydroxycyclohexyl)oxyphenyl]methanesulfonamide |
| 435 | 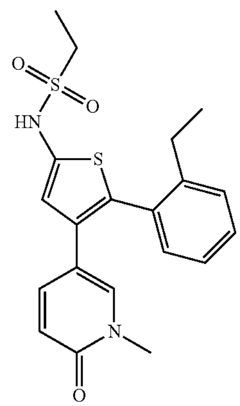 [SMILES: CCc1ccccc1-c1sc(NS(=O)(=O)CC)cc1-c1ccc(=O)n(C)c1] | N-[5-(2-ethylphenyl)-4-(1-methyl-6-oxopyridin-3-yl)thiophen-2-yl]ethanesulfonamide |
| 436 | 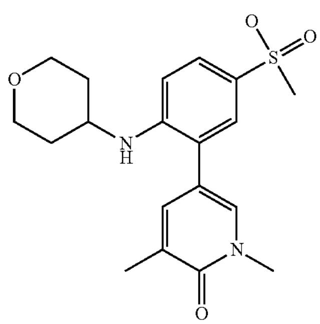 | 1,3-dimethyl-5-[5-methylsulfonyl-2-(oxan-4-ylamino)phenyl]pyridin-2-one |
| 437 | 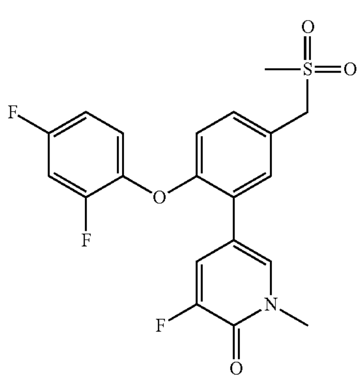 [SMILES: Cn1cc(-c2cc(CS(C)(=O)=O)ccc2Oc2ccc(F)cc2F)cc(F)c1=O] | 5-[2-(2,4-difluorophenoxy)-5-(methylsulfonylmethyl)phenyl]-3-fluoro-1-methylpyridin-2-one |

TABLE 1-continued
| Chemical Synthesis Example | Structure | Name |
|---|---|---|
| 438 | 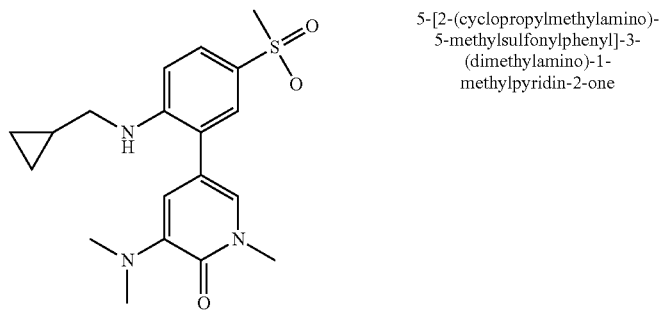 | 5-[2-(cyclopropylmethylamino)-5-methylsulfonylphenyl]-3-(dimethylamino)-1-methylpyridin-2-one |
| 439 | 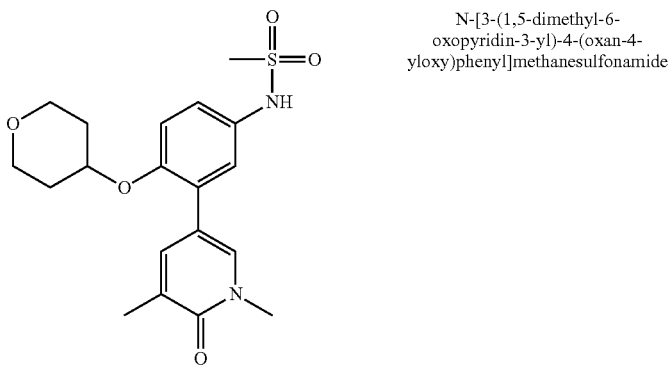 | N-[3-(1,5-dimethyl-6-oxopyridin-3-yl)-4-(oxan-4-yloxy)phenyl]methanesulfonamide |
| 440 | 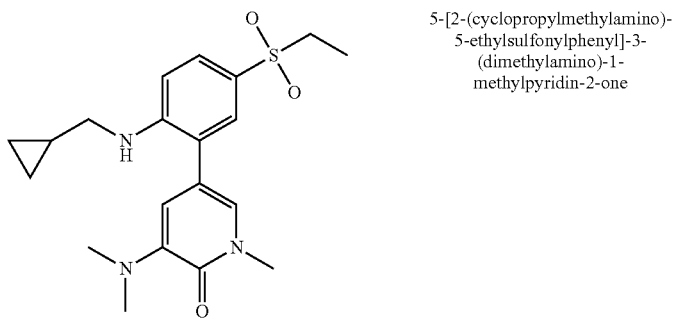 | 5-[2-(cyclopropylmethylamino)-5-ethylsulfonylphenyl]-3-(dimethylamino)-1-methylpyridin-2-one |
| 441 | 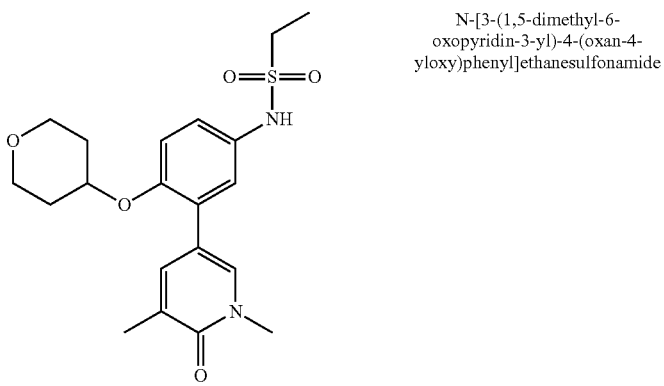 | N-[3-(1,5-dimethyl-6-oxopyridin-3-yl)-4-(oxan-4-yloxy)phenyl]ethanesulfonamide |

TABLE 1-continued

| Chemical Synthesis Example | Structure | Name |
|---|---|---|
| 442 | 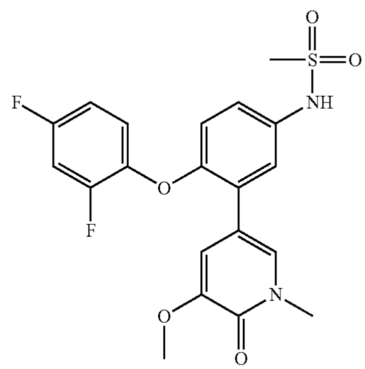 [SMILES: COc1cc(-c2cc(NS(C)(=O)=O)ccc2Oc2ccc(F)cc2F)cn(C)c1=O] | N-[4-(2,4-difluorophenoxy)-3-(5-methoxy-1-methyl-6-oxopyridin-3-yl)phenyl]methanesulfonamide |
| 443 | 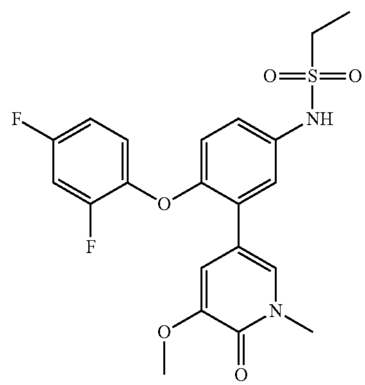 [SMILES: CCS(=O)(=O)Nc1ccc(Oc2ccc(F)cc2F)c(-c2cc(OC)c(=O)n(C)c2)c1] | N-[4-(2,4-difluorophenoxy)-3-(5-methoxy-1-methyl-6-oxopyridin-3-yl)phenyl]ethanesulfonamide |
| 444 | 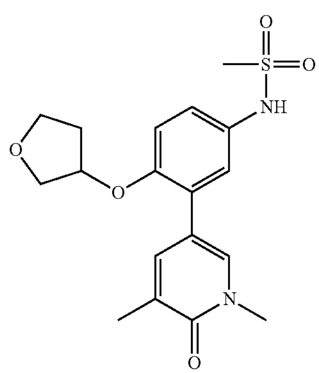 [SMILES: Cc1cc(-c2cc(NS(C)(=O)=O)ccc2OC2CCOC2)cn(C)c1=O] | N-[3-(1,5-dimethyl-6-oxopyridin-3-yl)-4-(oxolan-3-yloxy)phenyl]methanesulfonamide |
| 445 | 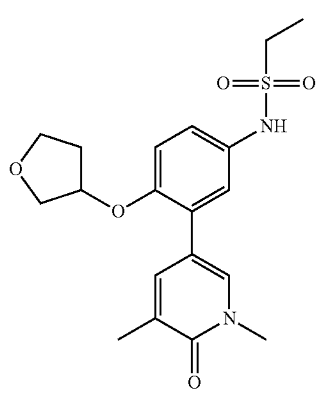 [SMILES: CCS(=O)(=O)Nc1ccc(OC2CCOC2)c(-c2cc(C)c(=O)n(C)c2)c1] | N-[3-(1,5-dimethyl-6-oxopyridin-3-yl)-4-(oxolan-3-yloxy)phenyl]ethanesulfonamide |

TABLE 1-continued

| Chemical Synthesis Example | Structure | Name |
|---|---|---|
| 446 | 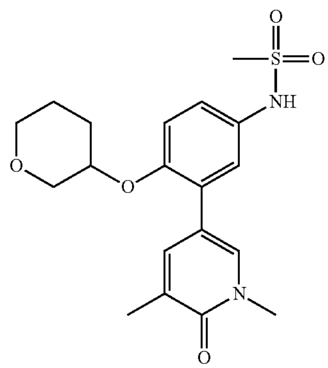 [SMILES: Cc1cc(-c2cc(NS(C)(=O)=O)ccc2OC2CCCOC2)cn(C)c1=O] | N-[3-(1,5-dimethyl-6-oxopyridin-3-yl)-4-(oxan-3-yloxy)phenyl]methanesulfonamide |
| 447 | 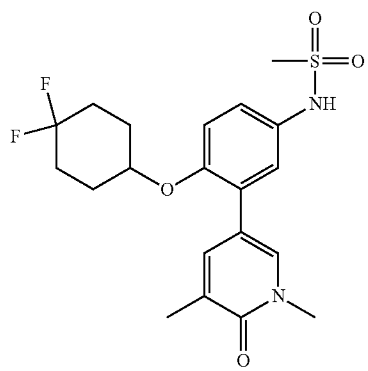 [SMILES: Cc1cc(-c2cc(NS(C)(=O)=O)ccc2OC2CCC(F)(F)CC2)cn(C)c1=O] | N-[4-(4,4-difluorocyclohexyl)oxy-3-(1,5-dimethyl-6-oxopyridin-3-yl)phenyl]methanesulfonamide |
| 448 | 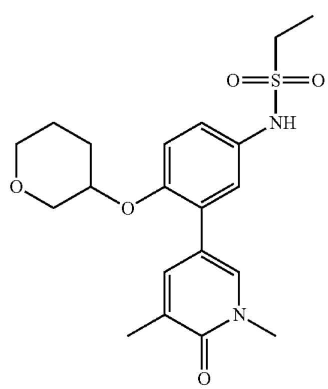 [SMILES: CCS(=O)(=O)Nc1ccc(OC2CCCOC2)c(-c2cc(C)c(=O)n(C)c2)c1] | N-[3-(1,5-dimethyl-6-oxopyridin-3-yl)-4-(oxan-3-yloxy)phenyl]ethanesulfonamide |
| 449 | 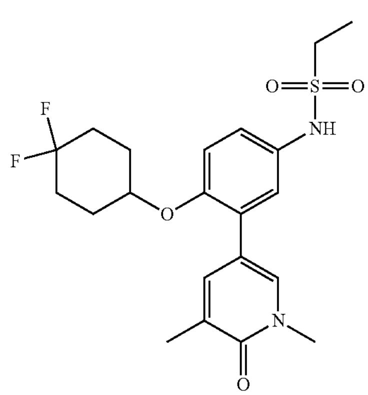 [SMILES: CCS(=O)(=O)Nc1ccc(OC2CCC(F)(F)CC2)c(-c2cc(C)c(=O)n(C)c2)c1] | N-[4-(4,4-difluorocyclohexyl)oxy-3-(1,5-dimethyl-6-oxopyridin-3-yl)phenyl]ethanesulfonamide |

TABLE 1-continued

| Chemical Synthesis Example | Structure | Name |
|---|---|---|
| 450 | 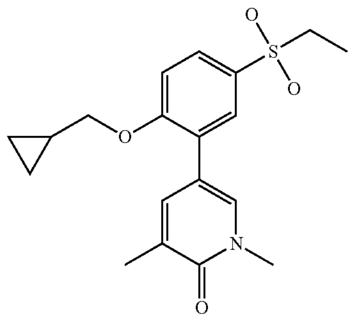 [SMILES: CCS(O)(O)c1ccc(OCC2CC2)c(-c2cc(C)c(=O)n(C)c2)c1] | 5-[2-(cyclopropylmethoxy)-5-ethylsulfonylphenyl]-1,3-dimethylpyridin-2-one |
| 451 | 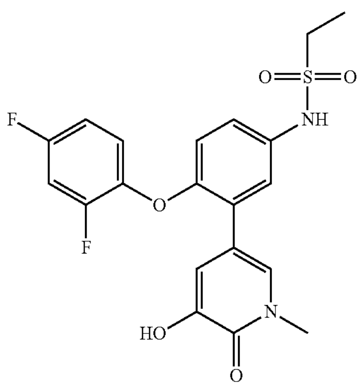 [SMILES: CCS(=O)(=O)Nc1ccc(Oc2ccc(F)cc2F)c(-c2cc(O)c(=O)n(C)c2)c1] | N-[4-(2,4-difluorophenoxy)-3-(5-hydroxy-1-methyl-6-oxopyridin-3-yl)phenyl]ethanesulfonamide |
| 452 | 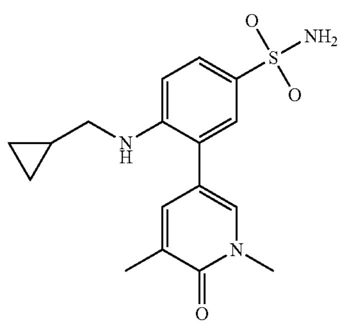 [SMILES: Cc1cc(-c2cc(S(N)(O)O)ccc2NCC2CC2)cn(C)c1=O] | 4-(cyclopropylmethylamino)-3-(1,5-dimethyl-6-oxopyridin-3-yl)benzenesulfonamide |
| 453 | 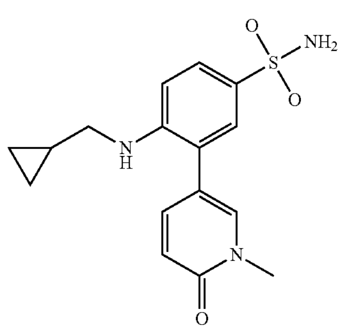 [SMILES: Cn1cc(-c2cc(S(N)(O)O)ccc2NCC2CC2)ccc1=O] | 4-(cyclopropylmethylamino)-3-(1-methyl-6-oxopyridin-3-yl)benzenesulfonamide |

TABLE 1-continued

| Chemical Synthesis Example | Structure | Name |
|---|---|---|
| 454 | 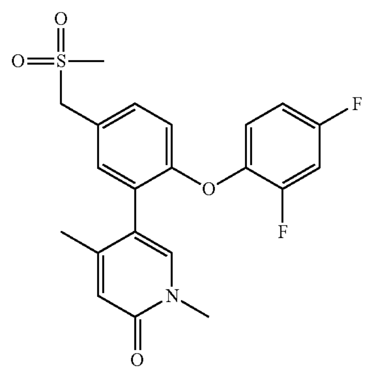 [SMILES: Cc1cc(=O)n(C)cc1-c1cc(CS(C)(=O)=O)ccc1Oc1ccc(F)cc1F] | 5-[2-(2,4-difluorophenoxy)-5-(methylsulfonylmethyl)phenyl]-1,4-dimethylpyridin-2-one |
| 455 | 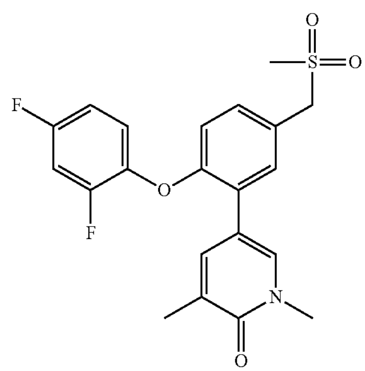 [SMILES: Cc1cc(-c2cc(CS(C)(=O)=O)ccc2Oc2ccc(F)cc2F)cn(C)c1=O] | 5-[2-(2,4-difluorophenoxy)-5-(methylsulfonylmethyl)phenyl]-1,3-dimethylpyridin-2-one |
| 456 | 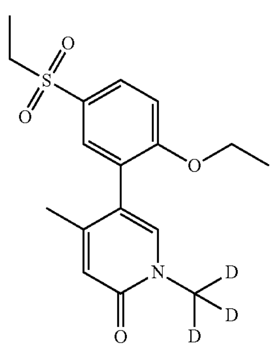 [SMILES: [2H]C([2H])([2H])n1cc(-c2cc(S(=O)(=O)CC)ccc2OCC)c(C)cc1=O] | 5-(2-ethoxy-5-ethylsulfonylphenyl)-1-($^2H_3$)methyl-4-methylpyridin-2-one |
| 457 | 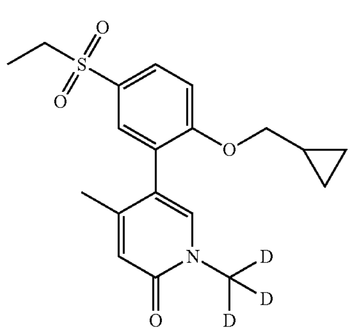 [SMILES: [2H]C([2H])([2H])n1cc(-c2cc(S(=O)(=O)CC)ccc2OCC2CC2)c(C)cc1=O] | 5[2-(cyclopropylmethoxy)-5-ethylsulfonylphenyl]-1-($^2H_3$)methyl-4-methylpyridin-2-one |

TABLE 1-continued

| Chemical Synthesis Example | Structure | Name |
|---|---|---|
| 458 | 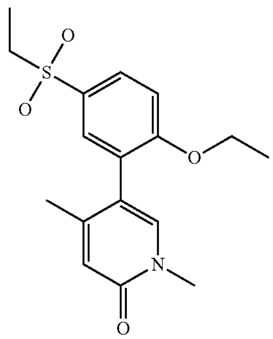 [SMILES: CCOc1ccc(S(O)(O)CC)cc1-c1cn(C)c(=O)cc1C] | 5-(2-ethoxy-5-ethylsulfonylphenyl)-1,4-dimethylpyridin-2-one |
| 459 | 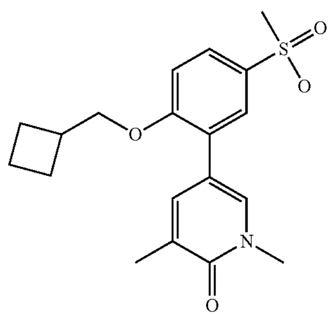 | 5-[2-(cyclobutylmethoxy)-5-methylsulfonylphenyl]-1,3-dimethylpyridin-2-one |
| 460 | 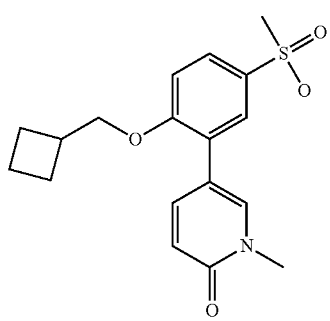 | 5-[2-(cyclobutylmethoxy)-5-methylsulfonylphenyl]-1-methylpyridin-2-one |
| 461 | 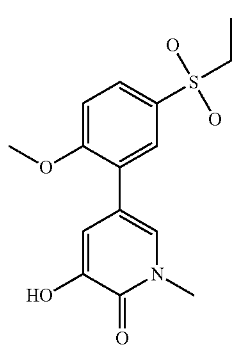 [SMILES: CCS(O)(O)c1ccc(OC)c(-c2cc(O)c(=O)n(C)c2)c1] | 5-(5-ethylsulfonyl-2-methoxyphenyl)-3-hydroxy-1-methylpyridin-2-one |

TABLE 1-continued

| Chemical Synthesis Example | Structure | Name |
|---|---|---|
| 462 | 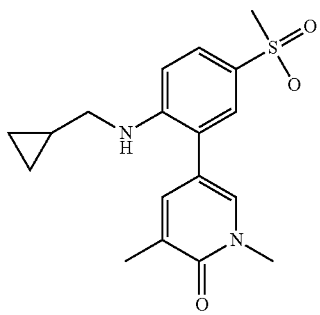 | 5-[2-(cyclopropylmethylamino)-5-methylsulfonylphenyl]-1,3-dimethylpyridin-2-one |
| 463 | 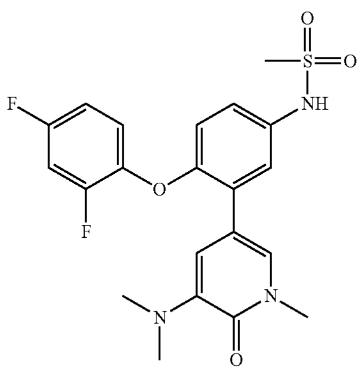 [SMILES: CN(C)c1cc(-c2cc(NS(C)(=O)=O)ccc2Oc2ccc(F)cc2F)cn(C)c1=O] | N-[4-(2,4-difluorophenoxy)-3-[5-(dimethylamino)-1-methyl-6-oxopyridin-3-yl]phenyl]methanesulfonamide |
| 464 | 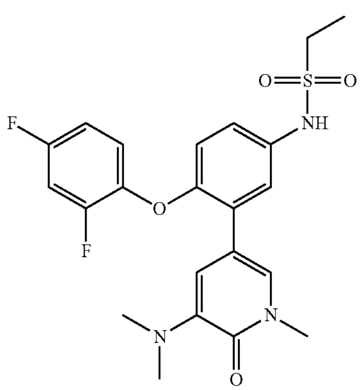 [SMILES: CCS(=O)(=O)Nc1ccc(Oc2ccc(F)cc2F)c(-c2cc(N(C)C)c(=O)n(C)c2)c1] | N-[4-(2,4-difluorophenoxy)-3-[5-(dimethylamino)-1-methyl-6-oxopyridin-3-yl]phenyl]ethanesulfonamide |
| 465 | 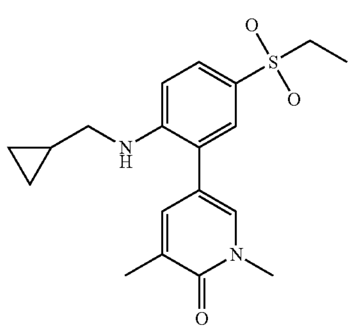 [SMILES: CCS(O)(O)c1ccc(NCC2CC2)c(-c2cc(C)c(=O)n(C)c2)c1] | 5-[2-(cyclopropylmethylamino)-5-ethylsulfonylphenyl]-1,3-dimethylpyridin-2-one |

TABLE 1-continued

| Chemical Synthesis Example | Structure | Name |
|---|---|---|
| 466 | 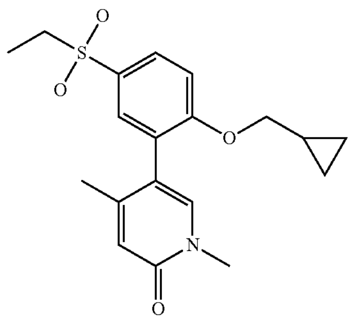 [SMILES: CCS(O)(O)c1ccc(OCC2CC2)c(-c2cn(C)c(=O)cc2C)c1] | 5-[2-(cyclopropylmethoxy)-5-ethylsulfonylphenyl]-1,4-dimethylpyridin-2-one |
| 467 | 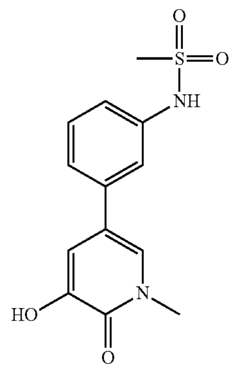 [SMILES: Cn1cc(-c2cccc(NS(C)(=O)=O)c2)cc(O)c1=O] | N-[3-(5-hydroxy-1-methyl-6-oxopyridin-3-yl)phenyl]methanesulfonamide |
| 468 | 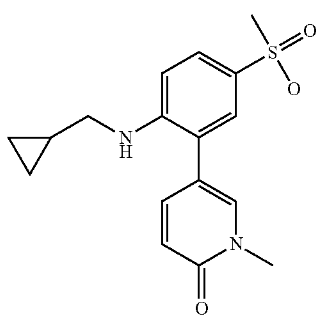 | 5-[2-(cyclopropylmethylamino)-5-methylsulfonylphenyl]-1-methylpyridin-2-one |
| 469 | 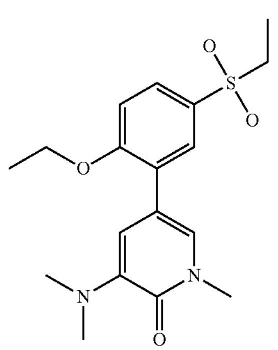 [SMILES: CCOc1ccc(S(O)(O)CC)cc1-c1cc(N(C)C)c(=O)n(C)c1] | 3-(dimethylamino)-5-(2-ethoxy-5-ethylsulfonylphenyl)-1-methylpyridin-2-one |

TABLE 1-continued

| Chemical Synthesis Example | Structure | Name |
|---|---|---|
| 470 | 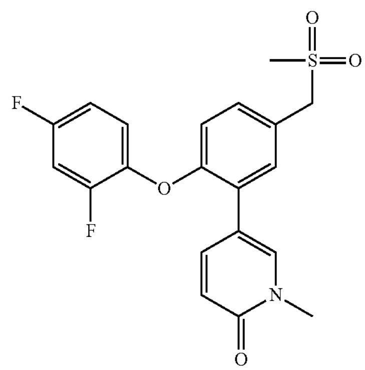 [SMILES: Cn1cc(-c2cc(CS(C)(=O)=O)ccc2Oc2ccc(F)cc2F)ccc1=O] | 5-[2-(2,4-difluorophenoxy)-5-(methylsulfonylmethyl)phenyl]-1-methylpyridin-2-one |
| 471 | 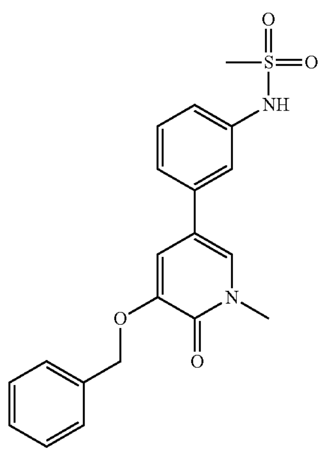 [SMILES: Cn1cc(-c2cccc(NS(C)(=O)=O)c2)cc(OCc2ccccc2)c1=O] | N-[3-(1-methyl-6-oxo-5-phenylmethoxypyridin-3-yl)phenyl]methanesulfonamide |
| 472 | 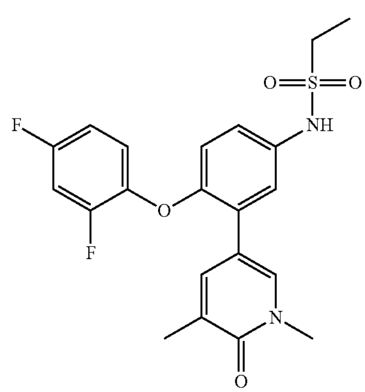 [SMILES: CCS(=O)(=O)Nc1ccc(Oc2ccc(F)cc2F)c(-c2cc(C)c(=O)n(C)c2)c1] | N-[4-(2,4-difluorophenoxy)-3-(1,5-dimethyl-6-oxopyridin-3-yl)phenyl]ethanesulfonamide |
| 473 | 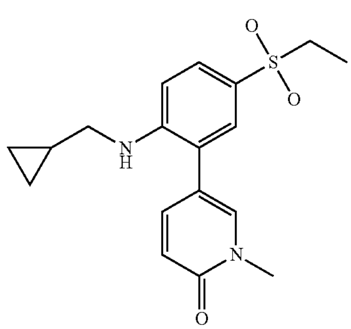 [SMILES: CCS(O)(O)c1ccc(NCC2CC2)c(-c2ccc(=O)n(C)c2)c1] | 5-[2-(cyclopropylmethylamino)-5-ethylsulfonylphenyl]-1-methylpyridin-2-one |

TABLE 1-continued

| Chemical Synthesis Example | Structure | Name |
|---|---|---|
| 474 | 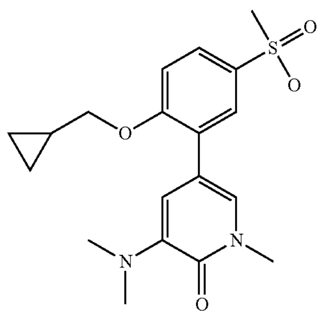 | 5-[2-(cyclopropylmethoxy)-5-methylsulfonylphenyl]-3-(dimethylamino)-1-methylpyridin-2-one |
| 475 | 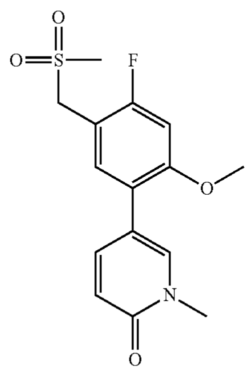 [SMILES: COc1cc(F)c(CS(C)(=O)=O)cc1-c1ccc(=O)n(C)c1] | 5-[4-fluoro-2-methoxy-5-(methylsulfonylmethyl)phenyl]-1-methylpyridin-2-one |
| 476 | 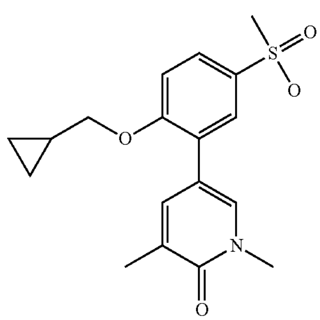 | 5-[2-(cyclopropylmethoxy)-5-methylsulfonylphenyl]-1,3-dimethylpyridin-2-one |
| 477 | 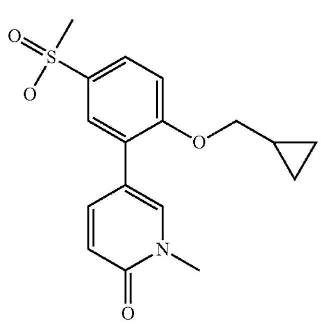 | 5-[2-(cyclopropylmethoxy)-5-methylsulfonylphenyl]-1,4-dimethylpyridin-2-one |

TABLE 1-continued
| Chemical Synthesis Example | Structure | Name |
|---|---|---|
| 478 | 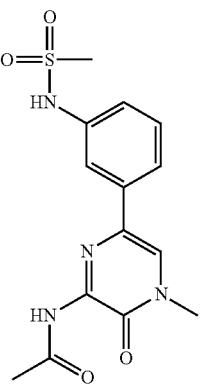 [SMILES: CC(=O)Nc1nc(-c2cccc(NS(C)(=O)=O)c2)cn(C)c1=O] | N-[6-[3-(methanesulfonamido)phenyl]-4-methyl-3-oxopyrazin-2-yl]acetamide |
| 479 | 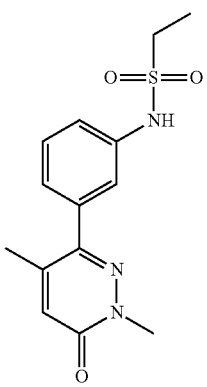 [SMILES: CCS(=O)(=O)Nc1cccc(-c2nn(C)c(=O)cc2C)c1] | N-[3-(1,4-dimethyl-6-oxopyridazin-3-yl)phenyl]ethanesulfonamide |
| 480 | 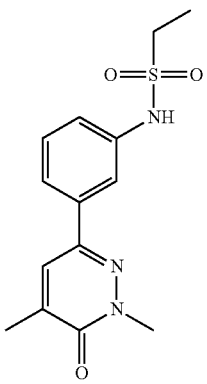 [SMILES: CCS(=O)(=O)Nc1cccc(-c2cc(C)c(=O)n(C)n2)c1] | N-[3-(1,5-dimethyl-6-oxopyridazin-3-yl)phenyl]ethanesulfonamide |
| 481 | 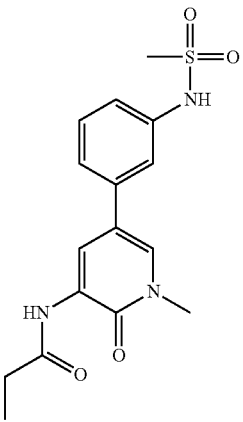 [SMILES: CCC(=O)Nc1cc(-c2cccc(NS(C)(=O)=O)c2)cn(C)c1=O] | N-[5-[3-(methanesulfonamido)phenyl]-1-methyl-2-oxopyridin-3-yl]propanamide |

TABLE 1-continued

| Chemical Synthesis Example | Structure | Name |
|---|---|---|
| 482 | 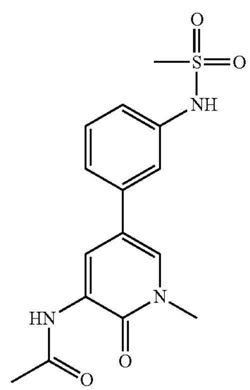 [SMILES: CC(=O)Nc1cc(-c2cccc(NS(C)(=O)=O)c2)cn(C)c1=O] | N-[5-[3-(methanesulfonamido)phenyl]-1-methyl-2-oxopyridin-3-yl]acetamide |
| 483 | 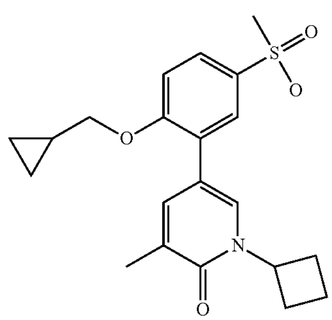 | 1-cyclobutyl-5-[2-(cyclopropylmethoxy)-5-methylsulfonylphenyl]-3-methylpyridin-2-one |
| 484 | 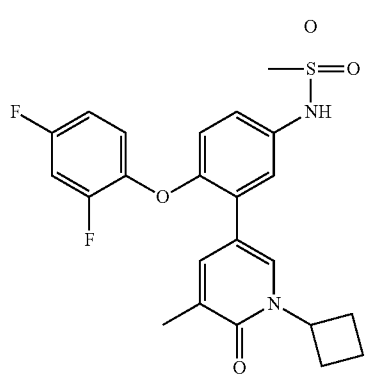 | N-[3-(1-cyclobutyl-5-methyl-6-oxopyridin-3-yl)-4-(2,4-difluorophenoxy)phenyl]methanesulfonamide |
| 485 | 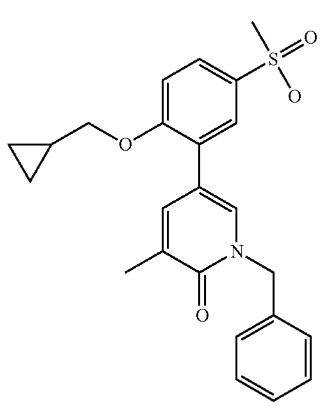 | 1-benzyl-5-[2-(cyclopropylmethoxy)-5-methylsulfonylphenyl]-3-methylpyridin-2-one |

TABLE 1-continued

| Chemical Synthesis Example | Structure | Name |
|---|---|---|
| 486 | 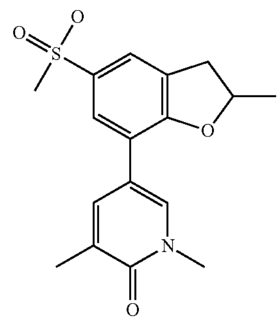 | 1,3-dimethyl-5-(2-methyl-5-methylsulfonyl-2,3-dihydro-1-benzofuran-7-yl)pyridin-2-one |
| 487 | 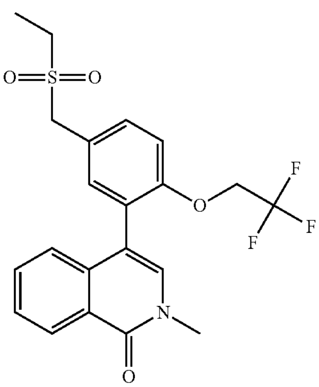 [SMILES: CCS(=O)(=O)Cc1ccc(OCC(F)(F)F)c(-c2cn(C)c(=O)c3ccccc23)c1] | 4-[5-(ethylsulfonylmethyl)-2-(2,2,2-trifluoroethoxy)phenyl]-2-methylisoquinolin-1-one |
| 488 | 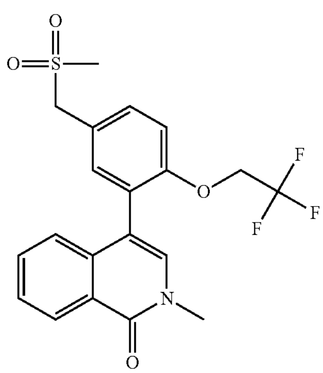 [SMILES: Cn1cc(-c2cc(CS(C)(=O)=O)ccc2OCC(F)(F)F)c2ccccc2c1=O] | 2-methyl-4-[5-(methylsulfonylmethyl)-2-(2,2,2-trifluoroethoxy)phenyl]isoquinolin-1-one |
| 489 | 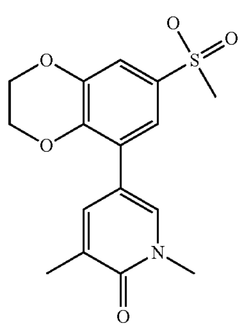 | 1,3-dimethyl-5-(7-methylsulfonyl-2,3-dihydro-1,4-benzodioxin-5-yl)pyridin-2-one |

TABLE 1-continued

| Chemical Synthesis Example | Structure | Name |
|---|---|---|
| 490 | 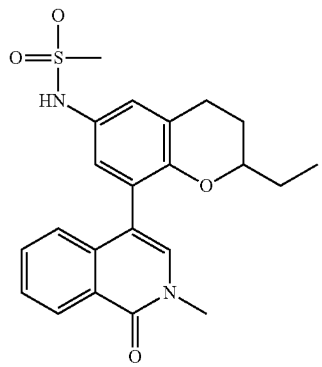 | N-[2-ethyl-8-(2-methyl-1-oxoisoquinolin-4-yl)-3,4-dihydro-2H-chromen-6-yl]methanesulfonamide |
| 491 | 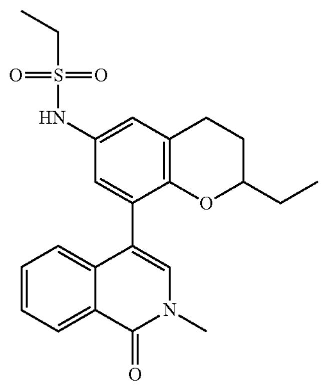 [SMILES: CCC1CCc2cc(NS(=O)(=O)CC)cc(-c3cn(C)c(=O)c4ccccc34)c2O1] | N-[2-ethyl-8-(2-methyl-1-oxoisoquinolin-4-yl)-3,4-dihydro-2H-chromen-6-yl]ethanesulfonamide |
| 492 | 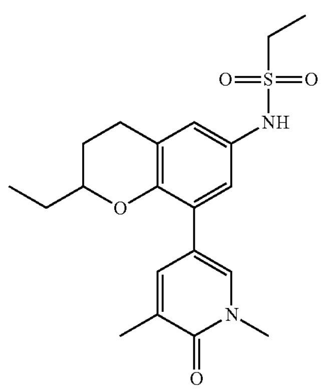 [SMILES: CCC1CCc2cc(NS(=O)(=O)CC)cc(-c3cc(C)c(=O)n(C)c3)c2O1] | N-[8-(1,5-dimethyl-6-oxopyridin-3-yl)-2-ethyl-3,4-dihydro-2H-chromen-6-yl]ethanesulfonamide |
| 493 | 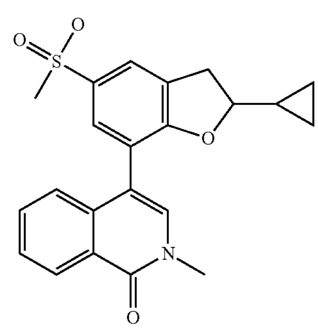 | 4-(2-cyclopropyl-5-methylsulfonyl-2,3-dihydro-1-benzofuran-7-yl)-2-methylisoquinolin-1-one |

TABLE 1-continued

| Chemical Synthesis Example | Structure | Name |
|---|---|---|
| 494 | 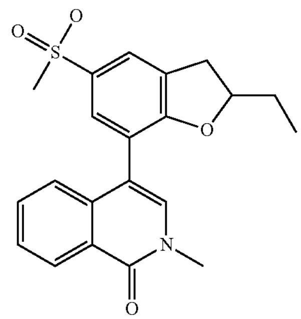 | 4-(2-ethyl-5-methylsulfonyl-2,3-dihydro-1-benzofuran-7-yl)-2-methylisoquinolin-1-one |
| 495 | 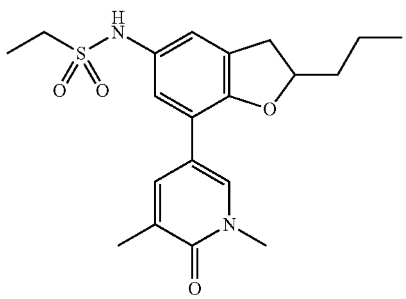 [SMILES: CCCC1Cc2cc(NS(=O)(=O)CC)cc(-c3cc(C)c(=O)n(C)c3)c2O1] | N-[7-(1,5-dimethyl-6-oxopyridin-3-yl)-2-propyl-2,3-dihydro-1-benzofuran-5-yl]ethanesulfonamide |
| 496 | 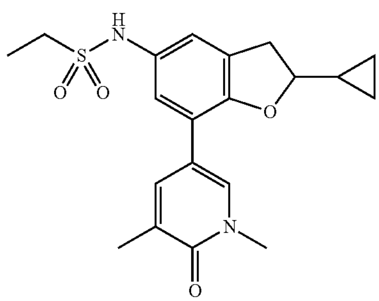 [SMILES: CCS(=O)(=O)Nc1cc2c(c(-c3cc(C)c(=O)n(C)c3)c1)OC(C1CC1)C2] | N-[2-cyclopropyl-7-(1,5-dimethyl-6-oxopyridin-3-yl)-2,3-dihydro-1-benzofuran-5-yl]ethanesulfonamide |
| 497 | 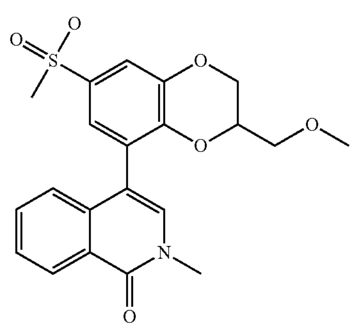 | 4[3-(methoxymethyl)-7-methylsulfonyl-2,3-dihydro-1,4-benzodioxin-5-yl]-2-methylisoquinolin-1-one |
| 498 | 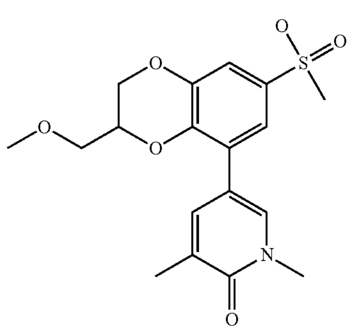 | 5-[3-(methoxymethyl)-7-methylsulfonyl-2,3-dihydro-1,4-benzodioxin-5-yl]-1,3-dimethylpyridin-2-one |

TABLE 1-continued

| Chemical Synthesis Example | Structure | Name |
|---|---|---|
| 499 | 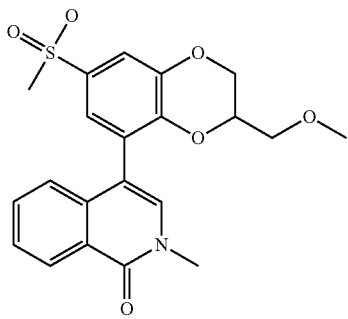 | 4-[3-(methoxymethyl)-7-methylsulfonyl-2,3-dihydro-1,4-benzodioxin-5-yl]-2-methylisoquinolin-1-one |
| 500 | 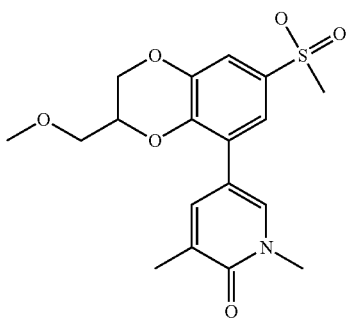 | 5-[3-(methoxymethyl)-7-methylsulfonyl-2,3-dihydro-1,4-benzodioxin-5-yl]-1,3-dimethylpyridin-2-one |
| 501 | 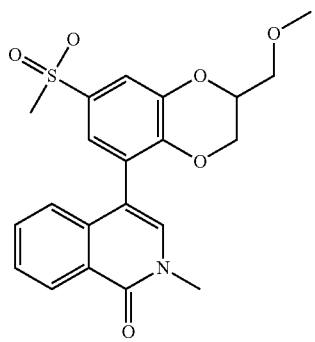 | 4-[2-(methoxymethyl)-7-methylsulfonyl-2,3-dehydro-1,4-benzodioxin-5-yl]-2-methylisoquinolin-1-one |
| 502 | 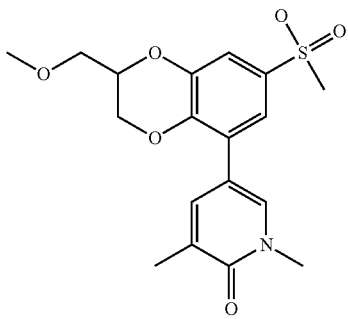 | 5[2-(methoxymethyl)-7-methylsulfonyl-2,3-dihydro-1,4-benzodioxin-5-yl]-1,3-dimethylpyridin-2-one |

TABLE 1-continued

| Chemical Synthesis Example | Structure | Name |
|---|---|---|
| 503 | 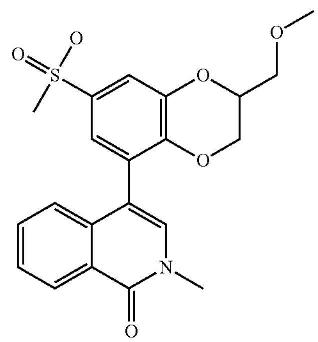 | 4-[2-(methoxymethyl)-7-methylsulfonyl-2,3-dihydro-1,4-benzodioxin-5-yl]-2-methylisoquinolin-1-one |
| 504 | 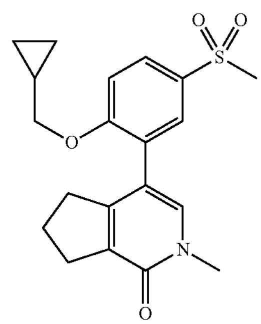 [SMILES: Cn1cc(-c2cc(S(C)(=O)=O)ccc2OCC2CC2)c2c(c1=O)CCC2] | 4-[2-(cyclopropylmethoxy)-5-methylsulfonylphenyl]-2-methyl-6,7-dihydro-5H-cyclopenta[c]pyridin-1-one |
| 505 | 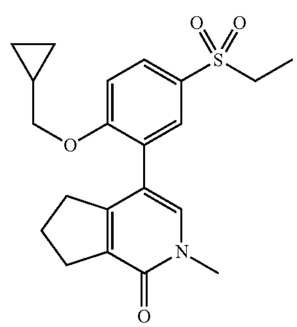 [SMILES: CCS(=O)(=O)c1ccc(OCC2CC2)c(-c2cn(C)c(=O)c3c2CCC3)c1] | 4-[2-(cyclopropylmethoxy)-5-ethylsulfonylphenyl]-2-methyl-6,7-dihydro-5H-cyclopenta[c]pyridin-1-one |
| 506 | 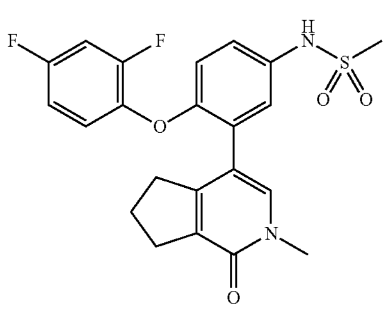 [SMILES: Cn1cc(-c2cc(NS(C)(=O)=O)ccc2Oc2ccc(F)cc2F)c2c(c1=O)CCC2] | N-[4-(2,4-difluorophenoxy)-3-(2-methyl-1-oxo-6,7-dihydro-5H-cyclopenta[c]pyridin-4-yl)phenyl]methanesulfonamide |

TABLE 1-continued

| Chemical Synthesis Example | Structure | Name |
|---|---|---|
| 507 | 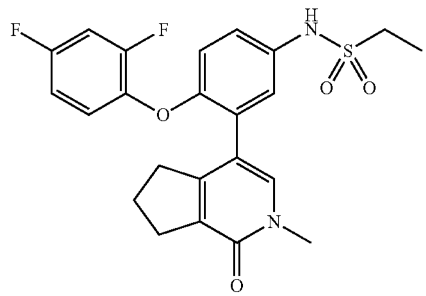 [SMILES: CCS(=O)(=O)Nc1ccc(Oc2ccc(F)cc2F)c(-c2cn(C)c(=O)c3c2CCC3)c1] | N-[4-(2,4-difluorophenoxy)-3-(2-methyl-1-oxo-6,7-dihydro-5H-cyclopenta[c]pyridin-4-yl)phenyl]ethanesulfonamide |
| 508 | 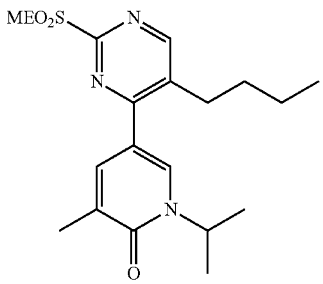 | 5-(5-butyl-2-methylsulfonylpyrimidin-4-yl)-3-methyl-1-propan-2-ylpyridin-2-one |
| 509 | 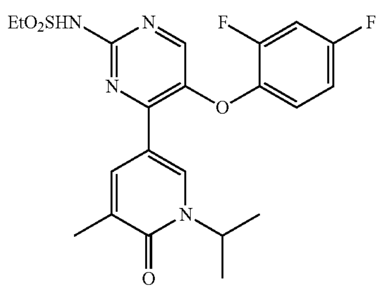 | N-[5-(2,4-difluorophenoxy)-4-(5-methyl-6-oxo-1-propan-2-ylpyridin-3-yl)pyrimidin-2-yl]ethanesulfonamide |
| 510 | 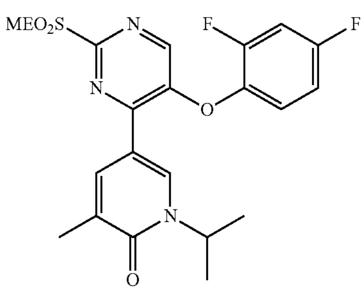 | 5-[5-(2,4-difluorophenoxy)-2-methylsulfonylpyrimidin-4-yl]-3-methyl-1-propan-2-ylpyridin-2-one |
| 511 | 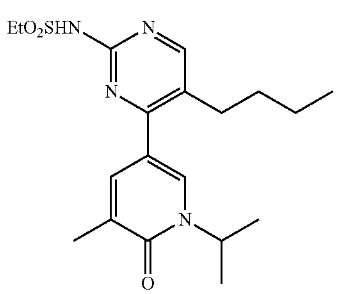 | N-[5-butyl-4-(5-methyl-6-oxo-1-propan-2-ylpyridin-3-yl)pyrimidin-2-yl]ethanesulfonamide |

TABLE 1-continued

| Chemical Synthesis Example | Structure | Name |
|---|---|---|
| 512 | 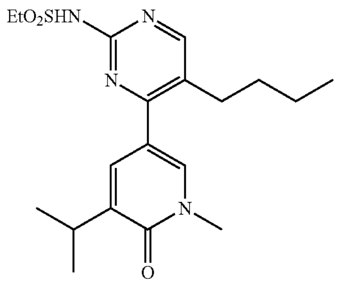 | N-[5-butyl-4-(1-methyl-6-oxo-5-propan-2-ylpyridin-3-yl)pyrimidin-2-yl]ethanesulfonamide |
| 513 | 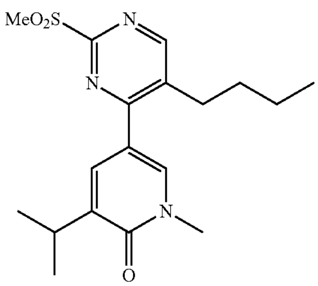 [SMILES: CCCCc1cnc(S(C)(=O)=O)nc1-c1cc(C(C)C)c(=O)n(C)c1] | 5-(5-butyl-2-methylsulfonylpyrimidin-4-yl)-1-methyl-3-propan-2-ylpyridin-2-one |
| 514 | 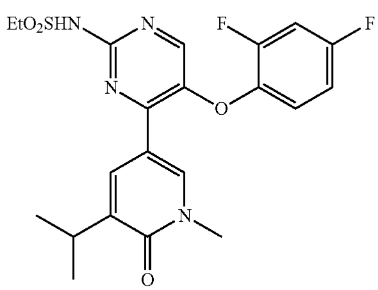 | N-[5-(2,4-difluorophenoxy)-4-(1-methyl-6-oxo-5-propan-2-ylpyridin-3-yl)pyrimidin-2-yl]ethanesulfonamide |

In some embodiments, the substituted heterocyclic derivative compound disclosed herein has the structure provided in Table 2.

TABLE 2

TABLE 2-continued

TABLE 2-continued
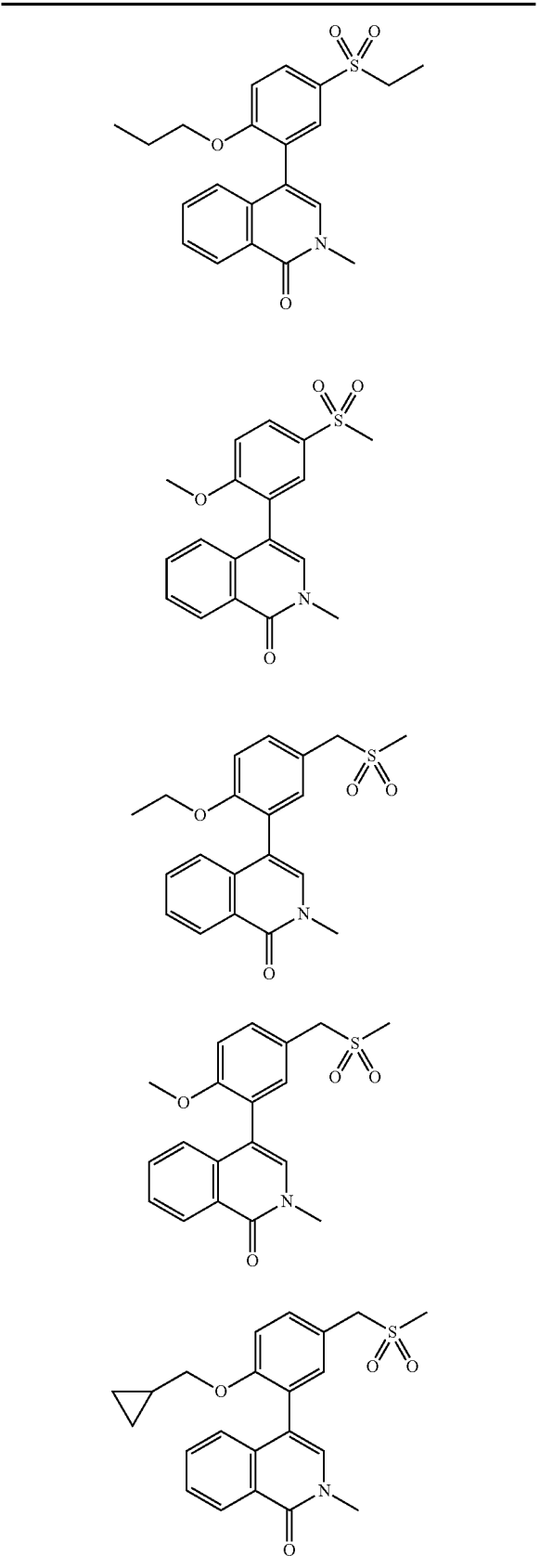
TABLE 2-continued
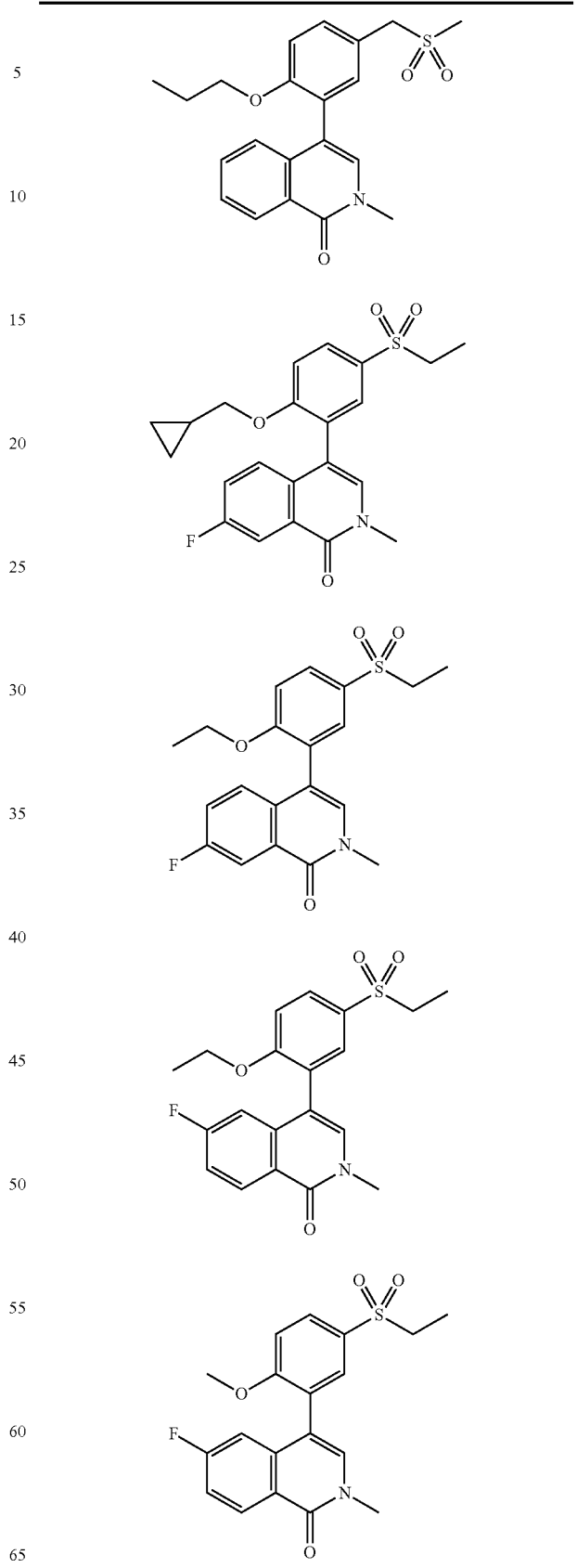

TABLE 2-continued
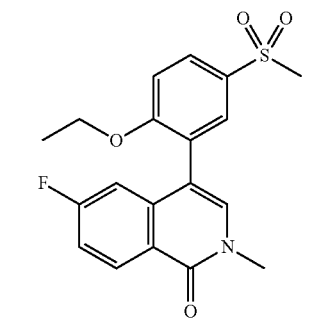 [SMILES: CCOc1ccc(S(C)(=O)=O)cc1-c1cn(C)c(=O)c2ccc(F)cc12]
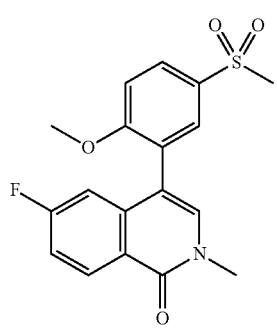
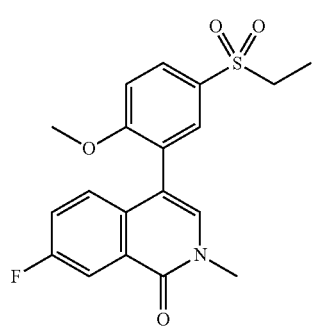 [SMILES: CCS(=O)(=O)c1ccc(OC)c(-c2cn(C)c(=O)c3cc(F)ccc23)c1]
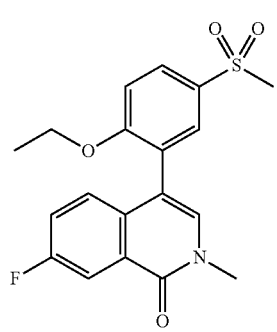
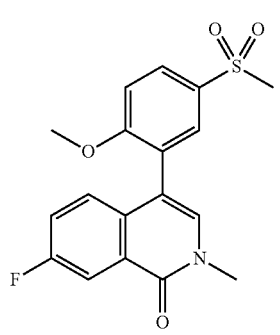 [SMILES: COc1ccc(S(C)(=O)=O)cc1-c1cn(C)c(=O)c2cc(F)ccc12]
TABLE 2-continued
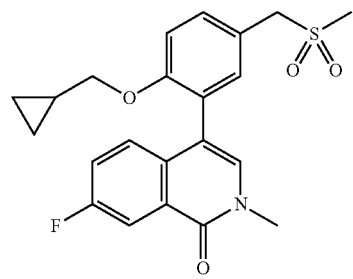 [SMILES: Cn1cc(-c2cc(CS(C)(=O)=O)ccc2OCC2CC2)c2ccc(F)cc2c1=O]
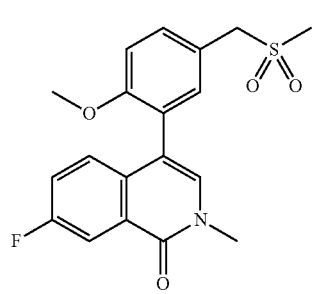 [SMILES: COc1ccc(CS(C)(=O)=O)cc1-c1cn(C)c(=O)c2cc(F)ccc12]
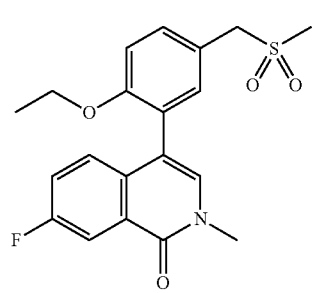 [SMILES: CCOc1ccc(CS(C)(=O)=O)cc1-c1cn(C)c(=O)c2cc(F)ccc12]
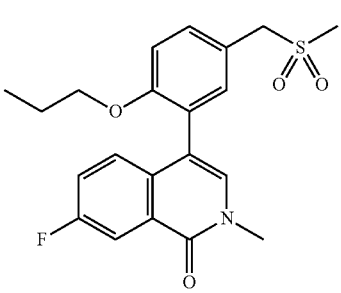 [SMILES: CCCOc1ccc(CS(C)(=O)=O)cc1-c1cn(C)c(=O)c2cc(F)ccc12]
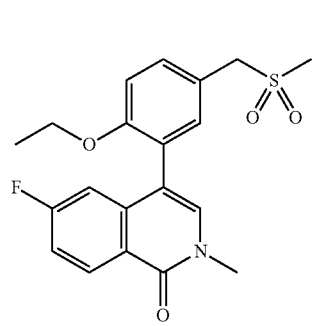 [SMILES: CCOc1ccc(CS(C)(=O)=O)cc1-c1cn(C)c(=O)c2ccc(F)cc12]

TABLE 2-continued
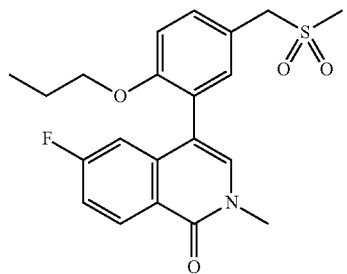 [SMILES: CCCOc1ccc(CS(C)(=O)=O)cc1-c1cn(C)c(=O)c2ccc(F)cc12]
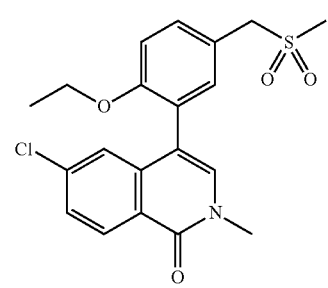 [SMILES: CCOc1ccc(CS(C)(=O)=O)cc1-c1cn(C)c(=O)c2ccc(Cl)cc12]
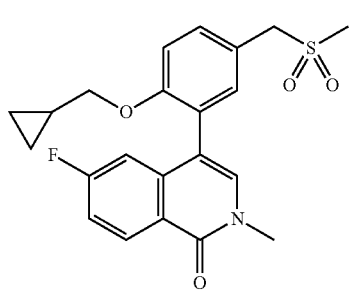 [SMILES: Cn1cc(-c2cc(CS(C)(=O)=O)ccc2OCC2CC2)c2cc(F)ccc2c1=O]
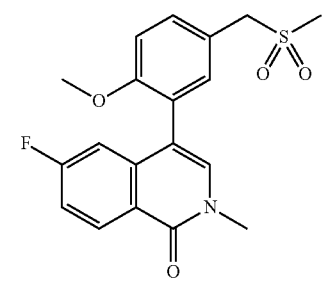 [SMILES: COc1ccc(CS(C)(=O)=O)cc1-c1cn(C)c(=O)c2ccc(F)cc12]
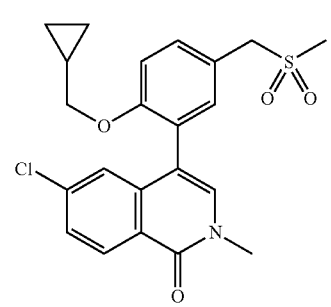 [SMILES: Cn1cc(-c2cc(CS(C)(=O)=O)ccc2OCC2CC2)c2cc(Cl)ccc2c1=O]
TABLE 2-continued
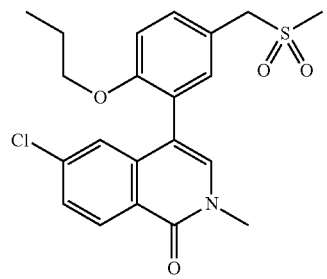 [SMILES: CCCOc1ccc(CS(C)(=O)=O)cc1-c1cn(C)c(=O)c2ccc(Cl)cc12]
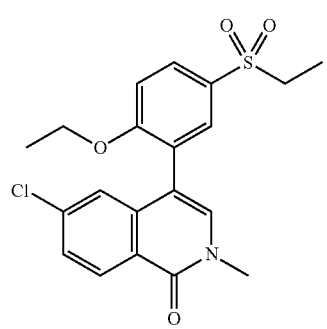 [SMILES: CCOc1ccc(S(=O)(=O)CC)cc1-c1cn(C)c(=O)c2ccc(Cl)cc12]
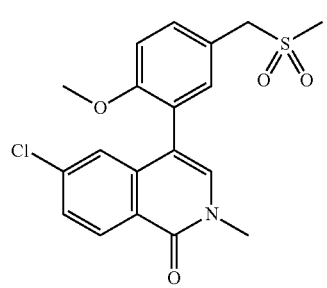 [SMILES: COc1ccc(CS(C)(=O)=O)cc1-c1cn(C)c(=O)c2ccc(Cl)cc12]
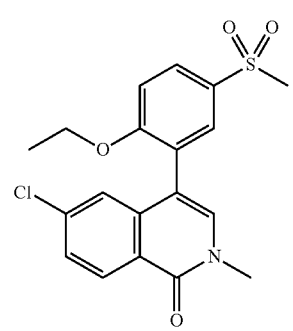 [SMILES: CCOc1ccc(S(C)(=O)=O)cc1-c1cn(C)c(=O)c2ccc(Cl)cc12]
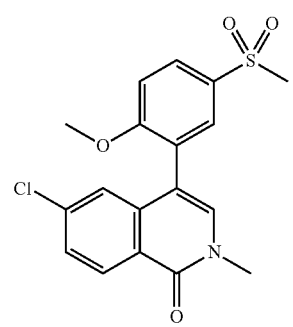 [SMILES: COc1ccc(S(C)(=O)=O)cc1-c1cn(C)c(=O)c2ccc(Cl)cc12]

TABLE 2-continued
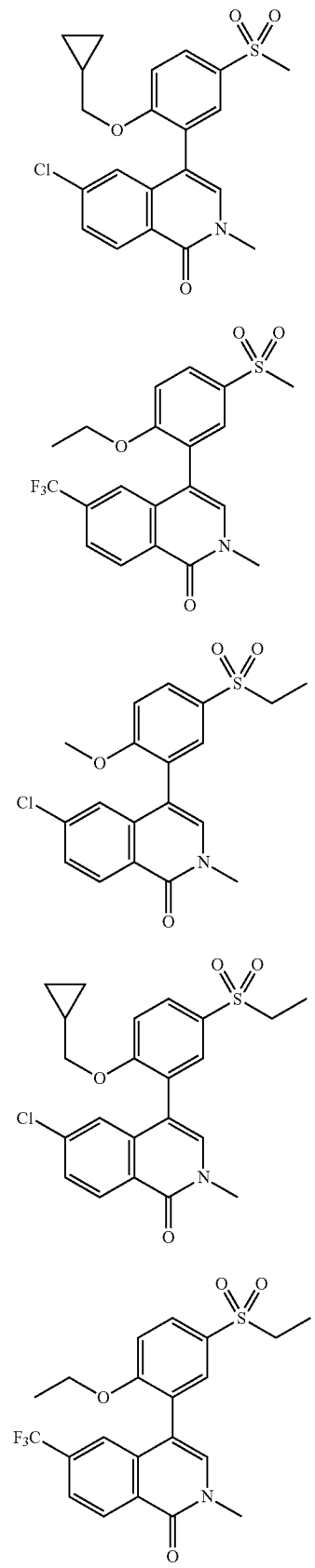
TABLE 2-continued
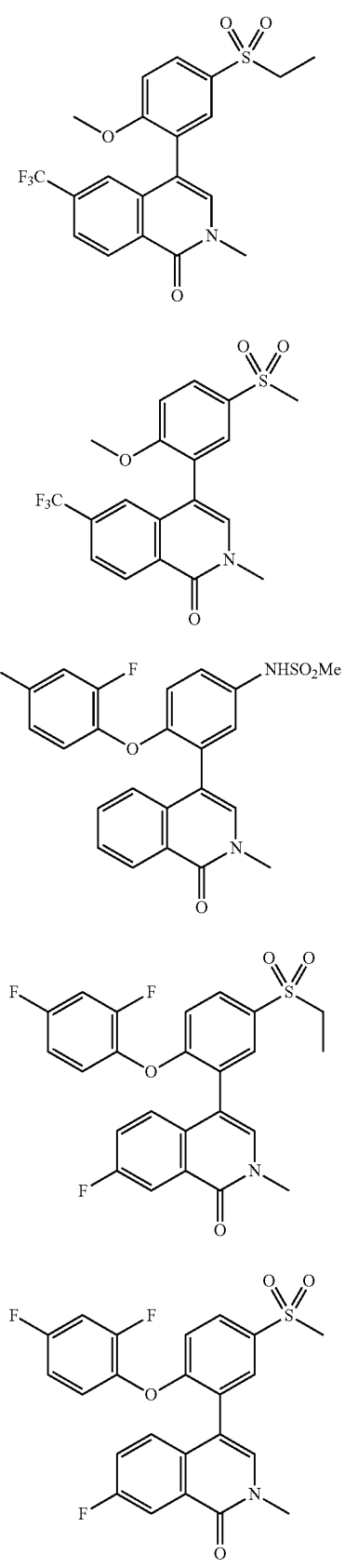

TABLE 2-continued
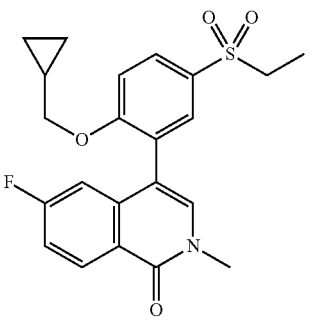 [SMILES: CCS(=O)(=O)c1ccc(OCC2CC2)c(-c2cn(C)c(=O)c3ccc(F)cc23)c1]
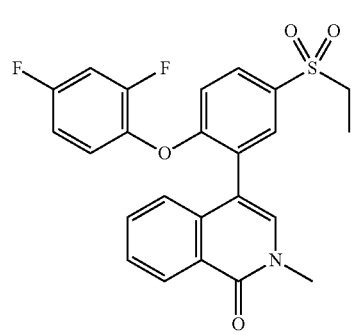 [SMILES: CCS(=O)(=O)c1ccc(Oc2ccc(F)cc2F)c(-c2cn(C)c(=O)c3ccccc23)c1]
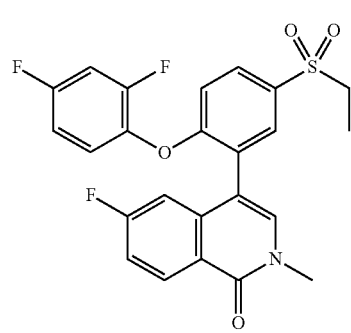 [SMILES: CCS(=O)(=O)c1ccc(Oc2ccc(F)cc2F)c(-c2cn(C)c(=O)c3ccc(F)cc23)c1]
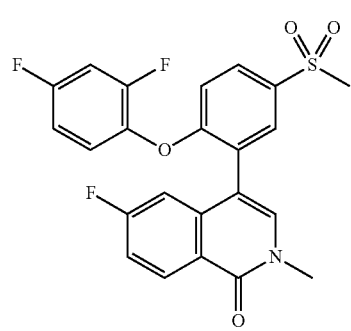 [SMILES: Cn1cc(-c2cc(S(C)(=O)=O)ccc2Oc2ccc(F)cc2F)c2cc(F)ccc2c1=O]
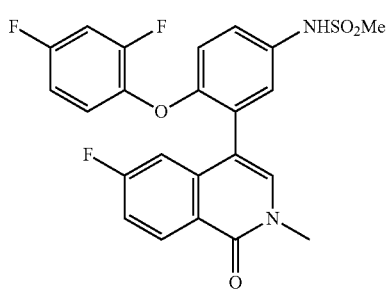
TABLE 2-continued
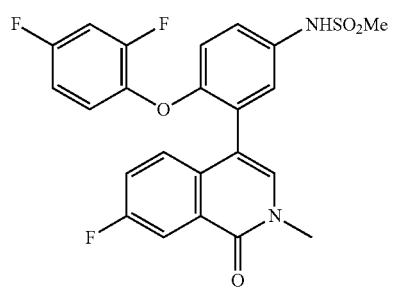
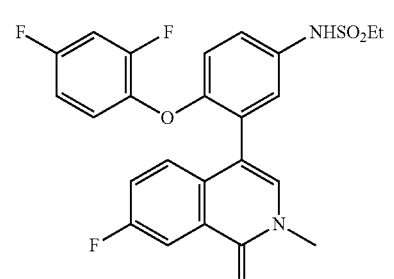
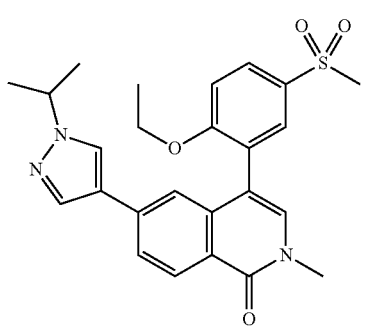 [SMILES: CCOc1ccc(S(C)(=O)=O)cc1-c1cn(C)c(=O)c2ccc(-c3cnn(C(C)C)c3)cc12]
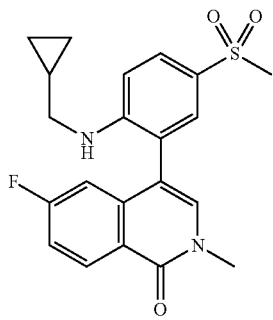
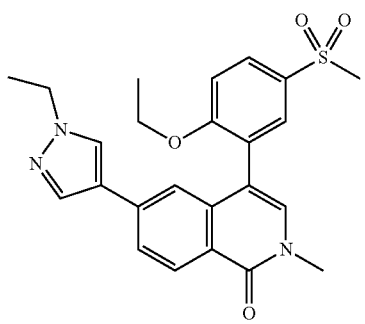 [SMILES: CCOc1ccc(S(C)(=O)=O)cc1-c1cn(C)c(=O)c2ccc(-c3cnn(CC)c3)cc12]

353
TABLE 2-continued
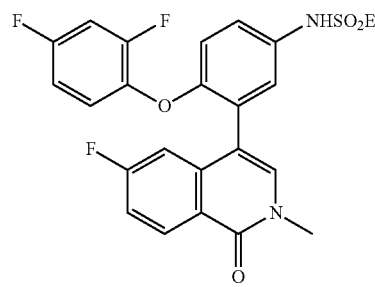
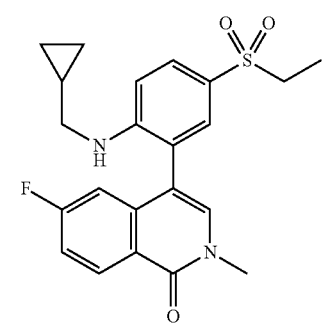 [SMILES: CCS(=O)(=O)c1ccc(NCC2CC2)c(-c2cn(C)c(=O)c3ccc(F)cc23)c1]
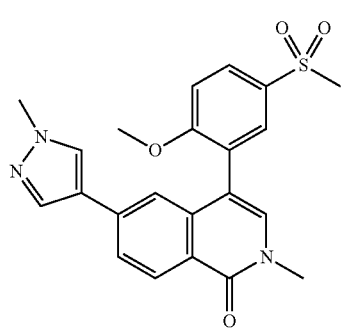
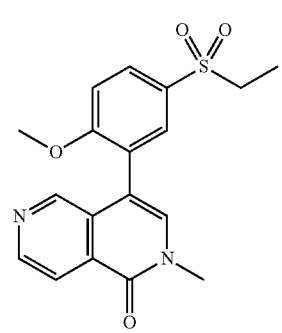 [SMILES: CCS(=O)(=O)c1ccc(OC)c(-c2cn(C)c(=O)c3ccncc23)c1]
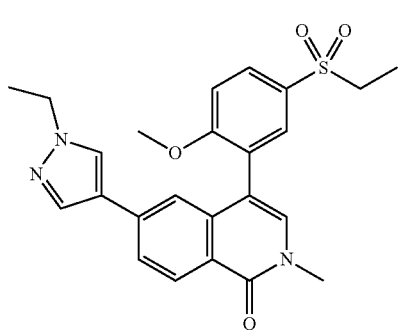 [SMILES: CCn1cc(-c2ccc3c(=O)n(C)cc(-c4cc(S(=O)(=O)CC)ccc4OC)c3c2)cn1]
354
TABLE 2-continued
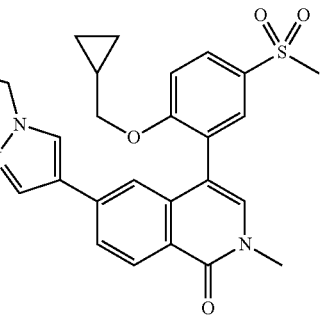
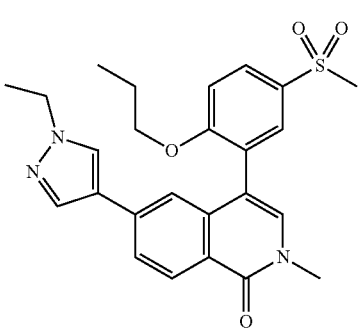 [SMILES: CCCOc1ccc(S(C)(=O)=O)cc1-c1cn(C)c(=O)c2ccc(-c3cnn(CC)c3)cc12]
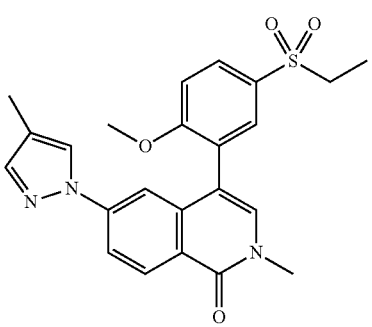
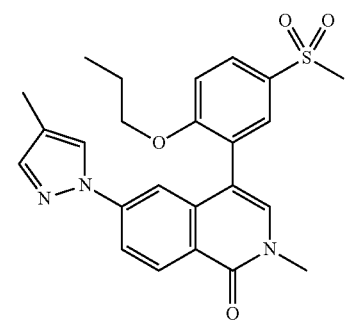 [SMILES: CCCOc1ccc(S(C)(=O)=O)cc1-c1cn(C)c(=O)c2ccc(-n3cc(C)cn3)cc12]
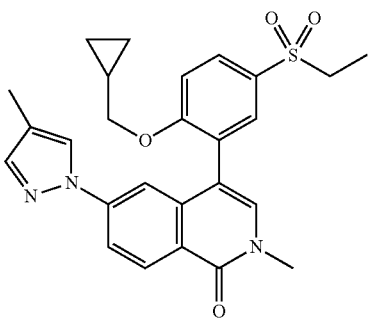

TABLE 2-continued
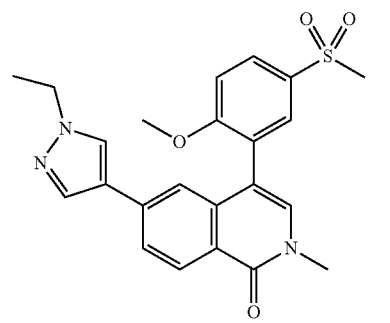 [SMILES: CCn1cc(-c2ccc3c(=O)n(C)cc(-c4cc(S(C)(=O)=O)ccc4OC)c3c2)cn1]
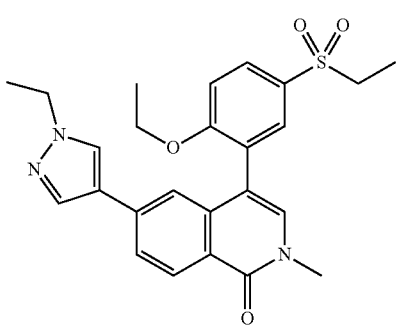 [SMILES: CCOc1ccc(S(=O)(=O)CC)cc1-c1cn(C)c(=O)c2ccc(-c3cnn(CC)c3)cc12]
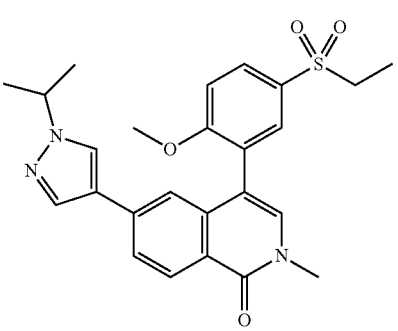 [SMILES: CCS(=O)(=O)c1ccc(OC)c(-c2cn(C)c(=O)c3ccc(-c4cnn(C(C)C)c4)cc23)c1]
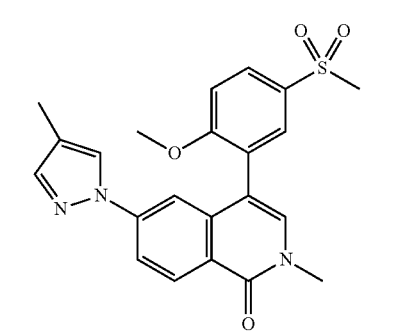 [SMILES: COc1ccc(S(C)(=O)=O)cc1-c1cn(C)c(=O)c2ccc(-n3cc(C)cn3)cc12]
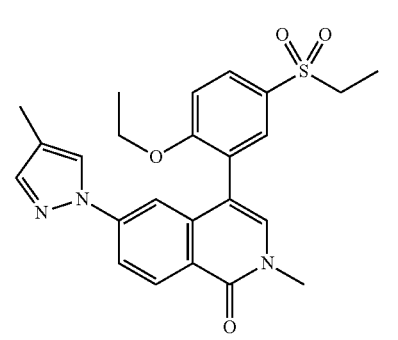
TABLE 2-continued
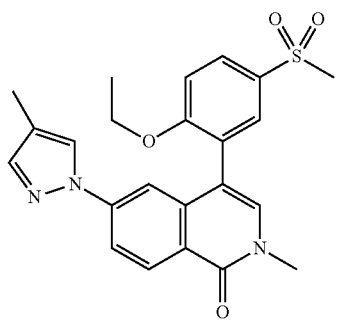 [SMILES: CCOc1ccc(S(C)(=O)=O)cc1-c1cn(C)c(=O)c2ccc(-n3cc(C)cn3)cc12]
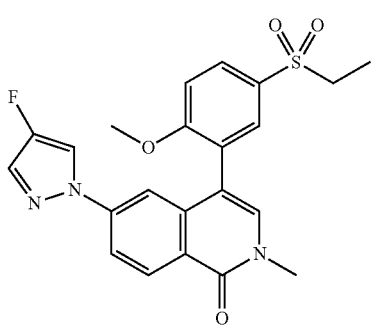
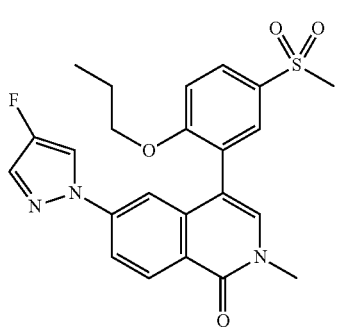
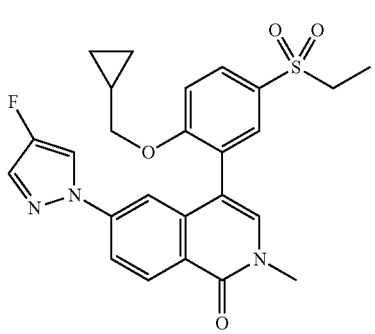 [SMILES: CCS(=O)(=O)c1ccc(OCC2CC2)c(-c2cn(C)c(=O)c3ccc(-n4cc(F)cn4)cc23)c1]
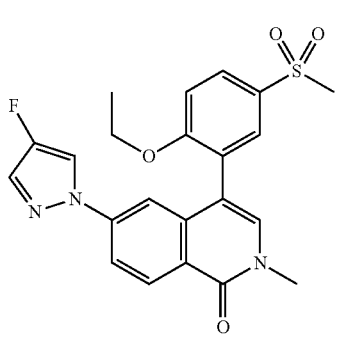

TABLE 2-continued
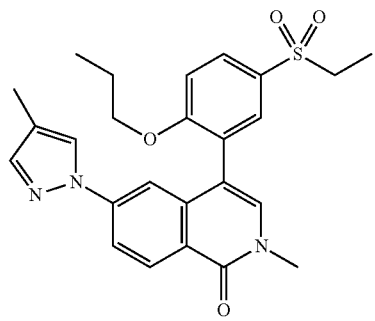 [SMILES: CCCOc1ccc(S(=O)(=O)CC)cc1-c1cn(C)c(=O)c2ccc(-n3cc(C)cn3)cc12]
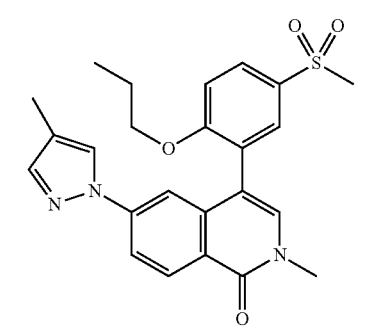 [SMILES: CCCOc1ccc(S(C)(=O)=O)cc1-c1cn(C)c(=O)c2ccc(-n3cc(C)cn3)cc12]
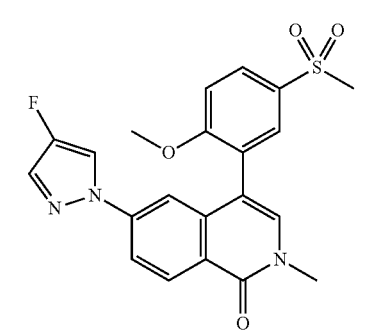 [SMILES: COc1ccc(S(C)(=O)=O)cc1-c1cn(C)c(=O)c2ccc(-n3cc(F)cn3)cc12]
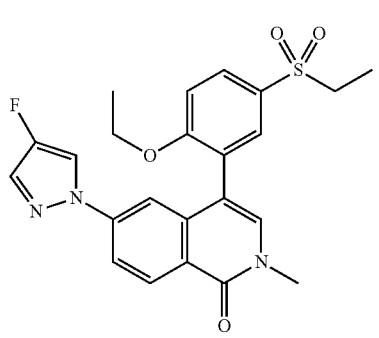 [SMILES: CCOc1ccc(S(=O)(=O)CC)cc1-c1cn(C)c(=O)c2ccc(-n3cc(F)cn3)cc12]
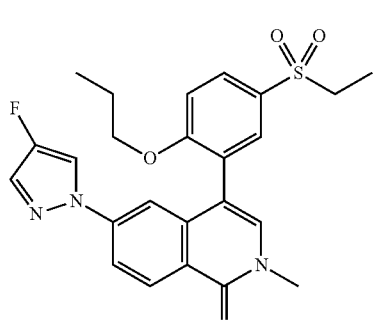
TABLE 2-continued
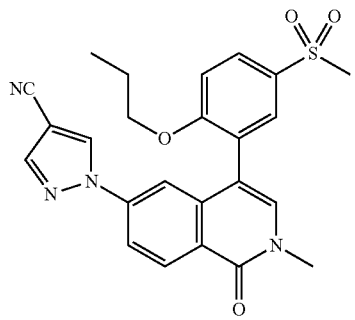 [SMILES: CCCOc1ccc(S(C)(=O)=O)cc1-c1cn(C)c(=O)c2ccc(-n3cc(C#N)cn3)cc12]
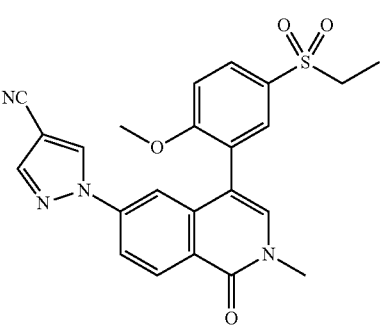 [SMILES: CCS(=O)(=O)c1ccc(OC)c(-c2cn(C)c(=O)c3ccc(-n4cc(C#N)cn4)cc23)c1]
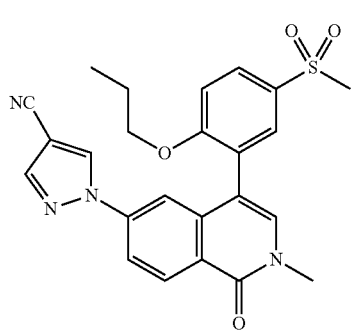 [SMILES: CCCOc1ccc(S(C)(=O)=O)cc1-c1cn(C)c(=O)c2ccc(-n3cc(C#N)cn3)cc12]
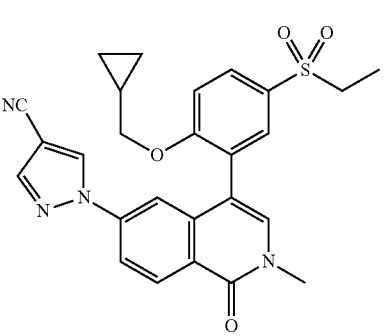 [SMILES: CCS(=O)(=O)c1ccc(OCC2CC2)c(-c2cn(C)c(=O)c3ccc(-n4cc(C#N)cn4)cc23)c1]
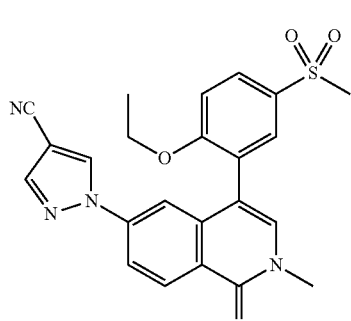

TABLE 2-continued
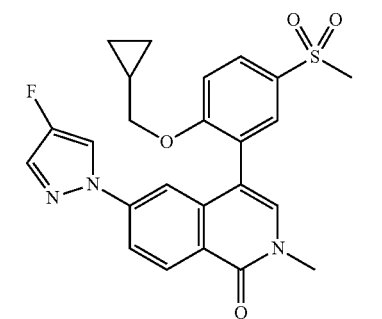 [SMILES: Cn1cc(-c2cc(S(C)(=O)=O)ccc2OCC2CC2)c2cc(-n3cc(F)cn3)ccc2c1=O]
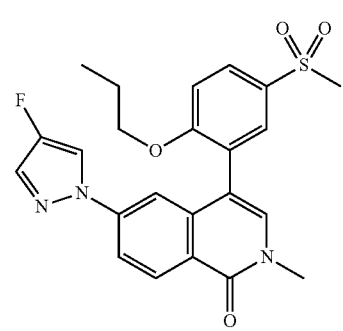 [SMILES: CCCOc1ccc(S(C)(=O)=O)cc1-c1cn(C)c(=O)c2ccc(-n3cc(F)cn3)cc12]
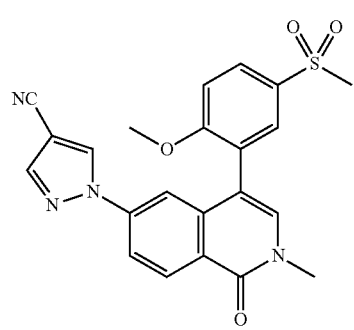 [SMILES: COc1ccc(S(C)(=O)=O)cc1-c1cn(C)c(=O)c2ccc(-n3cc(C#N)cn3)cc12]
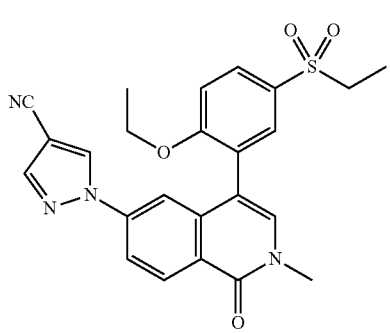 [SMILES: CCOc1ccc(S(=O)(=O)CC)cc1-c1cn(C)c(=O)c2ccc(-n3cc(C#N)cn3)cc12]
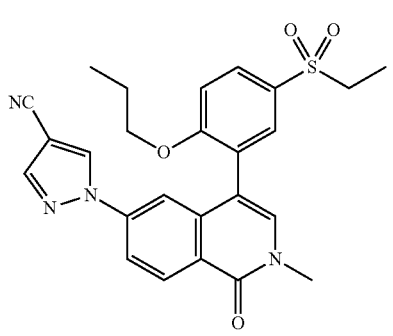 [SMILES: CCCOc1ccc(S(=O)(=O)CC)cc1-c1cn(C)c(=O)c2ccc(-n3cc(C#N)cn3)cc12]
TABLE 2-continued
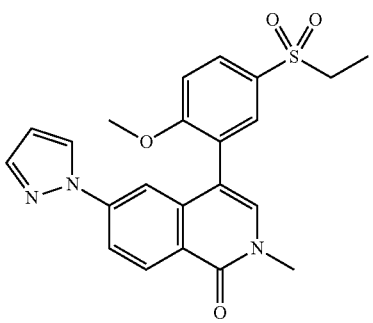 [SMILES: CCS(=O)(=O)c1ccc(OC)c(-c2cn(C)c(=O)c3ccc(-n4cccn4)cc23)c1]
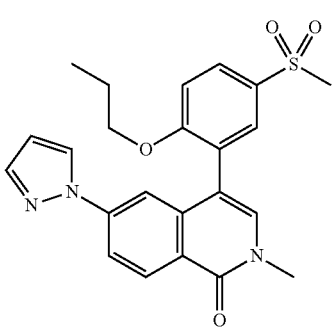 [SMILES: CCCOc1ccc(S(C)(=O)=O)cc1-c1cn(C)c(=O)c2ccc(-n3cccn3)cc12]
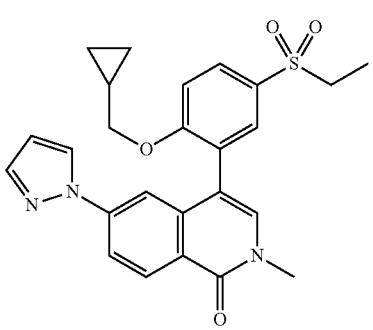 [SMILES: CCS(=O)(=O)c1ccc(OCC2CC2)c(-c2cn(C)c(=O)c3ccc(-n4cccn4)cc23)c1]
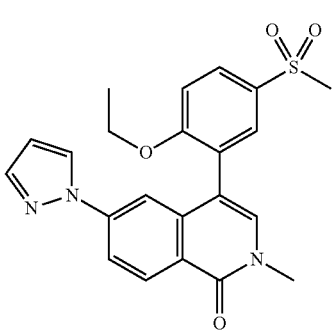 [SMILES: CCOc1ccc(S(C)(=O)=O)cc1-c1cn(C)c(=O)c2ccc(-n3cccn3)cc12]
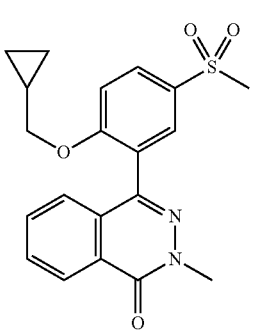

361
TABLE 2-continued
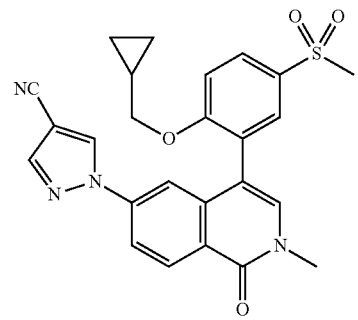 [SMILES: Cn1cc(-c2cc(S(C)(=O)=O)ccc2OCC2CC2)c2cc(-n3cc(C#N)cn3)ccc2c1=O]
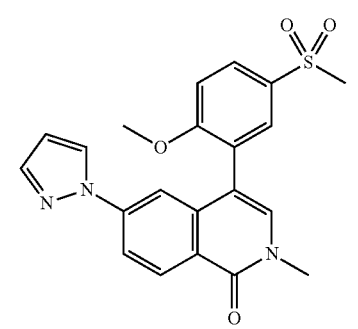 [SMILES: COc1ccc(S(C)(=O)=O)cc1-c1cn(C)c(=O)c2ccc(-n3cccn3)cc12]
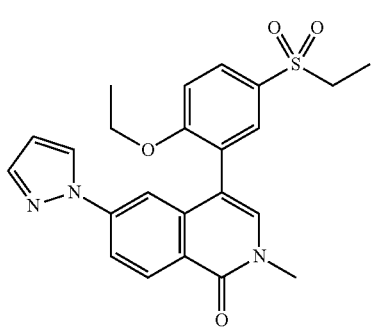 [SMILES: CCOc1ccc(S(=O)(=O)CC)cc1-c1cn(C)c(=O)c2ccc(-n3cccn3)cc12]
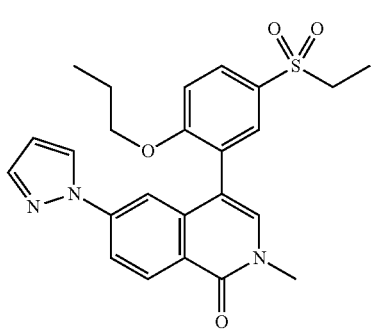 [SMILES: CCCOc1ccc(S(=O)(=O)CC)cc1-c1cn(C)c(=O)c2ccc(-n3cccn3)cc12]
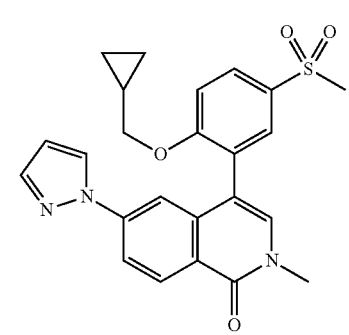 [SMILES: Cn1cc(-c2cc(S(C)(=O)=O)ccc2OCC2CC2)c2cc(-n3cccn3)ccc2c1=O]
362
TABLE 2-continued
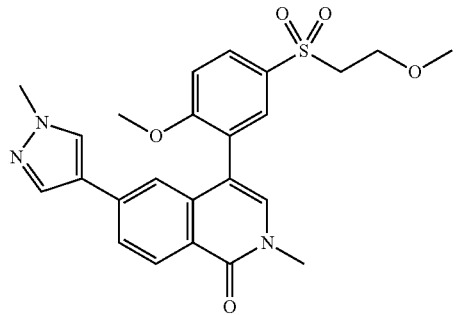 [SMILES: COCCS(=O)(=O)c1ccc(OC)c(-c2cn(C)c(=O)c3ccc(-c4cnn(C)c4)cc23)c1]
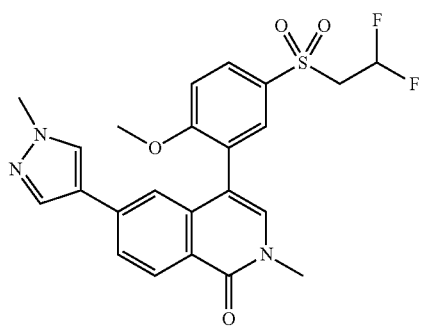 [SMILES: COc1ccc(S(=O)(=O)CC(F)F)cc1-c1cn(C)c(=O)c2ccc(-c3cnn(C)c3)cc12]
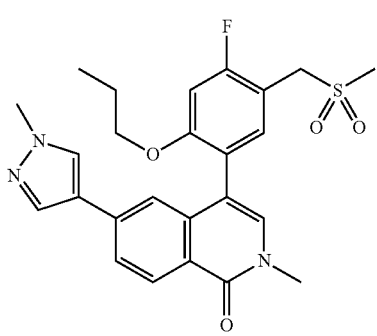 [SMILES: CCCOc1cc(F)c(CS(C)(=O)=O)cc1-c1cn(C)c(=O)c2ccc(-c3cnn(C)c3)cc12]
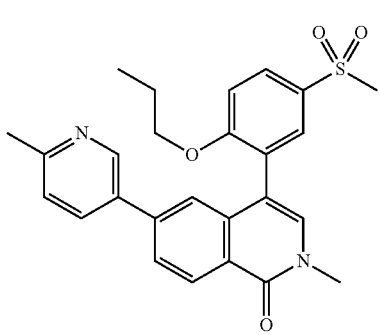

TABLE 2-continued
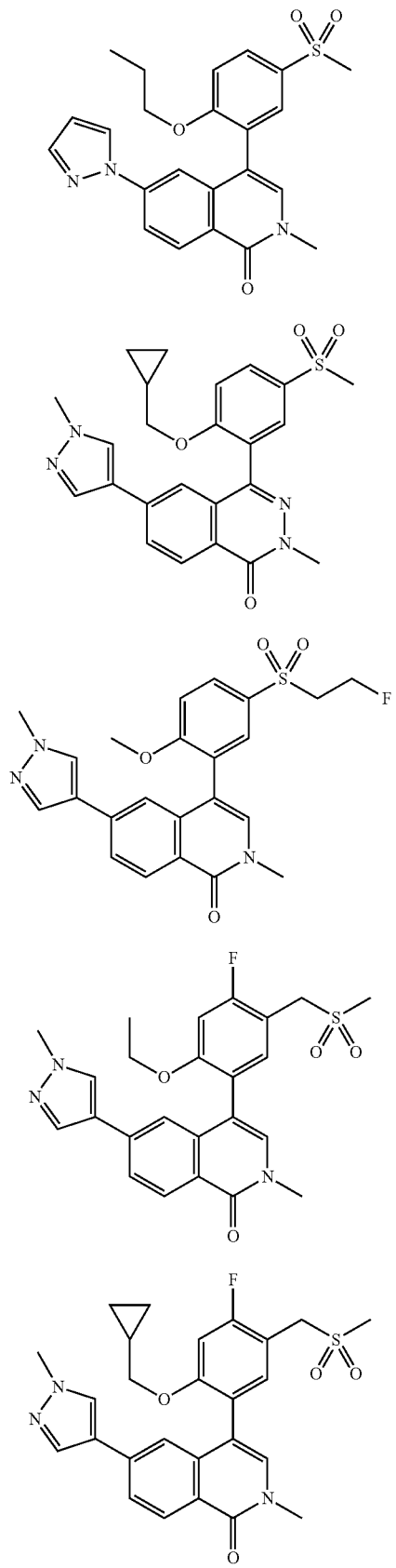
TABLE 2-continued
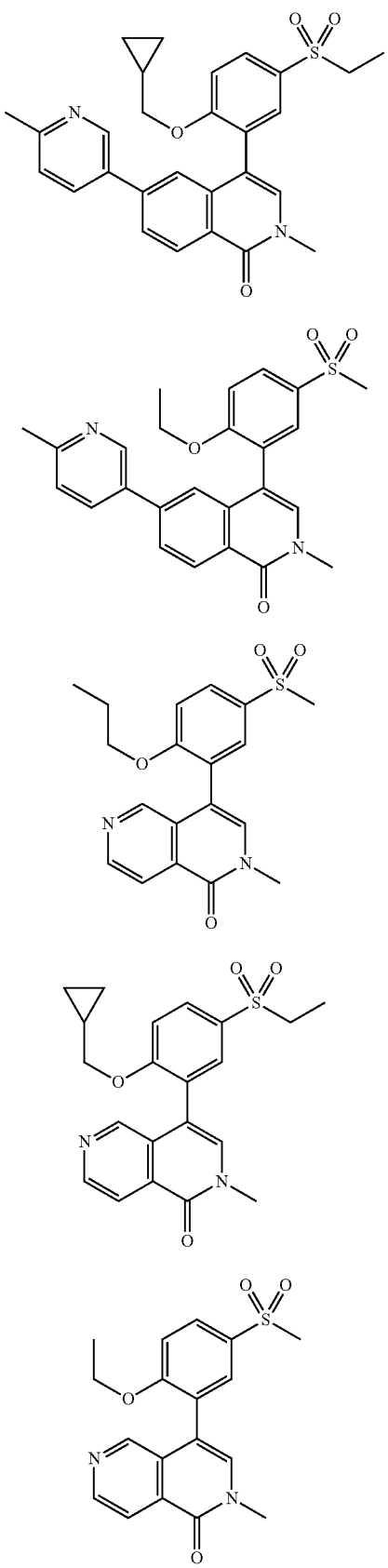

TABLE 2-continued
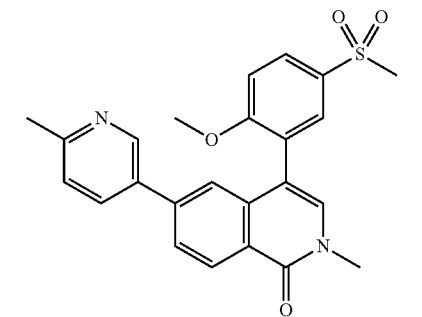
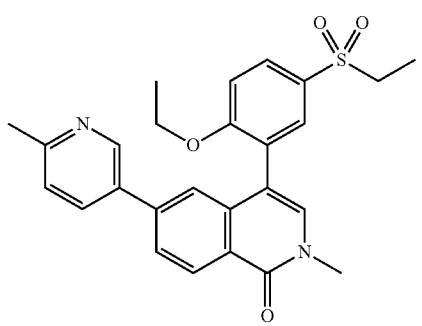 [SMILES: CCOc1ccc(S(=O)(=O)CC)cc1-c1cn(C)c(=O)c2ccc(-c3ccc(C)nc3)cc12]
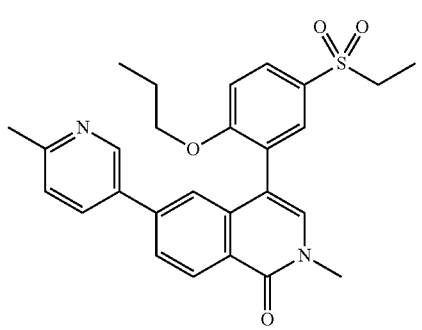 [SMILES: CCCOc1ccc(S(=O)(=O)CC)cc1-c1cn(C)c(=O)c2ccc(-c3ccc(C)nc3)cc12]
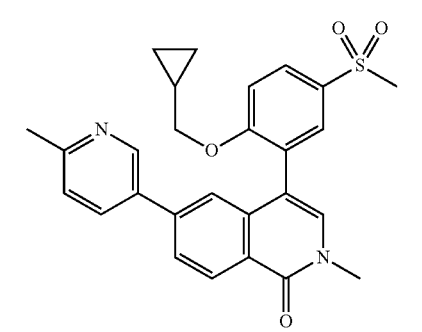
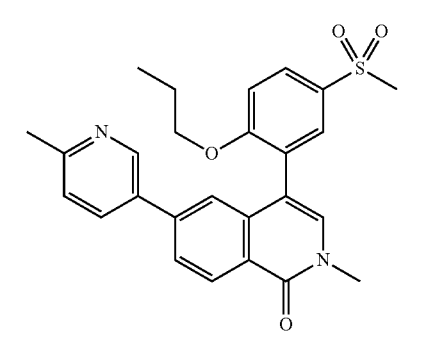
TABLE 2-continued
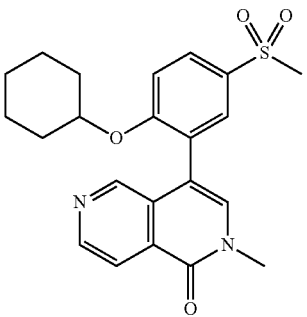 [SMILES: Cn1cc(-c2cc(S(C)(=O)=O)ccc2OC2CCCCC2)c2cnccc2c1=O]
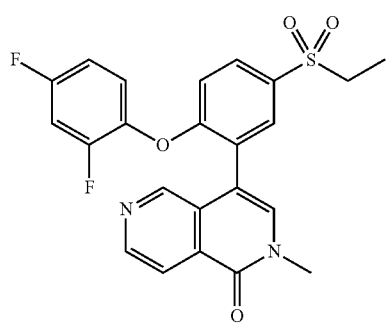 [SMILES: CCS(=O)(=O)c1ccc(Oc2ccc(F)cc2F)c(-c2cn(C)c(=O)c3ccncc23)c1]
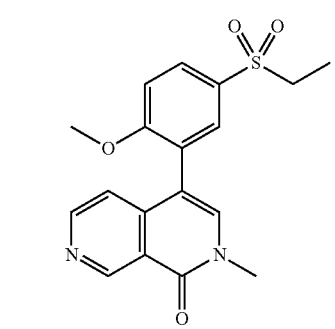 [SMILES: CCS(=O)(=O)c1ccc(OC)c(-c2cn(C)c(=O)c3cnccc23)c1]
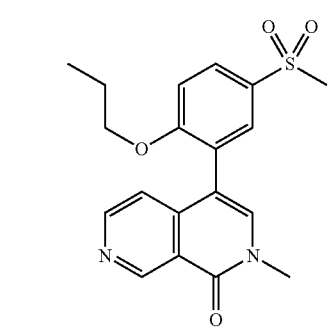
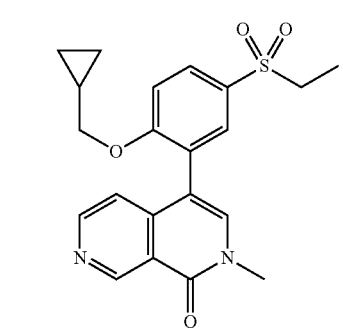 [SMILES: CCS(=O)(=O)c1ccc(OCC2CC2)c(-c2cn(C)c(=O)c3cnccc23)c1]

TABLE 2-continued
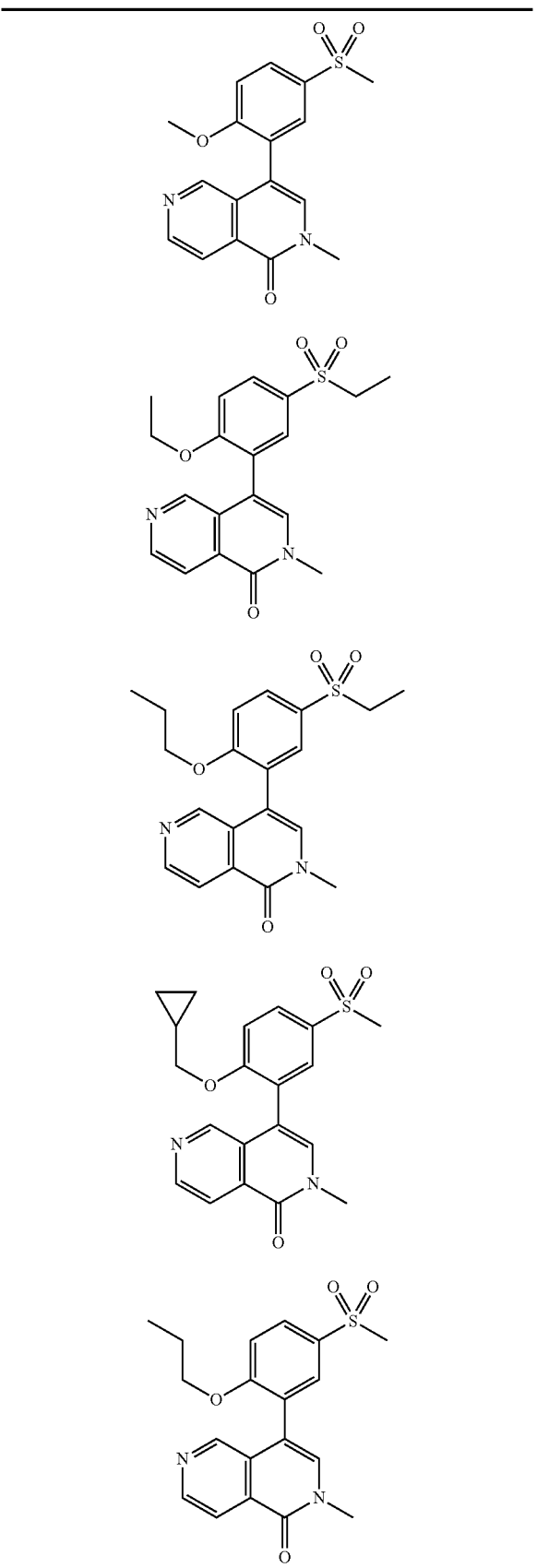
TABLE 2-continued
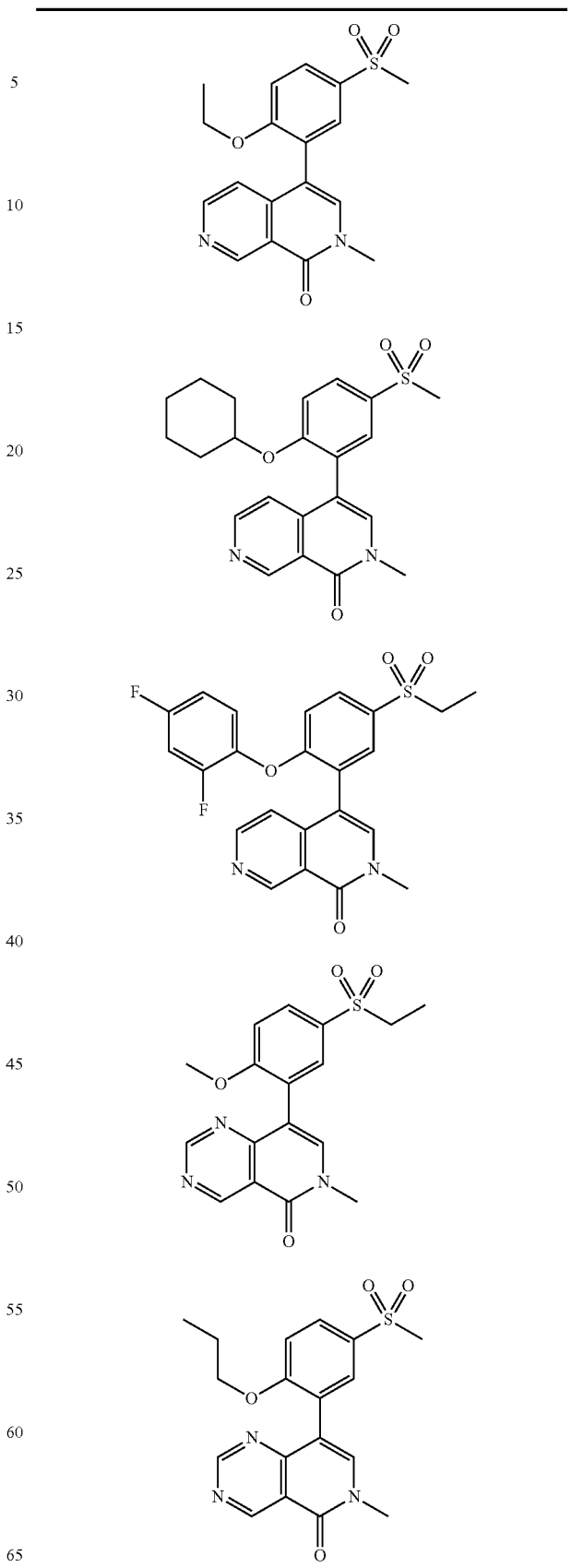

TABLE 2-continued
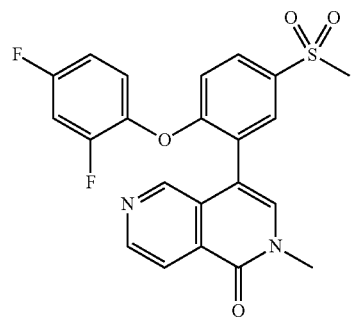 [SMILES: Cn1cc(-c2cc(S(C)(=O)=O)ccc2Oc2ccc(F)cc2F)c2cnccc2c1=O]
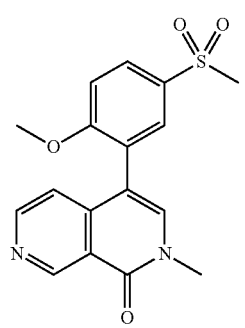 [SMILES: COc1ccc(S(C)(=O)=O)cc1-c1cn(C)c(=O)c2cnccc12]
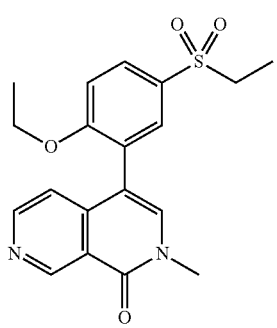 [SMILES: CCOc1ccc(S(=O)(=O)CC)cc1-c1cn(C)c(=O)c2cnccc12]
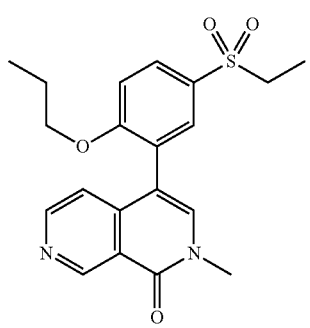 [SMILES: CCCOc1ccc(S(=O)(=O)CC)cc1-c1cn(C)c(=O)c2cnccc12]
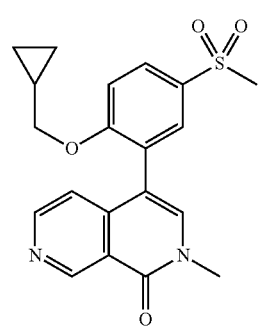 [SMILES: Cn1cc(-c2cc(S(C)(=O)=O)ccc2OCC2CC2)c2ccncc2c1=O]
TABLE 2-continued
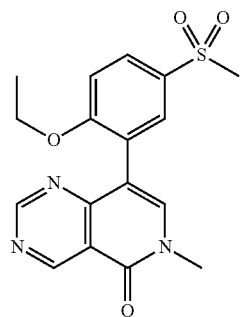 [SMILES: CCOc1ccc(S(C)(=O)=O)cc1-c1cn(C)c(=O)c2cncnc12]
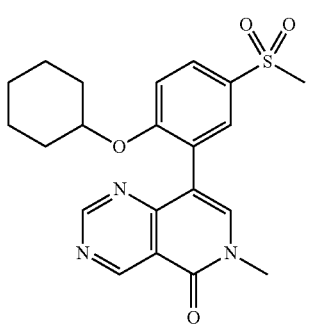 [SMILES: Cn1cc(-c2cc(S(C)(=O)=O)ccc2OC2CCCCC2)c2ncncc2c1=O]
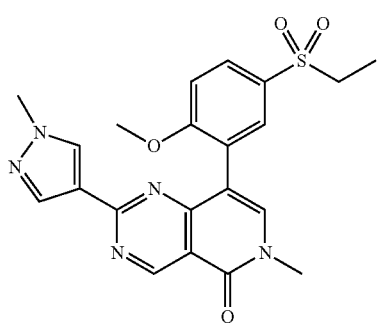 [SMILES: CCS(=O)(=O)c1ccc(OC)c(-c2cn(C)c(=O)c3cnc(-c4cnn(C)c4)nc23)c1]
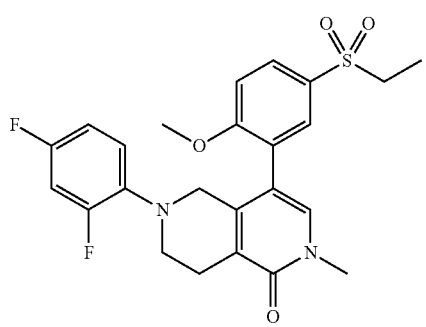 [SMILES: CCS(=O)(=O)c1ccc(OC)c(-c2cn(C)c(=O)c3c2CN(c2ccc(F)cc2F)CC3)c1]
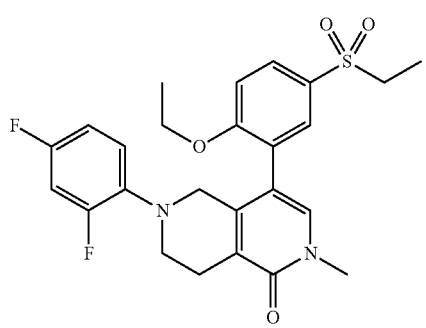 [SMILES: CCOc1ccc(S(=O)(=O)CC)cc1-c1cn(C)c(=O)c2c1CN(c1ccc(F)cc1F)CC2]

TABLE 2-continued
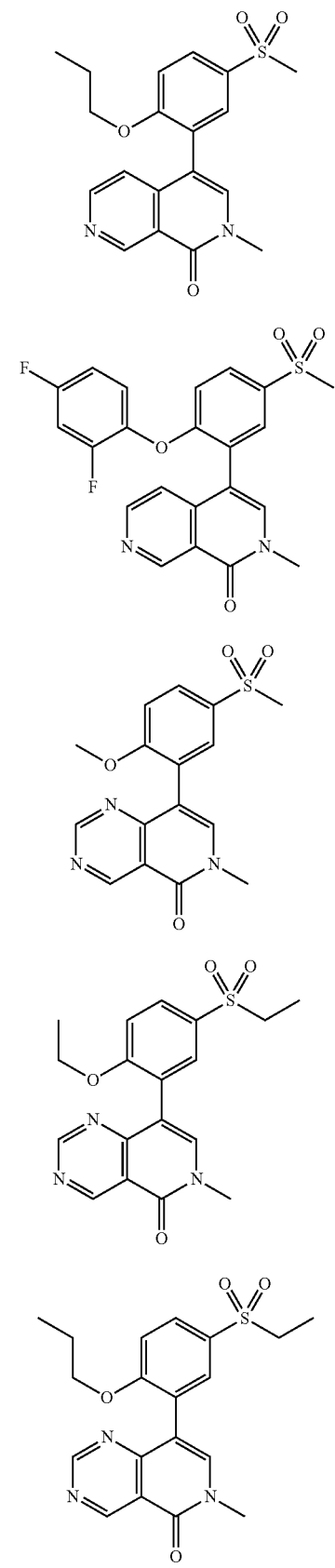
TABLE 2-continued
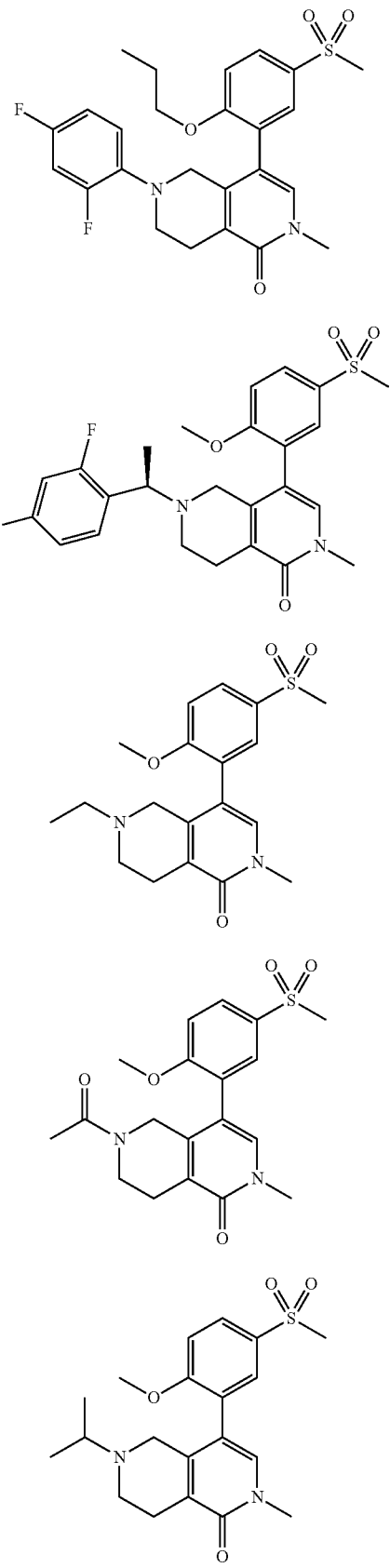

TABLE 2-continued
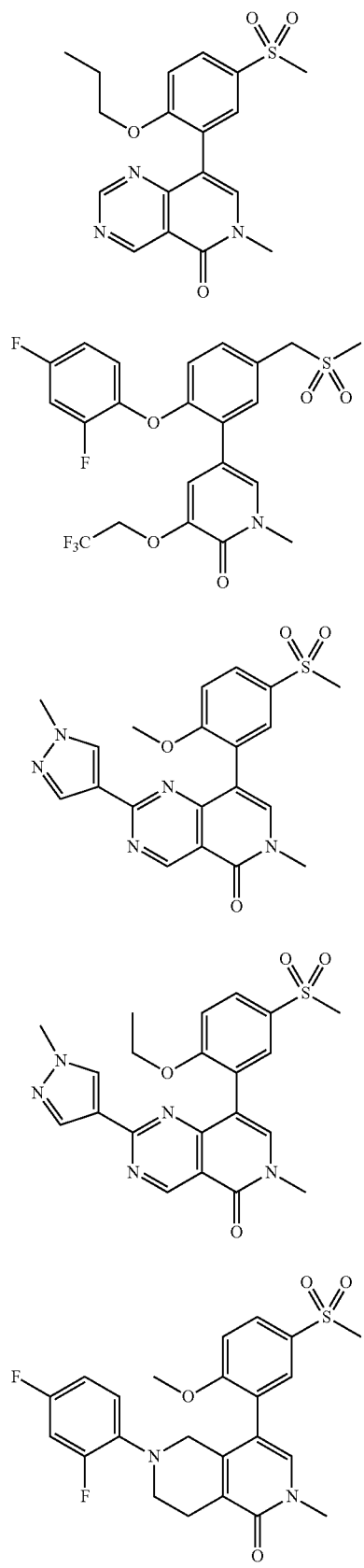
TABLE 2-continued
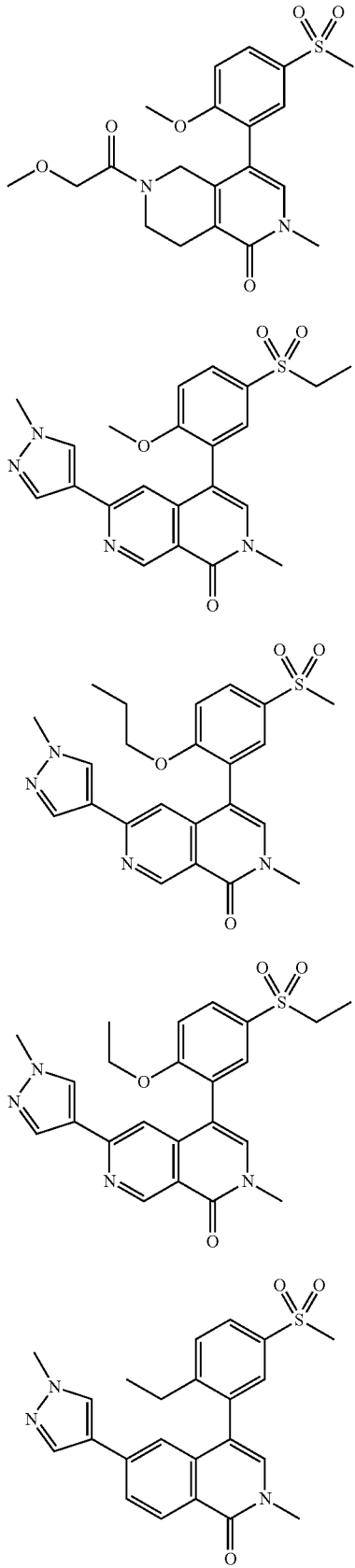

TABLE 2-continued
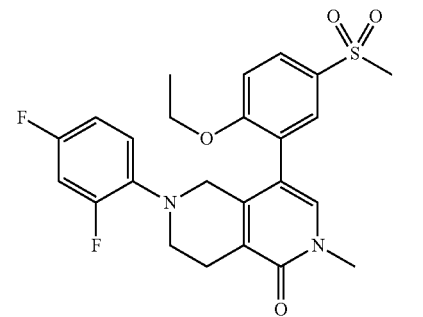 [SMILES: CCOc1ccc(S(C)(=O)=O)cc1-c1cn(C)c(=O)c2c1CN(c1ccc(F)cc1F)CC2]
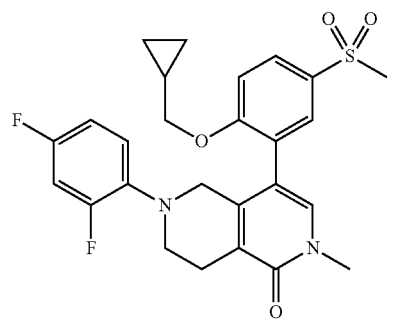 [SMILES: Cn1cc(-c2cc(S(C)(=O)=O)ccc2OCC2CC2)c2c(c1=O)CCN(c1ccc(F)cc1F)C2]
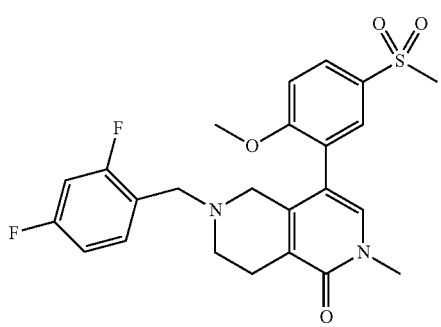 [SMILES: COc1ccc(S(C)(=O)=O)cc1-c1cn(C)c(=O)c2c1CN(Cc1ccc(F)cc1F)CC2]
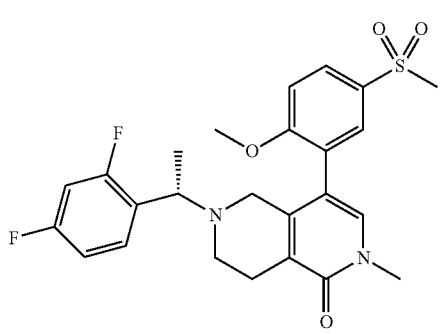 [SMILES: COc1ccc(S(C)(=O)=O)cc1-c1cn(C)c(=O)c2c1CN([C@@H](C)c1ccc(F)cc1F)CC2]
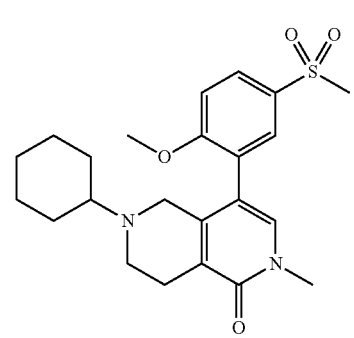 [SMILES: COc1ccc(S(C)(=O)=O)cc1-c1cn(C)c(=O)c2c1CN(C1CCCCC1)CC2]
TABLE 2-continued
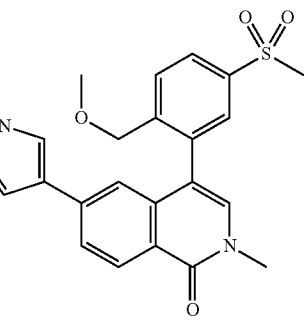
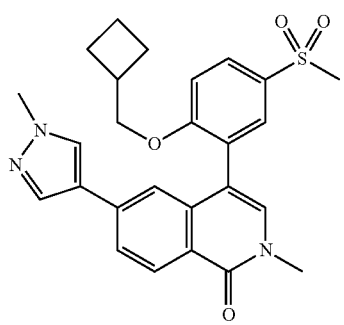 [SMILES: Cn1cc(-c2ccc3c(=O)n(C)cc(-c4cc(S(C)(=O)=O)ccc4OCC4CCC4)c3c2)cn1]
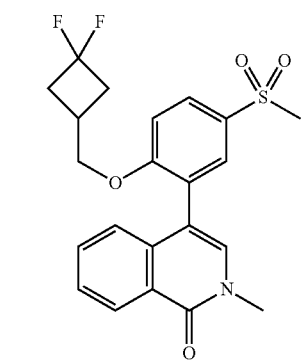 [SMILES: Cn1cc(-c2cc(S(C)(=O)=O)ccc2OCC2CC(F)(F)C2)c2ccccc2c1=O]
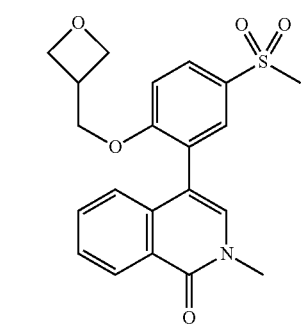 [SMILES: Cn1cc(-c2cc(S(C)(=O)=O)ccc2OCC2COC2)c2ccccc2c1=O]
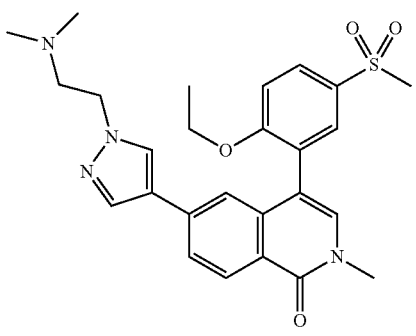

TABLE 2-continued
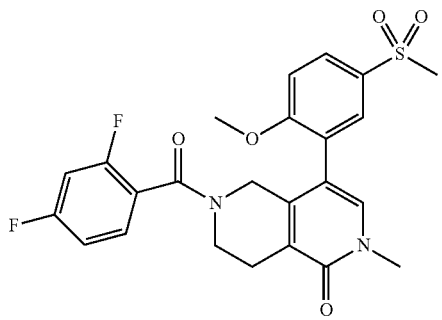 [SMILES: COc1ccc(S(C)(=O)=O)cc1-c1cn(C)c(=O)c2c1CN(C(=O)c1ccc(F)cc1F)CC2]
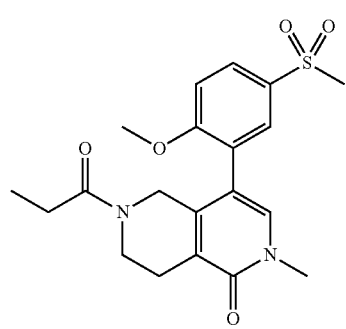 [SMILES: CCC(=O)N1CCc2c(c(-c3cc(S(C)(=O)=O)ccc3OC)cn(C)c2=O)C1]
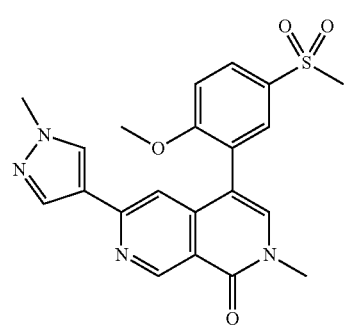 [SMILES: COc1ccc(S(C)(=O)=O)cc1-c1cn(C)c(=O)c2cnc(-c3cnn(C)c3)cc12]
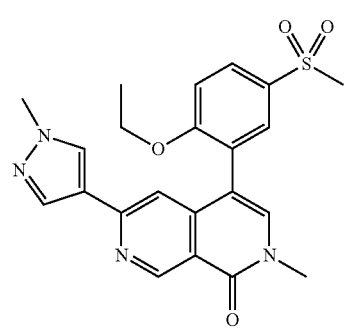 [SMILES: CCOc1ccc(S(C)(=O)=O)cc1-c1cn(C)c(=O)c2cnc(-c3cnn(C)c3)cc12]
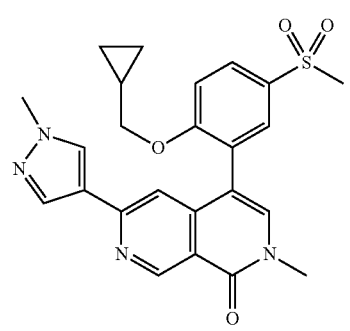 [SMILES: Cn1cc(-c2cc3c(-c4cc(S(C)(=O)=O)ccc4OCC4CC4)cn(C)c(=O)c3cn2)cn1]
TABLE 2-continued
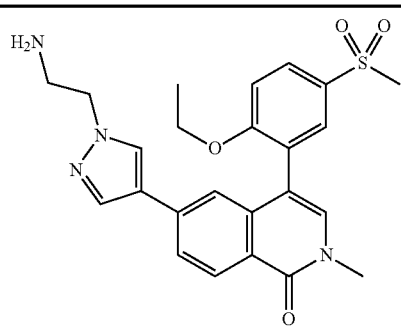
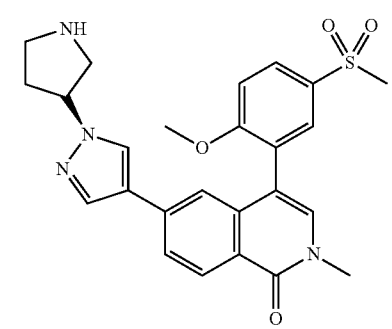
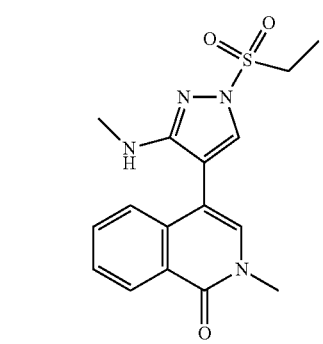 [SMILES: CCS(=O)(=O)n1cc(-c2cn(C)c(=O)c3ccccc23)c(NC)n1]
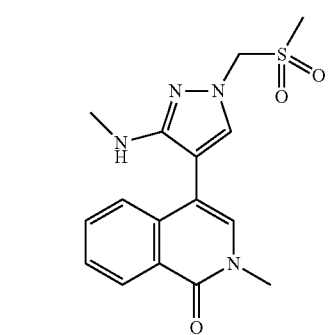 [SMILES: CNc1nn(CS(C)(=O)=O)cc1-c1cn(C)c(=O)c2ccccc12]
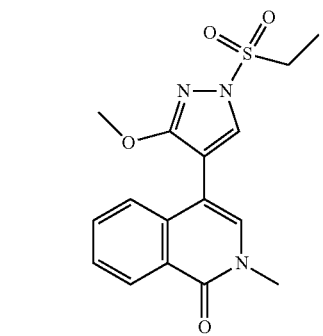 [SMILES: CCS(=O)(=O)n1cc(-c2cn(C)c(=O)c3ccccc23)c(OC)n1]

TABLE 2-continued
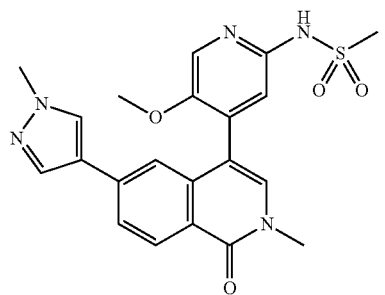 [SMILES: COc1cnc(NS(C)(=O)=O)cc1-c1cn(C)c(=O)c2ccc(-c3cnn(C)c3)cc12]
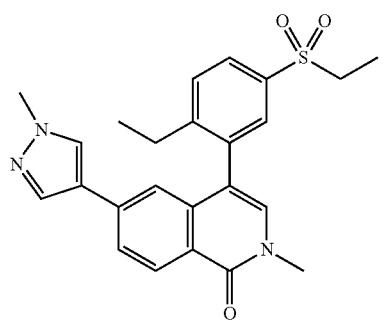 [SMILES: CCc1ccc(S(=O)(=O)CC)cc1-c1cn(C)c(=O)c2ccc(-c3cnn(C)c3)cc12]
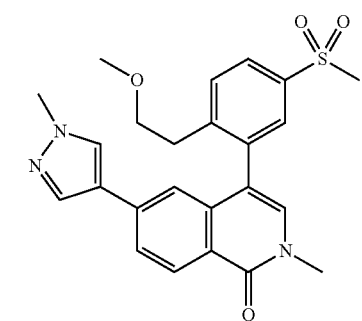 [SMILES: COCCc1ccc(S(C)(=O)=O)cc1-c1cn(C)c(=O)c2ccc(-c3cnn(C)c3)cc12]
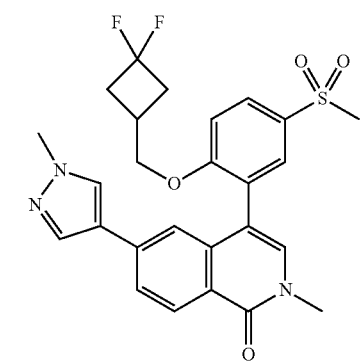 [SMILES: Cn1cc(-c2ccc3c(=O)n(C)cc(-c4cc(S(C)(=O)=O)ccc4OCC4CC(F)(F)C4)c3c2)cn1]
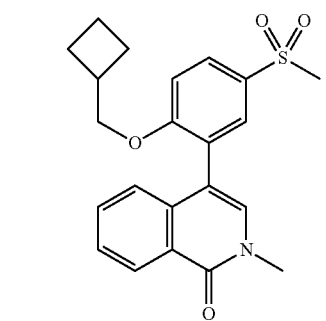 [SMILES: Cn1cc(-c2cc(S(C)(=O)=O)ccc2OCC2CCC2)c2ccccc2c1=O]
TABLE 2-continued
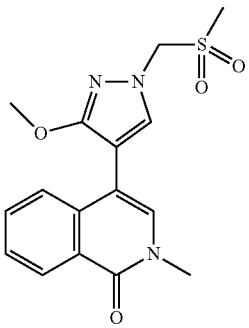 [SMILES: COc1nn(CS(C)(=O)=O)cc1-c1cn(C)c(=O)c2ccccc12]
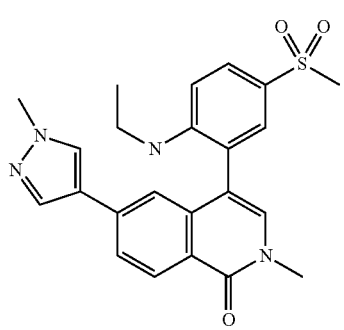 [SMILES: CCNc1ccc(S(C)(=O)=O)cc1-c1cn(C)c(=O)c2ccc(-c3cnn(C)c3)cc12]
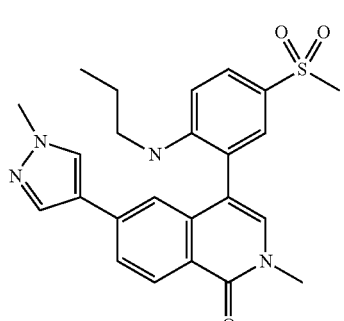
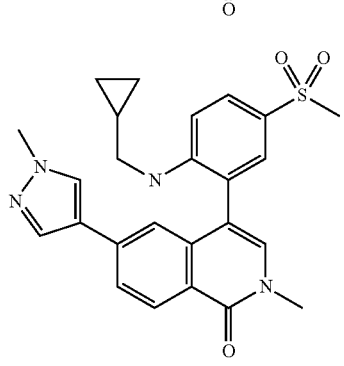
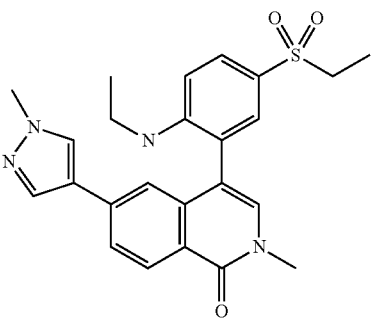 [SMILES: CCNc1ccc(S(=O)(=O)CC)cc1-c1cn(C)c(=O)c2ccc(-c3cnn(C)c3)cc12]

TABLE 2-continued
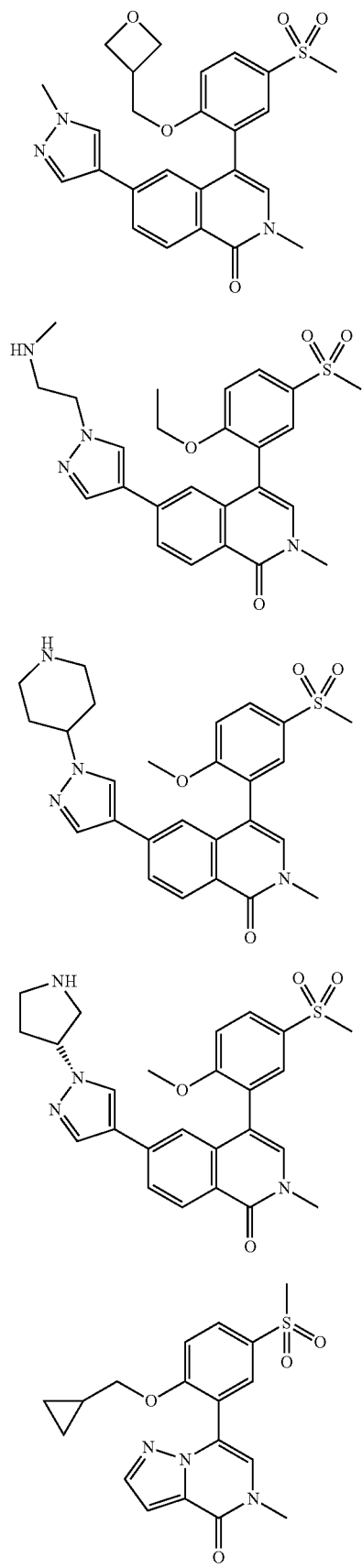
TABLE 2-continued
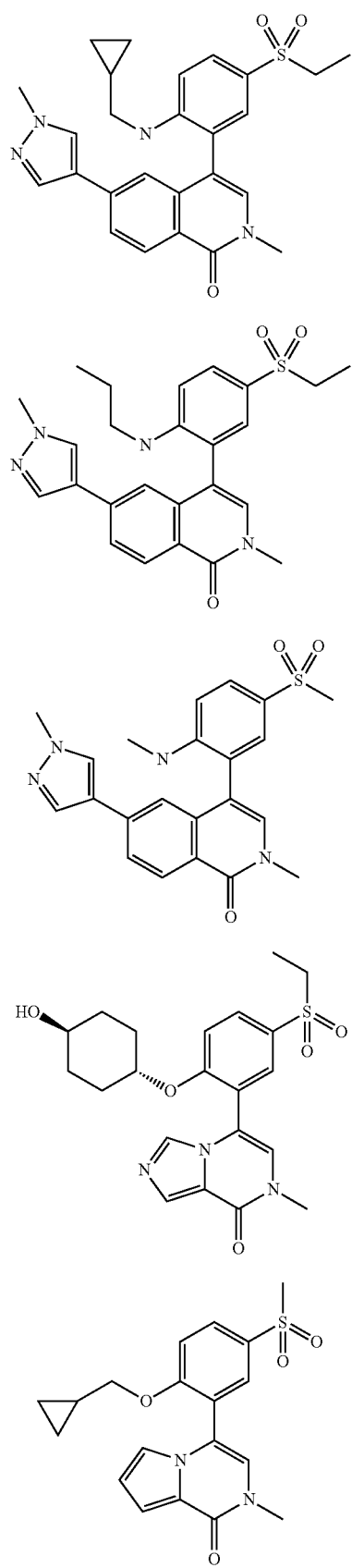

TABLE 2-continued
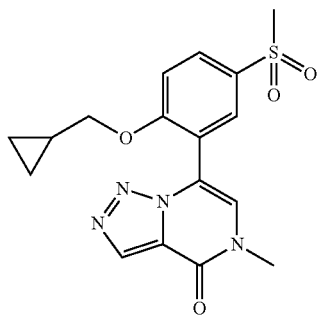
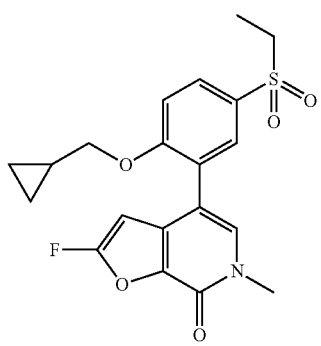 [SMILES: CCS(=O)(=O)c1ccc(OCC2CC2)c(-c2cn(C)c(=O)c3oc(F)cc23)c1]
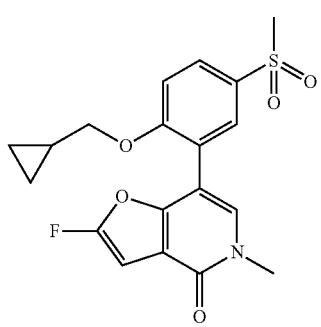 [SMILES: Cn1cc(-c2cc(S(C)(=O)=O)ccc2OCC2CC2)c2oc(F)cc2c1=O]
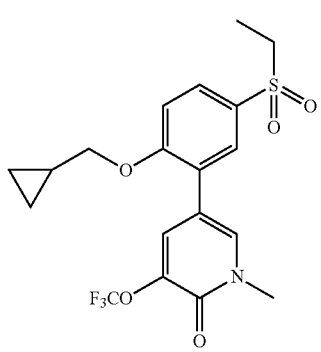 [SMILES: CCS(=O)(=O)c1ccc(OCC2CC2)c(-c2cc(OC(F)(F)F)c(=O)n(C)c2)c1]
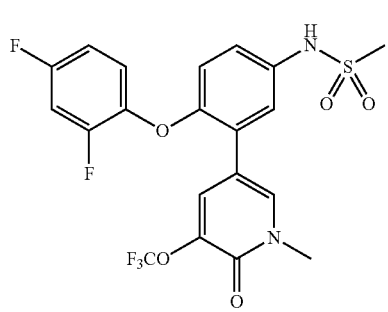 [SMILES: Cn1cc(-c2cc(NS(C)(=O)=O)ccc2Oc2ccc(F)cc2F)cc(OC(F)(F)F)c1=O]
TABLE 2-continued
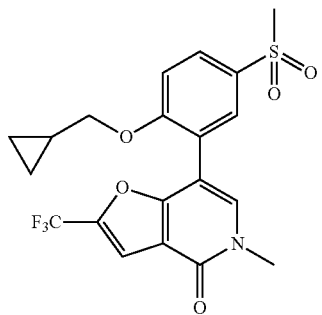 [SMILES: Cn1cc(-c2cc(S(C)(=O)=O)ccc2OCC2CC2)c2oc(C(F)(F)F)cc2c1=O]
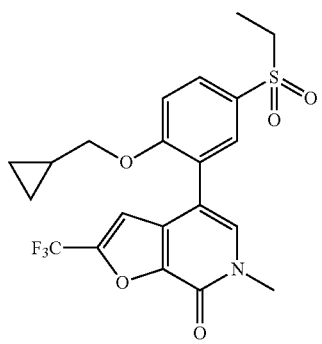 [SMILES: CCS(=O)(=O)c1ccc(OCC2CC2)c(-c2cn(C)c(=O)c3oc(C(F)(F)F)cc23)c1]
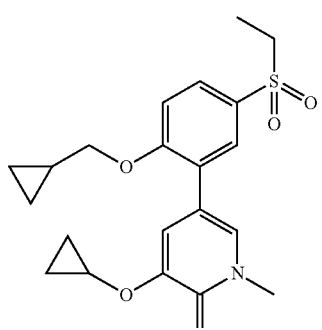
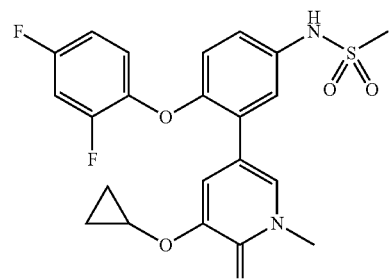
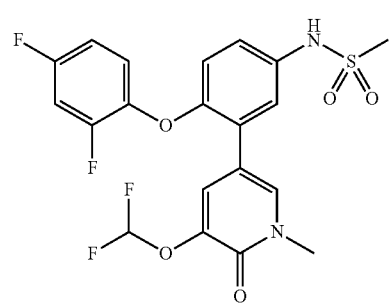 [SMILES: Cn1cc(-c2cc(NS(C)(=O)=O)ccc2Oc2ccc(F)cc2F)cc(OC(F)F)c1=O]

TABLE 2-continued
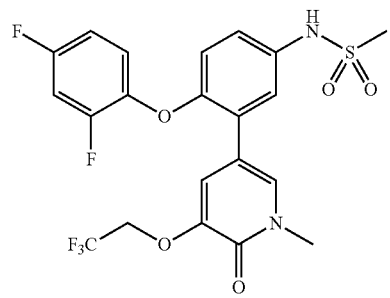 [SMILES: Cn1cc(-c2cc(NS(C)(=O)=O)ccc2Oc2ccc(F)cc2F)cc(OCC(F)(F)F)c1=O]
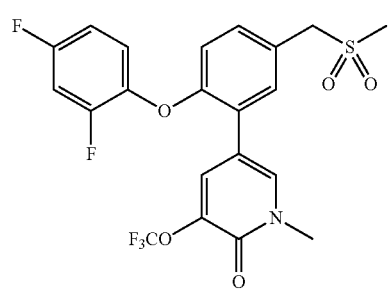 [SMILES: Cn1cc(-c2cc(CS(C)(=O)=O)ccc2Oc2ccc(F)cc2F)cc(OC(F)(F)F)c1=O]
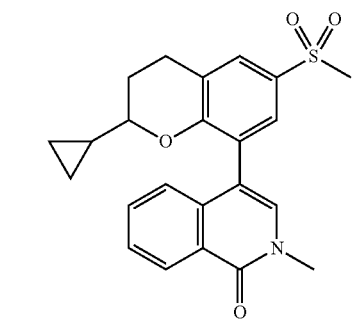 [SMILES: Cn1cc(-c2cc(S(C)(=O)=O)cc3c2OC(C2CC2)CC3)c2ccccc2c1=O]
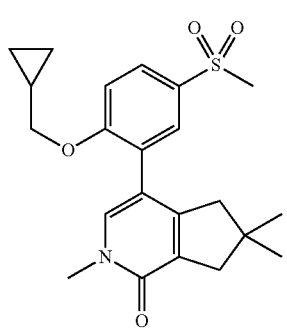 [SMILES: Cn1cc(-c2cc(S(C)(=O)=O)ccc2OCC2CC2)c2c(c1=O)CC(C)(C)C2]
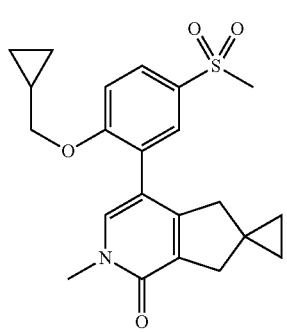 [SMILES: Cn1cc(-c2cc(S(C)(=O)=O)ccc2OCC2CC2)c2c(c1=O)CC1(CC1)C2]
TABLE 2-continued
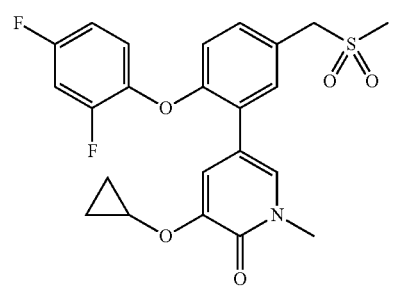 [SMILES: Cn1cc(-c2cc(CS(C)(=O)=O)ccc2Oc2ccc(F)cc2F)cc(OC2CC2)c1=O]
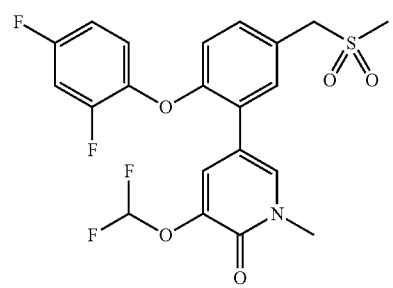 [SMILES: Cn1cc(-c2cc(CS(C)(=O)=O)ccc2Oc2ccc(F)cc2F)cc(OC(F)F)c1=O]
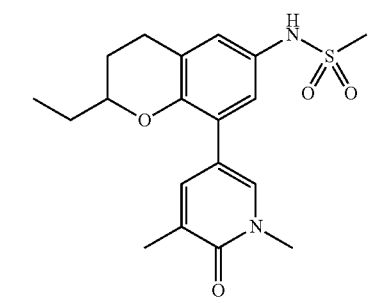 [SMILES: CCC1CCc2cc(NS(C)(=O)=O)cc(-c3cc(C)c(=O)n(C)c3)c2O1]
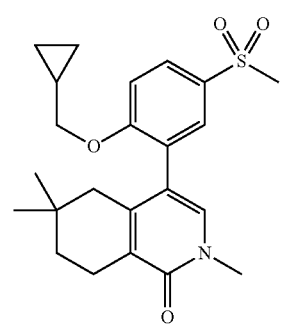
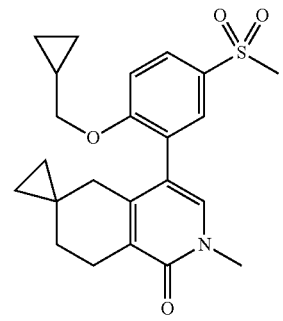 [SMILES: Cn1cc(-c2cc(S(C)(=O)=O)ccc2OCC2CC2)c2c(c1=O)CCC1(CC1)C2]

TABLE 2-continued
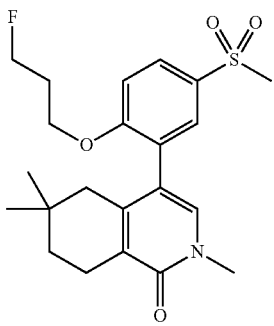
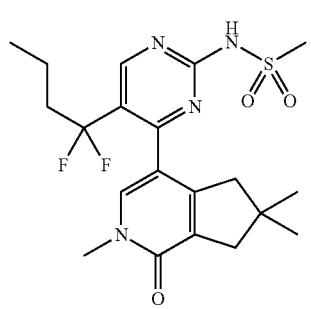 [SMILES: CCCC(F)(F)c1cnc(NS(C)(=O)=O)nc1-c1cn(C)c(=O)c2c1CC(C)(C)C2]
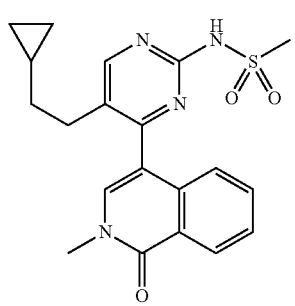 [SMILES: Cn1cc(-c2nc(NS(C)(=O)=O)ncc2CCC2CC2)c2ccccc2c1=O]
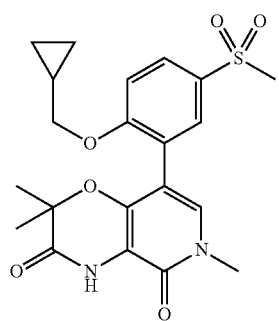
TABLE 2-continued
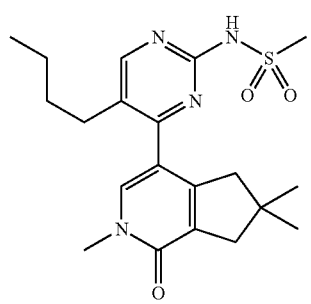 [SMILES: CCCCc1cnc(NS(C)(=O)=O)nc1-c1cn(C)c(=O)c2c1CC(C)(C)C2]
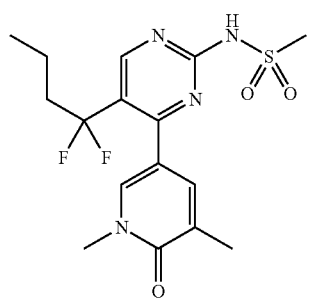 [SMILES: CCCC(F)(F)c1cnc(NS(C)(=O)=O)nc1-c1cc(C)c(=O)n(C)c1]
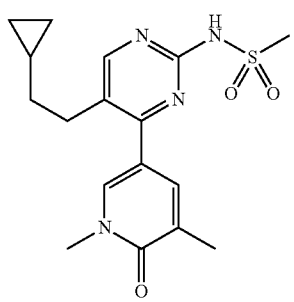 [SMILES: Cc1cc(-c2nc(NS(C)(=O)=O)ncc2CCC2CC2)cn(C)c1=O]
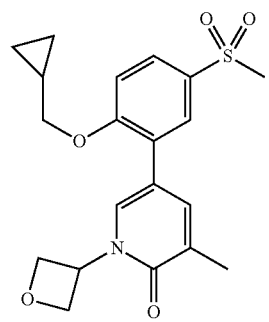 [SMILES: Cc1cc(-c2cc(S(C)(=O)=O)ccc2OCC2CC2)cn(C2COC2)c1=O]
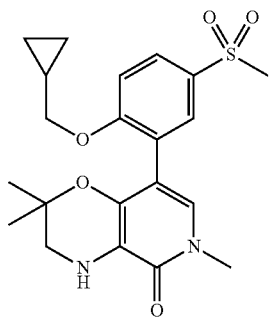

TABLE 2-continued
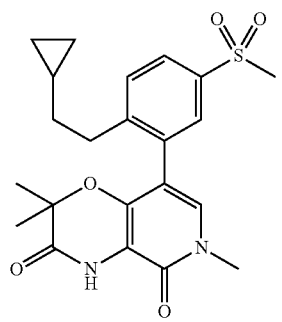
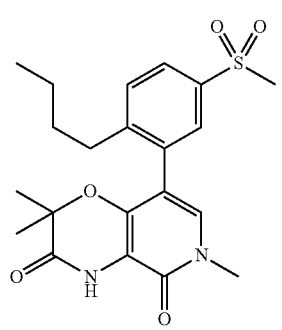
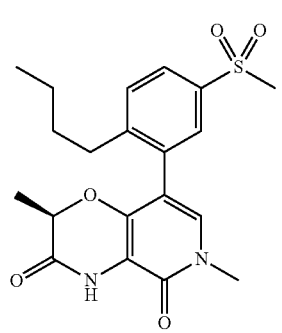
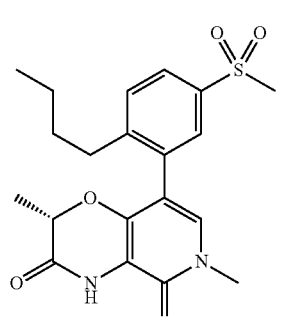
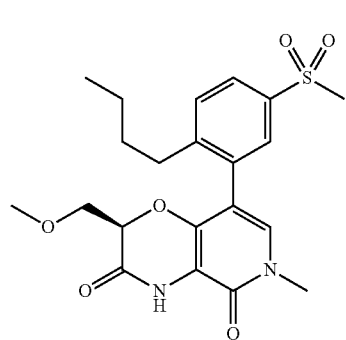
TABLE 2-continued
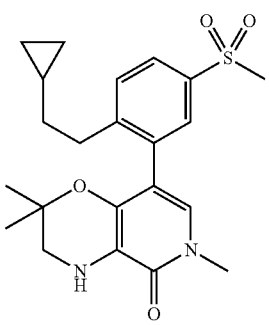
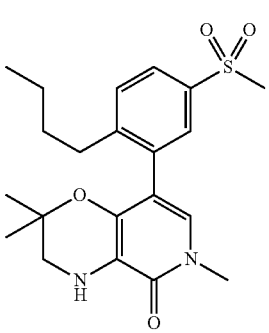
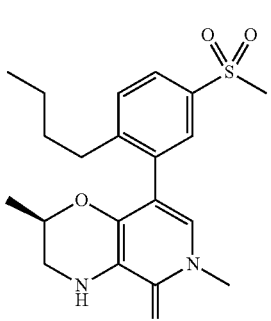
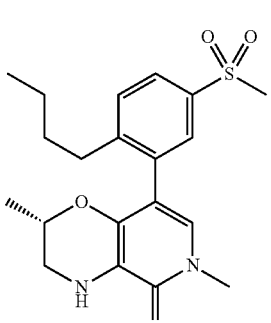
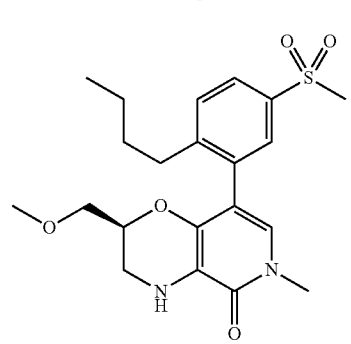

TABLE 2-continued
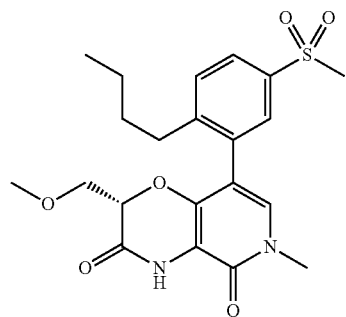
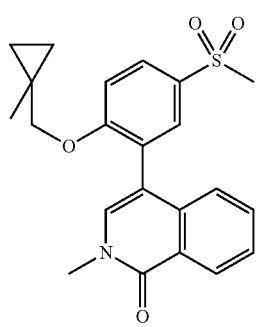 [SMILES: Cn1cc(-c2cc(S(C)(=O)=O)ccc2OCC2(C)CC2)c2ccccc2c1=O]
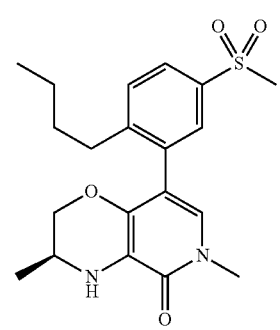 [SMILES: CCCCc1ccc(S(C)(=O)=O)cc1-c1cn(C)c(=O)c2c1OC[C@H](C)N2]
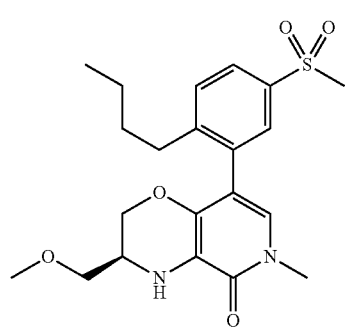
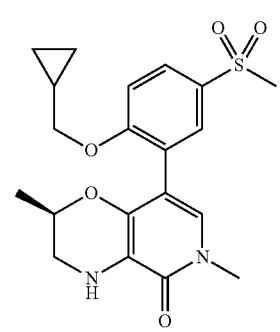
TABLE 2-continued
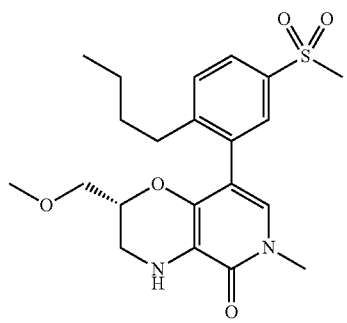
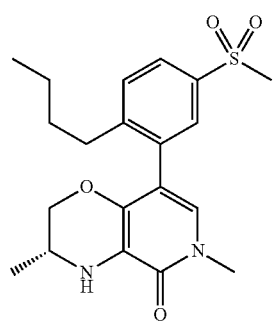 [SMILES: CCCCc1ccc(S(C)(=O)=O)cc1-c1cn(C)c(=O)c2c1OC[C@@H](C)N2]
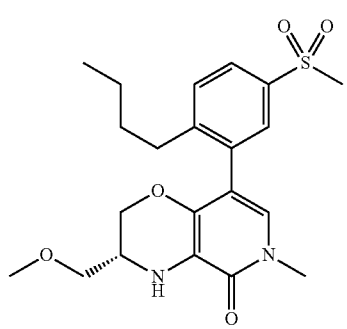
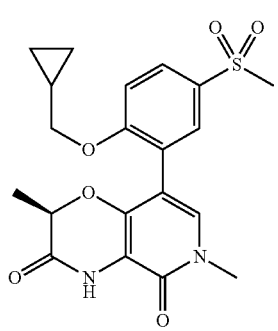
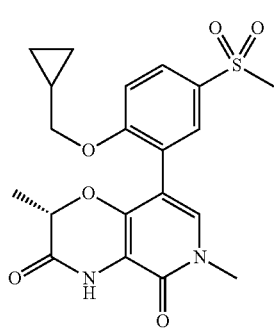

TABLE 2-continued
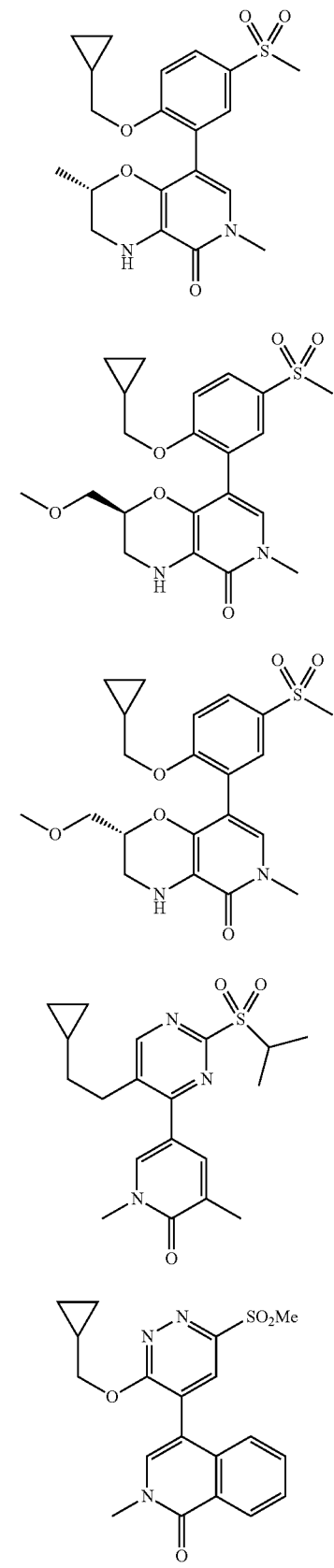
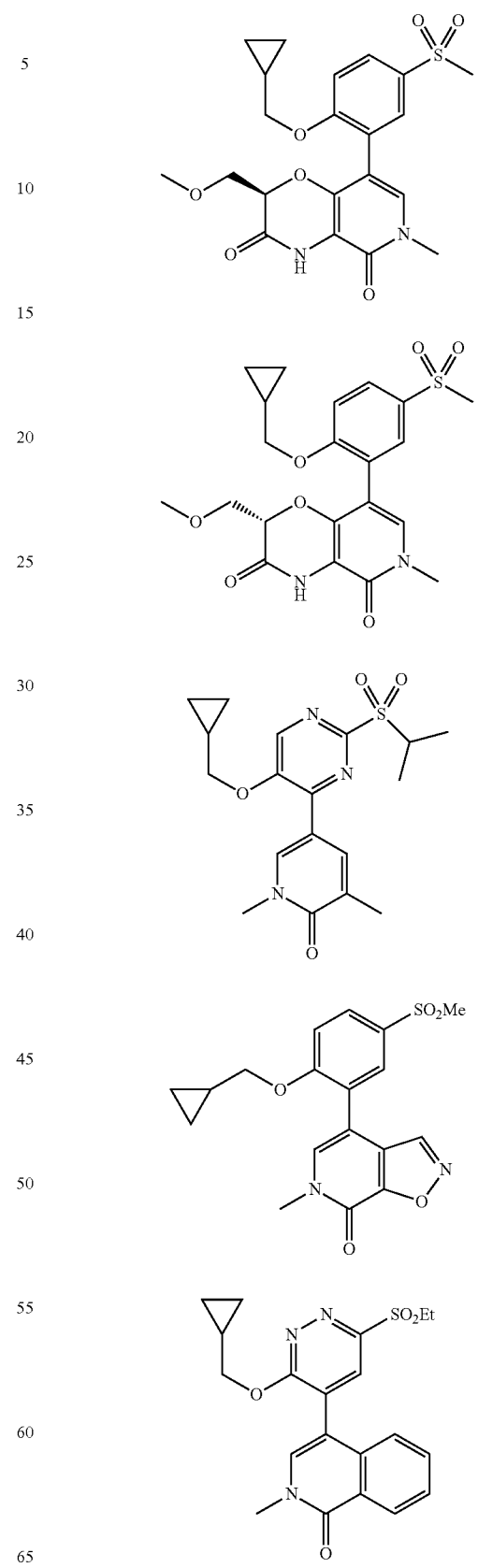

TABLE 2-continued
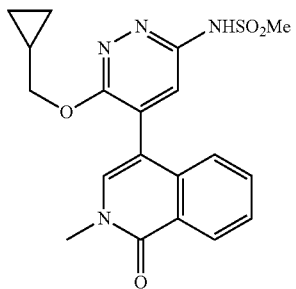
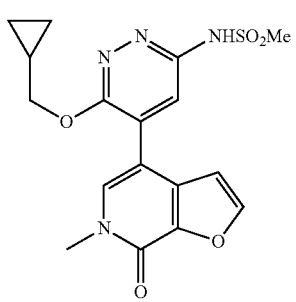
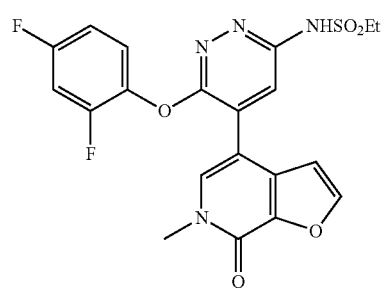
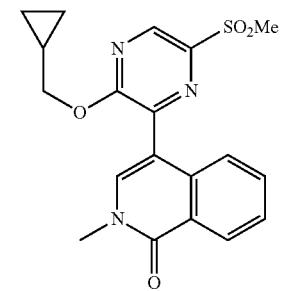 [SMILES: Cn1cc(-c2nc(S(C)(=O)=O)cnc2OCC2CC2)c2ccccc2c1=O]
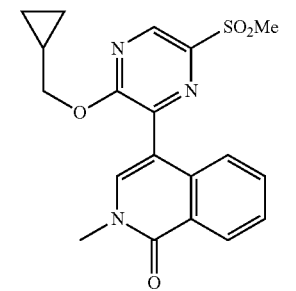
TABLE 2-continued
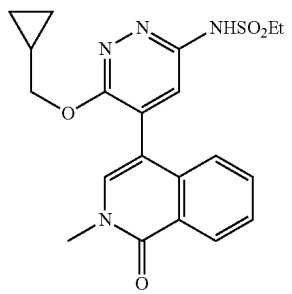
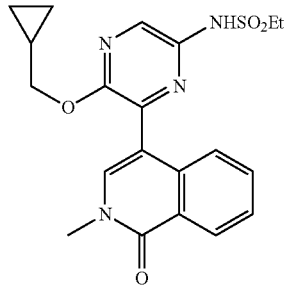
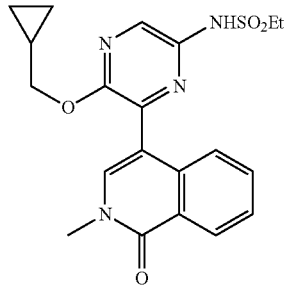
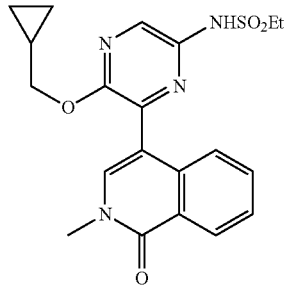
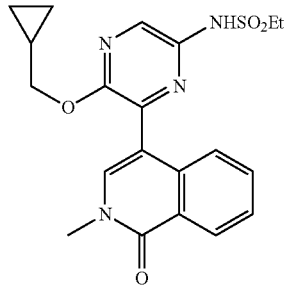

TABLE 2-continued
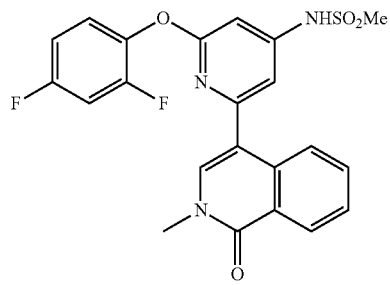
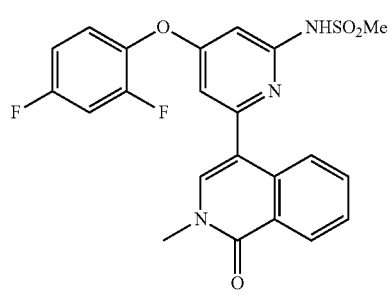
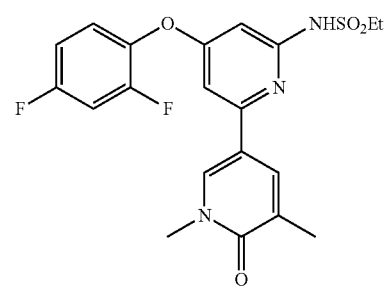
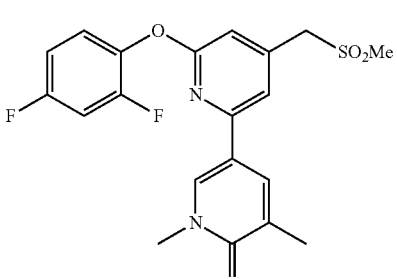
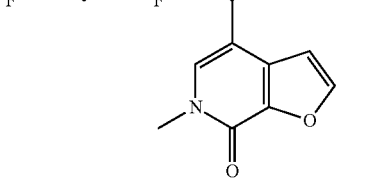
TABLE 2-continued
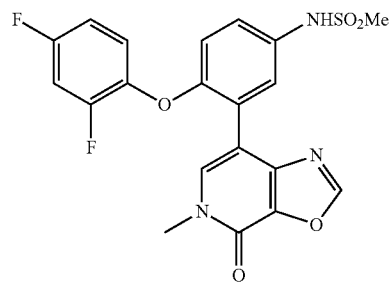
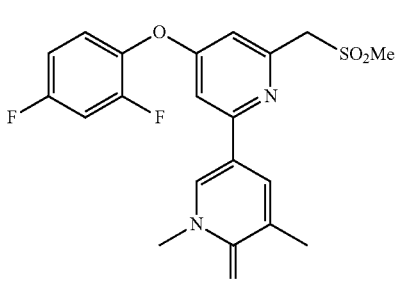
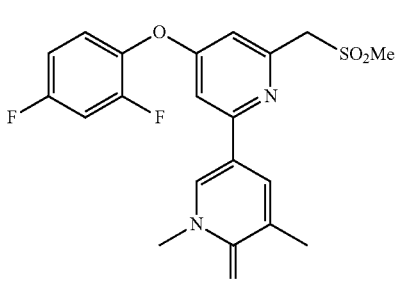
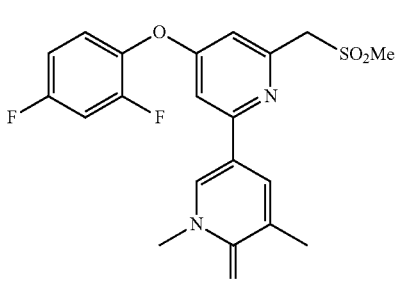
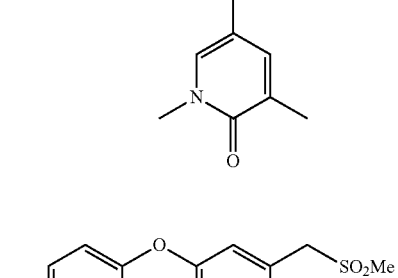

TABLE 2-continued
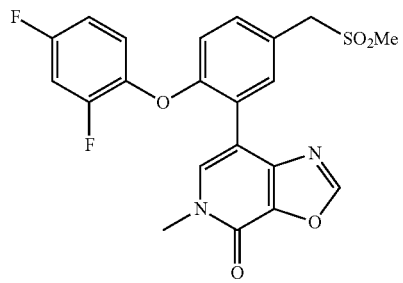 [SMILES: Cn1cc(-c2cc(CS(C)(=O)=O)ccc2Oc2ccc(F)cc2F)c2ncoc2c1=O]
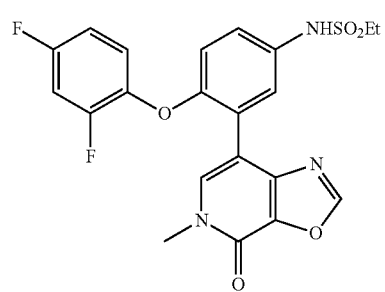
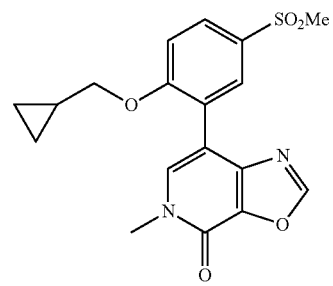
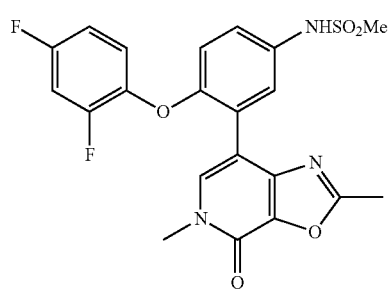
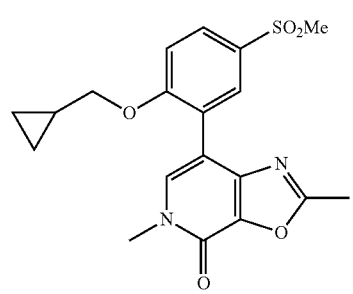 [SMILES: Cc1nc2c(-c3cc(S(C)(=O)=O)ccc3OCC3CC3)cn(C)c(=O)c2o1]
TABLE 2-continued
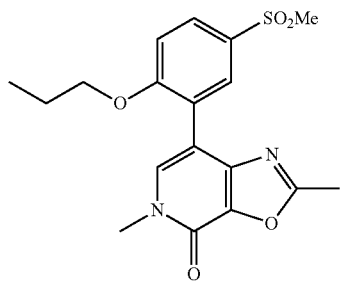 [SMILES: CCCOc1ccc(S(C)(=O)=O)cc1-c1cn(C)c(=O)c2oc(C)nc12]
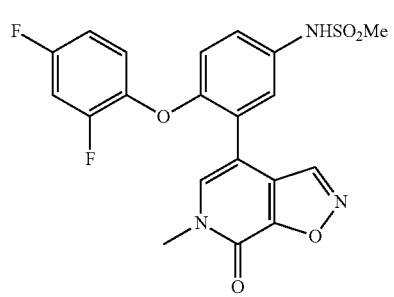
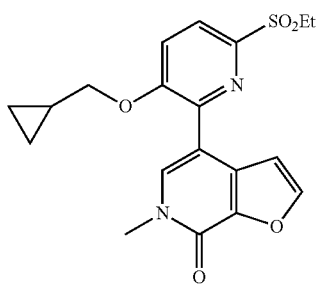
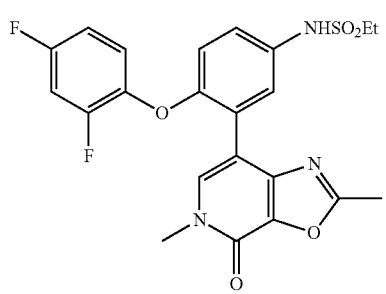
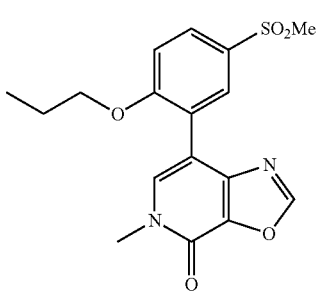 [SMILES: CCCOc1ccc(S(C)(=O)=O)cc1-c1cn(C)c(=O)c2ocnc12]

TABLE 2-continued
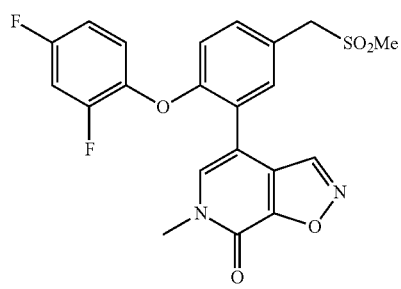 [SMILES: Cn1cc(-c2cc(CS(C)(=O)=O)ccc2Oc2ccc(F)cc2F)c2cnoc2c1=O]
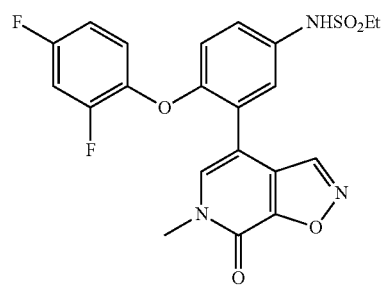
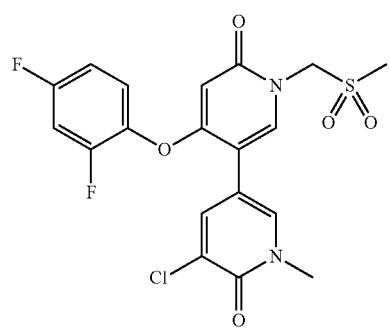 [SMILES: Cn1cc(-c2cn(CS(C)(=O)=O)c(=O)cc2Oc2ccc(F)cc2F)cc(Cl)c1=O]
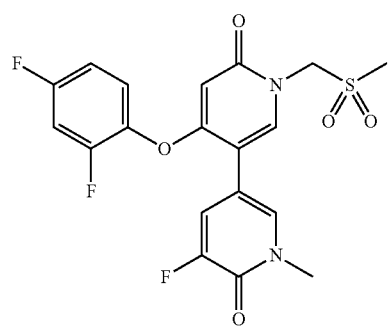
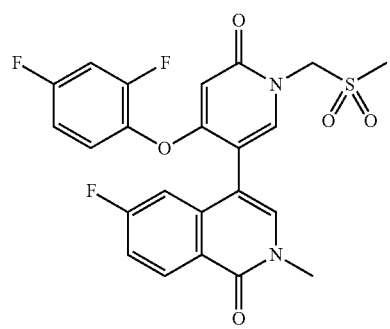 [SMILES: Cn1cc(-c2cn(CS(C)(=O)=O)c(=O)cc2Oc2ccc(F)cc2F)c2cc(F)ccc2c1=O]
TABLE 2-continued
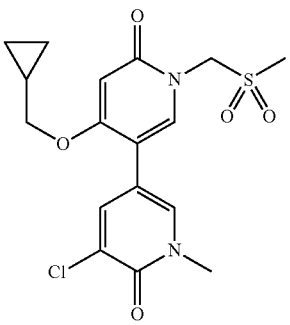 [SMILES: Cn1cc(-c2cn(CS(C)(=O)=O)c(=O)cc2OCC2CC2)cc(Cl)c1=O]
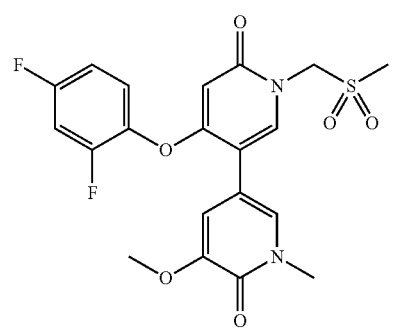 [SMILES: COc1cc(-c2cn(CS(C)(=O)=O)c(=O)cc2Oc2ccc(F)cc2F)cn(C)c1=O]
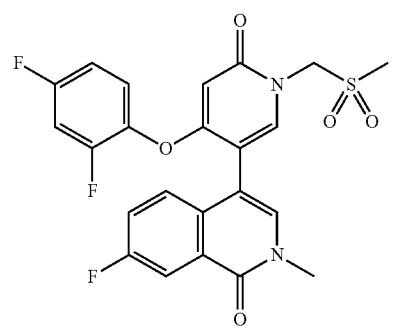 [SMILES: Cn1cc(-c2cn(CS(C)(=O)=O)c(=O)cc2Oc2ccc(F)cc2F)c2ccc(F)cc2c1=O]
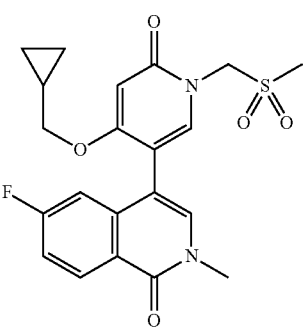 [SMILES: Cn1cc(-c2cn(CS(C)(=O)=O)c(=O)cc2OCC2CC2)c2cc(F)ccc2c1=O]
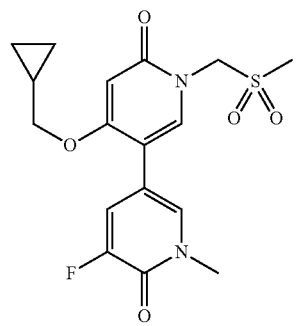 [SMILES: Cn1cc(-c2cn(CS(C)(=O)=O)c(=O)cc2OCC2CC2)cc(F)c1=O]

403
TABLE 2-continued
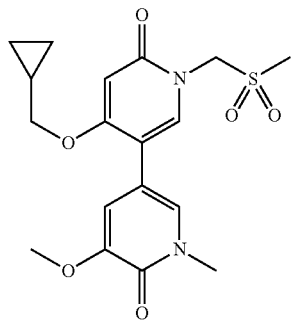 [SMILES: COc1cc(-c2cn(CS(C)(=O)=O)c(=O)cc2OCC2CC2)cn(C)c1=O]
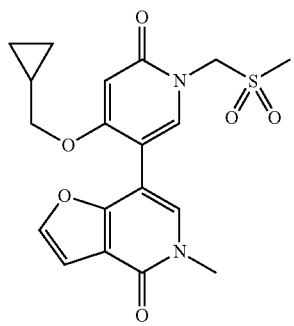 [SMILES: Cn1cc(-c2cn(CS(C)(=O)=O)c(=O)cc2OCC2CC2)c2occc2c1=O]
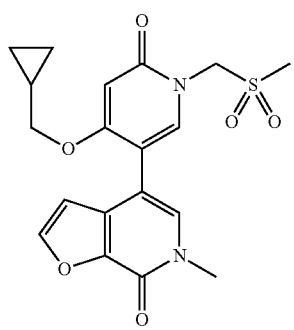 [SMILES: Cn1cc(-c2cn(CS(C)(=O)=O)c(=O)cc2OCC2CC2)c2ccoc2c1=O]
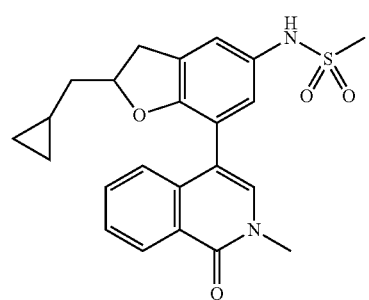 [SMILES: Cn1cc(-c2cc(NS(C)(=O)=O)cc3c2OC(CC2CC2)C3)c2ccccc2c1=O]
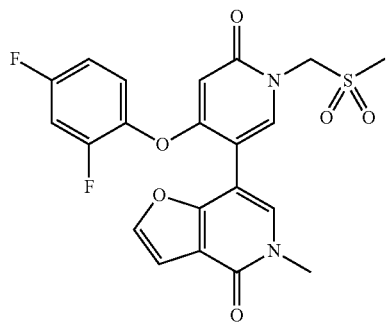 [SMILES: Cn1cc(-c2cn(CS(C)(=O)=O)c(=O)cc2Oc2ccc(F)cc2F)c2occc2c1=O]
404
TABLE 2-continued
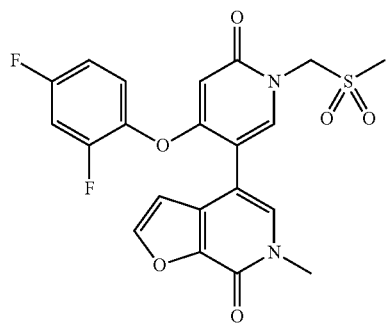 [SMILES: Cn1cc(-c2cn(CS(C)(=O)=O)c(=O)cc2Oc2ccc(F)cc2F)c2ccoc2c1=O]
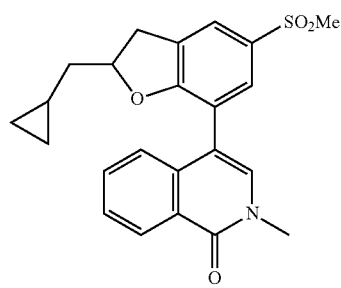 [SMILES: Cn1cc(-c2cc(S(C)(=O)=O)cc3c2OC(CC2CC2)C3)c2ccccc2c1=O]
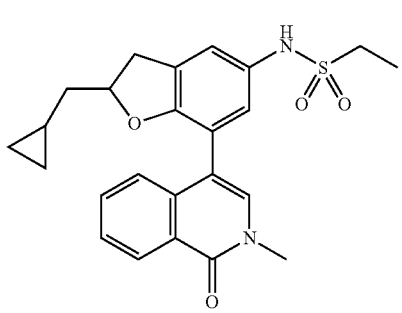 [SMILES: CCS(=O)(=O)Nc1cc2c(c(-c3cn(C)c(=O)c4ccccc34)c1)OC(CC1CC1)C2]
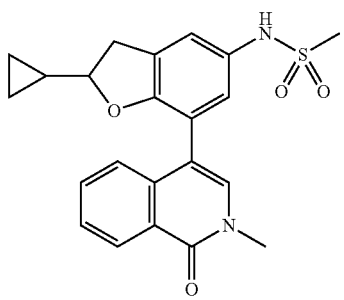 [SMILES: Cn1cc(-c2cc(NS(C)(=O)=O)cc3c2OC(C2CC2)C3)c2ccccc2c1=O]
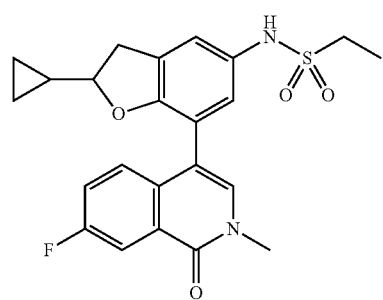 [SMILES: CCS(=O)(=O)Nc1cc2c(c(-c3cn(C)c(=O)c4cc(F)ccc34)c1)OC(C1CC1)C2]

TABLE 2-continued
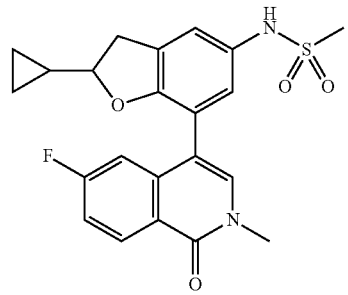 [SMILES: Cn1cc(-c2cc(NS(C)(=O)=O)cc3c2OC(C2CC2)C3)c2cc(F)ccc2c1=O]
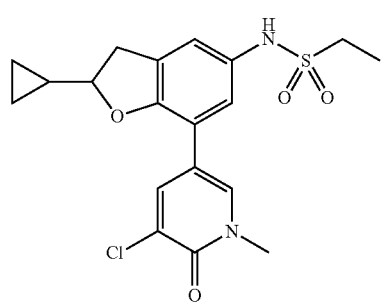 [SMILES: CCS(=O)(=O)Nc1cc2c(c(-c3cc(Cl)c(=O)n(C)c3)c1)OC(C1CC1)C2]
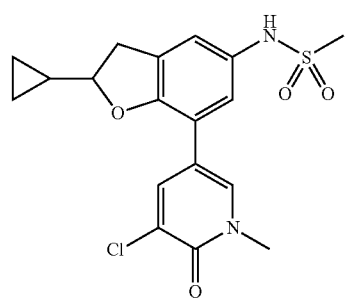 [SMILES: Cn1cc(-c2cc(NS(C)(=O)=O)cc3c2OC(C2CC2)C3)cc(Cl)c1=O]
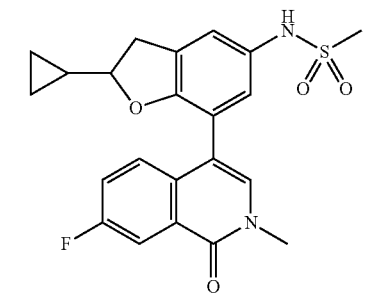 [SMILES: Cn1cc(-c2cc(NS(C)(=O)=O)cc3c2OC(C2CC2)C3)c2ccc(F)cc2c1=O]
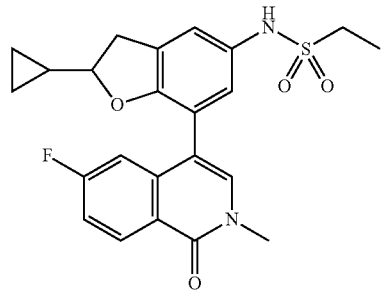 [SMILES: CCS(=O)(=O)Nc1cc2c(c(-c3cn(C)c(=O)c4ccc(F)cc34)c1)OC(C1CC1)C2]
TABLE 2-continued
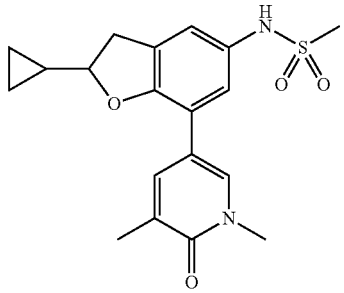
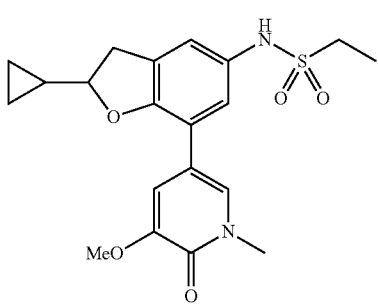 [SMILES: CCS(=O)(=O)Nc1cc2c(c(-c3cc(OC)c(=O)n(C)c3)c1)OC(C1CC1)C2]
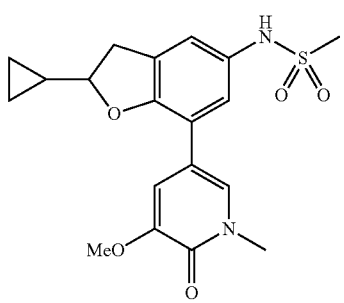 [SMILES: COc1cc(-c2cc(NS(C)(=O)=O)cc3c2OC(C2CC2)C3)cn(C)c1=O]
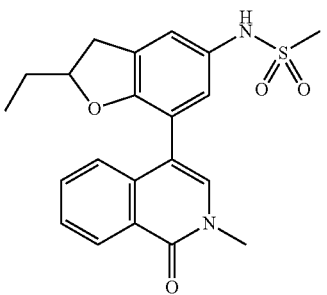 [SMILES: CCC1Cc2cc(NS(C)(=O)=O)cc(-c3cn(C)c(=O)c4ccccc34)c2O1]
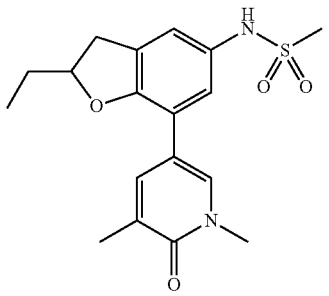 [SMILES: CCC1Cc2cc(NS(C)(=O)=O)cc(-c3cc(C)c(=O)n(C)c3)c2O1]

TABLE 2-continued

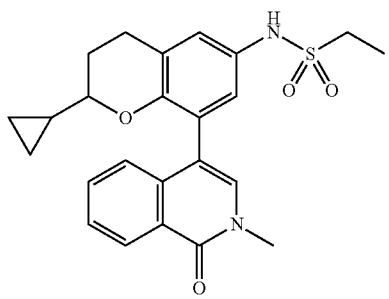 [SMILES: CCS(=O)(=O)Nc1cc2c(c(-c3cn(C)c(=O)c4ccccc34)c1)OC(C1CC1)CC2]

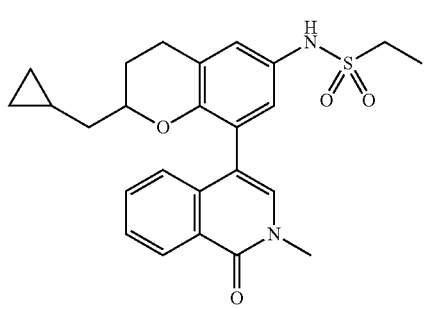 [SMILES: CCS(=O)(=O)Nc1cc2c(c(-c3cn(C)c(=O)c4ccccc34)c1)OC(CC1CC1)CC2]

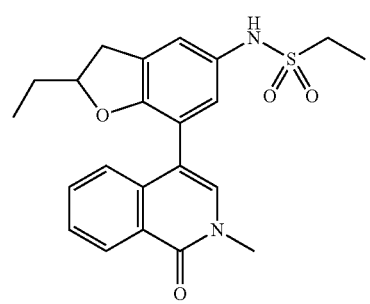 [SMILES: CCC1Cc2cc(NS(=O)(=O)CC)cc(-c3cn(C)c(=O)c4ccccc34)c2O1]

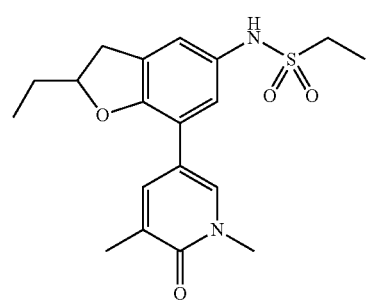 [SMILES: CCC1Cc2cc(NS(=O)(=O)CC)cc(-c3cc(C)c(=O)n(C)c3)c2O1]

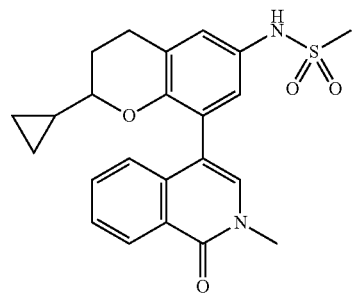 [SMILES: Cn1cc(-c2cc(NS(C)(=O)=O)cc3c2OC(C2CC2)CC3)c2ccccc2c1=O]

TABLE 2-continued

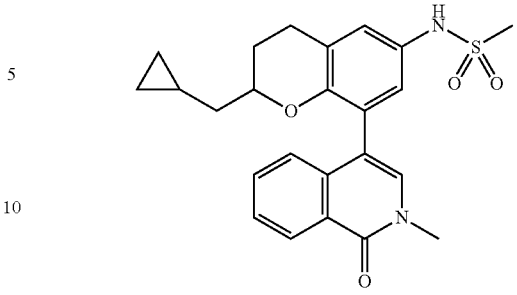

Preparation of the Substituted Heterocyclic Derivative Compounds

The compounds used in the reactions described herein are made according to organic synthesis techniques known to those skilled in this art, starting from commercially available chemicals and/or from compounds described in the chemical literature. "Commercially available chemicals" are obtained from standard commercial sources including Acros Organics (Pittsburgh, Pa.), Aldrich Chemical (Milwaukee, Wis., including Sigma Chemical and Fluka), Apin Chemicals Ltd. (Milton Park, UK), Avocado Research (Lancashire, U.K.), BDH Inc. (Toronto, Canada), Bionet (Cornwall, U.K.), Chemservice Inc. (West Chester, Pa.), Crescent Chemical Co. (Hauppauge, N.Y.), Eastman Organic Chemicals, Eastman Kodak Company (Rochester, N.Y.), Fisher Scientific Co. (Pittsburgh, Pa.), Fisons Chemicals (Leicestershire, UK), Frontier Scientific (Logan, Utah), ICN Biomedicals, Inc. (Costa Mesa, Calif.), Key Organics (Cornwall, U.K.), Lancaster Synthesis (Windham, N.H.), Maybridge Chemical Co. Ltd. (Cornwall, U.K.), Parish Chemical Co. (Orem, Utah), Pfaltz & Bauer, Inc. (Waterbury, Conn.), Polyorganix (Houston, Tex.), Pierce Chemical Co. (Rockford, Ill.), Riedel de Haen AG (Hanover, Germany), Spectrum Quality Product, Inc. (New Brunswick, N.J.), TCI America (Portland, Oreg.), Trans World Chemicals, Inc. (Rockville, Md.), and Wako Chemicals USA, Inc. (Richmond, Va.).

Methods known to one of ordinary skill in the art are identified through various reference books and databases. Suitable reference books and treatise that detail the synthesis of reactants useful in the preparation of compounds described herein, or provide references to articles that describe the preparation, include for example, "Synthetic Organic Chemistry", John Wiley & Sons, Inc., New York; S. R. Sandler et al., "Organic Functional Group Preparations," 2nd Ed., Academic Press, New York, 1983; H. O. House, "Modern Synthetic Reactions", 2nd Ed., W. A. Benjamin, Inc. Menlo Park, Calif. 1972; T. L. Gilchrist, "Heterocyclic Chemistry", 2nd Ed., John Wiley & Sons, New York, 1992; J. March, "Advanced Organic Chemistry: Reactions, Mechanisms and Structure", 4th Ed., Wiley-Interscience, New York, 1992. Additional suitable reference books and treatise that detail the synthesis of reactants useful in the preparation of compounds described herein, or provide references to articles that describe the preparation, include for example, Fuhrhop, J. and Penzlin G. "Organic Synthesis: Concepts, Methods, Starting Materials", Second, Revised and Enlarged Edition (1994) John Wiley & Sons ISBN: 3-527-29074-5; Hoffman, R. V. "Organic Chemistry, An Intermediate Text" (1996) Oxford University Press, ISBN 0-19-509618-5; Larock, R. C. "Comprehensive Organic Transformations: A Guide to Functional Group Preparations" 2nd Edition (1999) Wiley-VCH, ISBN: 0-471-19031-

4; March, J. "Advanced Organic Chemistry: Reactions, Mechanisms, and Structure" 4th Edition (1992) John Wiley & Sons, ISBN: 0-471-60180-2; Otera, J. (editor) "Modern Carbonyl Chemistry" (2000) Wiley-VCH, ISBN: 3-527-29871-1; Patai, S. "Patai's 1992 Guide to the Chemistry of Functional Groups" (1992) Interscience ISBN: 0-471-93022-9; Solomons, T. W. G. "Organic Chemistry" 7th Edition (2000) John Wiley & Sons, ISBN: 0-471-19095-0; Stowell, J. C., "Intermediate Organic Chemistry" 2nd Edition (1993) Wiley-Interscience, ISBN: 0-471-57456-2; "Industrial Organic Chemicals: Starting Materials and Intermediates: An Ullmann's Encyclopedia" (1999) John Wiley & Sons, ISBN: 3-527-29645-X, in 8 volumes; "Organic Reactions" (1942-2000) John Wiley & Sons, in over 55 volumes; and "Chemistry of Functional Groups" John Wiley & Sons, in 73 volumes.

Specific and analogous reactants may also be identified through the indices of known chemicals prepared by the Chemical Abstract Service of the American Chemical Society, which are available in most public and university libraries, as well as through on-line databases (the American Chemical Society, Washington, D.C., may be contacted for more details). Chemicals that are known but not commercially available in catalogs may be prepared by custom chemical synthesis houses, where many of the standard chemical supply houses (e.g., those listed above) provide custom synthesis services. A reference for the preparation and selection of pharmaceutical salts of the substituted heterocyclic derivative compounds described herein is P. H. Stahl & C. G. Wermuth "Handbook of Pharmaceutical Salts", Verlag Helvetica Chimica Acta, Zurich, 2002.

General methods for the synthesis of substituted heterocyclic derivatives are provided in, but not limited to, the following references: WO 2009/158396; WO 2005/63768; WO 2006/112666; Briet et. al., Tetrahedron (2002), 58(29), 5761-5766; WO 2008/77550; WO 2008/77551; WO 2008/77556; WO 2007/12421; WO 2007/12422; US 2007/99911; WO 2008/77550; Havera et al., J. Med. Chem. (1999), 42, 3860-3873; WO 2004/29051; and US 2009/0054434. Additional examples of the synthesis of substituted heterocyclic derivatives are found in the following references: WO 2012/171337; WO 2011/044157; WO 2009/097567; WO 2005/030791; EP 203216; Becknell et al., Bioorganic & Medicinal Chemistry Letters (2011), 21(23), 7076-7080; Svechkarev et al., Visnik Kharkivs'kogo Natsional'nogo Universitetu im. V. N. Karazina (2007), 770, 201-207; Coskun et al., Synthetic Communications (2005), 35(18), 2435-2443; Alvarez et al., Science of Synthesis (2005), 15, 839-906; Kihara et al., Heterocycles (2000), 53(2), 359-372; Couture et al., Journal of the Chemical Society, Perkin Transactions 1: Organic and Bio-Organic Chemistry (1999), (7), 789-794; Kihara et al., Heterocycles (1998), 48(12), 2473-2476; Couture et al., Tetrahedron (1996), 52(12), 4433-48; Couturre et al., Tetrahedron Letters (1996), 37(21), 3697-3700; Natsugari et al., Journal of Medicinal Chemistry (1995), 38(16), 3106-20; Moehrle et al., Archiv der Pharmazie (Weinheim, Germany) (1988), 321(10), 759-64; Gore et al., Journal of the Chemical Society, Perkin Transactions 1: Organic and Bio-Organic Chemistry (1972-1999) (1988), (3), 481-3; Narasimhan et al., Journal of the Chemical Society, Chemical Communications (1987), (3), 191-2; Henry et al., Journal of Organic Chemistry (1975), 40(12), 1760-6; Berti, Gazzetta Chimica Italiana (1960), 90, 559-72; Berti et al., Annali di Chimica (Rome, Italy) (1959), 49, 2110-23; Berti et al., Annali di Chimica (Rome, Italy) (1959), 49, 1253-68; WO 2012/000595; Couture et al., Tetrahedron (1996), 52(12), 4433-48; WO 2010/069504; WO 2010/069504; WO 2006/030032; WO 2005/095384; US 2005/0222159; WO 2013/064984; Mishra et al., European Journal of Organic Chemistry (2013), 2013(4), 693-700; Vachhani et al., Tetrahedron (2013), 69(1), 359-365; Xie et al., European Journal of Medicinal Chemistry (2010), 45(1), 210-218; Mukaiyama et al., Bioorganic & Medicinal Chemistry (2007), 15(2), 868-885; JP 2005/089352; Wang et al., Molecules (2004), 9(7), 574-582; WO 2000/023487; US 2006/0287341; CN 103183675; Hares et al., Egyptian Journal of Pharmaceutical Sciences (1991), 32(1-2), 303-14; DE 2356005; DE 2133898; DE 2133998; U.S. Pat. No. 3,816, 422; DE 2011970; and Staehle et al., Justus Liebigs Annalen der Chemie (1973), (8), 1275-81.

In some embodiments, the substituted heterocyclic derivative compounds disclosed herein are prepared by the general synthetic routes described below in Schemes 1-6. These schemes are intended to exemplary to one of skill in the art and are not limiting. Additional methods for the synthesis of the substituted heterocyclic derivative compounds disclosed herein are readily available to one of skill in the art.

Scheme 1

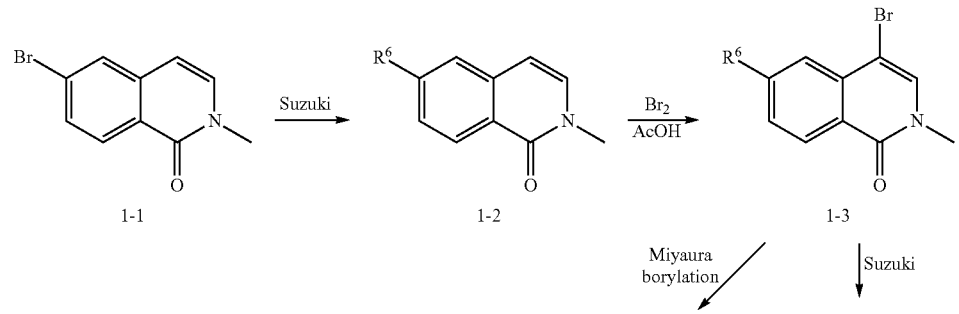

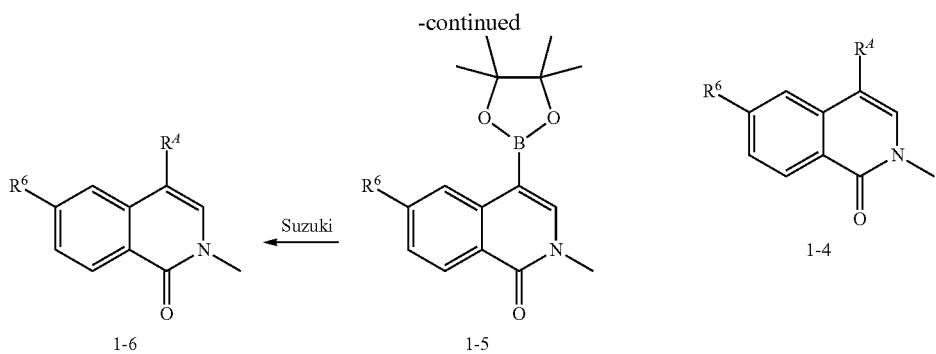

A method for preparing compounds of Formula (I) is provided in Scheme 1. 6-Bromo-2-methylisoquinolin-1(2H)-one (1-1) is subjected to a palladium-catalyzed cross coupling reaction to provide isoquinolinone 1-2. Bromination under acidic conditions provides compound 1-3. Further palladium-catalyzed cross coupling reaction with a boronic acid, or ester, provides the isoquinolinone 1-4. Alternatively, palladium-catalyzed cross coupling of compound 1-3 with 4,4,5,5-tetramethyl-2-(tetramethyl-1,3,2-dioxaborolan-2-yl)-1,3,2-dioxaborolane under the conditions described by Miyaura (Ishiyama et al., J. Org. Chem. 1995, 60, 7508-7510) provides the boron ester 1-5. Further palladium-catalyzed cross coupling reaction of compound 1-5 with a suitable halide provides the isoquinolinone 1-6.

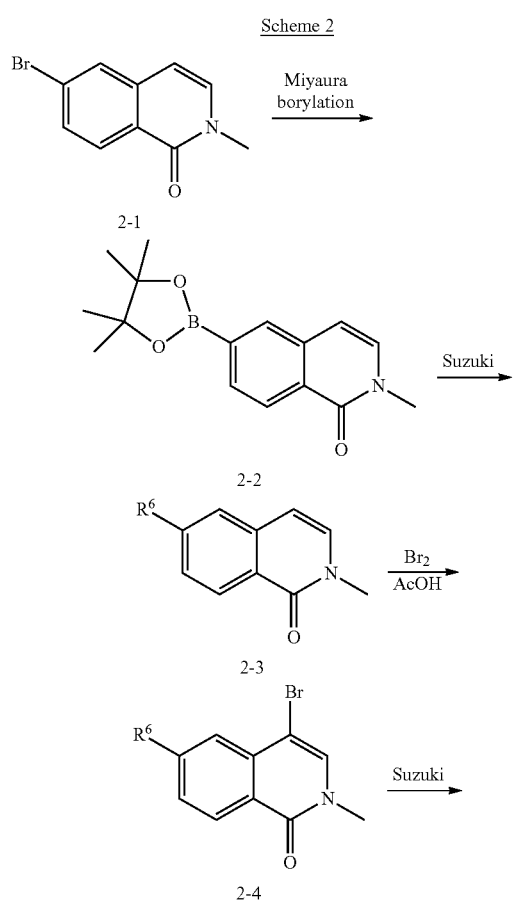

A method for preparing compounds of Formula (I) is provided in Scheme 2. 6-Bromo-2-methylisoquinolin-1(2H)-one (2-1) is subjected to a palladium-catalyzed cross coupling reaction with 4,4,5,5-tetramethyl-2-(tetramethyl-1,3,2-dioxaborolan-2-yl)-1,3,2-dioxaborolane to provide boron ester 2-2. Further palladium-catalyzed cross coupling reaction of compound 2-2 with a suitable halide provides compound 2-3. Bromination under acidic conditions provides compound 2-4. Further palladium-catalyzed cross coupling reaction with a boronic acid, or ester, provides the isoquinolinone 2-5.

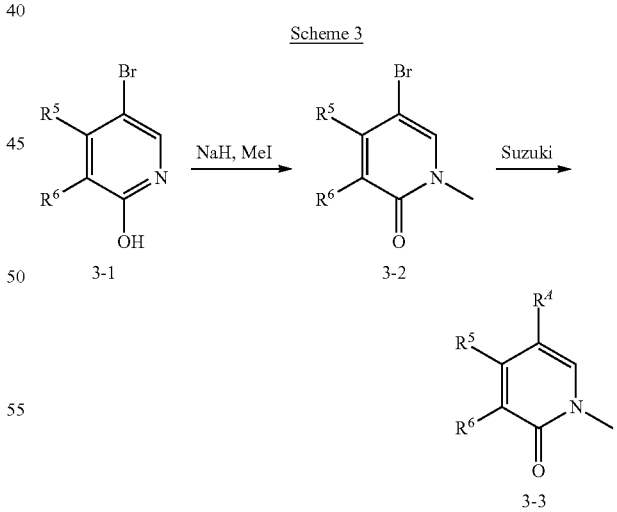

A method for preparing compounds of Formula (II) is provided in Scheme 3. 5-Bromopyridin-2-ol derivative (3-1) is subjected to alkylation with methyl iodide under basic conditions to provide the related 5-bromo-1-methylpyridin-2(1H)-one derivative (3-2). Further palladium-catalyzed cross coupling reaction of compound 3-2 with a suitable halide provides compound 3-3.

Scheme 4

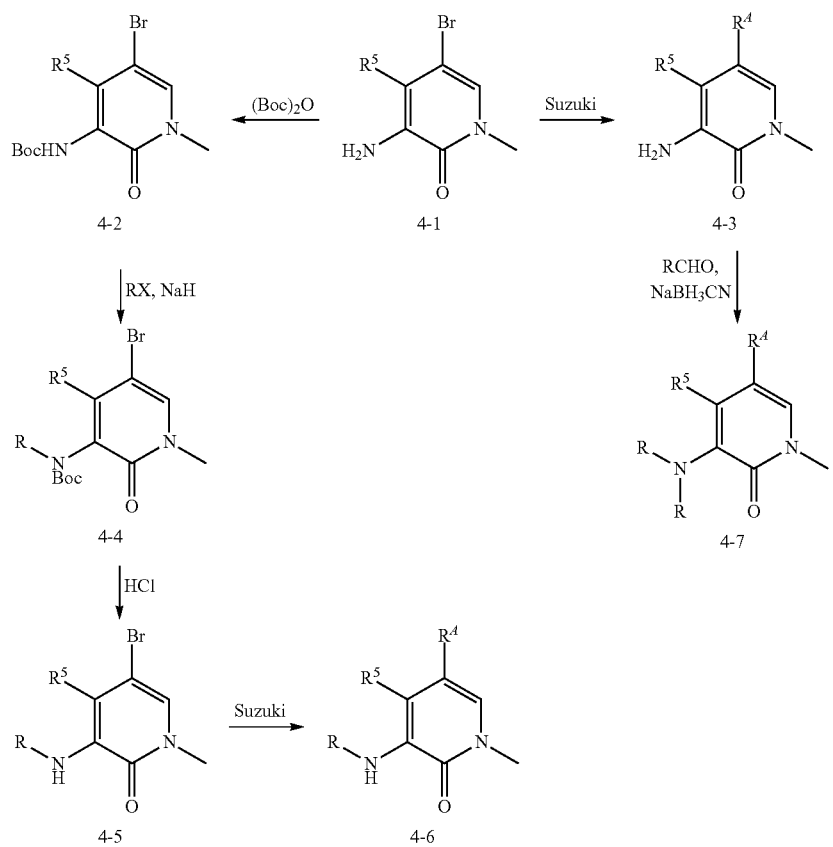

A method for preparing compounds of Formula (II) is provided in Scheme 4. 3-Amino-5-bromo-1-methylpyridin-2(1H)-one derivative 4-1 is used as a starting material for several routes. In one route, compound 4-1 is directly subjected to a palladium-catalyzed cross coupling reaction to provide pyridone 4-3. The amino group of compound 4-3 is subjected to a reductive amination with an aldehyde and a reducing agent, such as sodium cyanoborohydride, to provide the substituted amino derivative compound 4-7. A second route involving selective alkylation of the amino group of compound 4-1 begins with protection of the amino group as the BOC carbamate. Alkylation of the carbamate under basic conditions followed by removal of the BOC carbamate under acidic conditions provides the secondary amine compound 4-5. Treatment of 4-5 with a suitable halide under palladium-catalyzed cross coupling conditions affords compound 4-6.

Scheme 5

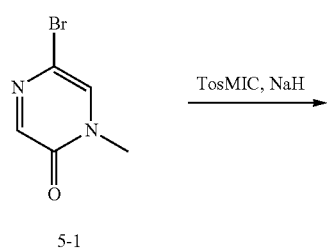

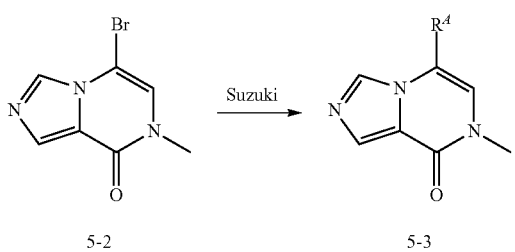

A method for preparing compounds of Formula (IV) is provided in Scheme 5. 5-Bromo-1-methylpyrazin-2(1H)-one (5-1) is subjected to an imidazole annulation reaction by treatment with tosylmethisocyanide (TosMIC) under basic conditions (Hoogenboom et al., Organic Syntheses, Coll. Vol. 6, p. 987 (1988)) to provide 5-bromo-7-methylimidazo[1,5-a]pyrazin-8(7H)-one (5-2). Palladium-catalyzed cross coupling reaction of compound 5-2 with a suitable halide provides the compound 5-3.

Scheme 6

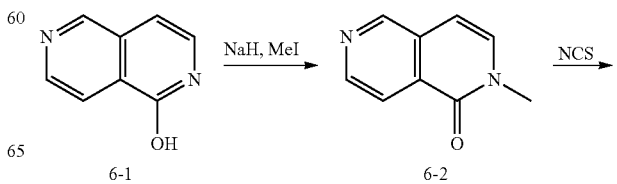

-continued

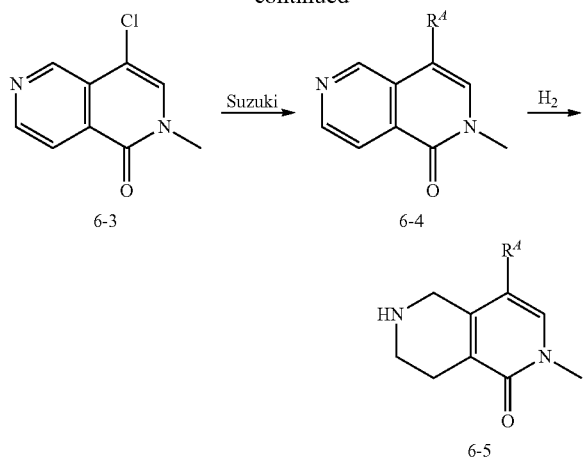

A method for preparing compounds of Formula (III) is provided in Scheme 6. 2,6-Naphthyridin-1-ol (6-1) is subjected to alkylation with methyl iodide under basic conditions to provide 2-methyl-2,6-naphthyridin-1(2H)-one (6-2). Chlorination of 6-2 with N-chlorosuccinimide provides chloro compound 6-3. Treatment of 6-3 under palladium-catalyzed cross coupling conditions with a suitable halide provides compound 6-4. Selective reduction of the 2,6-naphthyridinone derivative provides the 5,6,7,8-tetrahydro-2,6-naphthyridin-1(2H)-one derivative 6-5.

In each of the above reaction procedures or schemes, the various substituents may be selected from among the various substituents otherwise taught herein.

Pharmaceutical Compositions

In certain embodiments, the substituted heterocyclic derivative compound as described herein is administered as a pure chemical. In other embodiments, the substituted heterocyclic derivative compound described herein is combined with a pharmaceutically suitable or acceptable carrier (also referred to herein as a pharmaceutically suitable (or acceptable) excipient, physiologically suitable (or acceptable) excipient, or physiologically suitable (or acceptable) carrier) selected on the basis of a chosen route of administration and standard pharmaceutical practice as described, for example, in Remington: The Science and Practice of Pharmacy (Gennaro, 21$^{st}$ Ed. Mack Pub. Co., Easton, Pa. (2005)).

Accordingly, provided herein is a pharmaceutical composition comprising at least one substituted heterocyclic derivative compound, or a stereoisomer, pharmaceutically acceptable salt, hydrate, solvate, or N-oxide thereof, together with one or more pharmaceutically acceptable carriers. The carrier(s) (or excipient(s)) is acceptable or suitable if the carrier is compatible with the other ingredients of the composition and not deleterious to the recipient (i.e., the subject) of the composition.

One embodiment provides a pharmaceutical composition comprising a compound of Formula (I), (Ia), or (Ib), or a pharmaceutically acceptable salt thereof, and a pharmaceutically acceptable excipient. One embodiment provides a pharmaceutical composition comprising a compound of Formula (II), (IIa), or (IIb), or a pharmaceutically acceptable salt thereof, and a pharmaceutically acceptable excipient. One embodiment provides a pharmaceutical composition comprising a compound of Formula (III), or (IIIa), or a pharmaceutically acceptable salt thereof, and a pharmaceutically acceptable excipient. One embodiment provides a pharmaceutical composition comprising a compound of Formula (IV), or a pharmaceutically acceptable salt thereof, and a pharmaceutically acceptable excipient. One embodiment provides a pharmaceutical composition comprising a compound of Formula (V), or a pharmaceutically acceptable salt thereof, and a pharmaceutically acceptable excipient. One embodiment provides a pharmaceutical composition comprising a compound of Formula (VIa), (VIb), (VIc), (VId), or (VIe), or a pharmaceutically acceptable salt thereof, and a pharmaceutically acceptable excipient. One embodiment provides a pharmaceutical composition comprising a compound of Formula (VII), or (VIIa), or a pharmaceutically acceptable salt thereof, and a pharmaceutically acceptable excipient. One embodiment provides a pharmaceutical composition comprising a compound of Formula (VIII), or (VIIIa), or a pharmaceutically acceptable salt thereof, and a pharmaceutically acceptable excipient. One embodiment provides a pharmaceutical composition comprising a compound of Formula (IX), or a pharmaceutically acceptable salt thereof, and a pharmaceutically acceptable excipient. One embodiment provides a pharmaceutical composition comprising a compound of Formula (XII), or a pharmaceutically acceptable salt thereof, and a pharmaceutically acceptable excipient. One embodiment provides a pharmaceutical composition comprising a compound of Formula (XIII), or a pharmaceutically acceptable salt thereof, and a pharmaceutically acceptable excipient. One embodiment provides a pharmaceutical composition comprising a compound of Formula (XIV), or a pharmaceutically acceptable salt thereof, and a pharmaceutically acceptable excipient. One embodiment provides a pharmaceutical composition comprising a compound of Formula (XV), or a pharmaceutically acceptable salt thereof, and a pharmaceutically acceptable excipient. One embodiment provides a pharmaceutical composition comprising a compound of Formula (XVI), or a pharmaceutically acceptable salt thereof, and a pharmaceutically acceptable excipient. One embodiment provides a pharmaceutical composition comprising a compound of Formula (XVII), or a pharmaceutically acceptable salt thereof, and a pharmaceutically acceptable excipient. One embodiment provides a pharmaceutical composition comprising a compound of Formula (XVIII), or a pharmaceutically acceptable salt thereof, and a pharmaceutically acceptable excipient. One embodiment provides a pharmaceutical composition comprising a compound of Formula (XIX), or a pharmaceutically acceptable salt thereof, and a pharmaceutically acceptable excipient. One embodiment provides a pharmaceutical composition comprising a compound of Formula (XX), or a pharmaceutically acceptable salt thereof, and a pharmaceutically acceptable excipient. One embodiment provides a pharmaceutical composition comprising a compound of Formula (XXI), or a pharmaceutically acceptable salt thereof, and a pharmaceutically acceptable excipient. One embodiment provides a pharmaceutical composition comprising a compound of Formula (XXII), or a pharmaceutically acceptable salt thereof, and a pharmaceutically acceptable excipient. One embodiment provides a pharmaceutical composition comprising a compound of Formula (XXIII), or a pharmaceutically acceptable salt thereof, and a pharmaceutically acceptable excipient. One embodiment provides a pharmaceutical composition comprising a compound of Formula (XXIV), or a pharmaceutically acceptable salt thereof, and a pharmaceutically acceptable excipient. One embodiment provides a pharmaceutical composition comprising a compound of Formula (XXV), or a pharmaceutically acceptable salt thereof, and a pharmaceutically acceptable excipient.

In certain embodiments, the substituted heterocyclic derivative compound as described herein is substantially pure, in that it contains less than about 5%, or less than about 1%, or less than about 0.1%, of other organic small molecules, such as contaminating intermediates or by-products that are created, for example, in one or more of the steps of a synthesis method.

Suitable oral dosage forms include, for example, tablets, pills, sachets, or capsules of hard or soft gelatin, methylcellulose or of another suitable material easily dissolved in the digestive tract. Suitable nontoxic solid carriers are used which include, for example, pharmaceutical grades of mannitol, lactose, starch, magnesium stearate, sodium saccharin, talcum, cellulose, glucose, sucrose, magnesium carbonate, and the like. (See, e.g., *Remington: The Science and Practice of Pharmacy* (Gennaro, 21$^{st}$ Ed. Mack Pub. Co., Easton, Pa. (2005)).

The dose of the composition comprising at least one substituted heterocyclic derivative compound as described herein may differ, depending upon the patient's (e.g., human) condition, that is, stage of the disease, general health status, age, and other factors that a person skilled in the medical art will use to determine dose.

Pharmaceutical compositions may be administered in a manner appropriate to the disease to be treated (or prevented) as determined by persons skilled in the medical arts. An appropriate dose and a suitable duration and frequency of administration will be determined by such factors as the condition of the patient, the type and severity of the patient's disease, the particular form of the active ingredient, and the method of administration. In general, an appropriate dose and treatment regimen provides the composition(s) in an amount sufficient to provide therapeutic and/or prophylactic benefit (e.g., an improved clinical outcome, such as more frequent complete or partial remissions, or longer disease-free and/or overall survival, or a lessening of symptom severity. Optimal doses may generally be determined using experimental models and/or clinical trials. The optimal dose may depend upon the body mass, weight, or blood volume of the patient.

Oral doses typically range from about 1.0 mg to about 1000 mg, one to four times, or more, per day.

Bromodomain Inhibition

Chromatin is the complex of DNA and protein that makes up chromosomes. Histones are the major protein component of chromatin, acting as spools around which DNA winds. Changes in chromatin structure are affected by covalent modifications of histone proteins and by non-histone binding proteins. Several classes of enzymes are known which modify histones at various sites.

Epigenetics is the study of heritable changes in gene expression caused by mechanisms other than the underlying DNA sequence. Molecular mechanisms that play a role in epigenetic regulation include DNA methylation and chromatin/histone modifications.

The genomes of eukaryotic organisms are highly organized within the nucleus of the cell. Tremendous compaction is required to package the 3 billion nucleotides of the human genome into the nucleus of a cell.

Histones are the chief protein components of chromatin. There are a total of six classes of histones (H1, H2A, H2B, H3, H4, and H5) organized into two classes: core histones (H2A, H2B, H3, and H4) and linker histones (H1 and H5). The basic unit of chromatin is the nucleosome, which consists of about 147 base pairs of DNA wrapped around the core histone octamer, consisting of two copies each of the core histones H2A, H2B, H3, and H4.

Basic nucleosome units are then further organized and condensed by the aggregation and folding of nucleosomes to form a highly condensed chromatin structure. A range of different states of condensation are possible, and the tightness of chromatin structure varies during the cell cycle, being most compact during the process of cell division.

Chromatin structure plays a critical role in regulating gene transcription, which cannot occur efficiently from highly condensed chromatin. The chromatin structure is controlled by a series of post translational modifications to histone proteins, notably histones H3 and H4, and most commonly within the histone tails which extend beyond the core nucleosome structure. These modifications include acetylation, methylation, phosphorylation, ribosylation sumoylation, ubiquitination, citrullination, deimination, and biotinylation. The core of histones H2A and H3 can also be modified. Histone modifications are integral to diverse biological processes such as gene regulation, DNA repair, and chromosome condensation.

Histone Acetylation and Bromodomains

Histone acetylation is generally associated with the activation of gene transcription, as the modification is known to loosen the interaction of the DNA and the histone octamer by changing the electrostatics. In addition to this physical change, specific proteins are known to bind to acetylated lysine residues within histones in order to read the epigenetic code. Bromodomains are small (~110 amino acid) distinct domains within proteins that are known to bind to acetylated lysine residues commonly, but not exclusively, in the context of histones. Around 50 proteins are known to contain bromodomains, and they have a range of functions within the cell.

The BET family of bromodomain containing proteins comprises 4 proteins (BRD2, BRD3, BRD4 and BRD-t) which contain tandem bromodomains capable of binding to two acetylated lysine resides in close proximity, increasing the specificity of the interaction.

Bromodomain-containing proteins that recognize acetylated lysines on histones (such as BET proteins and non-BET proteins) have been implicated in proliferative disease. BRD4 knockout mice die shortly after implantation and are compromised in their ability to maintain an inner cell mass, and heterozygotes display pre- and postnatal growth defects associated with reduced proliferation rates. BRD4 regulates genes expressed during M/G1, including growth-associated genes, and remains bound to chromatin throughout the cell cycle (Dey, et al. (2009) Mol. Biol. Cell 20:4899-4909). BRD4 also physically associates with Mediator and P-TEFb (CDK9/cyclin T1) to facilitate transcriptional elongation (Yang, et al. (2005) Oncogene 24:1653-1662; Yang, et al. (2005) Mol. Cell 19:535-545). CDK9 is a validated target in chronic lymphocytic leukemia (CLL), and is linked to c-Myc-dependent transcription (Phelps, et al. Blood 113: 2637-2645; Rahl, et al. (2010) Cell 141:432-445).

BRD4 is translocated to the NUT protein in patients with lethal midline carcinoma, an aggressive form of human squamous carcinoma (French, et al. (2001) Am. J. Pathol. 159:1987-1992; French, et al. (2003) Cancer Res. 63:304-307). In vitro analysis with RNAi supports a causal role for BRD4 in this recurrent t(15; 19) chromosomal translocation. Also, inhibition of the BRD4 bromodomains has been found to result in growth arrest/differentiation of BRD4-NUT cell lines in vitro and in vivo (Filippakopoulos, et al. "Selective Inhibition of BET Bromodomains," Nature (published online Sep. 24, 2010)).

Bromodomain-containing proteins (such as BET proteins) have also been implicated in inflammatory diseases. BET proteins (e.g., BRD2, BRD3, BRD4, and BRDT) regulate assembly of histone acetylation-dependent chromatin complexes that control inflammatory gene expression (Hargreaves, et al. (2009) Cell 138:129-145; LeRoy, et al. (2008) Mol. Cell 30:51-60; Jang, et al. (2005) Mol. Cell 19:523-534; Yang, et al. (2005) Mol. Cell 19:535-545). Key inflammatory genes (secondary response genes) are down-regulated upon bromodomain inhibition of the BET subfamily, and non-responsive genes (primary response genes) are poised for transcription. BET bromodomain inhibition protects against LPS-induced endotoxic shock and bacteria-induced sepsis in vivo (Nicodeme, et al. "Suppression of Inflammation by a Synthetic Histone Mimic," Nature (published online Nov. 10, 2010)).

Bromodomain-containing proteins (such as BET proteins) have also been found to play a role in viral infection. For example, BRD4 is implicated in the primary phase of human papilloma virus (HPV) infection, in which the viral genome is maintained in an extra-chromosomal episome in basal epithelia. In some strains of HPV, BRD4 binding to the HPV E2 protein functions to tether the viral genome to chromosomes. E2 is critical for both the repression of E6/E7 and the activation of HPV viral genes. Disruption of BRD4 or the BRD4-E2 interaction blocks E2-dependent gene activation. BRD4 also functions to tether other classes of viral genomes to host chromatin (e.g., Herpes virus, Epstein-Barr virus).

Bromodomain-containing proteins has also been found to bind to acetylated lysine residues on proteins other than histones. For example, the bromodomain of CREB binding protein transcriptional coactivator (CBP) allows for recognition of p53 with acetylated Lys382. The interaction between the bromodomain and acetyl-p53 follows DNA damage and promotes p53-induced transcriptional activation of the CDK inhibitor p21 and cell cycle arrest.

Another novel bromodomain-containing protein is BAZ2B, whose biological function, is believed to function similarly to ACF1, the Drosophila BAZ2B ortholog. ACF complexes play roles in establishing regular nucleosome spacing during chromatin assembly and influencing different remodeling outcomes at target loci.

One embodiment provides a method of regulating gene transcription in a cell comprising exposing a bromodomain containing protein to a compound of Formula (I), (Ia), or (Ib). One embodiment provides a method of regulating gene transcription in a cell comprising exposing a bromodomain containing protein to a compound of Formula (II), (IIa), or (IIb). One embodiment provides a method of regulating gene transcription in a cell comprising exposing a bromodomain containing protein to a compound of Formula (III), or (IIIa). One embodiment provides a method of regulating gene transcription in a cell comprising exposing a bromodomain containing protein to a compound of Formula (IV). One embodiment provides a method of regulating gene transcription in a cell comprising exposing a bromodomain containing protein to a compound of Formula (V). One embodiment provides a method of regulating gene transcription in a cell comprising exposing a bromodomain containing protein to a compound of Formula (VIa), (VIb), (VIc), (VId), or (VIe). One embodiment provides a method of regulating gene transcription in a cell comprising exposing a bromodomain containing protein to a compound of Formula (VII) or (VIIa). One embodiment provides a method of regulating gene transcription in a cell comprising exposing a bromodomain containing protein to a compound of Formula (VIII), or (VIIIa). One embodiment provides a method of regulating gene transcription in a cell comprising exposing a bromodomain containing protein to a compound of Formula (IX). One embodiment provides a method of regulating gene transcription in a cell comprising exposing a bromodomain containing protein to a compound of Formula (XII). One embodiment provides a method of regulating gene transcription in a cell comprising exposing a bromodomain containing protein to a compound of Formula (XIII). One embodiment provides a method of regulating gene transcription in a cell comprising exposing a bromodomain containing protein to a compound of Formula (XIV). One embodiment provides a method of regulating gene transcription in a cell comprising exposing a bromodomain containing protein to a compound of Formula (XV). One embodiment provides a method of regulating gene transcription in a cell comprising exposing a bromodomain containing protein to a compound of Formula (XVI). One embodiment provides a method of regulating gene transcription in a cell comprising exposing a bromodomain containing protein to a compound of Formula (XVII). One embodiment provides a method of regulating gene transcription in a cell comprising exposing a bromodomain containing protein to a compound of Formula (XVIII). One embodiment provides a method of regulating gene transcription in a cell comprising exposing a bromodomain containing protein to a compound of Formula (XIX). One embodiment provides a method of regulating gene transcription in a cell comprising exposing a bromodomain containing protein to a compound of Formula (XX). One embodiment provides a method of regulating gene transcription in a cell comprising exposing a bromodomain containing protein to a compound of Formula (XXI). One embodiment provides a method of regulating gene transcription in a cell comprising exposing a bromodomain containing protein to a compound of Formula (XXII). One embodiment provides a method of regulating gene transcription in a cell comprising exposing a bromodomain containing protein to a compound of Formula (XXIII). One embodiment provides a method of regulating gene transcription in a cell comprising exposing a bromodomain containing protein to a compound of Formula (XXIV). One embodiment provides a method of regulating gene transcription in a cell comprising exposing a bromodomain containing protein to a compound of Formula (XXV).

One embodiment provides a method of inhibiting bromodomain-mediated recognition of an acetyl lysine region of a protein comprising exposing the bromodomain to a compound of Formula (I), (Ia), or (Ib). One embodiment provides a method of inhibiting bromodomain-mediated recognition of an acetyl lysine region of a protein comprising exposing the bromodomain to a compound of Formula (II), (IIa), or (IIb). One embodiment provides a method of inhibiting bromodomain-mediated recognition of an acetyl lysine region of a protein comprising exposing the bromodomain to a compound of Formula (III), or (IIIa). One embodiment provides a method of inhibiting bromodomain-mediated recognition of an acetyl lysine region of a protein comprising exposing the bromodomain to a compound of Formula (IV). One embodiment provides a method of inhibiting bromodomain-mediated recognition of an acetyl lysine region of a protein comprising exposing the bromodomain to a compound of Formula (V). One embodiment provides a method of inhibiting bromodomain-mediated recognition of an acetyl lysine region of a protein comprising exposing the bromodomain to a compound of Formula (VIa), (VIb), (VIc), (VId), or (VIe). One embodiment provides a method of inhibiting bromodomain-mediated recognition of an acetyl lysine region of a protein comprising exposing the bromodomain to a compound of Formula (VII), or (VIIa). One embodiment provides a method of inhibiting bromodomain-mediated recognition of an acetyl lysine region of a protein comprising exposing the bromodomain to a compound of Formula (VIII), or (VIIIa). One embodiment provides a method of inhibiting bromodomain-mediated recognition of an acetyl lysine region of a protein comprising exposing the bromodomain to a compound of Formula (IX). One embodiment provides a method of inhibiting bromodomain-mediated recognition of an acetyl lysine region of a protein comprising exposing the bromodomain to a compound of Formula (XII). One embodiment provides a method of inhibiting bromodomain-mediated recognition of an acetyl lysine region of a protein comprising exposing the bromodomain to a compound of Formula (XIII). One embodiment provides a method of inhibiting bromodomain-mediated recognition of an acetyl lysine region of a protein comprising exposing the bromodomain to a compound of Formula (XIV). One embodiment provides a method of inhibiting bromodomain-mediated recognition of an acetyl lysine region of a protein comprising exposing the bromodomain to a compound of Formula (XV). One embodiment provides a method of inhibiting bromodomain-mediated recognition of an acetyl lysine region of a protein comprising exposing the bromodomain to a compound of Formula (XVI). One embodiment provides a method of inhibiting bromodomain-mediated recognition of an acetyl lysine region of a protein comprising exposing the bromodomain to a compound of Formula (XVII). One embodiment provides a method of inhibiting bromodomain-mediated recognition of an acetyl lysine region of a protein comprising exposing the bromodomain to a compound of Formula (XVIII). One embodiment provides a method of inhibiting bromodomain-mediated recognition of an acetyl lysine region of a protein comprising exposing the bromodomain to a compound of Formula (XIX). One embodiment provides a method of inhibiting bromodomain-mediated recognition of an acetyl lysine region of a protein comprising exposing the bromodomain to a compound of Formula (XX). One embodiment provides a method of inhibiting bromodomain-mediated recognition of an acetyl lysine region of a protein comprising exposing the bromodomain to a compound of Formula (XXI). One embodiment provides a method of inhibiting bromodomain-mediated recognition of an acetyl lysine region of a protein comprising exposing the bromodomain to a compound of Formula (XXII). One embodiment provides a method of inhibiting bromodomain-mediated recognition of an acetyl lysine region of a protein comprising exposing the bromodomain to a compound of Formula (XXIII). One embodiment provides a method of inhibiting bromodomain-mediated recognition of an acetyl lysine region of a protein comprising exposing the bromodomain to a compound of Formula (XXIV). One embodiment provides a method of inhibiting bromodomain-mediated recognition of an acetyl lysine region of a protein comprising exposing the bromodomain to a compound of Formula (XXV).

One embodiment provides a method of regulating gene transcription in a cell comprising exposing a bromodomain-containing protein to a compound of Formula (X), or a pharmaceutically acceptable salt thereof,

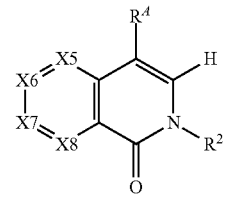

Formula (X)

wherein,
$R^2$ is selected from $CH_3$, $CH_2CH_3$, $CH_2CF_3$, $CH_2F$, $CHF_2$, $CF_3$, $CH_2D$, $CHD_2$, or $CD_3$;
X5 is C—$R^5$ or N;
X6 is C—$R^6$ or N;
X7 is C—$R^7$ or N;
X8 is C—$R^8$ or N; wherein no more than two of X5, X6, X7, or X8 may be N;
$R^5$ is hydrogen, halogen, —OH, —CN, —$OR^{61}$, —$NHR^{61}$, —$N(R^{61})_2$, alkyl, cycloalkyl, cycloalkylalkyl, aryl, aralkyl, heterocyclyl, heterocyclylalkyl, heteroaryl, or heteroarylalkyl, wherein each $R^{61}$ is independently selected from alkyl, cycloalkyl, cycloalkylalkyl, aryl, aralkyl, heterocyclyl, heterocyclylalkyl, heteroaryl, or heteroarylalkyl;
$R^6$ is hydrogen, halogen, —OH, —CN, —$OR^{61}$, —$NHR^{61}$, —$N(R^{61})_2$, alkyl, cycloalkyl, cycloalkylalkyl, aryl, aralkyl, heterocyclyl, heterocyclylalkyl, heteroaryl, or heteroarylalkyl, wherein each $R^{61}$ is independently selected from alkyl, cycloalkyl, cycloalkylalkyl, aryl, aralkyl, heterocyclyl, heterocyclylalkyl, heteroaryl, or heteroarylalkyl;
$R^7$ is hydrogen, halogen, —OH, —CN, —$OR^{61}$, —$NHR^{61}$, —$N(R^{61})_2$, alkyl, cycloalkyl, cycloalkylalkyl, aryl, aralkyl, heterocyclyl, heterocyclylalkyl, heteroaryl, or heteroarylalkyl, wherein each $R^{61}$ is independently selected from alkyl, cycloalkyl, cycloalkylalkyl, aryl, aralkyl, heterocyclyl, heterocyclylalkyl, heteroaryl, or heteroarylalkyl;
$R^8$ is hydrogen, halogen, or alkyl; and
$R^4$ is an aryl group or a heteroaryl group.

Another embodiment provides the method of regulating gene transcription in a cell, wherein the compound of Formula (X) has the structure wherein $R^4$ is a substituted phenyl group.

Another embodiment provides a method of inhibiting of bromodomain-mediated recognition of an acetyl lysine region of a protein comprising exposing the bromodomain to a compound of Formula (X). Another embodiment provides the method of inhibiting of bromodomain-mediated recognition of an acetyl lysine region of a protein, wherein the compound of Formula (X) has the structure wherein $R^4$ is a substituted phenyl group.

One embodiment provides a method of regulating gene transcription in a cell comprising exposing a bromodomain-containing protein to a compound of Formula (XI), or a pharmaceutically acceptable salt thereof,

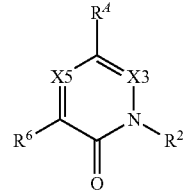

Formula (XI)

wherein, $R^2$ is $CH_3$, $CH_2CH_3$, $CH_2CF_3$, $CH_2F$, $CHF_2$, $CF_3$, $CH_2D$, $CHD_2$, or $CD_3$;

X3 is C—H or N;

X5 is C—$R^5$ or N; provided that if X3 is N, then X5 is C—$R^5$, and if X5 is N, then X3 is CH;

$R^5$ is hydrogen, halogen, —OH, —CN, —$OR^{61}$, —$NHR^{61}$, —$N(R^{61})_2$, alkyl, cycloalkyl, cycloalkylalkyl, aryl, aralkyl, heterocyclyl, heterocyclylalkyl, heteroaryl, or heteroarylalkyl, wherein each $R^{61}$ is independently selected from alkyl, cycloalkyl, cycloalkylalkyl, aryl, aralkyl, heterocyclyl, heterocyclylalkyl, heteroaryl, or heteroarylalkyl;

$R^6$ is hydrogen, halogen, —OH, —CN, alkyl, cycloalkyl, cycloalkylalkyl, amino, alkylamino, dialkylamino, cycloalkylalkylamino, alkoxy, or cycloalkylalkoxy; and $R^4$ is an aryl group or a heteroaryl group.

Another embodiment provides the method of regulating gene transcription in a cell, wherein the compound of Formula (XI) has the structure wherein $R^4$ is a substituted phenyl group.

Another embodiment provides a method of inhibiting of bromodomain-mediated recognition of an acetyl lysine region of a protein comprising exposing the bromodomain to a compound of Formula (XI). Another embodiment provides the method of inhibiting of bromodomain-mediated recognition of an acetyl lysine region of a protein, wherein the compound of Formula (XI) has the structure wherein $R^4$ is a substituted phenyl group.

Methods of Treatment

Compounds and compositions described herein are generally useful for the inhibition of activity of one or more proteins involved in epigenetic regulation. Thus, one embodiment provides a method of modulating epigenetic regulation mediated by one or more proteins containing acetyl-lysine recognition motifs, also known as bromodomains (e.g., BET proteins, such as BRD2, BRD3, BRD4, and/or BRDT, and non-BET proteins, such as CBP, ATAD2A, GCN5L, BAZ2B, FALZ, TAF1, and/or BRPF1), by administering a substituted heterocyclic derivative compound as described herein.

In some embodiments, the substituted heterocyclic derivative compounds as described herein are capable of inhibiting the activity of a bromodomain-containing protein, such as a BET protein (BRD2, BRD3, BRD4 and/or BRDT), non-BET proteins (such as CBP, ATAD2A, GCN5L, BAZ2B, FALZ, TAF1, and/or BRPF1) or a mutant thereof, in a biological sample in manner useful for a variety of purposes that are known to one of skill in the art. Examples of such purposes include, but are not limited to, blood transfusion, organ-transplantation, biological specimen storage, and biological assays.

In some embodiments is provided a method of inhibiting the activity of a bromodomain-containing protein, such as a BET protein (BRD2, BRD3, BRD4 and/or BRDT), non-BET proteins (such as CBP, ATAD2A, GCN5L, BAZ2B, FALZ, TAF1, and/or BRPF1) or a mutant thereof, in a patient comprising the step of administering to said patient a substituted heterocyclic derivative compound as described herein, or a composition comprising said compound.

In some embodiments is provided a method of inhibiting the activity of a bromodomain-containing protein, such as a BET protein (BRD2, BRD3, BRD4 and/or BRDT), non-BET proteins (such as CBP, ATAD2A, GCN5L, BAZ2B, FALZ, TAF1, and/or BRPF1) or a mutant thereof, in a biological sample comprising the step of contacting said biological sample with a substituted heterocyclic derivative compound as described herein. In some embodiments, the bromodomain-containing protein is a BET protein. In some embodiments, the BET protein is BRD4.

In some embodiments is provided a method of inhibiting the activity of a bromodomain-containing protein, such as a BET protein (BRD2, BRD3, BRD4 and/or BRDT), non-BET proteins (such as CBP, ATAD2A, GCN5L, BAZ2B, FALZ, TAF1, and/or BRPF1) or a mutant thereof, in a patient in need thereof, comprising the step of administering to said patient a substituted heterocyclic derivative compound as described herein. In some embodiments, the bromodomain-containing protein is a BET protein. In some embodiments, the BET protein is BRD4.

Diseases and conditions treatable according to the methods of this invention include cancer, neoplastic disease and other proliferative disorders. Thus, one aspect is a method of treating a subject having cancer, a neoplastic disease and other proliferative disorder, the method comprising administration of a substituted heterocyclic derivative compound as described herein to the subject. In one embodiment, a human patient is treated with a substituted heterocyclic derivative compound as described herein and a pharmaceutically acceptable excipient, wherein said compound is present in an amount to measurably inhibit bromodomain-containing protein activity (such as BRD2, BRD3, BRD4, and/or BRDT) in the patient.

The invention further provides a method of treating a subject, such as a human, suffering from cancer, a neoplastic disease and other proliferative disorder. The method comprises administering to a subject in need of such treatment a therapeutically effective amount of one or more substituted heterocyclic derivative compound as described herein, which function by inhibiting a bromodomain and, in general, by modulating gene expression, to induce various cellular effects, in particular induction or repression of gene expression, arresting cell proliferation, inducing cell differentiation and/or inducing apoptosis.

The invention further provides a therapeutic method of modulating protein methylation, gene expression, cell proliferation, cell differentiation and/or apoptosis in vivo in conditions, illnesses, disorders or diseases disclosed herein, in particular cancer, inflammatory disease, and/or viral disease comprising administering to a subject in need of such therapy a pharmacologically active and therapeutically effective amount of one or more substituted heterocyclic derivative compound as described herein.

The invention further provides a method of regulating endogenous or heterologous promoter activity by contacting a cell with a substituted heterocyclic derivative compound as described herein.

The invention further relates to a method for treating or ameliorating cancer, neoplastic disease, or another proliferative disorder by administration of an effective amount of a substituted heterocyclic derivative compound as described herein, to a mammal, in particular a human, in need of such treatment. In some aspects of the invention, the disease to be treated by the methods of the present invention is cancer.

In certain embodiments, the cancer is NUT midline carcinoma, prostate cancer, breast cancer, bladder cancer, lung cancer, or melanoma. In another embodiment the cancer is Burkitts lymphoma.

One embodiment provides a method of treating cancer in a patient in need thereof, comprising administering to the patient a compound of Formula (I), (Ia), or (Ib), or a pharmaceutically acceptable salt thereof. One embodiment provides a method of treating cancer in a patient in need thereof, comprising administering to the patient a compound of Formula (II), (IIa), or (IIb), or a pharmaceutically acceptable salt thereof. One embodiment provides a method of treating cancer in a patient in need thereof, comprising administering to the patient a compound of Formula (III), or (IIIa), or a pharmaceutically acceptable salt thereof. One embodiment provides a method of treating cancer in a patient in need thereof, comprising administering to the patient a compound of Formula (IV), or a pharmaceutically acceptable salt thereof. One embodiment provides a method of treating cancer in a patient in need thereof, comprising administering to the patient a compound of Formula (V), or a pharmaceutically acceptable salt thereof. One embodiment provides a method of treating cancer in a patient in need thereof, comprising administering to the patient a compound of Formula (VIa), (VIb), (VIc), (VId), or (VIe), or a pharmaceutically acceptable salt thereof. One embodiment provides a method of treating cancer in a patient in need thereof, comprising administering to the patient a compound of Formula (VII), or (VIIa), or a pharmaceutically acceptable salt thereof. One embodiment provides a method of treating cancer in a patient in need thereof, comprising administering to the patient a compound of Formula (VIII), or (VIIIa), or a pharmaceutically acceptable salt thereof. One embodiment provides a method of treating cancer in a patient in need thereof, comprising administering to the patient a compound of Formula (IX), or a pharmaceutically acceptable salt thereof. One embodiment provides a method of treating cancer in a patient in need thereof, comprising administering to the patient a compound of Formula (XII), or a pharmaceutically acceptable salt thereof. One embodiment provides a method of treating cancer in a patient in need thereof, comprising administering to the patient a compound of Formula (XIII), or a pharmaceutically acceptable salt thereof. One embodiment provides a method of treating cancer in a patient in need thereof, comprising administering to the patient a compound of Formula (XIV), or a pharmaceutically acceptable salt thereof. One embodiment provides a method of treating cancer in a patient in need thereof, comprising administering to the patient a compound of Formula (XV), or a pharmaceutically acceptable salt thereof. One embodiment provides a method of treating cancer in a patient in need thereof, comprising administering to the patient a compound of Formula (XVI), or a pharmaceutically acceptable salt thereof. One embodiment provides a method of treating cancer in a patient in need thereof, comprising administering to the patient a compound of Formula (XVII), or a pharmaceutically acceptable salt thereof. One embodiment provides a method of treating cancer in a patient in need thereof, comprising administering to the patient a compound of Formula (XVIII), or a pharmaceutically acceptable salt thereof. One embodiment provides a method of treating cancer in a patient in need thereof, comprising administering to the patient a compound of Formula (XIX), or a pharmaceutically acceptable salt thereof. One embodiment provides a method of treating cancer in a patient in need thereof, comprising administering to the patient a compound of Formula (XX), or a pharmaceutically acceptable salt thereof. One embodiment provides a method of treating cancer in a patient in need thereof, comprising administering to the patient a compound of Formula (XXI), or a pharmaceutically acceptable salt thereof. One embodiment provides a method of treating cancer in a patient in need thereof, comprising administering to the patient a compound of Formula (XXII), or a pharmaceutically acceptable salt thereof. One embodiment provides a method of treating cancer in a patient in need thereof, comprising administering to the patient a compound of Formula (XXIII), or a pharmaceutically acceptable salt thereof. One embodiment provides a method of treating cancer in a patient in need thereof, comprising administering to the patient a compound of Formula (XXIV), or a pharmaceutically acceptable salt thereof. One embodiment provides a method of treating cancer in a patient in need thereof, comprising administering to the patient a compound of Formula (XXV), or a pharmaceutically acceptable salt thereof.

Other embodiments and uses will be apparent to one skilled in the art in light of the present disclosures. The following examples are provided merely as illustrative of various embodiments and shall not be construed to limit the invention in any way.

EXAMPLES

I. Chemical Synthesis

Unless otherwise noted, reagents and solvents were used as received from commercial suppliers. Anhydrous solvents and oven-dried glassware were used for synthetic transformations sensitive to moisture and/or oxygen. Yields were not optimized. Reaction times are approximate and were not optimized. Column chromatography and thin layer chromatography (TLC) were performed on silica gel unless otherwise noted. Spectra are given in ppm (δ) and coupling constants (J) are reported in Hertz. For $^1$H NMR spectra, the solvent peak was used as the reference peak.

Chemistry Example 1 is 2-methyl-4-phenylisoquinolin-1-one which was purchased from a commercial vendor.

Example 2

4-(3-methoxyphenyl)-2-methylisoquinolin-1-one

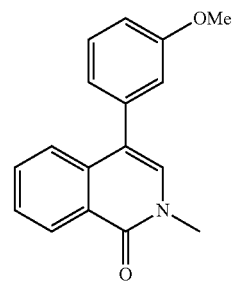 [SMILES: COc1cccc(-c2cn(C)c(=O)c3ccccc23)c1]

A mixture of 4-bromo-2-methylisoquinolin-1(2H)-one (100 mg, 0.42 mmol), and (3-methoxyphenyl)boronic acid (70 mg, 0.46 mmol), PPh$_3$ (66 mg, 0.25 mmol), Na$_2$CO$_3$ (133 mg, 1.26 mmol), and Pd(dppf)Cl$_2$ (62 mg, 0.084 mmol) in dioxane (2.5 mL) and water (0.5 mL) was heated overnight at 90° C. Extractive work up with ethyl acetate followed by preparative TLC (PE:EA=1:1) gave the title compound (18 mg, 0.07 mmol) as a white solid in 17% yield. $^1$H NMR (DMSO, 400 MHz): δ 8.30 (d, 1H, J=7.68), 7.68 (t, 1H, J=7.56), 7.50-7.55 (m, 3H), 7.40 (t, 1H, J=7.44), 6.97-7.00 (m, 3H), 3.78 (s, 3H), 3.54 (s, 3H). MS (m/z, relative intensity): 266 (M$^+$, 1).

Examples 3-14 in Table 3 were prepared from 4-bromo-2-methylisoquinolin-1(2H)-one and the appropriate boronic acid/ester in a manner similar to Example 2.

TABLE 3

| Ex. No. | R¹ | Name | ¹H NMR (ppm (δ), 400 MHz) | MS (M + H) |
|---|---|---|---|---|
| 3 | 2-fluorophenyl | 4-(2-fluorophenyl)-2-methylisoquinolin-1-one | (DMSO-d₆) 3.57 (s, 3 H) 7.20 (d, J = 7.42 Hz, 1 H) 7.31-7.41 (m, 2 H) 7.42-7.61 (m, 4 H) 7.64-7.73 (m, 1 H) 8.32 (d, J = 7.81 Hz, 1 H) | 254 |
| 4 | 2-methoxyphenyl | 4-(2-methoxyphenyl)-2-methylisoquinolin-1-one | (DMSO-d₆) 3.54 (s, 3 H) 3.67 (s, 3 H) 7.00-7.11 (m, 2 H) 7.15 (d, J = 8.20 Hz, 1 H) 7.25 (d, J = 6.83 Hz, 1 H) 7.40 (s, 1 H) 7.48 (dt, J = 15.91, 7.86 Hz, 2 H) 7.61 (d, J = 7.42 Hz, 1 H) 8.28 (d, J = 8.20 Hz, 1 H) | 266 |
| 5 | 3-aminophenyl | 4-(3-aminophenyl)-2-methylisoquinolin-1-one | (DMSO-d₆) 3.55 (s, 3 H) 5.19 (br. s., 2 H) 6.55 (d, J = 7.33 Hz, 1 H) 6.60-6.64 (m, 2 H) 7.12 (t, J = 7.83 Hz, 1 H) 7.43 (s, 1 H) 7.51-7.62 (m, 2 H) 7.66-7.72 (m, 1 H) 8.31 (d, J = 7.83 Hz, 1 H) | 251 |
| 6 | 3-(N-cyclopropylsulfamoyl)phenyl | N-cyclopropyl-3-(2-methyl-1-oxoisoquinolin-4-yl)benzenesulfonamide | (DMSO-d₆) 0.36-0.41 (m, 2 H) 0.47-0.52 (m, 2 H) 2.16 (br. s., 1 H) 3.57 (s, 3 H) 7.44 (d, J = 8.20 Hz, 1 H) 7.54-7.61 (m, 2 H) 7.68-7.77 (m, 3 H) 7.83-7.88 (m, 2 H) 7.96 (br. s., 1 H) 8.34 (d, J = 7.81 Hz, 1 H) | 355 |
| 7 | 3-(pyrrolidin-1-ylsulfonyl)phenyl | 2-methyl-4-(3-pyrrolidin-1-ylsulfonylphenyl)isoquinolin-1-one | (DMSO-d₆) 1.67 (t, J = 6.64 Hz, 4 H) 3.18 (t, J = 6.44 Hz, 4 H) 3.57 (s, 3 H) 7.42 (d, J = 8.20 Hz, 1 H) 7.56 (t, J = 7.61 Hz, 1 H) 7.61 (s, 1 H) 7.68-7.80 (m, 4 H) 7.85 (d, J = 6.83 Hz, 1 H) 8.33 (d, J = 8.20 Hz, 1 H). | 369 |
| 8 | 3-((methanesulfonamido)methyl)phenyl | N-[[3-(2-methyl-1-oxoisoquinolin-4-yl)phenyl]methyl]methanesulfonamide | (DMSO-d₆) 2.87 (s, 3 H) 3.56 (s, 3 H) 4.22 (d, J = 6.05 Hz, 2 H) 7.31-7.44 (m, 3 H) 7.45-7.62 (m, 5 H) 7.64-7.72 (m, 1 H) 8.32 (d, J = 7.61 Hz, 1 H) | 343 |
| 9 | 3-(methanesulfonamido)phenyl | N-[3-(2-methyl-1-oxoisoquinolin-4-yl)phenyl]methanesulfonamide | (DMSO-d₆) 3.03 (s, 3 H) 3.55 (s, 3 H) 7.16 (d, J = 7.61 Hz, 1 H) 7.23-7.28 (m, 2 H) 7.45 (t, J = 8.30 Hz, 1 H) 7.48-7.57 (m, 3 H) 7.67-7.72 (m, 1 H) 8.31 (d, J = 7.03 Hz, 1 H) 9.88 (br. s., 1 H) | 329 |
| 10 | 3-(N-ethylsulfamoyl)phenyl | N-ethyl-3-(2-methyl-1-oxoisoquinolin-4-yl)benzenesulfonamide | (DMSO-d₆) 0.92-1.02 (m, 3 H) 2.76-2.86 (m, 2 H) 3.56 (s, 3 H) 7.43 (d, J = 8.20 Hz, 1 H) 7.53-7.60 (m, 2 H) 7.64 (t, J = 5.66 Hz, 1 H) 7.68-7.75 (m, 3 H) 7.80-7.88 (m, 2 H) 8.29-8.36 (m, 1 H) | 343 |

TABLE 3-continued

| Ex. No. | R[1] | Name | $^1$H NMR (ppm (δ), 400 MHz) | MS (M + H) |
|---|---|---|---|---|
| 11 | | 4-(3-ethylsulfonylphenyl)-2-methylisoquinolin-1-one | (CHLOROFORM-d) 1.33 (t, J = 7.42 Hz, 3 H) 3.18 (q, J = 7.42 Hz, 2 H) 3.65-3.69 (m, 3 H) 7.10 (s, 1 H) 7.43 (d, J = 8.01 Hz, 1 H) 7.51-7.57 (m, 1 H) 7.60-7.76 (m, 3 H) 7.93-7.98 (m, 2 H) 8.53 (dd, J = 8.01, 0.98 Hz, 1 H) | 328 |
| 12 | | 4-[3-(dimethylsulfamoylamino)phenyl]-2-methyl-1-oxoisoquinoline | (DMSO-d6) 2.71 (s, 6 H) 3.55 (s, 3 H) 7.10 (d, J = 7.03 Hz, 1 H) 7.22-7.25 (m, 2 H) 7.41 (t, J = 7.71 Hz, 1 H) 7.48 (s, 1 H) 7.50-7.56 (m, 2 H) 7.67-7.72 (m, 1 H) 8.31 (d, J = 7.81 Hz, 1 H) 10.02 (br. s., 1 H) | 358 |
| 13 | | N-[3-(2-methyl-1-oxoisoquinolin-4-yl)phenyl]ethanesulfonamide | (DMSO-d6) 1.20 (t, J = 7.13 Hz, 3 H) 3.13 (q, J = 7.29 Hz, 2 H) 3.55 (s, 3 H) 7.14 (d, J = 7.03 Hz, 1 H) 7.25 (br. s., 2 H) 7.38-7.59 (m, 4 H) 7.69 (t, J = 7.61 Hz, 1 H) 8.31 (d, J = 8.01 Hz, 1 H) 9.92 (s, 1 H) | 343 |
| 14 | | 2-methyl-4-(3-morpholin-4-ylsulfonylphenyl)isoquinolin-1-one | (DMSO-d6) 3.02-3.09 (m, 4 H) 3.68 (s, 3 H) 3.73-3.80 (m, 4 H) 7.09 (s, 1 H) 7.43 (d, J = 7.81 Hz, 1 H) 7.53-7.58 (m, 1 H) 7.61-7.73 (m, 3 H) 7.78-7.84 (m, 2 H) 8.55 (d, J = 7.03 Hz, 1 H) | 385 |

Example 15

N-benzyl-2-methoxy-5-(2-methyl-1-oxoisoquinolin-4-yl)benzenesulfonamide

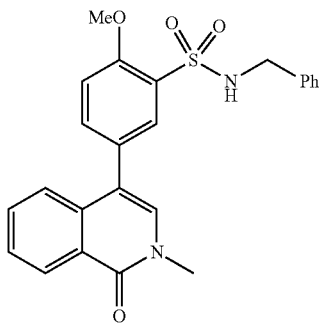 [SMILES: COc1ccc(-c2cn(C)c(=O)c3ccccc23)cc1S(=O)(=O)NCc1ccccc1]

For about 3 min, $N_2$ was bubbled through the mixture of 4-bromo-2-methylisoquinolin-1(2H)-one (56 mg, 0.24 mmol), [3-(benzylsulfamoyl)-4-methoxyphenyl]boronic acid (83 mg, 0.26 mmol), aqueous 2M $Na_2CO_3$ (0.375 mL) and Pd(dppf)Cl$_2$ (9 mg, 0.001 mmol) in dioxane (1.5 mL) which was then microwaved at 120° C. for 1 h and then filtered through a plug of anhydrous $Na_2SO_4$ using ethyl acetate to transfer and rinse. Silica gel chromatography, eluting with 0-60% EA in hexane over 6 min and continuing 60% isocratic EA gave the title compound (60 mg, 0.14 mmol) as a white solid in 58% yield. $^1$H NMR (400 MHz, DMSO-d$_6$) δ 3.57 (s, 3H), 3.89 (s, 3H), 4.11 (d, J=6.32 Hz, 2H), 7.16-7.23 (m, 6H), 7.34 (d, J=8.08 Hz, 1H), 7.47 (s, 1H), 7.53-7.59 (m, 2H), 7.65 (d, J=2.27 Hz, 1H), 7.72-7.77 (m, 1H), 7.94 (t, J=6.32 Hz, 1H), 8.34 (d, J=7.33 Hz, 1H). LCMS (M+H)[+] 435.

Examples 16-17 in Table 4 were prepared from 4-bromo-2-methylisoquinolin-1(2H)-one and the appropriate boronic acid/ester in a manner similar to Example 15.

TABLE 4

[Structure: 4-R1-2-methyl-isoquinolin-1(2H)-one core]

| Ex. No. | R¹ | Name | ¹H NMR (ppm (δ), 400 MHz) | MS (M + H) |
|---|---|---|---|---|
| 16 | [3-SO₂NH₂-4-OMe-phenyl] | 2-methoxy-5-(2-methyl-1-oxoisoquinolin-4-yl)benzenesulfonamide | (DMSO-d₆) 3.57 (s, 3 H) 3.97 (s, 3 H) 7.18 (s, 2 H) 7.35 (d, J = 8.59 Hz, 1 H) 7.44 (d, J = 8.08 Hz, 1 H) 7.50 (s, 1 H) 7.57 (t, J = 7.45 Hz, 1 H) 7.65 (dd, J = 8.46, 2.15 Hz, 1 H) 7.71 (t, J = 7.58 Hz, 1 H) 7.76 (d, J = 2.27 Hz, 1 H) 8.34 (d, J = 8.34 Hz, 1 H) | 345 |
| 17 | [3-NHSO₂Me-4-Me-phenyl] | N-[2-methyl-5-(2-methyl-1-oxoisoquinolin-4-yl)phenyl]methanesulfonamide | (DMSO-d₆) 2.38 (s, 3 H) 3.02 (s, 3 H) 3.57 (s, 3 H) 7.24 (dd, J = 7.83, 1.77 Hz, 1 H) 7.34 (d, J = 1.52 Hz, 1 H) 7.38 (d, J = 7.83 Hz, 1 H) 7.50 (s, 1 H) 7.53-7.58 (m, 2 H) 7.67-7.72 (m, 1 H) 8.30-8.36 (m, 1 H) 9.18 (s, 1 H) | 343 |

Example 18

N-benzyl-2-methoxy-5-(2-methyl-1-oxoisoquinolin-4-yl)benzamide

Step 1: N-benzyl-5-bromo-2-methoxybenzamide

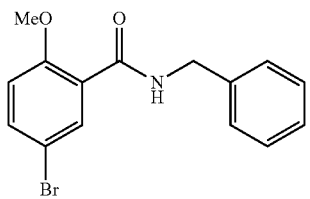 [SMILES: COc1ccc(Br)cc1C(=O)NCc1ccccc1]

To an ice bath cooled mixture of 5-bromo-2-methoxybenzoic acid (439 mg, 1.9 mmol) in 1:1 CH₂Cl₂:DMF (4 mL) was added benzylamine (0.228 mL, 2.1 mmol), EDCI (438 mg, 2.3 mmol), HOBt (311 mg, 2.3 mmol) and NEtiPr₂ (0.496 mL, 2.85 mmol). The mixture was then stirred at room temperature until the reaction was complete. Extractive work up with ethyl acetate, washing with saturated aqueous NaHCO₃, H₂O, saturated aqueous KHSO₄ and brine, gave the title compound (550 mg) after isolation which was carried forward without purification. LCMS (M+H)⁺ 320, 322.

Step 2: N-benzyl-2-methoxy-5-(tetramethyl-1,3,2-dioxaborolan-2-yl)benzamide

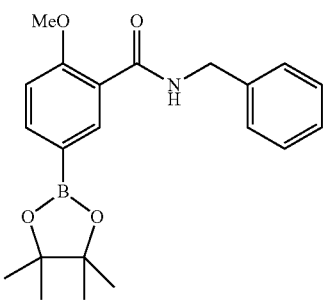 [SMILES: COc1ccc(B2OC(C)(C)C(C)(C)O2)cc1C(=O)NCc1ccccc1]

For about 3 min, N₂ was bubbled through a mixture of the title compound of N-benzyl-5-bromo-2-methoxybenzamide (174 mg, 0.54 mmol), 4,4,5,5-tetramethyl-2-(tetramethyl-1,3,2-dioxaborolan-2-yl)-1,3,2-dioxaborolane (166 mg, 0.65 mmol), potassium acetate (159 mg, 1.62 mmol) and Pd(dppf)Cl₂ (20 mg, 0.03 mmol) in anhydrous DMF (4.2 mL). After heating at 90° C. for about 2 h under N₂, silica gel chromatography, eluting with 0-40% EA in hexane over 7 min and continuing 40% isocratic EA gave the title compound (138 mg, 0.38 mmol) as a white solid in 70% yield. LCMS (M+H)⁺ 368.

Step 3: N-benzyl-2-methoxy-5-(2-methyl-1-oxoisoquinolin-4-yl)benzamide

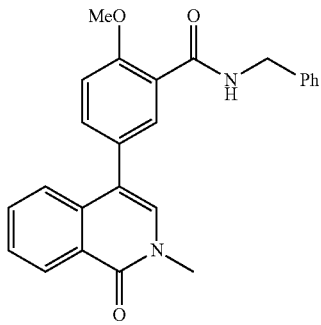 [SMILES: COc1ccc(-c2cn(C)c(=O)c3ccccc23)cc1C(=O)NCc1ccccc1]

For about 3 min, N₂ was bubbled through a mixture of N-benzyl-2-methoxy-5-(tetramethyl-1,3,2-dioxaborolan-2-yl)benzamide (51 mg, 0.14 mmol), 4-bromo-2-methylisoquinolin-1(2H)-one (30 mg, 0.13 mmol), aqueous 1M K₃PO₄ (0.3 mL) and Pd(dppf)Cl₂ (10 mg, 0.013 mmol) in dioxane (1.15 mL) which was then microwaved at 100° C. for 1 h. Work up similar to Example 15 and purification by silica gel chromatography, eluting with 5-50% EA in hexane over 4 min and continuing 50% isocratic EA gave the title compound (37 mg, 0.14 mmol) as a tan solid in 71% yield. ¹H NMR (400 MHz, DMSO-d₆) δ 3.57 (s, 3H), 3.97 (s, 3H), 4.52 (d, J=6.06 Hz, 2H), 7.21-7.37 (m, 6H), 7.47-7.51 (m, 2H), 7.56 (td, J=5.37, 2.15 Hz, 2H), 7.68-7.73 (m, 1H), 7.79 (d, J=2.27 Hz, 1H), 8.33 (d, J=7.83 Hz, 1H), 8.79 (t, J=6.06 Hz, 1H). LCMS (M+H)⁺ 399.

Examples 19-31 in Table 5 were prepared from 4-bromo-2-methylisoquinolin-1(2H)-one and the appropriate boronic acid/ester in a manner similar to Example 18, step 3. For Examples 20-26 the microwave temperature was increased to 120° C. Aniline hydrochlorides were prepared by treating the aniline with anhydrous HCl in methanol as the final step.

TABLE 5

| Ex. No. | R¹ | Name | ¹H NMR (ppm (δ), 400 MHz) | MS (M + H) |
|---|---|---|---|---|
| 19 | (3,4-dihydro-2H-1,4-benzoxazin-6-yl) | 4-(3,4-dihydro-2H-1,4-benzoxazin-6-yl)-2-methylisoquinolin-1-one | (DMSO-d₆) 3.50-3.59 (m, 3 H) 4.14-4.19 (m, 2 H) 5.87 (br. s., 1 H) 6.51 (dd, J = 8.08, 2.02 Hz, 1 H) 6.61 (d, J = 2.02 Hz, 1 H) 6.74 (d, J = 8.08 Hz, 1 H) 7.38 (s, 1 H) 7.50-7.55 (m, 1 H) 7.58 (d, J = 7.83 Hz, 1 H) 7.66-7.72 (m, 1 H) 8.30 (d, J = 8.08 Hz, 1 H) | 293 |
| 20 | (2-oxo-1,3-dihydroindol-6-yl) | 2-methyl-4-(2-oxo-1,3-dihydroindol-6-yl)isoquinolin-1-one | (DMSO-d₆) 3.55 (s, 2 H) 3.56 (s, 3 H) 6.85 (s, 1 H) 7.00 (dd, J = 7.58, 1.52 Hz, 1 H) 7.32 (d, J = 7.58 Hz, 1 H) 7.49 (s, 1 H) 7.53-7.58 (m, 2 H) 7.67-7.72 (m, 1 H) 8.31-8.35 (m, 1 H) 10.47 (s, 1 H) | 291 |
| 21 | 3-SO₂NH₂-phenyl | 3-(2-methyl-1-oxoisoquinolin-4-yl)benzenesulfonamide | (DMSO-d₆) 3.59 (s, 3 H) 7.43 (s, 2 H) 7.48 (d, J = 8.08 Hz, 1 H) 7.56-7.61 (m, 2 H) 7.67-7.75 (m, 3 H) 7.87-7.92 (m, 2 H) 8.36 (d, J = 8.08 Hz, 1 H) | 315 |
| 22 | 3-SO₂NH(CH₂)₂OH-phenyl | N-(2-hydroxyethyl)-3-(2-methyl-1-oxoisoquinolin-4-yl)benzenesulfonamide | (DMSO-d₆) 2.85 (q, J = 6.06 Hz, 2 H) 3.39 (q, J = 6.06 Hz, 2 H) 3.59 (s, 3 H) 4.70 (t, J = 5.56 Hz, 1 H) 7.47 (d, J = 8.08 Hz, 1 H) 7.56-7.59 (m, 1 H) 7.61 (s, 1 H) 7.66-7.77 (m, 4 H) 7.83-7.88 (m, 2 H) 8.36 (d, J = 8.08 Hz, 1 H) | 359 |
| 23 | 4-F-3-NH₂·HCl-phenyl | 4-(5-amino-2-fluorophenyl)-2-methylisoquinolin-1-one hydrochloride | (DMSO-d₆) 3.57 (s, 3 H partially obscured) 7.08-7.22 (m, 2 H) 7.24 (d, J = 9.60 Hz, 1 H) 7.32 (t, J = 9.09 Hz, 1 H) 7.54-7.60 (m, 2 H) 7.67-7.73 (m, 1 H) 8.32 (d, J = 7.83 Hz, 1 H | 269 |

TABLE 5-continued

| Ex. No. | R¹ | Name | ¹H NMR (ppm (δ), 400 MHz) | MS (M + H) |
|---|---|---|---|---|
| 24 | 2,4-difluoro-5-aminophenyl (NH₂·HCl) | 4-(5-amino-2,4-difluorophenyl)-2-methylisoquinolin-1-one hydrochloride | (DMSO-d₆) 3.55 (s, 3 H) 6.83 (dd, J = 9.73, 7.96 Hz, 1 H) 7.19-7.28 (m, 2 H) 7.51-7.58 (m, 2 H) 7.67-7.72 (m, 1 H) 8.30 (d, J = 8.08 Hz, 1 H) | 287 |
| 25 | 3-fluoro-5-aminophenyl (NH₂·HCl) | 4-(3-amino-5-fluorophenyl)-2-methylisoquinolin-1-one hydrochloride | (DMSO-d₆) 3.55 (s, 3 H) 6.47-6.56 (m, 2 H) 6.59 (s, 1 H) 7.51 (s, 1 H) 7.52-7.62 (m, 2 H) 7.69-7.75 (m, 1 H) 8.32 (d, J = 8.08 Hz, 1 H) | 269 |
| 26 | 3-amino-4-fluorophenyl (NH₂·HCl) | 4-(3-amino-4-fluorophenyl)-2-methylisoquinolin-1-one hydrochloride | (DMSO-d₆) 3.55 (s, 3 H) 6.64 (d, J = 2.53 Hz, 1 H) 6.89 (dd, J = 8.59, 2.02 Hz, 1 H) 7.13 (dd, J = 11.49, 8.21 Hz, 1 H) 7.45 (s, 1 H) 7.52-7.58 (m, 2 H) 7.67-7.74 (m, 1 H) 8.32 (d, J = 7.07 Hz, 1 H) | 269 |
| 27 | 3-(N-benzylsulfamoyl)phenyl | N-benzyl-3-(2-methyl-1-oxoisoquinolin-4-yl)benzenesulfonamide | (DMSO-d₆) 3.59 (s, 3 H) 4.08 (d, J = 6.06 Hz, 2 H) 7.17-7.29 (m, 5 H) 7.40 (d, J = 7.83 Hz, 1 H) 7.54 (s, 1 H) 7.58 (t, J = 7.58 Hz, 1 H) 7.68-7.76 (m, 3 H) 7.80 (s, 1 H) 7.85 (td, J = 4.48, 1.89 Hz, 1 H) 8.26 (t, J = 6.32 Hz, 1 H) 8.35 (d, J = 8.08 Hz, 1 H) | 405 |
| 28 | 3-(propane-1-sulfonamido)phenyl | N-[3-(2-methyl-1-oxoisoquinolin-4-yl)phenyl]propane-1-sulfonamide | (DMSO-d₆) 0.96 (t, J = 7.45 Hz, 3 H) 1.72 (sxt, J = 7.48 Hz, 2 H) 3.10-3.15 (m, 2 H) 3.57 (s, 3 H) 7.16 (d, J = 7.58 Hz, 1 H) 7.26-7.30 (m, 2 H) 7.43-7.59 (m, 4 H) 7.68-7.73 (m, 1 H) 8.34 (d, J = 7.83 Hz, 1 H) 9.91 (s, 1 H) | 357 |
| 29 | 3-(butane-1-sulfonamido)phenyl | N-[3-(2-methyl-1-oxoisoquinolin-4-yl)phenyl]butane-1-sulfonamide | (DMSO-d₆) 0.84 (t, J = 7.33 Hz, 3nH) 1.37 (sxt, J = 7.38 Hz, 2 H) 1.67 (dt, J = 15.35, 7.61 Hz, 2 H) 3.10-3.18 (m, 2 H) 3.57 (s, 3 H) 7.16 (d, J = 7.58 Hz, 1 H) 7.24-7.33 (m, 2 H) 7.41-7.60 (m, 4 H) 7.64-7.74 (m, 1 H) 8.34 (d, J = 8.08 Hz, 1 H) 9.91 (s, 1 H) | 371 |
| 30 | 2-methoxy-5-(methanesulfonamido)phenyl | N-[2-methoxy-5-(2-methyl-1-oxoisoquinolin-4-yl)phenyl]methanesulfonamide | (DMSO-d₆) 3.00 (s, 3 H) 3.57 (s, 3 H) 3.90 (s, 3 H) 7.18-7.23 (m, 1 H) 7.24-7.30 (m, 1 H) 7.33 (d, J = 2.27 Hz, 1 H) 7.47 (s, 1 H) 7.55 (dd, J = 7.58, 5.05 Hz, 2 H) 7.65-7.73 (m, 1 H) 8.31-8.37 (m, 1 H) 9.04 (s, 1 H) | 359 |
| 31 | 3-[N(Me)CO₂tBu]phenyl | tert-butyl N-methyl-N-[3-(2-methyl-1-oxoisoquinolin-4-yl)phenyl]carbamate | (DMSO-d₆) 1.41 (s, 9 H) 3.24 (s, 3 H) 3.57 (s, 3 H) 7.25 (d, J = 7.33 Hz, 1 H) 7.32-7.38 (m, 2 H) 7.44-7.60 (m, 4 H) 7.67-7.73 (m, 1 H) 8.34 (d, J = 7.83 Hz, 1 H) | 365 |

Example 32

2-methyl-4-[3-(methylamino)phenyl]isoquinolin-1-one hydrochloride

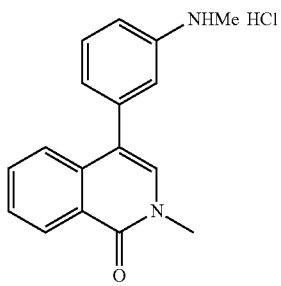 [SMILES: Cl ; CNc1cccc(-c2cn(C)c(=O)c3ccccc23)c1]

To the title compound of Example 31 (48 mg, 0.13 mmol) was added 4 M HCl in dioxane (3 mL). After stirring about 1 h, the volatile components were removed under vacuum. Hexane was added and evaporated (×2). The resulting white solid was dried under vacuum to give the title compound (39 mg, 0.13 mmol) in quantitative yield. $^1$H NMR (400 MHz, DMSO-d$_6$) δ ppm 2.85 (s, 3H), 3.57 (s, 3H), 7.10 (br. s., 3H), 7.44 (br. s., 1H), 7.51-7.60 (m, 3H), 7.68-7.74 (m, 1H), 8.34 (d, J=7.58 Hz, 1H). LCMS (M+H)$^+$ 265.

Example 33

N-methyl-N-[3-(2-methyl-1-oxoisoquinolin-4-yl)phenyl]methanesulfonamide

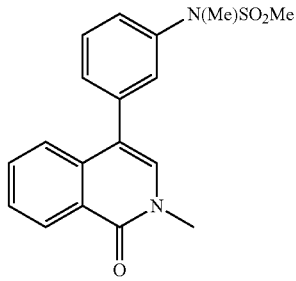

To the title compound of Example 32 (35 mg, 0.12 mmol) in anhydrous CH$_2$Cl$_2$ (0.3 mL), pyridine (0.1 mL) and NEtiPr$_2$ (0.021 mL, 0.12 mmol) was added methanesulfonyl chloride (0.011 mL, 0.14 mmol). After 0.5-1 h, ice was added to the mixture followed by water and ethyl acetate. Extractive work up, washing with H$_2$O, a 1:1 aqueous saturated KHSO$_4$:H$_2$O, and brine, and purification on silica gel eluting with 35-80% EA in hexane over 6 min and continuing 80% isocratic EA gave the title compound (22 mg, 0.06 mmol) as a cream solid in 54% yield. $^1$H NMR (400 MHz, DMSO-d$_6$) δ ppm 3.00 (s, 3H), 3.30 (s, 3H), 3.58 (s, 3H), 7.40 (d, J=7.58 Hz, 1H), 7.45-7.61 (m, 6H), 7.71 (td, J=7.58, 1.26 Hz, 1H), 8.34 (dd, J=8.21, 1.14 Hz, 1H). LCMS (M+H)$^+$ 343.

Examples 34-40 in Table 6 were prepared in one step by sulfonylation of the aniline Examples 23-26 from Table 5 using methanesulfonyl chloride in a manner similar to Example 33 (1 step from the indicated Example No.) or in two steps from 4-bromo-2-methylisoquinolin-1(2H)-one and the appropriate aniline boronic acid/ester in a manner similar to Example 23 followed by sulfonylation of the aniline with methanesulfonyl chloride in a manner similar to Example 33 (2 steps).

TABLE 6

| Ex. No. | R$^1$ | Name | No. of steps (from Ex. No.) | $^1$H NMR (ppm (δ), 400 MHz) | MS (M + H) |
|---|---|---|---|---|---|
| 34 | F-phenyl with NHSO$_2$Me | N-[4-fluoro-3-(2-methyl-1-oxoisoquinolin-4-yl)phenyl]methanesulfonamide | 1 step (from Ex. 23) | $^1$H NMR (400 MHz, DMSO-d$_6$) δ ppm 3.04 (s, 3 H) 3.57 (s, 3 H) 7.22-7.27 (m, 2 H) 7.30-7.40 (m, 2 H) 7.53-7.59 (m, 1 H) 7.61 (s, 1 H) 7.66-7.74 (m, 1 H) 8.32 (d, J = 8.08 Hz, 1 H) 9.83 (s, 1 H) | 347 |

TABLE 6-continued

| Ex. No. | R¹ | Name | No. of steps (from Ex. No.) | ¹H NMR (ppm (δ), 400 MHz) | MS (M + H) |
|---|---|---|---|---|---|
| 35 | 2,4-difluoro-5-(NHSO₂Me)phenyl | N-[2,4-difluoro-5-(2-methyl-1-oxoisoquinolin-4-yl)phenyl]methanesulfonamide | 1 step (from Ex. 24) | ¹H NMR (400 MHz, DMSO-d₆) δ ppm 3.08 (s, 3 H) 3.57 (s, 3 H) 7.24 (d, J = 8.08 Hz, 1 H) 7.45 (t, J = 8.21 Hz, 1 H) 7.53-7.60 (m, 2 H) 7.62 (s, 1 H) 7.70 (t, J = 7.58 Hz, 1 H) 8.32 (d, J = 7.83 Hz, 1 H) 9.70 (s, 1 H) | 365 |
| 36 | 3-fluoro-5-(NHSO₂Me)phenyl | N-[3-fluoro-5-(2-methyl-1-oxoisoquinolin-4-yl)phenyl]methanesulfonamide | 1 step (from Ex. 25) | ¹H NMR (400 MHz, DMSO-d₆) δ ppm 3.12 (s, 3 H) 3.57 (s, 3 H) 7.01-7.13 (m, 3 H) 7.54-7.63 (m, 3 H) 7.70-7.77 (m, 1 H) 8.33 (d, J = 8.08 Hz, 1 H) 10.16 (s, 1 H) | 347 |
| 37 | 2-fluoro-5-(NHSO₂Me)phenyl | N-[2-fluoro-5-(2-methyl-1-oxoisoquinolin-4-yl)phenyl]methanesulfonamide | 1 step (from Ex. 26) | ¹H NMR (400 MHz, DMSO-d₆) δ ppm 3.09 (s, 3 H) 3.57 (s, 3 H) 7.28-7.36 (m, 1 H) 7.39-7.48 (m, 2 H) 7.49-7.60 (m, 3 H) 7.67-7.74 (m, 1 H) 8.34 (d, J = 8.08 Hz, 1 H) 9.75 (s, 1 H) | 347 |
| 38 | 4-chloro-3-(NHSO₂Me)phenyl | N-[4-chloro-3-(2-methyl-1-oxoisoquinolin-4-yl)phenyl]methanesulfonamide | 2 steps | ¹H NMR (400 MHz, DMSO-d₆) δ ppm 3.08 (s, 3 H) 3.56 (s, 3 H) 7.07 (d, J = 7.83 Hz, 1 H) 7.23 (d, J = 2.78 Hz, 1 H) 7.33 (dd, J = 8.72, 2.65 Hz, 1 H) 7.51-7.62 (m, 3 H) 7.64-7.70 (m, 1 H) 8.28-8.36 (m, 1 H) 10.04 (s, 1 H) | 363, 365 |
| 39 | 4-methyl-3-(NHSO₂Me)phenyl | N-[4-methyl-3-(2-methyl-1-oxoisoquinolin-4-yl)phenyl]methanesulfonamide | 2 steps | ¹H NMR (400 MHz, DMSO-d₆) δ ppm 2.01 (s, 3 H) 3.00 (s, 3 H) 3.56 (s, 3 H) 7.02 (d, J = 8.08 Hz, 1 H) 7.06 (d, J = 2.53 Hz, 1 H) 7.22 (dd, J = 8.21, 2.40 Hz, 1 H) 7.33 (d, J = 8.34 Hz, 1 H) 7.45 (s, 1 H) 7.51-7.56 (m, 1 H) 7.63-7.68 (m, 1 H) 8.32 (d, J = 8.08 Hz, 1 H) 9.71 (s, 1 H) | 343 |
| 40 | 3-(CF₃)-5-(NHSO₂Me)phenyl | N-[3-(2-methyl-1-oxoisoquinolin-4-yl)-5-(trifluoromethyl)phenyl]methanesulfonamide | 2 steps | ¹H NMR (400 MHz, DMSO-d₆) δ ppm 3.14 (s, 3 H) 3.58 (s, 3 H) 7.49-7.52 (m, 2 H) 7.54-7.61 (m, 3 H) 7.64 (s, 1 H) 7.70-7.76 (m, 1 H) 8.35 (d, J = 8.08 Hz, 1 H) 10.29 (s, 1 H) | 397 |

Example 41

N-[4-fluoro-3-[2-methyl-6-(1-methylpyrazol-4-yl)-1-oxoisoquinolin-4-yl]phenyl]methanesulfonamide Step 1: 2-methyl-6-(1-methylpyrazol-4-yl)isoquinolin-1-one

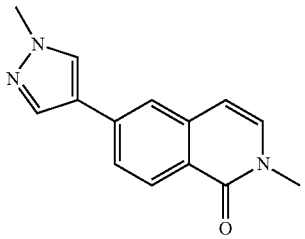 [SMILES: Cn1cc(-c2ccc3c(=O)n(C)ccc3c2)cn1]

A mixture of 6-bromo-2-methylisoquinolin-1-one (3.8 g, 16 mmol), 1-methyl-4-(tetramethyl-1,3,2-dioxaborolan-2-yl)-1H-pyrazole (6.69 g, 32 mmol), CsF (7.29 g, 48 mmol), Pd(PPh$_3$)$_2$Cl$_2$ (0.4 g, 1 mmol) in dioxane/H$_2$O (60/10 mL) was stirred at 90° C. for 12 h under N$_2$. The mixture was concentrated and the residue was purified by silica gel chromatography (PE:EA=2:1) to give the title compound (3.1 g, 81%) as a yellow solid. $^1$H NMR (CDCl$_3$, 400 MHz) δ 8.40 (d, J=12 Hz, 1H), 7.87 (s, 1H), 7.74 (s, 1H), 7.59-7.56 (dt, J$_1$=4 Hz, J$_2$=8 Hz, 2H), 7.07 (d, J=4 Hz, 1H), 6.48 (d, J=8 Hz, 1H) 3.98 (s, 3H), 3.61 (s, 3H). LCMS: 240.0 (M+H)$^+$ Step 2: 4-bromo-2-methyl-6-(1-methylpyrazol-4-yl)isoquinolin-1-one

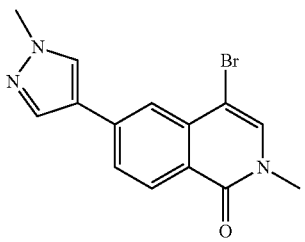 [SMILES: Cn1cc(-c2ccc3c(=O)n(C)cc(Br)c3c2)cn1]

Bromine (1.8 g, 11.25 mmol) in HOAc (6 mL) was added to the title compound of 2-methyl-6-(1-methylpyrazol-4-yl)isoquinolin-1-one (3 g, 12.5 mmol) in HOAc (24 mL) at 0° C. The mixture was stirred at 30° C. for 15 min, quenched with H$_2$O (100 mL), and the resulting yellow solid was collected by filtration to give the title compound (2.04 g, 56%). $^1$H NMR (CDCl$_3$, 400 MHz) δ 8.42 (d, J=8.4 Hz, 1H), 7.87 (d, J=28.8 Hz, 2H), 7.82 (d, J=15.6 Hz, 2H), 7.65 (d, J=8 Hz, 2H), 7.38 (s, 1H), 4.00 (s, 3H), 3.61 (s, 3H). LCMS: 318.0 (M+H)$^+$ Step 3: 4-(5-amino-2-fluorophenyl)-2-methyl-6-(1-methylpyrazol-4-yl)isoquinolin-1-one

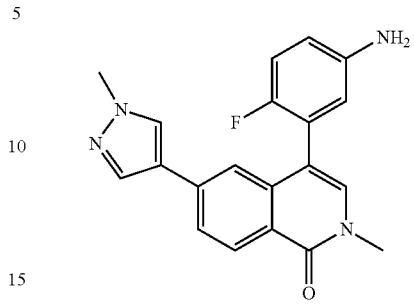

4-Bromo-2-methyl-6-(1-methylpyrazol-4-yl)isoquinolin-1-one (35 mg, 0.11 mmol), 4-fluoro-3-(4,4,5,5-tetramethyl-1,3,2-dioxaborolan-2-yl)aniline (29 mg, 0.12 mmol), Pd(dppf)Cl$_2$ (8 mg, 0.01 mmol) and aqueous 1 M K$_3$PO$_4$ (0.3 mL) in dioxane (1.2 mL) were microwaved at 120° C. for 1.25 h. Work up was similar to that described for Example 18, step 3. Silica gel chromatography, eluting with 100% EA followed by 10% methanol in EA, gave the title compound (25 mg, 0.07 mmol) as a cream solid in 64% yield. LCMS (M+H)$^+$ 349.

Step 4: N-[4-fluoro-3-[2-methyl-6-(1-methylpyrazol-4-yl)-1-oxoisoquinolin-4-yl]phenyl]methanesulfonamide

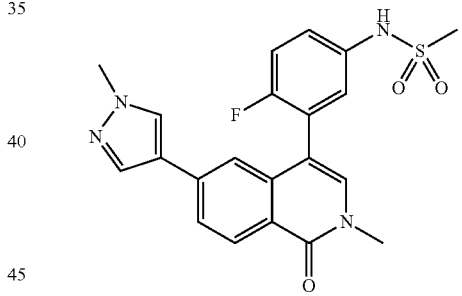

4-(5-Amino-2-fluorophenyl)-2-methyl-6-(1-methylpyrazol-4-yl)isoquinolin-1-one (25 mg, 0.07 mmol) in pyridine (0.1 mL) and anhydrous CH$_2$Cl$_2$ (0.3 mL) was treated with methanesulfonyl chloride (0.007 mL, 0.09 mmol) in a manner similar to Example 33. After a similar work up, silica gel chromatography, eluting with 50-100% EA in hexane over 4 min and continuing isocratic 100% EA, gave the title compound (24 mg, 0.06 mmol) as a white solid in 78% yield. $^1$H NMR (400 MHz, DMSO-d$_6$) δ 3.06 (s, 3H), 3.56 (s, 3H), 3.85 (s, 3H), 7.22-7.45 (m, 4H), 7.59 (s, 1H), 7.76 (dd, J=8.34, 1.52 Hz, 1H), 7.85 (s, 1H), 8.16 (s, 1H), 8.29 (d, J=8.34 Hz, 1H), 9.82 (s, 1H). LCMS (M+H)$^+$ 427.

Examples 42-45 in Table 7 were prepared from title compound of Example 41, step 2, in one step using the appropriate phenyl boronic acid/ester in a manner similar to Example 18, step 3, (1 step) or in two steps from the aniline boronic acid/ester followed sulfonylation of the aniline with the either methanesulfonyl chloride or ethanesulfonyl chloride in a manner similar to Example 41, steps 3 and 4, (2 steps).

TABLE 7

| Ex. No. | R¹ | Name | No. of steps (from Ex. No.) | ¹H NMR (ppm (δ), 400 MHz) | MS (M + H) |
|---|---|---|---|---|---|
| 42 | (3-NHSO₂Me-phenyl) | N-[3-[2-methyl-6-(1-methylpyrazol-4-yl)-1-oxoisoquinolin-4-yl]phenyl]methanesulfonamide | 1 step | (DMSO-d₆) 3.07 (s, 3 H) 3.56 (s, 3 H) 3.85 (s, 3 H) 7.23 (d, J = 7.83 Hz, 1 H) 7.28 (d, J = 8.08 Hz, 1 H) 7.34 (s, 1 H) 7.41-7.54 (m, 2 H) 7.66 (s, 1 H) 7.72-7.80 (m, 1 H) 7.86 (s, 1 H) 8.16 (s, 1 H) 8.30 (d, J = 8.34 Hz, 1 H) 9.87 (s, 1 H) | 409 |
| 43 | (2,4-difluoro-5-NHSO₂Me-phenyl) | N-[2,4-difluoro-5-[2-methyl-6-(1-methylpyrazol-4-yl)-1-oxoisoquinolin-4-yl]phenyl]methanesulfonamide | 2 steps | (DMSO-d₆) 3.10 (s, 3 H) 3.55 (s, 3 H) 3.85 (s, 3 H) 7.33 (s, 1 H) 7.44-7.63 (m, 3 H) 7.77 (dd, J = 8.59, 1.52 Hz, 1 H) 7.89 (s, 1 H) 8.19 (s, 1 H) 8.28 (d, J = 8.34 Hz, 1 H) 9.71 (s, 1 H) | 445 |
| 44 | (3-SO₂Et-phenyl) | 4-(3-ethylsulfonylphenyl)-2-methyl-6-(1-methylpyrazol-4-yl)isoquinolin-1-one | 1 step | (DMSO-d₆) 1.17 (t, J = 7.33 Hz, 3 H) 3.40 (q, J = 7.41 Hz, 2 H) 3.58 (s, 3 H) 3.85 (s, 3 H) 7.56 (s, 1 H) 7.63 (s, 1 H) 7.75-8.00 (m, 6 H) 8.16 (s, 1 H) 8.32 (d, J = 8.34 Hz, 1 H) | 409 |
| 45 | (4-Cl-3-NHSO₂Et-phenyl) | N-[4-chloro-3-[2-methyl-6-(1-methylpyrazol-4-yl)-1-oxoisoquinolin-4-yl]phenyl]ethanesulfonamide | 2 steps | (DMSO-d₆) 1.14-1.28 (m, 3 H) 3.11-3.28 (m, 2 H) 3.55 (s, 3 H) 3.84 (s, 3 H) 7.13 (s, 1 H) 7.26 (d, J = 2.53 Hz, 1 H) 7.36 (dd, J = 8.72, 2.65 Hz, 1 H) 7.54 (s, 1 H) 7.61 (d, J = 8.84 Hz, 1 H) 7.72-7.77 (m, 1 H) 7.81 (s, 1 H) 8.12 (s, 1 H) 8.28 (d, J = 8.34 Hz, 1 H) 10.08 (s, 1H) | 457, 459 |

Example 46

4-[2-(cyclopropylmethoxy)-5-methylsulfonylphenyl]-2-methyl-6-(1-methylpyrazol-4-yl)isoquinolin-1-one Step 1: 2-bromo-1-(cyclopropylmethoxy)-4-methanesulfonylbenzene

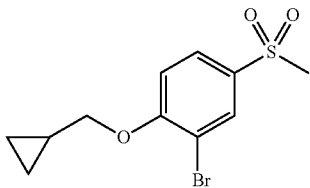 [SMILES: CS(=O)(=O)c1ccc(OCC2CC2)c(Br)c1]

A mixture of 2-bromo-4-methanesulfonylphenol (7.2 g, 29 mmol), (chloromethyl)cyclopropane (4.3 g, 32 mmol) and K₂CO₃ (8 g, 58 mmol) in acetone (80 mL) was stirred at 80° C. for 5 h. The mixture was quenched with water (40 mL). Extractive work up with ethyl acetate and purification by preparative HPLC gave the title compound (2.5 g, 28.6%). ¹H NMR (CDCl₃, 400 MHz) δ 8.12 (d, J=2.3 Hz, 1H), 7.84 (dd, J₁=2.3 Hz, J₂=8.7 Hz, 1H), 6.97 (d, J=8.8 Hz, 1H), 3.99 (d, J=6.7 Hz, 2H), 3.05 (s, 3H), 1.23-1.43 (m, 1H), 0.70 (d, J=7.9 Hz, 2H), 0.44 (d, J=5.4 Hz, 2H).

Step 2: 2-methyl-6-(1-methylpyrazol-4-yl)-4-(4,4,5,5-tetramethyl-1,3,2-dioxaborolan-2-yl)isoquinolin-1-one

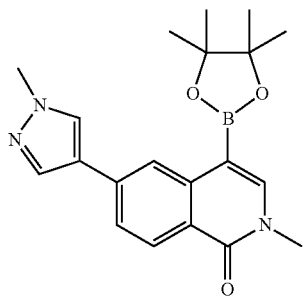 [SMILES: Cn1cc(-c2ccc3c(=O)n(C)cc(B4OC(C)(C)C(C)(C)O4)c3c2)cn1]

A mixture of the title compound of Example 41, step 2 (1.4 g, 4.41 mmol), 4,4,5,5-tetramethyl-2-(tetramethyl-1,3,2-dioxaborolan-2-yl)-1,3,2-dioxaborolane (2.24 g, 8.83 mmol), KOAc (1.08 g, 11.08 mmol), Pd(dppf)Cl₂ (100 mg, 0.137 mmol) in dioxane (50 mL) was stirred at 90° C. for 12 h under N₂. Purification by column chromatography on silica gel (PE:EA=3:1) gave the title compound (200 mg, 12%) as a yellow solid. ¹H NMR (CDCl₃, 400 MHz) δ 8.55 (d, J=1.5 Hz, 1H), 8.40 (d, J=8.4 Hz, 1H), 7.90 (s, 1H), 7.71 (d, J=16.8 Hz, 2H), 4.00 (s, 3H), 3.63 (s, 3H), 1.40 (s, 12H)

Step 3: 4-[2-(cyclopropylmethoxy)-5-methylsulfonylphenyl]-2-methyl-6-(1-methylpyrazol-4-yl)isoquinolin-1-one

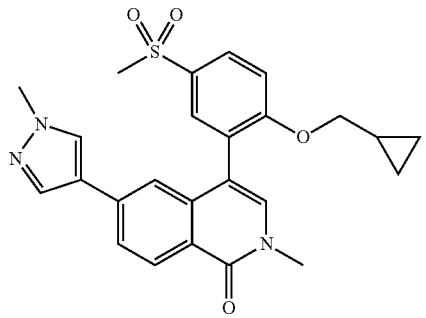 [SMILES: Cn1cc(-c2ccc3c(=O)n(C)cc(-c4cc(S(C)(=O)=O)ccc4OCC4CC4)c3c2)cn1]

A mixture of 2-bromo-1-(cyclopropylmethoxy)-4-methanesulfonylbenzene (20.8 mg, 0.068 mmol), 2-methyl-6-(1-methylpyrazol-4-yl)-4-(4,4,5,5-tetramethyl-1,3,2-dioxaborolan-2-yl)isoquinolin-1-one (30 mg, 0.08 mmol), NaHCO₃ (14.28 mg, 0.17 mmol), and Pd(dppf)Cl₂ (10 mg, 0.014 mmol) in dioxane (2.0 mL) and H₂O (0.5 mL) was microwaved under N₂ at 100° C. for 30 min. Purification by preparative HPLC gave the title compound (11 mg, 28%) as a white solid. ¹H NMR (CDCl₃, 400 MHz) δ 8.48 (d, J=8.4 Hz, 1H), 7.98-8.04 (m, 1H), 7.89 (d, J=2.4 Hz, 1H), 7.68 (s, 1H), 7.63 (s, 1H), 7.58-7.62 (m, 1H), 7.19-7.21 (m, 1H), 7.11-7.15 (m, 1H), 7.09 (s, 1H), 3.93 (s, 3H), 3.83-3.91 (m, 2H), 3.66 (s, 3H), 3.12 (s, 3H), 0.94-1.04 (m, 1H), 0.30-0.40 (m, 2H), 0.00-0.12 (m, 2H). LCMS: 464.1 (M+H)⁺

Example 47

N-[3-(6-fluoro-2-methyl-1-oxoisoquinolin-4-yl)phenyl]methanesulfonamide

Step 1: 6-fluoro-2-methylisoquinolin-1-one

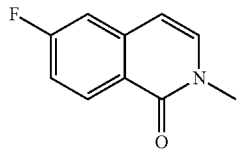

Sodium hydride (60% in mineral oil) (211 mg, 5.27 mmol) was added to 6-fluoro-1,2-dihydroisoquinolin-1-one (716 mg, 4.39 mmol) in anhydrous DMF (6 mL) cooled in an ice bath. The mixture was stirred for about 30 min at room temperature and methyl iodide (0.328 mL, 5.27 mmol) was added dropwise. After 1 h, the reaction was judged to be about 60% complete and additional methyl iodide (0.2 mL, 3.2 mmol) was added. After about 1 h, ice and water and ethyl acetate were added to the mixture. After extractive work up with ethyl acetate, the title compound (836 mg) was obtained as a cream solid and carried on without purification.

Step 2: 4-bromo-6-fluoro-2-methylisoquinolin-1-one

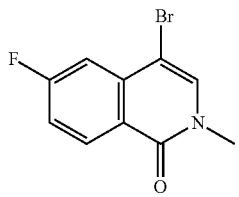

Bromine (232 mg, 1.45 mmol, 0.097 mL) in acetic acid (1.0 mL) was added dropwise, quickly to 6-fluoro-2-methylisoquinolin-1-one (283 mg, 1.61 mmol) in acetic acid (7.0 mL) under $N_2$ and cooled in an ice bath. The ice bath was removed and the thick suspension was stirred for 10 min at room temperature. Ice and water and ethyl acetate were added. Extractive work up with ethyl acetate, washing with aqueous 0.5 N NaOH, $H_2O$, saturated aqueous $KHSO_4$ and brine, gave the title compound as a cream solid (313 mg) which was carried on without purification.

Step 3: N-[3-(6-fluoro-2-methyl-1-oxoisoquinolin-4-yl)phenyl]methanesulfonamide

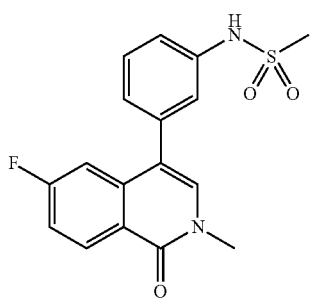 [SMILES: Cn1cc(-c2cccc(NS(C)(=O)=O)c2)c2cc(F)ccc2c1=O]

For about 3 min $N_2$ was bubbled through a mixture of 4-bromo-6-fluoro-2-methylisoquinolin-1-one (41 mg, 0.16 mmol), (3-methanesulfonamidophenyl)boronic acid (38 mg, 0.18 mmol), aqueous 1 M $K_3PO_4$ (0.3 mL) and $Pd(dppf)Cl_2$ (12 mg, 0.016 mmol) in dioxane (1.2 mL) which was then microwaved for 1 h at 120° C. Work up was similar to that described for Example 18, step 3. Purification using silica gel chromatography, eluting with 40-80% EA in hexane over 5 min and continuing 80% isocratic EA gave the title compound (28 mg, 0.08 mmol) as a cream solid in a combined yield of 38% over steps 1-3. $^1$H NMR (400 MHz, DMSO-$d_6$) 3.06 (s, 3H), 3.56 (s, 3H), 7.15-7.22 (m, 2H), 7.25-7.31 (m, 2H), 7.41 (td, J=8.65, 2.65 Hz, 1H), 7.45-7.52 (m, 1H), 7.61 (s, 1H), 8.40 (dd, J=9.09, 6.06 Hz, 1H), 9.88 (s, 1H). LCMS $(M+H)^+$ 347.

Examples 48-50 in Table 8 were prepared from title compound of Example 47, step 2, in one step using the appropriate phenyl boronic acid/ester in a manner similar to Example 47, step 3 (1 step) or in two steps from the appropriate aniline boronic acid/ester in a manner similar to Example 47, step 3 followed by sulfonylation of the aniline with either methanesulfonyl chloride or ethanesulfonyl chloride in a manner similar to Example 41, step 4 (2 steps).

TABLE 8

| Ex. No. | R$^1$ | Name | No. of steps (from Ex. No.) | $^1$H NMR (ppm (δ), 400 MHz) | MS (M + H) |
|---|---|---|---|---|---|
| 48 | (3-sulfamoylphenyl, SO$_2$NH$_2$) | 3-(6-fluoro-2-methyl-1-oxoisoquinolin-4-yl)benzenesulfonamide | 1 | (DMSO-$d_6$) 3.58 (s, 3 H) 7.11 (dd, J = 10.61, 2.53 Hz, 1 H) 7.41-7.49 (m, 3 H) 7.65-7.76 (m, 3 H) 7.87-7.93 (m, 2 H) 8.42 (dd, J = 8.84, 6.06 Hz, 1 H) | 333 |
| 49 | (3-(N-ethylsulfamoyl)phenyl) | N-ethyl-3-(6-fluoro-2-methyl-1-oxoisoquinolin-4-yl)benzenesulfonamide | 1 | (DMSO-$d_6$) 1.00 (t, J = 7.33 Hz, 3 H) 2.81-2.89 (m, 2 H) 3.58 (s, 3 H) 7.09 (dd, J = 10.36, 2.53 Hz, 1 H) 7.44 (td, J = 8.65, 2.40 Hz, 1 H) 7.65 (t, J = 5.68 Hz, 1 H) 7.69 (s, 1 H) 7.72-7.79 (m, 2 H) 7.82-7.90 (m, 2 H) 8.42 (dd, J = 9.09, 6.06 Hz, 1 H) | 361 |

TABLE 8-continued

| Ex. No. | R[1] | Name | No. of steps (from Ex. No.) | $^1$H NMR (ppm (δ), 400 MHz) | MS (M + H) |
|---|---|---|---|---|---|
| 50 | 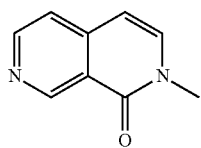 | N-[4-chloro-3-(6-fluoro-2-methyl-1-oxoisoquinolin-4-yl)phenyl]ethanesulfonamide | 2 | (DMSO-$d_6$) 1.22 (t, J = 7.33 Hz, 3 H) 3.16-3.24 (m, 2 H) 3.56 (s, 3 H) 6.72 (dd, J = 10.23, 2.40 Hz, 1 H) 7.24 (d, J = 2.53 Hz, 1 H) 7.34 (dd, J = 8.59, 2.78 Hz, 1 H) 7.40 (td, J = 8.72, 2.53 Hz, 1 H) 7.60 (d, J = 8.84 Hz, 1 H) 7.65 (s, 1 H) 8.38 (dd, J = 8.84, 5.81 Hz, 1 H) 9.86-10.28 (m, 1 H) | 395, 397 |

Example 51

N-[3-(2-methyl-1-oxo-2,7-naphthyridin-4-yl)phenyl]methanesulfonamide

Step 1: 2-methyl-2,7-naphthyridin-1-one

Sodium hydride (2.9 g, 72.5 mmol, 60% in oil) was added in portions to 2H-2,7-naphthyridin-1-one (3.5 g, 24.0 mmol) in dry DMF (50 mL) at 0° C. After stirring at 0° C. for 30 min, MeI (17.0 g, 118.7 mmol) was added and the mixture was stirred for an additional 30 min. Saturated aqueous NH$_4$Cl (250 mL) and ethyl acetate (100 mL) were added. Extractive work up with ethyl acetate and purification by silica gel chromatography (DCM:MeOH=100:1 to 10:1) gave the title compound (0.5 g, 13.1%) as a yellow solid. $^1$H NMR (CDCl3, 400 MHz) δ 9.54 (1H, s), 8.64-8.62 (1H, d, J=5.6 Hz), 7.27-7.26 (1H, d, J=5.2 Hz), 7.22-7.20 (1H, d, J=5.6 Hz), 6.37-6.35 (1H, d, J=7.2 Hz), 3.54 (3H, s).

Step 2: 4-bromo-2-methyl-2,7-naphthyridin-1-one

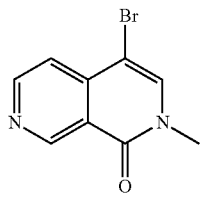

Bromine (1.1 g, 6.87 mmol) in acetic acid (10 mL) was added dropwise to 2-methyl-2,7-naphthyridin-1-one (1.1 g, 6.87 mmol) in acetic acid (60 mL) at 10-15° C. After stirring at 15° C. for 1 h, the mixture was concentrated under vacuum. Purification by silica gel chromatography (DCM:MeOH=50:1 to 10:1) gave the title compound (0.45 g, 27.4%) as a yellow solid. $^1$H NMR (CDCl3, 400 MHz) δ 9.61 (1H, s), 8.86-8.85 (1H, d, J=5.6 Hz), 7.62-7.60 (1H, d, J=5.6 Hz), 7.56 (1H, s), 3.63 (3H, s).

Step 3: N-[3-(2-methyl-1-oxo-2,7-naphthyridin-4-yl)phenyl]methanesulfonamide

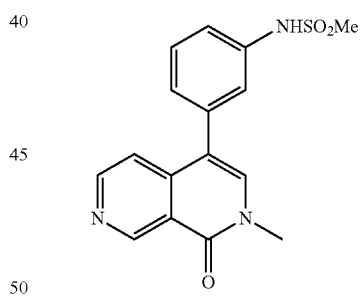

A mixture of 4-bromo-2-methyl-2,7-naphthyridin-1-one (50 mg, 0.21 mmol), [3-(methanesulfonamido)phenyl]boronic acid (68 mg, 0.31 mmol), Pd(dppf)Cl$_2$ (15.3 mg, 0.021 mmol) and aqueous K$_3$PO$_4$ (1 M, 0.3 mL, 0.3 mmol) in dioxane (3 mL) was microwaved at 90° C. for 40 min. Purification by silica gel chromatography (PE:EA=100:1 to 1:1) followed by preparative HPLC gave the title compound (48.1 mg, 69.8%) as a white solid. $^1$H NMR (400 MHz, Methanol-d4) δ 9.56 (s, 1H), 8.68 (d, J=6.4 Hz, 1H), 7.96 (s, 1H), 7.81 (d, J=6.4 Hz, 1H), 7.51 (t, J=7.6 Hz, 1H), 7.37 (d, J=2.0 Hz, 1H), 7.34 (d, J=1.6 Hz, 1H), 7.26 (d, J=7.6 Hz, 1H), 3.71 (s, 3H), 3.03 (s, 3H). LCMS: 330.0 (M+H)[+]

Examples 52-56 in Table 9 were prepared from title compound of Example 51, step 2, in one step using the appropriate phenyl boronic acid/ester in a manner similar to Example 51, step 3.

TABLE 9

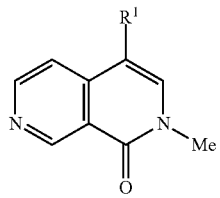

| Ex. No. | R¹ | Name | ¹H NMR (ppm (δ), 400 MHz) | MS (M + H) |
|---|---|---|---|---|
| 52 | 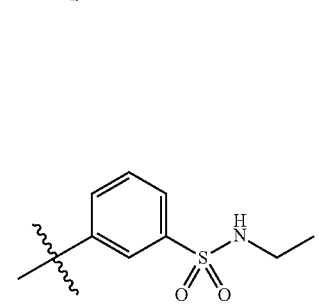 | N-[3-(2-methyl-1-oxo-2,7-naphthyridin-4-yl)phenyl]ethane-sulfonamide | ¹H NMR (400 MHz, CDCl₃) δ 9.71 (s, 1 H), 8.72 (d, J = 6.0 Hz, 1 H), 7.48 (t, J = 7.6 Hz, 1 H), 7.37 (d, J = 6.0 Hz, 1 H), 7.29-7.26 (m, 3 H), 7.20 (d, J = 7.6 Hz, 1 H), 6.74 (s, 1 H), 3.69 (s, 3 H), 3.21 (q, J = 7.6 Hz, 2 H), 1.43 (t, J = 7.6 Hz, 3 H) | 344 |
| 53 | 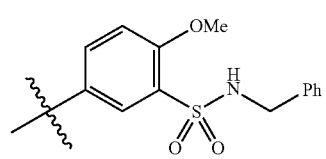 [SMILES: *c1ccc(OC)c(S(=O)(=O)NCc2ccccc2)c1] | N-ethyl-3-(2-methyl-1-oxo-2,7-naphthyridin-4-yl)benzene-sulfonamide | ¹H NMR (400 MHz, CDCl₃) δ 9.72 (s, 1 H), 8.73 (d, J = 5.6 Hz, 1 H), 7.95 (d, J = 7.2 Hz, 1 H), 7.92 (s, 1 H), 7.67-7.62 (m, 2 H), 7.33 (s, 1 H), 7.30 (d, J = 5.6 Hz, 1 H), 4.48 (s, 1 H), 3.70 (s, 3 H), 3.13-3.12 (m, 2 H), 1.18 (t, J = 7.2 Hz, 3 H) | 344 |
| 54 | 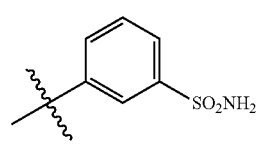 [SMILES: *c1cccc(S(N)(=O)=O)c1] | N-benzyl-2-methoxy-5-(2-methyl-1-oxo-2,7-naphthyridin-4-yl)benzene-sulfonamide | ¹H NMR (400 MHz, CDCl₃) δ 9.72 (s, 1 H), 8.74 (d, J = 5.6 Hz, 1 H), 7.93 (s, 1 H), 7.54 (dd, J₁ = 8.4 Hz, J₂ = 2.4 Hz, 1 H), 7.27-7.26 (s, 6 H), 7.19 (d, J = 3.2 Hz, 1 H) 7.06 (d, J = 8.4 Hz, 1 H), 5.26 (s, 1 H), 4.20 (d, J = 5.2 Hz, 2 H), 3.96 (s, 3 H), 3.70 (s, 3 H) | 436 |
| 55 | 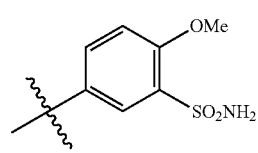 [SMILES: *c1ccc(OC)c(S(N)(=O)=O)c1] | 3-(2-methyl-1-oxo-2,7-naphthyridin-4-yl)benzene-sulfonamide | ¹H NMR (400 MHz, DMSO-d6) δ 9.46 (d, J = 9.2 Hz,1 H), 8.73 (d, J = 5.6 Hz, 1 H), 7.89-7.88 (m, 3 H), 7.73-7.69 (m, 2 H), 7.39-7.38 (d, J = 5.2 Hz, 1 H), 3.60 (s, 3 H) | 316 |
| 56 |  | 2-methoxy-5-(2-methyl-1-oxo-2,7-naphthyridin-4-yl)benzene-sulfonamide | ¹H NMR (400 MHz, DMSO-d6) δ 9.44 (s, 1 H), 8.72 (d, J = 5.6 Hz, 1 H), 7.80 (s, 1 H), 7.77 (d, J = 2.4 Hz, 1 H), 7.65-7.63 (dd, J₁ = 8.4 Hz, J₂ = 2.4 Hz, 1 H), 7.34 (d, J = 8.4 Hz, 1 H), 7.33 (d, J = 5.2 Hz, 1 H), 3.97 (s, 3 H), 3.59 (s, 3 H) | 346 |

Example 57

N-[4-(2,4-difluorophenoxy)-3-(2-methyl-1-oxo-2,7-naphthyridin-4-yl)phenyl]ethanesulfonamide

Step 1: 4-(2,4-difluorophenoxy)-3-(4,4,5,5-tetramethyl-1,3,2-dioxaborolan-2-yl)aniline

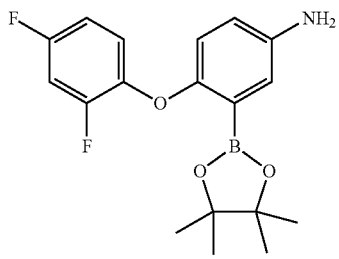 [SMILES: CC1(C)OB(c2cc(N)ccc2Oc2ccc(F)cc2F)OC1(C)C]

A mixture of 3-bromo-4-(2,4-difluorophenoxy)aniline (300 mg, 1 mmol), 4,4,5,5-tetramethyl-2-(4,4,5,5-tetramethyl-1,3,2-dioxaborolan-2-yl)-1,3,2-dioxaborolane (518 mg, 2 mmol), KOAc (300 mg, 3 mmol) and Pd(dppf)Cl$_2$ (73.2 mg, 0.1 mmol) in dioxane (6 mL) was microwaved at 100° C. for 2 h. Purification by silica gel chromatography (PE:EA=10:1 to 5:1) gave the title compound (200 mg, 56%). LCMS: 348.0 (M+H)$^+$

Step 2: 4-[5-amino-2-(2,4-difluorophenoxy)phenyl]-2-methyl-2,7-naphthyridin-1-one

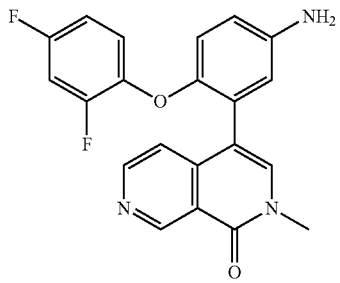 [SMILES: Cn1cc(-c2cc(N)ccc2Oc2ccc(F)cc2F)c2ccncc2c1=O]

For 5 min, N$_2$ was bubbled through a mixture of 4-(2,4-difluorophenoxy)-3-(4,4,5,5-tetramethyl-1,3,2-dioxaborolan-2-yl)aniline (64.8 mg, 0.187 mmol), the title compound of Example 51, step 2 (30.0 mg, 0.124 mmol), K$_2$CO$_3$ (51.6 mg, 0.374 mmol) and Pd(dppf)Cl$_2$ (18.3 mg, 0.025 mmol) in dioxane (2.0 mL) and water (0.2 mL) which was then microwaved at 100° C. for 1 h. Purification by preparative TLC (DCM:MeOH=20:1, Rf=0.5) gave the title compound (25.0 mg, 53%) as yellow gum. LCMS: 380.0 (M+H)$^+$

Step 3: N-[4-(2,4-difluorophenoxy)-3-(2-methyl-1-oxo-2,7-naphthyridin-4-yl)phenyl]ethanesulfonamide

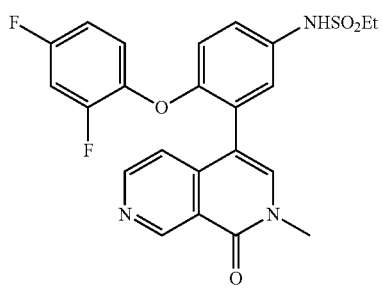

Ethanesulfonyl chloride (25.4 mg, 0.198 mmol) was added to 4-[5-amino-2-(2,4-difluorophenoxy)phenyl]-2-methyl-2,7-naphthyridin-1-one (25.0 mg, 0.066 mmol) and TEA (20.0 mg, 0.198 mmol) in DCM (5 mL) at 0° C. The mixture was stirred at room temperature for 18 h and then purified by preparative HPLC to give the title compound (8.5 mg, 27.4%) as yellow gum. $^1$H NMR (Methanol-d4, 400 MHz) δ 9.54 (s, 1H), 8.68 (d, J=4.4 Hz, 1H), 8.00 (s, 1H), 7.66 (d, J=8.4 Hz, 1H), 7.38-7.33 (m, 2H), 7.09-6.99 (m, 2H), 6.96-6.94 (d, J=8.4 Hz, 1H), 6.91-6.85 (m, 1H), 3.70 (s, 3H), 3.15 (q, J=7.6 Hz, 2H), 1.35 (t, J=7.6 Hz, 3H). LCMS: 472.1 (M+H)$^+$

Example 58

N-[3-(7-fluoro-2-methyl-1-oxoisoquinolin-4-yl)phenyl]methanesulfonamide

Step 1: 7-fluoro-2-methylisoquinolin-1-one

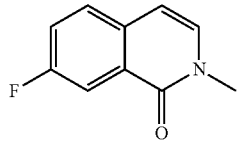

Under N$_2$, sodium hydride (710 mg, 29.4 mmol) was added to 7-fluoro-2H-isoquinolin-1-one (4 g, 24.55 mmol) in dry DMF (40 mL) at 0° C. After stirring at 0° C. for 20 min, CH$_3$I (5.2 g, 36.7 mmol) was added. The mixture was stirred at 26° C. for 2 h. Saturated aqueous NH$_4$Cl (20 mL) was added and after extractive work up with ethyl acetate, purification by silica gel chromatography (PE:EA=10:1) gave the title compound (2.2 g, 50%) as an off-white solid. $^1$H NMR (CDCl$_3$, 400 MHz) δ 8.06 (dd, J$_1$=9.6 Hz, J$_2$=2.8 Hz, 1H), 7.50 (dd, J$_1$=8.8 Hz, J$_2$=5.2 Hz, 1H), 7.38-7.36 (m, 1H), 7.03 (d, J=7.6 Hz, 1H), 6.48 (d, J=7.2 Hz, 1H), 3.61 (s, 3H). LCMS: 178.1 [M+H]$^+$

Step 2: 4-bromo-7-fluoro-2H-isoquinolin-1-one

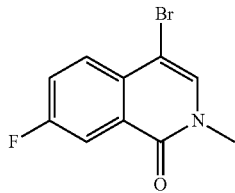

Bromine (3.8 g, 24 mmol) in acetic acid (6 mL) was added slowly to a mixture of 7-fluoro-2-methylisoquinolin-1-one (4 g, 22.4 mmol) in acetic acid (8 mL) at 0° C. After stirring at 26° C. for 2 h, the mixture was poured into water (100 mL) and the solid was collected by filtration. Purification by silica gel chromatography (PE:EA=20:1) gave the title compound (1.4 g, 44%) as an off-white solid. $^1$H NMR (CDCl$_3$, 400 MHz) δ 8.11 (d, J=9.2 Hz, 1H), 7.84 (dd, $J_1$=9.6 Hz, $J_2$=4.8 Hz, 1H), 7.49-7.45 (m, 1H), 7.34 (s, 1H), 3.62 (3H, s). LCMS: 255.9 [M+H]$^+$

Step 3: N-[3-(7-fluoro-2-methyl-1-oxoisoquinolin-4-yl)phenyl]methanesulfonamide

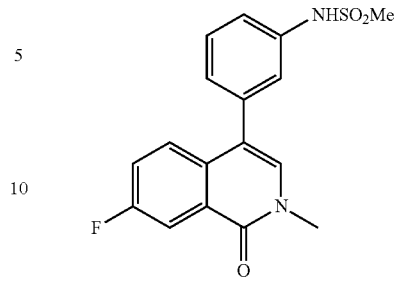

4-Bromo-7-fluoro-2H-isoquinolin-1-one was treated with [3-(methanesulfonamido)phenyl]boronic acid in a manner similar to Example 51, step 3. Isolation and purification also in a similar manner gave the title compound (18 mg, 26.5%) a white solid. $^1$H NMR (400 MHz, CDCl$_3$) δ 8.17 (dd, $J_1$=9.2 Hz, $J_2$=2.8 Hz, 1H), 7.52 (dd, J1=8.0 Hz, J2=4.0 Hz 1H), 7.50-7.45 (m, 1H), 7.38-7.32 (m, 1H), 7.31-7.27 (m, 2H), 7.26-7.21 (m, 1H), 7.03 (s, 1H), 6.72 (brs, 1H), 3.67 (s, 3H), 3.09 (s, 3H). LCMS: 347.0 (M+H)$^+$.

Examples 59-64 in Table 10 were prepared from title compound of Example 58, step 2 using the appropriate phenyl boronic acid/ester in a manner similar to Example 18, step 3.

TABLE 10

| Ex. No. | R$^1$ | Name | $^1H$ NMR ppm (δ) 400 Hz | MS (M + H) |
|---|---|---|---|---|
| 59 | ![3-SO2NHEt phenyl] | N-ethyl-3-(7-fluoro-2-methyl-1-oxoisoquinolin-4-yl)benzenesulfonamide | (CDCl$_3$) 8.17 (dd, $J_1$ = 9.6 Hz, $J_2$ = 2.4 Hz, 1 H), 7.93-7.92 (m, 2 H), 7.64-7.63 (s, 2 H), 7.46-7.45 (m, 1 H), 7.36-7.35 (m, 1 H), 7.06 (s, 1 H), 4.58 (brs, 1 H), 3.14-3.07 (m, 2 H), 1.16 (t, J = 7.2 Hz, 3 H) | 361 |
| 60 | ![4-OMe-3-SO2NHBn phenyl] | N-benzyl-5-(7-fluoro-2-methyl-1-oxoisoquinolin-4-yl)-2-methoxybenzenesulfonamide | (CDCl$_3$) 8.20 (dd, $J_1$ = 9.3 Hz, $J_2$ = 2.8 Hz, 1 H), 7.96 (d, J = 2.4 Hz, 1 H), 7.54 (dd, $J_1$ = 8.5 Hz, $J_2$ = 2.3 Hz, 1 H), 7.47-7.44 (m, 1 H), 7.41-7.36 (m, 1 H), 7.30-7.25 (m, 3 H), 7.22-7.20 (m, 2 H), 7.06 (d, J = 8.5 Hz, 1 H), 7.04 (s, 1 H), 5.34 (t, J = 6.0 Hz, 1 H), 4.21 (d, J = 6.3 Hz, 2 H), 3.97 (s, 3 H), 3.70 (s, 3 H) | 453 |
| 61 | ![3-SO2NH2 phenyl] | 3-(7-fluoro-2-methyl-1-oxoisoquinolin-4-yl)benzenesulfonamide | (CDCl$_3$) 7.13 (dd, $J_1$ = 9.6 Hz, $J_2$ = 2.8 Hz, 1 H), 7.03-7.01 (m, 2 H), 6.84-6.82 (m, 2 H), 6.76-6.74 (m, 1 H), 6.69 (s, 1 H), 6.67-6.66 (m, 1 H), 6.58-6.56 (m, 2 H), 2.71 (s, 3 H) | 333 |

TABLE 10-continued

| Ex. No. | R¹ | Name | ¹H NMR ppm (δ) 400 Hz | MS (M + H) |
|---|---|---|---|---|
| 62 | ![3-(NHSO2Et)phenyl] | N-[3-(7-fluoro-2-methyl-1-oxoisoquinolin-4-yl)phenyl]ethanesulfonamide | (CDCl$_3$) 8.17 (dd, J$_1$ = 9.2 Hz, J$_2$ = 2.8 Hz, 1 H), 7.53 (dd, J$_1$ = 8.8 Hz, J$_2$ = 3.6 Hz, 1 H), 7.44 (t, J = 8.4 Hz, 1 H), 7.28-7.27 (m, 3 H), 7.20 (d, J = 7.6 Hz, 1 H), 7.03 (s, 1 H), 6.79 (s, 1 H), 3.67 (s, 3 H), 3.20 (q, J = 7.2 Hz, 2 H), 1.43 (t, J = 7.2 Hz, 3 H) | 361 |
| 63 | ![3-(SO2Et)phenyl] | 4-(3-ethylsulfonylphenyl)-7-fluoro-2-methylisoquinolin-1-one | (CDCl$_3$) 1.15 (t, J = 7.45 Hz, 3 H) 3.38 (q, J = 7.41 Hz, 2 H) 3.60 (s, 3 H) 7.52-7.57 (m, 1 H) 7.61-7.67 (m, 2 H) 7.78-7.87 (m, 2 H) 7.91-8.03 (m, 3 H) | 346 |
| 64 | ![4-OMe-3-SO2NH2 phenyl] | 5-(7-fluoro-2-methyl-1-oxoisoquinolin-4-yl)-2-methoxybenzenesulfonamide | (DMSO-d6) 7.98 (d, J = 7.2 Hz, 1 H), 7.74 (s, 1 H), 7.65-7.61 (m, 2 H), 7.51-7.48 (m, 2 H), 7.35 (d, J = 8.4 Hz, 1 H), 7.18 (s, 2 H), 3.97 (s, 3 H), 3.57 (s, 3 H) | 363 |

Example 65

2-methyl-4-(1-methylpyrazol-4-yl)isoquinolin-1-one

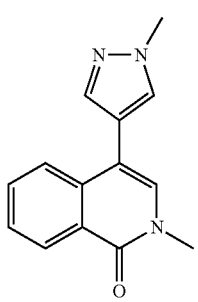 [SMILES: Cn1cc(-c2cn(C)c(=O)c3ccccc23)cn1]

For 3 min, N$_2$ was bubbled through a mixture of 4-bromo-2-methylisoquinolin-1(2H)-one (54 mg, 0.23 mmol), (1-methylpyrazol-4-yl)boronic acid (31 mg, 0.25 mmol), aqueous 2M Na$_2$CO$_3$ (0.375 mL) and Pd(dppf)Cl$_2$ (8 mg, 0.01 mmol) in 1,4-dioxane (1.5 mL) which was then microwaved at 120° C. for 1 h. Work up in a manner similar to Example 18, step 3, and two successive silica gel chromatographies, eluting with 15-80% EA in hexane over 6 min and continuing 80% isocratic EA followed by a second chromatography 15-100% EA in hexane over 6 min and continuing 100% isocratic EA gave the title compound (28 mg, 0.12 mmol) as a cream solid in 51% yield. $^1$H NMR (400 MHz, DMSO-d$_6$) δ ppm 3.54 (s, 3H) 3.92 (s, 3H) 7.50 (s, 1H) 7.55 (ddd, J=8.02, 5.87, 2.27 Hz, 1H) 7.60-7.64 (m, 1H) 7.70-7.80 (m, 2H) 7.95 (s, 1H) 8.31 (d, J=7.83 Hz, 1H). LCMS (M+H)$^+$ 240.

Examples 66-71

In Table 11 were prepared from 4-bromo-2-methylisoquinolin-1(2H)-one in a similar manner to Example 65 using commercially available boronic acids/esters or from commercially available tin compounds using standard Stille-type coupling conditions.

TABLE 11

| Ex No. | R¹ | Name | ¹H NMR (ppm (δ), 400 MHz) | MS (M + H) |
|---|---|---|---|---|
| 66 | ![furan-2-yl] | 4-(furan-2-yl)-2-methylisoquinolin-1-one | (CHLOROFORM-d) 3.61-3.70 (m, 3 H) 6.50-6.57 (m, 2 H) 7.37 (s, 1 H) 7.50-7.58 (m, 2 H) 7.69 (ddd, J = 8.30, 7.03, 1.46 Hz, 1 H) 7.93 (d, J = 8.20 Hz, 1 H) 8.51 (dd, J = 8.01, 0.98 Hz, 1 H) | 226 |

TABLE 11-continued

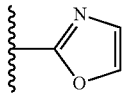

| Ex No. | R[1] | Name | $^1$H NMR (ppm (δ), 400 MHz) | MS (M+H) |
|---|---|---|---|---|
| 67 | 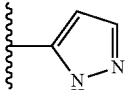 | 2-methyl-4-(1,3-oxazol-2-yl)isoquinolin-1-one | (CHLOROFORM-d) 3.72 (s, 3 H) 7.30 (s, 1 H) 7.56-7.61 (m, 1 H) 7.74 (s, 1 H) 7.79 (ddd, J = 8.40, 7.03, 1.37 Hz, 1 H) 7.99 (s, 1 H) 8.52 (dd, J = 8.01, 0.98 Hz, 1 H) 8.93 (d, J = 8.40 Hz, 1 H) | 227 |
| 68 | 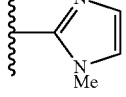 | 2-methyl-4-(1 H-pyrazol-5-yl)isoquinolin-1-one | (CHLOROFORM-d) 3.61-3.71 (m, 3 H) 6.66 (br. s., 1 H) 7.34 (s, 1 H) 7.57 (t, J = 7.42 Hz, 1 H) 7.68 (t, J = 7.52 Hz, 1 H) 7.76 (d, J = 8.01 Hz, 1 H) 7.83 (br. s., 1 H) 8.52 (d, J = 7.81 Hz, 1 H) | 226 |
| 69 | 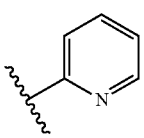 [SMILES: *c1ccccn1] | 2-methyl-4-(1-methyl-imidazol-2-yl)isoquinolin-1-one | (METHANOL-d4) 3.55 (s, 3 H) 3.65 (s, 3 H) 7.10 (br. s., 1 H) 7.17 (br. s., 1 H) 7.28 (s, 1 H) 7.54-7.62 (m, 2 H) 7.71 (t, J = 7.61 Hz, 1 H) 8.41 (d, J = 8.20 Hz, 1 H) | 240 |
| 70 | 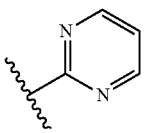 [SMILES: *c1ncccn1] | 2-methyl-4-pyridin-2-ylisoquinolin-1-one | (METHANOL-d4) 3.69 (s, 3 H) 7.48 (d, J = 5.86 Hz, 1 H) 7.58 (br. s., 2 H) 7.65 (d, J = 7.81 Hz, 1 H) 7.71 (t, J = 7.22 Hz, 1 H) 7.76-7.80 (m, 1 H) 7.98 (t, J = 7.03 Hz, 1 H) 8.42 (d, J = 7.81 Hz, 1 H) 8.68 (d, J = 3.32 Hz, 1 H) | 237 |
| 71 | 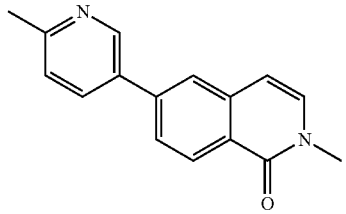 | 2-methyl-4-pyrimidin-2-ylisoquinolin-1-one | (METHANOL-d4) 3.73 (s, 3 H) 7.41 (t, J = 4.88 Hz, 1 H) 7.59 (t, J = 7.71 Hz, 1 H) 7.76 (t, J = 7.71 Hz, 1 H) 8.27 (t, 1 H) 8.42 (d, J = 8.20 Hz, 1 H) 8.82 (d, J = 8.40 Hz, 1 H) 8.90 (d, J = 4.88 Hz, 2 H) | 238 |

Example 72

N-[3-[2-methyl-6-(6-methylpyridin-3-yl)-1-oxoisoquinolin-4-yl]phenyl]ethanesulfonamide Step 1: 2-methyl-6-(6-methylpyridin-3-yl)isoquinolin-1-one

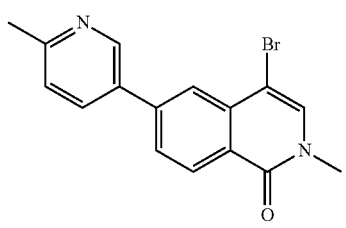

A mixture of 6-bromo-2-methylisoquinolin-1-one (160 mg, 0.67 mmol), (6-methylpyridin-3-yl)boronic acid (166 mg, 0.32 mmol), Pd(dppf)Cl$_2$ (60 mg, 0.08 mmol) and saturated aqueous NaHCO$_3$ (0.6 mL) in dioxane (6.5 mL) was microwaved at 110° C. for 1.5 h. Purification using silica gel chromatography (PE:EA=3:1 to 2:3) gave the title compound (160 mg, 95.2%) as a yellow solid. LCMS: 251.2 (M+H)$^+$ Step 2: 4-bromo-2-methyl-6-(6-methylpyridin-3-yl)isoquinolin-1-one

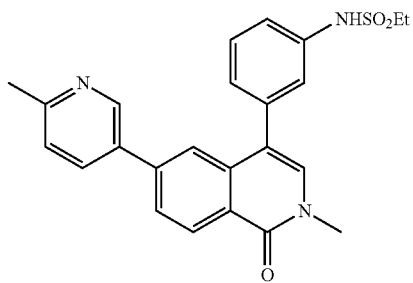

Bromine (97 mg, 0.61 mmol) in acetic acid (0.61 mL) was added dropwise to 2-methyl-6-(6-methylpyridin-3-yl)isoquinolin-1-one (160 mg, 0.64 mmol) in acetic acid (6 mL) at 0° C. After stirring at room temperature for 17 min, water (22 mL) was added and the pH was adjusted to 7-8 with 1M NaOH. Extractive work up with ethyl acetate and purification by silica gel chromatography (PE:EA=2:1 to 3:2) gave the title compound (135 mg, 64.3%) as a yellow solid. LCMS: 329.0 (M+H)$^+$ Step 3: N-[3-[2-methyl-6-(6-methylpyridin-3-yl)-1-oxoisoquinolin-4-yl]phenyl]ethanesulfonamide A mixture of 4-bromo-2-methyl-6-(6-methylpyridin-3-yl)isoquinolin-1-one (135 mg, 0.41 mmol), [3-(ethylsulfonylamino)phenyl]boronic acid (141 mg, 0.62 mmol), Pd(dppf)Cl$_2$ (35 mg, 0.05 mmol) and aqueous 1M K$_3$PO$_4$ (1.03 mL) in dioxane (6 mL) was microwaved at 100° C. for 1 h. Purification by silica gel chromatography (PE:EA=3:1 to 1:2) followed by preparative HPLC gave the title compound (25 mg, 14.1%) as a white solid. $^1$H NMR (CDCl$_3$, 400 MHz) δ 8.74 (d, J=2.0 Hz, 1H), 8.41 (d, J=8.4 Hz, 1H), 7.96 (d, J=8.0 Hz, 1H), 7.86 (d, J=8.8 Hz, 1H), 7.75 (s, 1H), 7.58 (s, 1H), 7.47 (t, J=8.0 Hz, 1H), 7.39 (s, 1H), 7.35 (d, J=8.4 Hz, 1H), 7.30 (d, J=8.4 Hz, 1H), 7.24 (d, J=8.4 Hz, 1H), 3.59 (s, 3H), 3.59 (s, 3H), 3.15 (q, J=7.2 Hz, 2H), 1.19 (t, J=7.2 Hz, 3H). LCMS: 434.1 (M+H)$^+$.

Examples 73-74 in Table 12 were prepared from 6-bromo-2-methylisoquinolin-1-one and phenylboronic acid in three steps in a manner similar to Example 72, steps 1-3. For Example 74, [3-methanesulfonamido)phenyl]boronic acid was substituted for [3-(ethylsulfonylamino)phenyl]boronic acid in step 3.

TABLE 12

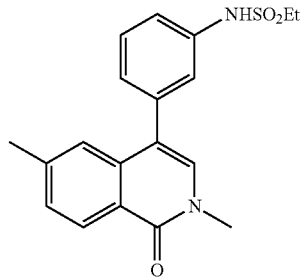

| Ex. No. | R$^1$ | Name | $^1$H NMR ppm (δ), 400 MHz | MS (M+H) |
|---|---|---|---|---|
| 73 | Ethyl | N-[3-(2-methyl-1-oxo-6-phenylisoquinolin-4-yl)phenyl]-ethanesulfonamide | (DMSO-d$_6$) 9.94 (brs, 1 H), 8.41 (d, J = 8.4 Hz, 1 H), 7.85 (d, J = 8.4 Hz, 1 H), 7.74 (s, 1 H), 7.67 (d, J = 7.6 Hz, 2 H), 7.57 (s, 1 H), 7.50-7.45 (m, 3 H), 7.42 (d, J = 7.6 Hz, 1 H), 7.38 (s, 1 H), 7.30 (d, J = 8.0 Hz, 1 H), 7.23 (d, J = 7.6 Hz, 1 H), 3.59 (s, 3 H), 3.14 (q, J = 7.2 Hz, 2 H), 1.19 (t, J = 7.2 Hz, 3 H). | 419 |
| 74 | Methyl | N-[3-(2-methyl-1-oxo-6-phenylisoquinolin-4-yl)phenyl]-methanesulfonamide | (CHLOROFORM-d) 8.60 (d, J = 8.4 Hz, 1 H), 7.78 (dd, J$_1$ = 8.4 Hz, J$_2$ = 1.6 Hz, 1 H), 7.72 (d, J = 1.2 Hz, 1 H), 7.60-7.58 (m, 2 H), 7.49-7.36 (m, 5H), 7.31 (d, J = 7.6 Hz, 1 H), 7.26-7.23 (m, 1 H), 7.10 (s, 1 H), 6.47 (s, 1 H), 3.70 (s, 3 H), 3.08 (s, 3 H) | 405 |

Example 75

N-[3-(2,6-dimethyl-1-oxoisoquinolin-4-yl)phenyl] ethanesulfonamide

Step 1: 2,6-dimethylisoquinolin-1-one

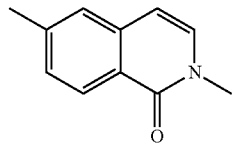

A mixture of 6-bromo-2-methylisoquinolin-1-one (200.0 mg, 0.84 mmol), methylboronic acid (251.0 mg, 4.2 mmol), Pd(PPh$_3$)$_4$ (93.0 mg, 0.08 mmol), K$_2$CO$_3$ (232.0 mg, 1.68 mmol) and H$_2$O (2 drops) in dioxane (10.0 mL) was microwaved at 120° C. for 1 h. Purification by silica gel chromatography (PE:EA=5:1) gave the title compound (120.0 mg, 82.8%) as a light yellow solid. LCMS: 174.3 (M+H)$^+$.

Step 2: 4-bromo-2,6-dimethylisoquinolin-1-one

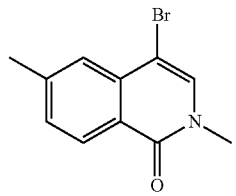

2,6-Dimethylisoquinolin-1-one (120.0 mg, 0.60 mmol) in acetic acid (4 mL) was treated with Br$_2$ (96 mg, 0.6 mmol) in acetic acid (0.6 mL) at 0° C. in a manner similar to Example 72, step 2. Isolation, also in a similar manner, gave the title compound (145.0 mg, 82.9%) as a white yellow solid. $^1$H NMR (CDCl$_3$, 400 MHz) δ 8.33 (d, J=8.0 Hz, 1H), 7.60 (s, 1H), 7.37 (d, J=8.0 Hz, 1H), 7.35 (s, 1H), 3.60 (s, 3H), 2.54 (s, 3H). LCMS: 252.1 (M+H)$^+$ Step 3: N-[3-(2,6-dimethyl-1-oxoisoquinolin-4-yl) phenyl]ethanesulfonamide NHSO$_2$Et 4-Bromo-2,6-dimethylisoquinolin-1-one (75.0 mg, 0.30 mmol), [3-(ethylsulfonylamino)phenyl]boronic acid (82.0 mg, 0.36 mmol), Pd(dppf)Cl$_2$ (22 mg, 0.03 mmol) and aqueous 1M K$_3$PO$_4$ (0.75 mL) in dioxane (4 mL) were reacted in a manner similar to Example 72, step 3. Isolation, also in a similar manner, gave the title compound (60.0 mg, 48.1%) as a white solid. $^1$H NMR (CDCl$_3$, 400 MHz) δ 8.42 (d, J=8.4 Hz, 1H), 7.46 (t, J=8.0 Hz, 1H), 7.34 (d, J=8.0 Hz, 1H), 7.29-7.27 (m, 2H), 7.24 (d, J=8.0 Hz, 1H), 7.03 (s, 1H), 6.68 (s, 1H), 3.65 (s, 3H), 3.21 (q, J=7.2 Hz, 2H), 2.42 (s, 3H), 1.43 (t, J=7.2 Hz, 3H). LCMS: 357.0 (M+H)$^+$ Examples 76-78 in Table 13 were prepared in three steps in a similar manner to Example 75 steps 1-3. For Examples 76 and 77, ethylboronic acid was substituted for methylboronic acid in step 1. For Examples 77 and 78, [3-(methanesulfonamido)phenyl]boronic acid was substituted for [3-(ethylsulfonylamino)phenyl]boronic acid in step 3.

TABLE 13

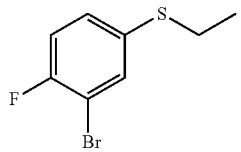

| Ex. No. | R$^1$ | R$^2$ | Name | $^1H$ NMR (ppm (δ), 400 MHz) | MS (M + H) |
|---|---|---|---|---|---|
| 76 | Ethyl | Ethyl | N-[3-(6-ethyl-2-methyl-1-oxoisoquinolin-4-yl)phenyl]-ethanesulfonamide | (CDCl$_3$) 8.41 (d, J = 8.4 Hz, 1 H), 7.42 (t, J = 8.4 Hz, 1 H), 7.38 (d, J = 8.4 Hz, 1 H), 7.29-7.25 (m, 2 H), 7.19 (d, J = 7.6 Hz, 1 H), 7.00 (s, 1 H), 6.90 (s, 1 H), 3.61 (s, 3 H), 3.17 (q, J = 7.6 Hz, 2 H), 2.67 (q, J = 7.6 Hz, 2 H), 1.39 (t, J = 7.6 Hz, 3 H), 1.19 (t, J = 7.6 Hz, 3 H) | 371 |
| 77 | Ethyl | Methyl | N-[3-(6-ethyl-2-methyl-1-oxoisoquinolin-4-yl)phenyl]-methanesulfonamide | (CDCl$_3$) 8.45 (d, J = 8.4 Hz, 1 H), 7.48 (t, J = 8.0 Hz, 1 H), 7.38 (d, J = 8.0 Hz, 1 H), 7.32-7.26 (m, 5H), 7.04 (s, 1 H), 6.66 (s, 1 H), 3.65 (s, 3 H), 3.10 (s, 3 H), 2.70 (q, J = 7.6 Hz, 2 H), 1.23 (t, J = 7.6 Hz, 3 H) | 357 |
| 78 | Methyl | Methyl | N-[3-(2,6-dimethyl-1-oxoisoquinolin-4-yl)phenyl]-methanesulfonamide | (DMSO-d$_6$) 9.88 (brs, 1 H), 8.23 (d, J = 8.0 Hz, 1 H), 7.49-7.45 (m, 2 H), 7.39 (d, J = 8.4 Hz, 1 H), 7.33 (s, 1 H), 7.28-7.24 (m, 2 H), 7.19 (d, J = 8.0 Hz, 1 H), 3.55 (s, 3 H), 3.06 (s, 3 H), 2.39 (s, 3 H) | 343 |

Example 79

4-(5-ethylsulfonyl-2-methoxyphenyl)-2-methyl-6-(1-methylpyrazol-4-yl)isoquinolin-1-one Step 1: 2-bromo-4-ethylsulfanyl-1-fluorobenzene

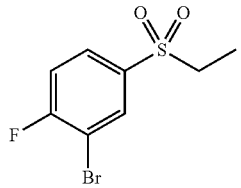

To a mixture of 3-bromo-4-fluorobenzenethiol (2.07 g, 10 mmol) and K$_2$CO$_3$ (4.14 g, 30 mmol) in acetone (20 mL) was added EtI (3.12 g, 20 mmol). The mixture was stirred at room temperature for 12 h, filtered, and the volatile components were removed under vacuum to give the title compound (2.34 g) as light yellow oil which was carried on without purification. $^1$H NMR (CDCl$_3$, 400 MHz): δ 7.54 (dd, J$_1$=6.4 Hz, J$_2$=2.4 Hz, 1H), 7.26-7.25 (m, 1H), 7.05 (t, J=8.4 Hz, 1H), 2.91 (q, J=7.6 Hz, 2H), 1.30 (t, J=7.6 Hz, 3H).

Step 2: 2-bromo-4-ethylsulfonyl-1-fluorobenzene

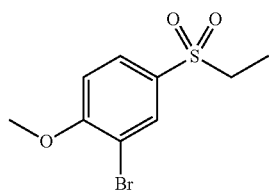

To 2-bromo-4-ethylsulfanyl-1-fluorobenzene (2.2 g, 9.36 mmol) in DCM (20 mL) was added m-CPBA (6.47 g, 37.4 mmol). The mixture was stirred at room temperature for 12 h. Aqueous saturated Na$_2$S$_2$O$_3$ (100 mL) was added, and extractive work up with CH$_2$Cl$_2$ gave the title compound (1.5 g, 50%) as a yellow solid which was carried on without purification. $^1$H NMR (CDCl$_3$, 400 MHz) δ 8.15 (dd, J1=6.4 Hz, J$_2$=2.4 Hz, 1H), 7.88-7.85 (m, 1H), 7.32 (t, J=8.4 Hz, 1H), 3.14 (q, J=7.2 Hz, 2H), 1.31 (t, J=7.6 Hz, 3H).

Step 3: 2-bromo-4-ethylsulfonyl-1-methoxybenzene

A mixture of 2-bromo-4-ethylsulfonyl-1-fluorobenzene (0.6 g, 2.25 mmol) and sodium methoxide (1.2 g, 22.2 mmol) in THF (20 mL) was stirred at room temperature for 18 h. Water (30 mL) was added and extractive work up with ethyl acetate followed by silica gel chromatography (PE: EA=10:1 to 1:1) gave the title compound (0.5 g, 79.4%) as a yellow solid. $^1$H NMR (CDCl$_3$, 400 MHz) δ 8.08 (d, J=2.4 Hz, 1H), 7.87-7.84 (dd, J$_1$=8.6 Hz, J$_2$=2.4 Hz, 1H), 7.04 (d, J=8.8 Hz, 1H), 3.99 (s, 3H), 3.11 (q, J=7.4 Hz, 2H), 1.30 (t, J=7.4 Hz, 3H).

Step 4: 4-(5-ethylsulfonyl-2-methoxyphenyl)-2-methyl-6-(1-methylpyrazol-4-yl)isoquinolin-1-one

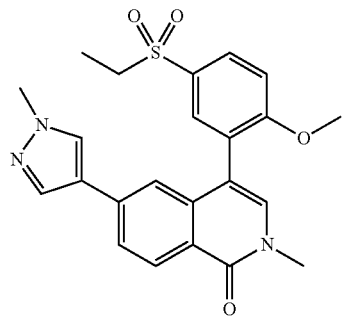 [SMILES: CCS(=O)(=O)c1ccc(OC)c(-c2cn(C)c(=O)c3ccc(-c4cnn(C)c4)cc23)c1]

For 5 min N$_2$ was bubbled into a mixture of 2-bromo-4-ethylsulfonyl-1-methoxybenzene (300 mg, 1.07 mmol), the title compound of Example 46, step 2 (300 mg, 0.82 mmol), K$_3$PO$_4$ (435.6 mg, 2.05 mmol) and Pd(dppf)Cl$_2$ (120.2 mg, 0.16 mmol) in dioxane (8 mL) and water (0.8 mL) which was then microwaved at 110° C. for 30 min. Purification by silica gel chromatography (DCM:MeOH=100:0 to 20:1) gave the title compound (200 mg, 55.7%) as a yellow solid. $^1$H NMR (CDCl$_3$, 400 MHz) δ 8.51 (d, J=8.4 Hz, 1H), 8.03 (dd, J$_1$=8.8 Hz, J$_2$=2.8 Hz, 1H), 7.86 (d, J=2.4 Hz, 1H), 7.72 (s, 1H), 7.64 (s, 1H), 7.63-7.61 (m, 1H), 7.19 (d, J=8.8 Hz, 1H), 7.15 (d, J=1.2 Hz, 1H), 7.09 (s, 1H), 3.97 (s, 3H), 3.85 (s, 3H), 3.68 (s, 3H), 3.18 (q, J=7.6 Hz, 2H), 1.35 (t, J=7.6 Hz, 3H). LCMS: 438.1 (M+H)$^+$ Example 80

4-(5-ethylsulfonyl-2-hydroxyphenyl)-2-methyl-6-(1-methylpyrazol-4-yl)isoquinolin-1-one

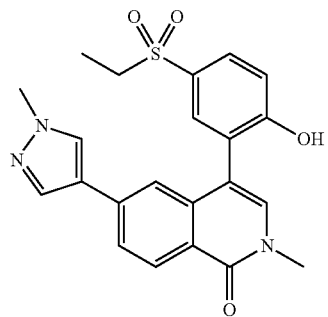 [SMILES: CCS(=O)(=O)c1ccc(O)c(-c2cn(C)c(=O)c3ccc(-c4cnn(C)c4)cc23)c1]

At −78° C., a 4 M solution of BBr$_3$ (2.3 mL, 9.2 mmol) in CH$_2$Cl$_2$ was added to the title compound of Example 79 (200.0 mg, 0.458 mmol) in dry CH$_2$Cl$_2$ (8 mL). The mixture was refluxed for 18 h. Extractive work up with CH$_2$Cl$_2$ and purification by silica gel chromatography (DCM: MeOH=100:1 to 20:1) gave the title compound (70 mg, 36.1%) as a brown solid. $^1$H NMR (CDCl$_3$, 400 MHz) δ 8.39 (d, J=8.4 Hz, 1H), 7.99 (s, 1H), 7.87 (dd, J$_1$=8.8 Hz, J$_2$=2.4 Hz, 1H), 7.80 (s, 1H), 7.79 (s, 1H), 7.76 (d, J=1.6 Hz, 1H), 7.39 (s, 1H), 7.35 (d, J=1.2 Hz, 1H), 7.18 (d, J=8.8 Hz, 1H), 3.91 (s, 3H), 3.67 (s, 3H), 3.25 (q, J=7.6 Hz, 2H), 1.27 (t, J=7.6 Hz, 3H). LCMS: 424.0 (M+H)$^+$ Example 81

4-(2-ethoxy-5-ethylsulfonylphenyl)-2-methyl-6-(1-methylpyrazol-4-yl)isoquinolin-1-one

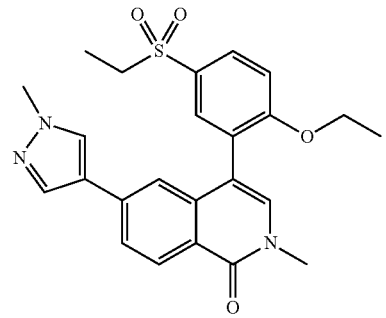 [SMILES: CCOc1ccc(S(=O)(=O)CC)cc1-c1cn(C)c(=O)c2ccc(-c3cnn(C)c3)cc12]

A mixture of the title compound of Example 80 (25.0 mg, 0.059 mmol), ethyl iodide (27.7 mg, 0.177 mmol), and K$_2$CO$_3$ (24.5 mg, 0.177 mmol) in acetone (2 mL) was stirred at room temperature for 18 h. After CH$_2$Cl$_2$ extractive work up, purification by preparative TLC (PE:EA=2:1) gave the title compound (15.8 mg, 60%) as a white solid. $^1$H NMR: (CDCl$_3$, 400 MHz) δ 8.48 (d, J=8.4 Hz, 1H), 7.97 (dd, J1=8.4 Hz, J$_2$=2.4 Hz, 1H), 7.86 (d, J=2.4 Hz, 1H), 7.68 (s, 1H), 7.62 (s, 1H), 7.61 (dd, J$_1$=8.4 Hz, J$_2$=1.6 Hz, 1H), 7.17 (d, J=1.2 Hz, 1H), 7.15 (d, J=8.4 Hz, 1H), 7.08 (s, 1H), 4.3 (q, J=7.2 Hz, 2H), 3.94 (s, 3H), 3.66 (s, 3H), 3.17 (q, J=7.6 Hz, 2H), 1.35 (t, J=7.6 Hz, 3H), 1.18 (t, J=7.2 Hz, 3H). LCMS: 452.1 (M+H)$^+$ Examples 82-84 in Table 14, the title compound of Example 80 was O-alkylated with the appropriate alkyl halide in a similar manner to Example 81. Example 85 in Table 14 was prepared in two steps by O-alkylation with tert-butyl N-(2-bromoethyl)carbamate in a similar manner to Example 81 followed by deprotection of the the Boc group in a manner similar to Example 32.

TABLE 14

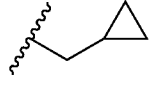

| Ex. No. | R¹ | Name | ¹H NMR (ppm (δ) 400 MHz) | MS (M + H) |
|---|---|---|---|---|
| 82 | 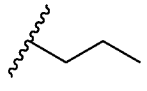 [SMILES: *CCC] | 4-[2-(cyclopropyl-methoxy)-5-ethylsulfonyl-phenyl]-2-methyl-6-(1-methylpyrazol-4-yl)isoquinolin-1-one | (CDCl₃) 8.51 (d, J = 8.4 Hz, 1 H), 7.97 (dd, J₁ = 8.4 Hz, J₂ = 2.4 Hz, 1 H), 7.88 (d, J = 2.8 Hz, 1 H), 7.70 (s, 1 H), 7.64 (s, 1 H), 7.62 (dd, J₁ = 8.4 Hz, J₂ = 1.6 Hz, 1 H), 7.21 (d, J = 1.6 Hz, 1 H), 7.13 (d, J = 8.8 Hz, 1 H), 7.11 (s, 1 H), 3.96 (s, 3 H), 3.91-3.86 (m, 2 H), 3.67 (s, 3 H), 3.17 (q, J = 7.6 Hz, 2 H), 1.34 (t, J = 7.6 Hz, 3 H), 0.99-0.96 (m, 1 H), 0.38-0.35 (m, 2 H), 0.10-0.02 (m, 2 H). | 478 |
| 83 | 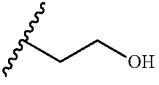 [SMILES: *CCO] | 4-(5-ethylsulfonyl-2-propoxyphenyl)-2-methyl-6-(1-methylpyrazol-4-yl)isoquinolin-1-one | (CDCl₃) 8.51 (d, J = 8.4 Hz, 1 H), 7.97 (dd, J₁ = 8.4 Hz, J₂ = 2.4 Hz, 1 H), 7.88 (d, J = 2.8 Hz, 1 H), 7.70 (s, 1 H), 7.64 (s, 1 H), 7.62 (dd, J₁ = 8.4 Hz, J₂ = 1.6 Hz, 1 H), 7.21 (d, J = 1.6 Hz, 1 H), 7.13 (d, J = 8.8 Hz, 1 H), 7.11 (s, 1 H), 3.96 (s, 3 H), 3.91-3.86 (m, 2 H), 3.67 (s, 3 H), 3.17 (q, J = 7.6 Hz, 2 H), 1.34 (t, J = 7.6 Hz, 3 H), 0.99-0.96 (m, 1 H), 0.38-0.35 (m, 2 H), 0.10-0.02 (m, 2 H). | 466 |
| 84 | 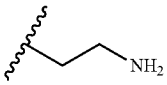 | 4-[5-ethylsulfonyl-2-(2-hydroxyethoxy)phenyl]-2-methyl-6-(1-methylpyrazol-4-yl)isoquinolin-1-one | (CDCl₃) 8.51 (d, J = 8.4 Hz, 1 H), 7.97 (dd, J₁ = 8.4 Hz, J₂ = 2.4 Hz, 1 H), 7.88 (d, J = 2.8 Hz, 1 H), 7.70 (s, 1 H), 7.64 (s, 1 H), 7.62 (dd, J₁ = 8.4 Hz, J₂ = 1.6 Hz, 1 H), 7.21 (d, J = 1.6 Hz, 1 H), 7.13 (d, J = 8.8 Hz, 1 H), 7.11 (s, 1 H), 3.96 (s, 3 H), 3.91-3.86 (m, 2 H), 3.67 (s, 3 H), 3.17 (q, J = 7.6 Hz, 2 H), 1.34 (t, J = 7.6 Hz, 3 H), 0.99-0.96 (m, 1 H), 0.38-0.35 (m, 2 H), 0.10-0.02 (m, 2 H). | 468 |
| 85 |  | 4-[2-(2-aminoethoxy)-5-ethylsulfonyl-phenyl]-2-methyl-6-(1-methylpyrazol-4-yl)isoquinolin-1-one | (Methanol-d4) 8.38 (d, J = 8.4 Hz, 1 H), 8.06 (dd, J₁ = 8.4 Hz, J₂ = 2.4 Hz, 1 H), 8.05 (s, 1 H), 7.89 (d, J = 2.4 Hz, 1 H), 7.83 (s, 1 H), 7.76 (dd, J₁ = 8.4 Hz, J₂ = 1.2 Hz, 1 H), 7.47 (d, J = 8.8 Hz, 1 H), 7.44 (s, 1 H), 7.27 (d, J = 1.2 Hz, 1 H), 4.46-4.32 (m, 2 H), 3.92 (s, 3 H), 3.67 (s, 3 H), 3.27 (q, J = 7.2 Hz, 2 H), 3.25-3.17 (m, 1 H), 3.04-2.96 (m, 1 H), 1.28 (t, J = 7.2 Hz, 3 H) | |

Example 86

N-[2-fluoro-4-methoxy-5-[2-methyl-6-(1-methyl-pyrazol-4-yl)-1-oxoisoquinolin-4-yl]phenyl]ethane-sulfonamide Step 1: 1-bromo-4-fluoro-2-methoxy-5-nitrobenzene and 1-bromo-2-fluoro-4-methoxy-5-nitrobenzene

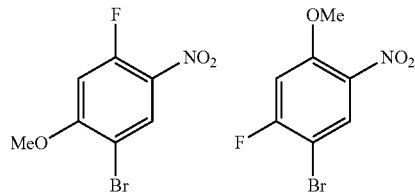 [SMILES: COc1cc(F)c([N+](=O)[O-])cc1Br ; COc1cc(F)c(Br)cc1[N+](=O)[O-]]

At 0° C., sodium methoxide (344 mg, 6.3 mmol) in dry MeOH (7 mL) was added dropwise to 1-bromo-2,4-difluoro-5-nitrobenzene (1 g, 4.2 mmol) in dry MeOH (18 mL). The mixture was stirred at room temperature for 10 h and then refluxed for 8 h. After extractive work up, purification by silica gel chromatography (PE:EA=1:0 to 10:1) gave a mixture of the two title compounds (765 mg, 72.9%) in about a 2:1 ratio as a yellow solid. LCMS: 249.9 (M+H)$^+$ Step 2: 5-bromo-2-fluoro-4-methoxyaniline

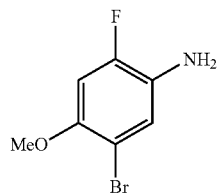 [SMILES: COc1cc(F)c(N)cc1Br]

Zinc dust (0.95 g, 14.5 mmol) was added to the mixture of two title compounds from step 1 (725 mg, 2.9 mmol) in 2:1 MeOH:saturated aqueous NH$_4$Cl (10 mL) at 0° C. After stirring at room temperature for 30 min, extractive work up with ethyl acetate and purification by silica gel chromatography (PE:EA=1:0 to 10:1) gave the title compound (260 mg, 41%) as a yellow solid free of the corresponding regioisomer. $^1$H NMR (400 MHz, DMSO-d$_6$) δ 7.00 (d, J=9.6 Hz, 1H), 6.94 (d, J=13.2 Hz, 1H), 4.88 (s, 2H), 3.72 (s, 3H). LCMS: 219.9 (M+H)$^+$ Step 3: N-(5-bromo-2-fluoro-4-methoxyphenyl)ethanesulfonamide

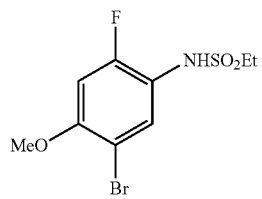

At 0° C., ethansulfonylchloride (1.4 g, 10.9 mmol) was added dropwise to a solution of 5-bromo-2-fluoro-4-methoxyaniline (3.5 g, 24.0 mmol) in pyridine (1.3 g, 16.4 mmol) and dry CH$_2$Cl$_2$ (20 mL). After stirring at room temperature for 10 h, CH$_2$Cl$_2$ extractive work up and purification by silica gel chromatography (PE:EA=10:0 to 3:1) gave the title compound (2.5 g, 73.5%) as a yellow solid. $^1$H NMR (400 MHz, CDCl$_3$) δ 7.77 (d, J=8.4 Hz, 1H), 6.73 (d, J=11.6 Hz, 1H), 6.27 (s, 1H), 3.89 (s, 3H), 3.10 (q, J=7.6 Hz, 2H), 1.40 (t, J=7.6 Hz, 3H). LCMS: 334.0 (M+Na)$^+$ Step 4: N-[2-fluoro-4-methoxy-5-[2-methyl-6-(1-methylpyrazol-4-yl)-1-oxoisoquinolin-4-yl]phenyl]ethanesulfonamide

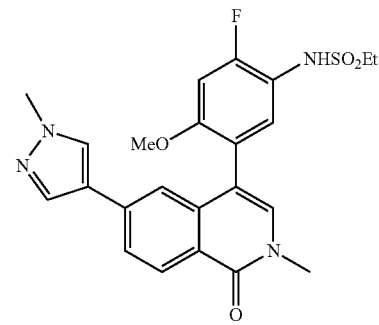

A mixture of N-(5-bromo-2-fluoro-4-methoxyphenyl)ethanesulfonamide (63 mg, 0.20 mmol), the title compound of Example 46, step 2 (75 mg, 0.21 mmol), Pd(dppf)Cl$_2$ (19 mg, 0.03 mmol) and aqueous K$_3$PO$_4$ (1 M, 0.5 mL, 0.5 mmol) in dioxane (3 mL) was microwaved at 100° C. for 1 h. Purification by silica gel chromatography (PE:EA=1:1 to 1:4) followed by preparative HPLC gave the title compound (25 mg, 26.3%) as a white solid. $^1$H NMR (400 MHz, CDCl$_3$) δ 8.48 (d, J=8.4 Hz, 1H), 7.72 (s, 1H), 7.69 (s, 1H), 7.58 (d, J=7.2 Hz, 1H), 7.49 (d, J=9.2 Hz, 1H), 7.25 (s, 1H), 7.04 (s, 1H), 6.85 (d, J=12.0 Hz, 1H), 6.37 (s, 1H), 3.94 (s, 3H), 3.75 (s, 3H), 3.65 (s, 3H), 3.17 (q, J=7.2 Hz, 2H), 1.46 (t, J=7.2 Hz, 3H). LCMS: 471.1 (M+H)$^+$

Example 87

N-[3-(2-methyl-1-oxo-6-pyridin-2-ylisoquinolin-4-yl)phenyl]ethanesulfonamide

Step 1: 2-methyl-6-(4,4,5,5-tetramethyl-1,3,2-dioxaborolan-2-yl)isoquinolin-1-one

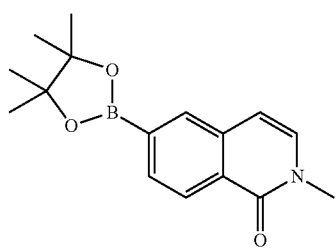

For 5 min N$_2$ was bubbled through a mixture of 6-bromo-2-methylisoquinolin-1-one (0.5 g, 2.1 mmol), 4,4,5,5-tetramethyl-2-(tetramethyl-1,3,2-dioxaborolan-2-yl)-1,3,2-dioxaborolane (0.8 g, 3.1 mmol), Pd(dppf)Cl$_2$ (153.6 mg, 0.21 mmol) and KOAc (0.51 g, 5.2 mmol) in dioxane (5 mL) which was then microwaved at 110° C. for 40 min. Purification by silica gel chromatography (PE:EA=20:1 to 5:1) gave the title compound (0.45 g, 75.0%) as yellow gum.

Step 2: 2-methyl-6-pyridin-2-ylisoquinolin-1-one

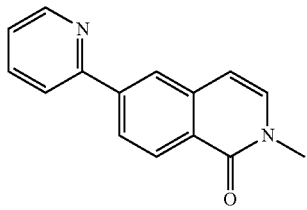 [SMILES: Cn1ccc2cc(-c3ccccn3)ccc2c1=O]

A mixture of 2-methyl-6-(4,4,5,5-tetramethyl-1,3,2-dioxaborolan-2-yl)isoquinolin-1-one (420 mg, 1.47 mmol), 2-bromopyridine (698 mg, 4.42 mmol), Pd(dppf)Cl$_2$ (107 mg, 0.15 mmol) and saturated aqueous NaHCO$_3$ (3.5 mL) in DMSO (25 mL) was microwaved at 150° C. for 45 min. After extractive work up with ethyl acetate, purification by silica gel chromatography (PE:EA=3:1 to 3:2) gave the title compound (160 mg, 46.0%) as a white solid. $^1$H NMR (CDCl$_3$, 400 MHz) δ 8.76 (d, J=4.8 Hz, 1H), 8.53 (d, J=8.0 Hz, 1H), 8.20 (d, J=1.2 Hz, 1H), 8.07 (dd, J$_1$=8.4 Hz, J$_2$=1.6 Hz, 1H), 7.85-7.82 (m, 2H), 7.34-7.30 (m, 1H), 7.11 (d, J=7.2 Hz, 1H), 6.6 (d, J=7.2 Hz, 1H), 3.64 (s, 3H). LCMS: 237.2 (M+H)$^+$ Step 3: 4-bromo-2-methyl-6-pyridin-2-ylisoquinolin-1-one

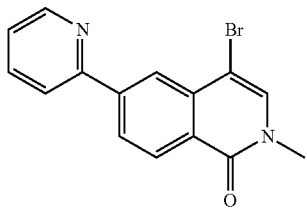 [SMILES: Cn1cc(Br)c2cc(-c3ccccn3)ccc2c1=O]

At 0° C., bromine (78 mg, 0.49 mmol) in acetic acid (0.3 mL) was added dropwise to 2-methyl-6-pyridin-2-ylisoquinolin-1-one (115 mg, 0.49 mmol) in acetic acid (20 mL). The mixture was stirred at room temperature for 20 min. Extractive work up with CH$_2$Cl$_2$ and purification by silica gel chromatography (PE:EA=5:1~1:1) gave the title compound (73.0 mg, 47.7%) as a yellow solid. $^1$H NMR (CDCl$_3$, 400 MHz) δ 8.79 (d, J=4.4 Hz, 1H), 8.55 (d, J=8.4 Hz, 1H), 8.44 (s, 1H), 8.19 (d, J=8.8 Hz, 1H), 7.90 (d, J=8.0 Hz, 1H), 7.85 (t, J=7.2 Hz, 1H), 7.42 (s, 1H), 7.36-7.34 (m, 1H), 3.64 (s, 3H). LCMS: 314.9 (M+H)$^+$ Step 4: N-[3-(2-methyl-1-oxo-6-pyridin-2-ylisoquinolin-4-yl)phenyl]ethanesulfonamide

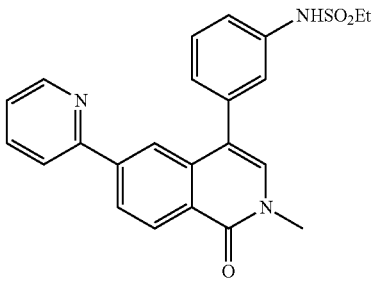

For 5 min, N$_2$ was bubbled through a mixture of 4-bromo-2-methyl-6-pyridin-2-ylisoquinolin-1-one (48.1 mg, 0.153 mmol), [3-(ethylsulfonylamino)phenyl]boronic acid (35.0 mg, 0.153 mmol), Pd(dppf)Cl$_2$ (22.3 mg, 0.03 mmol) and aqueous 1M K$_3$PO$_4$ (0.38 mL, 0.38 mmol, 1 M) in dioxane (5 mL) which was then microwaved at 80° C. for 20 min. Purification by silica gel chromatography (PE:EA=3:1 to 1:2) followed by preparative HPLC gave the title compound (2.5 mg, 3.9%) as a white solid. $^1$H NMR (Methanol-d4, 400 MHz) δ 8.69 (d, J=8.4 Hz, 1H), 8.59 (d, J=8.4 Hz, 1H), 8.23 (d, J=1.2 Hz, 1H), 8.15-8.22 (m, 1H), 8.10 (dd, J=8.4 Hz, J$_2$=1.6 Hz, 2H), 7.65-7.62 (m, 1H), 7.50-7.45 (m, 3H), 7.38-7.30 (m, 2H), 3.71 (s, 3H), 3.16 (q, J=7.2 Hz, 2H), 1.32 (t, J=7.2 Hz, 3H). LCMS: 420.1 (M+H)$^+$ Example 88

4-[4-fluoro-2-methoxy-5-(methylsulfonylmethyl)phenyl]-2-methyl-6-(1-methylpyrazol-4-yl)isoquinolin-1-one Step 1: 4-[4-fluoro-2-methoxy-5-(methylsulfonylmethyl)phenyl]-2-methyl-6-(1-methylpyrazol-4-yl)isoquinolin-1-one

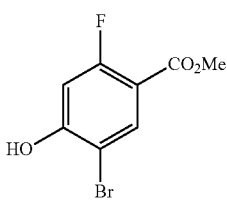

At 0-10° C., Br$_2$ (24 g, 150 mmol) in acetic acid (100 mL) was added drop-wise to a solution of methyl 2-fluoro-4-hydroxybenzoate (25.5 g, 150 mmol) in acetic acid (600 mL). The mixture was stirred at room temperature overnight. Extractive work up with ethyl acetate and purification by silica gel chromatography (100% DCM) gave the title compound (32.0 g, 86.5%) as a white solid. $^1$H NMR (Methanol-d4, 400 MHz) δ 8.03 (d, J=7.2 Hz, 1H), 6.68 (d, J=12.0 Hz, 1H), 3.86 (s, 3H). LCMS: 249.1 (M+H)$^+$

Step 2: 5-methyl 5-bromo-2-fluoro-4-methoxybenzoate

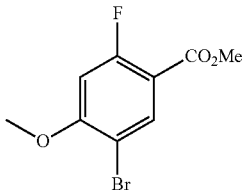

Methyl iodide (10.6 g, 74.9 mmol) was added drop-wise to 4-[4-fluoro-2-methoxy-5-(methylsulfonylmethyl)phenyl]-2-methyl-6-(1-methylpyrazol-4-yl)isoquinolin-1-one (6.0 g, 24.1 mmol) and $K_2CO_3$ (9.98 g, 72.3 mmol) in MeCN (120 mL). The mixture was heated at 80° C. overnight. Extractive work up with ethyl acetate and purification by silica gel chromatography (PE:EA=60:1 to 40:1) gave the title compound (5.1 g, 80.4%) as a white solid which was carried on without purification. $^1$H NMR (CDCl$_3$, 400 MHz) δ 8.15 (d, J=7.6 Hz, 1H), 6.66 (d, J=12.0 Hz, 1H), 3.94 (s, 3H), 3.91 (s, 3H). LCMS: 263.0 (M+H)$^+$

Step 3: (5-bromo-2-fluoro-4-methoxyphenyl)methanol

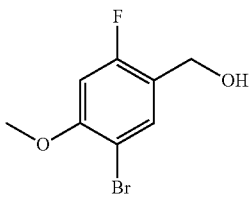

DIBAL-H (45.6 mL, 1M in toluene) was added drop-wise to a solution of 5-methyl 5-bromo-2-fluoro-4-methoxybenzoate (5.0 g, 19.0 mmol) in anhydrous CH$_2$Cl$_2$ (300 mL) at −78° C. The mixture was stirred at −78° C. for 3 h and then quenched with MeOH and water. The mixture was filtered and the filter cake rinsed with CH$_2$Cl$_2$. The filtrate was washed with brine, dried over Na$_2$SO$_4$, filtered, and concentrated to give the title compound (4.18 g, 94.4%) as a white solid which was carried on without purification. $^1$H NMR (DMSO-d6, 400 MHz) δ 7.59 (d, J=7.6 Hz, 1H), 7.02 (d, J=12.4 Hz, 1H), 5.25 (t, J=5.6 Hz, 1H), 4.45 (d, J=5.6 Hz, 2H), 3.84 (s, 3H).

Step 4: 1-bromo-5-(bromomethyl)-4-fluoro-2-methoxybenzene

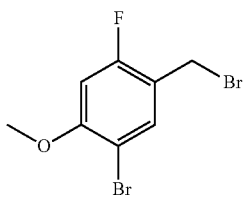

PBr$_3$ (4.7 g, 17.4 mmol) was added drop-wise to a solution of (5-bromo-2-fluoro-4-methoxyphenyl)methanol (4.1 g, 17.4 mmol) in anhydrous CH$_2$Cl$_2$ (40 mL) at 0° C. The mixture was stirred at room temperature for 3 h and poured into ice water. The pH was adjusted to 8 with saturated aqueous NaHCO$_3$. Extractive work up with CH$_2$Cl$_2$ gave the title compound (4.9 g, 94.8%) as a white solid which was carried on without purification. $^1$H NMR (DMSO-d$_6$, 400 MHz) δ 7.56 (d, J=8.0 Hz, 1H), 6.65 (d, J=11.6 Hz, 1H), 4.46 (s, 2H), 3.89 (s, 3H).

Step 5: 1-bromo-4-fluoro-2-methoxy-5-(methylsulfanylmethyl)benzene

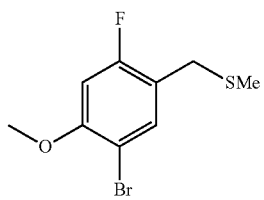

Thiomethoxide (1.19 g, 17.0 mmol) was added to a solution of 1-bromo-5-(bromomethyl)-4-fluoro-2-methoxybenzene (4.9 g, 16.4 mmol) in anhydrous DMF (25 mL) at 0° C. The mixture was stirred at room temperature for 5 h, and then poured into water (40 mL). Extractive work up with ethyl acetate gave the title compound (4.3 g, 99.0%) as colorless oil which was carried on without purification. $^1$H NMR (CDCl$_3$, 400 MHz) δ 7.50 (d, J=8.0 Hz, 1H), 6.64 (d, J=11.2 Hz, 1H), 3.88 (s, 3H), 3.63 (s, 2H), 2.04 (s, 3H).

Step 6: 1-bromo-4-fluoro-2-methoxy-5-(methylsulfonylmethyl)benzene

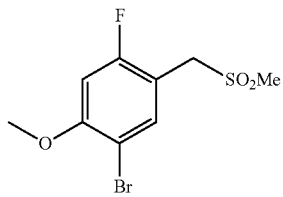

Oxone (20.9 g, 34.1 mmol) in H$_2$O (100 mL) was added drop-wise to a solution of 1-bromo-4-fluoro-2-methoxy-5-(methylsulfanylmethyl)benzene (4.3 g, 16.2 mmol) in MeOH (100 mL) at 0° C. The mixture was then stirred at room temperature for 3 h and then poured into water. Extractive work up with ethyl acetate, washing with saturated aqueous Na$_2$SO$_3$ (40 mL) and brine, gave a solid that was triturated with 1:10/EA:MTBE to give the title compound (4.40 g, 93.0%) as a white solid. $^1$H NMR (CDCl$_3$, 400 MHz) δ 7.66 (d, J=8.0 Hz, 1H), 6.72 (d, J=11.2 Hz, 1H), 4.22 (s, 2H), 3.92 (s, 3H), 2.83 (s, 3H). LCMS: 318.9 (M+Na)$^+$ Step 7: 4-[4-fluoro-2-methoxy-5-(methylsulfonylmethyl)phenyl]-2-methyl-6-(1-methylpyrazol-4-yl)isoquinolin-1-one

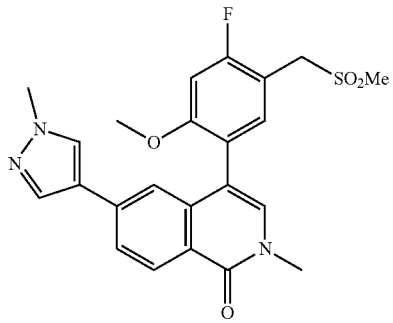 [SMILES: COc1cc(F)c(CS(C)(=O)=O)cc1-c1cn(C)c(=O)c2ccc(-c3cnn(C)c3)cc12]

1-Bromo-4-fluoro-2-methoxy-5-(methylsulfonylmethyl)benzene (34.0 mg, 0.114 mmol), the title compound of Example 46, step 2 (50.0 mg, 0.137 mmol), Pd(dppf)Cl$_2$ (20.0 mg, 0.027 mmol) and 1 M aqueous K$_3$PO$_4$ (0.47 mL, 0.47 mmol) in dioxane (3.0 mL) were microwaved at 100° C. for 40 min. Preparative HPLC gave the title compound (10.0 mg, 18%) as a light yellow solid. 1H NMR: (CDCl$_3$, 400 MHz) δ 8.47 (d, J=8.0 Hz, 1H), 7.74 (s, 1H), 7.73 (s, 1H), 7.60 (d, J=8.4 Hz, 1H), 7.42 (d, J=8.4 Hz, 1H), 7.27 (s, 1H), 7.05 (s, 1H), 6.85 (d, J=12.0 Hz, 1H), 4.32 (d, J=6.4 Hz, 2H), 3.93 (s, 3H), 3.77 (s, 3H), 3.64 (s, 3H), 2.93 (s, 3H). LCMS: 456.1 (M+H)$^+$.

Example 89

4-[2-(cyclopropylmethoxy)-5-methylsulfonylphenyl]-2-methylisoquinolin-1-one

Step 1: 2-methyl-4-(4,4,5,5-tetramethyl-1,3,2-dioxaborolan-2-yl)isoquinolin-1-one

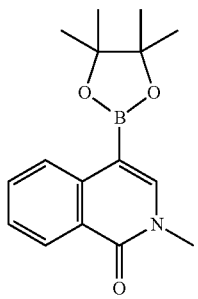 [SMILES: Cn1cc(B2OC(C)(C)C(C)(C)O2)c2ccccc2c1=O]

A suspension of 4-bromo-2-methylisoquinolin-1-one (100 mg, 0.42 mmol), bis(pinacolato)diboron (214 mg, 0.84 mmol), Pd(dppf)Cl$_2$ (31 mg, 0.04 mmol) and potassium acetate (104 mg, 1.05 mmol) in dioxane (2 mL) under nitrogen was warmed up to 90° C. for 135 minutes. It was then cooled down to room temperature and diluted with ethyl acetate (8 mL). The mixture was washed with aqueous saturated solution of NaHCO$_3$ (8 mL) and brine (8 mL). The organic phase was separated, dried over Na$_2$SO$_4$, filtered and concentrated under reduced pressure. The residue was purified by normal phase column chromatography (10-90% EtOAc/Hexanes) to give the title compound (44 mg, 37%).

$^1$H NMR (CDCl$_3$, 400 MHz) δ 8.43 (d, J=7.9 Hz, 1H), 8.40 (dd, J=8.2 Hz, 0.9 Hz, 1H), 7.68 (s, 1H), 7.65 (ddd, J=8.2, 8.2, 1.1 Hz, 1H), 7.46 (t, J=7.5 Hz, 1H), 3.63 (s, 3H), 1.38 (s, 12H). LCMS (M+H)$^+$ 286.

Step 2: 4-[2-(cyclopropylmethoxy)-5-methylsulfonylphenyl]-2-methylisoquinolin-1-one

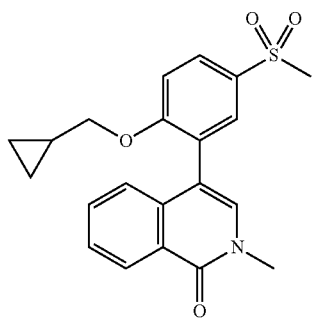

The title compound was prepared in a manner similar to Example 18, step 3, substituting 2-bromo-1-(cyclopropylmethoxy)-4-methylsulfonylbenzene for 4-bromo-2-methylisoquinolin-1(2H)-one and 2-methyl-4-(4,4,5,5-tetramethyl-1,3,2-dioxaborolan-2-yl)isoquinolin-1-one for N-benzyl-2-methoxy-5-(tetramethyl-1,3,2-dioxaborolan-2-yl)benzamide. $^1$H NMR (DMSO-d6, 400 MHz) δ 0.09 (m, 2H), 0.29 (m, 1H), 0.35 (m, 1H), 0.94 (m, 1H), 3.22 (s, 3H), 3.57 (s, 3H), 3.95 (m, 2H), 7.16 (d, J=7.9 Hz, 1H), 7.37 (d, J=8.8 Hz, 1H), 7.53 (m, 2H), 7.65 (t, J=7.6 Hz, 1H), 7.81 (d, J=2.4 Hz, 1H), 7.97 (dd, J=8.8, 2.4 Hz, 1H), 8.30 (d, J=8.1 Hz, 1H). LCMS (M+H)$^+$384.

Alternatively, 4-[2-(cyclopropylmethoxy)-5-methylsulfonylphenyl]-2-methylisoquinolin-1-one can be prepared as described below.

Step 1: 2-methyl-4-(4,4,5,5-tetramethyl-1,3,2-dioxaborolan-2-yl)isoquinolin-1-one

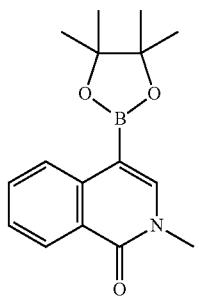 [SMILES: Cn1cc(B2OC(C)(C)C(C)(C)O2)c2ccccc2c1=O]

A mixture of 4-bromo-2-methylisoquinolin-1-one (8.0 g, 33.6 mmol), bis(pinacolato)diboron (17.1 g, 67.2 mmol), KOAc (6.6 g, 67.2 mmol), Pd$_2$(dba)$_3$ (3.1 g, 3.36 mmol) and X-Phos (1.6 g, 3.36 mmol) in anhydrous dioxane (200 mL) was stirred at 60° C. for 12 h. The reaction mixture was concentrated and the residue was purified by column chromatography on silica gel (PE:EA=15:1) to give the title compound (6.0 g, 62%) as a solid.

Step 2: 4-[2-(cyclopropylmethoxy)-5-methylsulfonylphenyl]-2-methylisoquinolin-1-one The title compound from Step 1 (5.0 g, 17.5 mmol), 2-bromo-1-(cyclopropylmethoxy)-4-methylsulfonylbenzene (6.4 g, 21 mmol), K$_3$PO$_4$ (9.3 g, 43.9 mmol) and Pd(dppf)Cl$_2$ (1.4 g, 1.75 mmol) in a dioxane/water (100 mL/10 mL) mixture were stirred at 60° C. for 12 hrs. The reaction mixture was concentrated under reduced pressure and the residue was purified by column chromatography on silica gel (EA:DCM=1:4). Appropriate fractions were combined and concentrated under reduce pressure. The resultant solid was recrystallized from DCM/MTBE (1:1, 50 mL) to give the title compound (4.0 g, 60%) as a white solid. $^1$H NMR: (CDCl$_3$, 400 MHz) δ 8.51 (dd, J$_1$=8.0 Hz, J$_2$=0.8 Hz, 1H), 7.98 (dd, J$_1$=8.4 Hz, J$_2$=2.4 Hz, 1H), 7.86 (d, J=2.4 Hz, 1H), 7.53 (m, 2H), 7.16 (d, J=7.6 Hz, 1H), 7.10 (m, 2H), 3.88 (m, 2H), 3.66 (s, 3H), 3.09 (s, 3H), 1.02-0.98 (m, 1H), 0.44-0.38 (m, 2H), 0.11-0.09 (m, 2H). LCMS: 384.1 (M+H)$^+$ Example 90

4-[2-(cyclopropylmethoxy)-5-methylsulfonylphenyl]-6-fluoro-2-methylisoquinolin-1-one Step 1: 2-[2-(cyclopropylmethoxy)-5-methylsulfonylphenyl]-4,4,5,5-tetramethyl-1,3,2-dioxaborolane

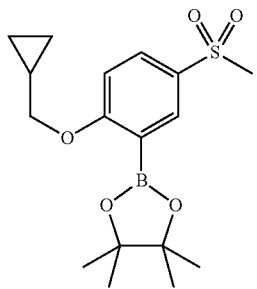 [SMILES: CC1(C)OB(c2cc(S(C)(=O)=O)ccc2OCC2CC2)OC1(C)C]

The title compound was prepared in a manner similar to Example 89, step 1, substituting 2-bromo-1-(cyclopropylmethoxy)-4-methylsulfonylbenzene for 4-bromo-2-methylisoquinolin-1-one. $^1$H NMR (CDCl$_3$, 400 MHz) δ 0.46 (m, 2H), 0.60 (m, 2H), 1.24 (m, 1H), 1.35 (s, 12H), 3.02 (s, 3H), 3.97 (d, J=6.0, 2H), 6.91 (d, J=8.7 Hz, 1H), 7.92 (dd, J=8.7, 2.5 Hz, 1H), 8.15 (d, J=2.4 Hz, 1H). LCMS (M+H)$^+$ 353.

Step 2: 4-[2-(cyclopropylmethoxy)-5-methylsulfonylphenyl]-6-fluoro-2-methylisoquinolin-1-one

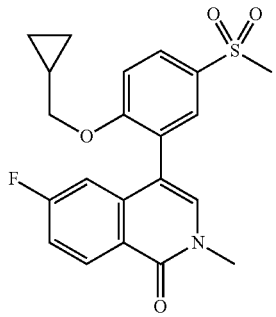 [SMILES: Cn1cc(-c2cc(S(C)(=O)=O)ccc2OCC2CC2)c2cc(F)ccc2c1=O]

The title compound was prepared in a manner similar to Example 18, step 3, substituting the title compound of Example 47, step 2 for 4-bromo-2-methylisoquinolin-1 (2H)-one and 2-[2-(cyclopropylmethoxy)-5-methylsulfonylphenyl]-4,4,5,5-tetramethyl-1,3,2-dioxaborolane for N-benzyl-2-methoxy-5-(tetramethyl-1,3,2-dioxaborolan-2-yl) benzamide. $^1$H NMR (DMSO-d6, 400 MHz) δ 0.12 (m, 2H), 0.32 (m, 1H), 0.39 (m, 1H), 0.99 (m, 1H), 3.22 (s, 3H), 3.56 (s, 3H), 3.97 (m, 2H), 6.82 (dd, J=10.5, 2.4 Hz, 1H), 7.39 (m, 2H), 7.61 (s, 1H), 7.82 (d, J=2.3 Hz, 1H), 7.98 (dd, J=8.74, 2.4 Hz, 1H), 8.36 (dd, J=8.9, 6.1 Hz, 1H). LCMS (M+H) 402.

Example 91

4-[2-(cyclopropylmethoxy)-5-methylsulfonylphenyl]-7-fluoro-2-methylisoquinolin-1-one

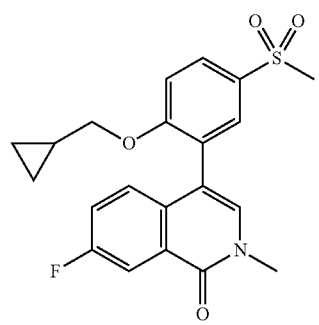 [SMILES: Cn1cc(-c2cc(S(C)(=O)=O)ccc2OCC2CC2)c2ccc(F)cc2c1=O]

The title compound was prepared in a manner similar to Example 18, step 3, substituting the title compound of Example 58, step 2 for 4-bromo-2-methylisoquinolin-1 (2H)-one and 2-[2-(cyclopropylmethoxy)-5-methylsulfonylphenyl]-4,4,5,5-tetramethyl-1,3,2-dioxaborolane for N-benzyl-2-methoxy-5-(tetramethyl-1,3,2-dioxaborolan-2-yl) benzamide. $^1$H NMR (DMSO-d6, 400 MHz) δ 0.10 (m, 2H), 0.30 (m, 1H), 0.39 (m, 1H), 0.94 (m, 1H), 3.22 (s, 3H), 3.58 (s, 3H), 3.95 (m, 2H), 7.24 (dd, J=9, 5.3 Hz, 1H), 7.38 (d, J=8.8 Hz, 1H), 7.54 (s, 1H), 7.56 (m, 1H), 7.81 (d, J=2.4 Hz, 1H), 7.96 (m, 2H). LCMS (M+H)$^+$ 402.

Example 92

4-[2-(2,4-difluorophenoxy)-5-methylsulfonylphenyl]-2-methylisoquinolin-1-one

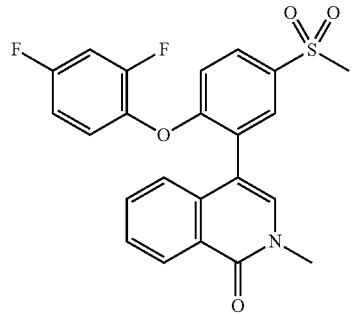 [SMILES: Cn1cc(-c2cc(S(C)(=O)=O)ccc2Oc2ccc(F)cc2F)c2ccccc2c1=O]

The title compound was prepared in a manner similar to Example 18, step 3, substituting 1-(2-bromo-4-methylsulfonylphenoxy)-2,4-difluorobenzene for 4-bromo-2-methylisoquinolin-1(2H)-one and 2-methyl-4-(4,4,5,5-tetramethyl-1,3,2-dioxaborolan-2-yl)isoquinolin-1-one for N-benzyl-2-methoxy-5-(tetramethyl-1,3,2-dioxaborolan-2-yl)benzamide. ¹H NMR (DMSO-d6, 400 MHz) δ 3.27 (s, 3H), 3.58 (s, 3H), 7.03 (d, J=9.2 Hz, 1H), 7.13 (m, 1H), 7.35 (m, 2H), 7.48 (m, 1H), 7.54 (t, J=7.5, 1H), 7.67 (s, 1H), 7.69 (m, 1H), 7.97 (m, 1H), 7.98 (s, 1H), 8.30 (d, J=8.1, 1H). LCMS (M+H)⁺ 442.

Example 93

N-[4-(2,4-difluorophenoxy)-3-(2-methyl-1-oxoisoquinolin-4-yl)phenyl]ethanesulfonamide

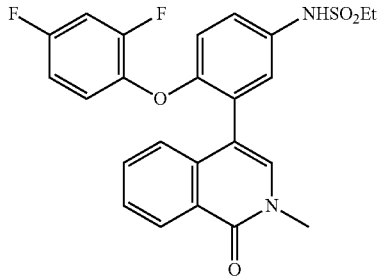

The title compound was prepared in a manner similar to Example 18, step 3, substituting N-[3-bromo-4-(2,4-difluorophenoxy)phenyl]ethanesulfonamide for 4-bromo-2-methylisoquinolin-1(2H)-one and 2-methyl-4-(4,4,5,5-tetramethyl-1,3,2-dioxaborolan-2-yl)isoquinolin-1-one for N-benzyl-2-methoxy-5-(tetramethyl-1,3,2-dioxaborolan-2-yl)benzamide. ¹H NMR (DMSO-d6, 400 MHz) δ 1.23 (t, J=7.3 Hz, 3H), 3.13 (q, J=7.8 Hz, 2H), 3.53 (s, 3H), 6.95 (m, 2H), 7.09 (m, 1H), 7.28 (m, 3H), 7.51 (m, 2H), 7.65 (t, J=6.9 Hz, 1H), 8.26 (d, J=0.8 Hz, 1H), 9.83 (s, 1H). LCMS (M+H)⁺ 471.

Example 94

N-[3-(1-methyl-6-oxopyridin-3-yl)phenyl]methanesulfonamide

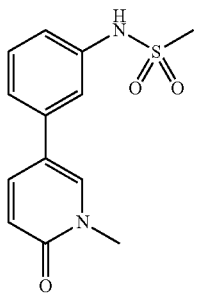 [SMILES: Cn1cc(-c2cccc(NS(C)(=O)=O)c2)ccc1=O]

A mixture of 5-bromo-1-methylpyridin-2-one (100 mg, 0.532 mmol), [3-(methanesulfonamido)phenyl]boronic acid (171.1 mg, 0.798 mmol), KOAc (130.0 mg, 1.326 mmol) and Pd(dppf)Cl₂ (38.9 mg, 0.05 mmol) in dioxane/H₂O (2 mL/0.5 mL) was stirred at 90° C. for 20 min. The mixture was concentrated and the residue was purified by column chromatography on silica gel (PE:EA=1:1) to give the title compound (30.0 mg, 20%) as a brown solid. ¹H NMR (CDCl₃, 400 MHz) δ 7.65-7.60 (dd, J₁=7.6 Hz, J₂=2.4 Hz, 1H), 7.54 (d, J=2.4 Hz, 1H), 7.41 (t, J=8.0 Hz, 1H), 7.33 (s, 1H), 7.24 (d, J=7.6 Hz, 1H), 7.17 (d, J=7.6 Hz, 1H), 6.86 (brs, 1H), 6.67 (d, J=9.2 Hz, 1H), 3.65 (s, 3H), 3.05 (s, 3H). LCMS (M+H)⁺ 279.

Example 95

N-[3-(1,4-dimethyl-6-oxopyridin-3-yl)phenyl]methanesulfonamide

Step 1: 5-bromo-1,4-dimethylpyridin-2-one

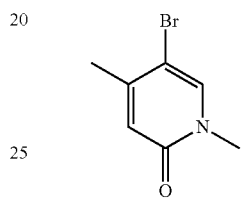

To a solution of 5-bromo-4-methylpyridin-2-ol (1.12 g, 6.0 mmol) in anhydrous THF (20 mL) was added NaH (288.0 mg, 12.0 mmol) and the reaction mixture was stirred at 0° C. for 30 min. Then, methyl iodide (1.7 g, 12.0 mmol) was added and stirred at room temperature for 3 h. Saturated NH₄Cl (100 mL) was added and the resulting mixture was extracted with ethyl acetate (100 mL×3). The combined organic layers were washed with brine (100 mL), dried over anhydrous Na₂SO₄ and concentrated. The residue was purified by column chromatography on silica gel (PE:EA=10:1 to 2:1) to give the title compound (1.0 g, 83.3%) as a yellow solid. 1H NMR (CDCl₃, 400 MHz) δ 7.44 (s, 1H), 6.94 (s, 1H), 3.51 (s, 3H), 2.24 (s, 3H). LCMS (M+H)⁺ 202.

Step 2: N-[3-(1-methyl-6-oxopyridin-3-yl)phenyl]methanesulfonamide

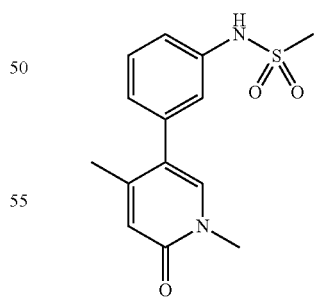

5-Bromo-1,4-dimethylpyridin-2-one was treated with [3-(methanesulfonamido)phenyl]boronic acid in a manner similar to Example 94 to give the title compound as a white solid. ¹H NMR (CDCl₃, 400 MHz) δ 7.43 (t, J=8.0 Hz, 1H), 7.20 (d, J=8.0 Hz, 1H), 7.16 (s, 1H), 7.07 (d, J=7.6 Hz, 1H), 6.71 (s, 1H), 6.69 (s, 1H), 3.67 (s, 3H), 3.07 (s, 3H), 2.16 (s, 3H). LCMS (M+H)⁺ 293.

Example 96

N-[3-(1,5-dimethyl-6-oxopyridin-3-yl)phenyl]methanesulfonamide

Step 1: 5-bromo-1,3-dimethylpyridin-2-one

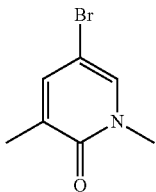

The title compound of step 1 was prepared in a manner similar to Example 95, step 1 using 5-bromo-3-methylpyridin-2-ol instead of 5-bromo-4-methylpyridin-2-ol to give 5-bromo-1,3-dimethylpyridin-2-one. $^1$H NMR (CDCl$_3$, 400 MHz): 7.30 (d, J=2.0 Hz, 1H), 7.26 (d, J=1.6 Hz, 1H), 3.53 (s, 3H), 2.16 (s, 3H). LCMS (M+H)$^+$ 202.

Step 2: N-[3-(1,5-dimethyl-6-oxopyridin-3-yl)phenyl]methanesulfonamide

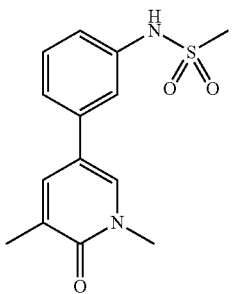

5-Bromo-1,3-dimethylpyridin-2-one was treated with [3-(methanesulfonamido)phenyl]boronic acid in a manner similar to Example 94 to give the title compound as a white solid. $^1$H NMR (DMSO-d6, 400 MHz): 9.74 (s, 1H), 7.91 (d, J=2.4 Hz, 1H), 7.62 (s, 1H), 7.37 (t, J=7.6 Hz, 1H), 7.32 (s, 1H), 7.29 (d, J=7.6 Hz, 1H), 7.13 (d, J=7.6 Hz, 1H), 3.52 (s, 3H), 3.02 (s, 3H), 2.08 (s, 3H). LCMS (M+H)$^+$ 293.

Example 97

N-[3-(1,4,5-trimethyl-6-oxopyridin-3-yl)phenyl]methanesulfonamide

Step 1: 5-bromo-3,4-dimethyl-1H-pyridin-2-one

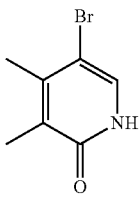

To a mixture of 5-bromo-3,4-dimethylpyridin-2-amine (0.6 g, 3.0 mmol) and H$_2$SO$_4$ (98%, 1.62 mL) and H$_2$O (18 mL) is added a solution of NaNO$_2$ (243.6 mg, 4.2 mmol) in H$_2$O (1.6 mL) drop-wise at 0° C. Then, it was stirred at 31° C. for 30 minutes and filtered. The resulting solid is washed with water to provide the title compound (375.0 mg, 62%) as a white solid. 1H NMR (CDCl$_3$, 400 MHz) δ 7.48 (s, 1H), 2.32 (s, 3H), 2.19 (s, 3H). LCMS (M+H)$^+$ 202.

Step 2: 5-bromo-1,3,4-trimethylpyridin-2-one

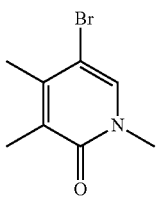

To a solution of 5-bromo-3,4-dimethyl-1H-pyridin-2-one (402.0 mg, 2.0 mmol) in anhydrous THF (20 mL) was added NaH (96.0 mg, 2.4 mmol). The resulting mixture was stirred at 0° C. for 30 min. Methyl iodide (568.0 mg, 4.0 mmol) was added and the reaction was stirred at 32° C. for 3 h. Then, saturated aqueous NH$_4$Cl (100 mL) was added and the mixture extracted with ethyl acetate (100 mL×3). The combined organic layers were washed with brine (100 mL), dried over Na$_2$SO$_4$, filtered and concentrated. The residue was purified by column chromatography on silica gel (PE:EA=10:1 to 2:1) to give the title compound (350.0 mg, 80%) as a white solid. $^1$H NMR (CDCl$_3$, 400 MHz) δ 7.38 (s, 1H), 3.52 (s, 3H), 2.27 (s, 3H), 2.20 (s, 3H). LCMS (M+H)$^+$ 216.

Step 3: N-[3-(1,4,5-trimethyl-6-oxopyridin-3-yl)phenyl]methanesulfonamide

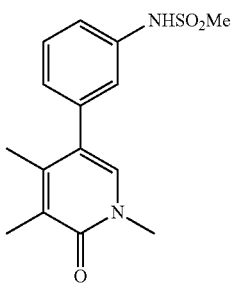

5-Bromo-1,3,4-trimethylpyridin-2-one was treated with [3-(methanesulfonamido)phenyl]boronic acid in a manner similar to Example 94 to give the title compound as a white solid. $^1$H NMR (CDCl$_3$, 400 MHz) δ 7.42 (s, 1H), 7.39 (t, J=7.6 Hz, 1H), 7.24 (s, 1H), 7.16 (s, 1H), 7.08 (s, 1H), 7.05 (d, J=7.6 Hz, 1H), 3.59 (s, 3H), 3.06 (s, 3H), 2.19 (s, 3H), 2.06 (s, 3H). LCMS (M+H)$^+$ 307.

Example 98

5-[2-(cyclopropylmethoxy)-5-methylsulfonylphenyl]-1-methylpyridin-2-one

Step 1: 1-methyl-5-(4,4,5,5-tetramethyl-1,3,2-dioxaborolan-2-yl)pyridin-2-one

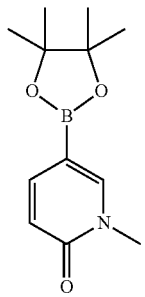

A solution of 5-bromo-1-methylpyridin-2-one (200.0 mg, 1.06 mmol), bis(pinacolato)diboron (410.0 mg, 1.61 mmol), potassium acetate (270 mg, 2.67 mmol), Pd (dppf)Cl$_2$ (80 mg, 0.11 mmol) in dioxane (5 mL) was heated at 100° C. for 2 h under microwave. The mixture was filtered, washed with water and extracted with ethyl acetate (20 mL×3). The combined organics were dried over Na$_2$SO$_4$, filtered and concentrated to give the crude title compound (59.0 mg, 23.6%). LCMS (M+H)$^+$ 236.

Step 2: 5-[2-(cyclopropylmethoxy)-5-methylsulfonylphenyl]-1-methylpyridin-2-one

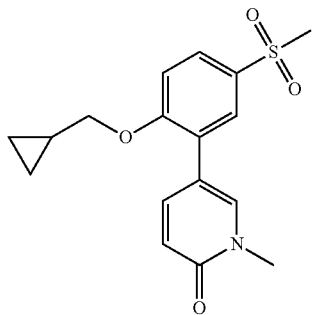 [SMILES: Cn1cc(-c2cc(S(C)(=O)=O)ccc2OCC2CC2)ccc1=O]

1-Methyl-5-(4,4,5,5-tetramethyl-1,3,2-dioxaborolan-2-yl)pyridin-2-one was treated with 2-bromo-1-(cyclopropylmethoxy)-4-methylsulfonylbenzene in a manner similar to Example 94 to give the title compound. $^1$H NMR (CDCl$_3$, 400 MHz): δ 7.86 (dd, J$_1$=8.8 Hz, J$_2$=2.4 Hz, 1H), 7.81 (d, J=2.0 Hz, 1H), 7.68-765 (m, 2H), 7.03 (d, J=8.4 Hz, 1H), 6.66 (d, J=8.8 Hz, 1H), 3.95 (d, J=6.8 Hz, 2H), 3.64 (s, 3H), 3.07 (s, 3H), 1.28-1.25 (m, 1H), 0.69-0.65 (m, 2H), 0.34-0.38 (m, 2H). LCMS (M+H)$^+$ 334.

Example 99

N-[4-(2,4-difluorophenoxy)-3-(1-methyl-6-oxopyridin-3-yl)phenyl]ethanesulfonamide Step 1: 5-[5-amino-2-(2,4-difluorohenoxy)phenyl]-1-methylpyridin-2-one

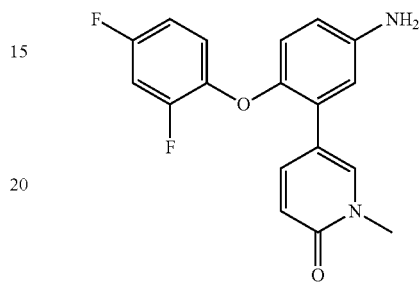

A mixture of the title compound of step 1 in Example 57 (100 mg, 0.289 mmol), 5-bromo-1-methylpyridin-2-one (45.27 mg, 0.240 mmol), K$_3$PO$_4$ (127.6 mg, 0.60 mmol) and Pd(dppf)Cl$_2$ (20 mg, 0.027 mmol) in dioxane/H$_2$O (4/0.5 mL) was stirred at 100° C. for 40 min under microwave. The mixture was concentrated and the residue was purified by column chromatography on silica gel (PE:EA=1:2) to give the title compound (60 mg, 76%). LCMS (M+H)$^+$ 328.

Step 2: N-[4-(2,4-difluorophenoxy)-3-(1-methyl-6-oxopyridin-3-yl)phenyl]ethanesulfonamide

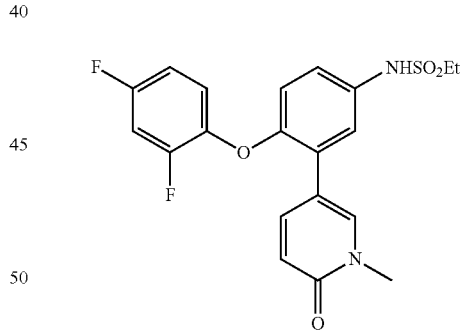

To a solution of 5-[5-amino-2-(2,4-difluorophenoxy)phenyl]-1-methylpyridin-2-one (30 mg, 0.09 mmol) in DCM (4 mL) was added TEA (27.3 mg, 0.27 mmol) and EtSO$_2$Cl (35.39 mg, 0.27 mmol). The mixture was stirred at 30° C. for 12 h. Water (4 mL) was added and the mixture was extracted with DCM (4 mL×3). The organic layer was concentrated and the residue was purified by prep-HPLC to give the title compound (10 mg, 26%) as light yellow gum. $^1$H NMR (CDCl$_3$, 400 MHz) δ7.68-7.66 (m, 2H), 7.28 (d, J=2.4 Hz, 1H), 7.13-7.10 (m, 1H), 7.09 (s, 1H), 7.00-6.92 (m, 2H), 6.84-6.86 (m, 1H), 6.78 (d, J=8.4 Hz, 1H), 6.73 (d, J=9.2 Hz, 1H), 3.65 (s, 3H), 3.14 (q, J=7.2 Hz, 2H), 1.41 (t, J=7.2 Hz, 3H). LCMS (M+H) 421.

Example 100

N-[4-(2,4-difluorophenoxy)-3-(1-methyl-6-oxopyridin-3-yl)phenyl]methanesulfonamide

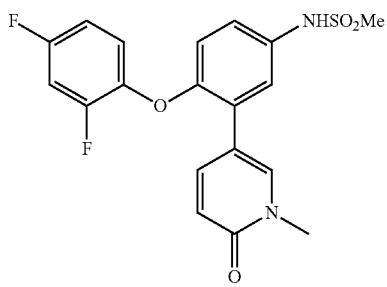

Preparation was carried out in a manner similar to Example 99, substituting methanesulfonyl chloride for ethanesulfonyl chloride in step 2 to give the title compound as a light yellow gum. $^1$H NMR (CDCl$_3$, 400 MHz) δ 7.64-7.62 (m, 2H), 7.29 (d, J=4.8 Hz, 1H), 7.13-7.12 (m, 1H), 6.69-6.95 (m, 2H), 6.79 (m, 1H), 6.79 (d, J=8.4 Hz, 1H), 6.62 (d, J=9.4 Hz, 1H), 3.61 (s, 3H), 3.04 (s, 3H). LCMS (M+H)$^+$ 407.

Example 101

N-[4-(2,4-difluorophenoxy)-3-(1,4-dimethyl-6-oxopyridin-3-yl)phenyl]methanesulfonamide

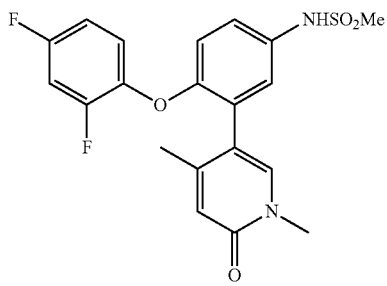

Preparation was carried out in a manner similar to Example 100, substituting 5-bromo-1,4-dimethylpyridin-2-one for 5-bromo-1-methylpyridin-2-one in step 1 to give the title compound. $^1$H NMR (CDCl$_3$, 400 MHz) δ 7.21-7.16 (m, 4H), 6.95-6.93 (m, 2H), 6.86-6.80 (m, 1H), 6.77 (d, J=8.8 Hz, 1H), 6.53 (s, 1H), 3.57 (s, 3H), 3.04 (s, 3H), 2.10 (s, 3H). LCMS (M+H)$^+$ 421.

Example 102

N-[4-(2,4-difluorophenoxy)-3-(1,5-dimethyl-6-oxopyridin-3-yl)phenyl]methanesulfonamide

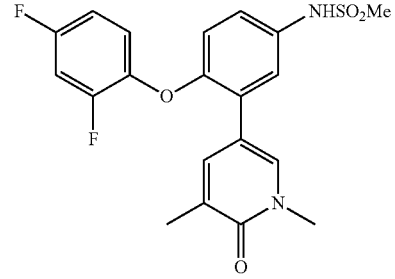

Preparation was carried out in a manner similar to Example 100, substituting 5-bromo-1,3-dimethylpyridin-2-one for 5-bromo-1-methylpyridin-2-one to give the title compound. $^1$H NMR (CDCl$_3$, 400 MHz) δ 7.53 (s, 2H), 7.40 (s., 1H), 7.31 (d, J=2.4 Hz, 1H), 7.17 (dd, J$_1$=8.8 Hz, J$_2$=2.4 Hz, 1H), 6.99-6.90 (m, 2H), 6.87-6.80 (m, 1H), 6.80 (d, J=8.8 Hz, 1H), 3.63 (s, 3H), 3.03 (s, 3H), 2.19 (s, 3H). LCMS (M+H)$^+$ 421.

Example 103

N-[4-(2,4-difluorophenoxy)-3-(1,4,5-trimethyl-6-oxopyridin-3-yl)phenyl]methanesulfonamide

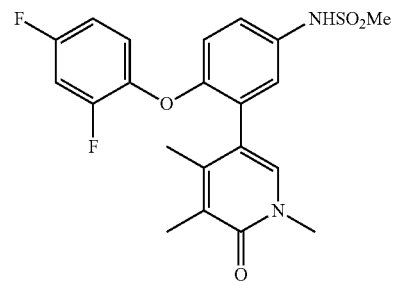

Preparation was carried out in a manner similar to Example 100, substituting 5-bromo-1,3,4-trimethylpyridin-2-one for 5-bromo-1-methylpyridin-2-one to give the title compound. $^1$H NMR (Methanol-d4, 400 MHz) δ 7.65 (dd, J$_1$=8.8 Hz, J$_2$=2.4 Hz, 1H), 7.58 (d, J=2.8 Hz, 1H), 7.39 (s, 1H), 7.05-7.01 (m, 2H), 6.94-6.91 (m, 2H), 3.55 (s, 3H), 3.31 (s, 3H), 2.13 (s, 3H), 2.08 (s, 3H). LCMS (M+18+H)$^+$ 453.

Example 104

3-amino-1-methyl-5-(3-methylsulfonylphenyl)pyrazin-2-one

Step 1: 3-amino-5-bromo-1-methylpyrazin-2-one

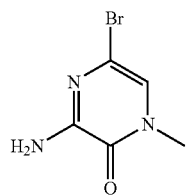

A solution of 3,5-dibromo-1-methylpyrazin-2-one (500.0 mg, 2.46 mmol), NH$_3$H$_2$O (5.0 mL) in dioxane (30.0 mL) was heated at 105° C. for 20 h. The mixture was concentrated, diluted with EtOAc (50 mL) and filtrated to give the title compound (300.0 mg, 79.0%) which was carried on without purification. LCMS (M+H)$^+$ 204.

Step 2: 3-amino-1-methyl-5-(3-methylsulfonylphenyl)pyrazin-2-one

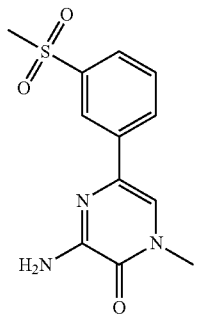

A solution of 3-amino-5-bromo-1-methylpyrazin-2-one (81.0 mg, 0.4 mmol), (3-methylsulfonylphenyl)boronic acid (120.0 mg, 0.6 mmol), Cs$_2$CO$_3$ (391.0 mg, 1.2 mmol), Pd(PPh$_3$)$_4$ (20.0 mg, 0.017 mmol) in dioxane (20.0 mL) and water (2.0 mL) was stirred at 95° C. for 12 h under N$_2$. The mixture was concentrated and purified by silica gel chromatography (PE:EA=3:2) to give the title compound (20.0 mg, 18%). $^1$H NMR (DMSO-d$_6$ 400 MHz): δ 8.35 (s, 1H), 8.11 (d, J=8.0 Hz, 1H), 7.80 (d, J=8.0 Hz, 1H), 7.73 (s, 1H), 7.66 (t, J=8.0 Hz, 1H), 6.93 (brs, 2H), 3.50 (s, 3H), 3.24 (s, 3H). LCMS (M+H)$^+$ 280.

Example 105

3-amino-5-(3-ethylsulfonylphenyl)-1-methylpyrazin-2-one

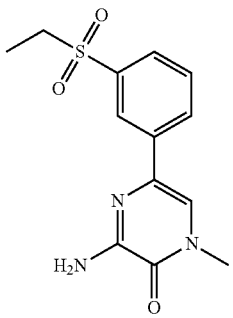 [SMILES: CCS(=O)(=O)c1cccc(-c2cn(C)c(=O)c(N)n2)c1]

Preparation was carried out in a manner similar to Example 104, step 2, substituting (3-ethylsulfonylphenyl)boronic acid for (3-methylsulfonylphenyl)boronic acid to give the title compound. $^1$H NMR (DMSO-d$_6$ 400 MHz): δ 8.30 (t, J=1.6 Hz, 1H), 8.11 (d, J=8.0 Hz, 1H), 7.74 (d, J=8.0 Hz, 1H), 7.71 (s, 1H), 7.65 (t, J=8.0 Hz, 1H), 6.90 (brs, 2H), 3.48 (s, 3H), 3.29 (q, J=7.2 Hz, 2H), 1.11 (t, J=7.2 Hz, 3H). LCMS (M+H)$^+$ 294.

Example 106

N-[5-(6-amino-4-methyl-5-oxopyrazin-2-yl)-2-methoxyphenyl]methanesulfonamide

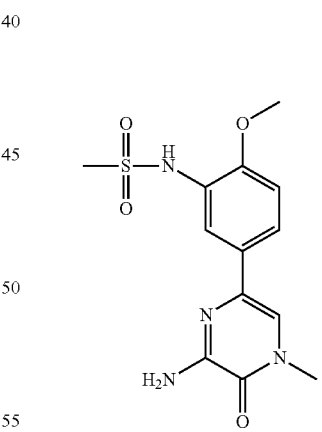

Preparation was carried out in a manner similar to Example 104, step 2, substituting [3-(methanesulfonamido)-4-methoxyphenyl]boronic acid for (3-methylsulfonylphenyl)boronic acid to give the title compound. $^1$H NMR (DMSO-d$_6$ 400 MHz): δ 8.91 (s, 1H), 7.68 (d, J=2.4 Hz, 1H), 7.61 (dd, J$_1$=8.8 Hz, J$_2$=2.4 Hz, 1H), 7.38 (s, 1H), 7.08 (d, J=8.8 Hz, 1H), 6.88-6.64 (m, 2H), 3.84 (s, 3H), 3.46 (s, 3H), 2.95 (s, 3H). LCMS (M+H)$^+$ 325.

Example 107

3-amino-1-methyl-5-(3-methylsulfonylphenyl)pyridin-2-one

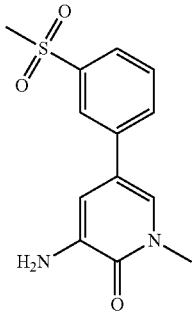

Preparation was carried out in a manner similar to Example 104, step 2, substituting 3-amino-5-bromo-1-methylpyridin-2-one for 3-amino-5-bromo-1-methylpyrazin-2-one to give the title compound. $^1$H NMR (Methanol-d4, 400 MHz) δ 8.06 (t, J=2.0 Hz, 1H), 7.89-7.85 (m, 2H), 7.67 (t, J=8.0 Hz, 1H), 7.39 (d, J=2.0 Hz, 1H), 7.03 (d, J=2.4 Hz, 1H), 3.67 (s, 3H), 3.17 (s, 3H). LCMS (M+H)$^+$ 279.

Example 108

3-amino-5-(3-ethylsulfonylphenyl)-1-methylpyridin-2-one

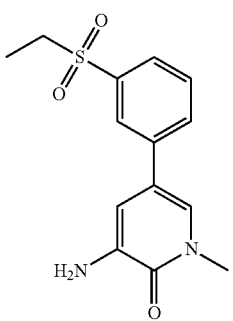

Preparation was carried out in a manner similar to Example 105, substituting 3-amino-5-bromo-1-methylpyridin-2-one for 3-amino-5-bromo-1-methylpyrazin-2-one to give the title compound. $^1$H NMR (Methanol-d4, 400 MHz) δ 8.01 (t, J=2.0 Hz, 1H), 7.88-7.83 (m, 2H), 7.68 (t, J=8.0 Hz, 1H), 7.39 (d, J=2.0 Hz, 1H), 7.03 (d, J=2.4 Hz, 1H), 3.67 (s, 3H), 3.26 (q, J=7.6 Hz, 2H), 1.25 (t, J=7.6 Hz, 3H). LCMS (M+H)$^+$ 293.

Example 109

N-[5-(5-amino-1-methyl-6-oxopyridin-3-yl)-2-methoxyphenyl]methanesulfonamide

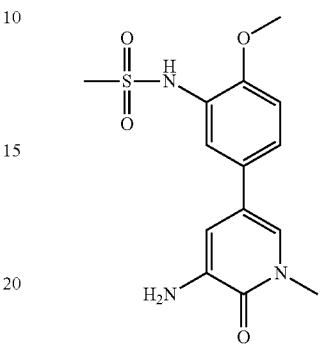

Preparation was carried out in a manner similar to Example 106, substituting 3-amino-5-bromo-1-methylpyridin-2-one for 3-amino-5-bromo-1-methylpyrazin-2-one to give the title compound. $^1$H NMR (Methanol-d4, 400 MHz) δ 7.53 (d, J=2.4 Hz, 1H), 7.34 (dd, J$_1$=8.8 Hz, J$_2$=2.4 Hz, 1H), 7.18 (d, J=2.4 Hz, 1H), 7.09 (d, J=8.8 Hz, 1H), 6.96 (d, J=2.4 Hz, 1H), 3.92 (s, 3H), 3.64 (s, 3H), 2.94 (s, 3H). LCMS (M+H)$^+$ 324.

Example 110

N-[2-methoxy-5-[1-methyl-5-(methylamino)-6-oxopyridin-3-yl]phenyl]methanesulfonamide

Step 1: tert-butyl N-(5-bromo-1-methyl-2-oxopyridin-3-yl)carbamate

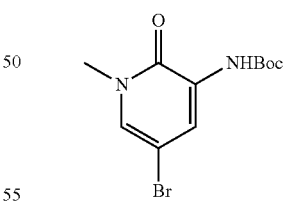

To a solution of 3-amino-5-bromo-1-methylpyridin-2-one (404.0 mg, 2.0 mmol) in DCM (30 mL) was added (Boc)$_2$O (654.0 mg, 3.0 mmol), Et$_3$N (606.0 mg, 6.0 mmol) dropwise and DMAP (123.0 mg, 1.0 mmol). The reaction mixture was stirred for 12 h at 30° C., quenched with saturated aqueous NH$_4$Cl (50 mL), extracted with EA (50 mL), dried over Na$_2$SO$_4$, filtered and concentrated. Silica gel chromatography (PE:EA=2:1) gave the impure title compound (400.0 mg) as a green solid, which was carried on to the next step. LCMS (M−55)$^+$ 247.

Step 2: tert-butyl N-(5-bromo-1-methyl-2-oxopyridin-3-yl)-N-methylcarbamate

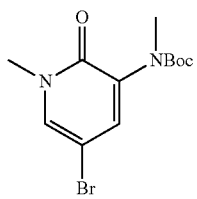 [SMILES: CN(C(=O)OC(C)(C)C)c1cc(Br)cn(C)c1=O]

To a solution of tert-butyl N-(5-bromo-1-methyl-2-oxopyridin-3-yl)carbamate (150.0 mg, impure) in DMF (10 mL) was added NaH (60.0 mg, 1.5 mol, 60% in oil) in portions at 0° C. It was stirred for 30 min. Then CH$_3$I (231.0 mg, 1.5 mmol) was added dropwise at 0° C. The reaction mixture was stirred for 2 h at 30° C. The reaction was quenched with saturated aqueous NH$_4$Cl (15 mL), extracted with EA (20 mL), washed with brine (20 mL), dried over Na$_2$SO$_4$, filtered and concentrated to give the title compound (120.0 mg, crude) as a green solid, which was used directly in the next step without purification.

Step 3: 5-bromo-1-methyl-3-(methylamino)pyridin-2-one

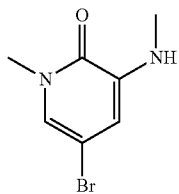

To a solution of tert-butyl N-(5-bromo-1-methyl-2-oxopyridin-3-yl)-N-methylcarbamate (94.8 mg, crude) in DCM (10 mL) was added HCl/dioxane (1 mL, 4 M) dropwise with stirring at 30° C. The reaction mixture was stirred at 30° C. for 30 min. The mixture was filtered and the filter cake collected. The filtrate was adjusted to pH=9 with saturated aqueous NaHCO$_3$, extracted with ethyl acetate (20 mL), dried over Na$_2$SO$_4$, filtered and concentrated to give a green solid which was combined with the filter cake to give the title compound (43.2 mg). 1H NMR (CDCl$_3$, 400 MHz): δ 6.74 (d, J=2.4 Hz, 1H), 6.18 (d, J=2.4 Hz, 1H), 5.15 (s, 1H), 3.53 (s, 3H), 2.83 (s, 3H). LCMS (M+H)$^+$ 217.

Step 4: N-[2-methoxy-5-[1-methyl-5-(methylamino)-6-oxopyridin-3-yl]phenyl]methanesulfonamide

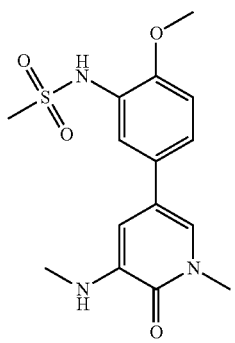

The title compound was prepared in a manner similar to Example 106, substituting the title compound of step 3 for 3-amino-5-bromo-1-methylpyrazin-2-one. $^1$H NMR (Methanol-d4, 400 MHz): δ 7.55 (d, J=2.0 Hz, 1H), 7.38 (dd, J$_1$=8.8, J$_2$=2.4 Hz, 1H), 7.13-7.08 (m, 2H), 6.52 (d, J=2.0 Hz, 1H), 3.93 (s, 3H), 3.63 (s, 3H), 2.94 (s, 3H), 2.88 (s, 3H). LCMS (M+H)$^+$338.

Example 111

N-[5-[5-(ethylamino)-1-methyl-6-oxopyridin-3-yl]-2-methoxyphenyl]methanesulfonamide Step 1: tert-butyl N-(5-bromo-1-methyl-2-oxopyridin-3-yl)-N-ethylcarbamate

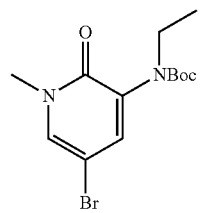 [SMILES: CCN(C(=O)OC(C)(C)C)c1cc(Br)cn(C)c1=O]

To a solution of the title compound from Example 110, step 1 (150.0 mg, crude) in DMF (10 mL) was added NaH (60.0 mg, 1.5 mmol, 60% in oil) in portions at 0° C. and stirred for 30 min. Then iodoethane (234.0 mg, 1.5 mmol) was added dropwise at 0° C. The reaction mixture was stirred for 2 h at 30° C. It was then quenched with saturated aqueous NH$_4$Cl (15 mL), extracted with ethyl acetate (20 mL), washed with brine (20 mL), dried over Na$_2$SO$_4$, filtered and concentrated to give the title compound (120.0 mg, crude) as a light green solid which was carried forward without purification.

Step 2: 5-bromo-3-(ethylamino)-1-methylpyridin-2-one

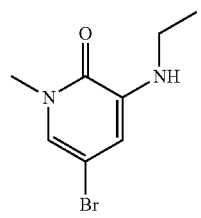

To a solution of tert-butyl N-(5-bromo-1-methyl-2-oxopyridin-3-yl)-N-ethylcarbamate (99.0 mg, crude) in DCM (10 mL) was added HCl/dioxane (1 mL, 4 M) dropwise with stirring at 30° C. The reaction mixture was stirred for 30 min at 30° C. Then the mixture was filtered and the filter cake collected. The filtrate was adjusted to pH=9 with saturated aqueous NaHCO$_3$, extracted with EA (20 mL), dried over Na$_2$SO$_4$, filtered and concentrated to give a light green solid which is combined with the filter cake to give the title compound (46.0 mg) which was carried forward without purification. $^1$H NMR (CDCl$_3$, 400 MHz): δ 6.72 (d, J=2.4 Hz, 1H), 6.20 (d, J=1.6 Hz, 1H), 3.51 (s, 3H), 3.09 (q, J=7.2 Hz, 2H), 1.27 (t, J=7.2 Hz, 3H). LCMS (M+H)$^+$ 231.

Step 3: N-[5-[5-(ethylamino)-1-methyl-6-oxopyridin-3-yl]-2-methoxyphenyl]methanesulfonamide

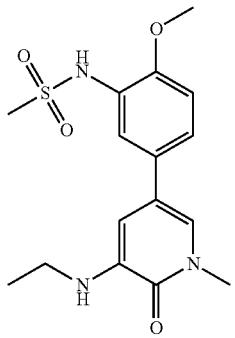

The title compound was prepared in a manner similar to Example 106, substituting the title compound of step 2 for 3-amino-5-bromo-1-methylpyrazin-2-one. $^1$H NMR (CDCl$_3$ 400 MHz): δ 7.63 (d, J=2.0 Hz, 1H), 6.16 (dd, J$_1$=8.4 Hz, J$_1$=2.4 Hz, 1H), 6.95 (d, J=8.4 Hz, 1H), 6.82-6.80 (m, 1H), 6.39 (d, J=2.4 Hz, 1H), 3.93 (s, 3H), 3.64 (s, 3H), 3.19 (q, J=7.2 Hz, 2H), 2.98 (s, 3H), 1.32 (t, J=7.2 Hz, 3H). LCMS (M+H)$^+$ 352.

Example 112

N-[5-[5-(cyclopropylmethylamino)-1-methyl-6-oxopyridin-3-yl]-2-methoxyphenyl]methanesulfonamide

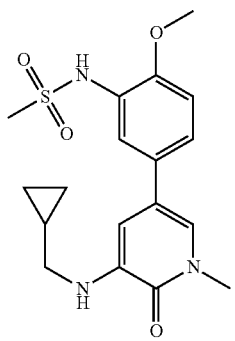

To a solution of compound from Example 109 (64.6 mg, 0.2 mmol) in MeOH (3 mL) and AcOH (0.3 mL) was added cyclopropanecarbaldehyde (14.0 mg, 0.2 mmol) dropwise with stirring at 30° C. NaBH$_3$CN (24.5 mg, 0.4 mol) was added in portions at 30° C. The reaction mixture was stirred for 2 h at 30° C. It was then quenched with saturated aqueous NH$_4$Cl (5 mL), extracted with EtOAc (20 mL), dried over Na$_2$SO$_4$, filtered and concentrated. The residue was purified by prep-HPLC to give the title compound (10.0 mg, 13.2%) as a light green solid. $^1$H NMR (Methanol-d4 400 MHz): δ 7.55 (d, J=2.4 Hz, 1H), 7.36 (dd, J=8.4, 2.4 Hz, 1H), 7.16-7.07 (m, 2H), 6.61 (d, J=2.4 Hz, 1H), 3.94 (s, 3H), 3.66 (s, 3H), 3.05 (s, 2H), 2.95 (s, 3H), 1.21-1.14 (m, 1H), 0.64-0.56 (m, 2H), 0.35-0.28 (m, 2H). LCMS (M+H)$^+$ 378.

Example 113

N-[5-[5-(dimethylamino)-1-methyl-6-oxopyridin-3-yl]-2-methoxyphenyl]methanesulfonamide

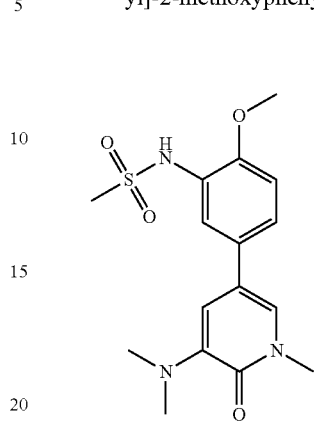

To a solution of compound from Example 109 (64.6 mg, 0.2 mmol) in MeOH (3 mL) and AcOH (0.3 mL) was added HCHO (30.0 mg, 1.0 mmol) dropwise with stirring at 30° C. NaBH$_3$CN (61 mg, 1.0 mol) was added in portions at 30° C. The reaction mixture was stirred for 2 h at 30° C. It was then quenched with saturated aqueous NH$_4$Cl (5 mL), extracted with EtOAc (20 mL), dried over Na$_2$SO$_4$, filtered and concentrated. The residue was purified by column chromatography on silica gel (PE:EA=2:3) to give the title compound (30 mg, 43%) as a light green solid. $^1$H NMR (Methanol-d4 400 MHz): δ 7.54 (d, J=2.4 Hz, 1H), 7.47 (d, J=2.4 Hz, 1H), 7.37 (dd, J$_1$=2.4, J$_2$=8.4 Hz, 1H), 7.11 (d, J=8.4 Hz, 1H), 7.04 (d, J=2.4 Hz, 1H), 3.93 (s, 3H), 3.63 (s, 3H), 2.94 (s, 3H), 2.86 (s, 6H). LCMS (M+H)$^+$ 352.

Example 114

N-[5-[5-(diethylamino)-1-methyl-6-oxopyridin-3-yl]-2-methoxyphenyl]methanesulfonamide

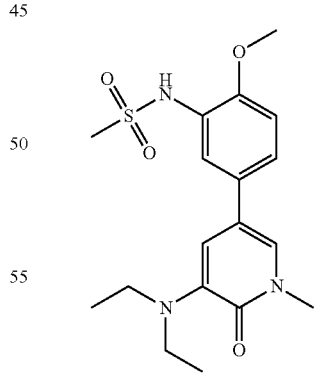

The title compound was prepared in a manner similar to Example 113, substituting acetaldehyde for formaldehyde. $^1$H NMR (Methanol-d4 400 MHz): δ 7.55 (d, J=2.4 Hz, 1H), 7.49 (d, J=2.4 Hz, 1H), 7.37 (dd, J$_1$=8.4 Hz, J$_2$=2.4 Hz, 1H), 7.17-7.11 (m, 1H), 7.06 (d, J=2.4 Hz, 1H), 3.95 (s, 3H), 3.65 (s, 3H), 3.34 (m, 4H), 2.97 (s, 3H), 1.11 (t, J=7.2 Hz, 6H). LCMS (M+H)$^+$ 380.

Example 115

N-[3-(5-amino-1-methyl-6-oxopyridin-3-yl)-4-(2,4-difluorophenoxy)phenyl]ethanesulfonamide Step 1: 3-amino-5-[5-amino-2-(2,4-difluorophenoxy)phenyl]-1-methylpyridin-2-one

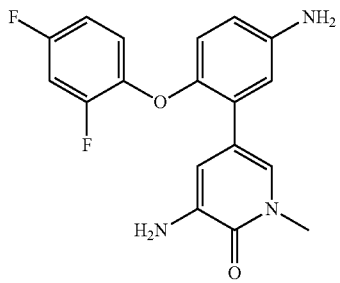 [SMILES: Cn1cc(-c2cc(N)ccc2Oc2ccc(F)cc2F)cc(N)c1=O]

The title compound of step 1 was prepared in a manner similar to Example 107, substituting the title compound of Example 57, step 1 for (3-methylsulfonylphenyl)boronic acid. LCMS (M+H)+ 344.

Step 2: N-[3-(5-amino-1-methyl-6-oxopyridin-3-yl)-4-(2,4-difluorophenoxy)phenyl]ethanesulfonamide

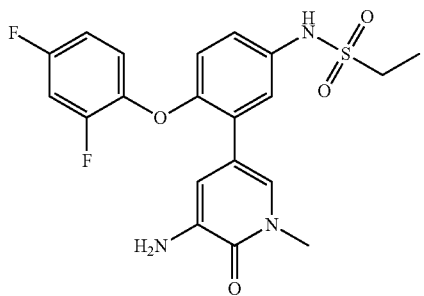 [SMILES: CCS(=O)(=O)Nc1ccc(Oc2ccc(F)cc2F)c(-c2cc(N)c(=O)n(C)c2)c1]

The title compound was prepared in a manner similar to Example 99, step 2. $^1$H NMR (DMSO-d6, 400 MHz) δ9.78 (s, 1H), 7.45-7.39 (m, 1H), 7.23-7.22 (m, 2H), 7.14 (dd, $J_1$=7.2 Hz, $J_2$=1.6 Hz, 1H), 7.10-7.02 (m, 2H), 6.85 (d, J=8.8 Hz, 1H), 6.79 (d, J=2.0 Hz, 1H), 3.49 (s, 3H), 3.09 (q, J=7.2 Hz, 2H), 1.21 (t, J=7.6 Hz, 3H). LCMS (M+H)+ 436.

Example 116

3-amino-5-[2-(cyclopropylmethoxy)-5-methylsulfonylphenyl]-1-methylpyridin-2-one

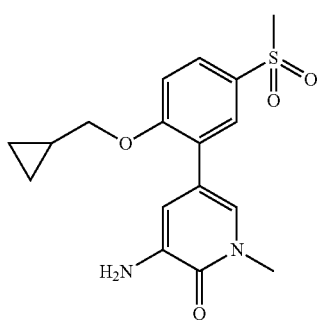 [SMILES: Cn1cc(-c2cc(S(C)(=O)=O)ccc2OCC2CC2)cc(N)c1=O]

The title compound was prepared in a manner similar to Example 107, substituting the title compound of Example 90, step 1 for (3-methylsulfonylphenyl)boronic acid. $^1$H NMR (CDCl$_3$, 400 MHz) δ 7.84-7.81 (m, 2H), 7.11 (d, J=2.0 Hz, 1H), 7.02 (d, J=2.4 Hz, 1H), 6.84 (d, J=2.4 Hz, 1H), 3.95 (d, J=6.8 Hz, 2H), 3.65 (s, 3H), 3.06 (s, 3H), 1.31-1.27 (m, 1H), 0.68 (q, J=5.6 Hz, 2H), 0.37 (q, J=5.2 Hz, 2H). LCMS (M+H)+ 349.

Example 117

4-ethoxy-3-(1-methyl-6-oxopyridin-3-yl)benzenesulfonamide

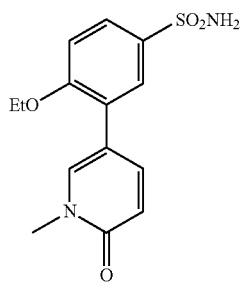 [SMILES: CCOc1ccc(S(N)(=O)=O)cc1-c1ccc(=O)n(C)c1]

A mixture of the title compound of Example 98, step 1 (40 mg, 0.17 mmol), Pd(dppf)Cl$_2$ (10 mg, 8%) and 3-bromo-4-ethoxybenzene-1-sulfonamide (48 mg, 0.17 mmol) was suspended in 1,4-dioxane (880 μL) and saturated bicarbonate solution (aq) (220 μL). The mixture was heated to 95° C. using microwave irradiation (normal) for 60 min. The crude reaction mixture was filtered through a short plug of celite, the plug was washed with additional 1,4-dioxane (1 ml), and the combined filtrate was purified by prep-HPLC. The fractions were combined and lyophilized to give the title compound (14 mg, 27%) as a white solid. 1HNMR (DMSO, 400 MHz): δ 1.33 (t, J=6.9, 3H), 3.49 (s, 3H), 4.15 (q, J=6.9, 2H), 6.45 (d, J=9.4 Hz, 1H), 7.20-7.23 (m, 3H), 7.64 (dd, J=2.6, 9.4 Hz, 1H), 7.72-7.74 (m, 2H), 7.89 (d, J=2.6 Hz, 1H). LCMS (M+H)+=309.

Example 118

4-(2,4-difluorophenoxy)-3-(1-methyl-6-oxopyridin-3-yl)benzenesulfonamide

Step 1: 3-bromo-4-fluorobenzenesulfonamide

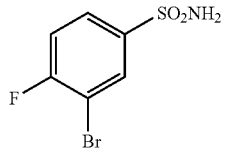 [SMILES: NS(=O)(=O)c1ccc(F)c(Br)c1]

A solution of 3-bromo-4-fluorobenzenesulfonyl chloride (1 g, 3.3 mmol, 90% pure) stirred at 0° C. in THF (15 ml) and DCM (5 ml) was treated with aqueous ammonium hydroxide (28%) by dropwise addition over 15 min. After stirring at 0° C. for 210 min, the mixture was acidified (pH=1) by addition of 1 N HCl (aq). After the mixture was concentrated in vacuo to near dryness, it was treated with water (50 ml), sonicated for 3 min and filtered. After the filter cake was washed sequentially with water (50 ml) and hexanes (100 ml), it was dried in vacuo to afford the title compound (503 mg, 60%) as a white solid which was carried forward without purification. LCMS (M–H)⁻=253.

Step 2: 3-bromo-4-(2,4-difluorophenoxy)benzenesulfonamide

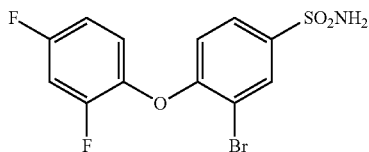 [SMILES: NS(=O)(=O)c1ccc(Oc2ccc(F)cc2F)c(Br)c1]

A solution of 3-bromo-4-fluorobenzenesulfonamide (400 mg, 1.6 mmol) and 2,4-difluorophenol (228 mg, 1.76 mmol) in DMSO (16 ml) was treated with cesium carbonate (1 g, 3.2 mmol). The resulting mixture was heated to 120° C. for 20 min by microwave irradiation (normal). The mixture was treated with water (100 ml) and extracted with EtOAc (3×50 ml). The combined organic extracts were washed with saturated bicarbonate solution (aq), dried over sodium sulfate, filtered and concentrated in vacuo to afford a tan solid. The solid was purified by silica gel chromatography (12 g ISCO, 30% EtOAc in hexanes 30 ml/min) to give the title compound (340 mg, 58%) as a tan solid LCMS (M–H)⁻=362.

Step 3: 4-(2,4-difluorophenoxy)-3-(1-methyl-6-oxopyridin-3-yl)benzenesulfonamide

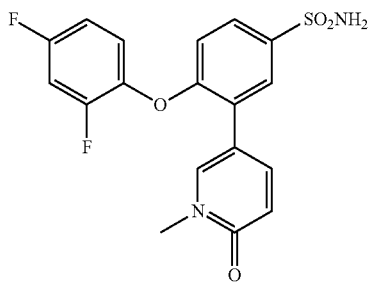

3-Bromo-4-(2,4-difluorophenoxy)benzenesulfonamide (1 eq., 62 mg), the title compound of Example 98, step 1 (40 mg, 0.17 mmol), Pd(dppf)Cl₂ (10 mg, 8%) in 1,4-dioxane (880 µL) and saturated bicarbonate solution (aq) (220 µL) were reacted at 105° C. for 30 min in a manner similar to Example 117. Work up and preparative HPLC, also in a similar manner, gave the title compound (12 mg, 18%) as a white solid. 1H NMR (DMSO, 400 MHz): δ3.51 (s, 3H), 6.49 (d, J=9.4, 1H), 4.15 (q, J=6.9, 2H), 6.45 (d, J=9.4 Hz, 1H), 7.20-7.23 (m, 3H), 7.64 (dd, J=2.6, 9.4 Hz, 1H), 7.72-7.74 (m, 2H), 7.89 (d, J=2.6 Hz, 1H). LCMS (M+H)⁺=393.

Example 119

5-[2-(cyclopropylmethoxy)-5-methylsulfonylphenyl]-3-fluoro-1-methylpyridin-2-one Step 1: 5-bromo-3-fluoro-1-methylpyridin-2-one

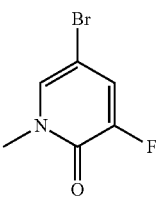

A mixture of 5-bromo-3-fluoropyridin-2-ol (1 g, 5.2 mmol), iodomethane (356 mg, 5.7 mmol) and K₂CO₃ (1.4 g, 10.4 mmol) in DMF (10 mL) was stirred at rt for 12 h. The mixture was treated with water (70 ml) and extracted with EtOAc (3×50 ml). The combined organic extracts were washed with saturated bicarbonate solution (aq), dried over sodium sulfate, filtered and concentrated in vacuo to afford the title compound (1 g, 93%) as a white solid which was carried forward without purification. LCMS (M+H)⁺=207.

Step 2: 3-fluoro-1-methyl-5-(4,4,5,5-tetramethyl-1,3,2-dioxaborolan-2-yl)pyridin-2-one

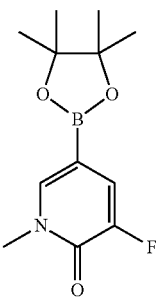 [SMILES: Cn1cc(B2OC(C)(C)C(C)(C)O2)cc(F)c1=O]

A mixture of 5-bromo-3-fluoro-1-methylpyridin-2-one (1 g, 4.9 mmol), 4,4,5,5-tetramethyl-2-(tetramethyl-1,3,2-dioxaborolan-2-yl)-1,3,2-dioxaborolane (2.5 g, 9.8 mmol), KOAc (1.2 g, 12.3 mmol), and Pd(dppf)Cl₂ (286 mg, 8%) was suspended in 1,4-dioxane (15 mL). After purging the reaction vial with nitrogen for 5 min, the capped vial was stirred at 80° C. for 1 h. The mixture was treated with water (70 ml) and extracted with EtOAc (3×40 ml). The combined organic extracts were washed with brine, dried over sodium sulfate, filtered and concentrated in vacuo to afford a dark residue. The residue was purified by silica gel chromatography (12 g ISCO, gradient 05-75% EtOAc in hexanes) to give the title compound (682 mg, 55%) as a reddish brown solid.

Step 3: 5-[2-(cyclopropylmethoxy)-5-methylsulfonylphenyl]-3-fluoro-1-methylpyridin-2-one

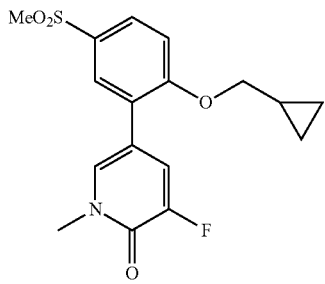 [SMILES: Cn1cc(-c2cc(S(C)(=O)=O)ccc2OCC2CC2)cc(F)c1=O]

3-Fluoro-1-methyl-5-(4,4,5,5-tetramethyl-1,3,2-dioxaborolan-2-yl)pyridin-2-one (40 mg, 0.16 mmol), 2-bromo-1-(cyclopropylmethoxy)-4-methanesulfonylbenzene (49 mg, 0.16 mmol), and Pd(dppf)Cl$_2$ (12 mg, 10%) in 1,4-dioxane (880 μL) and saturated bicarbonate solution (aq) (220 μL) were reacted, worked up, and purified in a manner similar to Example 117. The title compound (22 mg, 46%) was obtained as a tan solid. 1H NMR (400 MHz, DMSO-d6) δ 0.31-0.42 (m, 2H) 0.53-0.63 (m, 2H) 1.17-1.34 (m, 1H) 3.20 (s, 3H) 3.58 (s, 3H) 3.95-4.06 (m, 2H) 7.24-7.33 (m, 1H) 7.72-7.79 (m, 1H) 7.80-7.87 (m, 1H) 7.84 (s, 1H) 7.88-7.93 (m, 1H) LCMS (M+H)$^+$=351.

Example 120

5-[2-(2,4-difluorophenoxy)-5-methylsulfonylphenyl]-3-fluoro-1-methylpyridin-2-one

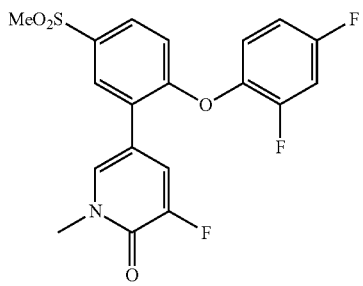 [SMILES: Cn1cc(-c2cc(S(C)(=O)=O)ccc2Oc2ccc(F)cc2F)cc(F)c1=O]

The title compound of Example 119, step 2 (40 mg, 0.16 mmol), 1-(2-bromo-4-methylsulfonylphenoxy)-2,4-difluorobenzene (58 mg, 0.16 mmol) and Pd(dppf)Cl$_2$ (12 mg, 10%) in 1,4-dioxane (880 μL) and saturated bicarbonate solution (aq) (220 μL) were reacted, worked up and purified in a manner similar to Example 117. The title compound (26 mg, 46%) was obtained as a tan solid. 1H NMR (400 MHz, DMSO-d6) δ 3.25 (s, 3H) 3.60 (s, 3H) 6.91-6.99 (m, 1H) 7.16-7.30 (m, 1H) 7.49-7.62 (m, 2H) 7.76-7.86 (m, 2H) 8.00 (m, 2H) LCMS (M+H)$^+$=410.

Example 121

5-[2-(2,4-difluorophenoxy)-5-ethylsulfonylphenyl]-3-fluoro-1-methylpyridin-2-one

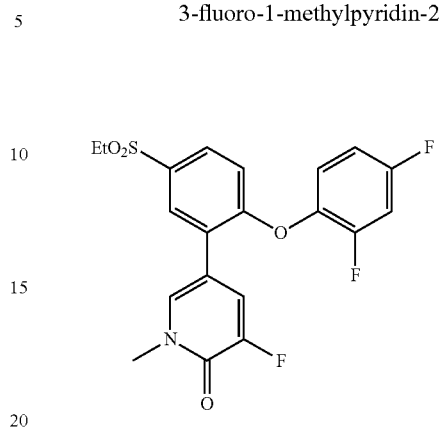

The title compound of Example 119, step 2 (40 mg, 0.16 mmol), 1-(2-bromo-4-ethylsulfonylphenoxy)-2,4-difluorobenzene (60 mg, 0.16 mmol), and Pd(dppf)Cl$_2$ (12 mg, 10%) in 1,4-dioxane (880 μL) and saturated bicarbonate solution (aq) (220 μL) were reacted, worked up and purified in a manner similar to Example 117. The title compound (18 mg, 27%) was obtained as a tan solid. 1H NMR (400 MHz, DMSO-d6) δ 1.13 (t, J=7.33 Hz, 3H) 3.34 (q, J=7.33 Hz, 2H) 3.59 (s, 3H) 6.92-6.98 (m, 1H) 7.19-7.27 (m, 1H) 7.50-7.61 (m, 2H) 7.76-7.84 (m, 2H) 7.92-7.96 (m, 1H) 7.97-8.01 (m, 1H) LCMS (M+H)$^+$=424.

Example 122

N-[4-(2,4-difluorophenoxy)-3-(5-fluoro-1-methyl-6-oxopyridin-3-yl)phenyl]ethanesulfonamide Step 1: N-[3-bromo-4-(2,4-difluorophenoxy)phenyl]ethanesulfonamide

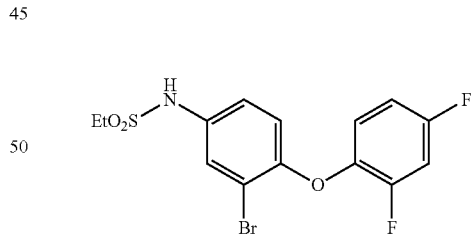

Ethylsulfonyl chloride (177 mg, 1.4 mmol) was added dropwise to a stirred solution of 3-bromo-4-(2,4-difluorophenoxy)aniline (328 mg, 1.1 mmol) and pyridine (178 μL, 2.2 mmol) in dichloromethane (2 ml) at 0° C. under nitrogen. After the mixture was allowed to warm to rt and stir overnight, it was treated with 1N HCl (10 ml) and extracted with dichloromethane (3×10 ml); the combined organic extracts were washed with saturated bicarbonate solution (aq), dried over sodium sulfate, filtered and concentrated in vacuo to give the title compound (430 mg, 99%) as a tan solid which was carried forward without purification. LCMS (M−H)$^−$=391.

Step 2: N-[4-(2,4-difluorophenoxy)-3-(5-fluoro-1-methyl-6-oxopyridin-3-yl)phenyl]ethanesulfonamide

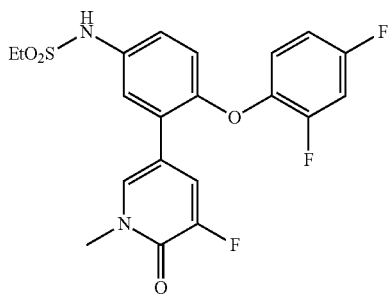

N-[3-Bromo-4-(2,4-difluorophenoxy)phenyl]ethanesulfonamide (77 mg, 0.2 mmol), the title compound of Example 119, step 2 (50 mg, 0.2 mmol), and Pd(dppf)Cl$_2$ (14 mg, 10%) in 1,4-dioxane (1 mL) and saturated bicarbonate solution (aq) (333 µL) were reacted, worked up and purified in a manner similar to Example 117. The title compound (31 mg, 27%) was obtained as a tan solid. 1H NMR (400 MHz, DMSO-d6) δ 1.22 (t, J=7.3, 3H) 3.11 (q, J=7.3 Hz, 2H) 3.55 (s, 3H) 6.86 (d, J=8.6 Hz, 1H) 7.02-7.12 (m, 1H) 7.13-7.23 (m, 2H) 7.26 (d, J=2.8 Hz, 1H) 7.35-7.52 (m, 1H) 7.60 (m, 1H) 7.79 (s, 1H) 9.48-9.96 (m, 1H). LCMS (M+H)$^+$=439.

Example 123

N-[3-(2-methyl-1-oxo-2,6-naphthyridin-4-yl)phenyl]ethanesulfonamide

Step 1: 4-chloro-2-methyl-2,6-naphthyridin-1-one

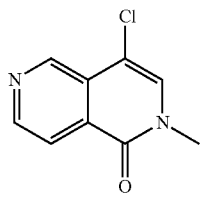

N-chlorosuccinimide (0.8 g, 6.2 mmol) was added in portions to a solution of 2-methyl-2,6-naphthyridin-1-one (1.0 g, 6.2 mmol) in acetonitrile (25 mL) which was then heated at 65° C. for 18 h. Extractive work up with ethyl acetate and purification by silica gel chromatography (PE:EA=5:1~1:1) gave the title compound of step 1 (0.6 g, 56%) as a yellow solid. $^1$H NMR: (CDCl3, 400 MHz) δ 9.29 (s, 1H), 8.81 (d, J=3.6 Hz, 1H), 8.21 (d, J=5.2 Hz, 1H), 7.31 (s, 1H), 3.63 (s, 3H). LCMS: 195.0 (M+H)$^+$.

Step 2: N-[3-(2-methyl-1-oxo-2,6-naphthyridin-4-yl)phenyl]ethanesulfonamide

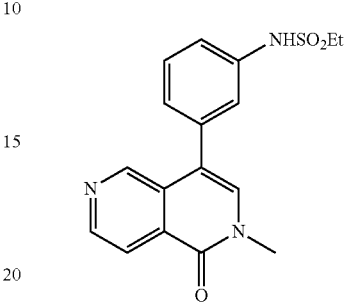

A mixture of 4-chloro-2-methyl-2,6-naphthyridin-1-one (50.0 mg, 0.26 mmol), [3-(ethylsulfonylamino)phenyl]boronic acid (88.0 mg, 0.38 mmol), Pd(dppf)Cl$_2$ (15.3 mg, 0.026 mmol) and K$_3$PO$_4$ (190 mg, 0.9 mmol) in dioxane (3 mL) and water (0.5 mL) was microwaved at 120° C. under microwave for 2 h. Purification by silica gel chromatography on (PE:EA=10:1 to 1:1) followed by preparative HPLC gave the title compound (5.9 mg, 6.8%) as a yellow solid. $^1$H NMR (Methanol-d4, 400 MHz) δ 8.99 (brs, 1H), 8.71 (d, J=6.0 Hz, 1H), 8.39 (d, J=5.6 Hz, 1H), 7.62 (s, 1H), 7.51 (t, J=8.0 Hz, 1H), 7.41-7.40 (m, 1H), 7.36 (dd, J$_1$=8.0 Hz, J$_2$=1.2 Hz, 1H), 7.29 (d, J=5.6 Hz, 1H), 3.72 (s, 3H), 3.17 (q, J=7.6 Hz, 2H), 1.35 (t, J=7.6 Hz, 3H). LCMS: 344.1 (M+H)$^+$.

Examples 124-126 in Table 15 were prepared from title compound of Example 123, step 1, using the appropriate phenyl boronic acid/ester in a manner similar to Example 123, step 2. Example 127 in Table 15 was prepared in two steps from the title compound of Example 123, step 1, and the title compound of Example 57, step 1, by coupling the aniline boronic ester in a manner similar to Example 123, step 1, except that the temperature was raised from 120° C. to 150° C. and NMP was used instead of dioxane (step 1), followed by sulfonylation of the aniline in a manner similar to Example 57, step 3 (step 2).

TABLE 15

| Ex. No. | R$^1$ | Name | $^1H$ NMR (ppm (δ), 400 Hz) | MS (M + H) |
|---|---|---|---|---|
| 124 | *phenyl-SO2NHEt group* | N-ethyl-3-(2-methyl-1-oxo-2,6-naphthyridin-4-yl)benzenesulfonamide | (Methanol-d4) 8.86 (d, J = 0.8 Hz, 1 H), 8.70 (d, J = 5.6 Hz, 1 H), 8.28 (dd, J$_1$ = 5.6 Hz, J$_2$ = 0.8 Hz, 1 H), 7.98-7.95 (m, 2 H), 7.78-7.75 (m, 2 H), 7.60 (s, 1 H), 3.71 (s, 3 H), 2.98 (q, J = 7.2 Hz, 2 H), 1.10 (t, J = 7.2 Hz, 3 H) | 344 |

TABLE 15-continued

| Ex. No. | R¹ | Name | ¹H NMR (ppm (δ), 400 Hz) | MS (M + H) |
|---|---|---|---|---|
| 125 | | N-[3-(2-methyl-1-oxo-2,6-naphthyridin-4-yl)phenyl]methanesulfonamide | (CD₃OD) 8.98 (s, 1 H), 8.70 (d, J = 5.2 Hz, 1 H), 8.34 (d, J = 5.2 Hz, 1 H), 7.60 (s, 1 H), 7.52 (t, J = 8.0 Hz, 1 H), 7.40 (s, 1 H), 7.36 (d, J = 8.0 Hz, 1 H), 7.31 (d, J = 8.0 Hz, 1 H), 3.71 (s, 3 H), 3.04 (s, 3 H) | 330 |
| 126 | | 4-(3-ethylsulfonylphenyl)-2-methyl-2,6-naphthyridin-1-one | (CD₃OD) 9.02 (s, 1 H), 8.78 (d, J = 5.2 Hz, 1 H), 8.57 (d, J = 5.2 Hz, 1 H), 8.09 (s, 1 H), 8.06 (d, J = 7.6 Hz, 1 H), 7.93 (d, J = 7.6 Hz, 1 H), 7.85 (t, J = 7.6 Hz, 1 H), 7.80 (s, 1 H), 3.74 (s, 3 H), 3.33 (q, J = 7.6 Hz, 2 H), 1.29 (t, J = 7.6 Hz, 3 H) | 329 |
| 127 | | N-[4-(2,4-difluorophenoxy)-3-(2-methyl-1-oxo-2,6-naphthyridin-4-yl)phenyl]ethanesulfonamide | (CD₃OD) 9.02 (s, 1 H), 8.78 (d, J = 5.2 Hz, 1 H), 8.57 (d, J = 5.2 Hz, 1 H), 8.09 (s, 1 H), 8.06 (d, J = 7.6 Hz, 1 H), 7.93 (d, J = 7.6 Hz, 1 H), 7.85 (t, J = 7.6 Hz, 1 H), 7.80 (s, 1 H), 3.74 (s, 3 H), 3.33 (q, J = 7.6 Hz, 2 H), 1.29 (t, J = 7.6 Hz, 3 H) | 472 |

Example 128

4-[2-(cyclopropylmethoxy)-5-methylsulfonylphenyl]-2-methyl-6-(4-methylpyrazol-1-yl)isoquinolin-1-one Step 1:
2-methyl-6-(4-methylpyrazol-1-yl)isoquinolin-1-one

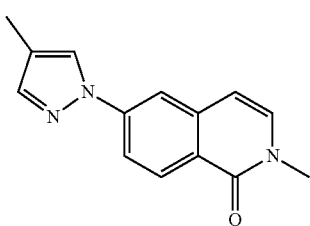

6-Bromo-2-methylisoquinolin-1-one (300.0 mg, 1.27 mmol), 4-methyl-1H-pyrazole (210.0 mg, 2.54 mmol), CuI (30.0 mg, 0.127 mmol) and K₂CO₃ (360.0 mg, 2.54 mmol) in NMP (3.0 mL) were microwaved at 195° C. for 5 h. Extractive work up with ethyl acetate followed by silica gel chromatography (PE:EA=5:1) gave the title compound of step 1 (160.0 mg, 52%) as a light yellow solid. ¹H NMR (CDCl₃, 400 MHz) δ 8.49 (d, J=8.8 Hz, 1H), 7.84 (s, 1H), 7.83 (d, J=2.0 Hz, 1H), 7.74 (dd, J1=8.8 Hz, J2=2.0 Hz, 1H), 7.59 (s, 1H), 7.10 (d, J=7.6 Hz, 1H), 6.52 (d, J=7.6 Hz, 1H), 3.62 (s, 3H), 2.19 (s, 3H). LCMS: 240.0 (M+H)⁺.

Step 2: 4-bromo-2-methyl-6-(4-methylpyrazol-1-yl)isoquinolin-1-one

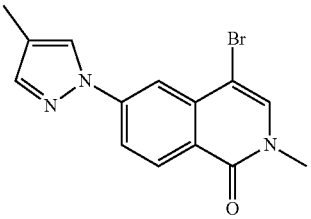

Bromine (94 mg, 0.59 mmol) in acetic acid (2 mL) was added drop-wise to a solution of 2-methyl-6-(4-methylpyrazol-1-yl)isoquinolin-1-one (140.0 mg, 0.583 mmol) in acetic acid (4 mL) at 0° C. The mixture was then stirred at room temperature for 17 min and quenched with water (10 mL). The pH was adjusted to about 7-8 with aqueous 1M NaOH. Extractive work up with ethyl acetate followed by purification using silica gel chromatography (PE:EA=1:1) gave the title compound of step 2 (120.0 mg, 56%) as a light yellow solid. $^1$H NMR (CDCl$_3$, 400 MHz) δ 8.51 (d, J=8.8 Hz, 1H), 8.06 (d, J=2.0 Hz, 1H), 7.89 (s, 1H), 7.87 (dd, J1=8.8 Hz, J2=2.0 Hz, 1H), 7.63 (s, 1H), 7.42 (s, 1H), 3.62 (s, 3H), 2.20 (s, 3H). LCMS: 319.8 (M+H)+.

Step 3: 4-[2-(cyclopropylmethoxy)-5-methylsulfonylphenyl]-2-methyl-6-(4-methylpyrazol-1-yl)isoquinolin-1-one

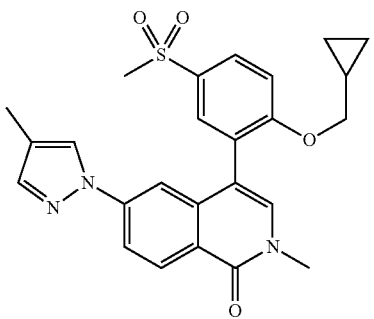 [SMILES: Cc1cnn(-c2ccc3c(=O)n(C)cc(-c4cc(S(C)(=O)=O)ccc4OCC4CC4)c3c2)c1]

4-Bromo-2-methyl-6-(4-methylpyrazol-1-yl)isoquinolin-1-one (40.0 mg, 0.126 mmol), the title compound of Example 90, step 1 (53.2 mg, 0.152 mmol), Pd(dppf)Cl$_2$ (200.0 mg, 0.05 mmol) and aqueous 1M K$_3$PO$_4$ (0.38 mL, 0.38 mmol) in dioxane (3 mL) were heat in a microwave at 100° C. for 1 h. Purification by preparative HPLC gave the title compound (15.0 mg, 25%) as a white solid. $^1$H NMR (CDCl$_3$, 400 MHz) δ 8.57 (d, J=8.4 Hz, 1H), 8.00 (d, J=8.4 Hz, 1H), 7.90 (s, 1H), 7.75 (d, J=7.6 Hz, 1H), 7.73 (s, 1H), 7.54 (s, 1H), 7.50 (s, 1H), 7.14 (s, 1H), 7.12 (s, J=9.2 Hz, 1H), 3.96-3.83 (m, 2H), 3.68 (s, 3H), 3.13 (s, 3H), 2.15 (s, 3H), 1.01-0.94 (m, 1H), 0.38-0.28 (m, 2H), 0.08-0.02 (m, 2H). LCMS: 464.1 (M+H)$^+$.

Example 129

N-[4-(2,4-difluorophenoxy)-3-(7-methyl-8-oxoimidazo[1,5-a]pyrazin-5-yl)phenyl]ethanesulfonamide Step 1: 5-bromo-7-methylimidazo[1,5-a]pyrazin-8-one

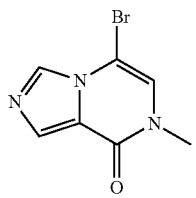

To a solution of 5-bromo-1-methylpyrazin-2-one (500.0 mg, 2.65 mmol) and (p-tolylsulfonyl)methyl isocyanide (573.0 mg, 2.94 mmol) in THF (4 mL) was added a suspension of NaH (235.0 mg, 5.9 mmol) in THF (2 mL) at 0° C. under N$_2$. After stirring at 0° C. for 30 min, the mixture was stirred at 30° C. for another 1.5 h. The reaction mixture was quenched with H$_2$O (20 mL) at 0° C., and extracted with EtOAc (30 mL×2). The organic phases were combined, washed with brine (30 mL), dried over Na$_2$SO$_4$, filtered and evaporated. The crude product was purified by column chromatography (PE:EA=1/1) to give the title compound (300.0 mg, 50%) as a light yellow solid. $^1$H NMR (CDCl$_3$ 400 MHz) δ 8.06 (d, J=4.4 Hz, 1H), 6.61 (s, 1H), 3.48 (s, 3H). LCMS (M+H)$^+$ 228.

Step 2: 5-[5-amino-2-(2,4-difluorophenoxy)phenyl]-7-methylimidazo[1,5-a]pyrazin-8-one

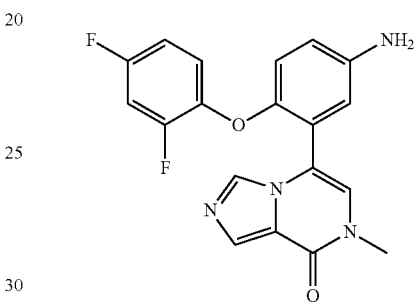

A solution of 5-bromo-7-methylimidazo[1,5-a]pyrazin-8-one (114.0 mg, 0.5 mmol), the title compound of Example 57, step 1 (208.0 mg, 0.6 mmol), Pd(dppf)$_2$Cl$_2$ (37.0 mg, 0.05 mmol), NaHCO$_3$ (126.0 mg, 1.5 mmol) in dioxane (10 mL) and H$_2$O (1 mL) was stirred in microwave at 110° C. with N$_2$ atmosphere for 3 hours. The solvent was evaporated to give the crude product, which was purified by column chromatography (PE:EA=3/1) to give the title compound (110 mg, 60%) as a yellow solid. $^1$H NMR (CDCl$_3$ 400 MHz) δ 7.94 (s, 1H), 7.82 (s, 1H), 6.93-6.82 (m, 2H), 6.79-6.74 (m, 4H), 6.41 (s, 1H), 3.50 (s, 3H). LCMS (M+H)$^+$ 369.

Step 3: N-[4-(2,4-difluorophenoxy)-3-(7-methyl-8-oxoimidazo[1,5-a]pyrazin-5-yl)phenyl]ethanesulfonamide

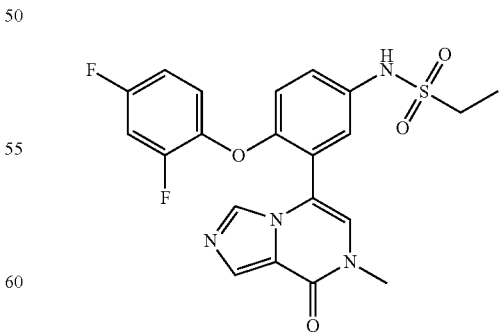

The title compound was prepared in a manner similar to Example 99, step 2, substituting the title compound of step 2 for the title compound of Example 99, step 1. $^1$H NMR (CDCl$_3$ 400 MHz) δ 8.57 (s, 1H), 8.14 (s, 1H), 7.50 (d, J=2.4

Hz, 1H), 7.30 (dd, J1=8.8 Hz, J₂=2.4, 1H), 7.20-7.16 (m, 1H), 6.99-6.87 (m, 2H), 6.83 (s, 1H), 6.55 (d, J=8.8 Hz, 1H), 3.59 (s, 3H), 3.13 (q, J=7.2 Hz, 2H), 1.39 (t, J=7.2 Hz, 3H). LCMS (M+H)⁺ 461.

Example 130

5-[2-(cyclopropylmethoxy)-5-methylsulfonylphenyl]-7-methylimidazo[1,5-a]pyrazin-8-one

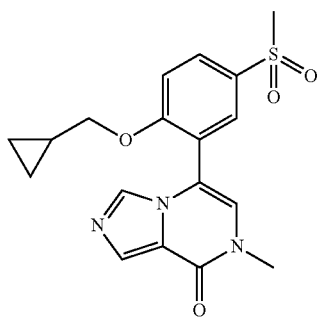 [SMILES: Cn1cc(-c2cc(S(C)(=O)=O)ccc2OCC2CC2)n2cncc2c1=O]

The title compound was prepared in a manner similar to Example 129, step 2, substituting 2-[2-(cyclopropylmethoxy)-5-methylsulfonylphenyl]-4,4,5,5-tetramethyl-1,3,2-dioxaborolane for 4-(2,4-difluorophenoxy)-3-(4,4,5,5-tetramethyl-1,3,2-dioxaborolan-2-yl)aniline to give the title compound. ¹H NMR (CDCl₃ 400 MHz) δ 8.08 (dd, J₁=8.8 Hz, J₂=2.4, 1H), 8.03 (s, 1H), 7.98 (d, J=2.4 Hz, 1H), 7.58 (s, 1H), 7.16 (d, J=8.8 Hz, 1H), 6.50 (s, 1H), 3.97 (d, J=7.2 Hz, 2H), 3.54 (s, 3H), 3.11 (s, 3H), 1.15-1.02 (m, 1H), 0.59-0.49 (m, 2H), 0.26-0.17 (m, 2H). LCMS (M+H)⁺ 374.

Example 131

7-methyl-5-(3-methylsulfonylphenyl)imidazo[1,5-a]pyrazin-8-one

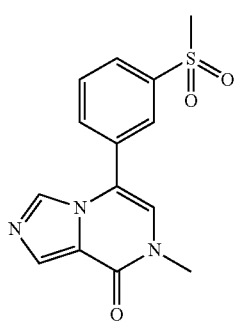 [SMILES: Cn1cc(-c2cccc(S(C)(=O)=O)c2)n2cncc2c1=O]

A solution of compound from Example 129, step 1 (80 mg, 0.35 mmol), (3-methylsulfonylphenyl)boronic acid (77 mg, 0.6 mmol), Na₂CO₃ (106 mg, 1 mmol), Pd(PPh₃)₂Cl₂ (30.0 mg) in dioxane (3 mL) and water (0.5 mL) was stirred at 120° C. for 18 h under N₂. After cooling to room temperature, the mixture was filtered, concentrated and purified by prep-HPLC to give the title compound (20.0 mg, 20%). ¹H NMR (Methanol-d₄ 400 MHz): δ 8.70-8.65 (m, 1H), 8.30-8.20 (m, 2H), 8.16 (d, J=8.0 Hz, 1H), 8.05 (d, J=8.0 Hz, 1H), 7.88 (t, J=8.0 Hz, 1H), 7.22 (s, 1H), 3.56 (s, 3H), 3.24 (s, 3H). LCMS (M+H)⁺ 304.

Example 132

N-[2-methoxy-5-(7-methyl-8-oxoimidazo[1,5-a]pyrazin-5-yl)phenyl]methanesulfonamide

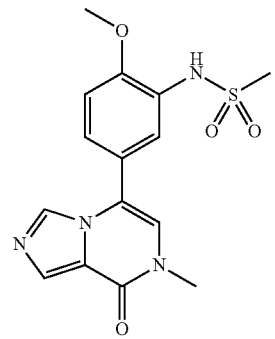 [SMILES: COc1ccc(-c2cn(C)c(=O)c3cncn23)cc1NS(C)(=O)=O]

The title compound was prepared in a manner similar to Example 131, substituting [3-(methanesulfonamido)-4-methoxyphenyl]boronic acid for (3-methylsulfonylphenyl)boronic acid to give the title compound. ¹H NMR (Methanol-d₄ 400 MHz): δ 8.81 (s, 1H), 8.29 (s, 1H), 7.70 (s, 1H), 7.50 (m, 2H), 7.28 (d, J=8.0 Hz, 1H), 7.12 (s, 1H), 4.01 (s, 3H), 3.56 (s, 3H), 3.08 (s, 3H). LCMS (M+H)⁺ 349.

Example 133

5-(3-ethylsulfonylphenyl)-7-methylimidazo[1,5-a]pyrazin-8-one

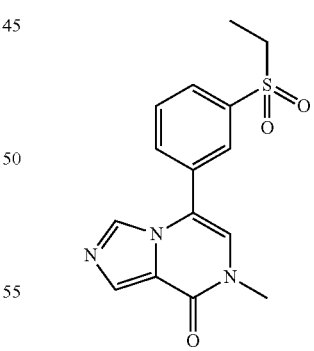

The title compound was prepared in a manner similar to Example 131, substituting (3-ethylsulfonylphenyl)boronic acid for (3-methylsulfonylphenyl)boronic acid to give the title compound. ¹H NMR (Methanol-d4 400 MHz): δ 8.83 (s, 1H), 8.27 (s, 1H), 8.21 (s, 1H), 8.10 (d, J=7.6 Hz, 1H), 8.05 (d, J=8.0 Hz, 1H), 7.89 (t, J=8.0 Hz, 1H), 7.24 (s, 1H), 3.56 (s, 3H), 3.31 (q, J=7.6 Hz, 2H), 1.28 (t, J=7.6 Hz, 3H). LCMS (M+H)⁺ 318.

Example 134

N-[3-(5-chloro-1-methyl-6-oxopyridin-3-yl)-4-(2,4-difluorophenoxy)phenyl]ethanesulfonamide

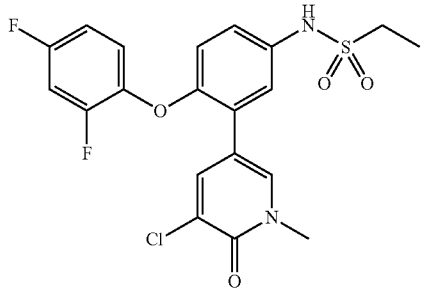 [SMILES: CCS(=O)(=O)Nc1ccc(Oc2ccc(F)cc2F)c(-c2cc(Cl)c(=O)n(C)c2)c1]

The title compound was prepared in a manner similar to Example 122, substituting 3-chloro-1-methyl-5-(4,4,5,5-tetramethyl-1,3,2-dioxaborolan-2-yl)pyridin-2-one for 3-fluoro-1-methyl-5-(4,4,5,5-tetramethyl-1,3,2-dioxaborolan-2-yl)pyridin-2-one. LCMS (M+H)$^+$ 455.

Example 135

4-[2-(cyclopropylmethoxy)-5-ethylsulfonylphenyl]-2-methylisoquinolin-1-one

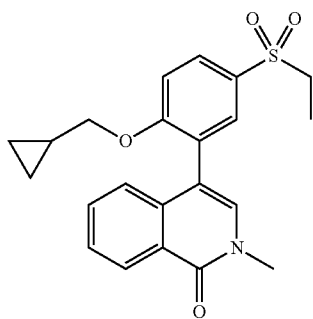 [SMILES: CCS(=O)(=O)c1ccc(OCC2CC2)c(-c2cn(C)c(=O)c3ccccc23)c1]

The title compound was prepared in a manner similar to Example 89, substituting 2-bromo-1-(cyclopropylmethoxy)-4-ethylsulfonylbenzene for 2-bromo-1-(cyclopropylmethoxy)-4-methylsulfonylbenzene. LCMS (M+H)$^+$ 398.

Example 136

6-[2-(cyclopropylmethoxy)-5-methylsulfonylphenyl]-2,4-dimethylpyridazin-3-one

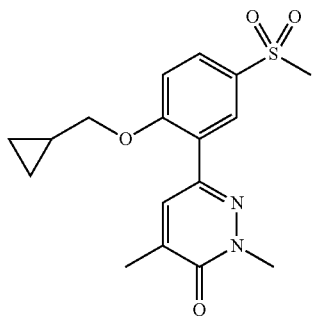 [SMILES: Cc1cc(-c2cc(S(C)(=O)=O)ccc2OCC2CC2)nn(C)c1=O]

The title compound was prepared in a manner similar to Example 90, substituting 6-chloro-2,4-dimethylpyridazin-3-one for 4-bromo-6-fluoro-2-methylisoquinolin-1-one. LCMS (M+H)$^+$ 349.

Example 137

6-[2-(cyclopropylmethoxy)-5-methylsulfonylphenyl]-2,5-dimethylpyridazin-3-one

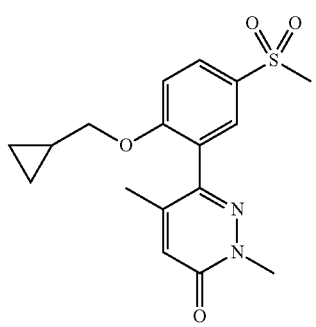 [SMILES: Cc1cc(=O)n(C)nc1-c1cc(S(C)(=O)=O)ccc1OCC1CC1]

The title compound was prepared in a manner similar to Example 90, substituting 6-chloro-2,5-dimethylpyridazin-3-one for 4-bromo-6-fluoro-2-methylisoquinolin-1-one. LCMS (M+H)$^+$ 349.

Example 138

N-[4-(2,4-difluorophenoxy)-3-[1-methyl-6-oxo-5-(trifluoromethyl)pyridin-3-yl]phenyl]ethanesulfonamide

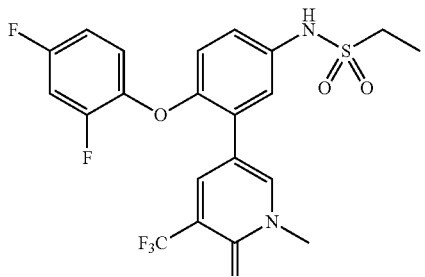

The title compound was prepared in a manner similar to Example 122, substituting 1-methyl-5-(4,4,5,5-tetramethyl-1,3,2-dioxaborolan-2-yl)-3-(trifluoromethyl)pyridin-2-one for 3-fluoro-1-methyl-5-(4,4,5,5-tetramethyl-1,3,2-dioxaborolan-2-yl)pyridin-2-one. LCMS (M+H)$^+$ 489.

Example 139

N-[4-(2,4-difluorophenoxy)-3-(4-fluoro-1-methyl-6-oxopyridin-3-yl)phenyl]ethanesulfonamide

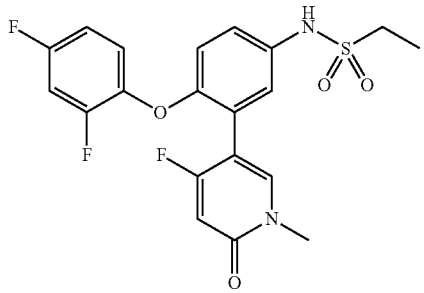 [SMILES: CCS(=O)(=O)Nc1ccc(Oc2ccc(F)cc2F)c(-c2cn(C)c(=O)cc2F)c1]

Step 1: 2-chloro-5-[2-(2,4-difluorophenoxy)-5-nitrophenyl]-4-fluoropyridine

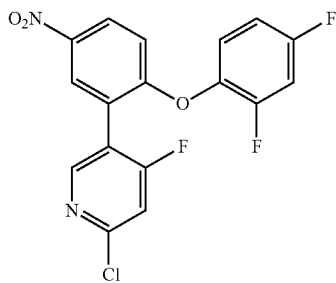 [SMILES: O=[N+]([O-])c1ccc(Oc2ccc(F)cc2F)c(-c2cnc(Cl)cc2F)c1]

A mixture of 2-chloro-4-fluoro-5-(4,4,5,5-tetramethyl-1,3,2-dioxaborolan-2-yl)pyridine (170 mg, 0.66 mmol), 2-bromo-1-(2,4-difluorophenoxy)-4-nitrobenzene (326 mg, 0.98 mmol), Pd$_2$(dba)$_3$ (30 mg, 5%), and tricyclohexylphosphine (280 mg, 10%) was suspended in 1,4-dioxane (4 mL) and aqueous 1M K$_3$PO$_4$ (2 mL). The mixture was heated to 70° C. using microwave irradiation (normal) for 45 min. The crude reaction mixture was filtered through a short plug of celite and the celite plug was washed with EtOAc (~50 mL). The filtrate was washed with water (2×30 mL), brine, dried over sodium sulfate, filtered and concentrated in vacuo. The resulting residue was purified by silica gel column chromatography (12 g ISCO, gradient 05-75% EtOAc in hexanes) to afford the free base of the desired product, 2-chloro-5-[2-(2,4-difluorophenoxy)-5-nitrophenyl]-4-fluoropyridine as a yellow solid (144 mg, 57%). LCMS (M+H)$^+$=381.

Step 2: 5-[2-(2,4-difluorophenoxy)-5-nitrophenyl]-4-fluoro-1-methylpyridin-2-one

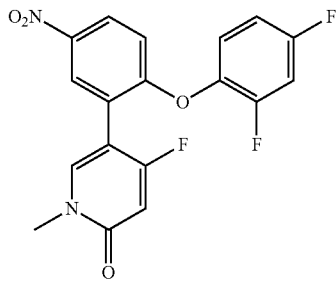

A mixture of 2-chloro-5-[2-(2,4-difluorophenoxy)-5-nitrophenyl]-4-fluoropyridine (140 mg, 0.37 mmol), KOH (62 mg, 1.11 mmol), Pd$_2$(dba)$_3$ (17 mg, 5%), and XPhos (18 mg, 10%) was suspended in 1,4-dioxane (1.9 mL) and water (316 μL). After purging the reaction vial with nitrogen for 5 min, the capped vial was stirred at 100° C. for 1 h. After the mixture cooled to rt, it was treated with 1N HCl (aq) (1 mL) and EtOAc (5 mL). The biphasic mixture was filtered through a short plug of celite and the celite plug was washed with EtOAc (~50 mL). The filtrate was washed with water (2×30 mL), brine, dried over sodium sulfate, filtered and concentrated in vacuo to afford a orange solid, 5-[2-(2,4-difluorophenoxy)-5-nitrophenyl]-4-fluoropyridin-2-ol (LCMS (M+H)$^+$=363). After the solid was diluted with DMF (2.4 mL), it was treated with K$_2$CO$_3$ (112 mg) and MeI (23 μL). After stirring at rt for 5 h, the mixture was treated with water (10 mL) and extracted with EtOAc (3×10 mL); the combined organic extracts were washed with saturated bicarbonate solution (aq), dried over sodium sulfate, filtered, concentrated in vacuo. The resulting residue was purified by silica gel column chromatography (4 g ISCO, gradient 05-95% EtOAc in hexanes) to afford the desired product, 5-[2-(2,4-difluorophenoxy)-5-nitrophenyl]-4-fluoro-1-methylpyridin-2-one as a tan solid (95 mg). LCMS (M+H)$^+$=377.

Step 3: 5-[5-amino-2-(2,4-difluorophenoxy)phenyl]-4-fluoro-1-methylpyridin-2-one

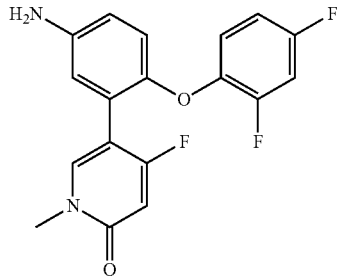 [SMILES: Cn1cc(-c2cc([N+](=O)[O-])ccc2Oc2ccc(F)cc2F)c(F)cc1=O]

A mixture of 5-[2-(2,4-difluorophenoxy)-5-nitrophenyl]-4-fluoro-1-methylpyridin-2-one (90 mg, 0.24 mmol), ammonium chloride (26 mg, 0.48 mmol), iron powder (67 mg, 1.2 mmol) suspended in THF (500 μL), water (180 μL) and ethanol (500 μL) was heated to 100° C. using microwave irradiation (normal) for 3 h. The crude reaction mixture was filtered through a short plug of celite and the celite plug was washed with heated (50° C.) MeOH (~10 mL). The resulting filtrate was concentrated in vacuo. The resulting residue was diluted with EtOAc (20 ml) and washed with saturated bicarbonate solution (aq), dried over anhydrous magnesium sulfate, filtered, and concentrated in vacuo to afford the desired product, 5-[5-amino-2-(2,4-difluorophenoxy)phenyl]-4-fluoro-1-methylpyridin-2-one (75 mg, 90%). LCMS (M+H)$^+$=347. The material was carried forward without any further purification.

Step 4: N-[4-(2,4-difluorophenoxy)-3-(4-fluoro-1-methyl-6-oxopyridin-3-yl)phenyl]ethanesulfonamide

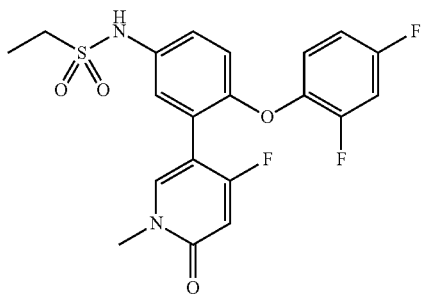 [SMILES: CCS(=O)(=O)Nc1ccc(Oc2ccc(F)cc2F)c(-c2cn(C)c(=O)cc2F)c1]

Ethylsulfonyl chloride (177 mg, 1.4 mmol) was added dropwise to a stirred solution of 5-[5-amino-2-(2,4-difluorophenoxy)phenyl]-4-fluoro-1-methylpyridin-2-one (72 mg, 0.21 mmol) and pyridine (50 μL, 0.63 mmol) in dichloromethane (500 μL) at 0° C. under nitrogen. After the mixture was allowed to warm to rt and stir for 2 h, it was treated with 1N HCl (3 mL) and extracted with dichloromethane (3×10 mL); the combined organic extracts were washed with saturated bicarbonate solution (aq), dried over sodium sulfate, filtered and concentrated in vacuo. The resulting residue was purified by silica gel column chromatography (4 g ISCO, gradient 0-10% MeOH in dichloromethane) to afford the desired product, N-[4-(2,4-difluorophenoxy)-3-(4-fluoro-1-methyl-6-oxopyridin-3-yl)phenyl]ethanesulfonamide (66 mg, 72%) as a white solid. $^1$H NMR (400 MHz, DMSO-d6) δ 1.18-1.26 (m, 3H), 3.07-3.16 (m, 2H), 3.45 (s, 3H), 6.22-6.33 (m, 1H), 6.82-6.93 (m, 1H), 7.01-7.16 (m, 2H), 7.18-7.28 (m, 2H), 7.38-7.49 (m, 1H), 7.95-8.05 (m, 1H), 9.77-9.87 (s, 1H). LCMS (M+H)$^+$=439.

Example 140

N-[3-(5-cyclopropyl-1-methyl-6-oxopyridin-3-yl)-4-(2,4-difluorophenoxy)phenyl]ethanesulfonamide

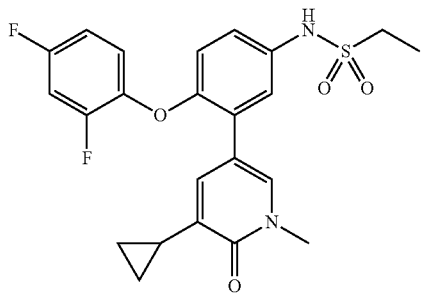 [SMILES: CCS(=O)(=O)Nc1ccc(Oc2ccc(F)cc2F)c(-c2cc(C3CC3)c(=O)n(C)c2)c1]

The title compound was prepared in a manner similar to Example 122, substituting 3-cyclopropyl-1-methyl-5-(4,4,5,5-tetramethyl-1,3,2-dioxaborolan-2-yl)pyridin-2-one for 3-fluoro-1-methyl-5-(4,4,5,5-tetramethyl-1,3,2-dioxaborolan-2-yl)pyridin-2-one. LCMS (M+H)$^+$ 461.

Example 141

N-{4-(2,4-difluorophenoxy)-3-[1-($^2$H$_3$)methyl-6-oxopyridin-3-yl]phenyl}ethanesulfonamide

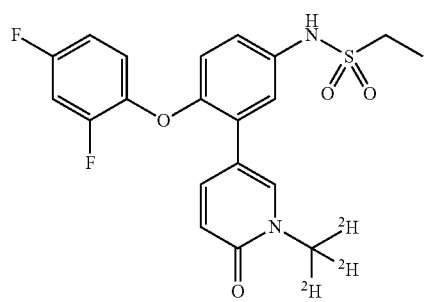 [SMILES: [2H]C([2H])([2H])n1cc(-c2cc(NS(=O)(=O)CC)ccc2Oc2ccc(F)cc2F)ccc1=O]

The title compound was prepared in a manner similar to Example 122, substituting 1-($^2$H$_3$)methyl-5-(4,4,5,5-tetramethyl-1,3,2-dioxaborolan-2-yl)pyridin-2-one for 3-fluoro-1-methyl-5-(4,4,5,5-tetramethyl-1,3,2-dioxaborolan-2-yl)pyridin-2-one. LCMS (M+H)$^+$ 424.

Example 142

N-[4-(2,4-difluorophenoxy)-3-(2-methyl-1-oxo-5,6,7,8-tetrahydro-2,6-naphthyridin-4-yl)phenyl]ethanesulfonamide

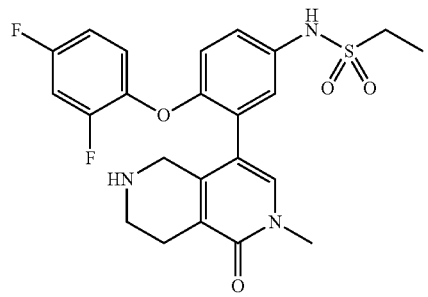 [SMILES: CCS(=O)(=O)Nc1ccc(Oc2ccc(F)cc2F)c(-c2cn(C)c(=O)c3c2CNCC3)c1]

The title compound of Example 127 (240 mg, 0.5 mmol) was hydrogenated (50 psi) at room temperature in anhydrous EtOH (30 mL) for 18 h using PtO$_2$ (0.1 g). Purification by preparative HPLC gave the title compound (40 mg, 16.7%) as a white solid. $^1$H NMR (Methanol-d4, 400 MHz) δ 7.36 (s., 1H), 7.23 (dd, J$_1$=8.8 Hz, J$_2$=2.8 Hz 1H), 7.14 (d, J=2.8 Hz, 1H), 7.06-6.96 (m, 2H), 6.91-6.86 (m, 2H), 3.83-3.49 (m, 2H), 3.53 (s, 3H), 3.16-2.89 (m, 2H), 3.08 (q, J=7.2 Hz, 2H), 2.55 (t, J=6.0 Hz, 2H), 2.55 (t, J=7.2 Hz, 3H). LCMS (M+H)$^+$476.

Example 143

4-[5-(cyclopropylmethoxy)-2-(methylsulfonylmethyl)pyrimidin-4-yl]-2-methylisoquinolin-1-one

Step 1: 5-(cyclopropylmethoxy)-2-(methylsulfonylmethyl)pyrimidin-4-ol

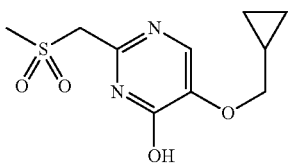 [SMILES: CS(=O)(=O)Cc1ncc(OCC2CC2)c(O)n1]

To the title compound of Example 152, step 1 (5.00 g, 31.6 mmol) in THF (50 mL) at 0° C. was added NaH (1.26 g, 31.6 mmol, 60% in mineral oil). Ethyl formate (2.57 g, 34.76 mmol) was added at 0° C. and the mixture was heated at 70° C. for 2 h. The mixture was then cooled to r.t and a pre-mixed solution of 2-(methylsulfonyl)-ethanimidamide (6.44 g 47.4 mmol) and EtONa (4.3 g, 63.2 mmol) in ethanol (50 mL) was added dropwise. The mixture was heated at 90° C. for 12 h, cooled to room temperature, and the solvent was removed under vacuum. Water (50 mL) was added to the residue and the pH was adjusted to 5 with 1M HCl. The resulting precipitate was collected and washed with water (100 ml), ethanol (50 ml) and methanol (30 mL) to give the title compound (1.9 g, yield: 23.4%) as a white solid. $^1$H NMR (DMSO-d6, 400 MHz) δ 11.49 (s, 1H), 6.83 (s, 1H), 6.49 (s, 2H), 3.63 (d, J=6.8 Hz, 2H), 3.04 (s, 3H), 1.14-1.10 (m, 1H), 0.52-0.49 (m, 2H), 0.27-0.24 (m, 2H). LCMS: 259.0 (M+1)$^+$

Step 2: 4-chloro-5-(cyclopropylmethoxy)-2-(methylsulfonylmethyl)pyrimidine

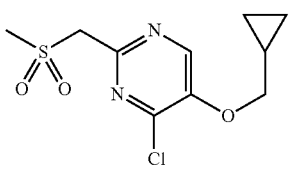 [SMILES: CS(=O)(=O)Cc1ncc(OCC2CC2)c(Cl)n1]

To the title compound of step 1 (1.9 g, 7.36 mmol) in MeCN (30 mL) was added Me$_4$NCl (1.6 g, 14.72 mmol) and POCl$_3$ (6.8 g, 44.16 mmol). The mixture was heated at 80° C. for 6 h. After concentration under vacuum, the residue was subjected to EA extractive work up. Trituration with methanol (20 mL) gave the title compound (1 g, yield: 49.3%) as a white solid. $^1$H NMR (CDCl$_3$, 400 MHz) δ 7.60 (s, 1H), 5.50 (s, 2H), 3.85 (d, J=6.8 Hz, 2H), 3.09 (s, 3H), 1.31-1.28 (m, 1H), 0.70-0.65 (m, 2H), 0.39-0.36 (m, 2H). LCMS: 277.1 (M+1)$^+$

Step 3: 4-[5-(cyclopropylmethoxy)-2-(methylsulfonylmethyl)pyrimidin-4-yl]-2-methylisoquinolin-1-one

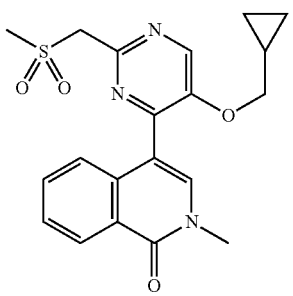 [SMILES: Cn1cc(-c2nc(CS(C)(=O)=O)ncc2OCC2CC2)c2ccccc2c1=O]

The title compound of step 2 (100 mg, 0.36 mmol), the title compound of Example 89, step 1 (124 mg, 0.43 mmol), Pd(dppf)Cl$_2$ (27 mg, 0.03 mmol) and K$_3$PO$_4$ (154 mg, 0.72 mmol) in dioxane (5 mL) and water (5 drops) were N$_2$ purged and heated to 70° C. for 18 h. After concentration under vacuum, the residue was purified using silica gel chromatography followed by prep-HPLC to give the title compound (61.7 mg, 42.7%) as a yellow solid. $^1$H NMR (DMSO-d6, 400 MHz) δ 8.29 (d, J=7.2 Hz, 1H), 7.69-7.65 (m, 3H), 7.53 (t, J=7.2 Hz, 1H), 7.44 (d, J=8.0 Hz, 1H), 3.76 (d, J=6.8 Hz, 2H), 3.58 (s, 3H), 3.26 (s, 3H), 0.94-0.88 (m, 1H), 0.35-0.31 (m, 2H), 0.10-0.08 (m, 2H). LCMS: 400.1 (M+1)$^+$

Example 144

5-[5-(cyclopropylmethoxy)-2-(methylsulfonylmethyl)pyrimidin-4-yl]-1,3-dimethylpyridin-2-one

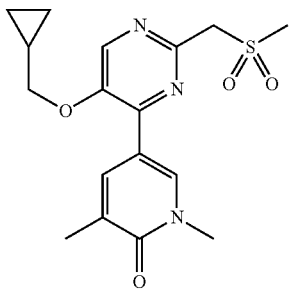 [SMILES: Cc1cc(-c2nc(CS(C)(=O)=O)ncc2OCC2CC2)cn(C)c1=O]

The title compound of Example 143, step 2 was reacted with 1,3-dimethyl-5-(4,4,5,5-tetramethyl-1,3,2-dioxaborolan-2-yl)pyridin-2-one in a manner similar to Example 143, step 3 to give the title compound. $^1$H NMR (CDCl$_3$, 400 MHz) δ 8.49 (d, J=2.0 Hz, 1H), 8.18 (s, 1H), 7.60 (s, 1H), 3.86 (d, J=6.8 Hz, 2H), 3.67 (s, 3H), 3.11 (s, 3H), 2.24 (s, 3H), 1.29-1.27 (m, 1H), 0.72-0.67 (m, 2H), 0.39-0.35 (m, 2H). LCMS: 364.1 (M+1)$^+$

Example 145

4-[5-(cyclopropylmethoxy)-2-(methylsulfonylmethyl)pyrimidin-4-yl]-2-methyl-6-(1-methylpyrazol-4-yl)isoquinolin-1-one

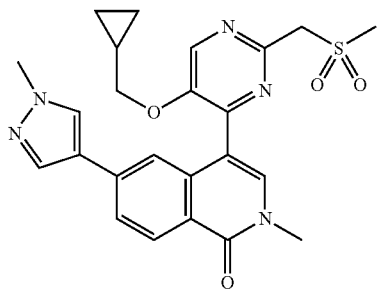 [SMILES: Cn1cc(-c2ccc3c(=O)n(C)cc(-c4nc(CS(C)(=O)=O)ncc4OCC4CC4)c3c2)cn1]

The title compound of Example 143, step 2 was reacted with the title compound of Example 46, step 2 in a manner similar to Example 143, step 3 to give the title compound. $^1$H NMR (DMSO-d6, 400 MHz) δ 8.26 (d, J=8.4 Hz, 1H), 8.23 (s, 1H), 7.91 (s, 1H), 7.5 (d, J=8.4 Hz, 1H), 7.70 (s, 1H), 7.66 (s, 1H), 7.52 (s, 1H), 3.87 (s, 3H), 3.85-3.80 (m, 4H), 3.57 (s, 3H), 3.28 (s, 3H), 0.88-0.87 (m, 1H), 0.30-0.25 (m, 2H), 0.07-0.04 (m, 2H). LCMS: 480.2 (M+1)$^+$

Example 146

5-[5-(2,4-difluorophenoxy)-2-(methylsulfonylmethyl)pyrimidin-4-yl]-3-methoxy-1-methylpyridin-2-one Step 1: 5-(2,4-difluorophenoxy)-2-(methylsulfonylmethyl)pyrimidin-4-ol

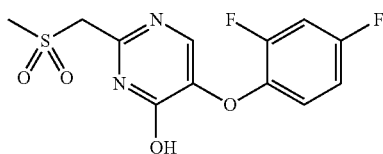 [SMILES: CS(=O)(=O)Cc1ncc(Oc2ccc(F)cc2F)c(O)n1]

To a stirred suspension of NaH (960 mg, 24 mmol, 60% in mineral oil) in anhydrous THF (33 mL) was added ethyl formate (1.8 g, 24.3 mmol) and 2-(2,4-difluorophenoxy)acetic acid ethyl ester (4.3 g, 19.9 mmol) in anhydrous THF (10 mL). The suspension was stirred at room temperature for 0.5 h and then refluxed for 3 h, cooled, and concentrated under vacuum. The residue was dissolved in EtOH (50 mL) and 2-(methylsulfonyl)-ethanimidamide (3.0 g, 22.1 mmol) was added and the mixture was refluxed for 18 h. After concentration under vacuum, water (50 mL) was added and the pH was adjusted to 5 with acetic acid. After EA extractive work up, the residue was dissolved in EA (20 mL) and PE (150 mL) was added. The resulting precipitate (3.0 g, crude) was collected as a grey solid to give the title compound. LCMS: 317.1 (M+1)$^+$ Step 2: 4-chloro-5-(2,4-difluorophenoxy)-2-(methylsulfonylmethyl)pyrimidine

To the title compound of step 1 (3.0 g) and N(CH$_3$)$_4$Cl (1.6 g, 14.2 mmol) in anhydrous MeCN (30 mL), POCl$_3$ (8.7 g, 56.9 mmol) was added dropwise. The mixture was stirred at r.t. for 0.5 h and then at 70° C. for 6 h. After concentration under vacuum, water was added and EA extractive work up was carried out to give the title compound (3.0 g) as a light yellow solid. LCMS: 335.1 (M+1)$^+$ Step 3: 5-[5-(2,4-difluorophenoxy)-2-(methylsulfonylmethyl)pyrimidin-4-yl]-3-methoxy-1-methylpyridin-2-one

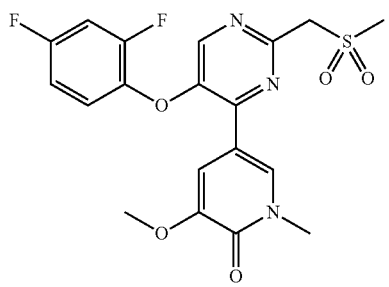 [SMILES: COc1cc(-c2nc(CS(C)(=O)=O)ncc2Oc2ccc(F)cc2F)cn(C)c1=O]

The title compound of Example 287, step 1 was treated with 4,4,5,5-tetramethyl-2-(tetramethyl-1,3,2-dioxaborolan-2-yl)-1,3,2-dioxaborolane in a manner similar to that outlined for Example 119, step 2 to give 3-methoxy-1-methyl-5-(4,4,5,5-tetramethyl-1,3,2-dioxaborolan-2-yl)pyridin-2-one which was then reacted with the title compound of step 2 in a manner similar to Example 143, step 3 to give the title compound. $^1$H NMR (DMSO-d6, 400 MHz) δ 8.37 (s, 1H), 8.36 (d, J=2.0 Hz, 1H), 7.62 (d, J=2.0 Hz, 1H), 7.60-7.54 (m, 1H), 7.51-7.45 (m, 1H), 7.22-7.18 (m, 1H), 4.78 (s, 2H), 3.77 (s, 3H), 3.56 (s, 3H), 3.20 (s, 3H). LCMS: 438.1 (M+1)$^+$

Example 147

5-[5-(2,4-difluorophenoxy)-2-(methylsulfonylmethyl)pyrimidin-4-yl]-1,3-dimethylpyridin-2-one

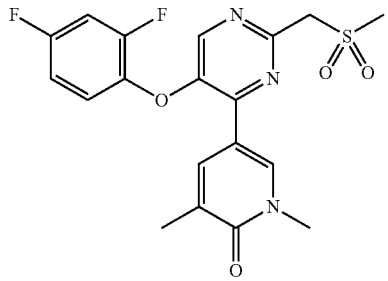 [SMILES: Cc1cc(-c2nc(CS(C)(=O)=O)ncc2Oc2ccc(F)cc2F)cn(C)c1=O]

The title compound of Example 146, step 2 was reacted with 1,3-dimethyl-5-(4,4,5,5-tetramethyl-1,3,2-dioxaborolan-2-yl)pyridin-2-one in a manner similar to Example 143, step 3 to give the title compound. ¹H NMR (DMSO-d6, 400 MHz) δ 8.58 (d, J=2.0 Hz, 1H), 8.35 (s, 1H), 8.13 (s, 1H), 7.60-7.54 (m, 1H), 7.52-7.46 (m, 1H), 7.22-7.17 (m, 1H), 4.76 (s, 2H), 3.56 (s, 3H), 3.18 (s, 3H), 2.08 (s, 3H). LCMS: 422.1 (M+1)⁺

Example 148

4-[5-(2,4-difluorophenoxy)-2-(methylsulfonylmethyl)pyrimidin-4-yl]-2-methylisoquinolin-1-one

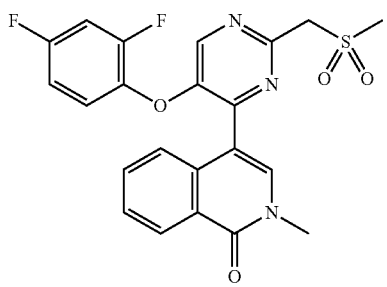 [SMILES: Cn1cc(-c2nc(CS(C)(=O)=O)ncc2Oc2ccc(F)cc2F)c2ccccc2c1=O]

The title compound of Example 146, step 2 was reacted with the title compound of Example 89, step 1 in a manner similar to Example 143, step 3 to give the title compound. ¹H NMR (DMSO-d6, 400 MHz) δ 8.62 (s, 1H), 8.28 (d, J=8.0 Hz, 1H), 7.91 (s, 1H), 7.69-7.68 (m, 2H), 7.58-7.54 (m, 1H), 7.45-7.34 (m, 2H), 7.07-7.03 (m, 1H), 4.83 (s, 2H), 3.58 (s, 3H), 3.17 (s, 3H). LCMS: 458.1 (M+1)⁺

Example 149

5-[5-(2,4-difluorophenoxy)-2-methylsulfonylpyrimidin-4-yl]-1,3-dimethylpyridin-2-one Step 1: 5-(2,4-difluorophenoxy)-2-methylsulfanylpyrimidin-4-ol

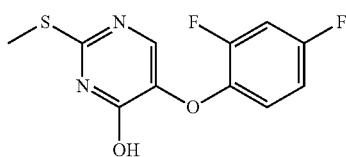 [SMILES: CSc1ncc(Oc2ccc(F)cc2F)c(O)n1]

To a solution of 2-(2,4-difluorophenoxy)acetic acid ethyl ester (8.0 g, 37.01 mmol) and ethyl formate (4.11 g, 55.51 mmol) in dry THF (200 mL) was added NaH (1.55 g, 38.75 mmol) slowly at 0° C. The mixture was then refluxed for 2 h. In a separate flask, sodium ethoxide (3.02 g, 44.41 mmol) and S-methylthiopseudourea hemisulfate (6.17 g, 44.41 mmol) in EtOH (100 mL) were stirred at 20° C. for 2 h and then the resulting mixture was added to the above THF solution. The combined mixture was refluxed for 12 h. After concentration under vacuum, water (20 mL) and HCl (10 mL, aq. 1N) were added. The suspended solids were collected and washed with water (50 mL×3) and EtOH (50 mL×3) and dried to give the title compound (6.0 g, 60.0% yield) as a light yellow solid. ¹H NMR (DMSO-d6, 400 MHz) δ 7.84 (s, 1H), 7.42-7.34 (m, 1H), 7.04-7.01 (m, 1H), 6.95 (t, J=9.6 Hz, 1H), 2.47 (s, 3H).
LCMS: 271.1 (M+1)⁺

Step 2: 4-chloro-5-(2,4-difluorophenoxy)-2-methylsulfanylpyrimidine

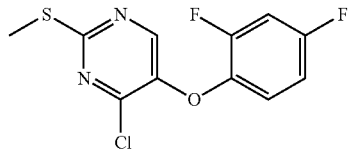 [SMILES: CSc1ncc(Oc2ccc(F)cc2F)c(Cl)n1]

The title compound of step 1 (5.30 g, 19.63 mmol), POCl₃ (18.06 g, 117.78 mmol), (Me)₄NCl (3.23 g, 29.47 mmol) in dry CH₃CN (60 mL) was refluxed for 12 h. The mixture was poured into ice-water (50 mL) and subjected to EA extractive work up. Concentration under vacuum gave impure title compound (4.0 g), which was carried on to the next step.
LCMS: 288.99 (M+1)⁺

Step 3: 4-chloro-5-(2,4-difluorophenoxy)-2-methylsulfonylpyrimidine

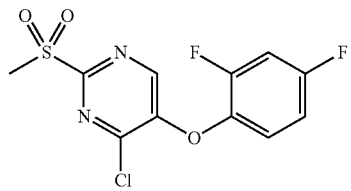 [SMILES: CS(=O)(=O)c1ncc(Oc2ccc(F)cc2F)c(Cl)n1]

To a solution of the title compound of step 2 (4.60 g, 15.93 mmol) in CH₂Cl₂ (200 mL) was added mCPBA (13.75 g, 79.68 mmol) slowly at 0° C. The mixture was stirred at 20° C. for 12 h and then sat. aq. Na₂SO₃ (200 mL) was added. EA extractive work up and silica gel chromatography gave the title compound (2.0 g, 39.1% yield) as a yellow solid. ¹H NMR (CDCl₃, 400 MHz) δ 8.18 (s, 1H), 7.31-7.27 (m, 1H), 7.10-7.01 (m, 2H), 3.36 (s, 3H). LCMS: 320.8 (M+1)⁺

Step 4: 5-[5-(2,4-difluorophenoxy)-2-methylsulfonylpyrimidin-4-yl]-1,3-dimethylpyridin-2-one

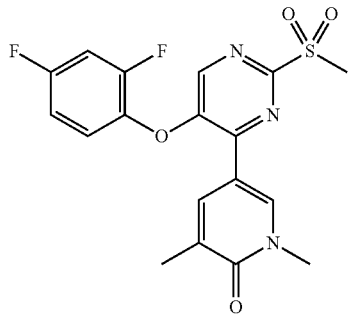 [SMILES: Cc1cc(-c2nc(S(C)(=O)=O)ncc2Oc2ccc(F)cc2F)cn(C)c1=O]

A mixture of the title compound from step 3 (100 mg, 0.31 mmol), 1,3-dimethyl-5-(4,4,5,5-tetramethyl-1,3,2-dioxaborolan-2-yl)pyridin-2-one (93 mg, 0.37 mmol), Pd(dppf)

Cl₂ (23 mg, 0.31 mmol) and K₃PO₄ (199 mg, 0.94 mmol) in dioxane/water (3 mL/0.5 mL) was N₂ purged and heated at 70° C. for 12 h. Concentration under vacuum and silica gel chromatography (PE:EA=3:1-0:1) followed by prep-HPLC gave the title compound (45 mg, 35.4%). ¹H NMR (CDCl₃, 400 MHz) δ 8.57 (s, 1H), 8.25 (s, 1H), 8.15 (s, 1H), 7.25-7.24 (m, 1H), 7.12-7.07 (m, 1H), 7.03 (t, J=8.0 Hz, 1H), 3.68 (s, 3H), 3.38 (s, 3H), 2.25 (s, 3H). LCMS: 407.9 (M+1)⁺

Example 150

5-[5-(2,4-difluorophenoxy)-2-methylsulfonylpyrimidin-4-yl]-3-methoxy-1-methylpyridin-2-one

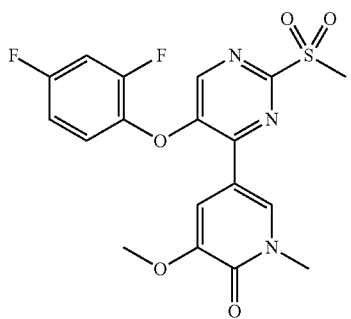 [SMILES: COc1cc(-c2nc(S(C)(=O)=O)ncc2Oc2ccc(F)cc2F)cn(C)c1=O]

The title compound of Example 149, step 3 was reacted with 3-methoxy-1-methyl-5-(4,4,5,5-tetramethyl-1,3,2-dioxaborolan-2-yl)pyridin-2-one (see Example 146, step 3) in a manner similar to Example 149, step 4 to give the title compound. ¹H NMR (CDCl₃, 400 MHz) δ 8.35 (d, J=2.0 Hz, 1H), 8.18 (s, 1H), 7.70 (d, J=2.0 Hz, 1H), 7.25-7.22 (m, 1H), 7.12-7.08 (m, 1H), 7.08-7.04 (m, 1H), 3.93 (s, 3H), 3.70 (s, 3H), 3.38 (s, 3H). LCMS: 423.9 (M+1)⁺

Example 151

4-[5-(2,4-difluorophenoxy)-2-methylsulfonylpyrimidin-4-yl]-2-methylisoquinolin-1-one

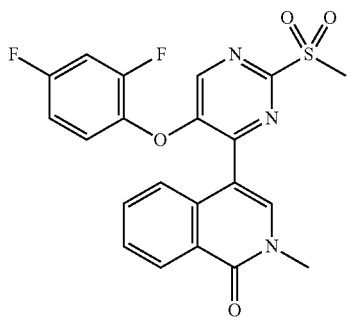 [SMILES: Cn1cc(-c2nc(S(C)(=O)=O)ncc2Oc2ccc(F)cc2F)c2ccccc2c1=O]

The title compound of Example 149, step 3 was reacted with the title compound of Example 89, step 1 in a manner similar to Example 149, step 4 to give the title compound. ¹H NMR (CDCl₃, 400 MHz) δ 8.52 (d, J=8.0 Hz, 1H), 8.32 (s, 1H), 7.68 (s, 1H), 7.59-7.56 (m, 1H), 7.14-7.08 (m, 1H), 7.05-7.00 (m, 1H), 6.96-6.92 (m, 1H), 3.72 (s, 3H), 3.39 (s, 3H). LCMS: 443.9 (M+1)⁺

Example 152

N-[5-(cyclopropylmethoxy)-4-(2-methyl-1-oxoisoquinolin-4-yl)pyrimidin-2-yl]methanesulfonamide Step 1: ethyl 2-(cyclopropylmethoxy)acetate

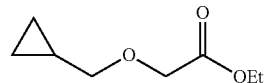 [SMILES: CCOC(=O)COCC1CC1]

Diazoacetic acid ethyl ester (80.00 g, 0.70 mol) was added dropwise to cyclopropanemethanol (60.66 g, 0.84 mol) and [Rh(Ac₂O)₂]₂ (3.1 g, 7.02 mmol) in anhydrous CH₂Cl₂ (800 mL) at 0° C. The mixture was stirred at 0° C. for 30 min and at room temperature for 4 h. CH₂Cl₂ extractive work up and silica gel chromatography (PE:EA=100:1-50:1) gave the title compound (100 g, 90.4% yield) as a colorless oil. ¹H NMR: (CDCl₃, 400 MHz) δ 4.23-4.19 (m, 2H), 4.09 (s, 2H), 3.38-3.36 (m, 2H), 1.27 (t, J=7.2 Hz, 3H), 1.10-1.07 (m, 1H), 0.57-0.52 (m, 2H), 0.24-0.20 (m, 2H).

Step 2: 5-(cyclopropylmethoxy)-2-methylsulfanylpyrimidin-4-ol

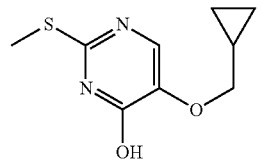

To a stirred suspension of NaH (35.20 g, 0.88 mol, 60% in mineral oil) in anhydrous THF (1000 mL) was added ethyl formate (88.80 g, 0.90 mol) and the title compound of step 1 (126.0 g, 0.80 mol) in anhydrous THF (100 mL). The mixture was stirred at r.t. for 0.5 hour and refluxed for 3 h. In a separate flask, S-methylthiopseudourea hemisulfate (133.44 g, 0.96 mol) and sodium ethoxide (65.28 g, 0.96 mol) in EtOH (200 mL) were stirred at r.t. for 1 h, whereupon this mixture was added to the above mixture. There combined mixture was refluxed for 15 h, cooled, and the pH was adjusted to 5 with acetic acid. After concentration under vacuum, silica gel chromatography (DCM: MeOH=50/1~10/1) gave the title compound (30.00 g, 17.7% yield) as a yellow solid. ¹H NMR (CDCl₃, 400 MHz) δ 12.08 (s, 1H), 7.49 (s, 1H), 3.83-3.80 (m, 2H), 2.55 (s, 3H), 1.37-1.28 (m, 1H), 0.65-0.62 (m, 2H), 0.37-0.34 (m, 2H).

Step 3: 4-chloro-5-(cyclopropylmethoxy)-2-methylsulfanylpyrimidine

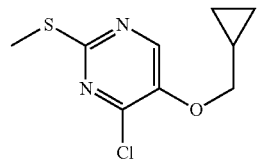

To the title compound of step 2 (29.00 g, 136.79 mmol) and N(CH₃)₄Cl (22.47 g, 205.19 mmol) in anhydrous MeCN (300 mL), was added POCl₃ (123.93 g, 820.74 mmol). The mixture was stirred at r.t. for 30 min and at 70° C. for 1 h. After concentration under vacuum, EA extractive work up and silica gel chromatography (PE:EA=50:1-5:1) gave the title compound (20 g, 63.6% yield) as a white solid. ¹H NMR (CDCl₃, 400 MHz) δ 8.16 (s, 1H), 3.95 (d, J=6.8 Hz, 2H), 2.56 (s, 3H), 1.33-1.28 (m, 1H), 0.72-0.70 (m, 2H), 0.41-0.37 (m, 2H). LCMS: 230.9 (M+1)⁺

Step 4: 4-chloro-5-(cyclopropylmethoxy)-2-methyl-sulfonylpyrimidine

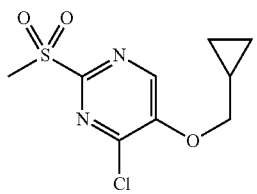 [SMILES: CS(=O)(=O)c1ncc(OCC2CC2)c(Cl)n1]

To the title compound of step 3 (19.0 g, 82.60 mmol) in dry CH₂Cl₂ (200 mL) at 0° C., m-CPBA (42.62 g, 247.80 mmol) was added over 15 min. The mixture was stirred at 0° C. for 30 min and at r.t. overnight. Sat. aq. Na₂SO₃ (100 mL) was added and CH₂Cl₂ extractive work up was carried out. Trituration with MTBE (300 mL) gave the title compound (17 g, 78.3% yield) as a white solid. ¹H NMR (CDCl₃, 400 MHz) δ 8.37 (s, 1H), 4.13 (d, J=6.8 Hz, 2H), 3.33 (s, 3H), 1.39-1.35 (m, 1H), 0.79-0.74 (m, 2H), 0.49-0.45 (m, 2H). LCMS: 263.0 (M+1)⁺

Step 5: 4-[5-(cyclopropylmethoxy)-2-methylsulfo-nylpyrimidin-4-yl]-2-methylisoquinolin-1-one

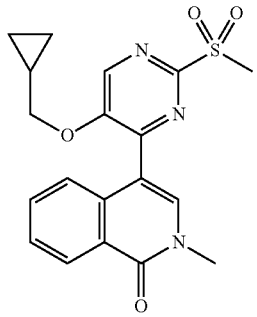 [SMILES: Cn1cc(-c2nc(S(C)(=O)=O)ncc2OCC2CC2)c2ccccc2c1=O]

The title compound of step 4 (5.00 g, 19.08 mmol), the title compound of Example 89, step 1 (5.98 g, 20.99 mmol), K₃PO₄ (12.13 g, 57.24 mmol), and Pd(dppf)Cl₂ (1.40 g, 1.91 mmol) in dioxane/H₂O (50 mL/5 mL) were N₂ purged and heated at 80° C. for 8 h. Silica gel chromatography (PE: EA=10/1~1/1) to gave the title compound (5.01 g, yield: 68%) as a yellow solid. ¹H NMR (CDCl₃, 400 MHz) δ 8.53 (s, 2H), 7.67-7.63 (m, 2H), 7.57-7.52 (m, 2H), 4.06 (d, J=6.8 Hz, 2H), 3.71 (s, 3H), 3.37 (s, 3H), 1.17 (m, 1H), 0.61 (m, 2H), 0.30 (m, 2H). LCMS: 386.1 (M+1)⁺

Step 6: N-[5-(cyclopropylmethoxy)-4-(2-methyl-1-oxoisoquinolin-4-yl)pyrimidin-2-yl]methanesulfona-mide

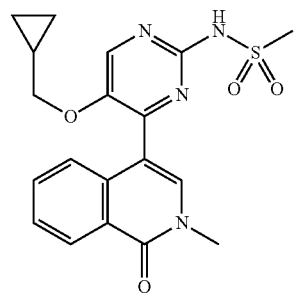 [SMILES: Cn1cc(-c2nc(NS(C)(=O)=O)ncc2OCC2CC2)c2ccccc2c1=O]

Sodium hydride (0.93 g, 23.37 mmol, 60% in mineral oil) was added to MeSO₂NH₂ (2.22 g, 23.37 mmol) in dry DMF (30 mL) at 0° C. over 15 min. The mixture was stirred at 0° C. for 1 h and the title compound of step 5 (3.00 g, 7.79 mmol) was added. The mixture was heated at 60° C. for 6 h. After cooling, ice water was added and the pH was adjusted to 5 with acetic acid. The suspended solids were collected and washed with MTBE (50 mL) to afford the title compound (3 g, yield: 96.7%) as an off-white solid. ¹H NMR (CDCl₃, 400 MHz) δ 9.80 (s, 1H), 8.53 (d, J=8.0 Hz, 1H), 8.42 (s, 1H), 7.97 (d, J=8.4 Hz, 1H), 7.70 (m, 2H), 7.56 (t, J=7.6 Hz, 1H), 3.87 (d, J=7.2 Hz, 2H), 3.70 (s, 3H), 3.39 (s, 3H), 1.12 (m, 1H), 0.58 (m, 2H), 0.24 (m, 2H). LCMS: 401.1 (M+1)⁺

Example 153

N-[5-(cyclopropylmethoxy)-4-(1,5-dimethyl-6-ox-opyridin-3-yl)pyrimidin-2-yl]methanesulfonamide

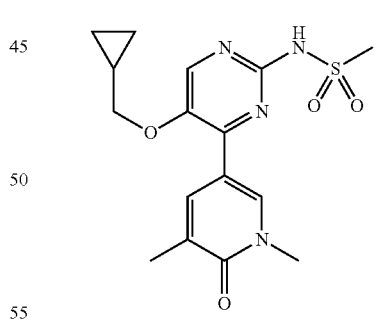

The title compound of Example 152, step 4 was reacted with 1,3-dimethyl-5-(4,4,5,5-tetramethyl-1,3,2-dioxaboro-lan-2-yl)pyridin-2-one in a manner similar to Example 152, step 5 and the resulting product was treated with MeSO₂NH₂ in a manner similar to Example 152, step 6 to give the title compound. ¹H NMR (DMSO-d6, 400 MHz) δ 10.97 (s, 1H), 8.67 (s, 1H), 8.42 (s, 1H), 8.14 (s, 1H), 4.03 (d, J=6.4 Hz, 2H), 3.54 (s, 3H), 3.35 (s, 3H), 2.08 (s, 3H), 1.33-1.31 (m, 1H), 0.63-0.61 (m, 2H), 0.38-0.37 (m, 2H). LCMS: 365.0 (M+1)⁺

Example 154

N-[5-(cyclopropylmethoxy)-4-[2-methyl-6-(1-methylpyrazol-4-yl)-1-oxoisoquinolin-4-yl]pyrimidin-2-yl]methanesulfonamide

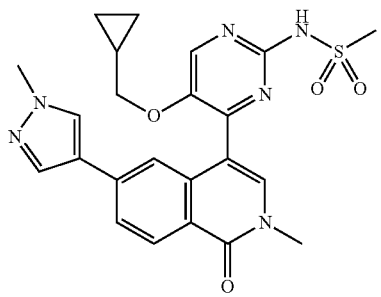 [SMILES: Cn1cc(-c2ccc3c(=O)n(C)cc(-c4nc(NS(C)(=O)=O)ncc4OCC4CC4)c3c2)cn1]

The title compound of Example 152, step 4 was reacted with the title compound of Example 46 step 2 in a manner similar to Example 152, step 5 and the resulting product was treated with MeSO$_2$NH$_2$ in a manner similar to Example 152, step 6 to give the title compound. $^1$H NMR (CDCl$_3$, 400 MHz) δ 11.15 (s, 1H), 8.56 (s, 1H), 8.27 (s, 1H), 8.25 (d, J=7.6 Hz, 1H), 7.98 (s, 1H), 7.79 (s, 1H), 7.77 (d, J=9.6 Hz, 1H), 7.70 (s, 1H), 3.95 (d, J=7.2 Hz, 2H), 3.85 (s, 3H), 3.57 (s, 3H), 3.32 (s, 3H), 1.00-0.99 (m, 1H), 0.37-0.32 (m, 2H), 0.14-0.12 (m, 2H). LCMS: 481.0 (M+1)$^+$

Example 155

N-[5-(cyclopropylmethoxy)-4-(2-methyl-1-oxoisoquinolin-4-yl)pyrimidin-2-yl]ethanesulfonamide

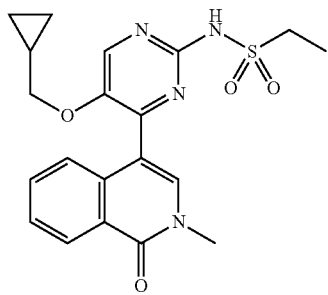 [SMILES: CCS(=O)(=O)Nc1ncc(OCC2CC2)c(-c2cn(C)c(=O)c3ccccc23)n1]

The title compound of Example 152, step 5 was treated with EtSO$_2$NH$_2$ instead of MeSO$_2$NH$_2$ in a manner similar to Example 152, step 6 to give the title compound. $^1$H NMR (CDCl$_3$, 400 MHz) δ 9.00 (s, 1H), 8.53 (d, J=8.0 Hz, 1H), 8.38 (s, 1H), 7.97 (d, J=8.0 Hz, 1H), 7.69 (m, 2H), 7.57 (t, J=7.6 Hz, 1H), 3.86 (d, J=6.8 Hz, 2H), 3.70 (s, 3H), 3.63 (q, J=7.2 Hz, 2H), 1.43 (t, J=7.2 Hz, 3H), 1.13 (m, 1H), 0.57 (m, 2H), 0.25 (m, 2H). LCMS: 415.0 (M+1)$^+$

Example 156

4-[5-(cyclopropylmethoxy)-2-(1,1-dioxo-1,2-thiazolidin-2-yl)pyrimidin-4-yl]-2-methylisoquinolin-1-one

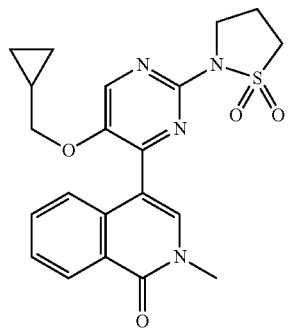 [SMILES: Cn1cc(-c2nc(N3CCCS3(=O)=O)ncc2OCC2CC2)c2ccccc2c1=O]

The title compound of Example 152, step 5 was treated with 1,1-dioxidoisothiazolidine instead of MeSO$_2$NH$_2$ in a manner similar to Example 152, step 6 to give the title compound. $^1$H NMR (DMSO-d6, 400 MHz) δ 8.56 (s, 1H), 8.30 (d, J=8.0 Hz, 1H), 7.86 (s, 1H), 7.77 (d, J=8.0 Hz, 1H), 7.67 (t, J=7.6 Hz, 1H), 7.55 (t, J=7.6 Hz, 1H), 3.93-3.91 (m, 4H), 3.59 (s, 3H), 2.38-2.31 (m, 2H), 1.06-1.01 (m, 1H), 0.44-0.39 (m, 2H), 0.20-0.16 (m, 2H). LCMS: 427.1 (M+H)$^+$

Example 157

N-[5-(cyclopropylmethoxy)-4-(6-fluoro-2-methyl-1-oxoisoquinolin-4-yl)pyrimidin-2-yl]ethanesulfonamide

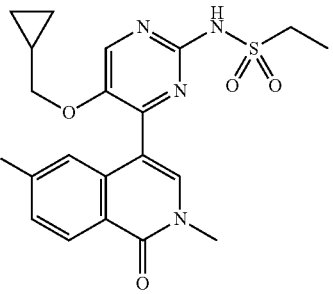

The title compound of Example 47, step 2 was treated with 4,4,5,5-tetramethyl-2-(tetramethyl-1,3,2-dioxaborolan-2-yl)-1,3,2-dioxaborolane in a manner similar to Example 89, step 1 and the resulting 6-fluoro-2-methyl-4-(4,4,5,5-tetramethyl-1,3,2-dioxaborolan-2-yl)isoquinolin-1-one was coupled to the title compound of Example 152, step 4 in a manner similar to Example 152, step 5 and the resulting 4-[5-(cyclopropylmethoxy)-2-methylsulfonylpyrimidin-4-yl]-6-fluoro-2-methylisoquinolin-1-one was treated with EtSO$_2$NH$_2$ instead of MeSO$_2$NH$_2$ in a manner similar to Example 152, step 6 to give the title compound. $^1$H NMR (DMSO-d6, 400 MHz) δ 11.04 (brs, 1H), 8.54 (s, 1H), 8.36 (dd, J$_1$=9.2 Hz, J$_2$=2.4 Hz, 1H), 8.01 (s, 1H), 7.65 (dd, J$_1$=11.2 Hz, J$_2$=2.4 Hz, 1H), 7.45-7.38 (m, 1H), 3.95 (d, J=6.8 Hz, 2H), 3.58 (s, 3H), 3.48 (q, J=7.2 Hz, 2H), 1.22 (t, J=7.2 Hz, 3H), 1.16-1.04 (m, 1H), 0.50-0.42 (m, 2H), 0.27-0.20 (m, 2H). LCMS: 433.0 (M+1)$^+$

Example 158

N-[5-(cyclopropylmethoxy)-4-(7-fluoro-2-methyl-1-oxoisoquinolin-4-yl)pyrimidin-2-yl]methanesulfonamide

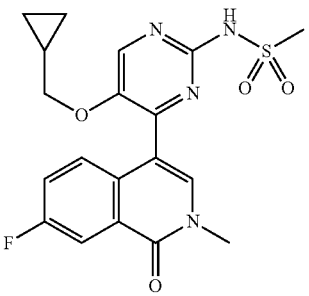 [SMILES: Cn1cc(-c2nc(NS(C)(=O)=O)ncc2OCC2CC2)c2ccc(F)cc2c1=O]

The title compound of Example 58, step 2 was treated with 4,4,5,5-tetramethyl-2-(tetramethyl-1,3,2-dioxaborolan-2-yl)-1,3,2-dioxaborolane in a manner similar to Example 89, step 1 and the resulting 7-fluoro-2-methyl-4-(4,4,5,5-tetramethyl-1,3,2-dioxaborolan-2-yl)isoquinolin-1-one was coupled to the title compound of Example 152, step 4 in a manner similar to Example 152, step 5 and the resulting 4-[5-(cyclopropylmethoxy)-2-methylsulfonylpyrimidin-4-yl]-7-fluoro-2-methylisoquinolin-1-one was treated with $MeSO_2NH_2$ in a manner similar to Example 152, step 6 to give the title compound. $^1$H NMR (DMSO-d6, 400 MHz) δ 11.15 (s, 1H), 8.55 (s, 1H), 8.36 (dd, $J_1$=9.2 Hz, $J_2$=6.0 Hz, 1H), 8.00 (s, 1H), 7.60 (dd, $J_1$=11.2 Hz, $J_2$=2.4 Hz, 1H), 7.44-7.37 (m, 1H), 3.95 (d, J=7.2 Hz, 2H), 3.58 (s, 3H), 3.32 (s, 3H), 1.15-1.03 (m, 1H), 0.49-0.42 (m, 2H), 0.26-0.20 (m, 2H). LCMS: 419.0 (M+1)$^+$

Example 159

N-[5-(cyclopropylmethoxy)-4-(6-fluoro-2-methyl-1-oxoisoquinolin-4-yl)pyrimidin-2-yl]methanesulfonamide

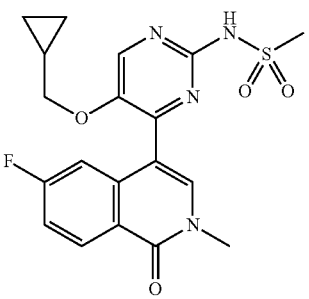 [SMILES: Cn1cc(-c2nc(NS(C)(=O)=O)ncc2OCC2CC2)c2cc(F)ccc2c1=O]

The title compound of Example 47, step 2 was treated with 4,4,5,5-tetramethyl-2-(tetramethyl-1,3,2-dioxaborolan-2-yl)-1,3,2-dioxaborolane in a manner similar to Example 89, step 1 and the resulting 6-fluoro-2-methyl-4-(4,4,5,5-tetramethyl-1,3,2-dioxaborolan-2-yl)isoquinolin-1-one was coupled to the title compound of Example 152, step 4 in a manner similar to Example 152, step 5 and the resulting 4-[5-(cyclopropylmethoxy)-2-methylsulfonylpyrimidin-4-yl]-6-fluoro-2-methylisoquinolin-1-one was treated with $MeSO_2NH_2$ in a manner similar to Example 152, step 6 to give the title compound. $^1$H NMR (DMSO-d6, 400 MHz) δ 11.14 (brs, 1H), 8.56 (s, 1H), 7.96 (dd, $J_1$=9.2 Hz, $J_2$=3.2 Hz, 1H), 7.88 (s, 1H), 7.85 (dd, $J_1$=9.2 Hz, $J_2$=3.6 Hz, 1H), 7.62-7.55 (m, 1H), 3.94 (d, J=6.8 Hz, 2H), 3.60 (s, 3H), 3.32 (s, 3H), 1.11-0.99 (m, 1H), 0.47-0.40 (m, 2H), 0.23-0.16 (m, 2H). LCMS: 419.0 (M+1)$^+$

Example 160

N-[5-(cyclopropylmethoxy)-4-(7-fluoro-2-methyl-1-oxoisoquinolin-4-yl)pyrimidin-2-yl]ethanesulfonamide

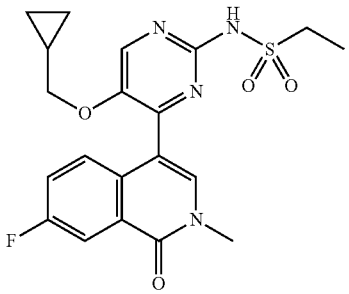 [SMILES: CCS(=O)(=O)Nc1ncc(OCC2CC2)c(-c2cn(C)c(=O)c3cc(F)ccc23)n1]

The title compound of Example 58, step 2 was treated with 4,4,5,5-tetramethyl-2-(tetramethyl-1,3,2-dioxaborolan-2-yl)-1,3,2-dioxaborolane in a manner similar to Example 89, step 1 and the resulting 7-fluoro-2-methyl-4-(4,4,5,5-tetramethyl-1,3,2-dioxaborolan-2-yl)isoquinolin-1-one was coupled to the title compound of Example 152, step 4 in a manner similar to Example 152, step 5 and the resulting 4-[5-(cyclopropylmethoxy)-2-methylsulfonylpyrimidin-4-yl]-7-fluoro-2-methylisoquinolin-1-one was treated with $EtSO_2NH_2$ instead of $MeSO_2NH_2$ in a manner similar to Example 152, step 6 to give the title compound. $^1$H NMR (CDCl3 400 MHz) δ 8.53 (dd, J1=8.8 Hz, $J_2$=6.0 Hz, 1H), 8.40 (s, 1H), 7.77 (s, 1H), 7.69 (dd, J=8.8 Hz, 1H), 7.27-7.23 (m, 1H), 3.88 (d, J=6.8 Hz, 2H), 3.69 (s, 3H), 3.60 (q, J=7.2 Hz, 2H), 1.43 (t, J=7.2 Hz, 3H), 1.16-1.13 (m, 1H), 0.62-0.56 (m, 2H), 0.27-0.26 (m, 2H). LCMS: 433.2 (M+1)$^+$

Example 161

N-[5-(cyclopropylmethoxy)-4-(2-methyl-1-oxoisoquinolin-4-yl)pyrimidin-2-yl]-N-ethylmethanesulfonamide

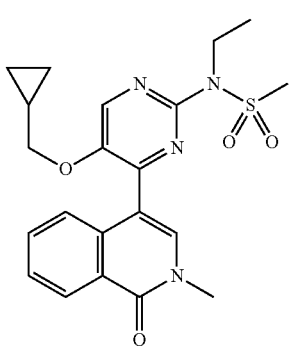 [SMILES: CCN(c1ncc(OCC2CC2)c(-c2cn(C)c(=O)c3ccccc23)n1)S(C)(=O)=O]

Ethyl iodide (95 mg, 0.6 mmol) and $K_2CO_3$ (55 mg, 0.4 mmol) were added to a solution of the title compound of Example 152 (80 mg, 0.2 mmol) in MeCN (5 mL). After refluxing 1 h, the mixture was cooled, concentrated under vacuum and subjected to CH$_2$Cl$_2$ extractive work up. HPLC purification gave the title compound (13.42 mg, yield: 15.2%) as a yellow solid. $^1$H NMR (DMSO-d6, 400 MHz) δ 8.63 (s, 1H), 8.32 (d, J=8.0 Hz, 1H), 7.90 (s, 1H), 7.77 (d, J=8.0 Hz, 1H), 7.69 (t, J=7.6 Hz, 1H), 7.56 (t, J=7.6 Hz, 1H), 4.02 (q, J=6.8 Hz, 2H), 3.97 (d, J=7.2 Hz, 1H), 3.60 (s, 3H), 3.43 (s, 3H), 1.25 (t, J=6.8 Hz, 1H), 1.10-1.07 (m, 1H), 0.46-0.42 (m, 2H), 0.24-0.20 (m, 2H). LCMS: 429.1 (M+H)$^+$ Example 162

N-[5-(cyclopropylmethoxy)-4-(1,5-dimethyl-6-oxopyridin-3-yl)pyrimidin-2-yl]-N-ethylmethanesulfonamide

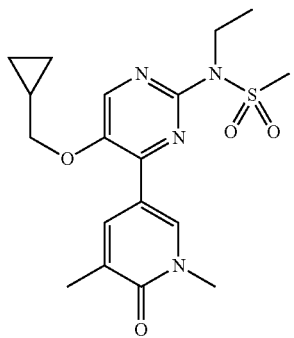 [SMILES: CCN(c1ncc(OCC2CC2)c(-c2cc(C)c(=O)n(C)c2)n1)S(C)(=O)=O]

The title compound of Example 153 was treated with ethyl iodide in a manner similar to Example 161 to give the title compound. $^1$H NMR (400 MHz, DMSO-d$_6$) δ ppm 0.36-0.42 (m, 2H) 0.60-0.66 (m, 2H) 1.25 (t, J=6.82 Hz, 3H) 1.29-1.40 (m, 1H) 2.09 (s, 3H) 3.48 (s, 3H) 3.56 (s, 3H) 3.88-4.20 (m, 4H) 8.13 (s, 1H) 8.49 (s, 1H) 8.69 (s, 1H). LCMS: 393 (M+H)$^+$ Example 163

N-[5-(cyclopropylmethoxy)-4-(2-methyl-1-oxo-5,6,7,8-tetrahydroisoquinolin-4-yl)pyrimidin-2-yl]methanesulfonamide Step 1:
2-methyl-5,6,7,8-tetrahydroisoquinolin-1-one

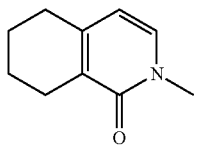

The title compound was prepared from the N-methylation of 5,6,7,8-tetrahydroisoquinolin-1(2H)-one in a manner similar to Example 47, step 1. $^1$H NMR (CDCl$_3$, 400 MHz): δ 7.02 (d, J=7.2 Hz, 1H), 5.90 (d, J=7.2 Hz, 1H), 3.49 (s, 3H), 2.54-2.45 (m, 4H), 1.74-1.69 (m, 4H).

Step 2: 4-bromo-2-methyl-5,6,7,8-tetrahydroisoquinolin-1-one

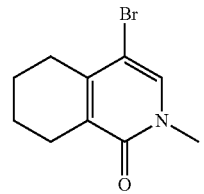

The title compound was prepared from the bromination of the title compound of step 1 in a manner similar to Example 47, step 2. LCMS: 241.9 (M+H)$^+$ Step 3: 2-methyl-4-(4,4,5,5-tetramethyl-1,3,2-dioxaborolan-2-yl)-5,6,7,8-tetrahydroisoquinolin-1-one

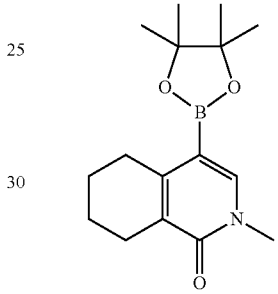

The title compound of step 2 (3.3 g, 13.7 mmol), 4,4,5,5-tetramethyl-2-(tetramethyl-1,3,2-dioxaborolan-2-yl)-1,3,2-dioxaborolane (6.96 g, 27.4 mmol), Pd$_2$(dba)$_3$ (400 mg, 0.43 mmol), X-phos (400 mg, 0.84 mmol) and anhydrous KOAc (1.02 g, 41.1 mmol) in anhydrous dioxane (50 mL) were heated at 50° C. under N$_2$ for 12 h. Silica gel chromatography (PE:EA=5:1) gave the title compound (1.5 g, yield: 38%) as a yellow solid. $^1$H NMR (CDCl$_3$, 400 MHz): δ 7.62 (s, 1H), 5.28 (s, 3H), 2.82-2.76 (m, 2H), 2.55-2.33 (m, 2H), 1.72-1.70 (m, 4H), 1.31 (s, 12H). LCMS: 290.0 (M+H)$^+$ Step 4: 4-[5-(cyclopropylmethoxy)-2-methylsulfonylpyrimidin-4-yl]-2-methyl-5,6,7,8-tetrahydroisoquinolin-1-one

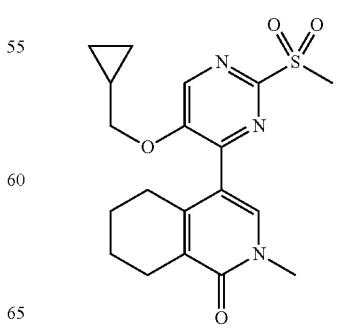

The title compound of step 3 (200 mg, 0.69 mmol), the title compound of Example 152, step 4 (218 mg, 0.83 mmol), $K_3PO_4$ (440 mg, 2.07 mmol) and Pd(dppf)Cl$_2$ (51 mg, 0.7 mmol) in 6:1 dioxane/water (7 mL) were purged with nitrogen and heated at 70° C. for 8 h. After silica gel chromatography (PE:EA=1:1), the title compound (180 mg, yield: 67%) was obtained as a light yellow solid. $^1$H NMR (CDCl$_3$, 400 MHz): δ 8.42 (s, 1H), 7.48 (s, 1H), 4.04 (d, J=7.2 Hz, 2H), 3.60 (s, 3H), 3.35 (s, 3H), 2.65-2.62 (m, 2H), 2.54-2.50 (m, 2H), 1.80-1.78 (m, 2H), 1.77-1.67 (m, 2H), 1.28-1.25 (m, 1H), 0.73-0.71 (m, 2H), 0.41-0.38 (m, 2H).

Step 5: N-[5-(cyclopropylmethoxy)-4-(2-methyl-1-oxo-5,6,7,8-tetrahydroisoquinolin-4-yl)pyrimidin-2-yl]methanesulfonamide

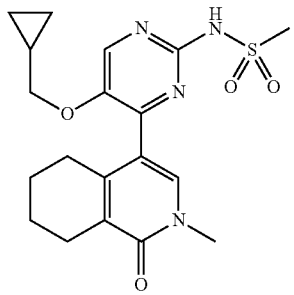 [SMILES: Cn1cc(-c2nc(NS(C)(=O)=O)ncc2OCC2CC2)c2c(c1=O)CCCC2]

The title compound of step 4 was treated with MeSO$_2$NH$_2$ in a manner similar to Example 152, step 6 to give the title compound. $^1$H NMR (CDCl$_3$, 400 MHz): δ 8.18 (s, 1H), 7.38 (s, 1H), 3.74 (d, J=6.4 Hz, 2H), 3.51 (s, 3H), 3.28 (s, 3H), 2.60-2.53 (m, 2H), 2.50-2.46 (m, 2H), 1.74-1.71 (m, 2H), 1.64-1.59 (m, 2H), 1.13-1.10 (m, 1H), 0.60-0.58 (m, 2H), 0.25-0.24 (m, 2H). LCMS: 405.1 (M+H)$^+$ Example 164

N-[5-(cyclopropylmethoxy)-4-(2-methyl-1-oxo-5,6,7,8-tetrahydroisoquinolin-4-yl)pyrimidin-2-yl]ethanesulfonamide

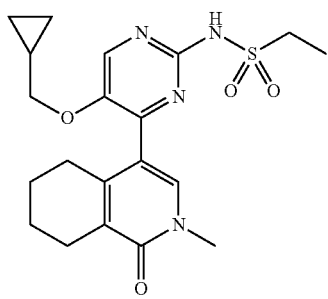 [SMILES: CCS(=O)(=O)Nc1ncc(OCC2CC2)c(-c2cn(C)c(=O)c3c2CCCC3)n1]

The title compound of Example 163, step 4 was treated with treated with EtSO$_2$NH$_2$ instead of MeSO$_2$NH$_2$ in a manner similar to Example 152, step 6 to give the title compound. $^1$H NMR (DMSO-d6, 400 MHz): δ 8.32 (s, 1H), 7.64 (s, 1H), 3.83 (d, J=6.8 Hz, 2H), 3.44 (s, 3H), 3.30-3.20 (m, 2H), 2.47-2.41 (m, 4H), 1.67-1.57 (m, 4H), 1.19-1.13 (m, 4H), 0.51-0.49 (m, 2H), 0.24-0.22 (m, 2H). LCMS: 419.1 (M+H)$^+$ Example 165

N-[5-(2,4-difluorophenoxy)-4-(2-methyl-1-oxoisoquinolin-4-yl)pyrimidin-2-yl]methanesulfonamide

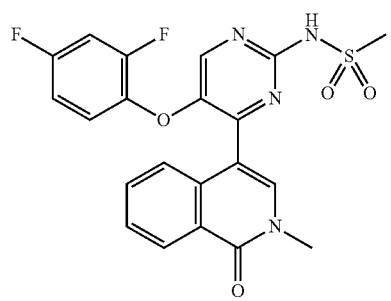 [SMILES: Cn1cc(-c2nc(NS(C)(=O)=O)ncc2Oc2ccc(F)cc2F)c2ccccc2c1=O]

The title compound of Example 151 was treated with MeSO$_2$NH$_2$ in a manner similar to Example 152, step 6 to give the title compound. $^1$H NMR (DMSO-d6, 400 MHz) δ 11.50 (s, 1H), 8.59 (s, 1H), 8.25 (s, J=8.0 Hz, 1H), 7.87 (s, 1H), 7.77 (d, J=8.0 Hz, 1H), 7.67 (t, J=8.0 Hz, 1H), 7.54 (t, J=7.2 Hz, 1H), 7.34-7.28 (m, 1H), 7.20-7.13 (m, 1H), 6.90 (t, J=8.8 Hz, 1H), 3.54 (s, 3H), 3.35 (s, 3H). LCMS: 459.0 (M+1)$^+$ Example 166

N-[5-(2,4-difluorophenoxy)-4-(1,5-dimethyl-6-oxopyridin-3-yl)pyrimidin-2-yl]methanesulfonamide

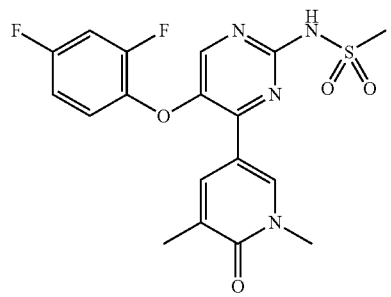 [SMILES: Cc1cc(-c2nc(NS(C)(=O)=O)ncc2Oc2ccc(F)cc2F)cn(C)c1=O]

The title compound of Example 149, step 4 was treated with MeSO$_2$NH$_2$ in a manner similar to Example 152, step 6 to give the title compound. $^1$H NMR (CDCl$_3$, 400 MHz) δ 8.42 (s, 1H), 8.36 (s, 1H), 8.10-8.12 (m, 2H), 6.98-7.05 (m, 2H), 6.87-6.92 (m, 1H), 3.64 (s, 3H), 3.45 (s, 3H), 2.22 (s, 3H). LCMS: 423.0 (M+1)$^+$

Example 167

N-[5-(2,4-difluorophenoxy)-4-(5-methoxy-1-methyl-6-oxopyridin-3-yl)pyrimidin-2-yl]methanesulfonamide

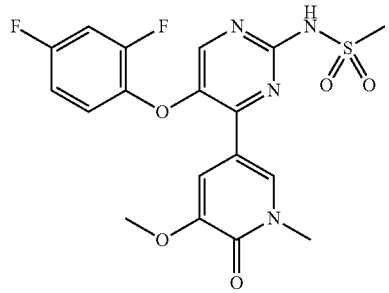 [SMILES: COc1cc(-c2nc(NS(C)(=O)=O)ncc2Oc2ccc(F)cc2F)cn(C)c1=O]

The title compound of Example 150 was treated with MeSO$_2$NH$_2$ in a manner similar to Example 152, step 6 to give the title compound. $^1$H NMR (DMSO-d6, 400 MHz) δ 11.37 (s, 1H), 8.34 (s, 1H), 8.26 (s, 1H), 7.58 (s, 1H), 7.54-7.50 (m, 1H), 7.28-7.23 (m, 1H), 7.10-7.06 (m, 1H), 3.74 (s, 3H), 3.52 (s, 3H), 3.39 (s, 3H). LCMS: 439.0 (M+1)$^+$

Example 168

N-[5-(2,4-difluorophenoxy)-4-(5-methoxy-1-methyl-6-oxopyridin-3-yl)pyrimidin-2-yl]ethanesulfonamide

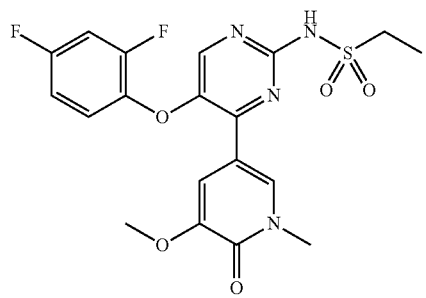 [SMILES: CCS(=O)(=O)Nc1ncc(Oc2ccc(F)cc2F)c(-c2cc(OC)c(=O)n(C)c2)n1]

The title compound of Example 150 was treated with EtSO$_2$NH$_2$ instead of MeSO$_2$NH$_2$ in a manner similar to Example 152, step 6 to give the title compound. $^1$H NMR (CDCl$_3$, 400 MHz) δ 8.35 (d, J=2.0 Hz, 1H), 8.18 (s, 1H), 7.70 (d, J=2.0 Hz, 1H), 7.25-7.22 (m, 1H), 7.12-7.07 (m, 1H), 7.04-7.01 (m, 1H), 3.93 (s, 3H), 3.70 (s, 3H), 3.38 (s, 3H). LCMS: 423.9 (M+1)$^+$

Example 169

N-[5-(2,4-difluorophenoxy)-4-(1,5-dimethyl-6-oxopyridin-3-yl)pyrimidin-2-yl]ethanesulfonamide

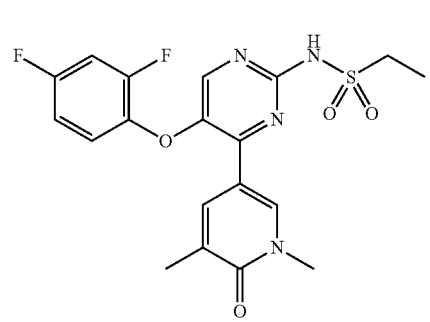 [SMILES: CCS(=O)(=O)Nc1ncc(Oc2ccc(F)cc2F)c(-c2cc(C)c(=O)n(C)c2)n1]

The title compound of Example 149, step 4 was treated with EtSO$_2$NH$_2$ instead of MeSO$_2$NH$_2$ in a manner similar to Example 152, step 6 to give the title compound. $^1$H NMR (DMSO-d6, 400 MHz) δ 9.07 (s, 1H), 8.42 (s, 1H), 8.15 (s, 1H), 8.11 (s, 1H), 7.03-6.97 (m, 1H), 6.91-6.87 (m, 1H), 3.66-3.61 (m, 5H), 2.22 (s, 3H), 1.44 (t, J=7.6 Hz, 3H). LCMS: 437.0 (M+1)$^+$

Example 170

N-[5-(2,4-difluorophenoxy)-4-(2-methyl-1-oxoisoquinolin-4-yl)pyrimidin-2-yl]ethanesulfonamide

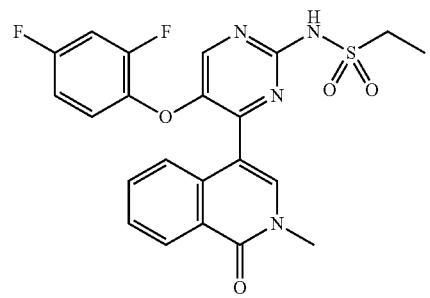 [SMILES: CCS(=O)(=O)Nc1ncc(Oc2ccc(F)cc2F)c(-c2cn(C)c(=O)c3ccccc23)n1]

The title compound of Example 151 was treated with with EtSO$_2$NH$_2$ instead of MeSO$_2$NH$_2$ in a manner similar to Example 152, step 6 to give the title compound. $^1$H NMR (CDCl$_3$, 400 MHz) δ 9.15 (s, 1H), 8.49 (d, J=7.6 Hz, 1H), 8.34 (s, 1H), 8.02 (d, J=8.0 Hz, 1H), 7.71-7.67 (m, 2H), 7.54 (t, J=7.6 Hz, 1H), 6.92-6.86 (m, 2H), 6.79-6.75 (m, 1H), 3.67 (s, 3H), 3.58 (q, J=7.6 Hz, 2H), 1.39 (t, J=7.6 Hz, 3H). LCMS: 473.0 (M+1)$^+$

Example 171

4-[5-(2,4-difluorophenoxy)-2-(1,1-dioxo-1,2-thiazolidin-2-yl)pyrimidin-4-yl]-2-methylisoquinolin-1-one

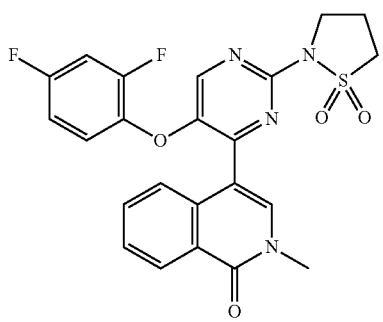 [SMILES: Cn1cc(-c2nc(N3CCCS3(=O)=O)ncc2Oc2ccc(F)cc2F)c2ccccc2c1=O]

The title compound of Example 151 was treated with 1,1-dioxoisothiazolidine instead of MeSO$_2$NH$_2$ in a manner similar to Example 152, step 6 to give the title compound. $^1$H NMR (DMSO-d6, 400 MHz) δ 8.63 (s, 1H), 8.24 (d, J=8.0 Hz, 1H), 7.86 (s, 1H), 7.83 (d, J=8.0 Hz, 1H), 7.65 (t, J=7.2 Hz, 1H), 7.53 (t, J=7.2 Hz, 1H), 7.31-7.26 (m, 1H), 7.13-7.07 (m, 1H), 6.89-6.87 (m, 1H), 3.97 (t, J=6.4 Hz, 2H), 3.57 (t, J=7.2 Hz, 2H), 3.54 (s, 3H), 2.40-2.33 (m, 2H). LCMS: 485.2 (M+H)$^+$

Example 172

N-[5-(2,4-difluorophenoxy)-4-(2-methyl-1-oxo-5,6,7,8-tetrahydroisoquinolin-4-yl)pyrimidin-2-yl]methanesulfonamide

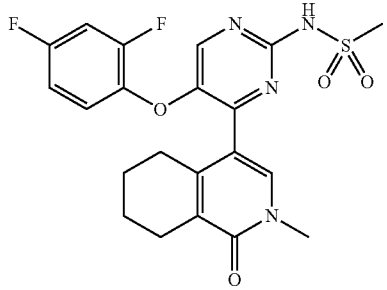 [SMILES: Cn1cc(-c2nc(NS(C)(=O)=O)ncc2Oc2ccc(F)cc2F)c2c(c1=O)CCCC2]

The title compound of Example 149, step 3 was reacted with the title compound of Example 163, step 3 in a manner similar to Example 163, step 4 and the resulting product was treated with MeSO$_2$NH$_2$ in a manner similar to Example 163, step 5 to give the title compound. $^1$H NMR (DMSO-d6, 400 MHz): δ 8.16 (s, 1H), 7.46 (s, 1H), 7.25-7.20 (m, 1H), 6.90-6.84 (m, 2H), 3.34 (s, 3H), 2.80 (s, 3H), 2.41-2.29 (m, 4H), 1.60-1.48 (m, 4H). LCMS: 463.1 (M+H)$^+$

Example 173

N-[5-(2,4-difluorophenoxy)-4-(2-methyl-1-oxo-5,6,7,8-tetrahydroisoquinolin-4-yl)pyrimidin-2-yl]ethanesulfonamide

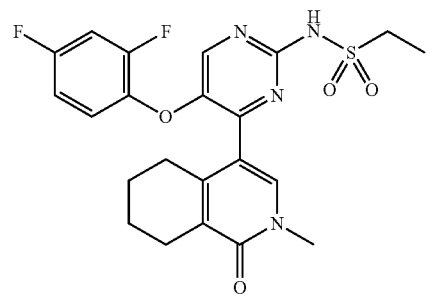 [SMILES: CCS(=O)(=O)Nc1ncc(Oc2ccc(F)cc2F)c(-c2cn(C)c(=O)c3c2CCCC3)n1]

The title compound of Example 149, step 3 was reacted with the title compound of Example 163, step 3 in a manner similar to Example 163, step 4 and the resulting 4-[5-(2,4-difluorophenoxy)-2-methylsulfonylpyrimidin-4-yl]-2-methyl-5,6,7,8-tetrahydroisoquinolin-1-one was treated with EtSO$_2$NH$_2$ instead of MeSO$_2$NH$_2$ in a manner similar to Example 163, step 5 to give the title compound. $^1$H NMR (DMSO-d6, 400 MHz): δ 8.38 (s, 1H), 7.61 (s, 1H), 7.35-7.31 (m, 1H), 7.04-6.95 (m, 2H), 3.41 (s, 3H), 3.30-3.20 (m, 2H), 2.42-2.40 (m, 2H), 2.32-2.30 (m, 2H), 1.61-1.51 (m, 4H), 1.18 (t, J=7.2 Hz, 3H). LCMS: 477.1 (M+H)$^+$

Example 174

4-[2-(cyclopropylmethoxy)-5-ethylsulfonylphenyl]-6-fluoro-2-methylisoquinolin-1-one

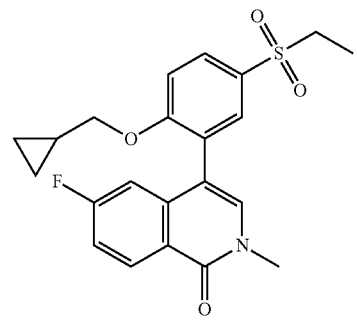 [SMILES: CCS(=O)(=O)c1ccc(OCC2CC2)c(-c2cn(C)c(=O)c3ccc(F)cc23)c1]

A mixture of 4-bromo-6-fluoro-2-methylisoquinolin-1-one (500.00 mg, 1.95 mmol), 2-[2-(cyclopropylmethoxy)-5-ethylsulfonylphenyl]-4,4,5,5-tetramethyl-1,3,2-dioxaborolane (1.07 g, 2.92 mmol), K$_3$PO$_4$ (1.24 g, 5.85 mmol) and Pd(dppf)Cl$_2$ (0.1 g, cat.) in dioxane/H$_2$O (30 mL/4 mL) was stirred at 70° C. for 12 hrs under Ar. The mixture was concentrated and the residue purified by column chromatography (PE:EA=1:1) to give a pink solid. The pink solid was further purified by column chromatography (DCM:EA=4:1) to afford the title compound (0.13 g, 16%) as a light yellow solid. $^1$H NMR (CDCl$_3$, 400 MHz) δ 8.54 (brs, 1H), 7.96 (dd, J$_1$=8.8 Hz, J$_2$=2.4 Hz, 1H), 7.81 (d, J=2.0 Hz, 1H), 7.22-7.20 (m, 1H), 7.15-7.13 (m, 1H), 7.1 (d, J=8.8 Hz, 1H), 6.78 (dd, J$_1$=10.4 Hz, J$_2$=2.4 Hz, 1H), 3.90 (t, J=7.6 Hz, 2H), 3.68 (s, 3H), 3.15 (q, J=7.6 Hz, 2H), 1.33 (t, J=7.6 Hz, 3H), 1.06-1.02 (m, 1H), 0.50-0.43 (m, 2H), 0.15-0.14 (m, 2H). LCMS (M+H)⁺=416.0 (M+1)⁺

Example 175

2-methyl-4-[5-methylsulfonyl-2-(oxolan-3-yloxy)phenyl]isoquinolin-1-one

Step 1: 4-(2-fluoro-5-methylsulfonylphenyl)-2-methylisoquinolin-1-one

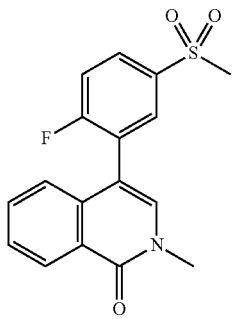 [SMILES: Cn1cc(-c2cc(S(C)(=O)=O)ccc2F)c2ccccc2c1=O]

A mixture of compound 2-methyl-4-(4,4,5,5-tetramethyl-1,3,2-dioxaborolan-2-yl)isoquinolin-1-one (4.1 g, 14.5 mmol), 2-bromo-4-methylsulfonyl-1-fluorobenzene (3.5 g, 13.8 mmol) prepared in a similar manner to Example 79 steps 1-2, CsF (6.3 g, 41.3 mmol), and Pd(dppf)Cl₂ (1.0 g, 1.38 mmol) in DME (70 mL) and MeOH (35 ml) was stirred at 70° C. for 12 h under N₂. The mixture was concentrated and the residue was purified by column chromatography on silica gel (PE:EA=2:1-0:1) to give the title compound (3.4 g, 74.4%) as a red solid. LCMS (M+H)⁺=331.9 (M+1)⁺

Step 2: 2-methyl-4-[5-methylsulfonyl-2-(oxolan-3-yloxy)phenyl]isoquinolin-1-one

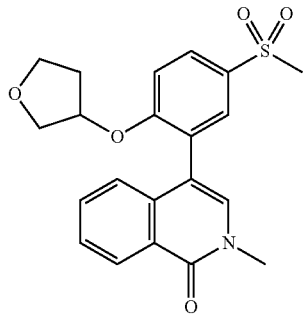 [SMILES: Cn1cc(-c2cc(S(C)(=O)=O)ccc2OC2CCOC2)c2ccccc2c1=O]

To a solution of oxolan-3-ol (175.0 mg, 1.99 mmol) in anhydrous DMF (3 mL) was added NaH (66.0 mg, 1.65 mmol, 60% in mineral oil) at 0° C. and then stirred at 0° C. for 0.5 hrs. 4-(2-fluoro-5-methylsulfonylphenyl)-2-methylisoquinolin-1-one (110.0 mg, 0.33 mmol) was added. The mixture was stirred at 0° C. for 0.5 h and then at r.t. for 3 hrs. It was then quenched with aqueous sat. NH₄Cl (20 mL) and extracted with EA (20 mL×3). The combined organic layers were washed with brine (40 mL), dried over Na₂SO₄, and concentrated under reduced pressure to afford a crude product which was purified by prep-HPLC to give the title compound (62.0 mg, 39.7%) as a light yellow solid. ¹H NMR (CDCl₃, 400 MHz) δ 8.51 (d, J=7.6 Hz, 1H), 8.00 (dd, J₁=8.8 Hz, J₂=2.4 Hz, 1H), 7.89 (d, J=2.4 Hz, 1H), 7.58-7.51 (m, 2H), 7.11-7.03 (m, 3H), 5.01-4.98 (m, 1H), 3.97 (dd, J₁=10.4 Hz, J₂=4.8 Hz, 1H), 3.76-3.70 (m, 2H), 3.67 (s, 3H), 3.61-3.42 (m, 1H), 3.11 (s, 3H), 2.18-1.88 (m, 2H). LCMS (M+H)⁺=400.0 (M+1)⁺

Example 176

2-methyl-4-[5-methylsulfonyl-2-(oxan-4-yloxy)phenyl]isoquinolin-1-one

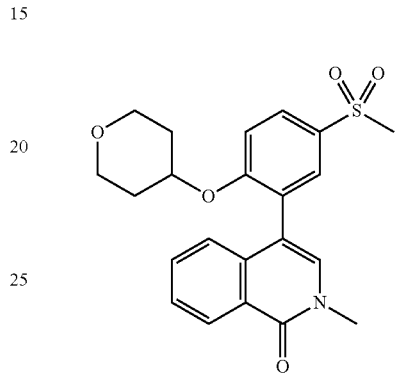

The title compound was prepared in a manner similar to Example 175, by substituting oxan-4-ol for oxolan-3-ol in step 2. ¹H NMR (CDCl₃, 400 MHz) δ 8.52 (d, J=7.6 Hz, 1H), 8.00 (dd, J1=8.8 Hz, J₂=2.4 Hz, 1H), 7.89 (d, J=2.4 Hz, 1H), 7.63-7.50 (m, 2H), 7.19 (d, J=7.6 Hz, 1H), 7.11 (d, J=8.8 Hz, 1H), 7.09 (s, 1H), 4.65-4.61 (m, 1H), 3.71 (s, 3H), 3.53-3.45 (m, 4H), 3.11 (s, 3H), 1.92-1.88 (m, 2H), 1.62-1.54 (m, 2H). LCMS (M+H)⁺=414.1 (M+1)⁺

Example 177

4-(2-ethoxy-5-methylsulfonylphenyl)-2-methylisoquinolin-1-one

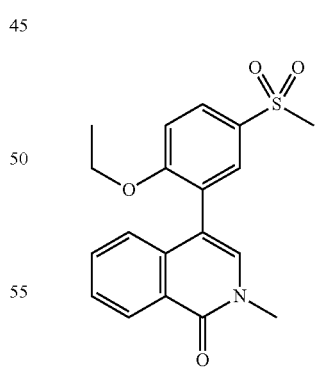

The title compound was prepared in a manner similar to Example 175, by substituting ethanol for oxolan-3-ol in step 2. ¹H NMR (CDCl₃, 400 MHz) δ 8.52 (d, J=8.0 Hz, 1H), 8.01 (dd, J₁=8.8 Hz, J₂=2.4 Hz, 1H), 7.86 (d, J=2.4 Hz, 1H), 7.57 (t, J=7.2 Hz, 1H), 7.52 (t, J=7.2 Hz, 1H), 7.13 (t, J=7.2 Hz, 2H), 7.08 (s, 1H), 4.12-4.09 (m, 2H), 3.68 (s, 3H), 3.10 (s, 3H), 1.18 (t, J=7.2 Hz, 1H). LCMS (M+H)⁺=358.0 (M+1)⁺

Example 178

2-methyl-4-(5-methylsulfonyl-2-propoxyphenyl)isoquinolin-1-one

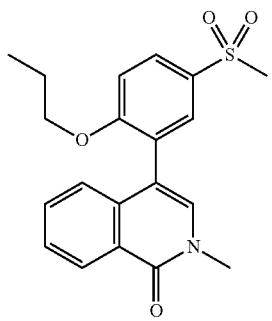

The title compound was prepared in a manner similar to Example 175, by substituting propan-1-ol for oxolan-3-ol in step 2. $^1$H NMR (CDCl$_3$, 400 MHz) δ 8.51 (d, J=8.0 Hz, 1H), 8.00 (dd, J$_1$=8.8 Hz, J$_2$=2.4 Hz, 1H), 7.86 (d, J=2.4 Hz, 1H), 7.56 (t, J=7.2 Hz, 1H), 7.50 (t, J=7.2 Hz, 1H), 7.14 (d, J=7.2 Hz, 1H), 7.12 (d, J=8.8 Hz, 1H), 7.07 (s, 1H), 4.00-3.94 (m, 2H), 3.67 (s, 3H), 3.10 (s, 3H), 1.60-1.52 (m, 2H), 0.68 (t, J=7.2 Hz, 1H). LCMS (M+H)$^+$=372.0 (M+1)$^+$

Example 179

2-methyl-4-[5-methylsulfonyl-2-(oxan-3-yloxy)phenyl]isoquinolin-1-one

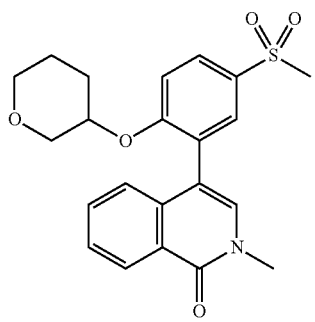 [SMILES: Cn1cc(-c2cc(S(C)(=O)=O)ccc2OC2CCCOC2)c2ccccc2c1=O]

The title compound was prepared in a manner similar to Example 175, by substituting oxan-3-ol for oxolan-3-ol in step 2. $^1$H NMR (CDCl$_3$, 400 MHz) δ 8.51 (d, J=8.0 Hz, 1H), 7.98 (dd, J$_1$=8.8 Hz, J$_2$=2.4 Hz, 1H), 7.88 (d, J=2.4 Hz, 1H), 7.56 (t, J=7.2 Hz, 1H), 7.52 (t, J=7.2 Hz, 1H), 7.18 (d, J=8.0 Hz, 1H), 7.12-7.06 (m, 2H), 4.43-4.41 (m, 1H), 3.79-3.78 (m, 1H), 3.67 (s, 3H), 3.66-3.63 (m, 1H), 3.39-3.34 (m, 2H), 3.10 (s, 3H), 2.02-1.93 (m, 2H), 1.59-1.48 (m, 2H). LCMS (M+H)$^+$=414.1 (M+1)$^+$

Example 180

4-[2-(trans-4-hydroxycyclohexyl)oxy-5-methylsulfonylphenyl]-2-methylisoquinolin-1-one Step 1: 4-[2-[4-[tert-butyl(dimethyl)silyl]oxycyclohexyl]oxy-5-methylsulfonylphenyl]-2-methylisoquinolin-1-one

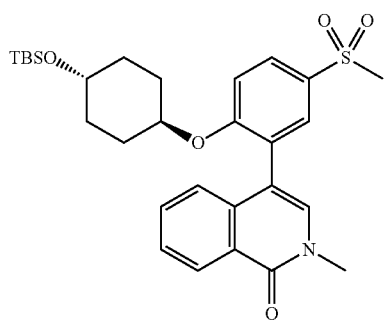 [SMILES: Cn1cc(-c2cc(S(C)(=O)=O)ccc2O[C@H]2CC[C@H](O[Si](C)(C)C(C)(C)C)CC2)c2ccccc2c1=O]

The title compound was prepared in a manner similar to Example 175, by substituting trans-4-[tert-butyl(dimethyl)silyl]oxycyclohexan-1-ol for oxolan-3-ol in step 2. LCMS (M+H)$^+$ =542.2 (M+1)$^+$ Step 2: 4-[2-(trans-4-hydroxycyclohexyl)oxy-5-methylsulfonylphenyl]-2-methylisoquinolin-1-one

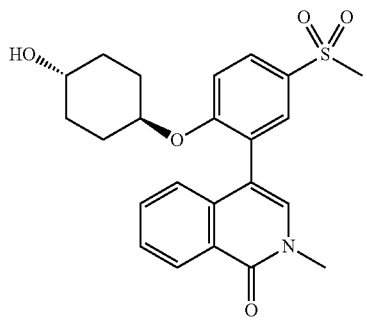

To a solution of the title compound from step 1 (180.0 mg, 0.33 mmol) in dry MeOH (5 mL) and DCM (3 mL) was added dropwise HCl/MeOH (0.3 mL, 1.2 mmol, 4M) at 0° C. and then stirred at r.t. for 20 min. TLC showed the starting material was consumed completely. The mixture was concentrated and the residue was purified by prep-HPLC to afford the title compound (130.0 mg, 97.8%) as a white solid. $^1$H NMR (CDCl$_3$, 400 MHz) δ 8.50 (d, J=7.6 Hz, 1H), 7.98 (dd, J$_1$=8.8 Hz, J$_2$=2.8 Hz, 1H), 7.86 (d, J=2.4 Hz, 1H), 7.55 (t, J=6.8 Hz, 1H), 7.51 (t, J=6.8 Hz, 1H), 7.16 (d, J=7.6 Hz, 1H), 7.11 (d, J=8.8 Hz, 1H), 7.05 (s, 1H), 4.42-4.35 (m, 1H), 3.67 (s, 3H), 3.65-3.62 (m, 1H), 3.10 (s, 3H), 2.01-1.89 (m, 2H), 1.71-1.65 (m, 2H), 1.36-1.34 (m, 4H). LCMS (M+H)$^+$=428.1 (M+1)$^+$

Example 181

4-[5-ethylsulfonyl-2-(trans-4-hydroxycyclohexyl)oxyphenyl]-2-methylisoquinolin-1-one Step 1: 4-[2-[4-[tert-butyl(dimethyl)silyl]oxycyclohexyl]oxy-5-ethylsulfonylphenyl]-2-methylisoquinolin-1-one

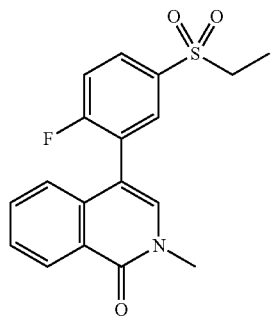 [SMILES: CCS(=O)(=O)c1ccc(F)c(-c2cn(C)c(=O)c3ccccc23)c1]

The title compound was prepared in a manner similar to Example 175 by substituting 2-bromo-4-ethylsulfonyl-1-fluorobenzene for 2-bromo-4-methylsulfonyl-1-fluorobenzene in step 1. LCMS (M+H)$^+$=345.9 (M+1)$^+$ Step 2: 4-[5-ethylsulfonyl-2-(trans-4-hydroxycyclohexyl)oxyphenyl]-2-methylisoquinolin-1-one

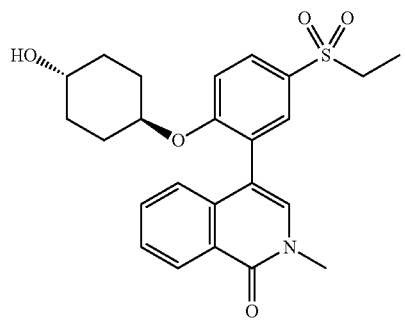 [SMILES: CCS(=O)(=O)c1ccc(O[C@H]2CC[C@H](O)CC2)c(-c2cn(C)c(=O)c3ccccc23)c1]

To a solution of trans-1,4-cyclohexanediol (504.0 mg, 4.34 mmol) in anhydrous DMF (4 mL) was added NaH (139.0 mg, 3.47 mmol, 60% in mineral oil) at 0° C. and then stirred at 0° C. for 1 h. The compound from step 1 (100.0 mg, 0.29 mmol) was added. The mixture was stirred at 0° C. for 0.5 h and then at r.t. 18 hrs. It was then quenched with MeOH (4 mL) and filtered. The filtrate was purified by prep-HPLC to give the title compound (37.0 mg, 30.0%) as an off-white solid. $^1$H NMR (CDCl$_3$, 40 MHz) δ 8.51 (d, J=7.6 Hz, 1H), 7.94 (dd, J$_1$=8.8 Hz, J$_2$=2.4 Hz, 1H), 7.83 (d, J=2.0 Hz, 1H), 7.56 (t, J=6.8 Hz, 1H), 7.51 (t, J=6.8 Hz, 1H), 7.16 (d, J=7.6 Hz, 1H), 7.11 (d, J=8.8 Hz, 1H), 7.05 (s, 1H), 4.43-4.18 (m, 1H), 3.67 (s, 3H), 3.65-3.62 (m, 1H), 3.16 (q, J=7.6 Hz, 2H), 2.00-1.90 (m, 2H), 1.71-1.65 (m, 2H), 1.42-1.30 (m, 7H). LCMS (M+H)$^+$=442.0 (M+1)$^+$

Example 182

4-[2-(trans-4-aminocyclohexyl)oxy-5-methylsulfonylphenyl]-2-methylisoquinolin-1-one

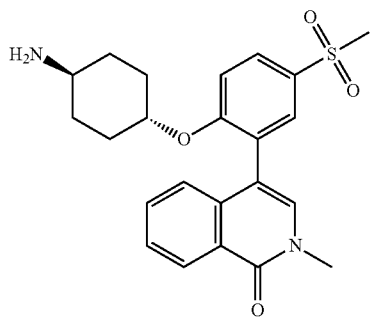 [SMILES: Cn1cc(-c2cc(S(C)(=O)=O)ccc2O[C@H]2CC[C@H](N)CC2)c2ccccc2c1=O]

A mixture of 4-(2-fluoro-5-methylsulfonylphenyl)-2-methylisoquinolin-1-one (200 mg, 0.60 mmol), trans-4-aminocyclohexan-1-ol (278 mg, 2.42 mmol) and Cs$_2$CO$_3$ (591 mg, 1.81 mmol) in DMSO (4 mL) was stirred at 120° C. for 12 hrs. Water (20 mL) was added and the mixture was extracted with EtOAc (3×20 mL). The combined organic layers were washed with brine (20 mL), dried over Na$_2$SO$_4$ and concentrated. The residue was purified by prep-HPLC to give the title compound (103.15 mg, 36.9%) as its hydrochloride salt. $^1$H NMR (DMSO-d6, 400 MHz) δ 8.28 (d, J=8.0 Hz, 1H), 8.10 (s, 3H), 7.95 (dd, J$_1$=8.8 Hz, J$_2$=2.4 Hz, 1H), 7.80 (d, J=2.4 Hz, 1H), 7.63 (t, J=7.2 Hz, 1H), 7.51-7.49 (m, 3H), 7.14 (d, J=8.0 Hz, 1H), 4.50-4.44 (m, 1H), 3.56 (s, 3H), 3.22 (s, 3H), 2.95-2.85 (m, 1H), 2.00-1.94 (m, 2H), 1.84 (d, J=11.2 Hz, 2H), 1.47-1.41 (m, 2H), 1.20-1.12 (m, 2H). LCMS (M+H)$^+$=427.1 (M+H)$^+$

Example 183

4-[2-(cis-4-aminocyclohexyl)oxy-5-methylsulfonylphenyl]-2-methylisoquinolin-1-one

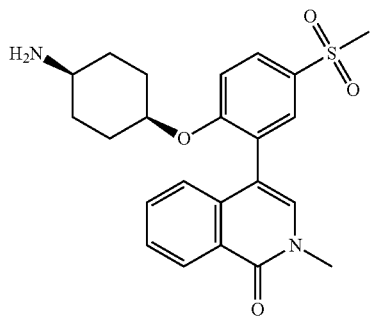 [SMILES: Cn1cc(-c2cc(S(C)(=O)=O)ccc2O[C@H]2CC[C@@H](N)CC2)c2ccccc2c1=O]

To compound cis-4-aminocyclohexan-1-ol (275 mg, 1.81 mmol) in DMF (3 mL), was added NaH (127 mg, 3.17 mmol, 60% in mineral oil) in one portion at 0° C. The mixture was stirred at 0° C. for 30 min, 4-(2-fluoro-5-methylsulfonylphenyl)-2-methylisoquinolin-1-one (150.00 mg, 0.45 mmol) was added in one portion and the mixture stirred at 0° C. for 2 hrs. The reaction was diluted with water (20 mL) and extracted with EA (3×20 mL). The combined organic layers were washed with saturated brine (2×20 mL), dried with anhydrous Na₂SO₄, filtered and concentrated in vacuum. The residue was purified by prep-HPLC to give the title compound as its hydrochloride salt (91.01 mg, 47.1%). ¹H NMR (DMSO-d6, 400 MHz) δ 8.29 (d, J=8.0 Hz, 1H), 8.00 (s, 3H), 7.95 (dd, J₁=8.8 Hz, J₂=2.0 Hz, 1H), 7.81 (d, J=2.0 Hz, 1H), 7.64 (t, J=7.2 Hz, 1H), 7.56 (s, 1H), 7.51 (t, J=7.2 Hz, 1H), 7.40 (d, J=8.8 Hz, 1H), 7.40 (d, J=8.0 Hz, 1H), 4.70 (s, 1H), 3.59 (s, 3H), 3.22 (s, 3H), 2.96-2.94 (m, 1H), 1.85-1.82 (m, 1H), 1.64-1.46 (m, 5H), 1.32-1.26 (m, 1H), 1.04-0.98 (m, 1H). LCMS (M+H)⁺=427.0 (M+H)⁺

Example 184

4-(2-but-2-ynoxy-5-methylsulfonylphenyl)-2-methylisoquinolin-1-one

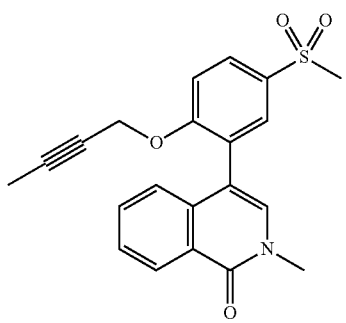 [SMILES: CCCCOc1ccc(S(C)(=O)=O)cc1-c1cn(C)c(=O)c2ccccc12]

The title compound was prepared in a manner similar to Example 175, by substituting but-2-yn-1-ol for oxolan-3-ol in step 2. ¹H NMR: (CDCl₃, 400 MHz) δ: 8.52 (d, J=7.6 Hz, 1H), 8.03 (d, J=8.8 Hz, 1H), 7.87 (s, 1H), 7.59-7.50 (m, 2H), 7.32 (d, J=8.8 Hz, 1H), 7.15 (d, J=8.4 Hz, 1H), 7.64 (t, J=8.0 Hz, 1H), 7.08 (s, 1H), 4.68 (s, 2H), 3.67 (s, 3H), 3.11 (s, 1H), 1.85 (s, 1H). LCMS (M+H)⁺=382.1 (M+H)⁺

Example 185

4-(2-but-2-ynoxy-5-ethylsulfonylphenyl)-2-methylisoquinolin-1-one

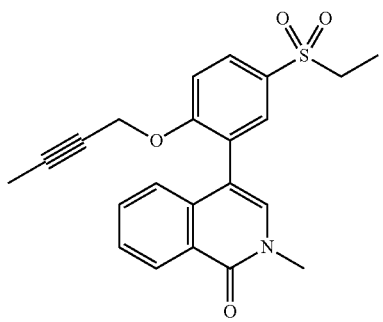 [SMILES: CCCCOc1ccc(S(=O)(=O)CC)cc1-c1cn(C)c(=O)c2ccccc12]

The title compound was prepared in a manner similar to Example 181, by substituting but-2-yn-1-ol for trans-1,4-cyclohexanediol in step 2. ¹H NMR: (CDCl₃, 400 MHz) δ: 8.51 (d, J=7.6 Hz, 1H), 8.00 (dd, J₁=8.8 Hz, J₂=2.0 Hz, 1H), 7.83 (s, 1H), 7.61 (d, J=7.6 Hz, 1H), 7.55 (d, J=7.6 Hz, 1H), 7.33 (d, J=8.8 Hz, 1H), 7.18 (d, J=8.0 Hz, 1H), 7.12 (s, 1H), 4.68 (s, 2H), 3.72 (s, 3H), 3.17 (q, J=7.2 Hz, 2H), 1.85 (s, 3H), 1.34 (t, J=7.2 Hz, 3H). LCMS (M+H)⁺=396.0 (M+H)⁺

Example 186

6-fluoro-4-[2-(trans-4-hydroxycyclohexyl)oxy-5-methylsulfonylphenyl]-2-methylisoquinolin-1-one Step 1: 6-fluoro-4-(2-fluoro-5-methylsulfonylphenyl)-2-methylisoquinolin-1-one

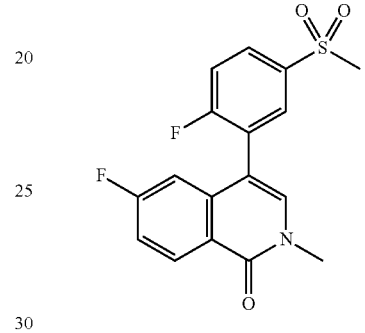

The title compound was prepared in a manner similar to Example 174, by substituting 2-(2-fluoro-5-methylsulfonylphenyl)-4,4,5,5-tetramethyl-1,3,2-dioxaborolane for 2-[2-(cyclopropylmethoxy)-5-ethylsulfonylphenyl]-4,4,5,5-tetramethyl-1,3,2-dioxaborolane. LCMS (M+H)⁺=349.9 (M+H)⁺

Step 2: 4-[2-[4-[tert-butyl(dimethyl)silyl]oxycyclohexyl]oxy-5-methylsulfonylphenyl]-6-fluoro-2-methylisoquinolin-1-one

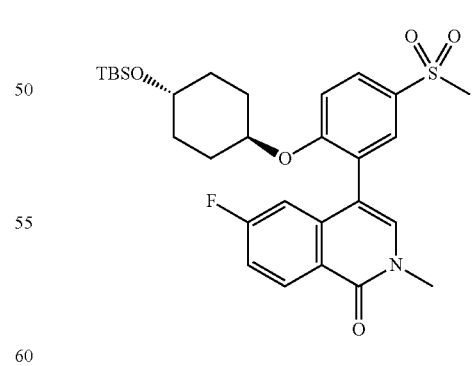

The title compound was prepared in a manner similar to Example 180 step 1, by substituting 6-fluoro-4-(2-fluoro-5-methylsulfonylphenyl)-2-methylisoquinolin-1-one for 4-(2-fluoro-5-methylsulfonylphenyl)-2-methylisoquinolin-1-one. The crude product was used directly in the next step without further purification. LCMS (M+H)⁺=560.3 (M+H)⁺

545

Step 3: 6-fluoro-4-[2-(trans-4-hydroxycyclohexyl)oxy-5-methylsulfonylphenyl]-2-methylisoquinolin-1-one

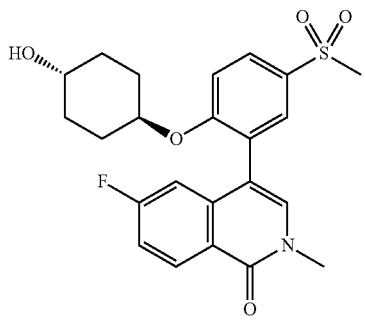 [SMILES: Cn1cc(-c2cc(S(C)(=O)=O)ccc2O[C@H]2CC[C@H](O)CC2)c2cc(F)ccc2c1=O]

The tert-butyl(dimethyl)silyl ether was deprotected in a manner similar to Example 180 step 2. ¹H NMR (CDCl₃, 400 MHz) δ 8.53-8.49 (m, 1H), 7.99 (dd, J₁=8.8 Hz, J₂=2.4 Hz, 1H), 7.85 (d, J=2.0 Hz, 1H), 7.21-7.18 (m, 1H), 7.12 (d, J=8.8 Hz, 1H), 7.08 (s, 1H), 6.78 (dd, J¹=10.0 Hz, J₂=2.4 Hz, 1H), 4.46-4.44 (m, 1H), 3.66-3.65 (m, 4H), 3.10 (s, 3H), 2.02-1.99 (m, 2H), 1.73-1.71 (m, 2H), 1.43-1.37 (m, 4H). LCMS (M+H)⁺=446.0 (M+H)⁺

Example 187

7-fluoro-4-[2-(trans-4-hydroxycyclohexyl)oxy-5-methylsulfonylphenyl]-2-methylisoquinolin-1-one

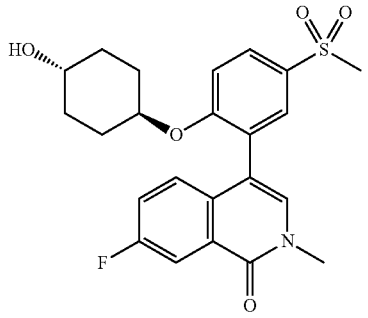 [SMILES: Cn1cc(-c2cc(S(C)(=O)=O)ccc2O[C@H]2CC[C@H](O)CC2)c2ccc(F)cc2c1=O]

The title compound was prepared in a manner similar to Example 186, by substituting 4-bromo-7-fluoro-2-methylisoquinolin-1-one for 4-bromo-6-fluoro-2-methylisoquinolin-1-one in step 1. ¹H NMR (CDCl₃, 400 MHz) δ 8.16-8.14 (m, 1H), 7.99 (dd, J=8.8 Hz, J₂=2.4 Hz, 1H), 7.86 (d, J=2.4 Hz, 1H), 7.28-7.27 (m, 1H), 7.18-7.12 (m, 2H), 7.01 (s, 1H), 4.43-4.42 (m, 1H), 3.67-3.66 (m, 4H), 3.10 (s, 3H), 1.98-1.97 (m, 2H), 1.72-1.71 (m, 2H), 1.39-1.32 (m, 4H). LCMS (M+H)⁺=446.0 (M+H)⁺

546

Example 188

4-[5-ethylsulfonyl-2-(trans-4-hydroxycyclohexyl)oxyphenyl]-6-fluoro-2-methylisoquinolin-1-one

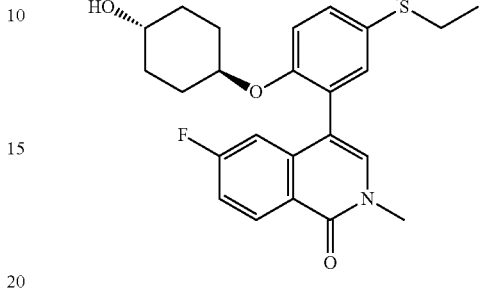

The title compound was prepared in a manner similar to Example 186, by substituting 2-(5-ethylsulfonyl-2-fluorophenyl)-4,4,5,5-tetramethyl-1,3,2-dioxaborolane for 2-(2-fluoro-5-methylsulfonylphenyl)-4,4,5,5-tetramethyl-1,3,2-dioxaborolane in step 1. ¹H NMR (CDCl₃, 400 MHz) δ 8.53-8.50 (m, 1H), 7.97-7.94 (m, 1H), 7.82 (d, J=2.4 Hz, 1H), 7.22-7.18 (m, 1H), 7.13 (d, J=8.8 Hz, 1H), 7.08 (s, 1H), 6.79-6.76 (m, 1H), 4.46-4.44 (m, 1H), 3.70-3.64 (m, 4H), 3.16 (q, J=7.6 Hz, 2H), 2.00-1.88 (m, 3H), 1.72-1.71 (m, 2H), 1.40-1.30 (m, 7H). LCMS (M+H)⁺=460.1 (M+H)⁺

Example 189

4-[5-ethylsulfonyl-2-(trans-4-hydroxycyclohexyl)oxyphenyl]-7-fluoro-2-methylisoquinolin-1-one Step 1: 4-(5-ethylsulfonyl-2-fluorophenyl)-7-fluoro-2-methylisoquinolin-1-one

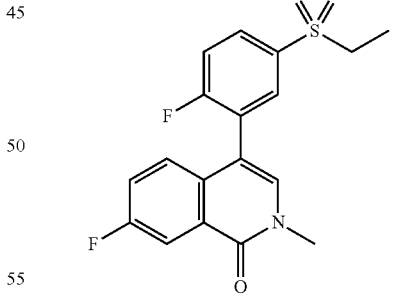

A mixture of 4-bromo-7-fluoro-2-methylisoquinolin-1-one (100 mg, 0.39 mmol), 2-(5-ethylsulfonyl-2-fluorophenyl)-4,4,5,5-tetramethyl-1,3,2-dioxaborolane (148 mg, 0.47 mmol), Pd(dppf)Cl₂ (29 mg, 0.04 mmol) and K₃PO₄ (207 mg, 0.98 mmol) in dioxane (6 mL) and H₂O (1 mL) was heated to 70° C. for 18 hrs under N₂. The mixture was concentrated and the residue was purified by column chromatography on silica gel (PE:EA=1:1) to give compound 12 (70 mg, yield: 49%) as a yellow solid. LCMS (M+H)⁺=364.1 (M+H)⁺

Step 2: 4-[2-[4-[tert-butyl(dimethyl)silyl]oxycyclohexyl]oxy-5-ethylsulfonylphenyl]-7-fluoro-2-methylisoquinolin-1-one

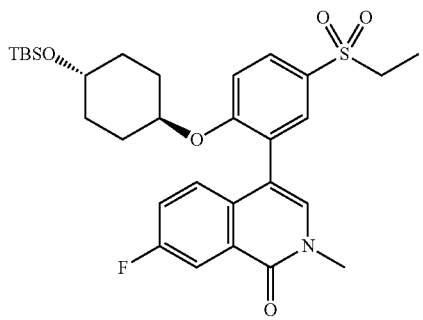 [SMILES: CCS(=O)(=O)c1ccc(O[C@H]2CC[C@H](O[Si](C)(C)C(C)(C)C)CC2)c(-c2cn(C)c(=O)c3cc(F)ccc23)c1]

To a solution of trans-4-[tert-butyl(dimethyl)silyl]oxycyclohexan-1-ol (87 mg, 0.38 mmol) in dry DMF (2 mL) was added NaH (15 mg, 0.38 mmol, 60% in mineral oil) in portions under $N_2$ at 0° C. and the mixture was stirred at 20° C. for 1 h. Then the title compound from step 1 (70 mg, 0.19 mmol) was added and the mixture was stirred at 20° C. for 4 hrs. The mixture was quenched with $H_2O$ (5 mL) and extracted with EtOAc (3×5 mL). The combined organic layers were dried over $Na_2SO_4$ and concentrated to give the title compound as a yellow gum (65 mg) which was used directly in the next step without further purification. LCMS $(M+H)^+=574.3$ $(M+H)^+$

Step 3: 4-[5-ethylsulfonyl-2-(trans-4-hydroxycyclohexyl)oxyphenyl]-7-fluoro-2-methylisoquinolin-1-one

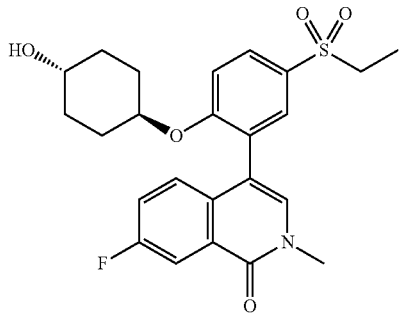 [SMILES: CCS(=O)(=O)c1ccc(O[C@H]2CC[C@H](O)CC2)c(-c2cn(C)c(=O)c3cc(F)ccc23)c1]

The tert-butyl(dimethyl)silyl ether was deprotected in a manner similar to Example 180 step 2. $^1$H NMR (CDCl$_3$, 400 MHz) δ 8.16 (dd, $J_1$=9.2 Hz, $J_2$=2.4 Hz, 1H), δ 7.96 (dd, $J_1$=8.4 Hz, $J_2$=2.4 Hz, 1H), 7.82 (d, J=2.4 Hz, 1H), 7.32-7.29 (m, 1H), 7.18-7.11 (m, 2H), 7.01 (s, 1H), 4.42-4.42 (m, 1H), 3.67 (s, 3H), 3.18 (q, J=7.6 Hz, 2H), 1.97-1.88 (m, 3H), 1.72-1.71 (m, 2H), 1.40-1.32 (m, 7H). LCMS (M+H)$^+$=460.1 (M+H)$^+$

Example 190

2-methyl-4-[5-methylsulfonyl-2-(oxolan-3-ylamino)phenyl]isoquinolin-1-one

Step 1: N-(2-bromo-4-methylsulfonylphenyl)oxolan-3-amine

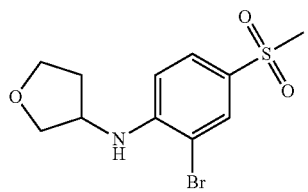 [SMILES: CS(=O)(=O)c1ccc(NC2CCOC2)c(Br)c1]

A mixture of 2-bromo-1-fluoro-4-methylsulfonylbenzene (0.8 g, 3.16 mmol), oxolan-3-amine (1.38 g, 15.8 mmol) and $K_2CO_3$ (0.87 g, 6.32 mmol) in DMSO (15 mL) was stirred at 100° C. for 5 hrs. It was cooled to r.t. and water (50 mL) was added. The mixture was extracted with EtOAc (50 mL×3) and the combined organic layers were washed with brine (50 mL), dried over $Na_2SO_4$, filtered and concentrated. The residue was purified by column chromatography (PE:EA=50:1-3:1) to give the title compound (0.7 g, yield: 69.16%). $^1$H NMR (CDCl$_3$, 400 MHz) δ 8.00 (d, J=1.2 Hz, 1H), 7.74 (d, J=8.8 Hz, 1H), 6.67 (d, J=8.8 Hz, 1H), 5.03 (d, J=6.4 Hz, 1H), 4.23-4.13 (m, 1H), 4.07-3.98 (m, 2H), 3.96-3.87 (m, 1H), 3.83-3.76 (m, 1H), 3.03 (s, 3H), 2.43-2.32 (m, 1H), 1.98-1.88 (m, 1H). LCMS $(M+H)^+$=320.0 $(M+H)^+$, 322.0

Step 2: 2-methyl-4-[5-methylsulfonyl-2-(oxolan-3-ylamino)phenyl]isoquinolin-1-one

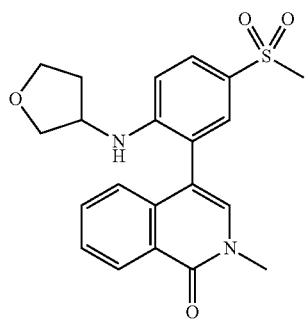 [SMILES: Cn1cc(-c2cc(S(C)(=O)=O)ccc2NC2CCOC2)c2ccccc2c1=O]

A mixture of 2-methyl-4-(4,4,5,5-tetramethyl-1,3,2-dioxaborolan-2-yl)isoquinolin-1-one (100 mg, 0.35 mmol), the compound from Step 1 (102 mg, 0.32 mmol), $K_3PO_4$ (186 mg, 0.88 mmol) and Pd(dppf)Cl$_2$ (29 mg, 0.04 mmol) in dioxane (5 mL) and $H_2O$ (1 mL) was purged 3 times with nitrogen and then stirred at 70° C. for 18 hrs under $N_2$. The mixture was filtered and concentrated. The residue was purified by prep-HPLC to give the title compound (56.02 mg, yield: 40.1%) as a light yellow solid. $^1$H NMR (CDCl$_3$, 400 MHz) δ 8.54 (d, J=8.0 Hz, 1H), 7.89 (dd, $J_1$=8.4 Hz, $J_2$=2.4 Hz, 1H), 7.69 (s, 1H), 7.64-7.52 (m, 2H), 7.13 (s, 1H), 7.13-7.08 (m, 1H), 6.78 (dd, $J_1$=8.8 Hz, $J_2$=5.6 Hz, 1H), 4.17 (s, 2H), 3.94-3.86 (m, 1H), 3.79-3.72 (m, 1H), 3.72-

3.64 (m, 1H), 3.67 (s, 3H), 3.58-3.49 (m, 1H), 3.07 (s, 3H), 2.32-2.18 (m, 1H), 1.76-1.63 (m, 1H). LCMS (M+H)⁺=399.1 (M+H)⁺

Example 191

2-methyl-4-[5-methylsulfonyl-2-(oxan-4-ylamino)phenyl]isoquinolin-1-one

Step 1: N-(2-bromo-4-methylsulfonylphenyl)oxan-4-amine

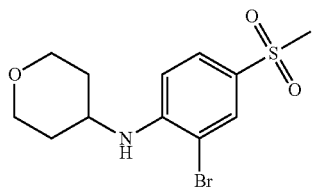 [SMILES: CS(=O)(=O)c1ccc(NC2CCOCC2)c(Br)c1]

The title compound was prepared in a manner similar to Example 190 step 1, by substituting oxan-3-amine for oxolan-3-amine. ¹H NMR (CDCl₃, 400 MHz) δ 7.98 (d, J=1.8 Hz, 1H), 7.70 (dd, J₁=8.8 Hz, J₂=1.8 Hz, 1H), 6.70 (d, J=8.8 Hz, 1H), 4.85 (d, J=7.2 Hz, 1H), 4.08-3.99 (m, 2H), 3.69-3.60 (m, 1H), 3.60-3.52 (m, 2H), 3.03 (s, 3H), 2.10-2.02 (m, 2H), 1.68-1.55 (m, 2H). LCMS (M+H)⁺=334.0 (M+H), 336.0

Step 2: 2-methyl-4-[5-methylsulfonyl-2-(oxan-4-ylamino)phenyl]isoquinolin-1-one

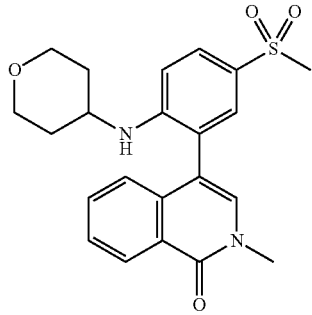 [SMILES: Cn1cc(-c2cc(S(C)(=O)=O)ccc2NC2CCOCC2)c2ccccc2c1=O]

The title compound was prepared in a manner similar to Example 190 step 2, by substituting N-(2-bromo-4-methylsulfonylphenyl)oxan-4-amine for N-(2-bromo-4-methylsulfonylphenyl)oxolan-3-amine. ¹H NMR (CDCl₃, 400 MHz) δ 8.52 (d, J=7.6 Hz, 1H), 7.85 (dd, J₁=8.8 Hz, J₂=2.0 Hz, 1H), 7.67 (d, J=2.0 Hz, 1H), 7.63-7.52 (m, 2H), 7.16-7.11 (m, 2H), 6.81 (d, J=8.8 Hz, 1H), 4.00 (d, J=7.6 Hz, 1H), 3.93-3.82 (m, 2H), 3.64 (s, 3H), 3.63-3.54 (m, 1H), 3.51-3.42 (m, 2H), 3.06 (s, 3H), 1.95-1.87 (m, 2H), 1.37-1.24 (m, 1H). LCMS (M+H)⁺=413.0 (M+H)⁺

Example 192

4-[2-[(trans-4-hydroxycyclohexyl)amino]-5-methylsulfonylphenyl]-2-methylisoquinolin-1-one

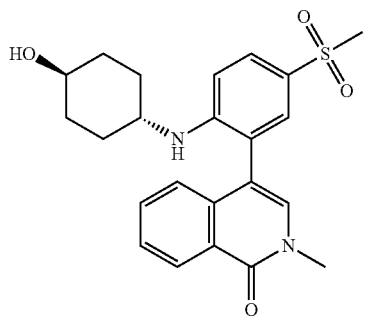

A mixture of 4-(2-fluoro-5-methylsulfonylphenyl)-2-methylisoquinolin-1-one (150 mg, 0.45 mmol) and trans-4-aminocyclohexan-1-ol (417 mg, 3.62 mmol) in NMP (0.2 mL) was heated for 20 min at 200-300° C. The cooled brownish residue was purified by prep-HPLC to give the title compound (55.64 mg, 28.8%) as a yellow solid. ¹H NMR (CDCl₃, 400 MHz) δ 8.54 (d, J=8.0 Hz, 1H), 7.86 (dd, J₁=8.8 Hz, J₂=2.4 Hz, 1H), 7.66 (d, J=2.4 Hz, 1H), 7.60-7.55 (m, 2H), 7.15-7.13 (m, 2H), 6.79 (d, J=8.8 Hz, 1H), 3.91-3.85 (m, 1H), 3.67 (s, 3H), 3.63-3.55 (m, 1H), 3.37-3.34 (m, 1H), 3.06 (s, 3H), 2.04-1.92 (m, 5H), 1.44-1.35 (m, 2H), 1.11-1.02 (m, 2H). LCMS (M+H)⁺=427.1 (M+H)⁺

Example 193

4-[2-(cyclopropylmethylamino)-5-ethylsulfonylphenyl]-2-methylisoquinolin-1-one

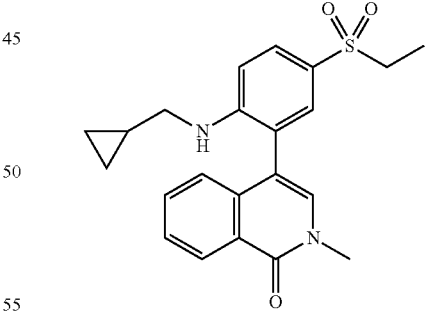

The title compound was prepared in a manner similar to Example 190 step 2, by substituting 2-bromo-N-(cyclopropylmethyl)-4-ethylsulfonylaniline for N-(2-bromo-4-methylsulfonylphenyl)oxolan-3-amine. ¹H NMR (CDCl₃, 400 MHz) δ 8.51 (d, J=7.6 Hz, 1H), 7.80 (dd, J₁=8.8 Hz, J₂=2.0 Hz, 1H), 7.61-7.51 (m, 3H), 7.15 (d, J=8.0 Hz, 1H), 7.13 (s, 1H), 6.76 (d, J=8.8 Hz, 1H), 4.32 (t, J=4.8 Hz, 1H), 3.62 (s, 3H), 3.09 (q, J=7.2 Hz, 2H), 3.01 (m, 2H), 1.29 (t, J=7.2 Hz, 3H), 0.95-0.89 (m, 1H), 0.46-0.38 (m, 2H), 0.12-0.05 (m, 2H). LCMS (M+H)⁺=397.1 (M+H)⁺

Example 194

4-[2-(cyclopropylmethylamino)-5-methylsulfonyl-phenyl]-2-methylisoquinolin-1-one

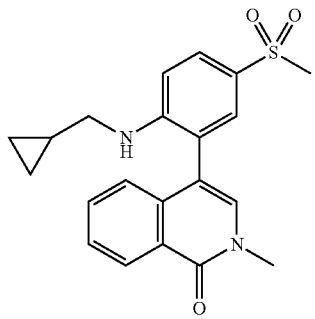 [SMILES: Cn1cc(-c2cc(S(C)(=O)=O)ccc2NCC2CC2)c2ccccc2c1=O]

The title compound was prepared in a manner similar to Example 190 step 2, by substituting 2-bromo-N-(cyclopropylmethyl)-4-methylsulfonylaniline for N-(2-bromo-4-methylsulfonylphenyl)oxolan-3-amine. $^1$H NMR (CDCl$_3$, 400 MHz) δ 8.54 (d, J=7.6 Hz, 1H), 7.80 (dd, J$_1$=8.8 Hz, J$_2$=2.4 Hz, 1H), 7.67 (d, J=2.4 Hz, 1H), 7.60-7.55 (m, 2H), 7.17 (d, J=8.0 Hz, 1H), 7.15 (s, 1H), 6.77 (d, J=8.8 Hz, 1H), 4.24-4.23 (m, 1H), 3.66 (s, 3H), 3.06 (s, 3H), 3.03-2.99 (m, 2H), 0.93-0.91 (m, 1H), 0.45-0.37 (m, 2H), 0.12-0.054 (m, 2H). LCMS (M+H)$^+$=383.1 (M+H)$^+$

Example 195

4-[2-(cyclopropylmethylamino)-5-ethylsulfonylphenyl]-7-fluoro-2-methylisoquinolin-1-one

Step 1: 7-fluoro-2-methyl-4-(4,4,5,5-tetramethyl-1,3,2-dioxaborolan-2-yl)isoquinolin-1-one

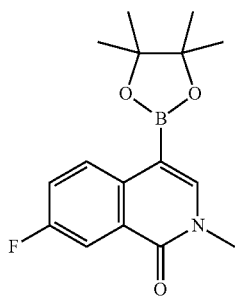 [SMILES: Cn1cc(B2OC(C)(C)C(C)(C)O2)c2ccc(F)cc2c1=O]

A mixture of compound 4-bromo-7-fluoro-2-methylisoquinolin-1-one (1.2 g, 4.69 mmol), bis(pinacolato)diboron (2.38 g, 9.37 mmol), AcOK (1.38 g, 14.07 mmol), Pd$_2$(dba)$_3$ (429 mg, 0.47 mmol) and X-phos (224 mg, 0.47 mmol) in dioxane (20 mL) was stirred at 70° C. for 18 hrs under N$_2$. The mixture was concentrated and the residue was purified by column chromatography to give the title compound (0.8 g, yield: 56.3%). $^1$H NMR (CDCl$_3$, 400 MHz) δ 8.42 (dd, J$_1$=9.2 Hz, J$_2$=4.2 Hz, 1H), 8.06 (dd, J$_1$=9.2 Hz, J$_2$=2.8 Hz, 1H), 7.65 (s, 1H), 7.42-7.35 (m, 1H), 3.64 (s, 3H), 1.38 (s, 12H). LCMS (M+H)$^+$=304.1 (M+H)$^+$

Step 2: 4-[2-(cyclopropylmethylamino)-5-ethylsulfonylphenyl]-7-fluoro-2-methylisoquinolin-1-one

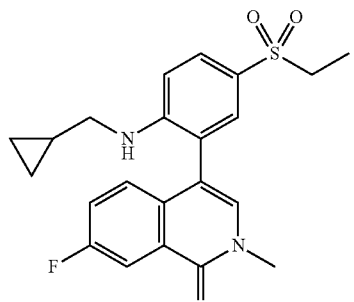

The title compound was prepared in a manner similar to Example 193, by substituting 7-fluoro-2-methyl-4-(4,4,5,5-tetramethyl-1,3,2-dioxaborolan-2-yl)isoquinolin-1-one for 2-methyl-4-(4,4,5,5-tetramethyl-1,3,2-dioxaborolan-2-yl)isoquinolin-1-one. $^1$H NMR (CDCl$_3$, 400 MHz) δ 8.17 (d, J=8.4 Hz, 1H), 7.82 (d, J=8.4 Hz, 1H), 7.61 (s, 1H), 7.38-7.29 (m, 1H), 7.21-7.13 (m, 1H), 7.11 (s, 1H), 6.77 (d, J=8.4 Hz, 1H), 3.67 (s, 3H), 3.11 (q, J=7.2 Hz, 2H), 3.01 (d, J=6.8 Hz, 2H), 1.31 (t, J=7.2 Hz, 3H), 0.99-0.85 (m, 1H), 0.51-0.36 (m, 2H), 0.17-0.02 (m, 2H). LCMS (M+H)$^+$=415.1 (M+H)$^+$

Example 196

4-[2-(cyclopropylmethylamino)-5-methylsulfonyl-phenyl]-7-fluoro-2-methylisoquinolin-1-one

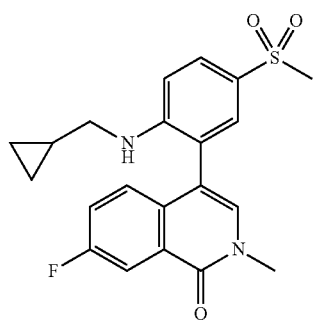 [SMILES: Cn1cc(-c2cc(S(C)(=O)=O)ccc2NCC2CC2)c2ccc(F)cc2c1=O]

The title compound was prepared in a manner similar to Example 195, by substituting 2-bromo-N-(cyclopropylmethyl)-4-methylsulfonylaniline for 2-bromo-N-(cyclopropylmethyl)-4-ethylsulfonylaniline in step 2. $^1$H NMR (CDCl$_3$, 400 MHz) δ 8.19 (dd, J$_1$=9.2 Hz, J$_2$=2.8 Hz, 1H), 7.86 (dd, J$_1$=8.8 Hz, J$_2$=2.0 Hz, 1H), 7.66 (d, J=2.4 Hz, 1H), 7.37-7.30 (m, 1H), 7.18 (dd, J$_1$=8.8 Hz, J$_2$=4.8 Hz, 1H), 7.11 (s, 1H), 6.77 (d, J=8.8 Hz, 1H), 4.14 (s, 1H), 3.68 (s, 3H), 3.06 (s, 3H), 3.01 (d, J=6.8 Hz, 2H), 0.98-0.84 (m, 1H), 0.51-0.37 (m, 2H), 0.16-0.02 (m, 2H). LCMS (M+H)$^+$=401.1 (M+H)$^+$

Example 197

4-[2-(cyclopropylmethoxy)-5-methylsulfonylphenyl]-2-methyl-6-(trifluoromethoxy)isoquinolin-1-one

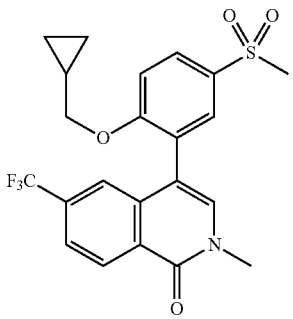 [SMILES: Cn1cc(-c2cc(S(C)(=O)=O)ccc2OCC2CC2)c2cc(C(F)(F)F)ccc2c1=O]

A mixture of 4-bromo-2-methyl-6-(trifluoromethyl)isoquinolin-1-one (40 mg, 0.13 mmol), 2-[2-(cyclopropylmethoxy)-5-methylsulfonylphenyl]-4,4,5,5-tetramethyl-1,3,2-dioxaborolane (46 mg, 0.13 mmol), $K_3PO_4$ (68 mg, 0.33 mmol) and Pd(dppf)Cl$_2$ (10 mg, 0.01 mmol) in dioxane (0.9 mL) and H$_2$O (0.09 mL) was degassed with N$_2$ for ten minutes and then stirred at 60° C. for 1.6 h. The reaction mixture was diluted with EtOAc (5 mL), dried over Na$_2$SO$_4$, filtered and concentrated under reduced pressure. The residue was purified by normal phase silica gel column chromatography to give the title compound (27 mg, 46%). $^1$H NMR (DMSO-d6, 400 MHz) δ 8.51 (d, $J_1$=8.4 Hz, 1H), 8.0 (dd, $J_1$=8.7 Hz, $J_2$=2.5 Hz, 1H), 7.87 (s, 1H), 7.85 (m, 1H), 7.72 (s, 1H), 7.39 (m, 2H), 4.02 (m, 1H), 3.86 (m, 1H), 3.61 (s, 3H), 3.23 (s, 3H), 0.90 (m, 1H), 0.31 (m, 2H), 0.09 (m, 2H). LCMS (M+H)$^+$=452.2

Example 198

4-(2-(cyclopropylmethoxy)-5-(methylsulfonyl)phenyl)-6-methoxy-2-methylisoquinolin-1(2H)-one

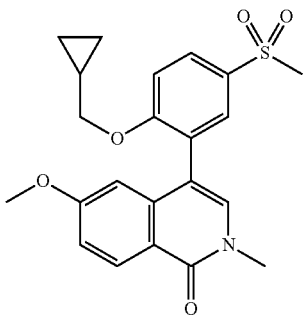

The title compound of Example 90, step 2 (30 mg, 0.075 mmol) in N,N-dimethylacetamide was treated with excess 25% sodium methoxide in methanol and heated at 85° C. until complete. Silica gel chromatography (40-80% EA in hexane over 8 min, then isocratic) gave the title compound 23 mg, 0.056 mmol, 74%) as a white solid. $^1$H NMR (400 MHz, DMSO-d$_6$) δ ppm 0.06-0.20 (m., 2H) 0.27-0.43 (m, 2H) 0.83-1.05 (m, 1H) 3.22 (s, 3H) 3.53 (s, 3H) 3.73 (s, 3H) 3.83-4.16 (m, 2H) 6.47 (s, 1H) 7.04-7.20 (m, 1H) 7.36 (d, J=8.59 Hz, 1H) 7.50 (s, 1H) 7.81 (s, 1H) 7.96 (d, J=6.82 Hz, 1H) 8.23 (d, J=8.59 Hz, 1H). LCMS: 414 (M+H)$^+$

Example 199

4-[3-(cyclopropylmethoxy)-6-methylsulfonylpyridin-2-yl]-2-methylisoquinolin-1-one

Step 1: 6-methylsulfonylpyridin-3-ol

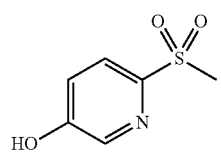

A mixture of 6-chloropyridin-3-ol (2.00 g, 15.44 mmol), MeSO$_2$Na (2.36 g, 23.16 mmol), CuI (882.16 mg, 4.63 mmol), L-proline (533.28 mg, 4.63 mmol), and K$_2$CO$_3$ (640.19 mg, 4.63 mmol) in DMSO (20 mL) were charged into a microwave tube. The sealed tube was heated at 140° C. for 3 hrs under microwave. After cooling to room temperature, water (100 mL) was added. The mixture was extracted with EtOAc (100 mL×3). The combined organic layers were washed with brine (100 mL), dried over Na$_2$SO$_4$, filtered and concentrated under reduced pressure. The residue was purified by column chromatography to give the title compound (1.2 g, 44.8%) as a yellow solid. $^1$H NMR (Methanol-d4, 400 MHz) δ 8.24 (d, J=2.4 Hz, 1H), 7.94 (d, J=8.4 Hz, 1H), 7.37 (dd, $J_1$=8.8 Hz, $J_2$=2.8 Hz, 1H), 3.15 (s, 3H).

Step 2: 2-iodo-6-methylsulfonylpyridin-3-ol and 4-iodo-6-methylsulfonylpyridin-3-ol

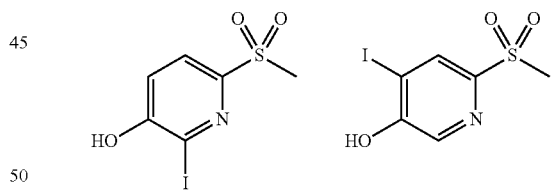

A mixture of the title compound from Step 1 (3.0 g, 17.34 mmol), I$_2$ (6.6 g, 26.01 mmol), NaHCO$_3$ (2.2 g, 26.20 mmol) and KI (0.72 g, 4.34 mmol) in THF (30 mL) and H$_2$O (30 mL) was stirred at 60° C. for 18 hrs. Water (100 mL) was added and the mixture was extracted with EtOAc (100 mL×3). The combined organic layers were washed with brine (100 mL), dried over Na$_2$SO$_4$, filtered and concentrated under reduced pressure. The residue was purified by preparative HPLC to give 4-iodo-6-methylsulfonylpyridin-3-ol (700.0 mg) and 2-iodo-6-methylsulfonylpyridin-3-ol (700.0 mg). 2-iodo-6-methylsulfonylpyridin-3-ol: $^1$H NMR (CDCl$_3$, 400 MHz) δ 12.08 (brs, 1H), 7.86 (d, J=8.4 Hz, 1H), 7.31 (d, J=8.4 Hz, 1H), 3.19 (s, 3H). 4-iodo-6-methylsulfonylpyridin-3-ol: $^1$H NMR (CDCl$_3$, 400 MHz) δ 12.0 (brs, 1H), 8.24 (s, 1H), 8.17 (s, 1H), 3.20 (s, 3H).

Step 3: 3-(cyclopropylmethoxy)-2-iodo-6-methyl-sulfonylpyridine

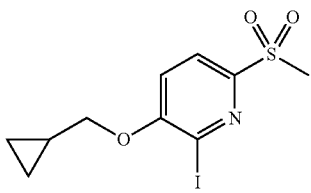 [SMILES: CS(=O)(=O)c1ccc(OCC2CC2)c(I)n1]

A mixture of 2-iodo-6-methylsulfonylpyridin-3-ol (500.0 mg, 1.67 mmol), bromomethylcyclopropane (248.4 mg, 1.84 mmol) and K₂CO₃ (461.3 mg, 33.4 mmol) in ACN (15 mL) was stirred at 80° C. for 4 hrs. Water (30 mL) was added and the mixture was extracted with EtOAc (30 mL×3). The combined organic layers were washed with brine (30 mL), dried over Na₂SO₄, filtered and concentrated to give the title compound (500.0 mg, 84.8%). ¹H NMR (CDCl₃, 400 MHz) δ 7.96 (d, J=8.8 Hz, 1H), 7.52 (d, J=8.4 Hz, 1H), 4.09 (d, J=6.8 Hz, 2H), 3.22 (s, 3H), 1.36-1.22 (m, 1H), 0.69-0.57 (m, 2H), 0.43-0.37 (m, 2H). LCMS: 354.0 (M+1)⁺

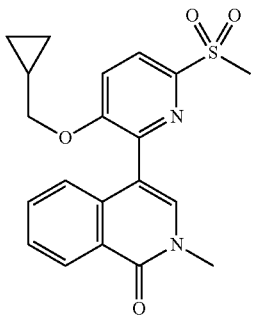 [SMILES: Cn1cc(-c2nc(S(C)(=O)=O)ccc2OCC2CC2)c2ccccc2c1=O]

A mixture of 3-(cyclopropylmethoxy)-2-iodo-6-methyl-sulfonylpyridine (140.0 mg, 0.40 mmol), 2-methyl-4-(4,4,5,5-tetramethyl-1,3,2-dioxaborolan-2-yl)isoquinolin-1-one (136.5 mg, 0.48 mmol), K₃PO₄ (252.7 mg, 1.19 mmol) and Pd(dppf)Cl₂ (29.2 mg, 0.04 mmol) in dioxane (5 mL) and H₂O (1 mL) was stirred at 70° C. for 18 hrs under N₂. The mixture was filtered and concentrated. The residue was purified by prep-HPLC to give the title compound (81.0 mg, 53.1%). ¹H NMR (CDCl₃, 400 MHz) δ 8.33 (dd, J₁=8.4 Hz, J₂=1.2 Hz, 1H), 8.07 (d, J=8.4 Hz, 1H), 7.83 (d, J=8.8 Hz, 1H), 7.74 (s, 1H), 7.67 (t, J=8.4 Hz, 1H), 7.55 (t, J=8.4 Hz, 1H), 7.39 (d, J=8.0 Hz, 1H), 4.01 (d, J=6.8 Hz, 2H), 3.60 (s, 3H), 3.25 (s, 3H), 1.10-0.98 (m, 1H), 0.45-0.37 (m, 2H), 0.23-0.17 (m, 2H). LCMS: 385.1 (M+1)⁺

Example 200

4-[5-(cyclopropylmethoxy)-2-methylsulfonylpyridin-4-yl]-2-methylisoquinolin-1-one

Step 1: 5-(cyclopropylmethoxy)-4-iodo-2-methyl-sulfonylpyridine

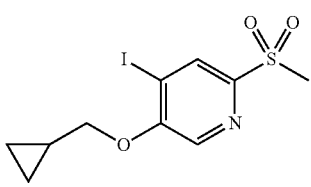 [SMILES: CS(=O)(=O)c1cc(I)c(OCC2CC2)cn1]

The title compound was prepared in a manner similar to Example 199 Step 3, by substituting 4-iodo-6-methylsulfonylpyridin-3-ol for 2-iodo-6-methylsulfonylpyridin-3-ol. ¹H NMR (CDCl₃, 400 MHz) δ 8.35 (s, 1H), 8.32 (s, 1H), 4.20 (d, J=7.2 Hz, 2H), 3.23 (s, 3H), 1.36-1.25 (m, 1H), 0.67-0.58 (m, 2H), 0.44-0.37 (m, 2H). LCMS: 354.0 (M+1)⁺

Step 2: 4-[5-(cyclopropylmethoxy)-2-methylsulfonylpyridin-4-yl]-2-methylisoquinolin-1-one

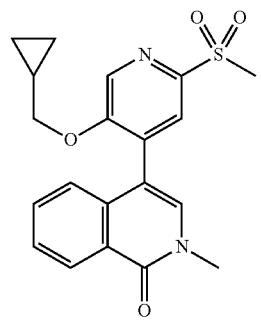 [SMILES: Cn1cc(-c2cc(S(C)(=O)=O)ncc2OCC2CC2)c2ccccc2c1=O]

The title compound was prepared in a manner similar to Example 199 Step 4, by substituting 5-(cyclopropylmethoxy)-4-iodo-2-methylsulfonylpyridine for 3-(cyclopropylmethoxy)-2-iodo-6-methylsulfonylpyridine. ¹H NMR (CDCl₃, 400 MHz) δ 8.66 (s, 1H), 8.31 (d, J=8.0 Hz, 1H), 7.96 (s, 1H), 7.70-7.66 (m, 2H), 7.57-7.54 (t, J=7.2 Hz, 1H), 7.22 (d, J=8.0 Hz, 1H), 4.12 (d, J=6.8 Hz, 2H), 3.57 (s, 3H), 3.28 (s, 3H), 1.05-0.92 (m, 1H), 0.43-0.27 (m, 2H), 0.18-0.10 (m, 2H). LCMS: 385.1 (M+1)⁺

Example 201

4-[3-(cyclopropylmethoxy)-6-methylsulfonylpyridin-2-yl]-7-fluoro-2-methylisoquinolin-1-one

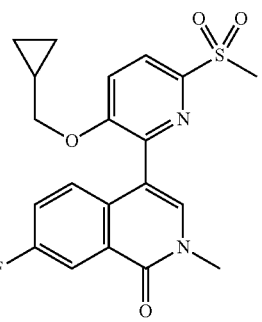

The title compound was prepared in a manner similar to Example 199 Step 4, by substituting 7-fluoro-2-methyl-4-(4,4,5,5-tetramethyl-1,3,2-dioxaborolan-2-yl)isoquinolin-1-one for 2-methyl-4-(4,4,5,5-tetramethyl-1,3,2-dioxaborolan-2-yl)isoquinolin-1-one. ¹H NMR (DMSO-d6, 400 MHz) δ 8.07 (d, J=8.4 Hz, 1H), 7.97 (d, J=7.6 Hz, 1H), 7.83 (d, J=8.4 Hz, 1H), 7.75 (s, 1H), 7.65-7.45 (m, 2H), 4.01 (d, J=6.4 Hz, 2H), 3.61 (s, 3H), 3.25 (s, 3H), 1.11-0.98 (m, 1H), 0.48-0.35 (m, 2H), 0.27-0.15 (m, 2H). LCMS: 403.1 (M+1)⁺

Example 202

4-[3-(cyclopropylmethoxy)-6-methylsulfonylpyridin-2-yl]-6-fluoro-2-methylisoquinolin-1-one

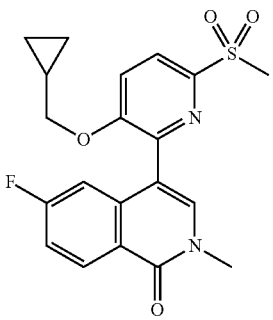 [SMILES: Cn1cc(-c2nc(S(C)(=O)=O)ccc2OCC2CC2)c2cc(F)ccc2c1=O]

The title compound was prepared in a manner similar to Example 199 Step 4, by substituting 6-fluoro-2-methyl-4-(4,4,5,5-tetramethyl-1,3,2-dioxaborolan-2-yl)isoquinolin-1-one for 2-methyl-4-(4,4,5,5-tetramethyl-1,3,2-dioxaborolan-2-yl)isoquinolin-1-one. $^1$H NMR (DMSO-d6, 400 MHz) δ 8.37 (dd, $J_1$=8.8 Hz, $J_2$=6.4 Hz, 1H), 8.07 (d, J=8.4 Hz, 1H), 7.84 (s, 1H), 7.82 (d, J=8.8 Hz, 1H), 7.45-7.36 (td, $J_1$=10.8 Hz, $J_2$=2.4 Hz, 1H), 7.18 (dd, $J_1$=10.8 Hz, $J_2$=2.4 Hz, 1H), 4.03 (d, J=7.2 Hz, 2H), 3.59 (s, 3H), 3.25 (s, 3H), 1.15-1.03 (m, 1H), 0.48-0.39 (m, 2H), 0.28-0.20 (m, 2H). LCMS: 403.1 (M+1)$^+$

Example 203

4-[5-(cyclopropylmethoxy)-2-methylsulfonylpyridin-4-yl]-7-fluoro-2-methylisoquinolin-1-one

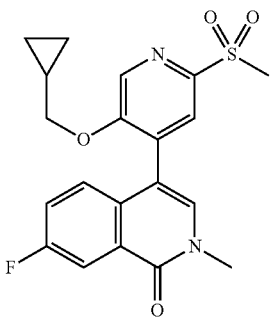 [SMILES: Cn1cc(-c2cc(S(C)(=O)=O)ncc2OCC2CC2)c2ccc(F)cc2c1=O]

The title compound was prepared in a manner similar to Example 200 Step 2, by substituting 7-fluoro-2-methyl-4-(4,4,5,5-tetramethyl-1,3,2-dioxaborolan-2-yl)isoquinolin-1-one for 2-methyl-4-(4,4,5,5-tetramethyl-1,3,2-dioxaborolan-2-yl)isoquinolin-1-one. $^1$H NMR (DMSO-d6, 400 MHz) δ 8.08 (d, J=8.4 Hz, 1H), 7.97 (dd, J1=9.2 Hz, $J_2$=2.8 Hz, 1H), 7.83 (d, J=8.4 Hz, 1H), 7.75 (s, 1H), 7.62-7.55 (td, $J_1$=9.2 Hz, $J_2$=2.4 Hz, 1H), 7.50 (dd, $J_1$=9.2 Hz, $J_2$=5.2 Hz, 1H), 4.01 (d, J=6.8 Hz, 2H), 3.61 (s, 3H), 3.25 (s, 3H), 1.11-0.99 (m, 1H), 0.46-0.39 (m, 2H), 0.24-0.18 (m, 2H). LCMS: 403.2 (M+1)$^+$

Example 204

4-(2-ethoxy-5-ethylsulfonylthiophen-3-yl)-2-methylisoquinolin-1-one

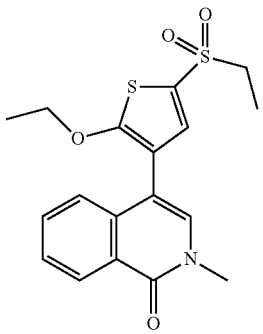 [SMILES: CCOc1sc(S(=O)(=O)CC)cc1-c1cn(C)c(=O)c2ccccc12]

A mixture of 3-bromo-2-ethoxy-5-ethylsulfonylthiophene (18.0 mg, 0.06 mmol), 2-methyl-4-(4,4,5,5-tetramethyl-1,3,2-dioxaborolan-2-yl)isoquinolin-1-one (24 mg, 0.08 mmol), $K_3PO_4$ (42 mg, 0.20 mmol) and Pd(dppf)Cl$_2$ (6 mg, 0.008 mmol) in dioxane (0.5 mL) and H$_2$O (0.05 mL) was stirred at 60° C. for 1.5 h. The reaction mixture was then poured over water (6 mL) and extracted with EtOAc (2×5 mL). The combined organic layers were dried over Na$_2$SO$_4$, filtered and concentrated under reduced pressure. The residue was purified by normal phase silica gel column chromatography to give the title compound (10.5 mg, 46%). $^1$H NMR (DMSO-d6, 400 MHz) δ 8.29 (d, J=7.9 Hz, 1H), 7.71 (dd, J=7.6, 7.6 Hz, 1H), 7.57 (m, 3H), 7.35 (d, J=7.9 Hz, 1H), 4.25 (m, 2H), 3.54 (s, 3H), 3.38 (m, 2H), 1.24 (m, 6H). LCMS: 378.05 (M+1)$^+$

Example 205

4-[2-(cyclopropylmethylamino)-5-ethylsulfonylthiophen-3-yl]-2-methylisoquinolin-1-one

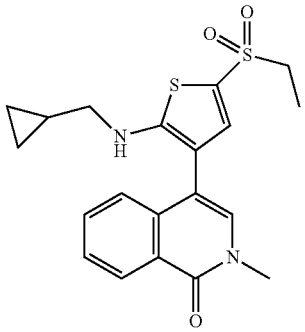 [SMILES: CCS(=O)(=O)c1cc(-c2cn(C)c(=O)c3ccccc23)c(NCC2CC2)s1]

The title compound was prepared in a manner similar to Example 204, by substituting 3-bromo-N-(cyclopropylmethyl)-5-ethylsulfonylthiophen-2-amine for 3-bromo-2-ethoxy-5-ethylsulfonylthiophene. $^1$H NMR (DMSO-d6, 400 MHz) δ 8.30 (d, J=8.0 Hz, 1H), 7.70 (m, 1H), 7.53 (dd, J=7.6, 7.6 Hz, 1H), 7.5 (s, 1H), 7.32 (s, 1H), 7.26 (d, J=8.0 Hz, 1H), 6.91 (m, 1H), 3.53 (s, 3H), 3.25 (m, 2H), 2.95 (m, 2H), 1.20 (dd, J=7.3, 7.3 Hz, 3H), 1.05 (m, 1H), 0.43 (m, 2H), 0.18 (m, 2H). LCMS: 403.1 (M+1)$^+$

Example 206

4-[3-(cyclopropylmethoxy)-6-ethylsulfonylpyridin-2-yl]-2-methylisoquinolin-1-one Step 1: 5-bromo-2-ethylsulfanylpyridine

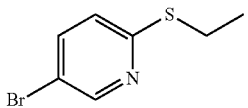

To a solution of 2,5-dibromopyridine (25 g, 105.5 mmol) in anhydrous DMSO (50 mL) at room temperature was added NaSEt (13.3 g, 158.3 mmol) in one portion. The mixture was stirred for 18 hrs. It was then diluted with water (500 mL) and extracted with ethyl acetate (200 mL×3). The combined organic layers were washed by brine and dried over $Na_2SO_4$, filtered and concentrated under reduced pressure. The residue was purified by column chromatography (PE:EA=20:1~10:1) to afford the title compound as light yellow oil (21 g yield: 91.3%). $^1$H NMR (CDCl$_3$, 400 MHz) δ 8.49 (dd, J$_1$=2.0 Hz, J$_2$=0.4 Hz, 1H), 7.59 (dd, J$_1$=8.8 Hz, J$_2$=2.4 Hz, 1H), 7.08 (dd, J$_1$=8.4 Hz, J$_2$=0.8 Hz, 1H), 3.16 (q, J=7.2 Hz, 2H), 1.38 (t, 3H). LCMS: 217.8 (M+1)$^+$; 219.8

Step 2: 5-bromo-2-ethylsulfonylpyridine

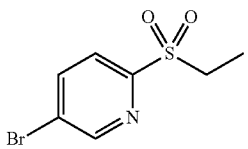

To a solution of the title compound form Step 1 (21 g, 96.3 mmol) in DCM (200 mL) was added m-CPBA (58.2 g, 289 mmol, 85% purity) slowly at 0° C. and then stirred at 20° C. for 3 hrs. The reaction mixture was quenched with sat. aq. $Na_2SO_3$ (200 mL) and then extracted with DCM (200 mL×2). The combined organic layers were washed with sat. aq. NaHCO$_3$ (200 mL), water (200 mL), and brine (200 mL), dried over $Na_2SO_4$, filtered and concentrated under reduced pressure to give 22 g of crude (~90% purity) title compound as a white solid that was used in the next step without further purification. $^1$H NMR (CDCl$_3$, 400 MHz) δ 8.82 (d, J=2.0 Hz, 1H), 8.13 (dd, J$_1$=8.4 Hz, J$_2$=2.0 Hz, 1H), 8.01 (d, J=8.0 Hz), 3.43 (q, J=7.2 Hz, 2H), 1.33 (t, J=7.2 Hz, 3H). LCMS: 249.8 (M+1)$^+$; 251.8

Step 3: 2-ethylsulfonyl-5-methoxypyridine

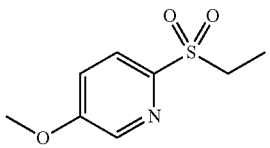

To a solution of the title compound form Step 2 (21 g, 84 mmol) in MeOH (150 mL) was added MeONa (11.3 g, 210 mmol). The mixture was refluxed for 5 hour. It was then cooled to room temperature and concentrated under reduced pressure. The residue was triturated with isopropyl ether and filtered. The filtrate was concentrated under reduced pressure to give the title compound (4.5 g, yield, 23% two steps.) as yellow oil. $^1$H NMR (CDCl$_3$, 400 MHz) δ 8.42 (d, J=2.8 Hz, 1H), 8.07 (d, J=8.4 Hz 1H), 7.37 (dd, J$_1$=8.8 Hz, J$_2$=2.8 Hz, 1H), 3.97 (s, 1H), 3.38 (q, J=7.2 Hz, 2H), 1.30 (t, J=7.2 Hz, 3H).

Step 4: 6-ethylsulfonylpyridin-3-ol

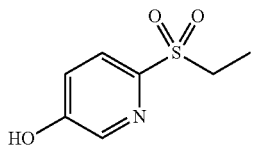

The title compound form Step 3 (4.5 g, 22.4 mmol) and pyridinium hydrochloride (26 g, 224 mmol) was heated to 160° C. for 4 hours. It was cooled to room temperature, diluted with water (100 mL) and extracted with EtOAc (100 mL×3). The combined organic layers were washed with brine (200 mL), dried over $Na_2SO_4$ and concentrated. The residue was purified by column chromatography to afford the title compound (3 g, 72%) as a yellow solid. $^1$H NMR (DMSO-d6, 400 MHz) δ: 8.87 (s, 1H), 8.86 (s, 1H), 8.45 (d, J=8.4 Hz, 1H), 7.93 (dd, J$_1$=8.8 Hz, J$_2$=2.4 Hz, 1H), 3.82 (q, J=7.2 Hz, 2H), 1.72 (t, J=7.2 Hz, 3H). LCMS: 187.9 (M+1)$^+$ Step 5: 6-ethylsulfonyl-2-iodopyridin-3-ol and 6-ethylsulfonyl-4-iodopyridin-3-ol

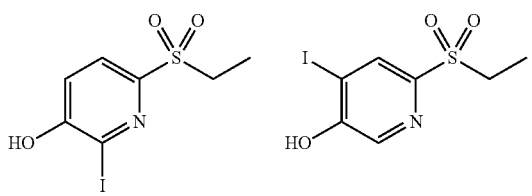

To a solution of the title compound from Step 4 (3 g, 16 mmol) in a mixture of THF (20 mL) and H$_2$O (20 mL) was added KI (662 mg, 4 mmol) and iodine (6.1 g, 24 mmol). The reaction was stirred at rt for 1 hour and then heated to 60° C. for another 17 hours. The reaction mixture was then cooled to room temperature and concentrated under reduced pressure to remove the THF. The mixture was diluted with water (100 mL) and extracted with DCM (10 mL×3). The combined organic layers were washed with brine, dried over $Na_2SO_4$, filtered and concentrated. The residue was purified by prep-HPLC to afford 6-ethylsulfonyl-2-iodopyridin-3-ol and 6-ethylsulfonyl-4-iodopyridin-3-ol as white solids. 6-ethylsulfonyl-2-iodopyridin-3-ol: $^1$H NMR (DMSO-d6, 400 MHz) δ 7.85 (d, J=8.4 Hz, 1H), 7.31 (d, J=8.4 Hz, 1H), 3.30 (q, J=7.2 Hz, 2H), 1.11 (t, J=7.2 Hz 3H). LCMS: 313.8 (M+1)⁺; 6-ethylsulfonyl-4-iodopyridin-3-ol: ¹H NMR (DMSO-d6, 400 MHz) δ 8.23 (s, 1H), 8.18 (s, 1H), 3.31 (q, J=7.2 Hz, 2H, overlapped with solvent peak), 1.10 (t, J=7.2 Hz 3H). LCMS: 313.8 (M+1)⁺

Step 6: 3-(cyclopropylmethoxy)-6-ethylsulfonyl-2-iodopyridine

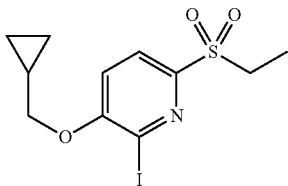 [SMILES: CCS(=O)(=O)c1ccc(OCC2CC2)c(I)n1]

The title compound was prepared in a manner similar to Example 199 Step 3, by substituting 6-ethylsulfonyl-2-iodopyridin-3-ol for 2-iodo-6-methylsulfonylpyridin-3-ol. ¹H NMR (CDCl₃, 400 MHz) δ 7.98 (d, J=8.4 Hz, 1H), 7.06 (d, J=8.4 Hz 1H), 4.02 (d, J=6.8 Hz 2H), 3.40 (q, J=7.2 Hz, 2H), 1.38-1.26 (m, 4H), 0.77-0.73 (m, 2H), 0.49-0.46 (m, 2H). LCMS: 367.8 (M+1)⁺

Step 7: 4-[3-(cyclopropylmethoxy)-6-ethylsulfonylpyridin-2-yl]-2-methylisoquinolin-1-one

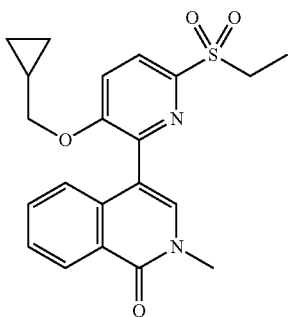 [SMILES: CCS(=O)(=O)c1ccc(OCC2CC2)c(-c2cn(C)c(=O)c3ccccc23)n1]

To a solution of the title compound from Step 6 (45 mg, 0.12 mmol) and 2-methyl-4-(4,4,5,5-tetramethyl-1,3,2-dioxaborolan-2-yl)isoquinolin-1-one (50 mg, 0.16 mmol) in dioxane (2.5 mL) and H₂O (0.5 mL) was added Pd(dppf)Cl₂ (9 mg, 0.013 mmol) and K₃PO₄ (86 mg, 0.4 mmol) in one portion at r.t. under N₂. The mixture was stirred for 12 hours at 90° C. under N₂. Water (15 mL) was added and the mixture was extracted with DCM (30 mL×3). The combined organic phases were dried over Na₂SO₄, filtered, concentrated under reduced pressure. The residue was purified by prep-HPLC to give the title compound (16 mg, yield: 32%) as a white solid. ¹H NMR (CDCl₃, 400 MHz) δ 8.52 (d, J=7.6 Hz, 1H), 8.11 (d, J=8.8 Hz 1H), 7.61-7.56 (m, 1H), 7.53-7.49 (m, 1H), 7.42 (d, J=8.8 Hz 1H), 7.38 (s, 1H), 7.34 (d, J=7.6 Hz 1H), 3.92 (d, J=7.2 Hz 2H), 3.68 (s, 3H), 3.41 (q, J=6.8 Hz, 2H), 1.33 (t, 3H), 1.08-1.02 (m, 1H), 0.54-0.48 (m, 2H), 0.22-0.21 (m, 2H). LCMS: 399.1 (M+1)⁺

Example 207

4-[5-(cyclopropylmethoxy)-2-ethylsulfonylpyridin-4-yl]-2-methylisoquinolin-1-one Step 1: 5-(cyclopropylmethoxy)-2-ethylsulfonyl-4-iodopyridine

The title compound was prepared in a manner similar to Example 199 Step 3, by substituting 6-ethylsulfonyl-4-iodopyridin-3-ol for 2-iodo-6-methylsulfonylpyridin-3-ol. ¹H NMR (CDCl₃, 400 MHz) δ 8.48 (s, 1H), 8.11 (s, 1H), 4.12 (d, J=6.8 Hz 2H), 3.37 (q, J=7.6 Hz, 2H), 1.39-1.27 (m, 4H), 0.76-0.73 (m, 2H), 0.48-0.46 (m, 2H). LCMS: 367.8 (M+1)⁺

Step 2: 4-[5-(cyclopropylmethoxy)-2-ethylsulfonylpyridin-4-yl]-2-methylisoquinolin-1-one

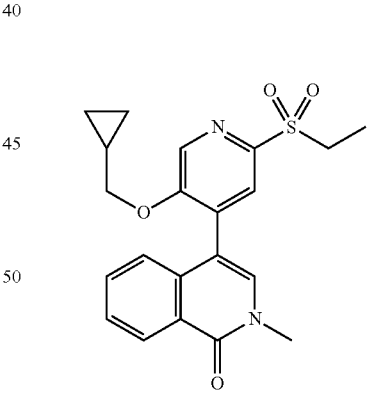

The title compound was prepared in a manner similar to Example 206 Step 7, by substituting 6-ethylsulfonyl-4-iodopyridin-3-ol for 3-(cyclopropylmethoxy)-6-ethylsulfonyl-2-iodopyridine. ¹H NMR (CDCl₃, 400 MHz) δ8.54-8.52 (m, 1H), 8.45 (s, 1H), 8.05 (s, 1H), 7.63-7.58 (m, 1H), 7.56-7.52 (m, 1H), 7.16 (d, J=8.8 Hz 1H), 4.01 (d, J=7.2 Hz 2H), 3.68 (s, 3H), 3.44 (q, J=7.2 Hz, 2H), 1.36 (t, 3H), 1.09-1.05 (m, 1H), 0.50-0.48 (m, 2H), 0.19-0.18 (m, 2H). LCMS: 399.1 (M+1)⁺

Example 208

4-[5-(2-hydroxyethylsulfonyl)-2-methoxyphenyl]-2-methyl-6-(1-methylpyrazol-4-yl)isoquinolin-1-one Step 1: 2-(4-methoxyphenyl)sulfanylethyl acetate

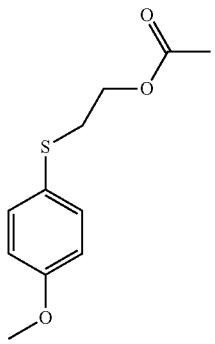

4-methoxybenzene-1-thiol (15.7 g, 0.11 mol), 2-bromoethyl acetate (18.8 g, 0.11 mol), and K₂CO₃ (46.6 g, 0.34 mol) in acetone (200 mL) were stirred at room temperature for 12 h. Then the mixture was filtered. After CH₂Cl₂ extractive work up and silica gel chromatography chromatography (PE:EA=1:0~10:1) the title compound (21.1 g, 83.3%) was obtained as a colorless oil. $^1$H NMR: (CDCl₃, 400 MHz) δ 7.40 (dd, J1=6.8 Hz, J₂=2.0 Hz, 2H), 6.86 (dd, J₁=6.8 Hz, J₂=2.0 Hz, 2H), 4.18 (t, J=7.2 Hz, 2H), 3.80 (s, 3H), 3.02 (t, J=7.2 Hz, 2H), 2.03 (s, 3H). LCMS: 139.0 (M−87)$^+$ Step 2: 2-(4-methoxyphenyl)sulfonylethyl acetate

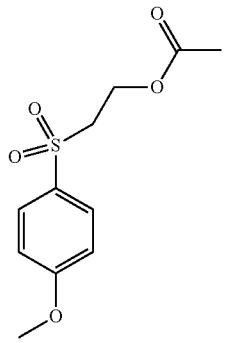 [SMILES: COc1ccc(S(=O)(=O)CCOC(C)=O)cc1]

m-CPBA (80.3 g, 467 mmol) was added to the title compound of step 1 (21.1 g, 93.4 mmol) in CH₂Cl₂ (500 mL). After stirring at r.t. for 12 h, the mixture was subjected to CH₂Cl₂ extractive work up & silica gel chromatography (PE:EA=1:0~1:1) to give the title compound (20.0 g, 83.3%) as a colorless oil. $^1$H NMR: (CDCl₃, 400 MHz) δ 7.85 (dd, J₁=6.8 Hz, J₂=2.0 Hz, 2H), 7.04 (dd, J₁=6.8 Hz, J₂=2.0 Hz, 2H), 4.39 (t, J=6.0 Hz, 2H), 3.90 (s, 3H), 3.43 (t, J=6.0 Hz, 2H), 1.89 (s, 3H). LCMS: 280.9 (M+Na)$^+$ Step 3: 2-(3-bromo-4-methoxyphenyl)sulfonylethanol

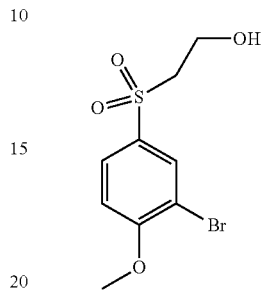

Br₂ (25 g, 155.0 mmol) was added dropwise over 30 min to the title compound of step 2 (8.0 g, 31.0 mmol) in acetic acid (100 mL) at 0° C. The mixture was heated at 50° C. for 12 h. Aqueous Na₂SO₃ (200 mL) was added and the pH was adjusted to 8 with sat. aq. NaHCO₃. The mixture was subjected to EA extractive work up and silica gel chromatography (PE:EA=1:0~1:1) to give the title compound (2.7 g, 27.3%) as a white solid. $^1$H NMR (CDCl₃, 400 MHz) δ 8.11 (d, J=2.4 Hz, 1H), 7.87 (dd, J₁=8.8 Hz, J₂=2.4 Hz, 1H), 7.04 (d, J=2.4 Hz, 1H), 4.05-4.00 (m, 5H), 3.34-3.67 (m, 3H). LCMS: 316.9, 318.9 (M+Na)$^+$ Step 4: 2-[2-(3-bromo-4-methoxyphenyl)sulfonylethoxy]oxane

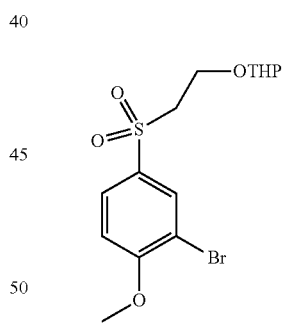

To the title compound of step 3 (1.0 g, 3.4 mmol) in CH₂Cl₂ (10 mL) was added 3,4-dihydro-2H-pyran (1.4 g, 17.0 mmol) followed by pyridinium p-toluensulfonate (64.6 mg, 0.34 mmol). After stirring at r.t. 12 h, the mixture was subjected to CH₂Cl₂ extractive work up & silica gel chromatography (PE:EA=1:0~5:1) to give the title compound (1.1 g, 85.6%) as a yellow oil. $^1$H NMR (CDCl₃, 400 MHz) δ 8.11 (d, J=2.4 Hz, 1H), 7.86 (dd, J₁=8.8 Hz, J₂=2.4 Hz, 1H), 7.00 (d, J=8.8 Hz, 1H), 4.51 (dd, J₁=4.0 Hz, J₂=2.4 Hz, 1H), 4.09-4.03 (m, 1H), 3.98 (s, 3H), 3.84-3.79 (m, 1H), 3.79-3.74 (m, 1H), 3.50-3.46 (m, 1H), 3.45-3.42 (m, 2H), 1.58-1.37 (m, 6H). LCMS: 401.0, 403.0 (M+Na)$^+$.

Step 5: 2-[2-methoxy-5-[2-(oxan-2-yloxy)ethylsulfonyl]phenyl]-4,4,5,5-tetramethyl-1,3,2-dioxaborolane

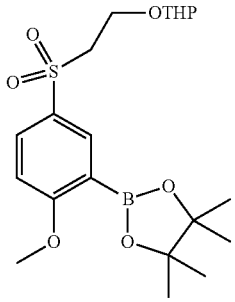

The title compound of step 4 (700 mg, 1.8 mmol), 4,4,5,5-tetramethyl-2-(tetramethyl-1,3,2-dioxaborolan-2-yl)-1,3,2-dioxaborolane (938 mg, 3.6 mmol) Pd(dppf)Cl$_2$ (263 mg, 0.36 mmol) and AcOK (1.05 g, 10.8 mmol) in 1,4-dioxane (7 mL) was stirred at 70° C. for 12 h. After silica gel column chromatography (PE:EA=1:0~1:1) the title compound (300 mg, 39.2%) was obtained as a yellow oil. $^1$H NMR (CDCl$_3$, 400 MHz) δ 8.20 (d, J=2.4 Hz, 1H), 7.94 (dd, J$_1$=8.8 Hz, J$_2$=2.8 Hz, 1H), 6.95 (d, J=8.8 Hz, 1H), 4.52 (t, J=4.0 Hz, 1H), 4.08-4.01 (m, 2H), 3.91 (s, 3H), 3.82-3.74 (m, 2H), 3.43 (t, J=2.4 Hz, 2H), 1.58-1.42 (m, 6H), 1.35 (s, 12H). LCMS: 343.0 (M+H-THP)$^+$.

Step 6: 4-[2-methoxy-5-[2-(oxan-2-yloxy)ethylsulfonyl]phenyl]-2-methyl-6-(1-methylpyrazol-4-yl)isoquinolin-1-one

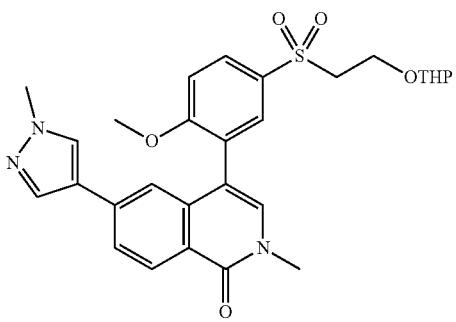

The title compound of step 5 (325 mg, 0.76 mmol), the title compound of Example 41, step 2 (201 mg, 0.64 mmol), Pd(dppf)Cl$_2$ (66 mg, 0.08 mmol) and AcOK (125 mg, 1.28 mmol) in 1,4-dioxane (6 mL) were heated at 70° C. for 12 h. After silica gel column chromatography (PE:EA=5:1-0:1) the title compound (80 mg, 23.6%) was obtained as a gray solid. $^1$H NMR: (CDCl$_3$, 400 MHz) δ 8.48 (d, J=8.4 Hz, 1H), 8.03 (dd, J$_1$=8.8 Hz, J$_2$=2.4 Hz, 1H), 7.88 (d, J=2.4 Hz, 1H), 7.58-7.69 (m, 2H), 7.14-7.18 (m, 2H), 7.06 (s, 1H), 4.50 (t, J=4.4 Hz, 2H), 4.06-4.15 (m, 1H), 3.93 (s, 3H), 3.84-3.90 (m, 1H), 3.84 (s, 3H), 3.71-3.80 (m, 2H), 3.65 (s, 3H), 3.49 (t, J=5.6 Hz, 2H), 3.41-3.47 (m, 1H), 1.25-1.67 (m, 6H). LCMS: 538.2 (M+H)$^+$; 454.1 (M+H-THP)$^+$.

Step 7: 4-[5-(2-hydroxyethylsulfonyl)-2-methoxyphenyl]-2-methyl-6-(1-methylpyrazol-4-yl)isoquinolin-1-one

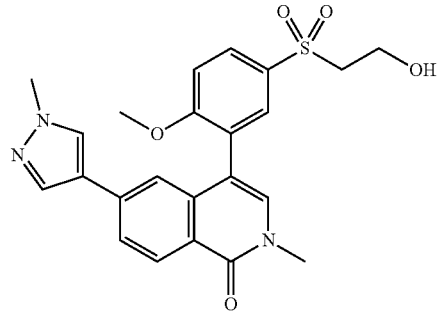 [SMILES: COc1ccc(S(=O)(=O)CCO)cc1-c1cn(C)c(=O)c2ccc(-c3cnn(C)c3)cc12]

The title compound of step 6 (80 mg, 0.15 mmol) and pyridinium p-toluensulfonate (59 mg, 0.31 mmol) in DCM (2 mL) were stirred at room temperature for 5 h. After purification by prep-TLC (DCM: MeOH=10:1), the title compound (16.47 mg, 24.4%) was obtained as an off-white solid. $^1$H NMR: (CDCl$_3$, 400 MHz) δ8.49 (d, J=8.4 Hz, 1H), 8.05 (dd, J$_1$=8.8 Hz, J$_2$=2.4 Hz, 1H), 7.88 (d, J=2.4 Hz, 1H), 7.68 (s, 1H), 7.59-7.62 (m, 2H), 7.20 (d, J=8.8 Hz, 1H), 7.12 (d, J=1.2 Hz, 1H), 7.07 (s, 1H), 4.03-4.11 (m, 2H), 3.94 (s, 3H), 3.86 (s, 3H), 3.66 (s, 3H), 4.16 (t, J=5.2 Hz, 2H), 2.72 (t, J=6.4 Hz, 1H). LCMS: 454.1 (M+H)$^+$

Example 209

N-[4-(cyclopropylmethoxy)-2-fluoro-5-[2-methyl-6-(1-methylpyrazol-4-yl)-1-oxoisoquinolin-4-yl]phenyl]ethanesulfonamide

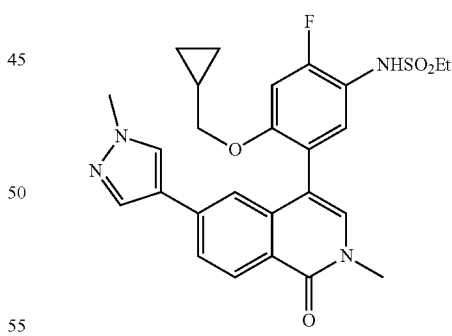

The title compound was prepared in 4 steps in a similar manner as Example 86 except that the alkoxide of cyclopropylmethanol was substituted for sodium methoxide in step 1. $^1$H NMR (DMSO-d6, 400 MHz) δ 9.46 (s, 1H), 8.26 (d, J=8.4 Hz, 1H), 8.17 (s, 1H), 7.84 (s, 1H), 7.34 (d, J=8.0 Hz, 1H), 7.42 (s, 1H), 7.27-7.25 (m, 1H), 7.16 (d, J=12.4 Hz, 1H), 3.97-3.96 (m, 2H, overlapped with solvent peak), 3.85 (s, 3H), 3.54 (s, 3H), 3.13-3.07 (m, 2H), 1.30-1.26 (m, 2H), 0.91-0.90 (m, 1H), 0.27-0.22 (m, 2H), 0.04-0.09 (m, 2H). LCMS: 511.1 (M+1)$^+$

Example 210

4-(5-ethylsulfonyl-2-methoxyphenyl)-2-methyl-6-(1H-pyrazol-4-yl)isoquinolin-1-one

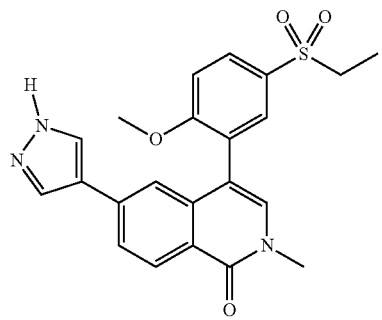 [SMILES: CCS(=O)(=O)c1ccc(OC)c(-c2cn(C)c(=O)c3ccc(-c4cn[nH]c4)cc23)c1]

The title compound was prepared in a similar manner to Example 79 using 4-(tetramethyl-1,3,2-dioxaborolan-2-yl)-1H-pyrazole instead of 1-methyl-4-(tetramethyl-1,3,2-dioxaborolan-2-yl)-1H-pyrazole. $^1$H NMR (DMSO-d6, 400 MHz) δ 8.26 (d, J=8.4 Hz, 1H), 8.02 (s, 2H), 7.97-8.00 (m, 1H), 7.75-7.79 (m, 2H), 7.50 (s, 1H), 7.42 (d, J=8.8 Hz, 1H), 7.16 (d, J=1.2 Hz, 1H), 3.82 (s, 3H), 3.54 (s, 3H), 3.31 (q, J=7.2, 2H), 1.13 (t, J=7.2 Hz, 3H). LCMS: 424.0 (M+1)$^+$

Example 211

4-(2-ethoxy-5-methylsulfonylphenyl)-2-methyl-6-(1-methylpyrazol-4-yl)isoquinolin-1-one

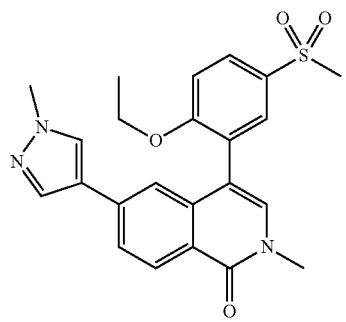 [SMILES: CCOc1ccc(S(C)(=O)=O)cc1-c1cn(C)c(=O)c2ccc(-c3cnn(C)c3)cc12]

2-(2-ethoxy-5-methanesulfonylphenyl)-4,4,5,5-tetramethyl-1,3,2-dioxaborolane was prepared in a similar manner to Example 90, step 1 and coupled to the title compound of Example 41, step 2 in a manner similar to Example 90, step 2 to give the title compound. $^1$H NMR (CDCl$_3$, 400 MHz) δ 8.48 (d, J=8.4 Hz, 1H), 8.06-8.02 (m, 1H), 7.89 (d, J=2.8 Hz, 1H), 7.68 (s, 1H), 7.62 (s, 1H), 7.61 (d, J=1.6 Hz, 1H), 7.18 (d, J=1.2 Hz, 1H), 7.14 (d, J=8.8 Hz, 1H), 7.08 (s, 1H), 4.12 (q, J=7.2 Hz, 2H), 3.94 (s, 3H), 3.66 (s, 3H), 3.12 (s, 3H), 1.17 (t, J=7.2 Hz, 3H). LCMS: 438.1 (M+1)$^+$

Example 212

2-methyl-6-(1-methylpyrazol-4-yl)-4-(5-methylsulfonyl-2-propoxyphenyl)isoquinolin-1-one

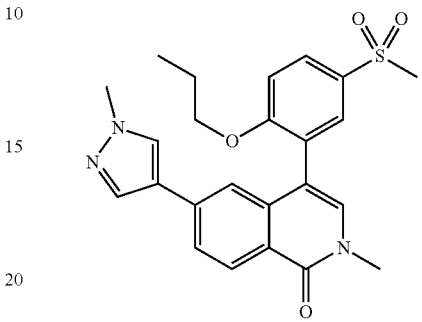

2-(5-methanesulfonyl-2-propoxyphenyl)-4,4,5,5-tetramethyl-1,3,2-dioxaborolane was prepared in a similar manner to Example 90, step 1 and coupled to the title compound of Example 41, step 2 in a manner similar to Example 90, step 2 to give the title compound. $^1$H NMR (CDCl$_3$, 400 MHz) δ 8.49 (d, J=8.4 Hz, 1H), 8.02 (s, J=6.8 Hz, 1H), 7.90 (d, J=2.4 Hz, 1H), 7.68 (s, 1H), 7.61 (s, 1H), 7.60 (d, J=6.8 Hz, 1H), 7.18 (s, 1H), 7.15 (d, J=8.8 Hz, 1H), 7.08 (s, 1H), 4.00 (m, 2H) 3.93 (s, 3H), 3.66 (s, 3H), 3.12 (s, 3H), 1.56 (m, 2H), 0.65 (t, J=7.2 Hz, 3H). LCMS: 452.0 (M+1)$^+$

Example 213

N-[2-[2-methyl-6-(1-methylpyrazol-4-yl)-1-oxoisoquinolin-4-yl]pyridin-4-yl]ethanesulfonamide

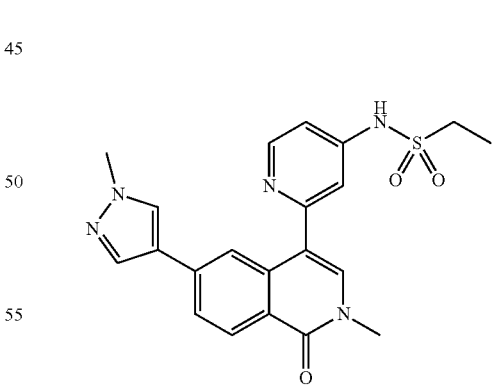

The title compound was prepared after 2-chloropyridin-4-amine was sulfonylated with ethanesulfonyl chloride and the resulting product was coupled to the title compound of Example 46, step 2. $^1$H NMR (CDCl$_3$, 400 MHz) δ 10.65 (brs, 1H), 8.56 (s, 1H), 8.29 (d, J=8.4 Hz, 1H), 8.22 (s, 1H), 8.01-7.73 (m, 4H), 7.37 (s, 1H), 7.18 (s, 1H), 3.87 (s, 3H), 3.59 (s, 3H), 1.25 (t, J=7.2 Hz, 3H). LCMS: 424.0 (M+1)$^+$

Example 214

[4-(cyclopropylmethoxy)-3-(2-methyl-1-oxoisoquinolin-4-yl)phenyl]sulfamate

Step 1:
[3-bromo-4-(cyclopropylmethoxy)phenyl]sulfamate

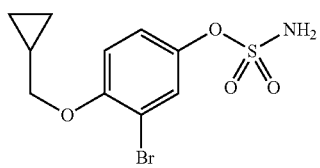 [SMILES: NS(=O)(=O)Oc1ccc(OCC2CC2)c(Br)c1]

3-bromo-4-(cyclopropylmethoxy)phenol (970 mg, 4.0 mmol) and sulfamoyl chloride (1.95 g, 16.0 mmol) in DMA (15 mL) were stirred at room temperature for 5 h. Extractive work up from EA and water gave the title compound (1.0 g, yield: 78.0%) which was carried on without purification. $^1$H NMR (CDCl$_3$, 400 MHz) δ 7.28 (d, J=2.8 Hz, 1H), 7.24 (dd, J1=8.8 Hz, J$_2$=2.8 Hz, 1H), 6.88 (d, J=8.8 Hz, 1H), 5.07 (s, 2H), 3.89 (d, J=6.8 Hz, 2H), 1.35-1.25 (m, 1H), 0.70-0.63 (m, 2H), 0.43-0.36 (m, 2H). LCMS: 322.0 (M+1)$^+$.

Step 2: [4-(cyclopropylmethoxy)-3-(2-methyl-1-oxoisoquinolin-4-yl)phenyl]sulfamate

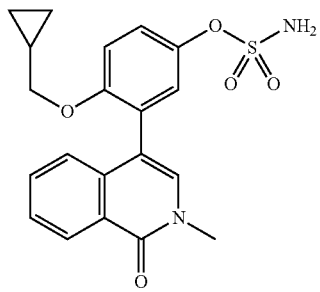 [SMILES: Cn1cc(-c2cc(OS(N)(=O)=O)ccc2OCC2CC2)c2ccccc2c1=O]

The title compound of step 1 (300 mg, 0.935 mmol), the title compound of Example 89, step 1 (293 mg, 1.028 mmol), K$_3$PO$_4$ (595 mg, 2.805 mmol) and Pd(dppf)Cl$_2$ (15 mg) in dioxane (5 mL) and H$_2$O (1 mL) were heated at 70° C. for 18 h under N$_2$ whereupon it was discovered that the sulfamoyl group had been cleaved to the phenol. HPLC purification gave the phenol (59 mg, 0.184 mmol) which was again treated with sulfamoyl chloride (100 mg, 0.87 mmol) in DMA (3 mL) in a manner similar to step 1. Preparative HPLC gave the title compound (64.21 mg, yield: 87.02%) as grey solid. $^1$H NMR (CDCl$_3$, 400 MHz) δ 8.48 (d, J=8.0 Hz, 1H), 7.56 (t, J=7.6 Hz, 1H), 7.49 (d, J=7.6 Hz, 1H), 7.35 (dd, J$_1$=9.2 Hz, J$_2$=2.4 Hz, 1H), 7.30-7.27 (m, 1H), 7.26-7.22 (m, 1H), 7.04 (s, 1H), 6.98 (d, J=9.2 Hz, 1H), 5.14 (s, 2H), 3.82-3.73 (m, 2H), 3.62 (s, 3H), 1.03-1.90 (m, 1H), 0.45-0.32 (m, 2H), 0.13-0.03 (m, 2H). LCMS: 401.0 (M+1)$^+$

Example 215

[4-(cyclopropylmethoxy)-3-(1,5-dimethyl-6-oxopyridin-3-yl)phenyl]sulfamate

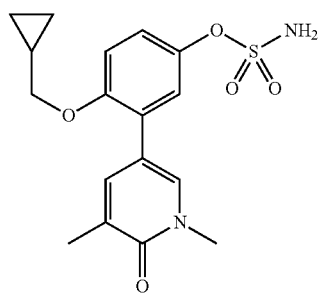 [SMILES: Cc1cc(-c2cc(OS(N)(=O)=O)ccc2OCC2CC2)cn(C)c1=O]

The title compound was prepared in a similar manner to Example 214, step 2 except that 1,3-dimethyl-5-(4,4,5,5-tetramethyl-1,3,2-dioxaborolan-2-yl)-2(1H)-pyridinone was substituted for the title compound of Example 89, step 1. $^1$H NMR (CDCl$_3$, 400 MHz) δ 7.54 (d, J=2.0 Hz, 1H), 7.50 (s, 1H), 7.23-7.18 (m, 2H), 6.92-6.87 (m, 1H), 5.20 (s, 2H), 3.84 (d, J=6.8 Hz, 2H), 3.61 (s, 3H), 2.20 (s, 3H), 1.25-1.17 (m, 1H), 0.66-0.59 (m, 1H), 0.36-0.29 (m, 1H). LCMS: 365.1 (M+1)$^+$

Example 216

4-(2-ethoxy-5-methylsulfonylphenyl)-2-methyl-5,6,7,8-tetrahydroisoquinolin-1-one

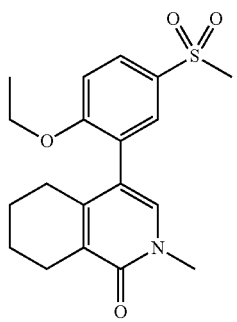 [SMILES: CCOc1ccc(S(C)(=O)=O)cc1-c1cn(C)c(=O)c2c1CCCC2]

2-bromo-1-ethoxy-4-methanesulfonylbenzene was prepared in a similar manner as Example 46, step 1 except that iodoethane was substituted for (chloromethyl)cyclopropane. The title compound of Example 163, step 3 and 2-bromo-1-ethoxy-4-methanesulfonylbenzene were reacted in a similar manner as in Example 89, step 2 to give the title compound. $^1$H NMR (CDCl$_3$, 400 MHz): δ 7.92 (dd, J1=8.8 Hz, J$_2$=2.0 Hz, 1H), 7.68 (d, J=2.0 Hz, 1H), 7.03 (d, J=8.8 Hz, 1H), 6.69 (d, J=8.8 Hz, 1H), 4.20 (q, J=7.2 Hz, 2H), 3.59 (s, 3H), 3.08 (s, 3H), 2.70-2.60 (m, 2H), 2.33-2.18 (m, 2H), 1.65-1.61 (m, 4H), 1.45-1.02 (t, J=7.2 Hz, 3H). LCMS: 362.0 (M+H)$^+$

Example 217

4-[2-(cyclopropylmethoxy)-5-methylsulfonylphenyl]-2-methyl-5,6,7,8-tetrahydroisoquinolin-1-one

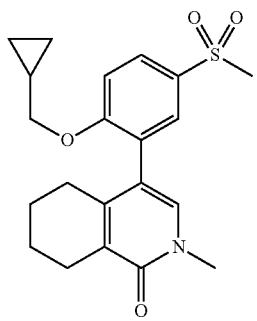 [SMILES: Cn1cc(-c2cc(S(C)(=O)=O)ccc2OCC2CC2)c2c(c1=O)CCCC2]

The title compound of Example 163, step 3 and 2-bromo-1-(cyclopropylmethoxy)-4-methylsulfonylbenzene were reacted in a similar manner as in Example 89, step 2 to give the title compound. $^1$H NMR (CDCl$_3$, 400 MHz): δ 7.92 (dd, J$_1$=8.4 Hz, J$_2$=2.0 Hz, 1H), 7.70 (d, J=2.0 Hz, 1H), 7.06 (s, 1H), 7.02 (d, J=8.4 Hz, 1H), 3.92-3.87 (m, 2H), 3.62 (s, 3H), 3.08 (s, 3H), 2.70-2.60 (m, 2H), 2.40-2.30 (m, 2H), 1.77-1.64 (m, 4H), 1.21-1.17 (m, 1H), 0.63-0.61 (m, 2H), 0.29-0.27 (m, 2H). LCMS: 388.1 (M+H)$^+$

Example 218

N-[4-(cyclopropylmethoxy)-2-fluoro-5-(2-methyl-1-oxo-5,6,7,8-tetrahydroisoquinolin-4-yl)phenyl]methanesulfonamide

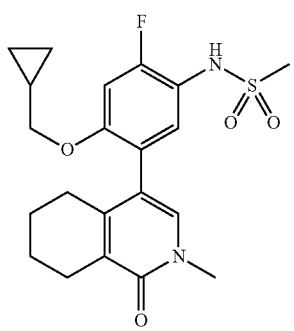 [SMILES: Cn1cc(-c2cc(NS(C)(=O)=O)c(F)cc2OCC2CC2)c2c(c1=O)CCCC2]

N-[5-bromo-4-(cyclopropylmethoxy)-2-fluorophenyl]methanesulfonamide was prepared in 3 steps in a similar manner as Example 86 except that the alkoxide of cyclopropylmethanol was substituted for sodium methoxide in step 1 and methanesulfonylchloride was substituted for ethanesulfonylchloride in step 3. The title compound of Example 163, step 3 and N-[5-bromo-4-(cyclopropylmethoxy)-2-fluorophenyl]methanesulfonamide were reacted in a similar manner as in Example 89, step 2 to give the title compound. $^1$H NMR (CDCl$_3$, 400 MHz): δ 7.29 (d, J=9.2 Hz, 1H), 6.96 (s, 1H), 6.70 (d, J=12.0 Hz, 1H), 6.21 (s, 1H), 3.76-3.75 (m, 2H), 3.56 (s, 3H), 3.02 (s, 3H), 2.70-2.60 (m, 2H), 2.36-2.17 (m, 2H), 1.80-1.70 (m, 2H), 1.69-1.64 (m, 2H), 1.20-1.10 (m, 1H), 0.60-0.50 (m, 2H), 0.27-0.25 (m, 2H). LCMS: 421.1 (M+H)$^+$

Example 219

4-[2-(cyclopropylmethoxy)-5-ethylsulfonylphenyl]-2-methyl-5,6,7,8-tetrahydroisoquinolin-1-one

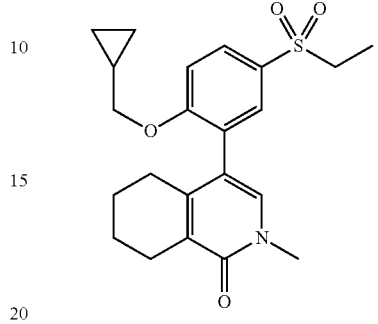

2-bromo-1-(cyclopropylmethoxy)-4-(ethanesulfonyl) benzene was prepared in a similar manner as Example 79, step 3 except that the alkoxide of cyclopropylmethanol was substituted for sodium methoxide. The title compound of Example 163, step 3 and 2-bromo-1-(cyclopropylmethoxy)-4-(ethanesulfonyl)benzene were reacted in a similar manner as in Example 89, step 2 to give the title compound. $^1$H NMR (DMSO-d6, 400 MHz): δ 7.83 (dd, J$_1$=8.8 Hz, J$_2$=2.4 Hz, 1H), 7.56 (d, J=2.4 Hz, 1H), 7.43 (s, 1H), 7.65 (d, J=8.8 Hz, 1H), 4.02-3.90 (m, 2H), 3.43 (s, 3H), 3.29-3.23 (m, 2H), 2.49-2.44 (m, 4H), 1.61-1.50 (m, 4H), 1.15-1.08 (m, 5H), 0.53-0.51 (m, 2H), 0.29-0.27 (m, 2H). LCMS: 402.0 (M+H)$^+$

Example 220

N-[2-(2-methyl-1-oxoisoquinolin-4-yl)-4-methylsulfonylphenyl]cyclopropanecarboxamide

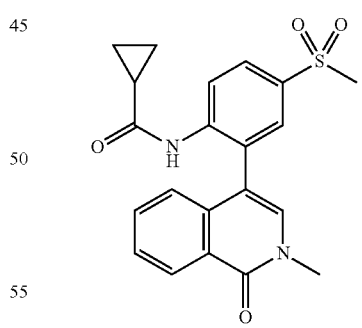

2-bromo-4-methanesulfonylaniline was coupled to the title compound of Example 89, step 1 in a manner similar to Example 89, step 2. The resulting product was reacted with cyclopropanecarbonyl chloride using diisopropylethylamine in THF to prepare the title compound. $^1$H NMR (CDCl$_3$, 400 MHz) δ 9.38 (s, 1H), 8.34 (d, J=8.0 Hz, 1H), 8.23 (d, J=8.8 Hz, 1H), 7.96 (d, J=8.8 Hz, 1H), 7.83 (s, 1H), 7.53-7.64 (m, 3H), 6.94 (d, J=8.0 Hz, 1H), 3.59 (s, 3H), 3.25 (m, 3H), 1.64 (brs, 1H), 0.52-0.75 (m, 4H). LCMS: 397.0 (M+1)$^+$

Example 221

N-[2-(2-methyl-1-oxoisoquinolin-4-yl)-4-methylsulfonylphenyl]propanamide

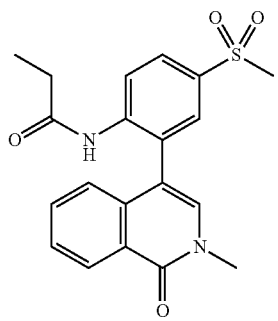 [SMILES: CCC(=O)Nc1ccc(S(C)(=O)=O)cc1-c1cn(C)c(=O)c2ccccc12]

The title compound was prepared in the same manner as Example 220 except that propanoyl chloride was substituted for cyclopropanecarbonyl chloride. $^1$H NMR (CDCl$_3$, 400 MHz) δ 8.70 (d, J=8.8 Hz, 1H), 8.57 (d, J=6.4 Hz, 1H), 8.04 (dd, J=2.0, 8.8 Hz, 1H), 7.88 (d, J=2.0 Hz, 1H), 7.55-7.65 (m, 2H), 7.19 (s, 1H), 7.01-7.20 (m, 2H), 3.67 (s, 3H), 3.11 (s, 3H), 2.00-2.21 (m, 2H), 0.93 (t, J=7.2 Hz, 3H). LCMS: 385.0 (M+1)$^+$

Example 222

N-[2-(2-methyl-1-oxoisoquinolin-4-yl)-4-methylsulfonylphenyl]acetamide

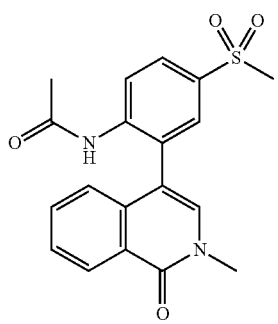 [SMILES: CC(=O)Nc1ccc(S(C)(=O)=O)cc1-c1cn(C)c(=O)c2ccccc12]

The title compound was prepared in the same manner as Example 220 except that acetyl chloride was substituted for cyclopropanecarbonyl chloride. $^1$H NMR (CDCl$_3$, 400 MHz) δ 8.67 (d, J=8.8 Hz, 1H), 8.51 (d, J=7.6 Hz, 1H), 8.03 (dd, J=2.0, 6.8 Hz, 1H), 7.86 (d, J=2.0 Hz, 1H), 7.62-7.67 (m, 1H), 7.57-7.62 (m, 1H), 7.36 (s, 1H), 7.16 (s, 1H), 7.07-7.10 (m, 1H), 3.54 (s, 3H), 3.10 (s, 3H), 1.96 (s, 3H). LCMS: 371.0 (M+1)$^+$

Example 223

4-[2-(cyclopropylmethylamino)-5-methylsulfonylphenyl]-2-methyl-5,6,7,8-tetrahydroisoquinolin-1-one

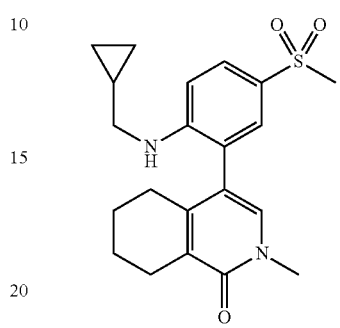

The sulfonyl compound of Example 194 was coupled as described in Example 163 to give the title compound. $^1$H NMR (CDCl$_3$, 400 MHz): δ 7.89 (dd, J$_1$=8.8 Hz, J$_2$=2.4 Hz, 1H), 7.51 (d, J=2.4 Hz, 1H), 7.10 (s, 1H), 6.69 (d, J=8.8 Hz, 1H), 3.62 (s, 3H), 3.04-3.02 (m, 5H), 2.67-2.62 (m, 2H), 2.26-2.24 (m, 2H), 1.78-1.76 (m, 2H), 1.75-1.74 (m, 2H), 1.05-1.02 (m, 1H), 0.58-0.54 (m, 2H), 0.23-0.21 (m, 2H). LCMS: 387.0 (M+H)$^+$

Example 224

8-[2-(cyclopropylmethoxy)-5-methylsulfonylphenyl]-6-methyl-2-(1-methylpyrazol-4-yl)pyrido[4,3-d]pyrimidin-5-one Step 1: ethyl 4-methyl-2-(1-methylpyrazol-4-yl)pyrimidine-5-carboxylate

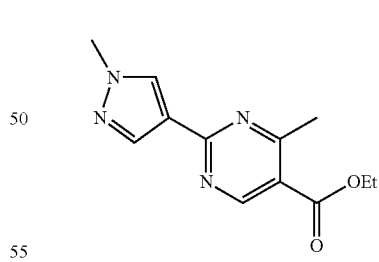

Ethyl 2-chloro-4-methylpyrimidine-5-carboxylate (1.0 g, 5.0 mmol), 1-methyl-4-(tetramethyl-1,3,2-dioxaborolan-2-yl)-1H-pyrazole (1.24 g, 6.0 mmol), K$_3$PO$_4$ (3.18 mg, 15.0 mmol) and Pd(dppf)Cl$_2$ (100 mg) in dioxane (15 mL) and H$_2$O (3 mL) were heated at 120° C. for 18 h under N$_2$. Silica gel chromatography (PE:EA=3:1 to 1:1) gave the title compound (72 mg, yield: 32.0%). $^1$H NMR (CDCl$_3$, 400 MHz) δ 9.08 (s, 1H), 8.22 (s, 1H), 8.15 (s, 1H), 4.40 (q, J=7.2 Hz, 2H), 3.98 (s, 3H), 2.82 (s, 3H), 1.42 (t, J=7.2 Hz, 3H). LCMS: 247.1 (M+1).

Step 2: ethyl 4-[(E)-2-(dimethylamino)ethenyl]-2-(1-methylpyrazol-4-yl)pyrimidine-5-carboxylate and ethyl 2-(1-methylpyrazol-4-yl)-4-[(E)-2-pyrrolidin-1-ylethenyl]pyrimidine-5-carboxylate

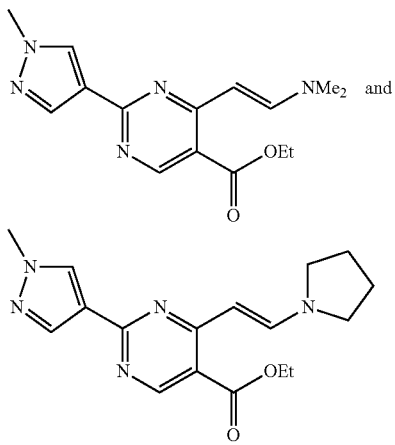

The title compound from step 1 (800 mg, 3.22 mmol), DMF-DMA (15.0 mL) and pyrrolidine (3.0 mL) were heated at 120° C. for 5 h. Extractive work up with EA gave a mixture of title compounds (500 mg, ~70:30 by LCMS) which were carried on without purification. LCMS: 328.1 (M+1)$^+$.

Step 3: 6-methyl-2-(1-methylpyrazol-4-yl)pyrido[4,3-d]pyrimidin-5-one

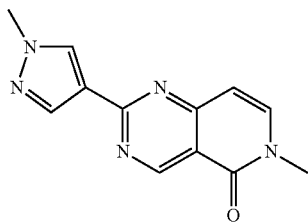

The mixture of title compounds from step 2 (500 mg) was treated with ethanolic methylamine (15 mL, 30% $CH_3NH_2$ in EtOH) and heated at 80° C. for 5 h. After concentration, the resulting solids were triturated with hexane (10 mL) and collected to give the title compound (220 mg, 55.0%). $^1$H NMR (CDCl$_3$, 400 MHz) δ 9.57 (s, 1H), 8.27 (s, 1H), 8.21 (s, 1H), 7.46 (d, J=7.6 Hz, 1H), 6.59 (d, J=7.6 Hz, 1H), 4.00 (s, 3H), 3.61 (s, 3H). LCMS: 242.0 (M+1).

Step 4: 8-bromo-6-methyl-2-(1-methylpyrazol-4-yl)pyrido[4,3-d]pyrimidin-5-one

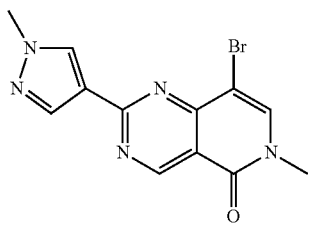

The title compound from step 3 (220 mg, 0.912 mmol) and Br$_2$ (146 mg, 0.912 mmol) in HOAc (15 mL) were stirred at room temperature for 2 h. Water (150 mL) was added, and the resulting solid was collected and triturated with DCM:PE=10:1 (10 mL) to give the title compound (200 mg, yield: 69.0%). $^1$H NMR (CDCl$_3$, 400 MHz) δ 9.54 (s, 1H), 8.33 (s, 1H), 8.27 (s, 1H), 7.77 (s, 1H), 4.01 (s, 3H), 3.62 (s, 3H).

Step 5: 8-[2-(cyclopropylmethoxy)-5-methylsulfonylphenyl]-6-methyl-2-(1-methylpyrazol-4-yl)pyrido[4,3-d]pyrimidin-5-one

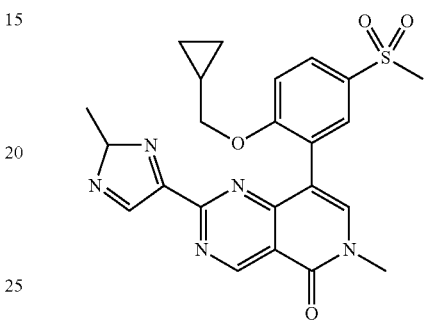

The title compound of step 4 (200 mg, 0.627 mmol), the title compound of Example 90, step 1 (266 mg, 0.752 mmol), K$_3$PO$_4$ (400 mg, 1.881 mmol) and Pd(dppf)Cl$_2$ (10 mg) in dioxane (4 mL) and H$_2$O (1 mL) were heated at 70° C. for 18 h under N$_2$. After preparative HPLC, the title compound (104.5 mg, 35.8%) was obtained as an off white solid. $^1$H NMR (CDCl$_3$, 400 MHz) δ 9.64 (s, 1H), 8.24-8.18 (m, 2H), 8.07 (s, 1H), 7.96 (dd, J$_1$=8.8 Hz, J$_2$=2.4 Hz, 1H), 7.77 (s, 1H), 7.10 (d, J=8.8 Hz, 1H), 3.95 (s, 3H), 3.91 (d, J=7.2 Hz, 2H), 3.68 (s, 3H), 3.12 (s, 3H), 1.13-1.01 (m, 1H), 0.54-0.44 (m, 2H), 0.21-0.14 (m, 1H). LCMS: 466.1 (M+1)$^+$ Example 225

8-(5-ethylsulfonyl-2-propoxyphenyl)-6-methyl-2-(1-methylpyrazol-4-yl)pyrido[4,3-d]pyrimidin-5-one Step 1: 2-bromo-4-ethylsulfonyl-1-propoxybenzene

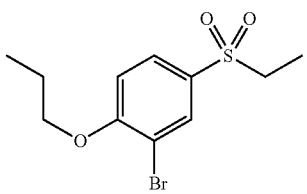 [SMILES: CCCOc1ccc(S(=O)(=O)CC)cc1Br]

To a solution of n-propanol (224 mg, 3.74 mmol) in THF (10 mL) was added NaH (112 mg, 2.80 mmol, 60% in mineral oil) at 0° C. After stirring at 0° C. for 30 min, 2-bromo-4-(ethanesulfonyl)-1-fluorobenzene (500 mg, 1.87 mmol) was added and the mixture was stirred at room temperature for 4 h. Addition of saturated NH$_4$Cl (10 mL) followed by EA extractive work up gave the title compound (300 mg, yield: 52.3%) which was carried on directly.

Step 2: 2-(5-ethylsulfonyl-2-propoxyphenyl)-4,4,5,5-tetramethyl-1,3,2-dioxaborolane

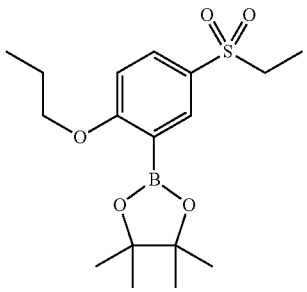 [SMILES: CCCOc1ccc(S(=O)(=O)CC)cc1B1OC(C)(C)C(C)(C)O1]

The title compound of step 1 (300 mg, 0.98 mmol), 4,4,5,5-tetramethyl-2-(tetramethyl-1,3,2-dioxaborolan-2-yl)-1,3,2-dioxaborolane (622 mg, 2.45 mmol), KOAc (288 mg, 2.94 mmol), Pd$_2$(dba)$_3$ (92 mg, 0.10 mmol), and X-Phos (62 mg, 0.13 mmol) in dioxane (5 mL) were purged with Ar and heated at 70° C. for 12 h. CH$_2$Cl$_2$ extractive work up and silica gel chromatography (PE:EA=20:1-5:1) gave the title compound (200 mg, yield: 57.7%) as a grey solid. $^1$H NMR (CDCl$_3$, 400 MHz) δ 8.13 (s, 1H), 7.91 (d, J=8.8 Hz, 1H), 6.95 (d, J=8.8 Hz, 1H), 4.02 (t, J=5.6 Hz, 2H), 3.13 (q, J=7.2 Hz, 2H), 1.89 (q, J=6.8 Hz, 2H), 1.36-1.25 (m, 15H), 1.12 (t, J=6.8 Hz, 3H). LCMS: 272.9 (M+1)$^+$.

Step 3: 8-(5-ethylsulfonyl-2-propoxyphenyl)-6-methyl-2-(1-methylpyrazol-4-yl)pyrido[4,3-d]pyrimidin-5-one

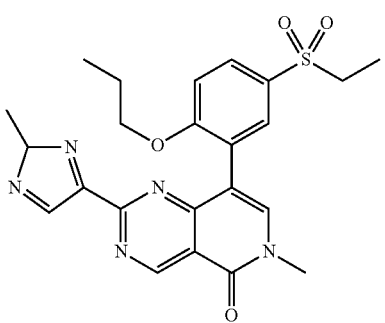 [SMILES: CCCOc1ccc(S(=O)(=O)CC)cc1-c1cn(C)c(=O)c2cnc(C3=NC(C)N=C3)nc12]

The title compound of step 2 (60 mg, 0.17 mmol), the title compound of Example 224, step 4 (64 mg, 0.20 mmol), K$_3$PO$_4$ (108 mg, 0.51 mmol), and Pd(dppf)Cl$_2$ (15 mg, 0.02 mmol) in dioxane (8 mL) were purged with N$_2$ and heated at 70° C. for 18 h. CH$_2$Cl$_2$ extractive work up and preparative HPLC gave the title compound (66.11 mg, yield: 83.3%) as a grey solid. $^1$H NMR (CDCl$_3$, 400 MHz) δ 9.64 (s, 1H), 8.19 (s, 1H), 8.12 (d, J=2.4 Hz, 1H), 8.06 (s, 1H), 7.96 (dd, J$_1$=8.8 Hz, J$_2$=2.4 Hz, 1H), 7.70 (s, 1H), 7.15 (d, J=8.4 Hz, 1H), 4.03-3.95 (m, 5H), 3.67 (s, 3H), 3.20 (q, J=7.2 Hz, 2H), 1.67-1.60 (m, 2H), 1.36 (t, J=7.2 Hz, 3H), 0.81 (t, J=7.2 Hz, 3H). LCMS: 468.2 (M+1)$^+$ Example 226

8-[2-(cyclopropylmethoxy)-5-ethylsulfonylphenyl]-6-methyl-2-(1-methylpyrazol-4-yl)pyrido[4,3-d]pyrimidin-5-one

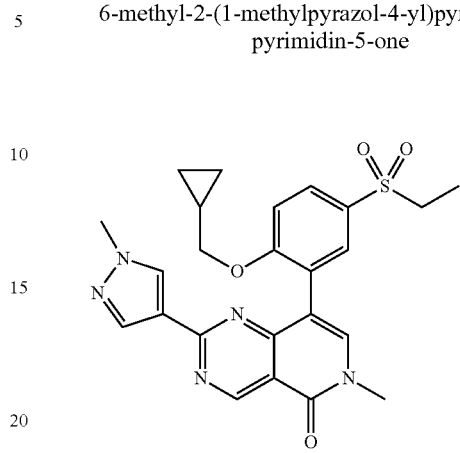

The title compound was prepared in three steps in a similar manner as Example 225 except that cyclopropylmethanol was substituted for n-propanol in step 1. $^1$H NMR (CDCl$_3$, 400 MHz) δ 9.64 (s, 1H), 8.22 (s, 1H), 8.17 (d, J=2.0 Hz, 1H), 8.07 (s, 1H), 7.92 (dd, J$_1$=8.4 Hz, J$_2$=2.0 Hz, 1H), 7.77 (s, 1H), 7.10 (d, J=8.4 Hz, 1H), 3.96 (s, 3H), 3.90 (d, J=6.8 Hz, 2H), 3.68 (s, 3H), 3.17 (q, J=7.2 Hz, 2H), 1.33 (t, J=7.2 Hz, 3H), 1.08-1.06 (m, 1H), 0.52-0.47 (m, 2H), 0.21-0.17 (m, 2H). LCMS: 480.2 (M+H)$^+$ Example 227

8-(2-ethoxy-5-ethylsulfonylphenyl)-6-methyl-2-(1-methylpyrazol-4-yl)pyrido[4,3-d]pyrimidin-5-one

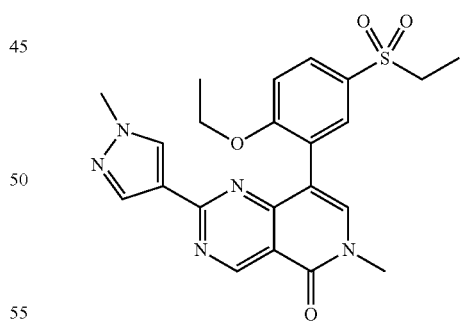

The title compound was prepared in three steps in a similar manner as Example 225 except that ethanol was substituted for n-propanol in step 1. $^1$H NMR (CDCl$_3$, 400 MHz) δ 9.64 (s, 1H), 8.19 (s, 1H), 8.10 (s, 1H), 8.06 (s, 1H), 7.94 (d, J=8.8 Hz, 1H), 7.69 (s, 1H), 7.13 (d, J=8.8 Hz, 1H), 4.13 (q, J=6.8 Hz, 2H), 3.95 (s, 3H), 3.67 (s, 3H), 3.17 (q, J=7.2 Hz, 2H), 1.34 (t, J=7.2 Hz, 3H), 0.81 (t, J=6.8 Hz, 3H). LCMS: 454.1 (M+H)$^+$

Example 228

8-(2-ethoxy-5-ethylsulfonylphenyl)-6-methyl-2-(1-methylpyrazol-4-yl)pyrido[4,3-d]pyrimidin-5-one

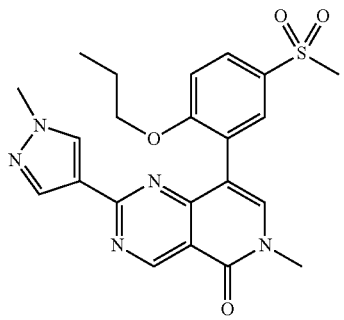 [SMILES: CCCOc1ccc(S(C)(=O)=O)cc1-c1cn(C)c(=O)c2cnc(-c3cnn(C)c3)nc12]

2-bromo-4-methylsulfonyl-1-propoxybenzene was prepared in a similar manner as Example 46, step 1 except that 1-chloropropane was substituted for (chloromethyl)cyclopropane and the resulting product was used to prepare 4,4,5,5-tetramethyl-2-(5-methylsulfonyl-2-propoxyphenyl)-1,3,2-dioxaborolane in a manner similar to Example 225, step 2 which was then used to prepare the title compound in a manner similar as Example 225, step 3. $^1$H NMR (CDCl$_3$, 400 MHz) δ 9.64 (s, 1H), 8.19 (s, 1H), 8.16 (d, J=2.4 Hz, 1H), 8.07 (s, 1H), 7.99 (dd, J$_1$=8.8 Hz, J$_2$=2.4 Hz, 1H), 7.70 (s, 1H), 7.14 (d, J=8.8 Hz, 1H), 4.01 (t, J=6.4 Hz, 2H), 3.96 (s, 3H), 3.68 (s, 3H), 3.12 (s, 3H), 1.67-1.61 (m, 2H), 0.78 (t, J=7.2 Hz, 3H). LCMS: 454.1 (M+H)$^+$

Example 229

N-[4-(2,4-difluorophenoxy)-3-(1,5-dimethyl-6-oxopyridin-3-yl)phenyl]-N-methylmethanesulfonamide

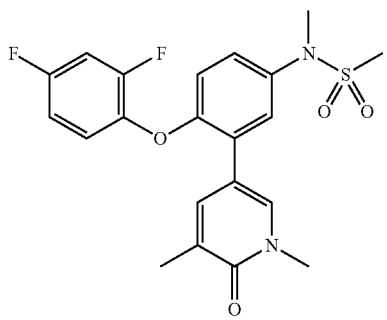 [SMILES: Cc1cc(-c2cc(N(C)S(C)(=O)=O)ccc2Oc2ccc(F)cc2F)cn(C)c1=O]

The title compound of Example 102 (56 mg, 0.13 mmol) in DMF (0.2 mL) was treated with NaH (60% dispersion in oil, 6 mg, 0.16 mmol). After about 15 min, methyl iodide (0.012 mL, 0.2 mmol) was added. After complete reaction, silica gel chromatography gave the title compound (55 mg, 0.13 mmol) as a cream colored solid. $^1$H NMR (400 MHz, DMSO-d$_6$) δ ppm 1.96-2.17 (s, 3H) 2.98 (s, 3H) 3.25 (s, 3H) 3.49 (s, 3H) 6.82 (d, J=8.84 Hz, 1H) 7.21-7.40 (m, 3H) 7.40-7.54 (m, 2H) 7.59 (s, 1H) 7.82 (d, J=2.53 Hz, 1H) LCMS (M+H)$^+$ 435

Example 230

N-[4-(2,4-difluorophenoxy)-3-(1,5-dimethyl-6-oxopyridin-3-yl)phenyl]-N-(oxetan-3-yl)methanesulfonamide

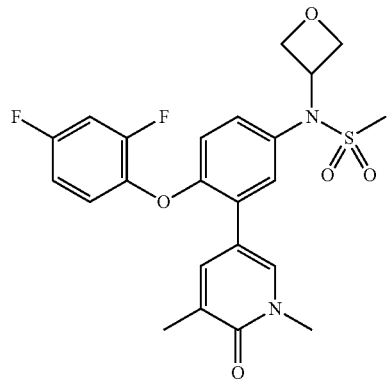 [SMILES: Cc1cc(-c2cc(N(C3COC3)S(C)(=O)=O)ccc2Oc2ccc(F)cc2F)cn(C)c1=O]

The title compound of Example 102 (46 mg, 0.11 mmol), Cs2CO3 (150 mg, 0.46 mmol), KI (10 mg, 0.06 mmol) and oxetan-3-yl 4-methylbenzenesulfonate (30 mg, 0.13 mmol) in DMF (0.9 mL) were microwaved at 130° C. for 2 h. Additional oxetan-3-yl 4-methylbenzenesulfonate (65 mg, 0.29 mmol) and Cs2CO3 (126 mg, 0.39 mmol) were added and microwave resumed at 130° C. for 2 h more. The mixture was purified by silica gel chromatography (EA) to give the title compound (20 mg, 0.04 mmol) as cream solids in 38% yield. $^1$H NMR (400 MHz, DMSO-d$_6$) δ ppm 2.03 (s, 3H) 2.98 (s, 3H) 3.50 (s, 3H) 4.41 (t, J=6.82 Hz, 2H) 4.58 (t, J=6.95 Hz, 2H) 5.30 (quin, J=7.01 Hz, 1H) 6.83 (d, J=8.84 Hz, 1H) 7.06-7.20 (m, 1H) 7.22-7.35 (m, 2H) 7.39 (d, J=2.53 Hz, 1H) 7.43-7.57 (m, 1H) 7.60 (s, 1H) 7.83 (d, J=2.27 Hz, 1H). LCMS (M+H)$^+$ 477

Example 231

8-[2-(cyclopropylmethoxy)-5-methylsulfonylphenyl]-6-methylpyrido[4,3-d]pyrimidin-5-one Step 1: 6H-pyrido[4,3-d]pyrimidin-5-one

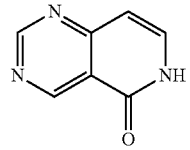 [SMILES: O=c1[nH]ccc2ncncc12]

Under N$_2$, ethyl 3-oxobutanoate (40.12 g, 0.31 mol) and 1,3,5-triazine (25.00 g, 0.31 mol) in dry EtOH (90 mL) were heated at 80° C. for 2 h and EtONa (8.39 g, 0.12 mol) was added and heating continued at 80° C. for 18 h. The mixture was concentrated and water (300 mL) was added. Acidification with concentrated HCl (50 mL) resulted in a precipitate which was collected and washed with cold acetone (20 mL) and dried under vacuum to give the title compound (1.20 g, yield: 2.6%) as a brown solid. $^1$H NMR: (DMSO-d6, 400 MHz) δ: 11.92 (brs, 1H), 9.41 (s, 1H), 9.32 (s, 1H), 7.72 (dd, J$_1$=7.6 Hz, J$_2$=6.4 Hz, 1H), 6.57 (d, J=7.6 Hz, 1H).

Step 2: 8-bromo-6H-pyrido[4,3-d]pyrimidin-5-one

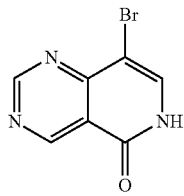

To the title compound of step 1 (200 mg, 1.36 mmol) in DMF (20 mL) was added NBS (242 mg, 1.36 mmol) at 0° C. The resulting mixture was stirred at 15° C. for 2 h and then concentrated and treated with acetone (20 mL). The resulting solid was collected to give the title compound (220 mg, yield: 71.6%) as a yellow solid. $^1$H NMR: (DMSO-d6, 400 MHz) δ: 12.25 (brs, 1H), 9.46 (s, 1H), 9.42 (s, H), 8.12 (d, J=6.0 Hz, 1H).

Step 3: 8-bromo-6-methylpyrido[4,3-d]pyrimidin-5-one

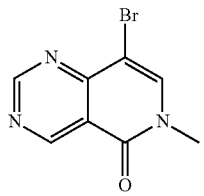

Sodium hydride (21 mg, 0.53 mmol, 60% in mineral oil) was added to the title compound of step 2 (100 mg, 0.44 mmol) in DMF (10 mL) at 0° C. After stirring 0.5 h, MeI (126 mg, 0.88 mmol) was added and stirring continued at 0° C. for 2 h. Following extractive work up with EA, the title compound (80 mg, yield: 75.3%) was obtained as a yellow solid. $^1$H NMR: (DMSO-d6, 400 MHz) δ: 9.47 (s, 1H), 9.46 (s, 1H), 8.53 (s, 1H), 3.54 (s, 3H). LCMS: 240.0, 242.0 (M+H)$^+$.

Step 4: 8-[2-(cyclopropylmethoxy)-5-methylsulfonylphenyl]-6-methylpyrido[4,3-d]pyrimidin-5-one

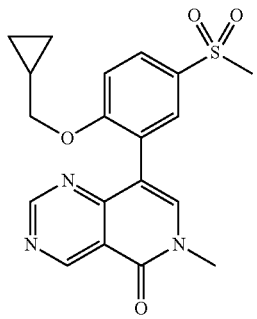 [SMILES: Cn1cc(-c2cc(S(C)(=O)=O)ccc2OCC2CC2)c2ncncc2c1=O]

The title compound of step 3 (100 mg, 0.42 mmol), the title compound of Example 90, step 1 (147 mg, 0.42 mmol), Pd(dppf)Cl$_2$ (62 mg, 0.08 mmol), K$_3$PO$_4$ (221 mg, 1.04 mmol) in dioxane (4 mL) and H$_2$O (0.5 mL) was purged with N$_2$ and heated at 100° C. for 18 h. Following CH$_2$Cl$_2$ extractive work up, silica gel chromatography (PE:EA=2:10:1) and preparative HPLC, the title compound (54.57 mg, yield: 34.2%) was obtained as a yellow solid. $^1$H NMR: (DMSO-d6, 400 MHz) δ: 9.54 (s, 1H), 9.30 (s, 1H), 8.18 (s, 1H), 7.93 (dd, J$_1$=8.8 Hz, J$_2$=2.4 Hz, 1H), 7.85 (d, J=2.4 Hz, 1H), 7.31 (d, J=8.8 Hz, 1H), 3.91 (d, J=6.8 Hz, 2H), 3.61 (s, 3H), 3.20 (s, 3H), 0.94-0.92 (m, 1H), 0.35-0.30 (m, 2H), 0.10-0.06 (m, 2H). LCMS: 386.0 (M+H)$^+$

Example 232

8-[2-(cyclopropylmethoxy)-5-ethylsulfonylphenyl]-6-methylpyrido[4,3-d]pyrimidin-5-one

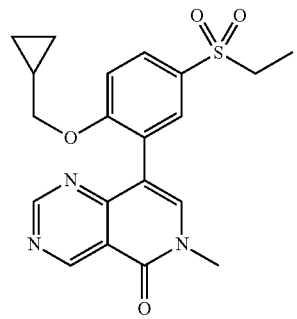 [SMILES: CCS(=O)(=O)c1ccc(OCC2CC2)c(-c2cn(C)c(=O)c3cncnc23)c1]

2-[2-(cyclopropylmethoxy)-5-ethylsulfonylphenyl]-4,4,5,5-tetramethyl-1,3,2-dioxaborolane as prepared in Example 226 was reacted with the title compound of 231, step 3 in a manner similar to 231, step 4 to give the title compound. $^1$H NMR: (DMSO-d6, 400 MHz) δ: 9.54 (s, 1H), 9.30 (s, 1H), 8.17 (s, 1H), 7.88 (dd, J1=8.8 Hz, J$_2$=2.4 Hz, 1H), 7.80 (d, J=2.4 Hz, 1H), 7.31 (d, J=8.8 Hz, 1H), 3.92 (d, J=6.8 Hz, 2H), 3.61 (s, 3H), 3.27 (q, J=7.2 Hz, 2H), 1.14 (t, J=7.2 Hz, 3H), 0.94-0.93 (m, 1H), 0.34-0.32 (m, 2H), 0.10-0.08 (m, 2H). LCMS: 400.0 (M+H)$^+$

Example 233

8-[2-(2,4-difluorophenoxy)-5-methylsulfonylphenyl]-6-methylpyrido[4,3-d]pyrimidin-5-one

Step 1: 8-(2-fluoro-5-methylsulfonylphenyl)-6-methylpyrido[4,3-d]pyrimidin-5-one

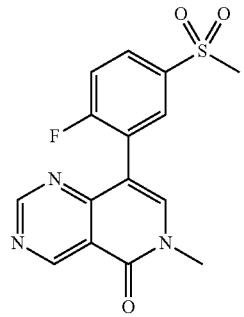 [SMILES: Cn1cc(-c2cc(S(C)(=O)=O)ccc2F)c2ncncc2c1=O]

2-bromo-1-fluoro-4-methylsulfonylbenzene was substituted for the title compound of Example 225, step 1 and was converted to 2-(2-fluoro-5-methylsulfonylphenyl)-4,4,5,5-tetramethyl-1,3,2-dioxaborolane in a manner similar to Example 225, step 2 and then reacted with the title compound of Example 231, step 3 in a manner similar to Example 231, step 4. LCMS: 333.9 (M+H)+.

Step 2: 8-[2-(2,4-difluorophenoxy)-5-methylsulfonylphenyl]-6-methylpyrido[4,3-d]pyrimidin-5-one

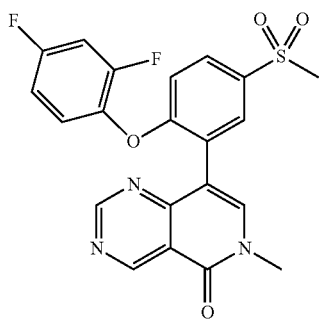 [SMILES: Cn1cc(-c2cc(S(C)(=O)=O)ccc2Oc2ccc(F)cc2F)c2ncncc2c1=O]

The title compound of step 2 (60 mg, crude), 2,4-difluorophenol (35 mg, 0.27 mmol) and Cs$_2$CO$_3$ (176 mg, 0.54 mmol) in DMSO (2 mL) was heated at 100° C. for 12 h. EA extractive work up and preparative HPLC gave the title compound (10.04 mg, yield: 13.6% for two steps) as a yellow solid. $^1$H NMR (CDCl$_3$, 400 MHz) δ 9.73 (s, 1H), 9.34 (s, 1H), 8.02 (d, J=2.4 Hz, 1H), 7.92 (dd, J$_1$=8.8 Hz, J$_2$=2.4 Hz, 1H), 7.72 (s, 1H), 7.19-7.17 (m, 1H), 6.97-6.89 (m, 3H), 3.72 (s, 3H), 3.12 (s, 3H). LCMS: 444.1 (M+H)+

Example 234

8-[2-(2,4-difluorophenoxy)-5-ethylsulfonylphenyl]-6-methylpyrido[4,3-d]pyrimidin-5-one Step 1: 1-(2-bromo-4-ethylsulfonylphenoxy)-2,4-difluorobenzene

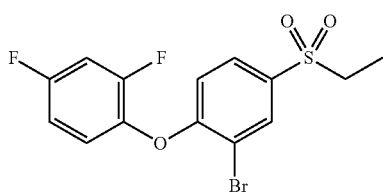 [SMILES: CCS(=O)(=O)c1ccc(Oc2ccc(F)cc2F)c(Br)c1]

2-bromo-1-fluoro-4-ethylsulfonylbenzene (130 mg, 0.49 mmol), 2,4-difluorophenol (78 mg, 0.60 mmol) and Cs$_2$CO$_3$ (478 mg, 1.47 mmol) in DMSO (5 mL) were heated at 100° C. for 12 h. EA extractive work up gave the title compound (150 mg, yield: 80.5%) as a grey solid. $^1$H NMR (CDCl$_3$, 400 MHz) δ 8.18 (d, J=2.0 Hz, 1H), δ 7.75 (dd, J$_1$=8.4 Hz, J$_2$=1.6 Hz, 1H), 7.22-7.16 (m, 1H), 7.06-6.95 (m, 2H), 6.80 (d, J=8.8 Hz, 1H), 3.16 (q, J=7.2 Hz, 2H), 1.33 (t, J=7.6 Hz, 3H). LCMS: 395.8 (M+NH$_4$)+.

Step 2: 2-[2-(2,4-difluorophenoxy)-5-ethylsulfonylphenyl]-4,4,5,5-tetramethyl-1,3,2-dioxaborolane

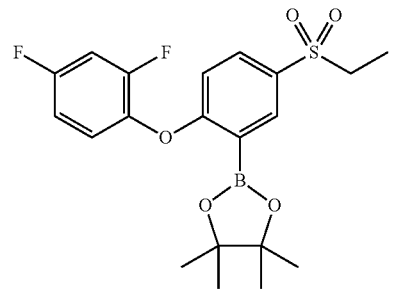 [SMILES: CCS(=O)(=O)c1ccc(Oc2ccc(F)cc2F)c(B2OC(C)(C)C(C)(C)O2)c1]

The title compound of step 1 was substituted for the title compound of Example 225, step 1 and reacted in a similar manner as Example 225, step 2. $^1$H NMR (CDCl$_3$, 400 MHz) δ 8.11 (d, J=2.8 Hz, 1H), δ 7.95 (dd, J$_1$=8.8 Hz, J$_2$=2.4 Hz, 1H), 7.55-7.50 (m, 1H), 7.29-7.23 (m, 1H), 7.16-7.12 (m, 1H), 6.99 (d, J=8.8 Hz, 1H), 3.32 (q, J=7.2 Hz, 2H), 1.26 (s, 12H), 1.12 (t, J=7.2 Hz, 3H). LCMS: 342.8 (M+H) (free boronic acid)+

Step 3: 8-[2-(2,4-difluorophenoxy)-5-ethylsulfonylphenyl]-6-methylpyrido[4,3-d]pyrimidin-5-one

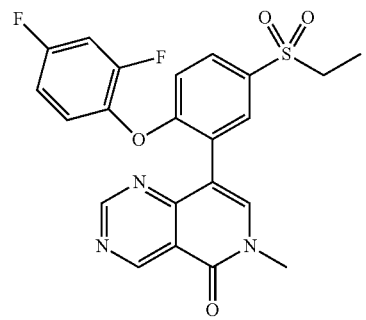 [SMILES: CCS(=O)(=O)c1ccc(Oc2ccc(F)cc2F)c(-c2cn(C)c(=O)c3cncnc23)c1]

The title compound of step 2 was substituted for the title compound of Example 225, step 2 and the title compound of Example 231, step 3 was substituted for the title compound of Example 224, step 4 and reacted in a similar manner as Example 225, step 3. $^1$H NMR (CDCl$_3$, 400 MHz) δ 9.60 (s, 1H), 9.27 (s, 1H), 8.12 (s, 1H), 8.02 (d, J=2.0 Hz, 1H), 7.94 (dd, J$_1$=8.8 Hz, J$_2$=2.0 Hz, 1H), 7.32-7.25 (m, 1H), 7.15-7.09 (m, 1H), 7.03-6.97 (m, 2H), 3.70 (s, 3H), 3.27 (q, J=7.6 Hz, 2H), 1.30 (t, J=7.2 Hz, 3H). LCMS: 458.0 (M+H)+

Example 235

5-[2-(cyclopropylmethoxy)-5-methylsulfonylphenyl]-7-methyl-[1,2,4]triazolo[4,3-a]pyrazin-8-one Step 1: 5-bromo-7H-[1,2,4]triazolo[4,3-a]pyrazin-8-one

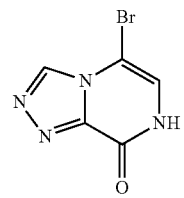 [SMILES: O=c1[nH]cc(Br)n2cnnc12]

To a solution of 5-bromo-8-methoxy-[1,2,4]triazolo[4,3-a]pyrazine (Borchardt WO2011/112766) (500 mg, 2.18 mmol) in HOAc (3 mL) was added HCl (1 N, 5.00 mL). The mixture was heated at 110° C. for 4 h and concentrated to give the title compound (400 mg, yield: 85%) as a yellow solid which was carried on without purification. $^1$H NMR (DMSO-d6, 400 MHz): δ 11.78 (s, 1H), 9.25 (s, 1H), 7.25 (d, J=6.0 Hz, 1H). LCMS: 214.9 (M+H)$^+$ Step 2: 5-bromo-7-methyl-[1,2,4]triazolo[4,3-a]pyrazin-8-one

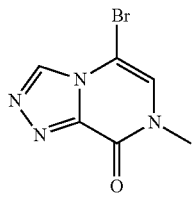

To a solution of the title compound of step 1 (400 mg, 1.86 mmol) in DMF (4 mL) was added NaH (149 mg, 3.72 mmol, 60% in mineral oil) in portions at 0° C. under N$_2$. The mixture was stirred at 20° C. for 1 h, and methyl iodide (792 mg, 5.58 mmol) was added. After stirring at 20° C. for 5 h, water was added. Methylene chloride: 2-propanol (10:1) extractive work up gave the title compound (200 mg, yield: 47%) as a light yellow solid which was carried on without purification. $^1$H NMR (DMSO-d6, 400 MHz): δ 9.26 (s, 1H), 7.60 (s, 1H), 3.42 (s, 3H). LCMS: 228.9 (M+H)$^+$ Step 3: 5-[2-(cyclopropylmethoxy)-5-methylsulfonylphenyl]-7-methyl-[1,2,4]triazolo[4,3-a]pyrazin-8-one

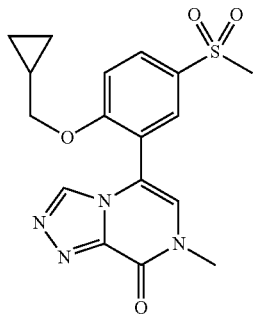 [SMILES: Cn1cc(-c2cc(S(C)(=O)=O)ccc2OCC2CC2)n2cnnc2c1=O]

The title compound of step 2 (40 mg, 0.175 mmol), the title compound of Example 90, step 1 (62 mg, 0.175 mmol), K$_3$PO$_4$ (93 mg, 0.438 mmol) and Pd(dppf)Cl$_2$ (13 mg, 0.018 mmol) in dioxane (2 mL) and H$_2$O (1 mL) was N$_2$ purged and microwaved at 70° C. for 2 h. Silica gel chromatography (PE:EA=1:4) followed by preparative HPLC gave the title compound (31.89 mg, yield: 48.6%) as an off-white solid. $^1$H NMR (DMSO-d6, 400 MHz): δ 8.91 (s, 1H), 8.06 (dd, J$_1$=8.8 Hz, J$_2$=2.4 Hz, 1H), 7.96 (d, J=2.4 Hz, 1H), 7.43-7.04 (m, 2H), 4.04 (d, J=6.8 Hz, 2H), 3.52 (s, 3H), 3.23 (s, 3H), 0.99-0.96 (m, 1H), 0.41-0.36 (m, 2H), 0.23-0.20 (m, 2H). LCMS: 375.0 (M+H)$^+$ Example 236

N-[4-(2,4-difluorophenoxy)-3-(7-methyl-8-oxo-[1,2,4]triazolo[4,3-a]pyrazin-5-yl)phenyl]ethanesulfonamide

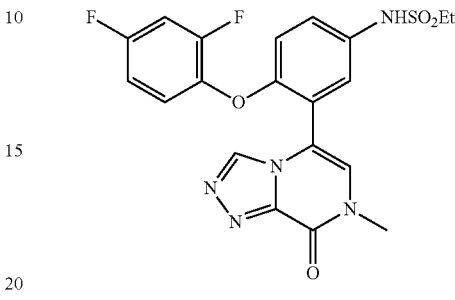

The title compound of Example 235, step 2 (40 mg, 0.175 mmol), N-[4-(2,4-difluorophenoxy)-3-(4,4,5,5-tetramethyl-1,3,2-dioxaborolan-2-yl)phenyl]ethanesulfonamide (77 mg, 0.175 mmol), K$_3$PO$_4$ (93 mg, 0.438 mmol) and Pd(dppf)Cl$_2$ (13 mg, 0.018 mmol) in dioxane (2 mL) and H$_2$O (1 mL) was N$_2$ purged and microwaved at 70° C. for 2 h. Preparative HPLC gave the title compound (38.75 mg, yield: 49.3%) as an off-white solid. $^1$H NMR (CDCl$_3$, 400 MHz): δ 8.60 (s, 1H), 7.64 (d, J=2.8 Hz, 1H), 7.45 (dd, J$_1$=8.8 Hz, J$_2$=2.8 Hz, 1H), 7.10-7.05 (m, 1H), 6.99-6.88 (m, 3H), 6.74 (d, J=8.8 Hz, 1H), 3.67 (s, 3H), 3.18 (q, J=7.2 Hz, 2H), 1.40 (t, J=7.2 Hz, 3H). LCMS: 462.0 (M+H)$^+$ Example 237

7-[2-(cyclopropylmethoxy)-5-methylsulfonylphenyl]-5-methyl-[1,3]oxazolo[4,5-c]pyridin-4-one Step 1: 3-nitro-4-hydroxy-1-methylpyridin-2-one

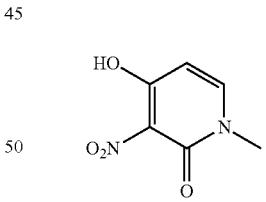

To 4-hydroxy-3-nitro-1H-pyridin-2-one (300 mg, 1.9 mmol) in DMF (5 mL) was added NaH (176 mg, 4.4 mmol, 60% in mineral oil) at 0° C. under N$_2$. After stirring at 0° C. for 30 min, CH$_3$I (272 mg, 1.9 mmol) in DMF (5 mL) was added dropwise, and the mixture was stirred for 2 h at 25° C. Saturated aqueous NH$_4$Cl was added, the pH was adjusted to ~3 with 1N HCl and EA extractive work up gave a residue that was triturated with MeOH (0.5 ml): EA (10 mL): PE (5 mL). After filtration, the trituratate was evaporated to give the title compound (300 mg, 91%) as a yellow solid. $^1$H NMR: (CDCl$_3$, 400 MHz) δ: 7.75 (d, J=7.2 Hz, 1H), 6.17 (d, J=7.2 Hz, 1H) 3.54 (s, 3H). LCMS: 171.0 (M+1)$^+$ Step 2:
1-methyl-3-nitro-4-phenylmethoxypyridin-2-one

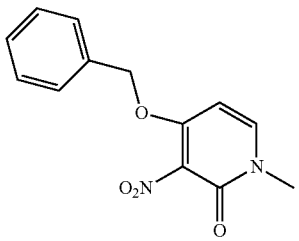 [SMILES: Cn1ccc(OCc2ccccc2)c([N+](=O)[O-])c1=O]

To the title compound of step 1 (300 mg, 1.7 mmol) in CH₃CN (15 mL) was added K₂CO₃ (726 mg, 5.2 mmol) at 25° C. under N₂. After stirring for 30 min, benzyl bromide (450 mg, 2.6 mmol) was added, and the mixture was heated at 50° C. for 20 h. Following CH₂Cl₂ extractive work up, the residue was triturated with PE:EA (3:1) to give the title compound (250 mg, 54%) as a yellow solid. ¹H NMR: (CDCl₃, 400 MHz) δ: 7.43-7.29 (m, 6H), 6.12 (d, J=7.2 Hz, 1H), 5.27 (s, 2H), 3.57 (s, 3H). LCMS: 261.0 (M+1)⁺

Step 3: 3-amino-4-hydroxy-1-methylpyridin-2-one hydrochloride

To the title compound of step 2 (2.00 g, 7.69 mmol, 1.00 Eq) in MeOH (50 mL)/EtOH (50 mL)/DMF (10 mL) was added Pd—C (10%, 0.2 g) under N₂. The suspension was purged with H₂ three times and hydrogenated under a balloon for 5 h. The catalyst was removed by filtration, and anhydrous HCl in methanol (10 mL, 1.25 M) was added. Concentration left a residue which was treated a second time with HCl in methanol. Evaporation of the volatile components and trituration with DCM (30 mL)/hexane (30 mL) gave the title compound (1.29 g, 7.30 mmol, yield: 95%) as a pink HCl salt after drying. ¹H NMR: (DMSO-d6, 400 MHz) δ: 9.45-8.02 (br, 3H), 7.64 (d, J=7.6 Hz, 1H), 3.27 (d, J=7.6 Hz, 1H), 3.43 (s, 3H). LCMS: 163.0 (M+Na)⁺

Step 4: 5-methyl-[1,3]oxazolo[4,5-c]pyridin-4-one

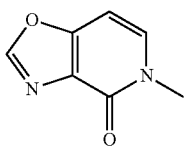

The title compound of step 3 (500 mg, 2.8 mmol) in triethyl orthoformate (10 mL) was heated to reflux for 5 h. The mixture was concentrated in vacuo at 55° C. and purified by silica gel chromatography (PE:EA=1:1) to give the title compound (130 mg, yield: 30%) as a yellow solid.

¹H NMR (CDCl₃, 400 MHz) δ 7.99 (s, 1H), 7.36 (d, J=8.0 Hz, 1H), 6.60 (d, J=8.0 Hz, 1H), 3.69 (s, 3H).

Step 5:
7-bromo-5-methyl-[1,3]oxazolo[4,5-c]pyridin-4-one

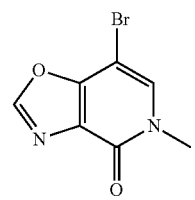

To the title compound of step 4 (100 mg, 0.7 mmol) in CH₃CN (5 mL) was added NBS (154 mg, 0.8 mmol) at 20° C. After 2 h, the mixture was concentrated in vacuum at 45° C. Purification by silica gel chromatography (PE:EA=5:1-2:1) to gave the title compound (70 mg, yield: 45%) as a yellow solid. ¹H NMR (CDCl₃, 400 MHz) δ 8.04 (s, 1H), 7.52 (s, 1H), 3.69 (s, 3H).

Step 6: 7-[2-(cyclopropylmethoxy)-5-methylsulfonylphenyl]-5-methyl-[1,3]oxazolo[4,5-c]pyridin-4-one

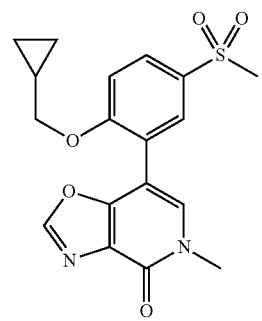 [SMILES: Cn1cc(-c2cc(S(C)(=O)=O)ccc2OCC2CC2)c2ocnc2c1=O]

The title compound of step 5 (60 mg, 0.3 mmol) in dioxane (2 mL) and H₂O (0.4 mL) was stirred at 15° C. under N₂ for 30 min. Pd(dppf)Cl₂ (19 mg, 0.026 mmol), the title compound of Example 90, step 1 (120 mg, 0.3 mmol) and K₃PO₄ (166 mg, 0.8 mmol,) were added at 15° C. under N₂. The reaction mixture was heated at 60° C. for 12 h. Purification by silica gel chromatography (EA) and preparative HPLC gave the title compound (20.63 mg, 20%) as a yellow solid. ¹H NMR (CDCl₃, 400 MHz) δ 8.03 (d, J=2.0 Hz, 1H), 8.02 (s, 1H), 7.96 (dd, J₁=8.4 Hz, J₂=2.0 Hz, 1H), 7.09 (d, J=8.4 Hz, 1H), 3.96 (d, J=6.8 Hz, 2H), 3.76 (s, 3H), 3.1 (s, 3H), 1.18 (m, 1H), 0.60 (m, 2H), 0.30 (m, 2H). LCMS: 375.1 (M+H)⁺

Example 238

7-[2-(cyclopropylmethoxy)-5-methylsulfonylphenyl]-2,5-dimethyl-[1,3]oxazolo[4,5-c]pyridin-4-one

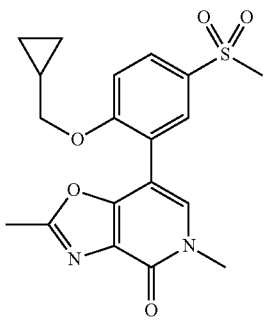

The title compound was prepared from the title compound of Example 237, step 3 in a similar manner as Example 237, steps 4-6 except that triethyl orthoacetate was substituted for triethyl orthoformate. $^1$H NMR (400 MHz, DMSO-d$_6$) δ ppm 0.25 (q, J=4.72 Hz, 2H) 0.48 (q, J=5.89 Hz, 2H) 1.11 (m, 1H) 2.54 (s, 3H) 3.21 (s, 3H) 3.60 (s, 3H) 4.00 (d, J=6.82 Hz, 2H) 7.34 (d, J=8.59 Hz, 1H) 7.88-7.98 (m, 3H). LCMS: 389 (M+H)$^+$

Example 239

5-methyl-7-[5-(methylsulfonylmethyl)-2-(2,2,2-trifluoroethoxy)phenyl]-[1,3]oxazolo[4,5-c]pyridin-4-one

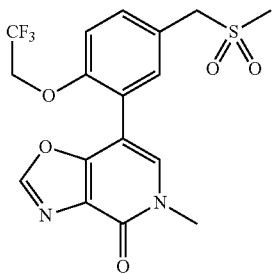 [SMILES: Cn1cc(-c2cc(CS(C)(=O)=O)ccc2OCC(F)(F)F)c2ocnc2c1=O]

The title compound of Example 237, step 5 and the title compound of Example 370, step 1 were reacted in a manner similar to Example 237, step 6 to give the title compound. $^1$H NMR (CDCl$_3$, 400 MHz) δ 8.00 (s, 1H), 7.62 (s, 1H), 7.60 (s, 1H), 7.47 (d, J=8.4 Hz, 1H), 7.02 (d, J=8.4 Hz, 1H), 4.42 (q, J=8.0 Hz, 2H), 4.28 (s, 2H), 3.74 (s, 3H), 2.87 (s, 3H). LCMS: 417.0 (M+H)$^+$

Example 240

N-[4-(2,4-difluorophenoxy)-3-(5-methyl-4-oxo-[1,3]oxazolo[4,5-c]pyridin-7-yl)phenyl]ethanesulfonamide

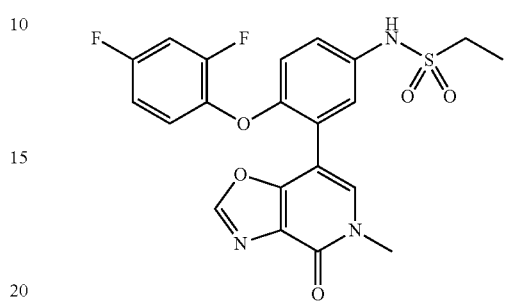

N-[4-(2,4-difluorophenoxy)-3-(4,4,5,5-tetramethyl-1,3,2-dioxaborolan-2-yl)phenyl]ethanesulfonamide was prepared from the title compound of Example 122, step 1 and 4,4,5,5-tetramethyl-2-(tetramethyl-1,3,2-dioxaborolan-2-yl)-1,3,2-dioxaborolane in a manner similar to Example 208, step 5 and reacted with the title compound of Example 237, step 5 in a manner similar to Example 237, step 6. $^1$H NMR (CDCl$_3$, 400 MHz) δ 8.01 (s, 1H), 7.31 (d, J=8.4 Hz, 1H), 7.67 (s, 1H), 7.48 (d, J=2.4 Hz, 1H), 7.22 (dd, J$_1$=8.8 Hz, J$_2$=2.4 Hz, 1H), 7.18 (m, 1H), 7.03 (m, 1H), 6.84 (m, 2H), 3.74 (s, 3H), 3.17 (q, J=7.2 Hz, 2H), 1.43 (t, J=7.2 Hz, 3H). LCMS: 462.1 (M+H)$^+$

Example 241

N-[4-(2,4-difluorophenoxy)-3-(2,5-dimethyl-4-oxo-[1,3]oxazolo[4,5-c]pyridin-7-yl)phenyl]ethanesulfonamide

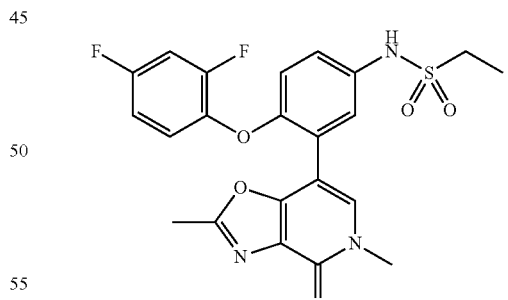

7-bromo-2,5-dimethyl-[1,3]oxazolo[4,5-c]pyridin-4-one prepared in Example 238 and N-[4-(2,4-difluorophenoxy)-3-(4,4,5,5-tetramethyl-1,3,2-dioxaborolan-2-yl)phenyl]ethanesulfonamide prepared in Example 240 were reacted in a manner similar to Example 237, step 6 to give the title compound. $^1$H NMR (400 MHz, DMSO-d$_6$) δ ppm 1.23 (t, J=6.95 Hz, 3H) 2.45 (s, 3H) 3.13 (d, J=7.83 Hz, 2H) 3.58 (s, 3H) 6.95 (d, J=8.59 Hz, 1H) 7.03-7.30 (m, 3H) 7.30-7.48 (m, 2H) 7.91 (s, 1H) 9.86 (s, 1H). LCMS: 476 (M+H)$^+$

Example 242

5-[2-(cyclopropylmethoxy)-5-methylsulfonylphenyl]-1-(cyclopropylmethyl)-3-methylpyridin-2-one Step 1: 5-[2-(cyclopropylmethoxy)-5-methylsulfonylphenyl]-3-methyl-1H-pyridin-2-one

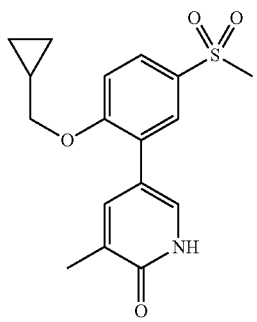 [SMILES: Cc1cc(-c2cc(S(C)(=O)=O)ccc2OCC2CC2)c[nH]c1=O]

5-bromo-3-methyl-1H-pyridin-2-one (950 mg, 5.05 mmol), the title compound of Example 90, step 1 (2.93 g, 5.95 mmol), Pd(dppf)Cl$_2$ (365 mg, 0.5 mmol) and K$_3$PO$_4$ (2.14 g, 10.1 mmol) in dioxane (30 mL) and water (5 mL) was purged with N$_2$ and heated at 70° C. for 12 h. Silica gel chromatography (PE:DCM:EA=3:0:1 to 0:1:3) gave impure title compound (990 mg) as a yellow solid which was used directly in the next step. $^1$H NMR (CDCl$_3$, 400 MHz) δ 12.57 (brs, 1H), 7.84 (d, J=8.8 Hz, 1H), 7.82 (s, 1H), 7.65 (s, 1H), 7.03 (d, J=8.8 Hz, 1H), 3.96 (d, J=7.2 Hz, 1H), 3.07 (s, 3H), 2.24 (s, 3H), 1.40-1.25 (m, 1H), 0.67-0.65 (m, 2H), 0.37-0.36 (m, 2H). LCMS: 334.1 (M+1)$^+$ Step 2: 5-[2-(cyclopropylmethoxy)-5-methylsulfonylphenyl]-1-(cyclopropylmethyl)-3-methylpyridin-2-one

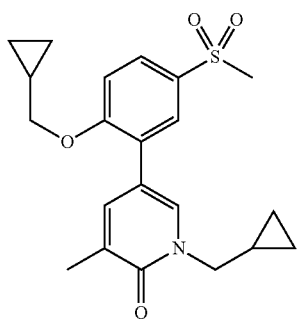 [SMILES: Cc1cc(-c2cc(S(C)(=O)=O)ccc2OCC2CC2)cn(CC2CC2)c1=O]

The title compound of step 1 (80 mg), K$_2$CO$_3$ (77 mg, 0.56 mmol) bromomethylcyclopropane (62 mg, 0.46 mmol) in DMF (2 mL) were heated at 70° C. for 4 h. EA extractive work up and preparative HPLC gave the title compound (17 mg) as a yellow solid. $^1$H NMR (CDCl$_3$, 400 MHz) δ 7.85-7.83 (m, 2H), 7.67 (d, J=2.0 Hz, 1H), 7.53 (s, 1H), 7.03 (d, J=9.2 Hz, 1H), 3.95 (d, J=6.8 Hz, 1H), 3.89 (d, J=7.2 Hz, 1H), 3.07 (s, 3H), 2.23 (s, 3H), 1.34-1.26 (m, 2H), 0.68-0.65 (m, 2H), 0.65-0.61 (m, 2H), 0.44-0.43 (m, 2H), 0.38-0.37 (m, 2H). LCMS: 388.2 (M+1)$^+$

Example 243

5-[2-(cyclopropylmethoxy)-5-methylsulfonylphenyl]-3-methyl-1-(2-methylpropyl)pyridin-2-one

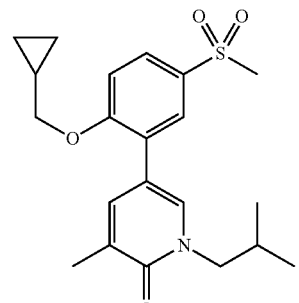

The title compound from Example 242, step 1 was reacted in a manner similar to Example 242, step 2 except that 1-bromo-2-methylpropane was substituted for bromomethylcyclopropane to give the title compound. $^1$H NMR (CDCl$_3$, 400 MHz) δ 7.85-7.82 (m, 2H), 7.56 (s, 1H), 7.53 (s, 1H), 7.03 (d, J=8.4 Hz, 1H), 3.94 (d, J=7.2 Hz, 1H), 3.83 (d, J=7.2 Hz, 1H), 3.07 (s, 3H), 2.30-2.26 (m, 1H), 2.23 (s, 3H), 1.28-1.27 (m, 1H), 1.00 (s, 3H), 0.98 (s, 3H), 0.69-0.65 (m, 2H), 0.38-0.35 (m, 2H). LCMS: 390.2 (M+1)$^+$

Example 244

5-[2-(cyclopropylmethoxy)-5-methylsulfonylphenyl]-1-(2-methoxyethyl)-3-methylpyridin-2-one

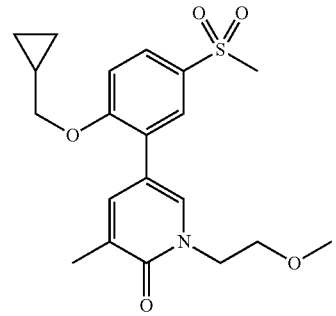 [SMILES: COCCn1cc(-c2cc(S(C)(=O)=O)ccc2OCC2CC2)cc(C)c1=O]

The title compound from Example 242, step 1 was reacted in a manner similar to Example 242, step 2 except that 1-bromo-2-methoxyethane was substituted for bromomethylcyclopropane to give the title compound. $^1$H NMR (CDCl$_3$, 400 MHz) δ 7.86-7.83 (m, 2H), 7.65 (d, J=1.6 Hz, 1H), 7.59 (s, 1H), 7.03 (d, J=8.4 Hz, 1H), 4.22 (t, J=4.8 Hz, 1H), 3.96 (d, J=6.8 Hz, 1H), 3.74 (t, J=4.8 Hz, 1H), 3.34 (s, 3H), 3.07 (s, 3H), 2.23 (s, 3H), 1.30-1.27 (m, 1H), 0.70-0.66 (m, 2H), 0.40-0.36 (m, 2H). LCMS: 392.2 (M+1)$^+$

Example 245

5-[2-(cyclopropylmethoxy)-5-methylsulfonylphenyl]-3-methyl-1-(oxetan-3-ylmethyl)pyridin-2-one

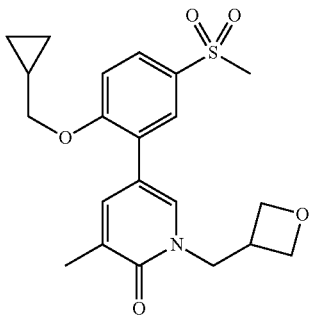 [SMILES: Cc1cc(-c2cc(S(C)(=O)=O)ccc2OCC2CC2)cn(CC2COC2)c1=O]

Sodium hydride (42 mg, 1.04 mmol, 60% in mineral oil) was added to the title compound from Example 242, step 1 (80 mg) in anhydrous DMF (4 mL) After stirring 1 h, oxetan-3-ylmethyl methanesulfonate (173 mg, 1.04 mmol) was added and stirring continued for 18 h. EA extractive work up from 1 M HCl and preparative HPLC purification gave the title compound (24.0 mg) as an off-white solid. $^1$H NMR (CDCl$_3$, 400 MHz) δ 7.85 (d, J=8.8 Hz, 1H), 7.82 (s, 1H), 7.62 (s, 1H), 7.51 (s, 1H), 7.03 (d, J=8.8 Hz, 1H), 4.83 (t, J=7.2 Hz, 1H), 4.57 (t, J=6.4 Hz, 1H), 4.30 (d, J=7.2 Hz, 1H), 3.95 (d, J=6.8 Hz, 1H), 3.62-3.56 (m, 1H), 3.07 (s, 3H), 2.21 (s, 3H), 1.32-1.27 (m, 1H), 0.72-0.68 (m, 2H), 0.40-0.36 (m, 2H). LCMS: 404.1 (M+1)$^+$

Example 246

5-[2-(cyclopropylmethoxy)-5-methylsulfonylphenyl]-3-methyl-1-(1,3-oxazol-4-ylmethyl)pyridin-2-one

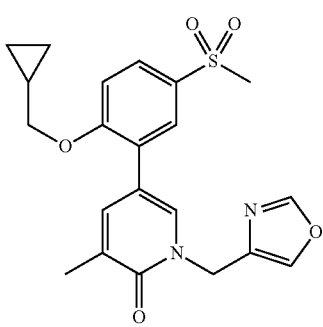 [SMILES: Cc1cc(-c2cc(S(C)(=O)=O)ccc2OCC2CC2)cn(Cc2cocn2)c1=O]

The title compound from Example 242, step 1 was reacted in a manner similar to Example 245 except that 1,3-oxazol-4-ylmethyl methanesulfonate was substituted for oxetan-3-ylmethyl methanesulfonate to give the title compound. $^1$H NMR (CDCl$_3$, 400 MHz) δ 7.82 (s, 5H), 7.52 (s, 1H), 7.01 (d, J=9.2 Hz, 1H), 5.11 (s, 2H), 3.94 (d, J=6.8 Hz, 1H), 3.06 (s, 3H), 2.21 (s, 3H), 1.27-1.24 (m, 1H), 0.68-0.65 (m, 2H), 0.37-0.36 (m, 2H). LCMS: 415.1 (M+1)$^+$

Example 247

N-[3-[1-(cyclopropylmethyl)-5-methyl-6-oxopyridin-3-yl]-4-(2,4-difluorophenoxy)phenyl]ethanesulfonamide

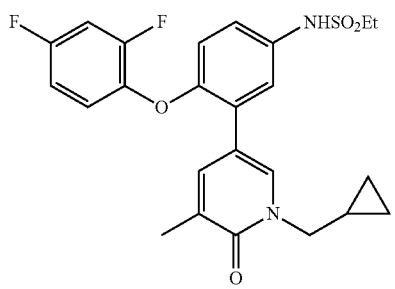

5-bromo-3-methyl-1H-pyridin-2-one was N-alkylated with bromomethylcyclopropane to give 5-bromo-1-(cyclopropylmethyl)-3-methylpyridin-2-one. 5-bromo-1-(cyclopropylmethyl)-3-methylpyridin-2-one (100 mg, 0.41 mmol), [2-(2,4-difluorophenoxy)-5-(ethylsulfonylamino)phenyl] boronic acid (217 mg, 0.5 mol), K$_3$PO$_4$ (263 mg, 1.24 mmol) and Pd(dppf)Cl$_2$ (30 mg, 41.3 umol) in dioxane (8 mL)/water (1 mL) were purged with N$_2$ and heated at 70-80° C. for 12 h. Preparative HPLC gave the title compound (56.0 mg, 28.6% yield) as dull-red semisolid. $^1$H NMR (CDCl$_3$, 400 MHz): δ 7.74 (s, 1H), 7.61 (s, 1H), 7.28 (d, J=2.0 Hz, 1H), 7.10-7.15 (m, 1H), 6.92-7.00 (m, 2H), 6.82-6.89 (m, 1H), 6.80 (d, J=8.8 Hz, 1H), 6.71 (br. s., 1H), 3.93 (d, J=7.2 Hz, 3H), 3.12-3.21 (m, 2H), 2.24 (s, 3H), 1.42 (t, J=7.2 Hz, 3H), 1.22-1.33 (m, 1H), 0.57-0.67 (m, 2H), 0.36-0.43 (m, 2H). LCMS: 475.1 (M+1)$^+$

Example 248

N-[4-[1-(cyclopropylmethyl)-5-methyl-6-oxopyridin-3-yl]-5-(2,4-difluorophenoxy)pyrimidin-2-yl]methanesulfonamide Step 1: 5-bromo-1-(cyclopropylmethyl)-3-methylpyridin-2-one

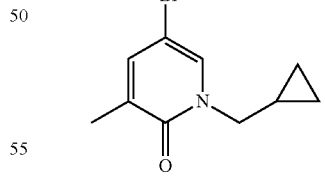

Potassium carbonate (1.32 g, 9.57 mmol) was added to 5-bromo-3-methyl-2-hydroxypyridine (600 mg, 3.19 mmol) and bromomethylcyclopropane (861 mg, 6.38 mmol) in DMF (6 mL). After heating at 70° C. for 3 h, EA extractive work up and silica gel chromatography (PE:EA=30:1~10:1), the title compound (510 mg, yield: 66.0%) was obtained as a white solid. $^1$H NMR: (CDCl$_3$, 400 MHz) δ: 7.39 (d, J=2.0 Hz, 1H), 7.26 (d, J=2.0 Hz, 1H), 3.77 (d, J=6.8 Hz, 2H), 2.15 (s, 3H), 0.65-0.60 (m, 2H), 0.40-0.37 (m, 2H). LCMS: 242.1; 244.1 (M+H)$^+$ Step 2: 1-(cyclopropylmethyl)-3-methyl-5-(4,4,5,5-tetramethyl-1,3,2-dioxaborolan-2-yl)pyridin-2-one

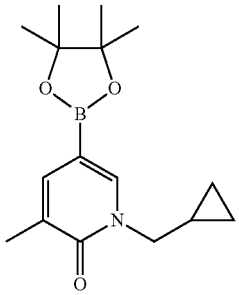 [SMILES: Cc1cc(B2OC(C)(C)C(C)(C)O2)cn(CC2CC2)c1=O]

The title compound of step 1 (480 mg, 1.98 mmol), 4,4,5,5-tetramethyl-2-(tetramethyl-1,3,2-dioxaborolan-2-yl)-1,3,2-dioxaborolane (1.01 g, 3.96 mmol), KOAc (582 mg, 5.94 mmol) and Pd(dppf)Cl$_2$ (146 mg, 0.20 mmol) in dioxane (9 mL) was purged with N$_2$ and heated to 70° C. for 8 h. After silica gel chromatography (PE:EA=30:1~10:1) the title compound (415 mg, ~70% purity on $^1$H NMR, yield: 55.1%) was obtained as light yellow oil. $^1$H NMR: (CDCl$_3$, 400 MHz) δ: 7.69 (s, 1H), 7.49 (s, 1H), 3.82 (d, J=6.8 Hz, 2H), 2.14 (s, 3H), 1.32 (s, 12H), 1.27-1.1.16 (m, 1H), 0.61-0.56 (m, 2H), 0.42-0.39 (m, 2H). LCMS: 290.3 (M+H)$^+$ Step 3: 1-(cyclopropylmethyl)-5-[5-(2,4-difluorophenoxy)-2-methylsulfonylpyrimidin-4-yl]-3-methylpyridin-2-one

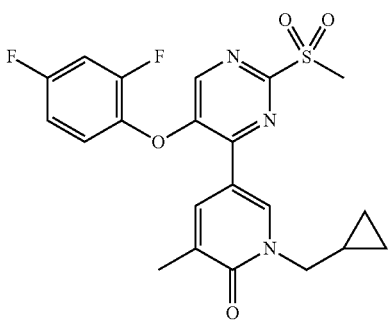 [SMILES: Cc1cc(-c2nc(S(C)(=O)=O)ncc2Oc2ccc(F)cc2F)cn(CC2CC2)c1=O]

The title compound of Example 149, step 3 (200 mg, 0.62 mmol), the title compound of step 2 (250 mg, 0.69 mmol, 70% purity), Pd(dppf)Cl$_2$ (88 mg, 0.12 mmol) and K$_3$PO$_4$ (3 M, 0.6 mL) in dioxane (6 mL) were purged with N$_2$ and heated to 70° C. for 4 h. After silica gel chromatography (PE:EA=3:1~1:1) the title compound (220 mg, yield: 78.8%) was obtained as a yellow solid. $^1$H NMR (CDCl$_3$, 400 MHz) δ 7.45 (d, J=2.0 Hz, 1H), 8.25 (s, 1H), 8.16 (s, 1H), 7.24-7.22 (m, 1H), 7.12-7.10 (m, 1H), 7.10-7.03 (m, 1H), 3.92 (d, J=7.2 Hz, 2H), 3.38 (s, 3H), 2.26 (s, 3H), 1.27-1.21 (m, 1H), 0.65-0.60 (m, 2H), 0.42-0.38 (m, 2H). LCMS: 448.1 (M+H)$^+$ Step 4: N-[4-[1-(cyclopropylmethyl)-5-methyl-6-oxopyridin-3-yl]-5-(2,4-difluorophenoxy)pyrimidin-2-yl]methanesulfonamide

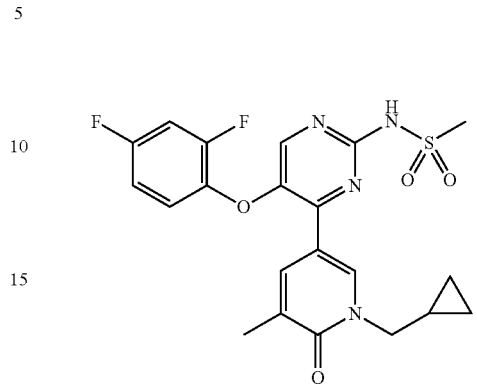

Methanesulfonamide (68 mg, 0.71 mmol), NaH (28 mg, 0.7 mmol, 60% in mineral oil) and the title compound from step 3 (80 mg, 0.18 mmol) in DMF (2 mL) were reacted in a similar manner as Example 152, step 6 to give the title compound (45.00 mg, yield: 54.4%) as an off-white solid. $^1$H NMR (CDCl$_3$, 400 MHz) δ 8.81 (s, 1H), 8.60 (d, J=2.0 Hz, 1H), 8.14 (s, 1H), 8.12 (s, 1H), 7.05-6.98 (m, 2H), 6.91-6.89 (m, 1H), 3.87 (d, J=7.2 Hz, 2H), 3.45 (s, 3H), 2.23 (s, 3H), 1.25-1.22 (m, 1H), 0.64-0.59 (m, 2H), 0.40-0.37 (m, 2H). LCMS: 463.1 (M+H)$^+$ Example 249

N-[4-[1-(cyclopropylmethyl)-5-methyl-6-oxopyridin-3-yl]-5-(2,4-difluorophenoxy)pyrimidin-2-yl]ethanesulfonamide

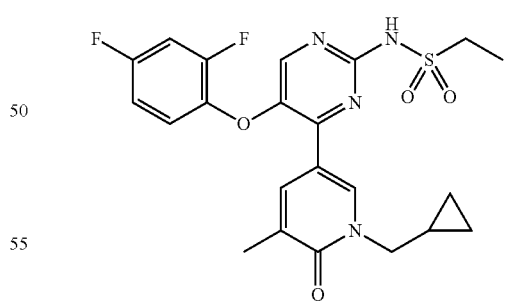

The title compound of Example 248, step 3 was treated with EtSO$_2$NH$_2$ instead of MeSO$_2$NH$_2$ in a manner similar to Example 248, step 4 to give the title compound. $^1$H NMR (CDCl$_3$, 400 MHz) δ 9.09 (s, 1H), 8.60 (s, 1H), 8.16 (s, 1H), 8.11 (s, 1H), 7.04-6.96 (m, 2H), 6.91-6.89 (m, 1H), 3.87 (d, J=7.2 Hz, 2H), 3.64 (q, J=7.2 Hz, 2H), 2.22 (s, 3H), 1.44 (t, J=7.2 Hz, 3H), 1.25-1.23 (m, 1H), 0.62-0.60 (m, 2H), 0.38-0.37 (m, 2H). LCMS: 477.2 (M+H)$^+$

Example 250

1-(cyclopropylmethyl)-5-[6-(2,4-difluorophenoxy)-3-(methylsulfonylmethyl)-4-oxocyclohexa-1,5-dien-1-yl]-3-methylpyridin-2-one

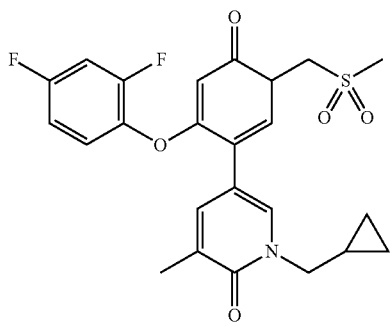 [SMILES: Cc1cc(C2=CC(CS(C)(=O)=O)C(=O)C=C2Oc2ccc(F)cc2F)cn(CC2CC2)c1=O]

The title compound from Example 248, step 2 was reacted with the title compound of Example 381, step 4 in a manner similar to Example 248, step 3 to give the title compound. $^1$H NMR (CDCl$_3$, 400 MHz) δ 7.47 (s, 1H), 7.41 (s, 1H), 7.37 (s, 1H), 7.18-7.16 (m, 1H), 7.04-7.02 (m, 1H), 7.01-6.98 (m, 1H), 5.69 (s, 1H), 5.17 (s, 2H), 3.86 (d, J=7.2 Hz, 2H), 2.99 (s, 3H), 2.20 (s, 3H), 1.28-1.27 (m, 1H), 0.65-0.60 (m, 2H), 0.42-0.39 (m, 2H). LCMS: 477.1 (M+H)$^+$

Example 251

1-cyclopropyl-5-[2-(cyclopropylmethoxy)-5-ethylsulfonylphenyl]-3-methylpyridin-2-one

Step 1: 5-bromo-1-cyclopropyl-3-methylpyridin-2-one

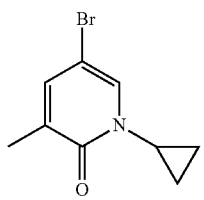

At room temperature, NBS (63 mg, 0.35 mmol) was added to 1-cyclopropyl-3-methylpyridin-2-one (Racine, et. al. Chemical Communications 2013, 49, 67, 7412-7414) (53 mg, 0.36 mmol) in CH$_3$CN (0.7 mL). After 1 h, EA extractive work up from saturated, aqueous NaHCO$_3$ gave the title compound as yellow solids in quantitative yield.

Step 2: 1-cyclopropyl-5-[2-(cyclopropylmethoxy)-5-ethylsulfonylphenyl]-3-methylpyridin-2-one

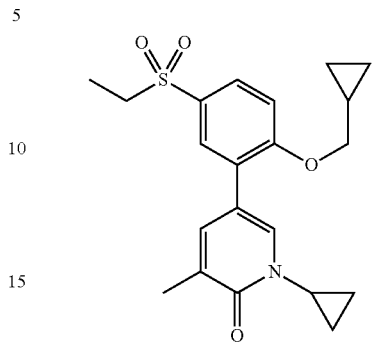

The title compound of step 1 was reacted with 2-[2-(cyclopropylmethoxy)-5-ethylsulfonylphenyl]-4,4,5,5-tetramethyl-1,3,2-dioxaborolane in a manner similar to Example 224, step 5. Silica gel chromatography (40-75% EA in hexane) gave the title compound (31 mg, 0.08 mmol, 42%) as a tan foam that turned to a glass upon standing. $^1$H NMR (400 MHz, CDCl$_3$) δ ppm 0.36-0.42 (m, 2H) 0.60-0.75 (m, 2H) 0.81-1.02 (m, 1H, partially obscured) 1.05-1.37 (m, 7H, partially obscured) 2.22 (s, 3H) 3.12 (q, J=7.41 Hz, 2H) 3.43 (br. s., 1H) 3.94 (d, J=6.82 Hz, 2H) 7.01 (d, J=9.35 Hz, 1H) 7.45-7.53 (m, 1H) 7.62 (br. s., 1H) 7.72-7.83 (m, 2H). LCMS: 388 (M+1)$^+$

Example 252

4-[2-(cyclopropylmethoxy)-5-ethylsulfonylphenyl]-6-methylfuro[2,3-c]pyridin-7-one

Step 1: 4-bromo-6H-furo[2,3-c]pyridin-7-one

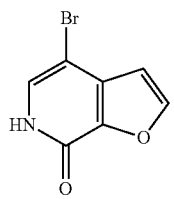

A mixture of 6H-furo[2,3-c]pyridin-7-one (1.0 g, 7.4 mmol) in DMF (30 mL) was treated with NBS (1.32 g, 7.4 mmol) in three equal portions at 0° C. After the resulting mixture was stirred at 15° C. for 2 h, it was treated with water (100 mL) and extracted with EtOAc (30 mL×3). The combined organic layers were washed with brine (30 mL), dried over Na$_2$SO$_4$, filtered, and concentrated in vacuo. The residue was purified by chromatography on silica gel (PE/EtOAc=3:1) to give the title compound (600 mg, 38%) as a yellow solid. $^1$H NMR (DMSO-d6, 400 MHz) δ 11.92 (s, 1H), 8.23 (s, J=2.0 Hz, 1H), 7.47 (s, 1H), 6.88 (m, 1H), 6.88 (s, 1H).

Step 2: 4-bromo-6-methylfuro[2,3-c]pyridin-7-one

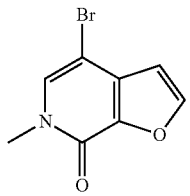

To a solution of the title compound of step 1 (500 mg, 2.3 mmol) stirred at 0° C. in DMF (5 mL) was added NaH (68 mg, 2.81 mmol, 60% in mineral oil). After stirring at 0° C. for 30 min, methyl iodide (400 mg, 2.8 mmol) was added dropwise. The ice bath was removed, and mixture was stirred at rt for 4 h. The reaction mixture was treated with saturated NH$_4$Cl (aq. 30 mL) and extracted with EtOAc (30 mL×2). The combined organic layers were washed with brine (30 mL), dried over Na$_2$SO$_4$, filtered, and concentrated in vacuo. The residue was purified by chromatography on silica gel (PE/EtOAc=10:1) to give the title compound (500 mg, 94%). $^1$H NMR (CDCl3, 400 MHz) δ 7.78 (d, J=2.0 Hz, 1H), 7.30 (s, 1H), 6.70 (d, J=2.0 Hz, 1H), 3.66 (s, 3H). LCMS (M+H)$^+$=229.

Step 3: 4-[2-(cyclopropylmethoxy)-5-ethylsulfonyl-phenyl]-6-methylfuro[2,3-c]pyridin-7-one

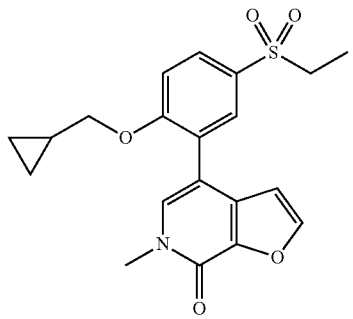 [SMILES: CCS(=O)(=O)c1ccc(OCC2CC2)c(-c2cn(C)c(=O)c3occc23)c1]

A mixture of the title compound of step 2 (150 mg, 0.66 mmol), 2-[2-(cyclopropylmethoxy)-5-ethylsulfonylphenyl]-4,4,5,5-tetramethyl-1,3,2-dioxaborolane (336 mg, 1.0 mmol), NaHCO$_3$ (167 mg, 1.99 mmol), Pd(dppf)Cl$_2$ (35 mg, 0.048 mmol) in dioxane/H$_2$O (10 mL/2.5 mL) was bubbled with argon for 5 min. The sealed vial was stirred at 80° C. for 18 h. The reaction mixture was concentrated, treated with DCM (30 mL), washed with water (30 mL) and brine (30 mL), dried over Na$_2$SO$_4$, filtered and concentrated in vacuo. The resulting residue was purified by prep-HPLC to give the title compound (63 mg, 25%) as a yellow solid. $^1$H NMR (CDCl$_3$, 400 MHz) δ 7.90-7.86 (m, 2H), 7.75 (d, J=1.6 Hz, 1H), 7.31 (s, 1H), 7.09 (d, J=8.4 Hz, 1H), 6.57 (d, J=1.6 Hz, 1H), 3.95 (d, J=6.8 Hz, 2H), 3.74 (s, 3H), 3.18-3.12 (q, J=7.6 Hz, 2H), 1.34 (t, J=7.6 Hz, 3H), 1.16-1.15 (m, 1H), 0.61-0.55 (m, 2H), 0.31-0.27 (m, 2H). LCMS (M+H)$^+$=388.

Example 253

N-[4-(2,4-difluorophenoxy)-3-(6-methyl-7-oxofuro[2,3-c]pyridin-4-yl)phenyl]ethanesulfonamide

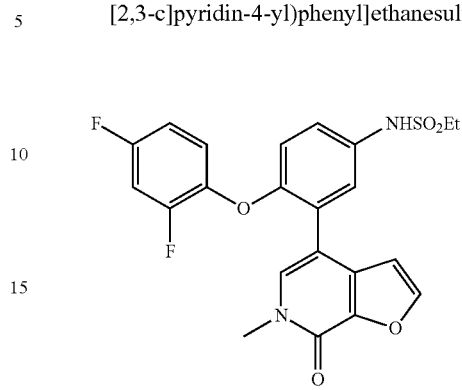

The title compound was prepared in a manner similar to step 3 of Example 252, by substituting N-[4-(2,4-difluorophenoxy)-3-(4,4,5,5-tetramethyl-1,3,2-dioxaborolan-2-yl)phenyl]ethanesulfonamide for 2-[2-(cyclopropylmethoxy)-5-ethylsulfonylphenyl]-4,4,5,5-tetramethyl-1,3,2-dioxaborolane. $^1$H NMR (CDCl$_3$, 400 MHz) δ 7.74 (s, 1H) 7.38 (m, 2H) 7.15 (m, 1H) 6.93-9.92 (m, 2H) 6.82-6.76 (m, 3H) 6.44 (s, 1H) 3.72 (s, 3H) 3.19-3.16 (q, J=7.2 Hz, 2H) 1.45 (t, J=7.2 Hz, 3H). LCMS (M+H)$^+$=461.

Example 254

4-[2-(cyclopropylmethoxy)-5-methylsulfonylphenyl]-6-methylfuro[2,3-c]pyridin-7-one

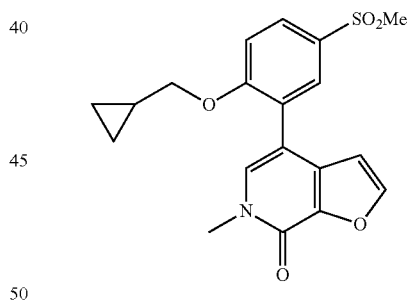

A mixture of 2-[2-(cyclopropylmethoxy)-5-methylsulfonylphenyl]-4,4,5,5-tetramethyl-1,3,2-dioxaborolane (115 mg, 0.33 mmol), 4-bromo-6-methyl-6H,7H-furo[2,3-c]pyridin-7-one (75 mg, 0.33 mmol), K$_3$PO$_4$ (175 mg, 0.83 mmol), Pd(dppf)Cl$_2$ (24 mg, 10%) in dioxane/H$_2$O (2.2 mL/200 uL) was bubbled with nitrogen for 5 min. The sealed vial was stirred at 70° C. for 90 min. The reaction mixture was filtered through a short plug of celite; the celite plug was washed with EtOAc (15 mL). The filtrate was washed with water and brine. The organic layer was dried over sodium sulfate, filtered and concentrated in vacuo to afford a brown residue. The resulting residue was purified by prep-HPLC to afford the title compound (60 mg, 49%) as a white solid. LCMS (M+H)$^+$=374.

Example 255

N-[4-(cyclopropylmethoxy)-3-(6-methyl-7-oxofuro[2,3-c]pyridin-4-yl)phenyl]ethanesulfonamide

Step 1: 2-bromo-1-(cyclopropylmethoxy)-4-nitrobenzene

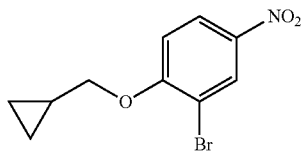

A 0.2 M solution of cyclopropyl methanol (441 uL, 5.5 mmol) in THF stirred at 0° C. under an atmosphere of nitrogen was treated with 2 equal portions of KOtBu (579 mg, 5.2 mmol). After 5 min the ice bath was removed; the mixture was stirred for 30 min at rt before resubmerging in the ice bath and cooling to 0° C. A solution of 2-bromo-1-fluoro-4-nitrobenzene (1 g, 4.5 mmol) in THF (3 mL) was added dropwise. After 20 min, the ice bath was removed and the mixture was stirred overnight. The reaction mixture was quenched with water (50 mL) and extracted with EtOAc (3×50 ml). The combined organic layers were washed brine (30 mL), dried over $Na_2SO_4$, filtered and concentrated in vacuo. The resulting residue was purified by silica gel column chromatography using a gradient of EtOAc (5 to 50%) in hexanes to afford the title compound (1.07 g, 88%) as a yellow solid.

Step 2: 3-bromo-4-(cyclopropylmethoxy)aniline

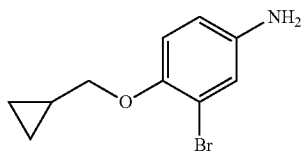 [SMILES: Nc1ccc(OCC2CC2)c(Br)c1]

A mixture of 2-bromo-1-(cyclopropylmethoxy)-4-nitrobenzene (1.07 g, 3.9 mmol), ammonium chloride (421 mg, 7.8 mmol), and iron powder (1.1 g, 20 mmol) suspended in THF (6.5 mL), water (2.5 mL) and ethanol (6.5 mL) was heated to 95° C. using microwave irradiation (normal) for 3 h. The crude reaction mixture was filtered through a short plug of celite; the celite plug was washed with MeOH (~10 mL). The resulting filtrate was concentrated in vacuo. The resulting residue was diluted with EtOAc (50 ml) and washed with saturated bicarbonate solution (aq), dried over anhydrous magnesium sulfate, filtered, and concentrated in vacuo to afford the title compound, (939 mg, 90%). The material was carried forward without any further purification. LCMS $(M+H)^+=242$.

Step 3: N-[3-bromo-4-(cyclopropylmethoxy)phenyl]ethane-1-sulfonamide

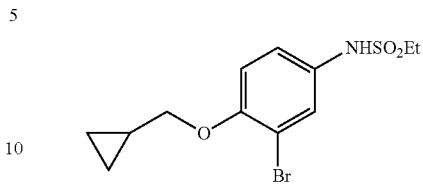

Ethylsulfonyl chloride (233 uL, 2.4 mmol) was added to a stirred solution of 3-bromo-4-(cyclopropylmethoxy)aniline (520 mg, 2.2 mmol) and pyridine (520 uL, 6.5 mmol) in DCM (4 mL) at 0° C. under nitrogen. After the mixture was allowed to warm to rt and stir for 12 h, it was treated with 1N HCl (15 mL) and extracted with DCM (3×15 mL); the combined organic extracts were washed with saturated bicarbonate solution (aq), dried over sodium sulfate, filtered and concentrated in vacuo. The resulting residue was purified by silica gel column chromatography using a gradient of EtOAc (10 to 100%) in hexanes to afford the title compound (711 mg, 98%) as a yellow solid. LCMS $(M+H)^+=335$.

Step 4: N-[4-(cyclopropylmethoxy)-3-(tetramethyl-1,3,2-dioxaborolan-2-yl)phenyl]ethane-1-sulfonamide

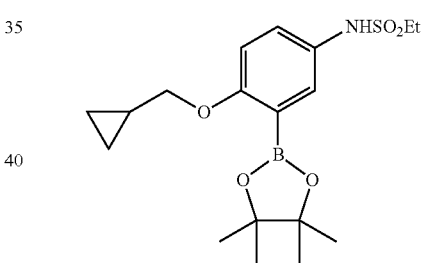

A mixture of N-[3-bromo-4-(cyclopropylmethoxy)phenyl]ethane-1-sulfonamide (711 mg, 2.1 mmol), 4,4,5,5-tetramethyl-2-(tetramethyl-1,3,2-dioxaborolan-2-yl)-1,3,2-dioxaborolane (1.1 g, 4.3 mmol), KOAc (470 mg, 4.8 mmol), $Pd_2(dba)_3$ (59 mg. 3%), and 1,3,5,7-Tetramethyl-6-phenyl-2,4,8-trioxa-6-phosphaadamantane (62 mg, 10%) was suspended in anhydrous dioxane (14 mL). The stirred mixture was capped and purged with nitrogen for 6 min using an oil bubbler as an outlet. After the nitrogen inlet and outlet were removed, the capped flask was stirred at 70° C. for 3 h. After cooling to about 35° C., the reaction mixture was filtered through a short plug of celite; the celite plug was washed with EtOAc (75 mL). The filtrate was treated with water and extracted with EtOAc; the combined organic layers were washed with brine, dried over sodium sulfate, filtered and concentrated in vacuo to afford a tan residue. The residue was purified by silica gel column chromatography using a gradient of EtOAc (5 to 100%) in hexanes to afford the title compound (527 mg, 65%). LCMS $(M+H)^+=382$.

Step 5: N-[4-(cyclopropylmethoxy)-3-(6-methyl-7-oxofuro[2,3-c]pyridin-4-yl)phenyl]ethanesulfonamide

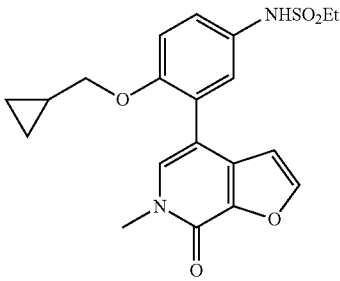

A mixture of N-[4-(cyclopropylmethoxy)-3-(tetramethyl-1,3,2-dioxaborolan-2-yl)phenyl]ethane-1-sulfonamide (138 mg, 0.38 mmol), 4-bromo-6-methyl-6H,7H-furo[2,3-c]pyridin-7-one (75 mg, 0.33 mmol), $K_3PO_4$ (175 mg, 0.83 mmol), Pd(dppf)Cl$_2$ (24 mg, 10%) in dioxane (2.2 mL) and H$_2$O (200 uL) was bubbled with nitrogen for 5 min. The sealed vial was stirred at 70° C. for 4 h. After the reaction mixture was filtered through a short plug of celite, the celite plug was washed with EtOAc (15 mL). The filtrate was washed with water and brine; the organic layer was dried over sodium sulfate, filtered and concentrated in vacuo to afford a tan residue. The resulting residue was purified by prep-HPLC to afford the title compound (21 mg, 16%) as a tan solid. 1H NMR (400 MHz, DMSO-d6) δ ppm 0.15-0.28 (m, 2H) 0.35-0.52 (m, 2H) 0.95-1.13 (m, 1H) 1.14-1.26 (m, 3H) 2.98-3.09 (m, 2H) 3.57-3.65 (m, 3H) 3.77-3.87 (m, 2H) 7.04-7.22 (m, 3H) 7.55-7.64 (m, 1H) 8.05-8.17 (m, 1H) 9.49-9.57 (m, 1H). LCMS (M+H)$^+$=403.

Example 256

N-[6-(2,4-difluorophenoxy)-5-(6-methyl-7-oxofuro[2,3-c]pyridin-4-yl)pyridin-3-yl]ethanesulfonamide

Step 1: 3-bromo-2-(2,4-difluorophenoxy)-5-nitropyridine

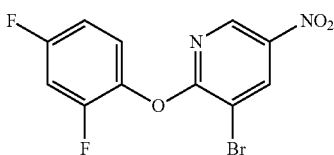 [SMILES: O=[N+]([O-])c1cnc(Oc2ccc(F)cc2F)c(Br)c1]

A solution of 3-bromo-2-chloro-5-nitropyridine (2.4 g, 10 mmol) and 2,4-difluorophenol (1 mL, 11 mmol) in NMP (20 ml) was treated with cesium carbonate (3.9 g, 12 mmol). The resulting mixture was heated to 60° C. for 12 h. The mixture was treated with water (100 ml) and extracted with EtOAc (3×50 ml); the combined organic extracts were washed with saturated bicarbonate solution (aq), dried over sodium sulfate, filtered and concentrated in vacuo to afford a yellow solid. The solid was purified by silica gel column chromatography (gradient of 5 to 30% EtOAc in hexanes) to afford the free base of the title compound (2 g, 59%) as a yellow solid. LCMS (M+H)$^+$=332.

Step 2: 5-bromo-6-(2,4-difluorophenoxy)pyridin-3-amine

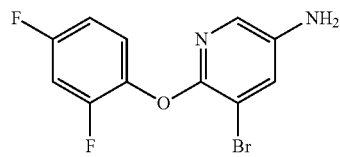 [SMILES: Nc1cnc(Oc2ccc(F)cc2F)c(Br)c1]

A mixture of 3-bromo-2-(2,4-difluorophenoxy)-5-nitropyridine (1.9 g, 5.9 mmol), ammonium chloride (637 mg, 11.8 mmol), and iron powder (1.65 g, 30 mmol) suspended in THF (10 mL), water (3 mL) and ethanol (10 mL) was heated to 90° C. using microwave irradiation (normal) for 5 h. The crude reaction mixture was filtered through a short plug of celite; the celite plug was washed with warm (50° C.) MeOH (~50 mL). The resulting filtrate was concentrated in vacuo. The resulting residue was diluted with EtOAc (100 ml) and washed with saturated bicarbonate solution (aq), dried over anhydrous magnesium sulfate, filtered, and concentrated in vacuo to afford the title compound, (824 mg, 46%). LCMS (M+H)$^+$=302.

Step 3: 6-(2,4-difluorophenoxy)-5-(4,4,5,5-tetramethyl-1,3,2-dioxaborolan-2-yl)pyridin-3-amine

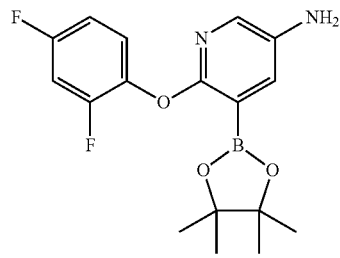 [SMILES: CC1(C)OB(c2cc(N)cnc2Oc2ccc(F)cc2F)OC1(C)C]

A mixture of 5-bromo-6-(2,4-difluorophenoxy)pyridin-3-amine (400 mg, 1.33 mmol), 4,4,5,5-tetramethyl-2-(tetramethyl-1,3,2-dioxaborolan-2-yl)-1,3,2-dioxaborolane (675 mg, 2.7 mmol), KOAc (325 mg, 3.3 mmol), Pd$_2$(dba)$_3$ (36 mg, 3%), and 1,3,5,7-tetramethyl-6-phenyl-2,4,8-trioxa-6-phosphaadamantane (38 mg, 10%) was suspended in dioxane (9 mL). The stirred reaction mixture was capped and purged with nitrogen for 5 to 7 min using an oil bubbler as an outlet. After the nitrogen inlet and outlet were removed, the capped vial was stirred at 80° C. for 3 h. After cooling to rt, the reaction mixture was filtered through a short plug of celite; the celite plug was washed with EtOAc (50 mL). The filtrate was treated with water and extracted with EtOAc; the combined organic layers were washed with brine, dried over sodium sulfate, filtered and concentrated in vacuo to afford a tan residue. The residue was purified by silica gel column chromatography using a gradient (20-70%) of EtOAc in hexanes to afford the title compound (163 mg, 35%). LCMS (M+H)$^+$=349.

Step 4: N-[6-(2,4-difluorophenoxy)-5-(4,4,5,5-tetramethyl-1,3,2-dioxaborolan-2-yl)pyridin-3-yl]ethanesulfonamide

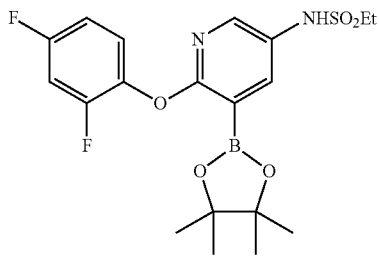

Ethylsulfonyl chloride (50 uL, 52 mmol) was added to a stirred solution of 6-(2,4-difluorophenoxy)-5-(4,4,5,5-tetramethyl-1,3,2-dioxaborolan-2-yl)pyridin-3-amine (163 mg, 0.5 mmol) and pyridine (113 uL) in DCM (2.4 mL) at 0° C. under nitrogen. After the mixture was allowed to warm to rt and stir for 12 h, it was treated with water (15 mL) and extracted with DCM (3×15 mL); the combined organic extracts were washed with saturated bicarbonate solution (aq), dried over sodium sulfate, filtered and concentrated in vacuo. The resulting residue was purified by silica gel column chromatography using a gradient of EtOAc (0 to 100%) in DCM to afford the title compound (181 mg, 88%) as a tan solid. LCMS (M+H)$^+$=441.

Step 5: N-[6-(2,4-difluorophenoxy)-5-(6-methyl-7-oxofuro[2,3-c]pyridin-4-yl)pyridin-3-yl]ethanesulfonamide

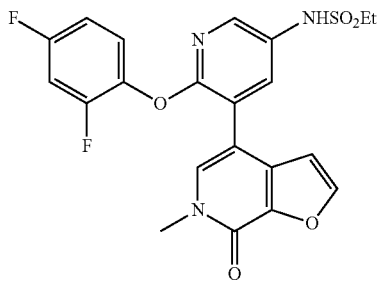

A mixture of N-[6-(2,4-difluorophenoxy)-5-(4,4,5,5-tetramethyl-1,3,2-dioxaborolan-2-yl)pyridin-3-yl]ethanesulfonamide (145 mg, 0.38 mmol), 4-bromo-6-methyl-6H,7H-furo[2,3-c]pyridin-7-one (75 mg, 0.33 mmol), K$_3$PO$_4$ (175 mg, 0.83 mmol), Pd(dppf)Cl$_2$ (24 mg, 10%) in dioxane/H$_2$O (2.2 mL/200 uL) was bubbled with nitrogen for 5 min. The sealed vial was stirred at 70° C. for 4 h. After the reaction mixture was filtered through a short plug of celite, the plug was washed with EtOAc (15 mL). The filtrate was washed with water and brine, the organic layer was dried over sodium sulfate, filtered and concentrated in vacuo to afford a tan residue. The resulting residue was purified by prep-HPLC to afford the title compound (50 mg, 33%) as a white solid. $^1$H NMR (400 MHz, DMSO-d6) δ ppm 1.18-1.28 (m, 3H) 3.10-3.21 (m, 2H) 3.59-3.65 (m, 3H) 6.85-6.95 (m, 1H) 7.07-7.19 (m, 1H) 7.35-7.51 (m, 2H) 7.73-7.79 (m, 1H) 7.80-7.85 (m, 1H) 7.90-7.97 (m, 1H) 8.14-8.20 (m, 1H) 9.78-10.09 (m, 1H). LCMS (M+H)$^+$=461.

Example 257

N-[6-(cyclopropylmethoxy)-5-(6-methyl-7-oxofuro[2,3-c]pyridin-4-yl)pyridin-3-yl]ethanesulfonamide

Step 1: 3-bromo-2-(cyclopropylmethoxy)-5-nitropyridine

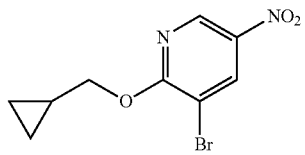 [SMILES: O=[N+]([O-])c1cnc(OCC2CC2)c(Br)c1]

A solution of 3-bromo-2-chloro-5-nitropyridine (2.4 g, 10 mmol) and cyclopropylmethanol (970 uL, 12 mmol) in THF (50 ml) was treated with KOtBu (3.3 g, 15 mmol). After stirring at rt for 12 h, the mixture was treated with water (150 ml) and extracted with EtOAc (3×50 ml); the combined organic extracts were washed with brine, dried over sodium sulfate, filtered and concentrated in vacuo to afford a yellow solid. The solid was purified by silica gel column chromatography using a gradient of EtOAc (5 to 30%) in hexanes to afford the title compound (1.3 g, 48%) as a yellow solid. LCMS (M+H)$^+$=274.

Step 2: 5-bromo-6-(cyclopropylmethoxy)pyridin-3-amine

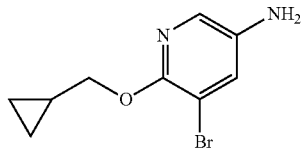 [SMILES: Nc1cnc(OCC2CC2)c(Br)c1]

A mixture of 3-bromo-2-(cyclopropylmethoxy)-5-nitropyridine (1 g, 3.7 mmol), ammonium chloride (600 mg, 11.1 mmol), and iron powder (1.05 g, 19 mmol) suspended in THF (6.2 mL), water (2.3 mL) and ethanol (6.2 mL) was heated to 100° C. using microwave irradiation (normal) for 5 h. The crude reaction mixture was filtered through a short plug of celite; the celite plug was washed with warm (50° C.) MeOH (50 mL). The resulting filtrate was concentrated in vacuo. The resulting residue was diluted with EtOAc (100 ml) and washed with saturated bicarbonate solution (aq), dried over anhydrous magnesium sulfate, filtered, and concentrated in vacuo to afford the title compound, (539 mg, 60%). LCMS (M+H)$^+$=244.

Step 3: N-[5-bromo-6-(cyclopropylmethoxy)pyridin-3-yl]ethanesulfonamide

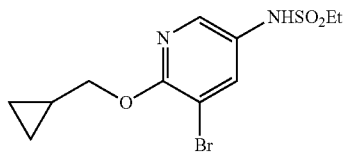

Ethylsulfonyl chloride (170 uL, 1.8 mmol) was added to a stirred solution of 5-bromo-6-(cyclopropylmethoxy)pyridin-3-amine (440 mg, 1.8 mmol) and pyridine (725 uL) in DCM (4.5 mL) at 0° C. under nitrogen. After the mixture was allowed to warm to rt and stir for 12 h, it was treated with 1N HCl (15 mL) and extracted with DCM (3×15 mL); the combined organic extracts were washed with saturated bicarbonate solution (aq), dried over sodium sulfate, filtered and concentrated in vacuo. The resulting residue was purified by silica gel column chromatography using a gradient of EtOAc (0 to 100%) in DCM to afford the title compound (181 mg, 88%) as a tan solid. LCMS (M+H)$^+$=336.

Step 4: N-[6-(cyclopropylmethoxy)-5-(4,4,5,5-tetramethyl-1,3,2-dioxaborolan-2-yl)pyridin-3-yl]ethanesulfonamide

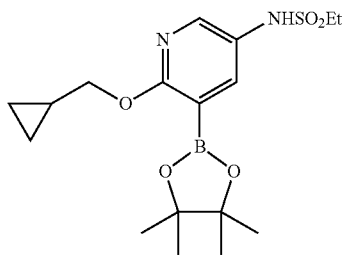

A mixture of N-[5-bromo-6-(cyclopropylmethoxy)pyridin-3-yl]ethanesulfonamide (150 mg, 0.45 mmol), 4,4,5,5-tetramethyl-2-(tetramethyl-1,3,2-dioxaborolan-2-yl)-1,3,2-dioxaborolane (285 mg, 1.13 mmol), KOAc (132 mg, 1.35 mmol), and Pd(dppf)$_2$(Cl)$_2$ (33 mg, 10%) was suspended in anhydrous dioxane (5 mL). The stirred reaction mixture was capped and purged with nitrogen for 5 min using an oil bubbler as an outlet. After the nitrogen inlet and outlet were removed, the capped vial was stirred at 70° C. for 3 h. After cooling to rt, the reaction mixture was filtered through a short plug of celite; the celite plug was washed with EtOAc. The filtrate was treated with water and separated; after the aqueous layer was washed with EtOAC (3×25 mL), the combined organic layers were washed with brine, dried over sodium sulfate, filtered and concentrated in vacuo to afford a dark tan residue. The residue was purified by silica gel column chromatography using a gradient of 5 to 70% EtOAc in hexanes to afford the title compound (112 mg, 65%). LCMS (M+H)$^+$=383.

Step 5: N-[6-(cyclopropylmethoxy)-5-(6-methyl-7-oxofuro[2,3-c]pyridin-4-yl)pyridin-3-yl]ethanesulfonamide

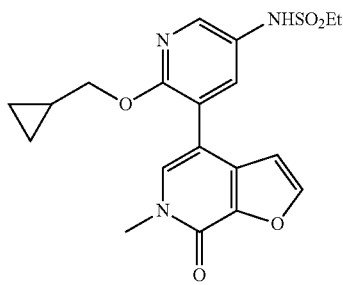

A mixture of N-[6-(cyclopropylmethoxy)-5-(4,4,5,5-tetramethyl-1,3,2-dioxaborolan-2-yl)pyridin-3-yl]ethanesulfonamide (145 mg, 0.38 mmol), 4-bromo-6-methyl-6H,7H-furo[2,3-c]pyridin-7-one (25 mg, 0.11 mmol), K$_3$PO$_4$ (58 mg, 0.28 mmol), Pd(dppf)Cl$_2$ (8 mg, 10%) in dioxane/H$_2$O (1 mL/100 uL) was bubbled with nitrogen for 5 min. The sealed vial was stirred at 65° C. for 12 h. The reaction mixture was filtered through a short plug of celite; the celite plug was washed with EtOAc (15 mL). The filtrate was washed with water and brine; the organic layer was dried over sodium sulfate, filtered and concentrated in vacuo to afford a tan residue. The resulting residue was purified by prep-HPLC to afford the title compound (21 mg, 48%) as a white solid. $^1$H NMR (400 MHz, DMSO-d6) δ ppm 0.23-0.32 (m, 2H) 0.41-0.52 (m, 2H) 1.08-1.19 (m, 1H) 1.20-1.29 (m, 3H) 3.05-3.16 (m, 2H) 3.58-3.63 (m, 3H) 3.64-3.66 (m, 1H) 4.08-4.17 (m, 2H) 6.72-6.82 (m, 1H) 7.58-7.65 (m, 1H) 7.67-7.73 (m, 1H) 7.95-8.06 (m, 1H) 8.10-8.18 (m, 1H) 9.41-9.86 (m, 1H). LCMS (M+H)$^+$=404.

Example 258

6-methyl-4-[5-(methylsulfonylmethyl)-2-(2,2,2-trifluoroethoxy)phenyl]furo[2,3-c]pyridin-7-one Step 1: 6-methyl-4-(4,4,5,5-tetramethyl-1,3,2-dioxaborolan-2-yl)furo[2,3-c]pyridin-7-one

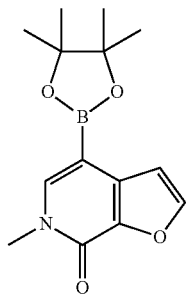 [SMILES: Cn1cc(B2OC(C)(C)C(C)(C)O2)c2ccoc2c1=O]

A solution of 4-bromo-6-methylfuro[2,3-c]pyridin-7-one (200 mg, 0.88 mmol), 4,4,5,5-tetramethyl-2-(tetramethyl-1,3,2-dioxaborolan-2-yl)-1,3,2-dioxaborolane (447 mg, 1.76 mmol), KOAc (259 mg, 2.64 mmol), Pd$_2$(dba)$_3$ (82 mg, 0.09 mmol), X-Phos (52 mg, 0.11 mmol) in dioxane (5 mL) was bubbled with nitrogen for 5 minutes and then stirred at 70° C. for 12 h. The reaction mixture was concentrated, treated with DCM (30 mL), washed with water (30 mL) and brine (30 mL), dried over Na$_2$SO$_4$, filtered and concentrated. The residue was purified by column chromatography (PE:EA=20:1-5:1) to give the title compound (130 mg, 54%) as a gray solid. $^1$H NMR (CDCl3, 400 MHz) δ 7.73 (s, 1H) 7.62 (s, 1H) 7.01 (s, 1H) 3.68 (s, 3H) 1.35 (s, 12H). LCMS (M+H)$^+$=276.

Step 2: 6-methyl-4-[5-(methylsulfonylmethyl)-2-(2,2,2-trifluoroethoxy)phenyl]furo[2,3-c]pyridin-7-one

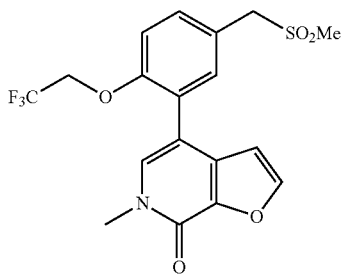 [SMILES: Cn1cc(-c2cc(CS(C)(=O)=O)ccc2OCC(F)(F)F)c2ccoc2c1=O]

A mixture of 2-bromo-4-(methylsulfonylmethyl)-1-(2,2,2-trifluoroethoxy)benzene (100 mg, 0.29 mmol), 6-methyl-4-(4,4,5,5-tetramethyl-1,3,2-dioxaborolan-2-yl)furo[2,3-c]pyridin-7-one (96 mg, 0.35 mmol), K$_3$PO$_4$ (184 mg, 0.87 mmol), Pd(dppf)Cl$_2$ (22 mg, 10%) in dioxane/H$_2$O (2 mL/1 mL) was bubbled with nitrogen for 5 min. The sealed vial was heated to 70° C. for 2 h. The reaction mixture was filtered through a short plug of celite; the celite plug was washed with EtOAc (15 mL). The filtrate was washed with water and brine; the organic layer was dried over sodium sulfate, filtered and concentrated in vacuo. The resulting residue was purified by prep-HPLC to afford the title compound (40 mg, 33%) as an off-white solid. $^1$H NMR (CDCl$_3$, 400 MHz) δ 7.76 (d, J=2.0 Hz, 1H) 7.53 (d, J=2.0 Hz, 1H) 7.41-7.38 (m, 1H) 7.37 (s, 1H) 7.02 (d, J=8.4, 1H) 6.72 (d, J=2.0 Hz, 2H) 4.37 (q, J=8.0 Hz, 2H) 4.27 (s, 2H) 3.73 (s, 3H) 2.89 (s, 3H). LCMS (M+H)$^+$=416.

Example 259

4-[3-(cyclopropylmethoxy)-6-methylsulfonylpyridin-2-yl]-6-methylfuro[2,3-c]pyridin-7-one

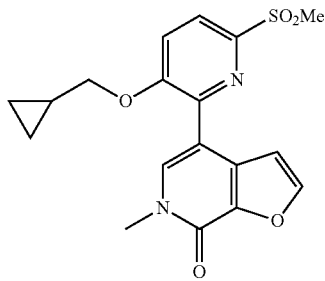 [SMILES: Cn1cc(-c2nc(S(C)(=O)=O)ccc2OCC2CC2)c2ccoc2c1=O]

A mixture of 6-methyl-4-(4,4,5,5-tetramethyl-1,3,2-dioxaborolan-2-yl)furo[2,3-c]pyridin-7-one (50 mg, 0.18 mmol), 3-(cyclopropylmethoxy)-2-iodo-6-methylsulfonylpyridine (53 mg, 0.15 mmol), K$_3$PO$_4$ (114 mg, 0.54 mmol), Pd(dppf)Cl$_2$ (13 mg, 0.018 mmol) in dioxane (5 mL) was bubbled with nitrogen for 5 min and then stirred at 70° C. for 12 h. The reaction mixture was concentrated, treated with DCM (30 mL), washed with water (30 mL) and brine (30 mL), dried over Na$_2$SO$_4$, filtered and concentrated. The residue was purified by prep-HPLC to give the title compound (35 mg, yield: 52%) as an off-white solid.

$^1$H NMR (CDCl$_3$, 400 MHz) δ 8.42 (s, 1H) 8.10 (s, 1H) 7.81 (d, J=1.6 Hz, 1H) 7.51 (s, 1H) 6.66 (d, J=1.6 Hz, 1H) 4.08 (d, J=7.6 Hz, 2H) 3.77 (s, 3H) 3.26 (s, 3H) 1.26-1.19 (m, 1H) 0.68-0.63 (m, 2H) 0.37-0.33 (m, 2H). LCMS (M+H)$^+$=375.

Example 260

2-chloro-4-[2-(cyclopropylmethoxy)-5-methylsulfonylphenyl]-6-methylfuro[2,3-c]pyridin-7-one Step 1: 2-chloro-7-methoxyfuro[2,3-c]pyridine

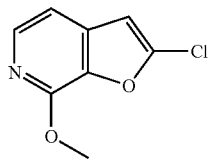

A 0.13 M solution of 7-methoxyfuro[2,3-c]pyridine (250 mg, 1.7 mmol) in THF stirred at −78° C. under an atmosphere of nitrogen was treated with n-BuLi (1.6M in hexanes, 450 uL, 5.2 mmol) dropwise over 30 sec. The mixture was warmed gradually to −15° C. over a period of 7 to 10 min. After 1 h at −15° C., the mixture was cooled to −65° C. and was treated with a 0.26 M solution of hexachloroethane (473 mg, 2 mmol) in THF by dropwise addition over 3 min. After stirring at −65° C. for 15 min, the mixture was allowed to gradually warm to rt. After the mixture was allowed to stir overnight, it was quenched with water (5 mL) and extracted with EtOAc (3×15 ml). The combined organic layers were washed brine (10 mL), dried over Na$_2$SO$_4$, filtered and concentrated in vacuo. The resulting residue was purified by silica gel column chromatography using a gradient of EtOAc (5 to 30%) in hexanes to afford the title compound (266 mg, 87%) as an amber oil. $^1$H NMR (400 MHz, DMSO-d$_6$) δ ppm 3.99-4.08 (m, 3H) 7.13 (s, 1H) 7.25 (d, J=5.31 Hz, 1H) 7.95 (d, J=5.31 Hz, 1H). LCMS (M+H)$^+$=184.

Step 2: 2-chlorofuro[2,3-c]pyridin-7-ol

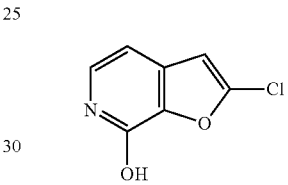

A 0.25M solution of 2-chloro-7-methoxyfuro[2,3-c]pyridine (263 mg, 1.4 mmol) in DCM stirred at −0° C. under an atmosphere of nitrogen was treated with BBr$_3$ (1 M in DCM, 4.3 mL, 4.3 mmol) dropwise over 5 min. The mixture was allowed to warm gradually to rt. After the mixture was allowed to stir overnight, it was poured into ice water and extracted with DCM (3×15 mL). The combined organic layers were washed with water and brine (10 mL), dried over Na$_2$SO$_4$, filtered and concentrated in vacuo. The resulting residue was purified by silica gel column chromatography using a gradient of EtOAc (15 to 75%) in hexanes to afford the title compound (115 mg, 47%) as light yellow solid. LCMS (M+H)$^+$=170.

Step 3: 4-bromo-2-chlorofuro[2,3-c]pyridin-7-ol

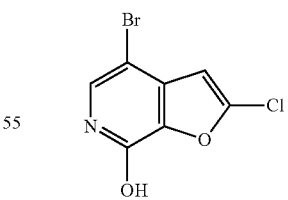

A 0.15 M solution of 2-chlorofuro[2,3-c]pyridin-7-ol (113 mg, 0.7 mmol) in DMF stirred in the dark at 0° C. under an atmosphere of nitrogen was treated with NBS (120 mg, 0.7 mmol) in three equal portions. The ice bath was removed; the mixture was stirred at rt for 3 h. The reaction mixture was treated with a 10% aqueous solution of sodium thiosulfate (5 ml) and was extracted with EtOAc (3×30 mL). The combined organic layers were washed with water (15 mL), brine (20 mL), dried over Na₂SO₄, filtered, and concentrated in vacuo. The residue was purified by chromatography on silica gel (hexanes/EtOAc=4:1) to afford the title compound (145 mg, 87%) as a white solid. LCMS (M+H)⁺=249.

Step 4:
4-bromo-2-chloro-6-methylfuro[2,3-c]pyridin-7-one

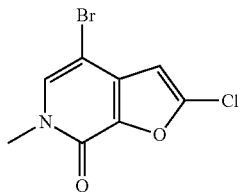

A 0.2 M solution of 4-bromo-2-chlorofuro[2,3-c]pyridin-7-ol (143 mg, 0.6 mmol) and K₂CO₃ (200 mg, 1.45 mmol) in DMF stirred at 0° C. under an atmosphere of nitrogen was treated with MeI (99 mg, 0.7 mmol). The ice bath was removed; the mixture was stirred at rt overnight. The reaction mixture was treated water (15 mL) and was extracted with EtOAc (3×10 mL). The combined organic layers were washed with water (15 mL), brine (20 mL), dried over Na₂SO₄, filtered, and concentrated in vacuo. The residue was purified by chromatography on silica gel using a gradient of EtOAc (10 to 100%) in hexanes to afford the title compound (113 mg, 85%) as a white solid. LCMS (M+H)⁺=263.

Step 5: 2-chloro-4-[2-(cyclopropylmethoxy)-5-methylsulfonylphenyl]-6-methylfuro[2,3-c]pyridin-7-one

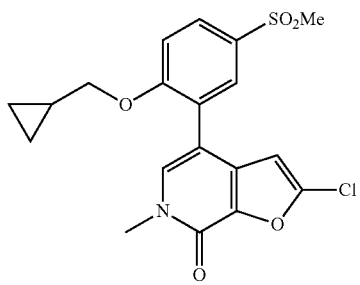 [SMILES: Cn1cc(-c2cc(S(C)(=O)=O)ccc2OCC2CC2)c2cc(Cl)oc2c1=O]

A mixture of 2-[2-(cyclopropylmethoxy)-5-methylsulfonylphenyl]-4,4,5,5-tetramethyl-1,3,2-dioxaborolane (33 mg, 0.09 mmol), 4-bromo-2-chloro-6-methylfuro[2,3-c]pyridin-7-one (25 mg, 0.09 mmol), K₃PO₄ (50 mg, 0.24 mmol), Pd(dppf)Cl₂ (7 mg, 10%) in dioxane/H₂O (700 uL/70 uL) was bubbled with nitrogen for 5 min. The sealed vial was stirred at 70° C. for 90 min. The reaction mixture was filtered through a short plug of celite; the celite plug was washed with EtOAc (10 mL). The filtrate was washed with water and brine; the organic layer was dried over sodium sulfate, filtered and concentrated in vacuo to afford a tan residue. The resulting residue was purified by prep-HPLC to afford the title compound (27 mg, 69%) as an off-white solid. ¹H NMR (400 MHz, DMSO-d₆) δ ppm 0.23-0.34 (m, 2H) 0.44-0.55 (m, 2H) 1.00-1.13 (m, 1H) 3.19-3.24 (m, 3H) 3.61 (s, 3H) 3.94-4.05 (m, 2H) 6.82-6.89 (m, 1H) 7.10-7.16 (m, 1H) 7.26-7.35 (m, 1H) 7.70-7.78 (m, 1H) 7.87-7.94 (m, 1H). LCMS (M+H)⁺=409.

Example 261

2-fluoro-4-[2-(cyclopropylmethoxy)-5-methylsulfonylphenyl]-6-methylfuro[2,3-c]pyridin-7-one Step 1: 2-fluoro-7-methoxyfuro[2,3-c]pyridine

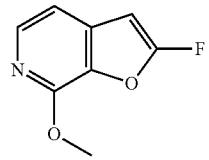

The title compound was prepared in a manner similar to step 1 of Example 260, by substituting N-Fluorobenzenesulfonamide for hexachloroethane. ¹H NMR (400 MHz, DMSO-d₆) δ ppm 4.01 (s, 3H) 6.46 (m, 1H) 7.25 (d, J=5.4 Hz, 1H) 7.96 (d, J=5.4 Hz, 1H). LCMS (M+H)⁺=168.

Step 2: 2-fluorofuro[2,3-c]pyridin-7-ol

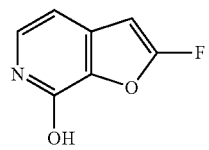 [SMILES: Oc1nccc2cc(F)oc12]

The title compound was prepared in a manner similar to step 2 of Example 260, by substituting 2-fluoro-7-methoxyfuro[2,3-c]pyridine for 2-chloro-7-methoxyfuro[2,3-c]pyridine. LCMS (M+H)⁺=154.

Step 3: 4-bromo-2-fluorofuro[2,3-c]pyridin-7-ol

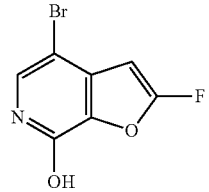 [SMILES: Oc1ncc(Br)c2cc(F)oc12]

The title compound was prepared in a manner similar to step 3 of Example 260, by substituting 2-fluorofuro[2,3-c]pyridin-7-ol for 2-chlorofuro[2,3-c]pyridin-7-ol. LCMS (M+H)⁺=233.

613

Step 4:
4-bromo-2-fluoro-6-methylfuro[2,3-c]pyridin-7-one

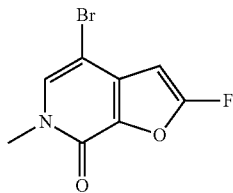

The title compound was prepared in a manner similar to step 4 of Example 260, by substituting 4-bromo-2-fluorofuro[2,3-c]pyridin-7-ol for 4-bromo-2-chlorofuro[2,3-c]pyridin-7-ol. LCMS (M+H)$^+$=247.

Step 5: 2-fluoro-4-[2-(cyclopropylmethoxy)-5-methylsulfonylphenyl]-6-methylfuro[2,3-c]pyridin-7-one

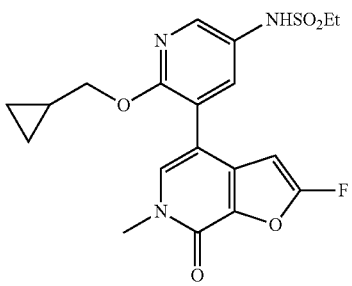

A mixture of N-[6-(cyclopropylmethoxy)-5-(4,4,5,5-tetramethyl-1,3,2-dioxaborolan-2-yl)pyridin-3-yl]ethanesulfonamide (31 mg, 0.08 mmol), 4-bromo-2-fluoro-6-methylfuro[2,3-c]pyridin-7-one (20 mg, 0.08 mmol), $K_3PO_4$ (36 mg, 0.17 mmol), Pd(dppf)Cl$_2$ (6 mg, 8%) in dioxane/H$_2$O (830 uL/100 uL) was bubbled with nitrogen for 10 min. The sealed vial was stirred at 67° C. for 90 min. The reaction mixture was filtered through a short plug of celite; the celite plug was washed with EtOAc (15 mL). The filtrate was washed with water and brine; the organic layer was dried over sodium sulfate, filtered and concentrated in vacuo to afford a tan residue. The resulting residue was purified by silica gel column chromatography using a gradient of MeOH (0 to 2%) in DCM. The fractions were combined and concentrated in vacuo to afford a white solid (10 mg). The solid had a minor impurity [LCMS (M+H)$^+$=578]; therefore, it was diluted in MeOH (1 mL) and 1N NaOH$_{(aq)}$ (500 uL) and purified by prep-HPLC to afford the title compound (6 mg, 17%) as a white solid. $^1$H NMR (400 MHz, DMSO-d$_6$) δ ppm 0.28 (m, 2H) 0.43-0.58 (m, 2H) 0.56-0.58 (m, 1H) 1.24 (m, 3H) 3.09 (m, 2H) 3.60 (s, 3H) 4.12 (m, 2H) 6.16-6.34 (m, 1H) 7.52-7.72 (m, 1H) 7.77 (s, 1H) 7.90-8.14 (m, 1H) 9.37-10.62 (bs, 1H). LCMS (M+H)$^+$=422.

614

Example 262

N-[5-(2,4-difluorophenoxy)-4-(6-methyl-7-oxofuro[2,3-c]pyridin-4-yl)pyrimidin-2-yl]methanesulfonamide Step 1: 4-[5-(2,4-difluorophenoxy)-2-methylsulfonylpyrimidin-4-yl]-6-methylfuro[2,3-c]pyridin-7-one

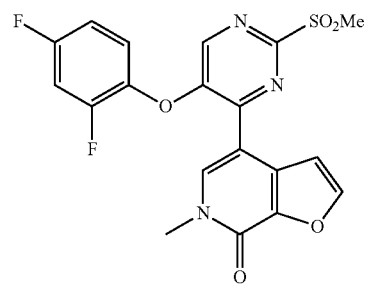 [SMILES: Cn1cc(-c2nc(S(C)(=O)=O)ncc2Oc2ccc(F)cc2F)c2ccoc2c1=O]

A mixture of 4-chloro-5-(2,4-difluorophenoxy)-2-methylsulfonylpyrimidine (155 mg, 0.48 mmol), 4-bromo-2-fluoro-6-methylfuro[2,3-c]pyridin-7-one (120 mg, 0.44 mmol), NaHCO$_3$ (92 mg, 1.1 mmol), Pd(dppf)Cl$_2$ (32 mg, 10%) in dioxane/H$_2$O (4 mL/200 uL) was bubbled with nitrogen for 7 min. The sealed vial was stirred at 70° C. for 8 h. LCMS analysis showed complete consumption of the limiting reagent. The reaction mixture was filtered through a short plug of celite; the celite plug was washed with DCM. The filtrate was concentrated in vacuo. The resulting residue was purified by silica gel column chromatography using a gradient of EtOAc (10 to 100%) in DCM to afford the title compound (151 mg, 79%) as a yellow solid. LCMS (M+H)$^+$=434.

Step 2: N-[5-(2,4-difluorophenoxy)-4-(6-methyl-7-oxofuro[2,3-c]pyridin-4-yl)pyrimidin-2-yl]methanesulfonamide

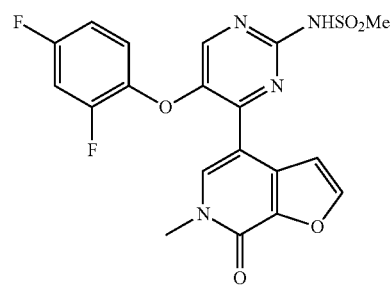

A solution of methanesulfonamide (61 mg, 0.65 mmol) in DMF (2 mL) stirred at 0° C. under an atmosphere of nitrogen was treated with NaH (99 mg, 0.7 mmol). After the ice bath was removed, the mixture was stirred at rt for 15 min. The resulting suspension was treated with a solution of 4-[5-(2,4-difluorophenoxy)-2-methylsulfonylpyrimidin-4-yl]-6-methylfuro[2,3-c]pyridin-7-one (70 mg, 0.16 mmol) in DMF (1 mL). After the nitrogen inlet was removed, the capped mixture was heated to 70° C. for 3 h. After cooling to 0° C., the reaction mixture was stirred vigorously and treated water (500 uL). After 5 min, the cooled mixture was treated with 1N HCl$_{(aq)}$ (1 mL). The resulting suspension was filtered; the filter cake was washed with additional 1N HCl$_{(aq)}$ (1 mL) and isopropyl ether (5 mL) to afford the title compound (50 mg, 70%) as an off-white solid. $^1$H NMR (400 MHz, DMSO-d6) δ ppm 3.34 (s, 3H) 3.60 (s, 3H) 7.06 (m, 1H) 7.28 (m, 1H) 7.49 (m, 1H) 7.80 (s, 1H) 8.23 (s, 1H) 8.43 (m, 2H) 11.50 (bs, 1H). LCMS (M+H)$^+$=449.

Example 263

N-[5-(2,4-difluorophenoxy)-4-(6-methyl-7-oxofuro[2,3-c]pyridin-4-yl)pyrimidin-2-yl]ethanesulfonamide

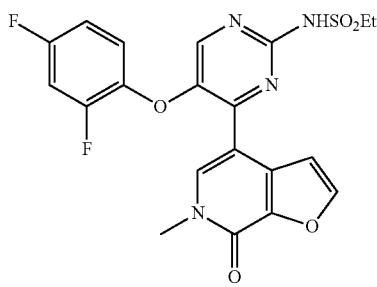

The title compound (46 mg, 62%) was prepared in a manner similar to step 2 of Example 262, by substituting ethanesulfonamide for methanesulfonamide. $^1$H NMR (400 MHz, DMSO-d$_6$) δ ppm 1.20-1.27 (m, 3H) 3.43-3.57 (m, 2H) 3.57-3.67 (s, 3H) 7.00-7.13 (m, 1H) 7.20-7.37 (m, 1H) 7.41-7.54 (m, 1H) 7.72-7.87 (m, 1H) 8.15-8.28 (m, 1H) 8.30-8.49 (m, 2H) 11.25-11.48 (bs, 1H). LCMS (M+H)$^+$=463.

Example 264

N-[5-(cyclopropylmethoxy)-4-(6-methyl-7-oxofuro[2,3-c]pyridin-4-yl)pyrimidin-2-yl]ethanesulfonamide Step 1: 4-[5-(cyclopropylmethoxy)-2-methylsulfonylpyrimidin-4-yl]-6-methylfuro[2,3-c]pyridin-7-one

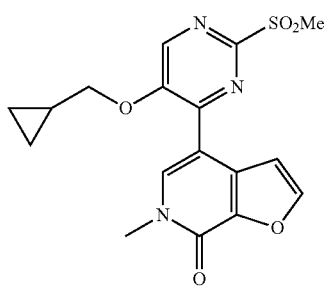 [SMILES: Cn1cc(-c2nc(S(C)(=O)=O)ncc2OCC2CC2)c2ccoc2c1=O]

The title compound was prepared in a manner similar to step 1 of Example 262, by substituting 4-chloro-5-(cyclopropylmethoxy)-2-methylsulfonylpyrimidine for 4-chloro-5-(2,4-difluorophenoxy)-2-methylsulfonylpyrimidine. LCMS (M+H)$^+$=376.

Step 2: N-[5-(cyclopropylmethoxy)-4-(6-methyl-7-oxofuro[2,3-c]pyridin-4-yl)pyrimidin-2-yl]ethanesulfonamide

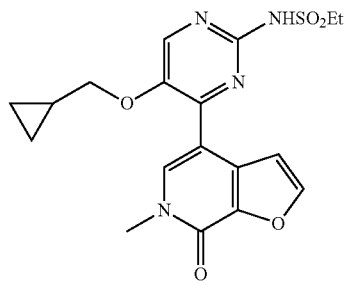

The title compound was prepared in a manner similar to step 2 of Example 262, by substituting ethanesulfonamide for methanesulfonamide and by substituting 4-[5-(cyclopropylmethoxy)-2-methylsulfonylpyrimidin-4-yl]-6-methylfuro[2,3-c]pyridin-7-one for 4-[5-(2,4-difluorophenoxy)-2-methylsulfonylpyrimidin-4-yl]-6-methylfuro[2,3-c]pyridin-7-one. LCMS (M+H)$^+$=405.

Example 265

4-[2-(cyclopropylmethoxy)-5-ethylsulfonylphenyl]-6-methyl-7-oxothieno[2,3-c]pyridine-2-carboxamide Step 1: methyl 4-bromo-6-methyl-7-oxothieno[2,3-c]pyridine-2-carboxylate

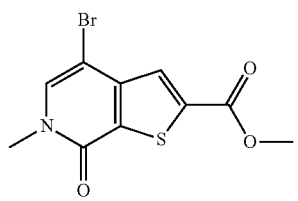

To a solution of methyl 4-bromo-7-hydroxythieno[2,3-c]pyridine-2-carboxylate (300 mg, 1.04 mmol) stirred at 0° C. in DMF (6.6 mL) under an atmosphere of nitrogen was added K$_2$CO$_3$ (358 mg, 2.6 mmol). After stirring at 0° C. for 15 min, methyl iodide (177 mg, 1.3 mmol) was added dropwise. The ice bath was removed, and mixture was stirred at rt for 20 min, 50° C. for 2 h, and rt for 10 h. The reaction mixture was treated with water (8 mL) and extracted with EtOAc (30 mL×3). The combined organic layers were washed with brine (30 mL), dried over Na$_2$SO$_4$, filtered, and concentrated in vacuo. The residue was purified by silica gel chromatography using a gradient of EtOAc (10 to 100%) in DCM to afford the title compound (284 mg, 90%) as a white solid. LCMS (M+H)$^+$=303.

Step 2: 4-bromo-6-methyl-7-oxothieno[2,3-c]pyridine-2-carboxamide

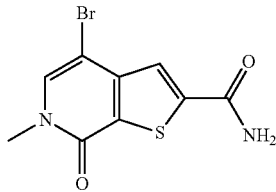

Using a sealed tube, a solution of methyl 4-bromo-6-methyl-7-oxothieno[2,3-c]pyridine-2-carboxylate (250 mg, 65 mmol) in MeOH (6 mL) stirred at rt was treated with 2N $NH_3$ in methanol (8 ml). The sealed tube was heated to 45° C. for 60 h. After cooling to 0° C., the resulting suspension was filtered; the filter cake was washed with cooled (0° C.) MeOH (3 mL) and isopropyl ether (3 mL) to afford the title compound (215 mg, 95%) as a white solid. LCMS (M+H)$^+$=288.

Step 3: 4-[2-(cyclopropylmethoxy)-5-ethylsulfonylphenyl]-6-methyl-7-oxothieno[2,3-c]pyridine-2-carboxamide

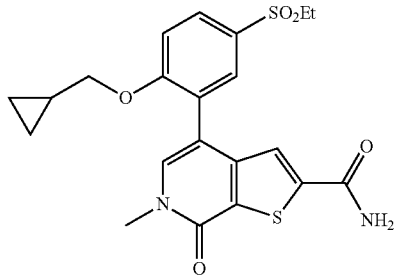

A mixture of 2-[2-(cyclopropylmethoxy)-5-ethylsulfonylphenyl]-4,4,5,5-tetramethyl-1,3,2-dioxaborolane (77 mg, 0.22 mmol), 4-bromo-6-methyl-7-oxothieno[2,3-c]pyridine-2-carboxamide (50 mg, 0.18 mmol), $K_3PO_4$ (93 mg, 0.44 mmol), Pd(dppf)Cl$_2$ (13 mg, 10%) in dioxane/H$_2$O (1.6 mL/160 uL) was bubbled with nitrogen for 5 min. The sealed vial was stirred at 65° C. for 3 h. The reaction mixture was filtered through a short plug of celite; the celite plug was washed with EtOAc (15 mL). The filtrate was washed with water and brine; the organic layer was dried over sodium sulfate, filtered and concentrated in vacuo to afford a tan residue. The resulting residue was purified by prep-HPLC to afford the title compound (20 mg, 26%) as a white solid. $^1$H NMR (400 MHz, DMSO-d$_6$) δ ppm 0.20 (m, 2H) 0.36 (m, 2H) 0.98 (m, 1H) 1.14 (m, 3H) 3.21-3.31 (m, 2H) 3.61 (s, 3H) 3.98 (m, 2H) 7.38 (d, J=8.6 Hz, 1H) 7.65-7.75 (m, 3H) 7.78 (d, J=2.0 Hz, 1H) 7.91 (dd, J=8.6, 2.0 Hz, 1H) 8.24 (s, 1H). LCMS (M+H)=447.

Example 266

4-[2-(cyclopropylmethoxy)-5-(ethylsulfonylamino)phenyl]-6-methyl-7-oxothieno[2,3-c]pyridine-2-carboxamide

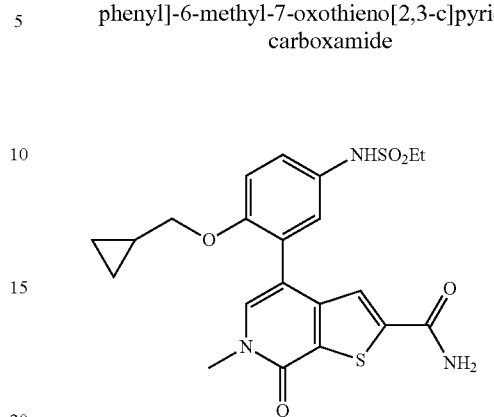

The title compound was prepared in a manner similar to step 3 of Example 265, by substituting N-[4-(cyclopropylmethoxy)-3-(tetramethyl-1,3,2-dioxaborolan-2-yl)phenyl]ethane-1-sulfonamide for 2-[2-(cyclopropylmethoxy)-5-ethylsulfonylphenyl]-4,4,5,5-tetramethyl-1,3,2-dioxaborolane. $^1$H NMR (400 MHz, DMSO-d$_6$) δ ppm 0.09-0.19 (m, 2H) 0.27-0.39 (m, 2H) 0.86-1.02 (m, 1H) 1.18-1.27 (m, 3H) 2.97-3.09 (m, 2H) 3.59 (s, 3H) 3.77-3.86 (m, 2H) 7.07-7.16 (m, 2H) 7.21-7.27 (m, 1H) 7.53-7.58 (m, 1H) 7.61-7.67 (m, 1H) 7.67-7.72 (m, 1H) 8.19-8.30 (m, 1H) 9.46-9.60 (m, 1H). LCMS (M+H)$^+$=462.

Example 267

4-[2-(cyclopropylmethoxy)-5-methylsulfonylphenyl]-6-methyl-7-oxothieno[2,3-c]pyridine-2-carboxamide

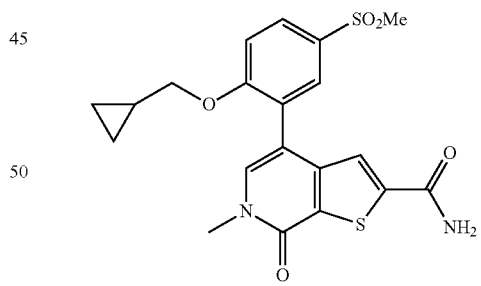

The title compound was prepared in a manner similar to step 3 of Example 265, by substituting 2-[2-(cyclopropylmethoxy)-5-methylsulfonylphenyl]-4,4,5,5-tetramethyl-1,3,2-dioxaborolane for 2-[2-(cyclopropylmethoxy)-5-ethylsulfonylphenyl]-4,4,5,5-tetramethyl-1,3,2-dioxaborolane. $^1$H NMR (400 MHz, DMSO-d$_6$) δ ppm 0.11-0.26 (m, 2H) 0.27-0.41 (m, 2H) 0.89-1.05 (m, 1H) 3.21 (s, 3H) 3.61 (s, 3H) 3.91-4.04 (m, 2H) 7.34-7.41 (m, 1H) 7.63-7.76 (m, 3H) 7.81-7.88 (m, 1H) 7.92-7.99 (m, 1H) 8.21-8.29 (m, 1H). LCMS (M+H)$^+$=433.

Example 268

4-[2-(cyclopropylmethoxy)-5-(ethylsulfonylamino)pyridin-3-yl]-6-methyl-7-oxothieno[2,3-c]pyridine-2-carboxamide

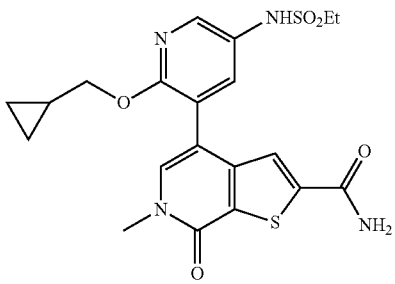

The title compound was prepared in a manner similar to step 3 of Example 265, by substituting N-[6-(cyclopropylmethoxy)-5-(4,4,5,5-tetramethyl-1,3,2-dioxaborolan-2-yl)pyridin-3-yl]ethanesulfonamide for 2-[2-(cyclopropylmethoxy)-5-ethylsulfonylphenyl]-4,4,5,5-tetramethyl-1,3,2-dioxaborolane. $^1$H NMR (400 MHz, DMSO-$d_6$) δ ppm 0.17-0.35 (m, 2H) 0.39-0.57 (m, 2H) 1.23 (m, 4H) 3.00-3.17 (m, 2H) 3.60 (s, 3H) 4.01-4.26 (m, 2H) 6.11-6.40 (m, 1H) 7.52-7.69 (m, 1H) 7.74-7.84 (m, 1H) 7.94-8.09 (m, 1H) 9.14-10.31 (m, 1H). LCMS (M+H)$^+$=463.

Example 269

N-[4-(2,4-difluorophenoxy)-3-(2,6-dimethyl-7-oxofuro[2,3-c]pyridin-4-yl)phenyl]ethanesulfonamide

Step 1: 7-methoxy-2-methylfuro[2,3-c]pyridine

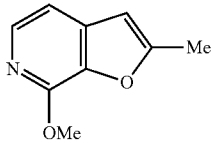 [SMILES: COc1nccc2cc(C)oc12]

To a solution of 7-methoxyfuro[2,3-c]pyridine (2.9 g, 19.6 mmol) in THF (20 mL) stirred under an atmosphere of argon was added n-BuLi (7.8 mL, 19.6 mmol) at −78° C.; the mixture was transferred to a −30° C. ice bath and was stirred for 2 h. The mixture was cooled to −78° C. and MeI (4.2 g, 29.4 mmol) was added. After the mixture was stirred at rt for 18 h, the reaction mixture was quenched with water (30 mL) and extracted with DCM (50 mL×3). The combined organic layers were washed with brine (30 mL×3), dried over Na$_2$SO$_4$ and concentrated in vacuo to afford the title compound (3.2 g, 100%) as a yellow solid. The material was carried forward without any further purification. LCMS (M+H)$^+$=164.

Step 2: 4-bromo-7-methoxy-2-methylfuro[2,3-c]pyridine

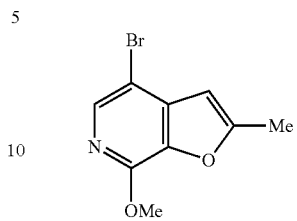

A solution of 7-methoxy-2-methylfuro[2,3-c]pyridine (3.2 g, 19.6 mmol) in ACN (30 mL) was treated with NBS (3.5 g, 19.7 mmol). After the mixture was stirred at rt for 18 h, it was concentrated in vacuo and purified by silica gel chromatography (PE/EA=30:1~5:1) to afford the title compound (3.0 g, 64%) as a yellow solid. LCMS (M+H)$^+$=243.

Step 3: 4-bromo-2-methyl-6H-furo[2,3-c]pyridin-7-one

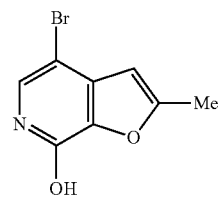 [SMILES: Cc1cc2c(Br)cnc(O)c2o1]

To a mixture of 4-bromo-7-methoxy-2-methylfuro[2,3-c]pyridine (3.0 g, 12.4 mmol) in DCM (30 mL) was stirred at 0° C. under an atmosphere of nitrogen was added BBr$_3$ (15.5 g, 62.0 mmol) dropwise. The mixture was stirred at 0° C. for 3 h. The mixture was concentrated in vacuo to afford the title compound (2.50 g, 88%). The material was immediately used in the next step without any further purification. LCMS (M+H)$^+$=229.

Step 4: 4-bromo-2,6-dimethylfuro[2,3-c]pyridin-7-one

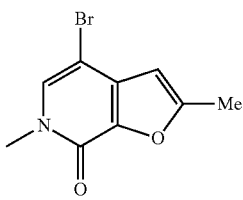

The title compound was prepared in a manner similar to step 2 of Example 252, by substituting 4-bromo-2-methyl-6H-furo[2,3-c]pyridin-7-one for 4-bromo-6H,7H-furo[2,3-c]pyridin-7-one. $^1$H NMR (CDCl$_3$, 400 MHz) δ 7.26 (s, 1H), 6.32 (s, 1H), 3.64 (s, 3H), 2.49 (s, 3H). LCMS (M+H)$^+$=243.

Step 5: N-[4-(2,4-difluorophenoxy)-3-(2,6-dimethyl-7-oxofuro[2,3-c]pyridin-4-yl)phenyl]ethanesulfonamide

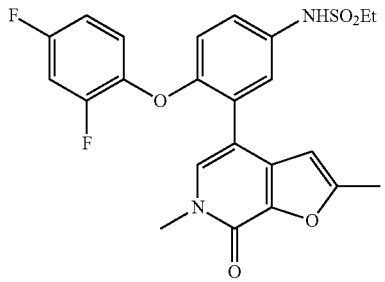

A mixture of 4-bromo-2,6-dimethylfuro[2,3-c]pyridin-7-one (200 mg, 0.83 mol), N-[4-(2,4-difluorophenoxy)-3-(4,4,5,5-tetramethyl-1,3,2-dioxaborolan-2-yl)phenyl]ethanesulfonamide (364 mg, 0.99 mmol), Pd(dppf)Cl$_2$ (66 mg, 0.09 mmol), K$_3$PO$_4$ (527 mg, 2.49 mmol) in dioxane/water (4 mL/1 mL) was bubbled with argon for 5 min. The mixture was heated to 70° C. for 18 h. After cooling to rt, the reaction mixture was poured into water (10 mL) and extracted with EtOAc (40 mL×3). The combined organic layers were washed with brine (20 mL×2), dried over Na$_2$SO$_4$, filtered, and concentrated in vacuo. The residue was purified by prep-HPLC to afford the title compound (49 mg, 12%) as a yellow solid. $^1$H NMR (CDCl$_3$, 400 MHz) δ 7.35-7.33 (m, 2H) 7.12 (m, 1H) 6.95-6.89 (m, 2H) 6.81 (m, 2H) 6.43 (s, 1H) 6.38 (s, 1H) 3.71 (s, 3H) 3.16 (q, J=7.2 Hz, 2H) 2.47 (s, 3H) 1.43 (t, J=7.2 Hz, 3H). LCMS (M+H)$^+$=475.

Example 270

4-[2-(cyclopropylmethoxy)-5-ethylsulfonylphenyl]-2,6-dimethylfuro[2,3-c]pyridin-7-one

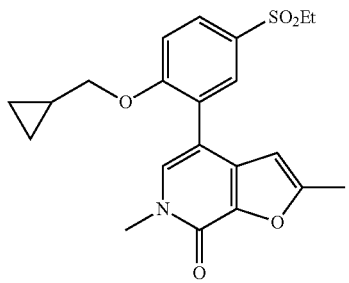

The title compound was prepared in a manner similar to step 5 of Example 269, by substituting 2-[2-(cyclopropylmethoxy)-5-ethylsulfonylphenyl]-4,4,5,5-tetramethyl-1,3,2-dioxaborolane for N-[4-(2,4-difluorophenoxy)-3-(4,4,5,5-tetramethyl-1,3,2-dioxaborolan-2-yl)phenyl]ethanesulfonamide. $^1$H NMR (CDCl$_3$, 400 MHz) δ 7.89 (dd, J$_1$=8.8 Hz, J$_2$=2.4 Hz, 1H) 7.85 (d, J=2.4 Hz, 1H) 7.34 (s, 1H) 7.09 (d, J=8.8 Hz, 1H) 6.24 (s, 1H) 3.94 (m, 2H) 3.78 (s, 3H) 3.14 (q, J=7.2 Hz, 2H) 2.48 (s, 3H) 1.32 (t, J=7.2 Hz, 3H) 1.18-1.16 (m, 1H) 0.64-0.59 (m, 2H) 0.32-0.28 (m, 2H). LCMS (M+H)$^+$=402.

Example 271

N-[4-(2,4-difluorophenoxy)-3-(5-fluoro-1-methyl-6-oxopyridin-3-yl)phenyl]methanesulfonamide

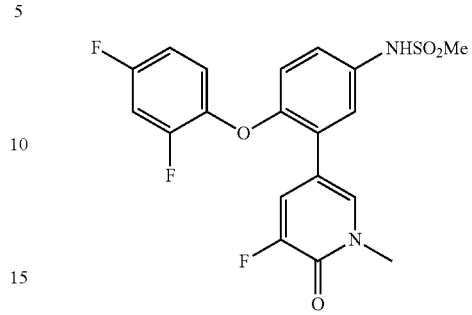

The title compound was prepared in a manner similar to Example 122, substituting N-[3-bromo-4-(2,4-difluorophenoxy)phenyl]methanesulfonamide for N-[3-Bromo-4-(2,4-difluorophenoxy)phenyl]ethanesulfonamide. $^1$H NMR (400 MHz, DMSO-d$_6$) δ ppm 2.98-3.07 (m, 3H) 3.52-3.60 (m, 3H) 6.80-6.94 (m, 1H) 7.10 (s, 1H) 7.14-7.24 (m, 2H) 7.24-7.28 (m, 1H) 7.38-7.51 (m, 1H) 7.57-7.66 (m, 1H) 7.76-7.86 (m, 1H) 9.67-9.76 (m, 1H). LCMS (M+H)$^+$=425.

Example 272

3-chloro-5-[2-(cyclopropylmethoxy)-5-ethylsulfonylphenyl]-1-methylpyridin-2-one

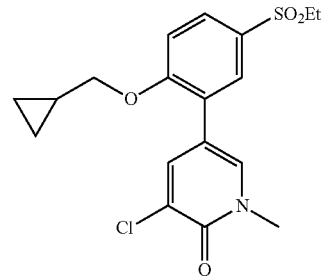

The title compound was prepared in a manner similar to Example 119, substituting 3-chloro-1-methyl-5-(4,4,5,5-tetramethyl-1,3,2-dioxaborolan-2-yl)pyridin-2-one for 3-Fluoro-1-methyl-5-(4,4,5,5-tetramethyl-1,3,2-dioxaborolan-2-yl)pyridin-2-one and 2-bromo-1-(cyclopropylmethoxy)-4-ethylsulfonylbenzene for 2-bromo-1-(cyclopropylmethoxy)-4-methanesulfonylbenzene. LCMS (M+H)$^+$=382.

Example 273

5-[5-(2,4-difluorophenoxy)-2-methylsulfonylpyrimidin-4-yl]-1-methyl-3-propan-2-ylpyridin-2-one

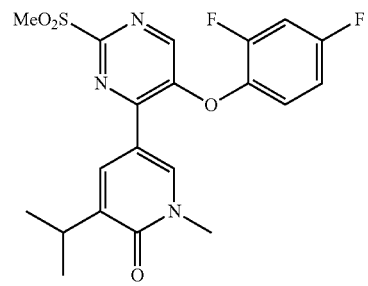 [SMILES: CC(C)c1cc(-c2nc(S(C)(=O)=O)ncc2Oc2ccc(F)cc2F)cn(C)c1=O]

The title compound was prepared in three steps. Using conditions similar to those described by Malhotra, et. al. in Organic Letters 2013, Vol. 15, No. 14, pp. 3698-3701 (supporting information, compounds 4c and 3a), 3,5-dibromo-1-methylpyridin-2-one was alkylated at the 3-position using isopropylmagnesium bromide to give 5-bromo-1-methyl-3-propan-2-ylpyridin-2-one which was then reacted with 4,4,5,5-tetramethyl-2-(tetramethyl-1,3,2-dioxaborolan-2-yl)-1,3,2-dioxaborolane using conditions similar to those described in Example 248, step 2 to give the pinacol ester, 1-methyl-3-propan-2-yl-5-(4,4,5,5-tetramethyl-1,3,2-dioxaborolan-2-yl)pyridin-2-one. This pinacol ester was then substituted for the pinacol ester of Example 149, step 4 and reacted in the same manner to obtain the title compound. LCMS (M+H)$^+$=436.

Example 274

5-[2-(cyclopropylmethoxy)-5-ethylsulfonylphenyl]-3-fluoro-1-methylpyridin-2-one

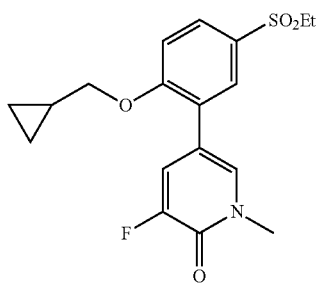

The title compound was prepared in a manner similar to Example 119, substituting 2-bromo-1-(cyclopropylmethoxy)-4-ethylsulfonylbenzene for 2-bromo-1-(cyclopropylmethoxy)-4-methanesulfonylbenzene. LCMS (M+H)$^+$=366.

Example 275

3-chloro-5-[2-(cyclopropylmethoxy)-5-ethylsulfonylphenyl]-1-methylpyridin-2-one

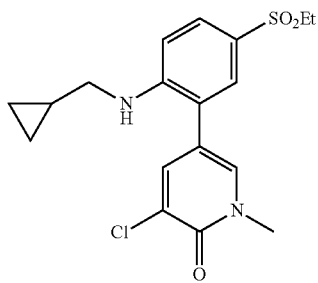

The title compound was prepared in a manner similar to Example 119, substituting 3-chloro-1-methyl-5-(4,4,5,5-tetramethyl-1,3,2-dioxaborolan-2-yl)pyridin-2-one for 3-Fluoro-1-methyl-5-(4,4,5,5-tetramethyl-1,3,2-dioxaborolan-2-yl)pyridin-2-one and N-(cyclopropylmethyl)-4-ethylsulfonyl-2-(4,4,5,5-tetramethyl-1,3,2-dioxaborolan-2-yl)aniline for 2-bromo-1-(cyclopropylmethoxy)-4-methanesulfonylbenzene. LCMS (M+H)$^+$=381.

Example 276

5-[2-(2,4-difluorophenoxy)-5-(methanesulfonylmethyl)phenyl]-3-($^2$H$_3$)methyl-1-methyl-1,2-dihydropyridin-2-one

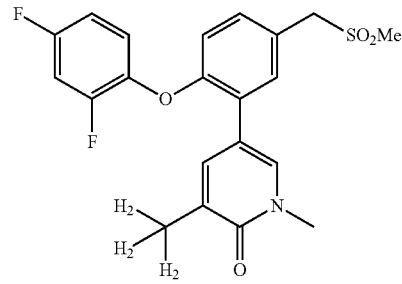

The title compound was prepared in a manner similar to Example 119, substituting 3-($^2$H$_3$)methyl-1-methyl-5-(tetramethyl-1,3,2-dioxaborolan-2-yl)-1,2-dihydropyridin-2-one for 3-Fluoro-1-methyl-5-(4,4,5,5-tetramethyl-1,3,2-dioxaborolan-2-yl)pyridin-2-one and 2-bromo-1-(2,4-difluorophenoxy)-4-(methylsulfonylmethyl)benzene for 2-bromo-1-(cyclopropylmethoxy)-4-methanesulfonylbenzene. $^1$H NMR (400 MHz, DMSO-d$_6$) δ ppm 2.93 (s, 3H) 3.49 (s, 3H) 4.42-4.52 (m, 2H) 6.81-6.89 (m, 1H) 7.04-7.16 (m, 1H) 7.20-7.29 (m, 1H) 7.30-7.35 (m, 1H) 7.43-7.51 (m, 2H) 7.53-7.57 (m, 1H) 7.75-7.82 (m, 1H) LCMS (M+H)$^+$ 423.

Example 277

N-[4-(2,4-difluorophenoxy)-3-[5-($^2$H$_3$)methyl-1-methyl-6-oxo-1,6-dihydropyridin-3-yl]phenyl]methanesulfonamide

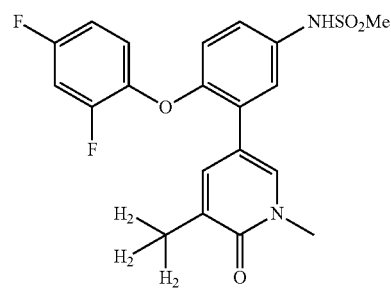

The title compound was prepared in a manner similar to Example 122, substituting N-[3-bromo-4-(2,4-difluorophenoxy)phenyl]methanesulfonamide for N-[3-Bromo-4-(2,4-difluorophenoxy)phenyl]ethanesulfonamide and 3-($^2$H$_3$)methyl-1-methyl-5-(tetramethyl-1,3,2-dioxaborolan-2-yl)-1,2-dihydropyridin-2-one for 3-fluoro-1-methyl-5-(4,4,5,5-tetramethyl-1,3,2-dioxaborolan-2-yl)pyridin-2-one. $^1$H NMR (400 MHz, DMSO-d$_6$) δ ppm 2.98-3.05 (m, 3H) 3.44-3.50 (m, 3H) 6.84-6.92 (m, 1H) 7.01-7.18 (m, 3H) 7.21-7.26 (m, 1H) 7.38-7.47 (m, 1H) 7.47-7.51 (m, 1H) 7.73-7.79 (m, 1H) 9.61-9.78 (bs, 1H). LCMS (M+H)$^+$=424.

Example 278

N-[4-(2,4-difluorophenoxy)-3-[5-($^2$H$_3$)methyl-1-methyl-6-oxo-1,6-dihydropyridin-3-yl]phenyl]ethane-1-sulfonamide

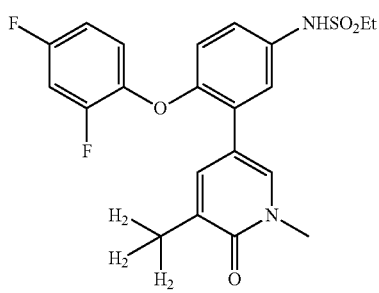

The title compound was prepared in a manner similar to Example 122, substituting 3-($^2$H$_3$)methyl-1-methyl-5-(tetramethyl-1,3,2-dioxaborolan-2-yl)-1,2-dihydropyridin-2-one for 3-fluoro-1-methyl-5-(4,4,5,5-tetramethyl-1,3,2-dioxaborolan-2-yl)pyridin-2-one. $^1$H NMR (400 MHz, DMSO-d$_6$) δ ppm 1.19-1.25 (m, 3H) 3.05-3.16 (m, 2H) 3.45-3.49 (m, 3H) 6.85-6.92 (m, 1H) 6.99-7.20 (m, 4H) 7.23 (m, 1H) 7.38-7.46 (m, 1H) 7.46-7.50 (m, 1H) 7.71-7.79 (m, 1H) 9.60-9.85 (m, 1H). LCMS (M+H)$^+$=438.

Example 279

N-[3-(5-cyclopropyl-1-methyl-6-oxopyridin-3-yl)-4-(2,4-difluorophenoxy)phenyl]methanesulfonamide

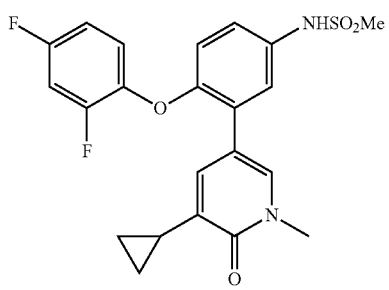

The title compound was prepared in a manner similar to Example 122, substituting 3-cyclopropyl-1-methyl-5-(4,4,5,5-tetramethyl-1,3,2-dioxaborolan-2-yl)pyridin-2-one for 3-Fluoro-1-methyl-5-(4,4,5,5-tetramethyl-1,3,2-dioxaborolan-2-yl)pyridin-2-one and N-[3-bromo-4-(2,4-difluorophenoxy)phenyl]methanesulfonamide for N-[3-Bromo-4-(2,4-difluorophenoxy)phenyl]ethanesulfonamide. $^1$H NMR (400 MHz, DMSO-d$_6$) δ ppm 0.46-0.54 (m, 2H) 0.77-0.88 (m, 2H) 1.93-2.07 (m, 1H) 2.98-3.05 (m, 3H) 3.44-3.51 (m, 3H) 6.89-6.95 (m, 1H) 7.00-7.12 (m, 3H) 7.13-7.19 (m, 1H) 7.21-7.25 (m, 1H) 7.39-7.48 (m, 1H) 7.71 (s, 1H) 9.56-9.82 (bs, 1H). LCMS (M+H)$^+$=447.

Example 280

3-cyclopropyl-5-[2-(cyclopropylmethoxy)-5-ethylsulfonylphenyl]-1-methylpyridin-2-one

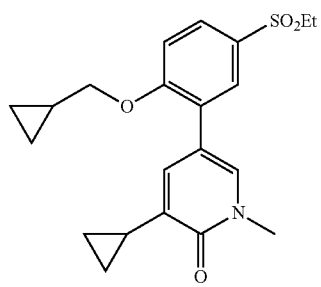

The title compound was prepared in a manner similar to Example 119, substituting 3-cyclopropyl-1-methyl-5-(4,4,5,5-tetramethyl-1,3,2-dioxaborolan-2-yl)pyridin-2-one for 3-Fluoro-1-methyl-5-(4,4,5,5-tetramethyl-1,3,2-dioxaborolan-2-yl)pyridin-2-one and 2-bromo-1-(cyclopropylmethoxy)-4-ethylsulfonylbenzene for 2-bromo-1-(cyclopropylmethoxy)-4-methanesulfonylbenzene. $^1$H NMR (400 MHz, DMSO-d$_6$) δ ppm 0.33-0.41 (m, 2H) 0.55-0.61 (m, 2H) 0.63-0.69 (m, 2H) 0.83-0.91 (m, 2H) 1.07-1.14 (m, 3H) 1.19-1.25 (m, 1H) 2.01-2.12 (m, 1H) 3.23-3.30 (m, 2H) 3.52 (s, 3H) 3.92-4.00 (m, 2H) 7.22-7.29 (m, 2H) 7.70-7.80 (m, 3H). LCMS (M+H)$^+$=388.

Example 281

N-[4-(2,4-difluorophenoxy)-3-(1-methyl-6-oxo-5-pyrrolidin-1-ylpyridin-3-yl)phenyl]methanesulfonamide

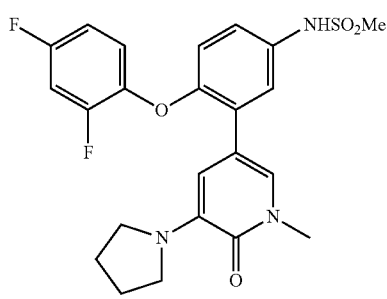

The title compound was prepared in a manner similar to Example 122, substituting 1-methyl-3-pyrrolidin-1-yl-5-(4,4,5,5-tetramethyl-1,3,2-dioxaborolan-2-yl)pyridin-2-one for 3-Fluoro-1-methyl-5-(4,4,5,5-tetramethyl-1,3,2-dioxaborolan-2-yl)pyridin-2-one and N-[3-bromo-4-(2,4-difluorophenoxy)phenyl]methanesulfonamide for N-[3-Bromo-4-(2,4-difluorophenoxy)phenyl]ethanesulfonamide. LCMS (M+H)$^+$=476.

Example 282

5-[2-(cyclopropylmethoxy)-5-ethylsulfonylphenyl]-1-methyl-3-pyrrolidin-1-ylpyridin-2-one

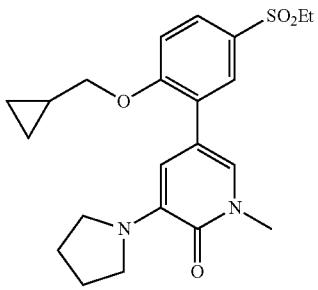

The title compound was prepared in a manner similar to Example 119, substituting 1-methyl-3-pyrrolidin-1-yl-5-(4,4,5,5-tetramethyl-1,3,2-dioxaborolan-2-yl)pyridin-2-one for 3-Fluoro-1-methyl-5-(4,4,5,5-tetramethyl-1,3,2-dioxaborolan-2-yl)pyridin-2-one and 2-bromo-1-(cyclopropylmethoxy)-4-ethylsulfonylbenzene for 2-bromo-1-(cyclopropylmethoxy)-4-methanesulfonylbenzene. $^1$H NMR (400 MHz, DMSO-$d_6$) δ ppm 0.33-0.40 (m, 2H) 0.53-0.61 (m, 2H) 1.08-1.14 (m, 3H) 1.20-1.29 (m, 1H) 1.81-1.90 (m, 4H) 3.23-3.30 (m, 2H) 3.35-3.35 (m, 1H) 3.35-3.40 (m, 3H) 3.48 (s, 3H) 3.94-4.03 (m, 2H) 6.60-6.66 (m, 1H) 7.21-7.28 (m, 1H) 7.31-7.38 (m, 1H) 7.68-7.79 (m, 2H). LCMS (M+H)$^+$=417.

Example 283

N-[4-(2,4-difluorophenoxy)-3-(5-ethynyl-1-methyl-6-oxopyridin-3-yl)phenyl]ethanesulfonamide Step 1: 5-bromo-3-iodo-1-methylpyridin-2-one

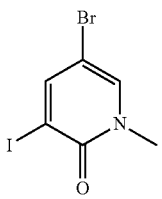

To a solution of 5-bromo-3-iodo-1H-pyridin-2-one (12.0 g, 40.01 mmol) stirred in dry DMF (120 mL) at 0° C. under an atmosphere of nitrogen was added NaH (2.4 g, 60.02 mmol, 60% in mineral oil). After the mixture was stirred at 0° C. for 1 h, iodomethane (11.4 g, 80.03 mmol) was added dropwise. The icebath was removed, and the reaction was stirred at rt for 1 h. The mixture was poured into ice water (200 mL); the resulting precipitate was filtered, collected and dried to give the title compound (12 g, 95%) as a light yellow solid. The material was used without any further purification. $^1$H NMR (CDCl$_3$, 400 MHz): δ 8.01 (d, J=3.2 Hz, 1H), 7.46 (d, J=3.2 Hz, 1H), 3.60 (s, 3H). LCMS (M+H)$^+$=315.

Step 2: 5-bromo-1-methyl-3-(2-trimethylsilylethynyl)pyridin-2-one

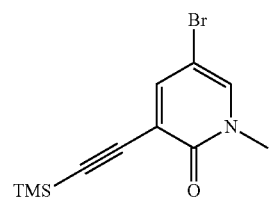

A mixture of 5-bromo-3-iodo-1-methylpyridin-2-one (8.0 g, 25.48 mmol), ethynyltrimethylsilane (2.7 g, 27.52 mmol), CuI (485 mg, 2.55 mmol), Pd(PPh$_3$)$_2$Cl$_2$ (1.79 g, 2.55 mmol) and triethylamine (12.9 g, 127.4 mmol) in dry THF (100 mL) was heated to 60° C. under an atmosphere of nitrogen for 2 h. The mixture was concentrated and the residue was purified by column chromatography on silica gel (PE:EA=5:1) to give the title compound (6 g, 82%) as a yellow solid. $^1$H NMR (CDCl$_3$, 400 MHz): δ 7.61 (d, J=2.4 Hz, 1H), 7.42 (d, J=2.4 Hz, 1H), 3.54 (s, 3H), 0.25 (s, 9H). LCMS (M+H)$^+$=285.

Step 3: 1-methyl-5-(4,4,5,5-tetramethyl-1,3,2-dioxaborolan-2-yl)-3-(2-trimethylsilylethynyl)pyridin-2-one

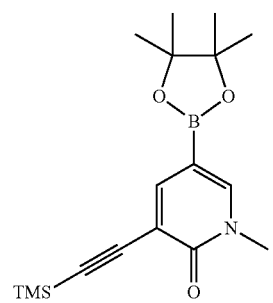 [SMILES: Cn1cc(B2OC(C)(C)C(C)(C)O2)cc(C#C[Si](C)(C)C)c1=O]

A mixture of 5-bromo-1-methyl-3-(2-trimethylsilylethynyl)pyridin-2-one (9.0 g, 31.67 mmol), 4,4,5,5-tetramethyl-2-(tetramethyl-1,3,2-dioxaborolan-2-yl)-1,3,2-dioxaborolane (20.1 g, 79.16 mmol), Pd$_2$(dba)$_3$ (1.8 g, 3.17 mmol), X-Phos (1.5 g, 3.17 mmol) and KOAc (18.65 g, 189.99 mmol) in anhydrous dioxane (200 mL) was stirred at 70° C. under an atmosphere of argon for 12 h. After the mixture was concentrated in vacuo, the residue was purified by column chromatography on silica gel (PE:EA=4:1) to give the title compound (3.5 g, 33%) as an off-white solid. $^1$H NMR (CDCl$_3$, 400 MHz): δ 7.88 (d, J=2.0 Hz, 1H), 7.75 (d, J=2.0 Hz, 1H), 3.56 (s, 3H), 1.31 (s, 12H), 0.25 (s, 9H). LCMS (M+H)$^+$=332 and 250.

Step 4: N-[4-(2,4-difluorophenoxy)-3-[1-methyl-6-oxo-5-(2-trimethylsilylethynyl)pyridin-3-yl]phenyl]ethanesulfonamide

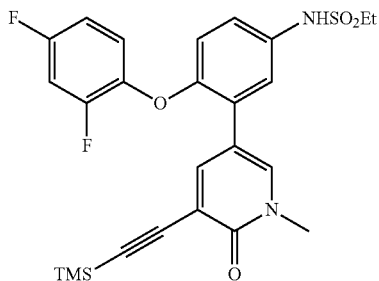

A mixture of 1-methyl-5-(4,4,5,5-tetramethyl-1,3,2-dioxaborolan-2-yl)-3-(2-trimethylsilylethynyl)pyridin-2-one (200 mg, 0.6 mmol), N-[3-Bromo-4-(2,4-difluorophenoxy)phenyl]ethanesulfonamide (197 mg, 0.5 mmol), Pd(dppf)Cl$_2$ (37 mg, 0.05 mmol) and K$_3$PO$_4$ (267 mg, 1.26 mmol) in dioxane (6 mL) and H$_2$O (0.6 mL) was stirred at 70° C. under an atmosphere of argon for 12 h. After the mixture was concentrated, the residue was purified by column chromatography on silica gel (PE:EA=2:1) to give the title compound (100 mg, 38%) as a yellow solid. $^1$H NMR (CDCl$_3$, 400 MHz): δ 7.82 (d, J=2.4 Hz, 1H), 7.67 (d, J=2.4 Hz, 1H), 7.23 (d, J=2.4 Hz, 1H), 7.16-7.12 (m, 1H), 6.99-6.91 (m, 2H), 6.87-6.83 (m, 1H), 6.78 (m, 1H), 6.65 (s, 1H), 3.61 (s, 3H), 3.14 (q, J=7.2 Hz, 2H), 1.42 (t, J=7.2 Hz, 3H), 024 (s, 9H). LCMS (M+H)$^+$=517.

Step 5: N-[4-(2,4-difluorophenoxy)-3-(5-ethynyl-1-methyl-6-oxopyridin-3-yl)phenyl]ethanesulfonamide

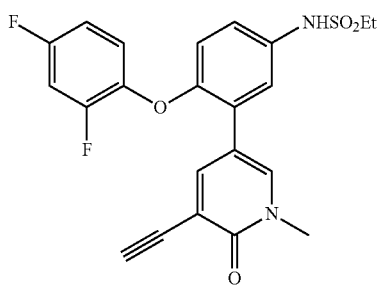

To a mixture of N-[4-(2,4-difluorophenoxy)-3-[1-methyl-6-oxo-5-(2-trimethylsilylethynyl)pyridin-3-yl]phenyl]ethanesulfonamide (100 mg, 0.19 mmol) in EtOH (10 mL) was added K$_2$CO$_3$ (157 mg, 1.14 mmol). The reaction was stirred at 20° C. for 12 h and poured into H$_2$O (30 mL) and extracted with DCM (20 mL×3). The organic phase was washed with brine (20 mL), dried over anhydrous MgSO$_4$ and concentrated in vacuo. The residue was purified by prep-HPLC to afford the title compound (48 mg, 56%) as an off-white solid. $^1$H NMR (CDCl$_3$, 400 MHz): δ 7.90 (d, J=2.4 Hz, 1H), 7.69 (d, J=2.4 Hz, 1H), 7.26 (d, J=2.8 Hz, 1H), 7.14-7.11 (m, 1H), 7.01-6.94 (m, 2H), 6.89-6.86 (m, 1H), 6.77 (d, J=8.8 Hz, 1H), 6.55 (s, 1H), 3.67 (s, 3H), 3.34 (s, 1H), 3.14 (q, J=7.2 Hz, 2H), 1.42 (t, J=7.2 Hz, 3H). LCMS (M+H)$^+$=445.

Example 284

5-[2-(cyclopropylmethoxy)-5-ethylsulfonylphenyl]-3-ethynyl-1-methylpyridin-2-one

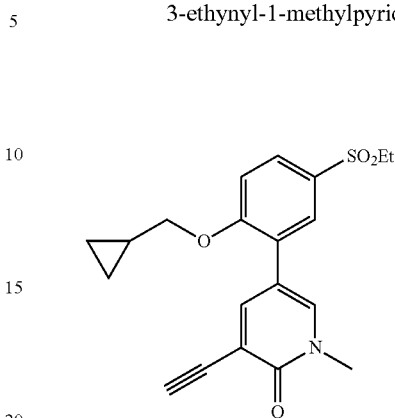

The title compound was prepared in a manner similar to Example 283, substituting 2-bromo-1-(cyclopropylmethoxy)-4-ethylsulfonylbenzene for N-[3-Bromo-4-(2,4-difluorophenoxy)phenyl]ethanesulfonamide in Step 4. $^1$H NMR (CDCl$_3$, 400 MHz): δ 7.93 (d, J=2.4 Hz, 1H), 7.84-7.81 (m, 1H), 7.76 (d, J=2.4 Hz, 1H), 7.68 (d, J=2.8 Hz, 1H), 7.03 (d, J=8.4 Hz, 1H), 3.96 (d, J=7.2 Hz, 2H), 3.66 (s, 3H), 3.35 (s, 1H), 3.13 (q, J=7.2 Hz, 2H), 1.32-1.27 (m, 4H), 0.71-0.67 (m, 2H), 0.40-0.37 (m, 2H). LCMS (M+H)$^+$=372.

Example 285

5-[2-(cyclopropylmethoxy)-5-methylsulfonylphenyl]-3-ethynyl-1-methylpyridin-2-one

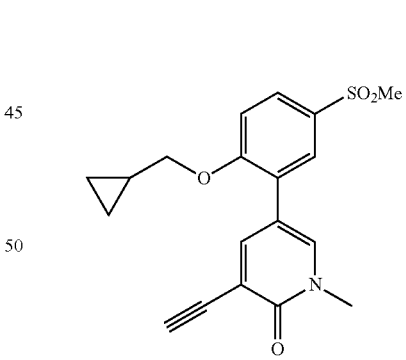

The title compound was prepared in a manner similar to Example 283, substituting 2-bromo-1-(cyclopropylmethoxy)-4-methylsulfonylbenzene for N-[3-Bromo-4-(2,4-difluorophenoxy)phenyl]ethanesulfonamide in Step 4. $^1$H NMR: (CDCl$_3$, 400 MHz) δ: 7.92 (d, J=2.0 Hz, 1H), 7.86 (d, J=8.8 Hz, 1H), 7.81 (s, 1H), 7.69 (d, J=1.6 Hz, 1H), 7.04 (d, J=8.4 Hz, 1H), 3.96 (d, J=6.8 Hz, 3H), 3.65 (s, 3H), 3.34 (s, 1H), 3.07 (s, 3H), 1.28-1.27 (m, 1H), 0.70-0.68 (m, 2H), 0.38-0.37 (m, 2H). LCMS (M+H)$^+$=358.

Example 286

N-[4-(2,4-difluorophenoxy)-3-(5-ethynyl-1-methyl-6-oxopyridin-3-yl)phenyl]methanesulfonamide

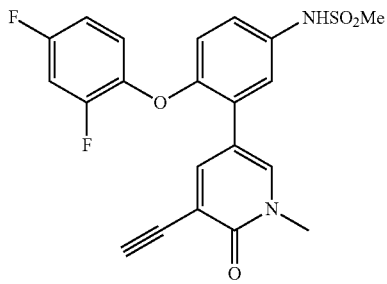

The title compound was prepared in a manner similar to Example 283, substituting N-[3-bromo-4-(2,4-difluorophenoxy)phenyl]methanesulfonamide for N-[3-Bromo-4-(2,4-difluorophenoxy)phenyl]ethanesulfonamide in Step 4. $^1$H NMR (CDCl$_3$, 400 MHz): δ 7.89 (d, J=3.2 Hz, 1H), 7.69 (d, J=3.2 Hz, 1H), 7.26-7.25 (m, 1H), 7.15-7.10 (m, 1H), 7.03-6.94 (m, 2H), 6.91-6.84 (m, 1H), 6.78 (d, J=11.6 Hz, 1H), 6.45 (s, 1H), 3.66 (s, 3H), 3.35 (s, 1H), 3.04 (s, 3H). LCMS (M+H)$^+$=431.

Example 287

5-[2-(cyclopropylmethoxy)-5-ethylsulfonylphenyl]-3-(difluoromethoxy)-1-methylpyridin-2-one Step 1: 5-bromo-3-methoxy-1-methylpyridin-2-one

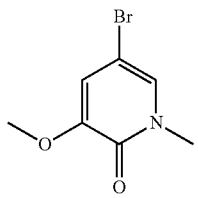

To a solution of 5-bromo-3-hydroxy-1H-pyridin-2-one (5.00 g, 26.31 mmol) in DMF (100 mL) stirred at 0° C. was added NaH (2.16 g, 53.95 mmol, 60% in mineral oil). After 30 min, iodomethane (9.33 g, 65.78 mmol) was added over a period of 5 min. After the mixture was stirred at rt for 12 h, it was quenched with water (20 mL) and extracted with EtOAc (100 mL×3). The combined organic layers were washed with brine (100 mL×3), dried over Na$_2$SO$_4$, and concentrated in vacuo to give the title compound (5.5 g, 96%). The material was carried forward without further purification. LCMS (M+H)$^+$=219.

Step 2: 5-bromo-3-hydroxy-1-methylpyridin-2-one

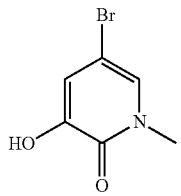

To a solution of 5-bromo-3-methoxy-1-methylpyridin-2-one (5.60 g, 25.7 mmol) stirred at 0° C. in DCM (100 mL) was added BBr$_3$ (12.87 g, 51.4 mmol). The icebath was removed and the mixture was stirred at rt for 5 h. After the mixture was cooled to 0° C., it was quenched with MeOH (5 mL), concentrated to near dryness and purified by column chromatography on silica gel to give title compound (3 g, 57%) as a white solid. $^1$H NMR (CDCl3, 400 MHz) δ 7.49 (s, 1H), 6.80 (s, 1H), 3.44 (s, 3H). LCMS (M+H)$^+$=205.

Step 3: 5-[2-(cyclopropylmethoxy)-5-ethylsulfonylphenyl]-3-hydroxy-1-methylpyridin-2-one

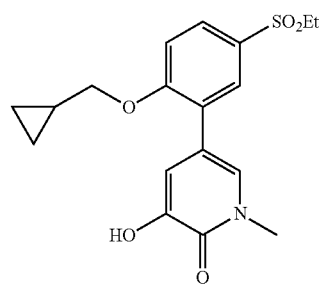

To a mixture of 5-bromo-3-hydroxy-1-methylpyridin-2-one (1.00 g, 4.9 mmol), 2-[2-(cyclopropylmethoxy)-5-ethylsulfonylphenyl]-4,4,5,5-tetramethyl-1,3,2-dioxaborolane (1.80 g, 4.9 mmol) in dioxane (30 mL) and H$_2$O (5 mL) was added K$_3$PO$_4$ (3.12 g, 14.7 mmol), Pd(dppf)Cl$_2$ (358 mg, 0.49 mmol). After purging the mixture with nitrogen, the mixture was stirred at 90° C. under microwave irradiation for 1 h. After the mixture was filtered, the filtrate was concentrated to dryness. The resulting residue was purified by prep-HPLC to give the title compound (0.9 g, 51%) as a purple solid. $^1$H NMR (CDCl3, 400 MHz) δ 7.81 (dd, J$_1$=8.8 Hz, J$_2$=2.4 Hz, 1H), 7.77 (d, J=2.4 Hz, 1H), 7.16-7.15 (m, 2H), 3.95 (d, J=6.8 Hz, 2H), 3.70 (s, 3H), 3.12 (q, J=7.6 Hz, 2H), 1.32-1.27 (m, 4H), 0.70-0.67 (m, 2H), 0.39-0.36 (m, 2H). LCMS (M+H)$^+$=364.

Step 4: 5-[2-(cyclopropylmethoxy)-5-ethylsulfonylphenyl]-3-(difluoromethoxy)-1-methylpyridin-2-one

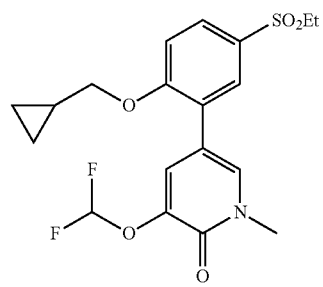

A mixture of 5-[2-(cyclopropylmethoxy)-5-ethylsulfonylphenyl]-3-hydroxy-1-methylpyridin-2-one (50 mg, 0.14 mmol), sodium chlorodifluoroacetate (252 mg, 1.65 mmol), K$_2$CO$_3$ (70 mg, 0.51 mmol) in dioxane (4 mL) was stirred at 100° C. for 18 h. After the mixture was filtered, the filtrate was concentrated in vacuo. The residue was purified by prep-HPLC to give the title compound (16 mg, 28%) as a light pink solid. ¹H NMR (CDCl₃, 400 MHz) δ 7.84 (m, 1H) 7.77 (d, J=2.4 Hz, 1H) 7.63 (d, J=2.4 Hz, 1H) 7.49 (d, J=2.4 Hz, 1H) 7.04 (m, 1H) 3.95 (m, 2H) 3.69 (s, 3H) 3.13 (m, 3H) 1.33-1.26 (m, 4H) 0.72-0.67 (m, 2H) 0.39-0.36 (m, 2H). LCMS (M+H)⁺=414.

Example 288

5-[2-(cyclopropylmethoxy)-5-ethylsulfonylphenyl]-1-methyl-3-(2,2,2-trifluoroethoxy)pyridin-2-one

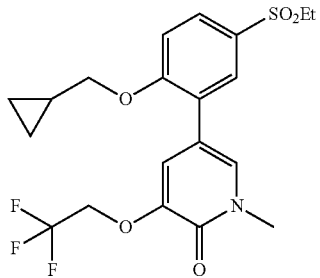

A mixture of 5-[2-(cyclopropylmethoxy)-5-ethylsulfonylphenyl]-3-hydroxy-1-methylpyridin-2-one (50 mg, 0.14 mmol), 2,2,2-trifluoroethyl trifluoromethanesulfonate (33 mg, 0.14 mmol), Cs₂CO₃ (134.48 mg, 0.42 mmol) in DMF (2 mL) was stirred at 20° C. for 2 h After the mixture was filtered, the filtrate was concentrated in vacuo. The residue was purified by prep-HPLC to give the title compound (29 mg, 47%) as an off-white solid. ¹H NMR (CDCl₃, 400 MHz) δ 7.84 (m, 1H), 7.77 (m, 1H), 7.41 (m, 2H), 7.04 (m, 1H), 4.58 (m, 2H), 3.95 (m, 2H), 3.70 (s, 3H), 3.14 (m, 2H), 1.33-1.27 (m, 4H), 0.72-0.69 (m, 2H), 0.39-0.35 (m, 2H). LCMS (M+H)⁺=446.

Example 289

N-[3-[5-(difluoromethoxy)-1-methyl-6-oxopyridin-3-yl]-4-(2,4-difluorophenoxy)phenyl]ethanesulfonamide Step 1: 5-bromo-3-(difluoromethoxy)-1-methylpyridin-2-one

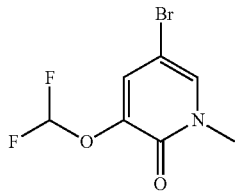

The title compound was prepared in a manner similar to step 4 in Example 287, substituting 5-bromo-3-hydroxy-1-methylpyridin-2-one for 5-[2-(cyclopropylmethoxy)-5-ethylsulfonylphenyl]-3-hydroxy-1-methylpyridin-2-one. LCMS (M+H)⁺=255.

Step 2: N-[3-[5-(difluoromethoxy)-1-methyl-6-oxopyridin-3-yl]-4-(2,4-difluorophenoxy)phenyl]ethanesulfonamide

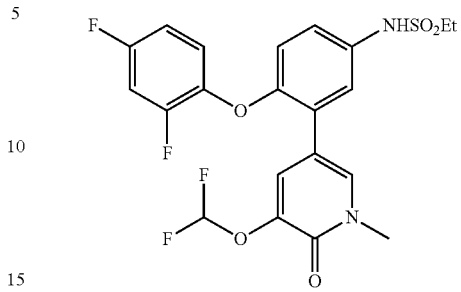

A mixture of 5-bromo-3-(difluoromethoxy)-1-methylpyridin-2-one (50 mg, 0.20 mmol), N-[4-(2,4-difluorophenoxy)-3-(4,4,5,5-tetramethyl-1,3,2-dioxaborolan-2-yl)phenyl]ethanesulfonamide (88 mg, 0.18 mmol), Pd(dppf)Cl₂ (11 mg) and K₃PO₄ (85 mg, 0.40 mmol) in dioxane (5 mL) and water (5 drops) was purged with nitrogen, capped, and heated to 70° C. for 8 h. After the mixture was filtered, the filtrate was concentrated in vacuo and purified by prep-HPLC to afford the title compound (13 mg, 13%) as a white solid. ¹H NMR (CDCl₃, 400 MHz) δ 7.53 (m, 2H) 7.25 (m, 1H) 7.05 (m, 1H) 7.12 (m, 1H) 7.02-6.97 (m, 2H) 6.97-6.95 (m, 1H) 6.77 (m, 1H) 6.48 (bs, 1H) 3.67 (s, 3H) 3.15 (q, J=7.4 Hz, 2H) 1.42 (t, J=7.4 Hz, 3H). LCMS (M+H)⁺=487.

Example 290

N-[4-(2,4-difluorophenoxy)-3-[1-methyl-6-oxo-5-(2,2,2-trifluoroethoxy)pyridin-3-yl]phenyl]ethanesulfonamide Step 1: 5-bromo-1-methyl-3-(2,2,2-trifluoroethoxy)pyridin-2-one

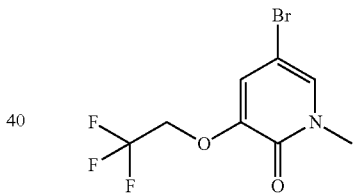

The title compound was prepared in a manner similar to Example 288, substituting 5-bromo-3-hydroxy-1-methylpyridin-2-one for 5-[2-(cyclopropylmethoxy)-5-ethylsulfonylphenyl]-3-hydroxy-1-methylpyridin-2-one. LCMS (M+H)⁺=287.

Step 2: N-[4-(2,4-difluorophenoxy)-3-[1-methyl-6-oxo-5-(2,2,2-trifluoroethoxy)pyridin-3-yl]phenyl]ethanesulfonamide

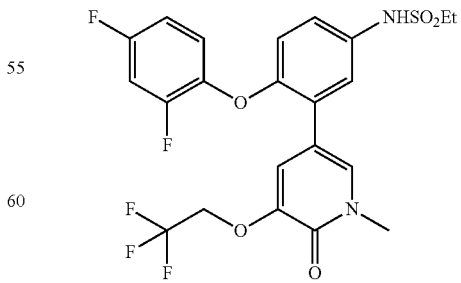

A mixture of 5-bromo-1-methyl-3-(2,2,2-trifluoroethoxy)pyridin-2-one (50 mg, 0.18 mmol), N-[4-(2,4-difluorophenoxy)-3-(4,4,5,5-tetramethyl-1,3,2-dioxaborolan-2-yl)phenyl]ethanesulfonamide (79 mg, 0.18 mmol), Pd(dppf)Cl$_2$ (11 mg) and K$_3$PO$_4$ (76 mg, 0.36 mmol) in dioxane (5 mL) and water (5 drops) was purged with nitrogen, capped, and heated to 70° C. for 8 h. After the mixture was filtered, the filtrate was concentrated in vacuo and purified by prep-HPLC to afford the title compound (11 mg, 11%) as a white solid. $^1$H NMR (CDCl$_3$, 400 MHz) δ 7.39 (m, 1H) 7.32 (m, 1H) 7.25 (d, J=2.8 Hz, 1H) 7.12 (dd, J$_1$=2.8 Hz, J$_2$=8.8 Hz, 1H) 6.99-6.93 (m, 2H) 6.88-6.83 (m, 1H) 6.79 (d, J=8.8 Hz, 1H) 6.47 (b.s., 1H), 4.56 (m, 2H), 3.65 (s, 3H) 3.15 (q, J=7.2 Hz, 2H) 1.42 (t, J=7.2 Hz, 3H). LCMS (M+H)$^+$=519.

Example 291

3-(difluoromethoxy)-5-[2-(2,4-difluorophenoxy)-5-(ethylsulfonylmethyl)phenyl]-1-methylpyridin-2-one

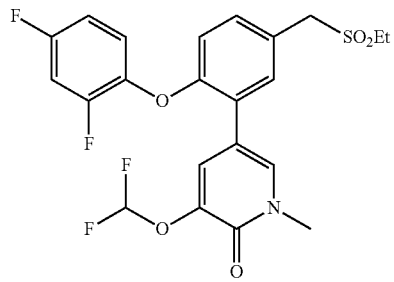

A mixture of 5-bromo-3-(difluoromethoxy)-1-methylpyridin-2-one (50 mg, 0.20 mmol), 2-[2-(2,4-difluorophenoxy)-5-(ethylsulfonylmethyl)phenyl]-4,4,5,5-tetramethyl-1,3,2-dioxaborolane (79 mg, 0.18 mmol), Pd(dppf)Cl$_2$ (11 mg) and K$_3$PO$_4$ (76 mg, 0.36 mmol) in dioxane (5 mL) and water (5 drops) was purged with nitrogen, capped, and heated to 70° C. for 8 h. After the mixture was filtered, the filtrate was concentrated in vacuo and purified by prep-HPLC to afford the title compound (21 mg, 22%) as a white solid. $^1$H NMR (CDCl$_3$, 400 MHz) δ 7.62 (d, J=2.0 Hz, 1H) 7.54 (d, J=2.0 Hz, 1H) 7.40 (d, J=2.0 Hz, 1H) 7.29 (d, J=2.0 Hz, 1H) 7.09-6.96 (m, 3H) 6.93-6.88 (m, 1H) 6.78 (m, 1H) 4.21 (s, 2H) 3.70 (s, 3H) 2.97 (q, J=7.6 Hz, 2H) 1.43 (t, J=7.6 Hz, 3H). LCMS (M+H)$^+$=486.

Example 292

5-[2-(2,4-difluorophenoxy)-5-(ethylsulfonylmethyl)phenyl]-1-methyl-3-(2,2,2-trifluoroethoxy)pyridin-2-one

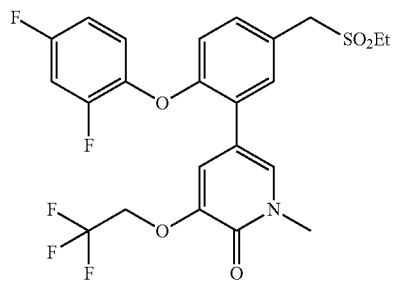

A mixture of 5-bromo-1-methyl-3-(2,2,2-trifluoroethoxy)pyridin-2-one (50 mg, 0.18 mmol), 2-[2-(2,4-difluorophenoxy)-5-(ethylsulfonylmethyl)phenyl]-4,4,5,5-tetramethyl-1,3,2-dioxaborolane (88 mg, 0.20 mmol), Pd(dppf)Cl$_2$ (11 mg) and K$_3$PO$_4$ (85 mg, 0.40 mmol) in dioxane (5 mL) and water (5 drops) was purged with nitrogen, capped, and heated to 70° C. for 8 h. After the mixture was filtered, the filtrate was concentrated in vacuo and purified by prep-HPLC to afford the title compound (21 mg, 22%) as a white solid. $^1$H NMR (CDCl$_3$, 400 MHz) δ 7.41 (m, 2H) 7.35 (m, 1H) 7.30 (m, 1H) 7.07-6.96 (m, 2H) 6.92-6.87 (m, 1H) 6.80 (m, 1H), 4.51 (m, 2H) 4.21 (s, 2H) 3.69 (s, 3H) 2.97 (m, 2H) 1.44 (m, 3H). LCMS (M+H)$^+$=518.

Example 293

5-[2-(cyclopropylmethoxy)-5-methylsulfonylphenyl]-1-methyl-3-(1-methylpyrazol-4-yl)oxypyridin-2-one Step 1: 5-bromo-1-methyl-3-(1-methylpyrazol-4-yl)oxypyridin-2-one

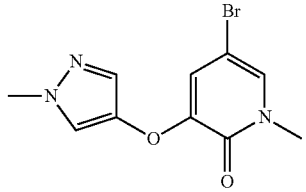

A 0.3M solution of 5-bromo-3-chloro-1-methylpyridin-2-one (124 mg, 0.56 mmol) in DMF was treated with Cs$_2$CO$_3$ (546 mg, 1.7 mmol). The mixture was sonicated for 30 sec before heating to 140° C. by microwave irradiation (normal) for 150 min. The resulting suspension was diluted with water and extracted with EtOAc (15 mL×3). The combined organic layers were washed with brine, dried over Na$_2$SO$_4$, and concentrated in vacuo. The resulting solid was purified by silica gel column chromatography using a gradient of EtOAc (5 to 60%) in hexanes to afford the title compound (33 mg, 19%) as a tan solid. LCMS (M+H)$^+$=285.

Step 2: 5-[2-(cyclopropylmethoxy)-5-methylsulfonylphenyl]-1-methyl-3-(1-methylpyrazol-4-yl)oxypyridin-2-one

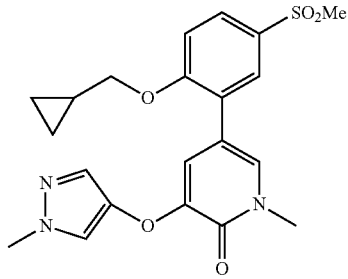 [SMILES: Cn1cc(Oc2cc(-c3cc(S(C)(=O)=O)ccc3OCC3CC3)cn(C)c2=O)cn1]

A mixture of 5-bromo-1-methyl-3-(1-methylpyrazol-4-yl)oxypyridin-2-one (30 mg, 0.11 mmol), 2-[2-(cyclopropylmethoxy)-5-methylsulfonylphenyl]-4,4,5,5-tetramethyl-1,3,2-dioxaborolane (44 mg, 0.16 mmol), Pd(dppf)Cl$_2$ (8 mg) and K$_3$PO$_4$ (57 mg, 0.26 mmol) in dioxane (1.5 mL) and water (200 uL) was purged with nitrogen, capped, and heated to 75° C. for 12 h. After the mixture was filtered through a short bed of celite, the filtrate was concentrated in vacuo and purified by prep-HPLC to afford the title compound (35 mg, 78%) as an off-white solid. $^1$H NMR (400 MHz, DMSO-d$_6$) δ ppm 0.12-0.36 (m, 2H) 0.46-0.61 (m, 2H) 0.99-1.17 (m, 1H) 3.14-3.23 (m, 3H) 3.55-3.60 (m, 3H) 3.75-3.83 (m, 3H) 3.88-3.96 (m, 2H) 7.18-7.32 (m, 2H) 7.32-7.40 (m, 1H) 7.68-7.91 (m, 4H). LCMS (M+H)$^+$=430.

Example 294

5-[2-(cyclopropylmethoxy)-5-methylsulfonylphenyl]-1-methyl-3-(1-propan-2-ylpyrazol-4-yl)oxypyridin-2-one Step 1: 1-propan-2-ylpyrazol-4-ol

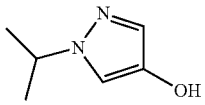

A 0.4 M solution of 1-propan-2-yl-4-(4,4,5,5-tetramethyl-1,3,2-dioxaborolan-2-yl)pyrazole (472 mg, 2 mmol) in THF stirred at 0° C. was treated with a 2.5 M aqueous solution of NaOH (1.6 mL, 4 mmol) and 30% $H_2O_2$ (aq) (453 μL, 4 mmol). The icebath was removed and the mixture was allowed to stir at rt for 1 h. After the pH was adjusted to 3 by the addition of aqueous 2N $H_2SO_4$, the mixture was extracted with DCM. The combined organic layers were washed with brine, dried over $MgSO_4$, filtered, and concentrated in vacuo. The resulting solid was purified by silica gel column chromatography using a gradient of EtOAc (5 to 90%) in hexanes to afford the title compound (240 mg, 95%) as a white solid. LCMS $(M+H)^+=127$.

Step 2: 5-[2-(cyclopropylmethoxy)-5-methylsulfonylphenyl]-3-iodo-1-methylpyridin-2-one

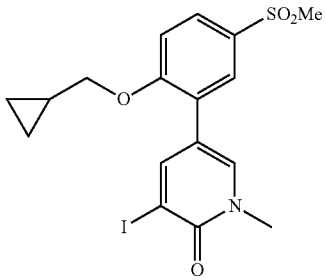 [SMILES: Cn1cc(-c2cc(S(C)(=O)=O)ccc2OCC2CC2)cc(I)c1=O]

A 0.2 M solution of the title compound (264 mg, 0.8 mmol) from Example 98 in DMF stirred at 0° C. was treated with three equal portions of N-iodosuccinimide (187 mg, 84 mmol). After 15 min, the icebath was removed and the mixture was stirred at rt for 2 h. The reaction mixture was treated with 10% sodium thiosulfate (aq) (5 mL) and extracted with EtOAc (20 mL×3). The combined organic layers were washed with water and brine, dried over $MgSO_4$, filtered, and concentrated in vacuo to afford a crude solid. The resulting solid was purified by silica gel column chromatography using a gradient of EtOAc (0 to 100%) in DCM to afford the title compound (333 mg, 91%) as a white solid. LCMS $(M+H)^+=460$.

Step 3: 5-[2-(cyclopropylmethoxy)-5-methylsulfonylphenyl]-1-methyl-3-(1-propan-2-ylpyrazol-4-yl)oxypyridin-2-one

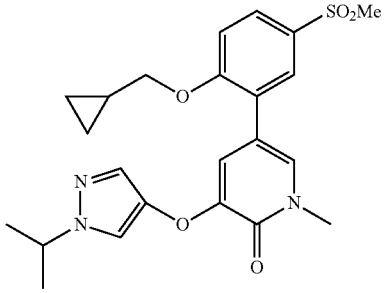 [SMILES: CC(C)n1cc(Oc2cc(-c3cc(S(C)(=O)=O)ccc3OCC3CC3)cn(C)c2=O)cn1]

A mixture of 5-[2-(cyclopropylmethoxy)-5-methylsulfonylphenyl]-3-iodo-1-methylpyridin-2-one (91 mg, 0.2 mmol), 1-propan-2-ylpyrazol-4-ol (45 mg, 0.36 mmol), CuI (4 mg, 10%), 2,2,6,6-tetramethyl-3,5-heptanedione (8 uL, 0.04 mmol) and $K_3PO_4$ (85 mg, 0.4 mmol) in DMSO (1 mL) was purged with nitrogen for 10 min, capped, and heated to 110° C. for 13 h. After the mixture was filtered through a short bed of celite, the filtrate was concentrated in vacuo and purified by prep-HPLC to afford the title compound (36 mg, 40%) as a white solid. $^1$H NMR (400 MHz, DMSO-$d_6$) δ ppm 0.18-0.26 (m, 2H) 0.44-0.53 (m, 2H) 1.03-1.10 (m, 1H) 1.37-1.43 (m, 6H) 3.17-3.21 (m, 3H) 3.54-3.61 (m, 3H) 3.87-3.93 (m, 2H) 4.33-4.46 (m, 1H) 7.20-7.25 (m, 1H) 7.25-7.28 (m, 1H) 7.33-7.36 (m, 1H) 7.70-7.74 (m, 1H) 7.76-7.85 (m, 4H). LCMS $(M+H)^+=458$.

Example 295

5-[2-(cyclopropylmethoxy)-5-methylsulfonylphenyl]-1-methyl-3-phenoxypyridin-2-one

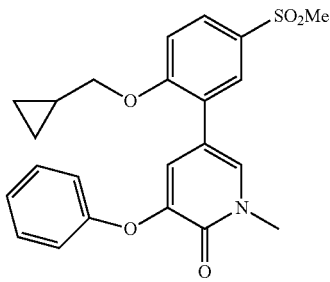 [SMILES: Cn1cc(-c2cc(S(C)(=O)=O)ccc2OCC2CC2)cc(Oc2ccccc2)c1=O]

The title compound was prepared in a manner similar to Step 3 of Example 294, substituting phenol for 1-propan-2-ylpyrazol-4-ol. $^1$H NMR (400 MHz, DMSO-$d_6$) δ ppm 0.23-0.30 (m, 2H) 0.41-0.50 (m, 2H) 1.05-1.16 (m, 1H) 3.17-3.22 (m, 3H) 3.54-3.61 (m, 3H) 3.88-3.97 (m, 2H) 6.95-7.01 (m, 2H) 7.04-7.11 (m, 1H) 7.21-7.27 (m, 1H) 7.30-7.37 (m, 2H) 7.49-7.54 (m, 1H) 7.77-7.83 (m, 1H) 7.83-7.92 (m, 2H). LCMS $(M+H)^+=426$

Example 296

N-[4-(1-butyl-5-methyl-6-oxopyridin-3-yl)-5-(2,4-difluorophenoxy)pyrimidin-2-yl]methanesulfonamide

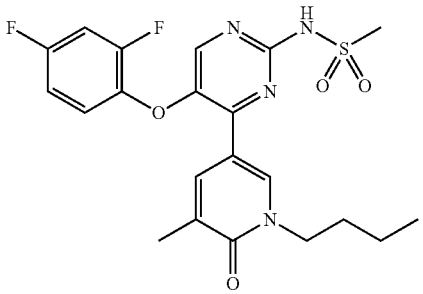

The title compound was prepared in four steps in a similar manner to Example 248 except that 1-iodobutane was sub-

Example 297

N-[4-(1-butyl-5-methyl-6-oxopyridin-3-yl)-5-(2,4-difluorophenoxy)pyrimidin-2-yl]ethanesulfonamide

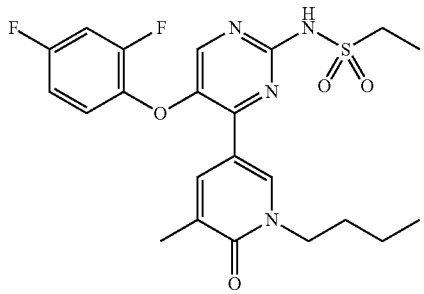 [SMILES: CCCCn1cc(-c2nc(NS(=O)(=O)CC)ncc2Oc2ccc(F)cc2F)cc(C)c1=O]

The title compound was prepared in four steps in a similar manner to Example 248 except that 1-iodobutane was substituted for bromomethylcyclopropane in step 1 and EtSO$_2$NH$_2$ was substituted for MeSO$_2$NH$_2$ in step 4. $^1$H NMR (CDCl$_3$, 400 MHz) δ 8.83 (s, 1H), 8.38 (s, 1H), 8.16 (s, 1H), 8.08 (s, 1H), 7.04-6.95 (m, 2H), 6.94-6.88 (m, 1H), 4.00 (t, J=7.2 Hz, 2H), 3.64 (q, J=7.2 Hz, 2H), 2.21 (s, 3H), 1.75-1.72 (m, 2H), 1.45 (t, J=7.2 Hz, 3H), 1.37-1.33 (m, 2H), 0.93 (t, J=7.2 Hz, 3H). LCMS: 479.1 (M+H)$^+$

Example 298

N-[4-[1-(cyclobutylmethyl)-5-methyl-6-oxopyridin-3-yl]-5-(2,4-difluorophenoxy)pyrimidin-2-yl]methanesulfonamide

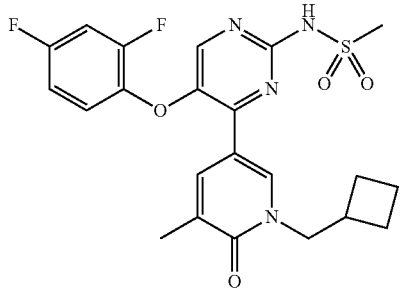 [SMILES: Cc1cc(-c2nc(NS(C)(=O)=O)ncc2Oc2ccc(F)cc2F)cn(CC2CCC2)c1=O]

The title compound was prepared in four steps in a similar manner to Example 248 except that 1-(bromomethyl)cyclobutane was substituted for bromomethylcyclopropane in step 1. $^1$H NMR (CDCl$_3$, 400 MHz) δ 8.96 (s, 1H), 8.39 (s, 1H), 8.14 (s, 1H), 8.09 (s, 1H), 7.02-6.96 (m, 2H), 6.91-6.89 (m, 1H), 4.03 (d, J=7.2 Hz, 2H), 3.44 (s, 3H), 2.82-2.74 (m, 1H), 2.21 (s, 3H), 2.04-2.03 (m, 2H), 1.89-1.85 (m, 2H), 1.79-1.74 (m, 2H). LCMS: 477.1 (M+H)$^+$

Example 299

N-[4-[1-(cyclobutylmethyl)-5-methyl-6-oxopyridin-3-yl]-5-(2,4-difluorophenoxy)pyrimidin-2-yl]ethanesulfonamide

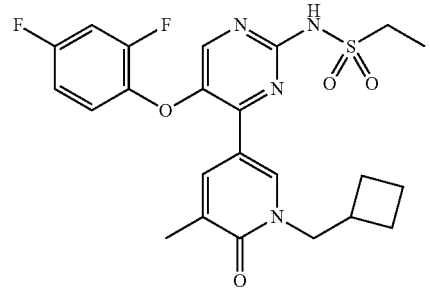 [SMILES: CCS(=O)(=O)Nc1ncc(Oc2ccc(F)cc2F)c(-c2cc(C)c(=O)n(CC3CCC3)c2)n1]

The title compound was prepared in four steps in a similar manner to Example 248 except that -(bromomethyl)cyclobutane was substituted for bromomethylcyclopropane in step 1 and EtSO$_2$NH$_2$ was substituted for MeSO$_2$NH$_2$ in step 4. $^1$H NMR (CDCl$_3$, 400 MHz) δ 8.38 (d, J=2.4 Hz, 1H), 8.13 (s, 1H), 8.08 (s, 1H), 7.04-6.98 (m, 2H), 6.97-6.88 (m, 1H), 4.02 (d, J=7.2 Hz, 2H), 3.63 (q, J=7.2 Hz, 2H), 2.80-2.76 (m, 1H), 2.20 (s, 3H), 2.04-2.03 (m, 2H), 1.89-1.76 (m, 4H), 1.44 (t, J=7.2 Hz, 3H). LCMS: 491.1 (M+H)$^+$

Example 300

N-[5-ethyl-4-(2-methyl-1-oxoisoquinolin-4-yl)pyrimidin-2-yl]ethanesulfonamide

Step 1

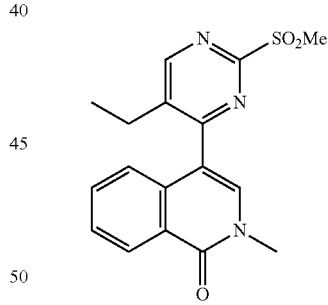

4-chloro-5-ethyl-2-methylsulfonylpyrimidine was prepared in a manner similar to Example 152, steps 2-4 except that ethyl butanoate was substituted for ethyl 2-(cyclopropylmethoxy)acetate in step 2. Thus prepared, 4-chloro-5-ethyl-2-methylsulfonylpyrimidine and the title compound of Example 89, step 1 were reacted in a similar manner as Example 152, step 5. Silica gel chromatography (PE:EA=1:1-0:1) gave the title compound (120 mg, yield: 77%) as a yellow solid. $^1$H NMR (CDCl$_3$, 400 MHz) δ 8.90 (s, 1H), 8.55 (d, J=8 Hz, 1H), 7.64-7.55 (m, 2H), 7.28 (s, 1H), 7.07 (d, J=8 Hz, 1H), 3.69 (s, 3H), 3.39 (s, 3H), 2.67 (q, J=8 Hz, 2H), 1.17 (t, J=8 Hz, 3H). LCMS: 344.0 (M+1)$^+$ Step 2: N-[5-ethyl-4-(2-methyl-1-oxoisoquinolin-4-yl)pyrimidin-2-yl]ethanesulfonamide

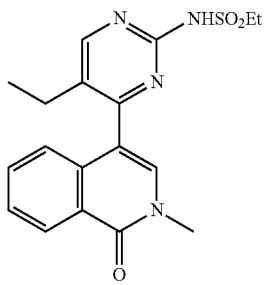

The title compound of step 1 was treated with EtSO$_2$NH$_2$ in a manner similar to Example 155 to give the title compound. $^1$H NMR (CDCl$_3$, 400 MHz) δ 8.59 (s, 1H), 8.53 (d, J=8 Hz, 1H), 7.63 (t, J=8 Hz, 1H), 7.55 (t, J=8 Hz, 1H), 7.23 (d, J=12 Hz, 1H), 7.17 (s, 1H), 3.68 (s, 3H), 3.64 (t, J=8 Hz, 2H), 2.52 (q, J=8 Hz, 2H), 1.44 (t, J=8 Hz, 3H), 1.09 (t, J=8 Hz, 3H).
LCMS: 373.0 (M+1)$^+$ Examples 301, 303-305 in Table 16 were prepared in a similar multi-step manner as Example 300, step 1 wherein ethyl pentanoate was converted to 4-chloro-2-methylsulfonyl-5-propylpyrimidine and ethyl hexanoate was converted to 5-butyl-4-chloro-2-methylsulfonylpyrimidine. Thus prepared, both the 4-chloro-2-methylsulfonyl-5-propylpyrimidine and the 5-butyl-4-chloro-2-methylsulfonylpyrimidine were each coupled to the title compound of Example 89, step 1 or 1,3-dimethyl-5-(4,4,5,5-tetramethyl-1,3,2-dioxaborolan-2-yl)-2(1H)-pyridinone in a manner similar to Example 152, step 5 to give the title compounds. Example 302 was prepared from 4-chloro-5-ethyl-2-methylsulfonylpyrimidine (described in Example 300, step 1) and 1,3-dimethyl-5-(4,4,5,5-tetramethyl-1,3,2-dioxaborolan-2-yl)-2(1H)-pyridinone which were also reacted in a manner similar to Example 152, step 5.

Example 302 in Table 16 was prepared from 4-chloro-5-ethyl-2-methylsulfonylpyrimidine (described in Example 300, step 1) and 1,3-dimethyl-5-(4,4,5,5-tetramethyl-1,3,2-dioxaborolan-2-yl)-2(1H)-pyridinone which were also reacted in a manner similar to Example 152, step 5.

TABLE 16

| Ex. No. | Structure | Name | $^1$H NMR (ppm (δ), 440 MHz) | MS (M + H) |
|---|---|---|---|---|
| 301 | 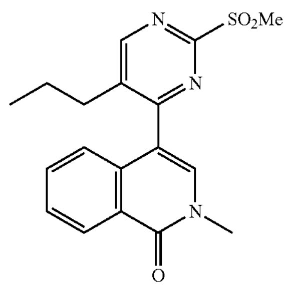 [SMILES: CCCc1cnc(S(C)(=O)=O)nc1-c1cn(C)c(=O)c2ccccc12] | 2-methyl-4-(2-methylsulfonyl-5-propylpyrimidin-4-yl)isoquinolin-1-one | (CDCl$_3$, 400 MHz) δ 8.88 (s, 1 H), 8.54 (d, J = 8 Hz, 1 H), 7.65-7.55 (m, 2 H), 7.06 (d, J = 8 Hz, 1 H), 3.69 (s, 3 H), 3.39 (s, 3 H), 2.61 (t, J = 8 Hz, 2 H), 1.56-1.50 (m, 2 H), 0.83 (t, J = 7.6 Hz, 3 H). | 358 |
| 302 | 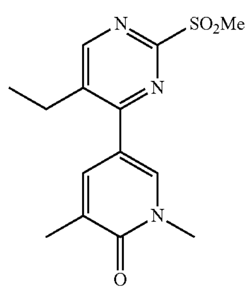 [SMILES: CCc1cnc(S(C)(=O)=O)nc1-c1cc(C)c(=O)n(C)c1] | 5-(5-ethyl-2-methylsulfonyl pyrimidin-4-yl)-1,3-dimethylpyridin-2-one | (CDCl$_3$, 400 MHz) δ 8.73 (s, 1 H), 7.84 (s, 1 H), 7.55 (s, 1 H), 3.67 (s, 3 H), 3.37 (s, 3 H), 2.90 (q, J = 7.6 Hz, 2 H), 2.23 (s, 3 H), 1.33 (t, J = 7.6 Hz, 3 H) | 308 |
| 303 | 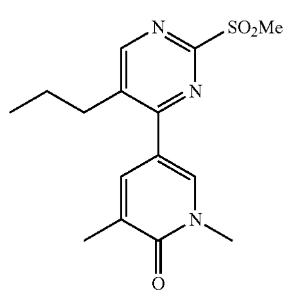 [SMILES: CCCc1cnc(S(C)(=O)=O)nc1-c1cc(C)c(=O)n(C)c1] | 1,3-dimethyl-5-(2-methylsulfonyl-5-propylpyrimidin-4-yl)pyridin-2-one | | 322 |

TABLE 16-continued

| Ex. No. | Structure | Name | $^1$H NMR (ppm (δ), 440 MHz) | MS (M + H) |
|---|---|---|---|---|
| 304 | 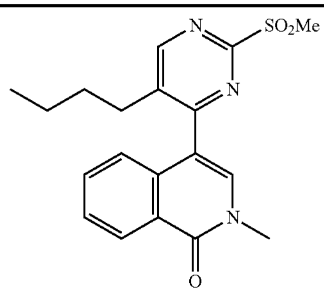 | 4-(5-butyl-2-methylsulfonyl pyrimidin-4-yl)-2-methylisoquinolin-1-one | | 372 |
| 305 | 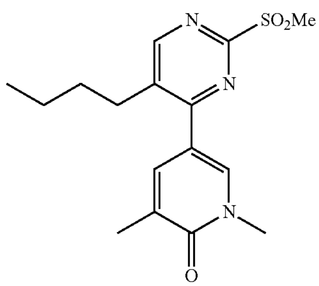 [SMILES: CCCCc1cnc(S(C)(=O)=O)nc1-c1cc(C)c(=O)n(C)c1] | 5-(5-butyl-2-methylsulfonyl pyrimidin-4-yl)-1,3-dimethylpyridin-2-one | (CDCl$_3$, 400 MHz) δ 8.70 (s, 1 H), 7.84 (s, 1 H), 7.55 (s, 1 H), 3.67 (s, 3 H), 3.37 (s, 3 H), 2.84 (t, J = 8.0 Hz, 2 H), 2.24 (s, 3 H), 1.68 (m, 2 H, overlapped with water peak), 1.41 (m, 2 H), 0.96 (t, J = 7.2 Hz, 3 H). | 336 |

Examples 306-310 in Table 17 were prepared in a similar manner as Example 300, step 2 wherein Examples 301-305 were each treated with EtSO$_2$NH$_2$ to give the title compound.

TABLE 17

| Ex. No. | Structure | Name | $^1$H NMR (ppm (δ), 400 MHz) | MS (M + H) | Prepared from Ex. No. |
|---|---|---|---|---|---|
| 306 | 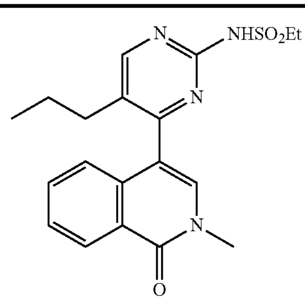 | N-[4-(2-methyl-1-oxoisoquinolin-4-yl)-5-propylpyrimidin-2-yl]ethanesulfonamide | (CDCl$_3$, 400 MHz) δ 8.58 (s, 1 H), 8.54 (d, J = 8 Hz, 1 H), 7.64 (t, J = 8 Hz, 1 H), 7.56 (t, J = 8 Hz, 1 H), 7.24 (s, 1 H), 7.18 (s, 1 H), 3.69 (s, 3 H), 3.67-3.61 (m, 2 H), 2.47 (t, J = 8 Hz, 2 H), 1.51-1.47 (t, J = 8 Hz, 2 H), 1.45-1.41 (t, J = 8 Hz, 3 H), 0.81 (t, J = 8 Hz, 3 H). | 387 | 301 |
| 307 | 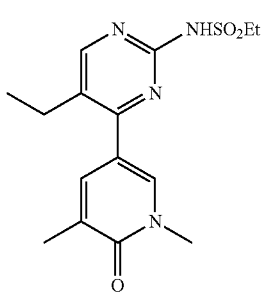 | N-[4-(1,5-dimethyl-6-oxopyridin-3-yl)-5-ethylpyrimidin-2-yl]ethanesulfonamide | (CDCl$_3$, 400 MHz) δ 8.47 (s, 1H), 7.69 (s, 1 H), 7.55 (s, 1 H), 3.67 (m, 5 H), 2.75 (q, J = 8 Hz, 2 H), 2.24 (s, 3 H), 1.45 (t, J = 8 Hz, 3 H), 1.26 (t, J = 8 Hz, 3 H) | 337 | 302 |

TABLE 17-continued

| Ex. No. | Structure | Name | ¹H NMR (ppm (δ), 400 MHz) | MS (M + H) | Prepared from Ex. No. |
|---|---|---|---|---|---|
| 308 | 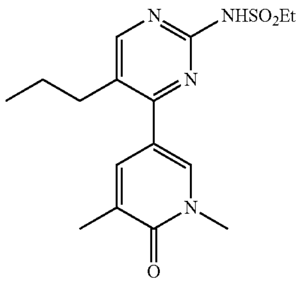 | N-[4-(1,5-dimethyl-6-oxopyridin-3-yl)-5-propylpyrimidin-2-yl]ethanesulfonamide | (CDCl$_3$, 400 MHz) δ 8.42 (s, 1 H), 7.67 (d, J = 2 Hz, 1 H), 7.53 (s, 1 H), 3.69 (t, J = 8 Hz, 2 H), 3.65 (d, J = 8 Hz, 3 H), 2.66 (q, J = 8 Hz, 2 H), 2.23 (s, 3 H), 1.62-1.60 (m, 2 H), 1.45 (t, J = 8 Hz, 3 H), 0.98 (t, J = 8 Hz, 3 H) | 351 | 303 |
| 309 | 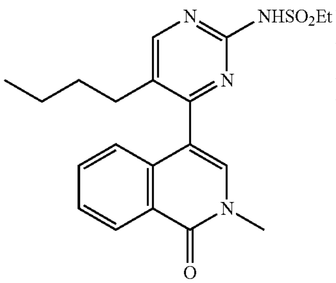 | N-[5-butyl-4-(2-methyl-1-oxoisoquinolin-4-yl)pyrimidin-2-yl]ethanesulfonamide | (CDCl$_3$, 400 MHz) δ 8.57 (s, 1 H), 8.53 (d, J = 8 Hz, 1 H), 7.65-7.61 (m, 1 H), 7.58-7.53 (m, 1 H), 7.24 (d, J = 8 Hz, 1 H), 7.17 (s, 1 H), 3.68 (s, 3 H), 3.67-3.61 (m, 2 H), 2.48 (t, J = 8 Hz, 2 H), 1.46-1.39 (m, 5 H), 1.23-1.16 (m, 2 H), 0.76 (t, J = 7.2 Hz, 3 H) | 401 | 304 |
| 310 | 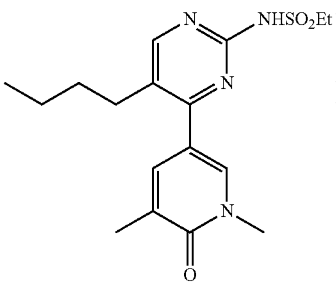 | N-[5-butyl-4-(1,5-dimethyl-6-oxopyridin-3-yl)pyrimidin-2-yl]ethanesulfonamide | (CDCl$_3$, 400 MHz) δ 8.47 (s, 1 H), 7.71 (s, 1 H), 7.55 (s, 1 H), 3.68-3.62 (m, 5 H), 2.69 (t, J = 8 Hz, 2 H), 2.23 (s, 3 H), 1.55-1.46 (m, 2 H), 1.40-1.37 (m, 5 H), 0.94 (t, J = 7.2 Hz, 3 H) | 365 | 305 |

Example 311

4-[5-(cyclopropylmethoxy)-2-methylsulfonylpyrimidin-4-yl]-2-methylisoquinolin-1-one

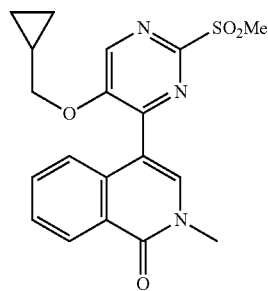 [SMILES: Cn1cc(-c2nc(S(C)(=O)=O)ncc2OCC2CC2)c2ccccc2c1=O]

The title compound of Example 152, step 5 was purified by preparative HPLC to give a cream colored powder. ¹H NMR (CDCl$_3$, 400 MHz) δ8.53 (s, 2H), 7.67-7.63 (m, 2H), 7.57-7.52 (m, 2H), 4.06 (d, J=6.8 Hz, 1H), 3.71 (s, 3H), 3.37 (s, 3H), 1.17 (m, 1H), 0.61 (m, 2H), 0.30 (m, 2H). LCMS: 386.1 (M+1)$^+$

Example 312

5-(2-ethyl-5-methylsulfonylphenyl)-1-methylpyridin-2-one

Step 1: 1-ethyl-4-methylsulfonyl-2-nitrobenzene

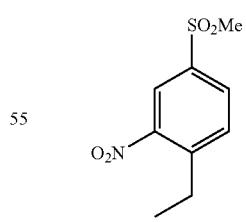

bromo-4-methylsulfonyl-2-nitrobenzene (2 g, 7.0 mmol), ethylboronic acid (0.57 g, 7.7 mmol), K$_2$CO$_3$ (3.0 g, 21 mmol), Pd(dppf)Cl$_2$ (0.29 g, 0.35 mmol) in 1,4-dioxane/water (4:1) (24 mL) were heated at 85° C. under N$_2$ overnight. Silica gel chromatography (PE:EA=6:1) gave the title compound (0.66 g, 40%) as a brown solid.

Step 2: 2-ethyl-5-methylsulfonylaniline

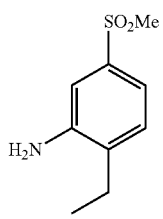

The title compound of step 1 (0.6 g, 2.6 mmol) and palladium on carbon (0.18 g) in CH₃OH (20 mL) was hydrogenated at 1 atm. for 6 h. Silica gel chromatography (PE:EA=6:1) gave the title compound (0.49 g, 94%) as a brown liquid.

Step 3: 1-ethyl-2-iodo-4-methylsulfonylbenzene

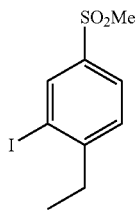

To the title compound of step 2 (155 mg, 0.8 mmol) in 5M HCl (3 mL) and H₂O (4 mL), cooled to 0° C., was added NaNO₂ (66 mg, 0.96 mmol). After stirring 0° C. for 30 min, KI (1.33 g, 8 mmol) in water (2 mL) was added and the mixture was warmed to rt & stirred 1 h. Silica gel chromatography (PE:EA=3:1) gave the title compound (213 mg, 86%) as a brown solid.

Step 4: 5-(2-ethyl-5-methylsulfonylphenyl)-1-methylpyridin-2-one

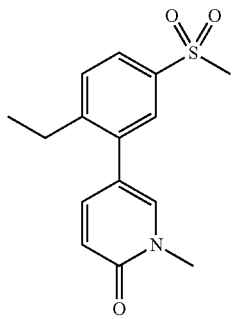 [SMILES: CCc1ccc(S(C)(=O)=O)cc1-c1ccc(=O)n(C)c1]

The title compound of step 3 (62 mg, 0.2 mmol), 1-methyl-5-(4,4,5,5-tetramethyl-1,3,2-dioxaborolan-2-yl)pyridin-2-one (57 mg, 0.24 mmol), K₂CO₃ (82 mg, 0.6 mmol), Pd(dppf)Cl₂ (6.2 mg) in 1,4-dioxane/water (4:1) (5 mL) were heated at 85° C. under N₂ overnight. Silica gel chromatography (PE:EA=1:1) gave the title compound (56.6 mg, 97%) as a brown oil. ¹H NMR (300 MHz, CDCl₃): δ 1.66 (3H, t, J=6.0 Hz), 2.63-2.71 (2H, m), 3.05 (3H, s), 3.60 (3H, s), 6.64 (1H, d, J=9.0 Hz), 7.28-7.33 (2H, m), 7.48 (1H, d, J=9.0 Hz), 7.70 (1H, s), 7.82-7.85 (1H, m). LCMS: 292 (M+1)⁺

Example 313

1-methyl-5-(5-methylsulfonyl-2-propylphenyl)pyridin-2-one

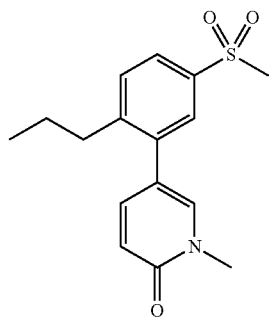 [SMILES: CCCc1ccc(S(C)(=O)=O)cc1-c1ccc(=O)n(C)c1]

The title compound was prepared in four steps in a similar manner to Example 312, steps 1-4 except that propylboronic acid was substituted for ethylboronic acid in step 1. ¹H NMR (CDCl3, 400 MHz): δ 7.91 (d, J=6.8 Hz, 1H), 7.77 (d, J=15.2 Hz, 2H), 7.62-7.58 (m, 2H), 6.66 (d, J=8.4 Hz, 1H), 3.67 (s, 3H), 3.16 (s, 3H), 2.74-2.78 (m, 2H), 1.63-1.58 (m, 2H), 0.93-0.90 (m, 3H). LCMS: 306 (M+1)⁺

Example 314

2-methyl-4-(5-methylsulfonyl-2-propylphenyl)isoquinolin-1-one

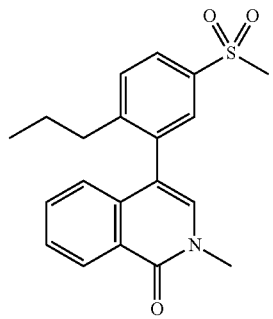 [SMILES: CCCc1ccc(S(C)(=O)=O)cc1-c1cn(C)c(=O)c2ccccc12]

The title compound was prepared in four steps in a similar manner to Example 312, steps 1-4 except that propylboronic acid was substituted for ethylboronic acid in step 1 and the title compound of Example 89, step 1 was substituted for 1-methyl-5-(4,4,5,5-tetramethyl-1,3,2-dioxaborolan-2-yl)pyridin-2-one in step 4. ¹H NMR (CD3OD, 400 MHz): δ 8.67 (d, J=8.0 Hz, 1H), 8.20 (dd, J₁=1.6 Hz, J₂=2.4 Hz, 1H), 7.84 (s, 1H), 7.71-7.67 (m, 2H), 7.63-7.59 (m, 1H), 7.42 (s, 1H), 7.08 (d, J=8.8 Hz, 1H), 3.71 (s, 3H), 3.18 (m, 3H), 2.64-2.57 (m, 1H), 2.51-2.44 (m, 1H), 1.59-1.50 (m, 2H), 0.82-0.78 (m, 3H). LCMS: 356 (M+1)⁺

Example 315

5-[2-(2-cyclopropylethyl)-5-methylsulfonylphenyl]-1-methylpyridin-2-one

Step 1: 2-(2-cyclopropylethynyl)-5-methylsulfonylaniline

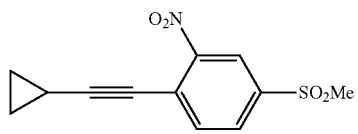 [SMILES: CS(=O)(=O)c1ccc(C#CC2CC2)c([N+](=O)[O-])c1]

bromo-4-methylsulfonyl-2-nitrobenzene (1.5 g, 5.36 mmol), ethynylcyclopropane (0.7 g, 10.72 mmol), $K_2CO_3$ (1.5 g, 10.72 mmol) in $CH_3CN$ (30 ml), $Pd(ACN)_2Cl_2$ (55.5 mg, 0.21 mmol) and X-phos (128 mg, 0.27 mmol) under $N_2$ were heated at 45° C. for 3 h. EA extractive work up and preparative TLC (PE: EtOAc=5:1) gave the title compound (1.2 g).

Step 2: 2-(2-cyclopropylethyl)-5-methylsulfonylaniline

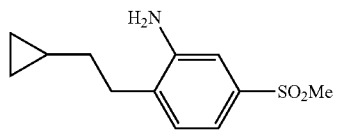 [SMILES: CS(=O)(=O)c1ccc(CCC2CC2)c(N)c1]

The title compound of step 1 (1.2 g) was hydrogenated in MeOH (45 mL) in a manner similar to Example 312, step 2. Preparative HPLC gave the title compound (422 mg, 41%). $^1H$ NMR (CDCl3, 400 MHz): δ 7.19-7.13 (m, 3H), 2.95 (s, 3H), 2.60-2.56 (m, 2H), 1.50-1.44 (m, 2H) 0.68-0.65 (m, 1H), 0.43-0.38 (m, 2H), 0.03-0.01 (m, 2H).

Step 3: 1-(2-cyclopropylethyl)-2-iodo-4-methylsulfonylbenzene

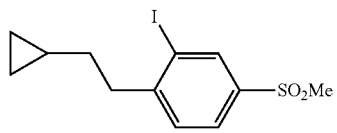 [SMILES: CS(=O)(=O)c1ccc(CCC2CC2)c(I)c1]

The title compound of step 2 (442 mg, 1.85 mmol) in 5M HCl (10 mL) was treated with $NaNO_2$ (167 mg, 2.41 mmol) followed by KI (3.07 g, 18.50 mmol) in $H_2O$ (8 ml) in a manner similar to Example 312, step 3. EA extractive work up & silica gel chromatography (PE:EA=10:1) gave the title compound (600 mg, 93%). $^1H$ NMR (CDCl3, 400 MHz): δ 8.27 (d, J=1.6 Hz, 1H), 7.74 (dd, $J_1$=1.6 Hz, $J_2$=6.4 Hz, 1H), 7.32 (d, J=7.6 Hz, 1H), 2.98 (s, 3H), 2.86-2.82 (m, 2H), 1.47-1.41 (m, 2H), 0.69-0.64 (m, 1H), 1.42-0.37 (m, 2H), 0.04-0.01 (m, 2H).

Step 4: 5-[2-(2-cyclopropylethyl)-5-methylsulfonylphenyl]-1-methylpyridin-2-one

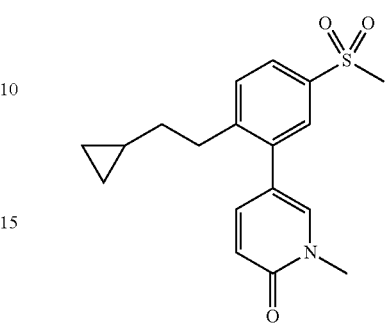

The title compound of step 3 (120 mg, 0.34 mmol), 1-methyl-5-(4,4,5,5-tetramethyl-1,3,2-dioxaborolan-2-yl)pyridin-2-one (89 mg, 0.37 mmol), $Na_2CO_3$ (72 mg, 0.68 mmol) and $Pd(dppf)Cl_2$ (15 mg) in $DMF/H_2O$ (6 ml/1.5 ml) under $N_2$ were heated at 100° C. for 1 h. EA extractive work up and preparative TLC (PE: EtOAc=0:1) gave the title compound (62 mg, 55%). $^1H$ NMR (CD3OD, 400 MHz): δ 7.92 (dd, $J_1$=2.4 Hz, $J_2$=5.6 Hz, 1H), 7.81 (d, J=2 Hz, 1H), 7.78 (d, J=2.4 Hz, 1H), 7.65-7.61 (m, 2H), 6.69 (m, J=9.2 Hz, 1H), 3.69 (s, 3H), 3.17 (s, 3H), 2.89-2.86 (m, 2H), 1.51-1.45 (m, 2H), 0.68-0.65 (m, 1H), 0.45-0.40 (m, 2H), 0.04-0.00 (m, 2H). LCMS: 332 $(M+1)^+$

Example 316

4-(2-ethyl-5-methylsulfonylphenyl)-2-methylisoquinolin-1-one

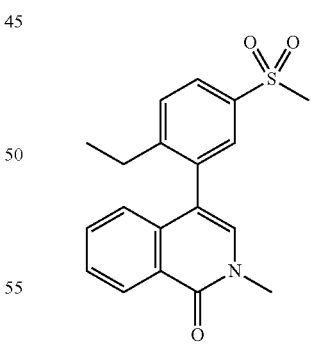

The title compound of Example 312, step 3 was reacted with the title compound of Example 89, step 1 in a manner similar to Example 312, step 4 to give the title compound. $^1H$ NMR (400 MHz, CDCl3): δ 1.10 (3H, t, J=8.0 Hz), 2.51-2.56 (2H, m), 3.10 (3H, s), 3.67 (3H, s), 6.97-7.02 (2H, m), 7.52-7.59 (3H, m), 7.80 (1H, s), 7.97 (1H, d, J=8.0 Hz), 8.54 (1H, d, J=8.0 Hz). LCMS: 342 $(M+1)^+$

Example 317

5-(2-butyl-5-methylsulfonylphenyl)-1-methylpyridin-2-one

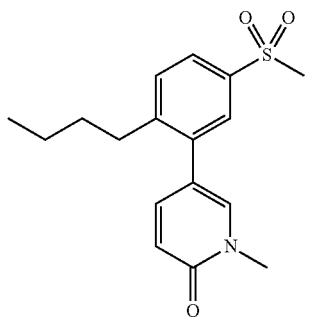 [SMILES: CCCCc1ccc(S(C)(=O)=O)cc1-c1ccc(=O)n(C)c1]

The title compound was prepared in four steps in a similar manner to Example 312, steps 1-4 except that butylboronic acid was substituted for ethylboronic acid in step 1. $^1$H NMR (400 MHz, MeOH-$d_4$): δ 0.89 (3H, t, J=8.0 Hz), 1.28-1.35 (2H, m), 1.54-1.58 (2H, m), 2.73-2.77 (2H, m), 3.16 (3H, s), 3.67 (3H, s), 6.67 (1H, d, J=4.0 Hz), 7.58-7.62 (2H, m), 7.78 (2H, d, J=12.0 Hz), 7.89-7.92 (1H, m). LCMS: 320 (M+1)$^+$

Example 318

4-(2-butyl-5-methylsulfonylphenyl)-2-methylisoquinolin-1-one

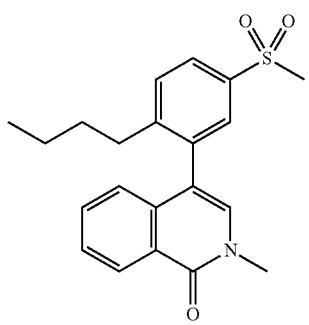 [SMILES: CCCCc1ccc(S(C)(=O)=O)cc1-c1cn(C)c(=O)c2ccccc12]

The title compound was prepared in four steps in a similar manner to Example 312, steps 1-4 except that butylboronic acid was substituted for ethylboronic acid in step 1 and the title compound of Example 89, step 1 was substituted for 1-methyl-5-(4,4,5,5-tetramethyl-1,3,2-dioxaborolan-2-yl)pyridin-2-one in step 4. $^1$H NMR (300 MHz, MeOH-$d_4$): δ 0.73 (3H, t, J=7.5 Hz), 1.14-1.21 (2H, m), 1.43-1.51 (2H, m), 2.45-2.64 (2H, m), 3.17 (3H, s), 3.70 (3H, s), 7.07 (1H, d, J=9.0 Hz), 7.41 (1H, s), 7.57-7.70 (3H, m), 7.82 (1H, d, J=3.0 Hz), 7.98-8.01 (1H, m), 8.44-8.47 (1H, m). LCMS: 370 (M+1)$^+$

Example 319

4-[2-(2-cyclopropylethyl)-5-methylsulfonylphenyl]-2-methylisoquinolin-1-one

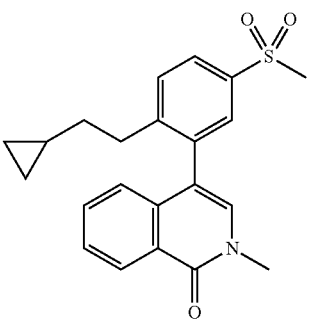 [SMILES: Cn1cc(-c2cc(S(C)(=O)=O)ccc2CCC2CC2)c2ccccc2c1=O]

The title compound of Example 315, step 3 was reacted with the title compound of Example 89, step 1 in a manner similar to Example 315, step 4 to give the title compound. 1H NMR (CD3OD, 400 MHz): δ 8.67 (d, J=8.0 Hz, 1H), 8.21 (dd, J1=2.0 Hz, J2=6.0 Hz, 1H), 8.03 (d, J=2.0 Hz, 1H), 7.92-7.86 (m, 2H), 7.82-7.79 (m, 1H), 7.61 (s, 1H), 7.28 (d, J=8.0 Hz, 1H), 3.91 (s, 3H), 3.38 (s, 3H), 2.94-2.89 (m, 1H), 2.83-2.77 (m, 1H), 1.64-1.55 (m, 2H), 0.75-0.71 (m, 1H), 0.51-0.47 (m, 2H), 0.01-0.00 (m, 2H). LCMS: 382 (M+1)$^+$

Example 320

N-[6-(cyclopropylmethoxy)-5-(2-methyl-1-oxoisoquinolin-4-yl)pyridin-3-yl]ethanesulfonamide

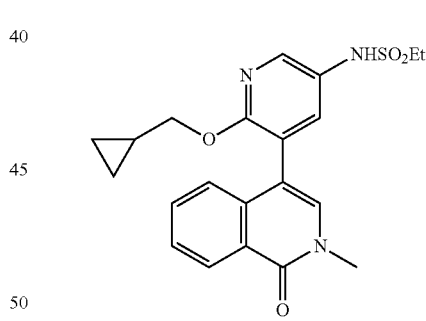

A mixture of N-[5-bromo-6-(cyclopropylmethoxy)pyridin-3-yl]ethanesulfonamide (60 mg, 0.21 mmol), 2-methyl-4-(4,4,5,5-tetramethyl-1,3,2-dioxaborolan-2-yl)isoquinolin-1-one (77 mg, 0.23 mmol), Pd$_2$(dba)$_3$ (7 mg), XPhos (7 mg), and K$_3$PO$_4$ (111 mg, 0.51 mmol) in dioxane (1.2 mL) and water (140 uL) was purged with nitrogen, capped, and heated to 70° C. for 2 h. After the mixture was filtered through a short bed of celite, the filtrate was concentrated in vacuo and purified by prep-HPLC to afford the title compound (45 mg, 52%) as a white solid. $^1$H NMR (400 MHz, DMSO-$d_6$) δ ppm 0.09-0.15 (m, 2H) 0.29-0.40 (m, 2H) 0.97-1.08 (m, 1H) 1.20-1.28 (m, 3H) 3.07-3.16 (m, 2H) 3.56 (s, 3H) 4.02-4.18 (m, 2H) 7.17-7.22 (m, 1H) 7.52 (s, 3H) 7.62-7.69 (m, 1H) 8.06-8.11 (m, 1H) 8.27-8.33 (m, 1H) 9.47-10.31 (m, 1H). LCMS (M+H)$^+$=414.

Example 321

4-[2-(cyclopropylmethoxy)-5-methylsulfonylpyridin-3-yl]-2-methylisoquinolin-1-one Step 1: 3-bromo-2-chloro-5-methylsulfonylpyridine

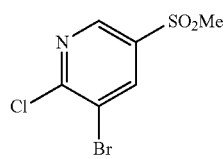 [SMILES: CS(=O)(=O)c1cnc(Cl)c(Br)c1]

A 0.5 M solution of 5-bromo-6-chloropyridine-3-sulfonyl chloride (1.5 g, 5.2 mmol) in THF was added dropwise to a mixture of NaHCO$_3$ (521 mg) and sodium sulfite (847 mg) stirred at rt in water (15 mL). The reaction mixture was heated to 70° C. for 2 h. After cooling to rt, the reaction mixture was treated with iodomethane (1.5 mL, 23 mmol) and then heated to 50° C. for for 12 h. The reaction mixture was extracted with EtOAc (20 mL×3); the combined organic layers were washed with water, brine, dried over MgSO$_4$, filtered, and concentrated in vacuo. The resulting solid was purified by silica gel column chromatography (20% EtOAc in hexanes) to afford the title compound (952 mg, 68%). LCMS (M+H)$^+$=271.

Step 2: 3-bromo-2-(cyclopropylmethoxy)-5-methylsulfonylpyridine

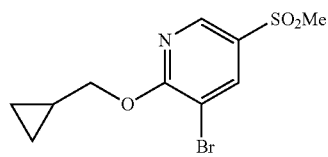 [SMILES: CS(=O)(=O)c1cnc(OCC2CC2)c(Br)c1]

A solution of cyclopropylmethanol (146 uL, 1.8 mmol) stirred in DMF (3 mL) at 0° C. was treated with NaH (75 mg, 1.9 mmol, 60% in mineral oil). After stirring at 0° C. for 30 min, the reaction mixture was treated with a solution of 3-bromo-2-chloro-5-methylsulfonylpyridine (400 mg, 1.5 mmol) in DMF (3 mL) by dropwise addition. After the ice bath was removed, the mixture was stirred at rt for 14 h. The reaction mixture was treated with water and extracted with EtOAc (30 mL×2). The combined organic layers were washed with brine, dried over Na$_2$SO$_4$, filtered, and concentrated in vacuo. The resulting residue was purified by silica gel column chromatography using a gradient of EtOAc (5 to 85%) in hexanes to give the title compound (298 mg, 65%). LCMS (M+H)$^+$=307.

Step 3: 4-[2-(cyclopropylmethoxy)-5-methylsulfonylpyridin-3-yl]-2-methylisoquinolin-1-one

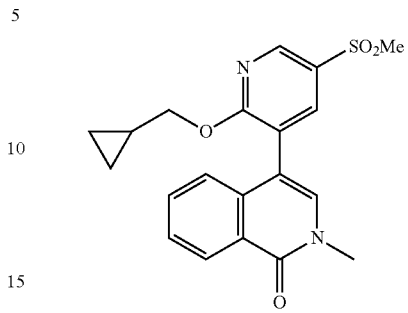

A mixture of 3-bromo-2-(cyclopropylmethoxy)-5-methylsulfonylpyridine (67 mg, 0.22 mmol), 2-methyl-4-(4,4,5,5-tetramethyl-1,3,2-dioxaborolan-2-yl)isoquinolin-1-one (60 mg, 0.21 mmol), Pd$_2$(dba)$_3$ (6 mg), XPhos (7 mg), and K$_3$PO$_4$ (111 mg, 0.51 mmol) in dioxane (1.2 mL) and water (140 uL) was purged with nitrogen, capped, and heated to 70° C. for 2 h. After the mixture was filtered through a short bed of celite, the filtrate was concentrated in vacuo and purified by prep-HPLC to afford the title compound (58 mg, 73%) as a white solid. $^1$H NMR (400 MHz, DMSO-d$_6$) δ ppm 0.12-0.26 (m, 2H) 0.28-0.47 (m, 2H) 1.02-1.15 (m, 1H) 3.30-3.32 (m, 3H) 3.54-3.62 (m, 3H) 4.02-4.41 (m, 2H) 7.17-7.27 (m, 1H) 7.52-7.59 (m, 1H) 7.60-7.64 (m, 1H) 7.64-7.71 (m, 1H) 8.16-8.22 (m, 1H) 8.26-8.35 (m, 1H) 8.70-8.79 (m, 1H). LCMS (M+H)$^+$=385.

Example 322

4-[2-(cyclopropylmethoxy)-5-ethylsulfonylpyridin-3-yl]-2-methylisoquinolin-1-one

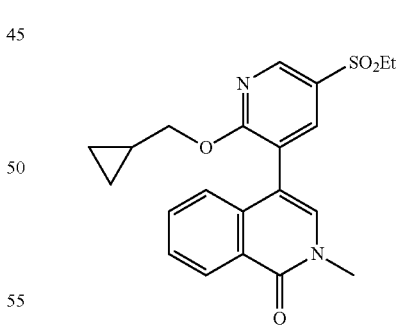

The title compound was prepared in a manner similar to Example 321, substituting iodoethane for iodomethane in Step 1. $^1$H NMR (400 MHz, DMSO-d$_6$) δ ppm 0.09-0.15 (m, 2H) 0.31-0.40 (m, 2H) 0.98-1.07 (m, 1H) 1.20-1.28 (m, 3H) 3.07-3.17 (m, 2H) 3.54-3.58 (m, 3H) 3.99-4.16 (m, 2H) 7.16-7.23 (m, 1H) 7.50-7.59 (m, 3H) 7.63-7.70 (m, 1H) 8.06-8.11 (m, 1H) 8.27-8.32 (m, 1H) 9.40-10.08 (m, 1H). LCMS (M+H)$^+$=399.

Example 323

5-[3-[(4-methoxyphenyl)methoxy]-5-methylsulfonylphenyl]-1,3-methylpyridin-2-one

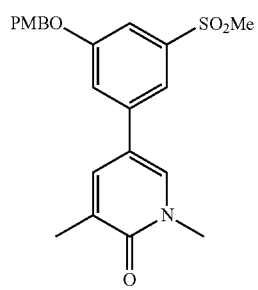

A mixture of 1-bromo-3-[(4-methoxyphenyl)methoxy]-5-methylsulfonylbenzene (450 mg, 1.2 mmol), 1,3-dimethyl-5-(4,4,5,5-tetramethyl-1,3,2-dioxaborolan-2-yl)pyridin-2-one (300 mg, 1.2 mmol), Pd(dppf)Cl$_2$ (88 mg) and K$_3$PO$_4$ (654 mg, 3 mmol) in dioxane (8 mL) and water (800 uL) was purged with nitrogen for 7 min, capped, and heated to 75° C. for 1 h. After the mixture was filtered through a short bed of celite, the filtrate was concentrated in vacuo and purified by silica gel column chromatography using a gradient of EtOAc (5 to 100%) in DCM to afford the title compound (416 mg, 83%) as a tan solid. $^1$H NMR (400 MHz, DMSO-d$_6$) δ ppm 2.05-2.14 (s, 3H) 3.25-3.28 (s, 3H) 3.49-3.57 (s, 3H) 3.74-3.81 (s, 3H) 5.12-5.22 (s, 2H) 6.93-7.03 (m, 2H) 7.34-7.47 (m, 3H) 7.52-7.59 (m, 1H) 7.64-7.72 (m, 1H) 7.82-7.90 (m, 1H) 8.14-8.22 (m, 1H). LCMS (M+H)$^+$=414.

Example 324

1,3-dimethyl-5-(3-methylsulfonyl-5-phenylmethoxyphenyl)pyridin-2-one

Step 1: 5-(3-hydroxy-5-methylsulfonylphenyl)-1,3-dimethylpyridin-2-one

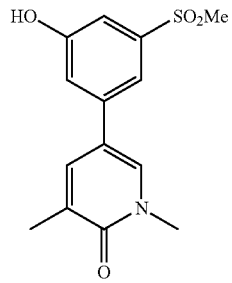 [SMILES: Cc1cc(-c2cc(O)cc(S(C)(=O)=O)c2)cn(C)c1=O]

A solution of 5-[3-[(4-methoxyphenyl)methoxy]-5-methylsulfonylphenyl]-1,3-dimethylpyridin-2-one (410 mg, 1 mmol) in AcOH (10 mL) was heated to 100° C. for 8 h. After cooling to rt, the reaction mixture was evaporated to dryness in vacuo. The resulting residue was diluted with water and extracted with EtOAc (50 ml×3); the combined organic layers were washed with brine, dried over MgSO$_4$, filtered, and concentrated in vacuo. The resulting solid was suspensed in ethyl ether, sonicated for 3 min, and filtered. The filter cake was collected to afford the title compound (290 mg, 68%) as a gray solid. LCMS (M+H)$^+$=294.

Step 2: 1,3-dimethyl-5-(3-methylsulfonyl-5-phenylmethoxyphenyl)pyridin-2-one

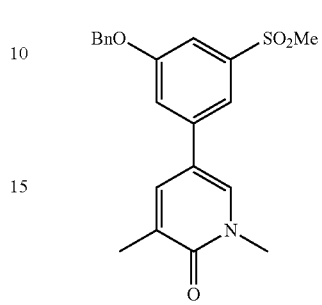

A capped mixture of 5-(3-hydroxy-5-methylsulfonylphenyl)-1,3-dimethylpyridin-2-one (25 mg, 0.085 mmol), benzyl bromide (20 mg, 0.12 mmol), and Na$_2$CO$_3$ (18 mg, 0.17 mmol) in DMF (600 uL) was heated to 80° C. for 90 min. The mixture was filtered and the filter cake was washed with ACN (500 uL), the filtrate was purified by prep-HPLC to afford the title compound (8 mg, 25%) as a tan solid. $^1$H NMR (400 MHz, DMSO-d$_6$) δ ppm 2.08-2.13 (m, 3H) 3.26-3.28 (m, 3H) 3.51-3.57 (m, 3H) 5.22-5.34 (m, 2H) 7.33-7.47 (m, 4H) 7.48-7.53 (m, 2H) 7.54-7.60 (m, 1H) 7.67-7.71 (m, 1H) 7.83-7.88 (m, 1H) 8.17-8.22 (m, 1H). LCMS (M+H)$^+$=384.

For Examples 325-340 in Table 18, the title compound of Step 1 in Example 324 was O-alkylated with the appropriate alkyl halide in a similar manner to Step 2 of Example 324. For Examples 332-340, Cs$_2$CO$_3$ is substituted for Na$_2$CO$_3$.

TABLE 18

| Ex. No. | R$^1$ | Name | MS (M + H) |
|---|---|---|---|
| 325 | ⟋△ | 5-[3-(cyclopropylmethoxy)-5-methylsulfonylphenyl]-1,3-dimethylpyridin-2-one | 348 |
| 326 | ⟋⟋Ph | 1,3-dimethyl-5-[3-methylsulfonyl-5-(2-phenylethoxy)phenyl]pyridin-2-one | 398 |

TABLE 18-continued (Structure: MeO2S and OR1 substituted phenyl attached to 1,3-dimethylpyridin-2-one)

| Ex. No. | R¹ | Name | MS (M + H) |
|---|---|---|---|
| 327 | -CH2CH2-cyclopropyl | 5-[3-(2-cyclopropylethoxy)-5-methylsulfonylphenyl]-1,3-dimethylpyridin-2-one | 362 |
| 328 | -CH2CF3 (2,2,2-trifluoroethyl) | 1,3-dimethyl-5-[3-methylsulfonyl-5-(2,2,2-trifluoroethoxy)phenyl]pyridin-2-one | 376 |
| 329 | -CH2-(3-methyloxetan-3-yl) | 1,3-dimethyl-5-[3-[(3-methyloxetan-3-yl)methoxy]-5-methylsulfonylphenyl]pyridin-2-one | 378 |
| 330 | -CH2-(pyridin-2-yl) | 1,3-dimethyl-5-[3-methylsulfonyl-5-(pyridin-2-ylmethoxy)phenyl]pyridin-2-one | 385 |
| 331 | -CH2-(2,6-dimethylphenyl) | 5-[3-[(2,6-dimethylphenyl)methoxy]-5-methylsulfonylphenyl]-1,3-dimethylpyridin-2-one | 412 |
| 332 | -CH2-(2-chlorophenyl) | 5-[3-[(2-chlorophenyl)methoxy]-5-methylsulfonylphenyl]-1,3-dimethylpyridin-2-one | 419 |
| 333 | -CH2-[2-(difluoromethoxy)phenyl] | 5-[3-[[2-(difluoromethoxy)phenyl]methoxy]-5-methylsulfonylphenyl]-1,3-dimethylpyridin-2-one | 450 |
| 334 | -CH2-(2-cyanophenyl) | 2-[[3-(1,5-dimethyl-6-oxopyridin-3-yl)-5-methylsulfonylphenoxy]methyl]benzonitrile | 409 |
| 335 | -CH2-(2,4-difluorophenyl) | 5-[3-[(2,4-difluorophenyl)methoxy]-5-methylsulfonylphenyl]-1,3-dimethylpyridin-2-one | 420 |
| 336 | -CH(CH3)-phenyl | 1,3-dimethyl-5-[3-methylsulfonyl-5-(1-phenylethoxy)phenyl]pyridin-2-one | 398 |
| 337 | -CH2-(2,3-dichlorophenyl) | 5-[3-[(2,3-dichlorophenyl)methoxy]-5-methylsulfonylphenyl]-1,3-dimethylpyridin-2-one | 453 |
| 338 | -CH2-(pyridin-3-yl) | 1,3-dimethyl-5-[3-methylsulfonyl-5-(pyridin-3-ylmethoxy)phenyl]pyridin-2-one | 385 |
| 339 | -CH2-(3-cyanophenyl) | 3-[[3-(1,5-dimethyl-6-oxopyridin-3-yl)-5-methylsulfonylphenoxy]methyl]benzonitrile | 409 |
| 340 | -CH2-C≡C-CH3 (but-2-ynyl) | 5-(3-but-2-ynoxy-5-methylsulfonylphenyl)-1,3-dimethylpyridin-2-one | 346 |

Example 341

1,3-dimethyl-5-[3-methylsulfonyl-5-[(1R)-1-phenylethoxy]phenyl]pyridin-2-one

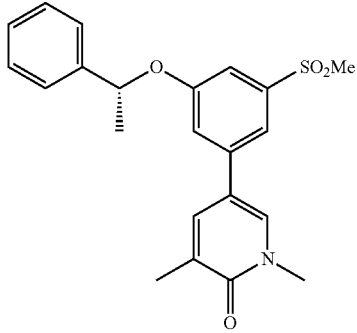 [SMILES: Cc1cc(-c2cc(O[C@H](C)c3ccccc3)cc(S(C)(=O)=O)c2)cn(C)c1=O]

A solution of (1S)-1-phenylethan-1-ol (14 mg, 0.11 mmol) in THF (1 mL) stirred at rt under an atmosphere of nitrogen was treated with triphenylphosphine (38 mg, 0.15 mmol) and 5-(3-hydroxy-5-methylsulfonylphenyl)-1,3-dimethylpyridin-2-one (33 mg, 0.11 mmol). After 30 min, the reaction mixture was treated with DIAD (29 mg, 0.15 mmol). The nitrogen inlet was removed and the mixture was stirred (closed system) for 18 h. After the reaction mixture was diluted with EtOAc (10 ml), it was washed with water, saturated sodium bicarbonate solution (aq), dried over $Na_2SO_4$, filtered, and concentrated in vacuo. The crude residue was diluted with ACN (1 mL) and was purified by prep-HPLC to afford the title compound (21 mg, 48%) as an off-white solid. 1H NMR (400 MHz, DMSO-d6) δ ppm 1.61 (d. J=6.4, 3H) 2.08 (s, 3H) 3.20 (s, 3H) 3.52 (s, 3H) 5.70-5.80 (q. J=6.4, 1H) 7.23-7.31 (m, 2H) 7.35-7.41 (m, 2H) 7.44-7.51 (m, 3H) 7.56-7.63 (m, 1H) 7.73-7.80 (m, 1H) 8.08-8.15 (m, 1H). LCMS $(M+H)^+=398$.

Example 342

N-[3-(2,4-difluorophenoxy)-5-(1,5-dimethyl-6-oxopyridin-3-yl)phenyl]ethanesulfonamide Step 1: 1-(3-bromo-5-nitrophenoxy)-2,4-difluorobenzene

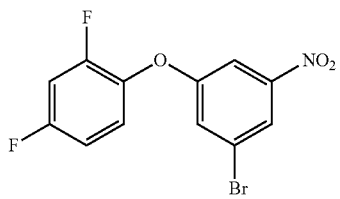 [SMILES: O=[N+]([O-])c1cc(Br)cc(Oc2ccc(F)cc2F)c1]

A mixture of 2,4-difluorophenol (286 mg, 2.2 mmol) and 1-bromo-3-fluoro-5-nitrobenzene (440 mg, 2 mmol) in DMF (4.5 mL) was treated with $K_2CO_3$ (304 mg, 2.2 mmol). The mixture was heated to 100° C. by microwave irradiation (normal) for 5 h. The resulting suspension was diluted with water and extracted with EtOAc (15 mL×3). The combined organic layers were washed with 1N NaOH (aq) (15 mL), water (15 mL), brine, dried over $MgSO_4$, and concentrated in vacuo. The crude solid was purified by silica gel column chromatography using a gradient of EtOAc (5 to 25%) in hexanes to afford the title compound (200 mg, 30%) as a yellow solid. LCMS $(M+H)^+=339$.

Step 2: 3-bromo-5-(2,4-difluorophenoxy)aniline

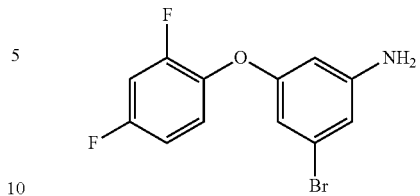

A mixture of 1-(3-bromo-5-nitrophenoxy)-2,4-difluorobenzene (54 mg, 0.16 mmol), ammonium chloride (18 mg, 0.32 mmol), and iron powder (45 mg, 0.80 mmol) suspended in THF (300 uL), water (100 uL) and ethanol (300 uL) was heated to 100° C. using microwave irradiation (normal) for 3 h. The crude reaction mixture was filtered through a short plug of celite; the celite plug was washed with MeOH (~5 mL). The resulting filtrate was concentrated in vacuo. The resulting residue was diluted with EtOAc (50 ml) and washed with saturated bicarbonate solution (aq), dried over anhydrous magnesium sulfate, filtered, and concentrated in vacuo. The crude solid was purified by silica gel column chromatography using a gradient of EtOAc (5 to 20%) in hexanes to afford the title compound (48 mg, 100%) as a yellow solid. LCMS $(M+H)^+=301$.

Step 3: N-[3-bromo-5-(2,4-difluorophenoxy)phenyl]ethanesulfonamide

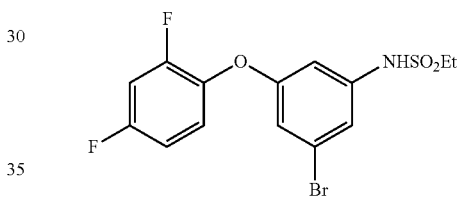

Ethylsulfonyl chloride (15 uL, 0.16 mmol) was added dropwise to a stirred solution of 3-bromo-5-(2,4-difluorophenoxy)aniline (48 mg, 0.16 mmol) and pyridine (40 uL, 0.48 mmol) in DCM (320 uL) at 0° C. under nitrogen. After the mixture was allowed to warm to rt and stir for 12 h, it was treated with 1N HCl (1 mL) and extracted with DCM (3×5 mL); the combined organic extracts were washed with saturated bicarbonate solution (aq), dried over sodium sulfate, filtered and concentrated in vacuo. The crude solid was purified by silica gel column chromatography using a gradient of EtOAc (5 to 60%) in hexanes to afford the title compound (60 mg, 95%) as a tan solid. LCMS $(M+H)^+=393$.

Step 4: N-[3-(2,4-difluorophenoxy)-5-(1,5-dimethyl-6-oxopyridin-3-yl)phenyl]ethanesulfonamide

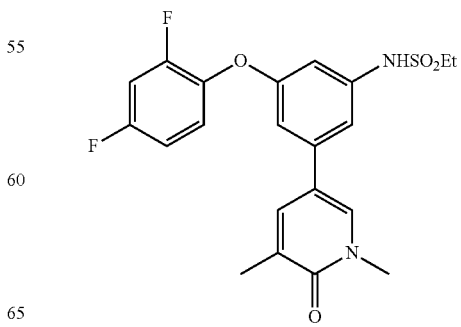

A mixture of N-[3-bromo-5-(2,4-difluorophenoxy)phenyl]ethanesulfonamide (70 mg, 0.17 mmol), 1,3-dimethyl-5-(4,4,5,5-tetramethyl-1,3,2-dioxaborolan-2-yl)pyridin-2-one (44 mg, 0.18 mmol), Pd(dppf)Cl$_2$ (12 mg) and K$_3$PO$_4$ (92 mg, 0.42 mmol) in dioxane (1 mL) and water (133 uL) was purged with nitrogen, capped, and heated to 75° C. for 1 h. After the mixture was filtered through a short bed of celite, the filtrate was concentrated in vacuo and purified by silica gel column chromatography using a gradient of MeOH (0 to 10%) in DCM to afford the title compound (69 mg, 94%) as an off-white solid. 1H NMR (400 MHz, DMSO-d6) δ ppm 1.13-1.22 (m, 3H) 2.07 (s, 3H) 3.08-3.20 (m, 2H) 3.50 (s, 3H) 6.65-6.70 (m, 1H) 6.92-6.96 (m, 1H) 7.05-7.10 (m, 1H) 7.12-7.19 (m, 1H) 7.28-7.37 (m, 1H) 7.47-7.55 (m, 1H) 7.56-7.59 (m, 1H) 7.87-7.95 (m, 1H) 9.76-9.94 (m, 1H). LCMS (M+H)$^+$=435.

Example 343

4-[3-[(4-methoxyphenyl)methoxy]-5-methylsulfonylphenyl]-2-methylisoquinolin-1-one

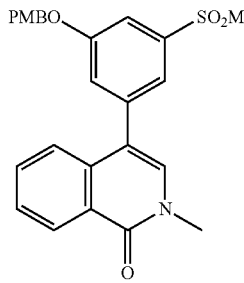

A mixture of 1-bromo-3-[(4-methoxyphenyl)methoxy]-5-methylsulfonylbenzene (103 mg, 0.28 mmol), 2-methyl-4-(4,4,5,5-tetramethyl-1,3,2-dioxaborolan-2-yl)isoquinolin-1-one (79 mg, 0.28 mmol), Pd(dppf)Cl$_2$ (20 mg) and K$_3$PO$_4$ (153 mg, 0.7 mmol) in dioxane (1.9 mL) and water (100 uL) was purged with nitrogen for 10 min, capped, and heated to 75° C. for 15 h. After the mixture was filtered through a short bed of celite, the filtrate was concentrated in vacuo and purified by silica gel column chromatography using a gradient of EtOAc (5 to 100%) in DCM to afford the title compound (100 mg, 80%) as a tan solid. $^1$H NMR (400 MHz, DMSO-d$_6$) δ ppm 3.30 (s, 3H) 3.58 (s, 3H) 3.77 (s, 3H) 5.14-5.28 (m, 2H) 6.88-7.04 (m, 2H) 7.32-7.80 (m, 9H) 8.29-8.43 (m, 1H). LCMS (M+H)$^+$=450.

Example 344

2-methyl-4-(3-methylsulfonyl-5-phenylmethoxyphenyl)isoquinolin-1-one

Step 1: 4-(3-hydroxy-5-methylsulfonylphenyl)-2-methylisoquinolin-1-one

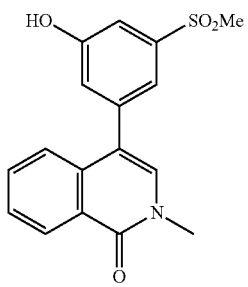 [SMILES: Cn1cc(-c2cc(O)cc(S(C)(=O)=O)c2)c2ccccc2c1=O]

The title compound was prepared in a manner similar to Example 324, substituting 4-[3-[(4-methoxyphenyl)methoxy]-5-methylsulfonylphenyl]-2-methylisoquinolin-1-one for 5-[3-[(4-methoxyphenyl)methoxy]-5-methylsulfonylphenyl]-1,3-dimethylpyridin-2-one in Step 1. LCMS (M+H)$^+$=330.

Step 2: 2-methyl-4-(3-methylsulfonyl-5-phenylmethoxyphenyl)isoquinolin-1-one

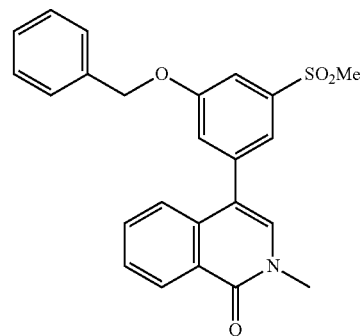 [SMILES: Cn1cc(-c2cc(OCc3ccccc3)cc(S(C)(=O)=O)c2)c2ccccc2c1=O]

A capped mixture of 4-(3-hydroxy-5-methylsulfonylphenyl)-2-methylisoquinolin-1-one (25 mg, 0.076 mmol), benzyl bromide (20 mg, 0.12 mmol), and Cs$_2$CO$_3$ (50 mg, 0.15 mmol) in DMF (600 uL) was heated to 80° C. for 3 h. The mixture was filtered and the filter cake was washed with ACN (500 uL), the filtrate was purified by prep-HPLC to afford the title compound (12 mg, 38%) as a tan solid. LCMS (M+H)$^+$=420.

Example 345

4-[3-(cyclopropylmethoxy)-5-methylsulfonylphenyl]-2-methylisoquinolin-1-one

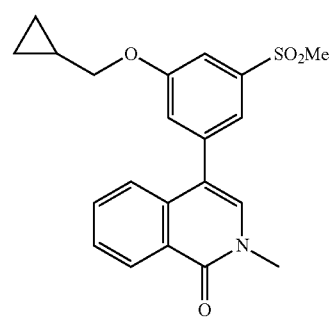 [SMILES: Cn1cc(-c2cc(OCC3CC3)cc(S(C)(=O)=O)c2)c2ccccc2c1=O]

The title compound was prepared in a manner similar to Example 344, substituting cyclopropylmethyl bromide for benzyl bromide in Step 2. LCMS (M+H)$^+$=384.

Example 346

N-[4-(2,4-difluorophenoxy)-6-(1,5-dimethyl-6-oxopyridin-3-yl)pyrimidin-2-yl]ethanesulfonamide Step 1: 5-(2,6-dichloropyrimidin-4-yl)-1,3-dimethylpyridin-2-one

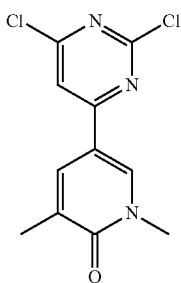 [SMILES: Cc1cc(-c2cc(Cl)nc(Cl)n2)cn(C)c1=O]

A mixture of 2,4,6-trichloropyrimidine (275 mg, 1.5 mmol), 1,3-dimethyl-5-(4,4,5,5-tetramethyl-1,3,2-dioxaborolan-2-yl)pyridin-2-one (246 mg, 1 mmol), Pd(OAc)$_2$ (20 mg), triphenylphosphine (16 mg), and 2M Na$_2$CO$_3$ (1 mL, 2 mmol) in THF (6.7 mL) was purged with nitrogen for 5 min, capped, and heated to 80° C. for 3 h. After the mixture was filtered through a short bed of celite, the filtrate was concentrated in vacuo and purified by silica gel column chromatography using a gradient (0 to 100%) EtOAc in DCM to afford the title compound (150 mg, 55%) as a white solid. LCMS (M+H)$^+$=271.

Step 2: 5-[2-chloro-6-(2,4-difluorophenoxy)pyrimidin-4-yl]-1,3-dimethylpyridin-2-one and 5-[6-chloro-2-(2,4-difluorophenoxy)pyrimidin-4-yl]-1,3-dimethylpyridin-2-one

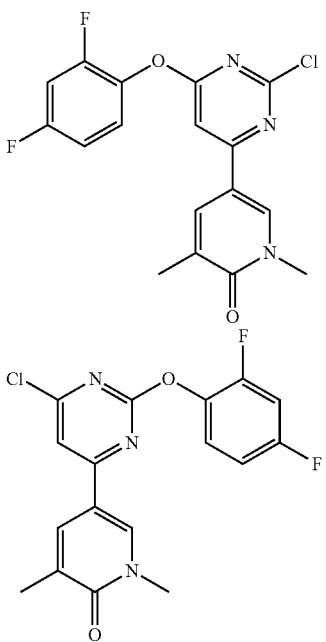

A mixture of 2,4-difluorophenol (25 mg, 0.19 mmol) and 5-(2,6-dichloropyrimidin-4-yl)-1,3-dimethylpyridin-2-one (50 mg, 0.19 mmol) in DMF (0.5 mL) and THF (0.5 mL) was treated with K$_2$CO$_3$ (304 mg, 0.23 mmol). The mixture was stirred at rt for 3 h. The resulting suspension was diluted with water and extracted with EtOAc (10 mL×3). The combined organic layers were washed with 1N NaOH (aq) (5 mL), water (15 mL), brine, dried over MgSO$_4$, and concentrated in vacuo. The crude solid was purified by silica gel column chromatography using a gradient of EtOAc (0 to 50%) in DCM to afford an unseparated mixture of regioisomeric title compounds (66 mg, 96% combined) as a white solid. LCMS (M+H)$^+$=364 for both regioisomers.

Step 3: N-[4-(2,4-difluorophenoxy)-6-(1,5-dimethyl-6-oxopyridin-3-yl)pyrimidin-2-yl]ethanesulfonamide

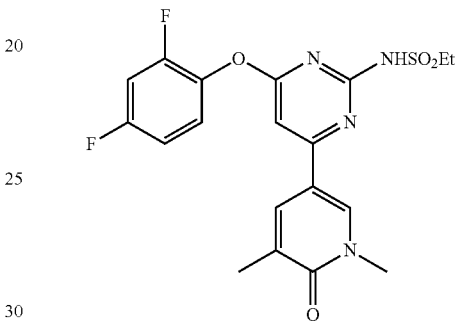

A solution of ethanesulfonamide (80 mg, 0.73 mmol) in DMF (2 mL) was treated with NaH (27 mg, 0.68 mmol, 60% by weight). After 15 min, the mixture was treated with a DMF (1 mL) solution of title compounds obtained from Step 2. The reaction mixture was stirred at 50° C. for 14 h. The resulting suspension was diluted with water and extracted with EtOAc (10 mL×3). The combined organic layers were washed with brine, dried over Na$_2$SO$_4$, and concentrated in vacuo. Preparative HPLC isolated both regioisomers as Examples 346 and 347. The title compound (6 mg, 8%) was obtained as a white solid. $^1$H NMR (400 MHz, DMSO-d$_6$) δ ppm 1.08 (t, J=7.1 Hz, 3H) 2.07 (s, 3H) 3.11 (q, J=7.1 Hz, 2H) 3.54 (s, 3H) 6.81 (s, 1H) 7.17 (m, 1H) 7.47 (s, 2H) 7.79 (s, 1H) 8.37 (s, 1H) 11.37 (bs, 1H). LCMS (M+H)$^+$=437.

Example 347

N-[2-(2,4-difluorophenoxy)-6-(1,5-dimethyl-6-oxopyridin-3-yl)pyrimidin-4-yl]ethanesulfonamide

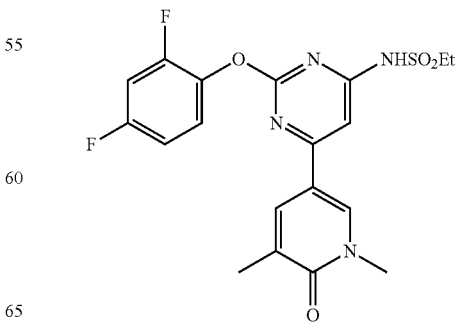

The preparative HPLC of Example 346, step 3 also isolated this regioisomer. The title compound (2 mg, 3%) was obtained as a white solid. ¹H NMR (400 MHz, DMSO-d₆) δ ppm 1.06-1.13 (m, 3H) 2.08-2.12 (m, 3H) 3.11-3.23 (m, 2H) 3.54-3.57 (m, 3H) 7.14-7.28 (m, 2H) 7.45-7.54 (m, 2H) 8.04-8.09 (m, 1H) 8.52-8.57 (m, 1H) 10.92-11.26 (m, 1H), both as a white solids. LCMS (M+H)⁺=437.

Example 348

4-[3-[[2-(difluoromethoxy)phenyl]methoxy]-5-methylsulfonylphenyl]-6-methylfuro[2,3-c]pyridin-7-one

Step 1: 4-[3-[(4-methoxyphenyl)methoxy]-5-methylsulfonylphenyl]-6-methylfuro[2,3-c]pyridin-7-one

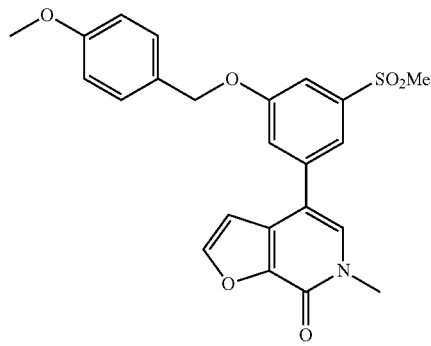 [SMILES: COc1ccc(COc2cc(-c3cn(C)c(=O)c4occc34)cc(S(C)(=O)=O)c2)cc1]

A mixture of 1-bromo-3-[(4-methoxyphenyl)methoxy]-5-methylsulfonylbenzene (470 mg, 1.27 mmol), 6-methyl-4-(4,4,5,5-tetramethyl-1,3,2-dioxaborolan-2-yl)furo[2,3-c]pyridin-7-one (316 mg, 1.15 mmol), Pd(dppf)Cl₂ (84 mg) and K₃PO₄ (610 mg, 2.9 mmol) in dioxane (7 mL) and water (700 uL) was purged with nitrogen for 7 min, capped, and heated to 70° C. for 2 h and rt for 48 h. After the mixture was diluted with EtOAc (5 mL) and water (5 mL), it was filtered through a short bed of celite. After the filtrate was separated, the aqueous layer was washed with EtOAc (25 mL×3). The combined organic layers were washed with water and brine, dried over MgSO₄, and concentrated in vacuo. The crude solid was purified by silica gel column chromatography using a gradient of EtOAc (0 to 100%) in DCM to afford the title compound (375 mg, 74%) as a white solid. LCMS (M+H)⁺=440.

Step 2: 4-(3-hydroxy-5-methylsulfonylphenyl)-6-methylfuro[2,3-c]pyridin-7-one

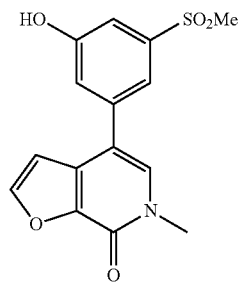 [SMILES: Cn1cc(-c2cc(O)cc(S(C)(=O)=O)c2)c2ccoc2c1=O]

A solution of 4-[3-[(4-methoxyphenyl)methoxy]-5-methylsulfonylphenyl]-6-methylfuro[2,3-c]pyridin-7-one (370 mg, 0.84 mmol) in AcOH (6 mL) was heated to 100° C. for 12 h. After cooling to rt, the reaction mixture was evaporated to dryness in vacuo. The resulting residue was diluted with water and extracted with EtOAc (20 mL×3); the combined organic layers were washed with brine, dried over MgSO₄, filtered, and concentrated in vacuo. The resulting solid was suspensed in a 1:1 mixture of EtOAc and hexanes, sonicated for 1 min, and filtered. The filter cake was collected to afford the title compound (210 mg, 78%) as a gray solid. LCMS (M+H)⁺=320.

Step 3: 4-[3-[[2-(difluoromethoxy)phenyl]methoxy]-5-methylsulfonylphenyl]-6-methylfuro[2,3-c]pyridin-7-one

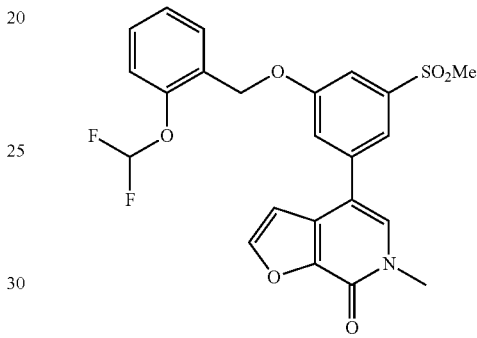

A capped mixture of 4-(3-hydroxy-5-methylsulfonylphenyl)-6-methylfuro[2,3-c]pyridin-7-one (25 mg, 0.08 mmol), 1-(bromomethyl)-2-(difluoromethoxy)benzene (28 mg, 0.12 mmol), and Cs₂CO₃ (50 mg, 0.15 mmol) in DMF (900 uL) was heated to 80° C. for 3 h. The mixture was filtered and the filter cake was washed with ACN (500 uL), the filtrate was purified by prep-HPLC to afford the title compound (22 mg, 58%) as a white solid. LCMS (M+H)⁺ =476.

Example 349

6-methyl-4-(3-methylsulfonyl-5-phenylmethoxyphenyl)furo[2,3-c]pyridin-7-one

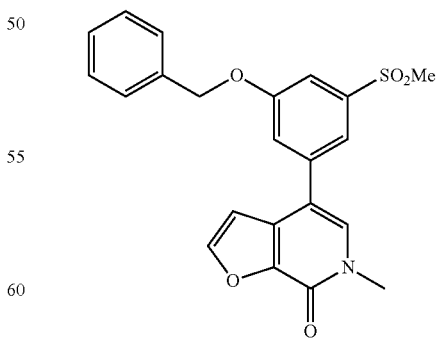

The title compound was prepared in a manner similar to Example 348, substituting benzyl bromide for 1-(bromomethyl)-2-(difluoromethoxy)benzene in Step 2. LCMS (M+H)⁺ =410.

Example 350

4-[3-(cyclopropylmethoxy)-5-methylsulfonylphenyl]-6-methylfuro[2,3-c]pyridin-7-one

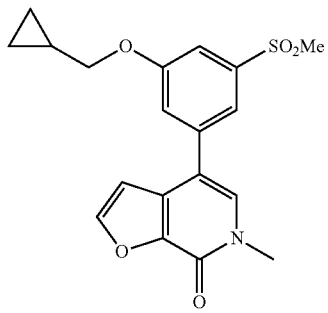 [SMILES: Cn1cc(-c2cc(OCC3CC3)cc(S(C)(=O)=O)c2)c2ccoc2c1=O]

The title compound was prepared in a manner similar to Example 348, substituting bromomethylcyclopropane for 1-(bromomethyl)-2-(difluoromethoxy)benzene in Step 3. LCMS (M+H)$^+$=374.

Examples 351-356 in Table 19 were prepared in a similar multi-step manner as Example 300, step 1 wherein either ethyl pentanoate was converted to 4-chloro-2-methylsulfonyl-5-propylpyrimidine or ethyl hexanoate was converted to 5-butyl-4-chloro-2-methylsulfonylpyrimidine which were then each reacted with a) 3-methoxy-1-methyl-5-(4,4,5,5-tetramethyl-1,3,2-dioxaborolan-2-yl)pyridin-2-one (described in Example 146, step 3), b) the title compound of Example 98, step 1, or c) 3-chloro-1-methyl-5-(4,4,5,5-tetramethyl-1,3,2-dioxaborolan-2-yl)pyridin-2-one (described in Example 134) in a manner similar to Example 152, step 5 to give the title compound.

TABLE 19

| Chemical Synthesis Example | Structure | Name | $^1$H NMR (ppm (δ), 400 MHz) | MS (M + H) |
|---|---|---|---|---|
| 351 | 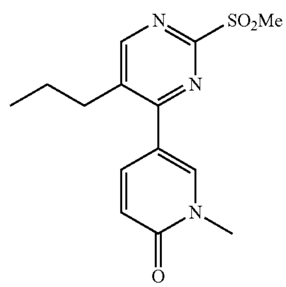 [SMILES: CCCc1cnc(S(C)(=O)=O)nc1-c1ccc(=O)n(C)c1] | 1-methyl-5-(2-methylsulfonyl-5-propylpyrimidin-4-yl)pyridin-2-one | (CDCl$_3$, 400 MHz) δ 8.72 (s, 1 H), 8.00 (s, 1 H), 7.67 (q, J = 6.8 Hz, 1 H), 6.67 (d, J = 9.6 Hz, 1 H), 3.68 (s, 3 H), 3.38 (s, 3 H), 2.82 (t, J = 8.0 Hz, 2 H), 1.73 (m, 2 H), 1.00 (t, J = 7.2 Hz, 3 H). | 308 |
| 352 | 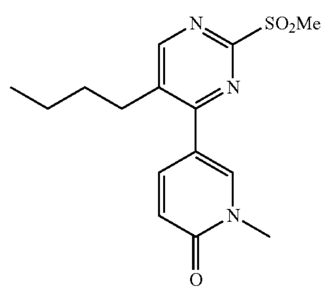 [SMILES: CCCCc1cnc(S(C)(=O)=O)nc1-c1ccc(=O)n(C)c1] | 5-(5-butyl-2-methylsulfonyl-pyrimidin-4-yl)-1-methylpyridin-2-one | | 322 |
| 353 | 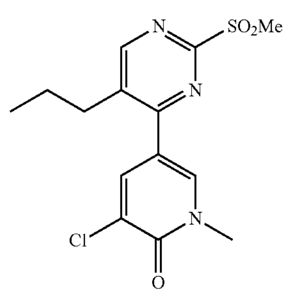 [SMILES: CCCc1cnc(S(C)(=O)=O)nc1-c1cc(Cl)c(=O)n(C)c1] | 3-chloro-1-methyl-5-(2-methylsulfonyl-5-propylpyrimidin-4-yl)pyridin-2-one | | 342 |

TABLE 19-continued

| Chemical Synthesis Example | Structure | Name | ¹H NMR (ppm (δ), 400 MHz) | MS (M + H) |
|---|---|---|---|---|
| 354 | 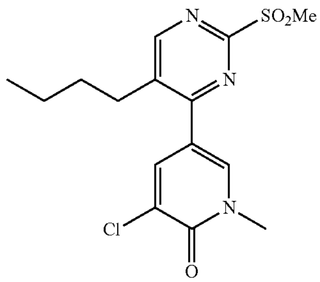 [SMILES: CCCCc1cnc(S(C)(=O)=O)nc1-c1cc(Cl)c(=O)n(C)c1] | 5-(5-butyl-2-methylsulfonyl-pyrimidin-4-yl)-3-chloro-1-methylpyridin-2-one | | 356 |
| 355 | 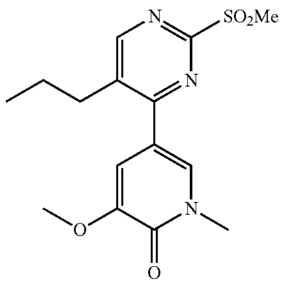 [SMILES: CCCc1cnc(S(C)(=O)=O)nc1-c1cc(OC)c(=O)n(C)c1] | 3-methoxy-1-methyl-5-(2-methylsulfonyl-5-propylpyrimidin-4-yl)pyridin-2-one | | 338 |
| 356 | 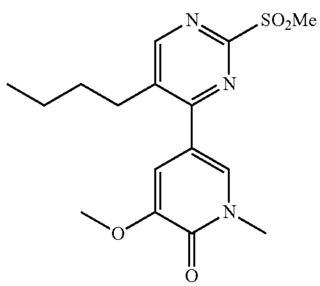 [SMILES: CCCCc1cnc(S(C)(=O)=O)nc1-c1cc(OC)c(=O)n(C)c1] | 5-(5-butyl-2-methylsulfonyl-pyrimidin-4-yl)-3-methoxy-1-methylpyridin-2-one | | 352 |

Examples 357-362 in Table 20 were prepared in a similar manner as Example 300, step 2 wherein Examples 351-356 were each treated with EtSO₂NH₂ to give the title compound.

Example 363 in Table 20 was prepared in a similar manner as Example 152, step 6 wherein Example 305 was treated with MeSO₂NH₂ to give the title compound.

TABLE 20

| Chemical Synthesis Example | Structure | Name | ¹H NMR (ppm (δ), 400 MHz) | MS (M + H) | Prepared from Ex. No. |
|---|---|---|---|---|---|
| 357 | 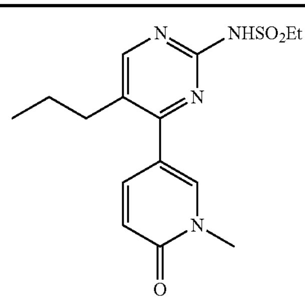 | N-[4-(1-methyl-6-oxopyridin-3-yl)-5-propylpyrimidin-2-yl]ethanesulfonamide | (CDCl₃, 400 MHz) δ 8.45 (s, 1 H), 7.84 (s, 1 H), 7.68 (d, J = 9.6 Hz, 1 H), 6.68 (d, J = 9.2 Hz, 1 H), 3.68 (s, 3 H), 3.64 (t, J = 7.6 Hz, 2 H), 2.67 (t, J = 8.0 Hz, 2 H), 1.64 (q, J = 7.6 Hz, 2 H), 1.45 (t, J = 7.2 Hz, 3 H), 0.98 (t, J = 7.2 Hz, 3H) | 337 | 351 |

TABLE 20-continued

| Chemical Synthesis Example | Structure | Name | ¹H NMR (ppm (δ), 400 MHz) | MS (M + H) | Prepared from Ex. No. |
|---|---|---|---|---|---|
| 358 | 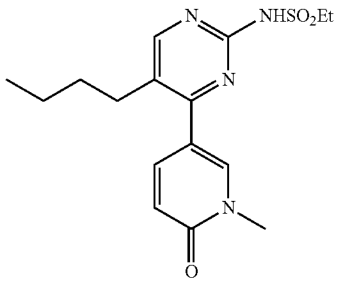 | N-[5-butyl-4-(1-methyl-6-oxopyridin-3-yl)pyrimidin-2-yl]ethanesulfonamide | (CDCl₃, 400 MHz) δ 8.44 (s, 1 H), 7.84 (s, 1 H), 7.69 (d, J = 9.6 Hz, 1 H), 6.68 (d, J = 9.2 Hz, 1 H), 3.68 (s, 3 H), 3.64 (t, J = 7.6 Hz, 2 H), 2.68 (t, J = 7.6 Hz, 2 H), 1.57 (t, J = 8.0 Hz, 2 H), 1.46 (d, J = 7.6 Hz, 3 H), 1.41 (t, J = 8.4 Hz, 2 H), 0.93 (t, J = 7.2 Hz, 3 H) | 351 | 352 |
| 359 | 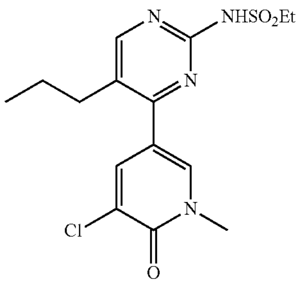 | N-[4-(5-chloro-1-methyl-6-oxopyridin-3-yl)-5-propylpyrimidin-2-yl]ethanesulfonamide | (CDCl₃, 400 MHz) δ 8.47 (s, 1 H), 7.87 (d, J = 2.8 Hz, 1 H), 7.78 (d, J = 2.0 Hz, 1 H), 3.72 (s, 3 H), 3.65 (q, J = 7.2 Hz, 2 H), 2.67 (t, J = 8.0 Hz, 2 H), 1.65 (d, J = 8.0 Hz, 2 H), 1.45 (t, J = 7.2 Hz, 3 H), 1.00 (t, J = 7.2 Hz, 3 H) | 371 | 353 |
| 360 | 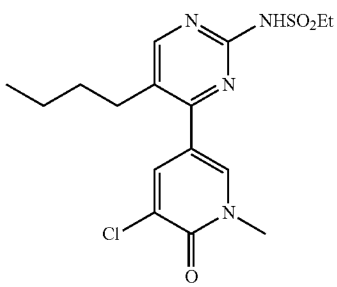 | N-[5-butyl-4-(5-chloro-1-methyl-6-oxopyridin-3-yl)pyrimidin-2-yl]ethanesulfonamide | (CDCl₃, 400 MHz) δ 8.48 (s, 1 H), 7.90 (d, J = 2.4 Hz, 1 H), 7.80 (d, J = 2.4 Hz, 1 H), 3.74 (s, 3 H), 3.66 (q, J = 7.2 Hz, 2 H), 2.70 (t, J = 8.0 Hz, 2 H), 1.61 (m, 2 H), 1.47 (t, J = 7.2 Hz, 3 H), 1.42 (q, J = 8.0 Hz, 2 H), 1.00 (t, J = 7.2 Hz, 3 H) | 385 | 354 |
| 361 | 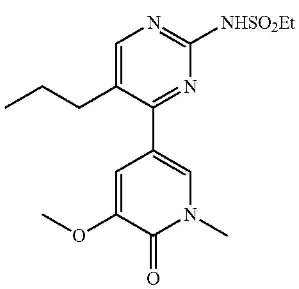 | N-[4-(5-methoxy-1-methyl-6-oxopyridin-3-yl)-5-propylpyrimidin-2-yl]ethanesulfonamide | (CDCl₃, 400 MHz) δ 8.46 (s, 1 H), 7.40 (d, J = 1.6 Hz, 1 H), 7.05 (s, 1 H), 3.89 (s, 3 H), 3.68 (s, 3 H), 3.65 (t, J = 8.0 Hz, 2 H), 2.69 (t, J = 8.0 Hz, 2 H), 1.67 (m, 2 H), 1.44 (t, J = 7.2 Hz, 3 H), 1.00 (t, J = 7.2 Hz, 3 H) | 367 | 355 |
| 362 | 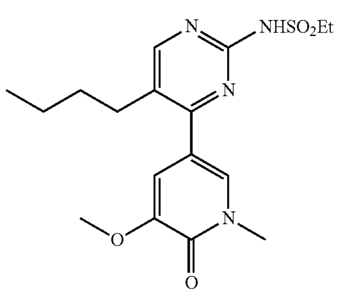 | N-[5-butyl-4-(5-methoxy-1-methyl-6-oxopyridin-3-yl)pyrimidin-2-yl]ethanesulfonamide | (CDCl₃, 400 MHz) δ 8.43 (s, 1 H), 7.39 (d, J = 2.0 Hz, 1 H), 7.03 (d, J = 2 Hz, 1 H), 3.89 (s, 3 H), 3.68 (s, 3 H), 3.64 (d, J = 8.0 Hz, 2 H), 2.71 (t, J = 8.0 Hz, 2 H), 1.67 (m, 2 H, overlapped with water peak), 1.45 (t, J = 7.2 Hz, 3 H), 1.39 (q, J = 7.2 Hz, 2 H), 0.94 (t, J = 7.2 Hz, 3 H) | 381 | 356 |

TABLE 20-continued

| Chemical Synthesis Example | Structure | Name | $^1$H NMR (ppm (δ), 400 MHz) | MS (M + H) | Prepared from Ex. No. |
|---|---|---|---|---|---|
| 363 | ![structure] | N-[5-butyl-4-(1,5-dimethyl-6-oxopyridin-3-yl)pyrimidin-2-yl]methanesulfonamide | (CDCl$_3$, 400 MHz) δ 8.47 (s, 1 H), 7.70 (d, J = 2 Hz, 1 H), 7.55 (s, 1 H), 3.66 (s, 3 H), 3.46 (s, 3 H), 2.69 (t, J = 8.0 Hz, 2 H), 2.23 (s, 3 H), 1.56 (q, J = 8.0 Hz, 2 H), 1.38 (q, J = 7.2 Hz, 2 H), 0.94 (t, J = 7.2 Hz, 3 H) | 351 | 305 |

Example 364

4-[2-(cyclopropylmethoxy)-5-propan-2-ylsulfonyl-phenyl]-2-methylisoquinolin-1-one Step 1:
5-bromo-7H-[1,2,4]triazolo[4,3-a]pyrazin-8-one

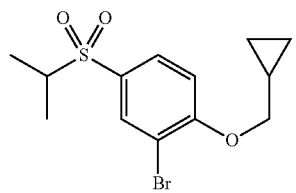 [SMILES: CC(C)S(=O)(=O)c1ccc(OCC2CC2)c(Br)c1]

The title compound was prepared in three steps from 3-bromo-4-fluorobenzenethiol in a manner similar to Example 79, steps 1-3 except that 2-iodopropane was substituted for ethyl iodide in step 1 and the alkoxide of cyclopropylmethanol was substituted for sodium methoxide in step 3. $^1$H NMR (CDCl$_3$, 400 MHz) δ 8.05 (d, J=2.4 Hz, 1H), 7.76 (dd, J$_1$=2.4 Hz, J$_2$=8.4, 1H), 6.97 (d, J=8.4 Hz, 1H), 3.18 (m, 1H), 1.29 (d, J=6.8 Hz, 6H), 0.86 (m, 1H), 0.71 (d, J=6.8 Hz, 2H), 0.45 (d, J=5.6 Hz, 2H). LCMS: (M+H+): 333.0; 335.0

Step 2: 4-[2-(cyclopropylmethoxy)-5-propan-2-yl-sulfonylphenyl]-2-methylisoquinolin-1-one

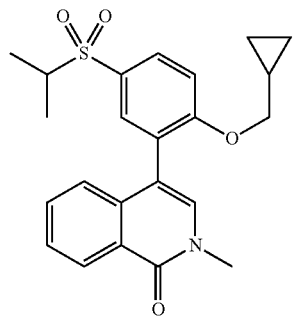 [SMILES: CC(C)S(=O)(=O)c1ccc(OCC2CC2)c(-c2cn(C)c(=O)c3ccccc23)c1]

The title compound of step 1 was coupled to the title compound of Example 89, step 1 in a manner similar Example 89, step 2 to give the title compound as a white solid. $^1$H NMR (CDCl$_3$, 400 MHz) δ 8.52 (d, J=7.2 Hz, 1H), 7.91 (dd, J$_1$=6.4 Hz, J$_2$=8.4, 1H), 7.80 (d, J=2.4 Hz, 1H), 7.51-7.57 (m, 2H), 7.15 (d, J=8.0 Hz, 1H), 7.09 (t, J=8.4 Hz, 1H), 3.89 (s, 2H), 3.67 (s, 3H), 3.18-3.25 (m, 1H), 1.33 (d, J=6.8 Hz, 6H), 0.99-1.02 (m, 1H), 0.414 (m, 2H), 0.11 (s, 2H). LCMS: (M+H+): 412

Example 365

8-[2-(cyclopropylmethoxy)-5-ethylsulfonylphenyl]-6-methyl-4H-pyrido[4,3-b][1,4]oxazine-3,5-dione Step 1:
6-methyl-4H-pyrido[4,3-b][1,4]oxazine-3,5-dione

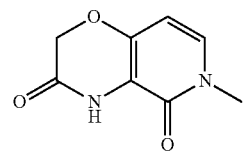

To a solution of the title compound of Example 237, step 3 (1.6 g, 9.01 mmol, 1.00 Eq) in CH$_2$Cl$_2$ (150 mL) at 0° C. under N$_2$ is added chloroacetyl chloride (0.75 mL, 9 mmol) dropwise. Pyridine (2.2 mL, 37 mmol) is then added, and the mixture was stirred for 5 h at room temperature. Saturated aqueous KHSO$_4$ (100 mL) is added and the aqueous layer was extracted a total of three times with CH$_2$Cl$_2$. The combined organic layers were dried over Na$_2$SO$_4$, filtered, and then acetone (200 mL) followed by cesium carbonate (14.6 g, 45 mmol) were added directly to the filtrate (250 mL). The mixture was then heated at 50° C. for 2 h. The volume was reduced and water was added. Extractive work up with 3:1 CH$_2$Cl$_2$:isopropanol followed by trituration with 1:2 EA/PE gave the title compound (400 mg, yield: 24.67%) as a yellow solid. $^1$H NMR: (CDCl$_3$, 400 MHz) δ: 8.17-8.14 (br, 1H), 7.01 (d, J=7.2 Hz, 1H), 6.07 (d, J=7.2 Hz, 1H), 4.69 (s, 1H), 3.59 (s, 3H). LCMS: 181.0 (M+H)$^+$ Step 2: 8-bromo-6-methyl-4H-pyrido[4,3-b][1,4]
oxazine-3,5-dione

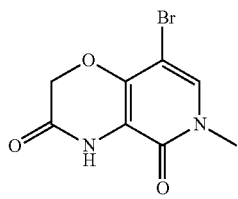

At room temperature, to the title compound of step 1 (90 mg, 0.5 mmol) in anhydrous CH$_3$CN (1 mL) was added NBS (89 mg, 0.5 mmol). After stirring about 2 h, additional NBS (75 mg, 0.4 mmol) was added and the reaction was complete within 20 min. EA extractive work up and silica gel chromatography gave the title compound (51 mg, 0.39 mmol) in 39% yield.

Step 3: 8-[2-(cyclopropylmethoxy)-5-ethylsulfonyl-
phenyl]-6-methyl-4H-pyrido[4,3-b][1,4]oxazine-3,5-
dione

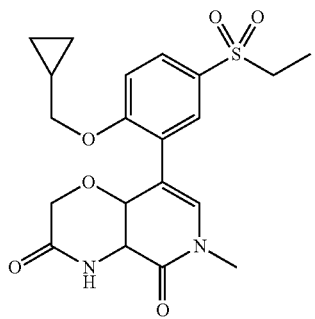 [SMILES: CCS(=O)(=O)c1ccc(OCC2CC2)c(C2=CN(C)C(=O)C3NC(=O)COC23)c1]

The title compound of step 2 was reacted with 2-[2-(cyclopropylmethoxy)-5-ethylsulfonylphenyl]-4,4,5,5-tetramethyl-1,3,2-dioxaborolane in a manner similar to Example 224, step 5. Silica gel chromatography (40-100% EA in hexane over 8 min) gave the title compound. $^1$H NMR: (DMSO-d6, 400 MHz) δ ppm 0.27-0.33 (m, 2H) 0.51-0.57 (m, 2H) 1.11 (t, J=7.33 Hz, 3H) 1.14-1.22 (m, 1H, partially obscured) 3.22-3.28 (m, 2H) 3.51 (s, 3H) 3.96 (d, J=7.07 Hz, 2H) 4.54 (s, 2H) 7.27 (d, J=8.84 Hz, 1H) 7.52 (s, 1H) 7.67 (d, J=2.02 Hz, 1H) 7.79-7.92 (m, 1H) 10.10 (s, 1H) LCMS: 419 (M+H)$^+$ Example 366

8-[2-(cyclopropylmethoxy)-5-ethylsulfonylphenyl]-
6-methyl-3,4,4a,8a-tetrahydro-2H-pyrido[4,3-b][1,4]
oxazin-5-one

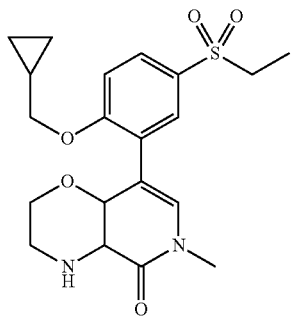 [SMILES: CCS(=O)(=O)c1ccc(OCC2CC2)c(C2=CN(C)C(=O)C3NCCOC23)c1]

The title compound of Example 365, step 3 in anhydrous THF was treated with excess 1M LAH in THF at room temperature. After about 30 min, ice, water, methanol and 1M HCl were added followed by saturated aqueous NaHCO3 and EA extractive work up. Silica gel chromatography (EA, followed by 5% methanol in EA) gave the title compound as a clear glass. $^1$H NMR: (DMSO-d6, 400 MHz) δ ppm 0.32 (br. s., 2H) 0.54 (br. s., 2H) 1.03-1.30 (m, 4H) 3.45 (br. s., 3H) 3.94 (br. s., 2H) 4.09 (br. s., 2H) 5.03 (br. s., 1H) 7.05 (br. s., 1H) 7.22 (br. s., 1H) 7.62 (br. s., 1H) 7.78 (br. s., 1H). $^1$H NMR: (DMSO-d6/DCl, 400 MHz) δ ppm 0.29 (br. s., 2H) 0.55 (br. s., 2H) 1.10 (br. s., 4H) 3.25 (br. s., 2H) 3.45 (br. s., 3H) 3.93 (br. s., 2H) 4.43 (br. s., 2H) 7.27 (br. s., 1H) 7.69 (br. s., 1H) 7.84 (br. s., 2H). LCMS: 405 (M+H)$^+$ Example 367

N-[4-(2,4-difluorophenoxy)-3-(7-methyl-8-oxoimi-
dazo[1,5-a]pyrazin-5-yl)phenyl]methanesulfonamide

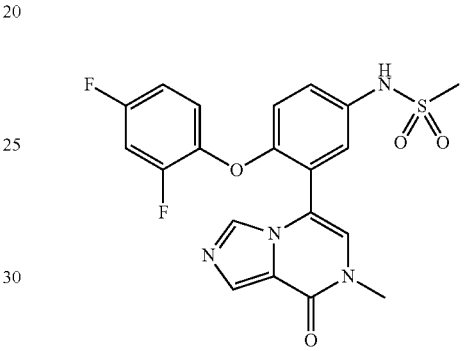

To a solution of the title compound from Example 129, Step 2 (140 mg, 0.38 mmol) in THF (20 ml) was added pyridine (152 mg, 1.90 mmol). Then methanesulfonyl chloride (48 mg, 0.46 mmol) was added to the solution at 0° C. The solution was allowed to warm up to room temperature and heated to reflux for overnight. The reaction mixture was concentrated under reduced pressure to yield the crude product that was purified by prep-HPLC to give the title compound (75.26 mg, 44%) as a yellow solid. $^1$H NMR (CDCl$_3$, 400 MHz) δ 8.60 (s, 1H), 8.15 (s, 1H), 7.50 (d, J=2.8 Hz, 1H), 7.30 (dd, J=8.8, 2.4 Hz, 1H), 7.18 (td, J=8.8, 5.3 Hz, 1H), 7.00-6.88 (m, 2H), 6.83 (s, 1H), 6.78 (d, J=8.8 Hz, 1), 3.60 (s, 3H), 3.03 (s, 3H). LCMS: 447.0 (M+1)$^+$.

Example 368

5-[2-(cyclopropylmethoxy)-5-ethylsulfonylphenyl]-
7-methylimidazo[1,5-a]pyrazin-8-one

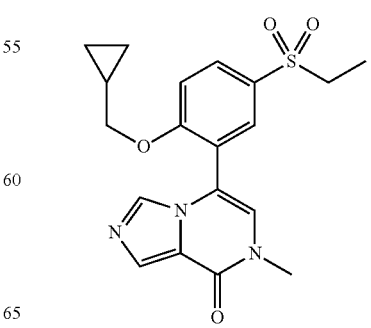

To a microwave vial containing 5-bromo-7-methylimidazo[1,5-a]pyrazin-8-one (150 mg, 0.66 mmol), 2-[2-(cyclopropylmethoxy)-5-ethylsulfonylphenyl]-4,4,5,5-tetramethyl-1,3,2-dioxaborolane (290 mg, 0.80 mmol) and NaHCO₃ (1 mL, 2M) in dioxane (3 mL) was added Pd(dppf)Cl₂ (80 mg, 0.10 mmol). The mixture was purge with N₂ for 2 min and sealed. The reaction was irradiated in microwave at 100° C. for 2 h. Water (20 mL) was added and the mixture was extracted with EtOAc (20 mL×3). The combined organic layers were washed with brine (20 mL), dried with Na₂SO₄, filtered and concentrated in vacuum. The residue was purified by column chromatography (PE:EA=5:1 to 1:1) to afford the title compound (55.3 mg, 22%) as a light yellow solid. ¹H NMR (CDCl₃, 400 MHz) δ 8.03 (dd, J1=8.4 Hz, J₂=2.0 Hz, 2H), 7.94 (d, J=2.0 Hz, 1H), 7.56 (s, 1H), 7.15 (d, J=8.8 Hz, 1H), 6.49 (s, 1H), 3.96 (d, J=6.4 Hz, 2H), 3.54 (s, 3H), 3.16 (q, J=7.6 Hz, 1H), 1.33 (t, J=7.6 Hz, 1H), 1.08 (s, 1H), 0.54 (d, J=7.2 Hz, 2H), 0.54 (d, J=4.4 Hz, 2H). LCMS: 388.1 (M+1)⁺

Example 369

5-[2-(2,4-difluorophenoxy)-5-(ethylsulfonylmethyl)phenyl]-7-methylimidazo[1,5-a]pyrazin-8-one Step 1: 2-[2-(2,4-difluorophenoxy)-5-(ethylsulfonylmethyl)phenyl]-4,4,5,5-tetramethyl-1,3,2-dioxaborolane

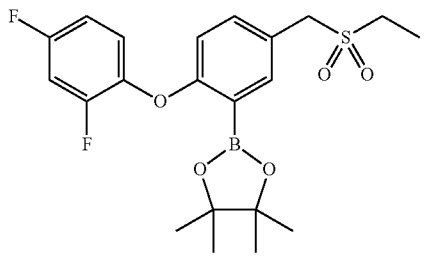 [SMILES: CCS(=O)(=O)Cc1ccc(Oc2ccc(F)cc2F)c(B2OC(C)(C)C(C)(C)O2)c1]

A mixture of 2-bromo-1-(2,4-difluorophenoxy)-4-(ethylsulfonylmethyl)benzene (250 mg, 0.64 mmol), bis(pinacolato)diboron (255 mg, 0.96 mmol), KOAc (189 mg, 1.92 mmol) and Pd(dppf)Cl₂ (44 mg, 0.06 mmol) in dioxane (5 mL) was stirred at 70° C. for 18 hrs under N₂. The mixture was concentrated and the residue was purified by column chromatography to give the title compound (150 mg, 53.4%) as yellow solid. LCMS: 439.2 (M+1)⁺

Step 2: 5-[2-(2,4-difluorophenoxy)-5-(ethylsulfonylmethyl)phenyl]-7-methylimidazo[1,5-a]pyrazin-8-one

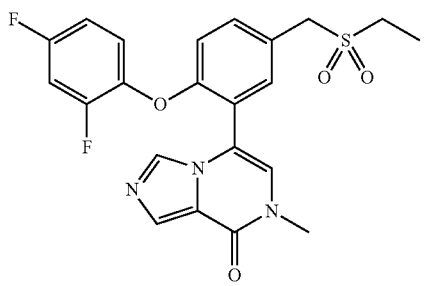 [SMILES: CCS(=O)(=O)Cc1ccc(Oc2ccc(F)cc2F)c(-c2cn(C)c(=O)c3cncn23)c1]

A mixture of the title compound from Step 1 (150 mg, 0.34 mmol), the title compound from Example 129 Step 1 (87 mg, 0.38 mmol), K₃PO₄ (217 mg, 1.02 mmol) and Pd(dppf)Cl₂ (22 mg, 0.03 mmol) in dioxane (5 mL) and H₂O (1 mL) was stirred at 70° C. for 18 hrs under N₂. The resulting mixture was filtered and concentrated. The residue was purified by prep-HPLC to give the title compound (70.0 mg, 45%) as a yellow solid. ¹H NMR (DMSO-d6, 400 MHz) δ 8.83 (s, 1H), 8.33 (s, 1H), 7.64 (d, J=2.0 Hz, 1H), 7.57 (dd, J₁=8.8 Hz, J₂=2.0 Hz, 1H), 7.53-7.41 (m, 2H), 7.37 (s, 1H), 7.20-7.12 (m, 1H), 6.93 (d, J=8.8 Hz, 1H), 4.54 (s, 2H), 3.45 (s, 3H), 3.09 (q, J=7.6 Hz, 2H), 1.23 (t, J=7.6 Hz, 3H). LCMS: 460.1 (M+1)⁺

Example 370

7-methyl-5-[5-(methylsulfonylmethyl)-2-(2,2,2-trifluoroethoxy)phenyl]imidazo[1,5-a]pyrazin-8-one Step 1: 4,4,5,5-tetramethyl-2-[5-(methylsulfonylmethyl)-2-(2,2,2-trifluoroethoxy)phenyl]-1,3,2-dioxaborolane

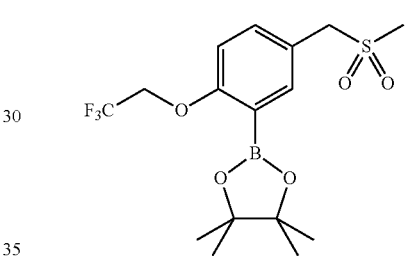

The title compound was prepared in a manner similar to Example 369 Step 1, by substituting 2-bromo-4-(methylsulfonylmethyl)-1-(2,2,2-trifluoroethoxy)benzene for 2-bromo-1-(2,4-difluorophenoxy)-4-(ethylsulfonylmethyl)benzene. LCMS: 395.2 (M+1)⁺

Step 2: 7-methyl-5-[5-(methylsulfonylmethyl)-2-(2,2,2-trifluoroethoxy)phenyl]imidazo[1,5-a]pyrazin-8-one

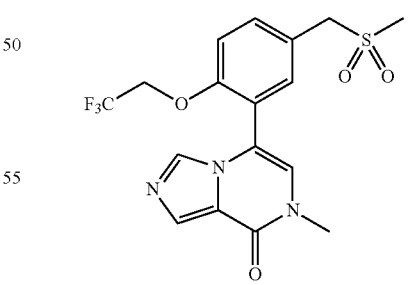

The title compound was prepared in a manner similar to Example 369 Step 2, by substituting 4,4,5,5-tetramethyl-2-[5-(methylsulfonylmethyl)-2-(2,2,2-trifluoroethoxy)phenyl]-1,3,2 dioxaborolane for 2-[2-(2,4-difluorophenoxy)-5-(ethylsulfonylmethyl)phenyl]-4,4,5,5-tetramethyl-1,3,2-dioxaborolane. ¹H NMR (DMSO-d6, 400 MHz) δ 8.64 (s, 1H), 8.32 (s, 1H), 7.64 (dd, J₁=8.8 Hz, J₂=2.0 Hz, 1H), 7.56

(s, 1H), 7.39 (d, J=8.8 Hz, 1H), 7.25 (s, 1H), 4.86 (q, J=8.8 Hz, 2H), 4.53 (s, 2H), 3.44 (s, 3H), 2.94 (s, 3H). LCMS: 416.1 (M+1)$^+$

Example 371

5-[5-(ethylsulfonylmethyl)-2-(2,2,2-trifluoroethoxy)phenyl]-7-methylimidazo[1,5-a]pyrazin-8-one Step 1: 2-[5-(ethylsulfonylmethyl)-2-(2,2,2-trifluoroethoxy)phenyl]-4,4,5,5-tetramethyl-1,3,2-dioxaborolane

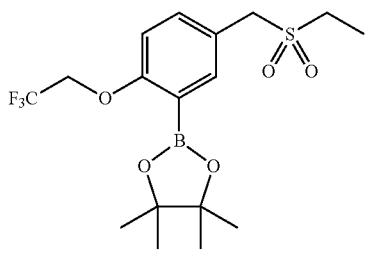 [SMILES: CCS(=O)(=O)Cc1ccc(OCC(F)(F)F)c(B2OC(C)(C)C(C)(C)O2)c1]

The title compound was prepared in a manner similar to Example 369 Step 1, by substituting 2-bromo-4-(ethylsulfonylmethyl)-1-(2,2,2-trifluoroethoxy)benzene for 2-bromo-1-(2,4-difluorophenoxy)-4-(ethylsulfonylmethyl)benzene. LCMS: 409.2 (M+1)$^+$ Step 2: 5-[5-(ethylsulfonylmethyl)-2-(2,2,2-trifluoroethoxy)phenyl]-7-methylimidazo[1,5-a]pyrazin-8-one

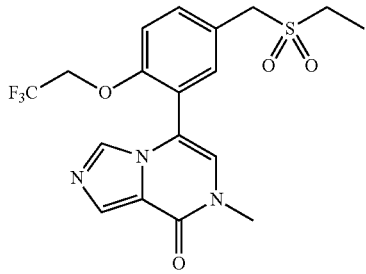 [SMILES: CCS(=O)(=O)Cc1ccc(OCC(F)(F)F)c(-c2cn(C)c(=O)c3cncn23)c1]

The title compound was prepared in a manner similar to Example 369 Step 2, by substituting 2-[5-(ethylsulfonylmethyl)-2-(2,2,2-trifluoroethoxy)phenyl]-4,4,5,5-tetramethyl-1,3,2-dioxaborolane for 2-[2-(2,4-difluorophenoxy)-5-(ethylsulfonylmethyl)phenyl]-4,4,5,5-tetramethyl-1,3,2-dioxaborolane. $^1$H NMR (DMSO-d6, 400 MHz) δ 8.99 (s, 1H), 8.47 (s, 1H), 7.61 (d, J=8.8 Hz, 1H), 7.52 (s, 1H), 7.35 (d, J=8.8 Hz, 1H), 7.31 (s, 1H), 4.82 (q, J=8.4 Hz, 2H), 4.48 (s, 2H), 3.42 (s, 3H), 3.04 (q, J=7.2 Hz, 2H), 2.94 (t, J=7.2 Hz, 3H). LCMS: 430.1 (M+1)$^+$

Example 372

5-[2-(2,4-difluorophenoxy)-5-(methylsulfonylmethyl)phenyl]-7-methylimidazo[1,5-a]pyrazin-8-one Step 1: 2-[2-(2,4-difluorophenoxy)-5-(methylsulfonylmethyl)phenyl]-4,4,5,5-tetramethyl-1,3,2-dioxaborolane

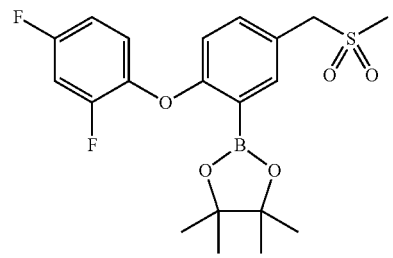 [SMILES: CC1(C)OB(c2cc(CS(C)(=O)=O)ccc2Oc2ccc(F)cc2F)OC1(C)C]

The title compound was prepared in a manner similar to Example 369 Step 1, by substituting 2-bromo-1-(2,4-difluorophenoxy)-4-(methylsulfonylmethyl)benzene for 2-bromo-1-(2,4-difluorophenoxy)-4-(ethylsulfonylmethyl)benzene. LCMS: 442.2 (M+18)$^+$ Step 2: 5-[2-(2,4-difluorophenoxy)-5-(methylsulfonylmethyl)phenyl]-7-methylimidazo[1,5-a]pyrazin-8-one

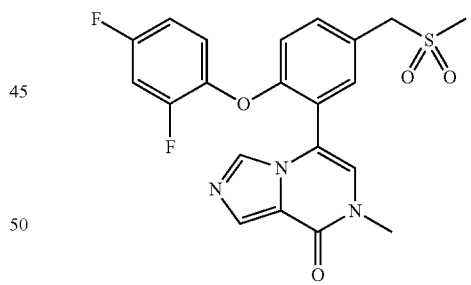

The title compound was prepared in a manner similar to Example 369 Step 2, by substituting 2-[2-(2,4-difluorophenoxy)-5-(methylsulfonylmethyl)phenyl]-4,4,5,5-tetramethyl-1,3,2-dioxaborolane for 2-[2-(2,4-difluorophenoxy)-5-(ethylsulfonylmethyl)phenyl]-4,4,5,5-tetramethyl-1,3,2-dioxaborolane. $^1$H NMR (DMSO-d6, 400 MHz) δ 8.59 (s, 1H), 8.19 (s, 1H), 7.65 (d, J=2.0 Hz, 1H), 7.57 (dd, J$_1$=8.8 Hz, J$_2$=2.0 Hz, 1H), 7.52-7.39 (m, 2H), 7.30 (s, 1H), 7.18-7.11 (m, 1H), 6.94 (d, J=8.8 Hz, 1H), 4.55 (s, 2H), 3.44 (s, 3H), 2.96 (s, 3H). LCMS: 446.1 (M+1)$^+$

Example 373

5-[2-(4,4-difluorocyclohexyl)oxy-5-ethylsulfonyl-phenyl]-7-methylimidazo[1,5-a]pyrazin-8-one Step 1: 2-(5-ethylsulfonyl-2-fluorophenyl)-4,4,5,5-tetramethyl-1,3,2-dioxaborolane

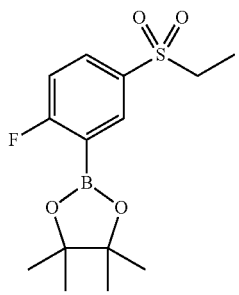 [SMILES: CCS(=O)(=O)c1ccc(F)c(B2OC(C)(C)C(C)(C)O2)c1]

bromo-4-ethylsulfonyl-1-fluorobenzene (5.00 g, 18.72 mmol), AcOK (3.88 g, 56.16 mmol, 3 eq), pinacol ester (9.51 g, 37.44 mmol, 2 eq), Pd$_2$(dba)$_3$ (17.14 g, 18.72 mmol, 1 eq) and XPhos (9.24 g, 18.72 mmol, 1 eq) in dioxane (300 mL) was degassed and then heated to 60° C. overnight under N$_2$. The reaction mixture was poured into H$_2$O (300 mL). The mixture was extracted with EA (3×250 mL). The combined organic phase were washed with saturated brine (300 mL), dried over anhydrous MgSO$_4$, filtered and concentrated under reduced pressure to give a residue that was purified by silica gel column chromatography to afford the title compound (1.87 g, 32%) as a gray solid. $^1$H NMR: (CDCl$_3$, 400 MHz) δ: 8.34-8.31 (m, 1H), 8.01-7.98 (m, 1H), 7.22 (d, J=8.8 Hz, 1H), 3.14 (q, J=7.6 Hz, 2H), 1.37 (s, 12H), 1.27 (t, J=7.6 Hz, 3H).

Step 2: 5-(5-ethylsulfonyl-2-fluorophenyl)-7-methylimidazo[1,5-a]pyrazin-8-one

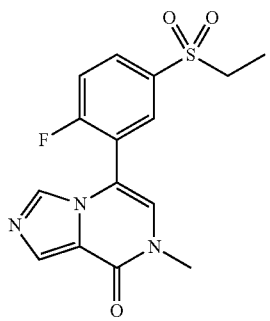 [SMILES: CCS(=O)(=O)c1ccc(F)c(-c2cn(C)c(=O)c3cncn23)c1]

5-bromo-7-methylimidazo[1,5-a]pyrazin-8-one (600 mg, 2.63 mmol, 0.83 Eq), the title compound from Step 2 (1.00 g, 3.18 mmol, 1.00 Eq), K$_3$PO$_4$ (2.03 g, 9.55 mmol, 3.00 Eq) and Pd(dppf)Cl$_2$ (118 mg, 0.16 mmol, 0.05 Eq) in dioxane (20 mL) was degassed and then heated to 60° C. overnight under N$_2$. The reaction mixture was poured into water. The mixture was extracted with EA (3×25 mL). The organic phase was washed with brine (30 mL), dried over anhydrous MgSO$_4$, filtered and concentrated under vacuum to give a residue which was purified by silica gel chromatography to afford the title compound (600 mg, yield: 56.24%). $^1$H NMR: (CDCl$_3$, 400 MHz) δ: 8.50 (s, 1H), 8.17 (s, 1H), 8.12-8.08 (m, 2H), 7.50 (t, J=8.8 Hz, 1H), 6.90 (s, 1H), 3.59 (s, 3H), 3.17 (q, J=7.2 Hz, 2H), 0.89-0.83 (m, 3H).

Step 3: 5-[2-(4,4-difluorocyclohexyl)oxy-5-ethylsulfonylphenyl]-7-methylimidazo[1,5-a]pyrazin-8-one

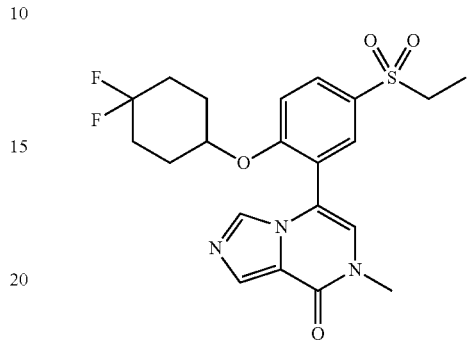

To a solution of 4,4-difluorocyclohexan-1-ol (162 mg, 1.19 mmol) in THF (10 mL) was added NaH (48 mg, 1.19 mmol, 60% in mineral oil) in one portion at 25° C. under N$_2$. The mixture was stirred at 25° C. for 30 minutes. Then the title compound from Step 2 (200 mg, 0.6 mmol) was added and the mixture was stirred at 25° C. for 18 hours. The reaction contents were poured into ice-water (v/v=1/1) (150 mL) and stirred for 20 minutes. The aqueous phase was extracted with EA (40 mL×3). The combined organic phase was washed with brine (20 mL×2), dried over anhydrous Na$_2$SO$_4$, filtered and concentrated under reduced pressure. The residue was purified by prep-HPLC to afford the title compound (57.35 mg, 22%) as a white solid. $^1$H NMR (DMSO-d6, 400 MHz) δ 8.63 (s, 1H), 8.26 (s, 1H), 8.04 (dd, J1=8.8 Hz, J 2=2.4 Hz 1H), 7.95 (d, J=2.4 Hz, 1H), 7.56 (d, J=8.8 Hz, 1H), 7.31 (s, 1H), 4.90-4.84 (brs, 1H), 3.44 (s, 3H), 3.32 (q, J=7.2 Hz, 2H), 1.85-1.83 (m, 4H), 1.69-1.61 (m, 4H), 1.15 (t, J=7.2 Hz, 3H). LCMS: 452.2 (M+H)$^+$

Example 374

5-(2-cyclopentyloxy-5-ethylsulfonylphenyl)-7-methylimidazo[1,5-a]pyrazin-8-one

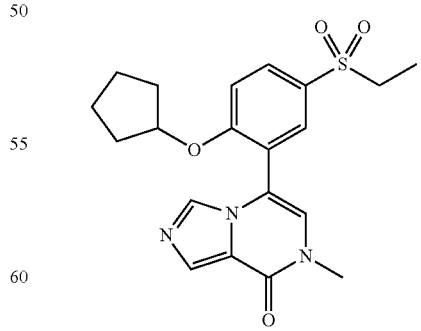

The title compound was prepared in a manner similar to Example 373, by substituting cyclopentanol for 4,4-difluorocyclohexan-1-ol in Step 3. $^1$H NMR (DMSO-d6, 400 MHz) δ 8.34 (s, 1H), 8.16 (s, 1H), 8.02 (d, J=8.8 Hz, 1H), 7.91 (s, 1H), 7.42 (d, J=8.8 Hz, 1H), 7.24 (s, 1H), 5.04-5.01 (brs, 1H), 3.43 (s, 3H), 3.31 (q, J=6.8 Hz, 2H), 1.91-1.80 (m, 2H), 1.62-1.30 (m, 6H), 1.14 (t, J=6.8 Hz, 3H). LCMS: 402.2 (M+H)+

Example 375

5-[2-(cyclopropylmethylamino)-5-ethylsulfonylphenyl]-7-methylimidazo[1,5-a]pyrazin-8-one

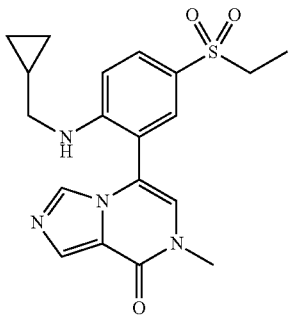 [SMILES: CCS(=O)(=O)c1ccc(NCC2CC2)c(-c2cn(C)c(=O)c3cncn23)c1]

The title compound was prepared in a manner similar to Example 373, by substituting cyclopropylmethanamine for 4,4-difluorocyclohexan-1-ol in Step 3. ¹H NMR (DMSO-d6, 400 MHz) δ 8.28-8.24 (m, 2H), 7.76 (d, J=8.8 Hz, 1H), 7.64 (s, 1H), 6.98 (d, J=8.8 Hz, 1H), 6.47-6.41 (brs, 1H), 3.44 (s, 3H), 3.18 (q, J=7.2 Hz, 2H), 3.06-3.01 (m, 2H), 1.12 (t, J=6.8 Hz, 3H), 1.06-0.98 (m, 1H), 0.42-0.37 (m, 2H), 0.16-0.11 (m, 2H). LCMS: 387.2 (M+H)+

Example 376

5-[2-(2,4-difluorophenoxy)-5-ethylsulfonylphenyl]-7-methylimidazo[1,5-a]pyrazin-8-one

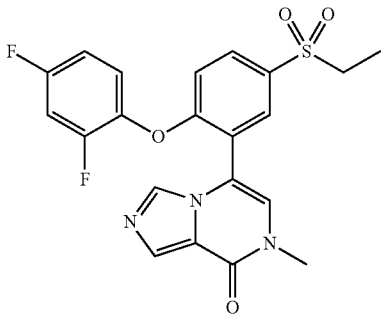 [SMILES: CCS(=O)(=O)c1ccc(Oc2ccc(F)cc2F)c(-c2cn(C)c(=O)c3cncn23)c1]

The title compound was prepared in a manner similar to Example 373, by substituting 2,4-difluorophenol for 4,4-difluorocyclohexan-1-ol in Step 3. ¹H NMR (CDCl3, 400 MHz) δ 8.05 (d, J=2.4 Hz, 1H), 8.03 (s, 1H), 7.97 (dd, J1=8.8 Hz, J 2=2.4 Hz 1H), 7.16-7.10 (m, 1H), 7.05-7.00 (m, 1H), 6.98-6.93 (m, 1H), 7.97 (dd, J1=8.8 Hz, J 2=1.2 Hz 1H), 3.55 (s, 3H), 3.18 (q, J=7.2 Hz, 2H), 1.36 (t, J=7.2 Hz, 3H). LCMS: 446.1 (M+H)+

Example 377

7-[2-(cyclopropylmethoxy)-5-methylsulfonylphenyl]-5-methylfuro[3,2-c]pyridin-4-one Step 1: 7-bromo-5-methylfuro[3,2-c]pyridin-4-one

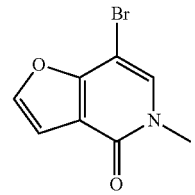

To a suspension of 7-bromo-5H-furo[3,2-c]pyridin-4-one (250 mg, 1.17 mmol) in DMF (5 mL) cooled to 0° C. was added HNa (56 mg, 1.4 mmol, 60% dispersion in mineral oil) in three portions. After stirring at room temperature for 45 min, MeI (87 μL, 1.4 mmol) was added drop wise over five minutes. The reaction was allowed to warm up to rt stirred for 2 h. It was then cooled to 0° C. followed by addition of sat. aq. NH4Cl (5 mL) drop wise. The resulting mixture was extracted with EtOAc (3×5 mL). The combined organic layers were dried over Na2SO4, filtered and concentrated under reduced pressure. The residue was purified by silica gel column chromatography to afford the title compound. LCMS: 227.9 (M+H)+

Step 2: 5-methyl-7-(4,4,5,5-tetramethyl-1,3,2-dioxaborolan-2-yl)furo[3,2-c]pyridin-4-one

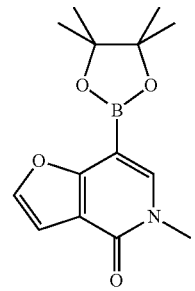 [SMILES: Cn1cc(B2OC(C)(C)C(C)(C)O2)c2occc2c1=O]

The title compound was prepared in a manner similar to Example 255, step 4, by substituting 7-bromo-5-methylfuro[3,2-c]pyridin-4-one for N-[4-(cyclopropylmethoxy)-3-(tetramethyl-1,3,2-dioxaborolan-2-yl)phenyl]ethane-1-sulfonamide. LCMS: 276.1 (M+H)+

Step 3: 7-[2-(cyclopropylmethoxy)-5-methylsulfonylphenyl]-5-methylfuro[3,2-c]pyridin-4-one

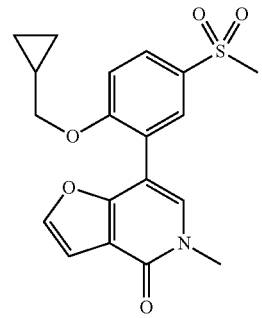 [SMILES: Cn1cc(-c2cc(S(C)(=O)=O)ccc2OCC2CC2)c2occc2c1=O]

The title compound was prepared in a manner similar to Example 197, by substituting 5-methyl-7-(4,4,5,5-tetramethyl-1,3,2-dioxaborolan-2-yl)furo[3,2-c]pyridin-4-one for 2-[2-(cyclopropylmethoxy)-5-methylsulfonylphenyl]-4,4,5,5-tetramethyl-1,3,2-dioxaborolane and 2-bromo-1-(cyclopropylmethoxy)-4-methylsulfonylbenzene for 4-bromo-2-methyl-6-(trifluoromethyl)isoquinolin-1-one. ¹H NMR (CDCl₃, 400 MHz) δ 8.05 (s, 1H), 7.92 (dd, J₁=8.6 Hz, J₂=1.8 Hz, 1H), 7.50 (m, 2H), 7.07 (m, 2H), 3.95 (d, J=6.7 Hz, 2H), 3.70 (s, 3H), 3.1 (s, 3H), 1.15 (m, 1H), 0.57 (m, 2H), 0.28 (m, 2H). LCMS: 374.1 (M+H)⁺

Example 378

7-[2-(cyclopropylmethoxy)-5-ethylsulfonylphenyl]-5-methylfuro[3,2-c]pyridin-4-one

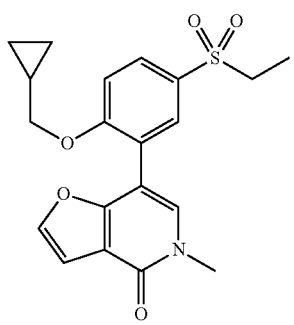 [SMILES: CCS(=O)(=O)c1ccc(OCC2CC2)c(-c2cn(C)c(=O)c3ccoc23)c1]

The title compound was prepared in a manner similar to Example 197, by substituting 2-[2-(cyclopropylmethoxy)-5-ethylsulfonylphenyl]-4,4,5,5-tetramethyl-1,3,2-dioxaborolane for 2-[2-(cyclopropylmethoxy)-5-methylsulfonylphenyl]-4,4,5,5-tetramethyl-1,3,2-dioxaborolane and 7-bromo-5-methylfuro[3,2-c]pyridin-4-one for 4-bromo-2-methyl-6-(trifluoromethyl)isoquinolin-1-one. ¹H NMR (DMSO-d6, 400 MHz) δ 7.88 (m, 4H), 7.33 (d, J=9.4 Hz, 1H), 7.01 (d, J=2.0 Hz, 1H), 4.02 (d, J=6.8 Hz, 2H), 3.58 (s, 3H), 3.28 (m, 2H), 1.12 (t, J=7.4 Hz, 3H), 1.08 (m, 1H), 0.45 (m, 2H), 0.24 (m, 2H). LCMS: 388.1 (M+H)⁺

Example 379

N-[4-(2,4-difluorophenoxy)-3-(5-methyl-4-oxofuro[3,2-c]pyridin-7-yl)phenyl]ethanesulfonamide

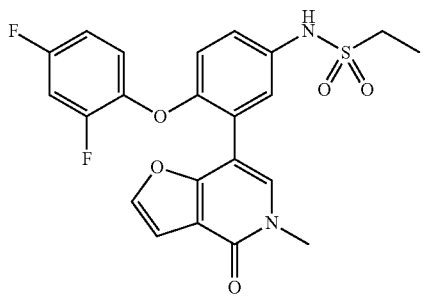 [SMILES: CCS(=O)(=O)Nc1ccc(Oc2ccc(F)cc2F)c(-c2cn(C)c(=O)c3ccoc23)c1]

The title compound was prepared in a manner similar to Example 197, by substituting N-[4-(2,4-difluorophenoxy)-3-(4,4,5,5-tetramethyl-1,3,2-dioxaborolan-2-yl)phenyl]ethanesulfonamide for 2-[2-(cyclopropylmethoxy)-5-methylsulfonylphenyl]-4,4,5,5-tetramethyl-1,3,2-dioxaborolane and 7-bromo-5-methylfuro[3,2-c]pyridin-4-one for 4-bromo-2-methyl-6-(trifluoromethyl)isoquinolin-1-one. ¹H NMR (DMSO-d6, 400 MHz) δ 9.83 (s, 1H), 7.85 (d, J=2.0 Hz, 1H), 7.78 (s, 1H), 7.37 (m, 2H), 7.24 (dd, J₁=8.8 Hz, J₂=2.7 Hz, 1H), 7.14 (m, 1H), 7.03 (m, 1H), 6.97 (d, J=2.1 Hz, 1H), 6.93 (d, J=8.8 Hz, 1H), 3.54 (s, 3H), 3.12 (q, J=7.3 Hz, 2H), 1.12 (t, J=7.3 Hz, 3H). LCMS: 461.2 (M+H)⁺

Example 380

N-[4-(2,4-difluorophenoxy)-3-(5-methyl-4-oxofuro[3,2-c]pyridin-7-yl)phenyl]methanesulfonamide

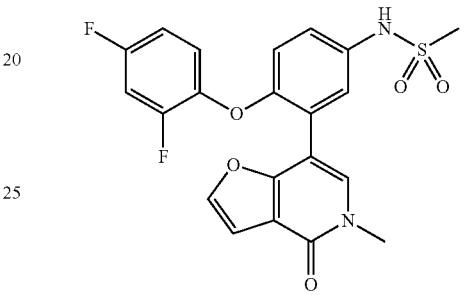

The title compound was prepared in a manner similar to Example 197, by substituting N-[4-(2,4-difluorophenoxy)-3-(4,4,5,5-tetramethyl-1,3,2-dioxaborolan-2-yl)phenyl]methanesulfonamide for 2-[2-(cyclopropylmethoxy)-5-methylsulfonylphenyl]-4,4,5,5-tetramethyl-1,3,2-dioxaborolane and 7-bromo-5-methylfuro[3,2-c]pyridin-4-one for 4-bromo-2-methyl-6-(trifluoromethyl)isoquinolin-1-one. ¹H NMR (DMSO-d6, 400 MHz) δ 9.77 (s, 1H), 7.85 (d, J=2.1 Hz, 1H), 7.79 (s, 1H), 7.38 (m, 2H), 7.25 (dd, J₁=8.8 Hz, J₂=2.8 Hz, 1H), 7.12 (m, 1H), 7.04 (m, 1H), 6.97 (d, J=2.1 Hz, 1H), 6.94 (d, J=8.8 Hz, 1H), 3.54 (s, 3H), 3.02 (s, 3H). LCMS: 447.1 (M+H)⁺

Example 381

4-(cyclopropylmethoxy)-5-(1-methyl-6-oxopyridin-3-yl)-1-(methylsulfonylmethyl)pyridin-2-one Step 1:
5-bromo-4-(cyclopropylmethoxy)-2-methoxypyridine

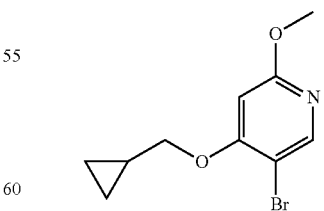

To a solution of cyclopropylmethanol (446 mg, 6.18 mmol) in THF (10 mL) was added NaH (247 mg, 6.18 mmol, 60% in mineral oil) in one portion at 0° C. The reaction mixture was warmed up to 20° C. over a period of 30 mins and stirred at 20° C. for 10 mins. Then 5-bromo- 4-chloro-2-methoxypyridine (550 mg, 2.47 mmol) was added in one portion and the mixture was stirred at 70° C. for 4 hours. The mixture was diluted with saturated ammonium aqueous solution (50 mL) and extracted by EtOAc (2×30 mL). The combined organic layers were dried over anhydrous sodium sulfate, filtered, and concentrated to give the crude product which was purified by silica gel column chromatography (PE:EA=20:1 to 10:1) to afford the title compound (450 mg, 70.6%) as colorless oil. $^1$H NMR: (CDCl$_3$, 400 MHz) δ: 8.11 (s, 1H), 6.18 (s, 1H), 3.90 (s, 3H), 3.89-3.88 (m, 2H), 1.39-1.27 (m, 1H), 0.70-0.67 (m, 2H), 0.46-0.43 (m, 2H). LCMS (M+H)$^+$=258.0 (M+1)$^+$; 260.0

Step 2: 5-bromo-4-(cyclopropylmethoxy)pyridin-2-ol

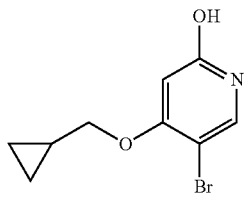 [SMILES: Oc1cc(OCC2CC2)c(Br)cn1]

To a solution of the title compound from step 1 (450 mg, 1.74 mmol) in DMF (5 mL) was added LiCl (370 mg, 8.72 mmol) and TsOH.H$_2$O (1.52 g, 8.72 mmol) at room temperature. The mixture was heated to 120° C. and stirred for 1 hour. The mixture was diluted with water (100 mL) and extracted with EtOAc (3×100 mL). The combined organic phase was washed with saturated brine (2×200 mL), dried over anhydrous Na$_2$SO$_4$, filtered and concentrated under reduced pressure to afford the title compound (380 mg, yield: 88.9%) as yellow solid which used directly for the next step without further purification. $^1$H NMR (CDCl$_3$, 400 MHz) δ 7.49 (s, 1H), 5.91 (s, 1H), 3.87 (d, J=6.8 Hz, 2H), 1.36-1.22 (m, 1H), 0.71-0.67 (m, 2H), 0.46-0.42 (m, 2H). LCMS: 244.0 (M+1)$^+$; 246.0

Step 3: 5-bromo-4-(cyclopropylmethoxy)-1-(methylsulfanylmethyl)pyridin-2-one

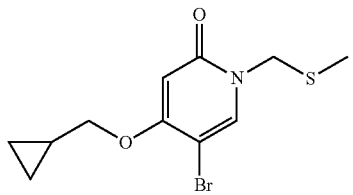 [SMILES: CSCn1cc(Br)c(OCC2CC2)cc1=O]

To a solution of the title compound from Step 2 (330 mg, 1.35 mmol) in DMF (5 mL) was added NaH (40 mg, 2 mmol, 60% in mineral oil) at 0° C. The mixture was stirred at 0° C. for 30 minutes. Then, chloromethyl methyl sulfide (131 mg, 1.35 mmol) was added. The mixture was warmed to room temperature and stirred for 5 hours. The mixture was quenched with saturated aqueous NH$_4$Cl (30 mL) and extracted with EA (10 mL×3). The combined organic layers were washed with saturated brine (20 mL×2), dried over anhydrous Na$_2$SO$_4$, filtered and concentrated under vacuum. The residue was purified by column chromatography on silica gel (PE:EA=3:1) to afford the title compound (205 mg, 50%) as yellow oil. $^1$H NMR (CDCl$_3$, 400 MHz) δ 7.60 (s, 1H), 5.86 (s, 1H), 4.96 (s, 1H), 3.84 (d, J=6.8 Hz, 2H), 2.17 (s, 3H), 1.32-1.25 (m, 1H), 0.70-0.67 (m, 2H), 0.41-0.39 (m, 2H).

Step 4: 5-bromo-4-(cyclopropylmethoxy)-1-(methylsulfonylmethyl)pyridin-2-one

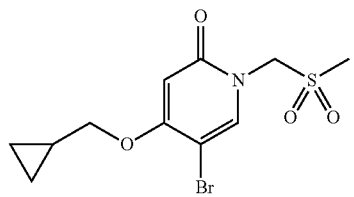 [SMILES: CS(=O)(=O)Cn1cc(Br)c(OCC2CC2)cc1=O]

To a solution of the title compound from Step 3 (150 mg, 0.5 mmoL) in DCM (5 mL), was added mCPBA (340 mg, 1.9 mmol). The mixture was stirred at 15° C. for 2.5 hours. Water (30 mL) was added and the resulting mixture was extracted with EtOAc (120 mL×3). The combined organic phases were washed with saturated brine (40 mL×2), dried over anhydrous Na$_2$SO$_4$, filtered and concentrated under reduced pressure. The residue was purified by column chromatography on silica gel (PE:EA=5:1 to 2:1) to afford the title compound (120 mg, 72%) as a yellow solid. $^1$H NMR (CDCl$_3$, 400 MHz) δ 7.60 (s, 1H), 5.91 (s, 1H), 5.10 (s, 2H), 3.89 (d, J=6.8 Hz, 2H), 2.98 (s, 3H), 0.90-0.86 (m, 1H), 0.75-0.70 (m, 2H), 0.45-0.42 (m, 2H). LCMS: 335.9 (M+1)$^+$; 337

Step 5: 4-(cyclopropylmethoxy)-5-(1-methyl-6-oxopyridin-3-yl)-1-(methylsulfonylmethyl)pyridin-2-one

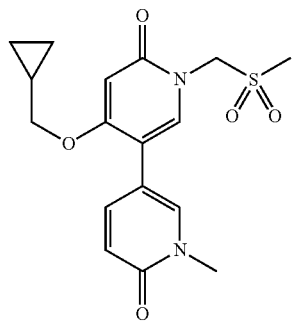 [SMILES: Cn1cc(-c2cn(CS(C)(=O)=O)c(=O)cc2OCC2CC2)ccc1=O]

The title compound from step 4 (50 mg, 0.15 mmol), 1-methyl-5-(4,4,5,5-tetramethyl-1,3,2-dioxaborolan-2-yl)pyridin-2-one (42 mg, 0.18 mmol), Pd(dppf)Cl$_2$ (11 mg, 14.9 umol) and K$_3$PO$_4$ (63 mg, 0.3 mmol) in dioxane (5 mL) and water (5 drops) were degassed and then heated to 70° C. under N$_2$ overnight. The reaction mixture was then concentrated under reduced pressure. The residue was purified by column chromatography (PE:DCM:EA=3:0:1 to 0:1:4) followed by preparative HPLC to afford the title compound (17.09 mg, 31.5%) as an off-white solid. $^1$H NMR (CDCl$_3$, 400 MHz) δ 7.50 (dd, J$_1$=9.2 Hz, J$_2$=2.4 Hz, 1H), 7.43 (d, J=2.4 Hz, 1H), 6.71 (d, J=9.2 Hz, 1H), 5.96 (s, 1H), 5.16 (s, 2H), 3.86 (d, J=6.8 Hz, 1H), 3.63 (s, 3H), 2.99 (s, 3H), 1.26-1.21 (m, 1H), 0.70-0.66 (m, 2H), 0.36-0.32 (m, 2H). LCMS: 365.0 (M+1)$^+$

Example 382

5-[4-(cyclopropylmethoxy)-1-(methylsulfonylmethyl)-6-oxopyridin-3-yl]-1,3-dimethylpyridin-2-one

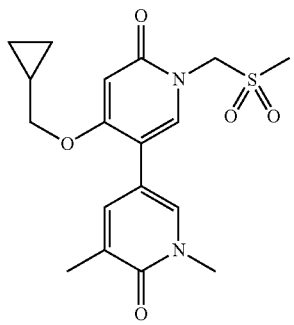 [SMILES: Cc1cc(-c2cn(CS(C)(=O)=O)c(=O)cc2OCC2CC2)cn(C)c1=O]

The title compound was prepared in a manner similar to Example 381, by substituting 1,3-dimethyl-5-(4,4,5,5-tetramethyl-1,3,2-dioxaborolan-2-yl)pyridin-2-one for 1-methyl-5-(4,4,5,5-tetramethyl-1,3,2-dioxaborolan-2-yl)pyridin-2-one in step 5. $^1$H NMR (CDCl$_3$, 400 MHz) δ 7.35 (s, 1H), 7.32 (s, 2H), 5.97 (s, 1H), 5.16 (s, 2H), 3.87 (s, J=7.2 Hz, 2H), 3.62 (s, 3H), 2.99 (s, 3H), 2.20 (s, 3H), 1.25-0.24 (m, 1H), 0.70-0.65 (m, 2H), 0.36-0.35 (m, 2H). LCMS: 379.0 (M+1)$^+$

Example 383

4-[4-(cyclopropylmethoxy)-1-(methylsulfonylmethyl)-6-oxopyridin-3-yl]-7-fluoro-2-methylisoquinolin-1-one

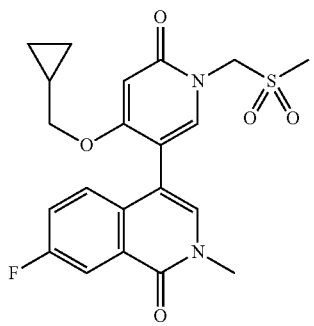 [SMILES: Cn1cc(-c2cn(CS(C)(=O)=O)c(=O)cc2OCC2CC2)c2ccc(F)cc2c1=O]

The title compound was prepared in a manner similar to Example 381, by substituting 7-fluoro-2-methyl-4-(4,4,5,5-tetramethyl-1,3,2-dioxaborolan-2-yl)isoquinolin-1-one for 1-methyl-5-(4,4,5,5-tetramethyl-1,3,2-dioxaborolan-2-yl)pyridin-2-one in step 5. $^1$H NMR (CDCl$_3$, 400 MHz) δ 8.13 (dd, J$_1$=9.2 Hz, J$_2$=2.4 Hz, 1H), 7.37 (s, 1H), 7.35-7.32 (m, 1H), 7.30-7.28 (m, 1H), 7.03 (s, 1H), 5.99 (s, 3H), 5.13 (d, J=13.6 Hz, 1H), 4.91 (d, J=13.6 Hz, 1H), 3.78 (t, J=6.4 Hz, 2H), 3.65 (s, 3H), 3.04 (s, 3H), 1.03-0.97 (m, 1H), 0.48-0.42 (m, 2H), 0.11 (s, 2H). LCMS: 433.1 (M+1)$^+$

Example 384

4-[4-(cyclopropylmethoxy)-1-(methylsulfonylmethyl)-6-oxopyridin-3-yl]-2-methylisoquinolin-1-one

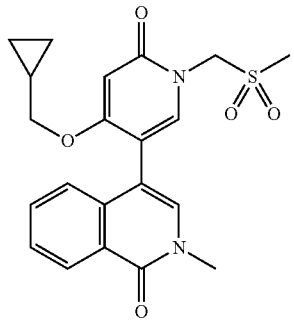 [SMILES: Cn1cc(-c2cn(CS(C)(=O)=O)c(=O)cc2OCC2CC2)c2ccccc2c1=O]

The title compound was prepared in a manner similar to Example 381, by substituting 2-methyl-4-(4,4,5,5-tetramethyl-1,3,2-dioxaborolan-2-yl)isoquinolin-1-one for 1-methyl-5-(4,4,5,5-tetramethyl-1,3,2-dioxaborolan-2-yl)pyridin-2-one in step 5. $^1$H NMR (CDCl$_3$, 400 MHz) δ 8.49 (d, J=8.0 Hz, 1H), 7.61 (t, J=7.2 Hz, 1H), 7.52 (t, J=7.2 Hz, 1H), 7.38 (s, 1H), 7.27 (d, J=8.0 Hz, 1H), 7.07 (s, 1H), 5.99 (s, 1H), 5.45 (d, J=14.4 Hz, 1H), 4.89 (d, J=14.4 Hz, 1H), 3.79 (t, J=8.0 Hz, 2H), 3.65 (s, 3H), 3.04 (s, 3H), 1.02-0.96 (m, 1H), 0.46-0.39 (m, 2H), 0.10 (s, 2H). LCMS: 415.1 (M+1)$^+$

Example 385

5-[4-(2,4-difluorophenoxy)-1-(methylsulfonylmethyl)-6-oxopyridin-3-yl]-1,3-dimethylpyridin-2-one Step 1: 5-bromo-4-(2,4-difluorophenoxy)-1-(methylsulfonylmethyl)pyridin-2-one

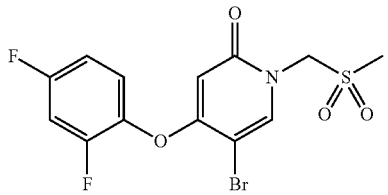 [SMILES: CS(=O)(=O)Cn1cc(Br)c(Oc2ccc(F)cc2F)cc1=O]

The title compound was prepared in a manner similar to Example 381 Steps 1 through 4, by substituting 2,4-difluorophenol for cyclopropylmethanol in step 1. $^1$H NMR (CDCl$_3$, 400 MHz) δ 7.71 (s, 1H), 7.21 (m, 1H), 7.01 (m, 2H), 5.66 (s, 1H), 5.1 (s, 2H), 2.96 (s, 3H).

Step 2: 5-[4-(2,4-difluorophenoxy)-1-(methylsulfonylmethyl)-6-oxopyridin-3-yl]-1,3-dimethylpyridin-2-one

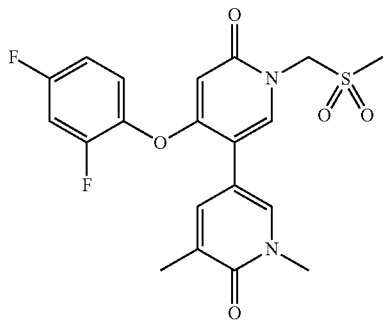

The title compound was prepared in a manner similar to Example 382, by substituting the title compound from Step 1 for 5-bromo-4-(cyclopropylmethoxy)-1-(methylsulfonylmethyl)pyridin-2-one. $^1$H NMR (CDCl$_3$, 400 MHz) δ 7.40 (s, 1H), 7.37 (s, 1H), 7.33 (s, 1H), 7.21-7.11 (m, 1H), 7.07-6.93 (m, 2H), 5.68 (s, 1H), 5.16 (s, 2H), 3.61 (s, 3H), 2.99 (s, 3H), 2.20 (s, 3H). LCMS: 437.0 (M+1)$^+$ Example 386

4-(2,4-difluorophenoxy)-5-(1-methyl-6-oxopyridin-3-yl)-1-(methylsulfonylmethyl)pyridin-2-one

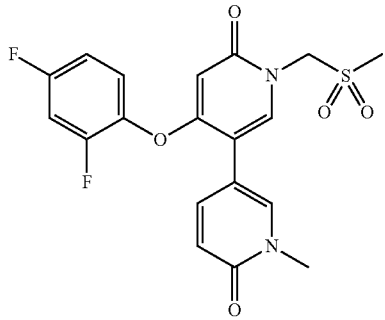 [SMILES: Cn1cc(-c2cn(CS(C)(=O)=O)c(=O)cc2Oc2ccc(F)cc2F)ccc1=O]

The title compound was prepared in a manner similar to Example 381, by substituting 5-bromo-4-(2,4-difluorophenoxy)-1-(methylsulfonylmethyl)pyridin-2-one for 5-bromo-4-(cyclopropylmethoxy)-1-(methylsulfonylmethyl)pyridin-2-one in step 5. $^1$H NMR (CDCl$_3$, 400 MHz) δ 7.53 (dd, J$_1$=2.4 Hz, J$_2$=9.6 Hz, 1H), 7.46 (d, J=2.4 Hz, 1H), 7.44 (s, 1H), 7.19-7.13 (m, 1H), 7.07-7.00 (m, 1H), 7.00-6.93 (m, 1H), 6.64 (d, J=9.2 Hz, 1H), 5.68 (s, 1H), 5.17 (s, 2H), 3.61 (s, 3H), 2.98 (s, 3H). LCMS: 423.0 (M+1)$^+$ Example 387

4-[4-(2,4-difluorophenoxy)-1-(methylsulfonylmethyl)-6-oxopyridin-3-yl]-2-methylisoquinolin-1-one

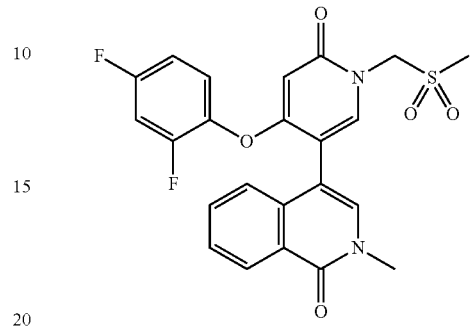

The title compound was prepared in a manner similar to Example 384, by substituting 5-bromo-4-(2,4-difluorophenoxy)-1-(methylsulfonylmethyl)pyridin-2-one for 5-bromo-4-(cyclopropylmethoxy)-1-(methylsulfonylmethyl)pyridin-2-one. $^1$H NMR (CDCl$_3$, 400 MHz) δ 8.50 (d, J=8.0 Hz, 1H), 7.72-7.67 (m, 1H), 7.57-7.52 (m, 1H), 7.49 (d, J=9.2 Hz, 2H), 7.20 (s, 1H), 7.08-7.02 (m, 1H), 7.01-6.94 (m, 1H), 6.93-6.86 (m, 1H), 5.74 (s, 1H), 5.46 (d, J=14.4 Hz, 1H), 4.92 (d, J=14.4 Hz, 1H), 3.68 (s, 3H), 3.05 (s, 3H). LCMS: 473.0 (M+1)$^+$ Example 388

5-(2-but-2-ynoxy-5-methylsulfonylphenyl)-1,3-dimethylpyridin-2-one

Step 1: 5-(2-fluoro-5-methylsulfonylphenyl)-1,3-dimethylpyridin-2-one

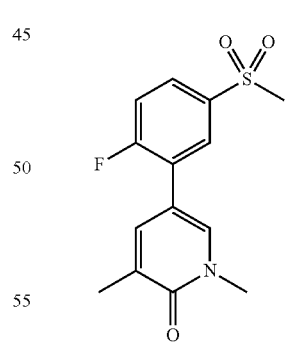

A mixture of 1,3-dimethyl-5-(4,4,5,5-tetramethyl-1,3,2-dioxaborolan-2-yl)pyridin-2-one (2.50 g, 10.0 mmol), 2-bromo-1-fluoro-4-methylsulfonylbenzene (2.54 g, 10.0 mmol), CsF (3.8 g, 25.0 mmol), Pd(dppf)Cl$_2$ (0.73 g, 1.0 mmol) in DME (50 mL) and MeOH (25 ml) was stirred at 80° C. for 18 hrs under N$_2$. The mixture was concentrated and the residue was purified by column chromatography on silica gel (PE:EA=2:1-0:1) to give the title compound (1.8 g, 61%) as a red solid. LCMS: 295.9 (M+H)$^+$ Step 2: 5-(2-but-2-ynoxy-5-methylsulfonylphenyl)-1,3-dimethylpyridin-2-one

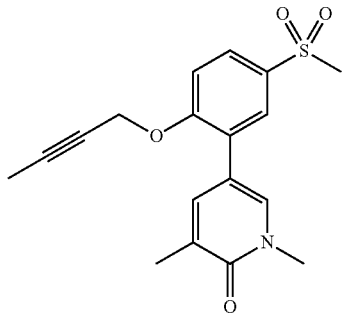 [SMILES: CC#CCOc1ccc(S(C)(=O)=O)cc1-c1cc(C)c(=O)n(C)c1]

To a solution of but-2-yn-1-ol (191 mg, 2.72 mmol) in anhydrous DMF (3 mL) was added NaH (109 mg, 2.72 mmol, 60% in mineral oil) at 0° C. The mixture was stirred at this temperature for 1 hr. The title compound from Step 1 (200 mg, 0.68 mmol) was added and the reaction mixture was stirred at 0° C. for 2 hrs. After this time, it was quenched with sat. $NH_4Cl$ solution (20 mL) and extracted with EtOAc (20 mL×3). The combined organic layers were washed with brine (40 mL), dried over $Na_2SO_4$, filtered and concentrated to give a crude product that was purified by prep-HPLC to give the title compound (56.01 mg, 23.9%) as a light yellow solid. $^1$H NMR ($CDCl_3$, 400 MHz) δ 7.88 (dd, $J_1$=8.8 Hz, $J_2$=2.0 Hz, 1H), 7.81 (d, J=2.0 Hz, 1H), 7.46 (s, 2H), 7.24 (d, J=8.8 Hz, 1H), 4.79 (d, J=2.0 Hz, 2H), 3.62 (s, 3H), 3.08 (s, 3H), 2.22 (s, 3H), 1.87 (s, 3H). LCMS: 346.0 $(M+H)^+$ Example 389

5-(2-but-2-ynoxy-5-ethylsulfonylphenyl)-3-methoxy-1-methylpyridin-2-one

Step 1: 5-(5-ethylsulfonyl-2-fluorophenyl)-3-methoxy-1-methylpyridin-2-one

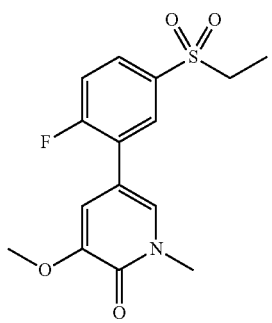 [SMILES: CCS(=O)(=O)c1ccc(F)c(-c2cc(OC)c(=O)n(C)c2)c1]

To a solution of 5-bromo-3-methoxy-1-methylpyridin-2-one (694 mg, 3.18 mmol), 2-(5-ethylsulfonyl-2-fluorophenyl)-4,4,5,5-tetramethyl-1,3,2-dioxaborolane (1 g, 3.18 mmol), Pd(dppf)Cl$_2$ (233 mg, 318.00 umol) in dioxane (26 mL) and H$_2$O (2.6 mL) was added K$_3$PO$_4$ (2.02 g, 9.54 mmol, 3.00 Eq). The reaction was stirred at 70° C. under N$_2$ for 6 hrs. The mixture was concentrated and the residue was purified by silica gel column chromatography (PE/EA=3/1 to 1/2) to afford the title compound (0.9 g, 87%) as a brown solid. $^1$H NMR ($CDCl_3$, 400 MHz) δ 7.93 (dd, J1=7.2 Hz, $J_2$=2.0 Hz, 1H), 7.88-7.84 (m, 1H), 7.35 (dd, J1=10.0 Hz, $J_2$=8.8 Hz, 1H), 7.23 (d, J=1.6 Hz, 1H), 6.83 (s, 1H), 3.89 (s, 3H), 3.67 (s, 3H), 3.16 (q, J=7.6 Hz, 2H), 1.33 (t, J=7.6 Hz, 3H). LCMS: 325.9 $(M+H)^+$ Step 2: 5-(2-but-2-ynoxy-5-ethylsulfonylphenyl)-3-methoxy-1-methylpyridin-2-one

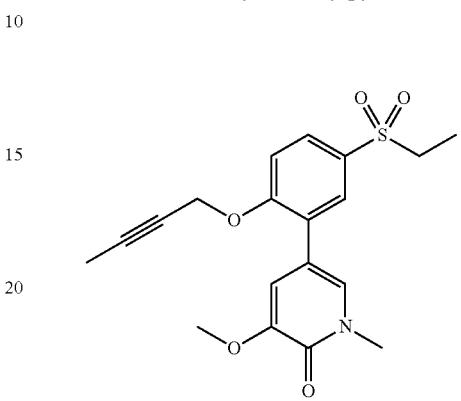

The title compound was prepared in a manner similar to Example 388 Step 2, by substituting 5-(5-ethylsulfonyl-2-fluorophenyl)-3-methoxy-1-methylpyridin-2-one for 5-(2-fluoro-5-methylsulfonylphenyl)-1,3-dimethylpyridin-2-one. $^1$H NMR ($CDCl_3$, 400 MHz) δ 7.88 (d, J=8.8 Hz, 1H), 7.80 (s, 1H), 7.23 (d, J=8.4 Hz, 1H), 7.19 (s, 1H), 6.97 (s, 1H), 4.78 (s, 2H), 3.83 (s, 3H), 3.70 (s, 3H), 3.15 (q, J=7.2 Hz, 2H), 1.87 (s, 3H), 1.32 (t, J=7.2 Hz, 3H). LCMS: 376.0 $(M+H)^+$ Example 390

5-(5-ethylsulfonyl-2-pent-2-ynoxyphenyl)-3-methoxy-1-methylpyridin-2-one

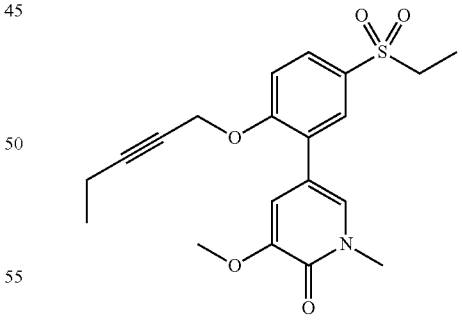

The title compound was prepared in a manner similar to Example 389, by substituting pent-2-yn-1-ol for but-2-yn-1-ol in Step 2. $^1$H NMR ($CDCl_3$, 400 MHz) δ 7.86 (dd, $J_1$=8.8 Hz, $J_2$=2.0 Hz, 1H), 7.79 (d, J=2.4 Hz, 1H), 7.23 (d, J=8.8 Hz, 1H), 7.18 (d, J=2.0 Hz, 1H), 6.94 (d, J=1.6 Hz, 1H), 4.80 (s, 2H), 3.87 (s, 3H), 3.67 (s, 3H), 3.15 (q, J=7.6 Hz, 2H), 2.24 (q, J=7.6 Hz, 2H), 1.32 (t, J=7.6 Hz, 3H), 1.14 (t, J=7.6 Hz, 3H). LCMS: 390.2 $(M+H)^+$

Example 391

5-[2-(3-cyclopropylprop-2-ynoxy)-5-ethylsulfonyl-phenyl]-3-methoxy-1-methylpyridin-2-one

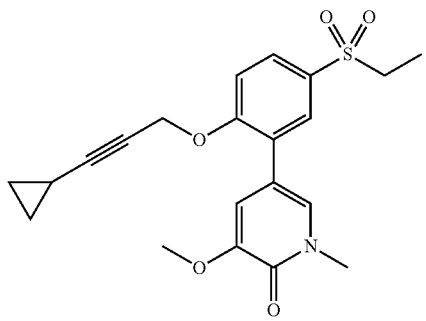 [SMILES: CCS(=O)(=O)c1ccc(OCC#CC2CC2)c(-c2cc(OC)c(=O)n(C)c2)c1]

The title compound was prepared in a manner similar to Example 389, by substituting 3-cyclopropylprop-2-yn-1-ol for but-2-yn-1-ol in Step 2. $^1$H NMR (CDCl$_3$, 400 MHz) δ 7.87 (d, J=8.8 Hz, 1H), 7.79 (s, 1H), 7.22-7.20 (m, 2H), 7.00 (s, 1H), 4.77 (s, 2H), 3.88 (s, 3H), 3.70 (s, 3H), 3.15 (q, J=7.2 Hz, 2H), 1.32 (t, J=7.2 Hz, 3H), 1.31-1.29 (m, 1H), 0.84-0.81 (m, 2H), 0.69-0.67 (m, 2H). LCMS: 402.0 (M+H)$^+$

Example 392

N-[4-(2,4-difluorophenoxy)-3-[1-methyl-6-oxo-5-(trifluoromethyl)pyridin-3-yl]phenyl]ethanesulfonamide

Step 1: 5-bromo-1-methyl-3-(trifluoromethyl)pyridin-2-one

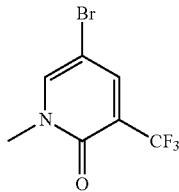

To a solution of 5-bromo-3-(trifluoromethyl)pyridin-2-ol (6 g, 25 mmol) stirred at rt in THF (5 mL) was added NaH (1.5 g, 37 mmol, 60% in mineral oil). After stirring for 30 min, methyl iodide (7.1 g, 50 mmol) was added. After stirring at rt for 3 h, the reaction mixture was treated with water (100 mL) and extracted with EtOAc (100 mL×3). The combined organic layers were washed with brine (100 mL), dried over Na$_2$SO$_4$, filtered, and concentrated in vacuo to afford the title compound (6 g, 97%) as a tan solid. The solid was carried forward without any further purification. $^1$H NMR (CDCl3, 400 MHz) δ 7.79 (d, J=2.0 Hz, 1H), 7.65 (d, J=2.0 Hz, 1H), 3.60 (s, 3H). LCMS (M+H)$^+$=256.

Step 2: 1-methyl-5-(3,3,4,4-tetramethylborolan-1-yl)-3-(trifluoromethyl)pyridin-2-one

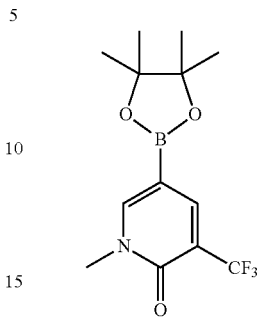

A suspension of compound 5-bromo-1-methyl-3-(trifluoromethyl)pyridin-2-one (3 g, 11.8 mmol), 4,4,5,5-tetramethyl-2-(tetramethyl-1,3,2-dioxaborolan-2-yl)-1,3,2-dioxaborolane (3.6 g, 14.1 mmol), KOAc (3 g, 30.6 mmol), and Pd(dppf)$_2$Cl$_2$ (200 mg) in dioxane (50 mL) was stirred at 90° C. for 4 h. After the reaction mixture was concentrated in vacuo, the resulting residue was purified by silica gel column chromatography (PE:EA=3:1~1:1) to give the title compound (1.2 g, 34%) as a red solid. $^1$H NMR (CDCl3, 400 MHz) δ 8.02 (d, J=2.0 Hz, 1H), 7.94 (d, J=2.0 Hz, 1H), 3.60 (s, 3H), 1.32 (s, 12H). LCMS (M+H)$^+$=304.

Step 3: 5-[2-(2,4-difluorophenoxy)-5-ethylsulfonyl-phenyl]-1-methyl-3-(trifluoromethyl)pyridin-2-one

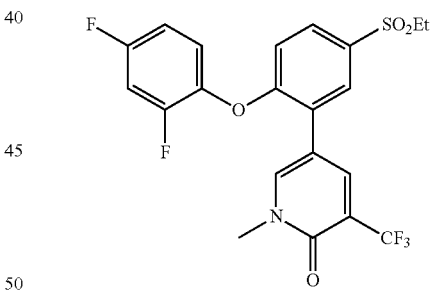

A mixture of 1-methyl-5-(3,3,4,4-tetramethylborolan-1-yl)-3-(trifluoromethyl)pyridin-2-one (100 mg, 0.33 mmol), 1-(2-bromo-4-ethylsulfonylphenoxy)-2,4-difluorobenzene (100 mg, 0.27 mmol), Pd(dppf)Cl$_2$ (24 mg) and K$_3$PO$_4$ (107 mg, 0.80 mmol) in dioxane (4 mL) and water (1 mL) was purged with nitrogen, capped, and heated to 90° C. for 4 h. After the mixture was filtered through a short bed of celite, the filtrate was concentrated in vacuo and purified by prep-HPLC afford the title compound (43 mg, 34%) as a white solid. 1H NMR (CDCl3, 400 MHz) □ppm 8.11 (s, 1H) 7.88 (s, 2H) 7.80 (m, 1H), 7.23-7.10 (m, 1H) 7.09-6.91 (m, 2H) 6.91-6.78 (m, 1H) 6.25 (s, 1H) 3.70 (s, 3H) 3.15 (q, J=7.2 Hz, 2H) 1.31 (t, J=7.2 Hz, 3H). LCMS (M+H)$^+$=474.

Example 393

4-[2-(cyclopropylmethoxy)-5-propan-2-ylsulfonyl-phenyl]-6-methoxy-2-methylisoquinolin-1-one

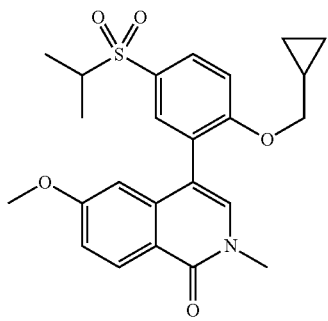 [SMILES: COc1ccc2c(=O)n(C)cc(-c3cc(S(=O)(=O)C(C)C)ccc3OCC3CC3)c2c1]

Bromo-6-methoxy-2-methylisoquinolin-1-one (previously prepared in WO 2013/142390) was reacted with 4,4,5,5-tetramethyl-2-(tetramethyl-1,3,2-dioxaborolan-2-yl)-1,3,2-dioxaborolane in a manner similar to Example 248, step 2 to give 6-methoxy-2-methyl-4-(4,4,5,5-tetramethyl-1,3,2-dioxaborolan-2-yl)isoquinolin-1-one which was then reacted with the title compound of Example 364, step 1 in a manner similar to Example 364, step 2 to give the title compound. 1H NMR (CDCl3, 400 MHz) δ 8.45 (d, J=8.4 Hz, 1H), 7.91 (dd, J1=2.0 Hz, J2=8.8, 1H), 7.06-7.27 (m, 3H), 6.53 (d, J=2.8 Hz, 1H), 3.89 (m, 2H), 3.78 (s, 3H), 3.65 (s, 3H), 3.22 (m, 1H), 1.33 (d, J=6.4 Hz, 6H), 1.03 (q, J=6.8 Hz, 1H), 0.45 (m, 2H), 0.14 (s, 2H). LCMS: 442.0 (M+H+)

Example 394

5-[2-(cyclopropylmethoxy)-5-propan-2-ylsulfonyl-phenyl]-1,3-dimethylpyridin-2-one

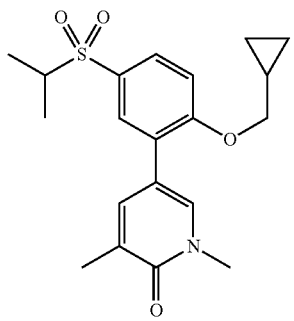 [SMILES: Cc1cc(-c2cc(S(=O)(=O)C(C)C)ccc2OCC2CC2)cn(C)c1=O]

The title compound of Example 364, step 1 was reacted with 1,3-dimethyl-5-(4,4,5,5-tetramethyl-1,3,2-dioxaborolan-2-yl)pyridin-2-one in a manner similar to Example 364, step 2 to give the title compound. 1H NMR (CDCl3, 400 MHz) δ 7.75-7.79 (m, 2H), 7.59 (s, 1H), 7.03 (d, J=8.4 Hz, 1H), 3.96 (d, J=6.8 Hz, 2H), 3.67 (s, 3H), 3.15-3.25 (m, 1H), 2.24 (s, 3H), 1.31 (d, J=7.2 Hz, 6H), 1.27 (d, J=7.2 Hz, 1H), 0.66-0.70 (m, 2H), 0.38 (q, J=5.2 Hz, 2H). LCMS: 376.0 (M+H+)

Example 395

N-[3-(1,5-dimethyl-6-oxopyridin-3-yl)-5-phenyl-methoxyphenyl]ethanesulfonamide

Step 1: N-(3-bromo-5-phenylmethoxyphenyl)ethanesulfonamide

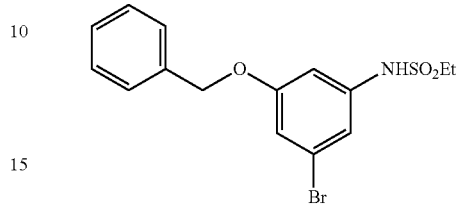

Ethylsulfonyl chloride (113 uL, 1.2 mmol) was added dropwise to a stirred solution of 3-bromo-5-phenyl-methoxyaniline (284 mg, 1.0 mmol) and pyridine (247 uL, 3.1 mmol) in DCM (5 mL) at 0° C. under nitrogen. After the mixture was allowed to warm to rt and stir for 14 h, it was treated with 1N HCl (1 mL) and extracted with DCM (3×5 mL); the combined organic extracts were washed with saturated bicarbonate solution (aq), dried over sodium sulfate, filtered and concentrated in vacuo. The crude solid was purified by silica gel column chromatography using a gradient of EtOAc (5 to 95%) in hexanes to afford the title compound (345 mg, 94%) as an amber oil that solidified upon standing. LCMS (M+H)+=371.

Step 2: N-[3-(1,5-dimethyl-6-oxopyridin-3-yl)-5-phenylmethoxyphenyl]ethanesulfonamide

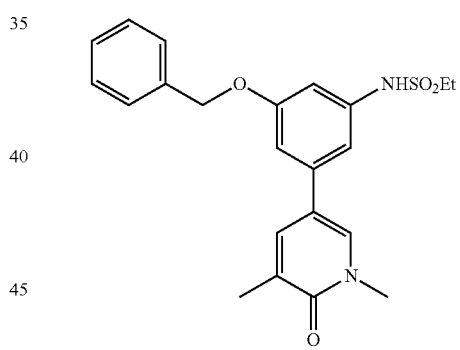

A mixture of N-(3-bromo-5-phenylmethoxyphenyl)ethanesulfonamide (60 mg, 0.16 mmol), 1,3-dimethyl-5-(4,4,5,5-tetramethyl-1,3,2-dioxaborolan-2-yl)pyridin-2-one (40 mg, 0.16 mmol), Pd(dppf)Cl2 (12 mg) and K3PO4 (88 mg, 0.40 mmol) in dioxane (1.5 mL) and water (150 uL) was purged with nitrogen, capped, and heated to 75° C. for 2 h. After the mixture was filtered through a short bed of celite, the filtrate was concentrated in vacuo and purified by silica gel column chromatography using a gradient of MeOH (0 to 10%) in DCM to afford the title compound (69 mg, 94%) as an off-white solid. 1H NMR (400 MHz, DMSO-d6) δ ppm 1.15-1.24 (m, 3H) 2.04-2.13 (m, 3H) 3.04-3.17 (m, 2H) 3.48-3.54 (m, 3H) 5.08-5.17 (m, 2H) 6.74-6.80 (m, 1H) 6.90-6.98 (m, 2H) 7.33-7.49 (m, 5H) 7.59-7.63 (m, 1H) 7.90-7.95 (m, 1H) 9.57-10.01 (b.s., 1H). LCMS (M+H)+=413.

Examples 396-482 in Table 21 were prepared using Suzuki conditions to append an appropriately substituted aryl group to an appropriately substituted pyridinone. Chemical manipulation subsequent to the Suzuki reaction was also carried out as needed to give the title compound.

TABLE 21

| Chemical Synthesis Example | Structure | Name | MS (M + H) |
|---|---|---|---|
| 396 | 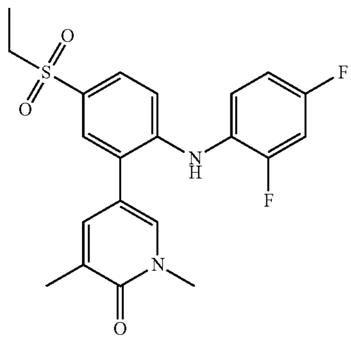 [SMILES: CCS(=O)(=O)c1ccc(Nc2ccc(F)cc2F)c(-c2cc(C)c(=O)n(C)c2)c1] | 5-[2-(2,4-difluoroanilino)-5-ethylsulfonylphenyl]-1,3-dimethylpyridin-2-one | 419.1 |
| 397 | 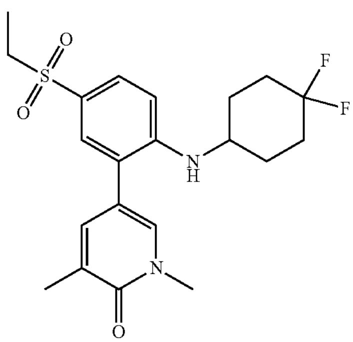 [SMILES: CCS(=O)(=O)c1ccc(NC2CCC(F)(F)CC2)c(-c2cc(C)c(=O)n(C)c2)c1] | 5-[2-[(4,4-difluorocyclohexyl)amino]-5-ethylsulfonylphenyl]-1,3-dimethylpyridin-2-one | 425.1 |
| 398 | 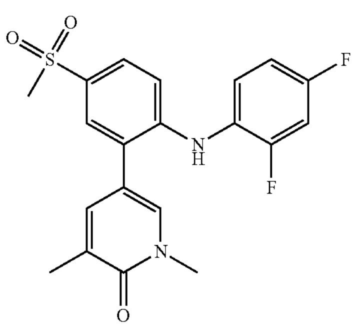 [SMILES: Cc1cc(-c2cc(S(C)(=O)=O)ccc2Nc2ccc(F)cc2F)cn(C)c1=O] | 5-[2-(2,4-difluoroanilino)-5-methylsulfonylphenyl]-1,3-dimethylpyridin-2-one | 405.1 |
| 399 | 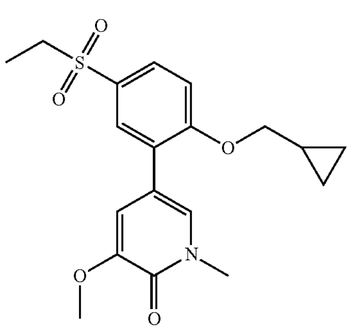 [SMILES: CCS(=O)(=O)c1ccc(OCC2CC2)c(-c2cc(OC)c(=O)n(C)c2)c1] | 5-[2-(cyclopropylmethoxy)-5-ethylsulfonylphenyl]-3-methoxy-1-methylpyridin-2-one | 378.1 |

TABLE 21-continued

| Chemical Synthesis Example | Structure | Name | MS (M + H) |
|---|---|---|---|
| 400 | 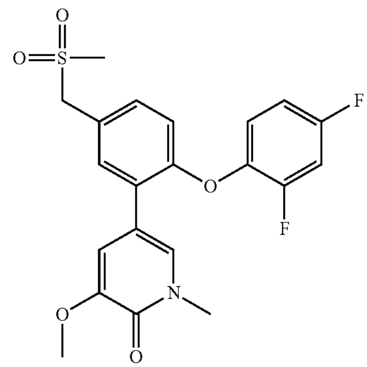 [SMILES: COc1cc(-c2cc(CS(C)(=O)=O)ccc2Oc2ccc(F)cc2F)cn(C)c1=O] | 5-[2-(2,4-difluorophenoxy)-5-(methylsulfonylmethyl)phenyl]-3-methoxy-1-methylpyridin-2-one | 436.0 |
| 401 | 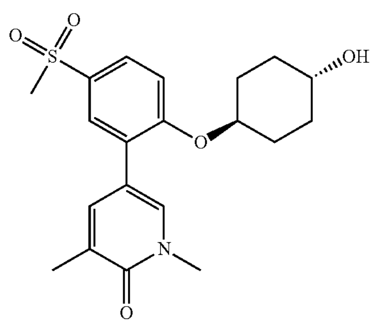 [SMILES: Cc1cc(-c2cc(S(C)(=O)=O)ccc2O[C@H]2CC[C@H](O)CC2)cn(C)c1=O] | 5-[2-(4-trans-hydroxycyclohexyl)oxy-5-methylsulfonylphenyl]-1,3-dimethylpyridin-2-one | 392.1 |
| 402 | 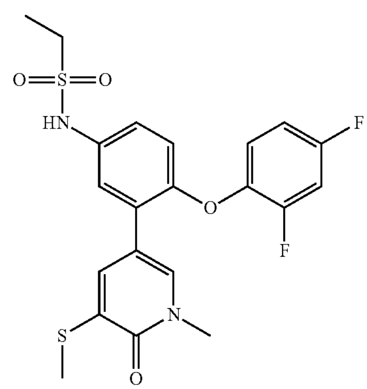 [SMILES: CCS(=O)(=O)Nc1ccc(Oc2ccc(F)cc2F)c(-c2cc(SC)c(=O)n(C)c2)c1] | N-[4-(2,4-difluorophenoxy)-3-(1-methyl-5-methylsulfanyl-6-oxopyridin-3-yl)phenyl]ethanesulfonamide | 467.10 |
| 403 | 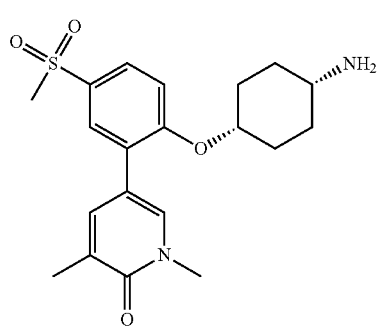 [SMILES: Cc1cc(-c2cc(S(C)(=O)=O)ccc2O[C@H]2CC[C@@H](N)CC2)cn(C)c1=O] | 5-[2-(4-cis-aminocyclohexyl)oxy-5-methylsulfonylphenyl]-1,3-dimethylpyridin-2-one | 391.2 |

TABLE 21-continued

| Chemical Synthesis Example | Structure | Name | MS (M + H) |
|---|---|---|---|
| 404 | 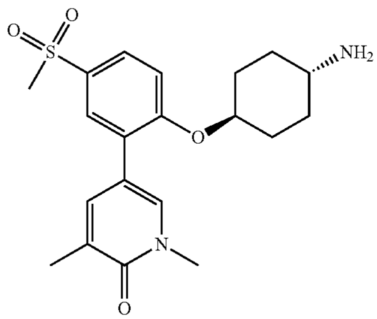 [SMILES: Cc1cc(-c2cc(S(C)(=O)=O)ccc2O[C@H]2CC[C@H](N)CC2)cn(C)c1=O] | 5-[2-(4-trans-aminocyclohexyl)oxy-5-methylsulfonylphenyl]-1,3-dimethylpyridin-2-one | 391.1 |
| 405 | 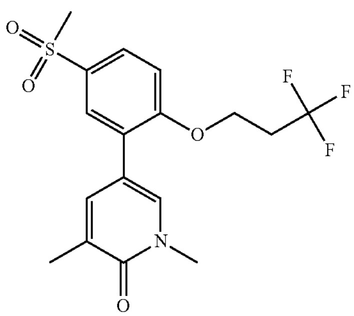 [SMILES: Cc1cc(-c2cc(S(C)(=O)=O)ccc2OCCC(F)(F)F)cn(C)c1=O] | 1,3-dimethyl-5-[5-methylsulfonyl-2-(3,3,3-trifluoropropoxy)phenyl]pyridin-2-one | 390.0 |
| 406 | 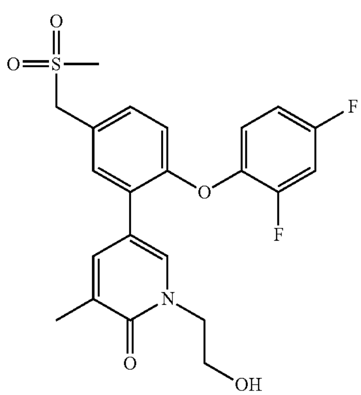 [SMILES: Cc1cc(-c2cc(CS(C)(=O)=O)ccc2Oc2ccc(F)cc2F)cn(CCO)c1=O] | 5-[2-(2,4-difluorophenoxy)-5-(methylsulfonylmethyl)phenyl]-1-(2-hydroxyethyl)-3-methylpyridin-2-one | 450.2 |
| 407 | 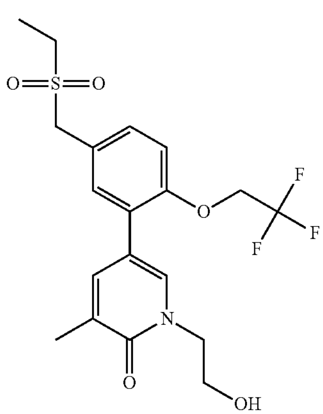 [SMILES: CCS(=O)(=O)Cc1ccc(OCC(F)(F)F)c(-c2cc(C)c(=O)n(CCO)c2)c1] | 5-[5-(ethylsulfonylmethyl)-2-(2,2,2-trifluoroethoxy)phenyl]-1-(2-hydroxyethyl)-3-methylpyridin-2-one | 434.1 |

TABLE 21-continued

| Chemical Synthesis Example | Structure | Name | MS (M + H) |
|---|---|---|---|
| 408 | 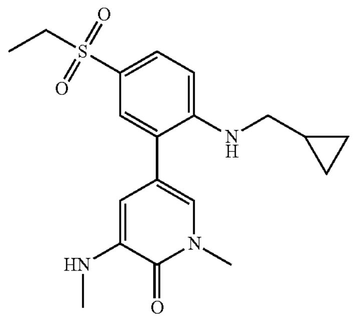 [SMILES: CCS(=O)(=O)c1ccc(NCC2CC2)c(-c2cc(NC)c(=O)n(C)c2)c1] | 5-[2-(cyclopropylmethylamino)-5-ethylsulfonylphenyl]-1-methyl-3-(methylamino)pyridin-2-one | 376.2 |
| 409 | 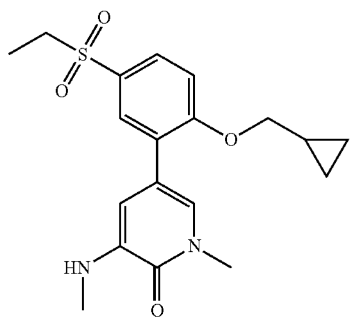 [SMILES: CCS(=O)(=O)c1ccc(OCC2CC2)c(-c2cc(NC)c(=O)n(C)c2)c1] | 5-[2-(cyclopropylmethoxy)-5-ethylsulfonylphenyl]-1-methyl-3-(methylamino)pyridin-2-one | 377.2 |
| 410 | 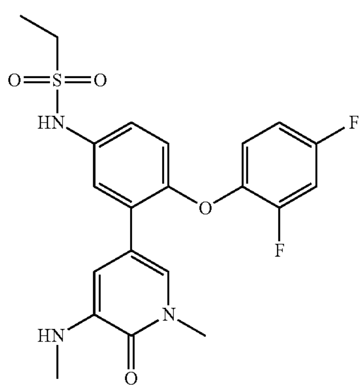 | N-[4-(2,4-difluorophenoxy)-3-[1-methyl-5-(methylamino)-6-oxopyridin-3-yl]phenyl]ethanesulfonamide | 450.1 |
| 411 | 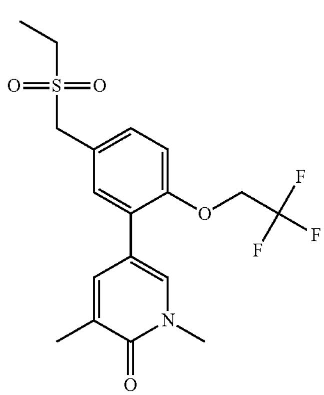 [SMILES: CCS(=O)(=O)Cc1ccc(OCC(F)(F)F)c(-c2cc(C)c(=O)n(C)c2)c1] | 5-[5-(ethylsulfonylmethyl)-2-(2,2,2-trifluoroethoxy)phenyl]-1,3-dimethylpyridin-2-one | 404.1 |

TABLE 21-continued

| Chemical Synthesis Example | Structure | Name | MS (M + H) |
|---|---|---|---|
| 412 | 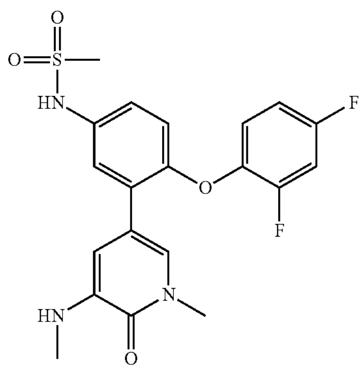 [SMILES: CNc1cc(-c2cc(NS(C)(=O)=O)ccc2Oc2ccc(F)cc2F)cn(C)c1=O] | N-[4-(2,4-difluorophenoxy)-3-[1-methyl-5-(methylamino)-6-oxopyridin-3-yl]phenyl]methanesulfonamide | 436.0 |
| 413 | 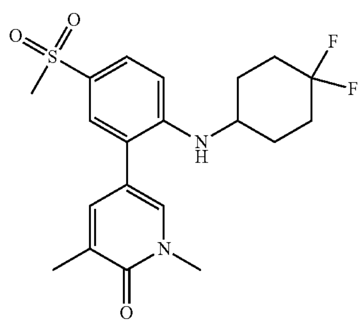 [SMILES: Cc1cc(-c2cc(S(C)(=O)=O)ccc2NC2CCC(F)(F)CC2)cn(C)c1=O] | 5-[2-[(4,4-difluorocyclohexyl)amino]-5-methylsulfonylphenyl]-1,3-dimethylpyridin-2-one | 411.0 |
| 414 | 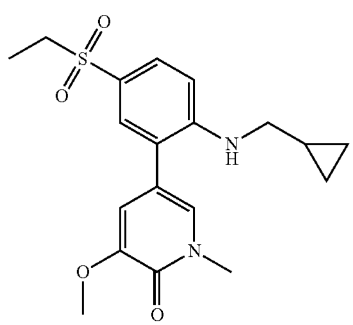 [SMILES: CCS(=O)(=O)c1ccc(NCC2CC2)c(-c2cc(OC)c(=O)n(C)c2)c1] | 5-[2-(cyclopropylmethylamino)-5-ethylsulfonylphenyl]-3-methoxy-1-methylpyridin-2-one | 377.1 |
| 415 | 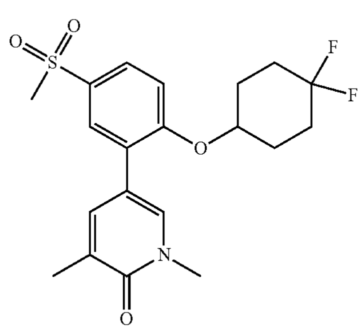 [SMILES: Cc1cc(-c2cc(S(C)(=O)=O)ccc2OC2CCC(F)(F)CC2)cn(C)c1=O] | 5-[2-(4,4-difluorocyclohexyl)oxy-5-methylsulfonylphenyl]-1,3-dimethylpyridin-2-one | 412.1 |

TABLE 21-continued

| Chemical Synthesis Example | Structure | Name | MS (M + H) |
|---|---|---|---|
| 416 | 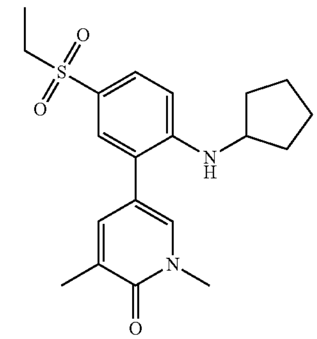 [SMILES: CCS(=O)(=O)c1ccc(NC2CCCC2)c(-c2cc(C)c(=O)n(C)c2)c1] | 5-[2-(cyclopentylamino)-5-ethylsulfonylphenyl]-1,3-dimethylpyridin-2-one | 375.2 |
| 417 | 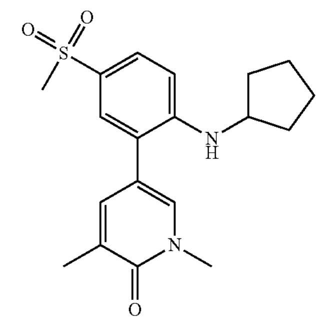 [SMILES: Cc1cc(-c2cc(S(C)(=O)=O)ccc2NC2CCCC2)cn(C)c1=O] | 5-[2-(cyclopentylamino)-5-methylsulfonylphenyl]-1,3-dimethylpyridin-2-one | 361.1 |
| 418 | 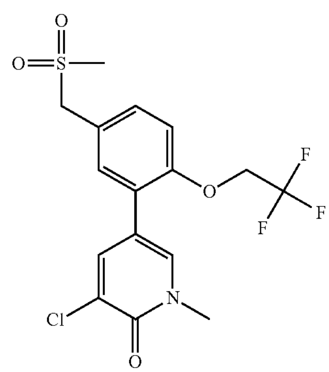 [SMILES: Cn1cc(-c2cc(CS(C)(=O)=O)ccc2OCC(F)(F)F)cc(Cl)c1=O] | 3-chloro-1-methyl-5-[5-(methylsulfonylmethyl)-2-(2,2,2-trifluoroethoxy)phenyl]pyridin-2-one | 410.0 |
| 419 | 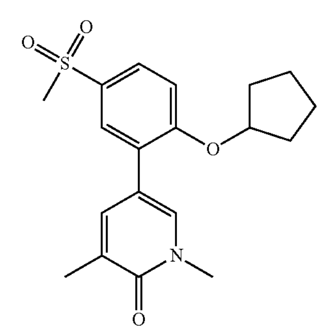 [SMILES: Cc1cc(-c2cc(S(C)(=O)=O)ccc2OC2CCCC2)cn(C)c1=O] | 5-(2-cyclopentyloxy-5-methylsulfonylphenyl)-1,3-dimethylpyridin-2-one | 362.1 |

TABLE 21-continued

| Chemical Synthesis Example | Structure | Name | MS (M + H) |
|---|---|---|---|
| 420 | 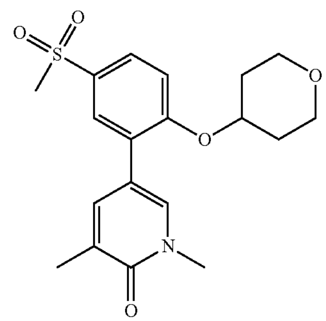 [SMILES: Cc1cc(-c2cc(S(C)(=O)=O)ccc2OC2CCOCC2)cn(C)c1=O] | 1,3-dimethyl-5-[5-methylsulfonyl-2-(oxan-4-yloxy)phenyl]pyridin-2-one | 378.1 |
| 421 | 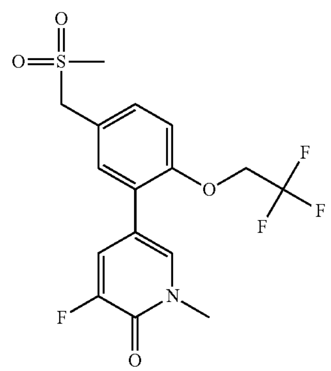 [SMILES: Cn1cc(-c2cc(CS(C)(=O)=O)ccc2OCC(F)(F)F)cc(F)c1=O] | 3-fluoro-1-methyl-5-[5-(methylsulfonylmethyl)-2-(2,2,2-trifluoroethoxy)phenyl]pyridin-2-one | 394.1 |
| 422 | 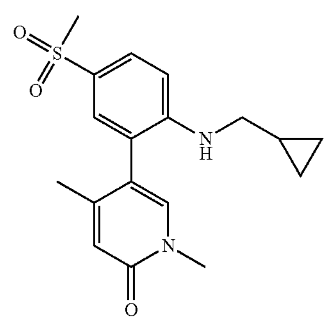 [SMILES: Cc1cc(=O)n(C)cc1-c1cc(S(C)(=O)=O)ccc1NCC1CC1] | 5-[2-(cyclopropylmethylamino)-5-methylsulfonylphenyl]-1,4-dimethylpyridin-2-one | 347.0 |
| 423 | 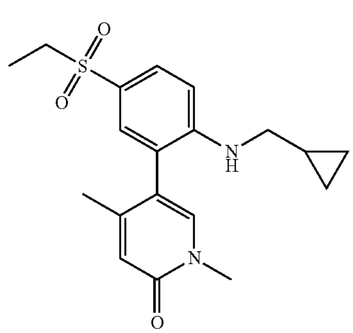 [SMILES: CCS(=O)(=O)c1ccc(NCC2CC2)c(-c2cn(C)c(=O)cc2C)c1] | 5-[2-(cyclopropylmethylamino)-5-ethylsulfonylphenyl]-1,4-dimethylpyridin-2-one | 361.1 |

TABLE 21-continued

| Chemical Synthesis Example | Structure | Name | MS (M + H) |
|---|---|---|---|
| 424 | 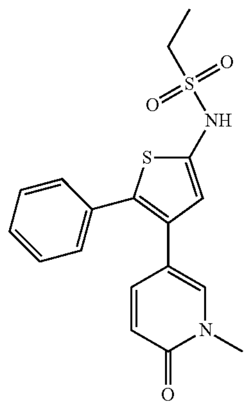 [SMILES: CCS(=O)(=O)Nc1cc(-c2ccc(=O)n(C)c2)c(-c2ccccc2)s1] | N-[4-(1-methyl-6-oxopyridin-3-yl)-5-phenylthiophen-2-yl]ethanesulfonamide | 375.0 |
| 425 | 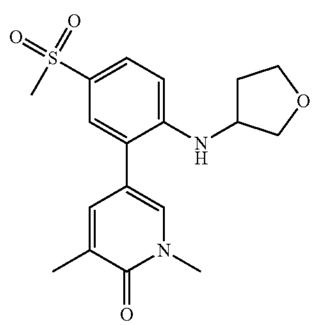 [SMILES: Cc1cc(-c2cc(S(C)(=O)=O)ccc2NC2CCOC2)cn(C)c1=O] | 1,3-dimethyl-5-[5-methylsulfonyl-2-(oxolan-3-ylamino)phenyl]pyridin-2-one | 363.1 |
| 426 | 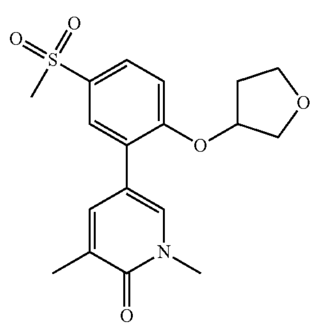 [SMILES: Cc1cc(-c2cc(S(C)(=O)=O)ccc2OC2CCOC2)cn(C)c1=O] | 1,3-dimethyl-5-[5-methylsulfonyl-2-(oxolan-3-yloxy)phenyl]pyridin-2-one | 364.0 |
| 427 | 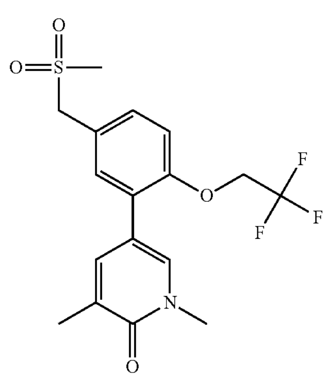 [SMILES: Cc1cc(-c2cc(CS(C)(=O)=O)ccc2OCC(F)(F)F)cn(C)c1=O] | 1,3-dimethyl-5-[5-(methylsulfonylmethyl)-2-(2,2,2-trifluoroethoxy)phenyl]pyridin-2-one | 390.0 |

TABLE 21-continued

| Chemical Synthesis Example | Structure | Name | MS (M + H) |
|---|---|---|---|
| 428 | 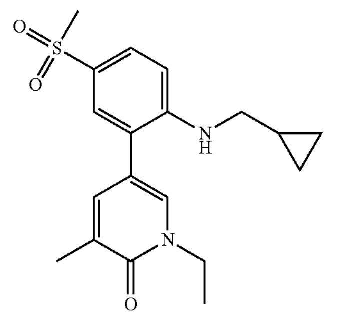 [SMILES: CCn1cc(-c2cc(S(C)(=O)=O)ccc2NCC2CC2)cc(C)c1=O] | 5-[2-(cyclopropylmethylamino)-5-methylsulfonylphenyl]-1-ethyl-3-methylpyridin-2-one | 361.1 |
| 429 | 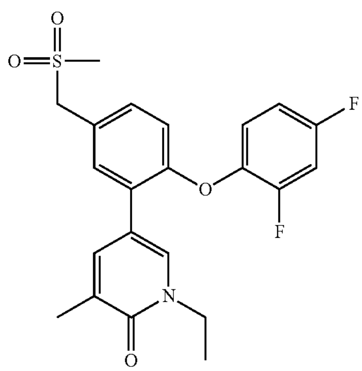 [SMILES: CCn1cc(-c2cc(CS(C)(=O)=O)ccc2Oc2ccc(F)cc2F)cc(C)c1=O] | 5-[2-(2,4-difluorophenoxy)-5-(methylsulfonylmethyl)phenyl]-1-ethyl-3-methylpyridin-2-one | 434.0 |
| 430 | 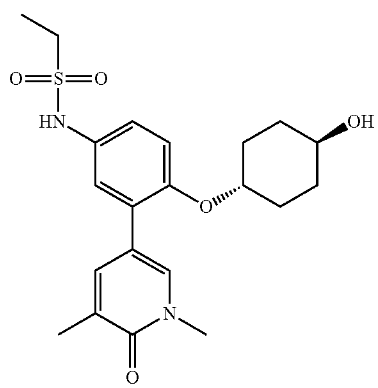 [SMILES: CCS(=O)(=O)Nc1ccc(O[C@H]2CC[C@H](O)CC2)c(-c2cc(C)c(=O)n(C)c2)c1] | N-[3-(1,5-dimethyl-6-oxopyridin-3-yl)-4-(4-trans-hydroxycyclohexyl)oxyphenyl]ethanesulfonamide | 421.1 |
| 431 | 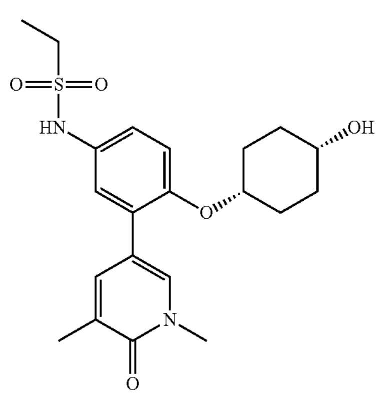 [SMILES: CCS(=O)(=O)Nc1ccc(O[C@H]2CC[C@@H](O)CC2)c(-c2cc(C)c(=O)n(C)c2)c1] | N-[3-(1,5-dimethyl-6-oxopyridin-3-yl)-4-(4-cis-hydroxycyclohexyl)oxyphenyl]ethanesulfonamide | 421.1 |

TABLE 21-continued

| Chemical Synthesis Example | Structure | Name | MS (M + H) |
|---|---|---|---|
| 432 | 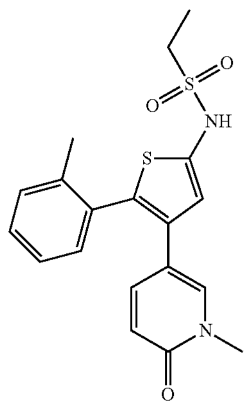 [SMILES: CCS(=O)(=O)Nc1cc(-c2ccc(=O)n(C)c2)c(-c2ccccc2C)s1] | N-[4-(1-methyl-6-oxopyridin-3-yl)-5-(2-methylphenyl)thiophen-2-yl]ethanesulfonamide | 389.1 |
| 433 | 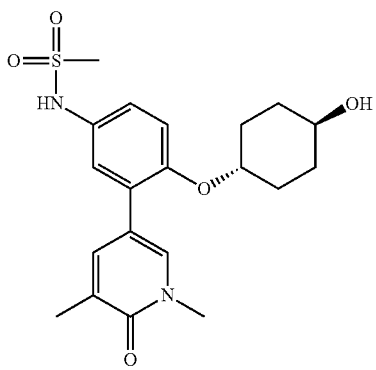 [SMILES: Cc1cc(-c2cc(NS(C)(=O)=O)ccc2O[C@H]2CC[C@H](O)CC2)cn(C)c1=O] | N-[3-(1,5-dimethyl-6-oxopyridin-3-yl)-4-(4-trans-hydroxycyclohexyl)oxyphenyl]methanesulfonamide | 407.1 |
| 434 | 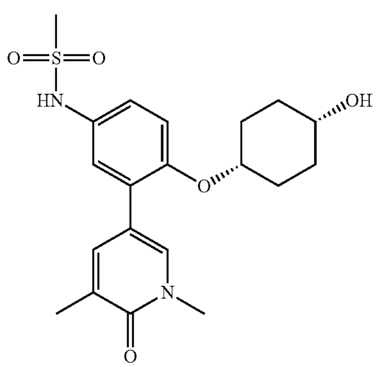 [SMILES: Cc1cc(-c2cc(NS(C)(=O)=O)ccc2O[C@H]2CC[C@@H](O)CC2)cn(C)c1=O] | N-[3-(1,5-dimethyl-6-oxopyridin-3-yl)-4-(4-cis-hydroxycyclohexyl)oxyphenyl]methanesulfonamide | 407.1 |
| 435 | 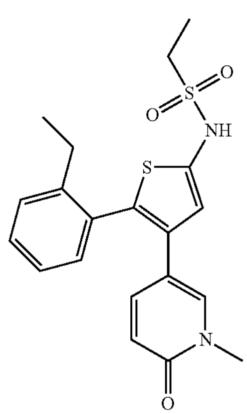 [SMILES: CCc1ccccc1-c1sc(NS(=O)(=O)CC)cc1-c1ccc(=O)n(C)c1] | N-[5-(2-ethylphenyl)-4-(1-methyl-6-oxopyridin-3-yl)thiophen-2-yl]ethanesulfonamide | 403.1 |

TABLE 21-continued

| Chemical Synthesis Example | Structure | Name | MS (M + H) |
|---|---|---|---|
| 436 | 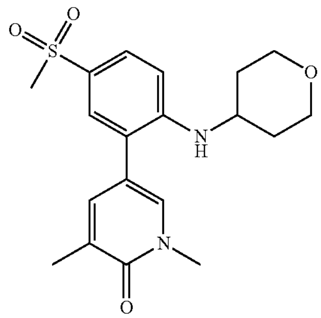 [SMILES: Cc1cc(-c2cc(S(C)(=O)=O)ccc2NC2CCOCC2)cn(C)c1=O] | 1,3-dimethyl-5-[5-methylsulfonyl-2-(oxan-4-yl)amino)phenyl]pyridin-2-one | 377.1 |
| 437 | 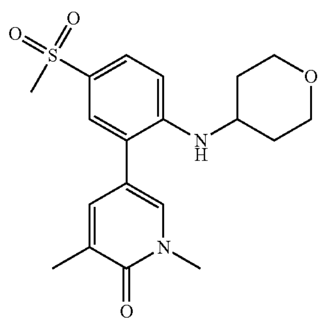 [SMILES: Cc1cc(-c2cc(S(C)(=O)=O)ccc2NC2CCOCC2)cn(C)c1=O] | 5-[2-(2,4-difluorophenoxy)-5-(methylsulfonylmethyl)phenyl]-3-fluoro-1-methylpyridin-2-one | 424.1 |
| 438 | 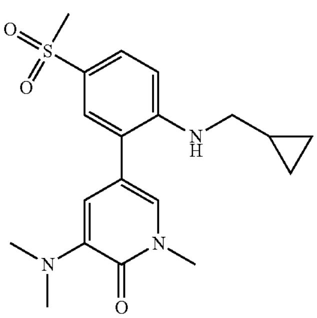 [SMILES: CN(C)c1cc(-c2cc(S(C)(=O)=O)ccc2NCC2CC2)cn(C)c1=O] | 5-[2-(cyclopropylmethylamino)-5-methylsulfonylphenyl]-3-(dimethylamino)-1-methylpyridin-2-one | 376.2 |
| 439 | 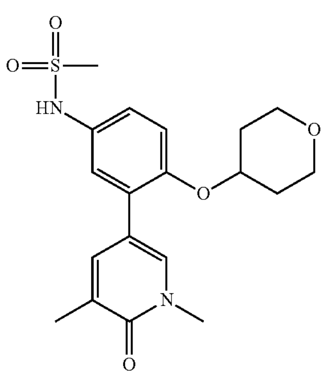 [SMILES: Cc1cc(-c2cc(NS(C)(=O)=O)ccc2OC2CCOCC2)cn(C)c1=O] | N-[3-(1,5-dimethyl-6-oxopyridin-3-yl)-4-(oxan-4-yloxy)phenyl]methanesulfonamide | 393.1 |

TABLE 21-continued

| Chemical Synthesis Example | Structure | Name | MS (M + H) |
|---|---|---|---|
| 440 | 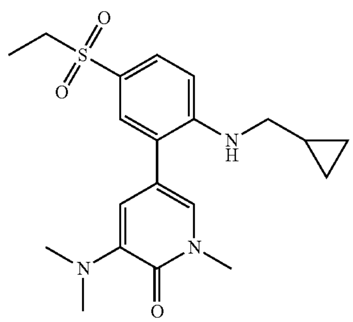 [SMILES: CCS(=O)(=O)c1ccc(NCC2CC2)c(-c2cc(N(C)C)c(=O)n(C)c2)c1] | 5-[2-(cyclopropylmethylamino)-5-ethylsulfonylphenyl]-3-(dimethylamino)-1-methylpyridin-2-one | 390.2 |
| 441 | 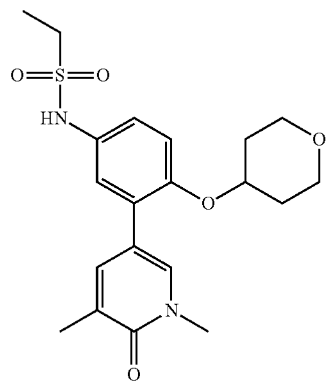 [SMILES: CCS(=O)(=O)Nc1ccc(OC2CCOCC2)c(-c2cc(C)c(=O)n(C)c2)c1] | N-[3-(1,5-dimethyl-6-oxopyridin-3-yl)-4-(oxan-4-yloxy)phenyl]ethanesulfonamide | 407.1 |
| 442 | 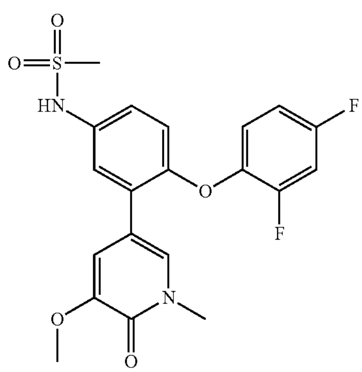 [SMILES: COc1cc(-c2cc(NS(C)(=O)=O)ccc2Oc2ccc(F)cc2F)cn(C)c1=O] | N-[4-(2,4-difluorophenoxy)-3-(5-methoxy-1-methyl-6-oxopyridin-3-yl)phenyl]methanesulfonamide | 437.1 |
| 443 | 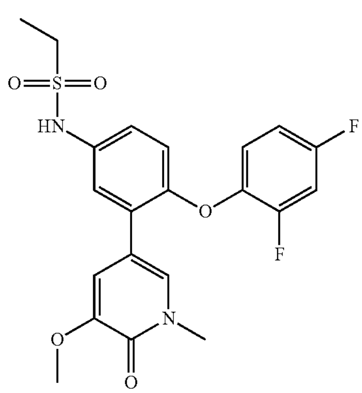 [SMILES: CCS(=O)(=O)Nc1ccc(Oc2ccc(F)cc2F)c(-c2cc(OC)c(=O)n(C)c2)c1] | N-[4-(2,4-difluorophenoxy)-3-(5-methoxy-1-methyl-6-oxopyridin-3-yl)phenyl]ethanesulfonamide | 451.1 |

TABLE 21-continued

| Chemical Synthesis Example | Structure | Name | MS (M + H) |
|---|---|---|---|
| 444 | 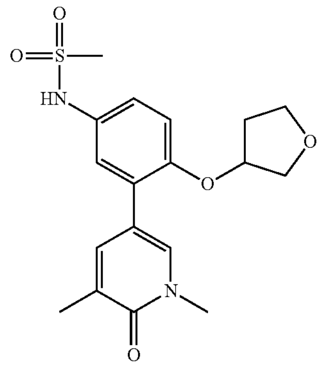 [SMILES: Cc1cc(-c2cc(NS(C)(=O)=O)ccc2OC2CCOC2)cn(C)c1=O] | N-[3-(1,5-dimethyl-6-oxopyridin-3-yl)-4-(oxolan-3-yloxy)phenyl]methanesulfonamide | 379.0 |
| 445 | 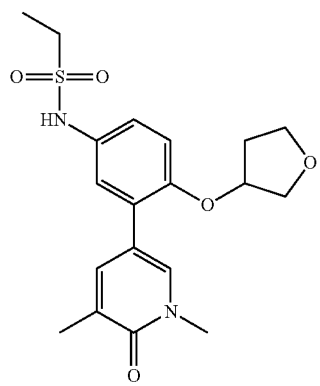 [SMILES: CCS(=O)(=O)Nc1ccc(OC2CCOC2)c(-c2cc(C)c(=O)n(C)c2)c1] | N-[3-(1,5-dimethyl-6-oxopyridin-3-yl)-4-(oxolan-3-yloxy)phenyl]ethanesulfonamide | 393.2 |
| 446 | 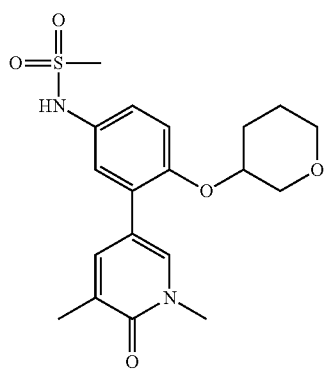 [SMILES: Cc1cc(-c2cc(NS(C)(=O)=O)ccc2OC2CCCOC2)cn(C)c1=O] | N-[3-(1,5-dimethyl-6-oxopyridin-3-yl)-4-(oxan-3-yloxy)phenyl]methanesulfonamide | 393.1 |
| 447 | 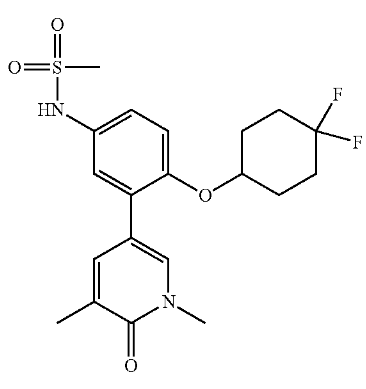 [SMILES: Cc1cc(-c2cc(NS(C)(=O)=O)ccc2OC2CCC(F)(F)CC2)cn(C)c1=O] | N-[4-(4,4-difluorocyclohexyl)oxy-3-(1,5-dimethyl-6-oxopyridin-3-yl)phenyl]methanesulfonamide | 427.1 |

TABLE 21-continued

| Chemical Synthesis Example | Structure | Name | MS (M + H) |
|---|---|---|---|
| 448 | 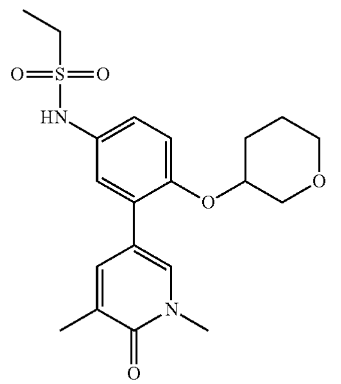 [SMILES: CCS(=O)(=O)Nc1ccc(OC2CCCOC2)c(-c2cc(C)c(=O)n(C)c2)c1] | N-[3-(1,5-dimethyl-6-oxopyridin-3-yl)-4-(oxan-3-yloxy)phenyl]ethanesulfonamide | 407.1 |
| 449 | 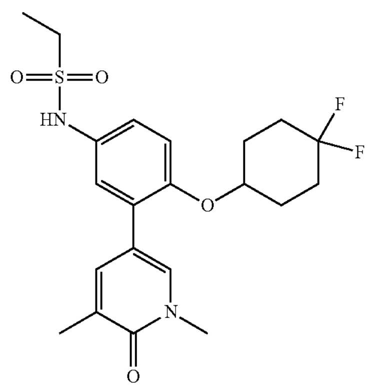 [SMILES: CCS(=O)(=O)Nc1ccc(OC2CCC(F)(F)CC2)c(-c2cc(C)c(=O)n(C)c2)c1] | N-[4-(4,4-difluorocyclohexyl)oxy-3-(1,5-dimethyl-6-oxopyridin-3-yl)phenyl]ethanesulfonamide | 441.1 |
| 450 | 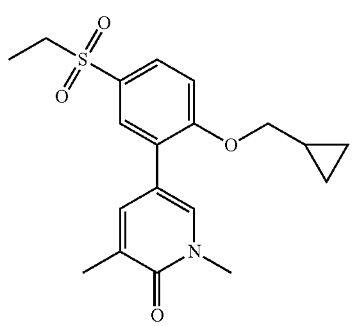 [SMILES: CCS(=O)(=O)c1ccc(OCC2CC2)c(-c2cc(C)c(=O)n(C)c2)c1] | 5-[2-(cyclopropylmethoxy)-5-ethylsulfonyl phenyl]-1,3-dimethylpyridin-2-one | 362.1 |
| 451 | 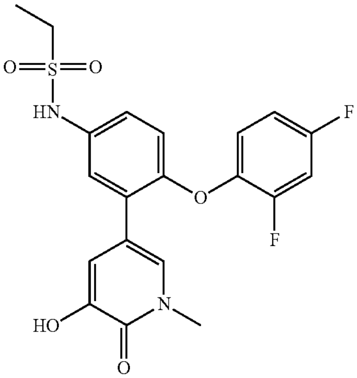 [SMILES: CCS(=O)(=O)Nc1ccc(Oc2ccc(F)cc2F)c(-c2cc(O)c(=O)n(C)c2)c1] | N-[4-(2,4-difluorophenoxy)-3-(5-hydroxy-1-methyl-6-oxopyridin-3-yl)phenyl]ethanesulfonamide | 437.0 |

TABLE 21-continued

| Chemical Synthesis Example | Structure | Name | MS (M + H) |
|---|---|---|---|
| 452 | 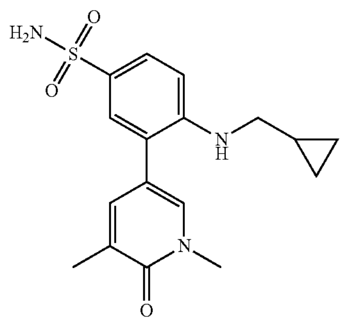 [SMILES: Cc1cc(-c2cc(S(N)(=O)=O)ccc2NCC2CC2)cn(C)c1=O] | 4-(cyclopropylmethylamino)-3-(1,5-dimethyl-6-oxopyridin-3-yl)benzenesulfonamide | 348.1 |
| 453 | 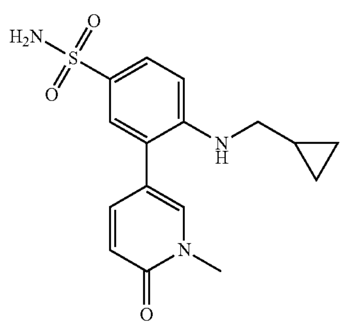 [SMILES: Cn1cc(-c2cc(S(N)(=O)=O)ccc2NCC2CC2)ccc1=O] | 4-(cyclopropylmethylamino)-3-(1-methyl-6-oxopyridin-3-yl)benzenesulfonamide | 334.1 |
| 454 | 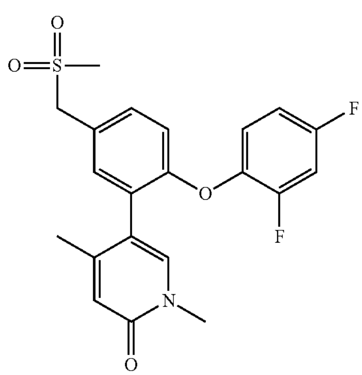 [SMILES: Cc1cc(=O)n(C)cc1-c1cc(CS(C)(=O)=O)ccc1Oc1ccc(F)cc1F] | 5-[2-(2,4-difluorophenoxy)-5-(methylsulfonylmethyl)phenyl]-1,4-dimethylpyridin-2-one | 420.0 |
| 455 | 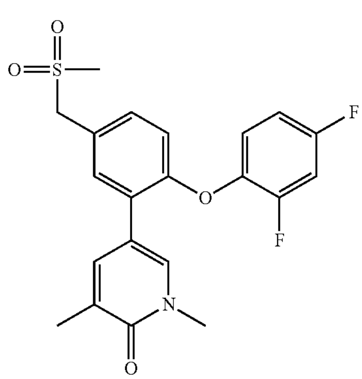 [SMILES: Cc1cc(-c2cc(CS(C)(=O)=O)ccc2Oc2ccc(F)cc2F)cn(C)c1=O] | 5-[2-(2,4-difluorophenoxy)-5-(methylsulfonylmethyl)phenyl]-1,3-dimethylpyridin-2-one | 420.1 |

TABLE 21-continued

| Chemical Synthesis Example | Structure | Name | MS (M + H) |
|---|---|---|---|
| 456 | 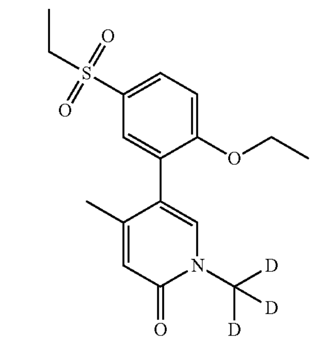 [SMILES: [2H]C([2H])([2H])n1cc(-c2cc(S(=O)(=O)CC)ccc2OCC)c(C)cc1=O] | 5-(2-ethoxy-5-ethylsulfonylphenyl)-1-(²H₃)methyl-4-methylpyridin-2-one | 339.0 |
| 457 | 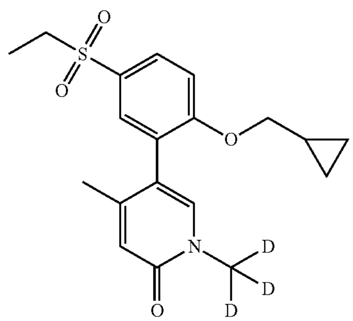 [SMILES: [2H]C([2H])([2H])n1cc(-c2cc(S(=O)(=O)CC)ccc2OCC2CC2)c(C)cc1=O] | 5-[2-(cyclopropylmethoxy)-5-ethylsulfonylphenyl]-1-(²H₃)methyl-4-methylpyridin-2-one | 365.0 |
| 458 | 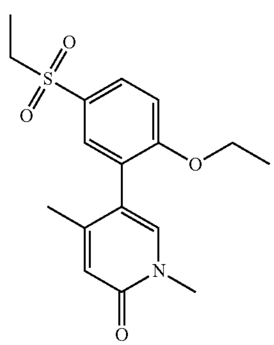 [SMILES: CCOc1ccc(S(=O)(=O)CC)cc1-c1cn(C)c(=O)cc1C] | 5-(2-ethoxy-5-ethylsulfonylphenyl)-1,4-dimethylpyridin-2-one | 336.1 |
| 459 | 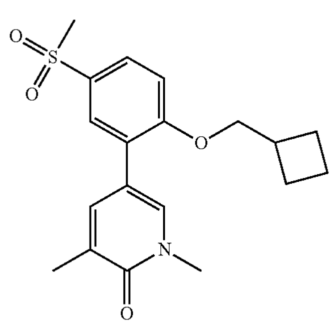 [SMILES: Cc1cc(-c2cc(S(C)(=O)=O)ccc2OCC2CCC2)cn(C)c1=O] | 5-[2-(cyclobutylmethoxy)-5-methylsulfonylphenyl]-1,3-dimethylpyridin-2-one | 362.1 |

TABLE 21-continued

| Chemical Synthesis Example | Structure | Name | MS (M + H) |
|---|---|---|---|
| 460 | 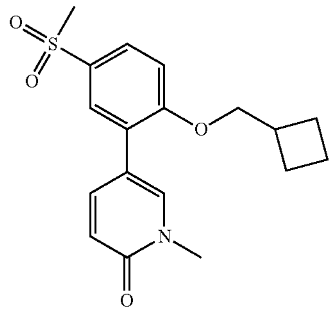 [SMILES: Cn1cc(-c2cc(S(C)(=O)=O)ccc2OCC2CCC2)ccc1=O] | 5-[2-(cyclobutylmethoxy)-5-methylsulfonylphenyl]-1-methylpyridin-2-one | 348.1 |
| 461 | 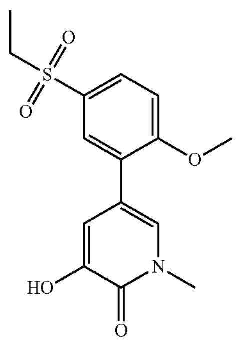 [SMILES: CCS(=O)(=O)c1ccc(OC)c(-c2cc(O)c(=O)n(C)c2)c1] | 5-(5-ethylsulfonyl-2-methoxyphenyl)-3-hydroxy-1-methylpyridin-2-one | 323.9 |
| 462 | 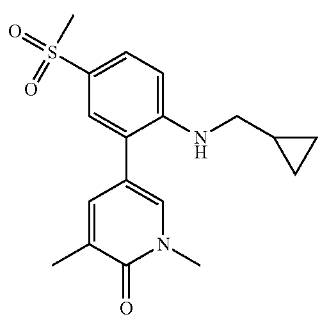 [SMILES: Cc1cc(-c2cc(S(C)(=O)=O)ccc2NCC2CC2)cn(C)c1=O] | 5-[2-(cyclopropylmethylamino)-5-methylsulfonylphenyl]-1,3-dimethylpyridin-2-one | 347.1 |
| 463 | 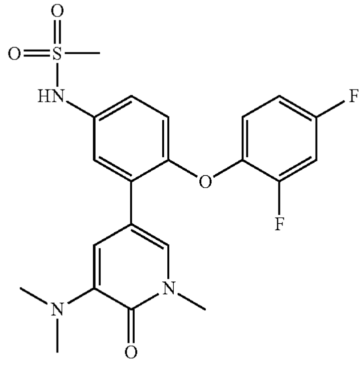 [SMILES: CN(C)c1cc(-c2cc(NS(C)(=O)=O)ccc2Oc2ccc(F)cc2F)cn(C)c1=O] | N-[4-(2,4-difluorophenoxy)-3-[5-(dimethylamino)-1-methyl-6-oxopyridin-3-yl]phenyl]methanesulfonamide | 450.1 |

TABLE 21-continued

| Chemical Synthesis Example | Structure | Name | MS (M + H) |
|---|---|---|---|
| 464 | 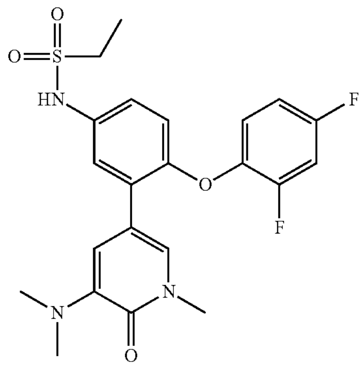 [SMILES: CCS(=O)(=O)Nc1ccc(Oc2ccc(F)cc2F)c(-c2cc(N(C)C)c(=O)n(C)c2)c1] | N-[4-(2,4-difluorophenoxy)-3-[5-(dimethylamino)-1-methyl-6-oxopyridin-3-yl]phenyl]ethanesulfonamide | 464.1 |
| 465 | 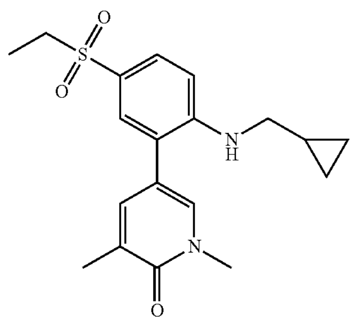 | 5-[2-(cyclopropylmethylamino)-5-ethylsulfonylphenyl]-1,3-dimethylpyridin-2-one | 361.1 |
| 466 | 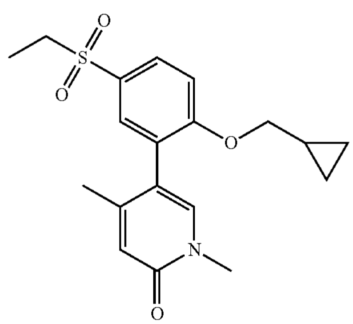 [SMILES: CCS(=O)(=O)c1ccc(OCC2CC2)c(-c2cn(C)c(=O)cc2C)c1] | 5-[2-(cyclopropylmethoxy)-5-ethylsulfonylphenyl]-1,4-dimethylpyridin-2-one | 362.1 |
| 467 | 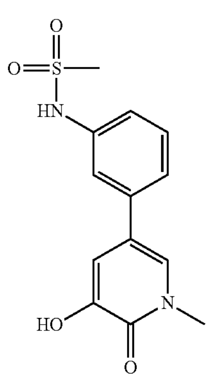 [SMILES: Cn1cc(-c2cccc(NS(C)(=O)=O)c2)cc(O)c1=O] | N-[3-(5-hydroxy-1-methyl-6-oxopyridin-3-yl)phenyl]methanesulfonamide | 295.0 |

TABLE 21-continued

| Chemical Synthesis Example | Structure | Name | MS (M + H) |
|---|---|---|---|
| 468 | 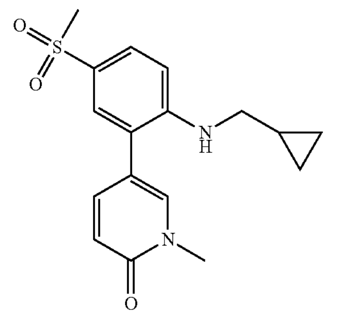 [SMILES: Cn1cc(-c2cc(S(C)(=O)=O)ccc2NCC2CC2)ccc1=O] | 5-[2-(cyclopropylmethylamino)-5-methylsulfonylphenyl]-1-methylpyridin-2-one | 333.1 |
| 469 | 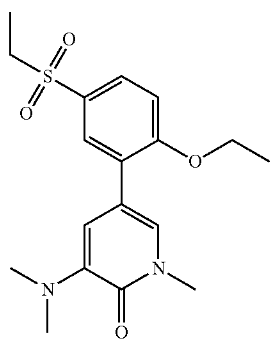 [SMILES: CCOc1ccc(S(=O)(=O)CC)cc1-c1cc(N(C)C)c(=O)n(C)c1] | 3-(dimethylamino)-5-(2-ethoxy-5-ethylsulfonylphenyl)-1-methylpyridin-2-one | 365.1 |
| 470 | 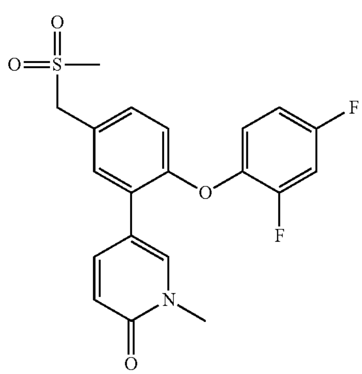 [SMILES: Cn1cc(-c2cc(CS(C)(=O)=O)ccc2Oc2ccc(F)cc2F)ccc1=O] | 5-[2-(2,4-difluorophenoxy)-5-(methylsulfonylmethyl)phenyl]-1-methylpyridin-2-one | 406.0 |
| 471 | 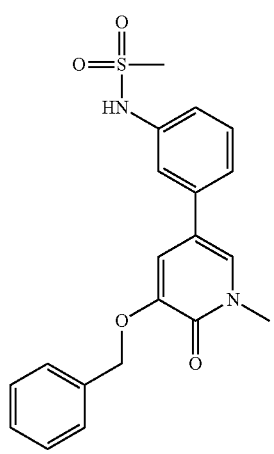 [SMILES: Cn1cc(-c2cccc(NS(C)(=O)=O)c2)cc(OCc2ccccc2)c1=O] | N-[3-(1-methyl-6-oxo-5-phenylmethoxypyridin-3-yl)phenyl]methanesulfonamide | 385.0 |

TABLE 21-continued

| Chemical Synthesis Example | Structure | Name | MS (M + H) |
|---|---|---|---|
| 472 | 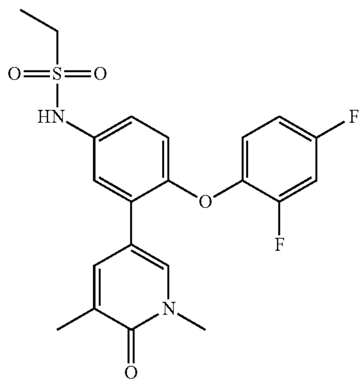 [SMILES: CCS(=O)(=O)Nc1ccc(Oc2ccc(F)cc2F)c(-c2cc(C)c(=O)n(C)c2)c1] | N-[4-(2,4-difluorophenoxy)-3-(1,5-dimethyl-6-oxopyridin-3-yl)phenyl]ethanesulfonamide | 435.1 |
| 473 | 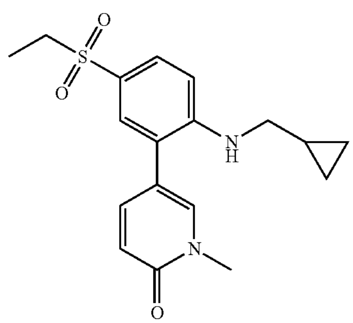 [SMILES: CCS(=O)(=O)c1ccc(NCC2CC2)c(-c2ccc(=O)n(C)c2)c1] | 5-[2-(cyclopropylmethylamino)-5-ethylsulfonylphenyl]-1-methylpyridin-2-one | 347.1 |
| 474 | 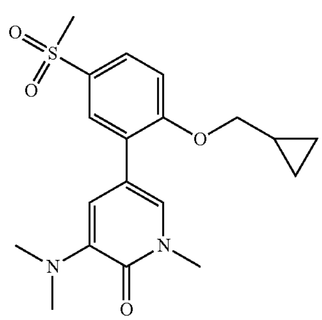 [SMILES: CN(C)c1cc(-c2cc(S(C)(=O)=O)ccc2OCC2CC2)cn(C)c1=O] | 5-[2-(cyclopropylmethoxy)-5-methylsulfonylphenyl]-3-(dimethylamino)-1-methylpyridin-2-one | 377.1 |
| 475 | 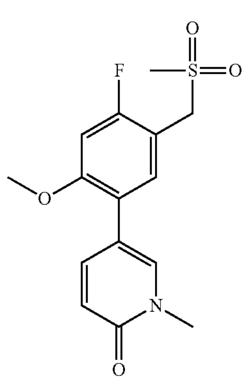 [SMILES: COc1cc(F)c(CS(C)(=O)=O)cc1-c1ccc(=O)n(C)c1] | 5-[4-fluoro-2-methoxy-5-(methylsulfonylmethyl)phenyl]-1-methylpyridin-2-one | 326.0 |

TABLE 21-continued

| Chemical Synthesis Example | Structure | Name | MS (M + H) |
|---|---|---|---|
| 476 | 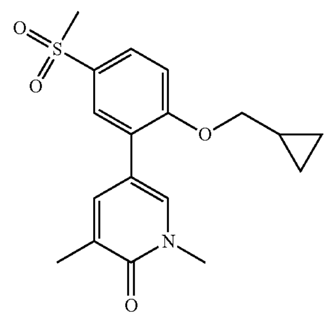 [SMILES: Cc1cc(-c2cc(S(C)(=O)=O)ccc2OCC2CC2)cn(C)c1=O] | 5-[2-(cyclopropylmethoxy)-5-methylsulfonylphenyl]-1,3-dimethylpyridin-2-one | 348.1 |
| 477 | 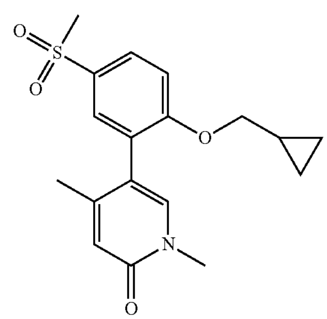 [SMILES: Cc1cc(=O)n(C)cc1-c1cc(S(C)(=O)=O)ccc1OCC1CC1] | 5-[2-(cyclopropylmethoxy)-5-methylsulfonylphenyl]-1,4-dimethylpyridin-2-one | 348.1 |
| 478 | 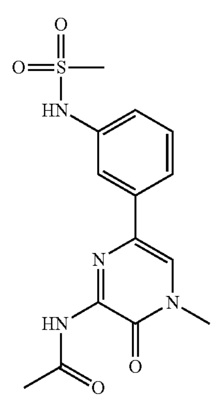 [SMILES: CC(=O)Nc1nc(-c2cccc(NS(C)(=O)=O)c2)cn(C)c1=O] | N-[6-[3-(methanesulfonamido)phenyl]-4-methyl-3-oxopyrazin-2-yl]acetamide | 337.0 |
| 479 | 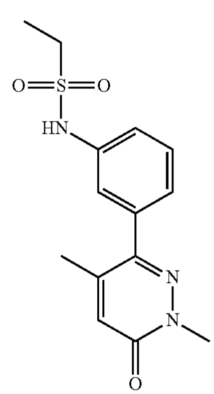 | N-[3-(1,4-dimethyl]-6-oxopyridazin-3-yl(phenyl)ethanesulfonamide | 308.0 |

TABLE 21-continued

| Chemical Synthesis Example | Structure | Name | MS (M + H) |
|---|---|---|---|
| 480 | 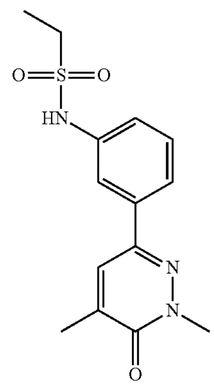 [SMILES: CCS(=O)(=O)Nc1cccc(-c2cc(C)c(=O)n(C)n2)c1] | N-[3-(1,5-dimethyl-6-oxopyridazin-3-yl)phenyl]ethanesulfonamide | 308.0 |
| 481 | 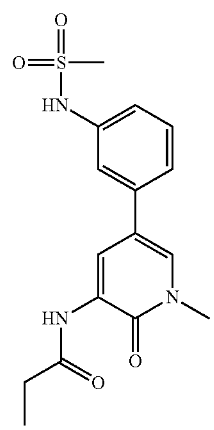 [SMILES: CCC(=O)Nc1cc(-c2cccc(NS(C)(=O)=O)c2)cn(C)c1=O] | N-[5-[3-(methanesulfonamido)phenyl]-1-methyl-2-oxopyridin-3-yl]propanamide | 350.0 |
| 482 | 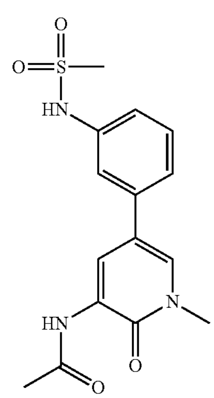 [SMILES: CC(=O)Nc1cc(-c2cccc(NS(C)(=O)=O)c2)cn(C)c1=O] | N-[5-[3-(methanesulfonamido)phenyl]-1-methyl-2-oxopyridin-3-yl]acetamide | 336.0 |

Example 483

1-cyclobutyl-5-[2-(cyclopropylmethoxy)-5-methyl-sulfonylphenyl]-3-methylpyridin-2-one

Step 1: 1-cyclobutyl-3-methylpyridin-1-ium chloride

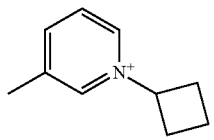

Cyclobutylamine (2.3 g, 32 mmol) was added to 1-(2,4-dinitrophenyl)-3-methylpyridinium chloride (J. Org. Chem. 1997, 62, 729-33) (8.0 g, 31 mmol) in n-butanol (120 mL) at 20° C. and the deep red solution was refluxed overnight. Concentration under vacuum left a residue that was treated with water (20 mL) and the precipitate was removed by filtration, and the operation was repeated twice. The combined aqueous phase was basified with concentrated ammonia (2 mL) and washed twice with EtOAc. Evaporation of the water to gave the title compound (3.2 g, 70%) as a brown oil. LCMS: 148 $M^+$

Step 2: 1-cyclobutyl-3-methylpyridin-2-one

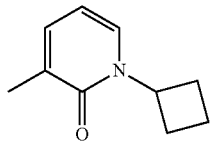

A stirred solution of the title compound from step 2 (2.8 g, 18.9 mmol) in water (30 mL) was cooled to 5° C. and $K_3Fe(CN)_6$ in water (30 mL) was added dropwise over 1 h. Then KOH (16.7 g, 298.6 mmol) in water (5 mL) and toluene (30 mL) were added, and the mixture was heated at 40° C. for 30 min. The organic layer was separated, and the aqueous layer was extracted with DCM. The combined organic layers were washed with water, brine and dried over $Na_2SO_4$, filtered and concentrated. Silica gel chromatography (DCM) gave the title compound (1.9 g, 62%) as a yellow oil. LCMS: 164 $(M+H)^+$

Step 3: 5-bromo-1-cyclobutyl-3-methylpyridin-2-one

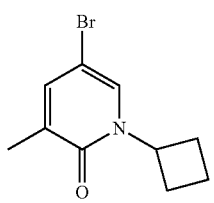

The title compound of step 3 (1.5 g, 9.2 mmol) in acetic acid (30 mL) was stirred at rt for 10 min. Bromine (1.51 g, 9.5 mmol) was then added slowly, and after about 2 h, the mixture was diluted with water and extracted with DCM. The organic solution was washed with water, brine and dried over $Na_2SO_4$, filtered, concentrated and purified by silica gel chromatography (DCM) to give the title compound (2.0 g, 82%) as a yellow oil. LCMS: 242, 244 $(M+H)^+$

Step 4: 1-cyclobutyl-5-[2-(cyclopropylmethoxy)-5-methylsulfonylphenyl]-3-methylpyridin-2-one

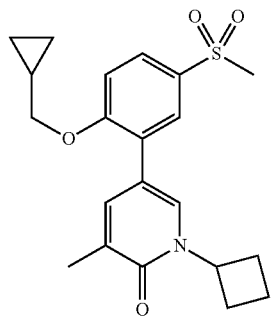 [SMILES: Cc1cc(-c2cc(S(C)(=O)=O)ccc2OCC2CC2)cn(C2CCC2)c1=O]

The title compound of step 4 (27 mg, 0.11 mmol), the title compound of Example 90, step 1 (46 mg, 0.13 mmol), $K_2CO_3$ (46 mg, 0.33 mmol) and $Pd(dppf)_2Cl_2$ (8 mg, 0.011 mmol) in DMF (2 mL) was $N_2$ purged and microwaved at 100° C. After 2 h, the mixture was concentrated under vacuum and DCM was added which was washed with water, brine and dried over $Na_2SO_4$. Purification by preparative TLC gave the title compound (25 mg, 58%) as a white solid. $^1$H NMR (CDCl$_3$, 400 MHz): δ 7.85-7.81 (m, 2H), 7.79 (d, J=1.6 Hz, 1H), 7.47 (s, 1H), 7.02 (d, J=8.4 Hz, 1H), 5.27-5.23 (m, 1H), 3.94 (d, J=8.0 Hz, 2H), 3.07 (s, 3H), 2.57-2.50 (m, 2H), 2.32-2.24 (m, 2H), 2.21 (s, 3H), 1.93-1.84 (m, 2H), 1.31-1.25 (m, 1H), 0.70-0.65 (m, 2H), 0.40-0.36 (m, 2H). LCMS: 388 $(M+H)^+$

Example 484

N-[3-(1-cyclobutyl-5-methyl-6-oxopyridin-3-yl)-4-(2,4-difluorophenoxy)phenyl]methanesulfonamide

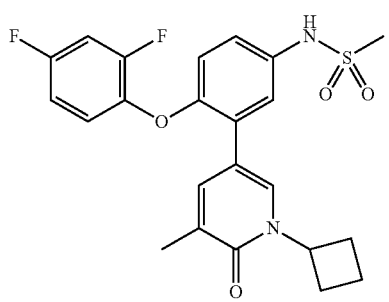 [SMILES: Cc1cc(-c2cc(NS(C)(=O)=O)ccc2Oc2ccc(F)cc2F)cn(C2CCC2)c1=O]

The title compound of Example 483, step 3 (27 mg, 0.11 mmol), N-[4-(2,4-difluorophenoxy)-3-(4,4,5,5-tetramethyl-1,3,2-dioxaborolan-2-yl)phenyl]methanesulfonamide (55 mg, 0.13 mmol), $K_2CO_3$ (46 mg, 0.33 mmol) and $Pd(dppf)_2Cl_2$ (8 mg, 0.011 mmol) in DMF (2 mL) were reacted and purified in a manner similar to Example 483, step 4 to give the title compound (16 mg, 32%) as a white solid. $^1$H NMR (CDCl$_3$, 400 MHz): δ 7.65 (s, 1H), 7.42 (s, 1H), 7.26-7.27 (m, 1H), 7.13 (dd, J=8.8, 2.8 Hz, 1H), 6.97-6.89 (m, 2H), 6.83 (d, J=9.2 Hz, 2H), 6.54 (s, 1H), 5.09-5.18 (m, 1H), 3.04 (s, 3H), 2.53-2.46 (m, 2H), 2.23-2.18 (m, 2H), 2.16 (s, 3H), 1.87-1.81 (m, 2H). LCMS: 461 (M+H)$^+$ Example 485

1-benzyl-5-[2-(cyclopropylmethoxy)-5-methylsulfonylphenyl]-3-methylpyridin-2-one

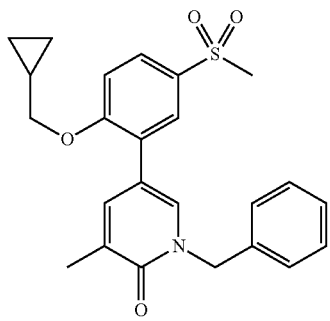 [SMILES: Cc1cc(-c2cc(S(C)(=O)=O)ccc2OCC2CC2)cn(Cc2ccccc2)c1=O]

The title compound was prepared in a manner similar to Example 483, steps 1-4 except that benzylamine was substituted for cyclobutylamine in step 1. $^1$H NMR (CDCl$_3$, 400 MHz): δ 7.79 (s, 1H), 7.62 (d, J=2.8 Hz, 1H), 7.49-7.51 (m, 1H), 7.34-7.38 (m, 4H), 7.29-7.32 (m, 2H), 6.98 (d, J=8.8 Hz, 1H), 5.20 (s, 2H), 3.89-3.94 (m, 2H), 3.04 (s, 3H), 2.22 (s, 3H), 1.13-1.18 (m, 1H), 0.58-0.62 (m, 2H), 0.28-0.34 (m, 2H). LCMS: 424 (M+H)$^+$ Example 486

1,3-dimethyl-5-(2-methyl-5-methylsulfonyl-2,3-dihydro-1-benzofuran-7-yl)pyridin-2-one Step 1: 2-methyl-5-methylsulfonyl-2,3-dihydro-1-benzofuran

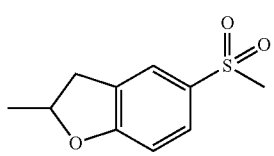

A mixture of 5-bromo-2-methyl-2,3-dihydro-1-benzofuran (1.0 g, 4.72 mmol), CH$_3$SO$_2$Na (730 mg, 7.08 mmol), L-proline (110 mg, 0.94 mmol), K$_2$CO$_3$ (120 mg, 0.94 mmol) and CuI (89 mg, 0.47 mmol) in DMSO (10 mL) was irradiated at 140° C. for 2 h under microwave. The mixture was extracted with EtOAc (2×30 mL). The combined organic layers were washed with brine (30 mL), dried over Na$_2$SO$_4$, filtered and concentrated to give the crude product that was purified by column chromatography on silica gel (PE/EA=2/1) to give the title compound (500 mg, 50%). $^1$H NMR (CDCl$_3$, 400 MHz) δ 7.71-7.70 (m, 2H), 6.86-6.82 (m, 1H), 5.08-5.03 (m, 1H), 3.41-3.35 (m, 1H), 3.02 (s, 3H), 2.89-2.83 (m, 1H), 1.56 (d, J=6.4 Hz, 3H).

Step 2: 7-bromo-2-methyl-5-methylsulfonyl-2,3-dihydro-1-benzofuran

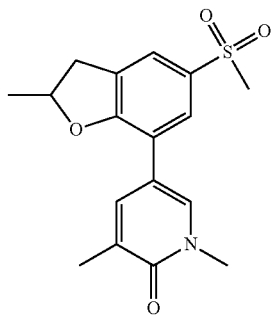 [SMILES: Cc1cc(-c2cc(S(C)(=O)=O)cc3c2OC(C)C3)cn(C)c1=O]

To a mixture of the title compound from Step 1 (300 mg, 1.42 mmol) in DCM (10 mL) was added Fe (159 mg, 2.84 mmol) and Br$_2$ (454 mg, 2.84 mmol) in one portion under N$_2$. The mixture was stirred at room temperature for 6 h. The reaction mixture was washed with saturated aqueous Na$_2$SO$_3$ (200 mL) and extracted with DCM (30 mL×2). The combined organic layers were washed with brine (20 mL×2), dried with anhydrous Na$_2$SO$_4$, filtered and concentrated under reduced pressure. The residue was purified by column chromatography on silica gel (PE/EA=3/1) to give the title compound (300 mg, 73%) as a yellow solid. $^1$H NMR (CDCl$_3$, 400 MHz) δ 7.90 (d, J=1.6 Hz, 1H), 7.64 (d, J=1.6 Hz, 1H), 5.20-5.14 (m, 1H), 3.53-3.47 (m, 1H), 3.01-2.95 (m, 1H), 3.04 (s, 3H), 1.56 (d, J=6.4 Hz, 3H). LCMS: 291.0 (M+1)$^+$; 293.0.

Step 3: 1,3-dimethyl-5-(2-methyl-5-methylsulfonyl-2,3-dihydro-1-benzofuran-7-yl)pyridin-2-one A solution of the title compound in Step 2 (300 mg, 1.03 mmol), 1,3-dimethyl-5-(4,4,5,5-tetramethyl-1,3,2-dioxaborolan-2-yl)pyridin-2-one (309 mg, 1.24 mmol), Pd(dppf)Cl$_2$ (76 mg, 0.103 mmol), Na$_2$CO$_3$ (328 mg, 3.09 mmol) in dioxane (8 mL) and H$_2$O (1 mL) was stirred at 80° C. under N$_2$ for 16 h. The solvent was removed under reduced pressure to give a residue that was purified by column chromatography on silica gel (PE/EA=1/2) to give the title compound (60.0 mg, 18%) as a yellow solid. $^1$H NMR (DMSO-d6, 400 MHz) δ 8.02 (s, 1H), 7.76 (s, 1H), 7.74 (s, 1H), 7.66 (s, 1H), 5.15-5.13 (m, 1H), 3.51 (s, 3H), 3.49-3.42 (m, 1H), 3.19 (s, 3H), 2.94-2.88 (m, 1H), 2.07 (s, 3H), 1.44 (d, J=5.2 Hz, 3H). LCMS: 334.1 (M+1)$^+$.

Example 487

4-[5-(ethylsulfonylmethyl)-2-(2,2,2-trifluoroethoxy)phenyl]-2-methylisoquinolin-1-one

Step 1: methyl 3-bromo-4-(2,2,2-trifluoroethoxy)benzoate

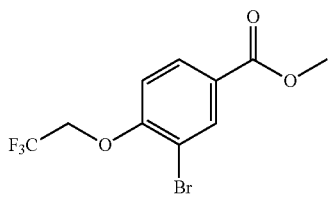 [SMILES: COC(=O)c1ccc(OCC(F)(F)F)c(Br)c1]

To a solution of methyl 3-bromo-4-fluorobenzoate (100 mg, 0.43 mmol) in DMF was added 2,2,2-trifluoroethanol (52 mg, 0.52 mmol), $K_2CO_3$ (119 mg, 0.86 mmol), and the mixture was stirred at 60° C. for 2 h. The mixture was cooled and water (50 mL) was added. The aqueous layer was extracted with EtOAc (30 mL×3). The combined organic layers were washed with water (30 mL×3), brine (30 mL), dried over anhydrous $Na_2SO_4$, filtered, concentrated and purified by silica gel chromatography (PE:EA=20:1) to afford compound 3 (95 mg, 88%) as a white solid. $^1$H NMR (CDCl3, 400 MHz) δ 8.29 (d, J=2.0 Hz, 1H), 8.00 (dd, $J_1$=8.4 Hz, $J_2$=2.0 Hz, 1H), 6.93 (d, J=8.4 Hz, 1H), 4.48 (q, J=8.0 Hz, 2H), 3.92 (s, 3H). LCMS: 313.0 (M+1)$^+$

Step 2: [3-bromo-4-(2,2,2-trifluoroethoxy)phenyl]methanol

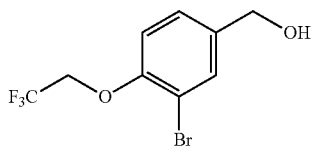 [SMILES: OCc1ccc(OCC(F)(F)F)c(Br)c1]

To solution of the title compound from Step 1 (2.00 g, 5.85 mmol) in THF (20.0 mL) was added LiAlH$_4$ (0.18 g, 4.68 mmol) in several portions at −40° C. The mixture was kept at −40° C. and stirred for 45 mins. The reaction was quenched with water (0.2 mL), 15% NaOH aqueous (0.2 mL) and additional water (0.6 mL). The mixture was stirred at room temperature for 15 min. It was then dried over Na$_2$SO$_4$ and filtered. The filtrate was concentrated and the residue purified by silica gel chromatography (PE:EA=5:1-3:1) to give the title compound (1.62 g, 89%) as a white solid. $^1$H NMR (DMSO-d6, 400 MHz) δ 7.55 (d, J=2.0 Hz, 1H), 7.31-7.28 (m, 1H), 7.19 (d, J=8.4 Hz, 1H), 4.83 (q, J=8.8 Hz, 2H), 4.44 (s, 2H).

Step 3: 2-bromo-4-(chloromethyl)-1-(2,2,2-trifluoroethoxy)benzene

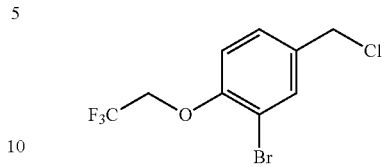

A solution of the title compound from Step 2 (300 mg, 1.05 mmol) in DCM (10 mL) was cooled to 0° C. and treated with triethylamine (91 mg, 1.15 mmol) and methanesulfonyl chloride (142 mg, 1.25 mmol). The reaction mixture was warmed to room temperature and stirred overnight. It was then diluted with DCM (10 mL) and washed with 1 M hydrochloric acid (10 mL) and sat. NaHCO$_3$ (10 mL). The organic phase was dried over Na$_2$SO$_4$, filtered and concentrated under reduced pressure. The crude residue was purified by silica gel chromatography to afford the title compound (260 mg, 82%) as a white solid. $^1$H NMR (CDCl3, 400 MHz) δ 7.63 (d, J=2.0 Hz, 1H), 7.32 (dd, J1=8.4 Hz, $J_2$=2.0 Hz, 1H), 6.92 (d, J=8.4 Hz, 1H), 4.53 (s, 2H), 4.42 (q, J=8.0 Hz, 2H)

Step 4: 2-bromo-4-(ethylsulfanylmethyl)-1-(2,2,2-trifluoroethoxy)benzene

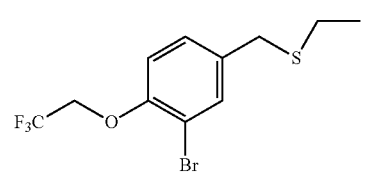 [SMILES: CCSCc1ccc(OCC(F)(F)F)c(Br)c1]

To a solution of the title compound from Step 3 (2.00 g, 6.59 mmol) in DCM (200 mL) was added TEA (1 g, 9.89 mmol), NaI (898 mg, 5.99 mmol) and EtSH (613 mg, 9.89 mmol). The mixture was stirred at 30° C. for 4 hrs. The reaction was poured into water (10 mL) and extracted with EtOAc (10 mL×3). The combined organic layers were washed with brine (30 mL), dried over anhydrous Na$_2$SO$_4$ and filtered. Solvents were removed under reduced pressure and the residue was purified by silica gel chromatography (PE:EA=1:0~3:1) to give the title compound (2.1 g, 96.8%) as a white solid. $^1$H NMR (CDCl3, 400 MHz) δ 7.55 (d, J=2.0 Hz, 1 H), 7.24 (dd, $J_1$=8.4 Hz, $J_2$=2.0 Hz, 1H), 6.89 (d, J=8.4 Hz, 1H), 4.42 (q, J=8.0 Hz, 2H), 3.66 (s, 2H), 2.47-2.41 (m, 2H), 1.26-1.22 (m, 3H).

Step 5: 2-bromo-4-(ethylsulfonylmethyl)-1-(2,2,2-trifluoroethoxy)benzene

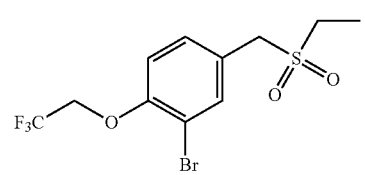 [SMILES: CCS(=O)(=O)Cc1ccc(OCC(F)(F)F)c(Br)c1]

To a solution of the title compound from Step 4 (2.10 g, 6.38 mmol) in DCM (210 mL) was added MCPBA (4.41 g, 25.53 mmol) in several portions. The mixture was stirred at 25° C. for 12 hrs. The reaction was poured into sat. aq. Na$_2$SO$_3$ (100 mL) and extracted with DCM (80 mL×3). The combined organic layers were washed with sat. NaHCO$_3$ (100 mL×2) and brine (100 mL), dried over anhydrous Na2SO$_4$, filtered and concentrated under reduced pressure. The residue was purified by silica gel chromatography (PE:EA=1:0~2:1) to give the title compound (2.10 g, 91%) as a white solid. $^1$H NMR (CDCl3, 400 MHz) δ 7.64 (d, J=2.0 Hz, 1H), 7.37 (dd, J$_1$=8.4 Hz, J$_2$=2.4 Hz, 1H), 6.95 (d, J=8.4 Hz, 1H), 4.43 (q, J=8.0 Hz, 2H), 4.15 (s, 2H), 2.91 (q, J=7.6 Hz, 2H), 1.39 (t, J=7.6 Hz, 3H).

Step 6: 4-[5-(ethylsulfonylmethyl)-2-(2,2,2-trifluoroethoxy)phenyl]-2-methylisoquinolin-1-one

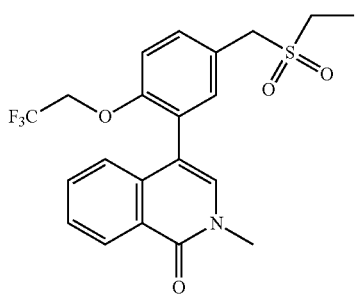 [SMILES: CCS(=O)(=O)Cc1ccc(OCC(F)(F)F)c(-c2cn(C)c(=O)c3ccccc23)c1]

The title compound from Step 5 (200 mg, 0.58 mmol), 2-methyl-4-(4,4,5,5-tetramethyl-1,3,2-dioxaborolan-2-yl)isoquinolin-1-one (197 mg, 0.69 mmol), Pd(PPh$_3$)$_4$ (67 mg, 58.0 umol) and Na$_2$CO$_3$ (184 mg, 1.74 mmol) in dioxane (6 mL) and water (6 drops) was degassed and then heated to 70° C. for 18 hours under N$_2$. The reaction mixture was concentrated under reduced pressure and the residue was purified by column chromatography (PE:EA=5:1~1:1) followed by prep-HPLC purification to afford the title compound (164.44 mg, 67%) as an off-white solid. $^1$H NMR (CDCl3, 400 MHz) δ 8.52 (d, J=8.0 Hz, 1H), 7.58-7.48 (m, 3H), 7.40 (d, J=2.4 Hz, 1H), 7.22 (d, J=8.0, 1H), 7.07 (t, J=8.0, 2H), 4.30 (q, J=8.0 Hz, 2H), 4.23 (s, 2H), 3.67 (s, 3H), 2.98 (q, J=7.6 Hz, 2H), 1.43 (t, J=7.6 Hz, 3H). LCMS: 440.0 (M+1)$^+$ Example 488

2-methyl-4-[5-(methylsulfonylmethyl)-2-(2,2,2-trifluoroethoxy)phenyl]isoquinolin-1-one Step 1: 2-bromo-4-(methylsulfanylmethyl)-1-(2,2,2-trifluoroethoxy)benzene

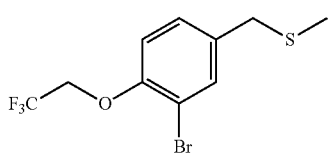 [SMILES: CSCc1ccc(OCC(F)(F)F)c(Br)c1]

The title compound was prepared in a manner similar to Example 487 Step 4, by substituting methanethiol for ethanethiol. $^1$H NMR (CDCl3, 400 MHz) δ 7.56 (d, J=2.0 Hz, 1H), 7.25 (dd, J$_1$=8.4 Hz, J$_2$=2.0 Hz, 1H), 6.93-6.90 (m, 1H), 4.44-4.35 (m, 2H), 3.63 (s, 2H), 2.02 (s, 3H).

Step 2: 2-bromo-4-(methylsulfonylmethyl)-1-(2,2,2-trifluoroethoxy)benzene

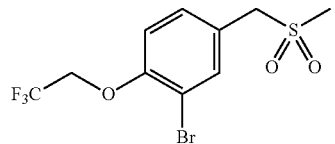 [SMILES: CS(=O)(=O)Cc1ccc(OCC(F)(F)F)c(Br)c1]

The title compound was prepared in a manner similar to Example 487 Step 5, by substituting 2-bromo-4-(methylsulfanylmethyl)-1-(2,2,2-trifluoroethoxy)benzene for 2-bromo-4-(ethylsulfanylmethyl)-1-(2,2,2-trifluoroethoxy)benzene. $^1$H NMR (CDCl3, 400 MHz) δ 7.65 (d, J=2.0 Hz, 1H), 7.38 (dd, J$_1$=8.4 Hz, J$_2$=2.4 Hz, 1H), 7.12-7.06 (m, 1H), 4.43 (q, J=8.0 Hz, 2H), 4.19 (s, 2H), 2.82 (s, 3H).

Step 3: 2-methyl-4-[5-(methylsulfonylmethyl)-2-(2,2,2-trifluoroethoxy)phenyl]isoquinolin-1-one

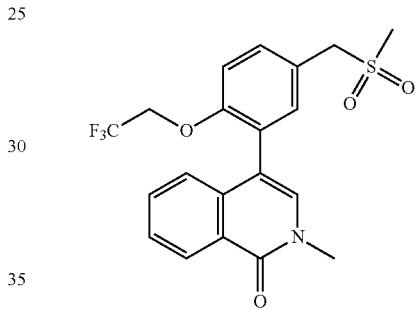

The title compound was prepared in a manner similar to Example 487 Step 6, by substituting 2-bromo-4-(methylsulfonylmethyl)-1-(2,2,2-trifluoroethoxy)benzene for 2-bromo-4-(ethylsulfonylmethyl)-1-(2,2,2-trifluoroethoxy)benzene. $^1$H NMR (CDCl3, 400 MHz) δ 8.52 (d, J=8.0 Hz, 1H), 7.60-7.49 (m, 3H), 7.41 (d, J=2.0 Hz, 1H), 7.22 (d, J=8.0, 1H), 7.08-7.06 (m, 2H), 4.33-4.27 (m, 4H), 3.67 (s, 3H), 2.87 (s, 3H). LCMS: 426.0 (M+1)$^+$ Example 489

1,3-dimethyl-5-(7-methylsulfonyl-2,3-dihydro-1,4-benzodioxin-5-yl)pyridin-2-one

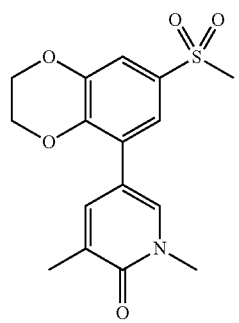 [SMILES: Cc1cc(-c2cc(S(C)(=O)=O)cc3c2OCCO3)cn(C)c1=O]

The title compound was prepared in a manner similar to Example 486, by substituting 6-bromo-2,3-dihydro-1,4-benzodioxine for 5-bromo-2-methyl-2,3-dihydro-1-benzofuran in step 1. $^1$H NMR (CDCl3, 400 MHz) δ 7.51 (m, 2H), 7.44 (d, J=2.4 Hz, 1H), 7.42 (d, J=2.4 Hz, 1H), 4.38 (m, 4H), 3.68 (s, 3H), 3.08 (s, 3H), 2.24 (s, 3H). LCMS: 336.0 (M+1)$^+$ Example 490

N-[2-ethyl-8-(2-methyl-1-oxoisoquinolin-4-yl)-3,4-dihydro-2H-chromen-6-yl]methanesulfonamide Step 1: 3,4-dihydro-2H-chromen-2-ylmethanol

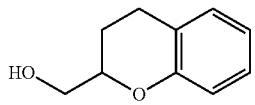

A mixture of 4-oxochromene-2-carboxylic acid (20.0 g, 105 mmol) and Pd/C (3.0 g, w/w=10%) in AcOH (200 mL) was placed in Parr hydrogenation apparatus under H$_2$ (50 psi) and stirred for 25 h at rt. It was then filtered and concentrated. The residue was suspended in water (300 mL), stirred for 10 min, filtered and dried to give 3,4-dihydro-2H-chromene-2-carboxylic acid (13.5 g, 72%) as a white solid. BH$_3$ (57 mL, 114 mmol, 2.0 M in THF) was added slowly to a solution of this carboxylic acid in THF (120 mL) at 0° C. The reaction mixture was then warmed to rt and stirred for 5 h at this temperature. THF/H$_2$O (30 mL, 1:1) was added drop wise while keeping the temperature between 0-5° C. and stirred for 20 min. K$_2$CO$_3$ (26.0 g, 189 mmol) was added and the reaction was vigorously stirred for 30 min. The THF layer was separated and concentrated to give the title compound (11.0 g, 89%) as a brown oil. $^1$H NMR (400 MHz, CDCl$_3$): δ 7.10-7.03 (m, 2H), 6.86-6.81 (m, 2H), 4.14-4.08 (m, 1H), 3.85-3.68 (m, 2H), 2.92-2.84 (m, 1H), 2.80-2.73 (m, 1H), 1.98-1.92 (m, 1H), 1.90-1.79 (m, 1H). LCMS: 165 (M+1)$^+$ Step 2: 3,4-dihydro-2H-chromen-2-ylmethyl trifluoromethanesulfonate

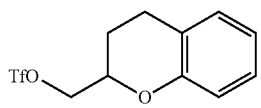 [SMILES: O=S(=O)(OCC1CCc2ccccc2O1)C(F)(F)F]

Trifluoromethanesulfonic anhydride (19.6 g, 69.5 mmol) in DCM (15 mL) was added to a solution of the title compound from Step 1 (9.50 g, 57.9 mmol) in DCM (100 mL) and pyridine (11.0 g, 139 mmol) cooled to −5° C. The reaction was then stirred at 0° C. for 1 h. Water (150 mL) was added and the reaction was extracted with DCM (150 mL). The organic layer was washed with 1 M HCl (180 mL), water (100 mL), and NaHCO$_3$ aqueous solution (100 mL). The organic phase was dried over Na$_2$SO$_4$, filtered and concentrated to give the title compound (13.5 g, 79%) as a pale-brown oil. $^1$H NMR (400 MHz, CDCl$_3$): δ 7.12-7.04 (m, 2H), 6.90-6.83 (m, 2H), 4.66-4.61 (m, 1H), 4.36-4.31 (m, 1H), 2.96-2.79 (m, 2H), 2.09-2.03 (m, 1H), 1.95-1.84 (m, 1H). LCMS: 314 (M+NH$_4$)$^+$ Step 3: 2-ethyl-3,4-dihydro-2H-chromene

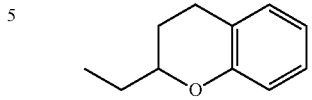

MeMgBr (45.6 mL, 137 mmol, 3M in ether) was added to a mixture of the title compound from Step 2 (13.5 g, 45.6 mmol) and CuBr-Me$_2$S (1.61 g, 7.74 mmol) in THF (150 mL) at −5° C. The reactions was stirred at rt for 2 h. It was then poured onto a solution of NH$_4$Cl (55 g, 1.04 mol) in water (200 mL) and extracted with DCM (3×150 mL). The organic layer was dried over Na$_2$SO$_4$, filtered and concentrated under reduced pressure to give the title compound (6.66 g, 90%) as a brown oil. $^1$H NMR (400 MHz, CDCl$_3$): δ 7.09-7.02 (m, 2H), 6.82-6.78 (m, 2H), 3.93-3.87 (m, 1H), 2.84-2.72 (m, 2H), 2.02-1.96 (m, 1H), 1.81-1.61 (m, 3H), 1.04 (t, J=7.2 Hz, 3H).

Step 4: 2-ethyl-6-nitro-3,4-dihydro-2H-chromene and 2-ethyl-8-nitro-3,4-dihydro-2H-chromene

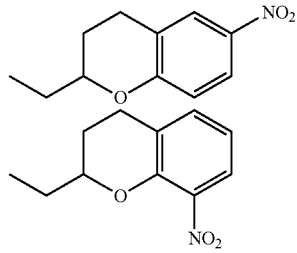

The title compound from Step 3 (1.0 g, 6.17 mmol) was added to HNO$_3$ (5 mL, 65-68%) at 0° C., warmed to rt and stirred for 1 h. It was then poured onto an ice-water mixture, extracted with EtOAc (50 mL), dried over Na$_2$SO$_4$ and concentrated under reduced pressure. The residue was purified by silica gel column chromatography (PE/EA 100:1 to 50:1) to give a mixture of the title compounds (600 mg) which was used in the next step.

Step 5: N-(2-ethyl-3,4-dihydro-2H-chromen-6-yl)methanesulfonamide

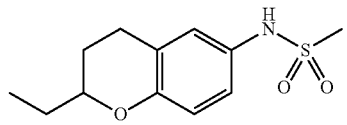 [SMILES: CCC1CCc2cc(NS(C)(=O)=O)ccc2O1]

The mixture of the title compounds from Step 4 (600 mg) was suspended in MeOH (6 mL) and sat. NH$_4$Cl solution (2 mL). Fe (810 mg, 14.5 mmol) was added and the mixture was heated to 85° C. for 2.5 h. It was then filtered and extracted with EtOAc. The organic layer was dried and concentrated under reduced pressure to give a crude mixture of 2-ethyl-3,4-dihydro-2H-chromen-6-amine and 2-ethyl-3,4-dihydro-2H-chromen-8-amine. This mixture was dissolved in DCM (10 mL) and TEA (0.8 mL) and methanesulfonyl chloride (400 mg, 3.50 mmol) were added. The mixture was stirred at rt for 1 h. It was then extracted with DCM (45 mL×2), dried over Na₂SO₄, filtered, concentrated under reduced pressure and purified by column chromatography (PE/EA 50:1 to 20:1 to 10:1) to give the title compound (190 mg, 12% for three steps) as a yellow solid. ¹H NMR (300 MHz, CDCl₃): δ 6.99-6.80 (m, 2H), 6.78 (d, J=8.7 Hz, 1H), 6.16 (s, 1H), 3.95-3.90 (m, 1H), 2.96 (s, 3H), 2.83-2.76 (m, 2H), 2.04-1.97 (m, 1H), 1.81-1.64 (m, 3H), 1.05 (t, J=7.2 Hz, 3H). LCMS: 273 (M+NH₄)⁺

Step 6: N-(8-bromo-2-ethyl-3,4-dihydro-2H-chromen-6-yl)methanesulfonamide

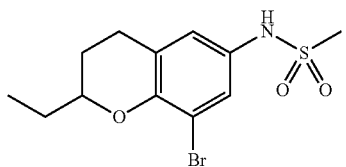 [SMILES: CCC1CCc2cc(NS(C)(=O)=O)cc(Br)c2O1]

To a solution of the title compound from Step 5 (170 mg, 0.667 mmol) in ACN (6 mL) was added NBS (156 mg, 0.867 mmol). The mixture was stirred for 7 h at rt. It was then extracted with DCM, dried over Na₂SO₄, filtered and concentrated under reduced pressure. The residue was purified with prep-TLC (PE/EA 3:1) to give the title compound (105 mg, 47%) as a gray solid. ¹H NMR (400 MHz, CDCl₃): δ 7.23 (d, J=2.4 Hz, 1H), 6.96 (d, J=2.4 Hz, 1H), 6.24 (s, 1H), 4.01-3.99 (m, 1H), 2.97 (s, 3H), 2.84-2.77 (m, 2H), 2.04-1.99 (m, 1H), 1.85-1.66 (m, 3H), 1.09 (t, J=7.2 Hz, 3H).

Step 7: N-[2-ethyl-8-(2-methyl-1-oxoisoquinolin-4-yl)-3,4-dihydro-2H-chromen-6-yl]methanesulfonamide

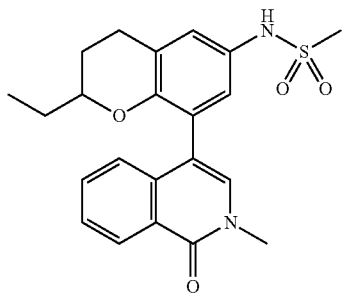 [SMILES: CCC1CCc2cc(NS(C)(=O)=O)cc(-c3cn(C)c(=O)c4ccccc34)c2O1]

A mixture of the title compound from Step 6 (105 mg, 0.315 mmol), 2-methyl-4-(4,4,5,5-tetramethyl-1,3,2-dioxaborolan-2-yl)isoquinolin-1-one (108 mg, 0.379 mmol), K₂CO₃ (131 mg, 0.949 mmol) and Pd(dppf)Cl₂ (23.1 mg, 0.032 mmol) in dioxane/H₂O (10 mL/3 mL) was heated to 85° C. for 2 h. It was then filtered and extracted with EtOAc. The organic layer was concentrated under reduced pressure. The residue was purified by silica gel column chromatography (PE/EA 50:1 to 20:1 to 10:1) to give the title compound (25 mg, 19%). ¹H NMR (400 MHz, CD₃OD) δ 8.31 (d, J=8.4 Hz, 1H), 7.59-7.55 (m, 1H), 7.47-7.43 (m, 1H), 7.31-7.23 (m, 2H), 7.05 (s, 1H), 6.95 (d, J=2.8 Hz, 1H), 3.77-3.71 (m, 1H), 3.60 (s, 3H), 2.95-2.75 (m, 5H), 1.95- 1.92 (m, 1H), 1.66-1.54 (m, 1H), 1.38-1.22 (m, 2H), 0.59-0.55 (m, 1.25H), 0.42-0.38 (m, 1.75H). LCMS: 413.0 (M+1)⁺.

Example 491

N-[2-ethyl-8-(2-methyl-1-oxoisoquinolin-4-yl)-3,4-dihydro-2H-chromen-6-yl]ethanesulfonamide

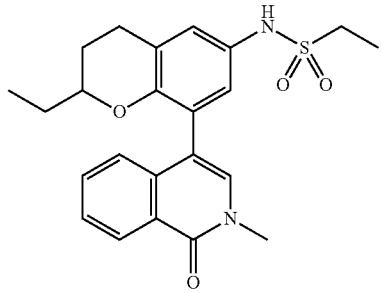 [SMILES: CCC1CCc2cc(NS(=O)(=O)CC)cc(-c3cn(C)c(=O)c4ccccc34)c2O1]

The title compound was prepared in a manner similar to Example 490 by substituting ethanesulfonyl chloride for methanesulfonyl chloride in Step 5. ¹H NMR (400 MHz, CD₃OD): δ 8.39 (d, J=7.6 Hz, 1H), 7.67-7.63 (m, 1H), 7.56-7.52 (m, 1H), 7.37-7.30 (m, 2H), 7.12 (s, 1H), 7.03 (d, J=2.8 Hz, 1H), 3.86-3.81 (m, 1H), 3.69 (s, 3H), 3.10 (q, J=7.2 Hz, 2H), 3.02-2.81 (m, 2H), 2.03-1.99 (m, 1H), 1.75-1.41 (m, 3H), 1.36 (t, J=7.6 Hz, 3H), 0.67-0.62 (m, 1.25H), 0.51-0.48 (m, 1.75H). LCMS: 427.0 (M+1)⁺.

Example 492

N-[8-(1,5-dimethyl-6-oxopyridin-3-yl)-2-ethyl-3,4-dihydro-2H-chromen-6-yl]ethanesulfonamide

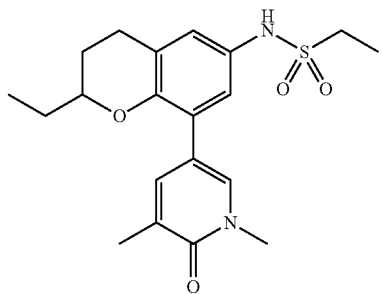 [SMILES: CCC1CCc2cc(NS(=O)(=O)CC)cc(-c3cc(C)c(=O)n(C)c3)c2O1]

The title compound was prepared in a manner similar to Example 491 by substituting 1,3-dimethyl-5-(4,4,5,5-tetramethyl-1,3,2-dioxaborolan-2-yl)pyridin-2-one for 2-methyl-4-(4,4,5,5-tetramethyl-1,3,2-dioxaborolan-2-yl)isoquinolin-1-one. ¹H NMR (400 MHz, CD₃OD): δ 7.69 (s, 1H), 7.66 (s, 1H), 7.02 (m, 1H), 7.0 (s, 1H), 3.96-3.93 (m, 1H), 3.65 (s, 3H), 3.07 (q, J=7.5 Hz, 2H), 2.93-2.82 (m, 2H), 2.18 (s, 3H), 2.08-2.04 (m, 1H), 1.72-1.66 (m, 3H), 1.34 (t, J=7.6 Hz, 3H), 1.04 (t, J=7.2 Hz, 3H). LCMS: 391.0 (M+1)⁺.

Example 493

4-(2-cyclopropyl-5-methylsulfonyl-2,3-dihydro-1-benzofuran-7-yl)-2-methylisoquinolin-1-one Step 1: 7-bromo-2-cyclopropyl-5-methylsulfonyl-1-benzofuran

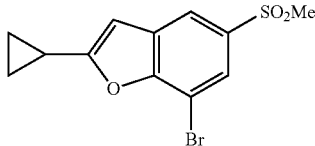 [SMILES: CS(=O)(=O)c1cc(Br)c2oc(C3CC3)cc2c1]

To a solution of 2,6-dibromo-4-methylsulfonylphenol (1 g, 3.30 mmol) in pyridine (40 mL) was added ethynylcyclopropane (240 mg, 3.64 mmol) and Cu$_2$O (260 mg, 1.82 mmol). The reaction mixture was degassed with N$_2$. The mixture was heated to 130° C. for 3 hours. It was then concentrated and purified by column chromatography (PE to PE/EA=3/1) to give the title product (510 mg, 53%) as a gray solid. $^1$H NMR (CDCl$_3$, 400 MHz) δ 7.99 (s, 1H), 7.93 (s, 1H), 6.52 (s, 1H), 3.07 (s, 3H), 2.13-2.11 (m, 1H), 1.13-1.05 (m, 4H).

Step 2: 7-bromo-2-cyclopropyl-5-methylsulfonyl-2,3-dihydro-1-benzofuran

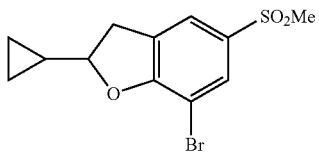 [SMILES: CS(=O)(=O)c1cc(Br)c2c(c1)CC(C1CC1)O2]

To a solution of the title compound from Step 1 (250 mg, 0.79 mmol) in Et$_3$SiH (516 mg, 4.44 mmol) at 0° C. was added TFA (5.43 g, 47.59 mmol) in one portion. The reaction mixture was warmed up to rt and stirred for 48 hours. Aqueous NaOH solution (10 mL, 1 N) was added slowly to the above solution. The mixture was extracted with EtOAc (10 mL). The organic layer was dried over Na$_2$SO$_4$, filtered and concentrated. The residue was purified by column chromatography (PE to PE/EA=2/1) to give the title compound (83 mg, 33%) as a white solid. $^1$H NMR (CDCl$_3$, 400 MHz) δ 7.90 (s, 1H), 7.64 (s, 1H), 4.47-4.43 (m, 1H), 3.51-3.47 (m, 1H), 3.23-3.17 (m, 1H), 3.04 (s, 3H), 1.24-1.22 (m, 1H), 0.74-0.55 (m, 3H), 0.44-0.41 (m, 1H).

Step 3: 4-(2-cyclopropyl-5-methylsulfonyl-2,3-dihydro-1-benzofuran-7-yl)-2-methylisoquinolin-1-one

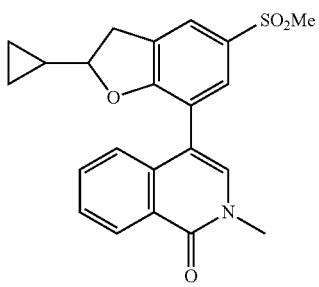 [SMILES: Cn1cc(-c2cc(S(C)(=O)=O)cc3c2OC(C2CC2)C3)c2ccccc2c1=O]

To a solution of the title compound from Step 2 (80 mg, 252 umol) in dioxane (10.00 mL) and H$_2$O (1.00 mL) was added Pd(dppf)Cl$_2$ (9 mg, 12.61 umol), K$_3$PO$_4$ (134 mg, 631 umol) and 2-methyl-4-(4,4,5,5-tetramethyl-1,3,2-dioxaborolan-2-yl)isoquinolin-1-one (79 mg, 278 umol) in one portion. The reaction mixture was degassed with N$_2$ and heated to 90° C. for 3 hours. It was then concentrated and purified by prep-HPLC to give the title compound (18.36 mg, 19% yield). $^1$H NMR (CDCl$_3$, 400 MHz) δ 8.53-8.51 (d, J=8.0 Hz, 1H), 7.79 (s, 1H), 7.75 (s, 1H), 7.63-7.56 (m, 2H), 7.33-7.31 (d, J=8.0 Hz, 1H), 7.15 (s, 1H), 4.43-4.37 (m, 1H), 3.68 (s, 3H), 3.50-3.46 (m, 1H), 3.32-3.16 (m, 1H), 3.09 (s, 3H), 1.21-1.06 (m, 1H), 0.60-0.59 (m, 2H), 0.39-0.32 (m, 2H). LCMS: 396.0 (M+1)$^+$

Example 494

4-(2-ethyl-5-methylsulfonyl-2,3-dihydro-1-benzofuran-7-yl)-2-methylisoquinolin-1-one Step 1: 2-ethyl-7-iodo-5-methylsulfonyl-1-benzofuran

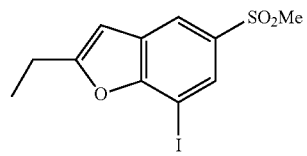 [SMILES: CCc1cc2cc(S(C)(=O)=O)cc(I)c2o1]

To a solution of 2,6-diiodo-4-methylsulfonylphenol (1.00 g, 2.36 mmol) in pyridine (10 mL) at 25° C. was added but-1-yne (128 mg, 2.36 mmol) and Cu$_2$O (135 mg, 0.944 mmol). The mixture was stirred at 130° C. for 3 h under a nitrogen atmosphere. The residue was cooled to 25° C., diluted with 1N HCl (200 ml) and extracted with EtOAc (30 mL×2). The combined organic layers were washed by brine (100 mL), dried over Na$_2$SO$_4$, filtered and concentrated. The residue was purified by column chromatography (PE: EA=10:1 to 5:1) to afford the title compound (400 mg, 48%) as a solid. $^1$H NMR (CDCl$_3$, 400 MHz) δ 8.14 (d, J=1.6 Hz, 1H), 8.06 (d, J=1.6 Hz, 1H), 6.62 (s, 1H), 3.09 (s, 3H), 2.90 (q, J=7.6 Hz, 2H), 1.38 (t, J=7.6 Hz, 3H). LCMS: 350.9 (M+H$^+$)

Step 2: 4-(2-ethyl-5-methylsulfonyl-1-benzofuran-7-yl)-2-methylisoquinolin-1-one

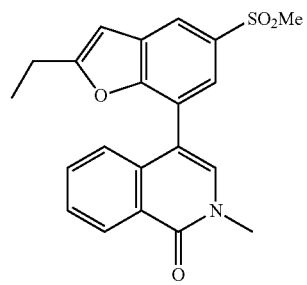 [SMILES: CCc1cc2cc(S(C)(=O)=O)cc(-c3cn(C)c(=O)c4ccccc34)c2o1]

To a solution of 2-methyl-4-(4,4,5,5-tetramethyl-1,3,2-dioxaborolan-2-yl)isoquinolin-1-one (82 mg, 286 umol) and the title compound from Step 1 (100 mg, 286 umol) in H$_2$O (2 mL) and dioxane (20 mL) was added Pd(dppf)Cl$_2$ (21 mg, 28.6 umol, 0.10 Eq) and Na$_2$CO$_3$ (61 mg, 572 umol). The mixture was degassed with nitrogen and heated to 90° C. for 4 h. It was then cooled to rt and concentrated under reduced pressure. The residue was purified by silica gel column chromatography (PE:EA=3:1 to 1:1) followed by prep-HPLC to afford the title compound (35.57 mg, 33%) as a white solid. ¹H NMR (CDCl₃, 400 MHz) δ 8.56 (d, J=7.2 Hz, 1H), 8.19 (d, J=1.6 Hz, 1H), 7.83 (d, J=1.6 Hz, 1H), 7.60-7.57 (m, 2H), 7.29-7.27 (m, 2H), 6.60 (s, 1H), 3.73 (s, 3H), 3.15 (s, 3H) 2.75 (q, J=7.2 Hz, 2H), 1.28 (t, J=7.2 Hz, 3H). LCMS: 382.0 (M+H⁺)

Step 3: 4-(2-ethyl-5-methylsulfonyl-2,3-dihydro-1-benzofuran-7-yl)-2-methylisoquinolin-1-one

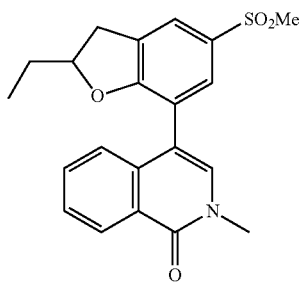 [SMILES: CCC1Cc2cc(S(C)(=O)=O)cc(-c3cn(C)c(=O)c4ccccc34)c2O1]

To a solution of the title compound from Step 2 (130 mg, 340 umol) in MeOH (3 mL) was added Pd/C (70 mg, 10% w/w) in one portion. The reaction mixture was stirred at 25° C. under H₂ atmosphere (15 psi) for 8 h. After this time, the mixture was filtered through celite. The solvent was removed under reduced pressure and the residue was purified by prep-HPLC to give the title compound (12.4 mg) as a gray solid. ¹H NMR (CDCl₃, 300 MHz) δ 8.54-8.51 (d, J=7.5 Hz, 1H), 7.79-7.75 (m, 2H), 7.75-7.54 (m, 2H), 7.32-7.29 (d, J=8.1 Hz, 1H), 7.16 (s, 1H), 4.90-4.85 (m, 1H), 3.69 (s, 3H), 3.49-3.41 (m, 1H), 3.06-3.00 (m, 1H), 1.85-1.70 (m, 2H), 0.96-0.91 (t, J=7.5 Hz, 3H). LCMS: 384.0 (M+1)⁺

Example 495

N-[7-(1,5-dimethyl-6-oxopyridin-3-yl)-2-propyl-2,3-dihydro-1-benzofuran-5-yl]ethanesulfonamide Step 1: 2-cyclopropyl-7-iodo-5-nitro-1-benzofuran

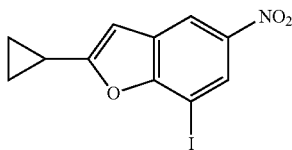 [SMILES: O=[N+]([O-])c1cc(I)c2oc(C3CC3)cc2c1]

A solution of 2,6-diiodo-4-nitrophenol (10 g, 25.6 mmol), ethynylcyclopropane (1.9 g, 28.8 mmol) and Cu₂O (1.9 mg, 13.2 mmol) in 100 mL of dry pyridine was refluxed for 2 h. The reaction mixture was poured into 1 L of water and stirred for 10 min. The resulting mixture was filtered. The cake was purified by column chromatography on silica gel eluting with EtOAc/PE (0-20%) to give the title compound (6.6 g, 78% yield) as a yellow solid. ¹H NMR (CDCl₃, 400 MHz): δ 8.47 (d, J=2.4 Hz, 1H), 8.32 (d, J=2.4 Hz, 1H), 6.58 (s, 1H), 2.13-2.07 (m, 1H), 1.14-1.04 (m, 4H).

Step 2: 2-cyclopropyl-7-iodo-1-benzofuran-5-amine

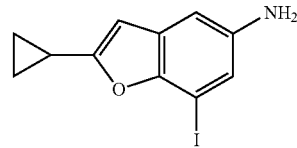 [SMILES: Nc1cc(I)c2oc(C3CC3)cc2c1]

To a solution of the title compound from Step 1 (2.0 g, 6.0 mmol) and Fe (1.0 g, 18 mmol) in MeOH (80 mL) was added sat. NH₄Cl solution (10 mL). The reaction mixture was refluxed for 1 h. The mixture was cooled to room temperature and poured into 400 mL of DCM. The resulting mixture was filtered and the filtrate was washed with water (100 mL) and brine. The organic layer was dried over anhydrous Na₂SO₄, filtered and concentrated under reduced pressure to give the crude title compound (1.5 g, 83% yield) as red oil that was used for the next step directly. ¹H NMR (CDCl₃, 400 MHz): δ 6.87 (d, J=2.4 Hz, 1H), 6.61 (d, J=2.0 Hz, 1H), 6.19 (s, 1H), 3.45 (br, 2H), 1.97-1.90 (m, 1H), 0.95-0.85 (m, 4H). LCMS: 300 (M+1)⁺.

Step 3: N-(2-cyclopropyl-7-iodo-1-benzofuran-5-yl) ethanesulfonamide

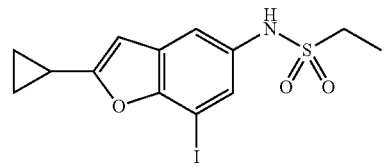 [SMILES: CCS(=O)(=O)Nc1cc(I)c2oc(C3CC3)cc2c1]

To a solution of the title compound from Step 2 (1.0 g, 3.3 mmol) in 20 mL of dry DCM was added a solution of pyridine (793 mg, 10 mmol) in DCM (10 mL), followed by addition of EtSO₂Cl (473 mg, 3.7 mmol). The reaction mixture was stirred at room temperature for 1 h. It was diluted with DCM (20 mL) and washed with water (20 mL×2) and brine. The organic layer was dried over Na₂SO₄, filtered and concentrated under reduced pressure to give the crude title compound (1.3 g, 100% yield) that was used directly in the next step. ¹H NMR (CDCl₃, 400 MHz): δ 7.42 (d, J=2.0 Hz, 1H), 7.38 (d, J=2.0 Hz, 1H), 6.88 (br, 1H), 6.40 (s, 1H), 3.09 (q, J=7.2 Hz, 2H), 1.37 (t, J=7.2 Hz, 3H), 2.04-2.08 (m, 1H), 1.06-0.97 (m, 4H). LCMS: 409 (M+18)⁺.

Step 4: N-[2-cyclopropyl-7-(1,5-dimethyl-6-oxopyridin-3-yl)-1-benzofuran-5-yl]ethanesulfonamide

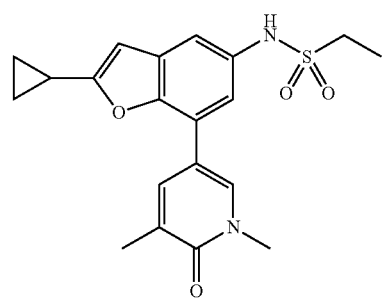

To a solution of the title compound from Step 3 (500 mg, 1.3 mmol) and 1,3-dimethyl-5-(4,4,5,5-tetramethyl-1,3,2-dioxaborolan-2-yl)pyridin-2-one (380 mg, 1.5 mmol) in 10 mL of DMF was added $K_2CO_3$ (50 mg, 3.8 mmol), water (2 mL) and Pd(dppf)$Cl_2$ (30 mg) under $N_2$. The reaction mixture was heated to 100° C. for 1 h. The resulting mixture was poured into 100 mL of water and extracted with DCM (100 mL×2). The combined organic layers were dried over anhydrous sodium sulfate, filtered and concentrated under reduced pressure. The residue was purified by column chromatography on silica gel eluting with EtOAc to give the title compound (230 mg, 47% yield) as a white solid. $^1$H NMR (CDCl$_3$, 400 MHz): δ 7.81 (d, J=3.6 Hz, 1H), 7.67-7.66 (m, 1H), 7.26 (t, J=1.2 Hz, 1H), 7.12 (d, J=3.2 Hz, 1H), 6.54 (br, 1H), 6.36 (d, J=0.8 Hz, 1H), 3.67 (s, 3H), 3.14-3.06 (m, 2H), 2.25 (s, 3H), 2.11-2.00 (m, 1H), 1.38-1.43 (m, 3H), 1.09-0.92 (m, 4H). LCMS: 387 (M+1)$^+$.

Step 5: N-[7-(1,5-dimethyl-6-oxopyridin-3-yl)-2-propyl-2,3-dihydro-1-benzofuran-5-yl]ethanesulfonamide

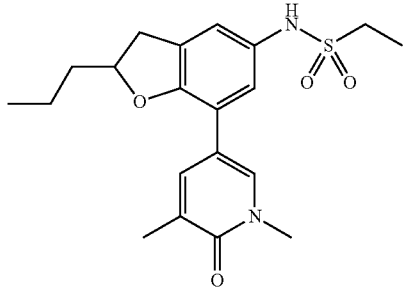 [SMILES: CCCC1Cc2cc(NS(=O)(=O)CC)cc(-c3cc(C)c(=O)n(C)c3)c2O1]

A mixture of the title compound from Step 4 (70 mg, 0.18 mmol) and 10 mg of Pd/C in 40 mL of MeOH was stirred under a $H_2$ atmosphere at room temperature for 1 h. The resulting mixture was filtered and the filtrate was concentrated under reduced pressure. The residue was purified by prep-HPLC to give the title compound (10 mg, 14% yield) as a white solid. $^1$H NMR (CDCl$_3$, 300 MHz): δ 7.77 (d, J=2.1 Hz, 1H), 7.56 (s, 1H), 7.04 (s, 1H), 7.01 (s, 1H), 6.26 (d, J=2.7 Hz, 1H), 4.88-4.84 (m, 1H), 3.61 (s, 3H), 3.34-3.26 (m, 1H), 3.09 (q, J=7.5 Hz, 2H), 2.90-2.84 (m, 1H), 2.21 (s, 3H), 1.87-1.82 (m, 1H), 1.72-1.63 (m, 1H), 1.56-1.43 (m, 2H), 1.38 (t, J=7.2 Hz, 3H), 0.98 (t, J=7.5 Hz, 3H). LCMS: 391 (M+1)$^+$.

Example 496

N-[2-cyclopropyl-7-(1,5-dimethyl-6-oxopyridin-3-yl)-2,3-dihydro-1-benzofuran-5-yl]ethanesulfonamide

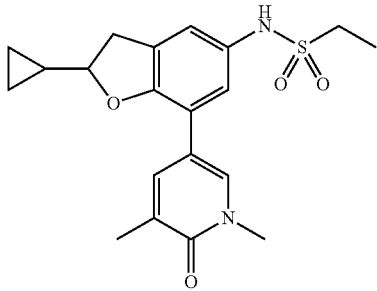

To a mixture of the title compound from Example 495, Step 4, (30 mg, 0.08 mmol) in Et$_3$SiH (1 mL) in a sealed tube was added TFA (0.2 mL) at 0° C. It was allowed to warm up to room temperature and stirred overnight. The resulting mixture was diluted with DCM (30 mL) and washed with 1 N NaOH, water and brine. The organic phase was dried over Na$_2$SO$_4$, filtered and concentrated under reduced pressure. The residue was recrystallized from EtOAc to give the title compound (3 mg, 10% yield) as a white solid. $^1$H NMR (CDCl$_3$, 300 MHz): δ 7.77 (s, 1H), 7.57 (s, 1H), 7.04 (d, J=3.0 Hz, 2H), 6.44 (s, 1H), 4.37-4.29 (m, 1H), 3.63 (s, 3H), 3.37-3.29 (m, 1H), 3.13-3.03 (m, 3H), 2.22 (s, 3H), 1.40 (t, J=7.5 Hz, 3H), 1.26-1.14 (m, 1H), 0.71-0.33 (m, 4H). LCMS: 389 (M+1)$^+$.

Example 497

4-[3-(methoxymethyl)-7-methylsulfonyl-2,3-dihydro-1,4-benzodioxin-5-yl]-2-methylisoquinolin-1-one Step 1: (6-bromo-2,3-dihydro-1,4-benzodioxin-2-yl)methanol and (6-bromo-2,3-dihydro-1,4-benzodioxin-3-yl)methanol

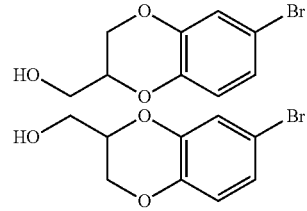

To a mixture of NaOH (1.6 g, 39.7 mmol) in THF (120 mL) and H$_2$O (40 mL) was added 4-bromobenzene-1,2-diol (5 g, 26.5 mmol). Oxiran-2-ylmethanol (7.35 g, 79.5 mmol) was added in portion wise at room temperature under N$_2$. The reaction was stirred at 100° C. for 4 hrs. It was then cooled down to rt and extracted with EtOAc (50 mL×2). The organic layers were washed with brine (40 mL×2), dried over anhydrous Na$_2$SO$_4$, filtered and concentrated under reduced pressure. The residue was purified by column chromatography on silica gel (PE/EA=5/1) to give a mixture of the title compounds (4.7 g, 73%). LCMS: 166 (M−80)$^+$.

Step 2: (6-methylsulfonyl-2,3-dihydro-1,4-benzodioxin-2-yl)methanol and (6-methylsulfonyl-2,3-dihydro-1,4-benzodioxin-3-yl)methanol

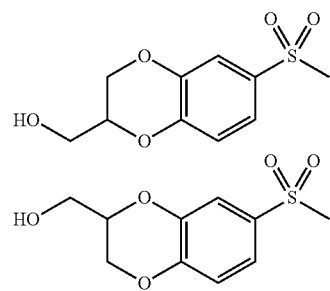

The mixture from Step 1 (1 g, 4.08 mmol) was submitted to the experimental conditions described in Example 486, Step 1, to give a mixture of the title compounds (650 mg, 65%). LCMS: 245.1 (M+1)⁺.

Step 3: 2-(methoxymethyl)-6-methylsulfonyl-2,3-dihydro-1,4-benzodioxine and 3-(methoxymethyl)-6-methylsulfonyl-2,3-dihydro-1,4-benzodioxine

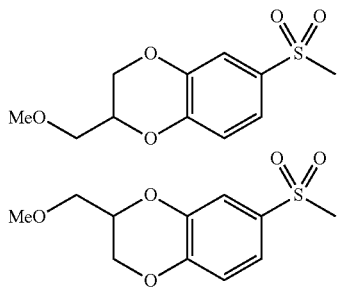

To a solution of the mixture from Step 2 (2.5 g, 10.23 mmol) in THF (30 mL) was added NaH (614 mg, 15.35 mmol) at 0° C. The reaction was stirred at 0° C. for 1 hr. CH₃I (1.45 g, 10.23 mmol) was added to the reaction mixture while keeping the internal temperature around 0° C. The reaction mixture was stirred at room temperature for another 3 hrs. It was then quenched with ice and extracted with EtOAc (30 mL×3). The combined organic phases were washed with saturated brine (20 mL×2), dried over anhydrous Na₂SO₄, filtered and concentrated under reduced pressure. The residue was purified by column chromatography on silica gel (PE/EA=3/1) to give a mixture of the title compounds (1.5 g, 57%) as an oil. The mixture was further separated into its four individual components by chiral phase SFC to give the two enantiomers of 2-(methoxymethyl)-6-methylsulfonyl-2,3-dihydro-1,4-benzodioxine (200 mgs each) and the two enantiomers of 3-(methoxymethyl)-6-methylsulfonyl-2,3-dihydro-1,4-benzodioxine (200 and 120 mgs, respectively). Their absolute stereochemistry was not assigned. 2-(methoxymethyl)-6-methylsulfonyl-2,3-dihydro-1,4-benzodioxine ¹H NMR (CDCl₃, 400 MHz) δ 7.44 (d, J=1.6 Hz, 1H), 7.41 (dd, J₁=8.8 Hz, J₂=2.0 Hz, 1H), 7.03 (d, J=8.0 Hz, 1H), 4.42-4.31 (m, 2H), 4.10 (dd, J₁=11.6 Hz, J₂=7.6 Hz, 1H), 3.71-3.58 (m, 2H), 3.42 (s, 3H), 3.01 (s, 3H). LCMS: 259 (M+1)⁺. 3-(methoxymethyl)-6-methylsulfonyl-2,3-dihydro-1,4-benzodioxine ¹H NMR (CDCl3, 400 MHz) δ 7.47 (d, J=2.0 Hz, 1H), 7.41 (dd, J₁=8.8 Hz, J₂=2.0 Hz, 1H), 7.00 (d, J=8.4 Hz, 1H), 4.40-4.30 (m, 2H), 4.18-4.10 (dd, J₁=11.2 Hz, J₂=7.2 Hz, 1H), 3.70-3.58 (m, 2H), 3.42 (s, 3H), 3.00 (s, 3H). LCMS: 259 (M+1)⁺.

Step 4: 5-bromo-3-(methoxymethyl)-7-methylsulfonyl-2,3-dihydro-1,4-benzodioxine

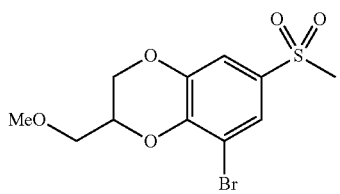 [SMILES: COCC1COc2cc(S(C)(=O)=O)cc(Br)c2O1]

The title compound (single enantiomer, absolute stereochemistry not assigned) was prepared in a manner similar to Example 486, Step 2, by substituting 2-(methoxymethyl)-6-methylsulfonyl-2,3-dihydro-1,4-benzodioxine for 2-methyl-5-methylsulfonyl-2,3-dihydro-1-benzofuran. ¹H NMR (CDCl₃, 400 MHz) δ 7.70 (d, J=2.0 Hz, 1H), 7.46 (d, J=2.0 Hz, 1H), 4.53 (dd, J₁=2.2 Hz, J₂=11.4 Hz, 1H), 4.39-4.34 (m, 1H), 4.26-4.21 (m, 1H), 3.73-3.63 (m, 2H), 3.45 (s, 3H), 3.03 (s, 3H).

Step 5: 4-[3-(methoxymethyl)-7-methylsulfonyl-2,3-dihydro-1,4-benzodioxin-5-yl]-2-methylisoquinolin-1-one

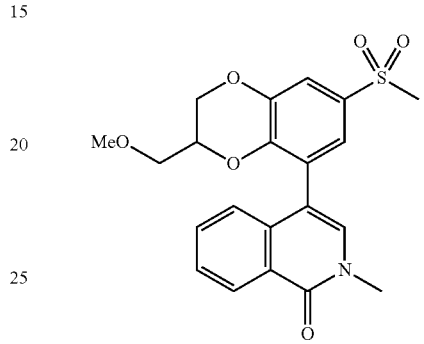

A mixture of the title compound from Step 4 (20 mg, 0.06 mmol), 2-methyl-4-(4,4,5,5-tetramethyl-1,3,2-dioxaborolan-2-yl)isoquinolin-1-one (20 mg, 0.07 mmol), Na₂CO₃ (19 mg, 0.18 mmol), Pd(dppf)Cl₂ (7 mg, 0.01 mmol) in dioxane (2 mL) and H₂O (0.2 mL) was stirred at 80° C. for 12 hrs under N₂. The reaction mixture was poured over H₂O (10 mL) and extracted with EtOAc (3×10 mL). The combined organic phases were washed with brine (10 mL), dried over anhydrous Na₂SO₄, filtered and concentrated under reduced pressure to give a residue that was purified by column chromatography followed by prep-HPLC to afford the title compound (12 mg, 24%). Absolute stereochemistry not assigned. ¹H NMR (DMSO-d6, 400 MHz) δ 8.30 (d, J=8.0 Hz, 1H), 7.68-7.63 (m, 1H), 7.55-7.52 (m, 3H), 7.42 (s, 1H), 7.28 (d, J=8.4 Hz, 1H), 4.43-4.35 (m, 2H), 4.21-4.12 (m, 1H), 3.56 (s, 3H), 3.44-3.41 (m, 2H), 3.23 (s, 3H), 3.09 (s, 3H). LCMS: 416.0 (M+H)⁺

Example 498

5-[3-(methoxymethyl)-7-methylsulfonyl-2,3-dihydro-1,4-benzodioxin-5-yl]-1,3-dimethylpyridin-2-one

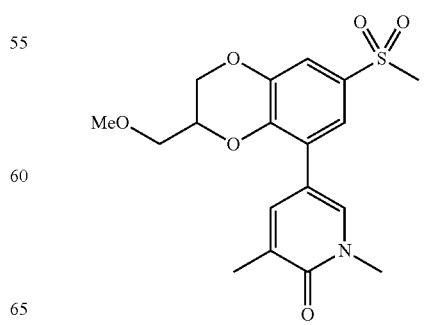

The title compound (single enantiomer, absolute stereochemistry not assigned) was prepared in a manner similar to Example 497, by substituting 1,3-dimethyl-5-(4,4,5,5-tetramethyl-1,3,2-dioxaborolan-2-yl)pyridin-2-one for 2-methyl-4-(4,4,5,5-tetramethyl-1,3,2-dioxaborolan-2-yl)isoquinolin-1-one in Step 5. $^1$H NMR (CDCl$_3$, 400 MHz) δ 7.53 (s, 1H), 7.49 (s, 1H), 7.43 (m, 2H), 4.45-4.37 (m, 2H), 4.18-4.17 (m, 1H), 3.68-3.62 (m, 5H), 3.44 (s, 3H), 3.07 (s, 3H), 2.21 (s, 3H). LCMS: 380 (M+H)$^+$ Example 499

4-[3-(methoxymethyl)-7-methylsulfonyl-2,3-dihydro-1,4-benzodioxin-5-yl]-2-methylisoquinolin-1-one

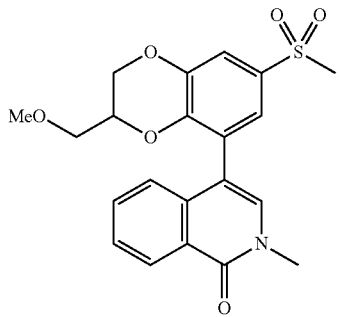 [SMILES: COCC1COc2cc(S(C)(=O)=O)cc(-c3cn(C)c(=O)c4ccccc34)c2O1]

The title compound (single enantiomer, absolute stereochemistry not assigned) was prepared in a manner similar to Example 497, by substituting the compound used in Step 4 for its enantiomer. $^1$H NMR (DMSO-d6, 400 MHz) δ 8.30 (d, J=8.0 Hz, 1H), 7.68 (t, J=8.0 Hz, 1H), 7.55-7.51 (m, 3H), 7.42 (s, 1H), 7.28 (d, J=8.0 Hz, 1H), 4.42-4.35 (m, 2H), 4.21-4.14 (m, 1H), 3.56 (s, 3H), 3.44-3.39 (m, 2H), 3.24 (s, 3H), 3.09 (s, 3H). LCMS: 416.0 (M+H)$^+$ Example 500

5-[3-(methoxymethyl)-7-methylsulfonyl-2,3-dihydro-1,4-benzodioxin-5-yl]-1,3-dimethylpyridin-2-one

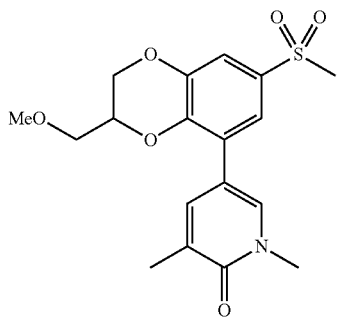 [SMILES: COCC1COc2cc(S(C)(=O)=O)cc(-c3cc(C)c(=O)n(C)c3)c2O1]

The title compound (single enantiomer, absolute stereochemistry not assigned) was prepared in a manner similar to Example 498 but using the other enantiomer of 5-bromo-3-(methoxymethyl)-7-methylsulfonyl-2,3-dihydro-1,4-benzodioxine. $^1$H NMR (CDCl$_3$, 400 MHz) δ 7.59 (s, 1H), 7.58 (s, 1H), 7.44 (m, 2H), 4.41-4.37 (m, 2H), 4.20-4.18 (m, 1H), 3.71-3.63 (m, 5H), 3.44 (s, 3H), 3.07 (s, 3H), 2.24 (s, 3H). LCMS: 380.0 (M+H)$^+$ Example 501

4-[2-(methoxymethyl)-7-methylsulfonyl-2,3-dihydro-1,4-benzodioxin-5-yl]-2-methylisoquinolin-1-one Step 1: 5-bromo-2-(methoxymethyl)-7-methylsulfonyl-2,3-dihydro-1,4-benzodioxine

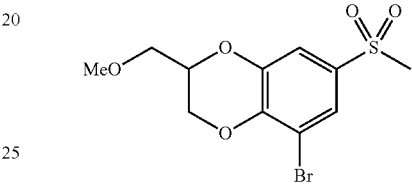

The title compound (single enantiomer, absolute stereochemistry not assigned) was prepared in a manner similar to Example 497, Step 4, by substituting 2-(methoxymethyl)-6-methylsulfonyl-2,3-dihydro-1,4-benzodioxine for 3-(methoxymethyl)-6-methylsulfonyl-2,3-dihydro-1,4-benzodioxine. LCMS: 359 (M+23)$^+$ Step 2: 4-[2-(methoxymethyl)-7-methylsulfonyl-2,3-dihydro-1,4-benzodioxin-5-yl]-2-methylisoquinolin-1-one

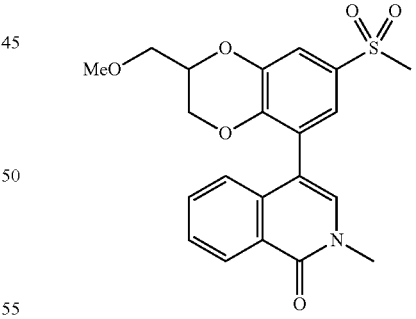

The title compound (single enantiomer, absolute stereochemistry not assigned) was prepared in a manner similar to Example 497, Step 5, by substituting 5-bromo-2-(methoxymethyl)-7-methylsulfonyl-2,3-dihydro-1,4-benzodioxine for 5-bromo-3-(methoxymethyl)-7-methylsulfonyl-2,3-dihydro-1,4-benzodioxine. $^1$H NMR (DMSO-d6, 400 MHz) δ 8.31 (d, J=8.0 Hz, 1H), 7.66-7.63 (m, 1H), 7.56-7.51 (m, 3H), 7.40 (s, 1H), 7.30-7.16 (m, 1H), 4.53-4.44 (m, 1H), 4.36-4.28 (m, 1H), 4.12-4.01 (m, 1H), 3.61-3.56 (m, 5H), 3.34 (s, 3H), 3.24 (s, 3H). LCMS: 416.0 (M+H)$^+$

Example 502

5-[2-(methoxymethyl)-7-methylsulfonyl-2,3-dihydro-1,4-benzodioxin-5-yl]-1,3-dimethylpyridin-2-one

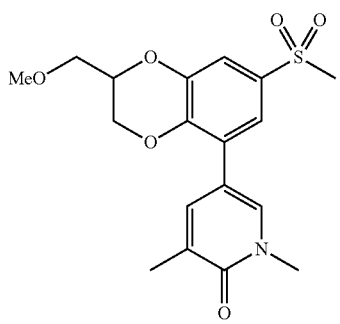 [SMILES: COCC1COc2c(cc(S(C)(=O)=O)cc2-c2cc(C)c(=O)n(C)c2)O1]

The title compound (single enantiomer, absolute stereochemistry not assigned) was prepared in a manner similar to Example 501, by substituting 1,3-dimethyl-5-(4,4,5,5-tetramethyl-1,3,2-dioxaborolan-2-yl)pyridin-2-one for 2-methyl-4-(4,4,5,5-tetramethyl-1,3,2-dioxaborolan-2-yl)isoquinolin-1-one. $^1$H NMR (CDCl$_3$, 400 MHz) δ 7.48 (m, 3H), 7.41 (d, J=2.4 Hz, 1H), 4.47-4.34 (m, 2H), 4.19-4.16 (m, 1H), 3.71-3.65 (m, 5H), 3.45 (s, 3H), 3.05 (s, 3H), 2.22 (s, 3H). LCMS: 380.0 (M+H)$^+$

Example 503

4-[2-(methoxymethyl)-7-methylsulfonyl-2,3-dihydro-1,4-benzodioxin-5-yl]-2-methylisoquinolin-1-one

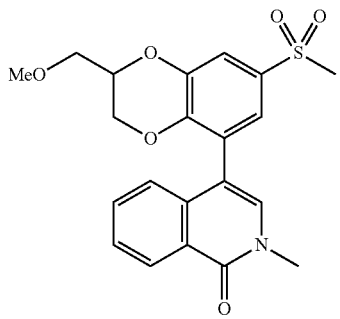 [SMILES: COCC1COc2c(cc(S(C)(=O)=O)cc2-c2cn(C)c(=O)c3ccccc23)O1]

The title compound (single enantiomer, absolute stereochemistry not assigned) was prepared in a manner similar to Example 501, by substituting the compound used in Step 1 for its enantiomer. $^1$H NMR (CD$_3$OD, 400 MHz) δ 8.41 (d, J=8.0 Hz, 1H), 7.70 (t, J=7.6 Hz, 1H), 7.58-7.54 (m, 2H), 7.48 (s, 1H), 7.42 (s, 1H), 7.33-7.30 (m, 1H), 4.52-4.41 (m, 2H), 4.20-4.12 (m, 1H), 3.67 (s, 3H), 3.47 (m, 2H), 3.19-3.15 (m, 6H). LCMS: 416.0 (M+H)$^+$

Example 504

4-[2-(cyclopropylmethoxy)-5-methylsulfonylphenyl]-2-methyl-6,7-dihydro-5H-cyclopenta[c]pyridin-1-one

Step 1: ethyl 6,7-dihydro-5H-cyclopenta[c]pyridine-1-carboxylate

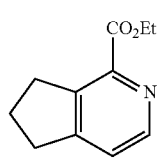 [SMILES: CCOC(=O)c1nccc2c1CCC2]

Ethyl 1,2,4-triazine-3-carboxylate (7 g, 45.8 mmol), cyclopentanone (4.9 mL, 55.0 mmol), and pyrrolidine (4.6 mL, 55.0 mmol) in toluene (100 mL) were heated to reflux for 12 h. The mixture was purified by column on silica gel chromatography (PE/EtOAc=5:1) to give the title compound (2.02 g, 25%) as a brown oil. LCMS: 192 (M+1)$^+$

Step 2: 6,7-dihydro-5H-cyclopenta[c]pyridine-1-carboxylic acid

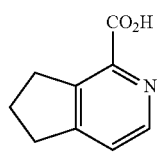 [SMILES: O=C(O)c1nccc2c1CCC2]

A 2N solution of LiOH (50 mL) in water was slowly added to the title compound of step 1 (10 g, 52.4 mmol) in MeOH (250 mL) at 0° C. The mixture was allowed to warm to rt and stirred for 30 min. The MeOH was reduced under vacuum and the residual aqueous solution was washed with EtOAc. The organic phase was re-extracted with water. The combined aqueous extracts were acidified to pH=2 with 1N HCl. The water was removed and preparative HPLC gave the title compound (5.4 g, 63%) as a white solid. $^1$H NMR (CD$_3$OD, 400 MHz): δ 8.45 (d, J=5.6 Hz, 1H), 7.88 (d, J=5.6 Hz, 1H), 3.39 (t, J=8.0, 7.6 Hz, 2H), 3.16 (d, t, J=8.0, 7.6 Hz, 2H), 2.16-2.20 (m, 2H).

Step 3: tert-butyl N-(6,7-dihydro-5H-cyclopenta[c]pyridin-1-yl)carbamate

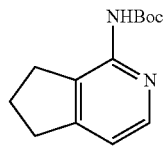 [SMILES: CC(C)(C)OC(=O)Nc1nccc2c1CCC2]

The title compound of step 2 (1.0 g, 6.1 mmol), diphenylphosphoryl azide (2.64 mL 12.2 mmol), and triethylamine (1.64 mL, 12.2 mmol) in tBuOH (50 mL) under N$_2$ were heated at 80° C. for 2 h. Silica gel chromatography (PE/

EtOAc=5:1) gave the title compound (570 mg, 40%) as a white solid. $^1$H NMR (CDCl$_3$, 300 MHz): δ 8.18 (d, J=4.8 Hz, 1H), 7.04 (d, J=4.8 Hz, 1H), 2.90-2.97 (m, 4H), 2.06-2.12 (m, 2H), 1.49 (s, 9H). LCMS: 235 (M+1)$^+$ Step 4:
6,7-dihydro-5H-cyclopenta[c]pyridin-1-amine hydrochloride

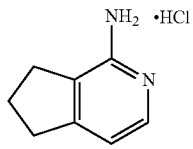

Anhydrous 1M HCl in DCM (20 mL) was added slowly to the title compound of step 3 (570 mg, 2.43 mmol) in DCM (10 mL) at 0° C. After stirring at rt for 1.5 h, evaporation of the volatile components gave the title compound (400 mg, 96%) as a white solid. $^1$H NMR (CD$_3$OD, 300 MHz): δ 7.66 (d, J=6.6 Hz, 1H), 6.88 (d, J=6.6 Hz, 1H), 3.04 (t, J=7.8, 7.2 Hz, 2H), 2.86 (t, J=7.8, 7.2 Hz, 2H), 2.17-2.27 (m, 2H). LCMS: 135 (M+1)$^+$ Step 5:
2,5,6,7-tetrahydrocyclopenta[c]pyridin-1-one

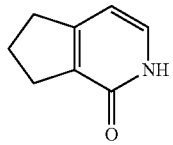

The title compound of step 4 (400 mg, 2.33 mmol) was dissolved in water (6.5 mL) and H$_3$PO$_2$ (2 mL, 50% w/w in water, 18.64 mmol) was added. The mixture was cooled to 0° C. and a solution of NaNO$_2$ (180 mg 2.68 mmol) in water (6.5 mL) was added dropwise. The mixture was stirred at 0° C. for 1 h and then at room temperature overnight. The pH was adjusted to about 7 by careful addition of NaHCO$_3$. Extractive work up using ethyl acetate gave the title compound (300 mg, 95%) as a yellow solid. $^1$H NMR (CDCl$_3$, 300 MHz): δ 12.55 (s, 1H), 7.24 (d, J=6.3 Hz, 1H), 6.26 (d, J=6.3 Hz, 1H), 2.84-2.89 (m, 4H), 2.04-2.11 (m, 2H). LCMS: 136 (M+1)$^+$ Step 6:
2-methyl-6,7-dihydro-5H-cyclopenta[c]pyridin-1-one

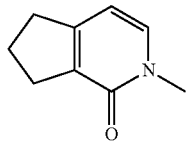

The title compound of step 5 (260 mg, 1.93 mmol) was dissolved in DMF (5 mL) and cooled to 0° C. NaH (94 mg, 2.31 mmol) was added and the mixture was stirred for 30 min. Methyl iodide (146 μL, 2.31 mmol) was added and the mixture stirred at rt for 2 h. The volatile components were removed under vacuum and silica gel chromatography (PE/EtOAc=1:1) gave the title compound (192.6 mg, 67%) as a brown oil. $^1$H NMR (CD$_3$Cl, 300 MHz): δ 7.13 (d, J=6.6 Hz, 1H), 6.13 (d, J=6.6 Hz, 1H), 3.53 (s, 3H), 2.79-2.85 (m, 4H), 2.01-2.11 (m, 2H). LCMS: 150 (M+1)$^+$ Step 7: 4-bromo-2-methyl-6,7-dihydro-5H-cyclopenta[c]pyridin-1-one

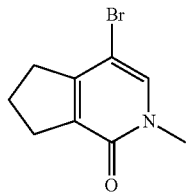

The title compound of step 6 (140 mg, 1.04 mmol) was dissolved in ACN (5 mL) and NBS (188 mg, 1.06 mmol) was added. After stirring at rt for 1.5 h, purification by silica gel chromatography (PE/EtOAc=1:1) gave the title compound (196 mg, 89.5%) as a white solid. $^1$H NMR (CD$_3$Cl, 300 MHz): δ 7.33 (s, 1H), 3.53 (s, 3H), 2.85-2.97 (m, 4H), 2.05-2.13 (m, 2H). LCMS: 228, 230 (M+1)$^+$ Step 8: 4-[2-(cyclopropylmethoxy)-5-methylsulfonylphenyl]-2-methyl-6,7-dihydro-5H-cyclopenta[c]pyridin-1-one

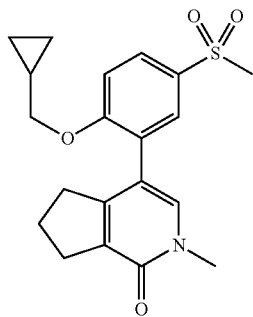 [SMILES: Cn1cc(-c2cc(S(C)(=O)=O)ccc2OCC2CC2)c2c(c1=O)CCC2]

To a solution of the title compound of step 7 (60 mg, 0.26 mmol), the title compound of Example 90, step 1 (111.2 mg, 0.32 mmol) and K$_2$CO$_3$ (107 mg, 0.78 mmol) in dioxane (4 mL) and water (1 mL) was added Pd(dppf)Cl$_2$ (6 mg) under N$_2$. The mixture was heated at 85° C. overnight. EA extractive work up followed by prep-TLC (DCM/MeOH=25:1) gave the title compound (47 mg, 48%) as a yellow solid. $^1$H NMR (DMSO-d$_6$, 300 MHz): δ 7.83 (dd, J=8.7, 2.7 Hz, 1H), 7.66 (d, J=2.9 Hz, 1H), 7.58 (s, 1H), 7.25 (d, J=8.7 Hz, 1H), 3.95 (d, J=6.9 Hz, 2H), 3.46 (s, 3H), 3.17 (s, 3H), 2.65-2.70 (m, 4H), 1.91-1.97 (m, 2H), 1.13-1.18 (m, 1H), 0.50-0.54 (m, 2H), 0.26-0.30 (m, 2H). LCMS: 374 (M+1)$^+$

Example 505

4-[2-(cyclopropylmethoxy)-5-ethylsulfonylphenyl]-2-methyl-6,7-dihydro-5H-cyclopenta[c]pyridin-1-one

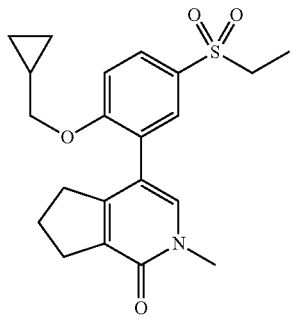 [SMILES: CCS(=O)(=O)c1ccc(OCC2CC2)c(-c2cn(C)c(=O)c3c2CCC3)c1]

The title compound was prepared in a similar manner to Example 504, step 8 except that 2-[2-(cyclopropylmethoxy)-5-ethylsulfonylphenyl]-4,4,5,5-tetramethyl-1,3,2-dioxaborolane was substituted for the title compound of Example 90, step 1. $^1$H NMR (CD3OD, 400 MHz): δ 7.91 (dd, J=8.4, 2.0 Hz, 1H), 7.73 (d, J=2.0 Hz, 1H), 7.56 (s, 1H), 7.27 (d, J=8.4 Hz, 1H), 4.01 (d, J=6.8 Hz, 2H), 3.66 (s, 3H), 3.23 (q, J=7.6 Hz, 2H), 2.88 (t, J=7.6 Hz, 2H), 2.82 (t, J=7.6 Hz, 2H), 2.08-2.14 (m, 2H), 1.26 (t, J=7.6 Hz, 3H), 1.08-1.27 (m, 1H), 0.60-0.65 (m, 2H), 0.33-0.37 (m, 2H). LCMS: 388 (M+1)$^+$

Example 506

N-[4-(2,4-difluorophenoxy)-3-(2-methyl-1-oxo-6,7-dihydro-5H-cyclopenta[c]pyridin-4-yl)phenyl]methanesulfonamide

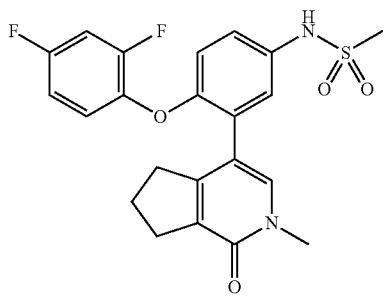 [SMILES: Cn1cc(-c2cc(NS(C)(=O)=O)ccc2Oc2ccc(F)cc2F)c2c(c1=O)CCC2]

The title compound was prepared in a similar manner to Example 504, step 8 except that N-[4-(2,4-difluorophenoxy)-3-(4,4,5,5-tetramethyl-1,3,2-dioxaborolan-2-yl)phenyl]methanesulfonamide was substituted for the title compound of Example 90, step 1. $^1$H NMR (DMSO-d6, 400 MHz): δ 9.72 (s, 1H), 7.58 (s, 1H), 7.34-7.42 (m, 1H), 7.24-7.10 (m, 2H), 7.00-7.08 (m, 2H), 6.91 (d, J=8.4 Hz, 1H), 3.43 (s, 3H), 3.01 (s, 3H), 2.71 (t, J=7.2 Hz, 2H), 2.65 (t, J=7.2 Hz, 2H), 1.88-1.96 (m, 2H). LCMS: 447 (M+1)$^+$

Example 507

N-[4-(2,4-difluorophenoxy)-3-(2-methyl-1-oxo-6,7-dihydro-5H-cyclopenta[c]pyridin-4-yl)phenyl]ethanesulfonamide

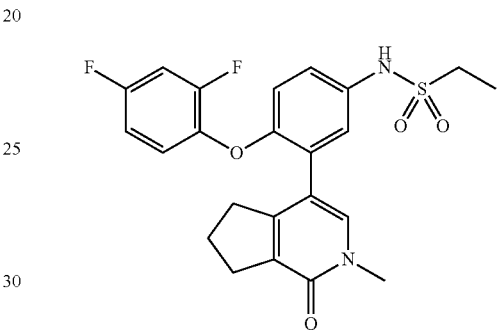

The title compound was prepared in a similar manner to Example 504, step 8 except that N-[4-(2,4-difluorophenoxy)-3-(4,4,5,5-tetramethyl-1,3,2-dioxaborolan-2-yl)phenyl]ethanesulfonamide was substituted for the title compound of Example 90, step 1. $^1$H NMR (CD$_3$Cl, 400 MHz): δ 7.30 (s, 1H), 7.19 (d, J=3.2 Hz, 1H), 7.14 (dd, J=8.8, 3.2 Hz, 1H), 6.89-6.96 (m, 2H), 6.79-6.85 (m, 1H); 6.77 (d, J=8.8 Hz, 1H), 6.60 (s, 1H), 3.65 (s, 3H), 3.15 (q, J=7.6 Hz, 2H), 2.96 (t, J=7.6 Hz, 2H), 2.82 (t, J=7.6 Hz, 2H), 2.02-2.06 (m, 2H), 1.41 (t, J=7.6 Hz, 3H). LCMS: 461 (M+1)$^+$

Examples 508-511

Examples 508-511 as described in Table 22 were prepared in three steps. Using conditions similar to those described in WO2005/40151 (Preparation 6), 5-bromo-3-methylpyridin-2-ol was N-alkylated with isopropyl bromide to give 5-bromo-3-methyl-1-propan-2-ylpyridin-2-one which was then reacted with 4,4,5,5-tetramethyl-2-(tetramethyl-1,3,2-dioxaborolan-2-yl)-1,3,2-dioxaborolane using conditions similar to those described in Example 248, step 2 to give the pinacol ester, 3-methyl-1-propan-2-yl-5-(4,4,5,5-tetramethyl-1,3,2-dioxaborolan-2-yl)pyridin-2-one. This pinacol ester was then substituted for the pinacol ester of the example shown under Synthetic Method in Table 22 and reacted in the same way as the example to obtain the title compounds.

TABLE 22

| Ex. No. | R¹ | Name | MS (M + H) | Synthetic Method |
|---|---|---|---|---|
| 508 | MeO₂S-pyrimidinyl-butyl | 5-(5-butyl-2-methylsulfonylpyrimidin-4-yl)-3-methyl-1-propan-2-ylpyridin-2-one | 364 | Example 305 |
| 509 | EtO₂SHN-pyrimidinyl-O-(2,4-difluorophenyl) | N-[5-(2,4-difluorophenoxy)-4-(5-methyl-6-oxo-1-propan-2-ylpyridin-3-yl)pyrimidin-2-yl]ethanesulfonamide | 465 | Example 169 |
| 510 | MeO₂S-pyrimidinyl-O-(2,4-difluorophenyl) | 5-[5-(2,4-difluorophenoxy)-2-methylsulfonylpyrimidin-4-yl]-3-methyl-1-propan-2-ylpyridin-2-one | 436 | Example 149, step 4 |
| 511 | EtO₂SHN-pyrimidinyl-butyl | N-[5-butyl-4-(5-methyl-6-oxo-1-propan-2-ylpyridin-3-yl)pyrimidin-2-yl]ethanesulfonamide | 393 | Example 310 |

Examples 512-514

Examples 512-514 as described in Table 23 were prepared in three steps. Using conditions similar to those described by Malhotra, et. al. in Organic Letters 2013, Vol. 15, No. 14, pp. 3698-3701 (supporting information, compounds 4c and 3a), 3,5-dibromo-1-methylpyridin-2-one was alkylated at the 3-position using isopropylmagnesium bromide to give 5-bromo-1-methyl-3-propan-2-ylpyridin-2-one which was then reacted with 4,4,5,5-tetramethyl-2-(tetramethyl-1,3,2-dioxaborolan-2-yl)-1,3,2-dioxaborolane using conditions similar to those described in Example 248, step 2 to give the pinacol ester, 1-methyl-3-propan-2-yl-5-(4,4,5,5-tetramethyl-1,3,2-dioxaborolan-2-yl)pyridin-2-one. This pinacol ester was then substituted for the pinacol ester of the example shown under Synthetic Method in Table 23 and reacted in the same way as the example to obtain the title compounds.

TABLE 23

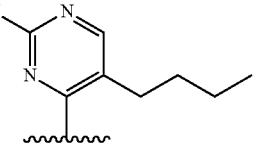

| Ex. No | R¹ | Name | MS (M + H) | Synthetic Method |
|---|---|---|---|---|
| 512 | 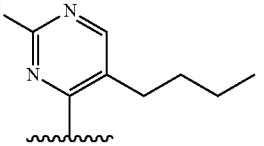 | N-[5-butyl-4-(1-methyl-6-oxo-5-propan-2-ylpyridin-3-yl)pyrimidin-2-yl]ethanesulfonamide | 393 | Example 310 |
| 513 | | 5-(5-butyl-2-methylsulfonylpyrimidin-4-yl)-1-methyl-3-propan-2-ylpyridin-2-one | 364 | Example 305 |
| 514 | 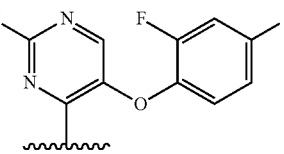 | N-[5-(2,4-difluorophenoxy)-4-(1-methy]-6-oxo-5-propan-2-ylpyridin-3-yl)pyrimidin-2-yl]ethanesulfonamide | 465 | Example 169 |

II. Biological Evaluation

Example 1

In Vitro Enzyme Inhibition Assay

Determination of the $IC_{50}$ for the heterocyclic derivative BRD4 inhibitors disclosed herein was performed as follows. His-tagged BRD4 was cloned, expressed and purified to homogeneity (P. Filipakopoulos et al. Nature 468, 1067-1073, 2010). BRD4 binding and inhibition was assessed by monitoring the interaction of biotinylated $H_4$-tetraacetyl peptide (AnaSpec, $H_4K5/8/12/16(Ac)$, biotin-labeled) with the target using the AlphaScreen technology (Life Technologies). In a 384-well ProxiPlate BRD4(BD1) (2 nM final) was combined with peptide (15 nM final) in 50 mM HEPES (pH 7.3), 10 mM NaCl, 0.25 mM TCEP, 0.1% (w/v) BSA, and 0.005% (w/v) Brij-35 either in the presence of DMSO (final 0.4% DMSO) or compound dilution series in DMSO. After 20 minute incubation at room temperature, Alpha streptavidin donor beads and Nickel Chelate acceptor beads were added to a final concentration of 5 g/mL. After two hours of equilibration, plates were read on an Envision instrument and the $IC_{50}$ was calculated using a four parameter non-linear curve fit. Chemistry Example 1 (2-methyl-4-phenylisoquinolin-1-one) had an $IC_{50}$ of 2.782 M in this assay format.

The ability of the compounds disclosed herein to inhibit BRD4 activity was quantified and the respective $IC_{50}$ value was determined. The $IC_{50}$ values of various compounds disclosed herein is provided in Table 24.

Example 2

In Vitro Cell-Based Assay

A colorimetric cellular proliferation assay (Cell-MTS assay) was performed to assess the ability of the heterocyclic derivative BRD4 inhibitors disclosed herein to effect the proliferation of established cancer cell lines.

Assay Principle

The Cell-MTS assay is a 7-day plate-based colorimetric assay which quantifies the amount of newly generated NADH in the presence or absence of test compound. The NADH level is used for the quantification of cancer cell proliferation.

Assay Method

Established cancer cell lines with a variety of driving mutations were obtained from American Type Culture Collection (ATCC) and routinely passaged according to ATCC protocols. For routine assay, these cells were seeded at densities which enabled ~90% confluence after 7 days of culture. Raji, human Burkitts lymphoma cells, (cMYC) were seeded at 15,000 cells per 96-well. HL-60, human proleukemia cells, (NRAS, p16, p53, c-Myc amplified) were seeded at 5,000 cells per 96-well. $NCI-H_{460}$, human non-small cell lung cancer cells, (KRAS, PIK3CA, STLK11, p16) were seeded at 3,000 cells per 96-well. 24 hours after plating, cells received an 11 point dilution of test compound with final concentration ranges from 100 M to 2.0 nM. Cells were incubated in the presence of compound for 168 hours at 37° C., and 5% $CO_2$. At the end of this incubation period, 80 L of media is removed and 20 L of CellTiter 96® AQueous Non-Radioactive Cell Proliferation Assay solution (Promega) was added. The cells were incubated until the OD490 was >0.6. $IC_{50}$ values were calculated using the IDBS XLfit software package and include background subtracted OD490 values and normalization to DMSO controls. Cellular proliferation $IC_{50}$ values were uploaded and archived using the Chem Biography Platform.

Table 24 provides the results of the in vitro enzyme inhibition assay experiments and the in vitro cell-based assay experiments performed with the compounds disclosed herein.

TABLE 24

| Chemistry Synthesis Example | Name | BRD4 IC50 (μM) | Raji IC50 (μM) | HL-60 IC50 (μM) | H460 IC50 (μM) |
|---|---|---|---|---|---|
| 1 | 4-(3-methoxyphenyl)-2-methylisoquinolin-1-one | B | | | |
| 2 | 2-methyl-4-phenylisoquinolin-1-one | B | | | |
| 3 | 4-(2-fluorophenyl)-2-methylisoquinolin-1-one | C | | | |
| 4 | 4-(2-methoxyphenyl)-2-methylisoquinolin-1-one | C | | | |
| 5 | 4-(3-aminophenyl)-2-methylisoquinolin-1-one | B | | | |
| 6 | N-cyclopropyl-3-(2-methyl-1-oxoisoquinolin-4-yl)benzenesulfonamide | B | | | |
| 7 | 2-methyl-4-(3-pyrrolidin-1-ylsulfonylphenyl)isoquinolin-1-one | B | A | B | |
| 8 | N-[[3-(2-methyl-1-oxoisoquinolin-4-yl)phenyl]methyl]methanesulfonamide | B | | | |
| 9 | N-[3-(2-methyl-1-oxoisoquinolin-4-yl)phenyl]methanesulfonamide | A | A | A | C |
| 10 | N-ethyl-3-(2-methyl-1-oxoisoquinolin-4-yl)benzenesulfonamide | B | | | |
| 11 | 4-(3-ethylsulfonylphenyl)-2-methylisoquinolin-1-one | B | A | B | |
| 12 | 4-[3-(dimethylsulfamoylamino)phenyl]-2-methyl-1-oxoisoquinoline | A | A | A | |
| 13 | N-[3-(2-methyl-1-oxoisoquinolin-4-yl)phenyl]ethanesulfonamide | A | A | A | |
| 14 | 2-methyl-4-(3-morpholin-4-ylsulfonylphenyl)isoquinolin-1-one | B | | | |
| 15 | N-benzyl-2-methoxy-5-(2-methyl-1-oxoisoquinolin-4-yl)benzenesulfonamide | B | A | B | |
| 16 | 2-methoxy-5-(2-methyl-1-oxoisoquinolin-4-yl)benzenesulfonamide | B | | | |
| 17 | N-[2-methyl-5-(2-methyl-1-oxoisoquinolin-4-yl)phenyl]methanesulfonamide | A | B | A | |
| 18 | N-benzyl-2-methoxy-5-(2-methyl-1-oxoisoquinolin-4-yl)benzamide | B | B | B | |
| 19 | 4-(3,4-dihydro-2H-1,4-benzoxazin-6-yl)-2-methylisoquinolin-1-one | B | | | |
| 20 | 2-methyl-4-(2-oxo-1,3-dihydroindol-6-yl)isoquinolin-1-one | C | A | A | |
| 21 | 3-(2-methyl-1-oxoisoquinolin-4-yl)benzenesulfonamide | B | B | B | |
| 22 | N-(2-hydroxyethyl)-3-(2-methyl-1-oxoisoquinolin-4-yl)benzenesulfonamide | B | B | B | |
| 23 | 4-(5-amino-2-fluorophenyl)-2-methylisoquinolin-1-one | B | | | |
| 24 | 4-(5-amino-2,4-difluorophenyl)-2-methylisoquinolin-1-one | B | | | |
| 25 | 4-(3-amino-5-fluorophenyl)-2-methylisoquinolin-1-one | B | | | |
| 26 | 4-(3-amino-4-fluorophenyl)-2-methylisoquinolin-1-one | B | | | |
| 27 | N-benzyl-3-(2-methyl-1-oxoisoquinolin-4-yl)benzenesulfonamide | B | | | |
| 28 | N-[3-(2-methyl-1-oxoisoquinolin-4-yl)phenyl]propane-1-sulfonamide | A | B | B | |
| 29 | N-[3-(2-methyl-1-oxoisoquinolin-4-yl)phenyl]butane-1-sulfonamide | A | B | B | |
| 30 | N-[2-methoxy-5-(2-methyl-1-oxoisoquinolin-4-yl)phenyl]methanesulfonamide | A | B | A | |

TABLE 24-continued

| Chemistry Synthesis Example | Name | BRD4 IC50 (μM) | Raji IC50 (μM) | HL-60 IC50 (μM) | H460 IC50 (μM) |
|---|---|---|---|---|---|
| 31 | tert-butyl N-methyl-N-[3-(2-methyl-1-oxoisoquinolin-4-yl)phenyl]carbamate | B | B | B | |
| 32 | 2-methyl-4-[3-(methylamino)phenyl]isoquinolin-1-one | B | | | |
| 33 | N-methyl-N-[3-(2-methyl-1-oxoisoquinolin-4-yl)phenyl]methanesulfonamide | A | B | B | |
| 34 | N-[4-fluoro-3-(2-methyl-1-oxoisoquinolin-4-yl)phenyl]methanesulfonamide | A | A | A | |
| 35 | N-[2,4-difluoro-5-(2-methyl-1-oxoisoquinolin-4-yl)phenyl]methanesulfonamide | B | B | B | |
| 36 | N-[3-fluoro-5-(2-methyl-1-oxoisoquinolin-4-yl)phenyl]methanesulfonamide | B | B | B | |
| 37 | N-[2-fluoro-5-(2-methyl-1-oxoisoquinolin-4-yl)phenyl]methanesulfonamide | A | B | B | |
| 38 | N-[4-chloro-3-(2-methyl-1-oxoisoquinolin-4-yl)phenyl]methanesulfonamide | A | B | A | |
| 39 | N-[4-methyl-3-(2-methyl-1-oxoisoquinolin-4-yl)phenyl]methanesulfonamide | A | B | A | |
| 40 | N-[3-(2-methyl-1-oxoisoquinolin-4-yl)-5-(trifluoromethyl)phenyl]methanesulfonamide | B | B | B | |
| 41 | N-[4-fluoro-3-[2-methyl-6-(1-methylpyrazol-4-yl)-1-oxoisoquinolin-4-yl]phenyl]methanesulfonamide | A | A | A | |
| 42 | N-[3-[2-methyl-6-(1-methylpyrazol-4-yl)-1-oxoisoquinolin-4-yl]phenyl]methanesulfonamide | A | A | A | |
| 43 | N-[2,4-difluoro-5-[2-methyl-6-(1-methylpyrazol-4-yl)-1-oxoisoquinolin-4-yl]phenyl]methanesulfonamide | A | A | A | |
| 44 | 4-(3-ethylsulfonylphenyl)-2-methyl-6-(1-methylpyrazol-4-yl)isoquinolin-1-one | A | B | A | C |
| 45 | N-[4-chloro-3-[2-methyl-6-(1-methylpyrazol-4-yl)-1-oxoisoquinolin-4-yl]phenyl]ethanesulfonamide | A | A | A | B |
| 46 | 4-[2-(cyclopropylmethoxy)-5-methylsulfonylphenyl]-2-methyl-6-(1-methylpyrazol-4-yl)isoquinolin-1-one | A | A | A | C |
| 47 | N-[3-(6-fluoro-2-methyl-1-oxoisoquinolin-4-yl)phenyl]methanesulfonamide | A | A | A | |
| 48 | 3-(6-fluoro-2-methyl-1-oxoisoquinolin-4-yl)benzenesulfonamide | B | B | B | |
| 49 | N-ethyl-3-(6-fluoro-2-methyl-1-oxoisoquinolin-4-yl)benzenesulfonamide | B | B | B | |
| 50 | N-[4-chloro-3-(6-fluoro-2-methyl-1-oxoisoquinolin-4-yl)phenyl]ethanesulfonamide | A | B | A | B |
| 51 | N-[3-(2-methyl-1-oxo-2,7-naphthyridin-4-yl)phenyl]methanesulfonamide | B | C | B | |
| 52 | N-[3-(2-methyl-1-oxo-2,7-naphthyridin-4-yl)phenyl]ethanesulfonamide | B | B | B | |
| 53 | N-ethyl-3-(2-methyl-1-oxo-2,7-naphthyridin-4-yl)benzenesulfonamide | B | C | C | |

TABLE 24-continued

| Chemistry Synthesis Example | Name | BRD4 IC50 (μM) | Raji IC50 (μM) | HL-60 IC50 (μM) | H460 IC50 (μM) |
|---|---|---|---|---|---|
| 54 | N-benzyl-2-methoxy-5-(2-methyl-1-oxo-2,7-naphthyridin-4-yl)benzenesulfonamide | C | C | B | C |
| 55 | 3-(2-methyl-1-oxo-2,7-naphthyridin-4-yl)benzenesulfonamide | C | | | |
| 56 | 2-methoxy-5-(2-methyl-1-oxo-2,7-naphthyridin-4-yl)benzenesulfonamide | C | | | |
| 57 | N-[4-(2,4-difluorophenoxy)-3-(2-methyl-1-oxo-2,7-naphthyridin-4-yl)phenyl]ethanesulfonamide | A | A | A | C |
| 58 | N-[3-(7-fluoro-2-methyl-1-oxoisoquinolin-4-yl)phenyl]methanesulfonamide | A | B | A | |
| 59 | N-ethyl-3-(7-fluoro-2-methyl-1-oxoisoquinolin-4-yl)benzenesulfonamide | B | B | B | |
| 60 | N-benzyl-5-(7-fluoro-2-methyl-1-oxoisoquinolin-4-yl)-2-methoxybenzenesulfonamide | B | A | B | C |
| 61 | 3-(7-fluoro-2-methyl-1-oxoisoquinolin-4-yl)benzenesulfonamide | A | B | B | |
| 62 | N-[3-(7-fluoro-2-methyl-1-oxoisoquinolin-4-yl)phenyl]ethanesulfonamide | A | B | A | |
| 63 | 4-(3-ethylsulfonylphenyl)-7-fluoro-2-methylisoquinolin-1-one | B | B | B | C |
| 64 | 5-(7-fluoro-2-methyl-1-oxoisoquinolin-4-yl)-2-methoxybenzenesulfonamide | B | | | |
| 65 | 2-methyl-4-(1-methylpyrazol-4-yl)isoquinolin-1-one | B | | | |
| 66 | 4-(furan-2-yl)-2-methylisoquinolin-1-one | C | | | |
| 67 | 2-methyl-4-(1,3-oxazol-2-yl)isoquinolin-1-one | C | | | |
| 68 | 2-methyl-4-(1H-pyrazol-5-yl)isoquinolin-1-one | C | | | |
| 69 | 2-methyl-4-(1-methylimidazol-2-yl)isoquinolin-1-one | C | | | |
| 70 | 2-methyl-4-pyridin-2-ylisoquinolin-1-one | C | | | |
| 71 | 2-methyl-4-pyrimidin-2-ylisoquinolin-1-one | C | | | |
| 72 | N-[3-[2-methyl-6-(6-methylpyridin-3-yl)-1-oxoisoquinolin-4-yl]phenyl]ethanesulfonamide | A | A | A | B |
| 73 | N-[3-(2-methyl-1-oxo-6-phenylisoquinolin-4-yl)phenyl]ethanesulfonamide | B | | | |
| 74 | N-[3-(2-methyl-1-oxo-6-phenylisoquinolin-4-yl)phenyl]methanesulfonamide | B | B | B | C |
| 75 | N-[3-(2,6-dimethyl-1-oxoisoquinolin-4-yl)phenyl]ethanesulfonamide | A | A | A | C |
| 76 | N-[3-(6-ethyl-2-methyl-1-oxoisoquinolin-4-yl)phenyl]ethanesulfonamide | A | | | |
| 77 | N-[3-(6-ethyl-2-methyl-1-oxoisoquinolin-4-yl)phenyl]methanesulfonamide | A | A | A | C |
| 78 | N-[3-(2,6-dimethyl-1-oxoisoquinolin-4-yl)phenyl]methanesulfonamide | A | A | A | C |
| 79 | 4-(5-ethylsulfonyl-2-methoxyphenyl)-2-methyl-6-(1-methylpyrazol-4-yl)isoquinolin-1-one | A | A | A | C |
| 80 | 4-(5-ethylsulfonyl-2-hydroxyphenyl)-2-methyl-6-(1-methylpyrazol-4-yl)isoquinolin-1-one | A | | | |

TABLE 24-continued

| Chemistry Synthesis Example | Name | BRD4 IC50 (µM) | Raji IC50 (µM) | HL-60 IC50 (µM) | H460 IC50 (µM) |
|---|---|---|---|---|---|
| 81 | 4-(2-ethoxy-5-ethylsulfonylphenyl)-2-methyl-6-(1-methylpyrazol-4-yl)isoquinolin-1-one | A | A | A | A |
| 82 | 4-[2-(cyclopropylmethoxy)-5-ethylsulfonylphenyl]-2-methyl-6-(1-methylpyrazol-4-yl)isoquinolin-1-one | A | A | A | B |
| 83 | 4-(5-ethylsulfonyl-2-propoxyphenyl)-2-methyl-6-(1-methylpyrazol-4-yl)isoquinolin-1-one | A | A | A | A |
| 84 | 4-[5-ethylsulfonyl-2-(2-hydroxyethoxy)phenyl]-2-methyl-6-(1-methylpyrazol-4-yl)isoquinolin-1-one | A | B | A | B |
| 85 | 4-[2-(2-aminoethoxy)-5-ethylsulfonylphenyl]-2-methyl-6-(1-methylpyrazol-4-yl)isoquinolin-1-one | A | C | B | C |
| 86 | N-[2-fluoro-4-methoxy-5-[2-methyl-6-(1-methylpyrazol-4-yl)-1-oxoisoquinolin-4-yl]phenyl]ethanesulfonamide | A | A | A | B |
| 87 | N-[3-(2-methyl-1-oxo-6-pyridin-2-ylisoquinolin-4-yl)phenyl]ethanesulfonamide | B | B | A | C |
| 88 | 4-[4-fluoro-2-methoxy-5-(methylsulfonylmethyl)phenyl]-2-methyl-6-(1-methylpyrazol-4-yl)isoquinolin-1-one | A | A | A | C |
| 89 | 4-[2-(cyclopropylmethoxy)-5-methylsulfonylphenyl]-2-methylisoquinolin-1-one | A | A | A | C |
| 90 | 4-[2-(cyclopropylmethoxy)-5-methylsulfonylphenyl]-6-fluoro-2-methylisoquinolin-1-one | A | A | A |  |
| 91 | 4-[2-(cyclopropylmethoxy)-5-methylsulfonylphenyl]-7-fluoro-2-methylisoquinolin-1-one | A | A | A | C |
| 92 | 4-[2-(2,4-difluorophenoxy)-5-methylsulfonylphenyl]-2-methylisoquinolin-1-one | A | A | A | C |
| 93 | N-[4-(2,4-difluorophenoxy)-3-(2-methyl-1-oxoisoquinolin-4-yl)phenyl]ethanesulfonamide | A | A | A | C |
| 94 | N-[3-(1-methyl-6-oxopyridin-3-yl)phenyl]methanesulfonamide | B | A | C |  |
| 95 | N-[3-(1,4-dimethyl-6-oxopyridin-3-yl)phenyl]methanesulfonamide | B |  |  |  |
| 96 | N-[3-(1,5-dimethyl-6-oxopyridin-3-yl)phenyl]methanesulfonamide | B |  |  |  |
| 97 | N-[3-(1,4,5-trimethyl-6-oxopyridin-3-yl)phenyl]methanesulfonamide | B |  |  |  |
| 98 | 5-[2-(cyclopropylmethoxy)-5-methylsulfonylphenyl]-1-methylpyridin-2-one | B | B | B | C |
| 99 | N-[4-(2,4-difluorophenoxy)-3-(1-methyl-6-oxopyridin-3-yl)phenyl]ethanesulfonamide | A | A | A | C |
| 100 | N-[4-(2,4-difluorophenoxy)-3-(1-methyl-6-oxopyridin-3-yl)phenyl]methanesulfonamide | A | A | A | C |
| 101 | N-[4-(2,4-difluorophenoxy)-3-(1,4-dimethyl-6-oxopyridin-3-yl)phenyl]methanesulfonamide | A | A | A | C |
| 102 | N-[4-(2,4-difluorophenoxy)-3-(1,5-dimethyl-6-oxopyridin-3-yl)phenyl]methanesulfonamide | A | A | A | C |
| 103 | N-[4-(2,4-difluorophenoxy)-3-(1,4,5-trimethyl-6-oxopyridin-3-yl)phenyl]methanesulfonamide | A | B | A | C |
| 104 | 3-amino-1-methyl-5-(3-methylsulfonylphenyl)pyrazin-2-one | C |  |  |  |
| 105 | 3-amino-5-(3-ethylsulfonylphenyl)-1-methylpyrazin-2-one | C |  |  |  |

TABLE 24-continued

| Chemistry Synthesis Example | Name | BRD4 IC50 (μM) | Raji IC50 (μM) | HL-60 IC50 (μM) | H460 IC50 (μM) |
|---|---|---|---|---|---|
| 106 | N-[5-(6-amino-4-methyl-5-oxopyrazin-2-yl)-2-methoxyphenyl]methanesulfonamide | C | | | |
| 107 | 3-amino-1-methyl-5-(3-methylsulfonylphenyl)pyridin-2-one | C | | | |
| 108 | 3-amino-5-(3-ethylsulfonylphenyl)-1-methylpyridin-2-one | C | | | |
| 109 | N-[5-(5-amino-1-methyl-6-oxopyridin-3-yl)-2-methoxyphenyl]methanesulfonamide | B | C | C | C |
| 110 | N-[2-methoxy-5-[1-methyl-5-(methylamino)-6-oxopyridin-3-yl]phenyl]methanesulfonamide | A | C | B | C |
| 111 | N-[5-[5-(ethylamino)-1-methyl-6-oxopyridin-3-yl]-2-methoxyphenyl]methanesulfonamide | B | | | |
| 112 | N-[5-[5-(cyclopropylmethylamino)-1-methyl-6-oxopyridin-3-yl]-2-methoxyphenyl]methanesulfonamide | B | | | |
| 113 | N-[5-[5-(dimethylamino)-1-methyl-6-oxopyridin-3-yl]-2-methoxyphenyl]methanesulfonamide | A | B | A | B |
| 114 | N-[5-[5-(diethylamino)-1-methyl-6-oxopyridin-3-yl]-2-methoxyphenyl]methanesulfonamide | B | | | |
| 115 | N-[3-(5-amino-1-methyl-6-oxopyridin-3-yl)-4-(2,4-difluorophenoxy)phenyl]ethanesulfonamide | A | A | A | C |
| 116 | 3-amino-5-[2-(cyclopropylmethoxy)-5-methylsulfonylphenyl]-1-methylpyridin-2-one | A | C | B | C |
| 117 | 4-ethoxy-3-(1-methyl-6-oxopyridin-3-yl)benzenesulfonamide | A | B | B | C |
| 118 | 4-(2,4-difluorophenoxy)-3-(1-methyl-6-oxopyridin-3-yl)benzenesulfonamide | A | A | A | C |
| 119 | 5-[2-(cyclopropylmethoxy)-5-methylsulfonylphenyl]-3-fluoro-1-methylpyridin-2-one | B | B | B | C |
| 120 | 5-[2-(2,4-difluorophenoxy)-5-methylsulfonylphenyl]-3-fluoro-1-methylpyridin-2-one | B | C | B | C |
| 121 | 5-[2-(2,4-difluorophenoxy)-5-ethylsulfonylphenyl]-3-fluoro-1-methylpyridin-2-one | A | B | A | C |
| 122 | N-[4-(2,4-difluorophenoxy)-3-(5-fluoro-1-methyl-6-oxopyridin-3-yl)phenyl]ethanesulfonamide | A | A | A | C |
| 123 | N-[3-(2-methyl-1-oxo-2,6-naphthyridin-4-yl)phenyl]ethanesulfonamide | B | B | B | C |
| 124 | N-ethyl-3-(2-methyl-1-oxo-2,6-naphthyridin-4-yl)benzenesulfonamide | B | | | |
| 125 | N-[3-(2-methyl-1-oxo-2,6-naphthyridin-4-yl)phenyl]methanesulfonamide | B | | | |
| 126 | 4-(3-ethylsulfonylphenyl)-2-methyl-2,6-naphthyridin-1-one | C | | | |
| 127 | N-[4-(2,4-difluorophenoxy)-3-(2-methyl-1-oxo-2,6-naphthyridin-4-yl)phenyl]ethanesulfonamide | A | A | A | C |
| 128 | 4-[2-(cyclopropylmethoxy)-5-methylsulfonylphenyl]-2-methyl-6-(4-methylpyrazol-1-yl)isoquinolin-1-one | A | A | A | C |
| 129 | N-[4-(2,4-difluorophenoxy)-3-(7-methyl-8-oxoimidazo[1,5-a]pyrazin-5-yl)phenyl]ethanesulfonamide | A | A | A | C |
| 130 | 5-[2-(cyclopropylmethoxy)-5-methylsulfonylphenyl]-7-methylimidazo[1,5-a]pyrazin-8-one | A | B | A | C |

TABLE 24-continued

| Chemistry Synthesis Example | Name | BRD4 IC50 (µM) | Raji IC50 (µM) | HL-60 IC50 (µM) | H460 IC50 (µM) |
|---|---|---|---|---|---|
| 131 | 7-methyl-5-(3-methylsulfonylphenyl)imidazo[1,5-a]pyrazin-8-one | C | | | |
| 132 | N-[2-methoxy-5-(7-methyl-8-oxoimidazo[1,5-a]pyrazin-5-yl)phenyl]methanesulfonamide | B | C | B | B |
| 133 | 5-(3-ethylsulfonylphenyl)-7-methylimidazo[1,5-a]pyrazin-8-one | C | | | |
| 134 | N-[3-(5-chloro-1-methyl-6-oxopyridin-3-yl)-4-(2,4-difluorophenoxy)phenyl]ethanesulfonamide | A | A | A | B |
| 135 | 4-[2-(cyclopropylmethoxy)-5-ethylsulfonylphenyl]-2-methylisoquinolin-1-one | A | A | A | B |
| 136 | 6-[2-(cyclopropylmethoxy)-5-methylsulfonylphenyl]-2,4-dimethylpyridazin-3-one | B | C | B | C |
| 137 | 6-[2-(cyclopropylmethoxy)-5-methylsulfonylphenyl]-2,5-dimethylpyridazin-3-one | B | | | |
| 138 | N-[4-(2,4-difluorophenoxy)-3-[1-methyl-6-oxo-5-(trifluoromethyl)pyridin-3-yl]phenyl]ethanesulfonamide | A | A | A | C |
| 139 | N-[4-(2,4-difluorophenoxy)-3-(4-fluoro-1-methyl-6-oxopyridin-3-yl)phenyl]ethanesulfonamide | A | A | A | C |
| 140 | N-[3-(5-cyclopropyl-1-methyl-6-oxopyridin-3-yl)-4-(2,4-difluorophenoxy)phenyl]ethanesulfonamide | A | A | A | C |
| 141 | N-{4-(2,4-difluorophenoxy)-3-[1-($^2$H$_3$)methyl-6-oxopyridin-3-yl]phenyl}ethanesulfonamide | A | | | |
| 142 | N-[4-(2,4-difluorophenoxy)-3-(2-methyl-1-oxo-5,6,7,8-tetrahydro-2,6-naphthyridin-4-yl)phenyl]ethanesulfonamide | B | | | |
| 143 | 4-[5-(cyclopropylmethoxy)-2-(methylsulfonylmethyl)pyrimidin-4-yl]-2-methylisoquinolin-1-one | A | B | B | C |
| 144 | 5-[5-(cyclopropylmethoxy)-2-(methylsulfonylmethyl)pyrimidin-4-yl]-1,3-dimethylpyridin-2-one | A | C | B | C |
| 145 | 4-[5-(cyclopropylmethoxy)-2-(methylsulfonylmethyl)pyrimidin-4-yl]-2-methyl-6-(1-methylpyrazol-4-yl)isoquinolin-1-one | A | B | A | C |
| 146 | 5-[5-(2,4-difluorophenoxy)-2-(methylsulfonylmethyl)pyrimidin-4-yl]-3-methoxy-1-methylpyridin-2-one | A | B | | C |
| 147 | 5-[5-(2,4-difluorophenoxy)-2-(methylsulfonylmethyl)pyrimidin-4-yl]-1,3-dimethylpyridin-2-one | A | B | | C |
| 148 | 4-[5-(2,4-difluorophenoxy)-2-(methylsulfonylmethyl)pyrimidin-4-yl]-2-methylisoquinolin-1-one | A | C | | |
| 149 | 5-[5-(2,4-difluorophenoxy)-2-methylsulfonylpyrimidin-4-yl]-1,3-dimethylpyridin-2-one | B | C | C | C |
| 150 | 5-[5-(2,4-difluorophenoxy)-2-methylsulfonylpyrimidin-4-yl]-3-methoxy-1-methylpyridin-2-one | A | B | B | C |
| 151 | 4-[5-(2,4-difluorophenoxy)-2-methylsulfonylpyrimidin-4-yl]-2-methylisoquinolin-1-one | A | | | |
| 152 | N-[5-(cyclopropylmethoxy)-4-(2-methyl-1-oxoisoquinolin-4-yl)pyrimidin-2-yl]methanesulfonamide | A | A | A | C |
| 153 | N-[5-(cyclopropylmethoxy)-4-(1,5-dimethyl-6-oxopyridin-3-yl)pyrimidin-2-yl]methanesulfonamide | A | B | B | C |

TABLE 24-continued

| Chemistry Synthesis Example | Name | BRD4 IC50 (μM) | Raji IC50 (μM) | HL-60 IC50 (μM) | H460 IC50 (μM) |
|---|---|---|---|---|---|
| 154 | N-[5-(cyclopropylmethoxy)-4-[2-methyl-6-(1-methylpyrazol-4-yl)-1-oxoisoquinolin-4-yl]pyrimidin-2-yl]methanesulfonamide | A | A | A | C |
| 155 | N-[5-(cyclopropylmethoxy)-4-(2-methyl-1-oxoisoquinolin-4-yl)pyrimidin-2-yl]ethanesulfonamide | A | A | A | C |
| 156 | 4-[5-(cyclopropylmethoxy)-2-(1,1-dioxo-1,2-thiazolidin-2-yl)pyrimidin-4-yl]-2-methylisoquinolin-1-one | A | | | |
| 157 | N-[5-(cyclopropylmethoxy)-4-(6-fluoro-2-methyl-1-oxoisoquinolin-4-yl)pyrimidin-2-yl]ethanesulfonamide | A | A | A | C |
| 158 | N-[5-(cyclopropylmethoxy)-4-(7-fluoro-2-methyl-1-oxoisoquinolin-4-yl)pyrimidin-2-yl]methanesulfonamide | A | A | A | C |
| 159 | N-[5-(cyclopropylmethoxy)-4-(6-fluoro-2-methyl-1-oxoisoquinolin-4-yl)pyrimidin-2-yl]methanesulfonamide | A | A | A | C |
| 160 | N-[5-(cyclopropylmethoxy)-4-(7-fluoro-2-methyl-1-oxoisoquinolin-4-yl)pyrimidin-2-yl]ethanesulfonamide | A | A | A | C |
| 161 | N-[5-(cyclopropylmethoxy)-4-(2-methyl-1-oxoisoquinolin-4-yl)pyrimidin-2-yl]-N-ethylmethanesulfonamide | A | A | A | C |
| 162 | N-[5-(cyclopropylmethoxy)-4-(1,5-dimethyl-6-oxopyridin-3-yl)pyrimidin-2-yl]-N-ethylmethanesulfonamide | A | A | A | C |
| 163 | N-[5-(cyclopropylmethoxy)-4-(2-methyl-1-oxo-5,6,7,8-tetrahydroisoquinolin-4-yl)pyrimidin-2-yl]methanesulfonamide | A | A | B | C |
| 164 | N-[5-(cyclopropylmethoxy)-4-(2-methyl-1-oxo-5,6,7,8-tetrahydroisoquinolin-4-yl)pyrimidin-2-yl]ethanesulfonamide | A | A | B | C |
| 165 | N-[5-(2,4-difluorophenoxy)-4-(2-methyl-1-oxoisoquinolin-4-yl)pyrimidin-2-yl]methanesulfonamide | A | B | | C |
| 166 | N-[5-(2,4-difluorophenoxy)-4-(1,5-dimethyl-6-oxopyridin-3-yl)pyrimidin-2-yl]methanesulfonamide | A | A | A | C |
| 167 | N-[5-(2,4-difluorophenoxy)-4-(5-methoxy-1-methyl-6-oxopyridin-3-yl)pyrimidin-2-yl]methanesulfonamide | A | B | | C |
| 168 | N-[5-(2,4-difluorophenoxy)-4-(5-methoxy-1-methyl-6-oxopyridin-3-yl)pyrimidin-2-yl]ethanesulfonamide | A | A | A | C |
| 169 | N-[5-(2,4-difluorophenoxy)-4-(1,5-dimethyl-6-oxopyridin-3-yl)pyrimidin-2-yl]ethanesulfonamide | A | A | A | C |
| 170 | N-[5-(2,4-difluorophenoxy)-4-(2-methyl-1-oxoisoquinolin-4-yl)pyrimidin-2-yl]ethanesulfonamide | A | A | A | C |
| 171 | 4-[5-(2,4-difluorophenoxy)-2-(1,1-dioxo-1,2-thiazolidin-2-yl)pyrimidin-4-yl]-2-methylisoquinolin-1-one | A | | | |
| 172 | N-[5-(2,4-difluorophenoxy)-4-(2-methyl-1-oxo-5,6,7,8-tetrahydroisoquinolin-4- | A | B | B | C |

TABLE 24-continued

| Chemistry Synthesis Example | Name | BRD4 IC50 (µM) | Raji IC50 (µM) | HL-60 IC50 (µM) | H460 IC50 (µM) |
|---|---|---|---|---|---|
| | yl)pyrimidin-2-yl]methanesulfonamide | | | | |
| 173 | N-[5-(2,4-difluorophenoxy)-4-(2-methyl-1-oxo-5,6,7,8-tetrahydroisoquinolin-4-yl)pyrimidin-2-yl]ethanesulfonamide | A | B | B | C |
| 174 | 4-[2-(cyclopropylmethoxy)-5-ethylsulfonylphenyl]-6-fluoro-2-methylisoquinolin-1-one | A | A | A | C |
| 175 | 2-methyl-4-[5-methylsulfonyl-2-(oxolan-3-yloxy)phenyl]isoquinolin-1-one | A | A | A | C |
| 176 | 2-methyl-4-[5-methylsulfonyl-2-(oxan-4-yloxy)phenyl]isoquinolin-1-one | A | A | A | C |
| 177 | 4-(2-ethoxy-5-methylsulfonylphenyl)-2-methylisoquinolin-1-one | A | B | A | C |
| 178 | 2-methyl-4-(5-methylsulfonyl-2-propoxyphenyl)isoquinolin-1-one | A | A | A | C |
| 179 | 2-methyl-4-[5-methylsulfonyl-2-(oxan-3-yloxy)phenyl]isoquinolin-1-one | A | A | A | C |
| 180 | 4-[2-(trans-4-hydroxycyclohexyl)oxy-5-methylsulfonylphenyl]-2-methylisoquinolin-1-one | A | A | A | C |
| 181 | 4-[5-ethylsulfonyl-2-(trans-4-hydroxycyclohexyl)oxyphenyl]-2-methylisoquinolin-1-one | A | A | A | C |
| 182 | 4-[2-(trans-4-aminocyclohexyl)oxy-5-methylsulfonylphenyl]-2-methylisoquinolin-1-one | A | A | A | C |
| 183 | 4-[2-(cis-4-aminocyclohexyl)oxy-5-methylsulfonylphenyl]-2-methylisoquinolin-1-one | A | C | B | C |
| 184 | 4-(2-but-2-ynoxy-5-methylsulfonylphenyl)-2-methylisoquinolin-1-one | A | B | A | B |
| 185 | 4-(2-but-2-ynoxy-5-ethylsulfonylphenyl)-2-methylisoquinolin-1-one | A | A | A | C |
| 186 | 6-fluoro-4-[2-(trans-4-hydroxycyclohexyl)oxy-5-methylsulfonylphenyl]-2-methylisoquinolin-1-one | A | A | A | C |
| 187 | 7-fluoro-4-[2-(trans-4-hydroxycyclohexyl)oxy-5-methylsulfonylphenyl]-2-methylisoquinolin-1-one | A | A | A | C |
| 188 | 4-[5-ethylsulfonyl-2-(trans-4-hydroxycyclohexyl)oxyphenyl]-6-fluoro-2-methylisoquinolin-1-one | A | A | | |
| 189 | 4-[5-ethylsulfonyl-2-(trans-4-hydroxycyclohexyl)oxyphenyl]-7-fluoro-2-methylisoquinolin-1-one | A | A | | |
| 190 | 2-methyl-4-[5-methylsulfonyl-2-(oxolan-3-ylamino)phenyl]isoquinolin-1-one | A | B | B | C |
| 191 | 2-methyl-4-[5-methylsulfonyl-2-(oxan-4-ylamino)phenyl]isoquinolin-1-one | A | A | A | C |
| 192 | 4-[2-[(trans-4-hydroxycyclohexyl)amino]-5-methylsulfonylphenyl]-2-methylisoquinolin-1-one | A | A | A | C |
| 193 | 4-[2-(cyclopropylmethylamino)-5-ethylsulfonylphenyl]-2-methylisoquinolin-1-one | A | A | A | C |
| 194 | 4-[2-(cyclopropylmethylamino)-5-methylsulfonylphenyl]-2-methylisoquinolin-1-one | A | A | A | C |
| 195 | 4-[2-(cyclopropylmethylamino)-5-ethylsulfonylphenyl]-7-fluoro-2-methylisoquinolin-1-one | A | A | A | C |

TABLE 24-continued

| Chemistry Synthesis Example | Name | BRD4 IC50 (µM) | Raji IC50 (µM) | HL-60 IC50 (µM) | H460 IC50 (µM) |
|---|---|---|---|---|---|
| 196 | 4-[2-(cyclopropylmethylamino)-5-methylsulfonylphenyl]-7-fluoro-2-methylisoquinolin-1-one | A | A | A | C |
| 197 | 4-[2-(cyclopropylmethoxy)-5-methylsulfonylphenyl]-2-methyl-6-(trifluoromethyl)isoquinolin-1-one | A | B | | C |
| 198 | 4-[2-(cyclopropylmethoxy)-5-methylsulfonylphenyl]-6-methoxy-2-methylisoquinolin-1-one | A | A | A | C |
| 199 | 4-[3-(cyclopropylmethoxy)-6-methylsulfonylpyridin-2-yl]-2-methylisoquinolin-1-one | A | A | A | C |
| 200 | 4-[5-(cyclopropylmethoxy)-2-methylsulfonylpyridin-4-yl]-2-methylisoquinolin-1-one | A | B | A | C |
| 201 | 4-[3-(cyclopropylmethoxy)-6-methylsulfonylpyridin-2-yl]-7-fluoro-2-methylisoquinolin-1-one | A | A | A | C |
| 202 | 4-[3-(cyclopropylmethoxy)-6-methylsulfonylpyridin-2-yl]-6-fluoro-2-methylisoquinolin-1-one | A | A | | C |
| 203 | 4-[5-(cyclopropylmethoxy)-2-methylsulfonylpyridin-4-yl]-7-fluoro-2-methylisoquinolin-1-one | A | A | A | C |
| 204 | 4-(2-ethoxy-5-ethylsulfonylthiophen-3-yl)-2-methylisoquinolin-1-one | A | B | B | C |
| 205 | 4-[2-(cyclopropylmethylamino)-5-ethylsulfonylthiophen-3-yl]-2-methylisoquinolin-1-one | A | B | B | C |
| 206 | 4-[3-(cyclopropylmethoxy)-6-ethylsulfonylpyridin-2-yl]-2-methylisoquinolin-1-one | A | A | A | C |
| 207 | 4-[5-(cyclopropylmethoxy)-2-ethylsulfonylpyridin-4-yl]-2-methylisoquinolin-1-one | A | A | A | C |
| 208 | 4-[5-(2-hydroxyethylsulfonyl)-2-methoxyphenyl]-2-methyl-6-(1-methylpyrazol-4-yl)isoquinolin-1-one | A | B | A | C |
| 209 | N-[4-(cyclopropylmethoxy)-2-fluoro-5-[2-methyl-6-(1-methylpyrazol-4-yl)-1-oxoisoquinolin-4-yl]phenyl]ethanesulfonamide | A | A | A | C |
| 210 | 4-(5-ethylsulfonyl-2-methoxyphenyl)-2-methyl-6-(1H-pyrazol-4-yl)isoquinolin-1-one | A | A | A | C |
| 211 | 4-(2-ethoxy-5-methylsulfonylphenyl)-2-methyl-6-(1-methylpyrazol-4-yl)isoquinolin-1-one | A | | | |
| 212 | 2-methyl-6-(1-methylpyrazol-4-yl)-4-(5-methylsulfonyl-2-propoxyphenyl)isoquinolin-1-one | A | | | |
| 213 | N-[2-[2-methyl-6-(1-methylpyrazol-4-yl)-1-oxoisoquinolin-4-yl]pyridin-4-yl]ethanesulfonamide | A | B | B | C |
| 214 | [4-(cyclopropylmethoxy)-3-(2-methyl-1-oxoisoquinolin-4-yl)phenyl] sulfamate | A | A | A | C |
| 215 | [4-(cyclopropylmethoxy)-3-(1,5-dimethyl-6-oxopyridin-3-yl)phenyl] sulfamate | A | A | A | C |
| 216 | 4-(2-ethoxy-5-methylsulfonylphenyl)-2-methyl-5,6,7,8-tetrahydroisoquinolin-1-one | A | | | |
| 217 | 4-[2-(cyclopropylmethoxy)-5-methylsulfonylphenyl]-2-methyl-5,6,7,8-tetrahydroisoquinolin-1-one | A | A | A | C |
| 218 | N-[4-(cyclopropylmethoxy)-2-fluoro-5-(2-methyl-1-oxo-5,6,7,8-tetrahydroisoquinolin-4-yl)phenyl]methanesulfonamide | A | B | A | C |

TABLE 24-continued

| Chemistry Synthesis Example | Name | BRD4 IC50 (μM) | Raji IC50 (μM) | HL-60 IC50 (μM) | H460 IC50 (μM) |
|---|---|---|---|---|---|
| 219 | 4-[2-(cyclopropylmethoxy)-5-ethylsulfonylphenyl]-2-methyl-5,6,7,8-tetrahydroisoquinolin-1-one | A | A | A | C |
| 220 | N-[2-(2-methyl-1-oxoisoquinolin-4-yl)-4-methylsulfonylphenyl]cyclopropane carboxamide | B | C | C | C |
| 221 | N-[2-(2-methyl-1-oxoisoquinolin-4-yl)-4-methylsulfonylphenyl]propanamide | C | C | C | C |
| 222 | N-[2-(2-methyl-1-oxoisoquinolin-4-yl)-4-methylsulfonylphenyl]acetamide | C | C | C | C |
| 223 | 4-[2-(cyclopropylmethylamino)-5-methylsulfonylphenyl]-2-methyl-5,6,7,8-tetrahydroisoquinolin-1-one | A | B | A | C |
| 224 | 8-[2-(cyclopropylmethoxy)-5-methylsulfonylphenyl]-6-methyl-2-(1-methylpyrazol-4-yl)pyrido[4,3-d]pyrimidin-5-one | A | A | A | C |
| 225 | 8-(5-ethylsulfonyl-2-propoxyphenyl)-6-methyl-2-(1-methylpyrazol-4-yl)pyrido[4,3-d]pyrimidin-5-one | A | A | A | C |
| 226 | 8-[2-(cyclopropylmethoxy)-5-ethylsulfonylphenyl]-6-methyl-2-(1-methylpyrazol-4-yl)pyrido[4,3-d]pyrimidin-5-one | A | A | A | C |
| 227 | 8-(2-ethoxy-5-ethylsulfonylphenyl)-6-methyl-2-(1-methylpyrazol-4-yl)pyrido[4,3-d]pyrimidin-5-one | A | B | A | C |
| 228 | 6-methyl-2-(1-methylpyrazol-4-yl)-8-(5-methylsulfonyl-2-propoxyphenyl)pyrido[4,3-d]pyrimidin-5-one | A | B | A | C |
| 229 | N-[4-(2,4-difluorophenoxy)-3-(1,5-dimethyl-6-oxopyridin-3-yl)phenyl]-N-methylmethanesulfonamide | A | A | A | C |
| 230 | N-[4-(2,4-difluorophenoxy)-3-(1,5-dimethyl-6-oxopyridin-3-yl)phenyl]-N-(oxetan-3-yl)methanesulfonamide | A | A | A | C |
| 231 | 8-[2-(cyclopropylmethoxy)-5-methylsulfonylphenyl]-6-methylpyrido[4,3-d]pyrimidin-5-one | B | | | |
| 232 | 8-[2-(cyclopropylmethoxy)-5-ethylsulfonylphenyl]-6-methylpyrido[4,3-d]pyrimidin-5-one | A | | | |
| 233 | 8-[2-(2,4-difluorophenoxy)-5-methylsulfonylphenyl]-6-methylpyrido[4,3-d]pyrimidin-5-one | B | | | |
| 234 | 8-[2-(2,4-difluorophenoxy)-5-ethylsulfonylphenyl]-6-methylpyrido[4,3-d]pyrimidin-5-one | B | | | |
| 235 | 5-[2-(cyclopropylmethoxy)-5-methylsulfonylphenyl]-7-methyl-[1,2,4]triazolo[4,3-a]pyrazin-8-one | C | C | C | C |
| 236 | N-[4-(2,4-difluorophenoxy)-3-(7-methyl-8-oxo-[1,2,4]triazolo[4,3-a]pyrazin-5-yl)phenyl]ethanesulfonamide | A | C | B | C |
| 237 | 7-[2-(cyclopropylmethoxy)-5-methylsulfonylphenyl]-5-methyl-[1,3]oxazolo[4,5-c]pyridin-4-one | A | | | |
| 238 | 7-[2-(cyclopropylmethoxy)-5-methylsulfonylphenyl]-2,5-dimethyl-[1,3]oxazolo[4,5-c]pyridin-4-one | A | B | A | C |

TABLE 24-continued

| Chemistry Synthesis Example | Name | BRD4 IC50 (μM) | Raji IC50 (μM) | HL-60 IC50 (μM) | H460 IC50 (μM) |
|---|---|---|---|---|---|
| 239 | 5-methyl-7-[5-(methylsulfonylmethyl)-2-(2,2,2-trifluoroethoxy)phenyl]-[1,3]oxazolo[4,5-c]pyridin-4-one | A | | | |
| 240 | N-[4-(2,4-difluorophenoxy)-3-(5-methyl-4-oxo-[1,3]oxazolo[4,5-c]pyridin-7-yl)phenyl]ethanesulfonamide | A | A | A | C |
| 241 | N-[4-(2,4-difluorophenoxy)-3-(2,5-dimethyl-4-oxo-[1,3]oxazolo[4,5-c]pyridin-7-yl)phenyl]ethanesulfonamide | A | A | A | C |
| 242 | 5-[2-(cyclopropylmethoxy)-5-methylsulfonylphenyl]-1-(cyclopropylmethyl)-3-methylpyridin-2-one | A | B | A | C |
| 243 | 5-[2-(cyclopropylmethoxy)-5-methylsulfonylphenyl]-3-methyl-1-(2-methylpropyl)pyridin-2-one | B | C | B | C |
| 244 | 5-[2-(cyclopropylmethoxy)-5-methylsulfonylphenyl]-1-(2-methoxyethyl)-3-methylpyridin-2-one | B | C | B | C |
| 245 | 5-[2-(cyclopropylmethoxy)-5-methylsulfonylphenyl]-3-methyl-1-(oxetan-3-ylmethyl)pyridin-2-one | B | C | C | C |
| 246 | 5-[2-(cyclopropylmethoxy)-5-methylsulfonylphenyl]-3-methyl-1-(1,3-oxazol-4-ylmethyl)pyridin-2-one | B | C | C | C |
| 247 | N-[3-[1-(cyclopropylmethyl)-5-methyl-6-oxopyridin-3-yl]-4-(2,4-difluorophenoxy)phenyl]ethanesulfonamide | A | A | A | C |
| 248 | N-[4-[1-(cyclopropylmethyl)-5-methyl-6-oxopyridin-3-yl]-5-(2,4-difluorophenoxy)pyrimidin-2-yl]methanesulfonamide | A | A | A | C |
| 249 | N-[4-[1-(cyclopropylmethyl)-5-methyl-6-oxopyridin-3-yl]-5-(2,4-difluorophenoxy)pyrimidin-2-yl]ethanesulfonamide | A | A | A | C |
| 250 | 1-(cyclopropylmethyl)-5-[4-(2,4-difluorophenoxy)-1-(methylsulfonylmethyl)-6-oxopyridin-3-yl]-3-methylpyridin-2-one | A | B | A | C |
| 251 | 1-cyclopropyl-5-[2-(cyclopropylmethoxy)-5-ethylsulfonylphenyl]-3-methylpyridin-2-one | A | B | A | C |
| 252 | 4-[2-(cyclopropylmethoxy)-5-ethylsulfonylphenyl]-6-methylfuro[2,3-c]pyridin-7-one | A | A | A | C |
| 253 | N-[4-(2,4-difluorophenoxy)-3-(6-methyl-7-oxofuro[2,3-c]pyridin-4-yl)phenyl]ethanesulfonamide | A | A | A | C |
| 254 | 4-[2-(cyclopropylmethoxy)-5-methylsulfonylphenyl]-6-methylfuro[2,3-c]pyridin-7-one | A | A | A | C |
| 255 | N-[4-(cyclopropylmethoxy)-3-(6-methyl-7-oxofuro[2,3-c]pyridin-4-yl)phenyl]ethanesulfonamide | A | A | A | C |
| 256 | N-[6-(2,4-difluorophenoxy)-5-(6-methyl-7-oxofuro[2,3-c]pyridin-4-yl)pyridin-3-yl]ethanesulfonamide | A | A | A | C |
| 257 | N-[6-(cyclopropylmethoxy)-5-(6-methyl-7-oxofuro[2,3-c]pyridin-4-yl)pyridin-3-yl]ethanesulfonamide | A | A | A | C |
| 258 | 6-methyl-4-[5-(methylsulfonylmethyl)-2-(2,2,2-trifluoroethoxy)phenyl]furo[2,3-c]pyridin-7-one | A | B | A | B |
| 259 | 4-[3-(cyclopropylmethoxy)-6-methylsulfonylpyridin-2-yl]-6-methylfuro[2,3-c]pyridin-7-one | A | B | A | C |

TABLE 24-continued

| Chemistry Synthesis Example | Name | BRD4 IC50 (μM) | Raji IC50 (μM) | HL-60 IC50 (μM) | H460 IC50 (μM) |
|---|---|---|---|---|---|
| 260 | 2-chloro-4-[2-(cyclopropylmethoxy)-5-methylsulfonylphenyl]-6-methylfuro[2,3-c]pyridin-7-one | A | A | A | B |
| 261 | N-[6-(cyclopropylmethoxy)-5-(2-fluoro-6-methyl-7-oxofuro[2,3-c]pyridin-4-yl)pyridin-3-yl]ethanesulfonamide | A | A | A | C |
| 262 | N-[5-(2,4-difluorophenoxy)-4-(6-methyl-7-oxofuro[2,3-c]pyridin-4-yl)pyrimidin-2-yl]methanesulfonamide | A | A | A | C |
| 263 | N-[5-(2,4-difluorophenoxy)-4-(6-methyl-7-oxofuro[2,3-c]pyridin-4-yl)pyrimidin-2-yl]ethanesulfonamide | A | A | A | C |
| 264 | N-[5-(cyclopropylmethoxy)-4-(6-methyl-7-oxofuro[2,3-c]pyridin-4-yl)pyrimidin-2-yl]ethanesulfonamide | A | A | A | C |
| 265 | 4-[2-(cyclopropylmethoxy)-5-ethylsulfonylphenyl]-6-methyl-7-oxothieno[2,3-c]pyridine-2-carboxamide | A | A | A | C |
| 266 | 4-[2-(cyclopropylmethoxy)-5-(ethylsulfonylamino)phenyl]-6-methyl-7-oxothieno[2,3-c]pyridine-2-carboxamide | A | A | A | C |
| 267 | 4-[2-(cyclopropylmethoxy)-5-methylsulfonylphenyl]-6-methyl-7-oxothieno[2,3-c]pyridine-2-carboxamide | A | B | A | C |
| 268 | 4-[2-(cyclopropylmethoxy)-5-(ethylsulfonylamino)pyridin-3-yl]-6-methyl-7-oxothieno[2,3-c]pyridine-2-carboxamide | A | B | A | C |
| 269 | N-[4-(2,4-difluorophenoxy)-3-(2,6-dimethyl-7-oxofuro[2,3-c]pyridin-4-yl)phenyl]ethanesulfonamide | A | A | A | C |
| 270 | 4-[2-(cyclopropylmethoxy)-5-ethylsulfonylphenyl]-2,6-dimethylfuro[2,3-c]pyridin-7-one | A | A | A | B |
| 271 | N-[4-(2,4-difluorophenoxy)-3-(5-fluoro-1-methyl-6-oxopyridin-3-yl)phenyl]methanesulfonamide | A | A | A | C |
| 272 | 3-chloro-5-[2-(cyclopropylmethoxy)-5-ethylsulfonylphenyl]-1-methylpyridin-2-one | A | A | A | C |
| 273 | 5-[5-(2,4-difluorophenoxy)-2-methylsulfonylpyrimidin-4-yl]-1-methyl-3-propan-2-ylpyridin-2-one | B | | | |
| 274 | 5-[2-(cyclopropylmethoxy)-5-ethylsulfonylphenyl]-3-fluoro-1-methylpyridin-2-one | A | B | B | C |
| 275 | 3-chloro-5-[2-(cyclopropylmethylamino)-5-ethylsulfonylphenyl]-1-methylpyridin-2-one | A | A | A | C |
| 276 | 5-[2-(2,4-difluorophenoxy)-5-(methanesulfonylmethyl)phenyl]-3-($^2$H$_3$)methyl-1-methyl-1,2-dihydropyridin-2-one | A | A | | |
| 277 | N-[4-(2,4-difluorophenoxy)-3-[5-($^2$H$_3$)methyl-1-methyl-6-oxo-1,6-dihydropyridin-3-yl]phenyl]methanesulfonamide | A | A | | |
| 278 | N-[4-(2,4-difluorophenoxy)-3-[5-($^2$H$_3$)methyl-1-methyl-6-oxo-1,6-dihydropyridin-3-yl]phenyl]ethane-1-sulfonamide | A | A | | |
| 279 | N-[3-(5-cyclopropyl-1-methyl-6-oxopyridin-3-yl)-4-(2,4-difluorophenoxy)phenyl]methanesulfonamide | A | A | A | C |

TABLE 24-continued

| Chemistry Synthesis Example | Name | BRD4 IC50 (μM) | Raji IC50 (μM) | HL-60 IC50 (μM) | H460 IC50 (μM) |
|---|---|---|---|---|---|
| 280 | 3-cyclopropyl-5-[2-(cyclopropylmethoxy)-5-ethylsulfonylphenyl]-1-methylpyridin-2-one | A | A | A | C |
| 281 | N-[4-(2,4-difluorophenoxy)-3-(1-methyl-6-oxo-5-pyrrolidin-1-ylpyridin-3-yl)phenyl]methanesulfonamide | B | | | |
| 282 | 5-[2-(cyclopropylmethoxy)-5-ethylsulfonylphenyl]-1-methyl-3-pyrrolidin-1-ylpyridin-2-one | B | | | |
| 283 | N-[4-(2,4-difluorophenoxy)-3-(5-ethynyl-1-methyl-6-oxopyridin-3-yl)phenyl]ethanesulfonamide | A | B | A | C |
| 284 | 5-[2-(cyclopropylmethoxy)-5-ethylsulfonylphenyl]-3-ethynyl-1-methylpyridin-2-one | A | B | B | C |
| 285 | 5-[2-(cyclopropylmethoxy)-5-methylsulfonylphenyl]-3-ethynyl-1-methylpyridin-2-one | B | | | |
| 286 | N-[4-(2,4-difluorophenoxy)-3-(5-ethynyl-1-methyl-6-oxopyridin-3-yl)phenyl]methanesulfonamide | A | B | | C |
| 287 | 5-[2-(cyclopropylmethoxy)-5-ethylsulfonylphenyl]-3-(difluoromethoxy)-1-methylpyridin-2-one | A | B | A | C |
| 288 | 5-[2-(cyclopropylmethoxy)-5-ethylsulfonylphenyl]-1-methyl-3-(2,2,2-trifluoroethoxy)pyridin-2-one | A | B | | |
| 289 | N-[3-[5-(difluoromethoxy)-1-methyl-6-oxopyridin-3-yl]-4-(2,4-difluorophenoxy)phenyl]ethanesulfonamide | A | A | A | C |
| 290 | N-[4-(2,4-difluorophenoxy)-3-[1-methyl-6-oxo-5-(2,2,2-trifluoroethoxy)pyridin-3-yl]phenyl]ethanesulfonamide | A | A | A | C |
| 291 | 3-(difluoromethoxy)-5-[2-(2,4-difluorophenoxy)-5-(ethylsulfonylmethyl)phenyl]-1-methylpyridin-2-one | A | A | A | C |
| 292 | 5-[2-(2,4-difluorophenoxy)-5-(ethylsulfonylmethyl)phenyl]-1-methyl-3-(2,2,2-trifluoroethoxy)pyridin-2-one | A | B | A | C |
| 293 | 5-[2-(cyclopropylmethoxy)-5-methylsulfonylphenyl]-1-methyl-3-(1-methylpyrazol-4-yl)oxypyridin-2-one | A | B | B | C |
| 294 | 5-[2-(cyclopropylmethoxy)-5-methylsulfonylphenyl]-1-methyl-3-(1-propan-2-ylpyrazol-4-yl)oxypyridin-2-one | A | C | B | C |
| 295 | 5-[2-(cyclopropylmethoxy)-5-methylsulfonylphenyl]-1-methyl-3-phenoxypyridin-2-one | A | B | B | B |
| 296 | N-[4-(1-butyl-5-methyl-6-oxopyridin-3-yl)-5-(2,4-difluorophenoxy)pyrimidin-2-yl]methanesulfonamide | A | | | |
| 297 | N-[4-(1-butyl-5-methyl-6-oxopyridin-3-yl)-5-(2,4-difluorophenoxy)pyrimidin-2-yl]ethanesulfonamide | A | | | |
| 298 | N-[4-[1-(cyclobutylmethyl)-5-methyl-6-oxopyridin-3-yl]-5-(2,4-difluorophenoxy)pyrimidin-2-yl]methanesulfonamide | B | | | |
| 299 | N-[4-[1-(cyclobutylmethyl)-5-methyl-6-oxopyridin-3-yl]-5-(2,4-difluorophenoxy)pyrimidin-2-yl]ethanesulfonamide | B | | | |
| 300 | N-[5-ethyl-4-(2-methyl-1-oxoisoquinolin-4-yl)pyrimidin-2-yl]ethanesulfonamide | A | | | |

TABLE 24-continued

| Chemistry Synthesis Example | Name | BRD4 IC50 (μM) | Raji IC50 (μM) | HL-60 IC50 (μM) | H460 IC50 (μM) |
|---|---|---|---|---|---|
| 301 | 2-methyl-4-(2-methylsulfonyl-5-propylpyrimidin-4-yl)isoquinolin-1-one | | | | |
| 302 | 5-(5-ethyl-2-methylsulfonylpyrimidin-4-yl)-1,3-dimethylpyridin-2-one | | | | |
| 303 | 1,3-dimethyl-5-(2-methylsulfonyl-5-propylpyrimidin-4-yl)pyridin-2-one | | | | |
| 304 | 4-(5-butyl-2-methylsulfonylpyrimidin-4-yl)-2-methylisoquinolin-1-one | A | | | |
| 305 | 5-(5-butyl-2-methylsulfonylpyrimidin-4-yl)-1,3-dimethylpyridin-2-one | A | | | |
| 306 | N-[4-(2-methyl-1-oxoisoquinolin-4-yl)-5-propylpyrimidin-2-yl]ethanesulfonamide | A | | | |
| 307 | N-[4-(1,5-dimethyl-6-oxopyridin-3-yl)-5-ethylpyrimidin-2-yl]ethanesulfonamide | A | A | A | C |
| 308 | N-[4-(1,5-dimethyl-6-oxopyridin-3-yl)-5-propylpyrimidin-2-yl]ethanesulfonamide | A | A | A | C |
| 309 | N-[5-butyl-4-(2-methyl-1-oxoisoquinolin-4-yl)pyrimidin-2-yl]ethanesulfonamide | A | A | A | C |
| 310 | N-[5-butyl-4-(1,5-dimethyl-6-oxopyridin-3-yl)pyrimidin-2-yl]ethanesulfonamide | A | A | A | C |
| 311 | 4-[5-(cyclopropylmethoxy)-2-methylsulfonylpyrimidin-4-yl]-2-methylisoquinolin-1-one | A | | | |
| 312 | 5-(2-ethyl-5-methylsulfonylphenyl)-1-methylpyridin-2-one | B | C | C | C |
| 313 | 1-methyl-5-(5-methylsulfonyl-2-propylphenyl)pyridin-2-one | B | C | B | C |
| 314 | 2-methyl-4-(5-methylsulfonyl-2-propylphenyl)isoquinolin-1-one | A | | | |
| 315 | 5-[2-(2-cyclopropylethyl)-5-methylsulfonylphenyl]-1-methylpyridin-2-one | A | | | |
| 316 | 4-(2-ethyl-5-methylsulfonylphenyl)-2-methylisoquinolin-1-one | A | | | |
| 317 | 5-(2-butyl-5-methylsulfonylphenyl)-1-methylpyridin-2-one | A | | | |
| 318 | 4-(2-butyl-5-methylsulfonylphenyl)-2-methylisoquinolin-1-one | A | | | |
| 319 | 4-[2-(2-cyclopropylethyl)-5-methylsulfonylphenyl]-2-methylisoquinolin-1-one | A | | | |
| 320 | N-[6-(cyclopropylmethoxy)-5-(2-methyl-1-oxoisoquinolin-4-yl)pyridin-3-yl]ethanesulfonamide | A | A | A | C |
| 321 | 4-[2-(cyclopropylmethoxy)-5-methylsulfonylpyridin-3-yl]-2-methylisoquinolin-1-one | A | A | A | C |
| 322 | 4-[2-(cyclopropylmethoxy)-5-ethylsulfonylpyridin-3-yl]-2-methylisoquinolin-1-one | A | A | A | C |
| 323 | 5-[3-[(4-methoxyphenyl)methoxy]-5-methylsulfonylphenyl]-1,3-dimethylpyridin-2-one | A | | | |
| 324 | 1,3-dimethyl-5-(3-methylsulfonyl-5-phenylmethoxyphenyl)pyridin-2-one | A | B | A | C |
| 325 | 5-[3-(cyclopropylmethoxy)-5-methylsulfonylphenyl]-1,3-dimethylpyridin-2-one | A | B | B | C |
| 326 | 1,3-dimethyl-5-[3-methylsulfonyl-5-(2-phenylethoxy)phenyl]pyridin-2-one | A | B | B | C |

TABLE 24-continued

| Chemistry Synthesis Example | Name | BRD4 IC50 (μM) | Raji IC50 (μM) | HL-60 IC50 (μM) | H460 IC50 (μM) |
|---|---|---|---|---|---|
| 327 | 5-[3-(2-cyclopropylethoxy)-5-methylsulfonylphenyl]-1,3-dimethylpyridin-2-one | A | B | B | C |
| 328 | 1,3-dimethyl-5-[3-methylsulfonyl-5-(2,2,2-trifluoroethoxy)phenyl]pyridin-2-one | A | | | |
| 329 | 1,3-dimethyl-5-[3-[(3-methyloxetan-3-yl)methoxy]-5-methylsulfonylphenyl]pyridin-2-one | A | | | |
| 330 | 1,3-dimethyl-5-[3-methylsulfonyl-5-(pyridin-2-ylmethoxy)phenyl]pyridin-2-one | A | | | |
| 331 | 5-[3-[(2,6-dimethylphenyl)methoxy]-5-methylsulfonylphenyl]-1,3-dimethylpyridin-2-one | A | B | A | C |
| 332 | 5-[3-[(2-chlorophenyl)methoxy]-5-methylsulfonylphenyl]-1,3-dimethylpyridin-2-one | A | | | |
| 333 | 5-[3-[[2-(difluoromethoxy)phenyl]methoxy]-5-methylsulfonylphenyl]-1,3-dimethylpyridin-2-one | A | B | A | C |
| 334 | 2-[[3-(1,5-dimethyl-6-oxopyridin-3-yl)-5-methylsulfonyl-phenoxy]methyl]benzonitrile | A | B | A | C |
| 335 | 5-[3-[(2,4-difluorophenyl)methoxy]-5-methylsulfonylphenyl]-1,3-dimethylpyridin-2-one | A | | | |
| 336 | 1,3-dimethyl-5-[3-methylsulfonyl-5-(1-phenylethoxy)phenyl]pyridin-2-one | A | B | A | C |
| 337 | 5-[3-[(2,3-dichlorophenyl)methoxy]-5-methylsulfonylphenyl]-1,3-dimethylpyridin-2-one | B | | | |
| 338 | 1,3-dimethyl-5-[3-methylsulfonyl-5-(pyridin-3-ylmethoxy)phenyl]pyridin-2-one | A | | | |
| 339 | 3-[[3-(1,5-dimethyl-6-oxopyridin-3-yl)-5-methylsulfonyl-phenoxy]methyl]benzonitrile | A | | | |
| 340 | 5-(3-but-2-ynoxy-5-methylsulfonylphenyl)-1,3-dimethylpyridin-2-one | A | | | |
| 341 | 1,3-dimethyl-5-[3-methylsulfonyl-5-(1-phenylethoxy)phenyl]pyridin-2-one | A | A | A | C |
| 342 | N-[3-(2,4-difluorophenoxy)-5-(1,5-dimethyl-6-oxopyridin-3-yl)phenyl]ethanesulfonamide | A | A | A | B |
| 343 | 4-[3-[(4-methoxyphenyl)methoxy]-5-methylsulfonylphenyl]-2-methylisoquinolin-1-one | B | | | |
| 344 | 2-methyl-4-(3-methylsulfonyl-5-phenylmethoxyphenyl)isoquinolin-1-one | A | | | |
| 345 | 4-[3-(cyclopropylmethoxy)-5-methylsulfonylphenyl]-2-methylisoquinolin-1-one | A | | | |
| 346 | N-[4-(2,4-difluorophenoxy)-6-(1,5-dimethyl-6-oxopyridin-3-yl)pyrimidin-2-yl]ethanesulfonamide | B | | | |
| 347 | N-[2-(2,4-difluorophenoxy)-6-(1,5-dimethyl-6-oxopyridin-3-yl)pyrimidin-4-yl]ethanesulfonamide | B | | | |
| 348 | 4-[3-[[2-(difluoromethoxy)phenyl]methoxy]-5-methylsulfonylphenyl]-6-methylfuro[2,3-c]pyridin-7-one | A | A | A | B |

TABLE 24-continued

| Chemistry Synthesis Example | Name | BRD4 IC50 (µM) | Raji IC50 (µM) | HL-60 IC50 (µM) | H460 IC50 (µM) |
|---|---|---|---|---|---|
| 349 | 6-methyl-4-(3-methylsulfonyl-5-phenylmethoxyphenyl)furo[2,3-c]pyridin-7-one | A | A | A | C |
| 350 | 4-[3-(cyclopropylmethoxy)-5-methylsulfonylphenyl]-6-methylfuro[2,3-c]pyridin-7-one | A | | | |
| 351 | 1-methyl-5-(2-methylsulfonyl-5-propylpyrimidin-4-yl)pyridin-2-one | | | | |
| 352 | 5-(5-butyl-2-methylsulfonylpyrimidin-4-yl)-1-methylpyridin-2-one | | | | |
| 353 | 3-chloro-1-methyl-5-(2-methylsulfonyl-5-propylpyrimidin-4-yl)pyridin-2-one | | | | |
| 354 | 5-(5-butyl-2-methylsulfonylpyrimidin-4-yl)-3-chloro-1-methylpyridin-2-one | | | | |
| 355 | 3-methoxy-1-methyl-5-(2-methylsulfonyl-5-propylpyrimidin-4-yl)pyridin-2-one | | | | |
| 356 | 5-(5-butyl-2-methylsulfonylpyrimidin-4-yl)-3-methoxy-1-methylpyridin-2-one | | | | |
| 357 | N-[4-(1-methyl-6-oxopyridin-3-yl)-5-propylpyrimidin-2-yl]ethanesulfonamide | A | | | |
| 358 | N-[5-butyl-4-(1-methyl-6-oxopyridin-3-yl)pyrimidin-2-yl]ethanesulfonamide | A | | | |
| 359 | N-[4-(5-chloro-1-methyl-6-oxopyridin-3-yl)-5-propylpyrimidin-2-yl]ethanesulfonamide | A | | | |
| 360 | N-[5-butyl-4-(5-chloro-1-methyl-6-oxopyridin-3-yl)pyrimidin-2-yl]ethanesulfonamide | A | | | |
| 361 | N-[4-(5-methoxy-1-methyl-6-oxopyridin-3-yl)-5-propylpyrimidin-2-yl]ethanesulfonamide | A | | | |
| 362 | N-[5-butyl-4-(5-methoxy-1-methyl-6-oxopyridin-3-yl)pyrimidin-2-yl]ethanesulfonamide | A | | | |
| 363 | N-[5-butyl-4-(1,5-dimethyl-6-oxopyridin-3-yl)pyrimidin-2-yl]methanesulfonamide | A | | | |
| 364 | 4-[2-(cyclopropylmethoxy)-5-propan-2-ylsulfonylphenyl]-2-methylisoquinolin-1-one | A | | | |
| 365 | 8-[2-(cyclopropylmethoxy)-5-ethylsulfonylphenyl]-6-methyl-4H-pyrido[4,3-b][1,4]oxazine-3,5-dione | A | A | A | C |
| 366 | 8-[2-(cyclopropylmethoxy)-5-ethylsulfonylphenyl]-6-methyl-3,4-dihydro-2H-pyrido[4,3-b][1,4]oxazin-5-one | A | | | |
| 367 | N-[4-(2,4-difluorophenoxy)-3-(7-methyl-8-oxoimidazo[1,5-a]pyrazin-5-yl)phenyl]methanesulfonamide | A | A | A | C |
| 368 | 5-[2-(cyclopropylmethoxy)-5-ethylsulfonylphenyl]-7-methylimidazo[1,5-a]pyrazin-8-one | A | A | A | B |
| 369 | 5-[2-(2,4-difluorophenoxy)-5-(ethylsulfonylmethyl)phenyl]-7-methylimidazo[1,5-a]pyrazin-8-one | A | B | A | C |
| 370 | 7-methyl-5-[5-(methylsulfonylmethyl)-2-(2,2,2-trifluoroethoxy)phenyl]imidazo[1,5-a]pyrazin-8-one | A | B | B | C |
| 371 | 5-[5-(ethylsulfonylmethyl)-2-(2,2,2-trifluoroethoxy)phenyl]-7-methylimidazo[1,5-a]pyrazin-8-one | B | B | B | C |
| 372 | 5-[2-(2,4-difluorophenoxy)-5-(methylsulfonylmethyl)phenyl]-7-methylimidazo[1,5-a]pyrazin-8-one | A | A | A | C |

TABLE 24-continued

| Chemistry Synthesis Example | Name | BRD4 IC50 (μM) | Raji IC50 (μM) | HL-60 IC50 (μM) | H460 IC50 (μM) |
|---|---|---|---|---|---|
| 373 | 5-[2-(4,4-difluorocyclohexyl)oxy-5-ethylsulfonylphenyl]-7-methylimidazo[1,5-a]pyrazin-8-one | A | B | A | C |
| 374 | 5-(2-cyclopentyloxy-5-ethylsulfonylphenyl)-7-methylimidazo[1,5-a]pyrazin-8-one | A | A | A | C |
| 375 | 5-[2-(cyclopropylmethylamino)-5-ethylsulfonylphenyl]-7-methylimidazo[1,5-a]pyrazin-8-one | A | | | |
| 376 | 5-[2-(2,4-difluorophenoxy)-5-ethylsulfonylphenyl]-7-methylimidazo[1,5-a]pyrazin-8-one | A | B | A | C |
| 377 | 7-[2-(cyclopropylmethoxy)-5-methylsulfonylphenyl]-5-methylfuro[3,2-c]pyridin-4-one | A | A | A | C |
| 378 | 7-[2-(cyclopropylmethoxy)-5-ethylsulfonylphenyl]-5-methylfuro[3,2-c]pyridin-4-one | A | A | A | B |
| 379 | N-[4-(2,4-difluorophenoxy)-3-(5-methyl-4-oxofuro[3,2-c]pyridin-7-yl)phenyl]ethanesulfonamide | A | A | A | C |
| 380 | N-[4-(2,4-difluorophenoxy)-3-(5-methyl-4-oxofuro[3,2-c]pyridin-7-yl)phenyl]methanesulfonamide | A | A | A | C |
| 381 | 4-(cyclopropylmethoxy)-5-(1-methyl-6-oxopyridin-3-yl)-1-(methylsulfonylmethyl)pyridin-2-one | A | C | B | C |
| 382 | 5-[4-(cyclopropylmethoxy)-1-(methylsulfonylmethyl)-6-oxopyridin-3-yl]-1,3-dimethylpyridin-2-one | A | B | A | C |
| 383 | 4-[4-(cyclopropylmethoxy)-1-(methylsulfonylmethyl)-6-oxopyridin-3-yl]-7-fluoro-2-methylisoquinolin-1-one | A | B | A | C |
| 384 | 4-[4-(cyclopropylmethoxy)-1-(methylsulfonylmethyl)-6-oxopyridin-3-yl]-2-methylisoquinolin-1-one | A | B | A | C |
| 385 | 5-[4-(2,4-difluorophenoxy)-1-(methylsulfonylmethyl)-6-oxopyridin-3-yl]-1,3-dimethylpyridin-2-one | A | A | A | C |
| 386 | 4-(2,4-difluorophenoxy)-5-(1-methyl-6-oxopyridin-3-yl)-1-(methylsulfonylmethyl)pyridin-2-one | A | B | B | C |
| 387 | 4-[4-(2,4-difluorophenoxy)-1-(methylsulfonylmethyl)-6-oxopyridin-3-yl]-2-methylisoquinolin-1-one | A | A | A | C |
| 388 | 5-(2-but-2-ynoxy-5-methylsulfonylphenyl)-1,3-dimethylpyridin-2-one | A | A | A | C |
| 389 | 5-(2-but-2-ynoxy-5-ethylsulfonylphenyl)-3-methoxy-1-methylpyridin-2-one | A | B | A | C |
| 390 | 5-(5-ethylsulfonyl-2-pent-2-ynoxyphenyl)-3-methoxy-1-methylpyridin-2-one | A | | | |
| 391 | 5-[2-(3-cyclopropylprop-2-ynoxy)-5-ethylsulfonylphenyl]-3-methoxy-1-methylpyridin-2-one | A | B | A | C |
| 392 | 5-[2-(2,4-difluorophenoxy)-5-ethylsulfonylphenyl]-1-methyl-3-(trifluoromethyl)pyridin-2-one | B | | | |
| 393 | 4-[2-(cyclopropylmethoxy)-5-propan-2-ylsulfonylphenyl]-6-methoxy-2-methylisoquinolin-1-one | A | | | |
| 394 | 5-[2-(cyclopropylmethoxy)-5-propan-2-ylsulfonylphenyl]-1,3-dimethylpyridin-2-one | A | | | |

TABLE 24-continued

| Chemistry Synthesis Example | Name | BRD4 IC50 (µM) | Raji IC50 (µM) | HL-60 IC50 (µM) | H460 IC50 (µM) |
|---|---|---|---|---|---|
| 395 | N-[3-(1,5-dimethyl-6-oxopyridin-3-yl)-5-phenylmethoxyphenyl]ethanesulfonamide | A | | | |
| 396 | 5-[2-(2,4-difluoroanilino)-5-ethylsulfonylphenyl]-1,3-dimethylpyridin-2-one | A | A | A | C |
| 397 | 5-[2-[(4,4-difluorocyclohexyl)amino]-5-ethylsulfonylphenyl]-1,3-dimethylpyridin-2-one | A | A | A | C |
| 398 | 5-[2-(2,4-difluoroanilino)-5-methylsulfonylphenyl]-1,3-dimethylpyridin-2-one | A | B | A | C |
| 399 | 5-[2-(cyclopropylmethoxy)-5-ethylsulfonylphenyl]-3-methoxy-1-methylpyridin-2-one | A | A | A | C |
| 400 | 5-[2-(2,4-difluorophenoxy)-5-(methylsulfonylmethyl)phenyl]-3-methoxy-1-methylpyridin-2-one | A | A | A | C |
| 401 | 5-[2-(4-hydroxycyclohexyl)oxy-5-methylsulfonylphenyl]-1,3-dimethylpyridin-2-one | A | B | A | C |
| 402 | N-[4-(2,4-difluorophenoxy)-3-(1-methyl-5-methylsulfanyl-6-oxopyridin-3-yl)phenyl]ethanesulfonamide | A | A | A | C |
| 403 | 5-[2-(cis-4-aminocyclohexyl)oxy-5-methylsulfonylphenyl]-1,3-dimethylpyridin-2-one | A | | | |
| 404 | 5-[2-(trans-4-aminocyclohexyl)oxy-5-methylsulfonylphenyl]-1,3-dimethylpyridin-2-one | A | C | A | C |
| 405 | 1,3-dimethyl-5-[5-methylsulfonyl-2-(3,3,3-trifluoropropoxy)phenyl]pyridin-2-one | A | | | |
| 406 | 5-[2-(2,4-difluorophenoxy)-5-(methylsulfonylmethyl)phenyl]-1-(2-hydroxyethyl)-3-methylpyridin-2-one | A | | | |
| 407 | 5-[5-(ethylsulfonylmethyl)-2-(2,2,2-trifluoroethoxy)phenyl]-1-(2-hydroxyethyl)-3-methylpyridin-2-one | B | | | |
| 408 | 5-[2-(cyclopropylmethylamino)-5-ethylsulfonylphenyl]-1-methyl-3-(methylamino)pyridin-2-one | A | | | |
| 409 | 5-[2-(cyclopropylmethoxy)-5-ethylsulfonylphenyl]-1-methyl-3-(methylamino)pyridin-2-one | A | | | |
| 410 | N-[4-(2,4-difluorophenoxy)-3-[1-methyl-5-(methylamino)-6-oxopyridin-3-yl]phenyl]ethanesulfonamide | A | | | |
| 411 | 5-[5-(ethylsulfonylmethyl)-2-(2,2,2-trifluoroethoxy)phenyl]-1,3-dimethylpyridin-2-one | A | | | |
| 412 | N-[4-(2,4-difluorophenoxy)-3-[1-methyl-5-(methylamino)-6-oxopyridin-3-yl]phenyl]methanesulfonamide | A | | | |
| 413 | 5-[2-[(4,4-difluorocyclohexyl)amino]-5-methylsulfonylphenyl]-1,3-dimethylpyridin-2-one | A | | | |
| 414 | 5-[2-(cyclopropylmethylamino)-5-ethylsulfonylphenyl]-3-methoxy-1-methylpyridin-2-one | A | | | |
| 415 | 5-[2-(4,4-difluorocyclohexyl)oxy-5-methylsulfonylphenyl]-1,3-dimethylpyridin-2-one | A | A | A | C |
| 416 | 5-[2-(cyclopentylamino)-5-ethylsulfonylphenyl]-1,3-dimethylpyridin-2-one | A | A | A | C |

TABLE 24-continued

| Chemistry Synthesis Example | Name | BRD4 IC50 (μM) | Raji IC50 (μM) | HL-60 IC50 (μM) | H460 IC50 (μM) |
|---|---|---|---|---|---|
| 417 | 5-[2-(cyclopentylamino)-5-methylsulfonylphenyl]-1,3-dimethylpyridin-2-one | A | A | A | C |
| 418 | 3-chloro-1-methyl-5-[5-(methylsulfonylmethyl)-2-(2,2,2-trifluoroethoxy)phenyl]pyridin-2-one | A | B | A | C |
| 419 | 5-(2-cyclopentyloxy-5-methylsulfonylphenyl)-1,3-dimethylpyridin-2-one | A | B | A | C |
| 420 | 1,3-dimethyl-5-[5-methylsulfonyl-2-(oxan-4-yloxy)phenyl]pyridin-2-one | A | B | A | C |
| 421 | 3-fluoro-1-methyl-5-[5-(methylsulfonylmethyl)-2-(2,2,2-trifluoroethoxy)phenyl]pyridin-2-one | A | | | |
| 422 | 5-[2-(cyclopropylmethylamino)-5-methylsulfonylphenyl]-1,4-dimethylpyridin-2-one | B | | | |
| 423 | 5-[2-(cyclopropylmethylamino)-5-ethylsulfonylphenyl]-1,4-dimethylpyridin-2-one | B | | | |
| 424 | N-[4-(1-methyl-6-oxopyridin-3-yl)-5-phenylthiophen-2-yl]ethanesulfonamide | C | | | |
| 425 | 1,3-dimethyl-5-[5-methylsulfonyl-2-(oxolan-3-ylamino)phenyl]pyridin-2-one | A | | | |
| 426 | 1,3-dimethyl-5-[5-methylsulfonyl-2-(oxolan-3-yloxy)phenyl]pyridin-2-one | A | B | B | C |
| 427 | 1,3-dimethyl-5-[5-(methylsulfonylmethyl)-2-(2,2,2-trifluoroethoxy)phenyl]pyridin-2-one | A | A | A | C |
| 428 | 5-[2-(cyclopropylmethylamino)-5-methylsulfonylphenyl]-1-ethyl-3-methylpyridin-2-one | A | B | B | C |
| 429 | 5-[2-(2,4-difluorophenoxy)-5-(methylsulfonylmethyl)phenyl]-1-ethyl-3-methylpyridin-2-one | A | A | A | C |
| 430 | N-[3-(1,5-dimethyl-6-oxopyridin-3-yl)-4-(trans-4-hydroxycyclohexyl)oxy-phenyl]ethanesulfonamide | A | A | A | C |
| 431 | N-[3-(1,5-dimethyl-6-oxopyridin-3-yl)-4-(cis-4-hydroxycyclohexyl)oxyphenyl]ethanesulfonamide | A | B | A | C |
| 432 | N-[4-(1-methyl-6-oxopyridin-3-yl)-5-(2-methylphenyl)thiophen-2-yl]ethanesulfonamide | C | | | |
| 433 | N-[3-(1,5-dimethyl-6-oxopyridin-3-yl)-4-(trans-4-hydroxycyclohexyl)oxyphenyl]methanesulfonamide | A | A | A | C |
| 434 | N-[3-(1,5-dimethyl-6-oxopyridin-3-yl)-4-(cis-4-hydroxycyclohexyl)oxyphenyl]methanesulfonamide | A | B | B | C |
| 435 | N-[5-(2-ethylphenyl)-4-(1-methyl-6-oxopyridin-3-yl)thiophen-2-yl]ethanesulfonamide | C | | | |
| 436 | 1,3-dimethyl-5-[5-methylsulfonyl-2-(oxan-4-ylamino)phenyl]pyridin-2-one | A | B | A | C |
| 437 | 5-[2-(2,4-difluorophenoxy)-5-(methylsulfonylmethyl)phenyl]-3-fluoro-1-methylpyridin-2-one | A | A | A | C |
| 438 | 5-[2-(cyclopropylmethylamino)-5-methylsulfonylphenyl]-3-(dimethylamino)-1-methylpyridin-2-one | A | A | A | C |
| 439 | N-[3-(1,5-dimethyl-6-oxopyridin-3-yl)-4-(oxan-4-yloxy)phenyl]methanesulfonamide | A | A | A | C |
| 440 | 5-[2-(cyclopropylmethylamino)-5-ethylsulfonylphenyl]-3-(dimethylamino)-1-methylpyridin-2-one | A | A | A | C |

TABLE 24-continued

| Chemistry Synthesis Example | Name | BRD4 IC50 (µM) | Raji IC50 (µM) | HL-60 IC50 (µM) | H460 IC50 (µM) |
|---|---|---|---|---|---|
| 441 | N-[3-(1,5-dimethyl-6-oxopyridin-3-yl)-4-(oxan-4-yloxy)phenyl]ethanesulfonamide | A | A | A | C |
| 442 | N-[4-(2,4-difluorophenoxy)-3-(5-methoxy-1-methyl-6-oxopyridin-3-yl)phenyl]methanesulfonamide | A | A | A | C |
| 443 | N-[4-(2,4-difluorophenoxy)-3-(5-methoxy-1-methyl-6-oxopyridin-3-yl)phenyl]ethanesulfonamide | A | A | A | C |
| 444 | N-[3-(1,5-dimethyl-6-oxopyridin-3-yl)-4-(oxolan-3-yloxy)phenyl]methanesulfonamide | A | A | A | C |
| 445 | N-[3-(1,5-dimethyl-6-oxopyridin-3-yl)-4-(oxolan-3-yloxy)phenyl]ethanesulfonamide | A | A | A | C |
| 446 | N-[3-(1,5-dimethyl-6-oxopyridin-3-yl)-4-(oxan-3-yloxy)phenyl]methanesulfonamide | A | A | A | C |
| 447 | N-[4-(4,4-difluorocyclohexyl)oxy-3-(1,5-dimethyl-6-oxopyridin-3-yl)phenyl]methanesulfonamide | A | A | A | C |
| 448 | N-[3-(1,5-dimethyl-6-oxopyridin-3-yl)-4-(oxan-3-yloxy)phenyl]ethanesulfonamide | A | A | A | C |
| 449 | N-[4-(4,4-difluorocyclohexyl)oxy-3-(1,5-dimethyl-6-oxopyridin-3-yl)phenyl]ethanesulfonamide | A | A | A | C |
| 450 | 5-[2-(cyclopropylmethoxy)-5-ethylsulfonylphenyl]-1,3-dimethylpyridin-2-one | A | A | A | C |
| 451 | N-[4-(2,4-difluorophenoxy)-3-(5-hydroxy-1-methyl-6-oxopyridin-3-yl)phenyl]ethanesulfonamide | A | ND | A | C |
| 452 | 4-(cyclopropylmethylamino)-3-(1,5-dimethyl-6-oxopyridin-3-yl)benzenesulfonamide | B | ND | B | C |
| 453 | 4-(cyclopropylmethylamino)-3-(1-methyl-6-oxopyridin-3-yl)benzenesulfonamide | C | C | C | C |
| 454 | 5-[2-(2,4-difluorophenoxy)-5-(methylsulfonylmethyl)phenyl]-1,4-dimethylpyridin-2-one | A | A | A | C |
| 455 | 5-[2-(2,4-difluorophenoxy)-5-(methylsulfonylmethyl)phenyl]-1,3-dimethylpyridin-2-one | A | A | A | C |
| 456 | 5-(2-ethoxy-5-ethylsulfonylphenyl)-1-($^{2}H_{3}$)methyl-4-methylpyridin-2-one | A | | | |
| 457 | 5-[2-(cyclopropylmethoxy)-5-ethylsulfonylphenyl]-1-($^{2}H_{3}$)methyl-4-methylpyridin-2-one | A | A | | |
| 458 | 5-(2-ethoxy-5-ethylsulfonylphenyl)-1,4-dimethylpyridin-2-one | A | | | |
| 459 | 5-[2-(cyclobutylmethoxy)-5-methylsulfonylphenyl]-1,3-dimethylpyridin-2-one | A | A | A | C |
| 460 | 5-[2-(cyclobutylmethoxy)-5-methylsulfonylphenyl]-1-methylpyridin-2-one | A | | | |
| 461 | 5-(5-ethylsulfonyl-2-methoxyphenyl)-3-hydroxy-1-methylpyridin-2-one | B | | | |
| 462 | 5-[2-(cyclopropylmethylamino)-5-methylsulfonylphenyl]-1,3-dimethylpyridin-2-one | A | A | A | C |
| 463 | N-[4-(2,4-difluorophenoxy)-3-[5-(dimethylamino)-1-methyl-6-oxopyridin-3-yl]phenyl]methanesulfonamide | A | A | A | C |
| 464 | N-[4-(2,4-difluorophenoxy)-3-[5-(dimethylamino)-1-methyl-6-oxopyridin-3-yl]phenyl]ethanesulfonamide | A | A | A | C |

TABLE 24-continued

| Chemistry Synthesis Example | Name | BRD4 IC50 (μM) | Raji IC50 (μM) | HL-60 IC50 (μM) | H460 IC50 (μM) |
|---|---|---|---|---|---|
| 465 | 5-[2-(cyclopropylmethylamino)-5-ethylsulfonylphenyl]-1,3-dimethylpyridin-2-one | A | A | A | C |
| 466 | 5-[2-(cyclopropylmethoxy)-5-ethylsulfonylphenyl]-1,4-dimethylpyridin-2-one | A | A | A | C |
| 467 | N-[3-(5-hydroxy-1-methyl-6-oxopyridin-3-yl)phenyl]methanesulfonamide | B | C | C | C |
| 468 | 5-[2-(cyclopropylmethylamino)-5-methylsulfonylphenyl]-1-methylpyridin-2-one | A | C | B | C |
| 469 | 3-(dimethylamino)-5-(2-ethoxy-5-ethylsulfonylphenyl)-1-methylpyridin-2-one | A | A | A | C |
| 470 | 5-[2-(2,4-difluorophenoxy)-5-(methylsulfonylmethyl)phenyl]-1-methylpyridin-2-one | A | A | A | B |
| 471 | N-[3-(1-methyl-6-oxo-5-phenylmethoxypyridin-3-yl)phenyl]methanesulfonamide | C | | | |
| 472 | N-[4-(2,4-difluorophenoxy)-3-(1,5-dimethyl-6-oxopyridin-3-yl)phenyl]ethanesulfonamide | A | A | A | C |
| 473 | 5-[2-(cyclopropylmethylamino)-5-ethylsulfonylphenyl]-1-methylpyridin-2-one | A | B | A | C |
| 474 | 5-[2-(cyclopropylmethoxy)-5-methylsulfonylphenyl]-3-(dimethylamino)-1-methylpyridin-2-one | A | A | A | C |
| 475 | 5-[4-fluoro-2-methoxy-5-(methylsulfonylmethyl)phenyl]-1-methylpyridin-2-one | B | | | |
| 476 | 5-[2-(cyclopropylmethoxy)-5-methylsulfonylphenyl]-1,3-dimethylpyridin-2-one | A | B | A | C |
| 477 | 5-[2-(cyclopropylmethoxy)-5-methylsulfonylphenyl]-1,4-dimethylpyridin-2-one | A | B | A | C |
| 478 | N-[6-[3-(methanesulfonamido)phenyl]-4-methyl-3-oxopyrazin-2-yl]acetamide | C | | | |
| 479 | N-[3-(1,4-dimethyl-6-oxopyridazin-3-yl)phenyl]ethanesulfonamide | C | | | |
| 480 | N-[3-(1,5-dimethyl-6-oxopyridazin-3-yl)phenyl]ethanesulfonamide | B | | | |
| 481 | N-[5-[3-(methanesulfonamido)phenyl]-1-methyl-2-oxopyridin-3-yl]propanamide | C | | | |
| 482 | N-[5-[3-(methanesulfonamido)phenyl]-1-methyl-2-oxopyridin-3-yl]acetamide | C | | | |
| 483 | 1-cyclobutyl-5-[2-(cyclopropylmethoxy)-5-methylsulfonylphenyl]-3-methylpyridin-2-one | A | | | |
| 484 | N-[3-(1-cyclobutyl-5-methyl-6-oxopyridin-3-yl)-4-(2,4-difluorophenoxy)phenyl]methanesulfonamide | A | | | |
| 485 | 1-benzyl-5-[2-(cyclopropylmethoxy)-5-methylsulfonylphenyl]-3-methylpyridin-2-one | B | | | |
| 486 | 1,3-dimethyl-5-(2-methyl-5-methylsulfonyl-2,3-dihydro-1-benzofuran-7-yl)pyridin-2-one | B | C | B | C |
| 487 | 4-[5-(ethylsulfonylmethyl)-2-(2,2,2-trifluoroethoxy)phenyl]-2-methylisoquinolin-1-one | A | A | A | C |
| 488 | 2-methyl-4-[5-(methylsulfonylmethyl)-2-(2,2,2- | A | A | A | C |

TABLE 24-continued

| Chemistry Synthesis Example | Name | BRD4 IC50 (μM) | Raji IC50 (μM) | HL-60 IC50 (μM) | H460 IC50 (μM) |
|---|---|---|---|---|---|
|  | trifluoroethoxy)phenyl]isoquinolin-1-one |  |  |  |  |
| 489 | 1,3-dimethyl-5-(7-methylsulfonyl-2,3-dihydro-1,4-benzodioxin-5-yl)pyridin-2-one | B |  |  |  |
| 490 | N-[2-ethyl-8-(2-methyl-1-oxoisoquinolin-4-yl)-3,4-dihydro-2H-chromen-6-yl]methanesulfonamide | A |  |  |  |
| 491 | N-[2-ethyl-8-(2-methyl-1-oxoisoquinolin-4-yl)-3,4-dihydro-2H-chromen-6-yl]ethanesulfonamide | A |  |  |  |
| 492 | N-[8-(1,5-dimethyl-6-oxopyridin-3-yl)-2-ethyl-3,4-dihydro-2H-chromen-6-yl]ethanesulfonamide | A |  |  |  |
| 493 | 4-(2-cyclopropyl-5-methylsulfonyl-2,3-dihydro-1-benzofuran-7-yl)-2-methylisoquinolin-1-one | A |  |  |  |
| 494 | 4-(2-ethyl-5-methylsulfonyl-2,3-dihydro-1-benzofuran-7-yl)-2-methylisoquinolin-1-one | A | B |  |  |
| 495 | N-[7-(1,5-dimethyl-6-oxopyridin-3-yl)-2-propyl-2,3-dihydro-1-benzofuran-5-yl]ethanesulfonamide | A |  |  |  |
| 496 | N-[2-cyclopropyl-7-(1,5-dimethyl-6-oxopyridin-3-yl)-2,3-dihydro-1-benzofuran-5-yl]ethanesulfonamide | A | A |  |  |
| 497 | 4-[3-(methoxymethyl)-7-methylsulfonyl-2,3-dihydro-1,4-benzodioxin-5-yl]-2-methylisoquinolin-1-one | A | B | B | C |
| 498 | 5-[3-(methoxymethyl)-7-methylsulfonyl-2,3-dihydro-1,4-benzodioxin-5-yl]-1,3-dimethylpyridin-2-one | A | C | B | C |
| 499 | 4-[3-(methoxymethyl)-7-methylsulfonyl-2,3-dihydro-1,4-benzodioxin-5-yl]-2-methylisoquinolin-1-one | A |  |  |  |
| 500 | 5-[3-(methoxymethyl)-7-methylsulfonyl-2,3-dihydro-1,4-benzodioxin-5-yl]-1,3-dimethylpyridin-2-one | A |  |  |  |
| 501 | 4-[2-(methoxymethyl)-7-methylsulfonyl-2,3-dihydro-1,4-benzodioxin-5-yl]-2-methylisoquinolin-1-one | A | B | B | C |
| 502 | 5-[2-(methoxymethyl)-7-methylsulfonyl-2,3-dihydro-1,4-benzodioxin-5-yl]-1,3-dimethylpyridin-2-one | A |  |  |  |
| 503 | 4-[2-(methoxymethyl)-7-methylsulfonyl-2,3-dihydro-1,4-benzodioxin-5-yl]-2-methylisoquinolin-1-one | A |  |  |  |
| 504 | 4-[2-(cyclopropylmethoxy)-5-methylsulfonylphenyl]-2-methyl-6,7-dihydro-5H-cyclopenta[c]pyridin-1-one | A | A |  |  |
| 505 | 4-[2-(cyclopropylmethoxy)-5-ethylsulfonylphenyl]-2-methyl-6,7-dihydro-5H-cyclopenta[c]pyridin-1-one | A |  |  |  |
| 506 | N-[4-(2,4-difluorophenoxy)-3-(2-methyl-1-oxo-6,7-dihydro-5H-cyclopenta[c]pyridin-4-yl)phenyl]methanesulfonamide | A |  |  |  |
| 507 | N-[4-(2,4-difluorophenoxy)-3-(2-methyl-1-oxo-6,7-dihydro-5H-cyclopenta[c]pyridin-4-yl)phenyl]ethanesulfonamide | A |  |  |  |
| 508 | 5-(5-butyl-2-methylsulfonylpyrimidin-4-yl)-3-methyl-1-propan-2-ylpyridin-2-one | A |  |  |  |

TABLE 24-continued

| Chemistry Synthesis Example | Name | BRD4 IC50 (μM) | Raji IC50 (μM) | HL-60 IC50 (μM) | H460 IC50 (μM) |
|---|---|---|---|---|---|
| 509 | N-[5-(2,4-difluorophenoxy)-4-(5-methyl-6-oxo-1-propan-2-ylpyridin-3-yl)pyrimidin-2-yl]ethanesulfonamide | A | A | | |
| 510 | 5-[5-(2,4-difluorophenoxy)-2-methylsulfonylpyrimidin-4-yl]-3-methyl-1-propan-2-ylpyridin-2-one | B | | | |
| 511 | N-[5-butyl-4-(5-methyl-6-oxo-1-propan-2-ylpyridin-3-yl)pyrimidin-2-yl]ethanesulfonamide | A | A | | |
| 512 | N-[5-butyl-4-(1-methyl-6-oxo-5-propan-2-ylpyridin-3-yl)pyrimidin-2-yl]ethanesulfonamide | A | A | | |
| 513 | 5-(5-butyl-2-methylsulfonylpyrimidin-4-yl)-1-methyl-3-propan-2-ylpyridin-2-one | A | | | |
| 514 | N-[5-(2,4-difluorophenoxy)-4-(1-methyl-6-oxo-5-propan-2-ylpyridin-3-yl)pyrimidin-2-yl]ethanesulfonamide | A | | | |

Note:
IC$_{50}$ data are designated within the following ranges:
A: ≤0.5 μM
B: >0.5 μM to ≤5.0 μM
C: >5.0 μM Example 3

In Vivo Xenograph Study—Antitumor Efficacy in Xenograft Models of Nut Midline Carcinoma (NMC)

Xenograft models of NMC in mice are used in this study. Matched cohorts of mice with established tumors are randomized to treatment with a test compound or vehicle, administered by daily intraperitoneal injection. Before randomization and after 4 days of therapy, mice are evaluated by $^{18}$F-fluorodeoxyglucose (FDG)-PET imaging. Tumor-volume measurements are also made, as are measures of toxicity or weight loss. Tumors are obtained and sectioned and immunohistochemically examined for the BRD4-NUT oncoprotein, cell spreading, keratin expression, nuclear Ki67, and TUNEL staining. Paired samples from treated and untreated mice are prepared and analyzed using standardized protocols and commercially available software (i.e., ImageScopt; Aperio Technologies).

Example 4

In Vivo Xenograph Study—Antitumor Efficacy in Xenograft Models of MCF-7 Breast Cancer Time release pellets containing 0.72 mg 17-β Estradiol are subcutaneously implanted into nu/nu mice. MCF-7 cells are grown in RPMI containing 10% FBS at 5% $CO_2$, 37° C. Cells are spun down and re-suspended in 50% RPMI (serum free) and 50% Matrigel at 1×10$^7$ cells/mL. MCF-7 cells are subcutaneously injected (100 μL/animal) on the right flank 2-3 days post pellet implantation and tumor volume (length×width$^2$/2) is monitored bi-weekly. When tumors reach an average volume of ~200 mm$^3$ animals are randomized and treatment is started. Animals are treated with a test compound or vehicle daily for 4 weeks. Tumor volume and body weight are monitored bi-weekly throughout the study. At the conclusion of the treatment period, plasma and tumor samples are taken for pharmacokinetic and pharmacodynamic analyses, respectively.

Example 5

In Vivo Xenograph Study—Antitumor Efficacy in Xenograft Model of Raji Human Burkitts Lymphoma Model Procedure: Female SCID CB17 mice (6-8 weeks old, Charles River Laboratories) were inoculated subcutaneously in the right flank region with Raji cells (at 3.5×10$^6$ cells/mouse) and the tumor was allowed to grow to approximately 150 mm$^3$. Mice were then randomized into treatment cohorts (N=8) and treated orally once daily with vehicle control or test compound for 21 days. Test compound was administered as a suspension in 1% Tween 80, 40% PEG400 and either: 59% of 0.5% HPMC, or 9% DMSO+50% of 0.5% HPMC. Tumors length and width were measured in millimeters three times per week. Tumor volumes were calculated by the formula V=L×W×W/2. Tumor growth inhibition (TGI) was calculated with the formula:

TGI=100−(median tumor volume of treatment group/
median tumor volume of vehicle control
group)×100

TGI measurements were performed until the volume of a tumor in the control group reached 3,000 mm$^3$. Statistical analysis was performed using 2-tailed T-test. P values <0.05 were considered as statistically significant.

Preliminary Results: Seven compounds from Table 1 were selected and administered at doses ranging from 5 mg/kg to 50 mg/kg. TGI was determined to range from 42% to 80%. Results are preliminary and do not reflect optimized dosing schedules.

III. Preparation of Pharmaceutical Dosage Forms

Example 1

Oral Tablet

A tablet is prepared by mixing 48% by weight of a compound of Formula (I), or a pharmaceutically acceptable salt thereof, 45% by weight of microcrystalline cellulose, 5% by weight of low-substituted hydroxypropyl cellulose, and 2% by weight of magnesium stearate. Tablets are prepared by direct compression. The total weight of the compressed tablets is maintained at 250-500 mg.

I claim:

1. A compound, or a pharmaceutically acceptable salt thereof, of Formula (XXIV)

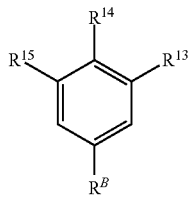

Formula (XXIV)

wherein, $R^{13}$ is —Y—Z; wherein Y is selected from a bond, or —CH$_2$—; and Z is selected from —SO$_2$R$^{21}$, —N(R$^{22}$)SO$_2$R$^{21}$, —SO$_2$N(R$^{22}$)$_2$, —N(R$^{22}$)SO$_2$N(R$^{22}$)$_2$, —CON(R$^{22}$)$_2$, —N(R$^{22}$)CO$_2$R$^{21}$, —N(R$^{22}$)CON (R$^{22}$)$_2$, —N(R$^{22}$)COR$^{21}$, —COR$^{21}$, —OC(O)N(R$^{22}$)$_2$, —OSO$_2$N(R$^{22}$)$_2$, —N(R$^{22}$)SO$_3$R$^{21}$, or —N(R$^{22}$)$_2$; and wherein each R$^{21}$ is independently selected from alkyl, cycloalkyl, cycloalkylalkyl, aryl, aralkyl, heterocyclyl, heterocyclylalkyl, heteroaryl, or heteroarylalkyl; and each R$^{22}$ is independently selected from hydrogen, alkyl, cycloalkyl, cycloalkylalkyl, aryl, aralkyl, heterocyclyl, heterocyclylalkyl, heteroaryl, or heteroarylalkyl;

$R^{14}$ is hydrogen, halogen, $C_1$-$C_3$ alkyl, or $C_1$-$C_3$ alkoxy;

$R^{15}$ is halogen or U-V, wherein U is a bond, —O—, or —CH$_2$—; and V is —CN, alkyl, alkynyl, aryl, aralkyl, cycloalkyl, cycloalkylalkyl, heterocyclyl, heterocyclylalkyl, heteroaryl, or heteroarylalkyl; and $R^B$ is

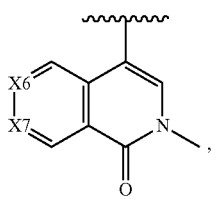

wherein X6 is C—R$^7$, wherein R$^7$ is hydrogen or halogen; X7 is C—R$^8$, wherein R$^8$ is hydrogen or halogen;

or $R^B$ is

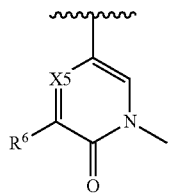

wherein X5 is C—R$^5$, wherein R$^5$ is hydrogen or halogen; and R$^6$ is hydrogen, alkyl, alkoxy, or halogen;

or $R^B$ is

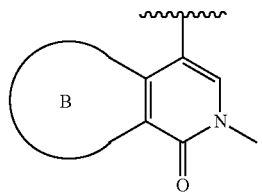

wherein Ring B is an optionally substituted 5-membered heterocyclyl ring containing at least one oxygen or sulfur atom.

2. The compound of claim 1, or a pharmaceutically acceptable salt thereof, wherein Y is —CH$_2$—.

3. The compound of claim 1, or a pharmaceutically acceptable salt thereof, wherein Y is a bond.

4. The compound of claim 1, or a pharmaceutically acceptable salt thereof, wherein Z is —SO$_2$R$^{21}$, —N(R$^{22}$) SO$_2$R$^{21}$, or —N(R$^{22}$)$_2$.

5. The compound of claim 1, or a pharmaceutically acceptable salt thereof, wherein Z is —SO$_2$R$^{21}$ or —N(R$^{22}$) SO$_2$R$^{21}$.

6. The compound of claim 1, or a pharmaceutically acceptable salt thereof, wherein Z is —N(R$^{22}$)SO$_2$R$^{21}$.

7. The compound of claim 1, or a pharmaceutically acceptable salt thereof, wherein Z is —SO$_2$R$^{21}$.

8. The compound of claim 1, or a pharmaceutically acceptable salt thereof, wherein R$^{21}$ is heterocyclyl or heterocyclylalkyl.

9. The compound of claim 1, or a pharmaceutically acceptable salt thereof, wherein R$^{21}$ is alkyl, cycloalkyl, or cycloalkylalkyl.

10. The compound of claim 1, or a pharmaceutically acceptable salt thereof, wherein R$^{21}$ is alkyl, and the alkyl is a $C_1$-$C_4$ alkyl.

11. The compound of claim 1, or a pharmaceutically acceptable salt thereof, wherein R$^{22}$ is alkyl, cycloalkyl, or aralkyl.

12. The compound of claim 1, or a pharmaceutically acceptable salt thereof, wherein R$^{22}$ is hydrogen or methyl.

13. The compound of claim 1, or a pharmaceutically acceptable salt thereof, wherein R$^{14}$ is hydrogen.

14. The compound of claim 1, or a pharmaceutically acceptable salt thereof, wherein U is a bond.

15. The compound of claim 1, or a pharmaceutically acceptable salt thereof, wherein U is —O—.

16. The compound of claim 1, or a pharmaceutically acceptable salt thereof, wherein U is —CH$_2$—.

17. The compound of claim 1, or a pharmaceutically acceptable salt thereof, wherein V is alkyl.

18. The compound of claim 1, or a pharmaceutically acceptable salt thereof, wherein V is aryl.

19. The compound of claim 1, or a pharmaceutically acceptable salt thereof, wherein V is aralkyl.

20. The compound of claim 1, or a pharmaceutically acceptable salt thereof, wherein V is cycloalkylalkyl.

21. The compound of claim 1, or a pharmaceutically acceptable salt thereof, wherein V is heterocyclylalkyl.

22. The compound of claim 1, or a pharmaceutically acceptable salt thereof, wherein V is heteroaryl.

23. The compound of claim 1, or a pharmaceutically acceptable salt thereof, wherein V is heteroarylalkyl.

24. The compound of claim 1, or a pharmaceutically acceptable salt thereof, wherein V is alkynyl.

25. The compound of claim 1, or a pharmaceutically acceptable salt thereof, wherein Y is a bond, Z is —N($R^{22}$)$SO_2R^{21}$, U is —O—, and V is aryl, aralkyl or cycloalkylalkyl.

26. The compound of claim 1, or a pharmaceutically acceptable salt thereof, wherein Y is a bond, Z is —$SO_2R^{21}$, U is —O—, and V is aryl, aralkyl or cycloalkylalkyl.

27. The compound of claim 1, or a pharmaceutically acceptable salt thereof, wherein $R^B$ is

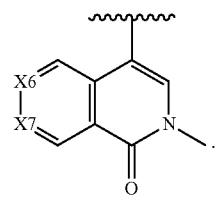

28. The compound of claim 1, or a pharmaceutically acceptable salt thereof, wherein $R^7$ is halogen and $R^8$ is hydrogen.

29. The compound of claim 1, or a pharmaceutically acceptable salt thereof, wherein $R^7$ is hydrogen and $R^8$ is halogen.

30. The compound of claim 1, or a pharmaceutically acceptable salt thereof, wherein both $R^7$ and $R^8$ are hydrogen.

31. A pharmaceutical composition comprising the compound of claim 1, or a pharmaceutically acceptable salt thereof, and at least one pharmaceutically acceptable excipient.

\* \* \* \* \*